US009090887B2

(12) United States Patent
Cuevas et al.

(10) Patent No.: US 9,090,887 B2
(45) Date of Patent: *Jul. 28, 2015

(54) VARIANT ALPHA-AMYLASES FROM *BACILLUS SUBTILIS* AND METHODS OF USE, THEREOF

(75) Inventors: William A Cuevas, San Francisco, CA (US); Sang-Kyu Lee, Palo Alto, CA (US); Sandra W Ramer, Sunnyvale, CA (US); Andrew Shaw, San Francisco, CA (US); Amr R Toppozada, San Francisco, CA (US); David E Estell, San Francisco, CA (US); Louise Wallace, Menlo Park, CA (US); Regina Chin, Palo Alto, CA (US); Carol A Requadt, Paradise, CA (US); Scott D Power, San Bruno, CA (US); Michael J Pepsin, Castro Valley, CA (US)

(73) Assignee: DANISCO US INC., Palo Alto, CA (US)

( * ) Notice: Subject to any disclaimer, the term of this patent is extended or adjusted under 35 U.S.C. 154(b) by 426 days.

This patent is subject to a terminal disclaimer.

(21) Appl. No.: 12/479,416

(22) Filed: Jun. 5, 2009

(65) Prior Publication Data
US 2010/0003366 A1 Jan. 7, 2010

Related U.S. Application Data

(60) Provisional application No. 61/059,618, filed on Jun. 6, 2008, provisional application No. 61/059,513, filed on Jun. 6, 2008.

(51) Int. Cl.
*C12N 9/26* (2006.01)
*C12N 9/28* (2006.01)
*G01N 11/00* (2006.01)

(52) U.S. Cl.
CPC .............. *C12N 9/26* (2013.01); *C12N 9/2408* (2013.01); *C12N 9/2417* (2013.01); *G01N 11/00* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 4,106,991 A | 8/1978 | Markussen et al. |
| 4,435,307 A | 3/1984 | Barbesgaard et al. |
| RE32,153 E | 5/1986 | Tamura et al. |
| 4,587,215 A | 5/1986 | Hirsh |
| 4,661,452 A | 4/1987 | Markussen et al. |
| 5,024,943 A | 6/1991 | Van Ee |
| 5,112,518 A | 5/1992 | Klugkist et al. |
| 5,141,664 A | 8/1992 | Corring et al. |
| 5,240,632 A | 8/1993 | Brumbaugh |
| 5,281,526 A | 1/1994 | Good et al. |
| 5,427,936 A | 6/1995 | Moeller et al. |
| 5,457,046 A | 10/1995 | Woldike et al. |
| 5,648,263 A | 7/1997 | Schulein et al. |
| 5,686,593 A | 11/1997 | Woldike et al. |
| 5,691,178 A | 11/1997 | Schulein et al. |
| 5,763,254 A | 6/1998 | Woldike et al. |
| 5,776,757 A | 7/1998 | Schulein et al. |
| 5,827,718 A | 10/1998 | Ishida et al. |
| 5,879,920 A | 3/1999 | Dale et al. |
| 5,942,431 A | 8/1999 | Yoneda et al. |
| 6,077,316 A | 6/2000 | Lund et al. |
| 6,287,841 B1 | 9/2001 | Mulleners et al. |
| 6,440,716 B1 | 8/2002 | Svendsen et al. |
| 6,475,762 B1 | 11/2002 | Stafford et al. |
| 7,037,704 B2 | 5/2006 | Dunn-Coleman et al. |
| 7,332,319 B2 | 2/2008 | Baldwin et al. |
| 2004/0018607 A1 | 1/2004 | Callen et al. |
| 2006/0014265 A1 | 1/2006 | Ferrari et al. |
| 2008/0220498 A1 | 9/2008 | Cervin et al. |
| 2009/0305360 A1 | 12/2009 | Breneman et al. |
| 2009/0305935 A1 | 12/2009 | Cascao-Pereira |
| 2010/0003366 A1 | 1/2010 | Cuevas et al. |
| 2010/0015686 A1 | 1/2010 | Cascao-Pereira et al. |

FOREIGN PATENT DOCUMENTS

| | | |
|---|---|---|
| CA | 2023529 A1 | 2/1991 |
| CA | 2006687 C | 12/1994 |
| CA | 2202553 A1 | 4/1996 |
| DE | 38 33 047 A1 | 4/1990 |
| DE | 41 37 470 A1 | 5/1993 |
| DE | 42 05 071 A1 | 8/1993 |
| DE | 42 12 166 A1 | 10/1993 |
| EP | 0 135 138 A2 | 3/1985 |
| EP | 0 214 761 A2 | 3/1987 |
| EP | 0 218 272 A1 | 4/1987 |
| EP | 0 238 023 A2 | 9/1987 |
| EP | 0 238 216 A1 | 9/1987 |

(Continued)

OTHER PUBLICATIONS

Rumbak et al. (J. Bacteriology, vol. 173, pp. 4203-4211, 1991).*
Mantsala et al. (JBC, vol. 254, No. 17, pp. 8540-8547, 1979).*
Orlando et al., "The purification of a novel amylase from *Bacillus subtilis* and its inhibition by wheat proteins," *Biochem. J.* (1983) 209: 561-64.
Kagawa et al., "Crystal Structure of *Bacillus subtilis* α-Amylase in Complex with Acarbose," *J. Bacteriol.* (2003) 185(23): 6981-84.
Mäntsälä et al., "Membrane-bound and Soluble Extracellular α-Amylase from *Bacillus subtilis*," *J. Biol. Chem.* (1979) 254(17): 8540-47.
Yang et al., "Nucleotide sequence of the amylase gene from *Bacillus subtilis*," *Nucl. Acids Res.* (1983) 11(2): 237-49.

(Continued)

*Primary Examiner* — Hope Robinson
(74) *Attorney, Agent, or Firm* — DANISCO US INC.

(57) ABSTRACT

Alpha-amylases from *Bacillus subtilis* (AmyE), variants thereof, nucleic acids encoding the same, and host cells comprising the nucleic acids are provided. Methods of using AmyE or variants thereof are disclosed, including liquefaction and/or saccharification of starch. Such methods may yield sugars useful for ethanol production or high fructose corn syrup production. In some cases, the amylases can be used at low pH, in the absence of calcium, and/or in the absence of a glucoamylase.

11 Claims, 16 Drawing Sheets

(56) References Cited

FOREIGN PATENT DOCUMENTS

| | | |
|---|---|---|
| EP | 0 258 068 A2 | 3/1988 |
| EP | 0 260 105 A2 | 3/1988 |
| EP | 0 271 155 A2 | 6/1988 |
| EP | 0 271 156 A2 | 6/1988 |
| EP | 0 305 216 A1 | 3/1989 |
| EP | 0 318 204 A1 | 5/1989 |
| EP | 0 318 279 A2 | 5/1989 |
| EP | 0 331 376 A2 | 9/1989 |
| EP | 0 346 136 A1 | 12/1989 |
| EP | 0 346 137 A1 | 12/1989 |
| EP | 0 407 225 A1 | 1/1991 |
| EP | 0 429 124 A1 | 5/1991 |
| EP | 0 481 547 A1 | 4/1992 |
| EP | 0 495 257 A1 | 7/1992 |
| EP | 0 516 553 A2 | 12/1992 |
| EP | 0 516 554 A2 | 12/1992 |
| EP | 0 516 555 A2 | 12/1992 |
| EP | 0 518 719 A1 | 12/1992 |
| EP | 0 518 720 A1 | 12/1992 |
| EP | 0 518 721 A1 | 12/1992 |
| EP | 0 530 635 A2 | 3/1993 |
| EP | 0 530 870 A1 | 3/1993 |
| EP | 0 533 239 A2 | 3/1993 |
| EP | 0 554 943 A2 | 8/1993 |
| EP | 0 561 446 A2 | 9/1993 |
| EP | 0 561 452 A1 | 9/1993 |
| GB | 1372034 A | 10/1974 |
| GB | 1483591 A | 8/1977 |
| GB | 2194546 A | 3/1988 |
| GB | 2200132 A | 7/1988 |
| GB | 2228945 A | 9/1990 |
| GB | 2234980 A | 2/1991 |
| IE | 911979 | 12/1991 |
| JP | 64-074992 | 3/1989 |
| WO | WO 84/02921 A2 | 8/1984 |
| WO | WO 86/01831 A1 | 3/1986 |
| WO | WO 88/02775 A1 | 4/1988 |
| WO | WO 89/01032 A1 | 2/1989 |
| WO | WO 89/06270 A1 | 7/1989 |
| WO | WO 89/06279 A1 | 7/1989 |
| WO | WO 89/09259 A1 | 10/1989 |
| WO | WO 91/17243 A1 | 11/1991 |
| WO | WO 91/17244 A1 | 11/1991 |
| WO | WO 91/19782 A1 | 12/1991 |
| WO | WO 92/00381 A1 | 1/1992 |
| WO | WO 92/01793 A1 | 2/1992 |
| WO | WO 92/05249 A1 | 4/1992 |
| WO | WO 92/06154 A1 | 4/1992 |
| WO | WO 92/06157 A1 | 4/1992 |
| WO | WO 92/08777 A1 | 5/1992 |
| WO | WO 92/17573 A1 | 10/1992 |
| WO | WO 92/19708 A1 | 11/1992 |
| WO | WO 92/19709 A1 | 11/1992 |
| WO | WO 92/19729 A1 | 11/1992 |
| WO | WO 93/03129 A1 | 2/1993 |
| WO | WO 93/04153 A1 | 3/1993 |
| WO | WO 93/10210 A1 | 5/1993 |
| WO | WO 93/17089 A1 | 9/1993 |
| WO | WO 93/18129 A1 | 9/1993 |
| WO | WO 93/21297 A1 | 10/1993 |
| WO | WO 93/21299 A1 | 10/1993 |
| WO | WO 93/24618 A1 | 12/1993 |
| WO | WO 93/25651 A1 | 12/1993 |
| WO | WO 94/01541 A1 | 1/1994 |
| WO | WO 94/07998 A1 | 4/1994 |
| WO | WO 94/25578 A1 | 11/1994 |
| WO | WO 94/25583 A1 | 11/1994 |
| WO | WO 95/00636 A1 | 1/1995 |
| WO | WO 95/10602 A1 | 4/1995 |
| WO | WO 95/14783 A1 | 6/1995 |
| WO | WO 95/22615 A1 | 8/1995 |
| WO | WO 95/24471 A1 | 9/1995 |
| WO | WO 95/26397 A1 | 10/1995 |
| WO | WO 95/30744 A2 | 11/1995 |
| WO | WO 95/35381 A1 | 12/1995 |
| WO | WO 96/00292 A1 | 1/1996 |
| WO | WO 96/11262 A1 | 4/1996 |
| WO | WO 96/13580 A1 | 5/1996 |
| WO | WO 96/29397 A1 | 9/1996 |
| WO | WO 96/34108 A2 | 10/1996 |
| WO | WO 97/04079 A1 | 2/1997 |
| WO | WO 97/07202 A1 | 2/1997 |
| WO | WO 98/08940 A1 | 3/1998 |
| WO | WO 98/12307 A1 | 3/1998 |
| WO | WO 98/15257 A1 | 4/1998 |
| WO | WO 98/20115 A1 | 5/1998 |
| WO | WO 98/22613 A1 | 5/1998 |
| WO | WO 99/01544 A1 | 1/1999 |
| WO | WO 99/25846 A2 | 5/1999 |
| WO | WO 99/28448 A1 | 6/1999 |
| WO | WO 99/49740 A1 | 10/1999 |
| WO | WO 00/04136 A1 | 1/2000 |
| WO | WO 01/14629 A1 | 3/2001 |
| WO | WO 01/34899 A1 | 5/2001 |
| WO | WO-02/068589 A2 | 9/2002 |
| WO | WO-2004/091544 A2 | 10/2004 |
| WO | WO 2005/056783 A1 | 6/2005 |
| WO | WO 2005/069849 | 8/2005 |
| WO | WO-2005/069849 A2 | 8/2005 |
| WO | WO 2005/111203 A2 | 11/2005 |
| WO | WO 2006/043178 A2 | 4/2006 |
| WO | WO 2006/060062 A2 | 6/2006 |
| WO | WO 2009/108941 A1 | 9/2009 |
| WO | WO-2009149395 A2 | 12/2009 |
| WO | WO-2009149419 A2 | 12/2009 |

OTHER PUBLICATIONS

Emori et al., "Molecular Cloning, Nucleotide Sequencing, and Expression of the *Bacillus subtilis* (*natto*) IAM1212 α-Amylase Gene, Which Encodes an α-Amylase Structurally Similar to but Enzymatically Distinct from That of *B. subtilis* 2633," *J. Bacteriol.* (1990) 172(9): 4901-08.

Kagawa M. et al., "Crystal structure of *Bacillus subtilis* alpha-amylase in complex with acarbose," J Bacteriol. Dec. 2003; 185 (23): pp. 6981-6984.

Fujimoto Z. et al., Crystal structure of a catalytic-site mutant alpha-amylase from *Bacillus subtilis* complexed with maltopentaose, J Mol Biol. Mar. 27, 1998: 277(2) pp. 393-407.

Mizuno H. et al., "Crystallization and preliminary X-ray studies of wild type and catalytic-site mutant alpha-amylase from *Bacillus subtilis*," J Mol Biol. Dec. 20, 1993; 234(4), pp. 1282-1283.

Barbe et al., "From a consortium sequence to a unified sequence: the *Bacillus subtilis* 168 reference genome a decade later," Microbiology 2009, 155 (PT 6), pp. 1756-1775.

Eichenberger et al., "The program of gene transcription for a single differentiating cell type during sporulation in *Bacillus subtilis*" PLoS Biol. 2 (10), E328 (2004).

Kunst et al., "The complete genome sequence of the gram-positive bacterium *Bacillus subtilis*" Nature 390 (6657), pp. 249-256 (1997).

Mizuno et al., "Systematic sequence of the 263 kb 210 degrees-232 degrees region of the *Bacillus subtilis* genome containing the skin element and many sporulation genes", Microbiology 142 (PT 111), pp. 3103-3111 (1996); NCBI Genome Project, "Direct Submission", submitted (Aug. 12, 2009) National Center for Biotechnology Information, NIH, Bethesda, MD 20894, USA.

GenBank: AL009126.3 region 90537-92086. Printed Jan. 27, 2012. https://rdp.cme.msu.edu/hierarchy/detail.jsp?format=genbank&seqid=S002289415.

NCBI Reference Sequence: YP_004206261.1. Printed Jan. 27, 2012. http://www.ncbi.nlm.nih.gov/protein/321313974?report=genbank&log$=protalign&blast_rank=1&RID=HHEG2BRJ01N.

NCBI Reference Sequence: NP_388186.2. Printed Jan. 27, 2012. http://www.ncbi.nlm.nih.gov/protein/255767082?report=genbank&log$=protalign&blast_rank=1&RID=HHEG2BRJ01N.

Swiss-Prot: P00691.2. Printed Jan. 27, 2012. http://www.ncbi.nlm.nih.gov/protein/239938593?report=genbank&log$=protalign&blast_rank=1&RID=HHEG2BRJ01N.

(56) References Cited

OTHER PUBLICATIONS

GenBank: ACM91731.1. Printed Jan. 27, 2012. http://www.ncbi.nlm.nih.gov/protein/223585727?report=genbank&log$=protalign&blast_rank=1&RID=HHEG2BRJ01N.
GenBank: CAB12098.2. Printed Jan. 27, 2012. http://www.ncbi.nlm.nih.gov/protein/225184709?report=genbank&log$=protalign&blast_rank=1&RID=HHEG2BRJ01N.
GenBank: ADV95234.1. Printed Jan. 27, 2012. http://www.ncbi.nlm.nih.gov/protein/320020248?report=genbank&log$=protalign&blast_rank=1&RID=HHEG2BRJ01N.
GenBank: EHA28753.1. Printed Jan. 27, 2012. http://www.ncbi.nlm.nih.gov/protein/351468537?report=genbank&log$=protalign&blast_rank=1&RID=HHEG2BRJ01N.
GenBank: ADH93704.1. Printed Jan. 27, 2012. http://www.ncbi.nlm.nih.gov/protein/296933184?report=genbank&log$=protalign&blast_rank=2&RID=HHEG2BRJ01N.
GenBank: ADH93705.1. Printed Jan. 27, 2012. http://www.ncbi.nlm.nih.gov/protein/296933186?report=genbank&log$=protalign&blast_rank=3&RID=HHEG2BRJ01N.
GenBank: ADH93703.1. Printed Jan. 27, 2012. http://www.ncbi.nlm.nih.gov/protein/296933182?report=genbank&log$=protalign&blast_rank=4&RID=HHEG2BRJ01N.
GenBank: AAF14358.1. Printed Jan. 27, 2012. http://www.ncbi.nlm.nih.gov/protein/6502575?report=genbank&log$=protalign&blast_rank=5&RID=HHEG2BRJ01N.
GenBank: ABK54355.1. Printed Jan. 27, 2012. http://www.ncbi.nlm.nih.gov/protein/117650733?report=genbank&log$=protalign&blast_rank=5&RID=HHEG2BRJ01N.
GenBank: AAT01440.1. Printed Jan. 27, 2012. http://www.ncbi.nlm.nih.gov/protein/46577901?report=genbank&log$=protalign&blast_rank=6&RID=HHEG2BRJ01N.
GenBank: ABW75769.1. Printed Jan. 27, 2012. http://www.ncbi.nlm.nih.gov/protein/158633403?report=genbank&log$=protalign&blast_rank=7&RID=HHEG2BRJ01N.
GenBank: AAZ30064.1. Printed Jan. 27, 2012. http://www.ncbi.nlm.nih.gov/protein/71362804?report=genbank&log$=protalign&blast_rank=8&RID=HHEG2BRJ01N.
GenBank: AEP89368.1. Printed Jan. 27, 2012. http://www.ncbi.nlm.nih.gov/protein/349593181?report=genbank&log$=protalign&blast_rank=9&RID=HHEG2BRJ01N.
GenBank: ADH93706.1. Printed Jan. 27, 2012. http://www.ncbi.nlm.nih.gov/protein/296933188?report=genbank&log$=protalign&blast_rank=10&RID=HHEG2BRJ01N.
NCBI Reference Sequence: ZP_03598671.1. Printed Jan. 27, 2012. http://www.ncbi.nlm.nih.gov/protein/221317377?report=genbank&log$=protalign&blast_rank=11&RID=HHEG2BRJ01N.
GenBank: CAA23437.1. Printed Jan. 27, 2012. http://www.ncbi.nlm.nih.gov/protein/39794?report=genbank&log$=protalign&blast_rank=12&RID=HHEG2BRJ01N.
GenBank: BAA08938.1. Printed Jan. 27, 2012. http://www.ncbi.nlm.nih.gov/protein/1805375?report=genbank&log$=protalign&blast_rank=12&RID=HHEG2BRJ01N.
NCBI Reference Sequence: YP_004875852.1. Printed Jan. 27, 2012. http://www.ncbi.nlm.nih.gov/protein/35026545?report=genbank&log$=protalign&blast_rank=13&RID=HHEG2BRJ01N.
GenBank: AEP85220.1. Printed Jan. 27, 2012. http://www.ncbi.nlm.nih.gov/protein/349597432?report=genbank&log$=protalign&blast_rank=13&RID=HHEG2BRJ01N.
Gene ID: 11238201. Printed Jan. 27, 2012. http://www.ncbi.nlm.nih.gov/sites/entrez?db=gene&cmd=search&term=11238201&RID=HHEG2BRJ01N&log$=geneexplicitprot&blast_rank=13.
NCBI Reference Sequence: ZP_06875121.1. Printed Jan. 27, 2012. http://www.ncbi.nlm.nih.gov/protein/296332661?report=genbank&log$=protalign&blast_rank=14&RID=HHEG2BRJ01N.
NCBI Reference Sequence: YP_003864677.1. Printed Jan. 27, 2012. http://www.ncbi.nlm.nih.gov/protein/305673005?report=genbank&log$=protalign&blast_rank=14&RID=HHEG2BRJ01N.
GenBank: EFG90830.1. Printed Jan. 27, 2012. http://www.ncbi.nlm.nih.gov/protein/296149941?report=genbank&log$=protalign&blast_rank=14&RID=HHEG2BRJ01N.
GenBank: ADM36368.1. Printed Jan. 27, 2012. http://www.ncbi.nlm.nih.gov/protein/305411249?report=genbank&log$=protalign&blast_rank=14&RID=HHEG2BRJ01N.
GenBank: ACD93218.3. Printed Jan. 27, 2012. http://www.ncbi.nlm.nih.gov/protein/288915565?report=genbank&log$=protalign&blast_rank=15&RID=HHEG2BRJ01N.
GenBank: AAQ83841.1. Printed Jan. 27, 2012. http://www.ncbi.nlm.nih.gov/protein/34979594?report=genbank&log$=protalign&blast_rank=16&RID=HHEG2BRJ01N.
NCBI Reference Sequence: YP_001419958.1. Printed Jan. 27, 2012. http://www.ncbi.nlm.nih.gov/protein/154684797?report=genbank&log$=protalign&blast_rank=17&RID=HHEG2BRJ01N.
GenBank: ABS72727.1. Printed Jan. 27, 2012. http://www.ncbi.nlm.nih.gov/protein/154350648?report=genbank&log$=protalign&blast_rank=17&RID=HHEG2BRJ01N.
Gene ID: 5462160. Printed Jan. 27, 2012. http://www.ncbi.nlm.nih.gov/sites/entrez?db=gene&cmd=search&term=5462160&RID=HHEG2BRJ01N&log$=geneexplicitprot&blast_rank=17.
GenBank: ADF47479.1. Printed Jan. 27, 2012. http://www.ncbi.nlm.nih.gov/protein/294906521?report=genbank&log$=protalign&blast_rank=18&RID=HHEG2BRJ01N.
GenBank: ADB81848.1. Printed Jan. 27, 2012. http://www.ncbi.nlm.nih.gov/protein/284178231?report=genbank&log$=protalign&blast_rank=19&RID=HHEG2BRJ01N.
GenBank: CCF03805.1. Printed Jan. 27, 2012. http://www.ncbi.nlm.nih.gov/protein/371566955?report=genbank&log$=protalign&blast_rank=20&RID=HHEG2BRJ01N.
GenBank: ABY73736.1. Printed Jan. 27, 2012. http://www.ncbi.nlm.nih.gov/protein/165909652?report=genbank&log$=protalign&blast_rank=21&RID=HHEG2BRJ01N.
GenBank: EHM06463.1. Printed Jan. 27, 2012. http://www.ncbi.nlm.nih.gov/protein/363726325?report=genbank&log$=protalign&blast_rank=22&RID=HHEG2BRJ01N.
GenBank: BAA31528.1. Printed Jan. 27, 2012. http://www.ncbi.nlm.nih.gov/protein/3298505?report=genbank&log$=protalign&blast_rank=23&RID=HHEG2BRJ01N.
GenBank: ADH93707.1. Printed Jan. 27, 2012. http://www.ncbi.nlm.nih.gov/protein/296933190?report=genbank&log$=protalign&blast_rank=24&RID=HHEG2BRJ01N.
GenBank: AAA72224.1. Printed Jan. 27, 2012. http://www.ncbi.nlm.nih.gov/protein/209058?report=genbank&log$=protalign&blast_rank=26&RID=HHEG2BRJ01N.
GenBank: AAA22234.1. Printed Jan. 27, 2012. http://www.ncbi.nlm.nih.gov/protein/142503?report=genbank&log$=protalign&blast_rank=27&RID=HHEG2BRJ01N.
GenBank: CAA30643.1. Printed Jan. 27, 2012. http://www.ncbi.nlm.nih.gov/protein/39790?report=genbank&log$=protalign&blast_rank=28&RID=HHEG2BRJ01N.
PRF: 226106. Printed Jan. 27, 2012. http://www.ncbi.nlm.nih.gov/protein/226106?report=genbank&log$=protalign&blast_rank=28&RID=HHEG2BRJ01N.
GenBank: CAA26086.1. Printed Jan. 27, 2012. http://www.ncbi.nlm.nih.gov/protein/39796?report=genbank&log$=protalign&blast_rank=29&RID=HHEG2BRJ01N.
GenBank: ACK37366.1. Printed Jan. 27, 2012. http://www.ncbi.nlm.nih.gov/protein/217315807?report=genbank&log$=protalign&blast_rank=30&RID=HHEG2BRJ01N.
GenBank: BAI83766.1. Printed Jan. 27, 2012. http://www.ncbi.nlm.nih.gov/protein/291482691?report=genbank&log$=protalign&blast_rank=31&RID=HHEG2BRJ01N.
PRF: 352984. Printed Jan. 27, 2012. http://www.ncbi.nlm.nih.gov/protein/352984?report=genbank&log$=protalign&blast_rank=32&RID=HHEG2BRJ01N.
GenBank: ABW34932.1. Printed Jan. 27, 2012. http://www.ncbi.nlm.nih.gov/protein/158342342?report=genbank&log$=protalign&blast_rank=33&RID=HHEG2BRJ01N.
GenBank: AAA22194.1. Printed Jan. 27, 2012. http://www.ncbi.nlm.nih.gov/protein/142435?report=genbank&log$=protalign&blast_rank=34&RID=HHEG2BRJ01N.

(56) References Cited

OTHER PUBLICATIONS

PDB: 1BAG_A. Printed Jan. 27, 2012. http://www.ncbi.nlm.nih.gov/protein/157830193?report=genbank&log$=protalign&blast_rank=35&RID=HHEG2BRJ01N.
GenBank: ACU57501.1. Printed Jan. 27, 2012. http://www.ncbi.nlm.nih.gov/protein/256033945?report=genbank&log$=protalign&blast_rank=36&RID=HHEG2BRJ01N.
PDB: 1UA7_A. Printed Jan. 27, 2012. http://www.ncbi.nlm.nih.gov/protein/49259314?report=genbank&log$=protalign&blast_rank=37&RID=HHEG2BRJ01N.
GenBank: CAJ01439.1. Printed Jan. 27, 2012. http://www.ncbi.nlm.nih.gov/protein/67624833?report=genbank&log$=protalign&blast_rank=38&RID=HHEG2BRJ01N.
PDB: 3DC0_A. Printed Jan. 27, 2012. http://www.ncbi.nlm.nih.gov/protein/190613740?report=genbank&log$=protalign&blast_rank=39&RID=HHEG2BRJ01N.
Yamazaki et al., "α-Amylase Genes (amyR2 and amyE') from an α-Amylase-Hyperproducing *Bacillus subtilis* Strain: Molecular Cloning and Nucleotide Sequences", Journal of Bacteriology, Oct. 1983, pp. 327-337.
Cho et al., "Molecular characterization of a dimeric intracellylar maltogenic amylase of *Bacillus subtilis* SUH4-2", Biochemica et Biophysica Acta 1478 (2000). pp. 333-340.
Boel, E. et al. "Glucoamylases G1 and G2 from *Aspergillus niger* are synthesized from two different but closely related mRNAs." *The EMBO Journal* 3(5): 1097-1102, 1984.
Broun, P., et al., Catalytic Plasticity of Fatty Acid Modification Enzymes Underlying Chemical Diversity of Plant Lipids. *Science* 282: 1315-1317, 1998.
Cayot, P. et al. "The Quantification of Protein Amino Groups by the Trinitrobenzenesulfonic Acid Method: A Reexamination." *Analytical Biochemistry* 249(2): 184-200, 1997.
Chen, H.-M. et al. "Identification and elimination by site-directed mutagenesis of thermolabile aspartyl bonds in *Aspergillus awamori* glucoamylase." *Protein Eng.* 8(6): 575-582, 1995.
Chen, H.-M. et al. "Effect of replacing helical glycine residues with alanines on reversible and irreversible stability and production of *Aspergillus awamori* glucoamylase." *Protein Eng.* 9(6): 499-505, 1996.
Chen, H.M. et al. "Substitution of asparagine residues in *Aspergillus awamori* glucoamylase by site-directed mutagenesis to eliminate N-glycosylation and inactivation by deamidation." *Biochem. J.* 301(Pt 1): 275-281, 1994.
Chica, R.A., et al., "Semi-rational approaches to engineering enzyme activity: combining the benefits of directed evolution and rational design." *Current Opinion in Biotechnology* 16: 378-384, 2005.
Cho, H.-Y., et al., "Molecular characterization of a dimeric intracellular maltogenic amylase of *Bacillus subtilis* SUH4-2." *Biochemica et Biophysica Acta* 1478(2): 333-340, 2000.
Christophersen, C., et al. "Enzymatic Characterisation of Novamyl®, a Thermostable α-Amylase." *Starch—Stärke* 50(1): 39-45, 1998.
Conti, M., et al. "Capillary isoelectric focusing: the problem of protein solubility." *Journal of Chromatography A.* 757(1-2): 237-245, 1997.
Dartois, V., et al. "Cloning, nucleotide sequence and expression in *Escherichia coli* of a lipase gene from *Bacillus subtilis* 168." *Biochimica et Biophysica Acta* 1131(3): 253-260, 1992.
Database GenBank. "alpha-amylase [*Bacillus subtilis*]." Accession No. ABW75769, 2007.
Database GenBank. "alpha-amylase [*Bacillus subtilis*]." Accession No. ABK54355, 2006.
Database GenBank. "alpha-amylase [*Bacillus subtilis*]." Accession No. AAF14358, 2000.
Database GenBank. "alpha-amylase [*Bacillus subtilis*]." Accession No. AAZ30064, 2005.
Database GenBank. "alpha-amylase [*Bacillus subtilis*]." Accession No. AAQ83841, 2003.
Database GenBank. "alpha-amylase precursor [*Bacillus subtilis*]." Accession No. BAA31528, 2000.
Database GenBank. "alpha-amylase protein [*Bacillus subtilis*]." Accession No. AAT01440, 2004.
Database NCBI Refseq. "alpha-amylase [*Bacillus subtilis* subsp. *subtilis* str. 168]." Accession No. NP_388186, 2009.
Database RCSB Protein Data Bank © "alpha-amylase from *Bacillus subtilis* complexed with 2 maltopentaose" Accession No. 1BAG, Jan. 30, 1998.
Database UniProt [Online] Accession No. Q9R9H7, May 1, 2000, Alpha-amylase—*Bacillus subtilis*, http://www.uniprot.org/uniprot/Q9R9H7.txt?version=1.
Database UniProt [Online] Accession No. P00691, Jul. 21, 1986, Alpha-amylase precursor—*Bacillus subtilis*, http://srs.ebi.ac.uk/srsbin/cgi-bin/wgetz?-e+[SWISSPROT-acc:P00691]+-vn+2.
Database UniProt. "Alpha-amylase." Accession No. O82953, 1998-2009.
Devos, D., et al., "Practical Limits of Function Prediction." *Proteins, Structure, Function, and Genetics* 41: 98-107, 2000.
Engelen, A.J. et al. "Simple and rapid determination of phytase activity." *Journal of AOAC International* 77(3): 760-764, 1994.
Fierobe, H.-P., et al. "Mutational Modulation of Substrate Bond-Type Specificity and Thermostability of Glucoamylase from *Aspergillus awamori* by Replacement with Short Homologue Active Site Sequences and Thiol/Disulfide Engineering." *Biochemistry* 35(26): 8696-8704, 1996.
Fogarty, W.M., et al. "Starch degrading enzymes of microbial origin." *Progress in Industrial Microbiology* 15: 87-150, particularly 112-115, 1979.
Freire, E. "Differential Scanning Calorimetry." In *Protein Stability and Folding: Theory and Practice*, Methods in Molecular Biology, No. 40, ed. B.A. Shirley. New York: Humana Press, pp. 191-218, 1995.
Fujimoto, Z., et al. "Crystal structure of a catalytic-site mutant aamylase from *Bacillus subtilis* complexed with maltopentaose." *Journal of Molecular Biology* 277(2): 393-407, 1998.
Hata, Y., et al. "The glucoamylase cDNA from *Aspergillus oryzae*: its cloning, nucleotide sequence, and expression in *Saccharomyces cerevisiae*." *Agric. Biol. Chem.* 55(4): 941-949, 1991.
International Search Report and the Written Opinion of the International Searching Authority for International Application No. PCT/US2009/046506 dated Mar. 3, 2010.
Kaushik, J.K., et al. "Why Is Trehalose an Exceptional Protein Stabilizer?: An analysis of the thermal stability of proteins in the presence of the compatible osmolyte trehalose." *J. Biol. Chem.* 278(29): 26458-26465, 2003.
Li, Y., et al. "Effect of introducing proline residues on the stability of *Aspergillus awamori*." *Protein Eng.* 10(10): 1199-1204, 1997.
McKenzie, T., et al. "The nucleotide sequence of pUB110: some salient features in relation to replication and its regulation." *Plasmid* 15(2): 93-103, 1986.
Morris, M.A., et al. "The Effect of Wash Temperature on Removal of Particulate and Oily Soil from Fabrics of Varying Fiber Content." *Textile Research Journal* 52(4): 280-286, 1982.
Ohdan, K., et al. "Characteristics of Two Forms of alpha-Amylases and Structural Implication." *Appl. Environ. Microbiol.* 65(10): 4652-4658, 1999.
Rumbak, E., et al., "Cloning, Nucleotide Sequence, and Enzymatic Characterization of an Alpha Amylase from the Ruminal Bacterium *Butyrivibrio fibrisolvens* H17c." *J. Bacteriol.* 173(13): 4203-4211, 1991.
Seffernick, J.L., et al., "Melamine Deaminase and Atrazine Chlorohydrolase: 98 Percent Identical but Functionally Different." *J. Bacteriol.* 183(8): 2405-2410, 2001.
Sen, S., et al., "Developments in Directed Evolution for Improving Enzyme Functions." *App. Biochem. Biotechol.* 143: 212-223, 2007.
Whisstock, J.C., et al., "Prediction of protein function from protein sequence and structure." *Quarterly Reviews of Biophysics* 36(3): 307-340, 2003.
Witkowski, A., et al., "Conversion of a β-Ketoacyl Synthase to a Malonyl Decarboxylase by Replacement of the Active-Site Cysteine with Glutamine." *Biochemistry* 38: 11643-11650, 1999.
Cleland, J.E. et al. "Baumé-Dry Substance Tables for Starch Suspensions." *Industrial & Engineering Chemistry Analytical Edition* 15(5):334-336, 1943.

(56) References Cited

OTHER PUBLICATIONS

De Moraes, L.M.P., et al. "Development of yeast strains for the efficient utilization of starch: evaluation of constructs that express alpha-amylase and glucoamylase separately or bifunctional fusion proteins." *Applied Microbiology and Biotechnology* 43: 1067-1076, 1995.

Konsoula, Z., et al. "Alpha-amylases and glucoamylases free or immobilized in calcium alginate gel capsules for synergistic hydrolysis of crude starches." *Amino Acids* 33, p. XIII, 2007.

Kunamneni, A., et al. "Response surface optimization of enzymatic hydrolysis of maize starch for higher glucose production." *Bichemical Engineering Journal* 27: 179-190, 2005.

Lassmann, T. et al. "Kalign—an accurate and fast multiple sequence alignment algorithm." *BMC Bioinformatics* 6(1):298, 2005.

Liu, X.-D., et al. "A novel raw starch digesting alpha-amylase from a newly isolated *bacillus* sp. YX-1: Purification and characterization." *Bioresource Technology* 99: 4315-4320, 2008.

MacGregor, E.A. et al. "Relationship of sequence and structure to specificity in the [alpha]-amylase family of enzymes." *Biochimica et Biophysica Acta (BBA)—Protein Structure and Molecular Enzymology* 1546(1): 1-20, 2001.

Sequence alignment of SEQ ID No: 2 with reference to Daniell H, WO2009/108941, published Sep. 3, 2009 (see PTO 892).

Sodhi, H.K., et al. "Production of a thermostable alpha-amylase from *Bacillus* sp. PS-7 by solid state fermentation and its synergistic use in the hydrolysis of malt starch for alcohol production." *Process Biochemistry* 40: 525-534, 2005.

Yeesang, C., et al. "Sago strach as a low-cost carbon source for exopolysaccharide production by *Lactobacillus kefiranofaciens*." *World Journal of Microbiology and Biotechnology* 24: 1195-1201, 2007.

Hayashida, S., et al. "Production and characteristics of raw-potato-starch-digesting alpha-amylase from *Bacillus subtilis* 65." *Applied and Environmental Microbiology* 54: 1516-1522, 1988.

\* cited by examiner

```
                                                                        9
     Amy31A    ..........  ..........  ..........  ..........  .VTASSVKNG
AmyE_full_length   ..........  ..........  ..........  ..........  .LTAPSIKSG 10
     Amy31A    TILHAWNWSF  NTLTQNMKDI  RDAGYAAIQT  SPINQVKEGN  QGDKSMSNWY
AmyE_full_length   TILHAWNWSF  NTLKHNMKDI  HDAGYTAIQT  SPINQVKEGN  QGDKSMSNWY 60
     Amy31A    WLYQPTSYQI  GNRYLGTEQE  FKDMCAAAEK  YGVKVIVDAV  VNHTTSDYGA
AmyE_full_length   WLYQPTSYQI  GNRYLGTEQE  FKEMCAAAEE  YGIKVIVDAV  INHTTSDYAA 110
     Amy31A    ISDEIKRIPN  WTHGNTQIKN  WSDRWDITQN  ALLGLYDWNT  QNTEVQAYLK
AmyE_full_length   ISNEVKSIPN  WTHGNTQIKN  WSDRWDVTQN  SLLGLYDWNT  QNTQVQSYLK 160
     Amy31A    GFLERALNDG  ADGFRYDAAK  HIELPDDGNY  GSQFWPNITN  TSAEFQYGEI
AmyE_full_length   RFLDRALNDG  ADGFRFDAAK  HIELPDDGSY  GSQFWPNITN  TSAEFQYGEI 210
     Amy31A    LQDSASRDTA  YANYMNVTAS  NYGHSIRSAL  KNRILSVSNI  SHYASDVSAD
AmyE_full_length   LQDSASRDAA  YANYMDVTAS  NYGHSIRSAL  KNRNLGVSNI  SHYASDVSAD 260
     Amy31A    KLVTWVESHD  TYANDDEEST  WMSDDDIRLG  WAVIGSRSGS  TPLFFSRPEG
AmyE_full_length   KLVTWVESHD  TYANDDEEST  WMSDDDIRLG  WAVIASRSGS  TPLFFSRPEG 310
     Amy31A    GGNGVRFPGK  SQIGDRGSAL  FKDQAITAVN  QFHNEMAGQP  EELSNPNGNN
AmyE_full_length   GGNGVRFPGK  SQIGDRGSAL  FEDQAITAVN  RFHNVMAGQP  EELSNPNGNN 360
     Amy31A    QIFMNQRGSK  GVVLANAGSS  SVTINTSTKL  PDGRYDNRAG  AGSFQVANGK
AmyE_full_length   QIFMNQRGSH  GVVLANAGSS  SVSINTATKL  PDGRYDNKAG  AGSFQVNDGK 410
     Amy31A    LTGTINARSA  AVLYPDDIGN  APHVFLENYQ  TEAVHSFNDQ  LTVTLRANAK
AmyE_full_length   LTGTINARSV  AVLYPDDIAK  APHVFLENYK  TGVTHSFNDQ  LTITLRADAN 460
     Amy31A    TTKAVYQINN  GQETAFKDGD  RLTIGKEDPI  GTTYNVKLTG  TNGEGASRTQ
AmyE_full_length   TTKAVYQINN  GPETAFKDGD  QFTIGKGDPF  GKTYTIMLKG  TNSDGVTRTE 510
     Amy31A    EYTFVKKDPS  QTNIIGYQNP  DHWGNVNAYI  YKHDGGGAIE  LTGSWPGKAM
AmyE_full_length   KYSFVKRDPA  SAKTIGYQNP  NHWSQVNAYI  YKHDGSRVIE  LTGSWPGKPM 560
     Amy31A    TKNADGIYTL  TLPANADTAD  AKVIFNNGSA  QVPGQNHPGF  DYVQNGLYNN
AmyE_full_length   TKNADGIYTL  TLPADTDTTN  AKVIFNNGSA  QVPGQNQPGF  DYVLNGLYND 610
     Amy31A    SGLNGYLPH   (SEQ ID NO: 3)
AmyE_full_length   SGLSGSLPH   (SEQ ID NO: 1)
```

FIG. 1

VARIANT ALPHA-AMYLASES FROM BACILLUS SUBTILIS AND METHODS OF USE, THEREOF

PRIORITY

The present application claims priority to U.S. Provisional Patent Applications 61/059,513 and 61/059,618, which were filed on Jun. 6, 2008, and which are incorporated by reference in their entirety.

FIELD OF THE INVENTION

Alpha-amylases from *Bacillus subtilis* (AmyE), variants thereof, nucleic acids encoding the same, and host cells comprising the nucleic acids are provided. Methods of using AmyE or variants thereof are disclosed, including liquefaction and/or saccharification of starch. Such methods may yield sugars useful for ethanol production or high fructose corn syrup production. In some cases, the amylases can be used at low pH, in the absence of calcium, and/or in the absence of a glucoamylase.

BACKGROUND

Grain, cereal, and vegetable starches, e.g., cornstarch, are widely used in the industrial manufacture of products such as syrups and biofuels. For example, high fructose corn syrup (HFCS) is a processed form of corn syrup having high fructose content and a sweetness comparable to sugar, making HFCS useful as a sugar substitute in soft drinks and other processed foods. HFCS production currently represents a billion dollar industry. The production of ethanol as a biofuel is also a growing industry.

Syrups and biofuels can be produced from starch by an enzymatic process that catalyzes the breakdown of starch into glucose. This enzymatic process typically involves a sequence of enzyme-catalyzed reactions:

(1) Liquefaction: Alpha ($\alpha$)-amylases (EC 3.2.1.1) first catalyze the degradation of a starch suspension, which may contain 30-40% w/w dry solids (ds), to maltodextrans. $\alpha$-amylases are endohydrolases that catalyze the random cleavage of internal $\alpha$-1,4-D-glucosidic bonds. Because liquefaction typically is conducted at high temperatures, e.g., 90-100° C., thermostable $\alpha$-amylases, such as an $\alpha$-amylase from *Bacillus* sp., are preferred for this step. $\alpha$-Amylases currently used for this step, e.g., $\alpha$-amylases from *B. licheniformis*, *B. amyloliquefaciens*, and *B. stearothermophilus* (AmyS), do not produce significant amounts of glucose. Instead, the resulting liquefact has a low dextrose equivalent (DE) and contains maltose and sugars with high degrees of polymerization (DPn).

(2) Saccharification: Glucoamylases and/or maltogenic $\alpha$-amylases catalyze the hydrolysis of non-reducing ends of the maltodextrans formed after liquefaction, releasing D-glucose, maltose and isomaltose. Saccharification produces either glucose-rich or high-maltose syrups. In the former case, glucoamylases typically catalyze saccharification under acidic conditions at elevated temperatures, e.g., 60° C., pH 4.3. Glucoamylases used in this process typically are obtained from fungi, e.g., *Aspergillus niger* glucoamylase used in OPTIDEX® L400 or *Humicula grisea* glucoamylase. De-branching enzymes, such as pullulanases, can aid saccharification.

Maltogenic $\alpha$-amylases alternatively may catalyze saccharification to form high-maltose syrups. Maltogenic $\alpha$-amylases typically have a higher optimal pH and a lower optimal temperature than glucoamylase, and maltogenic amylases typically require $Ca^{2+}$. Maltogenic $\alpha$-amylases currently used for this application include *B. subtilis* $\alpha$-amylases, plant amylases, and the $\alpha$-amylase from *Aspergillus oryzae*, the active ingredient of CLARASE® L. Exemplary saccharification reactions used to produce various products are depicted below:

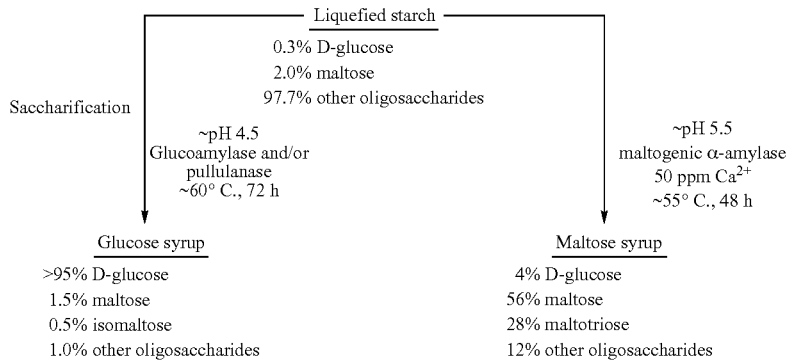

(3) Further processing: A branch point in the process occurs after the production of a glucose-rich syrup, shown on the left side of the reaction pathways above. If the final desired product is a biofuel, yeast can ferment the glucose-rich syrup to ethanol. On the other hand, if the final desired product is a fructose-rich syrup, glucose isomerase can catalyze the conversion of the glucose-rich syrup to fructose.

Saccharification is the rate-limiting step in the production of a glucose-rich syrup. Saccharification typically occurs over 48-72 hours, by which time many fungal glucoamylases lose significant activity. Further, although maltogenic $\alpha$-amylases and glucoamylases both can catalyze saccharification, the enzymes typically operate at different optimal pH and temperatures, as shown above. If both enzymes are used sequentially, the difference in reaction conditions between the two enzymes necessitates adjusting the pH and temperature, which slows down the overall the process and may give rise to the formation of insoluble amylose aggregates.

Accordingly, there is a need in the art for an improved process of making industrial products from starch. In particular, there is a need for improved efficiencies in a saccharification step.

SUMMARY

Described are compositions and methods relating to an α-amylase from *Bacillus subtilis* (AmyE) and related polypeptides. AmyE α-amylase is unique in that it exhibits high specific activity below pH 5.0, and even at about pH 4-4.5. Furthermore, $Ca^{2+}$ does not affect the thermal stability of AmyE, avoiding the need to add exogenous $Ca^{2+}$ to starch liquefaction or saccharification reactions. These features of AmyE polypeptides allow liquefaction and saccharification to be performed in the same reaction mixture (and optionally in the same reaction vessel) without the need to adjust the pH of the reaction mixture between liquefaction and saccharification. In particular, reaction conditions do not have to be adjusted when using AmyE and a glucoamylase, avoiding a step and time delays between liquefaction and saccharification, along with the potential formation of insoluble amylose aggregates. AmyE can, therefore, be used sequentially or simultaneously with a glucoamylase to liquefy and/or saccharify starch, and at a pH and $Ca^{2+}$ concentration that are optimal for the glucoamylase. AmyE also exhibits glucoamylase activity, reducing or eliminating the need for an additional polypeptide with glucoamylase activity to perform saccharification.

In one aspect, a method for liquefying and saccharifying starch in a starch conversion process, is provided, comprising contacting a starch substrate with an AmyE polypeptide to form a reaction mixture for liquefying and saccharifying the starch substrate in the reaction mixture to produce glucose, wherein the liquefying and saccharifying are performed in the same reaction mixture without a pH adjustment.

In some embodiments, the saccharifying (i.e., saccharification) is performed in the absence of an additional polypeptide having glucoamylase activity. In some embodiments, the liquefying (i.e., liquifaction) is performed at a pH suitable for the activity of a glucoamylase polypeptide. In some embodiments, the pH is 5.0 or lower. In some embodiments, the pH is 4.5 or lower. In particular embodiments, the pH is 4.0 or lower. In some embodiments, exogenous calcium is not added to the reaction mixture. In some embodiments, the calcium concentration in the reaction mixture is less than about 8 ppm.

In some embodiments, an additional polypeptide having glucoamylase activity is added to the reaction mixture before contacting the starch substrate with the AmyE polypeptide. In some embodiments, the additional polypeptide having glucoamylase activity is added to the reaction mixture after contacting the starch substrate with the AmyE polypeptide. In some embodiments, the additional polypeptide having glucoamylase activity is added to the reaction mixture simultaneously with contacting the starch substrate with the AmyE polypeptide.

In some embodiments, the method further comprises fermenting the glucose produced by the liquefying and saccharifying to produce a biofuel, such as an alcohol. In some embodiments, the alcohol is ethanol. In some embodiments, the alcohol is butanol. In some embodiments, at least a portion of the saccharifying and fermenting occur in the same reaction mixture simultaneously, as in the case of SSF.

In some embodiments, a batch fermentation process is used in a closed system, wherein the composition of the reacture mixture (including the pH) is selected at the beginning of the fermentation and is not altered during the fermentation. In another embodiment, a "fed-batch fermentation" system is used, wherein the starch substrate is added in increments as the fermentation progresses. In yet another embodiment, a continuous fermentation system is used, where a defined fermentation medium is added continuously to a bioreactor, and an equal amount of conditioned reaction mixture is removed for processing.

In some embodiments, the saccharified starch solution is converted to fructose-starch based syrup (HFSS), such as HFCS. The conversion to HFSS may be catalyzed at a pH of about 6.0 to about 8.0, e.g., pH 7.5, and the product may contain about 40-45% fructose. In some embodiments, the method further comprises contacting the glucose produced by the liquefying and saccharifying with a glucose isomerase to produce fructose (e.g., in the form of HFCS). In some embodiments, exogenous calcium is not added to the reaction mixture. In some embodiments, the calcium concentration in the reaction mixture is less than about 8 ppm. In some embodiments, the method further includes contacting the glucose produced by the liquefying and saccharifying with a glucose isomerase to produce fructose without reducing the amount of calcium in the reaction mixture.

In some embodiments, AmyE polypeptides are added to the reaction mixture in an amount of about 0.03-1 kg per metric ton of dry solids (ds). In some embodiments, the reaction mixture is a starch slurry having about 20-35% ds (w/w). The saccharification reaction may be performed at a temperature of about 60° C. to about 90° C., e.g., 70° C. to 85° C., or even 10, 12, 14, 16, 18, or even 20° C. below the starch gelation temperature (i.e., about 75° C.), and a pH of about 4.0 to about 6.0, e.g., about 4.2 to about 4.8. in some embodiments, the product of the saccharification reaction is a glucose-rich syrup. The glucose concentration may reach at least about 95% w/w ds.

In some embodiments, the AmyE polypeptides is any naturally-occurring AmyE polypeptide, for example, the AmyE polypeptides having the amino acid sequence of SEQ ID NO: 1 or SEQ ID NO: 3, or an amino acid sequence with at least about 85%, 90%, 91%, 92%, 93%, 94%, 95% 96%, 97%, 98%, 99%, sequence identity to SEQ ID NO: 1 or SEQ ID NO: 3, e.g., as measured with the BLAST sequence alignment algorithm. In particular embodiments, the AmyE polypeptide used in the method has at least 80% amino acid sequence identity with the amino acid sequence of SEQ ID NO: 1. In particular embodiments, the AmyE polypeptide used in the method has at least 90% amino acid sequence identity with the amino acid sequence of SEQ ID NO: 1.

In some embodiments, the AmyE polypeptide used in the method includes a deletion of the C-terminal starch binding domain. In particular embodiments, the AmyE polypeptides having the C-terminal deletion has the amino acid sequence of SEQ ID NO: 2, or an amino acid sequence with at least about 85%, 90%, 91%, 92%, 93%, 94%, 95% 96%, 97%, 98%, 99%, sequence identity to SEQ ID NO: 2. In particular embodiments, the AmyE polypeptide is truncated from residue D425 (referring to SEQ ID NO: 1).

In another aspect, AmyE variants having advantageous properties are provided. The AmyE variants may have an altered property or properties, compared to a wild-type AmyE polypeptide, for example an altered property with respect to specific activity towards starch, maltoheptaose, and/or maltotriose substrates, substrate specificity, thermostability, temperature optima, pH optima, pH and/or temperature range, oxidative stability, ability to reduce the viscosity of a starch composition, or the like. In some cases, the altered property of the AmyE variant relates to the specific activity on a particular corn flour, maltotriose, maltoheptaose substrate at particular pH (e.g., 4 or 5.8), heat stability at a particular temperature, (e.g., 60° C.), or cleaning performance at a particular pH (e.g., 8 or pH 10). The altered property may be characterized by a Performance Index (PI), where the PI is a ratio of performance of the AmyE variant compared to a wild-type AmyE. In some embodiments, the PI is greater than about 0.5, while in other embodiments, the PI is about 1 or is greater than 1.

In one aspect, the variant polypeptide has α-amylase activity and at least one altered characteristic that improves enzyme performance, the variant polypeptide comprising:

an amino acid sequence having at least 60% amino acid sequence identity to a parental α-amylase polypeptide selected from AmyE (SEQ ID NO: 1) or a truncated variant of AmyE (SEQ ID NO: 2), and a modification at one or more positions selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 121, 122, 123, 124, 125, 126, 127, 128, 129, 130, 131, 132, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 267, 268, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423; 424, and 425, wherein the modification produces a variant polypeptide having a performance index (PI) greater than 1.0 for at least one characteristic that improves enzyme performance.

In some embodiments, the variant polypeptide comprises a modification at one or more positions selected from the group consisting of 1, 2, 3, 4, 5, 6, 7, 8, 9, 10, 11, 12, 13, 14, 15, 16, 18, 19, 20, 21, 22, 23, 24, 25, 26, 27, 28, 29, 30, 31, 32, 33, 34, 35, 36, 37, 39, 42, 43, 44, 45, 46, 47, 48, 49, 50, 51, 52, 53, 54, 55, 56, 57, 58, 59, 60, 63, 64, 65, 66, 67, 68, 69, 72, 73, 74, 76, 77, 78, 79, 80, 81, 82, 83, 84, 85, 86, 87, 88, 89, 90, 91, 92, 93, 94, 95, 96, 98, 99, 100, 103, 104, 105, 106, 107, 108, 109, 110, 111, 112, 113, 114, 115, 116, 118, 119, 121, 124, 125, 126, 128, 129, 130, 131, 132, 134, 135, 136, 140, 141, 142, 143, 144, 147, 150, 151, 152, 153, 154, 155, 156, 157, 158, 159, 160, 162, 163, 164, 165, 166, 167, 168, 170, 171, 172, 175, 179, 180, 181, 184, 186, 187, 188, 189, 190, 192, 195, 196, 197, 198, 199, 200, 201, 202, 203, 204, 205, 207, 209, 211, 212, 213, 214, 217, 218, 219, 221, 222, 223, 224, 225, 226, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 267, 268, 270, 271, 272, 273, 274, 275, 276, 277, 279, 280, 281, 282, 283, 284, 285, 286, 287, 288, 289, 290, 291, 292, 293, 294, 295, 297, 298, 299, 300, 301, 302, 303, 304, 305, 307, 308, 309, 310, 311, 312, 313, 314, 315, 316, 317, 318, 319, 320, 321, 322, 324, 325, 327, 328, 329, 330, 331, 332, 333, 334, 335, 336, 337, 338, 339, 340, 341, 342, 343, 344, 345, 346, 347, 348, 349, 350, 351, 352, 353, 355, 356, 357, 358, 359, 360, 361, 362, 363, 364, 365, 366, 367, 368, 369, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, and 425, wherein the modification produces a variant polypeptide having a performance index (PI) greater than 0.5 for protein expression, and a PI greater than 1.1 for at least one characteristic that improves enzyme performance.

In some embodiments, the one or more positions are selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 76, 77, 78, 79, 80, 81, 82, 83, 84, 85, 86, 87, 88, 89, 90, 91, 92, 93, 94, 95, 96, 98, 99, 100, 103, 104, 105, 106, 107, 108, 109, 110, 111, 112, 113, 114, 115, 116, 117, 118, 119, 121, 122, 124, 125, 126, 127, 128, 129, 130, 131, 132, 134, 135, 136, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, and 425, which positions are non-fully restrictive for performance in either the full-length or truncated parental polypeptide.

In some embodiments, the modification is a substitution of one or more amino residues present in the parental polypeptide to different amino acid residues, at one or more positions selected from the group consisting of 1A, 1C, 1D, 1E, 1F, 1G, 1H, 1K, 1M, 1N, 1Q, 1R, 1S, 1T, 1V, 1W, 1Y, 2A, 2C, 2D, 2E, 2F, 2G, 2H, 2I, 2K, 2L, 2M, 2N, 2P, 2Q, 2R, 2S, 2V, 2W, 2Y, 3C, 3D, 3E, 3F, 3G, 3H, 3I, 3K, 3L, 3M, 3N, 3P, 3Q, 3R, 3S, 3V, 3W, 3Y, 4C, 4D, 4E, 4F, 4G, 4H, 4I, 4K, 4L, 4M, 4N, 4Q, 4S, 4T, 4V, 4W, 4Y, 5A, 5C, 5D, 5E, 5F, 5G, 5H, 5I, 5K, 5L, 5N, 5R, 5V, 5W, 5Y, 6C, 6D, 6E, 6H, 6K, 6L, 6M, 6N, 6P, 6Q, 6R, 6S, 6T, 6V, 6W, 7A, 7C, 7D, 7E, 7F, 7G, 7H, 7I, 7L, 7M, 7N, 7P, 7Q, 7R, 7S, 7T, 7W, 7Y, 8A, 8C, 8E, 8F, 8G, 8H, 8I, 8K, 8L, 8M, 8N, 8P, 8Q, 8R, 8T, 8V, 8W, 8Y, 9A, 9C, 9D, 9E, 9F, 9H, 9I, 9K, 9M, 9N, 9P, 9R, 9S, 9T, 9V, 9W, 9Y, 10A, 10I, 10L, 10M, 10N, 10P, 10Q, 10S, 10V, 11A, 11F, 11G, 11H, 11M, 11S, 11V, 11W, 11Y, 12I, 12M, 12V, 13A, 13C, 13D, 13E, 13F, 13G, 13I, 13L, 13M, 13Q, 13T, 13V, 13W, 13Y, 14C, 14F, 14G, 14M, 14N, 14S, 14T, 14V, 15A, 15F, 16A, 16D, 16E, 16F, 16G, 16H, 16I, 16L, 16M, 16Q, 16S, 16T, 16V, 17A, 17F, 17I, 17M, 17Q, 17Y, 18A, 18C, 18D, 18E, 18G, 18H, 18M, 18N, 18Q, 18R, 18T, 19A, 19C, 19H, 19L, 19M, 19N, 19S, 19W, 19Y, 20A, 20C, 20D, 20F, 20G, 20H, 20I, 20K, 20L, 20M, 20P, 20Q, 20R, 20S, 20T, 20V, 20W, 20Y, 21A, 21C, 21D, 21E, 21H, 21I, 21K, 21L, 21M, 21N, 21Q, 21R, 21S, 21V, 22I, 22M, 22Q, 22S, 22T, 22V, 23A, 23C, 23D, 23E, 23F, 23G, 23H, 23I, 23L, 23M, 23N, 23R, 23S, 23T, 23V, 23W, 23Y, 24A, 24C, 24D, 24F, 24G, 24L, 24N, 24P, 24Q, 24R, 24S, 24T, 24V, 24Y, 25A, 25C, 25D, 25E, 25F, 25G, 25H, 25I, 25K, 25L, 25R, 25S, 25T, 25V, 25W, 25Y, 26A, 26F, 26I, 26L, 26V, 27A, 27C, 27D, 27E, 27F, 27G, 27H, 27I, 27L, 27M, 27N, 27P, 27Q, 27R, 27S, 27T, 27V, 27W, 27Y, 28A, 28C, 28F, 28G, 28H, 28I, 28K, 28L, 28M, 28N, 28P, 28Q, 28R, 28S, 28T, 28V, 28W, 28Y, 29A, 29C, 29F, 29L, 29M, 29T, 29V, 30A, 30C, 30D, 30E, 30F, 30G, 30I, 30K, 30L, 30M, 30N, 30P, 30Q, 30R, 30S, 30T, 30V, 30W, 30Y, 31A, 31C, 31E, 31F, 31G, 31H, 31I, 31K, 31L, 31M, 31N, 31Q, 31S, 31T, 31V, 31W, 31Y, 32D, 32F, 32G, 32H, 32K, 32L, 32M, 32Q, 32S, 32T, 32V, 32Y, 33A, 33C, 33D, 33E, 33F, 33H, 33I, 33K, 33L, 33M, 33P, 33Q, 33S, 33T, 33W, 33Y, 34A, 34F, 34I, 34P, 34W, 35A, 35C, 35F, 35G, 35H, 35I, 35L, 35M, 35N, 35P, 35Q, 35R, 35S, 35V, 35W, 35Y, 36C, 36D, 36E, 36F, 36H, 36I, 36K, 36L, 36M, 36N, 36Q, 36R, 36S, 36T, 36Y, 37L, 37M, 37N, 37V, 38A, 38C, 38D, 38E, 38H, 38L, 38M, 38N, 38P, 38V, 39A, 39C, 39I, 39L, 39M, 39N, 39P, 39S, 39V, 40A, 40D, 40M, 40N, 40P, 40Q, 40T, 40V, 40W, 41A, 41C, 41E, 41G, 41N, 41S, 41V, 42A, 42L, 42M, 42P, 42V, 43A, 43G, 43H, 43L, 43M, 43Q, 43S, 43T, 43V, 44A, 44C, 44D, 44E, 44F, 44G, 44H, 44I, 44K, 44L, 44M, 44N, 44P, 44R, 44S, 44T, 44V, 44W, 44Y, 45A, 45C, 45F, 45G, 45H, 45I, 45L, 45M, 45N, 45P, 45Q, 45S, 45T, 45Y, 46A, 46C, 46D, 46E, 46F, 46H, 46I, 46L, 46M, 46N, 46Q, 46R, 46S, 46T, 46V, 46W, 46Y, 47A, 47C, 47D, 47F, 47G, 47H, 47I, 47K, 47L, 47N, 47P, 47R, 47S, 47T, 47V, 47Y, 48A, 48C, 48D, 48E, 48F, 48H, 48I, 48K, 48L, 48N, 48P, 48S, 48T, 48V, 48W, 49A, 49C, 49D, 49F, 49G, 49H, 49I, 49K, 49L, 49P, 49Q, 49R, 49S, 49T, 49V, 49W, 49Y, 50A, 50C, 50E, 50F, 50G, 50H, 50I, 50K, 50L, 50M, 50N, 50P, 50R, 50S, 50T, 50V, 50W, 50Y, 51A, 51C, 51D, 51E, 51F, 51H, 51K, 51L, 51M, 51N, 51P, 51Q, 51R, 51S, 51T, 51V, 51W, 52A, 52C, 52E, 52F, 52G, 52H, 52I, 52K, 52L, 52M, 52N, 52P, 52Q, 52R, 52S, 52T, 52V, 52W, 52Y, 53A, 53C, 53E, 53F, 53G, 53H, 53I, 53L, 53N, 53P, 53R, 53S, 53T, 53V, 53W, 53Y, 54A, 54C, 54D, 54F, 54G, 54H, 54I, 54L, 54M, 54N, 54P, 54Q, 54R, 54T, 54V, 54W, 54Y, 55A, 55C, 55D, 55E, 55F, 55G, 55H, 55I, 55N, 55P, 55Q, 55S, 55T, 55Y, 56A, 56D, 56E, 56F, 56G, 56I, 56K, 56L, 56M, 56N, 56P, 56Q, 56R, 56T, 56V, 56W, 56Y, 57A, 57C, 57D, 57E, 57F, 57H, 57I, 57K, 57L, 57M, 57Q, 57R, 57S, 57T, 57V, 57W, 57Y, 58A, 58F, 58H, 59A, 59C, 59D, 59E, 59F, 59G, 59H, 59K, 59L, 59N, 59P, 59R, 59S, 59T, 59V, 59W, 60A, 60C, 60D, 60E, 60G, 60I, 60K, 60L, 60M, 60N, 60Q, 60R, 60T, 60V, 61C, 61D, 61E, 61F, 61M, 61S, 61T, 61V, 62A, 62C, 62D, 62F, 62G, 62H, 62I, 62K, 62L, 62Q, 62S, 62T, 62V, 63A, 63C, 63D, 63F, 63G, 63H, 63K, 63M, 63N, 63R, 63S, 64A, 64G, 64H, 64I, 64L, 64M, 64N, 64S, 64V, 64Y, 65A, 65C, 65E, 65H, 65I, 65K, 65L, 65M, 65Q, 65R, 65S, 66D, 66E, 66F, 66G, 66H, 66I, 66K, 66L, 66M, 66N, 66Q, 66R, 66T, 66V, 66W, 66Y, 67A, 67C, 67D, 67E, 67F, 67G, 67I, 67K, 67L, 67N, 67P, 67Q, 67S, 67T, 67W, 68A, 68C, 68D, 68E, 68F, 68G, 68H, 68I, 68L, 68M, 68N, 68P, 68R, 68S, 68T, 68V, 68W, 68Y, 69A, 69C, 69M, 69P, 69T, 69V, 70A, 70E, 70H, 70N, 70S, 71S, 72C, 72D, 72E, 72F, 72G, 72H, 72I, 72K, 72L, 72P, 72Q, 72S, 72T, 72V, 72W, 72Y, 73A, 73C, 73E, 73F, 73H, 73I, 73K, 73L, 73M, 73P, 73S, 73T, 73V, 73W, 74A, 74E, 74F, 74M, 74S, 74T, 74Y, 75A, 75C, 75D, 75E, 75P, 76A, 76D, 76E, 76F, 76G, 76I, 76L, 76M, 76P, 76Q, 76R, 76S, 76V, 76Y, 77A, 77C, 77D, 77G, 77H, 77I, 77K, 77L, 77R, 77S, 77T, 77V, 77W, 77Y, 78A, 78C, 78D, 78E, 78F, 78G, 78H, 78I, 78K, 78L, 78M, 78N, 78P, 78R, 78S, 78T, 78V, 78W, 78Y, 79A, 79G, 79L, 79M, 79N, 79Q, 79S, 79T, 80A, 80L, 80M, 80W, 80Y, 81A, 81C, 81D, 81E, 81G, 81H, 81I, 81L, 81M, 81N, 81Q, 81R, 81S, 81T, 81V, 81W, 81Y, 82A, 82D, 82F, 82G, 82I, 82K, 82L, 82M, 82Q, 82R, 82S, 82T, 82V, 82W, 82Y, 83A, 83F, 83I, 83L, 83T, 83V, 84A, 84D, 84E, 84G, 84I, 84K, 84M, 84N, 84Q, 84S, 84T, 84V, 85D, 85E, 85F, 85G, 85I, 85K, 85L, 85M, 85N, 85R, 85S, 85T, 85V, 85W, 86C, 86D, 86E, 86F, 86G, 86I, 86K, 86L, 86M, 86N, 86Q, 86R, 86S, 86V, 86W, 86Y, 87F, 87G, 87T, 88A, 88C, 88D, 88F, 88G, 88H, 88I, 88K, 88L, 88M, 88N, 88Q, 88R, 88S, 88T, 88V, 88W, 88Y, 89A, 89C, 89D, 89F, 89G, 89H, 89I, 89K, 89L, 89M, 89N, 89P, 89Q, 89R, 89S, 89T, 89V, 89W, 89Y, 90C, 90D, 90E, 90F, 90G, 90H, 90I, 90K, 90L, 90M, 90N, 90Q, 90R, 90S, 90T, 90V, 90W, 91A, 91C, 91D, 91E, 91F, 91H, 91K, 91L, 91M, 91N, 91P, 91Q, 91R, 91S, 91T, 91W, 91Y, 92L, 92N, 92T, 92V, 93A, 93C, 93D, 93E, 93F, 93G, 93I, 93L, 93M, 93N, 93P, 93Q, 93R, 93S, 93T, 93V, 93W, 93Y, 94A, 94C, 94I, 94M, 94T, 95A, 95F, 95L, 95M, 95V, 95Y, 96A, 96C, 96I, 96L, 96M, 96P, 96T, 97A, 97E, 97M, 97W, 98C, 98G, 98I, 98L, 98M, 98T, 98V, 99A, 99C, 99E, 99F, 99G, 99I, 99L, 99M, 99N, 99P, 99S, 99T, 100A, 100C, 100F, 100M, 100N, 100P, 100T, 100V, 100Y, 101A, 102A, 102G, 102Q, 102S, 102W, 102Y, 103A, 103C, 103I, 103M, 103N, 103S, 103V, 104A, 104C, 104S, 105C, 105D, 105E, 105F, 105G, 105H, 105K, 105L, 105M, 105Q, 105R, 105T, 105V, 105W, 105Y, 106A, 106C, 106E, 106F, 106H, 106I, 106K, 106L, 106M, 106N, 106Q, 106R, 106S, 106T, 106V, 106W, 106Y, 107A, 107C, 107E, 107F, 107G, 107H, 107I, 107K, 107L, 107M, 107N, 107P, 107Q, 107R, 107S, 107T, 107V, 107W, 108C, 108D, 108E, 108F, 108G, 108H, 108I, 108K, 108L, 108N, 108P, 108R, 108S, 108T, 108V, 108W, 108Y, 109C, 109D, 109E, 109F, 109G, 109H, 109I, 109K, 109L, 109M, 109N, 109P, 109R, 109S, 109T, 109V, 109W, 109Y, 110L, 110M, 110V, 111A, 111C, 111E, 111F, 111G, 111H, 111I, 111K, 111L, 111M, 111N, 111P, 111Q, 111R, 111T, 111V, 111W, 111Y, 112A, 112C, 112D, 112E, 112F, 112G, 112I, 112K, 112L, 112M, 112P, 112Q, 112R, 112S, 112T, 112V, 112W, 112Y, 113A, 113D, 113F, 113G, 113I, 113K, 113L, 113M, 113N, 113P, 113Q, 113S, 113T, 113V, 113W, 113Y, 114F, 114L, 114P, 114T, 115A, 115C, 115F, 115G, 115H, 115I, 115L, 115M, 115N, 115Q, 115R, 115S, 115T, 115V, 115W, 115Y, 116A, 116D, 116E, 116F, 116G, 116H, 116I, 116L, 116N, 116Q, 116R, 116T, 116V, 116W, 116Y, 117F, 117L, 117N, 117Q, 117V, 117W, 117Y, 118A, 118C, 118D, 118E, 118F, 118G, 118H, 118I, 118K, 118L, 118M, 118N, 118Q, 118R, 118S, 118T, 118V, 118W, 118Y, 119A, 119C, 119D, 119E, 119F, 119G, 119H, 119I, 119K, 119L, 119M, 119Q, 119R, 119S, 119T, 119V, 119Y, 121A, 121M, 121N, 121S, 122R, 123E, 124A, 124C, 124D, 124E, 124F, 124G, 124I, 124K, 124M, 124Q, 124R, 124S, 124T, 124V, 124Y, 125A, 125D, 125E, 125F, 125G, 125H, 125I, 125K, 125L, 125M, 125N, 125P, 125Q, 125R, 125S, 125V, 125W, 125Y, 126A, 126C, 126D, 126F, 126G, 126H, 126I, 126K, 126L, 126N, 126P, 126R, 126S, 126T, 126V, 126W, 126Y, 127C, 127L, 127M, 127V, 128A, 128C, 128D, 128E, 128F, 128G, 128H, 128I, 128L, 128M, 128N, 128Q, 128R, 128S, 128T, 128V, 128Y, 129A, 129C, 129E, 129F, 129H, 129I, 129K, 129L, 129R, 129S, 129T, 129V, 129Y, 130A, 130C, 130D, 130F, 130G, 130H, 130I, 130K, 130L, 130M, 130P, 130R, 130T, 130V, 130Y, 131A, 131C, 131D, 131E, 131F, 131G, 131H, 131I, 131K, 131L, 131M, 131N, 131Q, 131R, 131T, 131V, 131W, 131Y, 132A, 132C, 132E, 132H, 132I, 132L, 132M, 132N, 132Q, 132S, 132W, 132Y, 134C, 134D, 134E, 134F, 134G, 134I, 134L, 134M, 134N, 134R, 134S, 134T, 134V, 134Y, 135A, 135C, 135E, 135M, 135N, 135Q, 135R, 136A, 136C, 136F, 136L, 136T, 136Y, 137C, 138A, 138C, 138F, 138H, 138N, 138R, 138W, 138Y, 139A, 139C, 139G, 139H, 139L, 139M, 139S, 140A, 140C, 140F, 140G, 141A, 141F, 141H, 141P, 141Q, 141S, 141T, 141V, 141Y, 142C, 142D, 142F, 142G, 142H, 142I, 142K, 142M, 142Q, 142R, 142S, 142T, 142W, 142Y, 143A, 143C, 143D, 143F, 143K, 143L, 143M, 143N, 143Q, 143R, 143S, 143W, 144G, 144S, 144T, 144V, 144W, 145W, 146A, 146E, 146M, 146T, 147C, 147F, 147H, 147I, 147L, 147N, 147P, 147Y, 148A, 148C, 148F, 148H, 148K, 148M, 148R, 148Y, 149S, 150A, 150H, 150N, 150S, 151A, 151C, 151D, 151E, 151F, 151G, 151H, 151I, 151K, 151L, 151M, 151Q, 151R, 151S, 151T, 151V, 151Y, 152A, 152C, 152D, 152E, 152F, 152G, 152H, 152I, 152K, 152L, 152M, 152N, 152P, 152Q, 152R, 152S, 152V, 152W, 152Y, 153A, 153C, 153D, 153E, 153F, 153G, 153H, 153I, 153K, 153L, 153M, 153N, 153P, 153R, 153S, 153T, 153V, 153W, 153Y, 154A, 154C, 154I, 154N, 154P, 154Q, 154S, 154T, 154Y, 155A, 155C, 155E, 155F, 155G, 155H, 155I, 155L, 155M, 155T, 155V, 155W, 156A, 156C, 156E, 156F, 156G, 156H, 156I, 156K, 156L, 156N, 156Q, 156R, 156T, 156V, 156W, 156Y, 157A, 157C, 157F, 157H, 157I, 157M, 157T, 157V, 158A, 158F, 158H, 158I, 158M, 158Q, 158S, 158T, 158V, 159A, 159C, 159E, 159F, 159G, 159H, 159I, 159L, 159M, 159N, 159R, 159S, 159T, 159V, 159W, 159Y, 160A, 160C, 160D, 160E, 160F, 160G, 160H, 160I, 160K, 160L, 160M, 160N, 160Q, 160S, 160T, 160V, 160W, 160Y, 161A, 161C, 161G, 161H, 161K, 161L, 161M, 161N, 161S, 162A, 162C, 162E, 162F, 162I, 162M, 162V, 163A, 163C, 163E, 163F, 163G, 163H, 163I, 163K, 163L, 163N, 163Q, 163R, 163S, 163T, 163V, 163W, 163Y, 164A, 164F, 164G, 164H, 164I, 164L, 164M, 164N, 164Q, 164S, 164T, 164V, 164W, 164Y, 165C, 165G, 165I, 165L, 165M, 165Q, 165S, 165T, 165V, 165W, 165Y, 166A, 166C, 166D, 166E, 166F, 166G, 166H, 166I, 166K, 166M, 166N, 166Q, 166R, 166S, 166T, 166V, 166W, 166Y, 167A, 167C, 167D, 167E, 167F, 167G, 167H, 167I, 167K, 167L, 167M, 167Q, 167R, 167S, 167T, 167V, 167W, 167Y, 168C, 168E, 168F, 168G, 168I, 168K, 168L, 168M, 168N, 168S, 168T, 168V, 168W, 168Y, 169L, 170C, 170G, 170V, 171A, 171C, 171E, 171F, 171G, 171H, 171I, 171L, 171M, 171N, 171Q, 171R, 171V, 172A, 172C, 172E, 172F, 172P, 173I, 173M, 173V, 173Y, 174D, 174E, 174G, 174H, 174L, 174Q, 174V, 174Y, 175H, 175M, 175W, 175Y, 176E, 176F, 176I, 176K, 176L, 176V, 176Y, 177C, 177G, 177M, 177Q, 177S, 178C, 178G, 178M, 178S, 178T, 179A, 179C, 179G, 179H, 179I, 179L, 179M, 179P, 179S, 179T, 179V, 179W, 179Y, 180A, 180D, 180M, 180N, 180Y, 181A, 181C, 181L, 181M, 181V, 182A, 183C, 183M, 184A, 184C, 184D, 184E, 184F, 184G, 184H, 184I, 184K, 184L, 184M, 184N, 184Q, 184R, 184S, 184T, 184V, 184W, 184Y, 185C, 185E, 185N, 185S, 185T, 186E, 187A, 187C, 187D, 187E, 187F, 187H, 187I, 187K, 187L, 187M, 187N, 187P, 187Q, 187R, 187S, 187T, 187V, 187W, 187Y, 188A, 188C, 188D, 188E, 188F, 188G, 188I, 188K, 188L, 188M, 188N, 188P, 188Q, 188R, 188T, 188V, 189F, 189W, 190A, 190C, 190E, 190F, 190H, 190K, 190L, 190M, 190Q, 190R, 190S, 190W, 190Y, 191A, 191L, 191T, 191Y, 192D, 192E, 192F, 192G, 192I, 192K, 192L, 192N, 192P, 192R, 192S, 192T, 192V, 193A, 193I, 193L, 193M, 194I, 195A, 195C, 195D, 195F, 195G, 195H, 195I, 195K, 195L, 195M, 195N, 195Q, 195R, 195S, 195T, 195V, 195W, 195Y, 196A, 196C, 196D, 196E, 196F, 196G, 196H, 196I, 196K, 196L, 196M, 196Q, 196R, 196S, 196T, 196V, 196W, 196Y, 197A, 197C, 197F, 197L, 197S, 197T, 197V, 198A, 198C, 198G, 198H, 198I, 198L, 198M, 198N, 198R, 198S, 198V, 199A, 199C, 199D, 199E, 199F, 199G, 199H, 199I, 199L, 199M, 199P, 199R, 199S, 199T, 199V, 199Y, 200A, 200C, 200D, 200E, 200F, 200G, 200H, 200I, 200K, 200L, 200M, 200N, 200P, 200Q, 200R, 200S, 200V, 200W, 200Y, 201A, 201C, 201D, 201E, 201F, 201G, 201H, 201I, 201K, 201L, 201M, 201N, 201P, 201Q, 201R, 201T, 201V, 201W, 201Y, 202C, 202F, 202G, 202I, 202K, 202L, 202M, 202N, 202P, 202Q, 202R, 202S, 202T, 202V, 202Y, 203A, 203C, 203F, 203G, 203I, 203K, 203L, 203N, 203P, 203Q, 203R, 203S, 203T, 203V, 203W, 203Y, 204A, 204C, 204E, 204I, 204L, 204M, 204T, 204V, 204W, 204Y, 205A, 205C, 205D, 205E, 205F, 205G, 205H, 205I, 205K, 205L, 205M, 205N, 205R, 205S, 205T, 205V, 205W, 205Y, 206F, 207A, 207C, 207M, 208K, 208N, 208R, 209C, 209F, 209L, 209M, 209T, 209V, 210F, 210I, 210V, 210W, 211A, 211C, 211D, 211E, 211G, 211H, 211M, 211P, 211S, 211T, 211W, 211Y, 212A, 212C, 212E, 212G, 212H, 212N, 212P, 212Q, 212S, 212T, 212Y, 213A, 213C, 213D, 213E, 213F, 213G, 213H, 213I, 213K, 213L, 213M, 213P, 213Q, 213R, 213T, 213V, 213Y, 214C, 214D, 214F, 214G, 214I, 214K, 214L, 214M, 214N, 214Q, 214R, 214S, 214T, 214V, 214W, 214Y, 215A, 215C, 215I, 215T, 216C, 216K, 216E, 217F, 217I, 217K, 217M, 217N, 217P, 217Q, 217R, 217S, 217T, 217V, 217Y, 218C, 218D, 218E, 218F, 218G, 218H, 218I, 218K, 218L, 218M, 218N, 218P, 218Q, 218R, 218S, 218T, 218V, 218W, 218Y, 219C, 219D, 219F, 219G, 219H, 219I, 219K, 219L, 219M, 219N, 219Q, 219R, 219S, 219T, 219V, 219W, 219Y, 220F, 221C, 221E, 221G, 221I, 221L, 221M, 221N, 221Q, 221R, 221S, 221T, 221V, 221Y, 222A, 222C, 222D, 222F, 222G, 222I, 222K, 222M, 222P, 222R, 222S, 222T, 222V, 223A, 223C, 223E, 223F, 223H, 223I, 223L, 223M, 223N, 223Q, 223V, 223W, 224I, 224L, 224V, 224Y, 225A, 225C, 225E, 225F, 225H, 225I, 225K, 225L, 225M, 225N, 225P, 225Q, 225S, 225T, 225V, 225W, 225Y, 226A, 226C, 226F, 226I, 226L, 226M, 226T, 227A, 227C, 227D, 227E, 227G, 227M, 227S, 228C, 228D, 228M, 228N, 228P, 228S, 228T, 228V, 229C, 229D, 229E, 229F, 229G, 229H, 229M, 229N, 229Q, 229R, 229T, 229V, 229Y, 230A, 230D, 230E, 230F, 230G, 230H, 230I, 230K, 230M, 230P, 230Q, 230R, 230S, 230V, 230Y, 231A, 231C, 231H, 231L, 231M, 231Q, 231W, 232A, 232C, 232M, 232N, 232Q, 232S, 232Y, 233A, 233C, 233D, 233E, 233F, 233G, 233I, 233K, 233L, 233M, 233N, 233P, 233Q, 233R, 233S, 233T, 233V, 233W, 233Y, 234A, 234C, 234D, 234E, 234F, 234G, 234H, 234I, 234L, 234M, 234N, 234Q, 234R, 234T, 234V, 234W, 234Y, 235A, 235C, 235F, 235L, 235M, 235T, 236A, 236C, 236D, 236E, 236G, 236H, 236I, 236K, 236L, 236M, 236N, 236Q, 236S, 236T, 237A, 237C, 237D, 237E, 237F, 237G, 237H, 237I, 237K, 237L, 237P, 237Q, 237R, 237T, 237V, 237W, 237Y, 238C, 238D, 238E, 238F, 238G, 238H, 238I, 238K, 238L, 238M, 238N, 238Q, 238R, 238S, 238T, 238V, 238W, 238Y, 239A, 239E, 239F, 239I, 239M, 239T, 240A, 240C, 240D, 240E, 240F, 240G, 240H, 240I, 240L, 240M, 240N, 240Q, 240R, 240S, 240T, 240V, 240W, 240Y, 241A, 241C, 241D, 241E, 241F, 241G, 241H, 241I, 241K, 241L, 241M, 241P, 241Q, 241R, 241S, 241T, 241V, 241W, 241Y, 242A, 242C, 242D, 242E, 242F, 242I, 242K, 242L, 242M, 242Q, 242S, 242T, 242V, 242W, 242Y, 243A, 243C, 243D, 243E, 243F, 243G, 243H, 243I, 243K, 243L, 243M, 243Q, 243R, 243S, 243T, 243V, 243W, 243Y, 244A, 244F, 244I, 244M, 244T, 244V, 244W, 244Y, 245A, 245C, 245D, 245F, 245H, 245I, 245L, 245M, 245N, 245P, 245R, 245T, 245V, 245W, 245Y, 246A, 246C, 246D, 246E, 246F, 246G, 246H, 246I, 246K, 246L, 246P, 246Q, 246R, 246S, 246T, 246W, 246Y, 247A, 247D, 247E, 247F, 247G, 247H, 247I, 247L, 247M, 247N, 247P, 247Q, 247T, 247V, 247Y, 248A, 248C, 248E, 248F, 248G, 248H, 248I, 248K, 248L, 248M, 248Q, 248R, 248S, 248T, 248V, 248W, 249A, 249C, 249E, 249F, 249H, 249L, 249M, 249P, 249S, 249V, 249Y, 250A, 250C, 250E, 250F, 250G, 250H, 250I, 250K, 250L, 250M, 250N, 250Q, 250R, 250T, 250V, 250W, 250Y, 251A, 251C, 251D, 251E, 251G, 251I, 251K, 251L, 251M, 251N, 251P, 251Q, 251R, 251V, 251Y, 252C, 252D, 252E, 252F, 252G, 252H, 252I, 252K, 252L, 252M, 252Q, 252R, 252S, 252T, 252V, 252W, 253C, 253E, 253F, 253G, 253H, 253I, 253K, 253L, 253M, 253P, 253R, 253S, 253T, 253V, 253W, 253Y, 254A, 254F, 254G, 254H, 254I, 254K, 254L, 254N, 254P, 254R, 254T, 254V, 254W, 254Y, 255A, 255C, 255E, 255F, 255G, 255I, 255K, 255L, 255N, 255P, 255Q, 255R, 255S, 255T, 255V, 255W, 255Y, 256A, 256C, 256I, 256M, 256N, 256T, 257A, 257D, 257E, 257F, 257G, 257H, 257I, 257K, 257L, 257M, 257N, 257P, 257Q, 257R, 257T, 257V, 257W, 258C, 258D, 258E, 258F, 258G, 258H, 258I, 258K, 258L, 258M, 258N, 258Q, 258R, 258S, 258T, 258V, 258Y, 259A, 259E, 259G, 259H, 259I, 259K, 259L, 259M, 259P, 259Q, 259R, 259S, 259T, 259W, 259Y, 260A, 260C, 260D, 260E, 260F, 260G, 260H, 260I, 260L, 260M, 260N, 260Q, 260R, 260S, 260T, 260V, 260W, 260Y, 261A, 261C, 261I, 261M, 261N, 261Q, 261S, 261T, 261V, 262A, 262C, 262I, 262M, 262T, 263A, 263C, 263L, 263M, 263N, 263P, 263S, 263V, 264D, 264E, 264G, 264H, 264I, 264L, 264N, 264Y, 265A, 265C, 265F, 265M, 265T, 265Y, 267A, 267C, 267D, 267F, 267G, 267H, 267M, 267N, 267Q, 267T, 267V, 268M, 268Q, 268R, 268V, 268Y, 270C, 270F, 270G, 270I, 270L, 270M, 270N, 270R, 270S, 270V, 270Y, 271F, 272G, 272I, 272L, 272M, 272N, 272S, 272T, 272V, 273D, 273G, 273I, 273K, 273L, 273P, 273Q, 273R, 273S, 273T, 273V, 273W, 273Y, 274A, 274C, 274F, 274G, 274H, 274I, 274K, 274L, 274M, 274N, 274P, 274Q, 274R, 274S, 274T, 274V, 274W, 274Y, 275A, 275C, 275E, 275F, 275G, 275H, 275I, 275K, 275L, 275M, 275N, 275P, 275Q, 275R, 275S, 275T, 275V, 275W, 275Y, 276A, 276C, 276D, 276F, 276G, 276H, 276I, 276K, 276L, 276M, 276N, 276P, 276Q, 276R, 276S, 276T, 276V, 276W, 276Y, 277A, 277C, 277D, 277F, 277G, 277H, 277I, 277K, 277L, 277M, 277N, 277P, 277Q, 277R, 277S, 277T, 277V, 277W, 277Y, 278A, 278C, 278T, 279D, 279E, 279G, 279H, 279I, 279K, 279L, 279M, 279N, 279P, 279Q, 279R, 279S, 279V, 279W, 279Y, 280A, 280D, 280E, 280F, 280G, 280H, 280K, 280L, 280M, 280N, 280Q, 280R, 280S, 280T, 280Y, 281C, 281F, 281L, 282A, 282C, 282D, 282E, 282F, 282G, 282H, 282I, 282K, 282L, 282M, 282N, 282P, 282Q, 282R, 282T, 282V, 282W, 282Y, 283A, 283C, 283F, 283G, 283R, 283I, 283L, 283M, 283N, 283P, 283R, 283S, 283T, 283V, 283W, 283Y, 284A, 284C, 284E, 284F, 284G, 284H, 284I, 284K, 284L, 284M, 284N, 284P, 284Q, 284R, 284S, 284T, 284V, 284W, 284Y, 285A, 285C, 285E, 285H, 285I, 285L, 285M, 285N, 285Q, 285S, 285T, 285V, 285Y, 286A, 286C, 286L, 286M, 286N, 286Q, 286T, 286V, 287A, 287C, 287D, 287E, 287F, 287G, 287H, 287I, 287K, 287L, 287M, 287N, 287P, 287Q, 287S, 287T, 287V, 287W, 287Y, 288A, 288C, 288I, 288M, 288T, 288V, 289A, 289S, 290F, 290H, 290M, 290Y, 291C, 291F, 291G, 291I, 291L, 291M, 291N, 291S, 291T, 291V, 292A, 292C, 292I, 292L, 292M, 292S, 292T, 292W, 293C, 293D, 293E, 293F, 293G, 293N, 293Q, 293S, 293V, 294C, 294G, 294M, 294N, 294S, 294T, 294V, 295A, 295C, 295G, 295T, 296A, 296C, 296F, 296G, 296H, 296K, 296M, 297A, 297C, 297D, 297E, 297F, 297G, 297H, 297I, 297K, 297L, 297M, 297N, 297P, 297Q, 297R, 297T, 297V, 297W, 297Y, 298C, 298D, 298E, 298F, 298H, 298I, 298K, 298L, 298M, 298N, 298P, 298Q, 298S, 298V, 298W, 299C, 299D, 299E, 299F, 299G, 299H, 299I, 299L, 299M, 299N, 299P, 299Q, 299V, 300A, 300C, 300F, 300H, 300I, 300K, 300L, 300M, 300N, 300Q, 300R, 300S, 300V, 300Y, 301C, 301D, 301F, 301H, 301I, 301K, 301L, 301M, 301Q, 301R, 301T, 301V, 302C, 302E, 302F, 302G, 302K, 302M, 302N, 302S, 302T, 303L, 303M, 303W, 303Y, 304C, 304E, 304G, 304L, 304N, 304Y, 305A, 305G, 305I, 305N, 305T, 305V, 307A, 307C, 307D, 307N, 307Q, 307T, 307V, 307Y, 308A, 308C, 308D, 308F, 308G, 308H, 308I, 308K, 308L, 308M, 308N, 308P, 308Q, 308R, 308S, 308T, 308V, 308W, 308Y, 309C, 309D, 309E, 309F, 309H, 309I, 309K, 309M, 309N, 309P, 309R, 309S, 309T, 309V, 309Y, 310A, 310D, 310E, 310F, 310H, 310I, 310L, 310M, 310N, 310P, 310Q, 310R, 310S, 310T, 310Y, 311A, 311C, 311D, 311E, 311F, 311H, 311K, 311L, 311M, 311N, 311P, 311Q, 311R, 311S, 311T, 311V, 311W, 311Y, 312A, 312C, 312D, 312E, 312F, 312G, 312H, 312I, 312K, 312L, 312M, 312P, 312Q, 312R, 312S, 312T, 312V, 312W, 312Y, 313A, 313C, 313D, 313E, 313F, 313H, 313I, 313K, 313L, 313M, 313N, 313P, 313Q, 313R, 313S, 313T, 313V, 313W, 313Y, 314A, 314C, 314D, 314F, 314G, 314H, 314K, 314L, 314M, 314Q, 314R, 314S, 314T, 314W, 314Y, 315C, 315D, 315E, 315G, 315H, 315I, 315K, 315L, 315M, 315N, 315P, 315Q, 315T, 315V, 316C, 316D, 316H, 316I, 316L, 316M, 316Y, 317A, 317C, 317D, 317E, 317F, 317G, 317H, 317I, 317K, 317L, 317N, 317Q, 317R, 317S, 317T, 317V, 317W, 317Y, 318F, 318H, 318I, 318K, 318L, 318M, 318N, 318R, 318S, 318T, 318V, 318W, 318Y, 319A, 319D, 319F, 319G, 319H, 319L, 319N, 319P, 319Q, 319S, 319V, 319W, 320A, 320C, 320D, 320F, 320G, 320H, 320I, 320K, 320L, 320M, 320N, 320P, 320Q, 320T, 320V, 320W, 320Y, 321A, 321C, 321D, 321E, 321F, 321G, 321H, 321I, 321K, 321L, 321M, 321N, 321P, 321R, 321S, 321T, 321V, 321W, 322L, 322M, 322V, 323A, 323C, 323H, 323N, 323R, 323S, 323T, 324A, 324C, 324E, 324F, 324G, 324H, 324I, 324K, 324L, 324M, 324N, 324P, 324Q, 324R, 324S, 324T, 324V, 324W, 324Y, 325A, 325C, 325D, 325F, 325G, 325H, 325I, 325K, 325L, 325M, 325N, 325P, 325T, 325V, 325W, 325Y, 326A, 326Q, 327C, 327D, 327F, 327G, 327H, 327K, 327N, 327P, 327R, 327T, 327V, 327Y, 328C, 328D, 328E, 328F, 328G, 328H, 328I, 328K, 328L, 328N, 328P, 328Q, 328R, 328S, 328T, 328V, 328W, 328Y, 329A, 329D, 329E, 329F, 329G, 329H, 329N, 329Q, 329R, 329S, 329T, 330A, 330C, 330H, 330L, 330M, 330S, 330W, 330Y, 331C, 331D, 331F, 331G, 331I, 331K, 331L, 331M, 331N, 331Q, 331R, 331S, 331T, 331V, 331Y, 332A, 332C, 332E, 332F, 332G, 332I, 332K, 332L, 332M, 332Q, 332R, 332S, 332V, 332Y, 333C, 333D, 333F, 333G, 333H, 333I, 333K, 333L, 333M, 333N, 333P, 333R, 333S, 333T, 333V, 333W, 333Y, 334C, 334D, 334F, 334G, 334H, 334I, 334L, 334M, 334N, 334Q, 334R, 334S, 334T, 334V, 334Y, 335A, 335L, 335M, 335Q, 335T, 335V, 336A, 336C, 336E, 336F, 336G, 336H, 336I, 336K, 336L, 336M, 336N, 336Q, 336R, 336S, 336V, 336W, 336Y, 337D, 337G, 337H, 337K, 337L, 337N, 337P, 337Q, 337R, 337S, 337V, 337W, 337Y, 338C, 338F, 338G, 338I, 338L, 338M, 338N, 338P, 338S, 338T, 339C, 339G, 339I, 339S, 339T, 339V, 340D, 340E, 340F, 340G, 340H, 340I, 340K, 340L, 340M, 340N, 340S, 340T, 340V, 340W, 341A, 341I, 341L, 341M, 341V, 341W, 341Y, 342A, 342D, 342E, 342F, 342G, 342K, 342L, 342M, 342N, 342R, 342S, 342V, 342Y, 343A, 343C, 343D, 343E, 343F, 343G, 343H, 343I, 343K, 343L, 343M, 343P, 343Q, 343S, 343T, 343V, 343W, 343Y, 344A, 344C, 344D, 344E, 344F, 344G, 344H, 344I, 344K, 344L, 344M, 344N, 344Q, 344R, 344S, 344T, 344W, 344Y, 345A, 345C, 345D, 345E, 345F, 345G, 345H, 345I, 345N, 345Q, 345S, 345T, 345V, 345W, 345Y, 346C, 346D, 346E, 346F, 346H, 346I, 346K, 346L, 346M, 346N, 346P, 346R, 346S, 346T, 346V, 346Y, 347A, 347C, 347D, 347E, 347F, 347H, 347I, 347K, 347L, 347M, 347N, 347P, 347Q, 347R, 347S, 347T, 347V, 347W, 347Y, 348C, 348F, 348G, 348H, 348I, 348K, 348M, 348N, 348P, 348R, 348S, 348T, 348V, 348W, 348Y, 349A, 349C, 349D, 349F, 349G, 349H, 349I, 349K, 349L, 349M, 349N, 349Q, 349R, 349S, 349T, 349V, 349W, 349Y, 350A, 350C, 350D, 350N, 350S, 351A, 351D, 351G, 351H, 351K, 351L, 351M, 351P, 351Q, 351R, 351S, 351T, 351V, 351W, 351Y, 352A, 352D, 352E, 352F, 352G, 352H, 352I, 352K, 352N, 352Q, 352R, 352T, 352V, 352W, 352Y, 353A, 353C, 353D, 353E, 353F, 353G, 353I, 353K, 353L, 353M, 353N, 353Q, 353R, 353T, 353V, 353W, 353Y, 354A, 354C, 354M, 354P, 354Q, 354S, 354T, 355C, 355D, 355E, 355F, 355G, 355I, 355K, 355L, 355M, 355N, 355T, 355V, 355W, 355Y, 356D, 356E, 356F, 356G, 356H, 356I, 356K, 356L, 356M, 356P, 356Q, 356T, 356W, 356Y, 357A, 357C, 357D, 357E, 357F, 357H, 357I, 357K, 357L, 357M, 357N, 357P, 357Q, 357R, 357S, 357T, 357V, 357W, 357Y, 358A, 358C, 358D, 358E, 358F, 358G, 358H, 358I, 358K, 358L, 358M, 358P, 358Q, 358R, 358S, 358T, 358V, 358W, 358Y, 359A, 359C, 359D, 359E, 359F, 359G, 359H, 359I, 359K, 359L, 359M, 359P, 359Q, 359R, 359S, 359T, 359V, 359W, 359Y, 360F, 360H, 360L, 360N, 360P, 360R, 360T, 360W, 361A, 361C, 361G, 361H, 361L, 361M, 361N, 361Q, 361S, 361T, 361V, 361W, 361Y, 362A, 362C, 362E, 362H, 362I, 362L, 362M, 362Q, 362S, 362T, 362V, 362Y, 363D, 363E, 363F, 363G, 363H, 363N, 363Q, 363R, 363S, 363V, 363W, 363Y, 364A, 364C, 364D, 364E, 364G, 364I, 364L, 364M, 364Q, 364S, 364T, 364V, 365A, 365C, 365D, 365F, 365G, 365I, 365K, 365L, 365M, 365N, 365R, 365S, 365T, 365V, 365W, 365Y, 366A, 366C, 366E, 366F, 366G, 366H, 366K, 366L, 366M, 366S, 366T, 366V, 367A, 367C, 367D, 367E, 367F, 367H, 367I, 367K, 367L, 367M, 367N, 367P, 367R, 367S, 367T, 367V, 367W, 367Y, 368D, 368F, 368G, 368I, 368K, 368L, 368M, 368N, 368P, 368Q, 368R, 368T, 368V, 368W, 368Y, 369A, 369C, 369D, 369E, 369F, 369G, 369I, 369K, 369L, 369M, 369N, 369P, 369Q, 369R, 369S, 369T, 369V, 369W, 369Y, 370A, 371A, 371C, 371F, 371G, 371H, 371I, 371L, 371M, 371N, 371Q, 371S, 371T, 371W, 371Y, 372A, 372C, 372G, 372I, 372L, 372M, 372N, 372Q, 372S, 372T, 373A, 373C, 373F, 373G, 373I, 373M, 373Q, 373S, 373T, 373V, 373W, 373Y, 374C, 374E, 374G, 374I, 374L, 374M, 374N, 374S, 374T, 374V, 375A, 375C, 375D, 375F, 375G, 375H, 375L, 375M, 375Q, 375S, 375T, 375V, 375W, 375Y, 376C, 376D, 376E, 376F, 376G, 376H, 376I, 376L, 376M, 376N, 376P, 376Q, 376S, 376T, 376V, 377F, 377H, 377I, 377K, 377L, 377P, 377T, 377W, 377Y, 378A, 378C, 378D, 378E, 378F, 378G, 378H, 378I, 378K, 378L, 378M, 378N, 378P, 378Q, 378R, 378T, 378V, 378W, 378Y, 379A, 379D, 379G, 379H, 379I, 379K, 379L, 379Q, 379T, 379W, 379Y, 380A, 380C, 380D, 380E, 380F, 380G, 380H, 380I, 380L, 380M, 380N, 380P, 380Q, 380R, 380T, 380V, 380W, 380Y, 381A, 381G, 381I, 381K; 381N, 381P, 381Q, 381R, 381S, 381T, 381W, 381Y, 382A, 382C, 382D, 382F, 382G, 382H, 382I, 382K, 382L, 382M, 382N, 382P, 382Q, 382R, 382T, 382V, 382W, 382Y, 383A, 383C, 383E, 383F, 383G, 383H, 383L, 383N, 383P, 383Q, 383S, 383T, 383V, 383W, 383Y, 384A, 384D, 384F, 384G, 384H, 384I, 384K, 384L, 384P, 384Q, 384S, 384T, 384V, 384W, 385A, 385C, 385D, 385E, 385F, 385G, 385H, 385I, 385K, 385L, 385M, 385N, 385P, 385Q, 385R, 385S, 385V, 385W, 385Y, 386C, 386D, 386F, 386G, 386H, 386I, 386L, 386N, 386P, 386R, 386S, 386T, 386V, 386W, 386Y, 387A, 387D, 387E, 387G, 387I, 387L, 387N, 387Q, 387S, 388A, 388C, 388D, 388E, 388F, 388G, 388H, 388I, 388L, 388M, 388N, 388P, 388Q, 388R, 388S, 388T, 388V, 388W, 388Y, 389C, 389E, 389F, 389H, 389I, 389K, 389M, 389N, 389Q, 389S, 389T, 389V, 389W, 389Y, 390A, 390C, 390D, 390E, 390F, 390G, 390H, 390I, 390K, 390L, 390M, 390N, 390R, 390S, 390T, 390V, 390W, 390Y, 391E, 391F, 391G, 391H, 391I, 391K, 391L, 391N, 391P, 391R, 391S, 391T, 391V, 391W, 391Y, 392A, 392C, 392D, 392E, 392F, 392H, 392K, 392L, 392M, 392N, 392Q, 392R, 392S, 392V, 392Y, 393A, 393C, 393D, 393F, 393G, 393H, 393I, 393L, 393M, 393P, 393Q, 393S, 393T, 393V, 393W, 393Y, 394A, 394C, 394E, 394F, 394H, 394I, 394K, 394L, 394M, 394N, 394P, 394Q, 394R, 394S, 394T, 394V, 394W, 394Y, 395A, 395C, 395E, 395F, 395G, 395H, 395I, 395K, 395L, 395M, 395N, 395P, 395Q, 395R, 395S, 395T, 395V, 395W, 395Y, 396A, 396C, 396D, 396E, 396G, 396M, 396P, 396S, 396T, 397A, 397C, 397D, 397E, 397F, 397G, 397H, 397I, 397L, 397M, 397P, 397R, 397S, 397T, 397V, 397W, 398C, 398D, 398E, 398F, 398G, 398I, 398L, 398M, 398N, 398P, 398Q, 398R, 398S, 398T, 398V, 398W, 398Y, 399A, 399C, 399D, 399E, 399F, 399H, 399I, 399K, 399L, 399P, 399R, 399S, 399T, 399V, 399W, 399Y, 400C, 400D, 400E, 400F, 400G, 400H, 400I, 400K, 400L, 400M, 400N, 400P, 400Q, 400R, 400S, 400T, 400V, 400W, 400Y, 401A, 401C, 401D, 401E, 401F, 401H, 401I, 401K, 401L, 401M, 401N, 401P, 401Q, 401R, 401S, 401T, 401V, 401W, 401Y, 402A, 402C, 402D, 402E, 402F, 402G, 402H, 402I, 402K, 402L, 402M, 402N, 402P, 402Q, 402R, 402T, 402V, 402W, 402Y, 403A, 403C, 403E, 403G, 403H, 403I, 403M, 403N, 403Q, 403S, 403T, 403V, 403W, 403Y, 404D, 404E, 404F, 404G, 404H, 404I, 404L, 404M, 404N, 404P, 404R, 404T, 404V, 404W, 404Y, 405E, 405F, 405G, 405H, 405I, 405K, 405Q, 405S, 405T, 406D, 406F, 406L, 406T, 406Y, 407A, 407C, 407E, 407F, 407G, 407H, 407I, 407K, 407M, 407N, 407P, 407Q, 407R, 407S, 407T, 407V, 407W, 407Y, 408A, 408D, 408E, 408F, 408H, 408I, 408K, 408N, 408P, 408Q, 408S, 408T, 408V, 408Y, 409A, 409C, 409D, 409E, 409F, 409H, 409I, 409L, 409M, 409Q, 409R, 409T, 409V, 409W, 409Y, 410F, 410G, 410I, 410K, 410Q, 410S, 410T, 410V, 410W, 410Y, 411A, 411D, 411E, 411F, 411G, 411H, 411I, 411L, 411M, 411N, 411Q, 411R, 411S, 411V, 411W, 411Y, 412A, 412D, 412E, 412H, 412I, 412K, 412L, 412M, 412N, 412R, 412S, 412T, 412V, 412Y, 413C, 413E, 413F, 413G, 413I, 413L, 413M, 413N, 413P, 413R, 413S, 413V, 413W, 413Y, 414A, 414C, 414E, 414F, 414G, 414H, 414L, 414M, 414N, 414P, 414Q, 414T, 414V, 414W, 415D, 415E, 415F, 415G, 415H, 415I, 415K, 415P, 415Q, 415R, 415V, 415W, 416F, 416I, 416L, 416P, 416Q, 416R, 416T, 416V, 416Y, 417A, 417C, 417D, 417F, 417G, 417H, 417I, 417K, 417M, 417N, 417P, 417Q, 417S, 417W, 417Y, 418C, 418D, 418E, 418F, 418H, 418I, 418K, 418N, 418Q, 418R, 418T, 418W, 418Y, 419C, 419D, 419E, 419F, 419G, 419H, 419I, 419L, 419P, 419Q, 419S, 419T, 419Y, 420D, 420E, 420F, 420G, 420H, 420I, 420K, 420L, 420M, 420N, 420Q, 420R, 420S, 420T, 420V, 420W, 420Y, 421A, 421C, 421G, 421I, 421L, 421M, 421S, 421T, 422A, 422F, 422G, 422H, 422I, 422M, 422N, 422Q, 422S, 422V, 422W, 422Y, 423A, 423D, 423G, 423H, 423I, 423K, 423P, 423Q, 423R, 423T, 423V, 423W, 424D, 424E, 424G, 424I, 424K, 424M, 424N, 424Q, 424R, 424S, 424T, 424V, 424W, 424Y, 425A, 425I, 425K, 425L, 425M, 425S, 425T, 425V, 425W, and 425Y.

In some embodiments, the modification is a substitution of one or more amino residues present in the parental polypeptide to different amino acid residues, at one or more positions selected from the group consisting of 1A, 1D, 1F, 1G, 1H, 1K, 1M, 1N, 1Q, 1R, 1S, 1T, 1V, 1W, 1Y, 2A, 2E, 2F, 2G, 2H, 2I, 2P, 2Q, 2R, 2S, 2W, 3D, 3E, 3F, 3G, 3H, 3I, 3K, 3L, 3M, 3N, 3P, 3Q, 3R, 3S, 3V, 3W, 3Y, 4D, 4E, 4F, 4G, 4I, 4K, 4L, 4Q, 4S, 4T, 4V, 4W, 5A, 5D, 5E, 5F, 5G, 5K, 5L, 5V, 5W, 6D, 6H, 6K, 6L, 6P, 6Q, 6S, 6V, 6W, 7A, 7D, 7E, 7H, 7N, 7Q, 7R, 7S, 8A, 8C, 8E, 8F, 8G, 8H, 8I, 8K, 8L, 8N, 8P, 8Q, 8R, 8T, 8V, 8W, 8Y, 9A, 9D, 9E, 9F, 9H, 9I, 9K, 9M, 9N, 9P, 9R, 9V, 9W, 9Y, 10I, 10L, 10M, 10P, 10S, 10V, 11A, 11F, 11M, 11V, 12I, 12M, 13A, 13D, 13Q, 14G, 14S, 14T, 14V, 15F, 16M, 16Q, 18G, 18N, 18R, 19H, 19W, 20A, 20D, 20F, 20G, 20H, 20I, 20K, 20M, 20R, 20S, 20V, 20W, 20Y, 21E, 21I, 21M, 21Q, 21S, 21V, 22I, 22T, 22V, 23A, 23D, 23E, 23F, 23G, 23H, 23I, 23L, 23M, 23N, 23R, 23S, 23T, 23V, 23W, 23Y, 24A, 24C, 24F, 24G, 24R, 24S, 24T, 24V, 24Y, 25E, 25F, 25K, 25L, 25R, 25S, 25T, 25V, 25W, 25Y, 26I, 26L, 27A, 27E, 27F, 27G, 27H, 27I, 27L, 27P, 27Q, 27R, 27S, 27T, 27V, 27W, 27Y, 28A, 28C, 28G, 28H, 28I, 28K, 28L, 28M, 28N, 28P, 28Q, 28R, 28S, 28V, 28W, 28Y, 29F, 29L, 29V, 30A, 30C, 30D, 30E, 30F, 30G, 30L, 30M, 30N, 30Q, 30R, 30S, 30T, 30V, 30W, 30Y, 31A, 31F, 31G, 31H, 31I, 31K, 31L, 31M, 31N, 31Q, 31S, 31T, 31V, 31Y, 32G, 32S, 33A, 33D, 33E, 33H, 33Q, 33S, 34W, 35A, 35F, 35G, 35H, 35I, 35L, 35M, 35N, 35Q, 35R, 35S, 35V, 35W, 36F, 36H, 36I, 36L, 36S, 36T, 36Y, 37L, 37V, 39A, 39P, 39S, 39V, 42V, 43A, 43S, 43T, 43V, 44A, 44D, 44E, 44F, 44G, 44H, 44I, 44K, 44N, 44R, 44S, 44T, 44Y, 45F, 45H, 45I, 45L, 45M, 45S, 45T, 46A, 46D, 46F, 46H, 46L, 46N, 46R, 47A, 47D, 47F, 47G, 47H, 47I, 47K, 47L, 47N, 47P, 47R, 47S, 47T, 47V, 47Y, 48A, 48E, 48F, 48H, 48N, 48P, 48W, 49A, 49F, 49G, 49H, 49K, 49L, 49Q, 49R, 49S, 49T, 49V, 49W, 49Y, 50E, 50F, 50H, 50I, 50K, 50L, 50M, 50P, 50R, 50S, 50T, 50V, 50W, 50Y, 51D, 51E, 51F, 51H, 51I, 51K, 51L, 51P, 51Q, 51R, 51S, 51T, 51V, 51W, 52E, 52F, 52G, 52H, 52I, 52K, 52L, 52M, 52N, 52Q, 52R, 52S, 52T, 52V, 52W, 52Y, 53A, 53E, 53F, 53H, 53I, 53L, 53P, 53R, 53S, 53T, 53V, 54A, 54C, 54F, 54G, 54H, 54L, 54N, 54P, 54R, 54T, 54W, 54Y, 55A, 55F, 55H, 55N, 55P, 55Q, 55S, 55T, 55Y, 56D, 56E, 56F, 56G, 56I, 56K, 56L, 56P, 56Q, 56R, 56T, 56V, 56W, 56Y, 57A, 57E, 57H, 57M, 57Q, 57R, 57S, 57Y, 58F, 59A, 59C, 59F, 59H, 59N, 59P, 59R, 59S, 59T, 59W, 60L, 60N, 63H, 63N, 64A, 64S, 65A, 65I, 65R, 66D, 66E, 66G, 66M, 66N, 66Q, 66R, 67A, 67F, 67G, 67I, 67L, 67N, 67Q, 67T, 67W, 68D, 68F, 68H, 68I, 68L, 68N, 68R, 68S, 68T, 68V, 68W, 69M, 69V, 72E, 72F, 72G, 72H, 72I, 72K, 72Q, 72S, 72T, 72V, 72W, 72Y, 73F, 73M, 73W, 74M, 74T, 76A, 76L, 76M, 76P, 76Q, 76R, 76Y, 77A, 77D, 77K, 77L, 77R, 77Y, 78D, 78E, 78F, 78G, 78H, 78I, 78K, 78L, 78P, 78R, 78S, 78T, 78W, 78Y, 79A, 79M, 79Q, 79S, 80M, 81E, 81G, 81H, 81L, 81M, 81N, 81Q, 81R, 81S, 81T, 81V, 81Y, 82D, 82F, 82G, 82I, 82K, 82L, 82M, 82Q, 82R, 82S, 82T, 82Y, 83A, 83F, 83L, 84A, 84N, 84S, 84T, 85D, 85E, 85F, 85G, 85I, 85K, 85R, 85S, 85T, 85V, 85W, 86D, 86E, 86F, 86G, 86I, 86K, 86L, 86M, 86N, 86Q, 86R, 86S, 86V, 86W, 86Y, 87G, 88A, 88D, 88F, 88G, 88H, 88K, 88L, 88M, 88N, 88Q, 88R, 88S, 88T, 88W, 88Y, 89D, 89F, 89G, 89H, 89I, 89K, 89L, 89M, 89N, 89P, 89Q, 89R, 89S, 89T, 89V, 89W, 89Y, 90D, 90E, 90F, 90H, 90I, 90K, 90M, 90N, 90R, 90S, 90T, 90V, 90W, 91D, 91E, 91H, 91K, 91N, 91Q, 91R, 91S, 92L, 92V, 93A, 93D, 93G, 93M, 93N, 93R, 93S, 93Y, 94I, 95F, 95M, 96I, 98C, 99I, 100C, 100F, 100M, 100V, 103A, 103C, 103V, 104A, 104S, 105C, 105D, 105E, 105F, 105G, 105M, 105W, 105Y, 106E, 106H, 106N, 106Q, 106S, 106T, 106Y, 107A, 107C, 107E, 107F, 107G, 107H, 107I, 107K, 107L, 107M, 107N, 107P, 107Q, 107R, 107S, 107T, 107V, 107W, 108C, 108D, 108E, 108F, 108G, 108H, 108I, 108K, 108L, 108N, 108P, 108R, 108S, 108T, 108V, 108W, 108Y, 109D, 109H, 109I, 109K, 109L, 109N, 109R, 109S, 109V, 109W, 109Y, 110V, 111C, 111E, 111F, 111G, 111H, 111K, 111L, 111M, 111N, 111Q, 111R, 111T, 112A, 112D, 112E, 112H, 112K, 112L, 112R, 112S, 112T, 112W, 112Y, 113A, 114L, 115A, 115H, 115I, 115L, 115R, 115V, 115Y, 116A, 116F, 116G, 116H, 116I, 116L, 116N, 116Q, 116R, 116T, 116V, 116W, 116Y, 118D, 118F, 118G, 118H, 118K, 118L, 118M, 118N, 118Q, 118R, 118S, 118T, 118V, 118W, 118Y, 119E, 119F, 119I, 119K, 119L, 119M, 119Q, 119S, 119T, 119Y, 121S, 124A, 124K, 124Q, 124R, 124S, 124T, 125A, 125D, 125F, 125I, 125K, 125Q, 125R, 125V, 125Y, 126A, 126C, 126D, 126F, 126G, 126H, 126I, 126K, 126L, 126N, 126P, 126R, 126S, 126T, 126V, 126W, 126Y, 128A, 128C, 128E, 128F, 128G, 128H, 128I, 128L, 128M, 128N, 128Q, 128R, 128S, 128T, 128V, 129C, 129D, 129E, 130A, 130F, 130L, 130T, 130Y, 131A, 131C, 131D, 131F, 131G, 131H, 131I, 131K, 131L, 131N, 131Q, 131T, 131V, 131W, 131Y, 132I, 132N, 132S, 132W, 134E, 134F, 134L, 134M, 134R, 134Y, 135E, 136L, 140A, 141F, 141H, 142C, 142D, 142F, 142G, 142H, 142I, 142K, 142M, 142Q, 142R, 142S, 142T, 142W, 142Y, 143C, 143D, 143K, 143L, 143N, 143Q, 143S, 144T, 147F, 147L, 150H, 151C, 151D, 151E, 151G, 151H, 151K, 151L, 151M, 151Q, 151S, 151T, 152A, 152C, 152E, 152F, 152G, 152H, 152I, 152K, 152L, 152M, 152N, 152P, 152Q, 152R, 152S, 152V, 152W, 152Y, 153E, 153F, 153H, 153K, 153L, 153N, 153R, 153T, 153V, 153W, 153Y, 154A, 155M, 156A, 156F, 156G, 156K, 156L, 156Q, 156R, 156V, 156Y, 157F, 157H, 158A, 158I, 158M, 158T, 158V, 159H, 159I, 159L, 159M, 160A, 160C, 160D, 160E, 160F, 160G, 160H, 160I, 160K, 160L, 160M, 160Q, 160S, 160T, 160V, 162I, 162M, 163A, 163E, 163F, 163G, 163H, 163I, 163K, 163L, 163N, 163Q, 163R, 163S, 163T, 163V, 163W, 163Y, 164G, 164H, 164L, 164N, 164S, 164T, 164V, 164W, 164Y, 165C, 165I, 165L, 165M, 165T, 165V, 166C, 166I, 166M, 166V, 167A, 167C, 167E, 167F, 167G, 167I, 167K, 167L, 167M, 167Q, 167R, 167S, 167T, 167V, 167W, 167Y, 168C, 168E, 168F, 168G, 168K, 168L, 168M, 168N, 168S, 168T, 168V, 168W, 168Y, 170C, 171E, 171H, 171I, 171M, 171N, 171Q, 171R, 172A, 175Y, 179A, 179C, 179G, 179H, 179S, 179W, 180M, 181V, 184D, 186E, 187E, 187F, 187H, 187I, 187K, 187M, 187Q, 187S, 187V, 187W, 188A, 188D, 188F, 188G, 188I, 188K, 188L, 188M, 188P, 188Q, 188R, 188T, 188V, 189F, 189W, 190H, 190K, 190Q, 190R, 190S, 192G, 192K, 192L, 192P, 192S, 192V, 195D, 195F, 195G, 195H, 195K, 195M, 195R, 195V, 195W, 196A, 196C, 196E, 196F, 196H, 196I, 196K, 196L, 196M, 196Q, 196R, 196S, 196T, 196V, 196Y, 197L, 197V, 198A, 198C, 198I, 198L, 198V, 199C, 199D, 199E, 199F, 199H, 199R, 199S, 199T, 199Y, 200I, 200N, 200S, 200V, 201C, 201D, 201E, 201F, 201G, 201H, 201I, 201K, 201L, 201N, 201Q, 201R, 201T, 201V, 201W, 201Y, 202C, 202V, 203A, 203C, 203F, 203G, 203I, 203K, 203L, 203Q, 203R, 203S, 203T, 203V, 203W, 203Y, 204I, 204M, 204W, 204Y, 205A, 205C, 205I, 205L, 205M, 205N, 205V, 207A, 209L, 209V, 211H, 211S, 211T, 212G, 212N, 213A, 213E, 213F, 213G, 213I, 213K, 213L, 213M, 213P, 213Q, 213R, 213T, 213V, 214C, 214D, 214F, 214G, 214I, 214K, 214L, 214M, 214N, 214Q, 214R, 214S, 214T, 214V, 214W, 214Y, 217I, 217Q, 217T, 218C, 218D, 218E, 218F, 218G, 218H, 218I, 218K, 218L, 218M, 218P, 218Q, 218R, 218S, 218T, 218V, 218W, 218Y, 219D, 219F, 219G, 219H, 219I, 219N, 219Q, 219S, 219T, 219V, 219Y, 221C, 221E, 221G, 221Q, 221S, 221V, 222F, 222T, 223H, 223L, 223M, 223W, 224I, 225E, 225F, 225N, 225P, 225Q, 225T, 225Y, 226I, 226L, 229D, 229E, 229N, 229T, 230A, 230D, 230E, 230F, 230H, 230I, 230K, 230M, 230Q, 230R, 230S, 230V, 230Y, 231H, 231W, 232S, 233A, 233D, 233E, 233F, 233G, 233I, 233K, 233L, 233M, 233N, 233Q, 233S, 233T, 233V, 233W, 233Y, 234A, 234F, 234G, 234H, 234I, 234L, 234M, 234N, 234Q, 234R, 234T, 234V, 234W, 234Y, 235L, 235M, 236A, 236G, 236I, 236L, 236M, 236N, 236Q, 237C, 237D, 237E, 237F, 237G, 237H, 237I, 237K, 237L, 237R, 237T, 237V, 237W, 237Y, 238C, 238E, 238G, 238N, 238R, 238S, 238W, 239I, 239M, 240A, 240E, 240F, 240G, 240L, 240Q, 240R, 240T, 240V, 240Y, 241F, 241G, 241H, 241I, 241K, 241L, 241R, 241S, 241T, 241V, 241W, 241Y, 242A, 242C, 242D, 242F, 242I, 242K, 242L, 242S, 242T, 242V, 242W, 242Y, 243D, 243E, 243F, 243G, 243H, 243I, 243K, 243L, 243M, 243Q, 243R, 243S, 243T, 243V, 243W, 243Y, 244I, 244M, 244V, 245C, 245F, 245H, 245I, 245L, 245M, 245N, 245P, 245R, 245T, 245V, 245W, 245Y, 246C, 246D, 246E, 246G, 246I, 246L, 246Q, 246W, 246Y, 247F, 247G, 247H, 247I, 247L, 247M, 247N, 247Q, 247T, 247V, 247Y, 248F, 248G, 248K, 248L, 248Q, 248R, 248S, 248T, 248V, 248W, 249A, 249C, 249F, 249L, 249M, 249V, 250C, 250E, 250F, 250G, 250H, 250I, 250K, 250L, 250M, 250T, 250V, 250W, 250Y, 251A, 251C, 251D, 251E, 251G, 251K, 251L, 251M, 251P, 251Q, 251V, 251Y, 252F, 252L, 252W, 253F, 253I, 253K, 253L, 253M, 253R, 253T, 253W, 253Y, 254A, 254F, 254G, 254H, 254I, 254L, 254N, 254T, 254V, 254Y, 255A, 255E, 255I, 255K, 255P, 255R, 255S, 255V, 256A, 256C, 256I, 257E, 257I, 257L, 257P, 258C, 258D, 258E, 258N, 258Q, 258R, 258S, 258V, 259A, 259G, 259H, 259K, 259Q, 259R, 259S, 259T, 259W, 260A, 260C, 260D, 260F, 260H, 260N, 260Q, 260R, 260S, 260Y, 261M, 262I, 263C, 263L, 263M, 263S, 263V, 264E, 264H, 264I, 264L, 264Y, 267A, 267C, 267N, 267T, 268M, 268Q, 270F, 270G, 270N, 270S, 270V, 271F, 272G, 272L, 272S, 272V, 273G, 273I, 273L, 273T, 273Y, 274F, 274G, 274H, 274I, 274K, 274L, 274M, 274N, 274P, 274Q, 274R, 274S, 274T, 274V, 274W, 274Y, 275F, 275G, 275H, 275K, 275P, 275Q, 275R, 275S, 275T, 275V, 276A, 276C, 276D, 276F, 276G, 276H, 276I, 276K, 276L, 276M, 276N, 276P, 276Q, 276R, 276S, 276T, 276Y, 277A, 277D, 277F, 277G, 277H, 277I, 277K, 277L, 277N, 277P, 277Q, 277R, 277S, 277T, 277V, 277Y, 279H, 279K, 279L, 279M, 279N, 279Q, 279Y, 280F, 280Y, 281C, 281L, 282A, 282D, 282I, 282K, 282L, 282M, 282N, 282Q, 282T, 282W, 282Y, 283C, 283G, 283H, 283P, 283R, 283S, 283T, 283V, 283W, 284A, 284C, 284E, 284F, 284G, 284H, 284I, 284K, 284L, 284N, 284R, 284S, 284T, 284V, 284W, 284Y, 285E, 285M, 286C, 286L, 286M, 286V, 287A, 287C, 287F, 287H, 287I, 287K, 287L, 287M, 287Q, 287S, 287T, 287V, 288C, 288I, 288M, 288V, 289A, 290Y, 291C, 291G, 291L, 291S, 291T, 292A, 292C, 292I, 292L, 292T, 293C, 293V, 294C, 294G, 294S, 294T, 295A, 295G, 297D, 297E, 297F, 297G, 297H, 297I, 297K, 297L, 297M, 297N, 297P, 297Q, 297R, 297T, 297V, 297W, 298C, 298D, 298E, 298F, 298H, 298I, 298K, 298L, 298M, 298N, 298P, 298Q, 298R, 298S, 298V, 298W, 299C, 299G, 299I, 299N, 299V, 300H, 300M, 300R, 300V, 301I, 301K, 301L, 301M, 301T, 302T, 303M, 304L, 304Y, 305T, 305V, 307C, 307N, 308C, 308F, 308G, 308H, 308I, 308K, 308L, 308M, 308N, 308P, 308Q, 308R, 308S, 308T, 308V, 308W, 308Y, 309D, 309E, 309F, 309H, 309K, 309R, 309S, 310A, 311A, 311H, 311K, 311R, 312D, 312F, 312G, 312H, 312I, 312K, 312L, 312M, 312P, 312Q, 312R, 312S, 312T, 312V, 312W, 312Y, 313A, 313D, 313E, 313F, 313K, 313L, 313N, 313Q, 313R, 313S, 313W, 313Y, 314A, 314F, 314H, 314K, 314L, 314M, 314Q, 314R, 314S, 314T, 314W, 314Y, 315K, 315N, 315P, 315T, 316Y, 317A, 317C, 317E, 317F, 317H, 317K, 317L, 317R, 317S, 317T, 317V, 317W, 317Y, 318D, 318F, 318H, 318I, 318K, 318L, 318M, 318N, 318R, 318S, 318T, 318V, 318W, 318Y, 319G, 319L, 319N, 319Q, 319V, 319W, 320C, 320F, 320G, 320I, 320K, 320L, 320M, 320P, 320Q, 320T, 320V, 320Y, 321C, 321D, 321E, 321F, 321G, 321H, 321I, 321K, 321L, 321R, 321S, 321T, 321V, 321W, 322L, 322M, 322V, 324A, 324F, 324G, 324H, 324I, 324K, 324L, 324M, 324N, 324Q, 324R, 324S, 324T, 324V, 324W, 324Y, 325C, 325D, 325G, 325H, 325I, 325K, 325L, 325M, 325N, 325P, 325T, 325V, 327C, 327D, 327G, 327H, 327N, 327T, 328D, 328E, 328F, 328L, 328N, 328Q, 328Y, 329F, 329H, 329Q, 330W, 330Y, 331D, 331F, 331G, 331I, 331L, 331Q, 331S, 331T, 331V, 331Y, 332A, 332C, 332G, 332Q, 332S, 333C, 333G, 333H, 333K, 333L, 333M, 333R, 333S, 333W, 333Y, 334C, 334H, 334I, 334L, 334M, 334N, 334R, 334T, 335V, 336A, 336C, 336F, 336G, 336I, 336M, 336N, 336Q, 336R, 336V, 336W, 336Y, 337H, 337N, 337S, 337V, 337W, 337Y, 338G, 338I, 338L, 338M, 338S, 338T, 339C, 340F, 340H, 340K, 340L, 340M, 340N, 340S, 340T, 340V, 340W, 341A, 341L, 341Y, 342A, 342K, 342N, 342R, 342Y, 343A, 343D, 343E, 343F, 343H, 343K, 343L, 343M, 343Q, 343S, 343T, 343W, 343Y, 344A, 344D, 344E, 344F, 344G, 344I, 344K, 344L, 344M, 344N, 344Q, 344R, 344S, 344T, 344W, 344Y, 345C, 345E, 345F, 345G, 345H, 345I, 345N, 345Q, 345S, 345T, 345V, 346C, 346D, 346E, 346I, 346K, 346L, 346M, 346N, 346S, 346T, 346V, 346Y, 347D, 347F, 347H, 347I, 347K, 347L, 347M, 347Q, 347R, 347S, 347T, 347V, 347W, 348F, 348H, 348I, 348K, 348R, 348S, 348T, 348V, 348W, 348Y, 349A, 349F, 349G, 349I, 349K, 349M, 349N, 349R, 349S, 349V, 349W, 349Y, 350D, 351A, 351D, 351G, 351H, 351K, 351L, 351M, 351P, 351Q, 351R, 351T, 351V, 351W, 351Y, 352A, 352H, 352Q, 352T, 352Y, 353A, 353D, 353E, 353G, 353I, 353K, 353L, 353M, 353Q, 353V, 353W, 353Y, 355C, 355F, 355I, 355L, 355M, 355V, 355Y, 356D, 356F, 356G, 356I, 356K, 356L, 356P, 356Q, 356T, 356W, 356Y, 357A, 357H, 357I, 357K, 357L, 357N, 357Q, 357R, 357S, 357T, 357V, 357W, 357Y, 358C, 358D, 358F, 358G, 358H, 358I, 358K, 358L, 358M, 358Q, 358R, 358S, 358T, 358V, 358Y, 359D, 359E, 359H, 359L, 359M, 359P, 359Q, 359R, 359T, 359V, 359W, 360F, 360P, 360T, 361C, 361L, 361M, 361N, 361Q, 361S, 361T, 361V, 362A, 362C, 362I, 362L, 362V, 362Y, 363D, 363G, 363H, 363Q, 363R, 363S, 363V, 363W, 363Y, 364A, 364C, 364G, 364I, 364L, 364M, 364Q, 364S, 364T, 364V, 365C, 365I, 365K, 365L, 365N, 365R, 365S, 365V, 366A, 366K, 367L, 367M, 367N, 367R, 367S, 367T, 367W, 367Y, 368G, 368I, 368K, 368L, 368R, 368T, 368V, 368W, 369C, 369D, 369E, 369F, 369G, 369I, 369K, 369L, 369N, 369Q, 369S, 369T, 369V, 369Y, 371A, 371C, 371F, 371I, 371L, 371M, 371N, 371S, 371T, 371Y, 372A, 372C, 372I, 372L, 372N, 372S, 372T, 373A, 373C, 373F, 373I, 373M, 373T, 373V, 374C, 374G, 374I, 374M, 374S, 374T, 374V, 375A, 375C, 375D, 375F, 375H, 375L, 375M, 375Q, 375S, 375T, 375Y, 376G, 376I, 376S, 376T, 376V, 377F, 377H, 377L, 377T, 377W, 377Y, 378C, 378E, 378F, 378G, 378H, 378I, 378K, 378L, 378M, 378N, 378Q, 378R, 378T, 378V, 378W, 378Y, 379A, 379G, 379H, 379I, 379K, 379L, 379Q, 379T, 379Y, 380C, 380E, 380F, 380G, 380H, 380L, 380M, 380N, 380P, 380Q, 380R, 380T, 380V, 380W, 380Y, 381G, 381I, 381Q, 381R, 381S, 381T, 381W, 381Y, 382A, 382C, 382F, 382I, 382K, 382Q, 382R, 382T, 382W, 382Y, 383A, 383F, 383L, 383P, 383Q, 383V, 384A, 384G, 384H, 384I, 384K, 384P, 384Q, 384V, 384W, 385C, 385F, 385H, 385I, 385L, 385M, 385N, 385P, 385Q, 385R, 385S, 385V, 385W, 385Y, 386D, 386F, 386G, 386H, 386L, 386N, 386R, 386S, 386T, 386V, 386W, 386Y, 387I, 387L, 388A, 388C, 388G, 388H, 388L, 388P, 388S, 388T, 388W, 388Y, 389C, 389F, 389I, 389M, 389Q, 389V, 390F, 390I, 390K, 390L, 390N, 390R, 390S, 390T, 390V, 390W, 390Y, 391F, 391K, 391N, 391P, 391R, 391T, 391W, 391Y, 392A, 392C, 392D, 392E, 392F, 392H, 392K, 392L, 392N, 392Q, 392R, 392S, 392V, 392Y, 393A, 393C, 393D, 393F, 393G, 393H, 393I, 393L, 393Q, 393S, 393T, 393V, 393W, 393Y, 394A, 394C, 394F, 394H, 394I, 394K, 394L, 394Q, 394V, 394W, 394Y, 395F, 395G, 395H, 395K, 395L, 395Q, 395R, 395S, 395T, 395V, 395Y, 396C, 396D, 396S, 397C, 397D, 397F, 397G, 397H, 397I, 397L, 397P, 397S, 397T, 397V, 397W, 398C, 398G, 398N, 398S, 398T, 398V, 399C, 399F, 399I, 399K, 399L, 399R, 399S, 399T, 399V, 399W, 399Y, 400C, 400D, 400E, 400F, 400G, 400H, 400I, 400K, 400L, 400M, 400Q, 400R, 400S, 400T, 400V, 400W, 400Y, 401A, 401C, 401D, 401E, 401F, 401I, 401K, 401L, 401M, 401N, 401Q, 401R, 401S, 401T, 401V, 401W, 401Y, 402A, 402C, 402D, 402E, 402F, 402G, 402H, 402I, 402K, 402L, 402M, 402N, 402P, 402Q, 402R, 402T, 402V, 402W, 402Y, 403A, 403C, 403H, 403I, 403M, 403V, 403W, 403Y, 404F, 404H, 404M, 404R, 404T, 404V, 404W, 404Y, 405G, 405Q, 405S, 405T, 406L, 406T, 407F, 407G, 407H, 407I, 407K, 407M, 407Q, 407R, 407S, 407T, 407V, 407W, 407Y, 408D, 408E, 408F, 408N, 408V, 409C, 409F, 409I, 409L, 409R, 409T, 409V, 409W, 409Y, 410V, 411E, 411F, 411M, 411Q, 411R, 411S, 411Y, 412N, 412T, 413C, 413F, 413G, 413I, 413L, 413P, 413R, 413S, 413V, 413W, 413Y, 414H, 414L, 414N, 414Q, 414T, 414V, 414W, 415D, 415E, 415G, 415I, 415R, 415V, 415W, 416F, 416L, 416Q, 416Y, 417A, 417C, 417D, 417F, 417G, 417H, 417I, 417K, 417M, 417N, 417Q, 418D, 418F, 418H, 418I, 418K, 418N, 418W, 418Y, 419E, 419F, 419H, 419I, 419L, 419S, 419T, 420D, 420E, 420F, 420G, 420H, 420I, 420K, 420L, 420Q, 420S, 420T, 420V, 420W, 420Y, 421C, 421L, 421M, 421S, 421T, 422F, 422I, 422S, 422W, 423D, 423I, 423Q, 423R, 423T, 424M, 424Q, 424R, 424V, 424Y, 425A, 425I, 425K, 425L, 425V, and 425Y.

In some embodiments, the substitution changes the amino acid residue present at position 153 to N, K or F, and the variant polypeptide exhibits increased ability to convert maltose and maltoheptaose substrates to glucose compared to the parental polypeptide. In some embodiments, the substitution changes the amino acid residue present at position 153 to K, and the variant polypeptide exhibits increased ability to convert a DP7 substrate to glucose compared to the parental polypeptide.

In some embodiments, the substitution is selected from the group consisting of L142F, L142G, L142Q, L142S, L142W, L142Y, A214I, A214V, S245Y, Q126F, Q126L, Q126P, Q126V, S131L, and S254I, and wherein the substitution improves the starch liquefaction performance of the variant polypeptides compared to the parental polypeptide of SEQ ID NO: 1. In some embodiments, the substitution is selected from the group consisting of W60L, W60M, W60N, I100F, I100M, S105M, S105W, G207A, T270A, T270E, T270L, T270N, T270V, and T279A, and wherein the substitution improves the starch liquefaction performance of the variant polypeptides compared to the parental polypeptide of SEQ ID NO: 2.

In some embodiments, the substitution is selected from the group consisting of 052D, 052E, 052I, 052K, 052L, 052N, 052Q, 052R, 052V, 056D, 056E, 056I, 056K, 056L, 056N, 056Q, 056R, 056V, 089D, 089E, 089I, 089K, 089L, 089N, 089Q, 089R, 089V, 152D, 152E, 152I, 152K, 152L, 152N, 152Q, 152R, 152V, 153D, 153E, 153I, 153K, 153L, 153N, 153Q, 153R, 153V, 201D, 201E, 201I, 201K, 201L, 201N, 201Q, 201R, 201V, 251D, 251E, 251I, 251K, 251L, 251N, 251Q, 251R, 251V, 284D, 284E, 284I, 284K, 284L, 284N, 284Q, 284R, 284V, 297D, 297E, 297I, 297K, 297L, 297N, 297Q, 297R, 297V, 308D, 308E, 308I, 308K, 308L, 308N, 308Q, 308R, 308V, 321D, 321E, 321I, 321K, 321L, 321N, 321Q, 321R, 321V, 328D, 328E, 328I, 328K, 328L, 328N, 328Q, 328R, 328V, 347D, 347E, 347I, 347K, 347L, 347N, 347Q, 347R, 347V, 357D, 357E, 357I, 357K, 357L, 357N, 357Q, 357R, 357V, 359D, 359E, 359I, 359K, 359L, 359N, 359Q, 359R, 359V, 369D, 369E, 369I, 369K, 369L, 369N, 369Q, 369R, 369V, 385D, 385E, 385I, 385K, 385L, 385N, 385Q, 385R, 385V, 388D, 388E, 388I, 388K, 388L, 388N, 388Q, 388R, 388V, 391D, 391E, 391I, 391K, 391L, 391N, 391Q, 391R, 391V, 400D, 400E, 400I, 400K, 400L, 400N, 400Q, 400R, 400V, 416D, 416E, 416I, 416K, 416L, 416N, 416Q, 416R, and 416V, which mutations have PI values >0.5 for both protein and activity.

In some embodiments, the variant polypeptide does not include a modification of the amino acid residue at a position selected from the group consisting of 75, 97, 101, 102, 120, 123, 133, 137, 182, 266, and 306, of the parental polypeptide. In some embodiments, the variant polypeptide does not include a modification of the amino acid residue at a position selected from the group consisting of 75 and 123, which were determined to be fully restrictive for performance in the truncated parental polypeptide. In some embodiments, the variant polypeptide does not include a modification of the amino acid residue at a position selected from the group consisting of 75, 97, 101, 102, 120, 133, 137, 182, 266, and 306, which were determined to be fully restrictive for performance in the full-length parental polypeptide.

In some embodiments, the parental polypeptide has at least 80% amino acid sequence identity to the amino acid sequence of SEQ ID NO: 1 or 2. In some embodiments, the parental polypeptide has at least 90% amino acid sequence identity to the amino acid sequence of SEQ ID NO: 1 or 2. In some embodiments, the parental polypeptide has at least 90% amino acid sequence identity to the amino acid sequence of SEQ ID NO: 3.

In some embodiments, the characteristic that improves enzyme performance is selected from the group consisting of increased thermal stability, increased specific activity, and increased protein expression.

In some embodiments, the characteristic that improves enzyme performance is selected from the group consisting of increased thermal stability, increased specific activity, and increased protein expression.

Also provided is a starch processing composition comprising an AmyE polypeptide (including a variant) and optionally a glucoamylase, a pullulanase, a β-amylase, a fungal α-amylase, a protease, a cellulase, a hemicellulase, a lipase, a cutinase, an isoamylase, or a combination thereof. In particular embodiments, the composition includes an additional polypeptide having glucoamylase activity.

Also provided is a baking composition comprising an AmyE polypeptide (including a variant) in a solution or in a gel. A method of baking comprises adding the baking composition to a substance to be baked, and baking the substance. In a related aspect, a method for reducing bread staling comprising adding to a bread dough an amount of AmyE polypeptide sufficient to reduce staling compared to the amount of staling observed with an equivalent bread dough lacking an AmyE polypeptide.

In another aspect, a cleaning composition is provided, comprising an AmyE polypeptide (including a variant) in an aqueous solution, and optionally another enzyme, a detergent and/or a bleach agent. The cleaning solution may used for laundering clothes, washing dishes, or cleaning other surfaces. In a related method, dishes, laundry, or other surfaces are contacted with the cleaning composition for a time sufficient for the article to be cleaned.

In another aspect, a textile desizing composition is provided, comprising an AmyE polypeptide (including a variant) in an aqueous solution, and optionally another enzyme. In a related method, a textile is contacted with the desizing composition for a time sufficient to desize the textile.

In another aspect, nucleic acids encoding AmyE variants, expression vectors comprising such polynucleotides, and host cells that express AmyE variants are provided. In yet another aspect, a nucleic acid complementary to a nucleic acid encoding any of the AmyE variants set forth herein is provided. Additionally, a nucleic acid capable of hybridizing to a nucleic acid encoding any of the AmyE variants set forth herein, or the complement, thereof, is provided. In another aspect, compositions and methods involving a synthetic nucleic acid encoding any of the AmyE variants set forth herein, wherein the codons are optionally optimized for expression in a particular host organism, are provided.

These and other aspects and embodiments of the compositions and methods will be apparent from the following description and accompanying Figures.

BRIEF DESCRIPTION OF THE DRAWINGS

FIG. 1 depicts a sequence alignment between AmyE having the amino acid sequence of SEQ ID NO: 1 (herein referred to as "AmyE full-length") and AmyE having the amino acid sequence of SEQ ID NO: 3 (herein referred to as "Amy31A").

Differences in the amino acid sequences are shown in bold. Residues are numbered from the first amino acid in the mature form of the enzymes.

Figure 2:
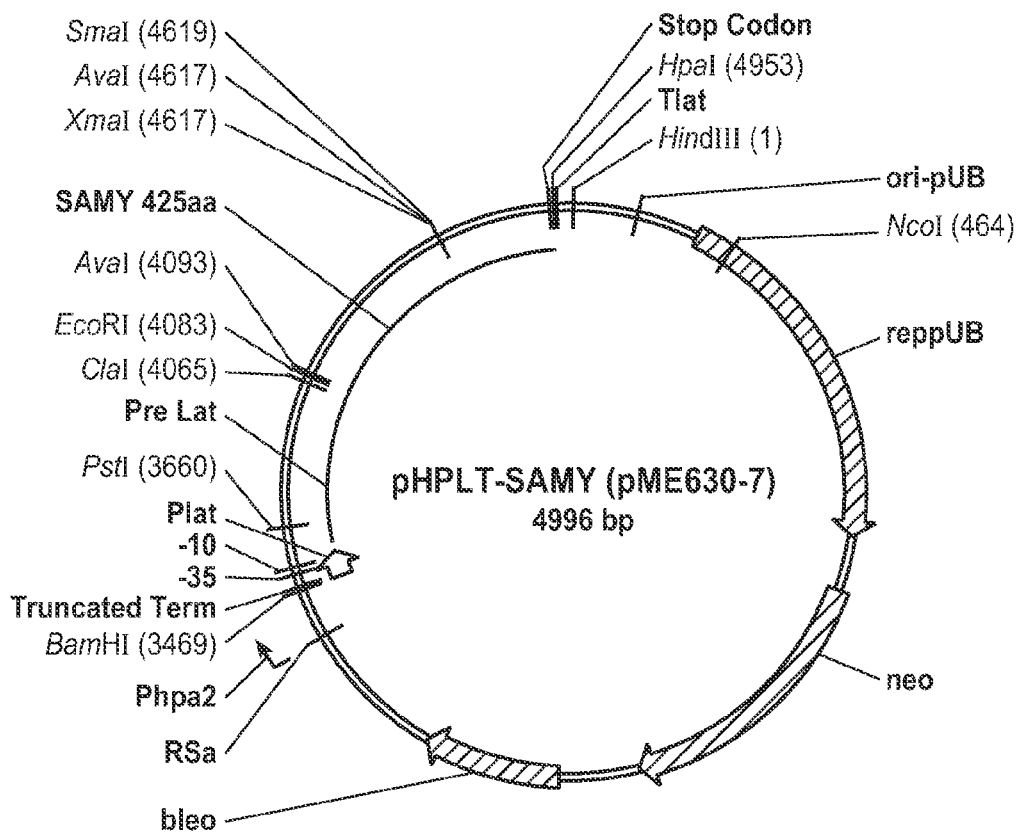

FIG. 2 depicts plasmid pME630-7, which comprises a polynucleotide (labeled "SAMY 425aa") that encodes AmyE-tr (SEQ ID NO: 2). The plasmid comprises a polynucleotide in-frame with the SAMY gene that encodes a signal sequence from *B. licheniformis* α-amylase (labeled "pre LAT").

Figure 3:
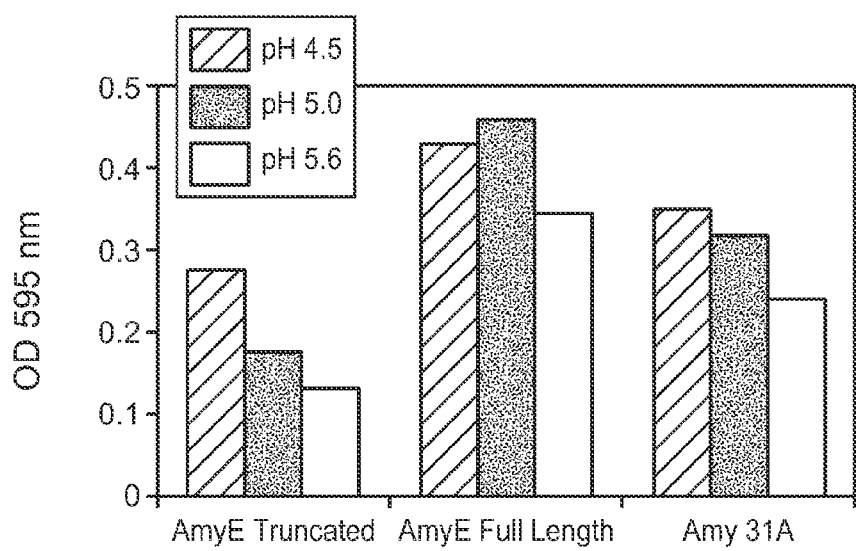

FIG. 3 depicts the relative specific activity of AmyE (SEQ ID NO: 1; "AmyE full length"), AmyE-tr (SEQ ID NO: 2; "AmyE truncated"), and Amy31A (SEQ ID NO: 3) toward an insoluble cornstarch substrate labeled with Remazol Brilliant Blue (RBB). Hydrolysis of the substrate was catalyzed for 30 minutes at 50° C. at pH 4.5, 5.0, or 5.6. Enzyme activity was determined by the absorbance at 595 nm of released RBB label.

Figure 4A:
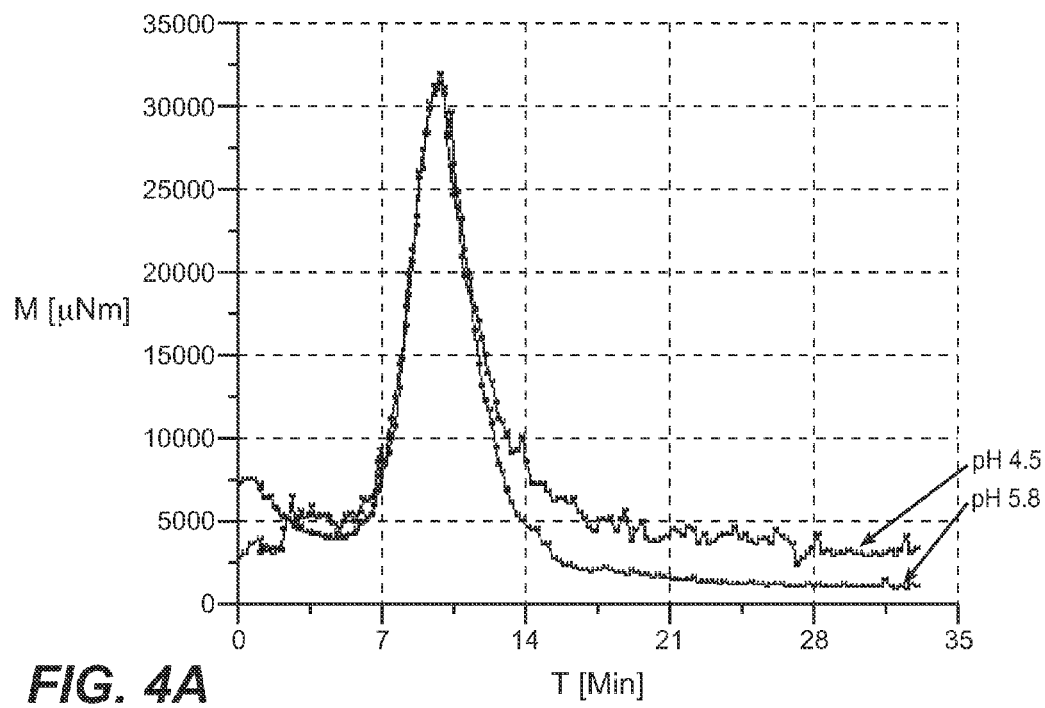
Figure 4B:
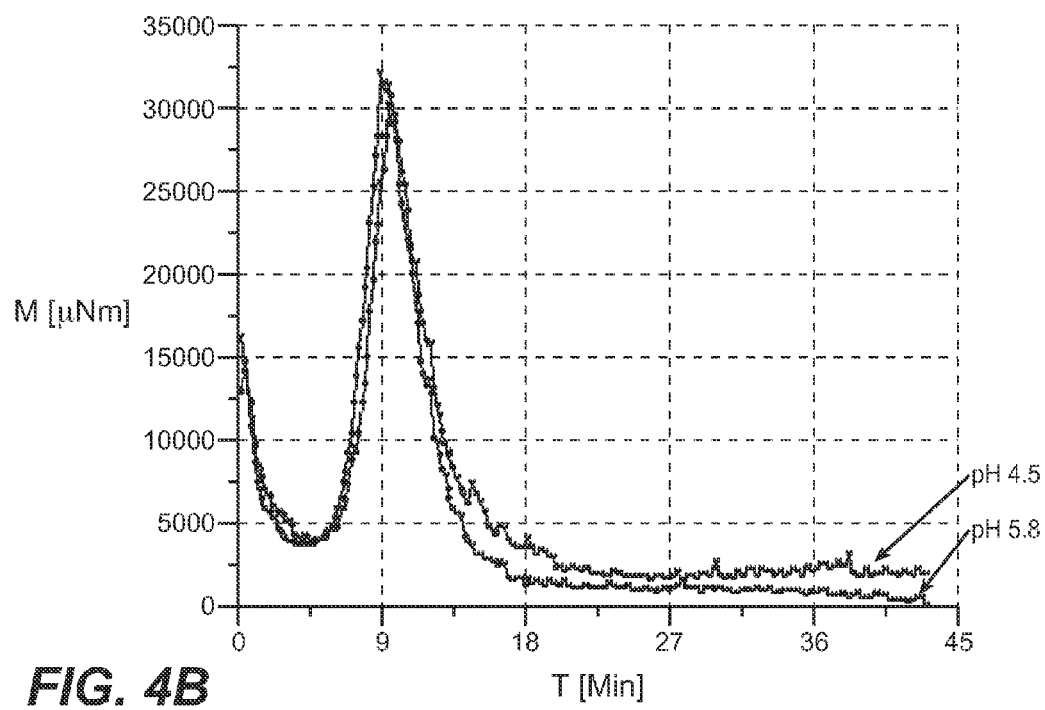
Figure 4C:
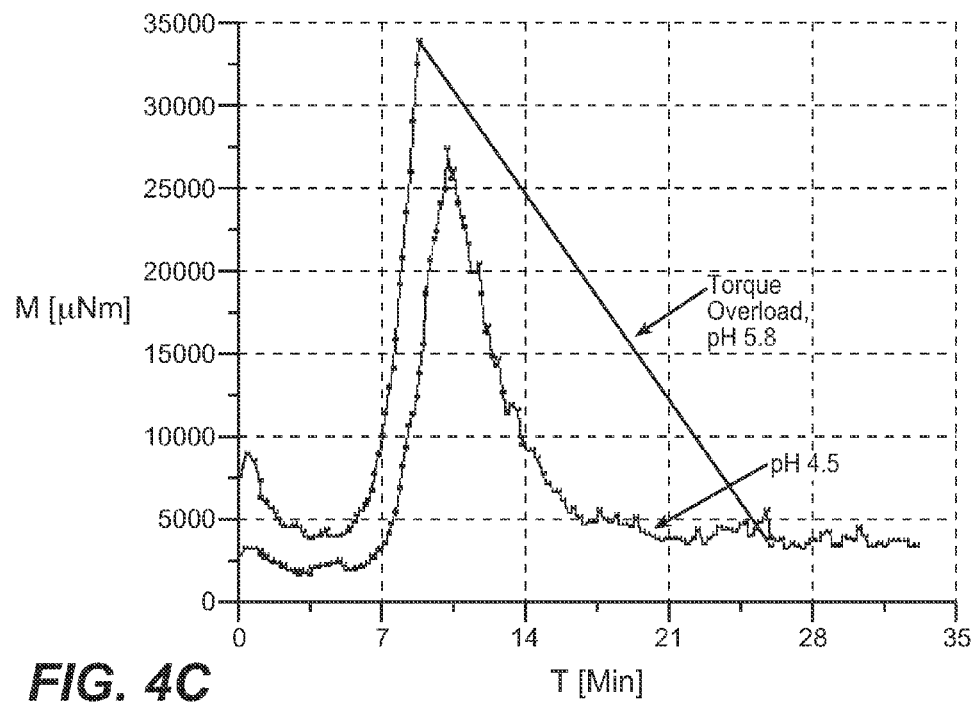
Figure 4D:
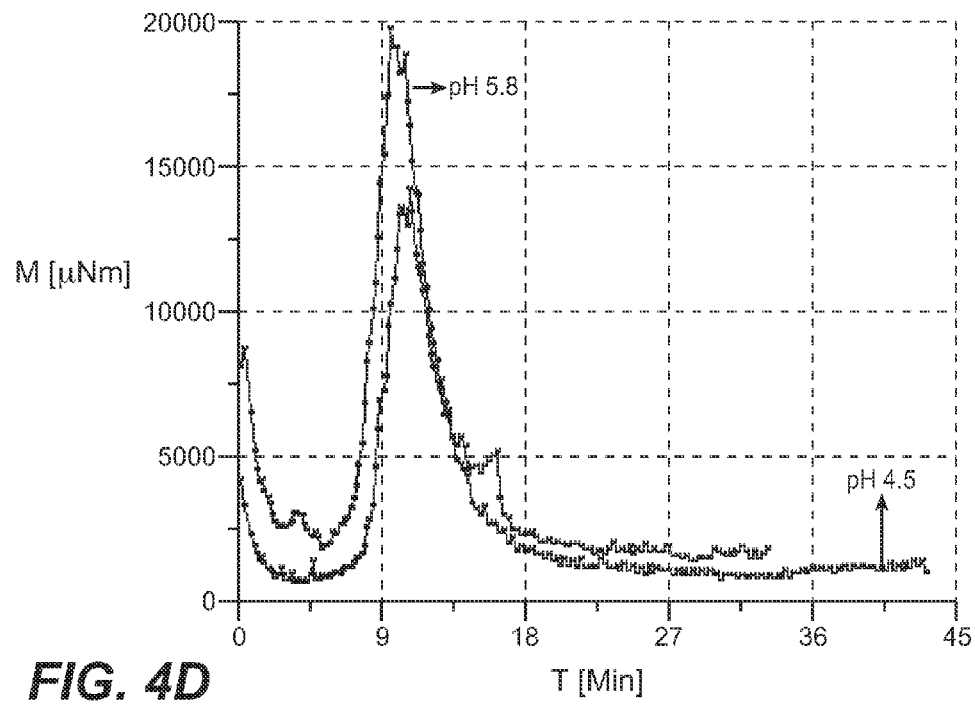

FIG. 4A depicts the viscosity (μNm) of 15 g ds starch substrate measured as a function of time (minutes) in the presence of 0.7 mg AmyE-tr (SEQ ID NO: 2) at pH of 4.5 or 5.8. FIG. 4B depicts substrate viscosity as a function of time in the presence of 2.2 mg AmyE (SEQ ID NO: 1) at pH of 4.5 or 5.8. FIG. 4C depicts substrate viscosity as a function of time in the presence of 1.4 mg Amy31A (SEQ ID NO: 3) at pH of 4.5 or 5.8. FIG. 4D depicts substrate viscosity as a function of time in the presence of 4.1 mg Amy31A at pH of 4.5 or 5.8.

Figure 5A:
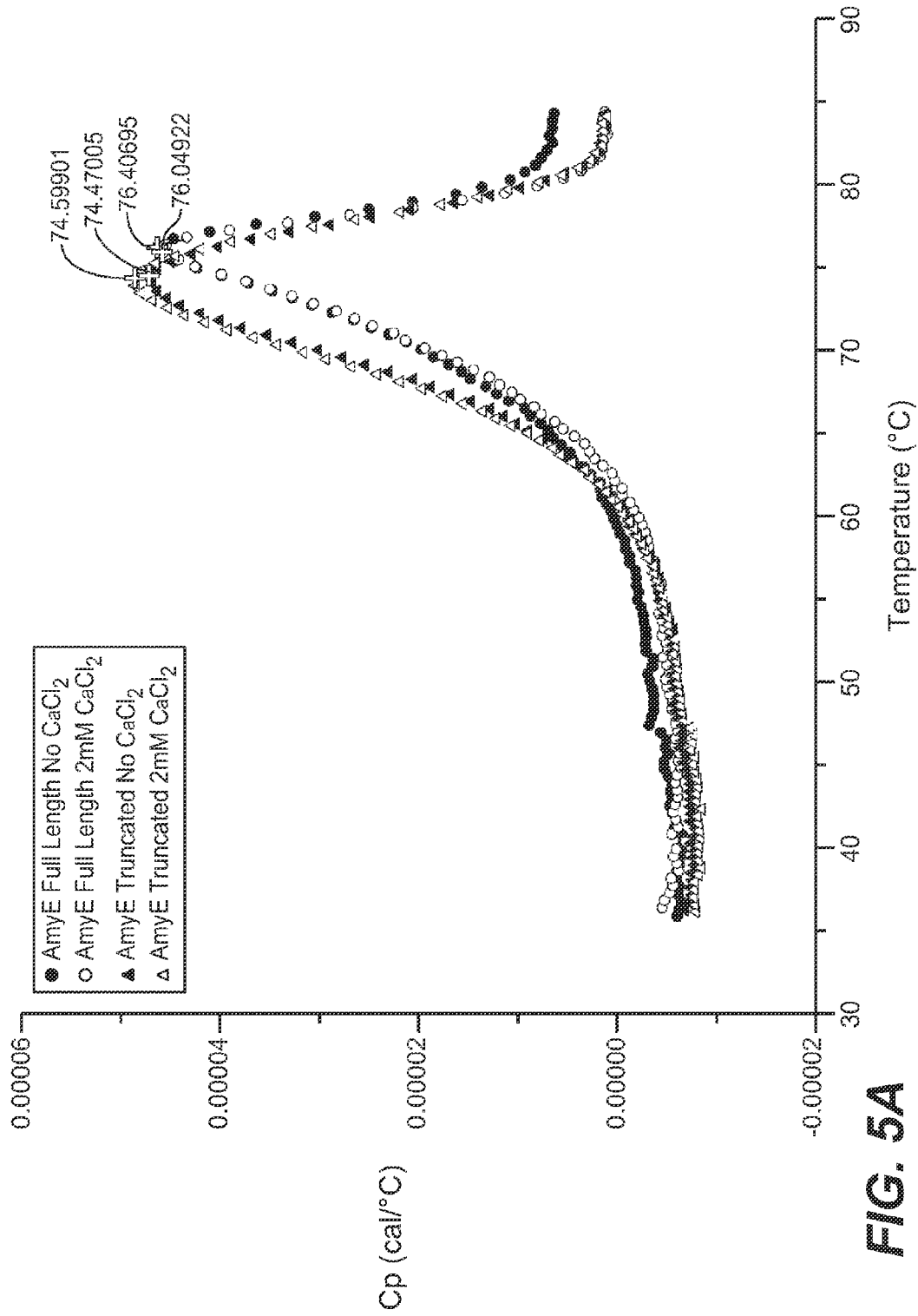
Figure 5B:
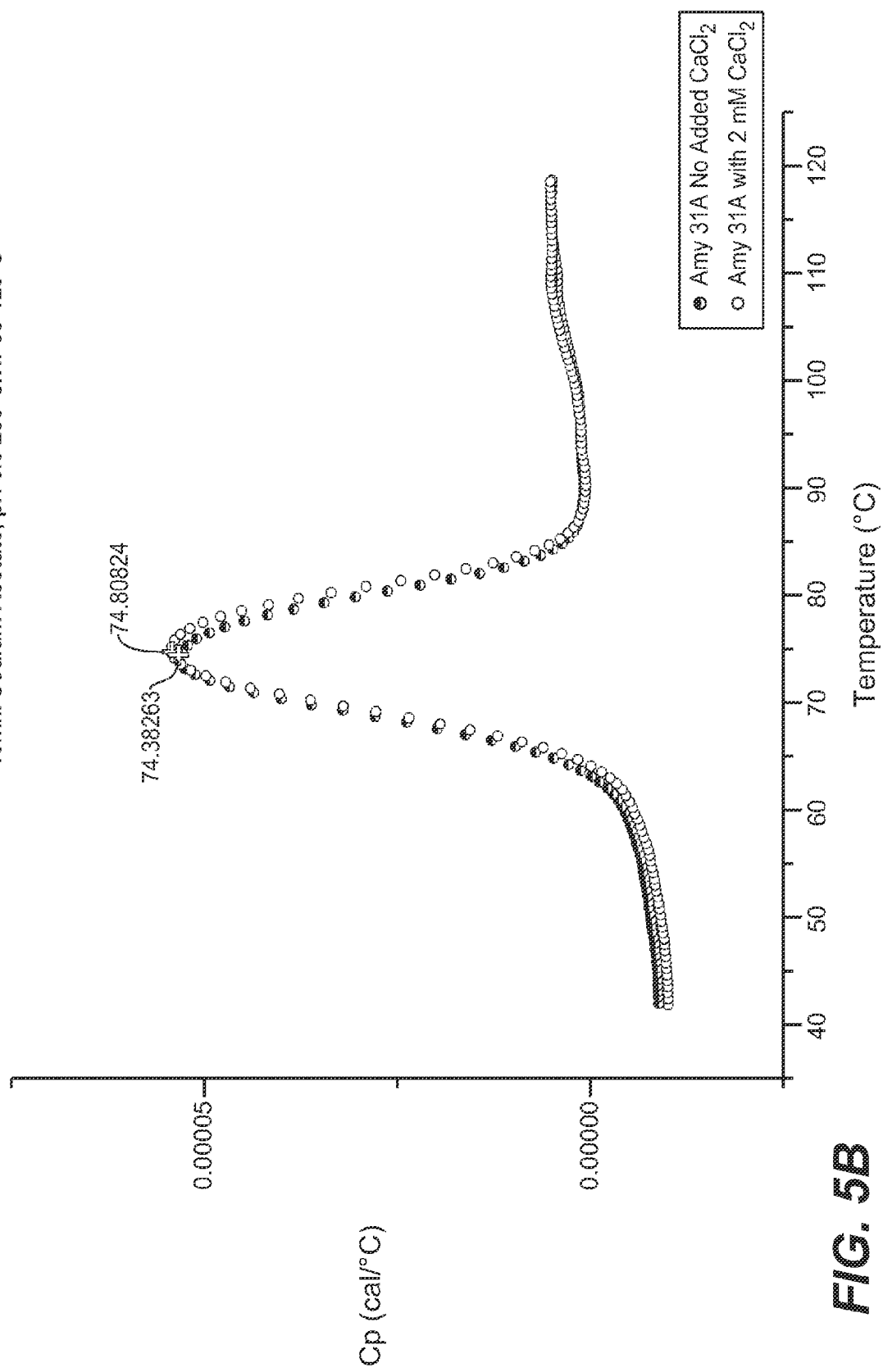
Figure 5C:
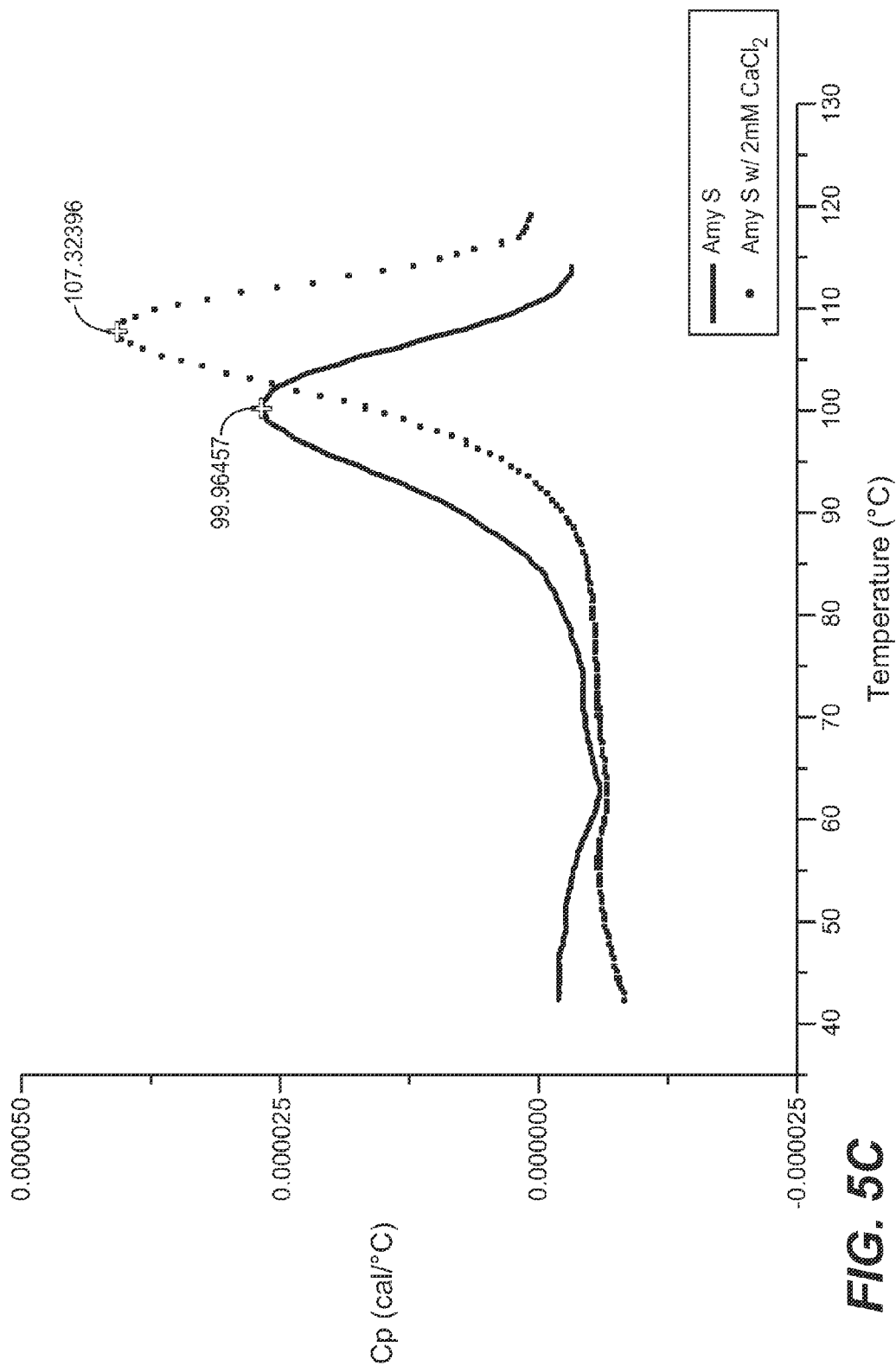

FIG. 5A depicts differential scanning calorimetric (DSC) analysis of excess heat capacity functions of AmyE (SEQ ID NO: 1; "AmyE full length") and AmyE-tr (SEQ ID NO: 2; AmyE truncated") in the presence or absence of 2 mM $Ca^{2+}$. FIG. 5B depicts DSC analysis of Amy31A (SEQ ID NO: 3) in the presence or absence of 2 mM $Ca^{2+}$. FIG. 5C depicts DSC analysis of *Geobacillus stearothermophilus* α-amylase (AmyS) in the presence or absence of 2 mM $Ca^{2+}$.

Figure 6:
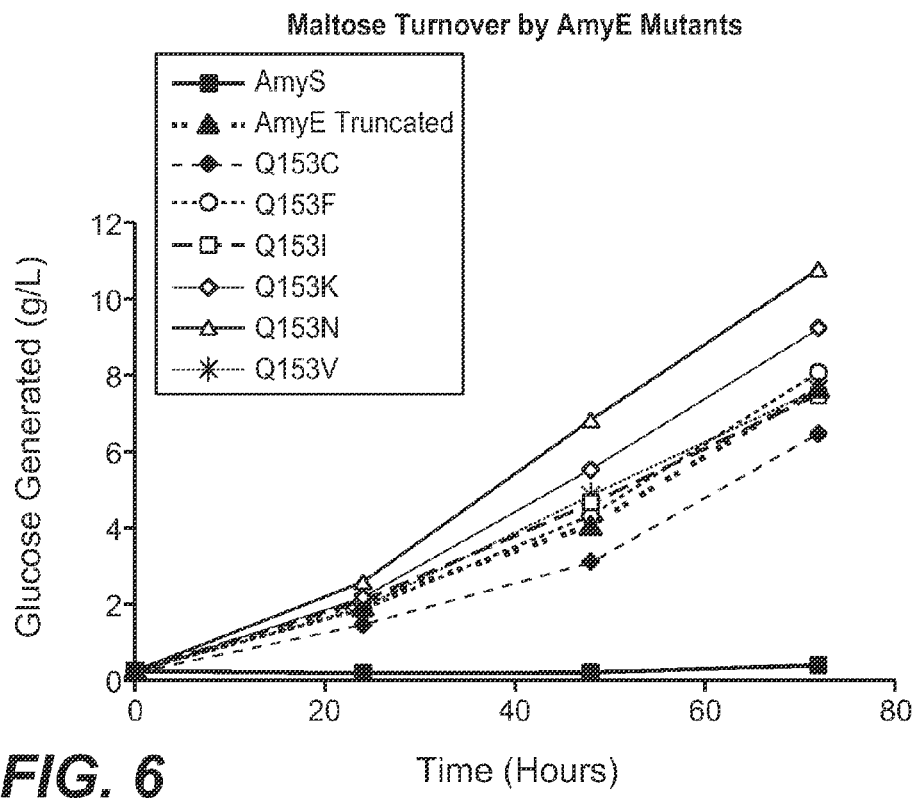

FIG. 6 depicts the results of glucose production from a maltose substrate by AmyE-tr (SEQ ID NO: 2) compared to AmyE position Q153 variants and truncated AmyS (SEQ ID NO: 4).

Figure 7:
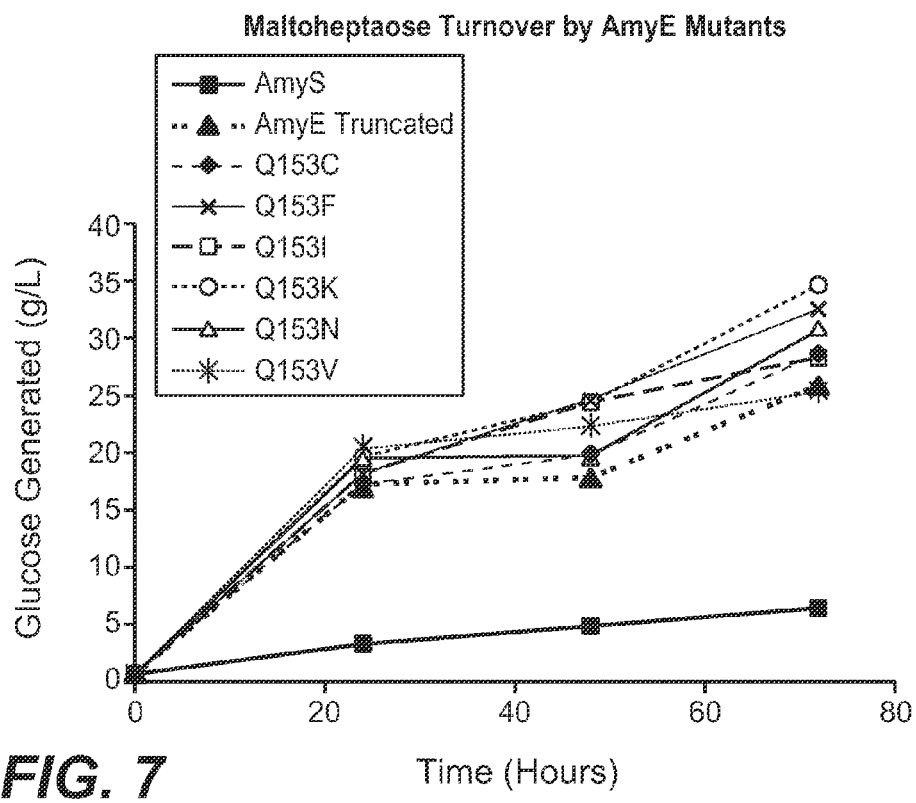

FIG. 7 depicts the results of glucose production from a maltoheptaose substrate by AmyE-tr (SEQ ID NO: 2) compared to AmyE position Q153 variants and truncated AmyS (SEQ ID NO: 4).

Figure 8:
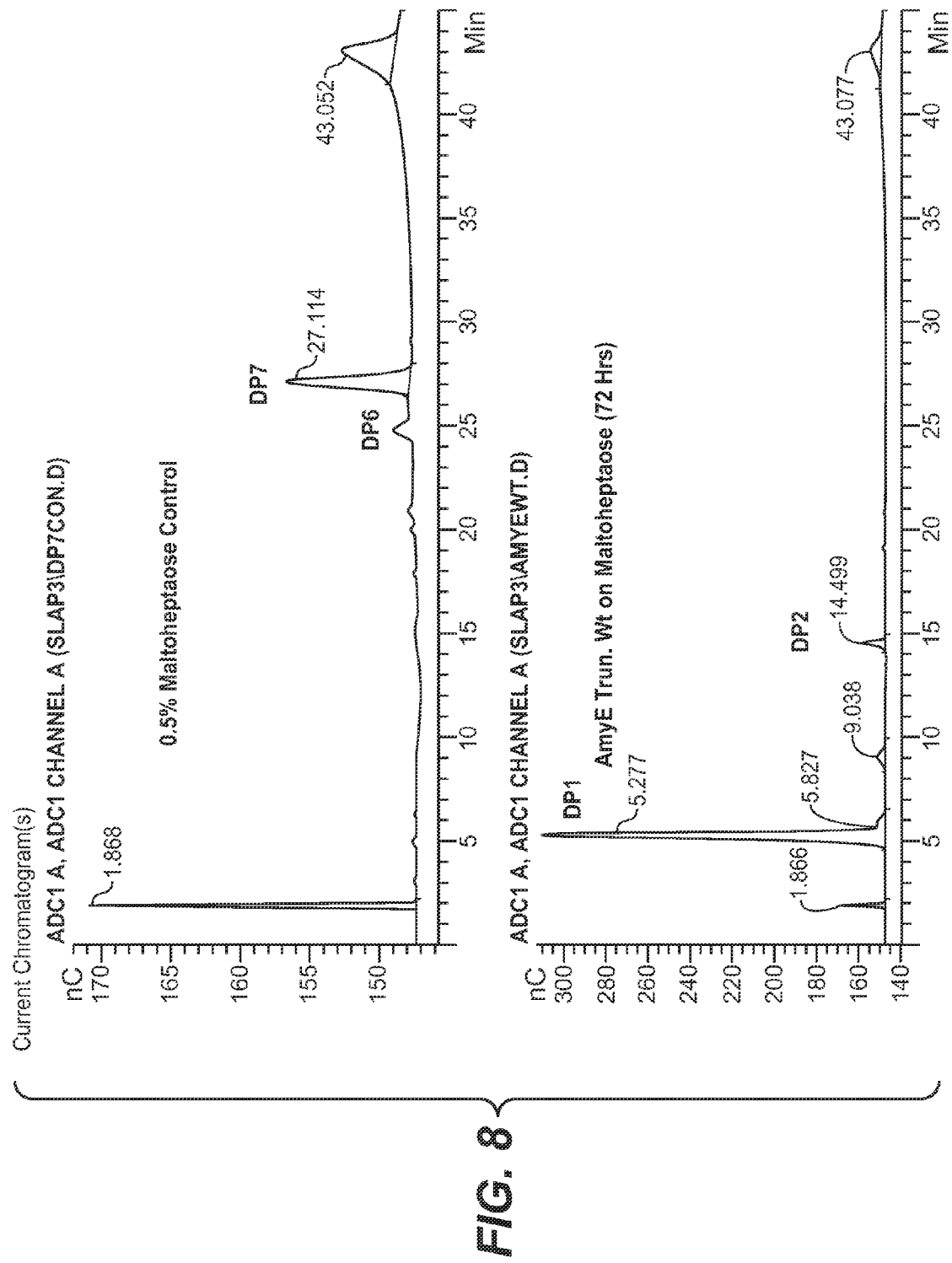

FIG. 8 depicts breakdown products detected by HPLC following a 0 h (top panel) and 72 h incubation (bottom panel) of AmyE-tr with maltoheptaose (DP7).

Figure 9:
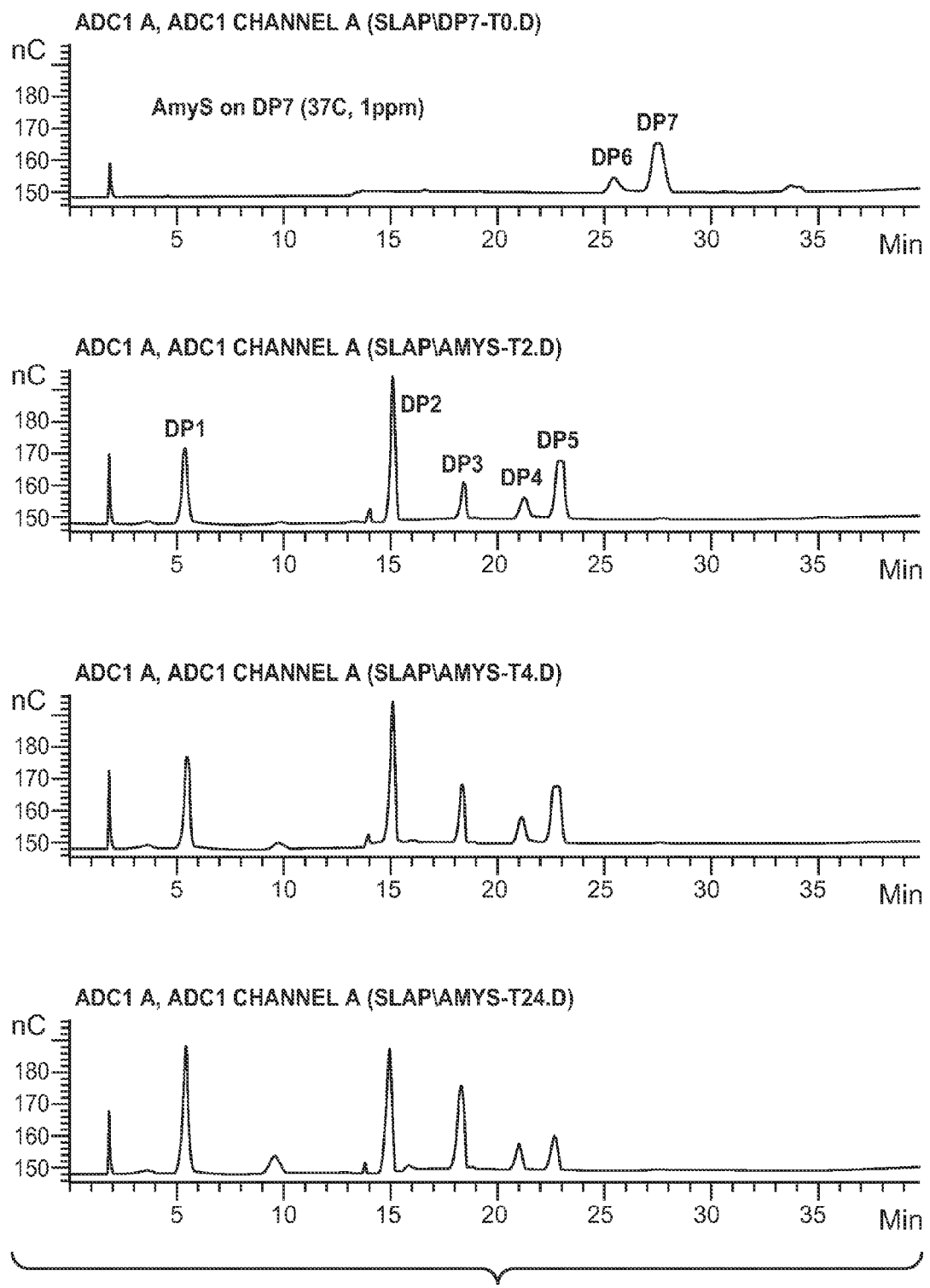

FIG. 9 depicts breakdown products detected by HPLC following a 0 h, 2 h, 4 h, and 24 h (panels from top to bottom) incubation of AmyS with a DP7 substrate.

Figure 10:
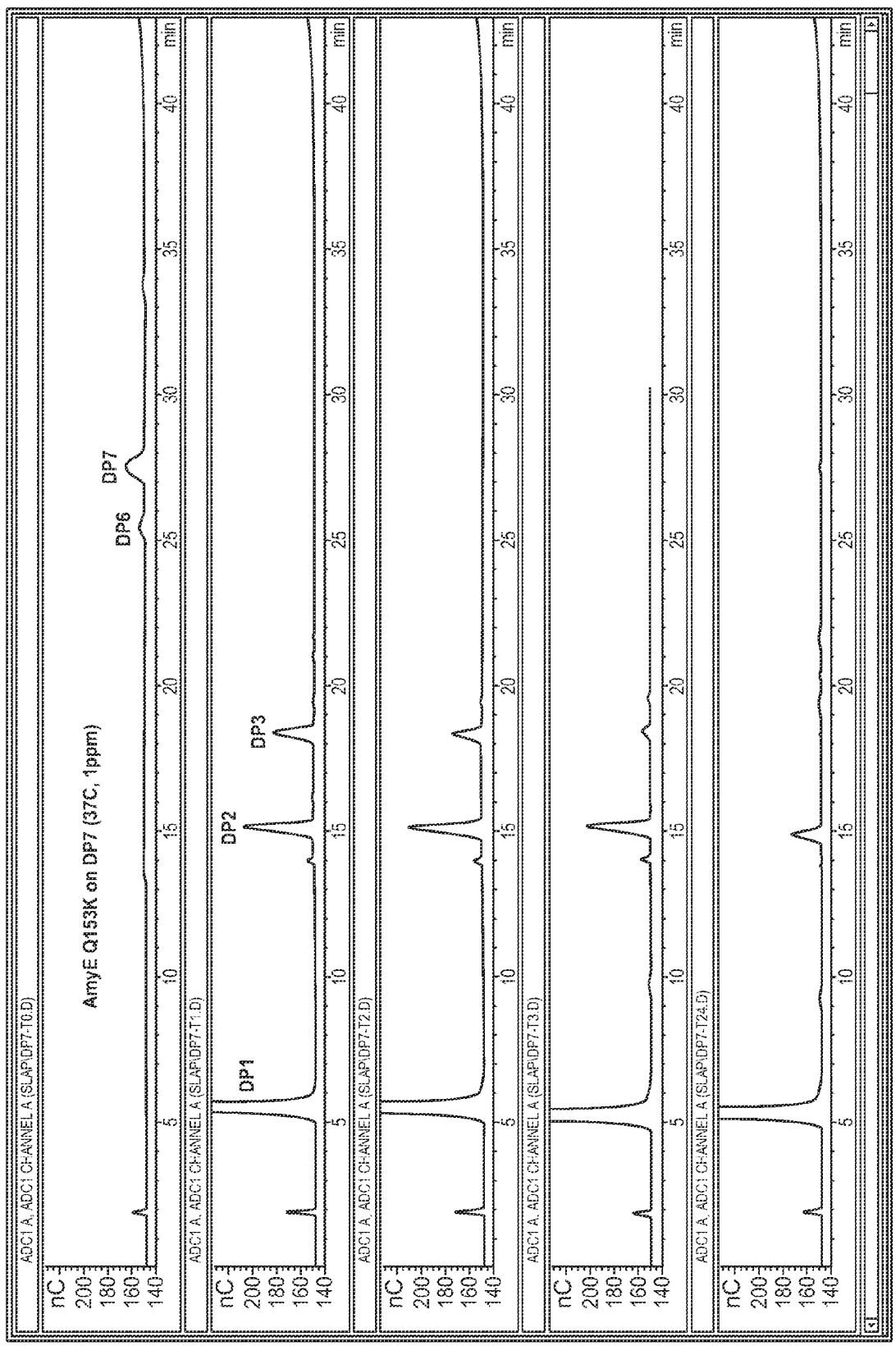

FIG. 10 depicts products formed by incubating AmyE-tr Q153K variant with maltoheptaose (DP7). HPLC traces shown from top to bottom correspond to time 0 h, 1 h, 2 h, 3 h, and 24 h.

Figure 11:
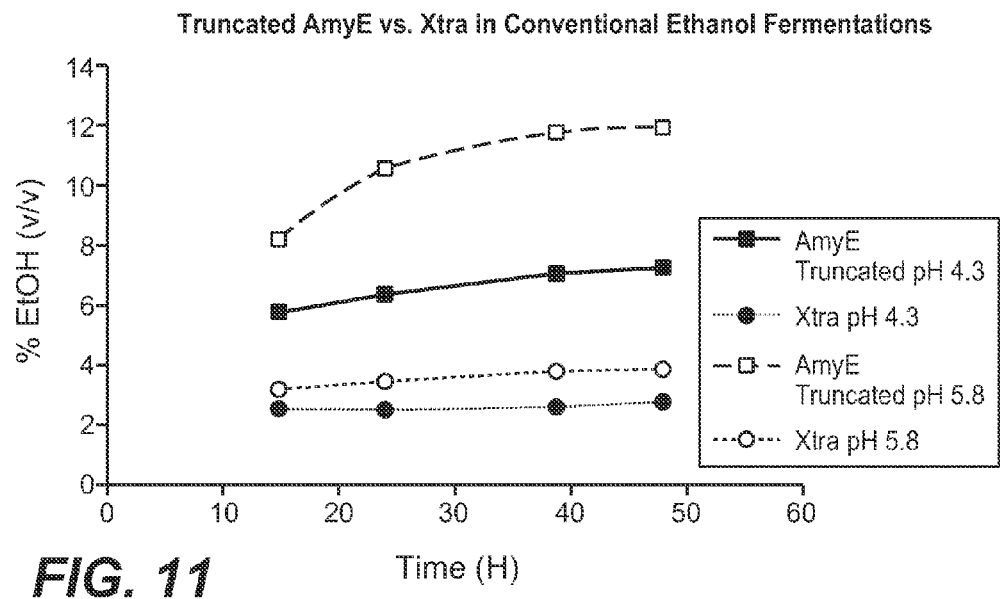

FIG. 11 shows ethanol formation by truncated AmyE and SPEZYME® Xtra amylase in conventional fermentation at pH 4.3 and 5.8.

Figure 12:
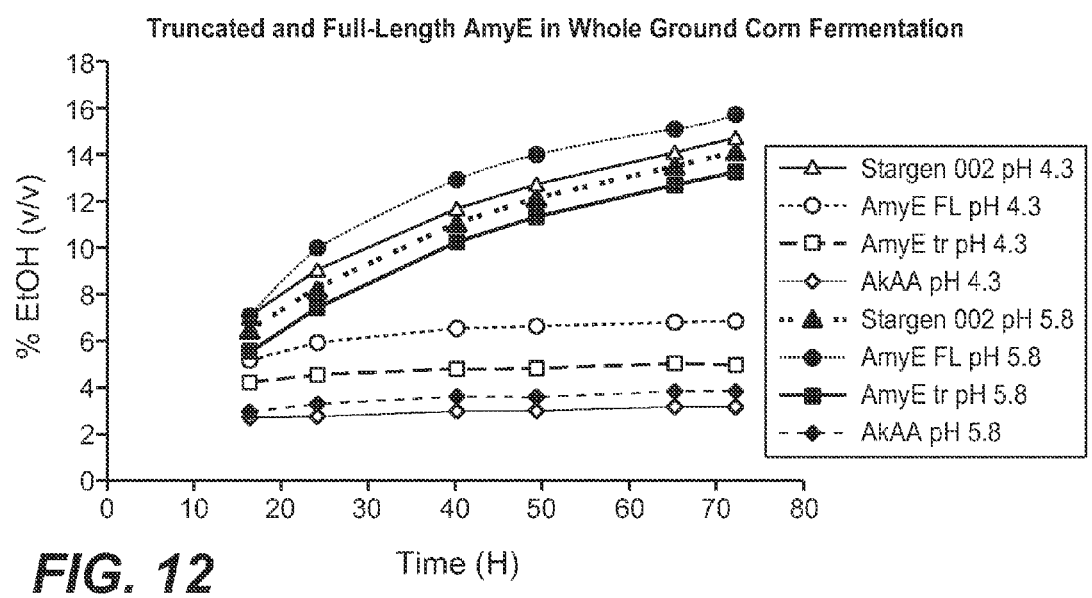

FIG. 12 shows hydrolysis of insoluble granular (uncooked) starch into ethanol by full length (FL) and truncated (tr) AmyE compared to AkAA alone or STARGEN™ 002 at pH 4.3 and pH 5.8.

Figure 13:
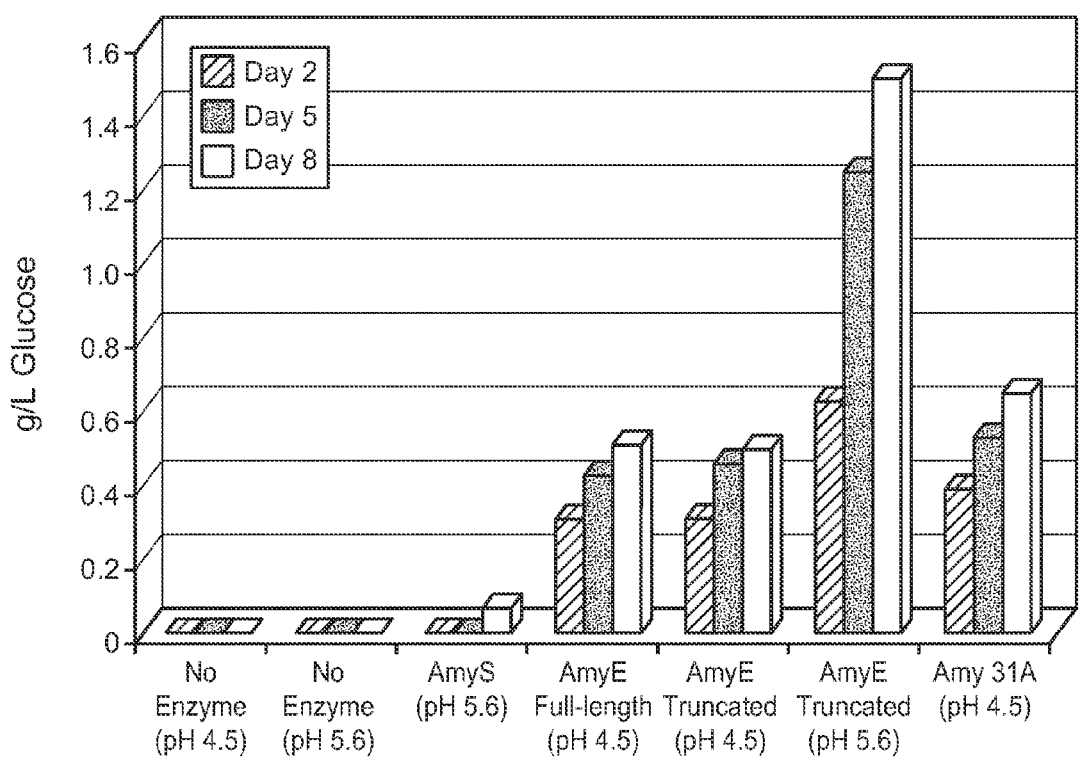

FIG. 13 shows glucose formation by *B. subtilis* AmyE full-length, AmyE truncated, and Amy 31A in comparison to AmyS at pH 4.5 and 5.6.

Figure 14:
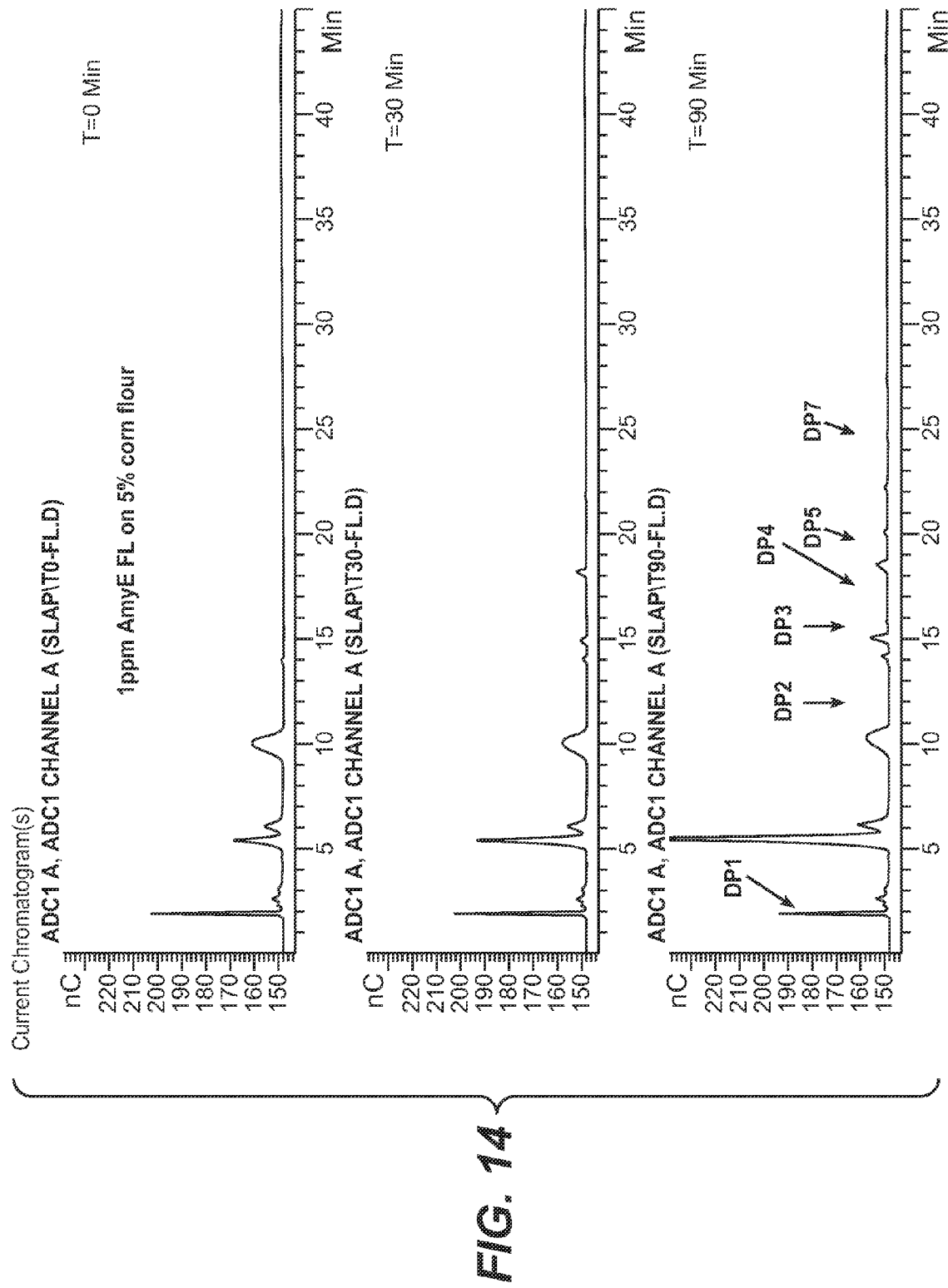

FIG. 14 shows the results of incubation of full length AmyE with raw starch (corn flour) and detection of oligosaccharides produced over time (0, 30, 90 minutes) by HPLC detection.

Figure 15:
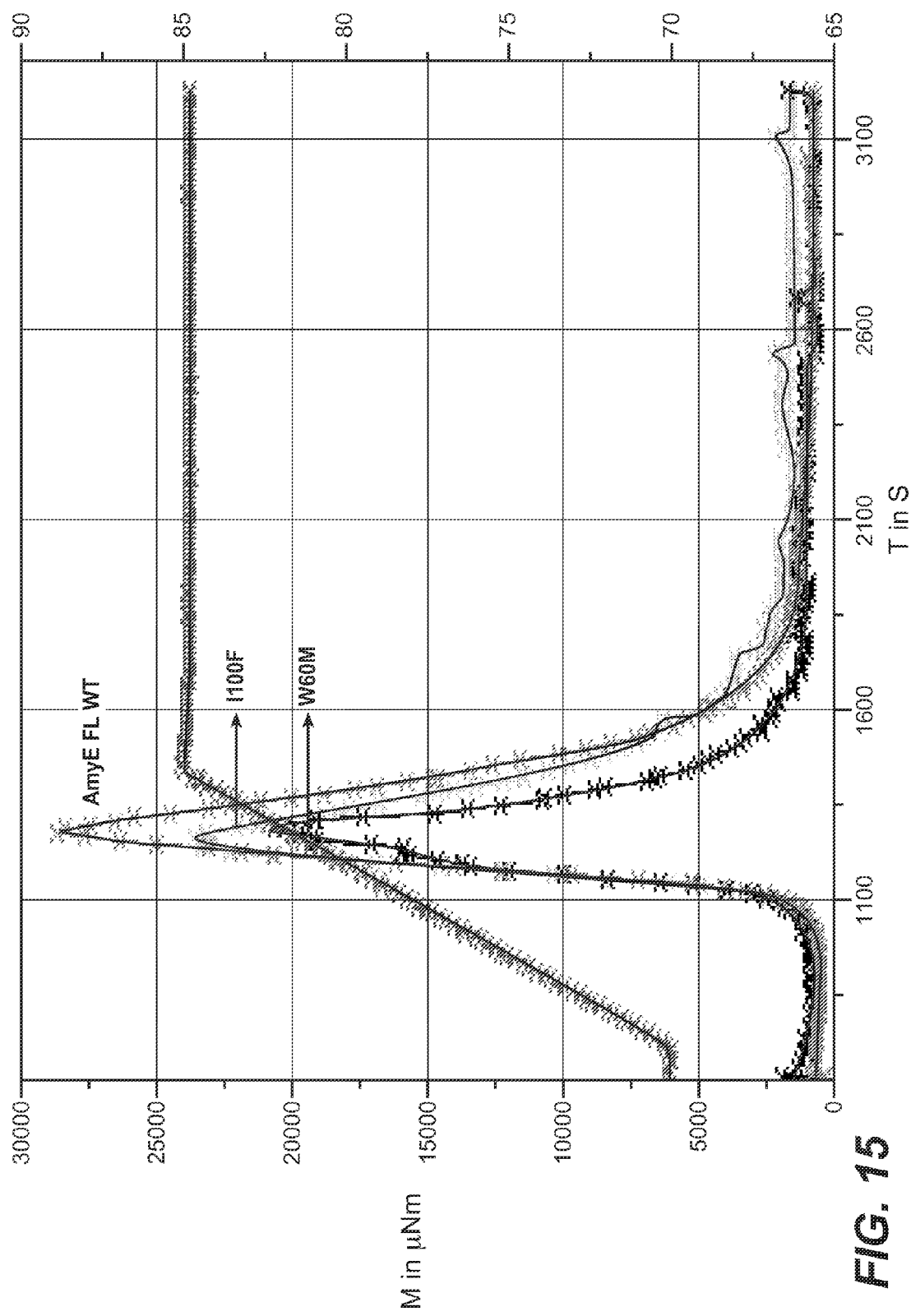

FIG. 15 shows the peak and final viscosity values obtained in a starch hydrolysis assay using AmyE polypeptides.

Figure 16:
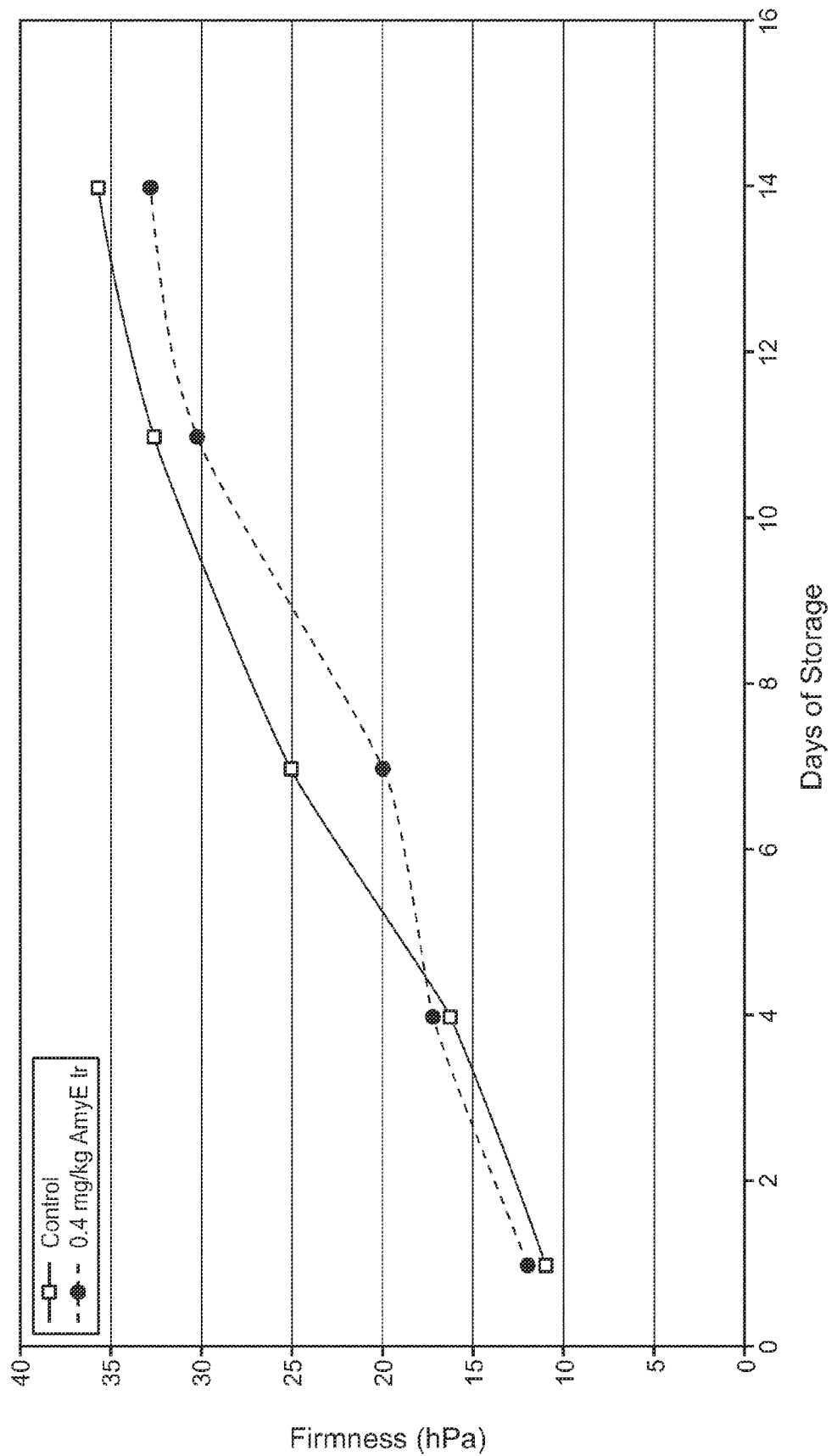

FIG. 16 shows the results of a bread staling assay using an AmyE polypeptide.

BRIEF DESCRIPTION OF THE SEQUENCES

The following sequences are referred to in the application:
SEQ ID NO: 1: Full length *Bacillus subtilis* AmyE amino acid sequence. The native signal sequence is not shown.

```
  1  LTAPSIKSGT ILHAWNWSFN TLKHNMKDIH DAGYTAIQTS PINQVKEGNQ

51  GDKSMSNWYW LYQPTSYQIG NRYLGTEQEF KEMCAAAEEY GIKVIVDAVI

101  NHTTSDYAAI SNEVKSIPNW THGNTQIKNW SDRWDVTQNS LLGLYDWNTQ

151  NTQVQSYLKR FLDRALNDGA DGFRFDAAKH IELPDDGSYG SQFWPNITNT

201  SAEFQYGEIL QDSASRDAAY ANYMDVTASN YGHSIRSALK NRNLGVSNIS

251  HYASDVSADK LVTWVESHDT YANDDEESTW MSDDDIRLGW AVIASRSGST

301  PLFFSRPEGG GNGVRFPGKS QIGDRGSALF EDQAITAVNR FHNVMAGQPE

351  ELSNPNGNNQ IFMNQRGSHG VVLANAGSSS VSINTATKLP DGRYDNKAGA

401  GSFQVNDGKL TGTINARSVA VLYPDDIAKA PHVFLENYKT GVTHSFNDQL

451  TITLRADANT TKAVYQINNG PETAFKDGDQ FTIGKGDPFG KTYTIMLKGT

501  NSDGVTRTEK YSFVKRDPAS AKTIGYQNPN HWSQVNAYIY KHDGSRVIEL

551  TGSWPGKPMT KNADGIYTLT LPADTDTTNA KVIFNNGSAQ VPGQNQPGFD

601  YVLNGLYNDS GLSGSLPH
```

SEQ ID NO: 2: Truncated *Bacillus subtilis* AmyE (AmyE-tr) amino acid sequence. The native signal sequence is not shown.

```
  1  LTAPSIKSGT ILHAWNWSFN TLKHNMKDIH DAGYTAIQTS PINQVKEGNQ
 51  GDKSMSNWYW LYQPTSYQIG NRYLGTEQEF KEMCAAAEEY GIKVIVDAVI
101  NHTTSDYAAI SNEVKSIPNW THGNTQIKNW SDRWDVTQNS LLGLYDWNTQ
151  NTQVQSYLKR FLDRALNDGA DGFRFDAAKH IELPDDGSYG SQFWPNITNT
201  SAEFQYGEIL QDSASRDAAY ANYMDVTASN YGHSIRSALK NRNLGVSNIS
251  HYASDVSADK LVTWVESHDT YANDDEESTW MSDDDIRLGW AVIASRSGST
301  PLFFSRPEGG GNGVRFPGKS QIGDRGSALF EDQAITAVNR FHNVMAGQPE
351  ELSNPNGNNQ IFMNQRGSHG VVLANAGSSS VSINTATKLP DGRYDNKAGA
401  GSFQVNDGKL TGTINARSVA VLYPD
```

SEQ ID NO: 3: *Bacillus subtilis* α-amylase variant Amy31A amino acid sequence (UniProtKB/TrEMBL Accession No. O82953). The native signal sequence is shown in bold.

```
  1  MFEKRFKTSL LPLFAGFLLL FHLVLSGPAA ANAETANKSN KVTASSVKNG
 51  TILHAWNWSF NTLTQNMKDI RDAGYAAIQT SPINQVKEGN QGDKSMSNWY
101  WLYQPTSYQI GNRYLGTEQE FKDMCAAAEK YGVKVIVDAV VNHTTSDYGA
151  ISDEIKRIPN WTHGNTQIKN WSDRWDITQN ALLGLYDWNT QNTEVQAYLK
201  GFLERALNDG ADGFRYDAAK HIELPDDGNY GSQFWPNITN TSAEFQYGEI
251  LQDSASRDTA YANYMNVTAS NYGHSIRSAL KNRILSVSNI SHYASDVSAD
301  KLVTWVESHD TYANDDEEST WMSDDDIRLG WAVIGSRSGS TPLFFSRPEG
351  GGNGVRFPGK SQIGDRGSAL FKDQAITAVN QFHNEMAGQP EELSNPNGNN
401  QIFMNQRGSK GVVLANAGSS SVTINTSTKL PDGRYDNRAG AGSFQVANGK
451  LTGTINARSA AVLYPDDIGN APHVFLENYQ TEAVHSFNDQ LTVTLRANAK
501  TTKAVYQINN GQETAFKDGD RLTIGKEDPI GTTYNVKLTG TNGEGASRTQ
551  EYTFVKKDPS QTNIIGYQNP DHWGNVNAYI YKHDGGGAIE LTGSWPGKAM
601  TKNADGIYTL TLPANADTAD AKVIFNNGSA QVPGQNHPGF DYVQNGLYNN
651  SGLNGYLPH
```

SEQ ID NO: 4: Truncated *Geobacillus stearothermophilus* α-amylase (AmyS) protein sequence (SPEZYME® Xtra amylase). The signal sequence is shown in bold.

```
  1  MLTFHRIIRK GWMFLLAFLL TASLFCPTGQ HAKAAAPFNG TMMQYFEWYL
 51  PDDGTLWTKV ANEANNLSSL GITALWLPPA YKGTSRSDVG YGVYDLYDLG
101  EFNQKGTVRT KYGTKAQYLQ AIQAAHAAGM QVYADVVFDH KGGADGTEWV
151  DAVEVNPSDR NQEISGTYQI QAWTKFDFPG RGNTYSSFKW RWYHFDGVDW
201  DESRKLSRIY KFIGKAWDWE VDTENGNYDY LMYADLDMDH PEVVTELKNW
251  GKWYVNTTNI DGFRLDAVKH IKFSFFPDWL SYVRSQTGKP LFTVGEYWSY
301  DINKLHNYIT KTNGTMSLFD APLHNKFYTA SKSGGAFDMR TLMTNTLMKD
351  QPTLAVTFVD NHDTEPGQAL QSWVDPWFKP LAYAFILTRQ EGYPCVFYGD
401  YYGIPQYNIP SLKSKIDPLL IARRDYAYGT QHDYLDHSDI IGWTREGVTE
```

451 KPGSGLAALI TDGPGGSKWM YVGKQHAGKV FYDLTGNRSD TVTINSDGWG

501 EFKVNGGSVS VWVPRKTT

SEQ ID NO: 5: Nucleotide sequence encoding the AmyE of SEQ ID NO: 1.

CTTACAGCACCGTCGATCAAAAGCGGAACCATTCTTCATGCATGGAATTG
GTCGTTCAATACGTTAAAACACAATATGAAGGATATTCATGATGCAGGAT
ATACAGCCATTCAGACATCTCCGATTAACCAAGTAAAGGAAGGGAATCAA
GGAGATAAAAGCATGTCGAACTGGTACTGGCTGTATCAGCCGACATCGTA
TCAAATTGGCAACCGTTACTTAGGTACTGAACAAGAATTTAAAGAAATGT
GTGCAGCCGCTGAAGAATATGGCATAAAGGTCATTGTTGACGCGGTCATC
AATCATACCACCAGTGATTATGCCGCGATTTCCAATGAGGTTAAGAGTAT
TCCAAACTGGACACATGGAAACACACAAATTAAAAACTGGTCTGATCGAT
GGGATGTCACGCAGAATTCATTGCTCGGGCTGTATGACTGGAATACACAA
AATACACAAGTACAGTCCTATCTGAAACGGTTCTTAGACAGGGCATTGAA
TGACGGGGCAGACGGTTTTCGATTTGATGCCGCCAAACATATAGAGCTTC
CAGATGATGGCAGTTACGGGAGTCAATTTTGGCCGAATATCACAAATACA
TCAGCAGAGTTCCAATACGGAGAAATCCTTCAGGATAGTGCCTCCAGAGA
TGCTGCATATGCGAATTATATGGATGTGACAGCGTCTAACTATGGGCATT
CCATAAGGTCCGCTTTAAAGAATCGTAATCTGGGCGTGTCGAATATCTCC
GACTATGCATCTGATGTGTCTGCGGACAAGCTAGTGACATGGGTAGAGTC
GCATGATACGTATGCCAATGATGATGAAGAGTCGACATGGATGAGCGATG
ATGATATCGGTTTAGGCTGGGCGGTGATAGCTTCTCGTTCAGGCAGTACG
CCTCTTTTCTTTTCCAGACCTGAGCGAGGCGGAAATGCTGTGAGGTTCCC
GGGGAAAAGCCAAATAGGCGATCGCGGGAGTGCTTTATTTGAAGATCAGG
CTATCACTGCGGTCAATAGATTTCACAATGTGATGGCTGGACAGCCTGAG
GAACTCTCGAACCGGAATGGAAACAACCAGATATTTATGAATCAGCGCGG
CTCACATGGCGTTGTGCTGGCAAATGCAGGTTCATCCTCTGTCTCTATCA
ATACGGCAACAAAATTGCCTGATGGCAGGTATGACAATAAAGCTGGAGCG
GGTTCATTTCAAGTGAACGATGGTAAACTGACAGGCACGATCAATGCCAG
GTCTGTAGCTGTGCTTTATCCTGATGATATTGCAAAAGCGCCTCATGTTT
TCCTTGAGAATTACAAAACAGGTGTAACACATTCTTTCAATGATCAACTG
ACGATTACCTTGCGTGCAGATGCGAATACAACAAAAGCCGTTTATCAAAT
CAATAATGGACCAGAGACGGCGTTTAAGGATGGAGATCAATTCACAATCG
GAAAAGGAGATCCATTTGGCAAAACATACACCATCATGTTAAAAGGAACG
AACAGTGATGGTGTAACGAGGACCGAGAAATACAGTTTTGTTAAAAGAGA
TCCAGGGTCGGCCAAAACCATCGGCTATCAAAATCCGAATCATTGGAGCC
AGGTAAATGCTTATATCTATAAACATGATGGGAGCCGAGTAATTGAATTG
ACCGGATCTTGGCCTGGAAAACCAATGACTAAAAATGCAGACGGAATTTA
CACGCTGACGCTGCCTGCGGACACGGATACAACCAACGCAAAAGTGATTT

TTAATAATGGCAGCGCCCAAGTGCCCGGTCAGAATCAGCCTGGCTTTGAT
TACGTGCTAAATGGTTTATATAATGACTCGGGCTTAAGCGGTTCTCTTCC
GCAT

SEQ ID NO: 6: Nucleotide sequence encoding AmyE-tr (SEQ ID NO: 2).

CTTACAGCACCGTCGATCAAAAGCGGAACCATTCTTCATGCATGGAATTG
GTCGTTCAATACGTTAAAACACAATATGAAGGATATTCATGATGCAGGAT
ATACAGCCATTCAGACATCTCCGATTAACCAAGTAAAGGAAGGGAATCAA
GGAGATAAAAGCATGTCGAACTGGTACTGGCTGTATCAGCCGACATCGTA
TCAAATTGGCAACCGTTACTTAGGTACTGAACAAGAATTTAAAGAAATGT
GTGCAGCCGCTGAAGAATATGGCATAAAGGTCATTGTTGACGCGGTCATC
AATCATACCACCAGTGATTATGCCGCGATTTCCAATGAGGTTAAGAGTAT
TCCAAACTGGACACATGGAAACACACAAATTAAAAACTGGTCTGATCGAT
GGGATGTCACGCAGAATTCATTGCTCGGGCTGTATGACTGGAATACACAA
AATACACAAGTACAGTCCTATCTGAAACGGTTCTTAGACAGGGCATTGAA
TGACGGGGCAGACGGTTTTCGATTTGATGCCGCCAAACATATAGAGCTTC
CAGATGATGGCAGTTACGGCAGTCAATTTTGGCCGAATATCACAAATACA
TCAGCAGAGTTCCAATACGGAGAAATCCTTCAGGATAGTGCCTCCAGAGA
TGCTGCATATGCGAATTATATGGATGTGACAGCGTCTAACTATGGGCATT
CCATAAGGTCCGCTTTAAAGAATCGTAATCTGGGCGTGTCGAATATCTCC
CACTATGCATCTGATGTGTCTGCGGACAAGCTAGTGACATGGGTAGAGTC
GCATGATACGTATGCCAATGATGATGAAGAGTCGACATGGATGAGCGATG
ATGATATCGGTTTAGGCTGGGCGGTGATAGCTTCTCGTTCAGGCAGTACG
CCTCTTTTCTTTTCCAGACCTGAGGGAGGCGGAAATGGTGTGAGGTTCCC
GGGGAAAAGCCAAATAGGCGATCGCGGGAGTGCTTTATTTGAAGATCAGG
CTATCACTGCGGTCAATAGATTTCACAATGTGATGGCTGGACAGCCTGAG
GAACTCTCGAACCGGAATGGAAACAACCAGATATTTATGAATCAGCGCGG
CTCACATGGCGTTGTGCTGGCAAATGCAGGTTCATCCTCTGTCTCTATCA
ATACGGCAACAAAATTGCCTGATGGCAGGTATGACAATAAAGCTGGAGCG
GGTTCATTTCAAGTGAACGATGGTAAACTGACAGGCACGATCAATGCCAG
GTCTGTAGCTGTGCTTTATCCTGAT

SEQ ID NO: 7: Nucleotide sequence encoding B. subtilis Amy31A (SEQ ID NO: 3).

TCTGTTAAAAACGGCACTATTCTGCATGCATGGAACTGCAGCTTTAACAC
GCTGACCCAGAACATGAAAGATATTCGTGACGCGGGCTATGCTGCGATCC
AAACCAGCCCTATCAACCAGGTCAAAGAAGGCAACCAAGGCGACAAATCC

```
ATGTCCAACTGGTACTGGCTGTATCAACCGACGTCCTATCAGATTGGCAA

CCGTTATCTGGGCACGGAGCAAGAGTTCAAAGACATGTGTGCTGCGGCTG

AGAAATATGGTGTGAAAGTTATCGTGGACGCTGTGGTAAACCACACGACC

TCTGATTATGGTGCTATTAGCGACGAGATTAAACGTATTCCAAATTGGAC

CCATGGTAATACCCAGATCAAAAATTGGAGCGACCGCTGGGACATTACCC

AGAATGCGCTGCTGGGTCTGTATGACTGGAACACGCAAAACACCGAAGTA

CAGGCATATCTGAAGGGCTTCCTGGAACGCGCTCTGAACGATGGTGCTGA

TGGTTTTCGCTACGACGCCGCAAAGCATATTGAGCTGCCGGATGACGGCA

ACTACGGTTCCCAATTCTGGCCGAACATCACCAACACCTCTGCCGAATTC

CAGTACGGCGAGATCCTGCAAGACTCCGCGAGCCGTGACACCGCTTATGC

CAACTATATGAACGTAACTGCCTCTAACTATGGCCATTCCATTCGTTCTG

CGCTGAAAAATCGTATCCTGTCCGTGTCCAATATCTCCCACTATGCATCC

GACGTTTCTGCTGACAAACTGGTAACTTGGGTCGAGTCTCACGACACCTA

TGCAAATGATGACGAGGAGAGCACCTGGATGAGCGATGATGATATTCGTC

TGGGTTGGGCGGTTATTGGTTCTCGCTCTGGTTCTACTCCGCTGTTCTTT

AGCCGTCCGGAAGGTGGCGGCAATGGCGTTCGTTTGCCGGGTAAATCTCA

AATTGGTGATCGTGGCTCTGCACTGTTTAAAGATCAAGCTATTACGGCGG

TGAATCAGTTCCATAATGAGATGGCAGGTCAACCTGAAGAACTGTCCAAT

CCAAACGGTAACAACCAATCTTCATGAACCAGCGTGGCAGCAAAGGCGT

CGTCCTGGCGAACGCCGGTAGCTCTTCTGTTACCATCAACACGTCTACCA

AACTGCCAGACGGCCGCTATGATAACCGTGCGGGTGCTGGTTCCTTTCAG

GTAGCCAACGGCAAGCTGACGGGCACCATCAACGCTCGTTCTGCTGCTGT

TCTGTACCCGGACGACATTGGCAACGCTCCGCACGTGTTCCTGGAGAATT

ACCAGACCGAAGCGGTACATAGCTTTAATGACCAGCTGACCGTCACTCTG

CGTGCCAACGCAAAAACCACGAAAGCAGTCTATCAGATCAATAATGGTCA

AGAAACTGCTTTCAAGGATGGCGACCGTCTGACTATTGGTAAGGAGGACC

CGATTGGCACCACTTATAACGTTAAACTGACTGGCACCAATGGCGAGGGC

GCTAGCCGCACTCAAGAGTATACGTTCGTAAAGAAAGACCCGTCTCAAAC

CAACATCATCGGTTACCAGAATCCTGACCACTGGGGTAATGTGAACGCTT

ACATCTATAAACATGATGGTGGCGGTGCTATCGAACTGACCGGCTCTTGG

CCAGGTAAAGCCATGACGAAAAACGCGGATGGCATCTATACCCTGACGCT

GGCGGCCAATGCGGATACCGCAGATGCGAAGGTTATCTTCAATAACGGCT

CCGCGCAGGTTCCGGGGCAAAACCATCCGGGCTTTGACTACGTACAAAAT

GGTCTGTATAACAACTCTGGCCTGAACGGTTACCTGCCGCAC
```

SEQ ID NO: 8: Nucleotide sequence encoding *Geobacillus stearothermophilus* AmyS (SEQ ID NO: 4).

```
GCCGCACCGTTTAACGGTACCATGATGCAGTATTTTGAATGGTACTTGCC

GGATGATGGCACGTTATGGACCAAAGTGGCCAATGAAGCCAACAACTTAT

CCAGCCTTGGCATCACCGCTCTTTGGCTGCCGCCCGCTTACAAAGGAACA

AGCCGCAGCGACGTAGGGTACGGAGTATACGACTTGTATGACCTCGGCGA

ATTCAATCAAAAAGGGACCGTCCGCACAAAATATGGAACAAAAGCTCAAT

ATCTTCAAGCCATTCAAGCCGCCCACGCCGCTGGAATGCAAGTGTACGCC

GATGTCGTGTTCGACCATAAAGGCGGCGCTGACGGCACGGAATGGGTGGA

CGCCGTCGAAGTCAATCCGTCCGACCGCAACCAAGAAATCTCGGGCACCT

ATCAAATCCAAGCATGGACGAAATTTGATTTTCCCGGGCGGGGCAACACC

TACTCCAGCTTTAAGTGGCGCTGGTACGATTTTGACGGCGTTGACTGGGA

CGAAAGCCGAAAATTAAGCCGCATTTACAAATTCATCGGCAAAGCGTGGG

ATTGGGAAGTAGACACAGAAAACGGAAACTATGACTACTTAATGTATGCC

GACCTTGATATGGATCATCCCGAAGTCGTGACCGAGCTGAAAAACTGGGG

GAAATGGTATGTCAACACAACGAACATTGATGGGTTCCGGCTTGATGCCG

TCAAGCATATTAAGTTCAGTTTTTTTCCTGATTGGTTGTCGTATGTGCGT

TCTCAGACTGGCAAGCCGCTATTTACCGTCGGGGAATATTGGAGCTATGA

CATCAACAAGTTGCACAATTACATTACGAAAACAAACGGAACGATGTCTT

TGTTTGATGCCCCGTTACACAACAAATTTTATAGCGCTTCCAAATCAGGG

GGCGCATTTGATATGCGCACGTTAATGACCAATACTCTCATGAAAGATGA

ACCGACATTGGCCGTCACCTTCGTTGATAATCATGACACCGAACCCGGCC

AAGCGCTGCAGTCATGGGTCGACCCATGGTTCAAACCGTTGGCTTACGCC

TTTATTCTAACTCGGCAGGAAGGATACCCGTGCGTCTTTTATGGTGACTA

TTATGGCATTCCACAATATAACATTCCTTCGCTGAAAAGCAAAATCGATC

CGCTCCTCATCGCGCAGGGATTATGCTTACGGAACGCAACATGATTAT

CTTGATCACTCCGACATCATCGGGTGGACAAGGGAAGGGGTCACTGAAAA

ACCAGGATCCGGGCTGGCCGCACTGATCACCGATGGGCCGGGAGGAAGCA

AATGGATGTACGTTGGCAAACAACACGCTGGAAAAGTGTTGTATGACCTT

ACCGGCAACCGGAGTGACACCGTCACCATCAACAGTGATGGATGGGGGGA

ATTCAAAGTCAATGGCGGTTCGGTTTCGGTTTGGGTTCCTAGAAAAACGA

CC
```

SEQ ID NO: 9: Native signal sequence of the AmyE of SEQ ID NO: 1.

MFAKRFKTSLLPLFAGFLLLFHLVLAGPAAASAETANKSNE

SEQ ID NO: 10: Primer PSTAMYE-F 5′

```
CTTCTTGCTGCCTCATTCTGCAGCTTCAGCACTTACAGCACCGTCGATCA

AAAGCGGAAC
```

SEQ ID NO: 11: Primer AMYENOPST-R 5′

```
CTGGAGGCACTATCCTGAAGGATTTCTCCGTATTGGAACTCTGCTGATGT

ATTTGTG
```

SEQ ID NO: 12: Primer AMYENOPST-F 5′

```
CACAAATACATCAGCAGAGTTCCAATACGGAGAAATCCTTCAGGATAGTG

CCTCCAG
```

SEQ ID NO: 13: Primer HPAIAMYE-R 5'

CAGGAAATCCGTCCTCTGTTAACTCAATGGGAAGAGAACCGCTTAAGCC
CGAGTC

SEQ ID NO: 14: Primer HPAIAMYE466-R 5'

CAGGAAATCCGTCCTCTGTTAACTCAATCAGGATAAAGCACAGCTACAGA
CCTGG

SEQ ID NO: 15: Primer AMYE SEQ-FL 5'

TACACAAGTACAGTCCTATCTG

SEQ ID NO: 16: Primer AMYE SEQ-F2 5'

CATCCTCTGTCTCTATCAATAC

SEQ ID NO: 17: BP-17 variant of *Buttiauxiella* phytase

```
NDTPASGYQV EKVVILSRHG VRAPTKMTQT MRDVTPNTWP
EWPVKLGYIT PRGEHLISLM GGFYRQKFQQ QGILSQGSCP
TPNSIYVWAD VDQRTLKTGE AFLAGLAPQC GLTIHHQQNL
EKADPLFHPV KAGTCSMDKT QVQQAVEKEA QTPIDNLNQH
YIPFLALMNT TLNFSTSAWC QKHSADKSCD LGLSMPSKLS
IKDNGNKVAL DGAIGLSSTL AEIFLLEYAQ GMPQAAWGNI
HSEQEWASLL KLHNVQFDLM ARTPYIARHN GTPLLQAISN
ALNPNATESK LPDISPDNKI LFIAGHDTNI ANIAGMLNMR
WTLPGQPDNT PPGGALVFER LADKSGKQYV SVSMVYQTLE
QLRSQTPLSL NQPAGSVQLK IPGCNDQTAE GYCPLSTFTR
VVSQSVEPGC QLQ
```

DETAILED DESCRIPTION

The present compositions and methods relate to an α-amylase from *Bacillus subtilis* (AmyE) and variants thereof (collectively referred to as AmyE polypeptides), which offer certain advantages compared to other α-amylases. For example, AmyE polypeptides exhibit high specific activity for starch substrates at an acidic pH, allowing AmyE polypeptides to be used for starch liquefaction under conditions that are also suitable for saccharification. This eliminates the need to adjust the pH of a starch slurry between liquefaction and saccharification. AmyE polypeptides also possesses glucoamylase activity, eliminating or reducing the need for the use of a separate glucoamylase to perform saccharifaction. In addition, AmyE polypeptides require little or no calcium for thermal stability, eliminating the need to subsequently remove added calcium prior to performing isomerization, thereby eliminating at least one step required for the production of high fructose corn syrup.

These and other features of the compositions and methods are described in more detail, below.

1. Definitions and Abbreviations

Unless defined otherwise, all technical and scientific terms and abbreviations should be accorded their ordinary meanings as understood by one of ordinary skill in the art. The following terms and abbreviations are defined for clarity.

1.1. Definitions

As used herein the term "starch" refers to any material comprised of the complex polysaccharide carbohydrates of plants, comprised of amylose and amylopectin with the formula $(C_6H_{10}O_5)_x$, wherein X can be any number. In particular, the term refers to any plant-based material including but not limited to grains, grasses, tubers and roots and more specifically wheat, barley, corn, rye, rice, sorghum, brans, cassava, millet, potato, sweet potato, and tapioca.

As used herein the term "oligosaccharide" refers to a carbohydrate molecule composed of 3-20 monosaccharides.

As used herein, an "amylase" refers to an enzyme capable of catalyzing the degradation of starch. Generally, α-amylases (EC 3.2.1.1; α-D-(1→4)-glucan glucanohydrolase) are endo-acting enzymes that cleave α-D-(1→4)O-glycosidic linkages within the starch molecule in a random fashion. In contrast, the exo-acting amylolytic enzymes, such as β-amylases (EC 3.2.1.2; α-D-(1→4)-glucan maltohydrolase), and some product-specific amylases like maltogenic α-amylase (EC 3.2.1.133), cleave the starch molecule from the non-reducing end of the substrate. β-amylases, α-glucosidases (EC 3.2.1.20; α-D-glucoside glucohydrolase), glucoamylases (EC 3.2.1.3; α-D-(1→4)-glucan glucohydrolase), and product-specific amylases can produce malto-oligosaccharides of a specific length from starch. As used herein, amylases include any/all amylases, including glucoamylases, α-amylases, β-amylases and wild-type α-amylases, such as those of *Bacillus* sp., e.g., *B. licheniformis* and *B. subtilis*, while α-amylases include the aforementioned subset of these enzymes.

As used herein, "α-amylase variants," and similar phrases, refer to variants/mutants of a reference α-amylase, which includes an amino acid substitution, insertion, and/or deletion with respect to the parent (wild-type; reference) amino acid sequence of the reference α-amylase. The term "variant" is used interchangeably with the term "mutant." The variant α-amylase may include mutations in the signal sequence with respect to parent signal sequence. In addition, the variant α-amylase can be in the form of a fusion protein containing a heterologous α-amylase signal sequence, such as from *B. licheniformis* (LAT).

A "parent nucleic acid/polynucleotide," "wild-type nucleic acid/polynucleotide," or "reference nucleic acid/polynucleotide," refers to a nucleic acid sequence encoding a parent polypeptide, and a nucleic acid complementary thereto.

A "variant nucleic acid/polynucleotide" refers to a nucleic acid sequence encoding a variant polypeptide or a nucleic acid complementary thereto, or a polynucleotide sequence having at least one base substitution, insertion, or deletion with respect to a parent polynucleotide sequence or a nucleic acid complementary thereto. Where specified such nucleic acids may include those having a specified degree of homology to a reference sequence, or that are capable of hybridizing to a reference sequence, for example, under stringent conditions [e.g., 50° C. and 0.2×SSC (1×SSC=0.15 M NaCl, 0.015 M Na$_3$ citrate, pH 7.0)] or highly stringent conditions [e.g., 65° C. and 0.1×SSC (1×SSC=0.15 M NaCl, 0.015 M Na$_3$ citrate, pH 7.0)]. A variant nucleic acid may be optimized to reflect preferred codon usage for a specified host organisms, such as the methylotrophic yeasts (e.g., *Pichia, Hansenula*, etc) or filamentous fungi (e.g., *Trichoderma* (e.g., *T. reesei*), etc) or other expression hosts (e.g., *Bacillus, Streptomyces*, etc.).

A "signal sequence" is a sequence of amino acids attached to the N-terminal portion of a protein, which facilitates the secretion of the protein outside the cell. The "signal sequence," may also be referred to as a "leader sequence" or a "pro-sequence."

As used herein, the "immature" or "full-length (FL)" form of an amylase includes the signal peptide. The immature form may include other post-translational modifications.

As used herein, the "mature" form of an extracellular protein (such as an amylase) lacks the signal sequence. The signal sequence may be cleaved off during the secretion process. Alternatively, a polypeptide may be expressed in its mature form, e.g., as an intracellular protein, or synthesized in its mature form.

As used herein, a "truncated" form of AmyE (i.e., "AmyE-tr") refers to an AmyE polypeptide with a deletion of all or part of the C-terminal starch binding domain. In the AmyE-tr of SEQ ID NO: 2, for example, the AmyE of SEQ ID NO: 1 is truncated at residue D425. A 2.5 Å resolution crystal structure of this AmyE-tr is available at Protein Databank Accession No. 1BAG, which is disclosed in Fujimoto et al., "Crystal structure of a catalytic-site mutant alpha-amylase from *B. subtilis* complexed with maltopentaose," *J. Mol. Biol.* 277: 393-407 (1998). AmyE-tr may be truncated at other positions, e.g., Y423, P424, D426 or I427 of the AmyE of SEQ ID NO: 1, provided all or part of the C-terminal starch binding domain is removed.

The term "recombinant," when used in reference to a subject cell, nucleic acid, protein or vector, indicates that the subject has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The terms "recovered," "isolated," and "separated," refer to a compound, protein, cell, nucleic acid or amino acid that is removed from at least one component with which it is naturally associated and found in nature.

As used herein, the term "purified" refers to material (e.g., an isolated polypeptide or polynucleotide) that is in a relatively pure state, e.g., at least about 90% pure, at least about 95% pure, at least about 98% pure, or even at least about 99% pure.

The terms "thermostable" and "thermostability" refer to the ability of an enzyme to retain activity after exposure to an elevated temperature. The thermostability of an enzyme, such as an α-amylase enzymes, is measured by its half-life ($t_{1/2}$) given in minutes, hours, or days, during which half the enzyme activity is lost under defined conditions. The half-life may be calculated by measuring residual α-amylase activity following exposure to (i.e., challenge by) an elevated temperature.

A "pH range" refers to the range of pH values under which an enzyme exhibits catalytic activity.

As used herein, the terms "pH stable" and "pH stability" relate to the ability of an enzyme to retain activity over a wide range of pH values for a predetermined period of time (e.g., 15 min., 30 min., 1 hour, and the like).

As used herein, the term "amino acid sequence" is synonymous with the terms "polypeptide," "protein," and "peptide," and are used interchangeably. Where such amino acid sequence exhibit activity, they may be referred to as an "enzyme." The conventional one-letter or three-letter code for amino acid residues are used herein.

The term "nucleic acid" encompasses DNA, RNA, heteroduplexes, and synthetic molecules capable of encoding a polypeptide. Nucleic acids may be single stranded or double stranded, and may be chemical modifications. The terms "nucleic acid" and "polynucleotide" are used interchangeably. Because the genetic code is degenerate, more than one codon may be used to encode a particular amino acid, and the present compositions and methods encompass nucleotide sequences which encode a particular amino acid sequence. Unless otherwise indicated, nucleic acids are written left to right in 5' to 3' orientation; amino acid sequences are written left to right in amino to carboxy orientation, respectively.

The term "homologue" refers to an amino acid or nucleotide sequence having a certain degree of identity to a reference amino acid or nucleotide sequences, or another specified common structural or functional feature. A homologous sequence is taken to include an amino acid sequence that is at least 75%, 80%, 81%, 82%, 83%, 84%, 85%, 86%, 87%, 88%, 89%, 90%, 91%, 92%, 93%, 94%, 95%, 96%, 97%, 98%, or even 99% identical to the subject sequence, using conventional sequence alignment tools (e.g., Clustal, BLAST, and the like). Typically, homologues will include the same active site residues as the subject amino acid sequence, unless otherwise specified.

As used herein, "hybridization" refers to the process by which one strand of nucleic acid base pairs with a complementary strand, as occurs during blot hybridization techniques and PCR techniques.

As used herein, a "degenerate sequence" in a nucleic acid contains is one in which a plurality of nucleotide sequences encode the same codon, i.e., due to the degeneracy of the genetic code. Degenerate sequences may be selected for optimal expression of an encoded polypeptide in a particular host organism, e.g., as a consequence of codon preferences.

As used herein, a "synthetic" molecule is produced by in vitro chemical or enzymatic synthesis rather than by an organism.

As used herein, the terms "transformed," "stably transformed," and "transgenic," used with reference to a cell means that the cell has a non-native (e.g., heterologous) nucleic acid sequence integrated into its genome or carried as an episomal plasmid that is maintained through multiple generations.

The term "introduced" in the context of inserting a nucleic acid sequence into a cell, means "transfection", "transformation" or "transduction," as known in the art.

A "host strain" or "host cell" is an organism into which an expression vector, phage, virus, or other DNA construct including a polynucleotide encoding a polypeptide of interest (e.g., a variant α-amylase) has been introduced. Exemplary host strains are bacterial cells. The term "host cell" includes protoplasts created from cells, such as those of a *Bacillus* sp.

The term "heterologous" with reference to a polynucleotide or protein refers to a polynucleotide or protein that does not naturally occur in a host cell.

The term "endogenous" with reference to a polynucleotide or protein refers to a polynucleotide or protein that occurs naturally in the host cell.

As used herein, the term "expression" refers to the process by which a polypeptide is produced based on the nucleic acid sequence of a gene. The process includes both transcription and translation.

A "selective marker" or "selectable marker" refers to a gene capable of being expressed in a host to facilitate selection of host cells carrying the gene. Examples of selectable markers include but are not limited to antimicrobials (e.g., hygromycin, bleomycin, or neomycin) and/or genes that confer a metabolic advantage, such as a nutritional advantage on the host cell.

"Culturing" refers to growing a population of microbial cells under suitable conditions in a liquid or solid medium. Culturing includes fermentative bioconversion of a starch substrate containing granular starch to an end-product (typically in a vessel or reactor).

"Fermentation" is the enzymatic breakdown of organic substances by microorganisms to produce simpler organic compounds. While fermentation generally occurs under anaerobic conditions it is not intended that the term be solely limited to strict anaerobic conditions, as fermentation also occurs in the presence of oxygen.

A "gene" refers to a DNA segment that is involved in producing a polypeptide, and includes coding regions, regions preceding and following the coding regions, and, intervening sequences (introns) between individual coding segments (exons).

A "vector" refers to a polynucleotide sequence designed to introduce nucleic acids into one or more cell types. Vectors include cloning vectors, expression vectors, shuttle vectors, plasmids, phage particles, cassettes and the like.

An "expression vector" refers to a DNA construct comprising a DNA sequence encoding a polypeptide of interest, which is operably linked to a suitable control sequence capable of effecting expression of the DNA in a suitable host. Such control sequences may include a promoter to effect transcription, an optional operator sequence to control transcription, a sequence encoding suitable ribosome binding sites on the mRNA, enhancers and sequences which control termination of transcription and translation.

A "promoter" is a regulatory sequence that is involved in binding RNA polymerase to initiate transcription of a gene. The promoter may be an inducible promoter or a constitutive promoter. An exemplary promoter is the *Bacillus licheniformis* α-amylase (AmyL) promoter.

The term "operably linked" means that specified components are in a relationship (including but not limited to juxtaposition) permitting them to function in an intended manner. For example, a regulatory sequence is operably linked to a coding sequence such that expression of the coding sequence is under control of the regulatory sequences.

The term, "under transcriptional control" means that transcription of a polynucleotide sequence, usually a DNA sequence, depends on its being operably linked to an element which contributes to the initiation of, or promotes transcription.

The term "under translational control" means that translation of a polynucleotide sequence, usually an RNA sequence, into a polypeptide depends on its being operably linked to an element which contributes to the initiation of, or promotes translation.

As used herein, "biologically active" refer to a sequence having a specified biological activity, such an enzymatic activity. In the case of the present amylases, the activity is α-amylase activity.

"Water hardness" is a measure of the minerals (e.g., calcium and magnesium) present in water.

"Gelatinization" refers to solubilization of a starch molecule by cooking to form a viscous suspension.

As used herein, the term "liquefaction" or "liquefy" means a process by which starch is converted to lower molecular weight (i.e., shorter) dextrins, which are generally more soluble and less viscous than the starting starch material. This process involves gelatinization of starch simultaneously with, or followed by, the addition of AmyE or a variant thereof.

As used herein, the term "primary liquefaction" refers to a step of liquefaction when the slurry's temperature is raised to or near its gelatinization temperature. Subsequent to the raising of the temperature, the slurry is sent through a heat exchanger or jet to temperatures from about 90-150° C., e.g., 100-110° C. (200-300° F., e.g., 220-235° F.). Subsequent to application to a heat exchange or jet temperature, the slurry is held for a period of 3-10 minutes at that temperature. This step of holding the slurry at 90-150° C. (200-300° F.) is termed primary liquefaction.

As used herein, the term "secondary liquefaction" refers the liquefaction step subsequent to primary liquefaction (heating to 90-150° C. (200-300° F.)), when the slurry is allowed to cool to room temperature. This cooling step can be 30 minutes to 180 minutes, e.g. 90 minutes to 120 minutes.

As used herein, the term "minutes of secondary liquefaction" refers to the time that has elapsed from the start of secondary liquefaction, to the time that the DE is measured.

"Saccharification" refers generally to the enzymatic conversion of maltodextrans formed after liquefaction to glucose.

The term "degree of polymerization (DP)" refers to the number (n) of anhydroglucopyranose units in a given saccharide. Examples of DP1 are the monosaccharides, such as glucose and fructose. Examples of DP2 are the disaccharides, such as maltose and sucrose. A DP>3 denotes polymers with a degree of polymerization of greater than 3.

With respect to starch conversion, the terms "end-product" or "desired end-product" refer to specified carbon-source-derived molecules, which are enzymatically converted from a starch substrate.

As used herein, the term "dry solids content (ds)" refers to the total solids in a slurry, expressed in % dry weight.

The term "slurry" refers to an aqueous mixture containing insoluble solids.

The term "residual starch" refers to the remaining starch (soluble or insoluble) in a composition after fermentation or enzymatic hydrolysis of a starch containing substrate.

As used herein "a recycling step" refers to the recycling of mash components, which may include residual starch, enzymes and/or microorganisms to ferment substrates comprising starch.

The term "mash" refers to an aqueous mixture including a fermentable carbon source (e.g., carbohydrate), which may be used to produce a fermented product, such as an alcohol. The terms "beer" and "mash" may be used interchangeability.

The term "stillage" refers to a mixture of non-fermented solids and water, which represents the residue following removal of alcohol from a fermented mash.

The terms "distillers dried grain (DDG)" and "distillers dried grain with solubles (DDGS)" refer to a useful by-product of grain fermentation.

As used herein "ethanologenic microorganism" refers to a microorganism with the ability to convert a sugar or oligosaccharide to ethanol. The ethanologenic microorganisms are ethanologenic by virtue of their ability to express one or more enzymes that individually or together convert sugar to ethanol.

As used herein the term "ethanol producer" or ethanol producing microorganism" refers to any organism or cell that is capable of producing ethanol from a hexose or pentose. Generally, ethanol-producing cells contain an alcohol dehydrogenase and a pyruvate decarboxylase. Examples of ethanol producing microorganisms include fungal microorganisms such as yeast. A preferred yeast includes strains of *Saccharomyces*, particularly, *S. cerevisiae*.

With respect to amylase enzymes and their substrates, the term "contacting" refers to the placing of the enzyme in sufficiently close proximity to the substrate to enable the enzyme to convert the substrate to an end-product. Contacting may include mixing.

The term "derived from" means "originated from," "based on," "obtained from," "obtainable from," or "isolated from," depending on context.

The term "enzymatic conversion" generally refers to the modification of a substrate (e.g., starch) by enzyme action (e.g., amylase).

As used herein, the term "disintegration" refers to the hydrolysis of polysaccharides in a biofilm matrix connecting and binding together individual microbial cells in the biofilm, whereby the microbial cells can be released and removed from the biofilm.

A "swatch" is a piece of material, such as a fabric, to which a stain may be applied for evaluating the cleaning efficiency of a composition.

As used herein the term "specific activity" refers to the number of moles of substrate converted to product by an enzyme preparation per unit time under specific conditions. Specific activity is expressed as units (U)/mg of protein.

As used herein, the term "biologically active" refers to a molecule that exhibits a preselected biological function.

The term "yield" refers to the amount of end-product produced by a process, e.g., expressed in concentration, volume, amount, or a percentage of staring material.

"ATCC" refers to American Type Culture Collection located at Manassas, Va. 20108 (ATCC).

As used herein, a "precipitation agent," for purposes of purification, refers to a compound effective to precipitate a polypeptide, such as AmyE or a variant thereof, from solution. The form of the precipitate may be, e.g., crystalline, amorphous, or a blend, thereof.

"NRRL" refers to the Agricultural Research Service Culture Collection, National Center for Agricultural Utilization Research (and previously known as USDA Northern Regional Research Laboratory), Peoria, Ill.

As used herein, a "swatch" is a piece of material, such as a fabric, to which a stain may be applied, or which has a stain applied. The material can be, for example, fabrics made of cotton, polyester or mixtures of natural and synthetic fibers. Alternatively, the material can be paper, such as filter paper or nitrocellulose, or a piece of a hard material, such as ceramic, metal, or glass. Exemplary stains include blood, milk, ink, grass, tea, wine, spinach, gravy, chocolate, egg, cheese, clay, pigment, oil, or combinations, thereof.

As used herein, a "smaller swatch" is a piece of the swatch that has been cut with a single hole punch device, or a custom manufactured 96-hole punch device, or equivalent, where the pattern of the multi-hole punch is matched to standard 96-well microtiter plates, or has been otherwise removed from the swatch. The swatch can be of textile, paper, metal, or other suitable material. The smaller swatch can have the stain affixed either before or after it is placed into the well of a 24-, 48- or 96-well microtiter plate.

As used herein, the term "food" encompasses both prepared food and ingredients for a food, such as flour, which are capable of providing a benefit to a food preparer of consumer. Food ingredients includes formulations that can be added to a food or foodstuff for the purposes of, e.g., acidifying or emulsifying. The food ingredient may be in the form of a solution or a solid, depending on the use and/or the mode of application and/or the mode of administration.

As used herein, the term "flour" refers to milled or ground cereal grain or Sago or tuber products that have been ground or mashed. In some embodiments, flour may also contain components in addition to the milled or mashed cereal or plant matter, such as a leavening agent. Cereal grains include wheat, oat, rye, and barley. Tuber products include tapioca flour, cassava flour, and custard powder. Flour also includes ground corn flour, maize-meal, rice flour, whole-meal flour, self-rising flour, tapioca flour, cassava flour, ground rice, enriched flower, and custard powder.

As used herein, the term "stock" refers to grains and plant components that are crushed or broken. For example, barley used in beer production is a grain that has been coarsely ground or crushed to yield a consistency appropriate for producing a mash for fermentation. A stock may include any of the aforementioned types of plants and grains in crushed or coarsely ground forms.

As used herein, the term "performance index (PI)" refers to the ratio of performance of a variant polypeptide to a parent polypeptide for a specified performance characteristic. Within this context, "up mutations" refer to mutations that have a PI>1; "neutral mutations" refer to mutations that have a PI>0.5; "non-deleterious mutations" refer to mutations that have a PI>0.05; and "deleterious mutations" refer to mutations that have a PI≤0.05.

As used herein, the terms "added (or additional) glucoamylase (or glucoamylase polypeptide)" or additional polypeptide having glucoamylase activity" refers to a glucoamylase enzyme that is not the same polypeptides as AmyE.

The singular forms "a," "an," and "the" include plural referents unless the context clearly dictates otherwise. Thus, for example, reference to "an enzyme" includes a plurality of such enzymes and reference to "the formulation" includes reference to one or more formulations and equivalents thereof known to those skilled in the art, and so forth.

Numeric ranges are inclusive of the numbers defining the range. Headings are descriptive and are not intended as limitations. All reference cited herein are incorporated by reference.

1.2. Abbreviations

The following abbreviations apply unless indicated otherwise:

AE alcohol ethoxylate
AEO alcohol ethoxylate
AEOS alcohol ethoxysulfate
AES alcohol ethoxysulfate
AGU glucoamylase activity unit
AkAA *Aspergillus kawachii* α-amylase
AmyE *Bacillus subtilis* α-amylase
AmyS *Geobacillus stearothermophilus* α-amylase
AS alcohol sulfate
BAA bacterial α-amylase
cDNA complementary DNA
CMC carboxymethylcellulose
DE Dextrose Equivalent
DI distilled, deionized
DNA deoxyribonucleic acid
DP3 degree of polymerization with three subunits
DPn degree of polymerization with n subunits
DS or ds dry solid
DTMPA diethyltriaminepentaacetic acid
EC enzyme commission for enzyme classification
EDTA ethylenediaminetetraacetic acid
EDTMPA ethylenediaminetetramethylene phosphonic acid
EO ethylene oxide
F&HC fabric and household care
GAU glucoamylase units
HFCS high fructose corn syrup
HFSS high fructose starch based syrup
IPTG isopropyl β-D-thiogalactoside LA Luria agar
LB Luria broth
LU Lipase Units
LIT leucine (L) residue at position 1 is replaced with a threonine (T) residue, where amino acids are designated by single letter abbreviations commonly known in the art
MW molecular weight
NCBI National Center for Biotechnology Information
nm nanometer
NOBS nonanoyloxybenzenesulfonate
NTA nitrilotriacetic acid
OD optical density
PCR polymerase chain reaction
PEG polyethylene glycol
pI isoelectric point
ppm parts per million
PVA poly(vinyl alcohol)
PVP poly(vinylpyrrolidone)
RAU Reference Amylase Units
RNA ribonucleic acid
SAS secondary alkane sulfonates
1×SSC 0.15 M NaCl, 0.015 M sodium citrate, pH 7.0
SSF simultaneous saccharification and fermentation
SSU soluble starch unit, equivalent to the reducing power of 1 mg of glucose released per minute
TAED tetraacetylethylenediamine
TNBS trinitrobenzenesulfonic acid
TrGA *Trichoderma reesei* glucoamylase
w/v weight/volume
w/w weight/weight
wt wild-type
μL microliter
μNm microNewton×meter.

2. AmyE Polypeptides 2.1. Parental AmyE Polypeptides

AmyE α-amylase refers to a naturally occurring α-amylase (EC 3.2.1.1; 1,4-α-D-glucan glucanohydrolase) from *B. subtilis*, as exemplified by SEQ ID NO: 1. Related polypeptides have amino acid sequences that differ from the sequence of a naturally occurring AmyE, for example, amino acid sequences that have at least about 85%, at least about 90%, at least about 91%, at least about 92%, at least about 93%, at least about 94%, at least about 95%, at least about 96%, at least about 97%, at least about 98%, or even at least about 99% sequence identity with SEQ ID NO: 1, as measured with the BLAST sequence alignment algorithm with default matching parameters.

Another exemplary AmyE polypeptide is Amy31A having the amino acid sequence of SEQ ID NO: 3 (Amy31A). Amy31A is described in Ohdan et al., "Characteristics of two forms of alpha-amylases and structural implication," *Appl. Environ. Microbiol.* 65(10): 4652-58 (1999) and UniProtKB/TrEMBL Accession No. 082953 (SEQ ID NO: 3). Amy31A has about 86% sequence identity to the AmyE of SEQ ID NO: 1, using the BLAST algorithm. Additional AmyE polypeptides include, but are not limited to, the AmyE having the amino acid sequence described in NCBI Accession Nos. ABW75769, ABK54355, AAF14358, AAT01440, AAZ30064, NP_388186, AAQ83841, and BAA31528, the contents of which are incorporated here by reference.

The representative AmyE amino acid sequence set forth in SEQ ID NO: 1 is that of a mature form, which lacks the native signal sequence. The mature form of an AmyE is referred to elsewhere as "AmyE full-length." Generally, the mature form of AmyE is of the most interest as an enzyme, although it may be desirable to express the immature form (with a signal sequence) to affect secretion from a host cell. The native signal sequence of this AmyE is 41 amino acid residues in length and is shown as SEQ ID NO: 9. The N-terminal 45 amino acid residues of SEQ ID NO: 3 are the signal sequence of Amy31A. A sequence alignment between AmyE (SEQ ID NO: 1) and Amy31A (without the signal sequence) is depicted in FIG. 1.

AmyE polypeptides may have a deletion of the C-terminal starch binding domain, as exemplified by the truncated AmyE polypeptide having the amino acid sequence of SEQ ID NO: 2 (AmyE-tr). This polypeptide is truncated from residue D425 (referring to SEQ ID NO: 1). A 2.5 Å resolution crystal structure of AmyE-tr is available at Protein Databank Accession No. 1BAG, which is disclosed in Fujimoto et al. (1998) "Crystal structure of a catalytic-site mutant alpha-amylase from *B. subtilis* complexed with maltopentaose," *J. Mol. Biol.* 277:393-407. AmyE may be truncated at other positions, e.g., Y423, P424, D426 or I427 of the AmyE of SEQ ID NO: 1, provided all or part of the C-terminal starch binding domain is removed. Similar truncations can be made to Amy31A and other AmyE polypeptides.

2.2. AmyE Variants

AmyE variants comprise at least one amino acid modification compared to the naturally-occurring AmyE of SEQ ID NO: 1, or compared to SEQ ID NO: 2 (the truncated polypeptide). Accordingly, the AmyE polypeptides of SEQ ID NO: 1 or SEQ ID NO: 2 may be referred to as "parental polypeptides," "parental enzymes," or "parental sequences," from which AmyE variants are derived. The amino acid residues that are not modified (i.e., the remaining contiguous amino acid sequences) may be identical to those of SEQ ID NOs: 1 or 2, identical to those of SEQ ID NO: 3, or identical to those of NCBI Accession Nos. ABW75769, ABK54355, AAF14358, AAT01440, AAZ30064, NP_388186, AAQ83841, and BAA31528. Alternatively, the remaining amino acid sequences may have a specified degree of sequence identity to one or more of these sequences as measured using, e.g., a BLAST alignment of the protein sequences with default alignment parameters. For example the remaining sequences may have at least about 85%, at least about 90%, at least about 91%, at least about 92%, at least about 93%, at least about 94%, at least about 95%, at least about 96%, at least about 97%, at least about 98%, or even at least about 99% sequence identity with the AmyE of SEQ ID NO: 1 or SEQ ID NO: 2.

AmyE variants may have a single amino acid modification or may have, e.g., 2, 3, 4, 5, 6, 7, 8, 9, 10, 15, 20 or more amino acid modifications compared to the amino acid sequence of SEQ ID NO: 1 or SEQ ID NO: 2. Modifications include substitutions, insertions, deletions, or combinations, thereof. In some cases, the modifications are to amino acid residues that are not required for biological function. The selection of amino acid residues to be modified may be guided by sequence homology among AmyE sequences. Generally, amino acids that are well conserved in AmyE sequences are more likely to be required for biological activity. Conversely, amino acid positions that vary among AmyE sequences are less likely to be required for biological activity. For example, amino acid residues that differ in the alignment between AmyE and Amy31A, shown in bold font in FIG. 1, likely can be modified in an AmyE variant without loss of biological activity.

Preferred AmyE variants have at least partial 1,4-α-D-glucan glucanohydrolase activity, compared to a naturally-occurring AmyE and at least one altered property compared to a naturally-occurring AmyE. The altered property may be with respect to specific activity towards starch, maltoheptaose, and/or maltotriose substrates, substrate specificity, thermostability, temperature optima, pH optima, pH and/or temperature range, oxidative stability, ability to reduce the viscosity of a starch composition, or the like. In some cases, the altered property of the AmyE variant relates to the specific activity on a particular corn flour, maltotriose, maltoheptaose substrate at particular pH (e.g., 4 or 5.8), heat stability at a particular temperature, (e.g., 60° C.), or cleaning performance at a particular pH (e.g., 8 or pH 10). The altered property may be characterized by a Performance Index (PI), where the PI is a ratio of performance of the AmyE variant compared to a wild-type AmyE. In some embodiments, the PI is greater than about 0.5, while in other embodiments, the PI is about 1 or is greater than 1.

Specific residues that may be substituted to impart beneficial properties on a resulting AmyE variant include one or more of the following: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 121, 122, 123, 124, 125, 126, 127, 128, 129, 130, 131, 132, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 267, 268, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, and 425. Modifications at any of these positions produces a variant polypeptide having a performance index (PI) greater than 0.5 for protein expression, and a PI greater than 1 for at least one characteristic that improves enzyme performance.

A subset of residues that may be substituted to impart beneficial properties on a resulting AmyE variant include one or more of the following: 1, 2, 3, 4, 5, 6, 7, 8, 9, 10, 11, 12, 13, 14, 15, 16, 18, 19, 20, 21, 22, 23, 24, 25, 26, 27, 28, 29, 30, 31, 32, 33, 34, 35, 36, 37, 39, 42, 43, 44, 45, 46, 47, 48, 49, 50, 51, 52, 53, 54, 55, 56, 57, 58, 59, 60, 63, 64, 65, 66, 67, 68, 69, 72, 73, 74, 76, 77, 78, 79, 80, 81, 82, 83, 84, 85, 86, 87, 88, 89, 90, 91, 92, 93, 94, 95, 96, 98, 99, 100, 103, 104, 105, 106, 107, 108, 109, 110, 111, 112, 113, 114, 115, 116, 118, 119, 121, 124, 125, 126, 128, 129, 130, 131, 132, 134, 135, 136, 140, 141, 142, 143, 144, 147, 150, 151, 152, 153, 154, 155, 156, 157, 158, 159, 160, 162, 163, 164, 165, 166, 167, 168, 170, 171, 172, 175, 179, 180, 181, 184, 186, 187, 188, 189, 190, 192, 195, 196, 197, 198, 199, 200, 201, 202, 203, 204, 205, 207, 209, 211, 212, 213, 214, 217, 218, 219, 221, 222, 223, 224, 225, 226, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 267, 268, 270, 271, 272, 273, 274, 275, 276, 277, 279, 280, 281, 282, 283, 284, 285, 286, 287, 288, 289, 290, 291, 292, 293, 294, 295, 297, 298, 299, 300, 301, 302, 303, 304, 305, 307, 308, 309, 310, 311, 312, 313, 314, 315, 316, 317, 318, 319, 320, 321, 322, 324, 325, 327, 328, 329, 330, 331, 332, 333, 334, 335, 336, 337, 338, 339, 340, 341, 342, 343, 344, 345, 346, 347, 348, 349, 350, 351, 352, 353, 355, 356, 357, 358, 359, 360, 361, 362, 363, 364, 365, 366, 367, 368, 369, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, and 425. Modifications at any of these positions produces a variant polypeptide having a performance index (PI) greater than 0.5 for protein expression, and a PI greater than 1.1 for at least one characteristic that improves enzyme performance.

In some case, one or more positions are selected from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 76, 77, 78, 79, 80, 81, 82, 83, 84, 85, 86, 87, 88, 89, 90, 91, 92, 93, 94, 95, 96, 98, 99, 100, 103, 104, 105, 106, 107, 108, 109, 110, 111, 112, 113, 114, 115, 116, 117, 118, 119, 121, 122, 124, 125, 126, 127, 128, 129, 130, 131, 132, 134, 135, 136, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, and 425, which positions are non-fully restrictive for performance in either the full-length or truncated parental polypeptide.

Some positions were determined to be non-fully restrictive for performance in the context of the truncated AmyE parental polypeptide (i.e., 1, 2, 3, 4, 5, 8, 18, 20, 23, 24, 25, 27, 28, 30, 35, 44, 45, 47, 49, 50, 51, 52, 54, 56, 59, 68, 73, 76, 78, 85, 88, 89, 90, 91, 106, 107, 108, 109, 112, 115, 116, 118, 119, 124, 125, 126, 127, 131, 132, 134, 142, 143, 152, 153, 156, 160, 163, 166, 167, 184, 185, 187, 188, 190, 192, 195, 199, 200, 201, 202, 203, 212, 213, 214, 218, 219, 221, 222, 223, 233, 234, 238, 240, 241, 243, 245, 247, 248, 250, 251, 252, 253, 254, 255, 257, 259, 260, 274, 275, 276, 277, 282, 283, 284, 287, 307, 308, 309, 310, 311, 312, 313, 314, 317, 318, 319, 320, 321, 323, 324, 325, 327, 328, 331, 333, 344, 346, 347, 349, 357, 358, 359, 367, 368, 369, 378, 380, 382, 385, 386, 388, 390, 393, 395, 400, 401, 402, and 406), and some positions were determined to be non-fully restrictive for performance in the context of the full-length AmyE parental polypeptide (i.e., 6, 7, 9, 10, 11, 12, 13, 14, 15, 16, 17, 19, 21, 22, 26, 27, 29, 30, 31, 32, 33, 34, 36, 37, 38, 39, 40, 41, 42, 43, 45, 46, 48, 52, 53, 55, 57, 58, 60, 61, 62, 63, 64, 65, 66, 67, 69, 70, 71, 72, 74, 77, 79, 80, 81, 82, 83, 84, 86, 87, 88, 89, 92, 93, 94, 95, 96, 98, 99, 100, 103, 104, 105, 110, 111, 113, 114, 117, 121, 122, 126, 128, 129, 130, 131, 135, 136, 138, 139, 140, 141, 144, 145, 146, 147, 148, 149, 150, 151, 154, 155, 157, 158, 159, 161, 162, 164, 165, 167, 168, 169, 170, 171, 172, 173, 174, 175, 176, 177, 178, 179, 180, 181, 183, 184, 186, 189, 191, 193, 194, 196, 197, 198, 204, 205, 206, 207, 208, 209, 210, 211, 215, 216, 217, 220, 223, 224, 225, 226, 227, 228, 229, 230, 231, 232, 235, 236, 237, 238, 239, 241, 242, 244, 246, 249, 256, 258, 260, 261, 262, 263, 264, 265, 267, 268, 269, 270, 271, 272, 273, 278, 279, 280, 281, 285, 286, 288, 289, 290, 291, 292, 293, 294, 295, 296, 297, 298, 299, 300, 301, 302, 303, 304, 305, 307, 312, 315, 316, 322, 326, 329, 330, 332, 334, 335, 336, 337, 338, 339, 340, 341, 342, 343, 344, 345, 348, 350, 351, 352, 353, 354, 355, 356, 360, 361, 362, 363, 364, 365, 366, 370, 371, 372, 373, 374, 375, 376, 377, 379, 380, 381, 383, 384, 387, 389, 391, 392, 394, 396, 397, 398, 399, 402, 403, 404, 405, 407, 408, 409, 410, 411, 412, 413, 414, 415, 416, 417, 418, 419, 420, 421, 422, 423, 424, 425).

In some cases, the modification is a substitution of one or more amino residues present in the parental polypeptide to different amino acid residues, for example: 1A, 1C, 1D, 1E, 1F, 1G, 1H, 1K, 1M, 1N, 1Q, 1R, 1S, 1T, 1V, 1W, 1Y, 2A, 2C, 2D, 2E, 2F, 2G, 2H, 2I, 2K, 2L, 2M, 2N, 2P, 2Q, 2R, 2S, 2V, 2W, 2Y, 3C, 3D, 3E, 3F, 3G, 3H, 3I, 3K, 3L, 3M, 3N, 3P, 3Q, 3R, 3S, 3V, 3W, 3Y, 4C, 4D, 4E, 4F, 4G, 4H, 4I, 4K, 4L, 4M, 4N, 4Q, 4S, 4T, 4V, 4W, 4Y, 5A, 5C, 5D, 5E, 5F, 5G, 5H, 5I, 5K, 5L, 5N, 5R, 5V, 5W, 5Y, 6C, 6D, 6E, 6H, 6K, 6L, 6M, 6N, 6P, 6Q, 6R, 6S, 6T, 6V, 6W, 7A, 7C, 7D, 7E, 7F, 7G, 7H, 7I, 7L, 7M, 7N, 7P, 7Q, 7R, 7S, 7T, 7W, 7Y, 8A, 8C, 8E, 8F, 8G, 8H, 8I, 8K, 8L, 8M, 8N, 8P, 8Q, 8R, 8T, 8V, 8W, 8Y, 9A, 9C, 9D, 9E, 9F, 9H, 9I, 9K, 9M, 9N, 9P, 9R, 9S, 9T, 9V, 9W, 9Y, 10A, 10I, 10L, 10M, 10N, 10P, 10Q, 10S, 10V, 11A, 11F, 11G, 11H, 11M, 11S, 11V, 11W, 11Y, 12I, 12M, 12V, 13A, 13C, 13D, 13E, 13F, 13G, 13I, 13L, 13M, 13Q, 13T, 13V, 13W, 13Y, 14C, 14F, 14G, 14M, 14N, 14S, 14T, 14V, 15A, 15F, 16A, 16D, 16E, 16F, 16G, 16H, 16I, 16L, 16M, 16Q, 16S, 16T, 16V, 17A, 17F, 17I, 17M, 17Q, 17Y, 18A, 18C, 18D, 18E, 18G, 18H, 18M, 18N, 18Q, 18R, 18T, 19A, 19C, 19H, 19L, 19M, 19N, 19S, 19W, 19Y, 20A, 20C, 20D, 20F, 20G, 20H, 20I, 20K, 20L, 20M, 20P, 20Q, 20R, 20S, 20T, 20V, 20W, 20Y, 21A, 21C, 21D, 21E, 21H, 21I, 21K, 21L, 21M, 21N, 21Q, 21R, 21S, 21V, 22I, 22M, 22Q, 22S, 22T, 22V, 23A, 23C, 23D, 23E, 23F, 23G, 23H, 23I, 23L, 23M, 23N, 23R, 23S, 23T, 23V, 23W, 23Y, 24A, 24C, 24D, 24F, 24G, 24L, 24N, 24P, 24Q, 24R, 24S, 24T, 24V, 24Y, 25A, 25C, 25D, 25E, 25F, 25G, 25H, 25I, 25K, 25L, 25R, 25S, 25T, 25V, 25W, 25Y, 26A, 26F, 26I, 26L, 26V, 27A, 27C, 27D, 27E, 27F, 27G, 27H, 27I, 27L, 27M, 27N, 27P, 27Q, 27R, 27S, 27T, 27V, 27W, 27Y, 28A, 28C, 28F, 28G, 28H, 28I, 28K, 28L, 28M, 28N, 28P, 28Q, 28R, 28S, 28T, 28V, 28W, 28Y, 29A, 29C, 29F, 29L, 29M, 29T, 29V, 30A, 30C, 30D, 30E, 30F, 30G, 30I, 30K, 30L, 30M, 30N, 30P, 30Q, 30R, 30S, 30T, 30V, 30W, 30Y, 31A, 31C, 31E, 31F, 31G, 31H, 31I, 31K, 31L, 31M, 31N, 31Q, 31S, 31T, 31V, 31W, 31Y, 32D, 32F, 32G, 32H, 32K, 32L, 32M, 32Q, 32S, 32T, 32V, 32Y, 33A, 33C, 33D, 33E, 33F, 33H, 33I, 33K, 33L, 33M, 33P, 33Q, 33S, 33T, 33W, 33Y, 34A, 34F, 34I, 34P, 34W, 35A, 35C, 35F, 35G, 35H, 35I, 35L, 35M, 35N, 35P, 35Q, 35R, 35S, 35V, 35W, 35Y, 36C, 36D, 36E, 36F, 36H, 36I, 36K, 36L, 36M, 36N, 36Q, 36R, 36S, 36T, 36Y, 37L, 37M, 37N, 37V, 38A, 38C, 38D, 38E, 38H, 38L, 38M, 38N, 38P, 38V, 39A, 39C, 39I, 39L, 39M, 39N, 39P, 39S, 39V, 40A, 40D, 40M, 40N, 40P, 40Q, 40T, 40V, 40W, 41A, 41C, 41E, 41G, 41N, 41S, 41V, 42A, 42L, 42M, 42P, 42V, 43A, 43G, 43H, 43L, 43M, 43Q, 43S, 43T, 43V, 44A, 44C, 44D, 44E, 44F, 44G, 44H, 44I, 44K, 44L, 44M, 44N, 44P, 44R, 44S, 44T, 44V, 44W, 44Y, 45A, 45C, 45F, 45G, 45H, 45I, 45L, 45M, 45N, 45P, 45Q, 45S, 45T, 45Y, 46A, 46C, 46D, 46E, 46F, 46H, 46I, 46L, 46M, 46N, 46Q, 46R, 46S, 46T, 46V, 46W, 46Y, 47A, 47C, 47D, 47F, 47G, 47H, 47I, 47K, 47L, 47N, 47P, 47R, 47S, 47T, 47V, 47Y, 48A, 48C, 48D, 48E, 48F, 48H, 48I, 48K, 48L, 48N, 48P, 48S, 48T, 48V, 48W, 49A, 49C, 49D, 49F, 49G, 49H, 49I, 49K, 49L, 49P, 49Q, 49R, 49S, 49T, 49V, 49W, 49Y, 50A, 50C, 50E, 50F, 50G, 50H, 50I, 50K, 50L, 50M, 50N, 50P, 50R, 50S, 50T, 50V, 50W, 50Y, 51A, 51C, 51D, 51E, 51F, 51H, 51I, 51K, 51L, 51M, 51N, 51P, 51Q, 51R, 51S, 51T, 51V, 51W, 52A, 52C, 52E, 52F, 52G, 52H, 52I, 52K, 52L, 52M, 52N, 52P, 52Q, 52R, 52S, 52T, 52V, 52W, 52Y, 53A, 53C, 53E, 53F, 53G, 53H, 53I, 53L, 53N, 53P, 53R, 53S, 53T, 53V, 53W, 53Y, 54A, 54C, 54D, 54F, 54G, 54H, 54I, 54L, 54M, 54N, 54P, 54Q, 54R, 54T, 54V, 54W, 54Y, 55A, 55C, 55D, 55E, 55F, 55G, 55H, 55I, 55N, 55P, 55Q, 55S, 55T, 55Y, 56A, 56D, 56E, 56F, 56G, 56I, 56K, 56L, 56M, 56N, 56P, 56Q, 56R, 56T, 56V, 56W, 56Y, 57A, 57C, 57D, 57E, 57F, 57H, 57I, 57K, 57L, 57M, 57Q, 57R, 57S, 57T, 57V, 57W, 57Y, 58A, 58F, 58H, 59A, 59C, 59D, 59E, 59F, 59G, 59H, 59K, 59L, 59N, 59P, 59R, 59S, 59T, 59V, 59W, 60A, 60C, 60D, 60E, 60G, 60I, 60K, 60L, 60M, 60N, 60Q, 60R, 60T, 60V, 61C, 61D, 61E, 61F, 61M, 61S, 61T, 61V, 62A, 62C, 62D, 62F, 62G, 62H, 62I, 62K, 62L, 62Q, 62S, 62T, 62V, 63A, 63C, 63D, 63F, 63G, 63H, 63K, 63M, 63N, 63R, 63S, 64A, 64G, 64H, 64I, 64L, 64M, 64N, 64S, 64V, 64Y, 65A, 65C, 65E, 65H, 65I, 65K, 65L, 65M, 65Q, 65R, 65S, 66D, 66E, 66F, 66G, 66H, 66I, 66K, 66L, 66M, 66N, 66Q, 66R, 66T, 66V, 66W, 66Y, 67A, 67C, 67D, 67E, 67F, 67G, 67I, 67K, 67L, 67N, 67P, 67Q, 67S, 67T, 67W, 68A, 68C, 68D, 68E, 68F, 68G, 68H, 68I, 68L, 68M, 68N, 68P, 68R, 68S, 68T, 68V, 68W, 68Y, 69A, 69C, 69M, 69P, 69T, 69V, 70A, 70E, 70H, 70N, 70S, 71S, 72C, 72D, 72F, 72G, 72H, 72I, 72K, 72L, 72P, 72Q, 72S, 72T, 72V, 72Y, 73A, 73C, 73E, 73F, 73H, 73I, 73K, 73L, 73M, 73P, 73S, 73T, 73V, 73W, 74A, 74E, 74F, 74M, 74S, 74T, 74Y, 75A, 75C, 75D, 75E, 75P, 76A, 76D, 76E, 76F, 76G, 76I, 76L, 76M, 76P, 76Q, 76R, 76S, 76V, 76Y, 77A, 77C, 77D, 77G, 77H, 77I, 77K, 77L, 77R, 77S, 77T, 77V, 77W, 77Y, 78A, 78C, 78D, 78E, 78F, 78G, 78H, 78I, 78K, 78L, 78M, 78N, 78P, 78R, 78S, 78T, 78V, 78W, 78Y, 79A, 79G, 79L, 79M, 79N, 79Q, 79S, 79T, 80A, 80L, 80M, 80W, 80Y, 81A, 81C, 81D, 81E, 81G, 81H, 81I, 81L, 81M, 81N, 81Q, 81R, 81S, 81T, 81V, 81W, 81Y, 82A, 82D, 82F, 82G, 82I, 82K, 82L, 82M, 82Q, 82R, 82S, 82T, 82V, 82W, 82Y, 83A, 83F, 83I, 83L, 83T, 83V, 84A, 84D, 84E, 84G, 84I, 84K, 84M, 84N, 84Q, 84S, 84T, 84V, 85D, 85E, 85F, 85G, 85I, 85K, 85L, 85M, 85N, 85R, 85S, 85T, 85V, 85W, 86C, 86D, 86E, 86F, 86G, 86I, 86K, 86L, 86M, 86N, 86Q, 86R, 86S, 86V, 86W, 86Y, 87F, 87G, 87T, 88A, 88C, 88D, 88F, 88G, 88H, 88I, 88K, 88L, 88M, 88N, 88Q, 88R, 88S, 88T, 88V, 88W, 88Y, 89A, 89C, 89D, 89F, 89G, 89H, 89I, 89K, 89L, 89M, 89N, 89P, 89Q, 89R, 89S, 89T, 89V, 89W, 89Y, 90C, 90D, 90E, 90F, 90G, 90H, 90I, 90K, 90L, 90M, 90N, 90Q, 90R, 90S, 90T, 90V, 90W, 91A, 91C, 91D, 91E, 91F, 91H, 91K, 91L, 91M, 91N, 91P, 91Q, 91R, 91S, 91T, 91W, 91Y, 92L, 92N, 92T, 92V, 93A, 93C, 93D, 93E, 93F, 93G, 93I, 93L, 93M, 93N, 93P, 93Q, 93R, 93S, 93T, 93V, 93W, 93Y, 94A, 94C, 94I, 94M, 94T, 95A, 95F, 95L, 95M, 95V, 95Y, 96A, 96C, 96I, 96L, 96M, 96P, 96T, 97A, 97E, 97M, 97W, 98C, 98G, 98I, 98L, 98M, 98T, 98V, 99A, 99C, 99E, 99F, 99G, 99I, 99L, 99N, 99P, 99S, 99T, 100A, 100C, 100F, 100M, 100N, 100P, 100T, 100V, 100Y, 101A, 102A, 102G, 102Q, 102S, 102W, 102Y, 103A, 103C, 103I, 103M, 103N, 103S, 103V, 104A, 104C, 104S, 105C, 105D, 105E, 105F, 105G, 105H, 105K, 105L, 105M, 105Q, 105R, 105T, 105V, 105W, 105Y, 106A, 106C, 106E, 106F, 106H, 106I, 106K, 106L, 106M, 106N, 106Q, 106R, 106S, 106T, 106V, 106W, 106Y, 107A, 107C, 107E, 107F, 107G, 107H, 107I, 107K, 107L, 107M, 107N, 107P, 107Q, 107R, 107S, 107T, 107V, 107W, 108C, 108D, 108E, 108F, 108G, 108H, 108I, 108K, 108L, 108N, 108P, 108R, 108S, 108T, 108V, 108W, 108Y, 109C, 109D, 109E, 109F, 109G, 109H, 109I, 109K, 109L, 109M, 109N, 109P, 109R, 109S, 109T, 109V, 109W, 109Y, 110L, 110M, 110V, 111A, 111C, 111E, 111F, 111G, 111H, 111I, 111K, 111L, 111M, 111N, 111P, 111Q, 111R, 111T, 111V, 111W, 111Y, 112A, 112C, 112D, 112E, 112F, 112G, 112H, 112I, 112K, 112L, 112M, 112P, 112Q, 112R, 112S, 112T, 112V, 112W, 112Y, 113A, 113D, 113F, 113G, 113I, 113K, 113L, 113M, 113N, 113P, 113Q, 113S, 113T, 113V, 113W, 113Y, 114F, 114L, 114P, 114T, 115A, 115C, 115F, 115G, 115H, 115I, 115L, 115M, 115N, 115Q, 115R, 115S, 115T, 115V, 115W, 115Y, 116A, 116D, 116E, 116F, 116G, 116H, 116I, 116L, 116N, 116Q, 116R, 116T, 116V, 116W, 116Y, 117F, 117L, 117N, 117Q, 117V, 117W, 117Y, 118A, 118C, 118D, 118E, 118F, 118G, 118H, 118I, 118K, 118L, 118M, 118N, 118Q, 118R, 118S, 118T, 118V, 118W, 118Y, 119A, 119C, 119D, 119E, 119F, 119G, 119H, 119I, 119K, 119L, 119M, 119Q, 119R, 119S, 119T, 119V, 119Y, 121A, 121M, 121N, 121S, 122R, 123E, 124A, 124C, 124D, 124E, 124F, 124G, 124I, 124K, 124M, 124Q, 124R, 124S, 124T, 124V, 124Y, 125A, 125D, 125E, 125F, 125G, 125H, 125I, 125K, 125L, 125M, 125N, 125P, 125Q, 125R, 125S, 125V, 125W, 125Y, 126A, 126C, 126D, 126F, 126G, 126H, 126I, 126K, 126L, 126N, 126P, 126R, 126S, 126T, 126V, 126W, 126Y, 127C, 127L, 127M, 127V, 128A, 128C, 128D, 128E, 128F, 128G, 128H, 128I, 128L, 128M, 128N, 128Q, 128R, 128S, 128T, 128V, 128Y, 129A, 129C, 129D, 129E, 129F, 129H, 129I, 129K, 129L, 129M, 129R, 129S, 129T, 129V, 129Y, 130A, 130C, 130D, 130F, 130G, 130H, 130I, 130K, 130L, 130M, 130P, 130R, 130T, 130V, 130Y, 131A, 131C, 131D, 131E, 131F, 131G, 131H, 131I, 131K, 131L, 131M, 131N, 131Q, 131R, 131T, 131V, 131W, 131Y, 132A, 132C, 132E, 132H, 132I, 132L, 132M, 132N, 132Q, 132S, 132W, 132Y, 134C, 134D, 134E, 134F, 134G, 134I, 134L, 134M, 134N, 134R, 134S, 134T, 134V, 134Y, 135A, 135C, 135E, 135M, 135N, 135Q, 135R, 136A, 136C, 136F, 136L, 136T, 136Y, 137C, 138A, 138C, 138F, 138H, 138N, 138R, 138W, 138Y, 139A, 139C, 139G, 139H, 139L, 139M, 139S, 140A, 140C, 140F, 140G, 141A, 141F, 141H, 141P, 141Q, 141S, 141T, 141V, 141Y, 142C, 142D, 142F, 142G, 142H, 142I, 142K, 142M, 142Q, 142R, 142S, 142T, 142W, 142Y, 143A, 143C, 143D, 143F, 143K, 143L, 143M, 143N, 143Q, 143R, 143S, 143W, 144G, 144S, 144T, 144V, 144W, 145W, 146A, 146E, 146M, 146T, 147C, 147F, 147H, 147I, 147L, 147N, 147P, 147Y, 148A, 148C, 148F, 148H, 148K, 148M, 148R, 148Y, 149S, 150A, 150H, 150N, 150S, 151A, 151C, 151D, 151E, 151F, 151G, 151H, 151I, 151K, 151L, 151M, 151Q, 151R, 151S, 151T, 151V, 151Y, 152A, 152C, 152D, 152E, 152F, 152G, 152H, 152I, 152K, 152L, 152M, 152N, 152P, 152Q, 152R, 152S, 152V, 152W, 152Y, 153A, 153C, 153D, 153E, 153F, 153G, 153H, 153I, 153K, 153L, 153M, 153N, 153P, 153R, 153S, 153T, 153V, 153W, 153Y, 154A, 154C, 154I, 154N, 154P, 154Q, 154S, 154T, 154Y, 155A, 155C, 155E, 155F, 155G, 155H, 155I, 155L, 155M, 155T, 155V, 155W, 156A, 156C, 156D, 156E, 156F, 156G, 156H, 156I, 156K, 156L, 156N, 156Q, 156R, 156T, 156V, 156W, 156Y, 157A, 157C, 157F, 157H, 157I, 157T, 157V, 158A, 158F, 158H, 158I, 158M, 158Q, 158S, 158T, 158V, 159A, 159C, 159E, 159F, 159G, 159H, 159I, 159L, 159M, 159N, 159R, 159S, 159T, 159V, 159W, 159Y, 160A, 160C, 160D, 160E, 160F, 160G, 160H, 160I, 160K, 160L, 160M, 160N, 160Q, 160S, 160T, 160V, 160W, 160Y, 161A, 161C, 161G, 161H, 161K, 161L, 161M, 161N, 161S, 162A, 162C, 162E, 162F, 162I, 162M, 162V, 163A, 163C, 163E, 163F, 163G, 163H, 163I, 163K, 163L, 163N, 163Q, 163R, 163S, 163T, 163V, 163W, 163Y, 164A, 164F, 164G, 164H, 164I, 164L, 164M, 164N, 164Q, 164S, 164T, 164V, 164W, 164Y, 165C, 165G, 165I, 165L, 165M, 165Q, 165S, 165T, 165V, 165W, 165Y, 166A, 166C, 166D, 166E, 166F, 166G, 166H, 166I, 166K, 166M, 166N, 166Q, 166R, 166S, 166T, 166V, 166W, 166Y, 167A, 167C, 167D, 167E, 167F, 167G, 167H, 167I, 167K, 167L, 167M, 167Q, 167R, 167S, 167T, 167V, 167W, 167Y, 168C, 168E, 168F, 168G, 168I, 168K, 168L, 168M, 168N, 168S, 168T, 168V, 168W, 168Y, 169L, 170C, 170G, 170V, 171A, 171C, 171E, 171F, 171G, 171H, 171I, 171L, 171M, 171N, 171Q, 171R, 171V, 172A, 172C, 172E, 172F, 172P, 173I, 173M, 173V, 173Y, 174E, 174G, 174H, 174L, 174Q, 174V, 174Y, 175H, 175M, 175W, 175Y, 176E, 176F, 176I, 176K, 176L, 176V, 176Y, 177C, 177G, 177M, 177Q, 177S, 178C, 178G, 178M, 178S, 178T, 179A, 179C, 179G, 179H, 179I, 179L, 179M, 179P, 179S, 179T, 179V, 179W, 179Y, 180A, 180D, 180M, 180N, 180Y, 181A, 181C, 181L, 181M, 181V, 182A, 183C, 183M, 184A, 184C, 184D, 184E, 184F, 184G, 184H, 184I, 184K, 184L, 184M, 184N, 184Q, 184R, 184S, 184T, 184V, 184W, 184Y, 185C, 185E, 185N, 185S, 185T, 186E, 187A, 187C, 187D, 187E, 187F, 187H, 187I, 187K, 187L, 187M, 187N, 187P, 187Q, 187R, 187S, 187T, 187V, 187W, 187Y, 188A, 188C, 188D, 188E, 188F, 188G, 188I, 188K, 188L, 188M, 188N, 188P, 188Q, 188R, 188T, 188V, 189F, 189W, 190A, 190C, 190E, 190F, 190H, 190K, 190L, 190M, 190Q, 190R, 190S, 190W, 190Y, 191A, 191L, 191T, 191Y, 192D, 192E, 192F, 192G, 192I, 192K, 192L, 192N, 192P, 192R, 192S, 192T, 192V, 193A, 193I, 193L, 193M, 194I, 195A, 195C, 195D, 195F, 195G, 195H, 195I, 195K, 195L, 195M, 195N, 195Q, 195R, 195S, 195T, 195V, 195W, 195Y, 196A, 196C, 196D, 196E, 196F, 196G, 196H, 196I, 196K, 196L, 196M, 196Q, 196R, 196S, 196T, 196V, 196W, 196Y, 197A, 197C, 197F, 197L, 197S, 197T, 197V, 198A, 198C, 198G, 198H, 198I, 198L, 198M, 198N, 198R, 198S, 198V, 199A, 199C, 199D, 199E, 199F, 199G, 199H, 199I, 199L, 199M, 199P, 199R, 199S, 199T, 199V, 199Y, 200A, 200C, 200D, 200E, 200F, 200G, 200H, 200I, 200K, 200L, 200M, 200N, 200P, 200Q, 200R, 200S, 200V, 200W, 200Y, 201A, 201C, 201D, 201E, 201F, 201G, 201H, 201I, 201K, 201L, 201M, 201N, 201P, 201Q, 201R, 201T, 201V, 201W, 201Y, 202C, 202F, 202G, 202I, 202K, 202L, 202M, 202N, 202P, 202Q, 202R, 202S, 202T, 202V, 202Y, 203A, 203C, 203F, 203G, 203I, 203K, 203L, 203N, 203P, 203Q, 203R, 203S, 203T, 203V, 203W, 203Y, 204A, 204C, 204E, 204I, 204L, 204M, 204T, 204V, 204W, 204Y, 205A, 205C, 205D, 205E, 205F, 205G, 205H, 205I, 205K, 205L, 205M, 205N, 205R, 205S, 205T, 205V, 205W, 205Y, 206F, 207A, 207C, 207M, 208K, 208N, 208R, 209C, 209F, 209L, 209M, 209T, 209V, 210F, 210I, 210V, 210W, 211A, 211C, 211D, 211E, 211G, 211H, 211M, 211P, 211S, 211T, 211W, 211Y, 212A, 212C, 212E, 212G, 212H, 212N, 212P, 212Q, 212S, 212T, 212Y, 213A, 213C, 213D, 213E, 213F, 213G, 213H, 213I, 213K, 213L, 213M, 213P, 213Q, 213R, 213T, 213V, 213Y, 214C, 214D, 214F, 214G, 214I, 214K, 214L, 214M, 214N, 214Q, 214R, 214S, 214T, 214V, 214W, 214Y, 215A, 215C, 215H, 215T, 216C, 216K, 217E, 217F, 217G, 217I, 217K, 217M, 217N, 217P, 217Q, 217R, 217S, 217T, 217V, 217Y, 218C, 218D, 218E, 218F, 218G, 218H, 218I, 218K, 218L, 218M, 218P, 218Q, 218R, 218S, 218T, 218V, 218W, 218Y, 219C, 219D, 219F, 219G, 219H, 219I, 219K, 219L, 219M, 219N, 219Q, 219R, 219S, 219T, 219V, 219W, 219Y, 220F, 221C, 221E, 221G, 221I, 221L, 221M, 221N, 221Q, 221R, 221S, 221T, 221V, 221Y, 222A, 222C, 222D, 222F, 222G, 222I, 222K, 222M, 222P, 222R, 222S, 222T, 222V, 223A, 223C, 223E, 223F, 223H, 223I, 223L, 223M, 223N, 223Q, 223V, 223W, 224I, 224L, 224V, 224Y, 225A, 225C, 225E, 225F, 225H, 225I, 225K, 225L, 225M, 225N, 225P, 225Q, 225S, 225T, 225V, 225W, 225Y, 226A, 226C, 226F, 226I, 226L, 226M, 226T, 227A, 227C, 227D, 227E, 227G, 227M, 227S, 228C, 228D, 228M, 228N, 228P, 228S, 228T, 228V, 229C, 229D, 229E, 229F, 229G, 229H, 229M, 229N, 229Q, 229R, 229T, 229V, 229Y, 230A, 230D, 230E, 230F, 230G, 230H, 230I, 230K, 230M, 230P, 230Q, 230R, 230S, 230V, 230Y, 231A, 231C, 231H, 231L, 231M, 231Q, 231W, 232A, 232C, 232M, 232N, 232Q, 232S, 232Y, 233A, 233C, 233D, 233E, 233F, 233G, 233I, 233K, 233L, 233M, 233N, 233P, 233Q, 233R, 233S, 233T, 233V, 233W, 233Y, 234A, 234C, 234D, 234E, 234F, 234G, 234H, 234I, 234L, 234M, 234N, 234Q, 234R, 234T, 234V, 234W, 234Y, 235A, 235C, 235F, 235L, 235M, 235T, 236A, 236C, 236D, 236E, 236G, 236H, 236I, 236K, 236L, 236M, 236N, 236Q, 236S, 236T, 237A, 237C, 237D, 237E, 237F, 237G, 237H, 237I, 237K, 237L, 237P, 237Q, 237R, 237T, 237V, 237W, 237Y, 238C, 238D, 238E, 238F, 238G, 238H, 238I, 238K, 238L, 238M, 238N, 238Q, 238R, 238S, 238T, 238V, 238W, 238Y, 239A, 239E, 239F, 239I, 239M, 239T, 240A, 240C, 240D, 240E, 240F, 240G, 240H, 240I, 240L, 240M, 240N, 240Q, 240R, 240S, 240T, 240V, 240W, 240Y, 241A, 241C, 241D, 241E, 241F, 241G, 241H, 241I, 241K, 241L, 241M, 241P, 241Q, 241R, 241S, 241T, 241V, 241W, 241Y, 242A, 242C, 242D, 242E, 242F, 242I, 242K, 242L, 242M, 242Q, 242S, 242T, 242V, 242W, 242Y, 243A, 243C, 243D, 243E, 243F, 243G, 243H, 243I, 243K, 243L, 243M, 243Q, 243R, 243S, 243T, 243V, 243W, 243Y, 244A, 244F, 244I, 244M, 244T, 244V, 244W, 244Y, 245A, 245C, 245D, 245F, 245H, 245I, 245L, 245M, 245N, 245P, 245R, 245T, 245V, 245W, 245Y, 246A, 246C, 246D, 246E, 246F, 246G, 246H, 246I, 246K, 246L, 246P, 246Q, 246R, 246S, 246T, 246W, 246Y, 247A, 247D, 247E, 247F, 247G, 247H, 247I, 247L, 247M, 247N, 247P, 247Q, 247T, 247V, 247Y, 248A, 248C, 248E, 248F, 248G, 248H, 248I, 248K, 248L, 248M, 248Q, 248R, 248S, 248T, 248V, 248W, 249A, 249C, 249E, 249F, 249H, 249L, 249M, 249P, 249S, 249V, 249Y, 250A, 250C, 250E, 250F, 250G, 250H, 250I, 250K, 250L, 250M, 250N, 250Q, 250R, 250T, 250V, 250W, 250Y, 251A, 251C, 251D, 251E, 251G, 251I, 251K, 251L, 251M, 251N, 251P, 251Q, 251R, 251V, 251Y, 252C, 252D, 252E, 252F, 252G, 252H, 252I, 252K, 252L, 252M, 252Q, 252R, 252S, 252T, 252V, 252W, 253C, 253E, 253F, 253G, 253H, 253I, 253K, 253L, 253M, 253P, 253R, 253S, 253T, 253V, 253W, 253Y, 254A, 254F, 254G, 254H, 254I, 254K, 254L, 254N, 254P, 254R, 254T, 254V, 254W, 254Y, 255A, 255C, 255E, 255F, 255G, 255I, 255K, 255L, 255N, 255P, 255Q, 255R, 255S, 255T, 255V, 255W, 255Y, 256A, 256C, 256I, 256M, 256N, 256T, 257A, 257D, 257E, 257F, 257G, 257H, 257I, 257K, 257L, 257M, 257N, 257P, 257Q, 257R, 257T, 257V, 257W, 258C, 258D, 258E, 258F, 258G, 258H, 258I, 258K, 258L, 258M, 258N, 258Q, 258R, 258S, 258T, 258V, 258Y, 259A, 259E, 259G, 259H, 259I, 259K, 259L, 259M, 259P, 259Q, 259R, 259S, 259T, 259W, 259Y, 260A, 260C, 260D, 260E, 260F, 260G, 260H, 260I, 260L, 260M, 260N, 260Q, 260R, 260S, 260T, 260V, 260W, 260Y, 261A, 261C, 261I, 261M, 261N, 261Q, 261S, 261T, 261V, 262A, 262C, 262I, 262M, 262T, 263A, 263C, 263L, 263M, 263N, 263P, 263S, 263V, 264D, 264E, 264G, 264H, 264I, 264L, 264N, 264Y, 265A, 265C, 265F, 265M, 265T, 265Y, 267A, 267C, 267D, 267F, 267G, 267H, 267M, 267N, 267Q, 267T, 267V, 268M, 268Q, 268R, 268V, 268Y, 270C, 270F, 270G, 270I, 270L, 270M, 270N, 270R, 270S, 270V, 270Y, 271F, 272G, 272I, 272L, 272M, 272N, 272S, 272T, 272V, 273D, 273G, 273I, 273K, 273L, 273P, 273Q, 273R, 273S, 273T, 273V, 273W, 273Y, 274A, 274C, 274F, 274G, 274H, 274I, 274K, 274L, 274M, 274N, 274P, 274Q, 274R, 274S, 274T, 274V, 274W, 274Y, 275A, 275C, 275E, 275F, 275G, 275H, 275I, 275K, 275L, 275M, 275N, 275P, 275Q, 275R, 275S, 275T, 275V, 275W, 275Y, 276A, 276C, 276D, 276F, 276G, 276H, 276I, 276K, 276L, 276M, 276N, 276P, 276Q, 276R, 276S, 276T, 276V, 276W, 276Y, 277A, 277C, 277D, 277F, 277G, 277H, 277I, 277K, 277L, 277M, 277N, 277P, 277Q, 277R, 277S, 277T, 277V, 277W, 277Y, 278A, 278C, 278T, 279D, 279E, 279G, 279H, 279I, 279K, 279L, 279M, 279N, 279P, 279Q, 279R, 279S, 279V, 279W, 279Y, 280A, 280D, 280E, 280F, 280G, 280H, 280K, 280L, 280M, 280N, 280Q, 280R, 280S, 280T, 280Y, 281C, 281F, 281L, 282A, 282C, 282D, 282E, 282F, 282G, 282H, 282I, 282K, 282L, 282M, 282N, 282P, 282Q, 282R, 282T, 282V, 282W, 282Y, 283A, 283C, 283F, 283G, 283H, 283I, 283L, 283N, 283P, 283R, 283S, 283T, 283V, 283W, 283Y, 284A, 284C, 284E, 284F, 284G, 284H, 284I, 284K, 284L, 284M, 284N, 284P, 284Q, 284R, 284S, 284T, 284V, 284W, 284Y, 285A, 285C, 285E, 285H, 285I, 285L, 285M, 285N, 285Q, 285S, 285T, 285V, 285Y, 286A, 286C, 286L, 286M, 286N, 286Q, 286T, 286V, 287A, 287C, 287D, 287E, 287F, 287G, 287H, 287I, 287K, 287L, 287M, 287N, 287P, 287Q, 287S, 287T, 287V, 287W, 287Y, 288A, 288C, 288I, 288M, 288T, 288V, 289A, 289S, 290F, 290H, 290M, 290Y, 291C, 291F, 291G, 291I, 291L, 291M, 291N, 291S, 291T, 291V, 292A, 292C, 292I, 292L, 292M, 292S, 292T, 292W, 293C, 293D, 293E, 293F, 293G, 293N, 293Q, 293S, 293V, 294C, 294G, 294M, 294N, 294S, 294T, 294V, 295A, 295C, 295G, 295T, 296A, 296C, 296F, 296G, 296H, 296K, 296M, 297A, 297C, 297D, 297E, 297F, 297G, 297H, 297I, 297K, 297L, 297M, 297N, 297P, 297Q, 297R, 297T, 297V, 297W, 297Y, 298C, 298D, 298E, 298F, 298H, 298I, 298K, 298L, 298M, 298N, 298P, 298Q, 298R, 298S, 298V, 298W, 299C, 299D, 299E, 299F, 299G, 299H, 299I, 299L, 299M, 299N, 299P, 299Q, 299V, 299W, 300A, 300C, 300F, 300H, 300I, 300K, 300L, 300M, 300N, 300Q, 300R, 300S, 300V, 300Y, 301C, 301D, 301F, 301H, 301I, 301K, 301L, 301M, 301Q, 301R, 301T, 301V, 302C, 302E, 302F, 302G, 302K, 302M, 302N, 302S, 302T, 303L, 303M, 303W, 303Y, 304C, 304E, 304G, 304L, 304N, 304Y, 305A, 305G, 305I, 305N, 305T, 305V, 307A, 307C, 307D, 307N, 307Q, 307T, 307V, 307Y, 308A, 308C, 308D, 308F, 308G, 308H, 308I, 308K, 308L, 308M, 308N, 308P, 308Q, 308R, 308S, 308T, 308V, 308W, 308Y, 309C, 309D, 309E, 309F, 309H, 309I, 309K, 309M, 309N, 309P, 309R, 309S, 309T, 309V, 309Y, 310A, 310D, 310E, 310F, 310H, 310I, 310L, 310M, 310N, 310P, 310Q, 310R, 310S, 310T, 310Y, 311A, 311C, 311D, 311E, 311F, 311H, 311K, 311L, 311M, 311N, 311P, 311Q, 311R, 311S, 311T, 311V, 311W, 311Y, 312A, 312C, 312D, 312E, 312F, 312G, 312H, 312I, 312K, 312L, 312M, 312P, 312Q, 312R, 312S, 312T, 312V, 312W, 312Y, 313A, 313C, 313D, 313E, 313F, 313H, 313I, 313K, 313L, 313M, 313N, 313P, 313Q, 313R, 313S, 313T, 313V, 313W, 313Y, 314A, 314C, 314D, 314F, 314G, 314H, 314K, 314L, 314M, 314Q, 314R, 314S, 314T, 314W, 314Y, 315C, 315D, 315E, 315H, 315I, 315K, 315L, 315M, 315N, 315P, 315Q, 315T, 315V, 316C, 316D, 316H, 316I, 316L, 316M, 316Y, 317A, 317C, 317D, 317E, 317F, 317G, 317H, 317I, 317K, 317L, 317N, 317Q, 317R, 317S, 317T, 317V, 317W, 317Y, 318D, 318F, 318H, 318I, 318K, 318L, 318M, 318N, 318R, 318S, 318T, 318V, 318W, 318Y, 319A, 319D, 319F, 319G, 319H, 319L, 319N, 319P, 319Q, 319S, 319V, 319W, 320A, 320C, 320D, 320F, 320G, 320H, 320I, 320K, 320L, 320M, 320N, 320P, 320Q, 320T, 320V, 320W, 320Y, 321A, 321C, 321D, 321E, 321F, 321G, 321H, 321I, 321K, 321L, 321M, 321N, 321P, 321R, 321S, 321T, 321V, 321W, 322L, 322M, 322V, 323A, 323C, 323H, 323N, 323R, 323S, 323T, 324A, 324C, 324E, 324F, 324G, 324H, 324I, 324K, 324L, 324M, 324N, 324P, 324Q, 324R, 324S, 324T, 324V, 324W, 324Y, 325A, 325C, 325D, 325F, 325G, 325H, 325I, 325K, 325L, 325M, 325N, 325P, 325T, 325V, 325W, 325Y, 326A, 326Q, 327C, 327D, 327F, 327G, 327H, 327K, 327N, 327P, 327R, 327T, 327V, 327Y, 328C, 328D, 328E, 328F, 328G, 328H, 328I, 328K, 328L, 328N, 328P, 328Q, 328R, 328S, 328T, 328V, 328W, 328Y, 329A, 329D, 329E, 329F, 329G, 329H, 329N, 329Q, 329R, 329S, 329T, 330A, 330C, 330H, 330L, 330M, 330S, 330W, 330Y, 331C, 331D, 331F, 331G, 331I, 331K, 331L, 331M, 331N, 331Q, 331R, 331S, 331T, 331V, 331Y, 332A, 332C, 332E, 332F, 332G, 332I, 332K, 332L, 332M, 332Q, 332R, 332S, 332V, 332Y, 333C, 333D, 333F, 333G, 333H, 333I, 333K, 333L, 333M, 333N, 333P, 333R, 333S, 333T, 333V, 333W, 333Y, 334C, 334D, 334F, 334G, 334H, 334I, 334L, 334M, 334N, 334Q, 334R, 334S, 334T, 334V, 334Y, 335A, 335L, 335M, 335Q, 335T, 335V, 336A, 336C, 336E, 336F, 336G, 336H, 336I, 336K, 336L, 336M, 336N, 336Q, 336R, 336S, 336V, 336W, 336Y, 337D, 337G, 337H, 337K, 337L, 337N, 337P, 337Q, 337R, 337S, 337V, 337W, 337Y, 338C, 338F, 338G, 338I, 338L, 338M, 338N, 338P, 338S, 338T, 339C, 339G, 339I, 339S, 339T, 339V, 340D, 340E, 340F, 340G, 340H, 340I, 340K, 340L, 340M, 340N, 340S, 340T, 340V, 340W, 341A, 341I, 341L, 341M, 341V, 341W, 341Y, 342A, 342D, 342E, 342F, 342G, 342K, 342L, 342M, 342N, 342R, 342S, 342V, 342Y, 343A, 343C, 343D, 343E, 343F, 343G, 343H, 343I, 343K, 343L, 343M, 343P, 343Q, 343S, 343T, 343V, 343W, 343Y, 344A, 344C, 344D, 344E, 344F, 344G, 344H, 344I, 344K, 344L, 344M, 344N, 344Q, 344R, 344S, 344T, 344W, 344Y, 345A, 345C, 345D, 345E, 345F, 345G, 345H, 345I, 345N, 345Q, 345S, 345T, 345V, 345W, 345Y, 346C, 346D, 346E, 346F, 346H, 346I, 346K, 346L, 346M, 346N, 346P, 346R, 346S, 346T, 346V, 346Y, 347A, 347C, 347D, 347E, 347F, 347H, 347I, 347K, 347L, 347M, 347N, 347P, 347Q, 347R, 347S, 347T, 347V, 347W, 347Y, 348C, 348F, 348G, 348H, 348I, 348K, 348M, 348N, 348P, 348R, 348S, 348T, 348V, 348W, 348Y, 349A, 349C, 349D, 349F, 349G, 349H, 349I, 349K, 349L, 349M, 349N, 349Q, 349R, 349S, 349T, 349V, 349W, 349Y, 350A, 350C, 350D, 350N, 350S, 351A, 351D, 351G, 351H, 351K, 351L, 351M, 351P, 351Q, 351R, 351S, 351T, 351V, 351W, 351Y, 352A, 352D, 352E, 352F, 352G, 352H, 352I, 352K, 352N, 352Q, 352R, 352T, 352V, 352W, 352Y, 353A, 353C, 353D, 353E, 353F, 353G, 353I, 353K, 353L, 353M, 353N, 353Q, 353R, 353T, 353V, 353W, 353Y, 354A, 354C, 354M, 354P, 354Q, 354S, 354T, 355C, 355D, 355E, 355F, 355G, 355I, 355K, 355L, 355M, 355N, 355T, 355V, 355W, 355Y, 356D, 356E, 356F, 356G, 356H, 356I, 356K, 356L, 356M, 356P, 356Q, 356T, 356W, 356Y, 357A, 357C, 357D, 357E, 357F, 357H, 357I, 357K, 357L, 357M, 357N, 357P, 357Q, 357R, 357S, 357T, 357V, 357W, 357Y, 358A, 358C, 358D, 358E, 358F, 358G, 358H, 358I, 358K, 358L, 358M, 358P, 358Q, 358R, 358S, 358T, 358V, 358W, 358Y, 359A, 359C, 359D, 359E, 359F, 359G, 359H, 359I, 359K, 359L, 359M, 359P, 359Q, 359R, 359S, 359T, 359V, 359W, 359Y, 360F, 360H, 360L, 360N, 360P, 360R, 360T, 360W, 361A, 361C, 361G, 361H, 361L, 361M, 361N, 361Q, 361S, 361T, 361V, 361W, 361Y, 362A, 362C, 362E, 362H, 362I, 362L, 362M, 362Q, 362S, 362T, 362V, 362Y, 363D, 363E, 363F, 363G, 363H, 363N, 363Q, 363R, 363S, 363V, 363W, 363Y, 364A, 364C, 364D, 364E, 364G, 364I, 364L, 364M, 364Q, 364S, 364T, 364V, 365A, 365C, 365D, 365F, 365G, 365I, 365K, 365L, 365M, 365N, 365R, 365S, 365T, 365V, 365W, 365Y, 366A, 366C, 366E, 366F, 366G, 366H, 366K, 366L, 366M, 366S, 366T, 366V, 367A, 367C, 367D, 367E, 367F, 367H, 367I, 367K, 367L, 367M, 367N, 367P, 367R, 367S, 367T, 367V, 367W, 367Y, 368D, 368F, 368G, 368I, 368K, 368L, 368M, 368N, 368P, 368Q, 368R, 368T, 368V, 368W, 368Y, 369A, 369C, 369D, 369E, 369F, 369G, 369I, 369K, 369L, 369M, 369N, 369P, 369Q, 369R, 369S, 369T, 369V, 369W, 369Y, 370A, 371A, 371C, 371F, 371G, 371H, 371I, 371L, 371M, 371N, 371Q, 371S, 371T, 371W, 371Y, 372A, 372C, 372G, 372I, 372L, 372M, 372N, 372Q, 372S, 372T, 373A, 373C, 373F, 373G, 373I, 373M, 373Q, 373S, 373T, 373V, 373W, 373Y, 374C, 374E, 374G, 374I, 374L, 374M, 374N, 374S, 374T, 374V, 375A, 375C, 375D, 375F, 375G, 375H, 375L, 375M, 375Q, 375S, 375T, 375V, 375W, 375Y, 376C, 376D, 376E, 376F, 376G, 376H, 376I, 376L, 376M, 376N, 376P, 376Q, 376S, 376T, 376V, 377F, 377H, 377I, 377K, 377L, 377P, 377T, 377W, 377Y, 378A, 378C, 378D, 378E, 378F, 378G, 378H, 378I, 378K, 378L, 378M, 378N, 378P, 378Q, 378R, 378T, 378V, 378W, 378Y, 379A, 379D, 379G, 379H, 379I, 379K, 379L, 379Q, 379T, 379W, 379Y, 380A, 380C, 380D, 380E, 380F, 380G, 380H, 380I, 380L, 380M, 380N, 380P, 380Q, 380R, 380T, 380V, 380W, 380Y, 381A, 381G, 381I, 381K, 381N, 381P, 381Q, 381R, 381S, 381T, 381W, 381Y, 382A, 382C, 382D, 382F, 382G, 382H, 382I, 382K, 382L, 382M, 382N, 382P, 382Q, 382R, 382T, 382V, 382W, 382Y, 383A, 383C, 383E, 383F, 383G, 383H, 383L, 383N, 383P, 383Q, 383S, 383T, 383V, 383W, 383Y, 384A, 384D, 384F, 384G, 384H, 384I, 384K, 384L, 384P, 384Q, 384S, 384T, 384V, 384W, 385A, 385C, 385D, 385E, 385F, 385G, 385H, 385I, 385K, 385L, 385M, 385N, 385P, 385Q, 385R, 385S, 385V, 385W, 385Y, 386C, 386D, 386F, 386G, 386H, 386I, 386L, 386N, 386P, 386R, 386S, 386T, 386V, 386W, 386Y, 387A, 387D, 387E, 387G, 387I, 387L, 387N, 387Q, 387S, 388A, 388C, 388D, 388E, 388F, 388G, 388H, 388I, 388L, 388M, 388N, 388P, 388Q, 388R, 388S, 388T, 388V, 388W, 388Y, 389C, 389E, 389F, 389H, 389I, 389K, 389M, 389N, 389Q, 389S, 389T, 389V, 389W, 389Y, 390A, 390C, 390D, 390E, 390F, 390G, 390H, 390I, 390K, 390L, 390M, 390N, 390R, 390S, 390T, 390V, 390W, 390Y, 391E, 391F, 391G, 391H, 391I, 391K, 391L, 391N, 391P, 391R, 391S, 391T, 391V, 391W, 391Y, 392A, 392C, 392D, 392E, 392F, 392H, 392K, 392L, 392M, 392N, 392Q, 392R, 392S, 392V, 392Y, 393A, 393C, 393D, 393F, 393G, 393H, 393I, 393L, 393M, 393P, 393Q, 393S, 393T, 393V, 393W, 393Y, 394A, 394C, 394E, 394F, 394H, 394I, 394K, 394L, 394M, 394N, 394P, 394Q, 394R, 394S, 394T, 394V, 394W, 395A, 395C, 395E, 395F, 395G, 395H, 395I, 395K, 395L, 395M, 395N, 395P, 395Q, 395R, 395S, 395T, 395V, 395W, 395Y, 396A, 396C, 396D, 396E, 396G, 396M, 396P, 396S, 396T, 397A, 397C, 397D, 397E, 397F, 397G, 397H, 397I, 397L, 397M, 397P, 397R, 397S, 397T, 397V, 397W, 398C, 398D, 398E, 398F, 398G, 398I, 398L, 398M, 398N, 398P, 398Q, 398R, 398S, 398T, 398V, 398W, 398Y, 399A, 399C, 399D, 399E, 399F, 399H, 399I, 399K, 399L, 399P, 399R, 399S, 399T, 399V, 399W, 399Y, 400C, 400D, 400E, 400F, 400G, 400H, 400I, 400K, 400L, 400M, 400N, 400P, 400Q, 400R, 400S, 400T, 400V, 400W, 400Y, 401A, 401C, 401D, 401E, 401F, 401H, 401I, 401K, 401L, 401M, 401N, 401P, 401Q, 401R, 401S, 401T, 401V, 401W, 401Y, 402A, 402C, 402D, 402E, 402F, 402G, 402H, 402I, 402K, 402L, 402M, 402N, 402P, 402Q, 402R, 402T, 402V, 402W, 402Y, 403A, 403C, 403E, 403G, 403H, 403I, 403M, 403N, 403Q, 403S, 403T, 403V, 403W, 403Y, 404D, 404E, 404F, 404G, 404H, 404I, 404L, 404M, 404N, 404P, 404R, 404T, 404V, 404W, 404Y, 405E, 405F, 405G, 405H, 405I, 405K, 405Q, 405S, 405T, 406D, 406F, 406L, 406T, 406Y, 407A, 407C, 407E, 407F, 407G, 407H, 407I, 407K, 407M, 407N, 407P, 407Q, 407R, 407S, 407T, 407V, 407W, 407Y, 408A, 408D, 408E, 408F, 408H, 408I, 408K, 408N, 408P, 408Q, 408S, 408T, 408V, 408Y, 409A, 409C, 409D, 409E, 409F, 409H, 409I, 409L, 409M, 409Q, 409R, 409T, 409V, 409W, 409Y, 410F, 410G, 410I, 410K, 410Q, 410S, 410T, 410V, 410W, 410Y, 411A, 411D, 411E, 411F, 411G, 411H, 411I, 411L, 411M, 411N, 411Q, 411R, 411S, 411V, 411W, 411Y, 412A, 412D, 412E, 412H, 412I, 412K, 412L, 412M, 412N, 412R, 412S, 412T, 412V, 412Y, 413C, 413E, 413F, 413G, 413I, 413L, 413M, 413N, 413P, 413R, 413S, 413V, 413W, 413Y, 414A, 414C, 414E, 414F, 414G, 414H, 414L, 414M, 414N, 414P, 414Q, 414T, 414V, 414W, 415D, 415E, 415F, 415G, 415H, 415I, 415K, 415P, 415Q, 415R, 415V, 415W, 416F, 416I, 416L, 416P, 416Q, 416R, 416T, 416V, 416Y, 417A, 417C, 417D, 417F, 417G, 417H, 417I, 417K, 417M, 417N, 417P, 417Q, 417S, 417W, 417Y, 418C, 418D, 418E, 418F, 418H, 418I, 418K, 418N, 418Q, 418R, 418T, 418W, 418Y, 419C, 419D, 419E, 419F, 419G, 419H, 419I, 419L, 419P, 419Q, 419S, 419T, 419Y, 420D, 420E, 420F, 420G, 420H, 420I, 420K, 420L, 420M, 420N, 420Q, 420R, 420S, 420T, 420V, 420W, 420Y, 421A, 421C, 421G, 421I, 421L, 421M, 421S, 421T, 422A, 422F, 422G, 422H, 422I, 422M, 422N, 422Q, 422S, 422V, 422W, 422Y, 423A, 423D, 423G, 423H, 423I, 423K, 423P, 423Q, 423R, 423T, 423V, 423W, 424D, 424E, 424G, 424I, 424K, 424M, 424N, 424Q, 424R, 424S, 424T, 424V, 424W, 424Y, 425A, 425I, 425K, 425L, 425M, 425S, 425T, 425V, 425W, and 425Y.

In some cases, the modification is a substitution of one or more amino residues present in the parental polypeptide to different amino acid residues as exemplified by: 1A, 1D, 1F, 1G, 1H, 1K, 1M, 1N, 1Q, 1R, 1S, 1T, 1V, 1W, 1Y, 2A, 2E, 2F, 2G, 2H, 2I, 2P, 2Q, 2R, 2S, 2W, 3D, 3E, 3F, 3G, 3H, 3I, 3K, 3L, 3M, 3N, 3P, 3Q, 3R, 3S, 3V, 3W, 3Y, 4D, 4E, 4F, 4G, 4I, 4K, 4L, 4Q, 4S, 4T, 4V, 4W, 5A, 5D, 5E, 5F, 5G, 5K, 5L, 5V, 5W, 6D, 6H, 6K, 6L, 6P, 6Q, 6S, 6V, 6W, 7A, 7D, 7E, 7H, 7N, 7Q, 7R, 7S, 8A, 8C, 8E, 8F, 8G, 8H, 8I, 8K, 8L, 8N, 8P, 8Q, 8R, 8T, 8V, 8W, 8Y, 9A, 9D, 9E, 9F, 9H, 9I, 9K, 9M, 9N, 9P, 9R, 9V, 9W, 9Y, 10I, 10L, 10M, 10P, 10S, 10V, 11A, 11F, 11M, 11V, 12I, 12M, 13A, 13D, 13Q, 14G, 14S, 14T, 14V, 15F, 16M, 16Q, 18G, 18N, 18R, 19H, 19W, 20A, 20D, 20F, 20G, 20H, 20I, 20K, 20M, 20R, 20S, 20V, 20W, 20Y, 21E, 21I, 21M, 21Q, 21S, 21V, 22I, 22T, 22V, 23A, 23D, 23E, 23F, 23G, 23H, 23I, 23L, 23M, 23N, 23R, 23S, 23T, 23V, 23W, 23Y, 24A, 24C, 24F, 24G, 24R, 24S, 24T, 24V, 24Y, 25E, 25F, 25K, 25L, 25R, 25S, 25T, 25V, 25W, 25Y, 26I, 26L, 27A, 27E, 27F, 27G, 27H, 27I, 27L, 27P, 27Q, 27R, 27S, 27T, 27V, 27W, 27Y, 28A, 28C, 28G, 28H, 28I, 28K, 28L, 28M, 28N, 28P, 28Q, 28R, 28S, 28V, 28W, 28Y, 29F, 29L, 29V, 30A, 30C, 30D, 30E, 30F, 30G, 30L, 30M, 30N, 30Q, 30R, 30S, 30T, 30V, 30W, 30Y, 31A, 31F, 31G, 31H, 31I, 31K, 31L, 31M, 31N, 31Q, 31S, 31T, 31V, 31Y, 32G, 32S, 33A, 33D, 33E, 33H, 33Q, 33S, 34W, 35A, 35F, 35G, 35H, 35I, 35L, 35M, 35N, 35Q, 35R, 35S, 35V, 35W, 36F, 36H, 36I, 36L, 36S, 36T, 36Y, 37L, 37V, 39A, 39P, 39S, 39V, 42V, 43A, 43S, 43T, 43V, 44A, 44D, 44E, 44F, 44G, 44H, 44I, 44K, 44N, 44R, 44S, 44T, 44Y, 45F, 45H, 45I, 45L, 45M, 45S, 45T, 46A, 46D, 46F, 46H, 46L, 46M, 46N, 46R, 47A, 47D, 47F, 47G, 47H, 47I, 47K, 47L, 47N, 47P, 47R, 47S, 47T, 47V, 47Y, 48A, 48E, 48F, 48H, 48N, 48P, 48W, 49A, 49F, 49G, 49H, 49K, 49L, 49Q, 49R, 49S, 49T, 49V, 49W, 49Y, 50E, 50F, 50H, 50I, 50K, 50L, 50M, 50P, 50R, 50S, 50T, 50V, 50W, 50Y, 51D, 51E, 51F, 51H, 51I, 51K, 51L, 51P, 51Q, 51R, 51S, 51T, 51V, 51W, 52E, 52F, 52G, 52H, 52I, 52K, 52L, 52M, 52N, 52Q, 52R, 52S, 52T, 52V, 52W, 52Y, 53A, 53E, 53F, 53H, 53I, 53L, 53P, 53R, 53S, 53T, 53V, 54A, 54C, 54F, 54G, 54H, 54L, 54N, 54P, 54R, 54T, 54W, 54Y, 55A, 55F, 55H, 55N, 55P, 55Q, 55S, 55T, 55Y, 56D, 56E, 56F, 56G, 56I, 56K, 56L, 56P, 56Q, 56R, 56T, 56V, 56W, 56Y, 57A, 57F, 57H, 57M, 57Q, 57R, 57S, 57Y, 58F, 59A, 59C, 59F, 59H, 59N, 59P, 59R, 59S, 59T, 59W, 60L, 60N, 63H, 63N, 64A, 64S, 65A, 65I, 65R, 66D, 66E, 66G, 66M, 66N, 66Q, 66R, 67A, 67F, 67G, 67I, 67L, 67N, 67Q, 67T, 67W, 68D, 68F, 68H, 68I, 68L, 68N, 68R, 68S, 68T, 68V, 68W, 69M, 69V, 72E, 72F, 72G, 72H, 72I, 72K, 72Q, 72S, 72T, 72V, 72W, 72Y, 73F, 73M, 73W, 74M, 74T, 76A, 76L, 76M, 76P, 76Q, 76R, 76Y, 77A, 77D, 77K, 77L, 77R, 77Y, 78D, 78E, 78F, 78G, 78H, 78I, 78K, 78L, 78P, 78R, 78S, 78T, 78W, 78Y, 79A, 79M, 79Q, 79S, 80M, 81E, 81G, 81H, 81L, 81M, 81N, 81Q, 81R, 81S, 81T, 81V, 81Y, 82D, 82F, 82G, 82I, 82K, 82L, 82M, 82Q, 82R, 82S, 82T, 82Y, 83A, 83F, 83L, 84A, 84N, 84S, 84T, 85D, 85E, 85F, 85G, 85I, 85K, 85R, 85S, 85T, 85V, 85W, 86D, 86E, 86F, 86G, 86I, 86K, 86L, 86M, 86N, 86Q, 86R, 86S, 86V, 86W, 86Y, 87G, 88A, 88D, 88F, 88G, 88H, 88K, 88L, 88M, 88N, 88Q, 88R, 88S, 88T, 88W, 88Y, 89D, 89F, 89G, 89H, 89I, 89K, 89L, 89M, 89N, 89P, 89Q, 89R, 89S, 89T, 89V, 89W, 89Y, 90D, 90E, 90F, 90H, 90I, 90K, 90M, 90N, 90P, 90S, 90T, 90V, 90W, 91D, 91E, 91H, 91K, 91N, 91Q, 91S, 92L, 92V, 93A, 93D, 93G, 93M, 93N, 93R, 93S, 93Y, 94I, 95F, 95M, 96I, 98C, 99I, 100C, 100F, 100M, 100V, 103A, 103C, 103V, 104A, 104S, 105C, 105D, 105E, 105F, 105G, 105M, 105W, 105Y, 106E, 106H, 106N, 106Q, 106S, 106T, 106Y, 107A, 107C, 107E, 107F, 107G, 107H, 107I, 107K, 107L, 107M, 107N, 107P, 107Q, 107R, 107S, 107T, 107V, 107W, 108C, 108D, 108E, 108F, 108G, 108H, 108I, 108K, 108L, 108N, 108P, 108R, 108S, 108T, 108V, 108W, 108Y, 109D, 109H, 109I, 109K, 109L, 109N, 109R, 109S, 109V, 109W, 109Y, 110V, 111C, 111E, 111F, 111G, 111H, 111K, 111L, 111M, 111N, 111Q, 111R, 111T, 112A, 112D, 112E, 112H, 112K, 112L, 112R, 112S, 112T, 112W, 112Y, 113A, 114L, 115A, 115H, 115I, 115L, 115R, 115V, 115Y, 116A, 116F, 116G, 116H, 116I, 116L, 116N, 116Q, 116R, 116T, 116V, 116W, 116Y, 118D, 118F, 118G, 118H, 118K, 118L, 118M, 118N, 118Q, 118R, 118S, 118T, 118V, 118W, 118Y, 119E, 119F, 119I, 119K, 119L, 119M, 119Q, 119S, 119T, 119Y, 121S, 124A, 124K, 124Q, 124R, 124S, 124T, 125A, 125D, 125F, 125I, 125K, 125Q, 125R, 125V, 125Y, 126A, 126C, 126D, 126F, 126G, 126H, 126I, 126K, 126L, 126N, 126P, 126R, 126S, 126T, 126V, 126W, 126Y, 128A, 128C, 128E, 128F, 128G, 128H, 128I, 128L, 128M, 128N, 128Q, 128R, 128S, 128T, 128V, 129C, 129D, 129E, 130A, 130F, 130L, 130T, 130Y, 131A, 131C, 131D, 131F, 131G, 131H, 131I, 131K, 131L, 131N, 131Q, 131T, 131V, 131W, 131Y, 132I, 132N, 132S, 132W, 134E, 134F, 134L, 134M, 134R, 134Y, 135E, 136L, 140A, 141F, 141H, 142C, 142D, 142F, 142G, 142H, 142I, 142K, 142M, 142Q, 142R, 142S, 142T, 142W, 142Y, 143C, 143D, 143K, 143L, 143N, 143Q, 143S, 144T, 147F, 147L, 150H, 151C, 151D, 151E, 151G, 151H, 151K, 151L, 151M, 151Q, 151S, 151T, 152A, 152C, 152E, 152F, 152G, 152H, 152I, 152K, 152L, 152M, 152N, 152P, 152Q, 152R, 152S, 152V, 152W, 152Y, 153E, 153F, 153H, 153K, 153L, 153N, 153R, 153T, 153V, 153W, 153Y, 154A, 155M, 156A, 156F, 156G, 156K, 156L, 156Q, 156R, 156V, 156Y, 157F, 157H, 158A, 158I, 158M, 158T, 158V, 159H, 159I, 159L, 159M, 160A, 160C, 160D, 160E, 160F, 160G, 160H, 160I, 160K, 160L, 160M, 160Q, 160S, 160T, 160V, 162I, 162M, 163A, 163E, 163F, 163G, 163H, 163I, 163L, 163N, 163Q, 163R, 163S, 163T, 163V, 163Y, 164H, 164L, 164N, 164S, 164T, 164V, 164W, 164Y, 165C, 165I, 165L, 165M, 165T, 165V, 166C, 166I, 166M, 166V, 167A, 167C, 167E, 167F, 167G, 167I, 167K, 167L, 167M, 167Q, 167R, 167S, 167T, 167V, 167W, 167Y, 168C, 168E, 168F, 168G, 168K, 168L, 168M, 168N, 168S, 168T, 168V, 168W, 168Y, 170C, 171E, 171H, 171I, 171M, 171N, 171Q, 171R, 172A, 175Y, 179A, 179C, 179G, 179H, 179S, 179W, 180M, 181V, 184D, 186E, 187E, 187F, 187H, 187I, 187K, 187M, 187Q, 187S, 187V, 187W, 188A, 188D, 188F, 188G, 188I, 188K, 188L, 188M, 188P, 188Q, 188R, 188T, 188V, 189F, 189W, 190H, 190K, 190Q, 190R, 190S, 192G, 192K, 192L, 192P, 192S, 192V, 195D, 195F, 195G, 195H, 195K, 195M, 195R, 195V, 195W, 196A, 196C, 196E, 196F, 196H, 196I, 196K, 196L, 196M, 196Q, 196R, 196S, 196T, 196V, 196Y, 197L, 197V, 198A, 198C, 198I, 198L, 198V, 199C, 199D, 199E, 199F, 199H, 199R, 199S, 199T, 199Y, 200I, 200N, 200S, 200V, 201C, 201D, 201E, 201F, 201G, 201H, 201I, 201K, 201L, 201N, 201Q, 201R, 201T, 201V, 201W, 201Y, 202C, 202V, 203A, 203C, 203F, 203G, 203I, 203K, 203L, 203Q, 203R, 203S, 203T, 203V, 203W, 203Y, 204I, 204M, 204W, 204Y, 205A, 205C, 205I, 205L, 205M, 205N, 205V, 207A, 209L, 209V, 211H, 211S, 211T, 212G, 212N, 213A, 213E, 213F, 213G, 213I, 213K, 213L, 213M, 213P, 213Q, 213R, 213T, 213V, 214C, 214D, 214F, 214G, 214I, 214K, 214L, 214M, 214N, 214Q, 214R, 214S, 214T, 214V, 214W, 214Y, 217I, 217Q, 217T, 218C, 218D, 218E, 218F, 218G, 218H, 218I, 218K, 218L, 218M, 218P, 218Q, 218R, 218S, 218T, 218V, 218W, 218Y, 219D, 219F, 219G, 219H, 219I, 219N, 219Q, 219S, 219T, 219V, 219Y, 221C, 221E, 221G, 221Q, 221S, 221V, 222F, 222T, 223H, 223L, 223M, 223W, 224I, 225E, 225F, 225N, 225P, 225Q, 225T, 225Y, 226I, 226L, 229D, 229E, 229N, 229T, 230A, 230D, 230E, 230F, 230H, 230I, 230K, 230M, 230Q, 230R, 230S, 230V, 230Y, 231H, 231W, 232S, 233A, 233D, 233E, 233F, 233G, 233I, 233K, 233L, 233M, 233N, 233Q, 233S, 233T, 233V, 233W, 233Y, 234A, 234F, 234G, 234H, 234I, 234L, 234M, 234N, 234Q, 234R, 234T, 234V, 234W, 234Y, 235L, 235M, 236A, 236G, 236I, 236L, 236M, 236N, 236Q, 237C, 237D, 237E, 237F, 237G, 237H, 237I, 237K, 237L, 237R, 237T, 237V, 237W, 237Y, 238C, 238E, 238G, 238N, 238R, 238S, 238W, 239I, 239M, 240A, 240E, 240F, 240G, 240L, 240Q, 240R, 240T, 240V, 240Y, 241F, 241G, 241H, 241I, 241K, 241L, 241R, 241S, 241T, 241V, 241W, 241Y, 242A, 242C, 242D, 242F, 242I, 242K, 242L, 242S, 242T, 242V, 242W, 242Y, 243D, 243E, 243F, 243G, 243H, 243I, 243K, 243L, 243M, 243Q, 243R, 243S, 243T, 243V, 243W, 243Y, 244I, 244M, 244W, 244V, 245C, 245F, 245H, 245I, 245L, 245M, 245N, 245P, 245R, 245T, 245V, 245W, 245Y, 246C, 246D, 246E, 246G, 246I, 246L, 246Q, 246W, 246Y, 247F, 247G, 247H, 247I, 247L, 247M, 247N, 247Q, 247T, 247V, 247Y, 248F, 248G, 248K, 248L, 248Q, 248R, 248S, 248T, 248V, 248W, 249A, 249C, 249F, 249L, 249M, 249V, 250C, 250E, 250F, 250G, 250H, 250I, 250K, 250L, 250M, 250T, 250V, 250W, 250Y, 251A, 251C, 251D, 251E, 251G, 251K, 251L, 251M, 251P, 251Q, 251V, 251Y, 252F, 252L, 252W, 253F, 253I, 253K, 253L, 253M, 253R, 253T, 253W, 253Y, 254A, 254F, 254G, 254H, 254I, 254L, 254N, 254T, 254V, 254Y, 255A, 255E, 255I, 255K, 255P, 255R, 255S, 255V, 256A, 256C, 256I, 257E, 257I, 257L, 257P, 258C, 258D, 258E, 258N, 258Q, 258R, 258S, 258V, 259A, 259G, 259H, 259K, 259Q, 259R, 259S, 259T, 259W, 260A, 260C, 260D, 260F, 260H, 260N, 260Q, 260R, 260S, 260Y, 261M, 262I, 263C, 263L, 263M, 263S, 263V, 264E, 264H, 264I, 264L, 264Y, 267A, 267C, 267N, 267T, 268M, 268Q, 270F, 270G, 270N, 270S, 270V, 271F, 272G, 272L, 272S, 272V, 273G, 273I, 273L, 273T, 273Y, 274F, 274G, 274H, 274I, 274K, 274L, 274M, 274N, 274P, 274Q, 274R, 274S, 274T, 274V, 274W, 274Y, 275G, 275H, 275K, 275P, 275Q, 275R, 275S, 275T, 275V, 276A, 276C, 276D, 276F, 276G, 276H, 276I, 276K, 276L, 276M, 276N, 276P, 276Q, 276R, 276S, 276T, 276Y, 277A, 277D, 277F, 277G, 277H, 277I, 277K, 277L, 277N, 277P, 277Q, 277R, 277S, 277T, 277V, 277Y, 279H, 279K, 279L, 279M, 279N, 279Q, 279Y, 280F, 280Y, 281C, 281L, 282A, 282D, 282I, 282K, 282L, 282M, 282N, 282Q, 282T, 282W, 282Y, 283C, 283G, 283H, 283P, 283R, 283S, 283T, 283V, 283W, 284A, 284C, 284E, 284F, 284G, 284H, 284I, 284K, 284L, 284N, 284R, 284S, 284T, 284V, 284W, 284Y, 285E, 285M, 286C, 286L, 286M, 286V, 287A, 287C, 287E, 287H, 287I, 287K, 287L, 287M, 287Q, 287S, 287T, 287V, 288C, 288I, 288M, 288V, 289A, 290Y, 291C, 291G, 291L, 291S, 291T, 292A, 292C, 292I, 292L, 292T, 293C, 293V, 294C, 294G, 294S, 294T, 295A, 295G, 297D, 297E, 297F, 297G, 297H, 297I, 297K, 297L, 297M, 297N, 297P, 297Q, 297R, 297T, 297V, 297W, 298C, 298D, 298E, 298F, 298H, 298I, 298K, 298L, 298M, 298N, 298P, 298Q, 298R, 298S, 298V, 298W, 299C, 299G, 299I, 299N, 299V, 300H, 300M, 300R, 300V, 301I, 301K, 301L, 301M, 301T, 302T, 303M, 304L, 304Y, 305T, 305V, 307C, 307N, 308C, 308F, 308G, 308H, 308I, 308K, 308L, 308M, 308N, 308P, 308Q, 308R, 308S, 308T, 308V, 308W, 308Y, 309D, 309E, 309F, 309H, 309K, 309R, 309S, 310A, 311A, 311H, 311K, 311R, 312D, 312F, 312G, 312H, 312I, 312K, 312L, 312M, 312P, 312Q, 312R, 312S, 312T, 312V, 312W, 312Y, 313A, 313D, 313E, 313F, 313K, 313L, 313N, 313Q, 313R, 313S, 313W, 313Y, 314A, 314F, 314H, 314K, 314L, 314M, 314Q, 314R, 314S, 314T, 314W, 314Y, 315K, 315N, 315P, 315T, 316Y, 317A, 317C, 317E, 317F, 317H, 317K, 317L, 317R, 317S, 317T, 317V, 317W, 317Y, 318D, 318F, 318H, 318I, 318K, 318L, 318M, 318N, 318R, 318S, 318T, 318V, 318W, 318Y, 319G, 319L, 319N, 319Q, 319V, 319W, 320C, 320F, 320G, 320I, 320K, 320L, 320M, 320P, 320Q, 320T, 320V, 320Y, 321C, 321D, 321E, 321F, 321G, 321H, 321I, 321K, 321L, 321R, 321S, 321T, 321V, 321W, 322L, 322M, 322V, 324A, 324F, 324G, 324H, 324I, 324K, 324L, 324M, 324N, 324Q, 324R, 324S, 324T, 324V, 324W, 324Y, 325C, 325D, 325G, 325H, 325I, 325K, 325L, 325M, 325N, 325P, 325T, 325V, 327C, 327D, 327G, 327H, 327N, 327T, 328D, 328E, 328F, 328L, 328N, 328Q, 328Y, 329F, 329H, 329Q, 330W, 330Y, 331D, 331F, 331G, 331I, 331L, 331Q, 331S, 331T, 331V, 331Y, 332A, 332C, 332G, 332Q, 332S, 333C, 333G, 333H, 333K, 333L, 333M, 333R, 333S, 333W, 333Y, 334D, 334H, 334I, 334L, 334M, 334N, 334R, 334T, 335V, 336A, 336C, 336F, 336G, 336I, 336M, 336N, 336Q, 336R, 336V, 336W, 336Y, 337H, 337N, 337S, 337V, 337W, 337Y, 338G, 338I, 338L, 338M, 338S, 338T, 339C, 340F, 340H, 340K, 340L, 340M, 340N, 340S, 340T, 340V, 340W, 341A, 341L, 341Y, 342A, 342K, 342N, 342R, 342Y, 343A, 343D, 343E, 343F, 343H, 343K, 343L, 343M, 343Q, 343S, 343T, 343W, 343Y, 344A, 344D, 344E, 344F, 344G, 344I, 344K, 344L, 344M, 344N, 344Q, 344R, 344S, 344T, 344W, 344Y, 345C, 345E, 345F, 345G, 345H, 345I, 345N, 345Q, 345S, 345T, 345V, 346C, 346D, 346E, 346I, 346K, 346L, 346M, 346N, 346S, 346T, 346V, 346Y, 347D, 347F, 347H, 347I, 347K, 347L, 347M, 347Q, 347R, 347S, 347T, 347V, 347W, 348F, 348H, 348I, 348K, 348R, 348S, 348T, 348V, 348W, 348Y, 349A, 349F, 349G, 349I, 349K, 349M, 349N, 349R, 349S, 349V, 349W, 349Y, 350D, 351A, 351D, 351G, 351H, 351K, 351L, 351M, 351P, 351Q, 351R, 351T, 351V, 351W, 351Y, 352A, 352H, 352Q, 352T, 352Y, 353A, 353D, 353E, 353G, 353I, 353K, 353L, 353M, 353Q, 353V, 353W, 353Y, 355C, 355F, 355I, 355L, 355M, 355V, 355Y, 356D, 356F, 356G, 356I, 356K, 356L, 356P, 356Q, 356T, 356W, 356Y, 357A, 357H, 357I, 357K, 357L, 357N, 357Q, 357R, 357S, 357T, 357V, 357W, 357Y, 358C, 358D, 358F, 358G, 358I, 358K, 358L, 358M, 358Q, 358R, 358S, 358T, 358V, 358Y, 359D, 359E, 359H, 359L, 359M, 359P, 359Q, 359R, 359T, 359V, 359W, 360F, 360P, 360T, 361C, 361L, 361M, 361N, 361Q, 361S, 361T, 361V, 362A, 362C, 362I, 362L, 362V, 362Y, 363D, 363G, 363H, 363Q, 363R, 363S, 363V, 363W, 363Y, 364A, 364C, 364G, 364I, 364L, 364M, 364Q, 364S, 364T, 364V, 365C, 365I, 365K, 365L, 365N, 365R, 365S, 365V, 366A, 366K, 367L, 367M, 367N, 367R, 367S, 367T, 367W, 367Y, 368G, 368I, 368K, 368L, 368R, 368T, 368V, 368W, 369C, 369D, 369E, 369F, 369G, 369I, 369K, 369L, 369N, 369Q, 369S, 369T, 369V, 369Y, 371A, 371C, 371F, 371I, 371L, 371M, 371N, 371S, 371T, 371Y, 372A, 372C, 372I, 372L, 372N, 372S, 372T, 373A, 373C, 373F, 373I, 373M, 373T, 373V, 374C, 374G, 374I, 374M, 374S, 374T, 374V, 375A, 375C, 375D, 375F, 375H, 375L, 375M, 375Q, 375S, 375T, 375Y, 376G, 376I, 376S, 376T, 376V, 377F, 377H, 377L, 377T, 377W, 377Y, 378C, 378E, 378F, 378G, 378H, 378I, 378K, 378L, 378M, 378N, 378Q, 378R, 378T, 378V, 378W, 378Y, 379A, 379G, 379H, 379I, 379K, 379L, 379Q, 379T, 379Y, 380C, 380E, 380F, 380G, 380H, 380L, 380M, 380N, 380P, 380Q, 380R, 380T, 380V, 380W, 380Y, 381G, 381I, 381Q, 381R, 381S, 381T, 381W, 381Y, 382A, 382C, 382F, 382I, 382K, 382Q, 382R, 382T, 382W, 382Y, 383A, 383F, 383L, 383P, 383Q, 383V, 384A, 384G, 384H, 384I, 384K, 384P, 384Q, 384V, 384W, 385C, 385F, 385H, 385I, 385K, 385L, 385N, 385P, 385Q, 385R, 385S, 385V, 385W, 385Y, 386D, 386F, 386G, 386H, 386L, 386N, 386R, 386S, 386T, 386V, 386W, 386Y, 387I, 387L, 388A, 388C, 388G, 388H, 388L, 388P, 388S, 388T, 388W, 388Y, 389C, 389F, 389I, 389M, 389Q, 389V, 390F, 390I, 390K, 390L, 390N, 390R, 390S, 390T, 390V, 390W, 390Y, 391F, 391K, 391N, 391P, 391R, 391T, 391W, 391Y, 392A, 392C, 392D, 392E, 392F, 392H, 392K, 392L, 392N, 392Q, 392R, 392S, 392V, 392Y, 393A, 393C, 393D, 393F, 393G, 393H, 393I, 393L, 393Q, 393S, 393T, 393V, 393W, 393Y, 394A, 394C, 394F, 394H, 394I, 394K, 394L, 394Q, 394V, 394W, 395F, 395G, 395H, 395K, 395L, 395Q, 395R, 395S, 395T, 395V, 395W, 395Y, 396C, 396D, 396S, 397C, 397D, 397F, 397G, 397H, 397I, 397L, 397P, 397S, 397T, 397V, 397W, 398C, 398G, 398N, 398S, 398T, 398V, 399C, 399F, 399I, 399K, 399L, 399R, 399S, 399T, 399V, 399W, 399Y, 400C, 400D, 400E, 400F, 400G, 400H, 400I, 400K, 400L, 400M, 400Q, 400R, 400S, 400T, 400V, 400W, 400Y, 401A, 401C, 401D, 401E, 401F, 401I, 401K, 401L, 401M, 401N, 401Q, 401R, 401S, 401T, 401V, 401W, 401Y, 402A, 402C, 402D, 402E, 402F, 402G, 402H, 402I, 402K, 402L, 402M, 402N, 402P, 402Q, 402R, 402T, 402V, 402W, 402Y, 403A, 403C, 403H, 403I, 403M, 403V, 403W, 403Y, 404F, 404H, 404M, 404R, 404T, 404V, 404W, 404Y, 405G, 405Q, 405S, 405T, 406L, 406T, 407F, 407G, 407H, 407I, 407K, 407M, 407Q, 407R, 407S, 407T, 407V, 407W, 407Y, 408D, 408E, 408F, 408N, 408V, 409C, 409F, 409I, 409L, 409R, 409T, 409V, 409W, 409Y, 410V, 411E, 411F, 411M, 411Q, 411R, 411S, 411Y, 412N, 412T, 413C, 413F, 413G, 413I, 413L, 413P, 413R, 413S, 413V, 413W, 413Y, 414H, 414L, 414N, 414Q, 414T, 414V, 414W, 415D, 415E, 415G, 415I, 415R, 415V, 415W, 416F, 416L, 416Q, 416Y, 417A, 417C, 417D, 417F, 417G, 417H, 417I, 417K, 417M, 417N, 417Q, 418D, 418F, 418H, 418I, 418K, 418N, 418W, 418Y, 419E, 419F, 419H, 419I, 419L, 419S, 419T, 420D, 420E, 420F, 420G, 420H, 420I, 420K, 420L, 420Q, 420S, 420T, 420V, 420W, 420Y, 421C, 421L, 421M, 421S, 421T, 422F, 422I, 422S, 422W, 423D, 423I, 423Q, 423R, 423T, 424M, 424Q, 424R, 424V, 424Y, 425A, 425I, 425K, 425L, 425V, and 425Y.

In some case, the substitution are selected from 052D, 052E, 052I, 052K, 052L, 052N, 052Q, 052R, 052V, 056D, 056E, 056I, 056K, 056L, 056N, 056Q, 056R, 056V, 089D, 089E, 089I, 089K, 089L, 089N, 089Q, 089R, 089V, 152D, 152E, 152I, 152K, 152L, 152N, 152Q, 152R, 152V, 153D, 153E, 153I, 153K, 153L, 153N, 153Q, 153R, 153V, 201D, 201E, 201I, 201K, 201L, 201N, 201Q, 201R, 201V, 251D, 251E, 251I, 251K, 251L, 251N, 251Q, 251R, 251V, 284D, 284E, 284I, 284K, 284L, 284N, 284Q, 284R, 284V, 297D, 297E, 297I, 297K, 297L, 297N, 297Q, 297R, 297V, 308D, 308E, 308I, 308K, 308L, 308N, 308Q, 308R, 308V, 321D, 321E, 321I, 321K, 321L, 321N, 321Q, 321R, 321V, 328D, 328E, 328I, 328K, 328L, 328N, 328Q, 328R, 328V, 347D, 347E, 347I, 347K, 347L, 347N, 347Q, 347R, 347V, 357D, 357E, 357I, 357K, 357L, 357N, 357Q, 357R, 357V, 359D, 359E, 359I, 359K, 359L, 359N, 359Q, 359R, 359V, 369D, 369E, 369I, 369K, 369L, 369N, 369Q, 369R, 369V, 385D, 385E, 385I, 385K, 385L, 385N, 385Q, 385R, 385V, 388D, 388E, 388I, 388K, 388L, 388N, 388Q, 388R, 388V, 391D, 391E, 391I, 391K, 391L, 391N, 391Q, 391R, 391V, 400D, 400E, 400I, 400K, 400L, 400N, 400Q, 400R, 400V, 416D, 416E, 416I, 416K, 416L, 416N, 416Q, 416R, and 416V, which mutations have PI values >0.5 for both protein and activity.

Substitutions that changed the amino acid residue present at position 153 of the parental AmyE polypeptide to N, K or F exhibited increased ability to convert maltose and maltoheptaose substrates to glucose. Substitutions that changed the amino acid residue present at position 153 of the parental AmyE polypeptide to K exhibited increased ability to convert a DP7 substrate to glucose.

The substitutions L142F, L142G, L142Q, L142S, L142W, L142Y, A2141, A214V, S245Y, Q126F, Q126L, Q126P, Q126V, S131L, and S2541, improved starch liquefaction performance in the context of the full-length AmyE polypeptide. The substitutions W60L, W60M, W60N, I100F, I100M, S105M, S105W, G207A, T270A, T270E, T270L, T270N, T270V, and T279A, improved starch liquefaction performance in the context of the truncated AmyE polypeptide.

Substitutions as one or more of positions 052D, 052E, 052I, 052K, 052L, 052N, 052Q, 052R, 052V, 056D, 056E, 056I, 056K, 056L, 056N, 056Q, 056R, 056V, 089D, 089E, 089I, 089K, 089L, 089N, 089Q, 089R, 089V, 152D, 152E, 152I, 152K, 152L, 152N, 152Q, 152R, 152V, 153D, 153E, 153I, 153K, 153L, 153N, 153Q, 153R, 153V, 201D, 201E, 201I, 201K, 201L, 201N, 201Q, 201R, 201V, 251D, 251E, 251I, 251K, 251L, 251N, 251Q, 251R, 251V, 284D, 284E, 284I, 284K, 284L, 284N, 284Q, 284R, 284V, 297D, 297E, 297I, 297K, 297L, 297N, 297Q, 297R, 297V, 308D, 308E, 308I, 308K, 308L, 308N, 308Q, 308R, 308V, 321D, 321E, 321I, 321K, 321L, 321N, 321Q, 321R, 321V, 328D, 328E, 328I, 328K, 328L, 328N, 328Q, 328R, 328V, 347D, 347E, 347I, 347K, 347L, 347N, 347Q, 347R, 347V, 357D, 357E, 357I, 357K, 357L, 357N, 357Q, 357R, 357V, 359D, 359E, 359I, 359K, 359L, 359N, 359Q, 359R, 359V, 369D, 369E, 369I, 369K, 369L, 369N, 369Q, 369R, 369V, 385D, 385E, 385I, 385K, 385L, 385N, 385Q, 385R, 385V, 388D, 388E, 388I, 388K, 388L, 388N, 388Q, 388R, 388V, 391D, 391E, 391I, 391K, 391L, 391N, 391Q, 391R, 391V, 400D, 400E, 400I, 400K, 400L, 400N, 400Q, 400R, 400V, 416D, 416E, 416I, 416K, 416L, 416N, 416Q, 416R, and 416V, have PI values >0.5 for both protein and activity, and are expected to be combinable for affecting various properties of AmyE polypeptides.

While many position of the AmyE polypeptides can be mutated, positions 75, 97, 101, 102, 120, 123, 133, 137, 182, 266, and 306, of AmyE polypeptides were restrictive, in the sense that mutations at these position generally decrease performance. In particular, positions 75 and 123 were determined to be fully restrictive for performance in a truncated version of the parental polypeptide, while positions 75, 97, 101, 102, 120, 133, 137, 182, 266, and 306 were determined to be fully restrictive for performance in a full-length version of the parental polypeptide.

Note that while many mutation are listed in the context of large groups and subgroups, each mutation is a separate entity and any one or more of the identified mutations can be included or excluded from a further subgroup of mutations. According, the composition and methods include AmyE variants having any one or more variants described herein, or combinations thereof.

3. Production of AmyE Polypeptides

A DNA sequence encoding an AmyE polypeptide can be expressed, in enzyme form, using an expression vector which typically includes control sequences encoding a suitable promoter, operator, ribosome binding site, translation initiation signal, and, optionally, a repressor gene or various activator genes.

Vectors comprising the nucleic acids encoding AmyE or variants thereof also are provided. Host cells comprising the vectors are provided. The host cell may express the polynucleotide encoding the AmyE variant. The host may be a *Bacillus* sp., e.g., *B. subtilis*.

3.1 Polynucleotides and Vectors

Aspect of the present compositions and methods include polynucleotides encoding AmyE polypeptides, as well as vectors and host cells useful for expressing AmyE polypeptides based on such polynucleotides. Nucleic acids encoding AmyE polypeptides include, but are not limited to, the polynucleotides of SEQ ID NO: 5 and SEQ ID NO: 6, which encode the AmyE of SEQ ID NO: 1 and AmyE-tr (SEQ ID NO: 2), respectively, and variants thereof. Further representative polynucleotides include that of SEQ ID NO: 7, which encodes Amy31A (SEQ ID NO: 3). The AmyE disclosed in NCBI Accession Nos. ABK54355, AAF14358, AAT01440, AAZ30064, NP_388186, AAQ83841, and BAA31528 are similarly encoded by polynucleotides disclosed in publicly accessible databases, which sequences are incorporated herein by reference. Nucleic acids may be DNA, mRNA, or cDNA sequences. Nucleic acids further include degenerate sequences corresponding to any of the aforementioned nucleic acids. Degenerate sequences may be designed for optimal expression by using codons preferred by a particular host organism.

Recombinant expression vector carrying DNA sequence encoding AmyE polypeptides (including variants) may be any vector that may conveniently be subjected to recombinant DNA procedures, and the choice of vector will often depend on the host cell into which it is to be introduced. Thus, the vector may be an autonomously replicating vector, i.e., a vector that exists as an extrachromosomal entity, the replication of which is independent of chromosomal replication, e.g., a plasmid, a bacteriophage or an extrachromosomal element, mini-chromosome or an artificial chromosome. Alternatively, the vector may be one which, when introduced into a host cell, is integrated into the host cell genome and replicated together with the chromosome(s) into which it has been integrated. The integrated gene may also be amplified to create multiple copies of the gene in the chromosome by use of an amplifiable construct driven by antibiotic selection or other selective pressure, such as an essential regulatory gene or by complementation of an essential metabolic pathway gene.

An expression vector typically includes the components of a cloning vector, e.g., an element that permits autonomous replication of the vector in the selected host organism and one or more phenotypically detectable markers for selection purposes. The expression vector normally comprises control nucleotide sequences encoding a promoter, operator, ribosome binding site, translation initiation signal and optionally, a repressor gene or one or more activator genes. In one aspect, all the signal sequences used target the material to the cell culture media for easier enzyme collection and optionally purification. The procedures used to ligate the DNA construct encoding an AmyE or variant thereof, the promoter, terminator and other elements, respectively, and to insert them into suitable vectors containing the information necessary for replication, are well known to persons skilled in the art (see e.g., Sambrook et al., MOLECULAR CLONING: A LABORATORY MANUAL, $2^{nd}$ ed., Cold Spring Harbor, 1989 and $3^{rd}$ ed., 2001).

In the vector, the DNA sequence should be operably connected to a suitable promoter sequence. The promoter may be any DNA sequence that shows transcriptional activity in the host cell of choice and may be derived from genes encoding proteins either homologous or heterologous to the host cell. Suitable promoters for directing the transcription of the DNA sequence encoding an AmyE or variant thereof, especially in a bacterial host, include various *Bacillus*-derived promoters, such as an α-amylase promoter derived from *B. subtilis*, *B. licheniformis*, *B. stearothermophilus*, or *B. amyloliquefaciens*, the promoter of the lac operon of *E. coli*, the *Streptomyces coelicolor* agarase gene dagA or celA promoters, and the promoters of the *Bacillus subtilis* xylA and xylB genes, etc. For transcription in a fungal host, examples of useful promoters are those derived from the gene encoding *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase, or *A. nidulans* acetamidase. When the gene encoding the AmyE or variant thereof is expressed in a bacterial species such as *E. coli*, a suitable promoter can be selected, for example, from a bacteriophage promoter including a T7 promoter and a phage lambda promoter. Examples of suitable promoters for the expression in a yeast species include but are not limited to the Gal 1 and Gal 10 promoters of *Saccharomyces cerevisiae* and the *Pichia pastoris* AOX1 or AOX2 promoters.

The expression vector may also comprise a suitable transcription terminator and, in eukaryotes, polyadenylation sequences operably connected to the DNA sequence encoding the α-amylase variant. Termination and polyadenylation sequences may suitably be derived from the same sources as the promoter. The vector may further comprise a DNA sequence enabling the vector to replicate in the host cell in question. Examples of such sequences are the origins of replication of plasmids pUC19, pACYC177, pUB110, pE194, pAMB1, pICatH, and pIJ702.

The vector may also comprise a selectable marker, e.g., a gene the product of which complements a defect in the host cell, such as the dal genes from *B. subtilis* or *B. licheniformis*, or a gene which confers antibiotic resistance, e.g., ampicillin, kanamycin, chloramphenicol or tetracyclin resistance. Furthermore, the vector may comprise *Aspergillus* selection markers such as amdS, argB, niaD, and xxsC, a marker giving rise to hygromycin resistance, or the selection may be accomplished by co-transformation as known in the art. See, e.g., WO 91/17243.

3.2 AmyE Polypeptide Expression and Host Organisms

It is generally advantageous if the AmyE polypeptide is secreted into the culture medium, when expressed in a host cell. To this end, the AmyE polypeptide may comprise a signal sequence that permits secretion of the expressed enzyme into the culture medium. The signal sequence may encoded by the same gene as the AmyE. For example, the AmyE set forth in SEQ ID NO: 1 is expressed naturally with a signal sequence and additional N-terminal amino acids having the sequence MFAKRFKTSLLPLFAGFLLLFHLV-LAGPAAASAETANKSNE (SEQ ID NO: 9). The signal sequence alternatively may be a *B. subtilis* sp. signal sequence from a different AmyE or even a different protein. Further, the signal sequence may be from a different species, e.g., *B. licheniformis*. The signal sequence may be chosen to provide optimal expression of the AmyE or variant thereof in a particular host cell, for example. The mature AmyE may be produced as a result of proteolytic cleavage of additional sequences from the N-terminus that are not signal sequences. For example, a 31-amino acid residue signal sequence from *B. licheniformis* ("LAT leader sequence") may be fused in frame with an AmyE sequence. For example, a nucleic acid encoding AmyE is operably linked to a *B. licheniformis* signal sequence in the expression vector shown in FIG. 2.

An isolated cell, either comprising a DNA construct or an expression vector, is advantageously used as a host cell in the recombinant production of an AmyE or variant thereof. The cell may be transformed with the DNA construct encoding the AmyE or variant thereof, optionally by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

Examples of suitable bacterial host organisms are Gram positive bacterial species such as Bacillaceae, including *B. subtilis, B. licheniformis, B. lentus, B. brevis, B. stearothermophilus, B. alkalophilus, B. amyloliquefaciens, B. coagulans, B. lautus, B. megaterium*, and *B. thuringiensis; Streptomyces* spp., such as *S. murinus*; lactic acid bacterial species including *Lactococcus* spp., such as *L. lactis; Lactobacillus* spp., including *L. reuteri; Leuconostoc* spp.; *Pediococcus* spp.; and *Streptococcus* spp. Still other useful hosts include *Bacillus* spp. A 7-7, for example. Alternatively, strains of a Gram negative bacterial species belonging to Enterobacteriaceae, including *E. coli*, or to Pseudomonadaceae can be selected as the host organism.

A suitable yeast host organism can be selected from biotechnologically relevant yeasts species, such as, but not limited to, *Pichia* spp., *Hansenula* spp., *Kluyveromyces* spp., *Yarrowinia* spp., *Saccharomyces* spp., including *S. cerevisiae*, or a species belonging to *Schizosaccharomyces*, such as *S. pombe*. A strain of the methylotrophic yeast species *Pichia pastoris* can be used as the host organism. Alternatively, the host organism can be a *Hansenula* spp. Suitable host organisms among filamentous fungi include species of *Aspergillus*, e.g., *A. niger, A. oryzae, A. tubigensis, A. awamori*, or *A. nidulans*. Alternatively, a strain of *Fusarium* spp., e.g., *Fusarium oxysporum* or *Rhizomucor* spp., such as *R. miehei*, can be used as the host organism. Other suitable yeasts include *Thermomyces* spp. and *Mucor* spp. Fungal cells may be transformed by a process involving protoplast formation and transformation of the protoplasts followed by regeneration of the cell wall in a manner known in the art. A suitable procedure for transforming *Aspergillus* host cells, for example, is described in EP 238023.

An aspect of the present compositions and methods is a method of producing an AmyE variant, which method comprises cultivating a host cell as described above under conditions conducive to the production of the variant and recovering the variant from the cells and/or culture medium. The medium used to cultivate the cells may be any conventional medium suitable for growing the host cell in question and obtaining expression of the AmyE variant. Suitable media and media components are available from commercial suppliers or may be prepared according to published recipes, e.g., as described in catalogues of the American Type Culture Collection (ATCC). Exemplary culture media include, but are not limited to, those for fed-batch fermentations performed in a three thousand liter (3,000 L) stirred tank fermentor. The growth medium in that case can consist of corn steep solids and soy flour as sources of organic compounds, along with inorganic salts as a source of sodium, potassium, phosphate, magnesium and sulfate, as well as trace elements. Typically, a carbohydrate source such as glucose is also part of the initial medium. Once the culture has established itself and begins growing, the carbohydrate is metered into the tank to maintain the culture as is known in the art. Samples are removed from the fermentor at regular intervals to measure enzyme titer using, for example, a colorimetric assay method. The fermentation process is halted when the enzyme production rate stops increasing according to the measurements.

An AmyE polypeptides secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

Host cells may be cultured under suitable conditions that allow expression of the AmyE polypeptides. Expression of the proteins may be constitutive such that they are continually produced, or inducible, requiring a stimulus to initiate expression. In the case of inducible expression, protein production can be initiated when required by addition of an inducer substance, e.g., dexamethasone, IPTG, or SEPHAROSE® polymer, to the culture medium, for example. Polypeptides can also be produced recombinantly in an in vitro cell-free system, such as the TNT™ (Promega) rabbit reticulocyte system.

A host for expressing an AmyE polypeptides can be cultured under aerobic conditions in the appropriate medium for the host. Shaking or a combination of agitation and aeration can be provided, with production occurring at the appropriate temperature for that host, e.g., from about 30° C. to about 75° C., depending on the needs of the host and production of the desired α-amylase variant. Culturing can occur from about 12 to about 100 hours or greater (and any hour value there between) or more particularly from 24 to 72 hours. Typically, the culture broth is at a pH of about 5.5 to about 8.0, again depending on the culture conditions needed for the host cell relative to production of the AmyE variant.

The amylolytic activity of the expressed enzyme may be determined using, e.g., potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

AmyE polypeptides may be expressed as a fusion protein that comprises sequences at the N- and/or C-terminus of the mature form of AmyE that facilitate expression, detection, and/or purification, e.g., a signal sequence or a His-tag. Such a sequence includes a signal sequence, which facilitates secretion and expression of the AmyE in a host organism. Additional amino acid residues may be cleaved from the N-terminus of an AmyE, following cleavage of the signal sequence, as discussed in Yang et al., "Nucleotide sequence of the amylase gene from *Bacillus subtilis*," *Nucleic Acids Res.* 11: 237-49 (1983).

4. Purification of AmyE Polypeptides

In some cases, conventional methods can be used in order to prepare a purified AmyE polypeptides. After growing a host organism in culture, a growth (or "fermentation") broth is obtained, and the microbial cells and various suspended solids, including residual raw fermentation materials, are removed by conventional separation techniques to obtain an amylase solution. Filtration, centrifugation, microfiltration, rotary vacuum drum filtration, followed by ultra-filtration, extraction or chromatography, or the like are generally used.

It is generally desirable to concentrate the solution containing the expressed AmyE or variant thereof to optimize recovery, since the use of un-concentrated solutions requires increased incubation time to collect precipitates containing the purified enzyme. The solution is concentrated using conventional techniques until the desired enzyme level is obtained. Concentration of the enzyme containing solution may be achieved by any of the techniques discussed above. In one embodiment, rotary vacuum evaporation and/or ultrafiltration is used. Alternatively, ultrafiltration can be used.

Precipitation can be performed using, for example, a metal halide precipitation agent. Metal halide precipitation agents include: alkali metal chlorides, alkali metal bromides and blends of two or more of these metal halides. The metal halide may be selected from the group consisting of sodium chloride, potassium chloride, sodium bromide, potassium bromide and blends of two or more of these metal halides. Suitable metal halides include sodium chloride and potassium chloride, particularly sodium chloride, which can further be used as a preservative. The selection of conditions of the precipitation for maximum recovery, including incubation time, pH, temperature and concentration of AmyE or variant thereof, will be readily apparent to one of ordinary skill in the art after routine testing.

Generally, at least about 5% w/v (weight/volume) to about 25% w/v of metal halide is added to the concentrated enzyme variant solution, and usually at least 8% w/v. Generally, no more than about 25% w/v of metal halide is added to the concentrated enzyme variant solution and usually no more than about 20% w/v. The optimal concentration of the metal halide precipitation agent will depend, among others, on the nature of the specific AmyE or variant thereof and on its concentration in solution.

An alternative to effect precipitation of the enzyme is to use of organic compounds, which can be added to the concentrated enzyme variant solution. The organic compound precipitating agent can include: 4-hydroxybenzoic acid, alkali metal salts of 4-hydroxybenzoic acid, alkyl esters of 4-hydroxybenzoic acid, and blends of two or more of these organic compounds. The addition of said organic compound precipitation agents can take place prior to, simultaneously with or subsequent to the addition of the metal halide precipitation agent, and the addition of both precipitation agents, organic compound and metal halide, may be carried out sequentially or simultaneously. For further descriptions, see, e.g., U.S. Pat. No. 5,281,526 to Danisco A/S, for example.

Generally, the organic compound precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitations agents can be for example linear or branched alkyl esters of 4-hydroxybenzoic acid, wherein the alkyl group contains from 1 to 10 carbon atoms, and blends of two or more of these organic compounds. Suitable organic compounds include linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl ester of 4-hydroxybenzoic acid, butyl ester of 4-hydroxybenzoic acid, ethyl ester of 4-hydroxybenzoic acid and blends of two or more of these organic compounds can also be used. Additional organic compounds also include, but are not limited to, 4-hydroxybenzoic acid methyl ester (methyl PARABEN) and 4-hydroxybenzoic acid propyl ester (propyl PARABEN), which are also amylase preservative agents. Addition of the such an organic compound precipitation agent provides the advantage of high flexibility of the precipitation conditions with respect to pH, temperature, enzyme concentration, precipitation agent concentration, and time of incubation. Generally, at least 0.01% w/v of organic compound precipitation agent is added to the concentrated enzyme variant solution and usually at least 0.02% w/v. Generally, no more than 0.3% w/v of organic compound precipitation agent is added to the concentrated enzyme variant solution and usually no more than 0.2% w/v.

The concentrated enzyme solution, containing the metal halide precipitation agent and, in one aspect, the organic compound precipitation agent, is adjusted to a pH that necessarily will depend on the enzyme variant to be purified. Generally, the pH is adjusted to a level near the isoelectric point (pI) of the amylase. For example, the pH can be adjusted within a range of about 2.5 pH units below the pI to about 2.5 pH units above the pI. The pH may be adjusted accordingly if the pI of the variant differs from the wild-type pI.

The incubation time necessary to obtain a purified enzyme precipitate depends on the nature of the specific enzyme, the concentration of enzyme, and the specific precipitation agent(s) and its (their) concentration. Generally, the time effective to precipitate the enzyme variant is between about 1 to about 30 hours; usually it does not exceed about 25 hours. In the presence of the organic compound precipitation agent, the time of incubation can still be reduced to less than about 10 hours, and in most cases even about 6 hours.

Generally, the temperature during incubation is between about 4° C. and about 50° C. Usually, the method is carried out at a temperature between about 10° C. and about 45° C., and particularly between about 20° C. and about 40° C. The optimal temperature for inducing precipitation varies according to the solution conditions and the enzyme or precipitation agent(s) used.

The overall recovery of purified enzyme precipitate, and the efficiency with which the process is conducted, is improved by agitating the solution comprising the enzyme, the added metal halide and the added organic compound. The agitation step is done both during addition of the metal halide and the organic compound, and during the subsequent incubation period. Suitable agitation methods include mechanical stirring or shaking, vigorous aeration, or any similar technique.

The purified enzyme may be further purified by conventional separation techniques, such as filtration, centrifugation, microfiltration, rotary vacuum filtration, ultrafiltration, press filtration, cross membrane microfiltration, cross flow membrane microfiltration, or the like. Cross membrane microfiltration can be one method used. Further purification of the purified enzyme precipitate can be obtained by washing the precipitate with water. For example, the purified enzyme precipitate may be washed with water containing the metal halide precipitation agent, for example, with water containing the metal halide and the organic compound precipitation agents.

During culturing, expressed enzyme may accumulate in the culture broth. For the isolation and purification of the expressed enzyme, the culture broth may be centrifuged or filtered to eliminate cells, and the resulting cell-free liquid may be used for the purification of the enzyme. In one embodiment, the cell-free broth is subjected to salting out using ammonium sulfate at about 70% saturation; the 70% saturation-precipitation fraction is then dissolved in a buffer and applied to a column such as a SEPHADEX® G-100 column, and eluted to recover the enzyme active fraction. For further purification, a conventional procedure such as ion exchange chromatography may be used.

Purified enzymes are useful for all applications in which the enzyme are generally utilized. For example, they can be used in laundry detergents and spot removers, in the food industry, in starch processing and baking, and in pharmaceutical compositions as digestive aids. They can be made into a final product that is either liquid (solution, slurry) or solid (granular, powder).

Alternatively, the enzyme product can be recovered and a flocculating agent is added to the media in order to remove cells and cell debris by filtration or centrifugation without further purification of the enzyme.

AmyE polypeptides produced and purified by the methods described above can be used in a variety of useful industrial applications. The enzymes possess valuable properties facilitating applications related to fabric and household care (F&HC). For example, AmyE polypeptides can be used as a component in washing, dishwashing and hard-surface cleaning detergent compositions. AmyE polypeptides are also useful in the production of sweeteners and ethanol from starch, and/or for textile desizing. AmyE polypeptides are particularly useful in starch-conversion processes, including starch liquefaction and/or saccharification processes, as described, for example, in WO 2005/111203 and U.S. Published Application No. 2006/0014265 (Danisco A/S). These uses of AmyE polypeptides are described in more detail below.

5. Compositions and Methods of Use of AmyE Polypeptides
    5.1. Starch Processing Compositions and Methods
        5.1.1. Overview AmyE polypeptides can be utilized for starch processing/conversion, which is central to producing sweeteners, producing alcohol for fuel or drinking (i.e., potable alcohol), producing a beverage, processing cane sugar, or producing desired organic compounds, e.g., citric acid, itaconic acid, lactic acid, gluconic acid, ketones, amino acids, antibiotics, enzymes, vitamins, hormones, and the like. Starch conversion generally involves the hydrolysis of a slurry of gelatinized or granular starch into a soluble starch hydrolysate. Conventions starch conversion involves three consecutive enzymatic processes: a liquefaction process, a saccharification process, and a further process to produce a desired product from glucose. Depending on the desired product, the further process may be isomerization, fermentation, and the like. In the process of converting starch to fructose syrup, the further process is isomerization.

5.1.2. Starch Compositions

The starch to be processed may be obtained from tubers, roots, stems, legumes, cereals or whole grain. More specifically, the granular starch may be obtained from corns, cobs, wheat, barley, rye, milo, sago, cassava, tapioca, sorghum, rice, peas, bean, banana, or potatoes. Specially contemplated are both waxy and non-waxy types of corn and barley. The starch may be a highly refined starch quality, for instance, at least 90%, at least 95%, at least 97%, or at least 99.5% pure. Alternatively, the starch can be a more crude starch containing material comprising milled whole grain, including non-starch fractions such as germ residues and fibers. The raw material, such as whole grain, is milled to open up the structure and allow further processing.

Two milling processes are suitable: wet and dry milling (dry grinding). In dry milling, the whole kernel is milled and used. Dry milled grain may include significant amounts of non-starch carbohydrate compounds, in addition to starch. When such a heterogeneous material is processed by jet cooking, often only a partial gelatinization of the starch is achieved. Wet milling gives a good separation of germ and meal (starch granules and protein) and is usually used in the production of syrups. The process may be conducted in an ultrafiltration system where the retentate is held under recirculation in presence of enzymes, raw starch and water, where the permeate is the soluble starch hydrolysate. The process may also be conducted in a continuous membrane reactor with ultrafiltration membranes, where the retentate is held under recirculation in presence of enzymes, raw starch and water, and where the permeate is the soluble starch hydrolysate. The process may further be conducted in a continuous membrane reactor with microfiltration membranes and where the retentate is held under recirculation in presence of enzymes, raw starch and water, and where the permeate is the soluble starch hydrolysate.

The starch slurry to be used in any of the above aspects may have about 20% to about 55% dry solids granular starch, about 25% to about 40% dry solids granular starch, or about 30% to about 35% dry solids granular starch. The enzyme variant converts the soluble starch into a soluble starch hydrolysate of the granular starch in the amount of at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

5.1.3. Liquefaction and Saccharification

During the liquefaction step, long-chained starch molecules present in the starch slurry are degraded into shorter branched and linear molecules (maltodextrins) by an α-amylase. Numerous α-amylases are available commercially, including SPEZYME® Xtra (Genencor) and LIQUOZYME® (Novozymes).

The liquefaction process is generally carried out at about 105-110° C. for about 5 to 10 minutes followed by 1-2 hours at 95° C. The pH of liquefaction is typically between about 5.0 and about 6.2, and usually above 5.5. To promote α-amylase stability under these conditions, 1 mM of calcium is typically added (40 ppm free calcium ions). Following this treatment, the liquefied starch composition will largely contain dextrins, and will have a "dextrose equivalent" (DE) of about 10-15.

Following the liquefaction process, the dextrins are typically converted, in a separate saccharification step, into dextrose, by addition of a glucoamylase (e.g., AMG™). A debranching enzyme, such as an isoamylase or a pullulanase (e.g., PROMOZYME®) may also be added. To prepare for the saccharification step, the pH of the slurry is typically reduced to a value below about 4.5, while maintaining the temperature at 95° C. or more, such that the liquefying α-amylase is denatured. The temperature then is lowered to about 60° C., and the glucoamylase and a debranching enzyme are added to affect glucose production from dextrins. The saccharification process proceeds typically for about 24 to about 72 hours.

5.1.4. Further Processing of Glucose Produced by Saccharification

After the saccharification process, the dextrose syrup may be converted into high fructose syrup using an immobilized glucose isomerase (such as SWEETZYME®, for example. In one regard, the soluble starch hydrolysate of the process is subjected to conversion into high fructose starch-based syrup (HFSS), such as high fructose corn syrup (HFCS). This conversion can be achieved using a glucose isomerase, particularly a glucose isomerase immobilized on a solid support. Contemplated isomerases included the commercial products SWEETZYME®, IT (Novozymes A/S); G-ZYME® IMGI, and G-ZYME® G993, KETOMAX®, G-ZYME® G993, G-ZYME® G993 liquid, and GENSWEET® IGI. While $Ca^{2+}$ increases the stability of conventional α-amylases, it strongly inhibits the activity of the glucose isomerase. Thus, $Ca^{2+}$ is typically removed prior to isomerization, e.g., by ion exchange, such that the level of $Ca^{2+}$ is below 3-5 ppm. This process is time consuming and expensive.

Alternatively, glucose produced by saccharification is used for fermentation to produce a fermentation product, e.g., ethanol, butanol, and other compound described herein and known in the art. A typical complete process for producing ethanol from starch-containing material by fermentation comprises: (i) liquefying the starch-containing material with an AmyE or variant thereof; (ii) saccharifying the liquefied mash obtained; and (iii) fermenting the material obtained in step (ii) in the presence of a fermenting organism. Optionally the process further comprises recovery of the ethanol. During the fermentation, the ethanol content reaches at least about 7%, at least about 8%, at least about 9%, at least about 10% such as at least about 11%, at least about 12%, at least about 13%, at least about 14%, at least 15%, or at least 16% ethanol.

The saccharification and fermentation processes may be carried out as a simultaneous saccharification and fermentation (SSF) process. When fermentation is performed simultaneously with the hydrolysis, the temperature can be between 30° C. and 35° C., particularly between 31° C. and 34° C. The process may be conducted in an ultrafiltration system where the retentate is held under recirculation in presence of enzymes, raw starch, yeast, yeast nutrients and water and where the permeate is an ethanol containing liquid. Also contemplated is the process conducted in a continuous membrane reactor with ultrafiltration membranes and where the retentate is held under recirculation in presence of enzymes, raw starch, yeast, yeast nutrients and water and where the permeate is an ethanol containing liquid.

Glucose produced by saccharification may also be used for production of a fermentation product such as ethanol, butanol, citric acid, monosodium glutamate, gluconic acid, sodium gluconate, calcium gluconate, potassium gluconate, glucono delta-lactone, or sodium erythorbate.

5.1.5. Advantages of AmyE α-amylase

AmyE polypeptides offer several advantages when used in starch hydrolysis, which distinguish them from other α-amylases and allow for the streamlining of starch hydrolysis methods. First, dextrins may be converted into dextrose by AmyE polypeptides under the same reaction conditions that are suitable for glucoamylases. This obviates the need to optimize the reaction mixture (e.g., slurry) pH and temperature for an α-amylase, and then adjust the reactions conditions to accommodate a glucoamylase, e.g., by reducing the pH and/or temperature of the slurry. In this manner, the use of AmyE in starch hydrolysis permits liquefaction and saccharification to be performed under the same slurry conditions, thereby eliminating a step in starch hydrolysis.

In some cases, both liquefaction and saccharification can be performed at a single pH between about 4-7, e.g., about 4-5, about 4-6, about 5-6, about 5-7, and about 6-7. Note that the single pH criterion ignores any minor changes to the pH of the reaction mixture that occur during liquefaction or saccharification, but which do not involve to the addition of acid or base to intentionally change the pH of the reaction mixture. In some cases, both liquefaction and saccharification can be performed at a pH below that which conventional liquefaction processes are performed, for example, a pH of less than about 5.0, less than about 4.8, less than about 4.6, less than about 4.4, less than about 4.2, or even a pH of about 4.0. The use of AmyE for liquefaction also allows the inclusion of a higher percentage of thin stillage in the starch composition used for liquefaction, for example, >50%, or even >60% of the reaction mix. In some cases, both liquefaction and saccharification can be performed at a temperature of about 20-105° C., for example, 60-85° C., or a temperature that is about 10, 12, 14, 16, 18, or even, 20° C. below the starch gelation temperature (i.e., about 75° C.). Importantly, liquefaction and saccharification can be performed entirely without an intervening pH adjustment. Alternatively, where pH adjustment is still desirable between liquefaction and saccharification, it can be performed using a reduced amount of acid or base, compared to the amount used in a conventional process, thereby introducing less salt in to the reaction mix.

In addition, AmyE polypeptides catalyze the breakdown of complex sugars, such as maltose, maltotriose, and maltoheptaose, into glucose. Such an enzymatic activity is conventionally associated with glucoamylases rather than α-amylases. This activity of AmyE polypeptides allows starch hydrolysis to glucose to be performed either in the absence of a separate glucoamylase, or in the presence of a reduced amount of a glucoamylase, compared to the amount required using a conventional α-amylase. In this manner, the use of AmyE polypeptides in starch hydrolysis permits liquefaction and saccharification to be performed simultaneously using a single enzyme that functions as both an α-amylase and a glucoamylase, thereby eliminating or reducing the need for separate enzymes.

AmyE polypeptides also require little or no $Ca^{2+}$ for stability, reducing or eliminating the need to add $Ca^{2+}$ to a liquefaction reaction. In addition to avoiding the step of adding $Ca^{2+}$, this avoids the need to subsequently remove $Ca^{2+}$ from a slurry (e.g., by ion exchange) prior to contacting the slurry with an enzyme such as glucose isomerase, which is sensitive to $Ca^{2+}$. Obviating $Ca^{2+}$ removal saves time and cost and increasing the efficiency of producing a high-fructose syrup.

Finally, AmyE polypeptides have a high activity towards ungelatinized starch, which can be recalcitrant to the enzymatic activity of conventional α-amylases. This permits the use of jet cooked dry milled starch for liquefaction and saccharification, where wet-milled starch is generally preferred to improve conversion efficiency.

It will be appreciated AmyE is suitable for use in a liquefaction/saccharification process that is tied to fermentation, isomerization, or any other subsequent process, including SSF.

5.1.6. Combination of AmyE with Glucoamylases and Other Enzymes

AmyE polypeptides can be used alone (e.g., as the only amylolytic enzyme in starch processing) or can be combined with other α- or β-amylases, or other enzymes to provide a "cocktail" with a broad spectrum of activity. For example, the starch may be contacted with one or more enzyme selected from the group consisting of a fungal α-amylase (EC 3.2.1.1), a bacterial α-amylase, e.g., a *Bacillus* α-amylase or a non-*Bacillus* α-amylase, or a β-amylase (EC 3.2.1.2). Another amylolytic enzyme or a debranching enzyme, such as an isoamylase (EC 3.2.1.68) or a pullulanases (EC 3.2.1.41) may be combined with AmyE polypeptides. Isoamylase hydrolyses α-1,6-D-glucosidic branch linkages in amylopectin and β-limit dextrins and can be distinguished from pullulanases by the inability of isoamylase to attack pullulan and by the limited action of isoamylase on α-limit dextrins.

β-Amylases are exo-acting maltogenic amylases, which catalyze the hydrolysis of 1,4-α-glucosidic linkages into amylose, amylopectin, and related glucose polymers, thereby releasing maltose. β-amylases have been isolated from various plants and microorganisms (Fogarty et al., PROGRESS IN INDUSTRIAL MICROBIOLOGY, Vol. 15, pp. 112-115, 1979). These β-amylases are characterized by having optimum temperatures in the range from 40° C. to 65° C., and optimum pH in the range from about 4.5 to about 7.0. Contemplated β-amylases include, but are not limited to, β-amylases from barley SPEZYME® BBA 1500, SPEZYME® DBA, OPTIMALT™ ME, OPTIMALT™ BBA (Danisco A/S); and NOVOZYM™ WBA (Novozymes A/S).

As described herein, AmyE polypeptides have glucoamylase activity and can be used in the absence of a separate glucoamylase. Alternatively, glucoamylases may be added in a reduced amount compared to that required for conventional starch hydrolysis methods. Preferably, glucoamylases are present in an amount of no more than (i.e., less than) 0.5 glucoamylase activity unit (AGU)/g DS (i.e., glucoamylase activity units per gram of dry solids), no more than 0.4 AGU/g DS, no more than 0.3 AGU/g DS, no more than 0.2 AGU/g DS, or even no more than 0.1 AGU/g DS. More generally, a glucoamylase may be added in an amount of 0.02-2.0 AGU/g DS or 0.1-1.0 AGU/g DS, although these ranges contemplate the use of more glucoamylase than is required in combination with AmyE. Because AmyE polypeptides are active at the same pH and temperature as glucoamylases, AmyE polypeptides may be added before or after addition of a glucoamylase, or simultaneously with a glucoamylase, e.g., by means of a cocktail including both AmyE and a glucoamylase. Thus, the order and manner of addition of an α-amylase and a glucoamylase are no longer critical, permitting increased flexibility in starch hydrolysis processes.

Glucoamylases (EC 3.2.1.3) may be derived from a microorganism or a plant. There are various known glucoamylases of fungal and bacterial origin. Exemplary bacterial glucoamylases are *Aspergillus* glucoamylases, in particular *A. niger* G1 or G2 glucoamylase (Boel et al. (1984), *EMBO J.* 3:1097-1102), or variants thereof, such as disclosed in WO 92/00381 and WO 00/04136; *A. awamori* glucoamylase (WO 84/02921); *A. oryzae* glucoamylase (*Agric. Biol. Chem.* (1991) 55(4): 941-949), or variants or fragments thereof. *Aspergillus* glucoamylase variants include those that enhance thermal stability: G137A and G139A (Chen et al. (1996) *Prot. Eng.* 9:499-505); D257E and D293E/Q (Chen et al. (1995) *Prot. Eng.* 8:575-582); N182 (Chen et al. (1994) *Biochem. J.* 301:275-281); disulphide bonds, A246C (Fierobe et al. (1996) *Biochemistry,* 35:8698-8704); and introduction of Pro residues in positions A435 and S436 (Li et al. (1997) *Protein Eng.* 10:1199-1204). Other glucoamylases include *Trichoderma reesie* glucoamylase (e.g., SEQ ID NO: 3 of WO 2006/060062; TrGA), *Talaromyces* glucoamylases, in particular derived from *T. emersonii* (WO 99/28448), *T. leycettanus* (U.S. Pat. No. RE 32,153), *T. duponti*, or *T. thermophilus* (U.S. Pat. No. 4,587,215). Bacterial glucoamylases include glucoamylases from the genus *Clostridium*, in particular *C. thermoamylolyticum* (EP 135138) and *C. thermohydrosulfuricum* (WO 86/01831). Other suitable glucoamylases include those derived from *Aspergillus oryzae*, such as a glucoamylase having 50%, 55%, 60%, 65%, 70%, 75%, 80%, 85%, or even 90% homology to the amino acid sequence shown in SEQ ID NO: 2 in WO 00/04136. Also suitable are commercial glucoamylases, such as AMG 200L; AMG 300L; SAN™ SUPER and AMG™ E (Novozymes); OPTIDEX® 300 (Genencor Division, Danisco US Inc.); AMIGASE™ and AMIGASE™ PLUS (from DSM); G-ZYME® G900 (Enzyme Bio-Systems); and G-ZYME® G990 ZR (*A. niger* glucoamylase and low protease content).

Phytases are enzymes capable of breaking down phytic acid (phytate) found in grains and oil seeds. Phytate, as well as intermediates in it degradation, are believed to destabilize or otherwise adversely affect α-amylases, thereby reducing their efficiency. Phytases that can be used in combination with variant α-amylases are capable of hydrolyzing phytic acid under the defined conditions of the incubation and liquefaction steps. In some embodiments, the phytase is capable of liberating at least one inorganic phosphate from an inositol hexaphosphate (phytic acid). Phytases can be grouped according to their preference for a specific position of the phosphate ester group on the phytate molecule at which hydrolysis is initiated, (e.g., as 3-phytases (EC 3.1.3.8) or as 6-phytases (EC 3.1.3.26)). A typical example of phytase is myo-inositol-hexakiphosphate-3-phosphohydrolase.

Phytases can be obtained from microorganisms such as fungal and bacterial organisms. Some of these microorganisms include e.g. *Aspergillus* (e.g., *A. niger, A. terreus, A. ficum* and *A. fumigatus*), *Myceliophthora* (*M. thermophila*), *Talaromyces* (*T. thermophilus*) *Trichoderma* spp (*T. reesei*). and *Thermomyces* (WO 99/49740). Also phytases are available from *Penicillium* species, e.g., *P. hordei* (ATCC No. 22053), *P. piceum* (ATCC No. 10519), or *P. brevi-compactum* (ATCC No. 48944). See, for example U.S. Pat. No. 6,475, 762. In addition, phytases are available from *Bacillus*(e.g., *B. subtilis, Pseudomonas, Peniophora, E. coli, Citrobacter, Enterbacter*and *Buttiauxella*(see WO2006/043178).

Commercial phytases are available such as NATUPHOS® (BASF), RONOZYME® P (Novozymes A/S), PHZYME® (Danisco A/S, Diversa) and FINASE® (AB Enzymes). The method for determining microbial phytase activity and the definition of a phytase unit has been published by Engelen et al. (1994) *J. AOAC Int*. 77:760-764. The phytase may be a wild-type phytase, a variant or fragment thereof.

Exemplary phytases are derived from species of the bacterium *Buttiauxella. Buttiauxella* spp. includes *B. agrestis, B. brennerae, B. ferragutiase, B. gaviniae, B. izardii, B. noackiae,* and *B. warmboldiae*. Strains of *Buttiauxella* species are available from DSMZ, the German National Resource Center for Biological Material (Inhoffenstrabe 7B, 38124 Braunschweig, DE). *Buttiauxella* sp. strain P1-29 deposited under accession number NCIMB 41248 is an example of a particularly useful strain from which a phytase may be obtained. The phytase may be BP-wild type, a variant thereof (such as BP-11) described in WO 06/043178, or a variant as described in U.S. Patent Pub. No. US20080220498, filed Mar. 6, 2007 (see, e.g., Table 1 and SEQ ID NO: 3).

The phytase may also be the BP-17 variant of *Buttiauxella* phytase, having the amino acid sequence of SEQ ID NO: 17, shown below, or a phytase having at least 75%, at least 80%, at least 85%, at least 88%, at least 90%, at least 91%, at least 92%, at least 93%, at least 94%, at least 95%, at least 96%, at least 97%, at least 98% and even at least 99% sequence identity to the amino acid sequence set forth in SEQ ID NO: 17.

The amount (dosage) of phytase used in the incubation and/or liquefaction processes may be in the range of about 0.001 to 50 FTU/g ds, (e.g., in the range of about 0.01 to 25 FTU/g ds, about 0.01 to 15 FTU/g ds, about 0.01 to 10 FTU/g ds, about 0.05 to 15 FTU/g ds, and about 0.05 to 5.0 FTU/g.

Other enzymes that may be used in combination with AmyE polypeptides include lipases, cutinases, proteases, cellulases/hemicellulases, peroxidase, pectinase, pectin lyases, laccases, or combinations, thereof. In some cases a carbohydrate-binding domain of the type disclosed in WO 98/22613 may be used.

5.2. Cleaning and Dishwashing Compositions and Methods

AmyE polypeptides can be formulated in detergent compositions for use in cleaning dishes or other hard surfaces. These compositions can be gels, powders or liquids. The compositions may include AmyE polypeptides as the single amylolytic enzymes in the composition. Alternatively, the composition may include other/additional amylolytic enzymes, other cleaning enzymes, and other components, many of which are common to cleaning compositions. The laundry detergent composition may additionally comprise one or more other enzymes, such as a lipase, a cutinase, a protease, a cellulase, a peroxidase, a pectinase, a pectin lyase, and/or a laccase, or a combination, thereof.

Dishwashing detergent compositions generally include one or more surfactants, which can be anionic, non-ionic, cationic, amphoteric or a mixture of these types. The detergent can contain 0% to about 90% by weight of a non-ionic surfactant, such as low- to non-foaming ethoxylated propoxylated straight-chain alcohols.

Liquid detergent compositions may include propylene glycol. AmyE polypeptides can be solubilized in propylene glycol, for example, by circulating in a 25% volume/volume propylene glycol solution containing 10% calcium chloride.

Dishwashing detergent compositions may include detergent builder salts of inorganic and/or organic types. Detergent builders may be subdivided into phosphorus-containing and non-phosphorus-containing types. Detergent compositions usually contain about 1% to about 90% of detergent builders. Examples of phosphorus-containing inorganic alkaline detergent builders are water-soluble salts, especially alkali metal pyrophosphates, orthophosphates, and polyphosphates. Examples of phosphorus-containing organic alkaline detergent builders are water-soluble salts of phosphonates. Examples of non-phosphorus-containing inorganic builders are water-soluble alkali metal carbonates, borates, and silicates, as well as the various types of water-insoluble crystalline or amorphous alumino silicates, of which zeolites are the best-known representatives.

Examples of suitable organic builders are the alkali metal; ammonium and substituted ammonium; citrates; succinates; malonates; fatty acid sulphonates; carboxymethoxy succinates; ammonium polyacetates; carboxylates; polycarboxylates; aminopolycarboxylates; polyacetyl carboxylates; and polyhydroxsulphonates. Other suitable organic builders include the higher molecular weight polymers and co-polymers known to have builder properties, for example appropriate polyacrylic acid, polymaleic and polyacrylic/polymaleic acid copolymers, and their salts.

Cleaning compositions may contain bleaching agents, e.g., of the chlorine/bromine-type or the oxygen-type. Examples of inorganic chlorine/bromine-type bleaches are lithium, sodium or calcium hypochlorite, and hypobromite, as well as chlorinated trisodium phosphate. Examples of organic chlorine/bromine-type bleaches are heterocyclic N-bromo- and N-chloro-imides such as trichloroisocyanuric, tribromoisocyanuric, dibromoisocyanuric, and dichloroisocyanuric acids, and salts thereof with water-solubilizing cations such as potassium and sodium. Hydantoin compounds are also suitable.

Cleaning compositions may contain oxygen bleaches, for example in the form of an inorganic persalt, optionally with a bleach precursor or as a peroxy acid compound. Typical examples of peroxy bleach compounds are alkali metal perborates, both tetrahydrates and monohydrates, alkali metal percarbonates, persilicates, and perphosphates. Suitable activator materials include tetraacetylethylenediamine (TAED) and glycerol triacetate. Enzymatic bleach activation systems may also be present, such as perborate or percarbonate, glycerol triacetate and perhydrolase, as disclosed in WO 2005/056783, for example.

Cleaning compositions may be stabilized using conventional stabilizing agents for the enzyme(s), e.g., a polyol such as, e.g., propylene glycol, a sugar or a sugar alcohol, lactic acid, boric acid, or a boric acid derivative (e.g., an aromatic borate ester). The cleaning composition may also contain other conventional detergent ingredients, e.g., deflocculant material, filler material, foam depressors, anti-corrosion agents, soil-suspending agents, sequestering agents, anti-soil redeposition agents, dehydrating agents, dyes, bactericides, fluorescent agents, thickeners, and perfumes.

Finally, AmyE polypeptides may be used in conventional dishwashing detergents, e.g., in any of the detergents described in the following patent publications, with the understanding that that AmyE polypeptides are used instead of, or in addition to, the α-amylases described in the following patents and published patent applications: CA 2006687, GB 2200132, GB 2234980, GB 2228945, DE 3741617, DE 3727911, DE 4212166, DE 4137470, DE 3833047, DE 4205071, WO 93/25651, WO 93/18129, WO 93/04153, WO 92/06157, WO 92/08777, WO 93/21299, WO 93/17089, WO 93/03129, EP 481547, EP 530870, EP 533239, EP 554943, EP 429124, EP 346137, EP 561452, EP 318204, EP 318279, EP 271155, EP 271156, EP 346136, EP 518719, EP 518720, EP 518721, EP 516553, EP 561446, EP 516554, EP 516555, EP 530635, EP 414197, and U.S. Pat. Nos. 5,112,518; 5,141, 664; and 5,240,632.

AmyE polypeptide-containing detergent compositions may be formulated for hand or machine dishwashing operations.

5.3. Laundry Detergent Compositions and Methods

AmyE polypeptides may be a component of a laundry detergent composition, e.g., in the form of a non-dusting granulate, a stabilized liquid, a protected enzyme, or the like. Non-dusting granulates may be produced, e.g., as described in U.S. Pat. Nos. 4,106,991 and 4,661,452 and may optionally be coated by methods known in the art. Examples of waxy coating materials are poly(ethylene oxide) products; (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are described in, e.g., GB Patent No. 1,483,591.

Liquid enzyme preparations may be stabilized by adding a polyol such as propylene glycol, a sugar or sugar alcohol, lactic acid or boric acid according to established methods.

Other enzyme stabilizers are known in the art. Protected enzymes may be prepared according to the method disclosed in U.S. Pat. No. 5,879,920 (Danisco A/S) or EP 238216, for example. Polyols have long been recognized as stabilizers of proteins as well as for improving the solubility of proteins. See, e.g., Kaushik et al., *J. Biol. Chem.* 278: 26458-65 (2003) and references cited therein; and M. Conti et al., *J. Chromatography* 757: 237-245 (1997).

Laundry detergent composition may be in any convenient form, e.g., as gels, powders, granules, pastes, or liquids. A liquid detergent may be aqueous, typically containing up to about 70% of water, and 0% to about 30% of organic solvent, it may also be in the form of a compact gel type containing only about 30% water.

Laundry detergent composition typically include one or more surfactants, which may be anionic, nonionic (including semi-polar), cationic, or zwitterionic, or a combination, thereof. The surfactants are typically present at a level of from 0.1% to 60% by weight. In some cases, the detergent will usually contain 0% to about 40% or to about 50% of anionic surfactant, such as linear alkylbenzenesulfonate; α-olefinsulfonate; alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, polyhydroxy alkyl fatty acid amide (as described in WO 92/06154), or N-acyl-N-alkyl derivatives of glucosamine ("glucamides").

The laundry detergent composition may additionally comprise one or more other enzymes, such as a lipase, a cutinase, a protease, a cellulase, a peroxidase, a pectinase, a pectin lyase, a laccase, and/or another amylolytic enzyme (e.g., another α-amylase), or a combination, thereof. In some cases, the 2,6-β-D-fructan hydrolase can be incorporated in a laundry detergent compositions and used for removal/cleaning of biofilm present on household and/or industrial textile/laundry.

The laundry detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst). The detergent may also be unbuilt, i.e., essentially free of detergent builder. Enzymes may be used in any composition compatible with the stability of the enzyme. Enzymes can be protected against generally deleterious components by known forms of encapsulation, as by granulation or sequestration in hydro gels, for example. Enzymes and specifically α-amylases either with or without the starch binding domains are not limited to laundry and dishwashing applications, but may bind use in surface cleaners and ethanol production from starch or biomass.

The laundry detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The laundry detergent may contain a bleaching system, which may comprise a $H_2O_2$ source such as perborate or percarbonate optionally combined with a peracid-forming bleach activator, such as TAED or nonanoyloxybenzenesulfonate (NOBS). Alternatively, the bleaching system may comprise peroxy acids of the amide, imide, or sulfone type, for example. The bleaching system can also be an enzymatic bleaching system where a perhydrolase activates peroxide, such as that described in WO 2005/056783.

The enzymes of the laundry detergent composition, including AmyE polypeptides may be stabilized using conventional stabilizing agents, e.g., a polyol such as propylene glycol or glycerol; a sugar or sugar alcohol; lactic acid; boric acid or a boric acid derivative, such as an aromatic borate ester; and the composition may be formulated as described, e.g., in WO 92/19709 and WO 92/19708.

The laundry detergent may also contain other conventional detergent ingredients such as fabric conditioners including clays, foam boosters, suds suppressors, anti-corrosion agents, soil-suspending agents, anti-soil redeposition agents, dyes, bactericides, optical brighteners, or perfume, for example. The pH (measured in aqueous solution at use concentration) is usually neutral or alkaline, e.g., pH about 7.0 to about 11.0, although AmyE polypeptides also work in low pH conditions, as in the case of starch hydrolysis.

One or more AmyE polypeptides may be present in laundry cleaning compositions at concentrations conventionally employed in such compositions, e.g., 0.00001-1.0 mg (calculated as pure enzyme protein) of AmyE polypeptide per liter of wash liquor. Exemplary detergent compositions include the following:

(1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5% to about 9%; sodium carbonate (e.g., $Na_2CO_3$) about 14% to about 20%; soluble silicate, about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6H_5Na_3O_7/C_6H_8O_7$) about 0% to about 15%; sodium perborate (e.g., $NaBO_3.H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

(2) A detergent composition formulated as a granulate having a bulk density of at least 600 g/L comprising linear alkylbenzenesulfonate (calculated as acid) about 6% to about 11%; alcohol ethoxysulfate (e.g., $C_{12-18}$ alcohol, 1-2 EO) or alkyl sulfate (e.g., $C_{16-18}$) about 1% to about 3%; alcohol ethoxylate (e.g., $C_{14-15}$ alcohol, 7 EO) about 5% to about 9%; sodium carbonate (e.g., $Na_2CO_3$) about 15% to about 21%; soluble silicate, about 1% to about 4%; zeolite (e.g., $NaAlSiO_4$) about 24% to about 34%; sodium sulfate (e.g., $Na_2SO_4$) about 4% to about 10%; sodium citrate/citric acid (e.g., $C_6H_5Na_3O_7/C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

(3) A detergent composition formulated as a granulate having a bulk density of at least 600 g/L comprising linear alkylbenzenesulfonate (calculated as acid) about 5% to about 9%; alcohol ethoxylate (e.g., $C_{12-15}$ alcohol, 7 EO) about 7% to about 14%; Soap as fatty acid (e.g., $C_{16-22}$ fatty acid) about 1 to about 3%; sodium carbonate (as $Na_2CO_3$) about 10% to about 17%; soluble silicate, about 3% to about 9%; zeolite (as $NaAlSiO_4$) about 23% to about 33%; sodium sulfate (e.g., $Na_2SO_4$) 0% to about 4%; sodium perborate (e.g., $NaBO_3.H_2O$) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

(4) A detergent composition formulated as a granulate having a bulk density of at least 600 g/L comprising linear alkylbenzenesulfonate (calculated as acid) about 8% to about 12%; alcohol ethoxylate (e.g., $C_{12-15}$ alcohol, 7 EO) about 10% to about 25%; sodium carbonate (as $Na_2CO_3$) about 14% to about 22%; soluble silicate, about 1% to about 5%; zeolite (e.g., $NaAlSiO_4$) about 25% to about 35%; sodium sulfate (e.g., $Na_2SO_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

(5) An aqueous liquid detergent composition comprising linear alkylbenzenesulfonate (calculated as acid) about 15% to about 21%; alcohol ethoxylate (e.g., $C_{12-15}$ alcohol, 7 EO or $C_{12-15}$ alcohol, 5 EO) about 12% to about 18%; soap as fatty acid (e.g., oleic acid) about 3% to about 13%; alkenyl-succinic acid ($C_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., $B_4O_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

(6) An aqueous structured liquid detergent composition comprising linear alkylbenzenesulfonate (calculated as acid) about 15% to about 21%; alcohol ethoxylate (e.g., $C_{12-15}$ alcohol, 7 EO, or $C_{12-15}$ alcohol, 5 EO) 3-9%; soap as fatty acid (e.g., oleic acid) about 3% to about 10%; zeolite (as $NaAlSiO_4$) about 14% to about 22%; potassium citrate about 9% to about 18%; borate (e.g., $B_4O_7$) 0% to about 2%; carboxymethylcellulose (CMC) 0% to about 2%; polymers (e.g., PEG, PVP) 0% to about 3%; anchoring polymers (e.g., lauryl methacrylate/acrylic acid copolymer); molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

(7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., $Na_2CO_3$) about 5% to about 10%; soluble silicate, about 1% to about 4%; zeolite (e.g., $NaAlSiO_4$) about 20% to about 40%; sodium sulfate (e.g., $Na_2SO_4$) about 2% to about 8%; sodium perborate (e.g., $NaBO_3.H_2O$) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

(8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., $Na_2CO_3$) about 4% to about 10%; soluble silicate, about 1% to about 4%; zeolite (e.g., $NaAlSiO_4$) about 30% to about 50%; sodium sulfate (e.g., $Na_2SO_4$) about 3% to about 11%; sodium citrate (e.g., $C_6H_5Na_3O_7$) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

(9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., $Na_2CO_3$) about 14% to about 22%; zeolite (e.g., $NaAlSiO_4$) about 18% to about 32%; sodium sulfate (e.g., $Na_2SO_4$) about 5% to about 20%; sodium citrate (e.g., $C_6H_5Na_3O_7$) about 3% to about 8%; sodium perborate (e.g., $NaBO_3.H_2O$) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

(10) An aqueous liquid detergent composition comprising linear alkylbenzenesulfonate (calculated as acid) about 15% to about 23%; alcohol ethoxysulfate (e.g., $C_{12-15}$ alcohol, 2-3 EO) about 8% to about 15%; alcohol ethoxylate (e.g., $C_{12-15}$ alcohol, 7 EO, or $C_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., $B_4O_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

(11) An aqueous liquid detergent composition comprising linear alkylbenzenesulfonate (calculated as acid) about 20% to about 32%; alcohol ethoxylate (e.g., $C_{12-15}$ alcohol, 7 EO, or $C_{12-15}$ alcohol, 5 EO) 6-12%; aminoethanol about 2% to about 6%; citric acid about 8% to about 14%; borate (e.g., $B_4O_7$) about 1% to about 3%; polymer (e.g., maleic/acrylic acid copolymer, anchoring polymer, such as lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

(12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., $Na_2CO_3$) about 8% to about 25%; soluble silicates, about 5% to about 15%; sodium sulfate (e.g., $Na_2SO_4$) 0% to about 5%; zeolite ($NaAlSiO_4$) about 15% to about 28%; sodium perborate (e.g., $NaBO_3.H_2O$) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

(13) Detergent compositions as described in compositions 1)-12) supra, wherein all or part of the linear alkylbenzenesulfonate is replaced by ($C_{12}$-$C_{18}$) alkyl sulfate.

(14) A detergent composition formulated as a granulate having a bulk density of at least 600 g/L comprising ($C_{12}$-$C_{18}$) alkyl sulfate about 9% to about 15%; alcohol ethoxylate about 3% to about 6%; polyhydroxy alkyl fatty acid amide about 1% to about 5%; zeolite (e.g., $NaAlSiO_4$) about 10% to about 20%; layered disilicate (e.g., SK56 from Hoechst) about 10% to about 20%; sodium carbonate (e.g., $Na_2CO_3$) about 3% to about 12%; soluble silicate, 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

(15) A detergent composition formulated as a granulate having a bulk density of at least 600 g/L comprising ($C_{12}$-$C_{18}$) alkyl sulfate about 4% to about 8%; alcohol ethoxylate about 11% to about 15%; soap about 1% to about 4%; zeolite MAP or zeolite A about 35% to about 45%; sodium carbonate (as $Na_2CO_3$) about 2% to about 8%; soluble silicate, 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

(16) Detergent formulations as described in 1)-15) supra, which contain a stabilized or encapsulated peracid, either as an additional component or as a substitute for already specified bleach systems.

(17) Detergent compositions as described supra in 1), 3), 7), 9), and 12), wherein perborate is replaced by percarbonate.

(18) Detergent compositions as described supra in 1), 3), 7), 9), 12), 14), and 15), which additionally contains a manganese catalyst.

(19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

AmyE-polypeptide-containing laundry detergent compositions may be formulated as hand or machine laundry detergent compositions, including laundry additive compositions suitable for pre-treatment of stained fabrics and rinse added fabric softener compositions, or may be formulated as detergent compositions for use in general household hard surface cleaning operations.

The detergent compositions may include 2,6-β-D-fructan hydrolase, one or more additional α-amylase enzymes, and one or more other cleaning enzymes, such as a protease, a lipase, a cutinase, a carbohydrase, a cellulase, a pectinase, a mannanase, an arabinase, a galactanase, a xylanase, an oxidase, a laccase, and/or a peroxidase, and/or combinations thereof. In general, the properties of the selected enzyme(s) should be compatible with the selected detergent, (e.g., pH-optimum, compatibility with other enzymatic and non-enzymatic ingredients, etc.), and the enzyme(s) should be present in effective amounts.

A detergent additive, i.e., a separate additive or a combined additive, can be formulated as a granulate, liquid, slurry, etc. Suitable granulate detergent additive formulations include non-dusting granulates.

It is contemplated that in the detergent compositions, AmyE polypeptides may be added in an amount corresponding to about 0.01 to about 100 mg of enzyme protein per liter of wash liquor, particularly about 0.05 to about 5.0 mg of enzyme protein per liter of wash liquor, or even more particularly in 0.1 to about 1.0 mg of enzyme protein per liter of wash liquor.

5.4. Enzymes for Use in Combination with AmyE Polypeptides

As described, above, AmyE polypeptide-containing cleaning compositions may include one or more additional enzymes, such as a protease, a lipase, a cutinase, a carbohydrase, a cellulase, a pectinase, a mannanase, an arabinase, a galactanase, a xylanase, an oxidase, a laccase, and/or a peroxidase, 2,6-β-D-fructan hydrolase, additional α-amylase enzymes, and combinations thereof. In general, the properties of the selected enzyme(s) should be compatible with the selected detergent, (e.g., pH-optimum, compatibility with other enzymatic and non-enzymatic ingredients, etc.), and the enzyme(s) should be present in effective amounts. Exemplary enzymes are described, below. Many of these enzymes can also be used in combination with AmyE polypeptides in compositions other than cleaning compositions.

Proteases: suitable proteases include those of animal, vegetable or microbial origin. Chemically modified or protein engineered mutants are also suitable. The protease may be a serine protease or a metalloprotease, e.g., an alkaline microbial protease or a trypsin-like protease. Examples of alkaline proteases are subtilisins, especially those derived from *Bacillus* sp., e.g., subtilisin Novo, subtilisin Carlsberg, subtilisin 309 (see, e.g., U.S. Pat. No. 6,287,841), subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729 and WO 98/20115. Suitable commercially available protease enzymes include ALCALASE®, SAVINASE®, PRIMASE™, DURALASE™, ESPERASE®, and KANNASE™ (Novo Nordisk A/S); MAXATASE®, MAXACAL™, MAXAPEM™, PROPERASE™, PURAFECT®, PURAFECT OXP™, FN2™, and FN3™ (Danisco A/S).

Lipases: suitable lipases include those of bacterial or fungal origin. Chemically modified or protein engineered mutants are included. Examples of useful lipases include, but are not limited to, lipases from *Humicola* (synonym *Thermomyces*), e.g. *H. lanuginosa* (*T. lanuginosus*) (see, e.g., EP 258068 and EP 305216) and *H. insolens* (see, e.g., WO 96/13580); a *Pseudomonas* lipase (e.g., from *P. alcaligenes* or *P. pseudoalcaligenes*; see, e.g., EP 218 272), *P. cepacia* (see, e.g., EP 331 376), *P. stutzeri* (see, e.g., GB 1,372,034), *P. fluorescens*, *Pseudomonas* sp. strain SD 705 (see, e.g., WO 95/06720 and WO 96/27002), *P. wisconsinensis* (see, e.g., WO 96/12012); a *Bacillus* lipase (e.g., from *B. subtilis*; see, e.g., Dartois et al. *Biochemica Biophysica Acta*, 1131: 253-360 (1993)), *B. stearothermophilus* (see, e.g., JP 64/744992), or *B. pumilus* (see, e.g., WO 91/16422). Additional lipase variants contemplated for use in the formulations include those described, for example, in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include LIPOLASE® and LIPOLASE® Ultra (Novo Nordisk A/S).

Polyesterases: Suitable polyesterases include, but are not limited to, those described in WO 01/34899 (Danisco A/S) and WO 01/14629 (Danisco A/S), and can be included in any combination with other enzymes discussed herein.

Amylases: The compositions can be combined with other α-amylases, such as a non-variant α-amylase. These can include commercially available amylases, such as but not limited to DURAMYL®, TERMAMYL™, FUNGAMYL® and BAN™ (Novo Nordisk A/S), RAPIDASE®, and PURASTAR® (Danisco A/S).

Cellulases: Cellulases can be added to the compositions. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307; 5,648,263; 5,691,178; 5,776,757; and WO 89/09259, for example. Exemplary cellulases contemplated for use are those having color care benefit for the textile. Examples of such cellulases are cellulases described in EP 0495257; EP 531 372; WO 99/25846 (Danisco A/S), WO 96/34108 (Danisco A/S), WO 96/11262; WO 96/29397; and WO 98/08940, for example. Other examples are cellulase variants, such as those described in WO 94/07998; WO 98/12307; WO 95/24471; PCT/DK98/00299; EP 531 315; U.S. Pat. Nos. 5,457,046; 5,686,593; and 5,763,254. Commercially available cellulases include CELLUZYME® and CAREZYME® (Novo Nordisk A/S); CLAZINASE™ and PURADAX® HA (Danisco A/S); and KAC-500(B)™ (Kao Corporation).

Peroxidases/Oxidases: Suitable peroxidases/oxidases contemplated for use in the compositions include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include GUARDZYME™ (Novo Nordisk A/S), for example.

5.5. Assays for Measuring AmyE Polypeptides Cleaning Performance

Exemplary assays for measuring AmyE polypeptides cleaning performance are described below and in the appended Examples. One standard assay that may be used to test the efficacy of a cleaning composition comprising an AmyE polypeptides involves a swatch test. Swatches having stains of known "strength" on various types of material are commercially available (EMPA, St. Gallen, Switzerland; wfk—Testgewebe GmbH, Krefeld Germany; or Center for Test Materials, Vlaardingen, The Netherlands) and/or can be made by the practitioner (Morris and Prato, *Textile Research Journal* 52(4): 280-286 (1982)). Swatches can comprise, for example, a cotton-containing fabric containing a stain made by blood/milk/ink (BMI), spinach, grass, or chocolate/milk/soot. A BMI stain can be fixed to cotton with 0.0003% to 0.3% hydrogen peroxide, for example. Other combinations include grass or spinach fixed with 0.001% to 1% glutaraldehyde, gelatin and Coomassie stain fixed with 0.001% to 1% glutaraldehyde, or chocolate, milk and soot fixed with 0.001% to 1% glutaraldehyde.

The swatch can also be agitated during incubation with an AmyE polypeptides and/or detergent formulation. Wash performance data is dependent on the orientation of the swatches in the wells (horizontal versus vertical), particularly in the 96-well plate. This would indicate that mixing was insufficient during the incubation period. Although there are a number of ways to ensure sufficient agitation during incubation, a plate holder in which the microtiter plate is sandwiched between two plates of aluminum can be constructed. This can be as simple as placing, for example, an adhesive plate sealer over the wells then clamping the two aluminum plates to the 96-well plate with any type of appropriate, commercially available clamps. It can then be mounted in a commercial incubator shaker. Setting the shaker to about 400 rpm results in very efficient mixing, while leakage or cross-contamination is efficiently prevented by the holder.

Trinitrobenzenesulfonic acid (TNBS) can be used to quantify the concentration of amino groups in the wash liquor. This can serve as a measure of the amount of protein that was removed from the swatch (see, e.g., Cayot and Tainturier, *Anal. Biochem.* 249: 184-200 (1997)). However, if a detergent or an enzyme sample leads to the formation of unusually small peptide fragments (for example, from the presence of peptidases in the sample), then one will obtain a larger TNBS signal, i.e., more "noise."

Another means of measuring wash performance of blood/milk/ink that is based on ink release that can be quantified by measuring the absorbance of the wash liquor. The absorbance can be measured at any wavelength between 350 and 800 nm, e.g, 410 nm or 620 nm. The wash liquor can also be examined to determine the wash performance on stains containing grass, spinach, gelatin or Coomassie stain. Suitable wavelengths for these stains include and 670 nm for spinach or grass and 620 nm for gelatin or Coomassie. For example, an aliquot of the wash liquor (typically 100-150 µL from a 96-well microplate, for example) is removed and placed in a cuvette or multiwell microplate. This is then placed in a spectrophotometer and the absorbance is read at an appropriate wavelength. The system also can be used to determine a suitable enzyme and/or detergent composition for dish washing, for example, using a blood/milk/ink stain on a suitable substrate, such as cloth, plastic or ceramic.

In one example, a BMI stain is fixed to cotton by applying 0.3% hydrogen peroxide to the BMI/cotton swatch for 30 minutes at 25° C. or by applying 0.03% hydrogen peroxide to the BMI/cotton swatch for 30 minutes at 60° C. Smaller swatches of approximately 0.25" are cut from the BMI/cotton swatch and placed in the wells of a 96-well microtiter plate. Into each well, a known mixture of a detergent composition and an enzyme, such as a variant protein, is placed. After placing an adhesive plate sealer onto the top of the microtiter plate, the microtiter plate is clamped to an aluminum plate and agitated on an orbital shaker at approximately 250 rpm for about 10 to 60 minutes. At the end of this time, the supernatants are transferred to wells in a new microtiter plate and the absorbance of the ink at 620 nm is measured. This can be similarly tests with spinach stains or grass stains fixed to cotton by applying 0.01% glutaraldehyde to the spinach/cotton swatch or grass/cotton swatch for 30 minutes at 25° C. The same can be done with chocolate, milk, and/or soot stains.

5.6. Textile Desizing Compositions and Methods

Also contemplated are compositions and methods of treating fabrics (e.g., to desize a textile) using one or more AmyE polypeptides. The AmyE polypeptides can be used in any fabric-treating method known in the art (see, e.g., U.S. Pat. No. 6,077,316). For example, the feel and appearance of a fabric can be improved using a method involving contacting the fabric with an AmyE polypeptides in solution, optionally under pressure.

AmyE polypeptides may be applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. AmyE polypeptides can be applied to remove these sizing starch or starch derivatives. After the textiles have been woven, a fabric can proceed to a desizing stage. This can be followed by one or more additional fabric processing steps. Desizing is the act of removing size from textiles. After weaving, the size coating should be removed before further processing the fabric in order to ensure a homogeneous and wash-proof result. AmyE polypeptides may then be used in a method for desizing fabric, comprising enzymatic hydrolysis of the size by the action of the AmyE polypeptides.

AmyE polypeptides can be used alone or with other desizing chemical reagents and/or desizing enzymes to desize fabrics, including cotton-containing fabrics. AmyE polypeptides can further be used in compositions and methods for producing a stonewashed look on indigo-dyed denim fabric and garments. For the manufacture of clothes, the fabric can be cut and sewn into clothes or garments, which are afterwards finished. In particular, for the manufacture of denim jeans, different enzymatic finishing methods have been developed. The finishing of denim garment normally is initiated with an enzymatic desizing step, during which garments are subjected to the action of amylolytic enzymes to provide softness to the fabric and make the cotton more accessible to the subsequent enzymatic finishing steps. AmyE polypeptides can be used in methods of finishing denim garments (e.g., a "bio-stoning process"), enzymatic desizing and providing softness to fabrics, and/or finishing process.

5.7. Compositions and Methods for Baking and Food Preparation

AmyE polypeptides may be used in compositions and methods for baking and food preparation. For the commercial and home use of flour for baking and food production, it is important to maintain an appropriate level of α-amylase activity in the flour. A level of activity that is too high may result in a product that is sticky and/or doughy and unmarketable. Conversely, flour with insufficient α-amylase activity may not contain enough sugar for proper yeast function, resulting in dry, crumbly bread. Accordingly, AmyE polypeptides, alone or in combination with another α-amylase(s), may be added to the flour to augment the level of endogenous α-amylase activity in flour. As described herein, AmyE polypeptides have a temperature optimum in the range of 30-90° C., 50-80° C., 55-75° C., or even 60-70° C., which make them well-suited for baking and food preparation applications. The temperature optimum of different AmyE variants may be measured, e.g., in a 1% solution of soluble starch at pH 5.5, or using other methods described herein or known in the art.

In addition to the use of grains and other plant products in baking, grains such as barley, oats, and wheat, as well as plant components, such as corn, hops, and rice, are used for both commercial and home brewing. The components used in brewing may be unmalted or may be malted, i.e., partially germinated, resulting in an increase in the levels of enzymes, including α-amylases. For successful brewing, adequate levels of α-amylase enzyme activity are necessary to ensure the appropriate levels of sugars for fermentation. AmyE polypeptides, alone or in combination with another α-amylase(s), may be added to wort or mash to improve starch conversion. As described elsewhere herein, AmyE polypeptides exhibit glucoamylase activity, allowing glucose to be generated from starch-containing grains without the use of an additional glucoamylase, or with a reduced amount of glucoamylase compared to that required using other α-amylases.

AmyE polypeptides can further be added alone or in a combination with other amylases to prevent or retard the staling, i.e., crumb-firming, of baked products. The amount of AmyE polypeptide used for anti-staling amylase will typically be in the range of 0.01-10 mg of enzyme protein per kg of flour, e.g., 1-10 mg/kg. Additional anti-staling amylases that can be used in combination with AmyE polypeptides include an endo-amylase, e.g., a bacterial endo-amylase from *Bacillus*. The additional amylase can also be a maltogenic α-amylase (EC 3.2.1.133), e.g., from *Bacillus*. NOVAMYL® is a suitable maltogenic α-amylase from *B. stearothermophilus* strain NCEB 11837 and is described in Christophersen et al. (1997) *Starch*, 50:39-45. Other examples of anti-staling endo-amylases include bacterial α-amylases derived from *Bacillus*, such as *B. licheniformis* or *B. amyloliquefaciens* and exo-amylase, such as β-amylase, e.g., from plant sources, such as soy bean, or from microbial sources, such as *Bacillus*.

Baking compositions comprising an AmyE polypeptides may further include a phospholipase. The phospholipase may have $A_1$ or $A_2$ activity to remove fatty acid from the phospholipids, forming a lyso-phospholipid. The phospholipase may or may not have lipase activity, i.e., activity on triglycerides. It typically has a temperature optimum in the range of 30-90° C., e.g., 30-70° C. The added phospholipases can be of animal origin, for example, from pancreas, e.g., bovine or porcine pancreas, snake venom or bee venom. Alternatively, the phospholipase may be of microbial origin, e.g., from filamentous fungi, yeast or bacteria, such as the genus or species *Aspergillus, A. niger; Dictyostelium, D. discoideum; Mucor, M. javanicus, M. mucedo, M. subtilissimus; Neurospora, N. crassa; Rhizomucor, R. pusillus; Rhizopus, R. arrhizus, R. japonicus, R. stolonifer; Sclerotinia, S. libertiana; Trichophyton, T. rubrum; Whetzelinia, W. sclerotiorum; Bacillus, B. megaterium, B. subtilis; Citrobacter, C. freundii; Enterobacter, E. aerogenes, E. cloacae; Edwardsiella, E. tarda; Etwinia, E. herbicola; Escherichia, E. coli; Klebsiella, K. pneumoniae; Proteus, P. vulgaris; Providencia, P. stuartii; Salmonella, S. typhimurium; Serratia, S. liquefasciens, S. marcescens; Shigella, S. flexneri; Streptomyces, S. violeceoruber; Yersinia, Y. enterocolitica; Fusarium, F. oxysporum*, strain DSM 2672), for example.

A phospholipase may be added in an amount that improves the softness of the bread during the initial period after baking, particularly the first 24 hours. The amount of phospholipase will typically be in the range of 0.01-10 mg of enzyme protein per kg of flour, e.g., 0.1-5 mg/kg. Phospholipase activity will generally be in the range of 20-1,000 Lipase Unit (LU)/kg of flour, where a Lipase Unit is defined as the amount of enzyme required to release 1 μmol butyric acid per minute at 30° C., pH 7.0, with gum arabic as emulsifier and tributyrin as substrate.

Compositions of dough generally include wheat meal or wheat flour and/or other types of meal, flour or starch such as corn flour, cornstarch, rye meal, rye flour, oat flour, oatmeal, soy flour, sorghum meal, sorghum flour, potato meal, potato flour or potato starch. The dough may be fresh, frozen or par-baked. The dough can be a leavened dough or a dough to be subjected to leavening. The dough may be leavened in various ways, such as by adding chemical leavening agents, e.g., sodium bicarbonate or by adding a leaven, i.e., fermenting dough. Dough also may be leavened by adding a suitable yeast culture, such as a culture of *Saccharomyces cerevisiae* (baker's yeast), e.g., a commercially available strain of 1*S. cerevisiae*.

The dough may further comprise other conventional dough ingredients, e.g., proteins, such as milk powder, gluten, and soy; eggs (either whole eggs, egg yolks or egg whites); an oxidant, such as ascorbic acid, potassium bromate, potassium iodate, azodicarbonamide (ADA) or ammonium persulfate; an amino acid such as L-cysteine; a sugar; or a salt, such as sodium chloride, calcium acetate, sodium sulfate or calcium sulfate. The dough may further comprise fat, e.g., triglycerides, such as granulated fat or shortening, and/or an emulsifier such as mono- or diglycerides, diacetyl tartaric acid esters of mono- or diglycerides, sugar esters of fatty acids, polyglycerol esters of fatty acids, lactic acid esters of monoglycerides, acetic acid esters of monoglycerides, polyoxyethylene stearates, or lysolecithin. The dough can also be made without the addition of an emulsifiers.

Optionally, an additional enzyme may be used together with the anti-staling amylase and the phospholipase. The additional enzyme may be a second (i.e., additional) amylase, such as an amyloglucosidase, a β-amylase, a cyclodextrin glucanotransferase; a peptidase, in particular an exopeptidase; a transglutaminase; a lipase; a cellulase; a hemicellulase, in particular a pentosanase such as xylanase; a protease; a protein disulfide isomerase, e.g., a protein disulfide isomerase as described in WO 95/00636; a glucanotransferase; a branching enzyme (1,4-α-glucan branching enzyme); a 4-α-glucanotransferase (dextrin glycosyltransferase); or an oxidoreductase, e.g., a peroxidase, a laccase, a glucose oxidase, a pyranose oxidase, a lipoxygenase, an L-amino acid oxidase or a carbohydrate oxidase. The additional enzyme may be of any origin, including mammalian and plant, and particularly of microbial (bacterial, yeast or fungal) origin and may be obtained by techniques conventionally used in the art.

The xylanase is typically of microbial origin, e.g., derived from a bacterium or fungus, such as a strain of *Aspergillus*, in particular of *A. aculeatus*, *A. niger* (e.g., WO 91/19782), *A. awamori* (e.g., WO 91/18977), or *A. tubigensis* (e.g., WO 92/01793); from a strain of *Trichoderma*, e.g., *T. reesei*, or from a strain of *Humicola*, e.g., *H. insolens* (e.g., WO 92/17573). PENTOPAN® and NOVOZYM 384® are commercially available xylanase preparations produced from *Trichoderma reesei*. The amyloglucosidase may be an *A. niger* amyloglucosidase (such as AMG®). Other useful amylase products include GRINDAMYL® A 1000 or A 5000 (available from Grindsted Products, Denmark) and AMYLASE® H or AMYLASE® P (available from Gist-Brocades, The Netherlands). The glucose oxidase may be a fungal glucose oxidase, in particular an *Aspergillus niger* glucose oxidase (such as GLUZYME®). An exemplary protease is Neutrase®. An exemplary lipase can be derived from strains of *Thermomyces* (*Humicola*), *Rhizomucor*, *Candida*, *Aspergillus*, *Rhizopus*, or *Pseudomonas*, in particular from *Thermomyces lanuginosus* (*Humicola lanuginosa*), *Rhizomucor miehei*, *Candida antarctica*, *Aspergillus niger*, *Rhizopus delemar* or *Rhizopus arrhizus* or *Pseudomonas cepacia*. The lipase may be Lipase A or Lipase B derived from *Candida antarctica* as described in WO 88/02775, for example, or the lipase may be derived from *Rhizomucor miehei* as described in EP 238,023, for example, or *Humicola lanuginosa*, described in EP 305,216, for example, or *Pseudomonas cepacia* as described in EP 214,761 and WO 89/01032, for example.

The AmyE polypeptide-containing enzyme preparation may optionally in the form of a granulate or agglomerated powder. The preparation can have a narrow particle size distribution with more than 95% (by weight) of the particles in the range from 25 to 500 μm. Granulates and agglomerated powders may be prepared by conventional methods, e.g., by spraying AmyE polypeptides onto a carrier in a fluid-bed granulator. The carrier may consist of particulate cores having a suitable particle size. The carrier may be soluble or insoluble, e.g., a salt (such as NaCl or sodium sulfate), a sugar (such as sucrose or lactose), a sugar alcohol (such as sorbitol), starch, rice, corn grits, or soy.

Particles comprising AmyE polypeptides may also be encapsulated using a food grade lipid, which may be any naturally organic compound that is insoluble in water but is soluble in non-polar organic solvents such as hydrocarbon or diethyl ether. Suitable food grade lipids include, but are not limited to, triglycerides either in the form of fats or oils which are either saturated or unsaturated. Examples of fatty acids and combinations thereof which make up the saturated triglycerides include, but are not limited to, butyric (derived from milk fat), palmitic (derived from animal and plant fat), and/or stearic (derived from animal and plant fat). Examples of fatty acids and combinations thereof which make up the unsaturated triglycerides include, but are not limited to, palmitoleic (derived from animal and plant fat), oleic (derived from animal and plant fat), linoleic (derived from plant oils), and/or linolenic (derived from linseed oil). Other suitable food grade lipids include, but are not limited to, monoglycerides and diglycerides derived from the triglycerides discussed above, phospholipids and glycolipids.

The food grade lipid, particularly in the liquid form, is contacted with a powdered form of AmyE polypeptides in such a fashion that the lipid material covers (envelops) at least a portion of the surface of at least a majority, e.g., 100% of the AmyE polypeptide particles. The advantages of enveloping the AmyE polypeptide particles are two-fold. First, the food grade lipid protects the enzyme from thermal denaturation during the baking process for those enzymes that are heat labile. Consequently, while the AmyE polypeptides are stabilized and protected during the proving and baking stages, they are released from the protective coating in the final baked good product, where they hydrolyzes glucosidic linkages in polyglucans. The loaded delivery vehicle also provides a sustained release of the active enzyme into the baked good. That is, following the baking process, active AmyE polypeptides are continually released from the protective coating at a rate that counteracts, and therefore reduces, the rate of staling.

In general, the amount of lipid applied to the AmyE polypeptide particles can vary from a few percent of the total weight of the α-amylase to many times that weight, depending upon the nature of the lipid, the manner in which it is applied to the particles, the composition of the dough mixture to be treated, and the severity of the dough-mixing operation involved.

The lipid-enveloped enzyme is added to the ingredients used to prepare a baked good in an effective amount to extend the shelf-life of the baked good. The baker computes the amount of enveloped α-amylase, prepared as discussed above, that will be required to achieve the desired anti-staling effect. The amount of the enveloped α-amylase required is calculated based on the concentration of enzyme enveloped and on the proportion of α-amylase to flour specified. A wide range of concentrations has been found to be effective, although, as has been discussed, observable improvements in anti-staling do not correspond linearly with the α-amylase concentration, but above certain minimal levels, large increases in α-amylase concentration produce little additional improvement. The α-amylase concentration actually used in a particular bakery production could be much higher than the minimum necessary in order to provide the baker with some insurance against inadvertent under-measurement errors by the baker. The lower limit of enzyme concentration is determined by the minimum anti-staling effect the baker wishes to achieve.

A method of preparing a baked good may comprise: (a) preparing lipid-coated AmyE polypeptide particles, wherein substantially 100 percent of the particles are coated; (b) mixing a dough containing flour; (c) adding the lipid-coated α-amylase to the dough before the mixing is complete and terminating the mixing before the lipid coating is removed from the α-amylase; (d) proofing the dough; and (e) baking the dough to provide the baked good, wherein the α-amylase is inactive during the mixing, proofing and baking stages and is active in the baked good. The enveloped AmyE polypeptides can be added to the dough during the mix cycle, e.g., near the end of the mix cycle to allow sufficient distribution throughout the dough; however, the mixing stage is terminated before the protective coating becomes stripped from the particle(s).

In some cases, bacterial α-amylase (BAA) can be added to the lipid-coated particles comprising AmyE polypeptides. BAA reduces bread to a gummy mass due to its excessive thermostability and retained activity in the fully baked loaf of bread; however, when BAA is incorporated into the lipid-coated particles, substantial additional anti-staling protection is obtained, even at very low BAA dosage levels.

Various modifications and variation can be made to the compositions and methods. All references cited herein are incorporated by reference in their entirety for all purposes.

EXAMPLES

In the foregoing description and examples that follows, the following abbreviations apply: wt % (weight percent); ° C. (degrees Centigrade); H$_2$O (water); dH$_2$O (deionized water); dIH$_2$O (deionized water, Milli-Q filtration); g or gm (grams); μg (micrograms); mg (milligrams); kg (kilograms); μL and μl (microliters); mL and ml (milliliters); mm (millimeters); μm (micrometer); M (molar); mM (millimolar); μM (micromolar); U (units); MW (molecular weight); sec (seconds); min(s) (minute/minutes); hr(s) (hour/hours); DO (dissolved oxygen); W/V (weight to volume); W/W (weight to weight); V/V (volume to volume); IKA (IKA Works Inc. 2635 North Chase Parkway SE, Wilmington, N.C.); Genencor (Danisco US Inc, Genencor Division, Palo Alto, Calif.); Ncm (Newton centimeter) and ETOH (ethanol). eq (equivalents); N (Normal); ds or DS (dry solids content), SAPU (spectrophotometric acid protease unit, wherein in 1 SAPU is the amount of protease enzyme activity that liberates one micromole of tyrosine per minute from a casein substrate under conditions of the assay) and GAU (glucoamylase unit, which is defined as the amount of enzyme that will produce 1 g of reducing sugar calculated as glucose per hour from a soluble starch substrate at pH 4.2 and 60° C.).

Example 1

Plasmid Construction and Protein Expression

The following general method were used for plasmid construction and protein expression.
1.1. Plasmid Construction Nucleic acids encoding the AmyE of SEQ ID NO: 1 or a C-terminal truncated AmyE variant, AmyE-tr (SEQ ID NO: 2), were cloned into the *B. subtilis* pHPLT expression vector, described in U.S. Pat. No. 5,024,943. FIG. 2 depicts the vector comprising a nucleic acid encoding AmyE-tr.

The pHPLT vector contained the *B. licheniformis* LAT promoter ("Plat"), a sequence encoding the LAT signal peptide ("preLAT"), followed by PstI and HpaI restriction sites for cloning. "ori-pUB" is the origin of replication from pUB110; "reppUB" is the replicase gene from pUB110, "neo" is the neomycin/kanamycin resistance gene from pUB110; "bleo" is the bleomycin resistance marker, "Tlat" is the transcriptional terminator from *B. licheniformis* amylase. These and other features of plasmid pUB110 are described in McKenzie et al., Plasmid 15(2): 93-103 (1986).

Plasmid constructs for the expression of AmyE and AmyE-tr were assembled using the AmyE-encoding sequence described by Yang et al, "Nucleotide sequence of the amylase gene from *Bacillus subtilis*," Nucl. Acids Res. 11(2): 237-49 (1983). Plasmid pME629.5 contains the nucleic acid encoding the full-length AmyE of SEQ ID NO: 1. The gene has a three base deletion in the sequence encoding the starch binding domain, compared to the sequence described by Yang et al.

Plasmid pME630.7, shown in FIG. 2, contained the truncated AmyE sequence (i.e., AmyE-tr). AmyE-tr is truncated at position D425 of SEQ ID NO: 1. AmyE-tr was designed based on a crystal structure of an AmyE variant that lacked the starch binding domain, as described in Fujimoto et al., "Crystal structure of a catalytic-site mutant alpha-amylase from *Bacillus subtilis* complexed with maltopentaose," *J. Mol. Biol.* 277: 393-407 (1998). See also, the RCSB Protein Data Bank© Accession No. 1BAG, "Alpha-Amylase From *Bacillus Subtilis* Complexed With Maltopentaose."

For expression plasmid construction, the nucleic acid encoding the AmyE polypeptide was PCR-amplified using HERCULASE® (Stratagene, La Jolla, Calif., USA) and purified using a column provided in a Qiagen QIAQUIK™ PCR purification kit (Qiagen, Valencia, Calif., USA), and resuspended in 50 μL of MELLI-Q™-purified water. 50 μL of the purified DNA was digested sequentially with HpaI (Roche) and PstI (Roche), and the resultant DNA fragments was resuspended in 30 μL of MILLI-Q™-purified water. 10-20 ng/μL DNA was cloned into plasmid pHPLT using the PstI and HpaI cloning sites. The ligation mixtures were directly transformed into competent *B. subtilis* cells (genotype: ΔaprE, ΔnprE, degUHy32 oppA, ΔspoIIE3501, amyE::xylRPxylAcomK-phleo). These *B. subtilis* cells had a competency gene (comK) placed under the control of a xylose-inducible promoter. Competency for DNA binding and uptake is induced by the addition of xylose. Because the amyE gene in the parent plasmid has two PstI sites, a PCR fusion reaction was performed to remove these sites prior to cloning. PCR fusion was performed after two separate PCR reactions. The following primers were used for making the pHPLT construct using HpaI and PstI sites:

SEQ ID NO: 10: Primer PSTAMYE-F'
5-CTTCTTGCTGCCTCATTCTGCAGCTTCAGCACTTACAGCACCGTCGA-TCAAAAGCGGAAC-3

SEQ ID NO: 11: Primer AMYENOPST-R'
5'-CTGGAGGCACTATCCTGAAGGATTTCTCCGTATTGGAACTCTGCTG-ATGTATTTGTG-3'

SEQ ID NO: 12: Primer AMYENOPST-F'
5'-CACAAATACATCAGCAGAGTTCCAATACGGAGAAATCCTTCAGGAT-AGTGCCTCCAG-3'

SEQ ID NO: 13: Primer HPAIAMYE-R'
5'-CAGGAAATCCGTCCTCTGTTAACTCAATGGGGAAGAGAACCGCTTA-AGCCCGAGTC-3'

SEQ ID NO: 14: Primer HPAIAMYE-R'
5'-CAGGAAATCCGTCCTCTGTTAACTCAATCAGGATAAAGCACAGCTA-CAGACCTGG-3'

SEQ ID NO: 15: Primer AMYE SEQ-F'
5'-TACACAAGTACAGTCCTATCTG-3'

SEQ ID NO: 16: Primer AMYE SEQ-F'
5'-CATCCTCTGTCTCTATCAATAC-3'

The plasmids pME629.5 and pME630.7 express AmyE with a 31 residue signal sequence, which is cleaved post-translationally. The subsequent 10 N-terminal amino acids are processed separately as proposed by Yang et al. (1983). pME629.5 encodes "full-length" AmyE and pME630.7 encodes "truncated" AmyE.

1.2. Protein Expression

Bacterial transformants harboring constructs encoding AmyE full-length and truncated polypeptides were selected on Luria agar (LA) with 10 µg/mL neomycin, 1% insoluble starch and incubated overnight at 37° C. Transformants showing a clearing (or halo) around the colony were selected for further studies. Precultures of each of the transformants were grown for 8 h in LB with 10 µg/mL neomycin. 30 µL of each pre-culture was added into a 250 mL flask filled with 30 mL of cultivation media (described below) supplemented with 10 µg/mL neomycin and 5 mM $CaCl_2$. The cultivation media was an enriched semi-defined media based on MOPs buffer, with urea as the major nitrogen source, glucose as the main carbon source, and supplemented with 1% soytone for robust cell growth. The shake flasks were incubated for 60-65 hours at 37° C., with mixing at 250 rpm. Cultures were harvested by centrifugation at 5,000 rpm for 20 minutes in conical tubes. Since both AmyE full-length and AmyE truncated proteins expressed at high levels, the culture supernatants were used for subsequent assays without further purification.

Example 2

Common Assays

The following assays were used in the examples described below. Deviations from the protocols provided below are indicated in the individual examples. In these experiments, a spectrophotometer was used to measure the absorbance of the products formed after the completion of the reactions.

2.1. Amylase Activity Assay

Amylase activity was measured spectrophotometrically. Insoluble corn starch covalently linked with the label Remazol Brilliant Blue R ("RBB-corn starch," Sigma S7776) was used as a substrate. 75 µL of 2% (wt ds) slurry of RBB-corn starch in 50 mM sodium acetate, pH 4.5, 5.0 or 5.6, was added to 10 µL of 100 µg/mL enzyme and thoroughly mixed. The mixture was then incubated at 50° C. for 30 minutes. The samples were then placed on ice and substrate was removed by centrifugation at 4,100 rpm for 20 minutes using a table-top centrifuge. The amount of product was determined by measuring the amount of blue dye released from the starch. The optical density (OD) of the dye was measured in triplicate at 595 nm.

2.2. Viscosity Measurement Assay

A viscometer was used to measure the viscosity of a corn starch substrate in the presence of an amylase at pH 4.5 and 5.8. A batch of 30% ds corn starch substrate slurry was freshly made, using sulfuric acid to lower the pH to either 4.5 or 5.8. For each reaction, 50 g of slurry (15 g ds) was weighed out and warmed for 10 minutes to 70° C. Upon addition of the α-amylase, the temperature was immediately increased from 70° C. to 85° C., and the reaction was stirred at 75 rpm. Once the temperature of the slurry and enzyme mixture reached 85° C., the viscosity was monitored for an additional 30 minutes.

2.3. Differential Scanning Calorimetry (DSC) to Measure Thermal Stability

The excess heat capacity function of AmyE or a variant thereof was measured in the presence or absence of 2 mM calcium chloride using an ultrasensitive scanning high-throughput microcalorimeter (VP-Capillary DSC; MicroCal, Inc., Northampton, Mass., USA). Approximately 500 µL of 0.5 mg/mL of AmyE or a variant thereof were scanned over 30-120° C. temperature range. Truncated *Geobacillus stearothermophilus* α-amylase (AmyS) was used as a control. The amino acid sequence of AmyS, including a 34 amino acid signal sequence, is shown in SEQ ID NO: 4. The same sample was then re-scanned to check the reversibility of the process. The buffer used was 10 mM sodium acetate, pH 5.5. A 200° C./hr scan rate was used to minimize any artifacts resulting from aggregation. The thermal midpoint ($T_m$) of the DSC curves was used as an indicator of thermal stability. The standard error in all the $T_m$ measurements was less than 1%.

2.4. Bradford Assay in 96-well Microtiter Plates

Protein concentration in sample supernatants was determined using the Bradford QUICKSTART™ Dye Reagent (Bio-Rad, Hercules, Calif., USA). Samples were obtained by filtering broths from cultures grown in microtiter plates (MTPs) for 3 days at 37° C. with shaking at 280 rpm and humidified aeration. 10 µL of the culture filtrate was combined with 200 µL Bradford QUICKSTART™ Dye Reagent in a well of a second MTP. After thorough mixing, the MTP were incubated for at least 10 minutes at room temperature. Air bubbles were removed and the OD (optical density) was measured at 595 nm. To determine the protein concentration, the background reading (from uninoculated wells) was subtracted from the sample readings.

2.5. Glucose Formation by HPLC Measurement

Hydrolysis of Maltose and Maltoheptaose 0.5% maltose or maltoheptaose solutions were prepared in 50 mM sodium acetate, pH 4.5 or 5.6, or in 50 mM malic acid pH 5.6, as specified for each experiment. All enzyme samples were initially diluted to 1 mg/mL. Reaction mixtures were prepared by diluting the enzyme using the appropriate substrate solutions to give a final enzyme concentration of 1 ppm, and then 200 µL aliquots were transferred to sterile screw top tubes and place in a 37° C. incubator. The reactions were stopped at the indicated times by diluting 10-fold into 10 mM sodium hydroxide.

Hydrolysis of Insoluble Starch

For measuring the hydrolysis of insoluble granular starch, purified Amy E or variants thereof (24.5 g/L) was diluted to a final concentration of 20.4 ppm in malic acid buffer, pH 5.6. The protein was then added to a 5% corn flour solution prepared in malic acid buffer, pH 5.6, to a final concentration of 1 ppm, and the mixture was incubated in a shaker at 32° C. Samples were periodically removed and diluted 10 fold into 50 mM NaOH to quench the reaction.

HPLC Detection Method

The formation of glucose and other breakdown products of the substrates were analyzed by HPLC using an Agilent 1100 LC system equipped with a Dionex PA-1 column and electrochemical detector. 10 µL samples were injected and a gradient of NaOH and sodium acetate was applied at 1.0 mL/min at 25° C. The distribution of saccharides was determined from previously run standards. Elution profiles were obtained over 45 minutes. Quantitation of glucose produced (reported as g/L) was obtained using authenticated glucose reference standard (Sigma, Mo., USA) to convert peak area for the sugars to actual sugar concentrations.

2.6. Glucose Formation Using Maltose and Maltoheptaose Substrates

The breakdown of maltose or maltoheptaose to glucose was assayed by HPLC. 0.5% maltose and maltoheptaose solution were made in a 50 mM sodium acetate buffer at pH 4.5 and pH 5.6. All enzyme samples were diluted to 1 mg/mL from purified stocks. The 1 mg/mL enzyme sample was further diluted into the maltose solution to give a final concentration of 1 µg/mL enzyme. 200 µL aliquots were then added to sterile screw-top tubes and placed in a 37° C. incubator. The reactions were stopped after 2, 5, and 8 days by the addition of sodium hydroxide. The formation of glucose and the breakdown of maltose were analyzed by HPLC against authentic standards, using the methods described in Example 2.5.

2.7 Triplex Assay

Standard total reducing sugars, glucose, and iodine assays were performed separately to characterize the products of amylopectin digestion. A 2.2% (w/w) corn amylopectin substrate was prepared in 55 mM sodium acetate buffer pH 5.8 by boiling the mixture with stirring for 30 minutes and then cooling to room temperature. One hundred μl of substrate was placed in wells of a 96 well medium binding polystyrene microtiter plate and 10 μl of diluted culture supernatants of AmyE variants were added to it. Plates were sealed (Nunc, cat. # 236366) and immediately placed in an iEMS shaking incubator and incubated at 50 C for 10 min, 1150 rpm. Amylase reactions were terminated via addition of 20 μl 0.5 N NaOH with mixing.

Total reducing sugars present were determined by mixing 20 μl 5% w/v 4-hydroxybenzhydrazide (Sigma H9882, prepared in 0.5 N HCl) with 80 μl 0.5 N NaOH followed by 20 μl of amylase reaction in an full skirt PCR plate (Axygen PCR-96-FS-C). The plate was sealed (Microseal B adhesive sealer, BioRad MSB-1001) and incubated at 95 C. for 2 minutes followed by immediate cooling to 25 C. on a PCR style thermocycling heating block. 80 μl of reaction sample was transferred to a polystyrene 96 well microtiter plate and the optical density was measured at 440 nm using a SpectraMax® plate reader.

Total glucose present in amylase reactions was determined in a microtiter plate by mixing 20 μl of reaction sample with 50 μl 5.8 mg/ml 2,2'-Azino-bis(3-ethylbenzothiazoline-6-sulfonic acid) diammonium salt (Sigma, A1888) in 50 mM potassium phosphate buffer pH 6.8, containing 0.005% v/v TWEEN-80™ followed by addition of 30 μl solution containing 0.33 U/ml peroxidase from horse radish type VI (Sigma, P8375), 3.33 U/ml OXYGO™ (Glucose Oxidase, Genencor) prepared in the same buffer. The microtiter plate was immediately placed in a SpectraMax® plate reader, shaken for 5 seconds and the optical density was monitored at 405 nm at 9 second intervals for the time period of 60-180 seconds.

Iodine analysis of amylase reactions was performed by mixing a 1:4 dilution (in water) of amylase reaction sample with 80 μl of Lugols reagent (5 g iodine, 10 g potassium iodide dissolved in 100 ml water) diluted 1:20 in water in a polystyrene microtiter plate. Optical density at 580 nm was determined using a SpectraMax® plate reader. Microsoft Excel was used to assemble data acquired from the SoftMax® Pro software (plate reader).

Iodine results are reported as total OD580; chain length/residual amylose is a function of total OD, therefore amylase activity is inversely proportional to total OD. Total reducing sugars are reported as total OD440 and are proportional to OD therefore amylase activity is directly proportional to OD. Total glucose is reported as a kinetic rate in the glucose assay and is directly proportional. OD and rates are reported in lieu of converting to known quantities using standard curves constructed from glucose. Ratios are reported using raw data and are therefore unit-less. The three types of data were combined graphically, as a ratio of iodine divided by the ratio of total reducing sugars to glucose.

2.8 High-throughput Viscometry Assay for Viscosity Reduction Rate Determination

A high-throughput viscometry assay was developed using the commercially available molecular rotor CCVJ (9-(2-carboxy-2-cyanovinyl) julolidine). A molecular rotor is a fluorescent species whose quantum yield (the number of photons emitted divided by the number of photons absorbed) is dependent on the free volume of the microenvironment, which is related in turn to viscosity. For such molecules, intramolecular rotation is the preferred mode of relaxation from the excited state. Intramolecular rotation is inhibited in a manner proportionate to the viscosity of the microenvironment, the balance of energy being dissipated through radiative relaxation (fluorescent emission).

For measuring the rate of viscosity reduction due to enzymatic activity, the molecular rotor CCVJ was incorporated into a buffered suspension of corn amylopectin as follows. A 100 mM stock solution of CCVJ was prepared by adding 186 μl of dimethyl sulfoxide to a vial containing 5 mg of lyophilized CCVJ (Sigma Aldrich Corporation, St. Louis, Mo.). The CCVJ stock solution was stored in the dark at room temperature and checked for precipitation prior to use. 90 g of amylopectin from corn (MP Biomedicals LLC, Solon, Ohio) were added to 2,850 mL of distilled water. This was heated to boiling with constant stirring, under which conditions the amylopectin gradually gelatinized and dissolved. The resulting, uniformly-viscous suspension of gelled amylopectin was removed from the heat source and stirred continuously as it returned to room temperature, at which point 150 mL of 1 M sodium acetate buffer pH 5.8 (previously prepared by titrating 1 molar sodium acetate with 1 M acetic acid) were added, followed by 150 μl of TWEEN-80™ (Sigma Aldrich Corporation, St. Louis, Mo.). When the TWEEN-80™ was completely dissolved, 150 μl of the 100 mM CCVJ stock solution were added and dissolved, at which point the amylopectin/CCVJ reagent was complete and ready for use. The reagent was stored in clear glass at room temperature with constant stirring for the three days that it took to complete the viscometry screen.

For the assay, all liquid-handling tasks were executed by a Biomek $FX^P$ robot equipped with a multichannel head that enabled the simultaneous pipetting of all 96 wells of a 96-well microtiter plate. 60 μl of amylopectin/CCVJ reagent were added to each well of a black untreated polystyrene 96-well microtiter plate (Corning Incorporated, Corning, N.Y.). 30 μl of enzyme sample were pipetted on top of this and the microtiter plate was immediately read on a SpectraMax® M2e fluorometer (Molecular Devices Corporation, Sunnyvale, Calif.) that was set up as follows: top-read fluorescence mode; excitation wavelength 435 nanometers (nm); emission wavelength 495 nm; cutoff wavelength 455 nm; kinetic read mode with 24-second read interval; 15-second shake before initial read, 3-second shake between reads; 192 seconds total read time with a 20-second lag period (eliminating from each kinetic rate calculation the first of the 9 data points collected).

In this assay, the rate of viscosity reduction was measured in terms of the rate of the drop in the fluorescent signal. Kinetic rates of fluorescent signal reduction were automatically calculated as "Vmax (milli-units per min)" by SoftMax® Pro, the software that comes packaged with SpectraMax® instruments.

2.9 High-throughput Viscometry Assay for Post-liquefaction Viscosity Determination For measuring the reduction in post-liquefaction viscosity due to enzymatic activity, the molecular rotor CCVJ was incorporated into a buffered slurry of corn flour as follows. A 100 mM stock solution of CCVJ was prepared by adding 186 μl of dimethyl sulfoxide to a vial containing 5 mg of lyophilized CCVJ (Sigma Aldrich Corporation, St. Louis, Mo.). The CCVJ stock solution was stored in the dark at room temperature and checked for precipitation prior to use. Organic corn flour (Azure Farm, Dufur, Oreg.) was passed through a 600-micrometer sieve, then baked at 95 degrees C.

for 16 hours and returned to room temperature. A 20% (weight/weight), pH 5.8 corn flour slurry was prepared in 2-kg batches by combining 1520 g of distilled water, 80 mL of 1 M sodium acetate buffer pH 5.6 (previously prepared by titrating 1 molar sodium acetate with 1 molar acetic acid), 80 µl of TWEEN-80™ (Sigma Aldrich Corporation, St. Louis, Mo.), 80 µl of the 100 mM CCVJ stock solution, and 400 g of sifted organic corn flour. The slurry was stirred vigorously and continuously for half an hour using a magnetic stir bar, at which point the pH was checked and confirmed to be 5.8. The slurry was stirred vigorously and continuously to keep the corn flour uniformly dispersed, while 90 µl of slurry were added to each well of a black untreated polystyrene 96-well microtiter plate (Corning Incorporated, Corning, N.Y.) using a multichannel pipet with 200-µl tips trimmed to an inner diameter of approximately 2.3 millimeters, determined by vernier caliper (Mitutoyo Corporation, Kure, Hiroshima, Japan). For each microtiter plate well, 10 µl of enzyme sample were pipetted on top of the corn flour slurry, after which the plate was sealed with an adhesive sealer (Bio-Rad Laboratories, Inc., Hercules, Calif.) and tightly sandwiched between pre-equilibrated metal plates in a high-temperature oven set to 80 degrees C. The plate was incubated for one hour, after which the plate was removed to room temperature and left overnight at room temperature. The following day, the plate sealer was removed and the plate was read on a SpectraMax® M2e fluorometer (Molecular Devices Corporation, Sunnyvale, Calif.) that was set up as follows: top-read fluorescence mode; excitation wavelength 435 nanometers (nm); emission wavelength 495 nm; cutoff wavelength 455 nm. In this assay, a decrease in fluorescent signal corresponded to a decrease in the density of the gelatinized corn flour, which in turn corresponded to an increase in liquefaction due to enzymatic activity.

Example 3

Specific Activity and pH Optima

The specific activity and pH optima of full-length AmyE (SEQ ID NO: 1), AmyE-tr (SEQ ID NO: 2), and variants, thereof, were measured using assays described in Example 2.1. The specific activities were determined by spectrophotometrically determining the amount of dye released from a RBB-corn starch substrate over 30 minutes at 50° C. and pH 4.5, 5.0, and 5.6. FIG. 3 shows that AmyE-tr and Amy31A have highest specific activities at pH 4.5, compared to pH 5 or 5.6. AmyE shows a higher specific activity at pH 5 than at pH 5.6.

Example 4

Reduction of the Viscosity of a Corn Starch Substrate

The ability of AmyE, AmyE-tr, and variants, thereof, to reduce the viscosity of a corn starch substrate was determined using the assay method described in Example 2.2. The viscosity was measured as a function of time at pH 4.5 and 5.8 for each enzyme. FIGS. 4A and 4B, respectively, show that AmyE-tr and AmyE reduced substrate viscosity at both pH 4.5 and 5.8. The peak viscosities were the same, while a lower final viscosity was observed at pH 5.8. FIGS. 4C and 4D, respectively, show that Amy31A has a better performance at pH 4.5 than pH 5.8.

Example 5

Thermal Stability

The thermal stabilities of AmyE, AmyE-tr, and variants, thereof, were measured in the presence and absence of $Ca^{2+}$ to determine whether $Ca^{2+}$ contributed to the stability of the enzymes, using differential scanning calorimetry (DSC) as described in Example 2.3. DSC revealed that the thermal unfolding process was irreversible. FIG. 5A shows the DSC unfolding profiles for AmyE and AmyE-tr, with and without 2 mM $Ca^{2+}$. FIG. 5B shows the DSC unfolding profiles for full length Amy31A variant. The absence of any effect of calcium on the thermal melting points suggests that neither AmyE, AmyE-tr, nor Amy31A bind $Ca^{2+}$ or are stabilized by $Ca^{2+}$ in the mM concentration range. Contrasting results were obtained for *G. stearothermophilus* α-amylase (AmyS), as shown in FIG. 5C. Table 1 summarizes the melting temperature of the tested enzymes. Addition of $Ca^{2+}$ did not significantly change the thermal stability of AmyE, AmyE-tr, or Amy31A, while $Ca^{2+}$ significantly increased the stability of AmyS.

TABLE 1

Summary of DSC $T_m$ measurements

| Sample | $T_m$ (°C.) | | |
|---|---|---|---|
| | Without added $CaCl_2$ | With 2 mM $CaCl_2$ | $\Delta T_m$ |
| AmyE truncated | 74.6 | 74.5 | −0.1 |
| AmyE full length | 76.4 | 76 | −0.4 |
| Amy31A variant | 74.8 | 74.4 | −0.4 |
| AmyS | 100 | 107.3 | 7.3 |

Example 6

Conversion of Maltose and Maltoheptaose to Glucose

The ability of AmyE-tr (SEQ ID NO: 2) and six AmyE variants of position Q153 (C, F, I, K, N, and V) of AmyE-tr to convert maltose and maltoheptaose substrates to glucose at pH 5.6 was tested, using the glucose formation assay described in Example 2.3. Glucose generated was measured after 1, 2, and 3 days. AmyE-tr and AmyE variants were used at 1 ppm. Truncated AmyS (SEQ ID NO: 4) was used for comparison at a similar dose.

FIG. 6 depicts the results of glucose production from a maltose substrate. The production of glucose by AmyS was minimal, while AmyE-tr and the Q153 position variants produced significant amounts of glucose. The variant Q153N was the best producer of glucose under these conditions. These results confirm that AmyE and a variant of AmyE efficiently produce glucose from maltose.

FIG. 7 depicts the results of glucose production from a maltoheptaose substrate. As was the case with maltose as a substrate, AmyS converted maltoheptaose to glucose with poor efficiency. By contrast, AmyE-tr and Q153 position variants converted maltoheptaose to glucose very effectively, with Q153K and F variants displaying the greatest conversion by day 3. This example demonstrates that AmyE and a variant of AmyE efficiently produce glucose from complex oligosaccharides.

Example 7

Conversion of Maltoheptaose to Glucose

The ability of AmyE-tr (SEQ ID NO: 2), AmyS, and AmyE variant Q153K to convert maltoheptaose (DP7) to glucose (DP1) was tested. The products of the reactions were analyzed using the HPLC method described in Example 2.2. Representative elution profiles are shown in FIGS. 8-10.

FIG. 8 shows that AmyE-tr converts DP7 predominately to DP1 and residual amounts of maltose (DP2) after a 72 h incubation. By contrast, FIG. 9 shows that AmyS converts DP7 to smaller oligosaccharides over time, producing a mixture of DP5, DP4, DP3, DP2 and DP1 oligosaccharides. FIG. 10 depicts a time course of the conversion of DP7 to smaller oligosaccharides in the presence of AmyE variant Q153K. Significant levels of DP1, DP2, and DP3 were detected in as little as 1 h. By 3 h, the Q153K variant converted DP7 predominately to DP1. These results show that AmyE and a variant thereof can efficiently produce glucose (DP1) from a DP7 substrate.

Example 8

Generation and Expression of Positional Variants

This example relates to the generation and expression of a library of positional variants.

8.1. Generation of Positional Libraries

Plasmid pME630.7 (FIG. 2, Example 1) was used to generate positional libraries at 150 different amino acid residues of AmyE-tr. Table 1 lists each residue for which a positional library was made. Residues are numbered based on their position in SEQ ID NO: 2. The amino acid listed at each position is the residue appearing in the AmyE of SEQ ID NO: 2 (i.e., the wild type residue).

TABLE 1

| Variant No. | SEQ ID NO: 2 Numbering | Wild type residue |
|---|---|---|
| 1 | 1 | L |
| 2 | 2 | T |
| 3 | 3 | A |
| 4 | 4 | P |
| 5 | 5 | S |
| 6 | 8 | S |
| 7 | 18 | S |
| 8 | 20 | N |
| 9 | 23 | K |
| 10 | 24 | H |
| 11 | 25 | N |
| 12 | 27 | K |
| 13 | 28 | D |
| 14 | 30 | H |
| 15 | 35 | T |
| 16 | 44 | Q |
| 17 | 45 | V |
| 18 | 47 | E |
| 19 | 49 | N |
| 20 | 50 | Q |
| 21 | 51 | G |
| 22 | 52 | D |
| 23 | 54 | S |
| 24 | 56 | S |
| 25 | 59 | Y |
| 26 | 68 | Q |
| 27 | 73 | Y |
| 28 | 75 | G |
| 29 | 76 | T |
| 30 | 78 | Q |

TABLE 1-continued

| Variant No. | SEQ ID NO: 2 Numbering | Wild type residue |
|---|---|---|
| 31 | 85 | A |
| 32 | 88 | E |
| 33 | 89 | E |
| 34 | 90 | Y |
| 35 | 91 | G |
| 36 | 106 | D |
| 37 | 107 | Y |
| 38 | 108 | A |
| 39 | 109 | A |
| 40 | 112 | N |
| 41 | 115 | K |
| 42 | 116 | S |
| 43 | 118 | P |
| 44 | 119 | N |
| 45 | 123 | G |
| 46 | 124 | N |
| 47 | 125 | T |
| 48 | 126 | Q |
| 49 | 127 | I |
| 50 | 131 | S |
| 51 | 132 | D |
| 52 | 134 | W |
| 53 | 142 | L |
| 54 | 143 | G |
| 55 | 152 | T |
| 56 | 153 | Q |
| 57 | 156 | S |
| 58 | 160 | R |
| 59 | 163 | E |
| 60 | 166 | L |
| 61 | 167 | N |
| 62 | 184 | P |
| 63 | 185 | D |
| 64 | 187 | G |
| 65 | 188 | S |
| 66 | 190 | G |
| 67 | 192 | Q |
| 68 | 195 | P |
| 69 | 199 | N |
| 70 | 200 | T |
| 71 | 201 | S |
| 72 | 202 | A |
| 73 | 203 | E |
| 74 | 212 | D |
| 75 | 213 | S |
| 76 | 214 | A |
| 77 | 218 | A |
| 78 | 219 | A |
| 79 | 221 | A |
| 80 | 222 | N |
| 81 | 223 | Y |
| 82 | 233 | H |
| 83 | 234 | S |
| 84 | 238 | A |
| 85 | 240 | K |
| 86 | 241 | N |
| 87 | 243 | N |
| 88 | 245 | G |
| 89 | 247 | S |
| 90 | 248 | N |
| 91 | 250 | S |
| 92 | 251 | H |
| 93 | 252 | Y |
| 94 | 253 | A |
| 95 | 254 | S |
| 96 | 255 | D |
| 97 | 257 | S |
| 98 | 259 | D |
| 99 | 260 | K |
| 100 | 274 | D |
| 101 | 275 | D |
| 102 | 276 | E |
| 103 | 277 | E |
| 104 | 282 | S |
| 105 | 283 | D |
| 106 | 284 | D |

TABLE 1-continued

| Variant No. | SEQ ID NO: 2 Numbering | Wild type residue |
|---|---|---|
| 107 | 287 | R |
| 108 | 307 | P |
| 109 | 308 | E |
| 110 | 309 | G |
| 111 | 310 | G |
| 112 | 311 | G |
| 113 | 312 | N |
| 114 | 313 | G |
| 115 | 314 | V |
| 116 | 317 | P |
| 117 | 318 | G |
| 118 | 319 | K |
| 119 | 320 | S |
| 120 | 321 | Q |
| 121 | 323 | G |
| 122 | 324 | D |
| 123 | 325 | R |
| 124 | 327 | S |
| 125 | 328 | A |
| 126 | 331 | E |
| 127 | 333 | Q |
| 128 | 344 | V |
| 129 | 346 | A |
| 130 | 347 | G |
| 131 | 349 | H |
| 132 | 357 | G |
| 133 | 358 | N |
| 134 | 359 | N |
| 135 | 367 | G |
| 136 | 368 | S |
| 137 | 369 | H |
| 138 | 378 | S |
| 139 | 380 | S |
| 140 | 382 | S |
| 141 | 385 | T |
| 142 | 386 | A |
| 143 | 388 | K |
| 144 | 390 | P |
| 145 | 393 | R |
| 146 | 395 | D |
| 147 | 400 | A |
| 148 | 401 | G |
| 149 | 402 | S |
| 150 | 406 | N |

The positional library for each of the 150 residues listed on Table 1 contained approximately 16 amino acid substitution variants. The libraries consisted of transformed *B. subtilis* cells containing expression plasmids encoding AmyE variant sequences at the 150 positions described. Each variant was confirmed by DNA sequencing analysis prior to protein activity evaluation. Individual clones were cultured as described below to obtain the different AmyE variants for functional characterization.

8.2. Protein Expression

The *B. subtilis* transformants containing AmyE substitution variants were cultured in 96 well plates for 8 hours in LB (Luria broth) with 10 μg/ml neomycin, and 30 μl of this pre-culture was added to a 250 mL flask filled with 30 mL of cultivation media (described below) supplemented with 25 ppm chloramphenicol and 5 mM $CaCl_2$. The flasks were incubated for 60-65 hours at 37° C. with constant rotational mixing at 250 rpm. Cultures were harvested by centrifugation at 5,000 rpm for 20 minutes in conical tubes. The culture supernatants were used for assays. The cultivation media was an enriched semi-defined media based on MOPs buffer, with urea as major nitrogen source, glucose as the main carbon source, and supplemented with 1% soytone for robust cell growth.

Example 9

Starch Hydrolysis Assay to Measure Specific Activity and Thermal Stability

The AmyE position variants were evaluated using a starch hydrolysis assay to measure specific activity and thermal stability. AmyE variants also were assayed using a cleaning swatch assay to measure stain removal performance. The pH stability of AmyE variants was evaluated by measuring amylase activity on a maltoheptaose substrate. Thermostability of each of the AmyE variants was determined by measuring amylase activity on a maltotriose substrate before and after heat stress.

9.1. Determination of Specific Activity and Thermal Stability

A starch hydrolysis assay was used to measure specific activity and stability of AmyE and AmyE variants. Conditions that closely mimic real-world applications in cleaning and grain processing were used. Activity is defined as reducing ends generated by enzymatic breakdown of corn flour. Reducing ends were determined using a PAHBAH (p-hydroxybenzoic acid hydrazide) assay, described below. Stability is defined as sustained activity at 80° C.

Hardware: Inheco Variomag Teleshake 95 heater shaker with PCR plate adapter (Hamilton Company, Reno Nev.); Thermo Electron Multidrop automated dispenser (Thermo Fisher Scientific, Inc., Waltham, Mass.); iEMS incubator (Thermo Fisher Scientific, Inc., Waltham, Mass.); V&P Scientific stir disc dispenser (model VP722B); Axygen PCR-96-FS-C full-skirt PCR plate (Axygen Scientific, Inc., Union City, Calif.); Tetrad thermocyclers (MJ Research, Waltham, Mass.), Biomek® FX liquid handlers (Beckman Coulter, Fullerton, Calif.).

Starch Hydrolysis: Azure Farms Organic Corn Flour (Norco, Calif, USA) was sifted to obtain the <600 micron fraction, baked 4 hours at 80° C., then allowed to equilibrate overnight at room temperature. The prepared dry corn flour was delivered into Axygen PCR plates using the VP722B unit as a powder flip dispenser. The mass of flour delivered to each well was determined to be approximately 5 mg. 100 μL 50 mM sodium acetate pH 5.6 (for a final suspension pH of ~5.8) were added to each well and mixed. Culture supernatants of AmyE and AmyE variants were diluted to approximately 20 μg/mL in dilution buffer (water+0.005% TWEEN-80™). 10 mL diluted supernatant were transferred to 8-minute and 30-minute reaction plates and mixed once by pipetting the sample up and down. An aliquot of 50 μL light mineral oil was transferred to each well. Plates were transferred to Inheco units pre-heated to 80° C. At various time points following incubation, the starch hydrolysis reaction was stopped by addition of 10 μL of 4 N NaOH to each well. The starch hydrolysis reaction products were analyzed by the PAHBAH assay.

PAHBAH assay: Aliquots of 80 μL of 0.5 N NaOH were added to all wells of an empty PCR plate (a "PAHBAH reaction plate"), followed by 20 μL of PAHBAH reagent (5% w/v p-hydroxybenzoic acid hydrazide (Sigma # H9882, St. Louis, Mo., USA), dissolved in 0.5 N HCl). The solutions were mixed by pipetting up and down. 10 μL of the starch hydrolysis reaction supernatants were added to each well of the PAHBAH reaction plate. The plates were sealed and placed in a thermocycler, programmed for 2 minutes at 95° C., and then cooled to 20° C. Samples of 80 μL of the developed PAHBAH reaction mixtures were transferred to a fresh plate, and absorbance was measured at 405 nm in a spectrophotometer.

9.2. Determination of Stain Removal Performance

The stain removal performance of AmyE and AmyE variants was determined using CS-28 rice starch stain microswatches. Microswatches of ¼-inch circular diameter were obtained from CFT Vlaardingen (Netherlands). Two microswatches were placed into each well of a 96-well microtiter plate.

The filtered culture broth samples were tested at an appropriate concentration by dilution with a mixture of 10 mM NaCl, 0.1 mM CaCl2, 0.005% TWEEN-80™ to 20× the desired final concentration in the performance test. The final concentration of enzyme was about 0.025-0.10 ppm. Amylase performance was measured at both pH 8 and pH 10.

Either 190 µl of (A) a buffer solution containing 25 mM HEPES (Sigma, H7523), 2 mM CaCl2, 0.005% TWEEN-80™, pH 8.0, or (B) a buffer solution containing 25 mM CAPS (Sigma, C2632), 2 mM CaCl2, 0.005% TWEEN-80™, pH 10.0 were added to each well of the plates containing microswatches. 10 µl of diluted amylase samples were added to each well to provide a total volume of 200 µl/well. The plate was covered with a plate seal and placed in an iEMS incubator for 60 minutes at 40° C. with agitation at 1,150 rpm. Following incubation under the appropriate conditions, 100 µl of solution from each well were removed and placed into a fresh microtiter plate, and absorbance was measured at 488 nm in a spectrophotometer. "Blank controls," containing 2 microswatches per well and detergent but no amylase samples, were also included in the test.

Calculation of the CS-28 rice starch hydrolysis performance: The obtained absorbance value was corrected for the blank control value. The resulting absorbance, "ΔOD488," was a measure for the amylase activity. For each AmyE or AmyE variant, the performance index was calculated by dividing the activity of the variant by the activity of the wild-type enzyme. The performance index thus represents a comparison of the performance of the variant (actual value) and the standard AmyE reference enzyme (theoretical value) at the same protein concentration. In addition, the theoretical values were calculated, using the parameters of the Langmuir equation of the standard AmyE enzyme.

Variants with performance differences over the wild-type enzyme were characterized by a performance index (PI). A PI greater than 1 (PI>1) identified a better variant compared to the standard, e.g., wild-type, while a PI of 1 (PI=1) identified a variant that performs the same as the standard. A PI less than 1 (PI<1) identified a variant that performs worse than the standard.

9.3. Determination of pH Stability

An amylase activity assay using maltoheptaose as a substrate was used to determine pH stability of AmyE and AmyE variants. Alpha amylase activity was measured by monitoring production of glucose at pH 5.8 and pH 4, using an enzyme-coupled colorimetric kinetic assay. Enzyme reactions were carried out in flat-bottom polystyrene 96-well microtiter plates at room temperature. For the assay conducted at pH 5.8, 5 µl of 5× diluted culture supernatant of AmyE or AmyE variants in 0.005% (w/v) TWEEN-20™ in water were mixed with 45 µl of buffer containing sodium acetate, pH 5.8, CaCl2, TWEEN-20™, horseradish peroxidase (Sigma-Aldrich, cat. # 8375) and glucose oxidase (OXYGO™; Genencor Division, Danisco US Inc.). The final 50 µl volume contained 50 mM, 2.6 mM, 0.005% (w/v), 20 U/ml and 50 U/ml of each component, respectively. Reactions were initiated by the addition of 50 µl of buffer containing 50 mM sodium acetate, pH 5.8, 5.4 mg/ml 2,2'-Azino-bis(3-ethylbenzothiazoline-6-sulfonic acid) diammonium salt (Sigma-Aldrich, cat. # A 1888) and 10 mM maltoheptaose (Sigma-Aldrich, cat. # M7753), and was followed by 5 seconds of mixing. Color formation in the reaction was monitored at 405 nm in 9 second intervals for 240 seconds using a SpectraMAX® 250 spectrophotometer (Molecular Devices, Union City, Calif.). Enzyme activity was reported as the rate of color formation during the 120-240 second interval of monitoring. For the assay conducted at pH 4.0, the method as described above was repeated exactly except using buffer at pH 4.0 and 20 µl of diluted AmyE or AmyE variant samples with 30 µl of peroxidase/glucose oxidase containing buffer, adjusting concentration of components appropriately.

9.4. Determination of Thermostability

The thermostability of AmyE and AmyE variants was measured by determining the amylase activity on maltotriose substrate at pH 5.8, monitoring the production of glucose using an enzyme-coupled colorimetric kinetic assay. The assay method used here was the same as described above using the maltoheptaose substrate. A 20 µl sample of diluted culture supernatants of AmyE or AmyE variants were used, and color formation was monitored during the 60-180 second interval of the reactions. In addition, 80 µl samples of diluted cultures were then transferred to fresh plates, fitted with plate sealers, and incubated for 30 minutes at 60° C. with 650 rpm shaking on an iEMS device (Thermo Fisher Scientific, Inc., Waltham, Mass.). Plates were cooled on ice for 4 minutes then 20 µl samples were assayed for activity on maltotriose substrate as described above. As in the previous assay, for each AmyE or AmyE variant, the performance index was calculated by dividing the activity of the variant by the activity of the wild-type enzyme. The performance index compared the performance of the variant (actual value) and the standard AmyE reference enzyme (theoretical value) at the same protein concentration.

Example 10

Relative Performance of AmyE Positional Variants

Using the procedures in Example 9, the relative performance or activity of AmyE-tr was compared to AmyE variants generated as described in Example 6. A total of 142 positional variants having six or more members were evaluated.

Definitions: The following definitions apply.
Performance Index (PI): ratio of performance of variant to parent protein
  Up mutations: PI>1
  Neutral mutations: PI>0.5
  Non-deleterious mutations: PI>0.05
  Deleterious mutations: PI≤0.05
Fully Restrictive Positions: No Neutral mutations for protein and activity
Non-Fully Restrictive Positions: At least one neutral mutation for one of the properties tested
Non-Restrictive Positions: ≥20% Neutral mutations for at least one property Table 2 summarizes the results of the site evaluation screens of AmyE-tr and AmyE variants. In Table 2, Column 1 indicates the amino acid position investigated. Column 2 shows the amino acid at that position in the wild-type enzyme. Column 3 indicates the number of variants at that position that were investigated in this study. The subsequent columns provide the number of variants, followed by the percent (%) of Neutral mutations identified by each assay performed. The properties tested were as follows: Columns 4 and 5 (corn flour ddG), specific activity on corn flour substrate; Columns 6 and 7 (DP3 ddG), maltotriose hydrolysis at pH 5.8; Columns 8 and 9 (DP7 pH 4 ddG), maltoheptaose hydrolysis at pH 4;

Columns 10 and 11 (DP7 pH 5.8 ddG) maltoheptaose hydrolysis at pH 5.8; Columns 12 and 13 (DP3 HS ddG), heat stability (30 min at 60° C.) using maltotriose hydrolysis assay; Columns 14 and 15 (Clean pH 8 ddG), rice starch stain microswatch assay at pH 8; Columns 16 and 17 (Clean pH 10 ddG), rice starch stain microswatch assay at pH 10. The 150 sites evaluated in truncated AmyE contained two fully restrictive positions, i.e., 75 and 123. The 295 sites evaluated in full-length AmyE contained 10 fully restrictive positions, i.e., 75, 97, 101, 102, 120, 133, 137, 182, 266, and 306.

TABLE 2

Number and percentage of Neutral mutations (PI > 0.5) at each position for each property tested.

| Position | WT amino acid | # at Position | corn flour ddG # | corn flour ddG % | DP3 ddG # | DP3 ddG % | DP7 pH 4 ddG # | DP7 pH 4 ddG % | DP7 pH 5.8 ddG # | DP7 pH 5.8 ddG % | DP3 HS ddG # | DP3 HS ddG % | Clean pH 8 ddG # | Clean pH 8 ddG % | Clean pH 10 ddG # | Clean pH 10 ddG % |
|---|---|---|---|---|---|---|---|---|---|---|---|---|---|---|---|---|
| 1 | L | 18 | 18 | 100% | 18 | 100% | 18 | 100% | 18 | 100% | 17 | 94% | 18 | 100% | 18 | 100% |
| 2 | T | 20 | 20 | 100% | 20 | 100% | 20 | 100% | 20 | 100% | 18 | 90% | 20 | 100% | 20 | 100% |
| 3 | A | 19 | 19 | 100% | 19 | 100% | 19 | 100% | 19 | 100% | 19 | 100% | 17 | 89% | 19 | 100% |
| 4 | P | 18 | 17 | 94% | 18 | 100% | 18 | 100% | 18 | 100% | 16 | 89% | 17 | 94% | 18 | 100% |
| 5 | S | 15 | 13 | 87% | 14 | 93% | 14 | 93% | 14 | 93% | 14 | 93% | 14 | 93% | 13 | 87% |
| 8 | S | 19 | 19 | 100% | 19 | 100% | 19 | 100% | 19 | 100% | 19 | 100% | 19 | 100% | 19 | 100% |
| 18 | S | 12 | 12 | 100% | 12 | 100% | 12 | 100% | 12 | 100% | 12 | 100% | 9 | 75% | 10 | 83% |
| 20 | N | 19 | 19 | 100% | 19 | 100% | 19 | 100% | 19 | 100% | 19 | 100% | 19 | 100% | 19 | 100% |
| 23 | K | 18 | 18 | 100% | 18 | 100% | 18 | 100% | 18 | 100% | 18 | 100% | 18 | 100% | 17 | 94% |
| 24 | H | 15 | 14 | 93% | 15 | 100% | 15 | 100% | 15 | 100% | 15 | 100% | 15 | 100% | 14 | 93% |
| 25 | N | 17 | 17 | 100% | 17 | 100% | 17 | 100% | 17 | 100% | 17 | 100% | 17 | 100% | 17 | 100% |
| 27 | K | 18 | 18 | 100% | 18 | 100% | 18 | 100% | 18 | 100% | 18 | 100% | 18 | 100% | 17 | 94% |
| 28 | D | 19 | 19 | 100% | 19 | 100% | 19 | 100% | 19 | 100% | 19 | 100% | 18 | 95% | 19 | 100% |
| 30 | H | 19 | 19 | 100% | 19 | 100% | 19 | 100% | 19 | 100% | 17 | 89% | 19 | 100% | 19 | 100% |
| 35 | T | 17 | 17 | 100% | 17 | 100% | 17 | 100% | 17 | 100% | 17 | 100% | 17 | 100% | 17 | 100% |
| 44 | Q | 20 | 18 | 90% | 20 | 100% | 20 | 100% | 20 | 100% | 20 | 100% | 20 | 100% | 20 | 100% |
| 45 | V | 14 | 14 | 100% | 14 | 100% | 13 | 93% | 14 | 100% | 10 | 71% | 14 | 100% | 7 | 50% |
| 47 | E | 17 | 17 | 100% | 17 | 100% | 17 | 100% | 17 | 100% | 17 | 100% | 17 | 100% | 17 | 100% |
| 49 | N | 18 | 17 | 94% | 18 | 100% | 18 | 100% | 18 | 100% | 18 | 100% | 18 | 100% | 15 | 83% |
| 50 | Q | 19 | 19 | 100% | 19 | 100% | 19 | 100% | 19 | 100% | 19 | 100% | 17 | 89% | 19 | 100% |
| 51 | G | 19 | 12 | 63% | 19 | 100% | 19 | 100% | 19 | 100% | 18 | 95% | 19 | 100% | 18 | 95% |
| 52 | D | 20 | 19 | 95% | 20 | 100% | 19 | 95% | 20 | 100% | 16 | 80% | 19 | 95% | 19 | 95% |
| 54 | S | 18 | 18 | 100% | 18 | 100% | 17 | 94% | 18 | 100% | 17 | 94% | 17 | 94% | 17 | 94% |
| 56 | S | 18 | 18 | 100% | 18 | 100% | 18 | 100% | 18 | 100% | 18 | 100% | 18 | 100% | 18 | 100% |
| 59 | Y | 17 | 7 | 41% | 17 | 100% | 10 | 59% | 8 | 47% | 15 | 88% | 17 | 100% | 3 | 18% |
| 68 | Q | 19 | 19 | 100% | 19 | 100% | 19 | 100% | 19 | 100% | 19 | 100% | 19 | 100% | 18 | 95% |
| 73 | Y | 15 | 5 | 33% | 14 | 93% | 8 | 53% | 14 | 93% | 10 | 67% | 14 | 93% | 13 | 87% |
| 76 | T | 15 | 14 | 93% | 14 | 93% | 15 | 100% | 15 | 100% | 15 | 100% | 13 | 87% | 11 | 73% |
| 78 | Q | 19 | 19 | 100% | 19 | 100% | 18 | 95% | 18 | 95% | 19 | 100% | 19 | 100% | 19 | 100% |
| 85 | A | 15 | 15 | 100% | 15 | 100% | 15 | 100% | 15 | 100% | 15 | 100% | 15 | 100% | 15 | 100% |
| 88 | E | 19 | 19 | 100% | 19 | 100% | 19 | 100% | 18 | 95% | 18 | 95% | 18 | 95% | 17 | 89% |
| 89 | E | 20 | 20 | 100% | 20 | 100% | 20 | 100% | 20 | 100% | 20 | 100% | 20 | 100% | 20 | 100% |
| 90 | Y | 18 | 18 | 100% | 18 | 100% | 18 | 100% | 18 | 100% | 18 | 100% | 18 | 100% | 18 | 100% |
| 91 | G | 18 | 13 | 72% | 17 | 94% | 17 | 94% | 17 | 94% | 17 | 94% | 15 | 83% | 15 | 83% |
| 106 | S | 18 | 9 | 50% | 18 | 100% | 9 | 50% | 18 | 100% | 6 | 33% | 18 | 100% | 14 | 78% |
| 107 | Y | 19 | 14 | 74% | 19 | 100% | 19 | 100% | 19 | 100% | 13 | 68% | 19 | 100% | 17 | 89% |
| 108 | A | 18 | 18 | 100% | 18 | 100% | 18 | 100% | 18 | 100% | 18 | 100% | 18 | 100% | 18 | 100% |
| 109 | A | 18 | 16 | 89% | 18 | 100% | 18 | 100% | 17 | 94% | 17 | 94% | 18 | 100% | 15 | 83% |
| 112 | N | 20 | 20 | 100% | 19 | 95% | 20 | 100% | 20 | 100% | 18 | 90% | 20 | 100% | 20 | 100% |
| 115 | K | 18 | 14 | 78% | 18 | 100% | 18 | 100% | 18 | 100% | 14 | 78% | 15 | 83% | 12 | 67% |
| 116 | S | 16 | 15 | 94% | 16 | 100% | 16 | 100% | 16 | 100% | 16 | 100% | 16 | 100% | 16 | 100% |
| 118 | P | 20 | 18 | 90% | 20 | 100% | 20 | 100% | 20 | 100% | 20 | 100% | 20 | 100% | 19 | 95% |
| 119 | N | 16 | 15 | 94% | 16 | 100% | 16 | 100% | 16 | 100% | 13 | 81% | 16 | 100% | 15 | 94% |
| 124 | N | 15 | 1 | 7% | 15 | 100% | 7 | 47% | 15 | 100% | 1 | 7% | 14 | 93% | 10 | 67% |
| 125 | T | 18 | 8 | 44% | 18 | 100% | 18 | 100% | 18 | 100% | 7 | 39% | 17 | 94% | 16 | 89% |
| 126 | Q | 17 | 9 | 53% | 16 | 94% | 14 | 82% | 16 | 94% | 13 | 76% | 16 | 94% | 12 | 71% |
| 131 | S | 17 | 15 | 88% | 17 | 100% | 17 | 100% | 17 | 100% | 15 | 88% | 17 | 100% | 16 | 94% |
| 132 | D | 16 | 2 | 13% | 16 | 100% | 15 | 94% | 14 | 88% | 2 | 13% | 16 | 100% | 6 | 38% |
| 134 | W | 14 | 0 | 0% | 14 | 100% | 14 | 100% | 14 | 100% | 0 | 0% | 13 | 93% | 12 | 86% |
| 142 | L | 15 | 6 | 40% | 15 | 100% | 3 | 20% | 3 | 20% | 13 | 87% | 9 | 60% | 3 | 20% |
| 143 | G | 13 | 1 | 8% | 13 | 100% | 2 | 15% | 13 | 100% | 1 | 8% | 2 | 15% | 2 | 15% |
| 152 | T | 20 | 20 | 100% | 20 | 100% | 20 | 100% | 20 | 100% | 19 | 95% | 20 | 100% | 20 | 100% |
| 153 | Q | 20 | 19 | 95% | 19 | 95% | 19 | 95% | 19 | 95% | 19 | 95% | 19 | 95% | 19 | 95% |
| 156 | S | 19 | 19 | 100% | 19 | 100% | 19 | 100% | 19 | 100% | 18 | 95% | 19 | 100% | 17 | 89% |
| 160 | R | 19 | 19 | 100% | 19 | 100% | 19 | 100% | 19 | 100% | 19 | 100% | 18 | 95% | 19 | 100% |
| 163 | D | 18 | 18 | 100% | 18 | 100% | 18 | 100% | 18 | 100% | 18 | 100% | 18 | 100% | 18 | 100% |
| 166 | L | 19 | 19 | 100% | 19 | 100% | 18 | 95% | 19 | 100% | 19 | 100% | 19 | 100% | 18 | 95% |
| 167 | N | 18 | 18 | 100% | 18 | 100% | 18 | 100% | 18 | 100% | 18 | 100% | 18 | 100% | 18 | 100% |
| 184 | P | 19 | 2 | 11% | 19 | 100% | 19 | 100% | 19 | 100% | 1 | 5% | 17 | 89% | 7 | 37% |
| 185 | D | 6 | 2 | 33% | 6 | 100% | 6 | 100% | 6 | 100% | 1 | 17% | 6 | 100% | 3 | 50% |
| 187 | G | 20 | 1 | 5% | 20 | 100% | 20 | 100% | 20 | 100% | 2 | 10% | 19 | 95% | 19 | 95% |
| 188 | S | 17 | 9 | 53% | 17 | 100% | 17 | 100% | 17 | 100% | 10 | 59% | 17 | 100% | 16 | 94% |
| 190 | G | 13 | 6 | 46% | 13 | 100% | 13 | 100% | 13 | 100% | 2 | 15% | 13 | 100% | 10 | 77% |
| 195 | P | 18 | 4 | 22% | 18 | 100% | 18 | 100% | 18 | 100% | 6 | 33% | 16 | 89% | 17 | 94% |
| 199 | N | 17 | 15 | 88% | 17 | 100% | 16 | 94% | 16 | 94% | 17 | 100% | 14 | 82% | 11 | 65% |
| 200 | T | 20 | 18 | 90% | 19 | 95% | 19 | 95% | 19 | 95% | 14 | 70% | 18 | 90% | 17 | 85% |

TABLE 2-continued

Number and percentage of Neutral mutations (PI > 0.5) at each position for each property tested.

| Position | WT amino acid | # at Position | corn flour ddG # | corn flour ddG % | DP3 ddG # | DP3 ddG % | DP7 pH 4 ddG # | DP7 pH 4 ddG % | DP7 pH 5.8 ddG # | DP7 pH 5.8 ddG % | DP3 HS ddG # | DP3 HS ddG % | Clean pH 8 ddG # | Clean pH 8 ddG % | Clean pH 10 ddG # | Clean pH 10 ddG % |
|---|---|---|---|---|---|---|---|---|---|---|---|---|---|---|---|---|
| 201 | S | 20 | 20 | 100% | 20 | 100% | 20 | 100% | 20 | 100% | 20 | 100% | 20 | 100% | 20 | 100% |
| 202 | A | 16 | 13 | 81% | 16 | 100% | 16 | 100% | 16 | 100% | 15 | 94% | 14 | 88% | 14 | 88% |
| 203 | E | 17 | 17 | 100% | 17 | 100% | 17 | 100% | 17 | 100% | 17 | 100% | 17 | 100% | 17 | 100% |
| 212 | D | 12 | 1 | 8% | 12 | 100% | 5 | 42% | 12 | 100% | 1 | 8% | 6 | 50% | 5 | 42% |
| 213 | S | 18 | 15 | 83% | 18 | 100% | 18 | 100% | 17 | 94% | 17 | 94% | 15 | 83% | 16 | 89% |
| 214 | A | 17 | 6 | 35% | 17 | 100% | 17 | 100% | 17 | 100% | 10 | 59% | 17 | 100% | 15 | 88% |
| 218 | A | 20 | 20 | 100% | 20 | 100% | 20 | 100% | 20 | 100% | 18 | 90% | 20 | 100% | 20 | 100% |
| 219 | A | 18 | 6 | 33% | 18 | 100% | 18 | 100% | 18 | 100% | 6 | 33% | 17 | 94% | 7 | 39% |
| 221 | A | 14 | 10 | 71% | 14 | 100% | 13 | 93% | 14 | 100% | 8 | 57% | 12 | 86% | 11 | 79% |
| 233 | H | 20 | 18 | 90% | 20 | 100% | 19 | 95% | 20 | 100% | 19 | 95% | 20 | 100% | 9 | 45% |
| 234 | S | 19 | 19 | 100% | 19 | 100% | 19 | 100% | 19 | 100% | 18 | 95% | 19 | 100% | 19 | 100% |
| 238 | A | 19 | 18 | 95% | 19 | 100% | 19 | 100% | 19 | 100% | 19 | 100% | 18 | 95% | 19 | 100% |
| 240 | K | 18 | 18 | 100% | 18 | 100% | 18 | 100% | 18 | 100% | 18 | 100% | 18 | 100% | 17 | 94% |
| 241 | N | 18 | 18 | 100% | 18 | 100% | 18 | 100% | 18 | 100% | 18 | 100% | 18 | 100% | 18 | 100% |
| 243 | N | 19 | 19 | 100% | 19 | 100% | 19 | 100% | 19 | 100% | 19 | 100% | 19 | 100% | 19 | 100% |
| 245 | G | 16 | 16 | 100% | 16 | 100% | 16 | 100% | 16 | 100% | 16 | 100% | 15 | 94% | 16 | 100% |
| 247 | S | 16 | 14 | 88% | 14 | 88% | 14 | 88% | 14 | 88% | 14 | 88% | 14 | 88% | 14 | 88% |
| 250 | S | 19 | 18 | 95% | 19 | 100% | 18 | 95% | 19 | 100% | 18 | 95% | 18 | 95% | 19 | 100% |
| 251 | H | 16 | 16 | 100% | 16 | 100% | 16 | 100% | 16 | 100% | 16 | 100% | 16 | 100% | 16 | 100% |
| 252 | Y | 18 | 14 | 78% | 18 | 100% | 16 | 89% | 18 | 100% | 9 | 50% | 14 | 78% | 17 | 94% |
| 253 | A | 17 | 17 | 100% | 17 | 100% | 17 | 100% | 17 | 100% | 15 | 88% | 17 | 100% | 16 | 94% |
| 254 | S | 15 | 12 | 80% | 13 | 87% | 13 | 87% | 15 | 100% | 9 | 60% | 15 | 100% | 12 | 80% |
| 259 | D | 16 | 15 | 94% | 16 | 100% | 15 | 94% | 15 | 94% | 16 | 100% | 15 | 94% | 14 | 88% |
| 260 | K | 19 | 19 | 100% | 19 | 100% | 19 | 100% | 19 | 100% | 19 | 100% | 16 | 84% | 18 | 95% |
| 274 | D | 19 | 18 | 95% | 19 | 100% | 1 | 5% | 19 | 100% | 19 | 100% | 19 | 100% | 19 | 100% |
| 275 | D | 20 | 19 | 95% | 20 | 100% | 8 | 40% | 20 | 100% | 20 | 100% | 20 | 100% | 18 | 90% |
| 276 | E | 20 | 19 | 95% | 18 | 90% | 14 | 70% | 18 | 90% | 18 | 90% | 19 | 95% | 16 | 80% |
| 277 | E | 20 | 19 | 95% | 20 | 100% | 10 | 50% | 20 | 100% | 18 | 90% | 20 | 100% | 15 | 75% |
| 282 | S | 20 | 18 | 90% | 20 | 100% | 19 | 95% | 20 | 100% | 20 | 100% | 20 | 100% | 20 | 100% |
| 283 | D | 17 | 14 | 82% | 16 | 94% | 7 | 41% | 16 | 94% | 16 | 94% | 15 | 88% | 16 | 94% |
| 284 | D | 20 | 19 | 95% | 19 | 95% | 19 | 95% | 19 | 95% | 19 | 95% | 19 | 95% | 20 | 100% |
| 287 | R | 20 | 18 | 90% | 20 | 100% | 20 | 100% | 20 | 100% | 20 | 100% | 18 | 90% | 20 | 100% |
| 307 | P | 6 | 4 | 67% | 6 | 100% | 3 | 50% | 6 | 100% | 6 | 100% | 6 | 100% | 6 | 100% |
| 308 | E | 20 | 20 | 100% | 20 | 100% | 20 | 100% | 20 | 100% | 20 | 100% | 20 | 100% | 19 | 95% |
| 309 | G | 17 | 14 | 82% | 16 | 94% | 11 | 65% | 16 | 94% | 16 | 94% | 11 | 65% | 17 | 100% |
| 310 | G | 17 | 5 | 29% | 17 | 100% | 2 | 12% | 17 | 100% | 16 | 94% | 15 | 88% | 14 | 82% |
| 311 | G | 20 | 18 | 90% | 19 | 95% | 2 | 10% | 20 | 100% | 19 | 95% | 17 | 85% | 19 | 95% |
| 312 | N | 20 | 19 | 95% | 20 | 100% | 19 | 95% | 19 | 95% | 20 | 100% | 20 | 100% | 18 | 90% |
| 313 | G | 20 | 17 | 85% | 20 | 100% | 17 | 85% | 20 | 100% | 20 | 100% | 20 | 100% | 20 | 100% |
| 314 | V | 16 | 15 | 94% | 15 | 94% | 15 | 94% | 15 | 94% | 15 | 94% | 16 | 100% | 15 | 94% |
| 317 | P | 19 | 19 | 100% | 19 | 100% | 14 | 74% | 19 | 100% | 19 | 100% | 19 | 100% | 17 | 89% |
| 318 | G | 16 | 15 | 94% | 15 | 94% | 15 | 94% | 15 | 94% | 15 | 94% | 14 | 88% | 15 | 94% |
| 319 | K | 12 | 12 | 100% | 12 | 100% | 12 | 100% | 12 | 100% | 12 | 100% | 12 | 100% | 12 | 100% |
| 320 | S | 18 | 18 | 100% | 18 | 100% | 13 | 72% | 18 | 100% | 18 | 100% | 18 | 100% | 18 | 100% |
| 321 | Q | 18 | 17 | 94% | 18 | 100% | 17 | 94% | 18 | 100% | 18 | 100% | 18 | 100% | 18 | 100% |
| 323 | G | 7 | 6 | 86% | 6 | 86% | 2 | 29% | 6 | 86% | 5 | 71% | 3 | 43% | 7 | 100% |
| 324 | D | 20 | 19 | 95% | 20 | 100% | 19 | 95% | 20 | 100% | 20 | 100% | 18 | 90% | 20 | 100% |
| 325 | R | 17 | 15 | 88% | 17 | 100% | 16 | 94% | 17 | 100% | 17 | 100% | 14 | 82% | 17 | 100% |
| 327 | S | 13 | 12 | 92% | 11 | 85% | 6 | 46% | 11 | 85% | 11 | 85% | 8 | 62% | 12 | 92% |
| 328 | A | 19 | 19 | 100% | 19 | 100% | 19 | 100% | 19 | 100% | 19 | 100% | 19 | 100% | 19 | 100% |
| 331 | E | 16 | 16 | 100% | 16 | 100% | 16 | 100% | 16 | 100% | 16 | 100% | 16 | 100% | 16 | 100% |
| 333 | Q | 18 | 18 | 100% | 18 | 100% | 18 | 100% | 18 | 100% | 18 | 100% | 18 | 100% | 18 | 100% |
| 344 | V | 18 | 15 | 83% | 18 | 100% | 18 | 100% | 18 | 100% | 18 | 100% | 18 | 100% | 18 | 100% |
| 346 | A | 16 | 16 | 100% | 16 | 100% | 16 | 100% | 16 | 100% | 16 | 100% | 16 | 100% | 16 | 100% |
| 347 | G | 20 | 20 | 100% | 20 | 100% | 20 | 100% | 20 | 100% | 20 | 100% | 20 | 100% | 20 | 100% |
| 349 | P | 19 | 19 | 100% | 19 | 100% | 19 | 100% | 19 | 100% | 19 | 100% | 19 | 100% | 19 | 100% |
| 357 | G | 20 | 20 | 100% | 20 | 100% | 20 | 100% | 20 | 100% | 20 | 100% | 20 | 100% | 20 | 100% |
| 358 | N | 19 | 19 | 100% | 19 | 100% | 19 | 100% | 19 | 100% | 19 | 100% | 19 | 100% | 18 | 95% |
| 359 | N | 20 | 20 | 100% | 20 | 100% | 20 | 100% | 20 | 100% | 20 | 100% | 20 | 100% | 20 | 100% |
| 367 | G | 19 | 19 | 100% | 19 | 100% | 19 | 100% | 19 | 100% | 19 | 100% | 19 | 100% | 19 | 100% |
| 368 | S | 16 | 16 | 100% | 16 | 100% | 16 | 100% | 16 | 100% | 16 | 100% | 16 | 100% | 16 | 100% |
| 369 | H | 20 | 20 | 100% | 20 | 100% | 20 | 100% | 20 | 100% | 20 | 100% | 20 | 100% | 20 | 100% |
| 378 | S | 20 | 20 | 100% | 20 | 100% | 20 | 100% | 20 | 100% | 20 | 100% | 20 | 100% | 20 | 100% |
| 380 | S | 18 | 18 | 100% | 18 | 100% | 18 | 100% | 18 | 100% | 18 | 100% | 18 | 100% | 18 | 100% |
| 382 | S | 19 | 19 | 100% | 19 | 100% | 19 | 100% | 19 | 100% | 19 | 100% | 19 | 100% | 19 | 100% |
| 385 | T | 20 | 20 | 100% | 20 | 100% | 20 | 100% | 20 | 100% | 20 | 100% | 20 | 100% | 20 | 100% |
| 386 | A | 16 | 16 | 100% | 16 | 100% | 16 | 100% | 16 | 100% | 16 | 100% | 16 | 100% | 15 | 94% |
| 388 | K | 19 | 19 | 100% | 19 | 100% | 19 | 100% | 19 | 100% | 19 | 100% | 19 | 100% | 19 | 100% |
| 390 | P | 19 | 19 | 100% | 19 | 100% | 19 | 100% | 19 | 100% | 19 | 100% | 19 | 100% | 19 | 100% |
| 393 | R | 17 | 17 | 100% | 17 | 100% | 17 | 100% | 17 | 100% | 17 | 100% | 17 | 100% | 17 | 100% |
| 395 | D | 20 | 20 | 100% | 19 | 95% | 19 | 95% | 20 | 100% | 19 | 95% | 20 | 100% | 20 | 100% |
| 400 | A | 20 | 20 | 100% | 20 | 100% | 20 | 100% | 20 | 100% | 20 | 100% | 20 | 100% | 20 | 100% |
| 401 | G | 20 | 20 | 100% | 20 | 100% | 20 | 100% | 20 | 100% | 20 | 100% | 20 | 100% | 20 | 100% |

TABLE 2-continued

Number and percentage of Neutral mutations (PI > 0.5) at each position for each property tested.

| Position | WT amino acid | # at Position | corn flour ddG # | corn flour ddG % | DP3 ddG # | DP3 ddG % | DP7 pH 4 ddG # | DP7 pH 4 ddG % | DP7 pH 5.8 ddG # | DP7 pH 5.8 ddG % | DP3 HS ddG # | DP3 HS ddG % | Clean pH 8 ddG # | Clean pH 8 ddG % | Clean pH 10 ddG # | Clean pH 10 ddG % |
|---|---|---|---|---|---|---|---|---|---|---|---|---|---|---|---|---|
| 402 | S | 18 | 18 | 100% | 18 | 100% | 18 | 100% | 18 | 100% | 18 | 100% | 18 | 100% | 18 | 100% |
| 406 | N | 6 | 6 | 100% | 6 | 100% | 6 | 100% | 6 | 100% | 6 | 100% | 6 | 100% | 6 | 100% |

Example 11

Ethanol Formation by AmyE

In this example, experiments were conducted to test the performance of truncated AmyE in conventional ethanol fermentation on Illinois River Energy (IRE) liquefact (31% DS) using a conventional ethanol fermentation assay. Briefly, batches of 31% DS Illinois River Energy (IRE) liquefact with 400 ppm urea were prepared and the pH of one batch adjusted to 4.3 and the other adjusted to pH 5.8 with 5 N $H_2SO_4$. 100 g substrate was used per flask (125 ml Erlenmeyer). Enzymes were dosed as indicated. Fermentations were inoculated with 0.2 ml of 10% (w/v) Red Start® Ethanol Red yeast (prehydrated ~45 min in DI water). Flasks were incubated at 32° C. with stir bars at 320 rpm for 48 h fermentation. The amount of ethanol produced was measured by HPLC analysis. The performance of truncated AmyE (SEQ ID NO: 2) was compared to SPEZYME® Xtra amylase (SEQ ID NO: 4) at pH 4.3 and pH 5.8. Truncated AmyE and SPEZYME® Xtra amylase were dosed at 0.2 mg/gDS.

As shown in FIG. 11, the final ethanol yield produced by truncated AmyE at pH 5.8 is 12.0% (v/v). Truncated AmyE at pH 4.3 yielded a final ethanol yield of 7.3% (v/v). Final ethanol yields in the presence of SPEZYME® Xtra amylase were 2.7% (v/v) at pH 4.3 and 3.9% (v/v) at pH 5.8.

Example 12

Comparison of Ethanol Formation by AmyE and Other α-amylases

In this example, experiments were conducted to compare the ability of full length AmyE (SEQ ID NO: 1) and truncated AmyE (SEQ ID NO: 2) to hydrolyze insoluble granular (uncooked) starch into ethanol at pH 4.3 and pH 5.8, using the ethanol fermentation on whole ground corn assay described in Example 11.

Using this assay, the ethanol forming performance of full length and truncated AmyE was compared to *A. kawachii* alpha amylase (AkAA, GC626), dosed at 1.5 SSU/g (one unit of the enzyme activity-SSU soluble starch unit is equivalent to the reducing power of 1 mg of glucose released per minute from the hydrolyssi of soluble potato starch substrate (4% ds) at pH 4.5 and 50° C.) and STARGEN™ 002 (*Aspergillus kawachi* alpha amylase expressed in *Trichoderma reesei* and a glucoamylase from *Trichoderma reesei* that work synergistically to hydrolyze granular starch substrate to glucose), dosed at 0.5 GAU/g, where one Glucoamylase Unit (GAU) is the amount of enzyme that will produce 1 μM of reducing sugar, calculated as glucose per hour from a soluble starch substrate (4% ds) at pH 4.2 and 60° C. The definitions of SSU and GAU are described in greater detail in U.S. Pat. No. 7,037,704. Both, AmyE full-length and truncated AmyE were dosed at 0.2 mg/gDS.

FIG. 12 shows the results observed when performance of these enzymes were compared, at pH 4.3 and 5.8, and reported as final ethanol yield produced. When tested at pH 5.8, both full length and truncated AmyE performed very comparably to the STARGEN™ 002, with full length AmyE actually surpassing the ethanol yields observed for STARGEN™ 002 at pH 4.3. The truncated AmyE when tested at pH 5.8 performed very comparably to STARGEN™ 002 tested at the same pH. In comparison, the *A. kawachii* alpha amylase performed very poorly at both pH 4.2 and pH 5.8.

Example 13

Glucose Formation by *Bacillus subtilis* Alpha Amylases

In this example, experiments were conducted to determine the ability of *Bacillus subtilis* alpha amylases to convert maltose to glucose at pH 4.5 and 5.6 using the glucose formation assay described in Example 2. The reactions were analyzed after 2, 5 and 8 days.

As shown in FIG. 13, *B. subtilis* AmyE full length (SEQ ID NO: 1), AmyE truncated (SEQ ID NO: 2), and variant α-amylase Amy 31A (SEQ ID NO: 3) effectively converted maltose to glucose, whereas the truncated *Geobacillus stearothermophilus* α-amylase, AmyS (SEQ ID NO: 4), showed only a minimal amount of glucose formation under these conditions.

Example 14

AmyE Action on Raw Starch

In this example, experiments were conducted to determine the ability of full-length AmyE (SEQ ID NO: 1), to hydrolyze insoluble granular (uncooked) starch. The HPLC method used for detection of saccharides produced from insoluble starch is as follows.

Purified Amy E (24.5 g/L) was diluted to a final concentration of 20.4 ppm in malic acid buffer, pH 5.6. The protein was then added to a 5% corn flour solution in malic acid buffer, pH 5.6 to a final concentration of 1 ppm. The mixture was then incubated in a shaker at 32° C. Samples were periodically removed and diluted into 50 mM NaOH to quench the reaction. 10 μL samples were then injected into an HPLC system (Agilent 1000) enabled with electrochemical detection. A PA1 column was used with a gradient of NaOH and Na-acetate run at 25° C. The distribution was determined from previously run standards.

Results: Incubation of raw starch with 1 ppm of full-length AmyE enzyme lead to a time-dependent release of numerous oligosaccharides (DP2, 3, 4, 5, 6, 7) as well as glucose (DP1). The appearance of these degradation products was quantified by HPLC analysis of digestion time points. Data for 0, 30 and 90 minute samples is shown in FIG. 14. Comparable results were observed for the truncated AmyE enzyme (data not shown).

Example 15

Positional Libraries in Full Length AmyE

Positional libraries were generated at 295 sites in full-length AmyE (SEQ ID NO: 1) by Geneart (Geneart GmbH, Josef-Engert-strasse 11, D-93053 Regensburg, Germany). Table 3 lists each residue for which a positional library was made. Residues are numbered based on their position in SEQ ID NO: 1.

TABLE 3

Positional libraries generated in full-length AmyE

| Variant No. | Residue number in full length AmyE | Wild type residue |
|---|---|---|
| 1 | 6 | I |
| 2 | 7 | K |
| 3 | 9 | G |
| 4 | 10 | T |
| 5 | 11 | I |
| 6 | 12 | L |
| 7 | 13 | H |
| 8 | 14 | A |
| 9 | 15 | W |
| 10 | 16 | N |
| 11 | 17 | W |
| 12 | 19 | F |
| 13 | 21 | T |
| 14 | 22 | L |
| 15 | 26 | M |
| 16 | 27 | K |
| 17 | 29 | I |
| 18 | 30 | H |
| 19 | 31 | D |
| 20 | 32 | A |
| 21 | 33 | G |
| 22 | 34 | Y |
| 23 | 36 | A |
| 24 | 37 | I |
| 25 | 38 | Q |
| 26 | 39 | T |
| 27 | 40 | S |
| 28 | 41 | P |
| 29 | 42 | I |
| 30 | 43 | N |
| 31 | 45 | V |
| 32 | 46 | K |
| 33 | 48 | G |
| 34 | 52 | D |
| 35 | 53 | K |
| 36 | 55 | M |
| 37 | 57 | N |
| 38 | 58 | W |
| 39 | 60 | W |
| 40 | 61 | L |
| 41 | 62 | Y |
| 42 | 63 | Q |
| 43 | 64 | P |
| 44 | 65 | T |
| 45 | 66 | S |
| 46 | 67 | Y |
| 47 | 69 | I |
| 48 | 70 | G |
| 49 | 71 | N |
| 50 | 72 | R |
| 51 | 74 | L |
| 52 | 75 | G |
| 53 | 77 | E |
| 54 | 79 | E |
| 55 | 80 | F |
| 56 | 81 | K |
| 57 | 82 | E |
| 58 | 83 | M |
| 59 | 84 | C |
| 60 | 86 | A |
| 61 | 87 | A |
| 62 | 88 | E |
| 63 | 89 | E |
| 64 | 92 | I |
| 65 | 93 | K |
| 66 | 94 | V |
| 67 | 95 | I |
| 68 | 96 | V |
| 69 | 97 | D |
| 70 | 98 | A |
| 71 | 99 | V |
| 72 | 100 | I |
| 73 | 101 | N |
| 74 | 102 | H |
| 75 | 103 | T |
| 76 | 104 | T |
| 77 | 105 | S |
| 78 | 110 | I |
| 79 | 111 | S |
| 80 | 113 | E |
| 81 | 114 | V |
| 82 | 117 | I |
| 83 | 120 | W |
| 84 | 121 | T |
| 85 | 122 | H |
| 86 | 126 | Q |
| 87 | 128 | K |
| 88 | 129 | N |
| 89 | 130 | W |
| 90 | 131 | S |
| 91 | 133 | R |
| 92 | 135 | D |
| 93 | 136 | V |
| 94 | 137 | T |
| 95 | 138 | Q |
| 96 | 139 | N |
| 97 | 140 | S |
| 98 | 141 | L |
| 99 | 144 | L |
| 100 | 145 | Y |
| 101 | 146 | D |
| 102 | 147 | W |
| 103 | 148 | N |
| 104 | 149 | T |
| 105 | 150 | Q |
| 106 | 151 | N |
| 107 | 154 | V |
| 108 | 155 | Q |
| 109 | 157 | Y |
| 110 | 158 | L |
| 111 | 159 | K |
| 112 | 161 | F |
| 113 | 162 | L |
| 114 | 164 | R |
| 115 | 165 | A |
| 116 | 167 | N |
| 117 | 168 | D |
| 118 | 169 | G |
| 119 | 170 | A |
| 120 | 171 | D |
| 121 | 172 | G |
| 122 | 173 | F |
| 123 | 174 | R |
| 124 | 175 | F |
| 125 | 176 | D |
| 126 | 177 | A |
| 127 | 178 | A |

TABLE 3-continued

Positional libraries generated in full-length AmyE

| Variant No. | Residue number in full length AmyE | Wild type residue |
|---|---|---|
| 128 | 179 | K |
| 129 | 180 | H |
| 130 | 181 | I |
| 131 | 182 | E |
| 132 | 183 | L |
| 133 | 184 | P |
| 134 | 186 | D |
| 135 | 189 | Y |
| 136 | 191 | S |
| 137 | 193 | F |
| 138 | 194 | W |
| 139 | 196 | N |
| 140 | 197 | I |
| 141 | 198 | T |
| 142 | 204 | F |
| 143 | 205 | Q |
| 144 | 206 | Y |
| 145 | 207 | G |
| 146 | 208 | E |
| 147 | 209 | I |
| 148 | 210 | L |
| 149 | 211 | Q |
| 150 | 215 | S |
| 151 | 216 | R |
| 152 | 217 | D |
| 153 | 220 | Y |
| 154 | 223 | Y |
| 155 | 224 | M |
| 156 | 225 | D |
| 157 | 226 | V |
| 158 | 227 | T |
| 159 | 228 | A |
| 160 | 229 | S |
| 161 | 230 | N |
| 162 | 231 | Y |
| 163 | 232 | G |
| 164 | 235 | I |
| 165 | 236 | R |
| 166 | 237 | S |
| 167 | 238 | A |
| 168 | 239 | L |
| 169 | 241 | N |
| 170 | 242 | R |
| 171 | 244 | L |
| 172 | 246 | V |
| 173 | 249 | I |
| 174 | 256 | V |
| 175 | 258 | A |
| 176 | 260 | K |
| 177 | 261 | L |
| 178 | 262 | V |
| 179 | 263 | T |
| 180 | 264 | W |
| 181 | 265 | V |
| 182 | 266 | E |
| 183 | 267 | S |
| 184 | 268 | H |
| 185 | 269 | D |
| 186 | 270 | T |
| 187 | 271 | Y |
| 188 | 272 | A |
| 189 | 273 | N |
| 190 | 278 | S |
| 191 | 279 | T |
| 192 | 280 | W |
| 193 | 281 | M |
| 194 | 285 | D |
| 195 | 286 | I |
| 196 | 288 | L |
| 197 | 289 | G |
| 198 | 290 | W |
| 199 | 291 | A |
| 200 | 292 | V |
| 201 | 293 | I |
| 202 | 294 | A |
| 203 | 295 | S |
| 204 | 296 | R |
| 205 | 297 | S |
| 206 | 298 | G |
| 207 | 299 | S |
| 208 | 300 | T |
| 209 | 301 | P |
| 210 | 302 | L |
| 211 | 303 | F |
| 212 | 304 | F |
| 213 | 305 | S |
| 214 | 306 | R |
| 215 | 307 | P |
| 216 | 312 | N |
| 217 | 315 | R |
| 218 | 316 | F |
| 219 | 322 | I |
| 220 | 326 | G |
| 221 | 329 | L |
| 222 | 330 | F |
| 223 | 332 | D |
| 224 | 334 | A |
| 225 | 335 | I |
| 226 | 336 | T |
| 227 | 337 | A |
| 228 | 338 | V |
| 229 | 339 | N |
| 230 | 340 | R |
| 231 | 341 | F |
| 232 | 342 | H |
| 233 | 343 | N |
| 234 | 344 | V |
| 235 | 345 | M |
| 236 | 348 | Q |
| 237 | 350 | E |
| 238 | 351 | E |
| 239 | 352 | L |
| 240 | 353 | S |
| 241 | 354 | N |
| 242 | 355 | P |
| 243 | 356 | N |
| 244 | 360 | Q |
| 245 | 361 | I |
| 246 | 362 | F |
| 247 | 363 | M |
| 248 | 364 | N |
| 249 | 365 | Q |
| 250 | 366 | R |
| 251 | 370 | G |
| 252 | 371 | V |
| 253 | 372 | V |
| 254 | 373 | L |
| 255 | 374 | A |
| 256 | 375 | N |
| 257 | 376 | A |
| 258 | 377 | G |
| 259 | 379 | S |
| 260 | 380 | S |
| 261 | 381 | V |
| 262 | 383 | I |
| 263 | 384 | N |
| 264 | 387 | T |
| 265 | 389 | L |
| 266 | 391 | D |
| 267 | 392 | G |
| 268 | 394 | Y |
| 269 | 396 | N |
| 270 | 397 | K |
| 271 | 398 | A |
| 272 | 399 | G |
| 273 | 402 | S |

TABLE 3-continued

Positional libraries generated in full-length AmyE

| Variant No. | Residue number in full length AmyE | Wild type residue |
|---|---|---|
| 274 | 403 | F |
| 275 | 404 | Q |
| 276 | 405 | V |
| 277 | 407 | D |
| 278 | 408 | G |
| 279 | 409 | K |
| 280 | 410 | L |
| 281 | 411 | T |
| 282 | 412 | G |
| 283 | 413 | T |
| 284 | 414 | I |
| 285 | 415 | N |
| 286 | 416 | A |
| 287 | 417 | R |
| 288 | 418 | S |
| 289 | 419 | V |
| 290 | 420 | A |
| 291 | 421 | V |
| 292 | 422 | L |
| 293 | 423 | Y |
| 294 | 424 | P |
| 295 | 425 | D |

Twenty libraries at positions 27, 30, 45, 52, 75, 88, 89, 126, 131, 167, 184, 223, 238, 241, 260, 307, 312, 344, 380 and 402 were generated in both full-length AmyE and AmyE-tr. The B. subtilis transformants containing full-length AmyE substitution variants were cultured as described in Example 8. Culture supernatants were used for assays.

Example 16

Performance of AmyE Variants

Using the procedures described in Examples 8 and 9, the relative performance or activity of full-length AmyE and truncated AmyE was compared to the variants generated in full length AmyE and truncated Amy E. Table 4 summarizes the results of the site evaluation screens of AmyE full length variants and Table 5 summarizes the results of the site evaluation screens of AmyE truncated variants. Column 1 shows the amino acid in the wildtype enzyme. Column 2 indicates the variant at the position that was investigated in this study. The subsequent columns show the performance index values of the variants for the properties tested. The properties tested were as follows: protein determination by Bradford assay (expression), viscosity reduction rate (peak viscosity), reduction in post-liquefaction viscosity (final viscosity), degree of polymerization (iodine), reducing ends generated (reducing ends), total glucose present (glucose), maltoheptahose hydrolysis at pH 5.8 (DP7 pH 5.8), heat stability (30 min at 60° C.) using maltoheptahose hydrolysis at pH 5.8 (DP7 pH 5.8 heated), maltoheptaose hydrolysis at pH 4 (DP7 pH 4), heat stability (30 min at 60° C.) using maltotriose hydrolysis at pH 5.8 (DP3 HS), specific activity on corn flour substrate for 30 min (corn flour 30 min), rice starch stain microswatch assay at pH 8 (Cleaning pH 8), and rice starch stain microswatch assay at pH 10 (cleaning, pH 10). Performance index (Pi) is defined as a ratio of performance of variant to parent protein

TABLE 4

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| I | 006A | 1.01 | 0.92 | −8.20 | 1.00 | 0.84 | 0.82 | 0.80 | 0.62 | 0.89 | 0.88 | 0.81 |
| I | 006C | 0.32 | 1.68 | −46.94 | 0.17 | 1.71 | 1.11 | 1.30 | 1.24 | 1.52 | 1.87 | 1.52 |
| I | 006D | 0.76 | 1.24 | 2.04 | 0.50 | 0.93 | 0.77 | 0.81 | 0.89 | 0.99 | 0.99 | 0.98 |
| I | 006E | 0.91 | 0.93 | −33.85 | 0.71 | 0.86 | 0.78 | 0.80 | 0.82 | 0.91 | 0.88 | 0.84 |
| I | 006H | 0.66 | 1.20 | −0.28 | 0.48 | 1.29 | 1.08 | 1.08 | 1.13 | 1.21 | 1.39 | 1.20 |
| I | 006K | 0.72 | 0.98 | 18.41 | 0.54 | 1.18 | 1.05 | 1.04 | 0.91 | 1.17 | 1.29 | 1.08 |
| I | 006L | 0.70 | 1.10 | −38.68 | 0.52 | 1.21 | 1.08 | 1.04 | 0.70 | 1.19 | 1.16 | 1.08 |
| I | 006M | 0.89 | 1.04 | −1.01 | 0.92 | 0.93 | 0.95 | 0.90 | 0.64 | 0.97 | 0.90 | 0.88 |
| I | 006N | 0.75 | 1.12 | −17.63 | 0.60 | 1.00 | 0.92 | 0.95 | 0.84 | 1.03 | 1.08 | 1.09 |
| I | 006P | 0.70 | 1.32 | 9.39 | 0.55 | 1.09 | 1.01 | 1.05 | 0.98 | 1.17 | 1.15 | 1.16 |
| I | 006Q | 0.68 | 1.25 | −1.61 | 0.51 | 1.14 | 1.07 | 1.09 | 1.08 | 1.20 | 1.17 | 1.21 |
| I | 006R | 0.30 | 1.99 | 24.30 | 0.12 | 1.86 | 1.13 | 1.35 | 1.33 | 1.58 | 2.28 | 1.94 |
| I | 006S | 0.66 | 1.22 | 26.23 | 0.46 | 1.28 | 1.08 | 1.10 | 1.10 | 1.23 | 1.17 | 1.26 |
| I | 006T | 0.85 | 1.00 | 21.53 | 0.59 | 1.00 | 0.86 | 0.91 | 0.89 | 0.98 | 0.95 | 1.01 |
| I | 006V | 0.73 | 1.18 | 8.95 | 0.51 | 1.20 | 1.03 | 1.10 | 0.99 | 1.15 | 1.01 | 1.23 |
| I | 006W | 0.62 | 1.30 | 50.59 | 0.41 | 1.32 | 1.07 | 1.13 | 0.95 | 1.28 | 1.30 | 1.09 |
| K | 007A | 0.75 | 1.08 | 1.35 | 0.68 | 1.08 | 1.03 | 1.03 | 0.77 | 1.00 | 1.27 | 0.81 |
| K | 007C | 0.25 | 1.87 | 7.71 | 0.13 | 2.11 | 1.34 | 1.67 | 1.54 | 1.74 | 2.72 | 2.25 |
| K | 007D | 0.64 | 1.31 | 3.57 | 0.58 | 1.34 | 1.26 | 1.29 | 1.21 | 1.27 | 1.48 | 1.45 |
| K | 007E | 0.65 | 1.31 | 4.22 | 0.49 | 1.28 | 1.16 | 1.20 | 1.17 | 1.18 | 1.37 | 1.29 |
| K | 007F | 0.40 | 1.67 | 3.49 | 0.22 | 1.80 | 1.34 | 1.52 | 1.50 | 1.43 | 2.23 | 1.72 |
| K | 007G | 0.46 | 1.40 | 4.63 | 0.28 | 1.74 | 1.38 | 1.47 | 1.47 | 1.43 | 1.87 | 1.92 |
| K | 007H | 0.61 | 1.08 | 1.85 | 0.36 | 1.31 | 1.06 | 1.14 | 1.09 | 1.13 | 1.52 | 2.08 |
| K | 007I | 0.16 | 2.22 | 12.83 | 0.06 | 3.53 | 2.01 | 2.62 | 2.56 | 2.66 | 4.61 | 3.86 |
| K | 007L | 0.27 | 1.64 | 4.80 | 0.12 | 2.33 | 1.42 | 1.72 | 1.43 | 1.71 | 2.83 | 2.22 |
| K | 007M | 0.51 | 1.33 | 4.28 | 0.40 | 1.52 | 1.24 | 1.27 | 0.82 | 1.21 | 1.68 | 1.46 |
| K | 007N | 0.71 | 1.11 | 1.78 | 0.62 | 1.19 | 1.09 | 1.06 | 0.75 | 1.02 | 1.36 | 1.32 |
| K | 007P | 0.47 | 1.31 | 5.21 | 0.27 | 1.53 | 1.17 | 1.26 | 1.00 | 1.19 | 1.74 | 1.54 |
| K | 007Q | 0.75 | 1.08 | 1.87 | 0.61 | 1.17 | 1.07 | 1.04 | 0.80 | 1.01 | 1.38 | 1.16 |
| K | 007R | 0.83 | 1.01 | 3.65 | 0.66 | 1.10 | 1.03 | 1.03 | 0.73 | 0.96 | 1.21 | 1.10 |
| K | 007S | 0.71 | 1.18 | 4.40 | 0.54 | 1.31 | 1.09 | 1.11 | 0.91 | 1.06 | 1.32 | 1.21 |
| K | 007T | 0.44 | 1.48 | 3.46 | 0.27 | 1.88 | 1.46 | 1.57 | 1.25 | 1.47 | 2.09 | 1.65 |
| K | 007W | 0.43 | 1.41 | 5.43 | 0.25 | 1.84 | 1.40 | 1.48 | 1.17 | 1.46 | 1.96 | 3.08 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| K | 007Y | 0.41 | 1.51 | 4.90 | 0.21 | 1.82 | 1.18 | 1.31 | 1.16 | 1.36 | 2.02 | 1.68 |
| G | 009A | 0.76 | 1.09 | −0.88 | 0.64 | 1.07 | 0.86 | 1.04 | 0.74 | 1.02 | 1.14 | 1.01 |
| G | 009C | 0.36 | 1.64 | −1.73 | 0.17 | 1.48 | 0.83 | 1.18 | 1.13 | 1.22 | 2.10 | 1.65 |
| G | 009D | 0.85 | 0.97 | −0.37 | 0.70 | 1.02 | 0.94 | 1.02 | 1.04 | 1.07 | 1.08 | 1.08 |
| G | 009E | 0.92 | 0.98 | −0.99 | 0.78 | 0.95 | 0.88 | 0.92 | 0.99 | 0.94 | 1.03 | 0.91 |
| G | 009F | 0.97 | 0.97 | 0.91 | 0.80 | 0.96 | 0.95 | 0.99 | 1.05 | 1.00 | 1.05 | 1.06 |
| G | 009H | 0.84 | 1.16 | 1.39 | 0.66 | 1.14 | 1.16 | 1.15 | 1.22 | 1.06 | 1.27 | 1.23 |
| G | 009I | 0.67 | 1.28 | 0.12 | 0.51 | 1.35 | 1.27 | 1.32 | 1.34 | 1.33 | 1.49 | 1.37 |
| G | 009K | 0.69 | 1.02 | 3.74 | 0.46 | 1.24 | 1.09 | 1.19 | 1.09 | 1.16 | 1.46 | 1.32 |
| G | 009M | 0.99 | 1.09 | −0.80 | 1.00 | 0.96 | 0.99 | 1.03 | 0.74 | 1.04 | 0.96 | 0.89 |
| G | 009N | 0.67 | 1.23 | −1.11 | 0.56 | 1.34 | 1.13 | 1.27 | 1.10 | 1.28 | 1.50 | 1.44 |
| G | 009P | 0.87 | 1.05 | 0.00 | 0.70 | 1.01 | 1.00 | 1.03 | 1.03 | 1.01 | 1.06 | 0.99 |
| G | 009R | 0.72 | 1.20 | 0.22 | 0.48 | 1.14 | 0.99 | 1.09 | 1.07 | 1.06 | 1.40 | 1.29 |
| G | 009S | 0.43 | 1.68 | 2.32 | 0.25 | 1.86 | 1.49 | 1.67 | 1.64 | 1.64 | 2.15 | 1.92 |
| G | 009T | 0.56 | 1.45 | 1.78 | 0.37 | 1.48 | 1.25 | 1.37 | 1.36 | 1.43 | 1.68 | 1.54 |
| G | 009V | 0.64 | 1.30 | 1.16 | 0.45 | 1.32 | 1.12 | 1.21 | 1.19 | 1.23 | 1.50 | 1.20 |
| G | 009W | 0.76 | 1.13 | 1.11 | 0.64 | 1.21 | 1.18 | 1.22 | 1.10 | 1.20 | 1.30 | 1.22 |
| G | 009Y | 0.71 | 1.46 | 2.12 | 0.62 | 1.46 | 1.52 | 1.47 | 1.12 | 1.51 | 1.43 | 1.27 |
| T | 010A | 1.09 | 1.00 | 2.26 | 1.36 | 0.97 | 0.93 | 0.87 | 0.57 | 0.89 | 0.90 | 0.85 |
| T | 010D | 0.02 | 27.05 | 63.29 | 0.01 | 9.79 | 2.09 | 6.22 | 6.56 | 6.99 | 26.82 | 8.96 |
| T | 010F | −0.04 | −14.28 | −37.79 | −0.01 | −3.89 | −0.70 | −2.96 | −3.34 | −3.51 | −15.15 | −2.88 |
| T | 010H | −0.14 | −4.46 | −15.98 | −0.03 | −1.31 | −0.14 | −1.01 | −1.15 | −1.19 | −5.22 | −1.05 |
| T | 010I | 0.88 | 1.05 | −3.51 | 0.84 | 1.15 | 1.10 | 1.05 | 0.73 | 1.03 | 0.91 | 0.97 |
| T | 010K | −0.23 | −1.05 | 9.05 | −0.06 | −0.60 | −0.06 | −0.55 | −0.65 | −0.68 | −2.96 | −0.20 |
| T | 010L | 1.02 | 0.92 | −1.25 | 1.17 | 1.00 | 1.10 | 1.02 | 0.74 | 1.01 | 1.04 | 0.98 |
| T | 010M | 0.75 | 1.10 | 3.73 | 0.64 | 1.09 | 0.92 | 0.94 | 0.60 | 0.91 | 1.26 | 1.01 |
| T | 010N | 0.47 | 1.42 | −3.00 | 0.35 | 1.57 | 1.20 | 1.32 | 1.12 | 1.26 | 2.19 | 1.49 |
| T | 010P | 0.66 | 1.27 | −1.82 | 0.60 | 1.33 | 1.20 | 1.18 | 1.11 | 1.21 | 1.55 | 1.33 |
| T | 010Q | 0.42 | 1.69 | −1.02 | 0.27 | 1.72 | 1.22 | 1.34 | 1.32 | 1.39 | 2.28 | 1.75 |
| T | 010R | 0.03 | 20.51 | 58.95 | 0.01 | 16.51 | 5.86 | 10.73 | 10.15 | 11.34 | 20.71 | 20.25 |
| T | 010S | 0.73 | 1.19 | −3.62 | 0.59 | 1.27 | 1.10 | 1.13 | 1.11 | 1.10 | 1.30 | 1.16 |
| T | 010V | 0.89 | 1.11 | −0.06 | 0.82 | 1.08 | 1.06 | 1.07 | 0.99 | 1.03 | 1.08 | 1.00 |
| T | 010W | −0.17 | −2.25 | −16.60 | −0.03 | −0.57 | −0.03 | −0.65 | −0.80 | −0.83 | −2.10 | −0.02 |
| I | 011A | 0.51 | 1.40 | 2.85 | 0.31 | 1.25 | 0.74 | 1.02 | 0.65 | 0.89 | 1.49 | 1.08 |
| I | 011D | −0.03 | −14.11 | −28.09 | −0.01 | −3.90 | −0.46 | −3.75 | −4.32 | −5.30 | −10.37 | 4.18 |
| I | 011E | −0.08 | −8.71 | −8.06 | −0.02 | −1.33 | −0.14 | −1.36 | −1.63 | −2.06 | −3.44 | 2.93 |
| I | 011F | 0.62 | 1.18 | 1.53 | 0.41 | 1.24 | 0.90 | 1.07 | 1.09 | 0.99 | 1.39 | 1.06 |
| I | 011G | 0.27 | 1.53 | 3.54 | 0.10 | 1.67 | 0.51 | 1.32 | 1.16 | 0.99 | 2.33 | 1.27 |
| I | 011H | 0.22 | 1.39 | 2.39 | 0.08 | 2.02 | 0.89 | 1.63 | 1.64 | 1.34 | 3.07 | 1.77 |
| I | 011K | 0.00 | 71.61 | 432.90 | 0.00 | 46.60 | 7.32 | 35.68 | 38.03 | 45.18 | 90.91 | −10.08 |
| I | 011M | 0.78 | 1.24 | 2.19 | 0.72 | 1.13 | 1.02 | 1.08 | 0.75 | 0.95 | 1.29 | 1.13 |
| I | 011N | 0.02 | 31.02 | 137.01 | 0.00 | 26.79 | 7.76 | 19.17 | 18.07 | 21.96 | 42.96 | 5.02 |
| I | 011P | −0.06 | −11.38 | −13.81 | −0.01 | −2.58 | −0.10 | −2.20 | −2.50 | −3.03 | −5.81 | 1.96 |
| I | 011Q | −0.05 | −9.42 | −7.32 | −0.01 | −3.57 | −0.34 | −2.96 | −3.24 | −3.68 | −7.80 | 1.42 |
| I | 011R | −0.10 | −3.55 | −15.14 | −0.02 | −1.75 | −0.22 | −1.36 | −1.52 | −1.77 | −3.53 | 1.73 |
| I | 011S | 0.15 | 2.43 | 5.11 | 0.05 | 2.98 | 1.21 | 2.24 | 2.26 | 2.00 | 4.00 | 2.29 |
| I | 011V | 0.60 | 1.22 | −0.27 | 0.41 | 1.36 | 1.21 | 1.33 | 1.31 | 1.29 | 1.54 | 1.61 |
| I | 011W | 0.32 | 1.53 | 3.37 | 0.15 | 1.81 | 0.98 | 1.50 | 1.25 | 1.18 | 2.41 | 1.84 |
| I | 011Y | 0.20 | 1.80 | 1.54 | 0.09 | 2.80 | 1.52 | 2.03 | 1.69 | 1.89 | 3.58 | 1.95 |
| L | 012A | −0.10 | −7.19 | 19.70 | −0.03 | −1.84 | −0.19 | −1.42 | −1.62 | −1.92 | −3.47 | −1.19 |
| L | 012D | −0.03 | −14.68 | −24.11 | −0.01 | −7.35 | −1.43 | −5.36 | −6.06 | −6.07 | −12.37 | −6.54 |
| L | 012E | −0.08 | −8.12 | −38.50 | −0.02 | −2.28 | −0.30 | −1.76 | −2.08 | −2.15 | −4.64 | −2.43 |
| L | 012G | −0.15 | −2.51 | −5.32 | −0.03 | −0.61 | −0.05 | −0.68 | −0.84 | −0.88 | −1.72 | −0.41 |
| L | 012H | −0.06 | −4.67 | 6.17 | −0.01 | −5.09 | −1.28 | −3.34 | −3.79 | −3.58 | −8.76 | −5.76 |
| L | 012I | 0.63 | 1.13 | 3.13 | 0.40 | 1.22 | 1.00 | 1.18 | 1.09 | 1.07 | 1.44 | 1.24 |
| L | 012K | −0.25 | 0.25 | −6.69 | −0.06 | −0.42 | −0.10 | −0.46 | −0.55 | −0.62 | −0.94 | −0.18 |
| L | 012M | 0.81 | 1.08 | 1.31 | 0.80 | 1.15 | 1.04 | 1.04 | 0.75 | 0.95 | 1.02 | 1.02 |
| L | 012N | −0.16 | −5.07 | 4.38 | −0.04 | −0.91 | −0.02 | −0.81 | −0.93 | −0.99 | −2.17 | −0.88 |
| L | 012P | −0.32 | −1.75 | 1.67 | −0.06 | −0.29 | 0.02 | −0.32 | −0.40 | −0.43 | −0.86 | −0.07 |
| L | 012Q | −0.17 | −5.38 | −12.20 | −0.04 | −0.68 | −0.06 | −0.67 | −0.81 | −0.85 | −1.55 | −0.44 |
| L | 012R | −0.19 | −0.51 | 8.70 | −0.04 | −0.51 | −0.07 | −0.57 | −0.69 | −0.73 | −1.27 | −0.45 |
| L | 012S | −0.16 | −3.15 | −0.52 | −0.03 | −0.62 | −0.12 | −0.66 | −0.83 | −0.86 | −1.41 | −0.21 |
| L | 012T | −0.17 | −0.50 | 1.47 | −0.03 | −0.64 | −0.09 | −0.67 | −0.80 | −0.84 | −1.69 | −0.44 |
| L | 012V | 0.43 | 1.54 | 3.91 | 0.21 | 1.61 | 1.10 | 1.34 | 1.23 | 1.23 | 1.91 | 1.54 |
| L | 012W | −0.22 | −0.03 | −3.32 | −0.04 | −0.42 | −0.12 | −0.50 | −0.61 | −0.61 | −0.96 | −0.24 |
| L | 012Y | −0.10 | −3.11 | −12.08 | −0.02 | −1.85 | −0.20 | −1.51 | −1.60 | −1.56 | −3.86 | −0.84 |
| H | 013A | 0.54 | 0.83 | −1.04 | 0.20 | 0.68 | 0.03 | 0.33 | 0.30 | 0.30 | 1.41 | 0.02 |
| H | 013C | 0.12 | 3.86 | 1.45 | 0.03 | 1.68 | 0.01 | 1.19 | 1.23 | 1.32 | 4.32 | 2.42 |
| H | 013D | 0.85 | 0.57 | −0.88 | 0.27 | 0.37 | 0.01 | 0.16 | 0.19 | 0.17 | 0.79 | 0.01 |
| H | 013E | 0.49 | 1.04 | −3.66 | 0.13 | 0.59 | 0.01 | 0.26 | 0.31 | 0.31 | 1.09 | 0.04 |
| H | 013F | 0.15 | 1.96 | −3.81 | 0.03 | 1.21 | 0.00 | 0.81 | 0.96 | 1.07 | 3.79 | 1.41 |
| H | 013G | 0.23 | 2.16 | −4.92 | 0.05 | 1.33 | 0.03 | 0.72 | 0.71 | 0.67 | 2.50 | 1.61 |
| H | 013I | 0.39 | 1.35 | 8.13 | 0.07 | 0.50 | −0.01 | 0.34 | 0.38 | 0.39 | 1.57 | 1.01 |
| H | 013K | −0.03 | 2.20 | 15.24 | −0.01 | −2.68 | −0.19 | −3.18 | −3.81 | −4.48 | −7.81 | −4.72 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| H | 013L | 0.27 | 1.41 | −6.49 | 0.07 | 1.12 | 0.04 | 0.60 | 0.56 | 0.66 | 2.08 | 0.94 |
| H | 013M | 0.48 | 1.11 | 2.62 | 0.18 | 0.85 | 0.07 | 0.46 | 0.35 | 0.37 | 1.46 | 0.88 |
| H | 013Q | 0.82 | 1.03 | −0.71 | 0.53 | 0.95 | 0.49 | 0.71 | 0.48 | 0.65 | 1.08 | 0.98 |
| H | 013R | 0.03 | 10.41 | −4.98 | 0.01 | 3.17 | 0.20 | 3.59 | 4.44 | 5.08 | 8.04 | 0.73 |
| H | 013S | −1.20 | −0.30 | 0.28 | −0.21 | −0.32 | −2.22 | −0.24 | −0.10 | −0.18 | −0.22 | −0.01 |
| H | 013T | 0.14 | 3.28 | −8.97 | 0.02 | 1.30 | −0.03 | 0.92 | 1.05 | 1.13 | 3.99 | 1.64 |
| H | 013V | 0.53 | 0.73 | 0.33 | 0.11 | 0.43 | 0.00 | 0.25 | 0.27 | 0.30 | 1.26 | 0.69 |
| H | 013W | 0.48 | 0.71 | −0.66 | 0.10 | 0.41 | −0.01 | 0.25 | 0.28 | 0.32 | 1.13 | 0.32 |
| H | 013Y | 0.20 | 0.89 | 5.35 | 0.03 | 0.60 | 0.04 | 0.59 | 0.68 | 0.78 | 2.23 | 1.02 |
| A | 014C | 0.46 | 0.65 | 2.16 | 0.21 | 1.16 | 0.62 | 0.85 | 0.84 | 0.91 | 1.63 | 1.31 |
| A | 014D | 0.03 | 14.12 | 46.14 | 0.01 | 3.39 | 0.26 | 3.76 | 4.64 | 5.42 | 10.17 | 3.69 |
| A | 014E | −0.02 | −22.64 | −60.00 | 0.00 | −6.48 | −0.84 | −7.47 | −9.21 | −10.68 | −18.26 | −7.43 |
| A | 014F | 0.08 | −5.45 | 11.87 | 0.02 | 1.26 | 0.18 | 1.45 | 1.80 | 2.06 | 3.99 | 0.63 |
| A | 014G | 0.74 | 1.21 | 2.44 | 0.71 | 1.23 | 1.15 | 1.16 | 1.21 | 1.13 | 1.38 | 1.21 |
| A | 014H | −0.03 | −8.97 | −20.31 | −0.01 | −3.54 | −0.73 | −4.09 | −5.03 | −5.86 | −11.19 | −3.44 |
| A | 014I | −0.14 | −0.65 | −1.42 | −0.03 | −0.98 | −0.04 | −0.98 | −1.18 | −1.29 | −2.43 | −0.84 |
| A | 014K | −0.02 | 24.41 | −9.58 | −0.01 | −4.35 | −0.47 | −5.06 | −6.30 | −7.23 | −13.14 | −4.17 |
| A | 014L | −0.09 | 4.73 | −8.12 | −0.02 | −1.33 | −0.18 | −1.63 | −1.81 | −2.00 | −3.75 | −1.46 |
| A | 014M | 0.09 | 1.83 | 12.05 | 0.02 | 1.14 | 0.01 | 1.34 | 1.64 | 1.97 | 3.03 | 1.12 |
| A | 014N | 0.08 | 7.18 | 13.71 | 0.02 | 2.89 | 0.52 | 2.12 | 2.45 | 2.45 | 5.72 | 2.53 |
| A | 014Q | −0.10 | −2.11 | −13.53 | −0.03 | −0.98 | −0.07 | −1.12 | −1.43 | −1.64 | −2.79 | −1.28 |
| A | 014R | −0.37 | −1.20 | −0.28 | −0.08 | −0.29 | −0.05 | −0.32 | −0.41 | −0.47 | −0.83 | −0.28 |
| A | 014S | 0.74 | 0.99 | 0.98 | 0.57 | 1.14 | 0.98 | 1.04 | 1.12 | 1.06 | 1.18 | 1.19 |
| A | 014T | 0.74 | 1.09 | 1.67 | 0.66 | 1.16 | 1.05 | 1.10 | 1.15 | 1.10 | 1.25 | 1.15 |
| A | 014V | 0.61 | 0.88 | 1.53 | 0.45 | 1.28 | 1.05 | 1.15 | 1.17 | 1.21 | 1.47 | 1.34 |
| A | 014W | −0.06 | 12.48 | −14.78 | −0.02 | −1.44 | −0.36 | −1.70 | −2.10 | −2.35 | −4.17 | −1.72 |
| A | 014Y | −0.15 | 5.60 | −3.29 | −0.04 | −0.66 | −0.08 | −0.82 | −0.98 | −1.17 | −2.02 | −0.88 |
| W | 015A | 0.17 | 3.90 | −18.75 | 0.06 | 1.38 | 0.08 | 1.04 | 1.03 | 1.11 | 2.44 | 1.65 |
| W | 015C | −0.05 | −12.63 | −76.11 | −0.02 | −2.36 | −0.13 | −2.65 | −2.90 | −3.69 | −6.31 | −2.33 |
| W | 015D | 0.00 | 9.85 | 2910.97 | 0.00 | −58.50 | −3.19 | −67.94 | −74.14 | −93.25 | −160.16 | −129.74 |
| W | 015E | 0.02 | −7.70 | 244.26 | 0.01 | 4.35 | 0.24 | 5.09 | 5.56 | 6.87 | 11.46 | 2.00 |
| W | 015F | 0.72 | 1.04 | −0.31 | 0.43 | 0.94 | 0.65 | 0.82 | 0.81 | 0.73 | 1.19 | 1.00 |
| W | 015G | −0.08 | 0.79 | −62.40 | −0.02 | −1.31 | −0.07 | −1.43 | −1.60 | −1.97 | −4.23 | −1.66 |
| W | 015H | −0.05 | 3.85 | −135.58 | −0.01 | −2.65 | −0.27 | −2.46 | −2.78 | −3.01 | −6.20 | −3.16 |
| W | 015I | −0.09 | −0.61 | −129.53 | −0.02 | −1.16 | −0.06 | −1.30 | −1.48 | −1.72 | −2.42 | −0.88 |
| W | 015K | −0.11 | −0.18 | −9.83 | −0.03 | −0.99 | −0.15 | −1.19 | −1.30 | −1.67 | −2.71 | −0.87 |
| W | 015N | −0.15 | 0.96 | −30.94 | −0.05 | −0.75 | −0.03 | −0.83 | −0.94 | −1.20 | −2.17 | −0.18 |
| W | 015P | −0.17 | 0.87 | −0.38 | −0.04 | −0.64 | −0.06 | −0.71 | −0.84 | −1.02 | −1.87 | −0.39 |
| W | 015Q | −0.13 | −1.29 | 18.55 | −0.03 | −0.84 | −0.08 | −0.93 | −1.07 | −1.31 | −2.06 | −0.71 |
| W | 015R | −0.09 | −0.05 | −13.01 | −0.02 | −1.18 | −0.26 | −1.36 | −1.56 | −1.94 | −3.42 | −0.61 |
| W | 015S | −0.18 | 0.52 | −42.42 | −0.05 | −0.74 | −0.07 | −0.73 | −0.81 | −0.92 | −2.07 | −0.54 |
| W | 015T | −0.16 | 0.70 | −27.70 | −0.03 | −0.68 | −0.05 | −0.74 | −0.86 | −1.01 | −1.77 | −0.69 |
| W | 015V | −0.11 | −1.45 | −107.01 | −0.03 | −1.10 | −0.05 | −1.15 | −1.32 | −1.56 | −2.69 | −0.20 |
| N | 016A | 0.51 | 0.93 | 11.53 | 0.35 | 1.35 | 0.58 | 0.79 | 0.61 | 0.40 | 1.43 | 0.73 |
| N | 016D | 0.24 | 1.99 | −19.06 | 0.11 | 2.14 | 0.76 | 1.33 | 1.28 | 1.22 | 2.70 | 1.85 |
| N | 016E | 0.22 | 0.69 | 11.32 | 0.08 | 1.91 | 0.43 | 1.03 | 1.03 | 0.82 | 2.49 | 0.65 |
| N | 016F | 0.10 | 9.36 | −9.38 | 0.03 | 1.62 | −0.02 | 1.27 | 1.45 | 1.65 | 3.22 | −0.02 |
| N | 016G | 0.40 | 1.19 | 1.89 | 0.25 | 1.85 | 1.09 | 1.31 | 1.08 | 0.66 | 2.10 | 1.80 |
| N | 016H | 0.32 | 1.45 | 0.62 | 0.13 | 1.38 | 0.13 | 0.77 | 0.68 | 0.52 | 2.34 | 2.26 |
| N | 016I | 0.15 | 0.97 | 19.48 | 0.06 | 3.30 | 0.71 | 1.69 | 1.47 | 1.23 | 3.17 | 1.39 |
| N | 016K | 0.01 | 23.15 | 21.55 | 0.00 | 10.74 | 0.83 | 9.88 | 11.12 | 12.28 | 25.73 | 1.70 |
| N | 016L | 0.38 | 1.23 | −0.67 | 0.27 | 1.92 | 0.74 | 1.08 | 0.78 | 0.52 | 1.99 | 1.21 |
| N | 016M | 0.65 | 1.16 | −7.38 | 0.56 | 1.24 | 0.61 | 0.89 | 0.68 | 0.36 | 1.37 | 0.93 |
| N | 016P | −0.02 | −67.95 | 25.58 | 0.00 | −7.80 | 0.84 | −7.96 | −9.71 | −11.05 | −21.06 | −4.58 |
| N | 016Q | 0.67 | 1.08 | −0.59 | 0.45 | 1.02 | 0.40 | 0.65 | 0.59 | 0.31 | 1.34 | 1.29 |
| N | 016R | 0.01 | −0.27 | 232.86 | 0.00 | 15.20 | −1.12 | 16.93 | 21.05 | 24.31 | 37.78 | −10.29 |
| N | 016S | 0.54 | 0.81 | 5.40 | 0.32 | 1.32 | 0.93 | 0.94 | 0.91 | 0.71 | 1.49 | 1.36 |
| N | 016T | 0.33 | 0.57 | 8.05 | 0.17 | 1.84 | 0.87 | 1.07 | 1.02 | 0.58 | 2.04 | 1.13 |
| N | 016V | 0.32 | 1.16 | 0.36 | 0.18 | 2.07 | 1.11 | 1.28 | 1.17 | 0.64 | 2.29 | 1.46 |
| N | 016W | −0.08 | 4.80 | 36.49 | −0.02 | −1.32 | −0.10 | −1.53 | −1.86 | −2.10 | −3.73 | 1.01 |
| N | 016Y | −0.15 | 6.70 | −25.51 | −0.04 | −0.83 | −0.10 | −0.87 | −1.00 | −1.21 | −1.48 | −0.01 |
| W | 017A | 0.16 | 6.14 | −13.16 | 0.05 | 0.82 | −0.01 | 0.89 | 1.06 | 1.22 | 1.98 | 0.70 |
| W | 017C | 0.05 | 14.42 | −141.99 | 0.02 | 2.32 | −0.04 | 2.64 | 3.32 | 3.72 | 6.44 | 1.08 |
| W | 017E | 0.04 | 17.97 | 4.67 | 0.01 | 2.65 | 0.00 | 2.95 | 3.66 | 3.97 | 7.20 | 2.27 |
| W | 017F | 0.25 | 2.34 | 12.70 | 0.08 | 1.50 | 0.52 | 1.08 | 1.23 | 1.10 | 2.21 | 1.63 |
| W | 017G | 0.00 | −26.02 | 444.64 | 0.00 | −14.26 | −0.66 | −16.15 | −20.34 | −21.81 | −37.09 | 16.44 |
| W | 017H | 0.04 | 17.29 | −403.45 | 0.01 | 5.52 | 0.67 | 4.62 | 5.66 | 5.27 | 12.48 | 4.26 |
| W | 017I | 0.23 | 0.85 | −29.36 | 0.04 | 0.47 | 0.02 | 0.54 | 0.69 | 0.77 | 1.32 | 0.32 |
| W | 017L | −0.05 | 0.91 | 177.50 | −0.01 | −2.38 | −0.36 | −2.82 | −3.51 | −4.08 | −7.39 | −1.42 |
| W | 017M | 0.11 | 8.80 | −58.20 | 0.04 | 1.51 | 0.11 | 1.33 | 1.53 | 1.67 | 3.33 | 0.56 |
| W | 017N | −0.04 | −67.42 | 220.33 | 0.00 | −11.87 | −0.30 | −10.77 | −12.71 | −13.54 | −22.61 | −4.46 |
| W | 017P | 0.04 | 25.62 | 291.46 | 0.01 | 3.57 | 0.11 | 4.20 | 5.29 | 5.84 | 9.62 | 2.62 |
| W | 017Q | 0.17 | 4.75 | −4.33 | 0.05 | 1.93 | 0.37 | 1.39 | 1.60 | 1.34 | 3.30 | 1.64 |
| W | 017R | −0.10 | −3.53 | −43.28 | −0.02 | −1.07 | 0.00 | −1.26 | −1.60 | −1.76 | −2.78 | −1.20 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| W | 017S | 0.02 | 19.46 | 5.46 | 0.00 | 11.17 | 0.37 | 11.56 | 14.48 | 14.65 | 27.67 | 15.19 |
| W | 017T | −0.07 | −3.47 | −15.67 | −0.02 | −1.80 | −0.15 | −1.79 | −2.17 | −2.14 | −5.00 | −1.16 |
| W | 017V | −0.06 | −3.27 | 112.72 | −0.02 | −2.03 | −0.18 | −2.06 | −2.52 | −2.53 | −4.29 | −1.71 |
| W | 017Y | 0.20 | 1.92 | −49.51 | 0.08 | 2.54 | 1.29 | 1.79 | 1.60 | 1.84 | 3.29 | 2.50 |
| F | 019A | 0.18 | 3.93 | −5.02 | 0.07 | 2.48 | 1.03 | 1.72 | 1.59 | 1.67 | 3.31 | 2.68 |
| F | 019C | 0.16 | 4.18 | 10.22 | 0.05 | 1.75 | 0.41 | 1.21 | 1.41 | 1.38 | 2.74 | 1.72 |
| F | 019D | −0.08 | −9.48 | −29.00 | −0.02 | −1.56 | −0.10 | −1.46 | −1.79 | −1.89 | −4.02 | −1.25 |
| F | 019E | −0.17 | −5.15 | −13.03 | −0.04 | −0.76 | −0.06 | −0.71 | −0.85 | −0.92 | −1.97 | −0.63 |
| F | 019G | −0.22 | −1.97 | −18.35 | −0.04 | −0.43 | −0.05 | −0.48 | −0.59 | −0.61 | −1.41 | −0.48 |
| F | 019H | 0.73 | 0.99 | 2.52 | 0.51 | 1.13 | 0.91 | 1.04 | 1.06 | 1.02 | 1.23 | 1.09 |
| F | 019I | −0.15 | −2.72 | −35.77 | −0.03 | −1.23 | −0.16 | −0.97 | −1.10 | −1.19 | −2.81 | −1.09 |
| F | 019K | −0.23 | −1.23 | −16.09 | −0.04 | −0.41 | −0.06 | −0.47 | −0.57 | −0.65 | −1.34 | −0.43 |
| F | 019L | 0.28 | 1.51 | 7.36 | 0.11 | 1.77 | 0.82 | 1.32 | 1.08 | 1.37 | 2.49 | 2.32 |
| F | 019M | 0.48 | 1.67 | 4.47 | 0.29 | 1.37 | 0.90 | 1.05 | 0.88 | 1.07 | 1.68 | 1.45 |
| F | 019N | 0.16 | 3.09 | 30.37 | 0.06 | 2.26 | 0.85 | 1.65 | 1.75 | 1.61 | 3.22 | 2.45 |
| F | 019P | −0.18 | −3.30 | −13.37 | −0.03 | −0.55 | 0.00 | −0.59 | −0.73 | −0.73 | −1.62 | −0.17 |
| F | 019R | −0.11 | −1.29 | −17.44 | −0.02 | −0.84 | −0.04 | −0.96 | −1.18 | −1.27 | −2.40 | −1.16 |
| F | 019S | 0.18 | 3.21 | 13.90 | 0.06 | 2.83 | 1.37 | 2.14 | 2.29 | 2.20 | 4.05 | 2.95 |
| F | 019T | −0.12 | −2.85 | −18.27 | −0.03 | −2.35 | −0.57 | −1.65 | −1.87 | −1.80 | −3.92 | −2.05 |
| F | 019V | −0.13 | −2.99 | −18.70 | −0.03 | −1.36 | −0.17 | −1.10 | −1.26 | −1.29 | −2.89 | −1.35 |
| F | 019W | 0.63 | 1.23 | 2.86 | 0.38 | 1.18 | 0.90 | 1.08 | 0.93 | 0.98 | 1.41 | 1.29 |
| F | 019Y | 0.31 | 1.83 | 14.98 | 0.15 | 2.05 | 1.33 | 1.62 | 1.36 | 1.61 | 2.68 | 2.05 |
| T | 021A | 0.83 | 1.14 | −1.76 | 0.87 | 1.13 | 1.01 | 0.96 | 0.64 | 0.87 | 1.00 | 0.60 |
| T | 021C | 0.06 | 8.47 | −15.22 | 0.03 | 8.75 | 5.52 | 6.03 | 5.28 | 5.81 | 6.40 | 2.67 |
| T | 021D | 0.29 | 1.90 | −3.48 | 0.16 | 2.08 | 1.47 | 1.51 | 1.38 | 1.29 | 3.19 | 2.10 |
| T | 021E | 0.65 | 1.36 | −1.03 | 0.48 | 1.28 | 1.11 | 1.15 | 1.01 | 1.06 | 1.03 | 1.12 |
| T | 021F | −0.09 | −3.33 | 25.16 | −0.02 | −2.85 | −0.70 | −1.94 | −2.10 | −1.74 | −7.58 | −2.28 |
| T | 021H | 0.39 | 1.48 | 1.75 | 0.21 | 1.76 | 1.14 | 1.33 | 1.22 | 1.02 | 2.41 | 2.03 |
| T | 021I | 0.69 | 1.23 | −2.25 | 0.49 | 1.26 | 1.04 | 1.08 | 0.96 | 1.01 | 1.51 | 1.28 |
| T | 021K | 0.53 | 1.43 | −1.21 | 0.31 | 1.45 | 1.08 | 1.17 | 1.00 | 0.84 | 1.85 | 1.58 |
| T | 021L | 0.36 | 1.21 | −3.53 | 0.17 | 1.83 | 1.14 | 1.34 | 1.05 | 1.06 | 2.91 | 1.90 |
| T | 021M | 0.88 | 1.01 | 2.42 | 0.92 | 1.09 | 0.97 | 0.88 | 0.49 | 0.81 | 1.28 | 0.97 |
| T | 021N | 1.05 | 0.90 | −1.83 | 1.19 | 0.98 | 0.89 | 0.82 | 0.53 | 0.77 | 0.80 | 0.92 |
| T | 021P | −0.07 | −8.45 | −3.25 | −0.02 | −1.84 | −0.08 | −1.76 | −2.05 | −2.07 | −9.22 | −0.68 |
| T | 021Q | 0.73 | 1.20 | −3.61 | 0.59 | 1.16 | 1.05 | 1.03 | 0.75 | 0.93 | 1.01 | 1.31 |
| T | 021R | 0.50 | 1.51 | 1.07 | 0.29 | 1.46 | 0.95 | 1.06 | 0.80 | 0.62 | 1.40 | 1.47 |
| T | 021S | 0.74 | 1.33 | −2.61 | 0.62 | 1.28 | 1.19 | 1.19 | 0.93 | 1.06 | 0.97 | 1.29 |
| T | 021V | 0.98 | 0.97 | −6.05 | 0.91 | 0.99 | 0.94 | 0.92 | 0.68 | 0.84 | 0.98 | 0.96 |
| T | 021Y | 0.01 | 18.98 | −148.98 | 0.01 | 26.25 | 8.86 | 15.97 | 13.93 | 12.79 | 52.31 | 19.48 |
| L | 022D | −0.08 | −7.83 | 3.61 | −0.02 | −1.71 | −0.13 | −1.57 | −1.91 | −1.85 | −5.25 | −0.94 |
| L | 022E | −0.05 | −9.07 | −135.03 | −0.01 | −4.27 | −0.65 | −3.26 | −3.82 | −3.77 | −10.04 | −3.42 |
| L | 022F | −0.09 | −5.58 | −5.73 | −0.02 | −2.19 | −0.27 | −1.72 | −2.01 | −1.71 | −4.37 | −2.00 |
| L | 022G | −0.14 | −1.77 | −10.32 | −0.03 | −2.03 | −0.41 | −1.33 | −1.57 | −1.51 | −4.05 | −1.55 |
| L | 022H | −0.16 | −1.54 | −18.09 | −0.03 | −0.92 | −0.05 | −0.75 | −0.92 | −0.84 | −3.00 | −0.74 |
| L | 022I | 0.99 | 0.91 | 0.95 | 1.03 | 1.00 | 1.05 | 1.02 | 1.01 | 0.99 | 0.90 | 1.09 |
| L | 022K | −0.18 | −0.67 | 1.97 | −0.04 | −0.58 | −0.10 | −0.62 | −0.75 | −0.76 | −1.80 | −0.50 |
| L | 022M | 1.03 | 0.91 | 2.19 | 1.28 | 1.00 | 1.03 | 0.94 | 0.71 | 0.86 | 0.76 | 0.90 |
| L | 022N | 0.02 | 23.57 | 37.86 | 0.01 | 9.49 | 1.60 | 6.50 | 7.15 | 7.11 | 19.24 | 5.78 |
| L | 022P | −0.30 | −1.21 | 3.78 | −0.06 | −0.34 | −0.06 | −0.36 | −0.46 | −0.46 | −1.06 | −0.21 |
| L | 022Q | 0.15 | 2.58 | 4.20 | 0.05 | 3.46 | 1.72 | 2.34 | 2.50 | 2.36 | 5.30 | 3.32 |
| L | 022R | −0.17 | −0.05 | −5.58 | −0.04 | −0.55 | −0.13 | −0.62 | −0.76 | −0.75 | −2.31 | −0.60 |
| L | 022S | 0.24 | 2.32 | 7.98 | 0.10 | 2.60 | 1.46 | 1.85 | 2.01 | 1.86 | 3.33 | 2.27 |
| L | 022T | 0.66 | 1.21 | −1.57 | 0.46 | 1.30 | 1.10 | 1.19 | 1.20 | 1.13 | 1.28 | 1.45 |
| L | 022V | 0.87 | 1.02 | −0.20 | 0.79 | 1.12 | 1.06 | 1.08 | 1.06 | 1.04 | 0.92 | 1.14 |
| L | 022Y | −0.09 | 0.80 | −24.02 | −0.02 | −1.08 | −0.11 | −1.27 | −1.55 | −1.59 | −5.99 | −0.79 |
| M | 026A | 0.32 | 1.56 | 2.86 | 0.15 | 1.72 | 0.90 | 1.17 | 1.01 | 1.21 | 2.26 | 1.24 |
| M | 026D | −0.07 | −7.02 | −29.74 | −0.01 | −1.34 | −0.12 | −1.50 | −1.86 | −2.24 | −4.14 | 2.77 |
| M | 026E | 0.00 | −107.31 | −161.29 | 0.00 | −63.43 | −4.83 | −68.45 | −82.58 | −101.38 | −167.63 | 106.20 |
| M | 026F | 0.25 | 1.52 | 5.31 | 0.10 | 2.13 | 1.07 | 1.46 | 1.61 | 1.57 | 2.49 | 1.73 |
| M | 026H | −0.05 | −1.51 | −14.45 | −0.01 | −1.96 | −0.41 | −2.03 | −2.45 | −3.02 | −5.02 | 4.74 |
| M | 026I | 0.59 | 1.24 | −0.68 | 0.39 | 1.35 | 1.16 | 1.24 | 1.25 | 1.21 | 1.50 | 1.23 |
| M | 026K | −0.07 | −0.98 | 2.19 | −0.01 | −1.49 | −0.13 | −1.60 | −1.93 | −2.40 | −4.06 | 2.24 |
| M | 026L | 0.65 | 1.06 | 0.59 | 0.43 | 1.25 | 1.10 | 1.07 | 0.84 | 1.08 | 1.43 | 1.41 |
| M | 026N | −0.07 | −8.40 | −5.82 | −0.02 | −1.90 | −0.13 | −1.71 | −1.98 | −2.47 | −4.94 | 3.19 |
| M | 026Q | −0.05 | −15.46 | −20.63 | −0.01 | −2.78 | −0.45 | −2.40 | −2.88 | −3.40 | −5.84 | 2.53 |
| M | 026R | −0.08 | −0.99 | −0.18 | −0.02 | −1.42 | −0.16 | −1.36 | −1.62 | −2.02 | −3.64 | 2.03 |
| M | 026S | −0.10 | −3.76 | −1.39 | −0.02 | −2.47 | −0.53 | −1.70 | −1.97 | −2.18 | −4.82 | 0.66 |
| M | 026T | 0.02 | 19.69 | −85.22 | 0.00 | 22.42 | 7.39 | 15.09 | 16.64 | 16.49 | 32.78 | 13.35 |
| M | 026V | 0.35 | 1.67 | 3.93 | 0.18 | 1.97 | 1.38 | 1.59 | 1.59 | 1.57 | 2.28 | 1.79 |
| M | 026W | −0.10 | 0.88 | −8.65 | −0.02 | −1.22 | −0.22 | −1.20 | −1.43 | −1.76 | −2.81 | 2.87 |
| M | 026Y | −0.15 | 1.04 | 13.59 | −0.03 | −0.85 | −0.20 | −0.81 | −0.93 | −1.16 | −2.41 | 0.63 |
| K | 027A | 1.14 | 0.93 | −0.20 | 1.47 | 0.90 | 0.93 | 0.86 | 0.58 | 0.91 | 0.87 | 0.83 |
| K | 027C | 0.45 | 1.24 | −0.89 | 0.26 | 1.20 | 0.64 | 0.87 | 0.76 | 0.95 | 1.40 | 1.38 |
| K | 027D | 1.12 | 0.75 | 0.21 | 1.23 | 0.89 | 0.85 | 0.83 | 0.69 | 0.83 | 0.82 | 0.85 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| K | 027G | 0.92 | 1.02 | −0.85 | 0.92 | 1.09 | 1.09 | 1.05 | 0.90 | 1.03 | 1.07 | 1.15 |
| K | 027H | 1.12 | 0.82 | 1.02 | 1.11 | 0.91 | 0.89 | 0.87 | 0.74 | 0.86 | 0.85 | 0.83 |
| K | 027M | 0.59 | 1.11 | −2.39 | 0.35 | 1.12 | 0.85 | 0.87 | 0.66 | 0.90 | 0.61 | 0.46 |
| K | 027P | 0.66 | 1.32 | 8.41 | 0.62 | 1.27 | 1.18 | 1.21 | 1.20 | 1.22 | 1.31 | 1.22 |
| K | 027Q | 0.94 | 1.11 | 2.24 | 0.93 | 0.99 | 0.95 | 0.98 | 0.97 | 0.95 | 0.97 | 1.09 |
| K | 027R | 1.14 | 0.87 | 0.40 | 1.04 | 0.84 | 0.79 | 0.81 | 0.79 | 0.78 | 0.82 | 0.79 |
| K | 027S | 1.07 | 0.85 | 3.78 | 0.92 | 0.89 | 0.84 | 0.84 | 0.83 | 0.83 | 0.85 | 0.85 |
| K | 027T | 0.84 | 0.97 | −5.49 | 0.64 | 1.02 | 0.87 | 0.95 | 0.88 | 0.94 | 1.07 | 1.06 |
| K | 027V | 0.87 | 0.96 | −5.35 | 0.66 | 1.00 | 0.87 | 0.92 | 0.85 | 0.88 | 0.98 | 0.99 |
| K | 027W | 0.58 | 1.28 | −2.27 | 0.41 | 1.26 | 0.99 | 1.08 | 0.99 | 1.05 | 1.49 | 1.32 |
| K | 027Y | 0.78 | 0.97 | −1.72 | 0.59 | 1.14 | 1.04 | 1.04 | 0.88 | 1.00 | 1.19 | 1.03 |
| I | 029A | 0.44 | 1.10 | 3.55 | 0.23 | 1.28 | 0.59 | 0.84 | 0.65 | 0.90 | 1.67 | 1.09 |
| I | 029C | 0.19 | 4.61 | −0.07 | 0.06 | 1.28 | 0.20 | 0.91 | 0.94 | 1.12 | 2.19 | 0.96 |
| I | 029D | 0.00 | −87.85 | −306.33 | 0.00 | −18.73 | 1.41 | −20.86 | −24.18 | −28.89 | −58.19 | −17.93 |
| I | 029E | 0.04 | 10.57 | 51.83 | 0.01 | 2.60 | −0.32 | 2.85 | 3.34 | 3.88 | 6.93 | 1.05 |
| I | 029F | 0.58 | 0.79 | 0.63 | 0.33 | 1.22 | 0.71 | 0.84 | 0.75 | 0.76 | 1.51 | 1.29 |
| I | 029G | −0.05 | −11.87 | 15.49 | −0.01 | −2.10 | −0.23 | −2.26 | −2.64 | −2.99 | −6.27 | −2.92 |
| I | 029H | −0.12 | 3.04 | −7.25 | −0.02 | −0.87 | −0.05 | −0.96 | −1.11 | −1.36 | −2.56 | −0.72 |
| I | 029L | 0.70 | 0.86 | 0.41 | 0.62 | 1.28 | 1.11 | 1.10 | 0.84 | 1.07 | 1.19 | 1.15 |
| I | 029M | 0.46 | 1.29 | 2.33 | 0.28 | 1.39 | 0.79 | 1.03 | 0.80 | 1.04 | 1.66 | 1.31 |
| I | 029Q | −0.01 | −107.58 | −305.14 | 0.00 | −16.76 | −0.26 | −18.50 | −22.07 | −26.86 | −53.06 | −21.75 |
| I | 029R | −0.08 | −5.11 | −13.89 | −0.02 | −1.19 | −0.13 | −1.31 | −1.54 | −1.92 | −3.68 | −2.39 |
| I | 029S | −0.02 | −36.21 | 12.51 | 0.00 | −8.00 | −0.91 | −7.21 | −8.09 | −9.23 | −18.75 | −7.29 |
| I | 029T | 0.11 | 2.63 | 0.74 | 0.03 | 2.93 | 0.82 | 1.96 | 2.13 | 2.14 | 4.41 | 3.07 |
| I | 029V | 0.82 | 1.05 | 0.02 | 0.71 | 1.11 | 1.01 | 1.05 | 1.00 | 1.01 | 1.15 | 1.07 |
| I | 029W | −0.04 | 5.17 | 17.32 | −0.01 | −2.55 | −0.27 | −2.97 | −3.42 | −4.00 | −7.41 | −0.69 |
| I | 029Y | −0.03 | 17.68 | 31.55 | −0.01 | −4.28 | −0.50 | −4.21 | −4.62 | −5.57 | −9.72 | −3.98 |
| H | 030A | 1.13 | 0.97 | 13.22 | 1.54 | 0.99 | 0.88 | 0.98 | 0.57 | 0.95 | 0.92 | 0.89 |
| H | 030C | 0.63 | 1.01 | −7.51 | 0.49 | 1.22 | 0.91 | 0.98 | 0.73 | 0.98 | 1.29 | 1.12 |
| H | 030D | 0.95 | 0.87 | −9.75 | 1.03 | 1.06 | 0.72 | 0.96 | 0.74 | 0.96 | 1.06 | 1.00 |
| H | 030E | 0.89 | 1.09 | −1.60 | 0.91 | 1.09 | 1.00 | 1.00 | 0.82 | 0.99 | 1.08 | 1.09 |
| H | 030F | 0.95 | 0.98 | −5.18 | 0.85 | 1.00 | 0.88 | 0.88 | 0.73 | 0.84 | 0.96 | 1.07 |
| H | 030G | 0.82 | 1.11 | −2.66 | 0.74 | 1.19 | 0.88 | 1.11 | 0.95 | 1.09 | 1.16 | 1.16 |
| H | 030I | 0.37 | 1.06 | −22.14 | 0.16 | 1.57 | 0.81 | 1.09 | 0.99 | 1.13 | 2.10 | 1.69 |
| H | 030L | 0.62 | 0.85 | −6.40 | 0.44 | 1.36 | 1.03 | 1.01 | 0.74 | 1.04 | 1.43 | 1.26 |
| H | 030N | 0.71 | 1.17 | 26.21 | 0.58 | 1.18 | 0.97 | 1.02 | 0.91 | 1.00 | 1.34 | 1.16 |
| H | 030P | 0.16 | 1.42 | −6.72 | 0.05 | 1.72 | −0.52 | 1.29 | 1.44 | 1.50 | 2.84 | 1.60 |
| H | 030Q | 0.83 | 1.12 | 17.10 | 0.82 | 1.14 | 1.17 | 1.10 | 1.07 | 1.08 | 1.16 | 1.13 |
| H | 030R | 0.86 | 1.25 | 3.57 | 0.78 | 1.17 | 1.00 | 1.11 | 1.09 | 1.11 | 1.20 | 1.20 |
| H | 030S | 0.78 | 1.23 | 9.20 | 0.71 | 1.28 | 1.11 | 1.26 | 1.20 | 1.24 | 1.27 | 1.22 |
| H | 030T | 0.55 | 1.31 | −3.88 | 0.38 | 1.55 | 1.29 | 1.32 | 1.32 | 1.32 | 1.56 | 1.64 |
| H | 030V | 0.52 | 1.44 | −12.76 | 0.37 | 1.58 | 1.18 | 1.38 | 1.27 | 1.35 | 1.61 | 1.68 |
| H | 030W | 0.60 | 1.03 | −11.26 | 0.38 | 1.30 | 1.02 | 1.11 | 0.87 | 1.05 | 1.41 | 1.30 |
| H | 030Y | 0.81 | 1.08 | 2.81 | 0.83 | 1.28 | 1.39 | 1.27 | 0.81 | 1.21 | 1.28 | 1.24 |
| D | 031A | 1.03 | 0.74 | 2.40 | 1.38 | 1.01 | 1.08 | 1.05 | 0.61 | 0.97 | 1.09 | 0.98 |
| D | 031C | 0.41 | 0.93 | 4.71 | 0.22 | 1.40 | 0.72 | 0.92 | 0.88 | 0.96 | 1.89 | 1.73 |
| D | 031E | 1.03 | 1.06 | 1.09 | 1.16 | 1.01 | 0.97 | 0.93 | 0.80 | 0.89 | 0.99 | 0.93 |
| D | 031F | 0.77 | 1.20 | 3.66 | 0.61 | 1.17 | 0.94 | 0.94 | 0.77 | 0.87 | 1.31 | 1.15 |
| D | 031G | 0.72 | 1.36 | 4.36 | 0.67 | 1.36 | 1.27 | 1.22 | 0.99 | 1.16 | 1.44 | 1.43 |
| D | 031H | 0.98 | 1.12 | 1.02 | 1.04 | 1.07 | 1.05 | 1.00 | 0.79 | 0.94 | 1.08 | 1.04 |
| D | 031I | 0.60 | 1.45 | 3.50 | 0.49 | 1.54 | 1.32 | 1.30 | 0.97 | 1.25 | 1.59 | 1.66 |
| D | 031K | 0.84 | 1.18 | 2.07 | 0.85 | 1.25 | 1.14 | 1.13 | 0.78 | 1.08 | 1.22 | 1.23 |
| D | 031L | 0.86 | 1.13 | 1.53 | 0.97 | 1.20 | 1.18 | 1.17 | 0.82 | 1.07 | 1.29 | 1.07 |
| D | 031M | 0.74 | 1.23 | 4.12 | 0.81 | 1.31 | 1.22 | 1.20 | 0.84 | 1.14 | 1.51 | 1.39 |
| D | 031N | 0.92 | 0.95 | 2.05 | 0.92 | 1.00 | 0.99 | 0.97 | 0.88 | 0.94 | 1.18 | 1.07 |
| D | 031P | −0.05 | −10.78 | −32.68 | −0.01 | −3.35 | −0.36 | −2.78 | −3.35 | −3.85 | −7.92 | −5.79 |
| D | 031Q | 0.81 | 1.21 | 1.28 | 0.81 | 1.15 | 1.10 | 1.09 | 1.07 | 1.04 | 1.19 | 1.24 |
| D | 031S | 0.78 | 1.15 | 2.82 | 0.63 | 1.18 | 1.08 | 1.10 | 1.03 | 1.08 | 1.20 | 1.14 |
| D | 031T | 0.76 | 1.11 | 2.70 | 0.60 | 1.18 | 1.04 | 1.08 | 1.01 | 1.07 | 1.27 | 1.14 |
| D | 031V | 0.73 | 1.04 | 3.29 | 0.53 | 1.15 | 1.01 | 1.04 | 0.95 | 1.02 | 1.23 | 1.12 |
| D | 031W | 0.40 | 1.72 | 7.60 | 0.26 | 1.92 | 1.54 | 1.64 | 1.38 | 1.58 | 2.30 | 2.36 |
| D | 031Y | 0.78 | 1.07 | 1.68 | 0.67 | 1.17 | 1.10 | 1.12 | 0.76 | 1.05 | 1.35 | 1.36 |
| A | 032C | −0.23 | −2.02 | −3.23 | −0.12 | −2.25 | −1.07 | −1.50 | −1.33 | −1.89 | −2.95 | −1.96 |
| A | 032D | 0.33 | 1.72 | 2.05 | 0.16 | 1.62 | 0.75 | 1.11 | 0.94 | 1.19 | 1.99 | 1.42 |
| A | 032E | 0.05 | 12.40 | 61.63 | 0.01 | 3.67 | 0.33 | 3.09 | 3.50 | 4.19 | 7.43 | 2.23 |
| A | 032F | 0.24 | 2.30 | 3.39 | 0.08 | 1.42 | 0.36 | 0.93 | 0.91 | 1.06 | 2.21 | 1.46 |
| A | 032G | 0.70 | 1.29 | 2.69 | 0.63 | 1.34 | 1.15 | 1.15 | 0.99 | 1.20 | 1.38 | 1.57 |
| A | 032H | 0.48 | 1.45 | 3.73 | 0.34 | 1.67 | 1.21 | 1.28 | 1.07 | 1.30 | 1.81 | 1.73 |
| A | 032I | −0.01 | −47.15 | −608.45 | 0.00 | −51.19 | −4.00 | −41.01 | −46.27 | −57.27 | −104.52 | −52.58 |
| A | 032K | 0.21 | 1.81 | 3.36 | 0.08 | 1.79 | 0.55 | 1.16 | 1.09 | 1.37 | 2.67 | 1.71 |
| A | 032L | 0.08 | 5.00 | 28.74 | 0.02 | 4.29 | 1.01 | 2.82 | 2.73 | 3.46 | 6.81 | 2.90 |
| A | 032M | 0.16 | 3.11 | 13.33 | 0.06 | 2.47 | 0.74 | 1.65 | 1.47 | 1.91 | 3.35 | 2.18 |
| A | 032P | −0.01 | −55.06 | −3.16 | 0.00 | −10.37 | 1.62 | −12.08 | −15.14 | −18.56 | −31.82 | −13.82 |
| A | 032Q | 0.08 | 6.31 | 16.94 | 0.03 | 3.19 | 0.62 | 2.39 | 2.59 | 2.98 | 5.97 | 5.15 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| A | 032S | 0.75 | 1.29 | 1.62 | 0.64 | 1.22 | 1.12 | 1.13 | 1.10 | 1.14 | 1.27 | 1.16 |
| A | 032T | 0.20 | 2.18 | 3.18 | 0.08 | 2.50 | 1.23 | 1.77 | 1.81 | 1.87 | 3.65 | 3.18 |
| A | 032V | 0.13 | 2.42 | 14.98 | 0.04 | 3.06 | 1.11 | 2.09 | 2.12 | 2.39 | 4.37 | 3.31 |
| A | 032W | −0.04 | 5.75 | −65.08 | −0.01 | −3.71 | −0.45 | −3.59 | −4.15 | −4.95 | −9.34 | −2.39 |
| A | 032Y | 0.18 | 1.87 | 9.67 | 0.06 | 2.36 | 0.90 | 1.59 | 1.43 | 1.80 | 3.21 | 2.20 |
| G | 033A | 0.57 | 1.13 | −0.63 | 0.34 | 1.12 | 0.65 | 0.78 | 0.69 | 0.81 | 1.20 | 1.11 |
| G | 033C | 0.17 | 3.10 | 61.70 | 0.05 | 1.42 | −0.01 | 1.14 | 1.26 | 1.31 | 2.42 | 1.05 |
| G | 033D | 0.79 | 0.90 | 5.64 | 0.59 | 0.96 | 0.49 | 0.86 | 0.84 | 0.81 | 1.16 | 1.12 |
| G | 033E | 0.70 | 0.94 | −0.11 | 0.49 | 1.09 | 0.86 | 0.96 | 0.96 | 0.91 | 1.27 | 1.28 |
| G | 033F | 0.16 | 2.51 | 24.89 | 0.04 | 1.43 | 0.18 | 1.17 | 1.34 | 1.37 | 2.90 | 1.42 |
| G | 033H | 0.82 | 1.03 | 9.20 | 0.62 | 1.07 | 0.96 | 0.97 | 0.97 | 0.94 | 1.22 | 1.21 |
| G | 033I | 0.06 | −4.79 | −95.00 | 0.01 | 1.93 | 0.10 | 2.30 | 2.77 | 2.93 | 5.75 | 2.04 |
| G | 033K | 0.37 | 1.38 | −18.95 | 0.18 | 1.83 | 0.83 | 1.41 | 1.25 | 1.43 | 2.34 | 2.30 |
| G | 033L | 0.07 | −2.72 | −47.96 | 0.02 | 2.57 | 0.42 | 2.35 | 2.52 | 2.85 | 5.86 | 3.29 |
| G | 033M | 0.27 | 1.00 | 9.88 | 0.10 | 1.21 | 0.12 | 0.92 | 0.90 | 1.04 | 1.99 | 0.92 |
| G | 033P | 0.08 | 0.95 | −59.03 | 0.02 | 1.35 | −1.27 | 1.68 | 1.99 | 2.11 | 3.52 | 0.25 |
| G | 033Q | 0.55 | 1.27 | −32.68 | 0.36 | 1.27 | 0.84 | 1.20 | 1.26 | 1.16 | 1.67 | 1.54 |
| G | 033S | 0.51 | 1.34 | −45.22 | 0.26 | 1.34 | 0.95 | 1.10 | 1.19 | 1.08 | 1.68 | 1.58 |
| G | 033T | 0.10 | 2.54 | −168.02 | 0.03 | 2.97 | −0.24 | 2.20 | 2.45 | 2.42 | 4.96 | 2.49 |
| G | 033V | −0.01 | 79.93 | 809.28 | 0.00 | −17.75 | 6.54 | −19.56 | −23.23 | −24.42 | −45.21 | −1.25 |
| G | 033W | 0.05 | −0.32 | −206.00 | 0.01 | 5.00 | 0.84 | 3.91 | 4.24 | 4.71 | 9.11 | 5.58 |
| G | 033Y | 0.22 | 1.32 | −42.04 | 0.08 | 2.05 | 0.21 | 1.41 | 1.23 | 1.51 | 2.95 | 1.60 |
| Y | 034A | 0.13 | 3.72 | 11.77 | 0.04 | 0.83 | 0.05 | 0.96 | 1.15 | 1.51 | 2.30 | 0.21 |
| Y | 034C | 0.03 | 15.69 | 26.09 | 0.01 | 2.90 | 0.17 | 3.36 | 4.12 | 5.26 | 8.00 | 2.79 |
| Y | 034D | 0.04 | 2.95 | 28.64 | 0.01 | 2.60 | −0.04 | 3.00 | 3.74 | 4.76 | 9.10 | 1.99 |
| Y | 034E | −0.13 | −0.66 | −14.31 | −0.03 | −0.73 | −0.02 | −0.85 | −1.04 | −1.26 | −1.99 | −0.63 |
| Y | 034F | 0.99 | 0.95 | 0.84 | 0.87 | 0.92 | 0.84 | 0.89 | 0.93 | 0.90 | 0.92 | 0.98 |
| Y | 034G | −0.01 | 52.37 | −381.43 | 0.00 | −89.51 | −3.54 | −102.27 | −128.08 | −149.61 | −263.93 | −119.90 |
| Y | 034H | 0.05 | 5.84 | 43.97 | 0.01 | 3.72 | 0.32 | 3.04 | 3.67 | 4.37 | 9.39 | 4.84 |
| Y | 034I | 0.13 | 3.25 | 13.63 | 0.04 | 2.33 | 0.53 | 1.55 | 1.71 | 1.88 | 4.13 | 2.94 |
| Y | 034K | −0.05 | −1.60 | −36.66 | −0.01 | −2.62 | −0.03 | −2.54 | −3.06 | −3.84 | −5.93 | −2.04 |
| Y | 034L | −0.04 | −2.76 | −39.04 | −0.01 | −4.91 | −0.51 | −3.93 | −4.42 | −5.57 | −10.14 | −3.46 |
| Y | 034M | 0.03 | 34.94 | 45.52 | 0.01 | 5.29 | −0.05 | 4.91 | 5.82 | 7.49 | 11.90 | 5.60 |
| Y | 034N | −0.05 | −14.46 | −43.59 | −0.01 | −2.47 | 0.04 | −2.63 | −3.15 | −3.90 | −5.69 | −0.86 |
| Y | 034P | 0.06 | 9.51 | 3.76 | 0.01 | 1.60 | −0.13 | 1.86 | 2.27 | 2.75 | 5.10 | 2.63 |
| Y | 034Q | −0.09 | −0.62 | −8.26 | −0.02 | −1.13 | 0.06 | −1.30 | −1.58 | −1.97 | −3.85 | −1.52 |
| Y | 034R | −0.01 | −26.29 | −112.14 | 0.00 | −14.94 | 0.27 | −17.62 | −21.99 | −26.77 | −41.47 | −2.83 |
| Y | 034S | −0.08 | 1.61 | −26.10 | −0.01 | −1.28 | −0.10 | −1.47 | −1.79 | −2.20 | −3.82 | −2.20 |
| Y | 034T | −0.11 | 1.45 | −8.56 | −0.02 | −1.04 | −0.08 | −1.19 | −1.38 | −1.70 | −3.12 | −0.92 |
| Y | 034V | −0.01 | −40.64 | −429.69 | 0.00 | −35.01 | −3.75 | −27.83 | −32.81 | −35.81 | −70.48 | −27.81 |
| Y | 034W | 0.85 | 1.00 | 2.80 | 0.62 | 1.03 | 0.92 | 0.99 | 0.96 | 0.99 | 1.06 | 0.96 |
| A | 036C | 0.32 | 1.96 | −10.86 | 0.15 | 1.45 | 0.77 | 1.11 | 1.01 | 1.23 | 2.06 | 1.40 |
| A | 036D | 0.30 | 2.01 | −1.33 | 0.15 | 1.81 | 1.05 | 1.35 | 1.29 | 1.43 | 2.37 | 2.04 |
| A | 036E | 0.09 | 6.99 | −20.80 | 0.03 | 4.59 | 2.18 | 3.30 | 3.40 | 3.75 | 5.87 | 5.56 |
| A | 036F | 0.75 | 1.32 | −6.85 | 0.67 | 1.15 | 1.06 | 1.06 | 1.03 | 1.05 | 1.14 | 1.08 |
| A | 036G | −0.25 | −3.96 | 19.73 | −0.09 | −1.98 | −0.87 | −1.34 | −1.39 | −1.67 | −2.77 | −1.77 |
| A | 036H | 0.67 | 1.41 | 5.16 | 0.48 | 1.29 | 1.02 | 1.02 | 1.01 | 1.00 | 1.29 | 1.23 |
| A | 036I | 0.64 | 1.29 | −10.19 | 0.50 | 1.47 | 1.24 | 1.22 | 1.13 | 1.29 | 1.37 | 1.24 |
| A | 036K | 0.51 | 1.48 | 6.64 | 0.33 | 1.60 | 1.19 | 1.24 | 1.13 | 1.27 | 1.77 | 1.56 |
| A | 036L | 0.80 | 1.09 | −0.70 | 0.73 | 1.29 | 1.08 | 1.02 | 0.84 | 1.04 | 1.19 | 1.16 |
| A | 036M | 1.08 | 0.96 | −12.13 | 1.49 | 0.94 | 1.01 | 0.90 | 0.55 | 0.94 | 0.92 | 0.89 |
| A | 036N | 0.42 | 1.31 | −17.38 | 0.25 | 1.58 | 1.08 | 1.08 | 0.81 | 1.18 | 1.43 | 1.09 |
| A | 036P | −0.03 | −3.87 | 133.88 | −0.01 | −4.79 | −0.55 | −4.03 | −4.62 | −6.10 | −8.71 | −2.10 |
| A | 036Q | 0.44 | 1.78 | −21.04 | 0.26 | 1.51 | 1.17 | 1.23 | 1.03 | 1.27 | 1.70 | 1.57 |
| A | 036R | 0.51 | 1.65 | −6.64 | 0.37 | 1.55 | 1.28 | 1.28 | 1.05 | 1.34 | 1.68 | 1.28 |
| A | 036S | 0.91 | 1.24 | 2.10 | 0.89 | 1.10 | 1.09 | 1.03 | 0.79 | 1.05 | 1.05 | 1.01 |
| A | 036T | 0.76 | 1.30 | 10.32 | 0.80 | 1.34 | 1.35 | 1.26 | 0.97 | 1.31 | 1.17 | 1.19 |
| A | 036V | 0.00 | −961.56 | −3185.86 | 0.00 | −681.63 | −698.73 | −23.71 | −325.53 | 1716.20 | −613.76 | −521.91 |
| A | 036Y | 0.72 | 1.30 | 3.78 | 0.86 | 1.47 | 1.33 | 1.23 | 1.03 | 1.23 | 1.28 | 1.19 |
| I | 037C | 0.05 | 10.56 | 41.18 | 0.01 | 3.72 | 0.25 | 3.05 | 3.55 | 4.18 | 7.10 | 4.01 |
| I | 037D | 0.02 | 1.82 | −6.29 | 0.01 | 3.87 | −0.30 | 4.54 | 5.68 | 6.82 | 13.33 | 2.74 |
| I | 037E | 0.04 | −0.13 | 17.77 | 0.01 | 2.16 | 0.03 | 2.55 | 3.14 | 3.84 | 7.16 | 2.53 |
| I | 037G | −0.08 | 2.14 | −6.40 | −0.02 | −1.14 | −0.14 | −1.31 | −1.59 | −1.92 | −3.48 | −1.02 |
| I | 037H | −0.01 | 14.14 | −22.57 | 0.00 | −14.39 | −2.04 | −16.56 | −20.45 | −24.98 | −43.54 | −15.84 |
| I | 037L | 0.72 | 1.12 | 1.93 | 0.59 | 1.30 | 1.21 | 1.13 | 0.99 | 1.23 | 1.32 | 1.23 |
| I | 037M | 0.44 | 1.15 | 0.56 | 0.23 | 1.29 | 0.71 | 0.91 | 0.82 | 1.02 | 1.62 | 1.37 |
| I | 037N | 0.06 | −0.44 | 23.22 | 0.01 | 1.56 | −0.08 | 1.83 | 2.31 | 2.79 | 4.18 | 1.30 |
| I | 037P | −0.47 | −1.53 | 1.79 | −0.09 | −0.29 | −0.52 | −0.31 | −0.94 | 1.52 | −0.55 | −0.13 |
| I | 037Q | −0.16 | −0.34 | −4.71 | −0.03 | −0.61 | −0.05 | −0.72 | −0.89 | −1.06 | −1.69 | −3.57 |
| I | 037R | −0.11 | −0.34 | −5.85 | −0.02 | −0.85 | −0.07 | −0.99 | −1.24 | −1.51 | −2.82 | 3.38 |
| I | 037S | −0.06 | 2.51 | −24.83 | −0.01 | −1.97 | −0.08 | −2.13 | −2.65 | −3.12 | −4.97 | −1.34 |
| I | 037T | −0.02 | −21.82 | −48.69 | 0.00 | −12.04 | −2.63 | −8.30 | −9.96 | −10.64 | −21.36 | −12.18 |
| I | 037V | 0.75 | 1.28 | 2.02 | 0.62 | 1.28 | 1.24 | 1.24 | 1.26 | 1.28 | 1.33 | 1.34 |
| I | 037W | 0.01 | 20.00 | 138.65 | 0.00 | 12.15 | 3.82 | 14.25 | 17.67 | 21.21 | 36.55 | 18.20 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| I | 037Y | −0.05 | −9.79 | −47.31 | −0.01 | −3.69 | −0.41 | −3.03 | −3.50 | −4.32 | −6.98 | −4.27 |
| Q | 038A | 0.24 | 2.55 | 6.18 | 0.06 | 0.74 | −0.03 | 0.62 | 0.64 | 0.77 | 1.64 | 0.57 |
| Q | 038C | 0.06 | 14.97 | 8.75 | 0.02 | 2.31 | −0.08 | 2.20 | 2.51 | 2.77 | 5.77 | 1.82 |
| Q | 038D | 0.14 | 6.76 | 9.40 | 0.03 | 0.71 | −0.01 | 0.83 | 1.02 | 1.18 | 2.14 | 0.51 |
| Q | 038E | 0.34 | 0.37 | 1.75 | 0.11 | 0.91 | 0.04 | 0.71 | 0.61 | 0.55 | 1.30 | 0.65 |
| Q | 038G | 0.05 | 6.14 | 1.26 | 0.01 | 3.66 | −0.07 | 2.91 | 3.14 | 3.25 | 8.83 | 3.73 |
| Q | 038H | 0.09 | 4.91 | 11.58 | 0.02 | 1.95 | 0.09 | 1.63 | 1.75 | 2.00 | 4.70 | 2.52 |
| Q | 038I | −0.06 | 0.03 | −17.34 | −0.01 | −1.98 | 0.02 | −1.99 | −2.42 | −2.73 | −5.93 | −2.25 |
| Q | 038K | −0.02 | 36.30 | −20.15 | 0.00 | −4.30 | −0.19 | −5.05 | −6.23 | −7.03 | −13.66 | −3.40 |
| Q | 038L | 0.10 | −1.84 | −2.87 | 0.03 | 2.41 | 0.20 | 1.79 | 1.67 | 1.87 | 3.89 | 1.60 |
| Q | 038M | 0.22 | 4.41 | 7.64 | 0.05 | 0.69 | −0.02 | 0.63 | 0.68 | 0.82 | 1.77 | 0.37 |
| Q | 038N | 0.36 | 0.79 | 1.00 | 0.10 | 0.77 | −0.01 | 0.51 | 0.53 | 0.53 | 1.32 | 0.77 |
| Q | 038P | 0.09 | 2.67 | 9.02 | 0.02 | 1.10 | 0.00 | 1.28 | 1.60 | 1.83 | 3.31 | −2.68 |
| Q | 038R | 0.02 | −15.84 | 83.19 | 0.00 | 6.23 | 0.97 | 7.43 | 9.09 | 10.11 | 18.14 | 4.57 |
| Q | 038S | −0.13 | 0.86 | −7.98 | −0.03 | −1.45 | −0.01 | −1.12 | −1.35 | −1.31 | −3.14 | −1.46 |
| Q | 038V | 0.15 | −0.34 | 9.64 | 0.04 | 1.77 | 0.13 | 1.18 | 1.30 | 1.22 | 2.82 | 1.17 |
| Q | 038W | −0.18 | 1.91 | −4.69 | −0.04 | −0.58 | −0.04 | −0.66 | −0.80 | −0.92 | −1.62 | −0.67 |
| Q | 038Y | 0.04 | −24.59 | 14.74 | 0.01 | 3.09 | 0.53 | 3.75 | 4.52 | 5.39 | 8.62 | −0.19 |
| T | 039A | 0.70 | 1.04 | 2.85 | 0.45 | 0.95 | 0.64 | 0.69 | 0.51 | 0.71 | 1.20 | 1.09 |
| T | 039C | 0.19 | 1.94 | 6.07 | 0.06 | 1.86 | 0.67 | 1.26 | 1.18 | 1.42 | 2.82 | 1.47 |
| T | 039D | −0.12 | −1.12 | −10.05 | −0.02 | −0.79 | −0.13 | −0.83 | −1.04 | −1.29 | −1.88 | 1.95 |
| T | 039E | −0.14 | 0.91 | −9.32 | −0.03 | −0.71 | −0.09 | −0.75 | −0.92 | −1.16 | −1.77 | 1.47 |
| T | 039F | −0.14 | −0.29 | −12.42 | −0.02 | −0.70 | −0.14 | −0.77 | −0.95 | −1.31 | −2.05 | 1.77 |
| T | 039G | −0.03 | −11.36 | −0.25 | −0.01 | −8.36 | −1.85 | −5.55 | −6.25 | −6.76 | −15.16 | −4.81 |
| T | 039H | −0.14 | 0.37 | 1.10 | −0.03 | −0.77 | −0.11 | −0.80 | −0.97 | −1.18 | −2.20 | 1.12 |
| T | 039I | 0.42 | 1.20 | 0.33 | 0.19 | 1.41 | 0.84 | 1.08 | 1.00 | 1.09 | 1.95 | 1.39 |
| T | 039K | −0.12 | 1.15 | −3.33 | −0.02 | −0.80 | −0.03 | −0.93 | −1.07 | −1.34 | −2.41 | 1.78 |
| T | 039L | 0.40 | 1.36 | −0.38 | 0.20 | 1.71 | 1.07 | 1.28 | 0.99 | 1.22 | 2.12 | 1.65 |
| T | 039M | 0.29 | 1.74 | 5.65 | 0.12 | 1.70 | 0.68 | 1.08 | 0.72 | 1.07 | 2.06 | 1.31 |
| T | 039N | 0.18 | 2.93 | 6.25 | 0.05 | 1.63 | 0.40 | 0.98 | 0.96 | 1.29 | 2.55 | 0.11 |
| T | 039P | 0.59 | 1.02 | 3.14 | 0.28 | 1.08 | 0.58 | 0.68 | 0.57 | 0.71 | 1.47 | 1.37 |
| T | 039Q | −0.06 | −2.99 | −22.55 | −0.01 | −1.78 | −0.17 | −1.91 | −2.27 | −2.78 | −4.83 | 4.03 |
| T | 039S | 0.47 | 1.51 | 2.19 | 0.27 | 1.71 | 1.22 | 1.31 | 1.07 | 1.30 | 1.85 | 1.83 |
| T | 039V | 0.63 | 1.24 | 2.04 | 0.40 | 1.32 | 1.05 | 1.06 | 0.79 | 1.02 | 1.49 | 1.14 |
| T | 039W | −0.09 | 1.72 | −1.97 | −0.02 | −1.02 | −0.09 | −1.20 | −1.42 | −1.84 | −2.72 | 2.04 |
| S | 040A | 0.35 | 1.38 | 4.02 | 0.19 | 1.78 | 0.81 | 1.24 | 0.85 | 0.76 | 2.14 | 1.74 |
| S | 040D | 0.08 | 7.32 | 8.10 | 0.02 | 3.49 | 0.02 | 2.31 | 2.46 | 2.28 | 5.36 | 1.87 |
| S | 040E | −0.01 | −83.15 | −56.33 | 0.00 | −22.56 | 1.38 | −16.29 | −18.87 | −21.61 | −49.14 | −17.43 |
| S | 040F | −0.12 | 0.48 | 6.55 | −0.03 | −0.77 | −0.16 | −0.91 | −1.13 | −1.36 | −2.94 | −0.77 |
| S | 040H | −0.02 | −7.09 | −11.57 | 0.00 | −6.78 | −2.13 | −7.93 | −9.64 | −11.83 | −19.98 | −4.39 |
| S | 040I | −0.10 | −1.47 | −11.43 | −0.02 | −1.07 | −0.09 | −1.15 | −1.43 | −1.73 | −3.26 | −1.39 |
| S | 040K | −0.04 | −5.11 | −17.08 | −0.01 | −2.87 | −0.08 | −3.40 | −4.26 | −5.16 | −9.79 | −3.57 |
| S | 040L | −0.01 | −8.25 | −204.65 | 0.00 | −12.03 | −1.12 | −13.61 | −16.55 | −21.42 | −31.87 | −9.89 |
| S | 040M | 0.33 | 0.79 | 0.93 | 0.11 | 1.37 | 0.17 | 0.74 | 0.58 | 0.74 | 1.62 | 1.05 |
| S | 040N | 0.24 | 1.48 | 1.14 | 0.07 | 1.58 | 0.17 | 1.02 | 0.86 | 0.82 | 2.31 | 1.07 |
| S | 040P | 0.09 | 5.78 | 0.12 | 0.02 | 3.09 | 0.42 | 2.13 | 2.07 | 2.14 | 5.63 | 2.45 |
| S | 040Q | 0.13 | 4.92 | 4.57 | 0.03 | 1.55 | 0.15 | 1.27 | 1.31 | 1.38 | 3.26 | 1.53 |
| S | 040R | −0.03 | 3.52 | −13.98 | −0.01 | −3.74 | −0.88 | −4.50 | −5.58 | −6.87 | −11.29 | −0.56 |
| S | 040T | 0.27 | 2.08 | 0.57 | 0.12 | 2.21 | 0.93 | 1.43 | 1.21 | 1.42 | 2.60 | 2.11 |
| S | 040V | 0.05 | 8.30 | 4.63 | 0.01 | 6.61 | 1.18 | 4.25 | 3.95 | 4.25 | 9.57 | 5.14 |
| S | 040W | 0.10 | 1.81 | 10.69 | 0.02 | 0.92 | 0.20 | 1.10 | 1.34 | 1.67 | 2.64 | 0.54 |
| S | 040Y | 0.02 | 5.62 | 32.73 | 0.00 | 4.03 | 1.21 | 4.84 | 5.89 | 7.88 | 12.45 | 4.61 |
| P | 041A | 0.32 | 1.34 | 29.01 | 0.15 | 1.65 | 0.07 | 1.20 | 1.00 | 0.80 | 1.83 | 0.95 |
| P | 041C | 0.08 | 6.42 | −213.36 | 0.02 | 2.33 | −1.68 | 2.15 | 2.33 | 2.27 | 4.33 | 2.31 |
| P | 041D | 0.00 | 9.81 | 929.02 | 0.00 | −14.15 | −0.68 | −17.89 | −21.76 | −23.05 | −42.15 | −12.88 |
| P | 041E | 0.11 | −3.24 | 28.13 | 0.02 | 0.95 | −0.49 | 1.24 | 1.49 | 1.59 | 2.90 | 1.14 |
| P | 041F | 0.02 | −11.44 | 136.40 | 0.01 | 4.33 | 0.46 | 5.65 | 6.66 | 7.28 | 13.74 | 1.44 |
| P | 041G | 0.07 | −4.63 | −106.11 | 0.02 | 2.19 | 0.21 | 2.03 | 2.39 | 2.31 | 4.62 | 1.02 |
| P | 041H | 0.01 | −15.22 | 84.41 | 0.00 | 7.04 | 1.58 | 8.62 | 10.99 | 11.68 | 19.28 | 10.46 |
| P | 041I | 0.03 | −12.42 | 76.12 | 0.01 | 4.08 | 0.49 | 4.42 | 5.11 | 5.09 | 9.52 | 2.79 |
| P | 041K | 0.01 | −13.42 | 152.89 | 0.00 | 6.25 | 1.65 | 8.14 | 9.93 | 10.66 | 20.50 | 3.99 |
| P | 041L | 0.02 | −15.05 | −459.84 | 0.00 | 4.74 | 0.92 | 6.67 | 7.94 | 9.10 | 15.04 | 3.20 |
| P | 041M | −0.01 | 31.75 | −3206.13 | 0.00 | −18.82 | 0.20 | −25.70 | −30.72 | −34.45 | −51.06 | −1.36 |
| P | 041N | 0.06 | 2.82 | 149.61 | 0.01 | 2.59 | −1.69 | 2.76 | 3.17 | 3.22 | 5.87 | 0.84 |
| P | 041Q | −0.11 | 1.97 | −13.33 | −0.03 | −0.91 | 0.02 | −1.19 | −1.44 | −1.61 | −2.69 | −0.40 |
| P | 041R | −0.04 | 6.52 | −470.72 | −0.01 | −2.76 | −0.19 | −3.50 | −4.28 | −4.52 | −9.39 | −0.72 |
| P | 041S | 0.05 | 7.53 | 41.42 | 0.01 | 6.29 | −1.63 | 4.78 | 5.09 | 3.78 | 9.15 | 4.41 |
| P | 041T | 0.01 | 17.56 | −252.33 | 0.00 | 22.81 | 4.27 | 20.02 | 20.62 | 19.07 | 47.46 | 23.95 |
| P | 041V | 0.12 | 0.76 | 66.77 | 0.03 | 1.80 | 0.22 | 1.55 | 1.64 | 1.58 | 3.85 | 1.91 |
| P | 041W | −0.05 | 2.88 | 301.31 | −0.01 | −2.05 | −0.83 | −2.50 | −3.19 | −3.29 | −7.00 | 0.01 |
| P | 041Y | −0.05 | 3.53 | 386.04 | −0.01 | −2.30 | −0.63 | −3.00 | −3.63 | −4.09 | −6.61 | −1.20 |
| I | 042A | 0.23 | 2.07 | −2.42 | 0.10 | 1.75 | 0.55 | 1.25 | 1.14 | 1.44 | 2.58 | 1.60 |
| I | 042C | 0.00 | 92.24 | 189.29 | 0.00 | 76.83 | 20.97 | 60.11 | 65.17 | 73.96 | 119.80 | 69.02 |
| I | 042D | −0.03 | −7.04 | 6.01 | −0.01 | −3.14 | 0.11 | −3.99 | −4.85 | −5.96 | −9.03 | −3.05 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| I | 042E | 0.00 | 63.77 | −453.64 | 0.00 | 20.89 | 0.94 | 25.80 | 32.39 | 37.56 | 53.46 | 9.77 |
| I | 042F | −0.02 | −15.40 | −12.13 | 0.00 | −7.75 | −0.50 | −7.14 | −8.76 | −9.89 | −15.98 | −8.56 |
| I | 042G | −0.03 | −1.37 | −69.76 | −0.01 | −4.36 | −0.36 | −4.39 | −5.50 | −5.93 | −12.08 | −3.07 |
| I | 042H | −0.02 | −5.10 | 41.72 | 0.00 | −8.08 | −0.69 | −7.00 | −8.76 | −9.37 | −20.10 | −8.38 |
| I | 042K | −0.07 | −1.73 | −28.46 | −0.01 | −1.61 | −0.34 | −1.91 | −2.46 | −2.80 | −5.36 | −2.95 |
| I | 042L | 0.35 | 1.68 | 6.13 | 0.17 | 1.80 | 1.14 | 1.30 | 1.08 | 1.43 | 2.16 | 1.71 |
| I | 042M | 0.22 | 2.40 | −3.56 | 0.09 | 1.73 | 0.54 | 1.23 | 1.18 | 1.49 | 2.48 | 1.73 |
| I | 042N | 0.03 | 13.54 | 47.92 | 0.01 | 3.53 | −0.23 | 3.83 | 4.76 | 5.53 | 8.88 | 4.37 |
| I | 042P | 0.18 | 2.25 | 3.65 | 0.08 | 2.67 | 1.37 | 2.08 | 2.18 | 2.19 | 4.04 | 2.65 |
| I | 042R | −0.01 | −39.10 | −58.17 | 0.00 | −7.40 | −1.35 | −8.83 | −11.31 | −12.73 | −20.41 | −6.87 |
| I | 042S | −0.02 | −12.30 | 57.58 | 0.00 | −7.96 | −0.95 | −6.96 | −8.63 | −9.29 | −16.30 | −7.93 |
| I | 042T | 0.03 | 15.41 | −18.16 | 0.01 | 12.03 | 3.95 | 8.47 | 9.41 | 9.79 | 18.10 | 12.81 |
| I | 042V | 0.72 | 1.19 | −0.60 | 0.51 | 1.17 | 1.01 | 1.08 | 0.99 | 1.05 | 1.27 | 1.27 |
| I | 042W | −0.17 | −0.51 | −8.54 | −0.04 | −0.62 | −0.28 | −0.72 | −0.93 | −1.02 | −1.89 | −0.54 |
| I | 042Y | −0.16 | 0.42 | −4.75 | −0.03 | −0.67 | −0.02 | −0.79 | −0.98 | −1.17 | −1.98 | −0.52 |
| N | 043A | 0.50 | 1.32 | −9.58 | 0.39 | 1.53 | 1.00 | 1.04 | 0.73 | 1.05 | 1.48 | 0.75 |
| N | 043C | −0.08 | −3.79 | 19.32 | −0.02 | −1.20 | −0.40 | −1.34 | −1.64 | −1.65 | −3.78 | −0.72 |
| N | 043D | −0.17 | −3.71 | −11.91 | −0.04 | −0.97 | −0.11 | −0.75 | −0.83 | −0.86 | −1.95 | −3.73 |
| N | 043E | 0.00 | −55.82 | 124.44 | 0.00 | −60.55 | −18.78 | −34.74 | −33.77 | −37.66 | −71.24 | −34.56 |
| N | 043F | −0.03 | −11.74 | 231.43 | −0.01 | −8.75 | −0.93 | −5.07 | −5.26 | −5.06 | −12.04 | −5.60 |
| N | 043G | 0.35 | 2.03 | −19.24 | 0.22 | 2.32 | 1.78 | 1.74 | 1.74 | 1.84 | 2.18 | 3.66 |
| N | 043H | 0.22 | 2.46 | −19.82 | 0.11 | 2.66 | 1.34 | 1.91 | 1.58 | 1.61 | 3.17 | 2.63 |
| N | 043K | −0.19 | 0.45 | −6.33 | −0.04 | −0.72 | −0.11 | −0.64 | −0.76 | −0.83 | −1.52 | −0.76 |
| N | 043L | 0.15 | 2.84 | −42.62 | 0.07 | 4.21 | 2.11 | 2.45 | 1.98 | 2.56 | 4.99 | 2.42 |
| N | 043M | 0.94 | 1.03 | 3.37 | 1.18 | 1.10 | 0.92 | 0.84 | 0.53 | 0.91 | 1.02 | 0.68 |
| N | 043P | −0.03 | −20.02 | 247.07 | −0.01 | −12.15 | −2.13 | −6.79 | −6.89 | −8.01 | −17.97 | −4.08 |
| N | 043Q | 0.49 | 1.74 | −6.11 | 0.35 | 1.74 | 1.23 | 1.21 | 0.81 | 1.29 | 1.70 | 1.42 |
| N | 043R | −0.11 | 1.13 | 78.87 | −0.02 | −0.90 | −0.18 | −0.96 | −1.16 | −1.17 | −2.03 | −0.18 |
| N | 043S | 0.63 | 1.41 | 0.25 | 0.65 | 1.70 | 1.64 | 1.50 | 1.22 | 1.53 | 1.53 | 1.20 |
| N | 043T | 0.86 | 1.09 | −7.30 | 0.85 | 1.09 | 1.21 | 1.13 | 0.83 | 1.06 | 1.04 | 0.84 |
| N | 043V | 0.61 | 1.27 | −14.46 | 0.55 | 1.65 | 1.26 | 1.29 | 1.01 | 1.22 | 1.50 | 0.77 |
| N | 043W | −0.08 | 0.47 | 4.97 | −0.02 | −1.70 | −0.11 | −1.40 | −1.58 | −1.69 | −3.49 | 0.66 |
| V | 045A | 0.50 | 1.16 | −0.97 | 0.29 | 1.33 | 1.00 | 1.03 | 0.65 | 1.01 | 0.92 | 0.47 |
| V | 045C | 0.29 | 1.62 | −0.48 | 0.13 | 1.75 | 0.87 | 1.25 | 1.15 | 1.31 | 2.23 | 1.78 |
| V | 045D | −0.15 | −4.42 | −0.99 | −0.04 | −0.95 | −0.05 | −0.88 | −1.03 | −1.12 | −2.44 | −0.79 |
| V | 045E | −0.04 | −28.02 | −8.41 | −0.01 | −3.52 | 0.02 | −3.83 | −4.51 | −5.12 | −10.42 | −3.06 |
| V | 045G | 0.07 | 5.79 | 2.41 | 0.02 | 5.24 | 1.38 | 3.06 | 2.84 | 3.20 | 7.88 | 5.95 |
| V | 045H | 0.43 | 1.44 | 3.12 | 0.25 | 1.66 | 1.02 | 1.19 | 1.12 | 1.11 | 2.02 | 1.66 |
| V | 045I | 0.41 | 1.55 | 0.07 | 0.25 | 1.81 | 1.27 | 1.45 | 1.35 | 1.46 | 2.10 | 2.14 |
| V | 045K | −0.10 | 2.90 | −18.10 | −0.02 | −1.25 | −0.20 | −1.35 | −1.62 | −1.72 | −3.72 | −1.40 |
| V | 045M | 0.49 | 1.61 | −0.51 | 0.30 | 1.34 | 0.68 | 0.97 | 0.67 | 0.98 | 1.54 | 1.47 |
| V | 045N | 0.26 | 2.25 | −2.40 | 0.16 | 2.38 | 1.39 | 1.65 | 1.41 | 1.82 | 3.25 | 2.09 |
| V | 045P | 0.10 | 3.84 | −3.06 | 0.04 | 4.25 | 1.21 | 2.57 | 2.69 | 3.01 | 6.30 | 8.64 |
| V | 045Q | 0.12 | 2.64 | −0.56 | 0.04 | 2.61 | 0.59 | 1.72 | 1.83 | 1.87 | 4.21 | 2.79 |
| V | 045S | 0.28 | 2.18 | 0.07 | 0.17 | 2.54 | 1.68 | 1.94 | 1.82 | 1.91 | 3.01 | 2.21 |
| V | 045T | 0.42 | 1.65 | 2.20 | 0.26 | 1.83 | 1.34 | 1.43 | 1.39 | 1.35 | 2.08 | 1.77 |
| V | 045W | −0.27 | 1.44 | −1.84 | −0.07 | −0.39 | −0.04 | −0.46 | −0.55 | −0.58 | −16.28 | −0.36 |
| K | 046A | 0.59 | 1.27 | 2.88 | 0.47 | 1.39 | 0.73 | 0.83 | 0.50 | 0.72 | 1.33 | 1.16 |
| K | 046C | 0.06 | 8.80 | 18.31 | 0.02 | 7.20 | 1.90 | 4.20 | 3.86 | 4.60 | 9.24 | 2.65 |
| K | 046D | 0.54 | 1.61 | 1.61 | 0.38 | 1.37 | 0.62 | 0.70 | 0.70 | 0.80 | 1.62 | 1.39 |
| K | 046E | 0.44 | 1.59 | 7.94 | 0.28 | 1.57 | 0.62 | 0.78 | 0.80 | 0.78 | 1.71 | 1.37 |
| K | 046F | 0.57 | 1.42 | 2.74 | 0.44 | 1.49 | 0.86 | 0.94 | 0.79 | 0.92 | 1.48 | 1.24 |
| K | 046G | 0.03 | 14.32 | 23.56 | 0.01 | 12.98 | 1.71 | 5.18 | 5.28 | 5.92 | 16.96 | 9.49 |
| K | 046H | 0.55 | 1.41 | 2.44 | 0.48 | 1.55 | 1.10 | 1.14 | 1.06 | 1.02 | 1.59 | 1.30 |
| K | 046I | 0.45 | 1.39 | 2.48 | 0.27 | 1.54 | 0.89 | 1.03 | 0.86 | 0.98 | 1.79 | 1.19 |
| K | 046L | 0.67 | 1.16 | 1.40 | 0.55 | 1.30 | 0.98 | 0.98 | 0.62 | 0.88 | 1.28 | 1.37 |
| K | 046M | 0.57 | 1.58 | 2.69 | 0.51 | 1.50 | 0.91 | 0.94 | 0.57 | 0.88 | 1.52 | 1.27 |
| K | 046N | 0.60 | 1.48 | 5.12 | 0.57 | 1.50 | 1.15 | 1.13 | 1.05 | 1.14 | 1.40 | 0.97 |
| K | 046Q | 0.35 | 2.24 | 7.62 | 0.28 | 2.23 | 1.13 | 1.21 | 1.20 | 1.04 | 2.13 | 2.14 |
| K | 046R | 0.60 | 1.43 | 2.27 | 0.47 | 1.34 | 0.97 | 1.05 | 1.01 | 0.92 | 1.45 | 1.30 |
| K | 046S | 0.25 | 2.11 | 17.03 | 0.12 | 2.53 | 1.02 | 1.46 | 1.23 | 1.29 | 3.05 | 1.94 |
| K | 046T | 0.10 | 4.60 | 17.44 | 0.05 | 5.68 | 2.35 | 3.27 | 2.84 | 3.04 | 7.12 | 3.95 |
| K | 046V | 0.34 | 1.67 | 0.16 | 0.19 | 2.01 | 1.23 | 1.43 | 1.21 | 1.26 | 2.46 | 1.79 |
| K | 046W | 0.07 | 8.11 | 44.98 | 0.03 | 7.59 | 2.30 | 3.74 | 3.17 | 3.68 | 9.20 | 7.73 |
| K | 046Y | 0.52 | 1.63 | 1.96 | 0.48 | 1.79 | 1.13 | 1.11 | 0.58 | 1.06 | 1.58 | 1.35 |
| G | 048A | 0.83 | 1.17 | 1.03 | 0.90 | 1.15 | 0.83 | 0.74 | 0.44 | 0.65 | 1.21 | 1.02 |
| G | 048C | 0.40 | 1.18 | −7.21 | 0.19 | 1.11 | 0.30 | 0.61 | 0.53 | 0.64 | 1.50 | 1.19 |
| G | 048D | 0.20 | 5.73 | 14.58 | 0.16 | 4.29 | 3.85 | 1.29 | −1.01 | −10.87 | 4.06 | 5.86 |
| G | 048E | 0.68 | 1.17 | −0.71 | 0.53 | 1.19 | 0.69 | 0.68 | 0.50 | 0.55 | 1.27 | 1.25 |
| G | 048F | 0.93 | 1.01 | 1.59 | 0.88 | 1.05 | 0.81 | 0.69 | 0.48 | 0.58 | 1.10 | 1.02 |
| G | 048H | 0.82 | 0.99 | 3.37 | 0.68 | 1.11 | 0.84 | 0.73 | 0.55 | 0.49 | 1.13 | 1.02 |
| G | 048I | 0.40 | 1.62 | 3.84 | 0.28 | 1.95 | 0.95 | 1.00 | 0.69 | 0.81 | 2.10 | 2.00 |
| G | 048K | 0.42 | 1.48 | 3.90 | 0.28 | 1.77 | 0.93 | 0.95 | 0.64 | 0.68 | 1.99 | 1.79 |
| G | 048L | 0.42 | 1.36 | 3.87 | 0.31 | 1.84 | 0.89 | 0.95 | 0.66 | 0.79 | 2.00 | 2.12 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| G | 048N | 0.65 | 1.12 | −0.66 | 0.51 | 1.17 | 0.69 | 0.74 | 0.57 | 0.61 | 1.30 | 1.17 |
| G | 048P | 0.69 | 1.25 | −0.15 | 0.54 | 1.14 | 0.65 | 0.69 | 0.54 | 0.56 | 1.27 | 1.17 |
| G | 048R | −0.07 | −12.43 | 1.99 | −0.04 | −10.69 | −9.67 | −2.54 | −8.23 | 57.53 | −13.10 | −11.25 |
| G | 048S | 0.50 | 1.33 | 5.90 | 0.32 | 1.53 | 0.89 | 0.94 | 0.80 | 0.77 | 1.74 | 1.73 |
| G | 048T | 0.32 | 2.03 | 2.72 | 0.19 | 2.20 | 1.02 | 1.18 | 1.00 | 0.96 | 2.61 | 1.99 |
| G | 048V | 0.49 | 1.24 | −4.70 | 0.30 | 1.46 | 0.76 | 0.81 | 0.64 | 0.66 | 1.62 | 1.42 |
| G | 048W | 0.73 | 1.18 | 0.36 | 0.55 | 1.13 | 0.90 | 0.81 | 0.60 | 0.71 | 1.34 | 1.24 |
| D | 052A | 1.07 | 1.08 | 2.22 | 1.42 | 0.97 | 0.97 | 0.91 | 0.60 | 0.83 | 0.93 | 0.87 |
| D | 052C | 0.31 | 1.97 | 6.29 | 0.15 | 1.50 | 0.63 | 0.97 | 0.87 | 1.01 | 1.97 | 1.10 |
| D | 052E | 1.09 | 0.96 | 2.20 | 1.20 | 0.88 | 0.83 | 0.79 | 0.66 | 0.69 | 0.88 | 0.82 |
| D | 052G | 0.81 | 1.12 | 3.21 | 0.75 | 1.19 | 1.04 | 1.03 | 0.85 | 0.92 | 1.29 | 1.45 |
| D | 052H | 0.77 | 1.14 | 2.92 | 0.67 | 1.21 | 1.01 | 1.01 | 0.82 | 0.86 | 1.29 | 1.35 |
| D | 052I | 0.82 | 1.06 | 1.91 | 0.72 | 1.12 | 0.98 | 1.00 | 0.83 | 0.92 | 1.21 | 1.24 |
| D | 052K | 0.93 | 0.92 | 3.10 | 0.96 | 1.03 | 0.98 | 0.95 | 0.75 | 0.80 | 1.14 | 1.19 |
| D | 052L | 0.89 | 0.94 | 4.07 | 0.91 | 1.04 | 0.94 | 0.93 | 0.76 | 0.86 | 1.14 | 1.20 |
| D | 052M | 0.97 | 1.04 | 3.72 | 1.09 | 0.88 | 0.89 | 0.85 | 0.63 | 0.75 | 0.98 | 1.15 |
| D | 052N | 0.80 | 0.93 | 2.87 | 0.62 | 0.92 | 0.70 | 0.77 | 0.68 | 0.70 | 1.19 | 1.12 |
| D | 052P | 0.31 | 1.83 | 5.17 | 0.15 | 1.64 | 0.55 | 0.90 | 0.81 | 0.66 | 2.37 | 1.46 |
| D | 052Q | 0.69 | 1.38 | 2.21 | 0.69 | 1.25 | 1.15 | 1.14 | 1.16 | 1.04 | 1.45 | 1.40 |
| D | 052R | 0.93 | 0.97 | 2.59 | 0.86 | 0.96 | 0.88 | 0.86 | 0.88 | 0.69 | 1.13 | 1.11 |
| D | 052S | 0.87 | 1.06 | 1.78 | 0.86 | 1.09 | 1.04 | 1.03 | 1.05 | 0.95 | 1.26 | 1.20 |
| D | 052T | 0.81 | 1.10 | 0.66 | 0.73 | 1.07 | 0.93 | 0.95 | 0.94 | 0.86 | 1.24 | 1.13 |
| D | 052V | 1.04 | 0.92 | 2.47 | 1.03 | 0.92 | 0.95 | 0.92 | 0.90 | 0.86 | 1.01 | 0.94 |
| D | 052W | 0.70 | 1.11 | 3.12 | 0.50 | 1.06 | 0.81 | 0.86 | 0.72 | 0.70 | 1.31 | 1.08 |
| D | 052Y | 0.74 | 1.11 | 2.18 | 0.62 | 1.14 | 0.96 | 1.00 | 0.75 | 0.85 | 1.24 | 1.54 |
| K | 053A | 0.91 | 0.76 | 1.20 | 0.84 | 0.95 | 0.81 | 0.81 | 0.58 | 0.83 | 1.01 | 0.87 |
| K | 053C | 0.51 | 0.54 | 1.04 | 0.23 | 1.09 | 0.61 | 0.82 | 0.80 | 0.89 | 1.45 | 1.11 |
| K | 053E | 0.83 | 0.98 | 1.34 | 0.63 | 0.93 | 0.78 | 0.84 | 0.84 | 0.88 | 1.06 | 0.96 |
| K | 053F | 0.84 | 0.80 | 0.57 | 0.65 | 0.95 | 0.81 | 0.85 | 0.86 | 0.85 | 1.05 | 0.90 |
| K | 053G | 0.45 | 1.18 | −0.42 | 0.33 | 1.68 | 1.37 | 1.48 | 1.55 | 1.46 | 1.93 | 1.97 |
| K | 053H | 0.77 | 1.23 | 0.85 | 0.70 | 1.14 | 1.02 | 1.05 | 1.05 | 1.04 | 1.29 | 1.10 |
| K | 053I | 0.67 | 0.90 | 0.43 | 0.60 | 1.27 | 1.13 | 1.16 | 1.19 | 1.24 | 1.35 | 1.10 |
| K | 053L | 0.82 | 0.84 | 1.71 | 0.88 | 1.15 | 1.12 | 1.07 | 0.86 | 1.12 | 1.18 | 1.06 |
| K | 053M | 1.09 | 0.81 | −0.06 | 1.15 | 0.89 | 0.87 | 0.84 | 0.60 | 0.89 | 0.78 | 0.80 |
| K | 053N | 1.18 | 0.67 | 0.77 | 1.35 | 0.83 | 0.79 | 0.76 | 0.66 | 0.79 | 0.84 | 0.77 |
| K | 053P | 0.87 | 0.81 | 1.01 | 0.70 | 0.96 | 0.82 | 0.85 | 0.82 | 0.88 | 1.02 | 0.94 |
| K | 053Q | 0.02 | 10.87 | 80.40 | 0.01 | 24.80 | 2.35 | 10.93 | 10.82 | 10.86 | 28.80 | 6.62 |
| K | 053R | 0.86 | 0.99 | 0.14 | 0.76 | 1.03 | 0.94 | 0.98 | 0.97 | 0.94 | 1.15 | 1.02 |
| K | 053S | 0.67 | 0.98 | 0.00 | 0.55 | 1.20 | 1.00 | 1.07 | 1.09 | 1.08 | 1.30 | 1.18 |
| K | 053T | 0.71 | 1.09 | 0.37 | 0.61 | 1.24 | 1.10 | 1.18 | 1.17 | 1.19 | 1.36 | 1.27 |
| K | 053V | 0.68 | 0.94 | 0.86 | 0.58 | 1.25 | 1.10 | 1.16 | 1.11 | 1.19 | 1.33 | 1.22 |
| K | 053W | 0.50 | 1.14 | 0.84 | 0.35 | 1.46 | 0.98 | 1.16 | 1.00 | 1.07 | 1.59 | 1.54 |
| K | 053Y | 0.51 | 1.05 | 0.42 | 0.42 | 1.64 | 1.28 | 1.36 | 1.05 | 1.42 | 1.63 | 1.55 |
| M | 055A | 0.66 | 0.96 | 0.72 | 0.51 | 1.15 | 0.81 | 0.99 | 0.76 | 0.73 | 1.32 | 0.77 |
| M | 055C | 0.34 | 1.39 | −0.26 | 0.15 | 1.41 | 0.65 | 1.03 | 0.96 | 1.00 | 2.01 | 1.44 |
| M | 055D | 0.21 | 2.15 | −7.25 | 0.06 | 1.73 | 0.50 | 1.20 | 1.21 | 1.19 | 2.70 | 1.74 |
| M | 055E | 0.47 | 1.42 | −3.89 | 0.25 | 1.40 | 0.97 | 1.18 | 1.07 | 1.13 | 1.59 | 1.40 |
| M | 055F | 0.78 | 1.15 | 1.12 | 0.66 | 1.17 | 1.01 | 1.10 | 0.93 | 0.86 | 1.12 | 1.00 |
| M | 055G | 0.28 | 1.88 | 1.53 | 0.13 | 2.32 | 1.32 | 1.73 | 1.59 | 1.15 | 2.66 | 2.53 |
| M | 055H | 0.69 | 1.41 | −0.29 | 0.52 | 1.25 | 1.03 | 1.14 | 0.95 | 0.47 | 1.44 | 1.28 |
| M | 055I | 0.17 | 3.72 | 3.60 | 0.06 | 2.69 | 0.93 | 1.81 | 1.56 | 1.72 | 3.55 | 2.32 |
| M | 055N | 0.60 | 1.28 | 0.23 | 0.37 | 1.26 | 0.83 | 0.99 | 0.75 | 0.77 | 1.34 | 1.21 |
| M | 055P | 0.55 | 1.20 | −0.58 | 0.34 | 1.33 | 0.74 | 0.96 | 0.71 | 0.60 | 1.60 | 1.48 |
| M | 055Q | 0.80 | 1.02 | −0.90 | 0.59 | 1.09 | 0.97 | 1.01 | 0.74 | 0.93 | 1.17 | 1.02 |
| M | 055R | 0.01 | 20.30 | 89.62 | 0.00 | 17.26 | 2.03 | 15.33 | 20.14 | 20.43 | 35.95 | 7.28 |
| M | 055S | 0.56 | 1.40 | −0.94 | 0.36 | 1.46 | 0.95 | 1.13 | 0.83 | 0.85 | 1.47 | 1.49 |
| M | 055T | 0.63 | 1.14 | −1.65 | 0.45 | 1.36 | 0.95 | 1.17 | 0.85 | 0.98 | 1.36 | 1.28 |
| M | 055Y | 0.83 | 1.20 | 0.96 | 0.89 | 1.26 | 1.07 | 1.13 | 0.79 | 0.83 | 1.12 | 1.17 |
| N | 057A | 0.67 | 0.91 | 0.52 | 0.57 | 1.17 | 0.83 | 0.89 | 0.59 | 0.77 | 1.18 | 0.84 |
| N | 057C | 0.44 | 0.87 | −0.29 | 0.21 | 1.14 | 0.69 | 0.78 | 0.67 | 0.77 | 1.62 | 1.11 |
| N | 057D | 0.43 | 0.92 | 1.24 | 0.27 | 1.44 | 0.88 | 1.08 | 0.88 | 1.08 | 1.76 | 1.31 |
| N | 057E | 0.66 | 1.00 | 1.30 | 0.52 | 1.21 | 1.00 | 1.07 | 0.94 | 1.01 | 1.32 | 1.39 |
| N | 057F | 0.51 | 1.18 | 1.37 | 0.33 | 1.30 | 0.70 | 0.86 | 0.75 | 0.69 | 1.68 | 1.53 |
| N | 057H | 0.58 | 1.22 | 1.17 | 0.47 | 1.33 | 0.86 | 0.96 | 0.84 | 0.63 | 1.44 | 1.30 |
| N | 057I | 0.23 | 1.28 | 3.81 | 0.10 | 2.09 | 0.48 | 1.08 | 0.98 | 0.91 | 3.10 | 2.17 |
| N | 057K | 0.54 | 0.88 | 1.60 | 0.39 | 1.26 | 0.64 | 0.86 | 0.67 | 0.47 | 1.64 | 1.49 |
| N | 057L | 0.38 | 1.11 | 0.26 | 0.27 | 1.85 | 0.87 | 1.18 | 0.84 | 0.99 | 2.31 | 2.27 |
| N | 057M | 0.90 | 0.76 | 0.72 | 0.95 | 0.99 | 0.76 | 0.78 | 0.39 | 0.69 | 1.01 | 0.89 |
| N | 057Q | 0.63 | 1.27 | 1.16 | 0.50 | 1.34 | 0.96 | 1.04 | 0.79 | 1.00 | 1.44 | 1.44 |
| N | 057R | 0.58 | 1.21 | 0.73 | 0.46 | 1.36 | 0.77 | 0.85 | 0.60 | 0.55 | 1.51 | 1.38 |
| N | 057S | 0.78 | 0.99 | 0.59 | 0.63 | 1.13 | 0.78 | 0.85 | 0.65 | 0.73 | 1.16 | 1.01 |
| N | 057T | 0.36 | 0.84 | 0.47 | 0.19 | 1.64 | 0.55 | 0.88 | 0.68 | 0.71 | 2.09 | 1.57 |
| N | 057V | 0.30 | 1.52 | 0.72 | 0.17 | 2.06 | 0.70 | 1.15 | 0.88 | 0.87 | 2.60 | 2.29 |
| N | 057W | 0.23 | 0.40 | 1.75 | 0.12 | 2.06 | 0.84 | 1.34 | 1.10 | 0.97 | 2.79 | 2.00 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| N | 057Y | 0.56 | 1.27 | 0.16 | 0.51 | 1.48 | 0.89 | 0.97 | 0.68 | 0.74 | 1.63 | 1.52 |
| W | 058A | 0.19 | 0.56 | 9.92 | 0.06 | 1.13 | -0.05 | 0.68 | 0.82 | 0.95 | 2.32 | 0.12 |
| W | 058C | -0.04 | -1.83 | -104.65 | -0.01 | -4.00 | 0.30 | -3.05 | -3.70 | -4.57 | -9.42 | 1.33 |
| W | 058D | 0.05 | 11.47 | 78.25 | 0.02 | 1.94 | 0.19 | 2.25 | 2.78 | 3.24 | 5.95 | -1.55 |
| W | 058E | -0.02 | -47.04 | -459.14 | 0.00 | -6.82 | -0.09 | -7.62 | -9.46 | -10.80 | -21.47 | 5.38 |
| W | 058F | 0.63 | 1.74 | 7.72 | 0.57 | 1.21 | 0.10 | 0.36 | 0.38 | 0.31 | 1.30 | 0.65 |
| W | 058G | 0.00 | -16.83 | 610.26 | 0.00 | -36.44 | 0.76 | -31.72 | -38.71 | -44.90 | -97.45 | 2.02 |
| W | 058H | 0.56 | 0.16 | -2.00 | 0.23 | 0.75 | 0.00 | 0.24 | 0.28 | 0.32 | 1.34 | 0.06 |
| W | 058I | -0.17 | -2.21 | 0.00 | -0.04 | -0.72 | -0.08 | -0.73 | -0.91 | -0.94 | -1.79 | 0.12 |
| W | 058K | -0.08 | -0.61 | 6.54 | -0.02 | -1.48 | -1.85 | -3.86 | -3.51 | 0.00 | -4.12 | 0.57 |
| W | 058L | -0.05 | 19.33 | 33.81 | -0.01 | -2.33 | -2.80 | -5.50 | -5.20 | 0.00 | -5.39 | 0.71 |
| W | 058M | 0.01 | 80.95 | 170.95 | 0.00 | 8.21 | -0.77 | 9.27 | 11.38 | 13.34 | 22.75 | -2.88 |
| W | 058N | 0.03 | 7.00 | 37.00 | 0.01 | 4.95 | -0.20 | 3.60 | 4.36 | 5.11 | 12.02 | -2.24 |
| W | 058P | -0.06 | -6.40 | -73.85 | -0.01 | -1.84 | 0.15 | -2.16 | -2.65 | -2.98 | -5.10 | -0.03 |
| W | 058Q | 0.03 | 25.16 | 75.75 | 0.01 | 3.93 | -0.39 | 4.11 | 5.20 | 5.73 | 13.47 | 0.74 |
| W | 058R | -0.10 | -5.20 | -1.63 | -0.03 | -0.99 | 0.01 | -1.17 | -1.41 | -1.69 | -2.89 | 0.71 |
| W | 058S | -0.03 | 5.44 | -162.29 | -0.01 | -10.48 | 0.14 | -5.13 | -6.26 | -6.67 | -13.66 | 3.66 |
| W | 058T | -0.04 | -0.62 | -75.60 | -0.01 | -2.92 | 0.24 | -2.77 | -3.45 | -3.85 | -8.00 | 1.25 |
| W | 058V | -0.07 | 0.65 | -20.19 | -0.01 | -1.58 | -0.12 | -1.95 | -2.37 | -2.97 | -4.48 | 0.23 |
| W | 060A | 0.38 | 1.28 | -7.91 | 0.24 | 1.45 | 0.22 | 0.46 | 0.42 | 0.43 | 1.89 | 0.37 |
| W | 060C | 0.45 | 1.36 | -5.04 | 0.24 | 1.22 | 0.26 | 0.44 | 0.42 | 0.42 | 1.67 | 1.19 |
| W | 060D | 0.48 | 1.61 | -1.05 | 0.36 | 1.46 | 0.30 | 0.45 | 0.39 | 0.42 | 1.57 | 1.29 |
| W | 060E | 0.36 | 2.10 | -0.23 | 0.23 | 1.74 | 0.34 | 0.55 | 0.48 | 0.51 | 2.18 | 1.72 |
| W | 060G | 0.24 | 2.09 | 5.95 | 0.10 | 2.28 | 0.30 | 0.70 | 0.70 | 0.62 | 2.84 | 2.44 |
| W | 060I | 0.35 | 2.22 | 4.38 | 0.22 | 1.92 | 0.37 | 0.58 | 0.50 | 0.52 | 2.27 | 2.26 |
| W | 060K | 0.23 | 2.82 | 4.65 | 0.14 | 2.81 | 0.41 | 0.78 | 0.71 | 0.71 | 3.39 | 2.86 |
| W | 060L | 0.57 | 1.78 | 0.01 | 0.62 | 1.76 | 0.73 | 0.66 | 0.46 | 0.46 | 1.72 | 1.75 |
| W | 060M | 1.07 | 0.95 | -0.50 | 1.37 | 0.90 | 0.51 | 0.44 | 0.24 | 0.29 | 0.89 | 0.80 |
| W | 060N | 0.77 | 1.45 | -0.88 | 0.94 | 1.25 | 0.51 | 0.48 | 0.29 | 0.32 | 1.19 | 1.27 |
| W | 060P | 0.05 | 16.51 | -7.27 | 0.01 | 3.47 | -0.02 | 2.63 | 3.21 | 3.30 | 8.87 | 5.30 |
| W | 060Q | 0.49 | 1.71 | 5.03 | 0.37 | 1.56 | 0.45 | 0.55 | 0.38 | 0.40 | 1.70 | 1.61 |
| W | 060R | 0.36 | 2.54 | -3.27 | 0.28 | 2.10 | 0.43 | 0.59 | 0.47 | 0.46 | 2.16 | 1.86 |
| W | 060T | 0.46 | 2.12 | 3.75 | 0.43 | 1.86 | 0.56 | 0.60 | 0.43 | 0.43 | 1.80 | 1.60 |
| L | 060V | 0.49 | 1.31 | -3.85 | 0.28 | 1.38 | 0.28 | 0.44 | 0.35 | 0.38 | 1.59 | 1.17 |
| L | 061C | 0.13 | 5.66 | -14.67 | 0.04 | 2.56 | 0.56 | 1.69 | 1.74 | 1.73 | 3.94 | 1.97 |
| L | 061D | 0.09 | 8.00 | 7.74 | 0.02 | 1.29 | 0.00 | 1.32 | 1.81 | 1.74 | 3.66 | 2.15 |
| L | 061E | 0.09 | 9.86 | 2.00 | 0.03 | 3.39 | 0.60 | 2.09 | 2.40 | 2.44 | 4.84 | 2.48 |
| L | 061F | 0.45 | 1.12 | 1.71 | 0.30 | 1.65 | 0.69 | 1.02 | 0.91 | 0.99 | 1.46 | 1.08 |
| L | 061K | -0.08 | 3.96 | -10.40 | -0.02 | -1.31 | -0.12 | -1.38 | -1.87 | -1.88 | -3.78 | -0.91 |
| L | 061M | 1.01 | 1.05 | -0.11 | 1.18 | 0.98 | 0.94 | 1.01 | 0.86 | 1.03 | 0.99 | 0.97 |
| L | 061N | 0.02 | 54.82 | 105.65 | 0.00 | 9.72 | -0.22 | 8.39 | 10.51 | 10.05 | 20.72 | 13.64 |
| L | 061P | -0.02 | -34.22 | -52.15 | -0.01 | -4.73 | 0.21 | -4.63 | -6.18 | -5.89 | -11.38 | -4.80 |
| L | 061R | -0.02 | -11.44 | -34.74 | 0.00 | -4.49 | 0.36 | -4.82 | -6.84 | -6.91 | -12.31 | -6.37 |
| L | 061S | 0.10 | 4.25 | 5.58 | 0.04 | 4.42 | 1.35 | 2.67 | 3.04 | 2.70 | 5.23 | 4.06 |
| L | 061T | 0.09 | 5.04 | 14.51 | 0.03 | 4.10 | 1.23 | 2.56 | 2.90 | 2.37 | 5.86 | 4.22 |
| L | 061V | 0.26 | 1.76 | 12.50 | 0.11 | 1.94 | 1.07 | 1.31 | 1.31 | 1.11 | 2.56 | 2.16 |
| L | 061W | 0.00 | -1826.68 | -32355.20 | 0.00 | -2369.74 | -154.86 | -2775.10 | -3809.88 | -3890.71 | -8744.19 | -2036.95 |
| L | 061Y | -0.01 | -5.04 | -147.46 | 0.00 | -12.57 | -2.21 | -14.14 | -18.77 | -18.82 | -35.15 | -6.25 |
| Y | 062A | 0.15 | 0.97 | 16.96 | 0.03 | 0.79 | -0.12 | 1.00 | 1.18 | 1.36 | 2.18 | -0.04 |
| Y | 062C | 0.21 | -1.65 | 50.09 | 0.05 | 0.48 | 0.02 | 0.64 | 0.78 | 0.89 | 1.36 | 0.41 |
| Y | 062D | 0.30 | 0.54 | 7.93 | 0.07 | 0.39 | -0.04 | 0.45 | 0.55 | 0.59 | 1.04 | 0.14 |
| Y | 062E | 0.59 | -0.21 | 29.03 | 0.14 | 0.17 | 0.01 | 0.22 | 0.27 | 0.29 | 0.45 | -0.03 |
| Y | 062F | 0.21 | 1.40 | 47.37 | 0.05 | 1.27 | -0.01 | 1.03 | 1.01 | 0.90 | 2.39 | 1.40 |
| Y | 062G | 0.10 | -2.43 | -78.42 | 0.02 | 1.12 | -0.29 | 1.44 | 1.72 | 1.82 | 3.56 | 1.09 |
| Y | 062H | 0.29 | -1.04 | -50.97 | 0.06 | 0.35 | -0.02 | 0.48 | 0.55 | 0.65 | 1.18 | 0.52 |
| Y | 062I | 0.07 | -0.30 | 33.28 | 0.01 | 1.43 | 0.19 | 1.83 | 2.21 | 2.36 | 3.57 | 1.35 |
| Y | 062K | 0.25 | -0.66 | -39.20 | 0.05 | 0.40 | 0.10 | 0.52 | 0.62 | 0.70 | 1.17 | 0.21 |
| Y | 062L | 0.13 | -0.69 | -10.05 | 0.03 | 0.76 | -0.05 | 1.03 | 1.18 | 1.29 | 2.55 | 0.22 |
| Y | 062M | 0.44 | 0.37 | -12.31 | 0.11 | 0.31 | -0.03 | 0.32 | 0.38 | 0.43 | 0.74 | 0.11 |
| Y | 062N | 0.47 | 0.58 | 32.16 | 0.10 | 0.24 | -0.04 | 0.30 | 0.34 | 0.41 | 0.77 | 0.06 |
| Y | 062P | -0.02 | 13.50 | -228.05 | -0.01 | -4.04 | -0.30 | -5.30 | -6.26 | -7.10 | -12.12 | -0.74 |
| Y | 062Q | 0.27 | -1.82 | 105.84 | 0.07 | 0.38 | -0.01 | 0.51 | 0.58 | 0.66 | 1.16 | 0.06 |
| Y | 062R | 0.42 | -0.73 | 18.63 | 0.09 | 0.24 | -0.17 | 0.32 | 0.38 | 0.43 | 0.68 | -0.10 |
| Y | 062S | 0.20 | -1.18 | 75.75 | 0.04 | 0.51 | 0.03 | 0.66 | 0.80 | 0.87 | 1.48 | 0.26 |
| Y | 062T | 0.13 | -0.63 | 139.77 | 0.03 | 0.78 | -0.36 | 1.02 | 1.21 | 1.34 | 2.27 | 0.08 |
| Y | 062V | 0.10 | -1.22 | -56.59 | 0.02 | 0.95 | 0.34 | 1.41 | 1.66 | 2.33 | 2.66 | 1.33 |
| Q | 063A | 0.50 | 1.82 | 11.53 | 0.37 | 1.28 | 0.16 | 0.40 | 0.33 | 0.41 | 1.66 | 1.18 |
| Q | 063C | 0.15 | 3.37 | 2.03 | 0.04 | 0.97 | -0.07 | 0.81 | 1.00 | 1.14 | 2.53 | 0.68 |
| Q | 063D | 0.13 | -0.24 | -4.31 | 0.04 | 1.25 | -0.11 | 0.89 | 1.09 | 1.28 | 2.94 | -0.20 |
| Q | 063E | 1.05 | 0.35 | -4.60 | 0.73 | 0.52 | 0.02 | 0.14 | 0.17 | 0.18 | 0.65 | -0.03 |
| Q | 063F | 0.06 | 4.54 | 61.70 | 0.01 | 1.66 | 0.07 | 1.97 | 2.39 | 2.80 | 5.18 | -1.66 |
| Q | 063G | 0.40 | 2.26 | -5.17 | 0.30 | 1.81 | 0.29 | 0.52 | 0.57 | 0.46 | 2.02 | 1.46 |
| Q | 063H | 0.89 | 1.02 | 2.61 | 0.59 | 0.69 | 0.03 | 0.18 | 0.21 | 0.20 | 1.06 | 0.54 |
| Q | 063I | -0.18 | 0.35 | -3.01 | -0.04 | -0.57 | -0.03 | -0.67 | -0.82 | -0.93 | -1.27 | 0.16 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| Q | 063K | 0.10 | -0.37 | 39.63 | 0.03 | 2.47 | -0.05 | 1.28 | 1.53 | 1.78 | 5.55 | 0.07 |
| Q | 063M | 0.24 | 1.50 | 24.70 | 0.09 | 1.36 | -0.03 | 0.58 | 0.65 | 0.79 | 2.61 | 0.68 |
| Q | 063N | 0.57 | 1.17 | -1.13 | 0.33 | 0.86 | 0.02 | 0.25 | 0.28 | 0.30 | 1.28 | 0.55 |
| Q | 063P | -0.06 | 2.16 | 42.24 | -0.01 | -1.65 | 0.10 | -1.90 | -2.38 | -2.58 | -4.78 | 1.28 |
| Q | 063R | 0.30 | -0.37 | -13.96 | 0.08 | 0.92 | 0.00 | 0.41 | 0.50 | 0.55 | 2.03 | 0.39 |
| Q | 063S | 0.33 | 2.96 | -9.16 | 0.24 | 2.23 | 0.21 | 0.62 | 0.58 | 0.53 | 2.63 | 1.05 |
| Q | 063T | 0.00 | -62.58 | -1751.62 | 0.00 | 92.24 | -0.74 | 59.16 | 71.67 | 80.40 | 240.48 | 49.54 |
| Q | 063V | -0.06 | 4.01 | -36.60 | -0.01 | -1.66 | -0.14 | -1.90 | -2.37 | -2.65 | -4.27 | 1.46 |
| Q | 063W | -0.03 | 23.88 | 91.81 | -0.01 | -3.67 | -0.38 | -4.44 | -5.49 | -6.20 | -12.78 | 3.97 |
| Q | 063Y | -0.04 | 9.30 | 12.61 | -0.01 | -2.57 | -0.26 | -3.18 | -3.86 | -4.62 | -6.40 | 0.59 |
| P | 064A | 0.76 | 0.72 | -3.91 | 0.42 | 0.77 | 0.30 | 0.60 | 0.43 | 0.72 | 1.09 | 0.65 |
| P | 064C | 0.05 | 11.62 | -53.74 | 0.01 | 4.56 | 0.16 | 3.54 | 3.73 | 4.74 | 10.43 | 3.90 |
| P | 064D | -0.15 | -0.99 | 39.77 | -0.03 | -0.70 | -0.02 | -0.82 | -1.01 | -1.16 | -1.86 | 0.76 |
| P | 064E | -0.06 | -4.96 | 74.27 | -0.01 | -2.13 | -0.08 | -2.26 | -2.74 | -3.13 | -5.58 | 0.23 |
| P | 064F | -0.06 | -7.24 | 27.99 | -0.01 | -2.26 | -0.14 | -2.03 | -2.40 | -2.69 | -5.54 | -0.41 |
| P | 064G | 0.28 | 0.96 | -11.98 | 0.10 | 1.74 | 0.51 | 1.17 | 1.19 | 1.17 | 2.63 | 2.35 |
| P | 064H | 0.07 | -3.77 | -101.97 | 0.02 | 1.86 | 0.06 | 1.73 | 2.09 | 2.43 | 5.45 | 0.88 |
| P | 064I | 0.22 | 0.55 | -12.03 | 0.06 | 1.35 | 0.09 | 0.81 | 0.78 | 0.75 | 2.68 | 1.68 |
| P | 064K | -0.12 | 2.99 | 59.81 | -0.03 | -0.90 | -0.07 | -1.02 | -1.25 | -1.45 | -2.73 | -0.15 |
| P | 064L | 0.13 | 0.33 | -38.85 | 0.04 | 2.63 | 0.23 | 1.51 | 1.43 | 1.83 | 4.86 | 2.94 |
| P | 064M | 0.12 | 6.77 | 5.76 | 0.03 | 1.78 | -0.01 | 1.26 | 1.29 | 1.68 | 3.85 | 0.85 |
| P | 064N | 0.21 | 3.89 | -13.92 | 0.05 | 0.87 | 0.04 | 0.70 | 0.74 | 0.91 | 2.05 | 0.80 |
| P | 064Q | 0.04 | 11.34 | 19.76 | 0.01 | 3.43 | 0.27 | 3.24 | 3.74 | 4.58 | 9.24 | -0.34 |
| P | 064R | -0.13 | 1.53 | -17.10 | -0.03 | -0.74 | -0.01 | -0.91 | -1.11 | -1.27 | -2.31 | -0.19 |
| P | 064S | 0.68 | 0.68 | 4.39 | 0.23 | 0.77 | 0.20 | 0.49 | 0.43 | 0.56 | 1.18 | 1.00 |
| P | 064V | 0.33 | 0.73 | -12.79 | 0.10 | 1.29 | 0.18 | 0.69 | 0.58 | 0.71 | 2.02 | 1.35 |
| P | 064W | -0.06 | 3.01 | 88.95 | -0.01 | -1.66 | -0.17 | -2.01 | -2.41 | -2.96 | -4.96 | 1.66 |
| P | 064Y | 0.06 | -1.17 | 4.01 | 0.01 | 1.87 | 0.11 | 2.16 | 2.57 | 3.06 | 4.68 | 0.29 |
| T | 065A | 0.56 | 1.17 | -0.66 | 0.38 | 1.38 | 0.99 | 1.04 | 0.70 | 1.00 | 1.52 | 1.18 |
| T | 065C | 0.06 | 5.66 | -23.23 | 0.02 | 4.64 | 1.23 | 3.03 | 2.91 | 2.97 | 7.59 | 3.47 |
| T | 065D | -0.06 | -12.48 | 7.29 | -0.01 | -3.27 | -0.57 | -2.31 | -2.30 | -2.36 | -6.13 | 5.95 |
| T | 065E | 0.26 | 2.03 | -4.18 | 0.10 | 1.98 | 0.95 | 1.29 | 1.20 | 1.24 | 2.59 | 1.87 |
| T | 065F | 0.02 | 6.67 | -27.06 | 0.01 | 11.39 | 3.00 | 6.63 | 6.38 | 6.85 | 17.98 | 9.08 |
| T | 065G | 0.00 | 213.52 | 381.26 | 0.00 | 240.33 | 67.25 | 147.84 | 153.26 | 145.01 | 408.39 | 192.30 |
| T | 065H | 0.24 | 1.89 | -3.66 | 0.09 | 2.26 | 1.39 | 1.49 | 1.61 | 1.54 | 2.92 | 2.20 |
| T | 065I | 0.72 | 1.02 | -0.58 | 0.56 | 1.25 | 1.19 | 1.20 | 1.21 | 1.12 | 1.47 | 1.27 |
| T | 065K | 0.40 | 1.40 | 5.04 | 0.23 | 1.71 | 1.19 | 1.33 | 1.14 | 1.14 | 2.19 | 1.68 |
| T | 065L | 0.37 | 1.28 | 0.56 | 0.19 | 1.82 | 1.22 | 1.45 | 1.05 | 1.24 | 2.30 | 1.90 |
| T | 065M | 0.37 | 1.50 | 0.31 | 0.21 | 1.80 | 1.18 | 1.25 | 0.87 | 1.25 | 2.02 | 1.65 |
| T | 065N | -0.31 | -3.96 | 0.41 | -0.11 | -1.53 | -0.64 | -0.98 | -0.84 | -1.07 | -2.34 | -1.43 |
| T | 065P | -0.16 | -2.99 | -0.85 | -0.03 | -0.63 | -0.08 | -0.65 | -0.77 | -0.73 | -2.04 | -2.38 |
| T | 065Q | 0.26 | 1.94 | 2.16 | 0.12 | 2.33 | 1.40 | 1.64 | 1.56 | 1.66 | 3.01 | 3.03 |
| T | 065R | 0.54 | 1.44 | -3.30 | 0.32 | 1.43 | 1.07 | 1.19 | 1.05 | 1.05 | 1.61 | 1.48 |
| T | 065S | 0.47 | 1.49 | -2.75 | 0.17 | 1.61 | 1.20 | 1.31 | 1.28 | 1.32 | 2.02 | 1.53 |
| T | 065W | -0.17 | -0.21 | 5.50 | -0.03 | -0.71 | -0.12 | -0.65 | -0.73 | -0.67 | -1.51 | -0.58 |
| T | 065Y | 0.02 | 12.14 | -36.10 | 0.01 | 15.90 | 5.01 | 8.94 | 7.07 | 8.99 | 27.23 | 13.56 |
| S | 066D | 0.84 | 0.94 | 2.11 | 0.69 | 0.96 | 0.83 | 0.87 | 0.66 | 0.90 | 1.04 | 1.77 |
| S | 066E | 0.69 | 1.17 | 0.70 | 0.45 | 1.14 | 0.94 | 1.02 | 0.95 | 1.08 | 1.28 | 1.66 |
| S | 066F | 0.13 | 4.05 | 2.66 | 0.06 | 3.73 | 1.96 | 2.54 | 2.62 | 2.85 | 5.08 | 3.56 |
| S | 066G | 0.82 | 1.32 | 0.69 | 0.70 | 1.18 | 0.96 | 0.99 | 0.64 | 0.94 | 1.11 | 1.18 |
| S | 066H | 0.45 | 1.56 | 0.31 | 0.27 | 1.61 | 1.23 | 1.22 | 1.07 | 1.35 | 1.81 | 1.64 |
| S | 066I | 0.19 | 3.02 | -12.79 | 0.10 | 3.34 | 2.56 | 2.29 | 2.52 | 2.68 | 3.63 | 3.04 |
| S | 066K | 0.46 | 1.69 | -2.48 | 0.34 | 1.82 | 1.54 | 1.55 | 1.54 | 1.75 | 2.11 | 1.49 |
| S | 066L | 0.33 | 1.91 | 2.88 | 0.20 | 2.27 | 1.68 | 1.60 | 1.39 | 1.91 | 2.49 | 2.00 |
| S | 066M | 0.69 | 1.19 | 1.18 | 0.64 | 1.36 | 0.94 | 1.01 | 0.73 | 1.12 | 1.29 | 1.03 |
| S | 066N | 0.93 | 0.86 | -0.02 | 0.91 | 1.02 | 0.88 | 0.83 | 0.55 | 0.89 | 0.94 | 0.87 |
| S | 066P | -0.01 | 19.48 | -271.79 | 0.00 | -19.42 | -2.73 | -23.74 | -30.07 | -36.18 | -48.94 | -11.19 |
| S | 066Q | 0.78 | 1.00 | 1.01 | 0.60 | 1.11 | 0.90 | 0.93 | 0.78 | 1.04 | 1.09 | 1.04 |
| S | 066R | 0.86 | 1.19 | 1.77 | 0.88 | 1.12 | 1.09 | 1.02 | 0.95 | 1.09 | 1.12 | 0.86 |
| S | 066T | 0.49 | 1.37 | 0.61 | 0.29 | 1.58 | 1.03 | 1.10 | 0.88 | 1.16 | 1.75 | 1.33 |
| S | 066V | 0.38 | 1.71 | 1.63 | 0.21 | 2.03 | 1.59 | 1.43 | 1.23 | 1.58 | 2.16 | 1.98 |
| S | 066W | 0.14 | 3.98 | -11.69 | 0.06 | 4.10 | 2.09 | 2.55 | 2.06 | 2.92 | 4.82 | 2.95 |
| S | 066Y | 0.33 | 1.51 | -4.56 | 0.15 | 1.97 | 1.12 | 1.21 | 0.98 | 1.43 | 2.26 | 1.80 |
| Y | 067A | 0.84 | 1.06 | -0.84 | 0.88 | 1.11 | 0.93 | 0.94 | 0.74 | 1.11 | 1.07 | 1.02 |
| Y | 067C | 0.29 | 1.86 | 2.02 | 0.13 | 1.63 | 0.65 | 1.08 | 1.06 | 1.25 | 2.18 | 1.38 |
| Y | 067D | 0.12 | 4.37 | -2.89 | 0.04 | 2.61 | 0.51 | 1.68 | 1.67 | 2.01 | 3.79 | 3.07 |
| Y | 067E | 0.19 | 2.58 | -0.22 | 0.07 | 2.17 | 0.82 | 1.37 | 1.43 | 1.71 | 2.95 | 2.06 |
| Y | 067F | 0.54 | 1.37 | 5.57 | 0.34 | 1.35 | 0.72 | 1.08 | 0.87 | 0.85 | 1.46 | 1.19 |
| Y | 067G | 0.58 | 1.31 | 1.60 | 0.41 | 1.42 | 1.05 | 1.20 | 1.08 | 1.33 | 1.46 | 1.35 |
| Y | 067I | 0.52 | 1.27 | 4.50 | 0.34 | 1.45 | 1.05 | 1.10 | 0.94 | 1.27 | 1.61 | 1.38 |
| Y | 067K | 0.40 | 1.27 | 5.58 | 0.22 | 1.71 | 1.11 | 1.33 | 1.18 | 1.58 | 2.06 | 1.73 |
| Y | 067L | 1.00 | 0.84 | 0.93 | 1.11 | 1.03 | 1.00 | 0.95 | 0.56 | 1.10 | 1.01 | 0.99 |
| Y | 067N | 0.56 | 1.37 | 2.18 | 0.46 | 1.45 | 1.16 | 1.25 | 1.03 | 1.35 | 1.46 | 1.44 |
| Y | 067P | 0.19 | 2.49 | 2.81 | 0.06 | 1.87 | 0.49 | 1.10 | 1.10 | 1.32 | 6.51 | 1.56 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| Y | 067Q | 0.73 | 1.15 | −0.22 | 0.60 | 1.14 | 0.93 | 0.97 | 0.96 | 1.20 | 1.25 | 1.36 |
| Y | 067S | 0.47 | 1.83 | 4.50 | 0.31 | 1.70 | 1.27 | 1.29 | 1.30 | 1.56 | 1.71 | 1.67 |
| Y | 067T | 0.52 | 1.53 | 1.64 | 0.42 | 1.67 | 1.45 | 1.48 | 1.39 | 1.71 | 1.77 | 1.51 |
| Y | 067W | 0.60 | 1.31 | 2.82 | 0.55 | 1.56 | 1.32 | 1.14 | 0.87 | 1.05 | 1.42 | 1.23 |
| I | 069A | 0.11 | 6.41 | 50.59 | 0.03 | 2.10 | 0.23 | 1.43 | 1.59 | 1.70 | 2.97 | 2.07 |
| I | 069C | 0.07 | 12.51 | 19.43 | 0.02 | 3.00 | 0.30 | 2.09 | 2.49 | 2.44 | 5.56 | 2.31 |
| I | 069D | 0.00 | −2116.48 | −8329.61 | 0.00 | −388.39 | −107.34 | −455.62 | −651.63 | −550.11 | −1109.99 | −384.96 |
| I | 069E | 0.00 | −330.94 | −662.83 | 0.00 | −43.49 | −6.24 | −43.67 | −60.19 | −50.69 | −93.78 | −72.09 |
| I | 069G | −0.01 | −23.18 | −77.55 | 0.00 | −10.42 | −1.26 | −10.26 | −13.92 | −12.27 | −32.06 | 0.03 |
| I | 069H | −0.01 | −27.81 | −371.66 | 0.00 | −9.33 | −1.94 | −8.77 | −11.89 | −9.92 | −28.07 | −9.66 |
| I | 069K | 0.04 | 3.20 | −61.34 | 0.01 | 3.20 | 0.62 | 3.13 | 4.33 | 3.70 | 8.97 | 0.49 |
| I | 069M | 0.66 | 1.08 | 0.00 | 0.47 | 1.12 | 0.80 | 0.85 | 0.67 | 0.88 | 1.22 | 1.13 |
| I | 069N | −0.01 | −87.67 | −273.44 | 0.00 | −13.40 | −0.91 | −13.13 | −17.88 | −16.30 | −37.54 | −11.76 |
| I | 069P | 0.16 | 3.13 | 31.86 | 0.06 | 2.33 | 0.75 | 1.52 | 1.65 | 1.59 | 3.34 | 2.32 |
| I | 069Q | −0.07 | −10.98 | −76.29 | −0.02 | −1.71 | −0.15 | −1.67 | −2.28 | −1.96 | −4.18 | −2.53 |
| I | 069R | −0.08 | −7.24 | −36.74 | −0.02 | −1.30 | −0.17 | −1.33 | −1.83 | −1.66 | −4.04 | −1.07 |
| I | 069S | −0.11 | −6.01 | −1.19 | −0.03 | −1.22 | −0.14 | −1.04 | −1.39 | −1.30 | −2.67 | −0.10 |
| I | 069T | 0.16 | 3.24 | 8.54 | 0.05 | 2.81 | 1.17 | 1.89 | 1.94 | 1.84 | 4.04 | 2.85 |
| I | 069V | 0.84 | 0.95 | 2.88 | 0.76 | 1.08 | 1.03 | 0.99 | 0.93 | 0.98 | 1.05 | 1.08 |
| I | 069W | −0.08 | −2.41 | −34.24 | −0.02 | −1.20 | −0.15 | −1.31 | −1.82 | −1.53 | −3.95 | −0.13 |
| I | 069Y | −0.06 | −1.62 | −7.99 | −0.01 | −3.09 | −0.50 | −2.43 | −3.00 | −2.85 | −5.92 | −4.79 |
| G | 070A | 0.18 | 3.68 | 13.19 | 0.06 | 1.76 | 0.37 | 1.15 | 1.18 | 1.26 | 2.85 | 1.69 |
| G | 070C | −0.04 | −19.25 | −80.47 | −0.01 | −4.03 | −0.26 | −3.47 | −4.53 | −4.26 | −8.69 | −5.56 |
| G | 070E | 0.13 | 4.37 | 24.32 | 0.04 | 1.85 | 0.37 | 1.29 | 1.63 | 1.41 | 3.73 | 2.60 |
| G | 070H | 0.06 | 6.41 | 20.10 | 0.01 | 4.45 | 1.06 | 3.00 | 3.61 | 3.24 | 7.41 | 5.81 |
| G | 070I | −0.01 | −9.31 | −195.34 | 0.00 | −8.00 | −1.02 | −7.89 | −11.02 | −8.97 | −19.31 | −11.92 |
| G | 070L | −0.09 | 0.66 | −27.70 | −0.02 | −1.16 | −0.27 | −1.23 | −1.65 | −1.53 | −3.63 | −1.38 |
| G | 070M | 0.01 | 77.51 | 446.17 | 0.00 | 16.20 | 1.41 | 13.45 | 17.09 | 16.19 | 36.32 | 21.45 |
| G | 070N | 0.12 | 3.03 | 25.71 | 0.04 | 2.42 | 0.69 | 1.63 | 1.85 | 1.79 | 4.25 | 2.19 |
| G | 070P | −0.23 | −2.31 | −3.84 | −0.04 | −0.42 | −0.03 | −0.47 | −0.67 | −0.58 | −1.48 | −0.29 |
| G | 070Q | 0.03 | 17.79 | 104.05 | 0.01 | 10.01 | 1.87 | 7.27 | 8.99 | 7.82 | 20.13 | 12.50 |
| G | 070R | 0.00 | −1730.77 | −8364.09 | 0.00 | −990.83 | −225.35 | −699.47 | −890.58 | −790.70 | −2141.50 | −924.39 |
| G | 070S | 0.10 | 6.18 | 36.60 | 0.03 | 4.14 | 1.56 | 2.85 | 3.38 | 2.96 | 5.99 | 4.32 |
| G | 070T | −0.05 | −8.16 | 3.27 | −0.01 | −3.47 | −0.61 | −2.60 | −3.35 | −2.98 | −5.62 | −3.36 |
| G | 070V | −0.15 | −1.51 | −17.79 | −0.03 | −0.74 | −0.11 | −0.73 | −1.00 | −0.85 | −1.66 | −0.37 |
| G | 070W | −0.15 | −0.13 | −35.55 | −0.01 | −0.72 | −0.13 | −0.72 | −1.00 | −0.84 | −1.97 | −0.94 |
| G | 070Y | −0.06 | −2.46 | −76.51 | −0.01 | −2.87 | −0.46 | −2.29 | −2.93 | −2.67 | −5.80 | −3.22 |
| N | 071A | −0.06 | −9.57 | 3.42 | −0.02 | −1.82 | −0.24 | −1.99 | −2.72 | −2.47 | −5.59 | −0.30 |
| N | 071D | −0.12 | −5.06 | 13.84 | −0.03 | −0.81 | −0.13 | −0.91 | −1.25 | −1.10 | −2.66 | −0.80 |
| N | 071E | −0.04 | −4.98 | −150.71 | −0.01 | −2.33 | −0.23 | −2.69 | −3.72 | −3.27 | −8.19 | −1.62 |
| N | 071F | −0.12 | −3.89 | −22.38 | −0.03 | −0.75 | −0.14 | −0.87 | −1.22 | −1.09 | −2.12 | −1.19 |
| N | 071I | −0.20 | −0.97 | −26.78 | −0.04 | −0.45 | −0.09 | −0.53 | −0.74 | −0.63 | −1.49 | −0.46 |
| N | 071K | −0.09 | −1.01 | 16.37 | −0.02 | −0.92 | −0.12 | −1.12 | −1.57 | −1.35 | −2.76 | −1.21 |
| N | 071L | −0.08 | 0.91 | −47.04 | −0.02 | −1.12 | −0.25 | −1.37 | −1.90 | −1.70 | −4.08 | −0.68 |
| N | 071M | −0.09 | −4.01 | 24.01 | −0.02 | −1.06 | −0.14 | −1.26 | −1.75 | −1.58 | −3.05 | −0.84 |
| N | 071Q | −0.16 | −4.73 | −24.10 | −0.03 | −0.93 | −0.13 | −0.80 | −1.06 | −0.89 | −2.51 | −0.83 |
| N | 071R | −0.06 | −2.56 | −13.71 | −0.01 | −1.35 | −0.44 | −1.55 | −2.18 | −1.90 | −4.02 | −1.56 |
| N | 071S | 0.25 | 2.69 | 6.06 | 0.14 | 2.81 | 1.91 | 2.12 | 2.14 | 2.00 | 3.04 | 2.71 |
| N | 071T | −0.09 | −3.83 | −7.05 | −0.02 | −1.96 | −0.27 | −1.49 | −2.00 | −1.65 | −4.21 | −1.49 |
| N | 071V | −0.23 | −0.63 | 10.02 | −0.05 | −0.41 | −0.08 | −0.46 | −0.65 | −0.55 | −1.11 | −0.30 |
| N | 071W | −0.21 | −0.66 | −4.12 | −0.04 | −0.43 | −0.07 | −0.49 | −0.68 | −0.60 | −1.37 | −0.60 |
| N | 071Y | −0.12 | 0.59 | −10.54 | −0.03 | −0.84 | −0.08 | −0.89 | −1.21 | −1.05 | −2.17 | −0.22 |
| R | 072A | 1.01 | 1.00 | −0.08 | 1.31 | 0.99 | 1.03 | 0.96 | 0.60 | 0.94 | 0.91 | 0.69 |
| R | 072C | 0.12 | 5.00 | 6.81 | 0.05 | 3.57 | 1.53 | 2.47 | 2.31 | 2.47 | 4.98 | 3.56 |
| R | 072D | 0.94 | 0.92 | −0.45 | 0.92 | 0.93 | 0.89 | 0.88 | 0.72 | 0.87 | 0.88 | 1.01 |
| R | 072E | 0.76 | 1.16 | −0.73 | 0.68 | 1.14 | 1.06 | 1.10 | 0.92 | 1.08 | 1.20 | 1.03 |
| R | 072F | 0.65 | 1.31 | −3.51 | 0.48 | 1.27 | 1.12 | 1.19 | 0.98 | 1.10 | 1.47 | 1.24 |
| R | 072G | 0.78 | 1.21 | −4.59 | 0.70 | 1.22 | 1.17 | 1.24 | 1.13 | 1.24 | 1.21 | 1.12 |
| R | 072H | 0.78 | 1.18 | −1.80 | 0.71 | 1.16 | 1.12 | 1.15 | 0.99 | 1.17 | 1.20 | 1.09 |
| R | 072I | 0.85 | 1.07 | 7.34 | 0.83 | 1.11 | 1.06 | 1.06 | 0.93 | 1.07 | 1.18 | 1.04 |
| R | 072K | 0.76 | 1.11 | −0.22 | 0.68 | 1.22 | 1.20 | 1.18 | 0.96 | 1.13 | 1.32 | 1.19 |
| R | 072L | 0.30 | 2.28 | −15.22 | 0.14 | 2.08 | 1.29 | 1.53 | 1.43 | 1.62 | 2.42 | 2.25 |
| R | 072M | 1.23 | 0.90 | 1.49 | 1.83 | 0.87 | 0.97 | 0.84 | 0.42 | 0.83 | 0.78 | 0.72 |
| R | 072N | 1.08 | 0.92 | −1.68 | 1.36 | 0.96 | 0.98 | 0.89 | 0.57 | 0.92 | 0.91 | 0.87 |
| R | 072P | 0.84 | 1.03 | −2.54 | 0.75 | 1.12 | 1.01 | 0.97 | 0.64 | 0.96 | 1.09 | 1.05 |
| R | 072Q | 0.86 | 1.12 | 2.13 | 0.78 | 1.08 | 1.02 | 1.00 | 0.70 | 0.95 | 1.02 | 1.10 |
| R | 072S | 0.86 | 1.13 | 2.71 | 0.80 | 1.16 | 1.10 | 1.08 | 0.84 | 1.08 | 1.14 | 0.90 |
| R | 072T | 0.73 | 1.17 | −2.81 | 0.56 | 1.20 | 1.13 | 1.13 | 0.87 | 1.13 | 1.30 | 1.03 |
| R | 072V | 0.82 | 1.12 | 1.63 | 0.73 | 1.24 | 1.16 | 1.11 | 0.77 | 1.07 | 1.19 | 0.74 |
| R | 072W | 0.70 | 1.09 | −6.05 | 0.64 | 1.37 | 1.26 | 1.14 | 0.78 | 1.11 | 1.27 | 1.20 |
| R | 072Y | 0.91 | 1.02 | 1.32 | 1.08 | 1.14 | 1.22 | 1.06 | 0.75 | 1.01 | 1.08 | 0.97 |
| L | 074A | 0.16 | 3.28 | 8.02 | 0.05 | 1.56 | 0.20 | 1.21 | 1.32 | 1.47 | 3.04 | 1.98 |
| L | 074D | 0.04 | 17.16 | 22.51 | 0.01 | 2.91 | 0.09 | 3.07 | 4.16 | 3.92 | 7.81 | 2.90 |
| L | 074E | 0.22 | 2.92 | 7.57 | 0.06 | 1.44 | 0.40 | 1.04 | 1.23 | 1.17 | 2.02 | 1.67 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| L | 074F | 0.47 | 1.51 | −1.20 | 0.28 | 1.60 | 1.03 | 1.39 | 1.35 | 1.42 | 1.79 | 1.52 |
| L | 074G | −0.06 | −12.70 | −32.61 | −0.01 | −2.14 | −0.25 | −2.05 | −2.78 | −2.66 | −5.38 | −3.69 |
| L | 074H | −0.12 | −0.78 | −19.94 | −0.03 | −0.98 | −0.08 | −0.97 | −1.32 | −1.23 | −2.70 | −1.12 |
| L | 074K | −0.07 | 0.70 | −21.53 | −0.01 | −1.54 | −0.20 | −1.81 | −2.53 | −2.45 | −4.51 | −2.04 |
| L | 074M | 0.86 | 0.96 | 0.08 | 0.73 | 0.94 | 0.76 | 0.84 | 0.68 | 0.83 | 1.03 | 1.06 |
| L | 074N | 0.05 | 21.39 | 8.45 | 0.01 | 3.73 | 0.22 | 3.24 | 4.10 | 3.79 | 7.92 | 4.17 |
| L | 074P | 0.00 | −135.49 | −145.85 | 0.00 | −79.78 | 10.65 | −88.57 | −123.72 | −120.16 | −226.12 | −39.69 |
| L | 074Q | −0.05 | −14.22 | −9.29 | −0.01 | −4.18 | −0.73 | −3.26 | −4.02 | −3.54 | −7.97 | −4.20 |
| L | 074R | 0.00 | 26.92 | 179.73 | 0.00 | 29.37 | 0.21 | 32.97 | 46.42 | 43.77 | 87.32 | 34.59 |
| L | 074S | 0.06 | 6.02 | 24.42 | 0.02 | 4.15 | 0.87 | 2.96 | 3.54 | 3.07 | 7.46 | 4.27 |
| L | 074T | 0.50 | 1.22 | 1.35 | 0.22 | 1.23 | 0.73 | 0.99 | 1.06 | 0.99 | 1.63 | 1.52 |
| L | 074W | −0.12 | −4.57 | −4.13 | −0.03 | −0.89 | −0.11 | −1.01 | −1.36 | −1.35 | −2.42 | −0.53 |
| L | 074Y | 0.06 | 6.25 | 19.04 | 0.02 | 7.40 | 1.66 | 4.78 | 4.41 | 5.17 | 9.70 | 5.84 |
| G | 075A | 0.09 | 3.65 | 22.46 | 0.02 | 1.12 | 0.01 | 1.34 | 1.35 | 2.15 | 2.59 | 0.39 |
| G | 075C | 0.13 | 3.20 | −32.94 | 0.03 | 0.81 | −0.07 | 0.91 | 0.99 | 1.48 | 1.95 | 0.98 |
| G | 075D | 0.11 | 3.48 | −0.38 | 0.03 | 1.08 | −0.02 | 1.20 | 1.22 | 1.76 | 2.65 | 1.03 |
| G | 075E | 0.07 | 3.02 | −6.58 | 0.01 | 1.69 | 0.17 | 1.93 | 1.97 | 2.81 | 4.04 | 1.02 |
| G | 075F | 0.04 | −2.53 | 6.03 | 0.01 | 2.48 | 0.10 | 2.92 | 3.02 | 4.28 | 6.87 | 0.75 |
| G | 075H | −0.08 | 5.56 | −29.50 | −0.02 | −1.56 | 0.03 | −1.74 | −1.74 | −2.49 | −4.30 | −1.58 |
| G | 075I | −0.07 | 5.21 | −32.04 | −0.02 | −1.42 | −0.14 | −1.61 | −1.63 | −2.44 | −3.55 | −1.35 |
| G | 075K | −0.07 | 4.69 | 71.42 | −0.01 | −1.75 | −0.15 | −1.93 | −1.96 | −2.80 | −3.94 | −0.48 |
| G | 075L | 0.02 | −6.90 | 179.80 | 0.00 | 6.04 | 0.73 | 6.66 | 6.65 | 9.99 | 15.87 | 5.74 |
| G | 075N | −0.04 | −15.39 | 71.79 | −0.01 | −3.71 | 0.17 | −4.11 | −4.15 | −6.03 | −10.03 | −3.34 |
| G | 075P | 0.06 | 3.65 | −73.26 | 0.01 | 1.70 | −0.10 | 1.98 | 2.05 | 2.91 | 4.39 | 0.95 |
| G | 075R | −0.01 | −15.46 | 595.02 | 0.00 | −25.07 | 2.95 | −27.87 | −28.72 | 40.62 | −62.59 | −32.88 |
| G | 075S | 0.02 | −5.59 | −238.78 | 0.00 | 7.16 | 0.63 | 7.40 | 7.53 | 11.05 | 17.34 | 10.11 |
| G | 075T | −0.04 | 3.07 | 111.28 | −0.01 | −2.27 | −0.23 | −2.60 | −2.63 | −3.66 | −5.49 | −1.56 |
| G | 075V | −0.06 | 1.52 | 197.13 | −0.01 | −1.90 | −0.49 | −2.21 | −2.24 | −3.24 | −5.37 | −1.21 |
| G | 075W | −0.14 | −2.64 | −39.76 | −0.03 | −0.72 | −0.22 | −0.84 | −0.84 | −1.24 | −2.05 | −0.40 |
| G | 075Y | −0.01 | 17.21 | −91.06 | 0.00 | −7.04 | −1.88 | −8.44 | −8.19 | −12.98 | −19.43 | −6.22 |
| E | 077A | 0.69 | 1.30 | −4.72 | 0.69 | 1.38 | 1.18 | 1.14 | 0.66 | 1.10 | 1.49 | 1.23 |
| E | 077C | 0.08 | 5.43 | −151.02 | 0.02 | 3.02 | 0.46 | 1.60 | 1.68 | 2.36 | 1.44 | 4.87 |
| E | 077D | 0.55 | 1.32 | −19.02 | 0.43 | 1.50 | 1.16 | 1.15 | 0.92 | 1.16 | 1.48 | 1.61 |
| E | 077G | 0.79 | 0.97 | −14.94 | 0.57 | 1.13 | 0.88 | 0.87 | 0.63 | 0.81 | 1.23 | 1.22 |
| E | 077H | 0.91 | 1.08 | −44.13 | 0.80 | 1.10 | 0.95 | 0.94 | 0.68 | 0.84 | 1.20 | 1.15 |
| E | 077I | 0.30 | 1.13 | −8.48 | 0.10 | 1.60 | 0.63 | 0.88 | 0.73 | 1.00 | 1.59 | 1.87 |
| E | 077K | 0.82 | 0.95 | −9.50 | 0.65 | 1.07 | 0.91 | 0.88 | 0.61 | 0.83 | 1.18 | 1.36 |
| E | 077L | 0.51 | 0.96 | 32.12 | 0.29 | 1.34 | 0.79 | 0.83 | 0.58 | 0.90 | 1.57 | 1.41 |
| E | 077M | 0.01 | 49.99 | 1009.47 | 0.00 | 13.43 | 0.71 | 7.81 | 9.27 | 14.95 | 4.35 | 0.16 |
| E | 077N | −0.21 | −1.91 | 20.54 | −0.05 | −0.48 | −0.04 | −0.37 | −0.50 | −0.73 | 0.19 | −0.32 |
| E | 077Q | 0.87 | 0.95 | 33.62 | 0.78 | 1.00 | 0.88 | 0.89 | 0.86 | 0.86 | 1.13 | 1.15 |
| E | 077R | 0.69 | 1.28 | 13.11 | 0.63 | 1.29 | 1.17 | 1.20 | 1.14 | 1.04 | 1.59 | 1.36 |
| E | 077S | 0.74 | 1.00 | 32.89 | 0.46 | 1.10 | 0.82 | 0.89 | 0.81 | 0.86 | 1.30 | 1.25 |
| E | 077T | 0.33 | 1.21 | 63.52 | 0.13 | 1.65 | 0.82 | 1.01 | 0.95 | 1.10 | 1.83 | 1.73 |
| E | 077V | 0.32 | 1.49 | 6.94 | 0.15 | 1.90 | 1.13 | 1.32 | 1.14 | 1.38 | 2.12 | 2.17 |
| E | 077W | 0.41 | 1.08 | 11.32 | 0.19 | 1.43 | 0.83 | 1.02 | 0.78 | 1.04 | 1.81 | 1.37 |
| E | 077Y | 0.54 | 1.08 | −21.38 | 0.31 | 1.34 | 0.84 | 0.94 | 0.59 | 0.98 | 1.42 | 1.49 |
| E | 079A | 0.85 | 1.07 | 2.47 | 0.75 | 1.09 | 0.87 | 0.85 | 0.53 | 0.80 | 1.13 | 1.11 |
| E | 079C | 0.04 | 15.47 | 12.70 | 0.01 | 5.95 | 1.07 | 3.79 | 3.69 | 3.88 | 9.71 | 6.92 |
| E | 079D | 1.01 | 0.90 | 3.68 | 1.07 | 1.01 | 0.93 | 0.89 | 0.71 | 0.84 | 0.92 | 0.92 |
| E | 079G | 0.48 | 1.37 | 7.09 | 0.27 | 1.57 | 1.04 | 1.13 | 1.01 | 1.07 | 1.77 | 1.65 |
| E | 079I | 0.02 | 15.37 | 203.72 | 0.00 | 16.07 | 4.22 | 9.95 | 9.86 | 9.67 | 25.92 | 16.49 |
| E | 079L | 0.09 | 4.45 | 19.57 | 0.03 | 4.74 | 1.63 | 2.86 | 2.52 | 2.59 | 7.32 | 4.70 |
| E | 079M | 0.58 | 1.15 | 8.28 | 0.30 | 1.10 | 0.66 | 0.76 | 0.59 | 0.68 | 1.38 | 1.17 |
| E | 079N | 0.46 | 1.20 | 10.83 | 0.23 | 1.36 | 0.80 | 0.99 | 0.91 | 0.94 | 1.73 | 1.51 |
| E | 079P | −0.03 | −30.26 | −173.40 | −0.01 | −5.19 | −0.40 | −4.13 | −4.74 | −4.59 | −12.36 | −4.12 |
| E | 079Q | 0.82 | 1.21 | 2.78 | 0.69 | 1.10 | 0.98 | 0.99 | 1.00 | 0.90 | 1.19 | 1.05 |
| E | 079S | 0.56 | 1.26 | 5.55 | 0.37 | 1.37 | 1.03 | 1.10 | 1.10 | 1.01 | 1.53 | 1.57 |
| E | 079T | 0.26 | 2.36 | −2.04 | 0.12 | 2.33 | 1.36 | 1.68 | 1.69 | 1.54 | 3.27 | 2.81 |
| E | 079V | 0.02 | 19.92 | 205.08 | 0.01 | 16.82 | 6.04 | 10.85 | 11.04 | 10.48 | 22.44 | 18.45 |
| E | 079W | −0.08 | −6.38 | −96.30 | −0.02 | −2.14 | −0.29 | −1.73 | −1.88 | −1.79 | −3.84 | −2.11 |
| E | 079Y | −0.01 | −17.04 | −305.85 | 0.00 | −19.49 | −5.34 | −12.44 | −12.08 | −12.27 | −33.45 | −20.75 |
| F | 080A | 0.18 | 4.17 | 11.19 | 0.06 | 0.80 | 0.01 | 0.77 | 0.94 | 1.20 | 2.02 | 1.02 |
| F | 080D | −0.05 | −12.18 | −25.17 | −0.01 | −1.98 | 0.00 | −2.36 | −3.11 | −3.55 | −5.53 | −2.10 |
| F | 080E | 0.03 | 18.20 | 70.28 | 0.01 | 3.17 | 0.07 | 3.77 | 4.81 | 5.70 | 8.74 | 3.58 |
| F | 080G | −0.07 | −9.11 | −5.30 | −0.01 | −1.43 | −0.05 | −1.61 | −2.07 | −2.38 | −4.11 | −1.43 |
| F | 080H | −0.18 | −1.90 | 6.79 | −0.05 | −0.70 | −0.08 | −0.74 | −0.92 | −1.04 | −2.08 | −0.44 |
| F | 080I | 0.02 | 13.10 | 51.17 | 0.01 | 6.44 | 0.77 | 5.75 | 7.16 | 7.84 | 14.50 | 8.40 |
| F | 080K | −0.01 | 15.76 | 361.83 | 0.00 | −15.23 | −2.71 | −18.40 | −22.84 | −25.95 | −42.97 | −16.20 |
| F | 080L | 0.55 | 1.04 | 11.26 | 0.41 | 1.50 | 1.16 | 1.19 | 1.00 | 1.26 | 1.65 | 1.44 |
| F | 080M | 0.58 | 1.17 | −1.08 | 0.41 | 1.23 | 0.83 | 0.94 | 0.83 | 1.03 | 1.50 | 1.22 |
| F | 080N | 0.05 | 13.25 | −4.51 | 0.01 | 2.22 | −0.32 | 2.66 | 3.31 | 3.84 | 5.72 | 10.28 |
| F | 080P | −0.07 | −6.41 | −22.15 | −0.02 | −1.54 | 0.13 | −1.79 | −2.34 | −2.81 | −4.83 | −1.82 |
| F | 080Q | −0.03 | −4.51 | −57.41 | −0.01 | −2.92 | 0.08 | −3.44 | −4.49 | −5.15 | −9.49 | −4.29 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| F | 080R | 0.02 | 18.58 | 3.48 | 0.00 | 4.96 | −0.23 | 5.95 | 7.58 | 8.76 | 15.09 | 4.89 |
| F | 080S | −0.11 | −1.21 | 0.17 | −0.02 | −0.89 | −0.03 | −1.16 | −1.50 | −1.72 | −3.09 | −0.52 |
| F | 080T | −0.05 | 0.31 | −19.20 | −0.01 | −2.10 | −0.17 | −2.42 | −3.17 | −3.47 | −6.35 | −2.20 |
| F | 080V | −0.09 | −3.57 | 10.55 | −0.02 | −1.60 | −0.08 | −1.52 | −1.85 | −2.00 | −3.89 | −1.53 |
| F | 080W | 0.41 | 1.38 | −2.64 | 0.22 | 1.62 | 1.06 | 1.33 | 1.04 | 1.37 | 1.85 | 1.84 |
| F | 080Y | 0.54 | 1.12 | 5.72 | 0.41 | 1.56 | 1.28 | 1.28 | 0.99 | 1.40 | 1.56 | 1.45 |
| K | 081A | 0.93 | 0.88 | 8.87 | 0.96 | 0.99 | 0.89 | 0.89 | 0.67 | 0.84 | 1.01 | 0.88 |
| K | 081C | 0.16 | 1.85 | −5.39 | 0.06 | 2.23 | 0.74 | 1.47 | 1.53 | 1.52 | 3.55 | 2.61 |
| K | 081D | 0.44 | 1.29 | 13.10 | 0.25 | 1.37 | 0.89 | 1.08 | 1.09 | 1.06 | 1.63 | 1.64 |
| K | 081E | 0.65 | 1.28 | 11.32 | 0.55 | 1.33 | 1.18 | 1.26 | 1.26 | 1.23 | 1.40 | 1.31 |
| K | 081G | 0.65 | 1.19 | −0.79 | 0.46 | 1.26 | 1.03 | 1.10 | 1.15 | 1.07 | 1.36 | 1.37 |
| K | 081H | 0.59 | 1.14 | 22.79 | 0.42 | 1.37 | 1.13 | 1.22 | 1.23 | 1.21 | 1.55 | 1.48 |
| K | 081I | 0.88 | 1.04 | 11.68 | 0.79 | 1.03 | 0.97 | 1.01 | 0.98 | 0.98 | 1.00 | 1.05 |
| K | 081L | 0.70 | 1.04 | 9.43 | 0.58 | 1.27 | 1.07 | 1.09 | 0.89 | 1.10 | 1.28 | 1.15 |
| K | 081M | 0.77 | 1.12 | 2.88 | 0.81 | 1.25 | 1.20 | 1.11 | 0.85 | 1.13 | 1.21 | 1.20 |
| K | 081N | 0.61 | 1.15 | 10.71 | 0.46 | 1.28 | 1.03 | 1.12 | 1.04 | 1.09 | 1.39 | 1.09 |
| K | 081P | −0.08 | −7.11 | −186.80 | −0.02 | −1.43 | −0.09 | −1.34 | −1.63 | −1.61 | −3.60 | −1.23 |
| K | 081Q | 0.72 | 1.16 | 2.89 | 0.64 | 1.22 | 1.12 | 1.15 | 1.17 | 1.16 | 1.38 | 1.15 |
| K | 081R | 0.81 | 1.06 | 3.63 | 0.70 | 1.10 | 1.07 | 1.11 | 1.16 | 1.07 | 1.17 | 1.13 |
| K | 081S | 0.65 | 1.20 | 22.10 | 0.49 | 1.33 | 1.16 | 1.23 | 1.30 | 1.23 | 1.36 | 1.32 |
| K | 081T | 0.60 | 1.44 | 12.38 | 0.49 | 1.47 | 1.31 | 1.41 | 1.43 | 1.38 | 1.54 | 1.47 |
| K | 081V | 0.74 | 1.10 | 6.85 | 0.57 | 1.18 | 1.08 | 1.16 | 1.14 | 1.15 | 1.20 | 1.16 |
| K | 081W | 0.29 | 2.14 | −10.83 | 0.16 | 2.27 | 1.55 | 1.81 | 1.73 | 1.77 | 2.86 | 2.64 |
| K | 081Y | 0.53 | 1.17 | 10.40 | 0.36 | 1.54 | 1.22 | 1.26 | 1.04 | 1.25 | 1.65 | 1.39 |
| E | 082A | 1.04 | 0.97 | 0.58 | 1.13 | 0.98 | 0.90 | 0.87 | 0.70 | 0.87 | 0.94 | 0.88 |
| E | 082C | −0.17 | −2.52 | −17.88 | −0.05 | −1.75 | −0.43 | −1.20 | −1.37 | −1.51 | −2.78 | −0.01 |
| E | 082D | 0.89 | 1.00 | 1.41 | 0.82 | 1.04 | 0.93 | 1.00 | 1.05 | 0.95 | 1.08 | 1.05 |
| E | 082F | 0.57 | 1.20 | 4.05 | 0.33 | 1.27 | 0.94 | 1.04 | 1.17 | 1.03 | 1.62 | 1.20 |
| E | 082G | 0.72 | 1.10 | 3.28 | 0.52 | 1.22 | 1.03 | 1.10 | 1.16 | 1.08 | 1.42 | 1.22 |
| E | 082I | 0.59 | 1.20 | 1.52 | 0.38 | 1.30 | 1.03 | 1.12 | 1.14 | 1.06 | 1.49 | 1.36 |
| E | 082K | 0.68 | 1.29 | −1.84 | 0.52 | 1.30 | 1.17 | 1.20 | 1.12 | 1.12 | 1.53 | 1.24 |
| E | 082L | 0.70 | 1.06 | 3.76 | 0.59 | 1.32 | 1.19 | 1.18 | 0.87 | 1.15 | 1.31 | 1.31 |
| E | 082M | 0.89 | 0.99 | −1.30 | 0.90 | 1.06 | 0.95 | 0.93 | 0.75 | 0.88 | 1.08 | 1.07 |
| E | 082Q | 0.75 | 1.20 | 2.18 | 0.64 | 1.23 | 1.12 | 1.16 | 1.21 | 1.11 | 1.17 | 1.27 |
| E | 082R | 0.69 | 1.29 | 0.62 | 0.49 | 1.25 | 1.03 | 1.13 | 1.16 | 1.01 | 1.45 | 1.30 |
| E | 082S | 0.78 | 1.11 | 2.84 | 0.65 | 1.16 | 1.06 | 1.11 | 1.10 | 1.10 | 1.25 | 1.24 |
| E | 082T | 0.71 | 1.17 | −2.19 | 0.47 | 1.17 | 0.98 | 1.09 | 1.10 | 1.07 | 1.35 | 1.04 |
| E | 082V | 0.51 | 1.42 | 3.16 | 0.33 | 1.54 | 1.23 | 1.36 | 1.35 | 1.30 | 1.71 | 1.52 |
| E | 082W | 0.53 | 1.31 | −2.99 | 0.32 | 1.46 | 1.13 | 1.24 | 1.13 | 1.20 | 1.79 | 1.19 |
| E | 082Y | 0.57 | 1.26 | −1.59 | 0.40 | 1.42 | 1.20 | 1.25 | 0.94 | 1.21 | 1.62 | 1.74 |
| M | 083A | 0.58 | 1.03 | −1.05 | 0.39 | 1.22 | 0.83 | 0.90 | 0.74 | 0.89 | 1.37 | 1.25 |
| M | 083D | −0.11 | −4.73 | −47.81 | −0.02 | −0.90 | −0.11 | −0.94 | −1.17 | −1.12 | −2.67 | −0.39 |
| M | 083E | 0.02 | 18.57 | 1207.87 | 0.00 | 6.93 | 1.23 | 7.23 | 8.71 | 8.27 | 19.76 | 5.68 |
| M | 083F | 0.59 | 1.05 | 4.72 | 0.34 | 1.25 | 0.96 | 1.08 | 1.09 | 1.06 | 1.52 | 1.27 |
| M | 083G | −0.14 | −3.70 | −72.97 | −0.03 | −0.89 | −0.19 | −0.84 | −0.99 | −0.96 | −2.18 | −0.76 |
| M | 083H | −0.16 | −1.05 | −22.05 | −0.04 | −0.64 | −0.08 | −0.67 | −0.80 | −0.78 | −1.99 | −0.60 |
| M | 083I | 0.08 | 2.82 | 94.71 | 0.02 | 4.53 | 1.57 | 3.12 | 3.27 | 3.16 | 7.66 | 4.77 |
| M | 083K | −0.19 | 0.07 | 8.60 | −0.04 | −0.50 | −0.04 | −0.55 | −0.67 | −0.67 | −1.37 | −0.54 |
| M | 083L | 0.58 | 1.14 | 9.33 | 0.38 | 1.46 | 1.23 | 1.25 | 0.97 | 1.25 | 1.60 | 1.50 |
| M | 083N | −0.08 | −5.93 | −1.38 | −0.02 | −1.44 | −0.16 | −1.48 | −1.77 | −1.73 | −3.83 | −0.11 |
| M | 083Q | −0.12 | −6.78 | −32.58 | −0.03 | −1.13 | −0.17 | −1.01 | −1.18 | −1.13 | −2.36 | −1.58 |
| M | 083R | −0.12 | −0.94 | 61.25 | −0.03 | −0.78 | −0.21 | −0.85 | −1.03 | −1.01 | −2.34 | −0.93 |
| M | 083T | 0.21 | 2.31 | 12.59 | 0.07 | 2.36 | 1.20 | 1.73 | 1.81 | 1.75 | 3.60 | 2.91 |
| M | 083V | 0.44 | 1.33 | 17.11 | 0.22 | 1.56 | 1.12 | 1.28 | 1.25 | 1.32 | 1.88 | 3.11 |
| M | 083W | −0.25 | 0.41 | 34.06 | −0.05 | −0.46 | −0.06 | −0.45 | −0.54 | −0.53 | −1.09 | −0.35 |
| M | 083Y | −0.05 | −6.94 | 121.48 | −0.01 | −6.25 | −1.40 | −4.07 | −3.83 | −4.37 | −10.71 | −5.96 |
| C | 084A | 0.89 | 1.08 | 0.51 | 0.88 | 1.01 | 0.91 | 0.98 | 0.70 | 1.00 | 1.04 | 1.00 |
| C | 084D | 0.28 | 2.15 | −1.80 | 0.14 | 1.79 | 1.06 | 1.41 | 1.39 | 1.52 | 2.38 | 1.94 |
| C | 084E | 0.40 | 1.50 | 0.80 | 0.17 | 1.11 | 0.53 | 0.82 | 0.81 | 0.94 | 1.53 | 1.33 |
| C | 084F | −0.12 | 1.82 | −10.50 | −0.04 | −0.91 | −0.08 | −1.02 | −1.05 | −1.50 | −2.64 | −0.51 |
| C | 084G | 0.44 | 1.17 | −5.65 | 0.21 | 1.44 | 0.92 | 1.10 | 1.15 | 1.20 | 1.85 | 1.42 |
| C | 084H | −0.02 | −27.86 | 297.57 | 0.00 | −19.90 | −5.25 | −14.12 | −14.17 | −17.81 | −34.93 | −14.77 |
| C | 084I | 0.43 | 1.21 | 3.86 | 0.20 | 1.42 | 0.91 | 1.13 | 1.05 | 1.23 | 1.72 | 1.37 |
| C | 084K | 0.08 | 3.66 | −23.92 | 0.02 | 3.68 | 0.92 | 2.65 | 2.52 | 3.39 | 5.72 | 3.61 |
| C | 084L | −0.13 | −4.95 | 2.86 | −0.06 | −4.37 | −4.81 | 0.00 | 0.00 | 16.47 | −4.69 | −7.29 |
| C | 084M | 0.33 | 1.85 | −12.13 | 0.13 | 1.21 | 0.41 | 0.88 | 0.59 | 1.06 | 1.67 | 1.37 |
| C | 084N | 0.88 | 1.08 | −1.26 | 0.78 | 1.00 | 0.88 | 0.96 | 0.83 | 0.94 | 0.98 | 0.91 |
| C | 084P | −0.06 | −0.24 | −30.99 | −0.01 | −1.94 | −0.03 | −2.24 | −2.35 | −3.34 | −5.13 | −1.73 |
| C | 084Q | 0.15 | 2.63 | −6.19 | 0.05 | 2.37 | 0.86 | 1.72 | 1.65 | 2.04 | 3.39 | 3.94 |
| C | 084R | −0.07 | −7.98 | 13.60 | −0.02 | −2.92 | −0.47 | −2.41 | −2.41 | −3.21 | −5.91 | −2.63 |
| C | 084S | 0.68 | 1.21 | 1.07 | 0.47 | 1.24 | 1.05 | 1.11 | 1.11 | 1.16 | 1.31 | 1.46 |
| C | 084T | 0.65 | 1.49 | 10.90 | 0.52 | 1.33 | 1.25 | 1.31 | 1.24 | 1.35 | 1.39 | 1.33 |
| C | 084V | 0.49 | 1.46 | 1.81 | 0.24 | 1.35 | 0.95 | 1.12 | 0.99 | 1.14 | 1.54 | 1.37 |
| C | 084W | −0.07 | −2.28 | −63.60 | −0.02 | −1.47 | −0.09 | −1.64 | −1.72 | −2.49 | −3.64 | −1.06 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| C | 084Y | −0.03 | 1.38 | 59.66 | −0.01 | −3.69 | −0.29 | −3.79 | −3.72 | −5.65 | −8.98 | −2.55 |
| A | 086C | 0.32 | 0.54 | 3.14 | 0.13 | 1.32 | 0.54 | 0.95 | 0.92 | 1.02 | 1.85 | 1.41 |
| A | 086D | 0.89 | 0.91 | 1.80 | 0.70 | 0.89 | 0.76 | 0.83 | 0.81 | 0.82 | 1.05 | 0.96 |
| A | 086E | 0.90 | 0.99 | 1.30 | 0.87 | 1.05 | 1.03 | 1.07 | 1.07 | 1.07 | 1.04 | 1.14 |
| A | 086F | 0.92 | 0.93 | 3.21 | 0.73 | 0.94 | 0.84 | 0.89 | 0.95 | 0.88 | 1.04 | 0.91 |
| A | 086G | 0.61 | 1.15 | −0.79 | 0.39 | 1.31 | 1.04 | 1.12 | 1.19 | 1.12 | 1.46 | 1.48 |
| A | 086I | 0.88 | 0.98 | −0.57 | 0.72 | 1.03 | 0.98 | 1.01 | 0.99 | 1.00 | 1.05 | 0.89 |
| A | 086K | 0.92 | 0.95 | 0.97 | 0.86 | 1.06 | 1.02 | 1.05 | 0.94 | 1.12 | 1.08 | 1.10 |
| A | 086L | 0.81 | 1.11 | −1.62 | 0.82 | 1.24 | 1.22 | 1.19 | 0.88 | 1.19 | 1.22 | 1.21 |
| A | 086M | 0.88 | 1.07 | −0.31 | 0.96 | 1.09 | 1.09 | 1.06 | 0.85 | 1.07 | 1.10 | 0.95 |
| A | 086N | 0.77 | 0.90 | −0.11 | 0.67 | 1.05 | 0.90 | 0.98 | 0.92 | 0.96 | 1.16 | 1.01 |
| A | 086P | 0.00 | 375.06 | 484.26 | 0.00 | 57.06 | 1.04 | 54.01 | 63.21 | 73.67 | 139.55 | 22.63 |
| A | 086Q | 0.96 | 1.06 | −1.12 | 0.84 | 0.95 | 0.93 | 0.95 | 1.00 | 0.95 | 1.02 | 1.00 |
| A | 086R | 0.75 | 1.22 | 1.41 | 0.67 | 1.25 | 1.22 | 1.25 | 1.35 | 1.21 | 1.29 | 1.21 |
| A | 086S | 0.73 | 1.18 | −1.54 | 0.60 | 1.25 | 1.17 | 1.24 | 1.31 | 1.21 | 1.30 | 1.26 |
| A | 086V | 0.83 | 1.13 | −1.27 | 0.69 | 1.11 | 1.13 | 1.11 | 1.12 | 1.09 | 1.21 | 1.13 |
| A | 086W | 0.63 | 0.93 | −0.27 | 0.40 | 1.25 | 1.00 | 1.09 | 0.97 | 1.05 | 1.47 | 1.30 |
| A | 086Y | 0.77 | 1.10 | −1.28 | 0.67 | 1.26 | 1.17 | 1.17 | 0.92 | 1.18 | 1.18 | 1.28 |
| A | 087C | −0.05 | −8.70 | 171.10 | −0.01 | −2.20 | −0.27 | −1.53 | −1.86 | −3.34 | 0.48 | −0.56 |
| A | 087D | −0.04 | −9.18 | 166.98 | −0.01 | −2.02 | −0.26 | −1.45 | −1.90 | −3.63 | 0.47 | −0.73 |
| A | 087E | −0.12 | −4.05 | 71.05 | −0.03 | −0.80 | −0.12 | −0.57 | −0.73 | −1.49 | −0.10 | −5.95 |
| A | 087F | 0.13 | 2.72 | −113.49 | 0.03 | 1.71 | 0.34 | 0.94 | 1.05 | 1.63 | 1.43 | 1.27 |
| A | 087G | 0.61 | 1.16 | 6.35 | 0.39 | 1.27 | 0.94 | 0.97 | 0.98 | 1.06 | 1.30 | 1.36 |
| A | 087H | −0.07 | −4.15 | −369.35 | −0.01 | −1.35 | −0.17 | −0.94 | −1.19 | −2.18 | −0.19 | −1.19 |
| A | 087I | −0.17 | 0.44 | −12.49 | −0.03 | −0.60 | −0.11 | −0.40 | −0.49 | −0.96 | −0.63 | −0.66 |
| A | 087K | −0.10 | −1.49 | 102.14 | −0.02 | −1.17 | −0.15 | −0.73 | −0.90 | −1.67 | −0.51 | −1.08 |
| A | 087M | 0.25 | 1.22 | −34.36 | 0.08 | 0.99 | 0.23 | 0.56 | 0.56 | 0.86 | 0.98 | 0.56 |
| A | 087N | −0.03 | −9.10 | 206.98 | −0.01 | −2.66 | −0.34 | −2.04 | −2.57 | −4.98 | 0.61 | 1.74 |
| A | 087P | 0.03 | 18.38 | −824.04 | 0.00 | 3.31 | −0.34 | 2.48 | 3.16 | 6.38 | −1.22 | 3.58 |
| A | 087Q | −0.16 | −2.15 | 58.69 | −0.03 | −0.58 | −0.07 | −0.41 | −0.52 | −1.02 | −0.41 | −0.06 |
| A | 087R | −0.06 | −4.37 | 33.42 | −0.02 | −1.45 | −0.03 | −0.99 | −1.26 | −2.49 | 0.15 | −5.83 |
| A | 087T | 0.17 | 2.11 | 82.36 | 0.05 | 2.56 | 1.07 | 1.52 | 1.56 | 1.99 | 3.37 | 2.10 |
| A | 087V | −0.12 | −1.79 | 48.13 | −0.02 | −1.00 | −0.13 | −0.62 | −0.78 | −1.46 | −0.50 | −1.33 |
| A | 087W | −0.15 | 1.71 | −88.84 | −0.03 | −0.62 | −0.04 | −0.44 | −0.57 | −1.12 | −0.12 | −0.40 |
| A | 087Y | −0.06 | −2.53 | 277.71 | −0.01 | −2.89 | −0.32 | −1.72 | −1.79 | −3.31 | −1.95 | −2.13 |
| E | 088A | 0.98 | 0.98 | 1.94 | 1.11 | 0.97 | 0.96 | 0.94 | 0.58 | 0.88 | 1.03 | 0.74 |
| E | 088C | 0.30 | 2.12 | −9.45 | 0.13 | 1.25 | 0.42 | 0.90 | 0.80 | 1.03 | 1.79 | 1.31 |
| E | 088D | 1.08 | 0.89 | −8.53 | 1.21 | 0.83 | 0.85 | 0.84 | 0.66 | 0.82 | 0.85 | 0.80 |
| E | 088F | 0.48 | 1.62 | 2.00 | 0.28 | 1.42 | 0.81 | 0.98 | 0.87 | 0.98 | 1.69 | 1.31 |
| E | 088G | 0.87 | 1.10 | 2.81 | 0.83 | 1.23 | 1.01 | 0.98 | 0.83 | 0.98 | 1.10 | 1.08 |
| E | 088H | 0.83 | 1.22 | 32.44 | 0.87 | 1.26 | 1.23 | 1.15 | 1.05 | 1.20 | 1.25 | 1.18 |
| E | 088I | 0.19 | 2.38 | 18.95 | 0.09 | 2.59 | 1.11 | 1.70 | 1.58 | 1.77 | 3.55 | 2.66 |
| E | 088L | 0.35 | 1.80 | 72.30 | 0.23 | 2.17 | 1.27 | 1.45 | 1.24 | 1.53 | 2.28 | 1.95 |
| E | 088M | 0.54 | 1.50 | −11.19 | 0.41 | 1.20 | 0.88 | 1.07 | 0.78 | 1.09 | 1.44 | 1.47 |
| E | 088N | 0.93 | 0.91 | −15.28 | 0.87 | 0.84 | 0.77 | 0.83 | 0.69 | 0.81 | 0.94 | 0.90 |
| E | 088P | 0.03 | 9.80 | −42.50 | 0.01 | 4.04 | −0.28 | 4.68 | 5.41 | 6.86 | 12.72 | 5.38 |
| E | 088Q | 0.79 | 1.27 | 0.89 | 0.78 | 1.06 | 1.07 | 1.08 | 1.08 | 1.09 | 1.09 | 1.19 |
| E | 088R | 0.67 | 1.26 | −6.03 | 0.57 | 1.26 | 1.19 | 1.16 | 1.21 | 1.19 | 1.27 | 1.29 |
| E | 088S | 0.68 | 1.33 | −3.37 | 0.58 | 1.36 | 1.15 | 1.18 | 1.18 | 1.17 | 1.37 | 1.24 |
| E | 088T | 0.60 | 1.39 | −1.69 | 0.45 | 1.65 | 1.13 | 1.17 | 1.21 | 1.20 | 1.56 | 1.46 |
| E | 088V | 0.00 | 61.85 | 1392.84 | 0.00 | 68.75 | 25.01 | 45.52 | 43.73 | 48.96 | 93.63 | 71.84 |
| E | 088W | 0.20 | 3.09 | 18.33 | 0.11 | 3.26 | 1.99 | 2.46 | 2.34 | 2.59 | 3.65 | 3.29 |
| E | 088Y | 0.46 | 1.66 | 3.40 | 0.35 | 1.88 | 1.43 | 1.48 | 1.29 | 1.51 | 1.84 | 1.79 |
| E | 089A | 1.29 | 0.84 | 0.08 | 1.48 | 0.82 | 0.80 | 0.82 | 0.50 | 0.78 | 0.85 | 0.77 |
| E | 089C | 0.26 | 2.00 | 3.15 | 0.10 | 1.64 | 0.61 | 1.15 | 1.01 | 1.21 | 2.29 | 1.99 |
| E | 089D | 0.89 | 1.19 | 1.75 | 0.94 | 1.18 | 1.12 | 1.12 | 0.88 | 1.07 | 1.16 | 1.12 |
| E | 089G | 0.84 | 1.08 | 1.72 | 0.83 | 1.21 | 1.15 | 1.10 | 0.93 | 1.10 | 1.14 | 1.22 |
| E | 089H | 0.94 | 1.08 | 1.85 | 0.93 | 1.07 | 1.04 | 1.02 | 0.92 | 0.98 | 1.01 | 1.21 |
| E | 089I | 0.76 | 1.18 | 1.52 | 0.69 | 1.34 | 1.25 | 1.23 | 0.99 | 1.20 | 1.36 | 1.33 |
| E | 089K | 0.97 | 0.99 | 1.52 | 1.05 | 1.08 | 1.11 | 1.09 | 0.80 | 1.05 | 1.18 | 1.12 |
| E | 089L | 0.95 | 1.00 | 1.40 | 1.03 | 1.08 | 1.09 | 1.06 | 0.87 | 1.07 | 1.21 | 1.01 |
| E | 089M | 1.00 | 1.03 | −0.90 | 1.05 | 0.95 | 0.87 | 0.93 | 0.67 | 0.91 | 0.97 | 0.95 |
| E | 089N | 1.21 | 0.76 | −0.15 | 1.22 | 0.80 | 0.76 | 0.81 | 0.68 | 0.79 | 0.68 | 0.86 |
| E | 089P | 0.74 | 1.08 | 0.85 | 0.55 | 1.10 | 0.89 | 0.98 | 0.97 | 0.97 | 1.27 | 1.22 |
| E | 089Q | 0.88 | 1.13 | 0.62 | 0.80 | 1.06 | 1.00 | 1.04 | 1.02 | 1.00 | 1.16 | 1.21 |
| E | 089R | 0.89 | 1.10 | 1.47 | 0.86 | 1.08 | 1.02 | 1.04 | 1.04 | 0.99 | 1.14 | 1.19 |
| E | 089S | 1.00 | 0.92 | 0.28 | 0.92 | 0.93 | 0.87 | 0.89 | 0.88 | 0.88 | 0.99 | 0.96 |
| E | 089T | 0.79 | 1.21 | 1.88 | 0.68 | 1.16 | 1.12 | 1.14 | 1.12 | 1.14 | 1.22 | 1.22 |
| E | 089V | 0.78 | 1.27 | 1.03 | 0.76 | 1.26 | 1.23 | 1.25 | 1.18 | 1.26 | 1.33 | 1.27 |
| E | 089W | 0.68 | 1.37 | 2.03 | 0.57 | 1.24 | 1.10 | 1.15 | 1.00 | 1.12 | 1.44 | 1.40 |
| E | 089Y | 0.87 | 1.19 | 2.10 | 0.92 | 1.14 | 1.17 | 1.14 | 0.90 | 1.11 | 1.12 | 1.25 |
| I | 092A | 0.04 | 7.26 | 5.29 | 0.01 | 7.36 | 1.92 | 4.81 | 4.44 | 4.93 | 11.68 | 2.13 |
| I | 092D | −0.14 | −5.91 | −16.22 | −0.03 | −0.94 | −0.09 | −0.90 | −1.02 | −1.00 | −2.28 | −0.77 |
| I | 092E | −0.01 | −70.53 | 1.50 | 0.00 | −50.58 | −19.88 | −33.30 | −34.29 | −31.52 | −75.06 | −53.63 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| I | 092F | −0.16 | −3.23 | −14.57 | −0.03 | −1.27 | −0.27 | −0.94 | −1.01 | −1.05 | −2.47 | −0.70 |
| I | 092G | −0.21 | −2.08 | 12.91 | −0.04 | −0.62 | −0.11 | −0.54 | −0.63 | −0.58 | −1.50 | −0.68 |
| I | 092H | −0.13 | 0.15 | −13.25 | −0.02 | −1.17 | −0.19 | −0.98 | −1.12 | −1.04 | −2.60 | −1.02 |
| I | 092K | −0.04 | −10.77 | 37.91 | −0.01 | −8.14 | −3.29 | −5.53 | −5.66 | −5.49 | −14.77 | −7.05 |
| I | 092L | 0.82 | 0.91 | 0.39 | 0.68 | 1.16 | 1.09 | 1.11 | 0.87 | 0.99 | 1.37 | 1.17 |
| I | 092M | 0.99 | 0.93 | 0.01 | 1.00 | 0.99 | 0.97 | 0.87 | 0.45 | 0.79 | 0.98 | 0.88 |
| I | 092N | 0.09 | 6.96 | 18.43 | 0.02 | 2.67 | 0.45 | 1.76 | 1.79 | 1.90 | 4.42 | 1.81 |
| I | 092P | 0.00 | 130.31 | −94.05 | 0.00 | 38.16 | 5.94 | 28.18 | 30.44 | 31.05 | 71.62 | 27.04 |
| I | 092Q | 0.05 | 10.76 | 27.94 | 0.01 | 7.64 | 2.41 | 4.87 | 4.58 | 4.63 | 12.73 | 6.87 |
| I | 092R | −0.06 | −9.31 | 6.16 | −0.01 | −2.66 | −0.36 | −2.14 | −2.38 | −2.33 | −6.41 | −1.44 |
| I | 092S | −0.11 | −2.48 | −3.08 | −0.02 | −2.01 | −0.32 | −1.39 | −1.46 | −1.41 | −3.97 | −1.65 |
| I | 092T | 0.20 | 2.41 | 4.66 | 0.08 | 3.23 | 1.89 | 2.17 | 1.83 | 1.98 | 4.11 | 2.88 |
| I | 092V | 0.83 | 1.02 | 1.06 | 0.76 | 1.19 | 1.10 | 1.07 | 0.80 | 0.98 | 1.23 | 1.07 |
| I | 092W | −0.09 | −1.36 | 10.97 | −0.02 | −1.25 | −0.23 | −1.33 | −1.53 | −1.44 | −3.60 | −0.90 |
| I | 092Y | −0.03 | −9.30 | −76.51 | −0.01 | −8.70 | −1.35 | −5.85 | −5.96 | −5.94 | −17.96 | −7.18 |
| K | 093A | 0.93 | 0.98 | 3.19 | 0.87 | 0.98 | 0.83 | 0.87 | 0.59 | 0.90 | 0.90 | 0.82 |
| K | 093C | 0.19 | 3.44 | 15.07 | 0.07 | 2.05 | 0.69 | 1.44 | 1.29 | 1.73 | 2.94 | 2.48 |
| K | 093D | 0.67 | 1.14 | 0.48 | 0.47 | 1.12 | 0.89 | 1.01 | 0.88 | 1.02 | 1.35 | 1.17 |
| K | 093E | 0.42 | 1.71 | 2.00 | 0.21 | 1.53 | 1.06 | 1.25 | 1.13 | 1.30 | 1.78 | 1.54 |
| K | 093F | 0.55 | 1.85 | 7.70 | 0.40 | 1.49 | 1.30 | 1.37 | 1.24 | 1.38 | 1.60 | 1.47 |
| K | 093G | 0.83 | 1.12 | 1.43 | 0.66 | 1.11 | 1.04 | 1.05 | 0.97 | 1.04 | 1.11 | 1.10 |
| K | 093I | 0.53 | 1.30 | −6.48 | 0.32 | 1.40 | 1.08 | 1.14 | 1.03 | 1.19 | 1.62 | 1.27 |
| K | 093L | 0.51 | 1.30 | 10.72 | 0.38 | 1.76 | 1.36 | 1.36 | 1.06 | 1.47 | 1.47 | 1.60 |
| K | 093M | 0.82 | 1.03 | 0.62 | 0.81 | 1.20 | 0.96 | 0.98 | 0.57 | 1.05 | 1.05 | 1.04 |
| K | 093N | 0.58 | 1.35 | 3.71 | 0.37 | 1.34 | 0.92 | 0.93 | 0.73 | 1.10 | 1.08 | 0.79 |
| K | 093P | 0.25 | 2.64 | 8.38 | 0.13 | 2.41 | 1.39 | 1.68 | 1.32 | 1.90 | 2.67 | 2.25 |
| K | 093Q | 0.51 | 1.61 | −0.62 | 0.36 | 1.64 | 1.32 | 1.35 | 1.03 | 1.38 | 1.49 | 1.61 |
| K | 093R | 0.83 | 1.15 | −5.04 | 0.82 | 1.19 | 1.15 | 1.12 | 0.85 | 1.15 | 1.04 | 1.04 |
| K | 093S | 0.63 | 1.64 | −1.47 | 0.49 | 1.44 | 1.25 | 1.26 | 0.93 | 1.22 | 1.49 | 1.44 |
| K | 093T | 0.37 | 1.98 | −1.46 | 0.19 | 2.01 | 1.33 | 1.45 | 1.18 | 1.50 | 2.21 | 2.02 |
| K | 093V | 0.22 | 2.91 | 3.83 | 0.12 | 3.03 | 2.00 | 2.20 | 1.73 | 2.44 | 3.32 | 3.08 |
| K | 093W | 0.49 | 1.74 | 6.25 | 0.36 | 1.76 | 1.40 | 1.42 | 1.08 | 1.53 | 1.68 | 1.61 |
| K | 093Y | 0.79 | 1.11 | −0.12 | 0.75 | 1.30 | 1.18 | 1.12 | 0.80 | 1.13 | 1.13 | 1.00 |
| V | 094A | 0.22 | 3.65 | 59.67 | 0.09 | 1.44 | 0.38 | 1.06 | 0.98 | 1.28 | 2.42 | 1.35 |
| V | 094C | 0.41 | 1.72 | 27.44 | 0.23 | 1.23 | 0.74 | 0.99 | 0.93 | 1.05 | 1.80 | 1.36 |
| V | 094D | 0.04 | 16.55 | −119.89 | 0.01 | 3.11 | 0.20 | 3.56 | 4.05 | 4.91 | 9.33 | 3.17 |
| V | 094E | 0.02 | 21.51 | 488.37 | 0.01 | 5.13 | 0.04 | 5.46 | 6.29 | 7.95 | 12.36 | 4.85 |
| V | 094F | 0.05 | 13.58 | 17.54 | 0.01 | 3.27 | 0.31 | 2.90 | 3.20 | 3.65 | 7.03 | 2.22 |
| V | 094G | −0.06 | −2.00 | −181.28 | −0.02 | −1.98 | −0.08 | −2.14 | −2.47 | −3.00 | −5.70 | −1.98 |
| V | 094H | −0.05 | 2.55 | −146.49 | −0.01 | −2.37 | −0.12 | −2.64 | −2.93 | −3.87 | −6.81 | −1.43 |
| V | 094I | 0.89 | 0.96 | 5.34 | 0.77 | 1.06 | 0.92 | 0.96 | 0.95 | 0.95 | 1.11 | 1.09 |
| V | 094K | −0.01 | 5.72 | −745.72 | 0.00 | −10.40 | −1.65 | −11.17 | −12.52 | −15.33 | −30.57 | −7.17 |
| V | 094M | 0.48 | 1.54 | 26.25 | 0.32 | 1.18 | 0.86 | 1.02 | 0.81 | 1.10 | 1.81 | 1.60 |
| V | 094N | 0.00 | 296.55 | 2308.32 | 0.00 | 57.07 | 6.78 | 49.78 | 52.46 | 64.74 | 116.38 | 28.69 |
| V | 094P | 0.02 | 32.65 | −16.94 | 0.01 | 6.39 | −0.05 | 6.35 | 7.18 | 8.58 | 14.42 | 0.39 |
| V | 094Q | 0.04 | 5.80 | 134.95 | 0.01 | 3.55 | 0.35 | 3.69 | 4.27 | 5.35 | 9.41 | 2.98 |
| V | 094R | −0.01 | 0.55 | 46.61 | 0.00 | −8.79 | −1.08 | −9.29 | −10.60 | −12.76 | −22.08 | −5.64 |
| V | 094S | −0.03 | −7.74 | −437.42 | −0.01 | −7.01 | −0.96 | −5.56 | −6.10 | −7.09 | −12.75 | −9.20 |
| V | 094T | 0.31 | 2.31 | 18.38 | 0.17 | 2.13 | 1.31 | 1.56 | 1.66 | 1.62 | 2.39 | 1.82 |
| V | 094W | −0.11 | 0.59 | −82.05 | −0.03 | −1.10 | −0.03 | −1.18 | −1.31 | −1.64 | −2.98 | −1.19 |
| I | 095A | 0.33 | 1.76 | 5.33 | 0.16 | 1.62 | 0.61 | 1.00 | 0.63 | 0.94 | 1.34 | 1.50 |
| I | 095C | −0.12 | −3.61 | 4.57 | −0.03 | −1.96 | −0.27 | −1.12 | −0.97 | −1.58 | −1.52 | −1.85 |
| I | 095D | −0.19 | −3.37 | −12.47 | −0.05 | −0.55 | −0.06 | −0.38 | −0.41 | −0.86 | 0.10 | −0.44 |
| I | 095E | −0.02 | −29.21 | −16.97 | −0.01 | −4.86 | −0.51 | −3.14 | −3.25 | −6.56 | −1.75 | −3.74 |
| I | 095F | 0.60 | 1.24 | 2.42 | 0.37 | 1.20 | 0.74 | 0.95 | 0.75 | 0.76 | 1.34 | 1.25 |
| I | 095G | −0.06 | −6.35 | −13.08 | −0.01 | −3.19 | −0.35 | −1.79 | −1.53 | −2.85 | −2.95 | −3.99 |
| I | 095H | −0.03 | −7.85 | −109.41 | −0.01 | −6.32 | −0.90 | −3.61 | −3.22 | −5.22 | −5.81 | −8.89 |
| I | 095K | −0.10 | −0.30 | −0.77 | −0.02 | −1.02 | −0.06 | −0.68 | −0.71 | −1.55 | −0.01 | −0.98 |
| I | 095L | 1.00 | 0.83 | 0.35 | 1.15 | 1.05 | 0.99 | 0.94 | 0.73 | 0.85 | 0.92 | 0.97 |
| I | 095M | 0.53 | 1.47 | 0.82 | 0.46 | 1.59 | 1.22 | 1.27 | 1.08 | 1.11 | 1.52 | 1.41 |
| I | 095N | −0.07 | −7.12 | −20.13 | −0.02 | −2.13 | −0.11 | −1.28 | −1.28 | −2.05 | −1.60 | −2.11 |
| I | 095P | −0.15 | −3.81 | −16.49 | −0.03 | −0.63 | −0.03 | −0.44 | −0.47 | −0.98 | 0.16 | −0.50 |
| I | 095Q | −0.20 | −1.78 | −15.22 | −0.05 | −0.56 | −0.02 | −0.36 | −0.42 | −0.79 | 0.15 | −0.62 |
| I | 095R | −0.26 | −0.67 | −5.95 | −0.05 | −0.38 | −0.03 | −0.27 | −0.28 | −0.45 | 0.00 | −0.54 |
| I | 095S | −0.21 | −1.73 | −4.62 | −0.04 | −0.96 | −0.10 | −0.58 | −0.53 | −0.78 | −0.73 | −0.45 |
| I | 095V | 0.90 | 0.92 | 6.32 | 0.67 | 0.96 | 0.87 | 0.89 | 0.80 | 0.88 | 1.06 | 1.06 |
| I | 095W | −0.36 | −1.53 | −5.10 | −0.09 | −0.83 | −0.34 | −0.73 | −0.60 | −4.04 | −0.86 | −0.90 |
| I | 095Y | 0.66 | 1.00 | 6.85 | 0.42 | 1.15 | 0.73 | 0.94 | 0.67 | 0.75 | 1.21 | 1.05 |
| V | 096A | 0.42 | 1.60 | 4.56 | 0.26 | 1.56 | 0.80 | 1.05 | 0.75 | 1.04 | 1.63 | 1.64 |
| V | 096C | 0.42 | 1.54 | 1.64 | 0.25 | 1.62 | 0.91 | 1.11 | 0.92 | 1.09 | 1.80 | 1.47 |
| V | 096D | −0.07 | −9.97 | −19.14 | −0.02 | −1.70 | −0.15 | −1.65 | −2.12 | −2.46 | −3.84 | 3.16 |
| V | 096E | −0.06 | −10.31 | −8.16 | −0.02 | −1.65 | −0.05 | −1.65 | −2.21 | −2.54 | −3.34 | 3.07 |
| V | 096G | −0.03 | −22.38 | −58.73 | −0.01 | −7.32 | −0.92 | −5.14 | −6.23 | −6.52 | −15.81 | 5.13 |
| V | 096H | −0.12 | −0.93 | −13.22 | −0.03 | −0.97 | −0.15 | −0.95 | −1.21 | −1.39 | −2.56 | 1.73 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| V | 096I | 0.89 | 1.06 | 1.58 | 0.96 | 1.21 | 1.17 | 1.18 | 0.94 | 1.02 | 1.03 | 1.04 |
| V | 096K | −0.08 | −1.01 | −14.24 | −0.02 | −1.25 | −0.07 | −1.38 | −1.75 | −2.20 | −3.33 | 2.91 |
| V | 096L | 0.28 | 2.54 | 1.27 | 0.14 | 2.13 | 1.12 | 1.49 | 1.00 | 1.36 | 2.72 | 1.74 |
| V | 096M | 0.31 | 1.72 | 4.53 | 0.17 | 1.89 | 0.97 | 1.23 | 1.11 | 1.33 | 2.08 | 1.47 |
| V | 096N | −0.06 | −11.13 | −14.25 | −0.02 | −3.16 | −0.09 | −2.28 | −2.69 | −3.03 | −6.13 | 0.41 |
| V | 096P | 0.06 | 7.29 | 19.31 | 0.02 | 5.91 | 1.35 | 4.27 | 4.67 | 4.41 | 9.68 | 3.93 |
| V | 096Q | −0.18 | −3.26 | −5.41 | −0.05 | −0.61 | −0.08 | −0.59 | −0.78 | −0.90 | −1.32 | 1.42 |
| V | 096R | −0.23 | −2.85 | −4.82 | −0.04 | −0.44 | −0.03 | −0.47 | −0.61 | −0.72 | −1.11 | 1.17 |
| V | 096S | −0.05 | −8.21 | −25.47 | −0.02 | −6.21 | −1.70 | −4.16 | −4.48 | −4.45 | −8.75 | −0.90 |
| V | 096T | 0.21 | 2.75 | 0.58 | 0.10 | 2.86 | 1.66 | 2.02 | 2.21 | 2.06 | 3.58 | 2.14 |
| V | 096W | −0.24 | −0.84 | −5.34 | −0.05 | −0.42 | −0.07 | −0.44 | −0.56 | −0.65 | −1.03 | 0.85 |
| V | 096Y | −0.19 | −1.02 | 4.99 | −0.04 | −0.70 | −0.14 | −0.60 | −0.75 | −0.89 | −1.35 | 0.95 |
| D | 097A | 0.23 | 2.92 | 1.37 | 0.06 | 0.43 | −0.06 | 0.55 | 0.67 | 0.79 | 1.25 | 0.24 |
| D | 097C | 0.00 | −254.82 | 769.47 | 0.00 | −43.58 | 0.72 | −49.63 | −60.66 | −65.75 | −114.54 | −35.39 |
| D | 097E | 0.31 | 2.42 | −11.24 | 0.08 | 0.31 | −0.03 | 0.38 | 0.47 | 0.51 | 1.25 | 0.27 |
| D | 097G | −0.03 | −12.47 | 194.48 | −0.01 | −3.24 | −0.16 | −3.79 | −4.67 | −4.96 | −9.69 | −1.54 |
| D | 097H | 0.03 | 5.74 | −203.36 | 0.00 | 5.14 | 1.34 | 6.06 | 7.67 | 8.18 | 14.35 | 1.84 |
| D | 097I | −0.03 | −2.25 | 394.31 | −0.01 | −3.95 | −1.28 | −4.76 | −6.04 | −6.36 | −10.08 | −5.77 |
| D | 097K | 0.00 | −4.21 | 480.47 | 0.00 | −14.21 | −2.19 | −18.01 | −21.83 | −24.31 | −46.61 | −15.64 |
| D | 097L | −0.13 | 0.92 | 20.01 | −0.03 | −0.82 | −0.10 | −1.07 | −1.30 | −1.41 | −2.45 | −1.45 |
| D | 097M | 0.11 | 5.14 | −46.51 | 0.02 | 1.00 | 0.10 | 1.26 | 1.60 | 1.82 | 2.49 | 0.46 |
| D | 097N | −0.01 | −69.38 | 697.64 | 0.00 | −24.11 | −0.28 | −28.27 | −35.85 | −40.12 | −69.42 | −19.42 |
| D | 097P | −0.02 | −12.84 | 354.81 | 0.00 | −11.11 | −0.92 | −12.85 | −16.34 | −17.69 | −32.56 | −0.19 |
| D | 097Q | 0.03 | 16.12 | −151.37 | 0.01 | 3.78 | 0.56 | 4.47 | 5.70 | 6.10 | 11.32 | 3.71 |
| D | 097R | −1.21 | −0.01 | −1.40 | −0.30 | −0.34 | −2.57 | −0.16 | −0.09 | −0.07 | −0.28 | −0.06 |
| D | 097S | −0.09 | −3.44 | −11.12 | −0.01 | −1.49 | −0.14 | −1.71 | −2.20 | −2.29 | −4.54 | −0.57 |
| D | 097T | −0.04 | 3.18 | −77.57 | −0.01 | −2.79 | −1.07 | −3.22 | −4.17 | −4.27 | −7.62 | −0.40 |
| D | 097V | −0.09 | 0.13 | −37.02 | −0.02 | −1.03 | −0.52 | −1.17 | −1.50 | −1.59 | −2.79 | −1.16 |
| D | 097W | 0.11 | 1.21 | 16.33 | 0.03 | 0.82 | 0.37 | 0.98 | 1.26 | 1.32 | 2.01 | 0.61 |
| D | 097Y | −0.17 | 0.44 | −18.70 | −0.04 | −0.63 | −0.25 | −0.78 | −0.96 | −1.09 | −2.14 | −0.43 |
| A | 098C | 0.52 | 1.36 | 0.25 | 0.36 | 1.56 | 0.91 | 1.25 | 0.91 | 0.81 | 1.75 | 1.40 |
| A | 098D | −0.04 | −25.19 | 8.83 | −0.01 | −3.90 | −0.25 | −3.80 | −4.22 | −3.74 | −12.34 | −4.17 |
| A | 098F | 0.00 | 97.70 | −22.57 | 0.00 | 14.59 | 2.36 | 16.41 | 18.39 | 25.32 | 50.05 | 8.43 |
| A | 098G | 0.23 | 1.90 | 1.52 | 0.09 | 2.25 | 1.01 | 1.50 | 1.35 | 1.24 | 3.34 | 2.18 |
| A | 098H | −0.05 | −10.26 | 11.44 | −0.01 | −3.48 | −0.17 | −2.70 | −2.89 | −2.43 | −8.56 | −3.94 |
| A | 098I | 0.36 | 1.37 | −8.81 | 0.21 | 1.94 | 0.93 | 1.33 | 1.00 | 0.75 | 2.58 | 1.88 |
| A | 098K | −0.06 | −1.94 | −17.27 | −0.01 | −1.72 | −0.29 | −1.85 | −2.07 | −1.86 | −4.54 | −0.23 |
| A | 098L | 0.13 | 2.55 | 16.79 | 0.05 | 3.44 | 0.82 | 2.07 | 1.49 | 1.22 | 5.53 | 3.32 |
| A | 098M | 0.28 | 2.06 | 5.67 | 0.14 | 2.30 | 1.22 | 1.76 | 1.24 | 4.67 | 2.75 | 2.04 |
| A | 098N | −0.04 | −20.69 | 4.40 | −0.01 | −6.29 | −1.77 | −6.66 | −6.01 | −33.55 | −12.44 | −6.16 |
| A | 098P | −0.12 | −6.32 | −8.95 | −0.03 | −1.24 | −0.26 | −1.28 | −1.32 | −4.00 | −3.38 | −1.44 |
| A | 098Q | −0.03 | −27.69 | 29.50 | −0.01 | −8.21 | −0.72 | −6.34 | −6.55 | −7.88 | −16.44 | −12.95 |
| A | 098R | −0.07 | −8.66 | 42.09 | −0.01 | −1.66 | −0.21 | −1.74 | −2.01 | −1.89 | −4.28 | −0.87 |
| A | 098T | 0.33 | 1.48 | −5.38 | 0.16 | 1.79 | 0.83 | 1.33 | 1.21 | 1.29 | 2.47 | 2.06 |
| A | 098V | 0.40 | 1.40 | −3.47 | 0.23 | 1.55 | 0.73 | 1.10 | 0.95 | 0.63 | 2.14 | 1.73 |
| A | 098W | −0.12 | −3.20 | 17.99 | −0.03 | −1.08 | −0.06 | −0.97 | −1.05 | −0.95 | −3.03 | −0.70 |
| A | 098Y | −0.05 | −2.37 | 16.04 | −0.01 | −3.67 | −0.31 | −2.69 | −2.65 | −2.43 | −7.82 | −3.30 |
| V | 099A | 0.39 | 2.35 | 6.49 | 0.11 | 0.46 | −0.01 | 0.34 | 0.36 | 0.44 | 1.32 | 0.59 |
| V | 099C | 0.47 | 1.75 | 7.78 | 0.13 | 0.37 | −0.02 | 0.29 | 0.32 | 0.37 | 1.15 | 0.85 |
| V | 099E | 0.13 | 4.71 | 13.90 | 0.04 | 0.74 | 0.03 | 0.86 | 1.03 | 1.21 | 2.73 | −0.96 |
| V | 099F | 0.07 | 2.95 | 31.65 | 0.02 | 1.41 | 0.03 | 1.59 | 1.96 | 2.27 | 3.69 | −5.10 |
| V | 099G | 0.15 | 4.33 | 5.87 | 0.03 | 1.03 | 0.06 | 0.83 | 0.98 | 1.11 | 3.14 | −0.61 |
| V | 099H | 0.04 | 18.35 | 27.13 | 0.01 | 4.93 | 0.74 | 3.80 | 4.39 | 4.67 | 10.36 | 0.02 |
| V | 099I | 0.53 | 0.88 | 2.53 | 0.22 | 0.95 | 0.40 | 0.67 | 0.65 | 0.56 | 1.39 | 1.13 |
| V | 099K | 0.00 | 365.21 | 493.16 | 0.00 | 252.70 | 27.16 | 293.14 | 359.38 | 420.57 | 682.58 | −263.60 |
| V | 099L | 0.18 | −0.13 | 14.59 | 0.04 | 0.70 | 0.05 | 0.68 | 0.77 | 0.99 | 2.34 | 0.24 |
| V | 099M | 0.10 | 5.71 | 23.19 | 0.03 | 0.92 | 0.02 | 1.10 | 1.33 | 1.58 | 2.99 | −2.23 |
| V | 099N | 0.12 | 5.48 | 29.95 | 0.02 | 0.78 | 0.08 | 0.91 | 1.06 | 1.20 | 2.60 | −2.80 |
| V | 099P | 0.41 | 1.09 | 4.63 | 0.15 | 0.88 | 0.12 | 0.48 | 0.44 | 0.51 | 1.61 | 0.98 |
| V | 099Q | 0.04 | 12.32 | 92.50 | 0.01 | 2.08 | −0.01 | 2.45 | 2.93 | 3.49 | 8.13 | −3.97 |
| V | 099R | −0.02 | −7.99 | −120.74 | −0.01 | −4.00 | −0.67 | −4.63 | −5.62 | −6.72 | −11.98 | 14.83 |
| V | 099S | 0.10 | 6.03 | 17.61 | 0.02 | 1.04 | 0.02 | 1.15 | 1.36 | 1.47 | 4.22 | 0.36 |
| V | 099T | 0.28 | 1.63 | 2.38 | 0.08 | 1.08 | 0.16 | 0.69 | 0.66 | 0.72 | 2.20 | 1.70 |
| V | 099Y | 0.03 | −4.91 | 65.79 | 0.01 | 3.67 | 0.48 | 4.62 | 5.48 | 6.05 | 11.49 | −10.01 |
| I | 100A | 0.56 | 1.87 | −1.53 | 0.52 | 1.53 | 0.81 | 1.13 | 0.76 | 1.01 | 1.47 | 1.32 |
| I | 100C | 0.75 | 1.35 | 2.58 | 1.04 | 1.35 | 1.19 | 1.24 | 1.22 | 1.16 | 1.12 | 1.10 |
| I | 100D | −0.06 | −17.03 | −6.80 | −0.02 | −2.41 | −0.06 | −2.26 | −2.77 | −2.37 | −4.86 | 3.69 |
| I | 100E | −0.10 | −8.11 | −5.30 | −0.03 | −1.89 | −0.20 | −1.47 | −1.75 | −1.54 | −3.20 | 1.46 |
| I | 100F | 1.27 | 1.35 | −0.57 | 2.87 | 1.15 | 1.03 | 1.17 | 1.08 | 0.61 | 0.80 | 0.74 |
| I | 100G | 0.05 | 11.52 | −60.44 | 0.02 | 11.14 | 3.24 | 6.44 | 6.28 | 6.14 | 13.59 | 3.97 |
| I | 100K | −0.09 | −2.39 | −20.56 | −0.03 | −1.45 | −0.24 | −1.44 | −1.74 | −1.48 | −3.15 | 1.72 |
| I | 100M | 1.28 | 1.20 | 2.41 | 2.94 | 1.07 | 1.32 | 1.27 | 1.12 | 0.99 | 0.72 | 0.77 |
| I | 100N | 0.12 | 4.57 | 33.74 | 0.06 | 3.79 | 1.11 | 2.45 | 2.52 | 2.28 | 4.58 | 1.12 |
| I | 100P | 0.23 | 4.15 | −5.73 | 0.07 | 0.98 | 0.05 | 0.77 | 0.86 | 0.81 | 2.46 | 2.81 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| I | 100Q | 0.03 | 15.91 | 12.49 | 0.01 | 16.18 | 4.59 | 9.57 | 10.28 | 8.98 | 15.92 | 5.63 |
| I | 100R | −0.18 | −3.67 | −9.41 | −0.05 | −0.55 | −0.07 | −0.61 | −0.78 | −0.68 | −1.32 | 1.50 |
| I | 100S | −0.01 | −35.93 | −272.59 | −0.01 | −29.57 | −9.13 | −18.65 | −19.11 | −16.89 | −31.09 | −6.53 |
| I | 100T | 0.54 | 1.90 | 10.30 | 0.60 | 1.85 | 1.51 | 1.62 | 1.60 | 1.38 | 1.62 | 1.51 |
| I | 100V | 0.86 | 1.28 | −2.49 | 1.03 | 1.20 | 1.23 | 1.23 | 1.22 | 1.06 | 1.15 | 1.22 |
| I | 100W | −0.24 | 0.01 | −11.98 | −0.07 | −0.44 | −0.07 | −0.49 | −0.62 | −0.53 | −1.16 | 0.90 |
| I | 100Y | 0.14 | 3.02 | 6.92 | 0.07 | 4.02 | 0.86 | 2.18 | 2.21 | 1.53 | 4.34 | 1.55 |
| N | 101A | 0.08 | 5.46 | 22.61 | 0.01 | 1.21 | 0.07 | 1.37 | 1.72 | 1.97 | 3.15 | 0.94 |
| N | 101C | −0.04 | −15.22 | −57.02 | −0.01 | −2.41 | −0.05 | −2.73 | −3.34 | −3.54 | −8.47 | −0.72 |
| N | 101D | −0.16 | −2.72 | −2.45 | −0.03 | −0.61 | 0.02 | −0.66 | −0.81 | −0.86 | −1.59 | −0.15 |
| N | 101E | −0.08 | −6.44 | 23.16 | −0.02 | −1.15 | −0.01 | −1.28 | −1.57 | −1.73 | −3.56 | −0.26 |
| N | 101G | −0.02 | −34.56 | −79.13 | 0.00 | −5.01 | −0.12 | −5.20 | −6.33 | −6.80 | −16.23 | −8.80 |
| N | 101H | −0.17 | −0.30 | −20.23 | −0.03 | −0.56 | −0.08 | −0.63 | −0.78 | −0.82 | −1.83 | 0.08 |
| N | 101I | −0.21 | −0.82 | −11.40 | −0.04 | −0.45 | −0.08 | −0.52 | −0.63 | −0.65 | −1.28 | −0.14 |
| N | 101M | −0.07 | −6.75 | −46.67 | −0.01 | −1.36 | 0.01 | −1.58 | −1.95 | −2.26 | −3.74 | −0.63 |
| N | 101Q | −0.11 | −6.48 | −3.28 | −0.03 | −1.00 | 0.07 | −1.02 | −1.20 | −1.36 | −2.80 | −0.87 |
| N | 101R | −0.09 | −3.41 | −1.96 | −0.02 | −1.07 | −0.16 | −1.15 | −1.46 | −1.63 | −2.99 | −1.02 |
| N | 101S | −0.17 | −1.32 | −0.99 | −0.03 | −0.54 | −0.07 | −0.60 | −0.73 | −0.80 | −1.61 | −0.19 |
| N | 101T | −0.18 | −1.24 | −9.21 | −0.03 | −0.52 | −0.07 | −0.57 | −0.70 | −0.76 | −1.43 | −0.11 |
| N | 101W | −0.18 | −0.77 | −9.30 | −0.04 | −0.51 | −0.07 | −0.60 | −0.73 | −0.81 | −1.35 | −0.16 |
| N | 101Y | −0.17 | 0.28 | −14.48 | −0.03 | −0.53 | −0.03 | −0.65 | −0.79 | −0.85 | −1.51 | −0.43 |
| H | 102A | 0.20 | 1.95 | 26.79 | 0.07 | 0.50 | −0.01 | 0.62 | 0.63 | 0.98 | 1.93 | 1.13 |
| H | 102D | 0.05 | 3.30 | 54.48 | 0.01 | 2.21 | −0.07 | 2.52 | 2.60 | 3.78 | 6.28 | 1.68 |
| H | 102E | 0.03 | −2.58 | 113.13 | 0.01 | 3.79 | −0.40 | 4.45 | 4.59 | 6.87 | 9.69 | 4.40 |
| H | 102G | 0.13 | −2.16 | −8.59 | 0.04 | 0.82 | 0.04 | 0.92 | 0.91 | 1.43 | 2.78 | 1.76 |
| H | 102K | −0.12 | 0.51 | −24.73 | −0.02 | −0.96 | −0.08 | −1.12 | −1.14 | −1.65 | −2.68 | −0.75 |
| H | 102L | −0.03 | −2.26 | −3.16 | −0.01 | −3.17 | −0.16 | −3.80 | −3.87 | −5.53 | −9.93 | −5.39 |
| H | 102M | 0.42 | 1.50 | 7.36 | 0.14 | 0.23 | −0.01 | 0.30 | 0.31 | 0.48 | 0.56 | 0.23 |
| H | 102N | −0.06 | −3.08 | 63.88 | −0.01 | −1.76 | 0.13 | −2.17 | −2.20 | −3.21 | −4.98 | 0.11 |
| H | 102P | −0.12 | −2.17 | 2.03 | −0.02 | −0.94 | 0.03 | −1.10 | −1.14 | −1.64 | −2.86 | −1.21 |
| H | 102Q | 0.14 | −0.58 | −90.86 | 0.04 | 0.75 | −0.08 | 0.87 | 0.93 | 1.35 | 2.76 | 1.24 |
| H | 102R | 0.01 | 12.77 | 263.32 | 0.00 | 18.94 | 0.76 | 22.27 | 23.05 | 31.95 | 44.37 | 11.01 |
| H | 102S | 0.07 | 10.03 | −58.26 | 0.02 | 1.78 | −0.12 | 2.05 | 2.06 | 2.91 | 6.18 | 3.40 |
| H | 102T | −0.08 | 0.73 | 83.30 | −0.02 | −1.28 | −0.30 | −1.48 | −1.54 | −2.14 | −3.76 | −0.65 |
| H | 102V | −0.12 | 0.56 | 6.20 | −0.03 | −0.80 | −0.31 | −0.95 | −0.96 | −1.38 | −2.34 | −0.65 |
| H | 102W | 0.20 | 0.00 | −33.72 | 0.04 | 0.51 | −0.01 | 0.61 | 0.60 | 0.74 | 1.46 | 0.42 |
| H | 102Y | 0.31 | 0.24 | 10.26 | 0.07 | 0.33 | 0.07 | 0.41 | 0.40 | 0.53 | 0.81 | 0.29 |
| T | 103A | 0.71 | 0.96 | 10.29 | 0.51 | 1.13 | 0.77 | 0.84 | 0.49 | 0.74 | 1.17 | 1.08 |
| T | 103C | 0.78 | 1.26 | 5.10 | 0.80 | 1.26 | 1.20 | 1.09 | 0.93 | 1.12 | 1.12 | 1.12 |
| T | 103E | −0.16 | −4.54 | 24.15 | −0.04 | −0.65 | −0.05 | −0.64 | −0.72 | −0.73 | −1.67 | −0.70 |
| T | 103F | −0.10 | −7.63 | −47.59 | −0.02 | −1.27 | −0.32 | −1.06 | −1.16 | −1.15 | −2.72 | −1.29 |
| T | 103G | 0.02 | 21.14 | 241.75 | 0.01 | 16.30 | 3.97 | 9.64 | 8.02 | 8.63 | 20.22 | 14.34 |
| T | 103H | −0.22 | −1.41 | −10.41 | −0.04 | −0.50 | −0.07 | −0.47 | −0.53 | −0.54 | −1.23 | −0.48 |
| T | 103I | 0.34 | 1.51 | 10.03 | 0.16 | 1.66 | 0.55 | 1.00 | 0.69 | 0.73 | 1.92 | 2.18 |
| T | 103K | −0.09 | −0.93 | 4.33 | −0.02 | −1.15 | −0.14 | −1.23 | −1.42 | −1.37 | −3.20 | −1.84 |
| T | 103M | 0.90 | 1.03 | 1.44 | 0.83 | 0.99 | 0.81 | 0.80 | 0.28 | 0.69 | 1.03 | 1.01 |
| T | 103N | 0.05 | 8.21 | 56.27 | 0.01 | 4.86 | 0.92 | 2.92 | 2.52 | 3.25 | 7.00 | 4.04 |
| T | 103P | −0.15 | −3.02 | 24.15 | −0.03 | −0.61 | −0.09 | −0.71 | −0.83 | −0.79 | −1.88 | −1.24 |
| T | 103Q | −0.02 | −20.43 | −370.43 | 0.00 | −16.53 | −3.31 | −9.34 | −8.65 | −9.90 | −24.36 | −21.19 |
| T | 103R | −0.14 | −2.30 | −35.18 | −0.03 | −0.64 | −0.10 | −0.71 | −0.83 | −0.81 | −1.68 | −0.82 |
| T | 103S | 0.21 | 2.27 | 50.00 | 0.08 | 2.56 | 1.21 | 1.75 | 1.74 | 1.69 | 3.12 | 2.82 |
| T | 103V | 0.91 | 1.03 | 4.69 | 0.87 | 1.04 | 1.09 | 1.06 | 1.09 | 1.08 | 1.03 | 1.04 |
| T | 103W | −0.19 | −0.75 | −53.40 | −0.04 | −0.45 | −0.03 | −0.52 | −0.62 | −0.58 | −1.06 | −0.19 |
| T | 103Y | −0.15 | −2.66 | −66.78 | −0.03 | −0.61 | −0.09 | −0.73 | −0.83 | −0.81 | −1.72 | −0.56 |
| T | 104A | 0.53 | 1.38 | 1.87 | 0.41 | 1.38 | 0.77 | 0.89 | 0.55 | 0.61 | 1.87 | 1.33 |
| T | 104C | 0.33 | 1.64 | 5.49 | 0.17 | 1.61 | 0.64 | 1.05 | 0.77 | 0.89 | 2.32 | 1.96 |
| T | 104D | 0.00 | 176.04 | 868.78 | 0.00 | 244.73 | −4.10 | 108.94 | 130.90 | 163.06 | 444.23 | 206.40 |
| T | 104E | −0.12 | −4.44 | −13.71 | −0.03 | −0.85 | −0.05 | −0.86 | −1.10 | −1.32 | −2.43 | −0.91 |
| T | 104F | −0.10 | −2.70 | −9.74 | −0.02 | −0.95 | −0.06 | −1.10 | −1.36 | −1.65 | −3.05 | −1.60 |
| T | 104G | −0.02 | −5.32 | −39.56 | −0.01 | −11.56 | −1.84 | −6.64 | −6.72 | −8.09 | −22.09 | −17.08 |
| T | 104H | 0.04 | 10.62 | 82.28 | 0.01 | 11.44 | 4.09 | 6.99 | 7.73 | 7.91 | 16.67 | 12.79 |
| T | 104I | −0.19 | −0.71 | −10.99 | −0.04 | −0.52 | −0.06 | −0.57 | −0.71 | −0.84 | −1.22 | −0.28 |
| T | 104K | −0.20 | 0.51 | −9.06 | −0.04 | −0.50 | −0.02 | −0.55 | −0.68 | −0.81 | −1.43 | −0.52 |
| T | 104L | −0.08 | −2.06 | −9.68 | −0.02 | −2.14 | −0.25 | −1.81 | −1.98 | −2.41 | −4.64 | −4.57 |
| T | 104M | −0.16 | −2.58 | −9.21 | −0.03 | −0.57 | −0.02 | −0.72 | −0.85 | −1.06 | −2.02 | −0.35 |
| T | 104N | −0.10 | −3.44 | −18.29 | −0.03 | −1.48 | 0.02 | −1.08 | −1.33 | −1.61 | −3.51 | −1.77 |
| T | 104P | −0.14 | −0.80 | −5.08 | −0.03 | −0.68 | −0.07 | −0.81 | −0.99 | −1.21 | −2.34 | −1.53 |
| T | 104Q | −0.11 | −2.61 | −13.29 | −0.03 | −0.87 | −0.03 | −0.98 | −1.21 | −1.50 | −2.99 | −1.35 |
| T | 104R | −0.16 | −0.33 | −6.50 | −0.03 | −0.59 | −0.03 | −0.67 | −0.85 | −1.05 | −2.12 | −0.94 |
| T | 104S | 0.85 | 1.03 | 2.35 | 0.68 | 1.10 | 0.97 | 1.07 | 1.16 | 1.05 | 1.07 | 1.01 |
| T | 104V | −0.15 | 0.13 | −17.33 | −0.03 | −0.83 | −0.03 | −0.76 | −0.93 | −1.09 | −1.94 | −1.68 |
| T | 104W | −0.26 | 1.12 | −6.13 | −0.05 | −0.36 | −0.05 | −0.43 | −0.52 | −0.64 | −1.13 | −1.15 |
| T | 104Y | −0.17 | 1.93 | −8.49 | −0.03 | −0.56 | −0.07 | −0.70 | −0.83 | −1.08 | −1.74 | 2.39 |
| S | 105C | 0.72 | 1.18 | 2.71 | 0.50 | 0.90 | 0.24 | 0.37 | 0.37 | 0.30 | 0.96 | 0.40 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| S | 105D | 0.93 | 0.95 | 2.67 | 0.75 | 0.85 | 0.71 | 0.71 | 0.76 | 0.82 | 0.94 | 1.02 |
| S | 105E | 0.62 | 1.61 | −6.13 | 0.47 | 1.17 | 0.58 | 0.66 | 0.62 | 0.62 | 1.33 | 1.29 |
| S | 105F | 0.63 | 1.98 | 1.39 | 0.56 | 1.33 | 0.40 | 0.59 | 0.52 | 0.42 | 1.50 | 1.40 |
| S | 105G | 0.94 | 1.26 | −1.51 | 0.96 | 0.97 | 0.52 | 0.61 | 0.41 | 0.46 | 1.04 | 1.06 |
| S | 105H | 0.61 | 1.74 | 3.18 | 0.50 | 1.28 | 0.47 | 0.54 | 0.50 | 0.33 | 1.40 | 1.56 |
| S | 105K | 0.58 | 1.79 | 5.60 | 0.45 | 1.17 | 0.30 | 0.43 | 0.41 | 0.27 | 1.37 | 0.48 |
| S | 105L | 0.29 | 3.21 | −7.14 | 0.19 | 2.19 | 0.32 | 0.77 | 0.71 | 0.74 | 2.62 | 1.38 |
| S | 105M | 0.72 | 1.84 | −8.31 | 0.90 | 1.17 | 0.30 | 0.43 | 0.34 | 0.36 | 1.21 | 1.00 |
| S | 105P | 0.04 | 16.65 | −85.83 | 0.01 | 12.12 | 1.99 | 5.71 | 5.03 | 5.66 | 17.14 | 9.31 |
| S | 105Q | 0.55 | 1.71 | −12.77 | 0.43 | 1.38 | 0.46 | 0.61 | 0.57 | 0.57 | 1.48 | 1.45 |
| S | 105R | 0.47 | 2.31 | −3.85 | 0.36 | 1.54 | 0.29 | 0.48 | 0.50 | 0.32 | 1.68 | 1.14 |
| S | 105T | 0.41 | 2.39 | 7.16 | 0.29 | 1.85 | 0.75 | 0.86 | 0.86 | 0.90 | 1.94 | 1.79 |
| S | 105V | 0.30 | 1.93 | −1.53 | 0.14 | 1.77 | 0.52 | 0.85 | 0.81 | 0.85 | 2.38 | 1.18 |
| S | 105W | 0.87 | 1.60 | −1.48 | 1.33 | 1.11 | 0.43 | 0.48 | 0.45 | 0.35 | 1.15 | 1.13 |
| S | 105Y | 0.66 | 1.77 | −4.95 | 0.74 | 1.45 | 0.57 | 0.71 | 0.50 | 0.50 | 1.62 | 1.69 |
| I | 110A | 0.04 | 12.57 | −3.99 | 0.01 | 7.40 | 2.06 | 4.44 | 4.19 | 5.60 | 11.01 | −1.32 |
| I | 110D | −0.24 | −1.07 | −3.06 | −0.05 | −0.41 | −0.08 | −0.44 | −0.57 | −0.66 | −1.04 | 0.67 |
| I | 110E | −0.26 | −0.46 | −4.92 | −0.05 | −0.38 | −0.03 | −0.41 | −0.53 | −0.62 | −1.11 | 0.86 |
| I | 110F | −0.20 | −0.73 | −0.62 | −0.04 | −0.48 | −0.09 | −0.51 | −0.66 | −0.77 | −1.65 | 1.24 |
| I | 110G | −0.23 | −0.15 | 4.71 | −0.05 | −0.44 | −0.07 | −0.45 | −0.60 | −0.70 | −1.16 | 0.57 |
| I | 110H | −0.18 | −0.22 | 0.09 | −0.03 | −0.55 | −0.07 | −0.58 | −0.75 | −0.85 | −1.75 | 1.48 |
| I | 110K | −0.23 | 0.36 | 9.34 | −0.05 | −0.46 | −0.05 | −0.45 | −0.58 | −0.70 | −1.21 | 0.97 |
| I | 110L | 0.11 | 3.76 | −14.46 | 0.03 | 4.29 | 1.55 | 2.81 | 2.08 | 2.88 | 6.08 | 3.22 |
| I | 110M | 0.52 | 1.23 | −0.89 | 0.23 | 0.99 | 0.33 | 0.54 | 0.37 | 0.57 | 1.24 | 0.81 |
| I | 110N | −0.07 | −1.27 | −4.02 | −0.02 | −1.45 | −0.17 | −1.50 | −1.94 | −2.31 | −3.36 | 2.35 |
| I | 110P | −0.08 | −4.79 | 18.63 | −0.02 | −1.23 | −0.22 | −1.31 | −1.74 | −2.00 | −3.38 | 1.52 |
| I | 110Q | −0.20 | −0.94 | 1.49 | −0.04 | −0.51 | −0.09 | −0.54 | −0.70 | −0.80 | −1.26 | 1.34 |
| I | 110R | −0.09 | −1.37 | −4.34 | −0.02 | −1.11 | −0.19 | −1.19 | −1.61 | −1.80 | −3.07 | 3.25 |
| I | 110S | −0.12 | 0.96 | −6.60 | −0.02 | −0.80 | −0.20 | −0.86 | −1.13 | −1.33 | −2.66 | 1.62 |
| I | 110T | −0.03 | −10.82 | 17.02 | −0.01 | −15.81 | −4.98 | −8.87 | −6.90 | −8.73 | −20.48 | −4.97 |
| I | 110V | 0.70 | 1.19 | −0.26 | 0.54 | 1.35 | 1.19 | 1.21 | 0.90 | 1.22 | 1.39 | 1.22 |
| I | 110W | −0.18 | −0.43 | 10.98 | −0.04 | −0.55 | −0.10 | −0.50 | −0.76 | −0.87 | −1.42 | 1.25 |
| I | 110Y | −0.13 | 0.96 | 11.56 | −0.03 | −0.79 | −0.09 | −0.85 | −1.11 | −1.33 | −2.40 | 1.63 |
| S | 111A | 1.13 | 0.80 | 0.95 | 1.27 | 0.82 | 0.73 | 0.74 | 0.52 | 0.70 | 0.84 | 0.89 |
| S | 111C | 0.84 | 0.72 | 1.88 | 0.61 | 0.86 | 0.67 | 0.71 | 0.74 | 0.71 | 0.98 | 0.92 |
| S | 111E | 0.87 | 1.10 | −0.03 | 0.69 | 0.95 | 0.79 | 0.85 | 0.89 | 0.83 | 1.06 | 1.05 |
| S | 111F | 0.70 | 0.87 | 3.35 | 0.39 | 0.94 | 0.62 | 0.73 | 0.74 | 0.72 | 1.15 | 1.06 |
| S | 111G | 0.81 | 0.93 | −1.92 | 0.60 | 1.03 | 0.85 | 0.90 | 0.88 | 0.87 | 1.09 | 1.05 |
| S | 111H | 0.88 | 0.94 | 6.13 | 0.70 | 0.99 | 0.80 | 0.92 | 0.88 | 0.97 | 1.13 | 1.03 |
| S | 111I | 0.32 | 1.29 | 1.83 | 0.13 | 1.69 | 0.85 | 1.14 | 1.00 | 1.13 | 2.20 | 2.07 |
| S | 111K | 0.69 | 0.79 | −0.97 | 0.55 | 1.22 | 1.01 | 1.10 | 0.96 | 1.01 | 1.43 | 1.50 |
| S | 111L | 0.68 | 0.66 | 0.90 | 0.45 | 1.14 | 0.85 | 0.92 | 0.67 | 0.90 | 1.22 | 1.35 |
| S | 111M | 0.78 | 0.81 | 1.90 | 0.66 | 0.99 | 0.78 | 0.80 | 0.66 | 0.82 | 1.08 | 1.02 |
| S | 111N | 1.02 | 0.68 | −0.10 | 0.90 | 0.78 | 0.63 | 0.68 | 0.63 | 0.68 | 0.95 | 1.12 |
| S | 111P | 0.23 | 2.20 | −1.79 | 0.09 | 1.85 | 0.66 | 1.19 | 1.04 | 1.15 | 2.62 | 1.86 |
| S | 111Q | 0.72 | 0.99 | 4.08 | 0.51 | 1.12 | 0.92 | 0.99 | 1.05 | 1.00 | 1.20 | 1.20 |
| S | 111R | 0.73 | 1.26 | 2.57 | 0.45 | 0.98 | 0.77 | 0.82 | 0.89 | 0.85 | 1.27 | 1.12 |
| S | 111T | 0.58 | 1.08 | 5.03 | 0.36 | 1.30 | 1.34 | 1.18 | 1.25 | 1.22 | 0.76 | 0.52 |
| S | 111V | 0.07 | −2.43 | 27.03 | 0.02 | 1.25 | 0.18 | 1.45 | 1.86 | 1.72 | 4.06 | −5.53 |
| S | 111W | 0.55 | 0.99 | 8.29 | 0.33 | 1.31 | 0.87 | 1.04 | 0.90 | 0.99 | 1.66 | 1.47 |
| S | 111Y | 0.35 | 1.00 | 9.22 | 0.20 | 1.95 | 1.23 | 1.43 | 1.04 | 1.47 | 2.37 | 2.12 |
| E | 113A | 0.57 | 1.08 | 7.05 | 0.35 | 1.30 | 0.87 | 0.92 | 0.61 | 0.89 | 1.40 | 1.26 |
| E | 113C | −1.07 | 0.29 | −5.24 | −0.20 | −0.33 | −2.24 | −0.18 | 0.00 | −0.25 | −0.23 | −0.04 |
| E | 113D | 0.84 | 1.04 | −3.26 | 0.59 | 0.99 | 0.86 | 0.91 | 0.87 | 0.86 | 1.01 | 0.96 |
| E | 113F | 0.16 | 2.69 | 35.81 | 0.05 | 2.77 | 1.21 | 1.60 | 1.61 | 1.64 | 3.81 | 2.53 |
| E | 113G | 0.24 | 1.46 | 17.35 | 0.08 | 2.17 | 1.06 | 1.25 | 1.32 | 1.23 | 3.01 | 2.21 |
| E | 113I | 0.26 | 1.54 | 12.30 | 0.11 | 2.20 | 1.30 | 1.51 | 1.51 | 1.42 | 2.63 | 2.43 |
| E | 113K | 0.11 | 1.69 | 32.52 | 0.03 | 2.64 | 0.63 | 1.28 | 1.35 | 1.43 | 3.74 | 1.90 |
| E | 113L | 0.10 | 4.46 | 64.89 | 0.04 | 5.92 | 2.92 | 3.49 | 2.75 | 3.47 | 7.41 | 6.11 |
| E | 113M | 0.36 | 1.19 | −9.16 | 0.16 | 1.65 | 0.89 | 1.03 | 0.74 | 1.02 | 1.91 | 1.53 |
| E | 113N | 0.42 | 1.29 | −3.73 | 0.18 | 1.28 | 0.67 | 0.76 | 0.64 | 0.76 | 1.69 | 1.29 |
| E | 113P | 0.17 | 2.87 | −34.45 | 0.06 | 2.79 | 1.29 | 1.71 | 1.47 | 1.77 | 3.82 | 2.68 |
| E | 113Q | 0.41 | 1.45 | −12.07 | 0.23 | 1.82 | 1.32 | 1.35 | 1.31 | 1.34 | 1.96 | 1.82 |
| E | 113R | 0.03 | 15.61 | 1212 | 0.01 | 5.43 | 0.92 | 3.33 | 3.77 | 3.69 | 11.41 | 6.01 |
| E | 113S | 0.36 | 1.47 | 23.72 | 0.18 | 1.80 | 1.15 | 1.27 | 1.19 | 1.21 | 2.23 | 1.88 |
| E | 113T | 0.27 | 2.36 | −2.77 | 0.13 | 2.61 | 1.77 | 1.87 | 1.83 | 1.82 | 3.03 | 2.79 |
| E | 113V | 0.30 | 1.75 | −3.45 | 0.15 | 2.10 | 1.32 | 1.44 | 1.43 | 1.39 | 2.45 | 2.27 |
| E | 113W | 0.06 | 5.60 | 10.10 | 0.02 | 5.30 | 1.62 | 2.90 | 2.54 | 2.96 | 8.06 | 4.90 |
| E | 113Y | 0.23 | 1.72 | 6.89 | 0.09 | 2.34 | 1.13 | 1.47 | 1.15 | 1.40 | 3.27 | 2.68 |
| V | 114A | 1.34 | 0.44 | 1.33 | 0.91 | 0.49 | 0.30 | 0.33 | 0.22 | 0.35 | 0.53 | 0.42 |
| V | 114C | 0.42 | 1.14 | 20.07 | 0.20 | 1.24 | 0.67 | 0.79 | 0.73 | 0.91 | 1.45 | 1.05 |
| V | 114D | −0.08 | −2.66 | 140.41 | −0.02 | −1.05 | −0.09 | −0.75 | −1.04 | −1.71 | 0.20 | −1.87 |
| V | 114F | 0.07 | 3.13 | −79.45 | 0.02 | 4.31 | 1.08 | 2.09 | 1.68 | 3.04 | 6.07 | 4.32 |
| V | 114G | −0.05 | −1.37 | −185.08 | −0.01 | −1.94 | −0.12 | −1.31 | −1.81 | −2.96 | 0.24 | −3.68 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| V | 114H | −0.09 | −0.17 | −33.43 | −0.02 | −1.06 | −0.10 | −0.76 | −1.06 | −1.75 | −0.25 | −3.06 |
| V | 114K | −0.01 | 30.19 | −7789.78 | 0.00 | −16.68 | −0.53 | −12.08 | −16.47 | −27.95 | 6.55 | −19.86 |
| V | 114L | 0.51 | 1.02 | 64.42 | 0.32 | 1.51 | 1.00 | 1.05 | 0.58 | 1.07 | 1.78 | 1.43 |
| V | 114N | −0.16 | −1.33 | −127.77 | −0.03 | −0.61 | −0.08 | −0.42 | −0.60 | −0.83 | 0.05 | −1.61 |
| V | 114P | 0.07 | 4.71 | −152.25 | 0.01 | 3.82 | 0.78 | 1.84 | 1.77 | 2.89 | 3.94 | 5.22 |
| V | 114Q | −0.06 | −1.80 | −111.68 | −0.01 | −1.55 | −0.43 | −1.09 | −1.52 | −2.39 | 0.18 | −3.45 |
| V | 114R | −0.01 | 3.70 | −342.75 | 0.00 | −7.26 | −2.14 | −5.15 | −7.12 | −11.06 | 0.16 | −14.57 |
| V | 114T | 0.23 | 1.42 | −6.56 | 0.06 | 1.79 | 0.66 | 0.96 | 0.87 | 1.22 | 2.07 | 2.56 |
| V | 114W | −0.10 | 0.25 | 65.34 | −0.02 | −1.10 | 0.03 | −0.80 | −1.04 | −1.71 | −0.63 | −0.90 |
| V | 114Y | 0.00 | 23.90 | −31054.19 | 0.00 | 128.14 | 14.82 | 100.95 | 135.72 | 213.57 | 10.88 | 144.05 |
| I | 117A | 0.04 | 17.56 | −136.92 | 0.01 | 3.25 | 0.33 | 2.85 | 3.09 | 3.33 | 6.99 | 0.12 |
| I | 117C | −0.09 | −6.99 | 3.43 | −0.02 | −2.58 | −0.54 | −1.67 | −1.53 | −1.84 | −4.08 | −2.28 |
| I | 117D | −0.12 | −4.37 | −21.86 | −0.02 | −0.95 | −0.15 | −0.90 | −0.99 | −1.02 | −2.28 | −1.20 |
| I | 117E | −0.02 | −24.37 | 205.99 | 0.00 | −10.68 | −1.96 | −6.91 | −6.69 | −7.90 | −19.24 | −10.85 |
| I | 117F | 0.10 | 4.94 | −62.66 | 0.03 | 4.68 | 2.07 | 2.81 | 2.49 | 3.00 | 6.52 | 4.88 |
| I | 117G | −0.21 | −0.88 | 12.68 | −0.03 | −0.43 | −0.07 | −0.56 | −0.65 | −0.53 | −1.27 | −0.36 |
| I | 117H | −0.11 | −3.36 | −7.06 | −0.03 | −2.88 | −0.82 | −1.91 | −1.78 | −2.07 | −4.13 | −2.96 |
| I | 117K | −0.17 | 0.69 | −2.89 | −0.03 | −0.70 | −0.07 | −0.63 | −0.70 | −0.68 | −1.65 | −0.77 |
| I | 117L | 0.47 | 1.25 | 2.66 | 0.29 | 1.62 | 1.17 | 1.35 | 0.99 | 1.27 | 1.90 | 1.74 |
| I | 117M | 0.90 | 0.82 | 1.75 | 0.79 | 0.96 | 0.81 | 0.76 | 0.43 | 0.76 | 0.95 | 0.91 |
| I | 117N | 0.13 | 4.24 | −25.88 | 0.03 | 2.53 | 0.56 | 1.45 | 1.05 | 1.57 | 3.54 | 1.91 |
| I | 117P | −0.04 | −8.45 | 161.82 | −0.01 | −2.28 | −0.76 | −2.62 | −3.16 | −3.18 | −7.51 | −1.61 |
| I | 117Q | 0.16 | 3.28 | −39.25 | 0.06 | 2.96 | 1.29 | 1.69 | 1.17 | 1.80 | 3.91 | 3.46 |
| I | 117R | −0.10 | −4.46 | 15.12 | −0.02 | −1.33 | −0.16 | −1.05 | −1.15 | −1.20 | −2.66 | −0.54 |
| I | 117S | −0.22 | 0.34 | 39.35 | −0.04 | −0.55 | −0.07 | −0.49 | −0.54 | −0.55 | −1.44 | −0.35 |
| I | 117T | 0.04 | 8.61 | −93.86 | 0.01 | 10.63 | 4.05 | 6.21 | 4.76 | 6.50 | 13.84 | 9.97 |
| I | 117V | 0.42 | 1.62 | −8.17 | 0.22 | 1.71 | 1.07 | 1.14 | 0.75 | 1.10 | 2.04 | 1.67 |
| I | 117W | 0.06 | 4.77 | −51.25 | 0.02 | 5.98 | 1.51 | 3.28 | 2.64 | 3.51 | 8.47 | 5.19 |
| I | 117Y | 0.11 | 3.61 | −27.33 | 0.03 | 3.29 | 1.06 | 1.89 | 1.38 | 2.00 | 4.70 | 3.06 |
| W | 120A | −0.10 | −6.00 | −24.58 | −0.03 | −1.17 | −0.06 | −1.35 | −1.68 | −1.55 | −2.89 | 2.93 |
| W | 120C | −0.13 | −3.83 | 23.86 | −0.03 | −0.81 | −0.11 | −0.96 | −1.20 | −1.09 | −2.21 | 2.62 |
| W | 120D | −0.19 | −3.29 | 13.43 | −0.05 | −0.52 | −0.07 | −0.61 | −0.79 | −0.69 | −1.51 | 1.23 |
| W | 120E | −0.10 | −1.50 | 20.25 | −0.03 | −0.91 | −0.29 | −1.15 | −1.47 | −1.28 | −3.18 | 3.44 |
| W | 120G | −0.16 | −2.70 | −34.01 | −0.04 | −0.69 | −0.13 | −0.77 | −0.97 | −0.91 | −1.76 | 1.12 |
| W | 120H | −0.12 | −3.44 | 20.88 | −0.03 | −2.04 | −0.38 | −1.40 | −1.38 | −1.25 | −3.20 | 0.60 |
| W | 120I | −0.20 | −0.15 | 6.21 | −0.05 | −0.49 | −0.05 | −0.57 | −0.72 | −0.63 | −1.51 | 1.26 |
| W | 120K | −0.21 | −0.69 | −30.09 | −0.05 | −0.47 | −0.07 | −0.56 | −0.86 | −0.62 | −1.36 | 1.22 |
| W | 120L | −0.20 | 0.08 | 15.32 | −0.05 | −0.50 | −0.04 | −0.61 | −0.77 | −0.69 | −1.43 | 1.37 |
| W | 120M | −0.07 | −8.13 | −13.16 | −0.02 | −1.86 | −0.25 | −2.06 | −2.49 | −2.34 | −4.11 | 5.65 |
| W | 120N | −0.14 | −5.67 | 39.86 | −0.04 | −0.92 | −0.04 | −0.88 | −1.08 | −1.00 | −2.00 | 2.49 |
| W | 120P | −0.18 | −2.21 | −8.85 | −0.04 | −0.58 | −0.04 | −0.66 | −0.84 | −0.74 | −1.42 | 1.37 |
| W | 120Q | −0.22 | −2.35 | 13.81 | −0.05 | −0.49 | −0.07 | −0.54 | −0.69 | −0.58 | −1.38 | 1.65 |
| W | 120R | −0.16 | −0.23 | 8.53 | −0.03 | −0.64 | −0.03 | −0.71 | −1.38 | −0.79 | −1.69 | 1.29 |
| W | 120S | −0.25 | −0.30 | 0.06 | −0.06 | −0.44 | −0.04 | −0.47 | −0.60 | −0.53 | −1.05 | 1.05 |
| W | 120T | −0.24 | 0.03 | −13.79 | −0.06 | −0.44 | −0.16 | −0.50 | −0.67 | −0.56 | −1.20 | 0.76 |
| W | 120V | −0.27 | −0.30 | −0.94 | −0.07 | −0.39 | −0.06 | −0.44 | −0.56 | −0.48 | −0.74 | 0.93 |
| W | 120Y | −0.16 | −1.98 | 16.34 | −0.04 | −1.48 | −0.22 | −1.08 | −1.01 | −1.14 | −2.51 | 0.99 |
| T | 121A | 0.09 | 5.68 | 6.42 | 0.04 | 4.55 | 1.31 | 2.87 | 1.64 | 2.70 | 6.30 | 1.03 |
| T | 121C | −0.03 | −20.71 | 6.67 | −0.01 | −12.35 | −3.69 | −8.24 | −5.10 | 7.86 | −17.62 | −4.56 |
| T | 121D | −0.12 | −6.81 | −11.71 | −0.03 | −1.49 | −0.21 | −1.17 | −1.21 | −1.30 | −3.01 | 1.10 |
| T | 121E | −0.17 | −3.82 | −23.83 | −0.04 | −0.91 | −0.11 | −0.82 | −0.90 | −0.79 | −1.80 | 1.61 |
| T | 121F | −0.11 | −5.07 | −65.94 | −0.04 | −1.87 | −0.25 | −1.38 | −1.32 | −1.33 | −3.61 | −0.14 |
| T | 121G | −0.19 | −2.75 | −39.86 | −0.04 | −1.01 | −0.14 | −0.77 | −0.82 | −0.84 | −1.92 | 1.12 |
| T | 121H | 0.02 | 24.16 | 256.09 | 0.01 | 15.75 | 3.15 | 9.67 | 7.26 | 8.05 | 22.83 | 8.78 |
| T | 121I | −0.26 | −0.30 | 5.13 | −0.05 | −0.40 | −0.04 | −0.44 | −0.57 | −0.50 | −1.04 | 0.93 |
| T | 121L | −0.14 | 0.38 | −6.41 | −0.03 | −1.08 | −0.19 | −0.97 | −1.05 | −1.07 | −2.78 | 1.33 |
| T | 121M | 0.12 | 6.14 | −11.62 | 0.04 | 2.46 | 0.42 | 1.55 | 1.28 | 1.63 | 3.71 | 0.18 |
| T | 121N | 0.06 | 10.30 | 20.20 | 0.02 | 4.81 | 1.02 | 3.13 | 3.22 | 3.10 | 7.85 | 3.23 |
| T | 121P | −0.03 | −17.92 | −118.06 | −0.01 | −4.02 | −0.34 | −4.29 | −5.25 | −4.78 | −10.53 | 8.22 |
| T | 121Q | −0.19 | −2.20 | −1.32 | −0.05 | −0.94 | −0.11 | −0.75 | −0.80 | −0.79 | −1.76 | 0.69 |
| T | 121R | −0.23 | −0.32 | −3.86 | −0.07 | −0.47 | −0.08 | −0.51 | −0.64 | −0.54 | −1.28 | 0.90 |
| T | 121S | 0.62 | 1.32 | −0.79 | 0.47 | 1.27 | 1.10 | 1.15 | 0.43 | 1.04 | 1.46 | 1.40 |
| T | 121V | −0.19 | −1.24 | −18.14 | −0.04 | −0.75 | −0.05 | −0.68 | −0.79 | −0.74 | −1.57 | 0.85 |
| T | 121W | −0.22 | −0.22 | −13.98 | −0.05 | −0.48 | −0.08 | −0.55 | −0.66 | −0.62 | −1.06 | 1.14 |
| T | 121Y | −0.01 | −45.90 | −127.81 | 0.00 | −26.43 | −4.10 | −17.37 | −14.94 | −16.19 | −41.78 | −2.00 |
| H | 122A | −0.01 | −47.08 | −266.99 | 0.00 | −12.66 | −1.94 | −14.30 | −16.91 | −16.80 | −34.94 | −3.53 |
| H | 122C | −0.03 | −17.18 | 13.08 | −0.01 | −3.59 | −0.50 | −4.27 | −4.76 | −7.04 | −10.71 | −2.40 |
| H | 122D | −0.07 | −5.82 | −3.26 | −0.01 | −1.44 | −0.27 | −1.56 | −1.82 | −1.67 | −4.79 | −1.98 |
| H | 122E | −0.06 | −8.03 | 68.94 | −0.01 | −1.82 | −0.22 | −1.97 | −2.30 | −2.15 | −4.28 | 0.22 |
| H | 122F | −0.05 | −3.16 | −23.85 | −0.01 | −1.97 | −0.20 | −2.16 | −2.52 | −2.29 | −6.10 | −3.56 |
| H | 122G | −0.12 | −0.02 | −10.21 | −0.02 | −0.83 | −0.22 | −1.01 | −1.14 | −2.33 | −2.50 | −0.88 |
| H | 122I | −0.21 | −0.09 | 12.63 | −0.04 | −0.46 | −0.05 | −0.49 | −0.58 | −0.53 | −1.37 | −0.53 |
| H | 122K | 0.03 | −2.23 | −24.86 | 0.01 | 2.94 | 0.57 | 2.94 | 3.29 | 3.06 | 9.39 | 3.39 |
| H | 122L | −0.31 | 0.48 | 4.86 | −0.05 | −0.30 | 0.00 | −0.36 | −0.41 | −0.39 | −0.97 | −0.08 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| H | 122N | 0.00 | 197.90 | −314.30 | 0.00 | 63.57 | 12.36 | 45.29 | 37.06 | 41.36 | 138.70 | 62.08 |
| H | 122P | −0.16 | −2.62 | −2.96 | −0.03 | −0.58 | −0.07 | −0.64 | −0.73 | −0.66 | −1.69 | −0.36 |
| H | 122Q | −0.08 | −6.69 | 8.89 | −0.02 | −1.16 | 0.00 | −1.23 | −1.48 | −1.35 | −3.60 | −1.42 |
| H | 122R | 0.06 | 5.53 | 13.31 | 0.02 | 5.64 | 1.80 | 3.16 | 2.02 | 2.67 | 7.50 | 4.53 |
| H | 122S | −0.16 | −1.00 | 11.86 | −0.03 | −0.61 | −0.09 | −0.67 | −0.76 | −0.69 | −1.80 | −0.55 |
| H | 122T | −0.12 | 0.15 | −11.49 | −0.03 | −0.94 | −0.16 | −0.93 | −1.04 | −0.93 | −2.52 | −0.99 |
| H | 122V | −0.15 | −1.21 | 7.20 | −0.03 | −0.64 | −0.06 | −0.71 | −0.82 | −0.74 | −2.00 | −0.41 |
| H | 122W | −0.20 | −0.12 | −1.55 | −0.04 | −0.47 | −0.07 | −0.54 | −0.60 | −0.53 | −1.60 | −0.63 |
| H | 122Y | −0.09 | 1.08 | −0.92 | −0.02 | −1.05 | −0.19 | −1.24 | −1.40 | −1.29 | −3.08 | −0.64 |
| Q | 126A | 1.24 | 0.93 | 4.02 | 1.79 | 0.88 | 0.79 | 0.75 | 0.35 | 0.70 | 0.83 | 0.73 |
| Q | 126C | 0.94 | 0.82 | −0.45 | 0.88 | 0.95 | 0.65 | 0.84 | 0.49 | 0.77 | 1.00 | 0.94 |
| Q | 126D | 0.75 | 1.26 | 0.79 | 0.84 | 1.21 | 0.64 | 0.53 | 0.21 | 0.44 | 1.15 | 1.19 |
| Q | 126E | 1.23 | 0.84 | 2.34 | 1.55 | 0.88 | 0.93 | 0.69 | 0.53 | 0.69 | 0.79 | 0.83 |
| Q | 126F | 1.13 | 1.12 | −1.17 | 1.47 | 0.94 | 0.57 | 0.79 | 0.40 | 0.87 | 0.86 | 0.99 |
| Q | 126G | 0.87 | 1.02 | 5.82 | 0.87 | 1.14 | 0.86 | 0.88 | 0.25 | 0.73 | 1.10 | 1.08 |
| Q | 126H | 1.14 | 1.04 | 3.17 | 1.42 | 0.96 | 0.83 | 0.87 | 0.74 | 0.68 | 0.88 | 1.05 |
| Q | 126I | 1.10 | 0.61 | 4.31 | 1.18 | 0.90 | 0.89 | 0.92 | 0.80 | 1.18 | 0.87 | 1.06 |
| Q | 126K | 1.12 | 0.60 | 5.29 | 1.04 | 0.86 | 0.86 | 0.97 | 0.79 | 0.73 | 0.87 | 0.91 |
| Q | 126L | 1.22 | 0.60 | 0.23 | 1.45 | 0.87 | 0.92 | 1.01 | 0.94 | 1.17 | 0.84 | 0.85 |
| Q | 126M | 1.23 | 0.86 | 0.71 | 1.63 | 0.84 | 0.75 | 0.84 | 0.66 | 0.91 | 0.76 | 0.92 |
| Q | 126P | 1.16 | 0.89 | 1.08 | 1.33 | 0.85 | 0.79 | 0.81 | 1.11 | 0.92 | 0.83 | 0.97 |
| Q | 126R | 1.11 | 0.70 | 0.53 | 0.96 | 0.81 | 0.58 | 0.97 | 1.04 | 0.57 | 0.93 | 0.96 |
| Q | 126S | 0.88 | 1.07 | 1.03 | 0.89 | 1.07 | 0.80 | 0.79 | 0.54 | 0.53 | 1.08 | 1.20 |
| Q | 126T | 0.98 | 0.85 | 0.74 | 0.96 | 0.94 | 0.83 | 0.89 | 0.71 | 0.65 | 1.01 | 0.92 |
| Q | 126V | 0.91 | 0.79 | 4.36 | 0.82 | 0.99 | 0.97 | 0.94 | 0.87 | 1.19 | 1.01 | 1.25 |
| Q | 126W | 0.93 | 1.19 | 3.55 | 1.15 | 1.07 | 0.55 | 1.17 | 1.09 | 0.71 | 1.12 | 1.05 |
| Q | 126Y | 0.99 | 1.07 | 1.32 | 1.20 | 1.04 | 0.67 | 0.91 | 0.34 | 0.94 | 0.95 | 1.21 |
| K | 128A | 0.81 | 1.42 | 0.13 | 0.85 | 1.27 | 1.11 | 1.09 | 0.33 | 1.33 | 1.24 | 1.12 |
| K | 128C | 0.70 | 1.15 | −0.02 | 0.55 | 1.20 | 0.91 | 0.92 | 0.27 | 0.94 | 1.15 | 1.18 |
| K | 128D | 0.38 | 2.07 | 1.75 | 0.22 | 1.83 | 0.99 | 1.10 | 0.32 | 1.33 | 2.07 | 2.00 |
| K | 128E | 0.80 | 1.27 | 1.41 | 0.72 | 1.17 | 1.02 | 0.93 | 0.30 | 1.06 | 1.16 | 1.29 |
| K | 128F | 0.70 | 1.20 | −0.85 | 0.52 | 1.23 | 0.87 | 0.89 | 0.22 | 0.94 | 1.31 | 1.18 |
| K | 128G | 0.56 | 1.34 | −0.25 | 0.41 | 1.51 | 1.13 | 1.11 | 0.26 | 1.28 | 1.60 | 1.77 |
| K | 128H | 0.66 | 1.34 | −0.83 | 0.53 | 1.33 | 1.05 | 1.14 | 0.40 | 1.14 | 1.58 | 1.35 |
| K | 128I | 0.75 | 1.18 | −0.54 | 0.70 | 1.29 | 1.13 | 1.07 | 0.57 | 1.17 | 1.34 | 1.33 |
| K | 128L | 0.74 | 1.23 | −0.55 | 0.71 | 1.28 | 1.15 | 1.15 | 0.46 | 1.18 | 1.41 | 1.37 |
| K | 128M | 0.84 | 1.19 | −0.49 | 0.84 | 1.12 | 1.00 | 0.96 | 0.52 | 1.03 | 1.15 | 1.08 |
| K | 128N | 0.63 | 1.59 | −1.48 | 0.54 | 1.33 | 1.03 | 1.08 | 0.41 | 1.28 | 1.43 | 1.45 |
| K | 128P | −0.07 | −5.34 | −11.40 | −0.01 | −1.41 | −0.02 | −1.50 | −1.72 | −2.05 | −4.06 | 4.54 |
| K | 128Q | 0.76 | 1.34 | −0.18 | 0.72 | 1.23 | 1.14 | 1.12 | 1.00 | 1.30 | 1.36 | 1.18 |
| K | 128R | 0.89 | 1.12 | −0.52 | 0.80 | 1.05 | 0.94 | 0.96 | 0.92 | 1.02 | 1.16 | 1.03 |
| K | 128S | 0.74 | 1.24 | 1.82 | 0.62 | 1.21 | 1.11 | 1.09 | 0.86 | 1.39 | 1.28 | 1.26 |
| K | 128T | 0.76 | 1.23 | −2.58 | 0.68 | 1.20 | 1.17 | 1.15 | 1.02 | 1.42 | 1.25 | 1.13 |
| K | 128V | 0.72 | 1.23 | 1.42 | 0.64 | 1.24 | 1.14 | 1.12 | 0.87 | 1.29 | 1.34 | 1.32 |
| K | 128Y | 0.40 | 1.69 | −5.80 | 0.25 | 1.74 | 1.17 | 1.32 | 0.37 | 1.41 | 2.26 | 1.71 |
| N | 129A | 0.38 | 1.27 | 2.96 | 0.22 | 1.60 | 0.77 | 1.10 | 0.36 | 0.99 | 2.04 | 1.57 |
| N | 129C | 0.74 | 0.81 | 1.94 | 0.53 | 1.04 | 0.82 | 0.94 | 0.53 | 0.83 | 1.15 | 1.05 |
| N | 129D | 0.79 | 1.32 | 1.32 | 0.71 | 1.19 | 1.21 | 1.16 | 1.16 | 1.20 | 1.29 | 1.25 |
| N | 129E | 0.51 | 1.21 | 2.93 | 0.33 | 1.40 | 1.02 | 1.17 | 0.35 | 1.27 | 1.61 | 1.52 |
| N | 129F | 0.33 | 1.73 | 2.87 | 0.16 | 1.70 | 0.85 | 1.21 | 0.45 | 1.08 | 2.26 | 1.94 |
| N | 129G | −0.11 | −2.56 | −3.48 | −0.03 | −2.30 | −0.29 | −1.52 | −1.32 | −1.58 | −4.48 | −1.81 |
| N | 129H | 0.42 | 1.29 | 4.06 | 0.25 | 1.63 | 1.04 | 1.32 | 0.44 | 1.04 | 1.96 | 1.67 |
| N | 129I | 0.25 | 2.25 | 7.84 | 0.13 | 2.61 | 1.55 | 1.98 | 0.68 | 1.87 | 3.01 | 3.63 |
| N | 129K | 0.38 | 1.23 | 5.02 | 0.20 | 1.67 | 0.94 | 1.29 | 0.39 | 1.07 | 2.02 | 1.66 |
| N | 129L | 0.33 | 1.42 | 4.10 | 0.17 | 1.97 | 1.08 | 1.44 | 0.45 | 1.36 | 2.50 | 2.17 |
| N | 129M | 0.33 | 1.39 | 4.73 | 0.20 | 1.94 | 1.05 | 1.35 | 0.42 | 1.24 | 2.29 | 2.11 |
| N | 129R | 0.25 | 2.13 | 5.38 | 0.11 | 2.61 | 1.56 | 2.11 | 0.82 | 1.70 | 3.23 | 2.62 |
| N | 129S | 0.46 | 1.36 | 3.29 | 0.27 | 1.40 | 1.04 | 1.34 | 0.54 | 1.21 | 1.81 | 1.66 |
| N | 129T | 0.25 | 1.74 | 4.35 | 0.11 | 2.40 | 1.35 | 1.88 | 0.61 | 1.79 | 2.91 | 2.78 |
| N | 129V | 0.42 | 1.34 | 4.48 | 0.23 | 1.64 | 1.13 | 1.39 | 0.51 | 1.31 | 1.94 | 1.67 |
| N | 129W | −0.06 | −5.75 | −26.96 | −0.02 | −6.62 | −2.02 | −4.28 | −2.25 | −3.89 | −9.79 | −6.20 |
| N | 129Y | 0.11 | 2.26 | 15.92 | 0.04 | 4.98 | 2.19 | 3.32 | 1.33 | 3.18 | 6.93 | 4.81 |
| W | 130A | 0.73 | 1.21 | −1.84 | 0.71 | 1.27 | 1.20 | 2.06 | 0.23 | 1.45 | 1.36 | 0.83 |
| W | 130C | 0.54 | 1.25 | −1.60 | 0.27 | 1.11 | 0.90 | 1.65 | 0.43 | 1.01 | 1.52 | 1.19 |
| W | 130D | 0.32 | 1.72 | −2.37 | 0.20 | 2.16 | 1.22 | 2.72 | 0.47 | 2.23 | 2.50 | 2.56 |
| W | 130E | −0.03 | −24.60 | 11.67 | −0.02 | −19.02 | −28.59 | 13.81 | 26.45 | 18.75 | −21.51 | −16.21 |
| W | 130F | 0.82 | 1.26 | 0.58 | 0.75 | 1.12 | 1.15 | 1.67 | 1.33 | 1.31 | 1.14 | 1.05 |
| W | 130G | 0.16 | 3.75 | 0.32 | 0.08 | 4.83 | 2.78 | 6.20 | 0.97 | 4.47 | 5.77 | 4.57 |
| W | 130H | 0.52 | 1.76 | 2.42 | 0.38 | 1.71 | 1.47 | 2.88 | 0.92 | 2.05 | 1.91 | 2.00 |
| W | 130I | 0.42 | 1.93 | 1.32 | 0.26 | 1.87 | 1.49 | 3.10 | 0.38 | 2.07 | 2.22 | 2.20 |
| W | 130K | 0.48 | 1.46 | 2.90 | 0.31 | 1.59 | 1.49 | 3.67 | 0.83 | 1.92 | 1.99 | 1.82 |
| W | 130L | 0.59 | 1.39 | 1.21 | 0.48 | 1.54 | 1.42 | 2.43 | 0.36 | 1.46 | 1.60 | 1.57 |
| W | 130M | 0.57 | 1.54 | −1.24 | 0.54 | 1.77 | 2.67 | −0.37 | −0.73 | −0.74 | 1.65 | 1.76 |
| W | 130P | 0.28 | 2.64 | 1.41 | 0.20 | 3.16 | 4.49 | −1.39 | −2.05 | −1.52 | 2.97 | 2.85 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| W | 130R | 0.30 | 2.06 | −1.10 | 0.16 | 2.21 | 1.56 | 3.93 | 0.75 | 1.65 | 2.78 | 2.11 |
| W | 130T | 0.70 | 1.27 | 1.77 | 0.60 | 1.38 | 1.39 | 2.40 | 0.26 | 1.76 | 1.32 | 1.34 |
| W | 130V | 0.45 | 1.70 | −1.73 | 0.33 | 1.84 | 1.73 | 3.16 | 0.34 | 2.29 | 2.03 | 1.87 |
| W | 130Y | 0.83 | 1.16 | 0.54 | 0.83 | 1.21 | 1.05 | 1.48 | 0.77 | 1.47 | 1.25 | 1.06 |
| S | 131A | 1.09 | 0.92 | −12.75 | 1.43 | 0.88 | 0.97 | 0.91 | 0.57 | 1.01 | 0.80 | 0.81 |
| S | 131C | 1.04 | 0.74 | 0.48 | 1.01 | 0.79 | 1.03 | 0.91 | 0.82 | 0.81 | 0.85 | 0.77 |
| S | 13W | 1.47 | 0.91 | −0.14 | 2.28 | 0.78 | 1.07 | 0.95 | 0.71 | 1.03 | 0.70 | 0.77 |
| S | 131E | 1.14 | 0.94 | −17.28 | 1.30 | 0.90 | 0.92 | 0.86 | 0.66 | 0.90 | 0.75 | 0.88 |
| S | 131F | 1.06 | 1.11 | −18.89 | 1.20 | 0.97 | 0.91 | 0.90 | 0.76 | 0.80 | 0.91 | 0.92 |
| S | 131H | 1.00 | 1.01 | −1.78 | 1.04 | 1.04 | 0.99 | 0.98 | 0.79 | 0.80 | 0.94 | 0.99 |
| S | 131I | 0.79 | 1.08 | 20.50 | 0.68 | 1.17 | 0.97 | 1.01 | 0.36 | 1.02 | 1.10 | 1.42 |
| S | 131K | 0.87 | 1.08 | 24.89 | 0.91 | 1.14 | 1.11 | 1.08 | 0.72 | 0.99 | 1.11 | 1.01 |
| S | 131L | 0.89 | 0.98 | 4.65 | 1.02 | 1.11 | 1.10 | 1.08 | 0.88 | 1.09 | 1.12 | 1.04 |
| S | 131M | 0.99 | 1.04 | −2.41 | 1.09 | 0.88 | 0.94 | 0.92 | 0.66 | 0.94 | 0.95 | 0.96 |
| S | 131N | 1.09 | 0.91 | 19.79 | 1.08 | 0.81 | 0.82 | 0.79 | 0.74 | 0.82 | 0.80 | 0.81 |
| S | 131P | −0.04 | −9.70 | −1.29 | −0.01 | −4.02 | 0.00 | −2.28 | −2.10 | −4.52 | −3.18 | −1.40 |
| S | 131Q | 0.90 | 1.18 | 3.52 | 0.89 | 1.02 | 1.00 | 1.03 | 0.98 | 0.98 | 0.98 | 1.03 |
| S | 131R | 0.87 | 1.22 | −6.73 | 0.79 | 1.04 | 0.93 | 1.00 | 0.90 | 0.79 | 0.98 | 0.87 |
| S | 131T | 0.77 | 1.43 | −7.75 | 0.72 | 1.22 | 1.15 | 1.14 | 1.06 | 1.23 | 1.19 | 1.08 |
| S | 131V | 0.73 | 1.29 | 21.56 | 0.57 | 1.16 | 1.00 | 1.06 | 0.52 | 1.08 | 1.21 | 1.14 |
| S | 131W | 0.77 | 1.30 | −128.06 | 0.69 | 1.13 | 0.91 | 1.21 | 0.85 | 0.97 | 0.99 | 0.98 |
| S | 131Y | 0.84 | 1.11 | 1.97 | 0.87 | 1.15 | 1.07 | 1.11 | 0.72 | 0.96 | 1.07 | 0.96 |
| R | 133A | 0.01 | 21.40 | 449.85 | 0.00 | 6.08 | 0.60 | 4.37 | 5.26 | 10.31 | 2.51 | −6.61 |
| R | 133C | −0.11 | 0.22 | 172.92 | −0.02 | −0.82 | −0.13 | −0.64 | −0.82 | −1.60 | −0.14 | −0.52 |
| R | 133D | −0.21 | −0.93 | −88.00 | −0.03 | −0.43 | −0.04 | −0.32 | −0.42 | −0.71 | 0.28 | −0.31 |
| R | 133E | −0.16 | 1.01 | −67.14 | −0.03 | −0.55 | −0.05 | −0.41 | −0.53 | −1.06 | −0.04 | −0.02 |
| R | 133F | −0.06 | −2.36 | −100.74 | −0.01 | −1.49 | −0.31 | −1.07 | −1.37 | −2.62 | 0.05 | −7.40 |
| R | 133G | −0.18 | 0.54 | −80.88 | −0.03 | −0.51 | −0.02 | −0.36 | −0.45 | −0.88 | −0.18 | −0.10 |
| R | 133I | −0.09 | 2.47 | 6.61 | −0.02 | −1.24 | −0.13 | −0.80 | −0.98 | −1.91 | −0.82 | −1.87 |
| R | 133K | −0.22 | 0.24 | 30.84 | −0.04 | −0.41 | −0.01 | −0.30 | −0.38 | −0.74 | 0.29 | −0.56 |
| R | 133L | −0.23 | −0.75 | 9.51 | −0.04 | −0.42 | −0.02 | −0.31 | −0.38 | −0.79 | 0.03 | −0.90 |
| R | 133M | 0.13 | 1.77 | 77.82 | 0.03 | 0.70 | 0.06 | 0.52 | 0.64 | 1.26 | −0.26 | −0.27 |
| R | 133N | 0.01 | −5.01 | −676.03 | 0.00 | 36.29 | 2.28 | 27.35 | 34.57 | 59.10 | 7.01 | −36.97 |
| R | 133P | −0.10 | −2.44 | −81.25 | −0.02 | −1.16 | −0.09 | −0.77 | −0.92 | −1.75 | −0.46 | −1.01 |
| R | 133Q | −0.04 | 4.51 | 45.96 | −0.01 | −2.32 | −0.24 | −1.80 | −2.23 | −4.46 | 0.06 | −0.36 |
| R | 133S | −0.11 | 1.22 | −143.22 | −0.02 | −0.99 | −0.09 | −0.61 | −0.76 | −1.44 | 0.08 | −0.71 |
| R | 133T | −0.11 | 0.99 | −61.84 | −0.02 | −0.91 | −0.10 | −0.62 | −0.76 | −1.49 | −0.12 | 0.36 |
| R | 133V | −0.05 | 3.97 | 37.07 | −0.01 | −2.00 | −0.19 | −1.24 | −1.48 | −2.85 | −1.14 | −0.53 |
| R | 133W | −0.06 | −1.22 | 125.95 | −0.01 | −1.61 | −0.17 | −1.19 | −1.50 | −2.95 | 0.66 | 1.10 |
| R | 133Y | −0.12 | −1.45 | −169.34 | −0.02 | −0.82 | −0.02 | −0.61 | −0.74 | −1.31 | −0.09 | −0.55 |
| D | 135A | 0.12 | 6.01 | 4.72 | 0.03 | 1.71 | 0.16 | 1.34 | 1.15 | 1.64 | 3.28 | 1.24 |
| D | 135C | 0.05 | 10.66 | −4.17 | 0.01 | 3.43 | 0.32 | 2.76 | 2.67 | 3.43 | 7.26 | 2.54 |
| D | 135E | 0.75 | 1.00 | −0.60 | 0.56 | 1.05 | 0.92 | 0.93 | 0.60 | 0.83 | 1.14 | 1.11 |
| D | 135F | −0.45 | −2.91 | 2.32 | −0.10 | −0.38 | −0.83 | 0.00 | 0.00 | 1.45 | −0.68 | −0.28 |
| D | 135G | 0.01 | 29.82 | −141.82 | 0.00 | 13.26 | 2.36 | 14.30 | 16.76 | 19.41 | 35.42 | 17.94 |
| D | 135H | 0.03 | 10.11 | 0.78 | 0.01 | 6.44 | 0.99 | 4.90 | 4.00 | 5.37 | 12.92 | 5.64 |
| D | 135K | −0.01 | 41.92 | 73.58 | 0.00 | −11.69 | −1.31 | −14.04 | −16.37 | −19.11 | −35.81 | −11.38 |
| D | 135L | −0.03 | −1.28 | 40.94 | −0.01 | −4.09 | −0.24 | −5.13 | −5.88 | −7.13 | −12.96 | −2.73 |
| D | 135M | 0.10 | 6.71 | 6.25 | 0.03 | 2.06 | 0.12 | 1.66 | 1.48 | 2.08 | 4.07 | 2.09 |
| D | 135N | 0.05 | 20.64 | 7.15 | 0.01 | 2.79 | 0.07 | 2.58 | 2.61 | 3.18 | 6.04 | 2.47 |
| D | 135P | −0.02 | −30.89 | −61.21 | 0.00 | −7.24 | −1.15 | −8.26 | −9.73 | −11.20 | −18.74 | −3.53 |
| D | 135Q | 0.40 | 0.84 | 1.20 | 0.19 | 1.47 | 0.84 | 1.06 | 0.34 | 0.94 | 1.92 | 1.60 |
| D | 135R | 0.06 | 11.55 | 20.92 | 0.01 | 3.33 | 0.56 | 2.60 | 2.60 | 3.14 | 7.13 | 2.94 |
| D | 135S | 0.01 | 45.71 | 6.88 | 0.00 | 37.82 | 8.25 | 24.73 | 16.87 | 26.89 | 61.73 | 37.17 |
| D | 135T | −0.12 | 0.91 | −3.24 | −0.03 | −0.97 | −0.05 | −1.00 | −1.11 | −1.30 | −2.25 | −0.65 |
| D | 135W | 0.01 | −11.21 | 68.26 | 0.00 | 18.07 | 0.99 | 16.63 | 17.02 | 21.17 | 40.29 | 13.94 |
| D | 135Y | −0.15 | 2.82 | 3.05 | −0.04 | −0.70 | −0.09 | −0.81 | −0.89 | −1.12 | −1.98 | −0.19 |
| V | 136A | 0.16 | 3.81 | 6.93 | 0.05 | 1.95 | 0.14 | 1.15 | 0.90 | 1.22 | 3.23 | 1.46 |
| V | 136C | 0.26 | 0.92 | 4.23 | 0.12 | 1.90 | 0.63 | 1.33 | 0.55 | 1.17 | 2.62 | 1.79 |
| V | 136D | −0.01 | −68.45 | −135.47 | 0.00 | −10.09 | −0.48 | −9.23 | −11.49 | −11.41 | −24.18 | −1.51 |
| V | 136E | −0.04 | −17.86 | −31.93 | −0.01 | −3.09 | −0.16 | −3.08 | −4.02 | −3.87 | −8.03 | −2.27 |
| V | 136F | 0.06 | 5.60 | 46.05 | 0.02 | 4.85 | 0.09 | 2.39 | 2.18 | 2.40 | 7.84 | 4.12 |
| V | 136G | −0.13 | −1.10 | −12.57 | −0.03 | −0.88 | −0.10 | −0.86 | −1.09 | −1.03 | −2.27 | −0.96 |
| V | 136H | −0.17 | 1.59 | −5.19 | −0.05 | −0.65 | −0.07 | −0.62 | −0.79 | −0.75 | −2.03 | −0.33 |
| V | 136K | −0.11 | −1.07 | −12.33 | −0.03 | −1.62 | −0.07 | −1.03 | −1.18 | −1.21 | −3.27 | −1.40 |
| V | 136L | 0.91 | 1.30 | 1.71 | 1.29 | 1.24 | 1.27 | 1.06 | 0.72 | 1.09 | 1.27 | 1.23 |
| V | 136N | −0.07 | −11.29 | −15.93 | −0.02 | −1.87 | 0.05 | −1.64 | −2.00 | −2.02 | −4.44 | −0.72 |
| V | 136Q | −0.05 | −17.41 | −23.09 | −0.01 | −6.69 | −1.07 | −4.10 | −3.38 | −4.11 | −12.24 | −6.46 |
| V | 136R | −0.18 | −2.76 | −1.11 | −0.05 | −1.08 | 0.01 | −0.63 | −0.74 | −0.74 | −2.03 | −0.83 |
| V | 136S | 0.03 | 7.68 | 15.61 | 0.01 | 9.96 | 1.37 | 5.34 | 4.14 | 5.02 | 15.49 | 7.66 |
| V | 136T | 0.37 | 1.47 | 1.03 | 0.21 | 1.71 | 1.02 | 1.15 | 0.44 | 0.79 | 2.10 | 1.49 |
| V | 136W | −0.23 | −0.01 | −10.61 | −0.04 | −0.41 | −0.07 | −0.46 | −0.58 | −0.57 | −1.17 | 0.06 |
| V | 136Y | 0.12 | 1.23 | 6.42 | 0.04 | 3.59 | 0.56 | 2.11 | 1.23 | 1.76 | 5.47 | 2.83 |
| T | 137C | 0.04 | 10.35 | −111.10 | 0.01 | 2.08 | 0.21 | 1.48 | 1.96 | 3.16 | 1.43 | 1.83 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| T | 137D | 0.02 | 6.15 | 970.47 | 0.00 | 4.13 | 0.44 | 2.88 | 3.94 | 6.22 | 0.13 | 8.82 |
| T | 137E | −0.16 | −3.16 | 76.20 | −0.03 | −0.60 | −0.05 | −0.41 | −0.59 | −0.93 | −0.18 | −0.90 |
| T | 137F | −0.09 | −3.77 | −308.72 | −0.02 | −1.03 | −0.10 | −0.71 | −1.02 | −1.59 | −0.41 | 0.01 |
| T | 137H | −0.07 | 4.03 | 61.23 | −0.01 | −1.29 | −0.03 | −0.89 | −1.23 | −1.71 | 0.91 | −1.14 |
| T | 137I | −0.12 | 1.13 | −87.71 | −0.02 | −0.88 | −0.09 | −0.64 | −0.83 | −1.36 | 0.05 | −1.50 |
| T | 137K | −0.10 | 1.03 | 191.65 | −0.02 | −1.02 | −0.03 | −0.77 | −1.00 | −1.69 | 0.06 | −1.15 |
| T | 137L | −0.10 | 1.34 | −225.14 | −0.02 | −1.07 | −0.04 | −0.88 | −1.16 | −1.84 | 0.17 | −1.57 |
| T | 137M | 0.01 | 18.95 | 2298.80 | 0.00 | 18.44 | 0.34 | 13.51 | 18.92 | 30.15 | −6.09 | −4.68 |
| T | 137N | −0.17 | −1.31 | −216.63 | −0.03 | −0.56 | −0.03 | −0.41 | −0.57 | −0.92 | 0.06 | −4.17 |
| T | 137P | −0.06 | −4.15 | −48.62 | −0.01 | −1.55 | −0.11 | −1.18 | −1.61 | −2.56 | 1.04 | −1.09 |
| T | 137Q | −0.18 | −1.53 | −169.16 | −0.03 | −0.52 | −0.03 | −0.36 | −0.50 | −0.70 | 0.08 | −0.79 |
| T | 137R | −0.08 | −3.20 | −379.88 | −0.01 | −1.11 | −0.14 | −0.81 | −1.09 | −1.83 | 0.95 | −0.33 |
| T | 137S | −0.02 | −14.80 | −219.58 | 0.00 | −7.26 | −0.86 | −3.80 | −3.86 | −7.08 | −7.31 | −13.78 |
| T | 137V | −0.12 | −0.04 | −145.01 | −0.03 | −0.90 | −0.07 | −0.60 | −0.81 | −1.34 | 0.09 | −1.00 |
| T | 137W | −0.03 | 4.34 | −493.82 | 0.00 | −3.39 | −0.43 | −2.64 | −3.50 | −5.79 | −0.05 | −8.58 |
| T | 137Y | 0.00 | 15.35 | −3765.02 | 0.00 | −21.72 | −2.80 | −17.42 | −23.64 | −36.21 | 2.26 | −19.39 |
| Q | 138A | 0.10 | −0.01 | 5.52 | 0.03 | 1.09 | 0.07 | 1.19 | 1.43 | 1.43 | 3.03 | 0.24 |
| Q | 138C | 0.09 | 9.67 | 19.48 | 0.02 | 1.72 | 0.06 | 1.51 | 1.55 | 1.66 | 4.08 | 0.72 |
| Q | 138D | 0.47 | 0.97 | −0.78 | 0.10 | 0.20 | 0.00 | 0.17 | 0.25 | 0.26 | 0.67 | 0.11 |
| Q | 138F | 0.28 | 2.88 | −5.10 | 0.08 | 0.96 | 0.15 | 0.66 | 0.49 | 0.62 | 1.69 | 1.25 |
| Q | 138G | −0.01 | −39.08 | −40.13 | 0.00 | −8.02 | −1.07 | −8.94 | −11.15 | −10.73 | −23.28 | −6.43 |
| Q | 138H | 0.15 | 3.98 | 5.02 | 0.05 | 2.42 | 0.47 | 1.48 | 0.91 | 1.17 | 3.63 | 2.39 |
| Q | 138I | −0.05 | −1.80 | −42.10 | −0.01 | −1.83 | −0.23 | −2.06 | −2.55 | −2.26 | −5.21 | −0.92 |
| Q | 138K | −0.09 | 2.74 | −54.67 | −0.02 | −1.13 | −0.10 | −1.30 | −1.60 | −1.56 | −3.43 | −0.94 |
| Q | 138L | −0.09 | 1.93 | −18.97 | −0.02 | −1.12 | −0.20 | −1.41 | −1.70 | −1.12 | −3.20 | −1.74 |
| Q | 138N | 0.33 | 2.08 | 1.07 | 0.09 | 0.47 | 0.00 | 0.31 | 0.35 | 0.42 | 1.02 | 0.28 |
| Q | 138P | 0.01 | 8.56 | 117.42 | 0.00 | 9.44 | 1.64 | 10.73 | 13.55 | 12.91 | 27.97 | 1.25 |
| Q | 138R | 0.12 | −0.36 | 7.27 | 0.03 | 1.16 | 0.06 | 1.02 | 1.18 | 1.14 | 3.16 | 1.53 |
| Q | 138S | −0.08 | −0.73 | 4.86 | −0.02 | −1.76 | −0.19 | −1.51 | −1.69 | −1.62 | −3.59 | −0.89 |
| Q | 138T | −0.08 | −7.76 | −1.14 | −0.02 | −2.61 | −0.23 | −1.88 | −1.87 | −1.89 | −5.20 | −2.56 |
| Q | 138W | 0.19 | 1.73 | 7.13 | 0.06 | 2.26 | 0.65 | 1.54 | 0.77 | 1.15 | 3.60 | 2.67 |
| Q | 138Y | 0.15 | 2.40 | −7.60 | 0.04 | 2.08 | 0.31 | 1.39 | 0.99 | 1.34 | 3.37 | 2.44 |
| N | 139A | 0.08 | 6.47 | 7.53 | 0.03 | 3.22 | 0.49 | 1.98 | 1.42 | 2.60 | 5.75 | 1.62 |
| N | 139C | 0.26 | 2.20 | 1.41 | 0.11 | 1.96 | 0.90 | 1.34 | 0.55 | 1.36 | 2.48 | 1.73 |
| N | 139D | −0.13 | −4.42 | −4.91 | −0.03 | −0.78 | −0.06 | −0.81 | −0.92 | −1.10 | −2.60 | 2.05 |
| N | 139E | −0.17 | −4.31 | −6.89 | −0.04 | −0.67 | −0.05 | −0.63 | −0.69 | −0.88 | −1.74 | 1.82 |
| N | 139G | 0.14 | 4.00 | 2.31 | 0.05 | 3.85 | 1.79 | 2.56 | 0.88 | 2.99 | 5.69 | 4.63 |
| N | 139H | 0.25 | 2.01 | 0.68 | 0.11 | 2.27 | 1.05 | 1.46 | 0.59 | 1.47 | 3.13 | 1.73 |
| N | 139I | −0.16 | −1.25 | 2.13 | −0.03 | −0.57 | −0.02 | −0.62 | −0.73 | −0.83 | −1.79 | 1.17 |
| N | 139K | 0.00 | −1692.57 | −615.79 | 0.00 | −1468.94 | −451.47 | −943.25 | −505.63 | −1031.39 | −2503.30 | −1092.35 |
| N | 139L | 0.42 | 1.29 | 2.73 | 0.20 | 1.47 | 0.92 | 1.07 | 0.34 | 1.21 | 1.95 | 1.51 |
| N | 139M | 0.45 | 1.55 | 1.02 | 0.26 | 1.49 | 0.97 | 1.02 | 0.28 | 1.32 | 1.78 | 1.46 |
| N | 139P | −0.11 | −4.83 | 2.62 | −0.02 | −0.89 | −0.07 | −0.98 | −1.15 | −1.36 | −2.84 | 2.20 |
| N | 139R | 0.00 | −137.90 | 106.42 | 0.00 | −96.85 | −24.60 | −62.95 | −51.01 | −76.80 | −178.05 | −25.70 |
| N | 139S | 0.23 | 1.81 | 10.27 | 0.09 | 2.37 | 1.28 | 1.61 | 0.55 | 2.03 | 3.20 | 3.01 |
| N | 139T | −0.15 | −2.49 | 2.72 | −0.03 | −0.99 | −0.12 | −0.80 | −0.80 | −1.06 | −2.43 | 0.98 |
| N | 139V | −0.16 | 0.34 | −13.25 | −0.03 | −0.60 | −0.06 | −0.65 | −0.77 | −0.92 | −2.02 | 1.66 |
| N | 139W | −0.25 | −0.43 | −3.33 | −0.06 | −0.43 | −0.10 | −0.42 | −0.47 | −0.56 | −1.27 | 0.89 |
| N | 139Y | −0.01 | −27.22 | −25.18 | 0.00 | −28.78 | −7.95 | −18.34 | −11.16 | −20.70 | −49.54 | −3.47 |
| S | 140A | 0.62 | 1.09 | 1.14 | 0.38 | 1.13 | 0.83 | 0.72 | 0.45 | 0.81 | 1.40 | 1.34 |
| S | 140C | 0.06 | 5.90 | 14.25 | 0.02 | 4.14 | 0.39 | 2.23 | 1.91 | 2.49 | 7.74 | 0.98 |
| S | 140D | −0.11 | −4.57 | −0.34 | −0.02 | −0.86 | −0.11 | −0.95 | −1.11 | −1.34 | −2.89 | 1.51 |
| S | 140E | −0.05 | −4.04 | −5.72 | −0.01 | −1.92 | −0.24 | −2.10 | −2.45 | −2.88 | −5.96 | 5.12 |
| S | 140F | 0.25 | 1.30 | 5.94 | 0.05 | 0.35 | −0.01 | 0.39 | 0.46 | 0.54 | 1.45 | −0.80 |
| S | 140G | 0.13 | 2.73 | −1.04 | 0.04 | 2.99 | 0.72 | 1.58 | 1.03 | 1.84 | 5.10 | 3.17 |
| S | 140H | −0.19 | −0.81 | −1.85 | −0.04 | −0.53 | −0.06 | −0.54 | −0.63 | −0.74 | −1.46 | 1.36 |
| S | 140I | −0.18 | −1.75 | −11.39 | −0.03 | −0.53 | −0.05 | −0.57 | −0.66 | −0.77 | −1.78 | 1.26 |
| S | 140K | −0.19 | 0.22 | 5.92 | −0.04 | −0.46 | 0.00 | −0.51 | −0.59 | −0.70 | −1.52 | 1.20 |
| S | 140L | −0.18 | 0.25 | −4.57 | −0.04 | −0.54 | −0.09 | −0.60 | −0.68 | −0.84 | −1.63 | 0.91 |
| S | 140M | −0.07 | −9.84 | 7.17 | −0.02 | −1.77 | −0.11 | −1.50 | −1.67 | −2.10 | −4.52 | 2.18 |
| S | 140N | −0.09 | −8.81 | 2.92 | −0.02 | −1.40 | −0.12 | −1.22 | −1.38 | −1.69 | −4.24 | 2.07 |
| S | 140P | −0.26 | −1.16 | 0.71 | −0.05 | −0.36 | −0.06 | −0.38 | −0.47 | −0.54 | −1.14 | 0.95 |
| S | 140Q | −0.14 | −1.59 | −2.09 | −0.02 | −0.69 | −0.12 | −0.74 | −0.86 | −1.03 | −2.57 | 1.13 |
| S | 140R | −0.14 | −0.19 | 4.03 | −0.03 | −0.73 | −0.12 | −0.76 | −0.89 | −1.07 | −2.66 | 1.02 |
| S | 140T | −0.03 | −8.00 | 17.42 | −0.01 | −5.93 | 0.11 | −3.03 | −3.38 | −3.87 | −16.89 | 1.08 |
| S | 140V | −0.18 | −0.98 | 2.81 | −0.03 | −0.53 | −0.06 | −0.56 | −0.66 | −0.78 | −1.48 | 0.98 |
| S | 140W | −0.24 | 0.55 | −0.30 | −0.04 | −0.38 | −0.02 | −0.41 | −0.48 | −0.56 | −1.06 | 0.96 |
| S | 140Y | 0.42 | −0.21 | −2.03 | 0.09 | 0.22 | 0.03 | 0.25 | 0.28 | 0.35 | 0.70 | −0.49 |
| L | 141A | 0.46 | 1.62 | 17.49 | 0.14 | 0.41 | −0.06 | 0.24 | 0.28 | 0.29 | 1.03 | 0.38 |
| L | 141C | 0.63 | 1.26 | 7.96 | 0.18 | 0.30 | −0.02 | 0.18 | 0.20 | 0.20 | 0.64 | 0.12 |
| L | 141D | 0.75 | 1.01 | −8.08 | 0.20 | 0.21 | −0.02 | 0.14 | 0.17 | 0.16 | 0.40 | 0.11 |
| L | 141E | 0.43 | 1.98 | 21.12 | 0.10 | 0.32 | −0.04 | 0.24 | 0.29 | 0.28 | 0.68 | 0.14 |
| L | 141F | 0.88 | 1.18 | 2.78 | 1.04 | 1.08 | 0.26 | 0.28 | 0.22 | 0.18 | 1.10 | 0.84 |
| L | 141G | −0.01 | −31.94 | −1495.61 | 0.00 | −17.02 | −2.21 | −17.20 | −20.75 | −21.08 | −46.49 | −18.52 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| L | 141H | 0.72 | 0.58 | 0.02 | 0.19 | 0.32 | −0.01 | 0.17 | 0.17 | 0.17 | 1.09 | 0.80 |
| L | 141I | 0.97 | 0.53 | 1.49 | 0.47 | 0.57 | 0.04 | 0.23 | 0.23 | 0.21 | 0.84 | 0.55 |
| L | 141K | 0.81 | 0.32 | −0.51 | 0.19 | 0.17 | 0.00 | 0.15 | 0.17 | 0.19 | 0.42 | 0.09 |
| L | 141M | 0.97 | 0.79 | −4.61 | 0.87 | 0.75 | 0.12 | 0.26 | 0.15 | 0.17 | 0.95 | 0.74 |
| L | 141N | 0.75 | 1.02 | −11.49 | 0.19 | 0.18 | −0.04 | 0.14 | 0.17 | 0.16 | 0.53 | 0.04 |
| L | 141P | 0.42 | 0.72 | −9.43 | 0.16 | 0.87 | −0.02 | 0.27 | 0.30 | 0.34 | 1.74 | 0.81 |
| L | 141Q | 0.45 | 0.62 | 11.75 | 0.11 | 0.37 | −0.03 | 0.24 | 0.28 | 0.27 | 1.07 | 0.28 |
| L | 141R | 0.75 | 0.88 | 2.53 | 0.18 | 0.15 | −0.01 | 0.14 | 0.16 | 0.18 | 0.49 | 0.25 |
| L | 141S | 0.21 | 2.37 | 16.81 | 0.05 | 0.58 | 0.01 | 0.48 | 0.57 | 0.57 | 1.48 | 0.24 |
| L | 141T | 0.42 | 0.97 | −6.28 | 0.09 | 0.33 | 0.00 | 0.26 | 0.30 | 0.30 | 15.22 | 0.36 |
| L | 141V | 0.20 | 1.53 | 17.75 | 0.05 | 0.78 | −0.03 | 0.55 | 0.64 | 0.65 | 2.13 | 0.37 |
| L | 141W | 0.81 | 0.29 | 22.60 | 0.36 | 0.48 | −0.01 | 0.14 | 0.16 | 0.16 | 0.70 | 0.20 |
| L | 141Y | 0.77 | 0.53 | −4.50 | 0.51 | 0.85 | 0.09 | 0.20 | 0.20 | 0.20 | 1.03 | 0.45 |
| L | 144A | 1.17 | 0.36 | −0.58 | 0.40 | 0.21 | −0.01 | 0.11 | 0.13 | 0.16 | 0.66 | 0.09 |
| L | 144C | 0.97 | 0.57 | 3.05 | 0.43 | 0.44 | 0.01 | 0.16 | 0.18 | 0.20 | 0.80 | 0.46 |
| L | 144D | 0.67 | 0.51 | −12.69 | 0.20 | 0.38 | −0.01 | 0.19 | 0.23 | 0.27 | 0.52 | 0.04 |
| L | 144E | 0.78 | 0.65 | 12.83 | 0.18 | 0.19 | −0.01 | 0.16 | 0.20 | 0.23 | 0.68 | 0.54 |
| L | 144F | 0.87 | 0.67 | 1.84 | 0.22 | 0.21 | −0.01 | 0.14 | 0.18 | 0.20 | 0.66 | 0.14 |
| L | 144G | 0.88 | 0.44 | 0.63 | 0.21 | 0.24 | −0.02 | 0.14 | 0.17 | 0.19 | 0.85 | 0.20 |
| L | 144H | 0.95 | 0.36 | 3.70 | 0.20 | 0.11 | −0.01 | 0.13 | 0.16 | 0.18 | 0.45 | 0.16 |
| L | 144I | −0.10 | −1.64 | −1.08 | −0.02 | −1.09 | −0.03 | −1.21 | −1.57 | −1.79 | −3.41 | −1.27 |
| L | 144K | 1.04 | 0.17 | −1.62 | 0.22 | 0.10 | 0.00 | 0.12 | 0.15 | 0.17 | 0.32 | 0.12 |
| L | 144N | 1.92 | 0.32 | 2.87 | 1.11 | 0.26 | 0.00 | 0.08 | 0.09 | 0.11 | 0.47 | 0.11 |
| L | 144P | 0.02 | 12.92 | −115.19 | 0.01 | 3.59 | 0.32 | 4.36 | 5.44 | 6.39 | 10.64 | 1.64 |
| L | 144Q | 1.10 | 0.62 | 4.05 | 0.25 | 0.09 | 0.00 | 0.11 | 0.14 | 0.16 | 0.43 | 0.23 |
| L | 144R | 1.20 | 0.17 | 1.47 | 0.29 | 0.09 | 0.01 | 0.10 | 0.13 | 0.15 | 0.25 | 0.03 |
| L | 144S | 1.02 | 0.51 | −0.66 | 0.25 | 0.24 | −0.01 | 0.13 | 0.15 | 0.17 | 0.84 | 0.29 |
| L | 144T | 1.00 | 0.97 | −0.52 | 0.86 | 0.77 | 0.05 | 0.19 | 0.17 | 0.19 | 0.99 | 0.52 |
| L | 144V | 0.33 | 0.97 | −8.16 | 0.08 | 0.65 | −0.03 | 0.40 | 0.49 | 0.56 | 1.64 | 0.58 |
| L | 144W | 0.50 | 0.60 | −6.22 | 0.10 | 0.21 | −0.01 | 0.25 | 0.30 | 0.36 | 0.82 | 0.16 |
| L | 144Y | 1.08 | −0.03 | −4.56 | 0.26 | 0.10 | 0.00 | 0.12 | 0.14 | 0.17 | 0.31 | 0.05 |
| Y | 145A | −0.13 | −6.42 | −4.92 | −0.03 | −0.98 | −0.04 | −0.89 | −1.11 | −1.13 | −2.87 | −0.70 |
| Y | 145C | −0.12 | −4.87 | −16.98 | −0.03 | −1.32 | −0.05 | −1.00 | −1.12 | −1.19 | −3.10 | −1.09 |
| Y | 145D | −0.16 | −1.32 | −4.18 | −0.03 | −0.64 | 0.01 | −0.70 | −0.91 | −0.86 | −1.86 | −0.08 |
| Y | 145G | −0.20 | −2.05 | −9.54 | −0.03 | −0.51 | −0.06 | −0.55 | −0.71 | −0.66 | −1.39 | −0.32 |
| Y | 145H | 0.03 | 10.68 | 30.72 | 0.01 | 14.73 | 3.49 | 8.10 | 5.02 | 5.63 | 20.12 | 9.97 |
| Y | 145I | −0.18 | −0.74 | −4.21 | −0.04 | −0.78 | −0.11 | −0.66 | −0.80 | −0.83 | −1.80 | −0.22 |
| Y | 145K | −0.25 | 0.23 | −4.53 | −0.04 | −0.40 | −0.03 | −0.43 | −0.56 | −0.54 | −1.22 | −2.03 |
| Y | 145L | −0.14 | −0.58 | −17.70 | −0.03 | −1.79 | −0.22 | −1.10 | −1.03 | −1.31 | −3.07 | −1.52 |
| Y | 145M | 0.00 | 113.96 | −94.83 | 0.00 | 68.53 | 7.44 | 38.40 | 32.75 | 44.42 | 109.49 | 38.82 |
| Y | 145N | −0.12 | −8.65 | −6.43 | −0.03 | −1.17 | −0.03 | −0.99 | −1.18 | −1.19 | −2.78 | −0.61 |
| Y | 145Q | −0.14 | −4.44 | −12.50 | −0.03 | −0.91 | −0.04 | −0.84 | −1.04 | −1.00 | −2.31 | 0.04 |
| Y | 145R | −0.20 | 0.63 | −2.02 | −0.05 | −0.53 | −0.04 | −0.53 | −0.67 | −0.63 | −1.44 | −0.49 |
| Y | 145S | −0.20 | −1.89 | −5.65 | −0.04 | −0.66 | −0.11 | −0.54 | −0.67 | −0.65 | −1.45 | −0.25 |
| Y | 145T | −0.27 | 0.63 | 0.10 | −0.06 | −0.41 | −0.05 | −0.39 | −0.43 | −0.48 | −1.04 | −0.41 |
| Y | 145V | −0.25 | 0.51 | −1.11 | −0.05 | −0.44 | −0.07 | −0.44 | −0.55 | −0.54 | −0.94 | −0.02 |
| Y | 145W | 1.26 | 0.73 | −0.40 | 1.37 | 0.84 | 0.99 | 0.80 | 0.90 | 0.89 | 0.83 | 0.76 |
| D | 146A | 0.19 | 2.78 | 14.95 | 0.05 | 0.95 | −0.01 | 0.58 | 0.69 | 0.78 | 1.55 | −1.57 |
| D | 146C | −0.08 | −9.23 | −40.90 | −0.03 | −1.23 | −0.11 | −1.38 | −1.62 | −1.96 | −4.09 | 2.81 |
| D | 146E | 0.24 | 1.80 | 14.96 | 0.07 | 1.18 | 0.31 | 0.80 | 0.55 | 0.88 | 2.01 | −0.16 |
| D | 146F | 0.04 | 5.17 | 10.92 | 0.01 | 2.10 | 0.30 | 2.50 | 2.95 | 3.39 | 5.99 | −7.27 |
| D | 146G | 0.00 | 384.58 | 2399.35 | 0.00 | 72.60 | −0.11 | 69.80 | 80.42 | 91.80 | 204.04 | −71.10 |
| D | 146H | −0.03 | −3.36 | −44.75 | −0.01 | −3.21 | −0.31 | −3.75 | −4.60 | −4.86 | −10.09 | 8.06 |
| D | 146I | −0.11 | 1.33 | −27.11 | −0.02 | −0.88 | −0.20 | −1.04 | −1.25 | −1.44 | −2.92 | 3.10 |
| D | 146K | −0.04 | −2.31 | −24.61 | −0.01 | −2.16 | −0.25 | −2.60 | −3.15 | −3.64 | −8.03 | 5.86 |
| D | 146L | 0.05 | 0.25 | 87.38 | 0.01 | 1.81 | 0.11 | 2.42 | 2.88 | 0.06 | 5.68 | −5.87 |
| D | 146M | 0.14 | 1.78 | 12.75 | 0.03 | 0.67 | 0.02 | 0.80 | 0.98 | 1.16 | 1.82 | −2.14 |
| D | 146N | 0.03 | 15.60 | 63.98 | 0.01 | 2.92 | 0.54 | 3.32 | 4.02 | 4.55 | 9.41 | −6.44 |
| D | 146P | −0.02 | 2.26 | −68.00 | 0.00 | −5.23 | −0.39 | −5.98 | −7.18 | −8.38 | −16.77 | 14.39 |
| D | 146Q | −0.03 | −8.02 | −67.05 | −0.01 | −2.67 | −0.42 | −3.08 | −3.79 | −4.11 | −8.11 | 7.26 |
| D | 146S | 0.02 | 2.44 | 69.42 | 0.00 | 6.72 | 0.89 | 5.95 | 6.83 | 7.70 | 16.58 | −13.72 |
| D | 146T | 0.05 | 1.73 | −17.53 | 0.01 | 1.86 | 0.22 | 2.12 | 2.55 | 2.73 | 5.43 | −4.71 |
| D | 146V | 0.01 | −1.24 | 101.10 | 0.00 | 13.34 | 1.15 | 14.31 | 17.14 | 18.74 | 37.55 | −44.06 |
| D | 146W | −0.05 | −1.68 | 30.41 | −0.01 | −1.77 | −0.73 | −2.12 | −2.61 | −2.89 | −5.47 | 0.19 |
| D | 146Y | −0.03 | −3.34 | −61.70 | −0.01 | −3.52 | −0.61 | −4.39 | −5.14 | −6.43 | −10.15 | 9.32 |
| W | 147C | 0.08 | 6.91 | 11.92 | 0.02 | 2.26 | 0.19 | 1.81 | 1.74 | 2.35 | 4.69 | 2.77 |
| W | 147D | −0.01 | −38.35 | −174.41 | 0.00 | −9.22 | −1.70 | −10.87 | −12.67 | −15.24 | −25.15 | −8.17 |
| W | 147E | −0.04 | 0.35 | −46.16 | −0.01 | −2.52 | −0.37 | −3.02 | −3.52 | −4.34 | −7.38 | 0.10 |
| W | 147F | 0.70 | 1.31 | 1.05 | 0.53 | 1.19 | 1.08 | 1.12 | 0.75 | 0.96 | 1.30 | 1.16 |
| W | 147G | −0.19 | −1.69 | 4.18 | −0.04 | −0.53 | −0.05 | −0.60 | −0.70 | −0.80 | −1.37 | −0.50 |
| W | 147H | 0.18 | 0.80 | −1.30 | 0.07 | 2.84 | 1.56 | 1.90 | 1.64 | 2.45 | 3.74 | 2.26 |
| W | 147I | 0.24 | 0.96 | −3.97 | 0.09 | 2.08 | 0.63 | 1.36 | 0.86 | 1.25 | 2.95 | 2.57 |
| W | 147K | −0.12 | −0.05 | −2.62 | −0.03 | −1.00 | −0.16 | −1.06 | −1.20 | −1.39 | −2.91 | −0.66 |
| W | 147L | 0.61 | 1.19 | −1.31 | 0.48 | 1.46 | 0.99 | 1.21 | 0.54 | 1.01 | 1.53 | 1.31 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| W | 147N | 0.33 | 0.99 | 6.14 | 0.13 | 1.45 | 0.47 | 0.93 | 0.56 | 1.04 | 1.88 | 1.39 |
| W | 147I | 0.08 | 3.88 | 18.47 | 0.02 | 1.31 | 0.21 | 1.59 | 1.82 | 2.27 | 3.96 | 1.04 |
| W | 147Q | 0.01 | 76.69 | 97.52 | 0.00 | 38.37 | 5.05 | 26.49 | 23.40 | 34.80 | 63.43 | 20.56 |
| W | 147S | −0.05 | −3.13 | −10.13 | −0.01 | −3.41 | −0.31 | −2.92 | −3.03 | −3.61 | −6.83 | −1.86 |
| W | 147T | −0.04 | −1.66 | −17.15 | −0.01 | −5.68 | −0.38 | −3.99 | −3.88 | −5.06 | −10.80 | −3.99 |
| W | 147V | 0.05 | 3.58 | −6.21 | 0.01 | 5.48 | 0.39 | 3.63 | 3.11 | 4.10 | 10.57 | 6.12 |
| W | 147Y | 0.12 | 1.37 | −3.10 | 0.04 | 4.37 | 1.62 | 2.51 | 1.55 | 2.41 | 5.42 | 3.12 |
| N | 148A | 0.29 | 1.51 | 16.38 | 0.19 | 2.12 | 1.20 | 1.39 | 0.93 | 1.47 | 2.24 | 2.01 |
| N | 148C | 0.35 | 1.30 | 8.71 | 0.20 | 1.71 | 0.96 | 1.25 | 1.05 | 1.28 | 1.67 | 1.68 |
| N | 148D | −0.17 | −3.53 | −6.38 | −0.04 | −1.37 | −0.17 | −0.93 | −0.88 | −1.12 | −4.28 | −1.47 |
| N | 148E | −0.07 | −7.87 | −32.69 | −0.02 | −2.62 | −0.29 | −1.86 | −1.86 | −2.24 | −8.91 | −2.36 |
| N | 148F | 0.07 | 6.13 | 38.63 | 0.03 | 5.17 | 2.06 | 3.39 | 3.76 | 3.55 | 8.95 | 5.63 |
| N | 148G | −0.11 | −3.33 | 12.87 | −0.03 | −2.51 | −0.53 | −1.68 | −1.81 | −1.87 | −3.92 | −2.26 |
| N | 148H | 0.31 | 1.65 | 15.86 | 0.15 | 2.11 | 1.27 | 1.57 | 1.54 | 1.67 | 2.78 | 2.42 |
| N | 148K | 0.09 | 3.80 | 19.15 | 0.03 | 5.16 | 1.80 | 3.20 | 2.32 | 3.46 | 8.47 | 6.16 |
| N | 148M | 0.07 | 6.29 | 71.15 | 0.03 | 4.94 | 1.38 | 2.99 | 2.33 | 3.48 | 6.80 | 3.70 |
| N | 148P | −0.20 | −1.68 | −16.35 | −0.04 | −0.49 | −0.10 | −0.54 | −0.68 | −0.69 | −3.04 | −0.66 |
| N | 148Q | −0.01 | −15.34 | −152.77 | −0.01 | −16.16 | −4.28 | −10.14 | −8.85 | −11.50 | −27.18 | −11.56 |
| N | 148R | 0.17 | 2.28 | 1.62 | 0.06 | 2.55 | 1.14 | 1.73 | 1.39 | 1.85 | 3.58 | 3.06 |
| N | 148T | −0.06 | −3.23 | −18.41 | −0.02 | −5.01 | −1.56 | −3.33 | −3.41 | −4.33 | −7.53 | −4.35 |
| N | 148V | −0.30 | −0.88 | 0.80 | −0.06 | −0.35 | −0.04 | −0.40 | −0.49 | −0.57 | −1.20 | −0.26 |
| N | 148W | −0.07 | −4.10 | −17.98 | −0.02 | −4.25 | −1.06 | −2.76 | −2.49 | −3.06 | −6.44 | −4.97 |
| N | 148Y | 0.06 | 4.58 | 79.23 | 0.03 | 8.37 | 4.14 | 5.67 | 5.26 | 6.49 | 9.98 | 8.30 |
| T | 149A | −0.11 | −3.52 | −3.34 | −0.02 | −0.87 | −0.05 | −0.99 | −1.28 | −1.33 | −2.68 | 0.80 |
| T | 149C | −0.20 | −0.60 | 1.81 | −0.04 | −0.49 | −0.09 | −0.53 | −0.67 | −0.66 | −1.40 | −0.54 |
| T | 149D | −0.24 | −0.83 | 2.21 | −0.06 | −0.40 | −0.06 | −0.44 | −0.56 | −0.55 | −1.07 | −0.64 |
| T | 149E | −0.25 | −0.22 | 0.82 | −0.05 | −0.39 | −0.06 | −0.42 | −0.54 | −0.53 | −1.20 | −0.38 |
| T | 149F | −0.28 | −1.12 | 1.14 | −0.06 | −0.35 | −0.05 | −0.37 | −0.48 | −0.46 | −0.97 | −0.53 |
| T | 149G | −0.24 | 0.90 | −0.36 | −0.05 | −0.41 | −0.05 | −0.45 | −0.57 | −0.52 | −1.24 | −0.07 |
| T | 149H | −0.23 | 0.18 | 1.19 | −0.04 | −0.44 | −0.05 | −0.47 | −0.60 | −0.60 | −1.24 | −0.25 |
| T | 149I | −0.26 | 1.55 | −3.24 | −0.05 | −0.37 | −0.04 | −0.39 | −0.52 | −0.49 | −0.90 | −0.35 |
| T | 149K | −0.26 | −0.27 | −1.10 | −0.05 | −0.37 | −0.04 | −0.42 | −0.54 | −0.54 | −0.97 | −0.41 |
| T | 149L | −0.20 | 0.46 | −3.02 | −0.04 | −0.48 | −0.05 | −0.56 | −0.71 | −0.74 | −1.21 | −0.27 |
| T | 149M | −0.07 | −1.09 | 0.75 | −0.02 | −1.25 | −0.16 | −1.44 | −1.86 | −1.98 | −3.18 | −0.44 |
| T | 149N | −0.27 | −3.89 | 3.55 | −0.05 | −0.36 | −0.04 | −0.40 | −0.52 | −0.56 | −0.99 | −0.10 |
| T | 149P | −0.13 | −1.07 | 3.21 | −0.02 | −0.76 | −0.21 | −0.87 | −1.11 | −1.15 | −2.29 | −0.28 |
| T | 149Q | −0.16 | 0.66 | 0.07 | −0.03 | −0.63 | −0.12 | −0.70 | −0.90 | −0.91 | −1.90 | −0.63 |
| T | 149R | −0.16 | 0.47 | 1.83 | −0.03 | −0.62 | −0.15 | −0.70 | −0.90 | −0.88 | −1.69 | −0.24 |
| T | 149S | 0.28 | 2.33 | −1.31 | 0.14 | 2.50 | 1.47 | 1.75 | 1.06 | 1.72 | 3.02 | 2.24 |
| T | 149V | −0.16 | 1.07 | −0.15 | −0.03 | −0.62 | −0.12 | −0.71 | −0.90 | −0.89 | −1.90 | −0.29 |
| T | 149W | −0.23 | −0.33 | −0.36 | −0.05 | −0.42 | −0.05 | −0.48 | −0.60 | −0.61 | −1.04 | −0.29 |
| Q | 150A | 0.39 | 1.84 | 0.30 | 0.24 | 1.69 | 0.90 | 1.14 | 0.33 | 1.31 | 2.01 | 1.06 |
| Q | 150C | −0.12 | −4.46 | −0.84 | −0.03 | −1.82 | −0.26 | −1.19 | −1.01 | −1.53 | −3.39 | 0.46 |
| Q | 150D | −0.10 | −4.65 | 1.47 | −0.02 | −2.44 | −0.30 | −1.56 | −1.28 | −1.84 | −4.73 | 0.38 |
| Q | 150F | −0.23 | −1.49 | −1.69 | −0.04 | −0.67 | −0.07 | −0.51 | −0.51 | −0.72 | −1.80 | 0.78 |
| Q | 150H | 0.60 | 1.54 | 1.42 | 0.42 | 1.40 | 1.08 | 1.09 | 0.35 | 1.04 | 1.64 | 1.61 |
| Q | 150I | −0.20 | −1.36 | −1.74 | −0.04 | −0.79 | −0.11 | −0.62 | −0.61 | −0.82 | −1.91 | 0.80 |
| Q | 150K | −0.10 | −4.28 | 28.87 | −0.02 | −3.46 | −0.89 | −2.03 | −1.23 | −2.51 | −5.91 | −1.99 |
| Q | 150L | −0.20 | 0.42 | 3.63 | −0.04 | −0.71 | −0.12 | −0.60 | −0.62 | −0.84 | −1.97 | 0.66 |
| Q | 150M | −0.04 | −16.10 | 17.66 | −0.01 | −5.54 | −0.60 | −3.41 | −2.92 | −4.62 | −12.01 | 2.54 |
| Q | 150N | 0.10 | 5.08 | 6.93 | 0.03 | 4.27 | 1.19 | 2.32 | 1.19 | 2.65 | 6.26 | 1.47 |
| Q | 150P | −0.08 | −5.89 | 13.05 | −0.02 | −1.39 | −0.19 | −1.37 | −1.55 | −1.87 | −4.06 | 1.77 |
| Q | 150S | 0.16 | 3.60 | −1.85 | 0.06 | 3.72 | 1.57 | 2.21 | 0.78 | 2.44 | 4.75 | 2.91 |
| Q | 150T | −0.10 | −2.04 | 9.14 | −0.02 | −2.15 | −0.29 | −1.36 | −1.19 | −1.80 | −3.45 | −0.24 |
| Q | 150V | −0.12 | −1.50 | 10.98 | −0.02 | −1.70 | −0.24 | −1.12 | −1.01 | −1.45 | −3.42 | 0.55 |
| Q | 150W | −0.11 | −0.27 | −4.95 | −0.02 | −1.36 | −0.09 | −1.08 | −1.09 | −1.46 | −3.10 | 1.72 |
| Q | 150Y | −0.06 | −3.19 | 7.84 | −0.01 | −3.10 | −0.38 | −2.22 | −2.12 | −2.96 | −6.74 | 1.70 |
| N | 151A | 0.87 | 1.04 | 0.55 | 0.86 | 1.10 | 0.95 | 0.90 | 0.45 | 0.91 | 1.06 | 0.87 |
| N | 151C | 0.62 | 1.28 | 2.44 | 0.48 | 1.30 | 1.04 | 1.01 | 0.67 | 1.01 | 1.60 | 1.15 |
| N | 151D | 0.84 | 1.13 | 1.89 | 0.77 | 1.10 | 0.93 | 0.87 | 0.60 | 0.90 | 1.21 | 1.25 |
| N | 151E | 0.89 | 1.06 | 0.53 | 0.76 | 1.05 | 0.86 | 0.86 | 0.61 | 0.87 | 0.97 | 1.07 |
| N | 151F | 0.27 | 1.85 | 1.56 | 0.09 | 1.70 | 0.63 | 0.95 | 0.73 | 1.07 | 2.31 | 1.31 |
| N | 151G | 0.47 | 1.27 | 2.68 | 0.25 | 1.45 | 0.87 | 0.95 | 0.71 | 0.99 | 1.66 | 1.52 |
| N | 151H | 0.48 | 1.41 | 1.97 | 0.30 | 1.49 | 1.04 | 1.08 | 0.89 | 1.06 | 1.85 | 1.26 |
| N | 151I | 0.38 | 1.54 | −0.58 | 0.22 | 1.71 | 1.16 | 1.24 | 0.92 | 1.27 | 2.09 | 1.91 |
| N | 151K | 0.54 | 1.09 | 4.63 | 0.33 | 1.39 | 0.99 | 0.97 | 0.71 | 0.97 | 1.76 | 1.27 |
| N | 151L | 0.60 | 1.15 | 1.77 | 0.48 | 1.38 | 1.20 | 1.08 | 0.67 | 1.12 | 1.50 | 1.53 |
| N | 151M | 0.62 | 1.23 | 1.05 | 0.46 | 1.24 | 0.96 | 0.95 | 0.69 | 0.97 | 1.49 | 1.10 |
| N | 151P | 0.04 | 18.05 | 8.53 | 0.01 | 3.20 | 0.24 | 2.84 | 3.26 | 4.24 | 8.28 | −2.03 |
| N | 151Q | 0.65 | 1.16 | 2.77 | 0.43 | 1.20 | 0.90 | 0.96 | 0.94 | 1.02 | 1.40 | 1.27 |
| N | 151R | 0.29 | 1.58 | 3.55 | 0.14 | 2.00 | 1.15 | 1.33 | 1.30 | 1.38 | 2.52 | 1.72 |
| N | 151S | 0.83 | 1.15 | 2.93 | 0.75 | 1.10 | 1.04 | 1.03 | 0.96 | 1.02 | 1.10 | 1.01 |
| N | 151T | 0.48 | 1.14 | 1.46 | 0.29 | 1.40 | 0.92 | 1.00 | 0.97 | 1.04 | 1.74 | 1.38 |
| N | 151V | 0.37 | 1.61 | −0.71 | 0.21 | 1.81 | 1.25 | 1.40 | 1.20 | 1.37 | 2.20 | 2.05 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| N | 151W | 0.04 | 8.21 | 49.30 | 0.01 | 6.36 | 1.58 | 4.17 | 4.03 | 5.14 | 11.22 | 1.12 |
| N | 151Y | 0.13 | 1.96 | −19.36 | 0.05 | 3.26 | 1.27 | 1.97 | 1.39 | 2.19 | 5.07 | 2.56 |
| V | 154A | 0.60 | 1.03 | 1.95 | 0.38 | 1.02 | 0.65 | 0.76 | 0.54 | 0.77 | 1.40 | 0.67 |
| V | 154C | 0.41 | 1.39 | 1.97 | 0.20 | 1.24 | 0.68 | 0.89 | 0.81 | 0.93 | 1.79 | 1.46 |
| V | 154D | −0.07 | −2.11 | 6.57 | −0.01 | −1.39 | 0.06 | −1.58 | −1.95 | −2.14 | −3.80 | 3.30 |
| V | 154E | −0.08 | 0.86 | 2.97 | −0.02 | −1.19 | −0.16 | −1.40 | −1.66 | −1.98 | −3.77 | 3.57 |
| V | 154G | −0.04 | −8.46 | 6.33 | −0.01 | −4.95 | −0.75 | −3.73 | −4.11 | −4.75 | −11.09 | 1.92 |
| V | 154H | 0.05 | 1.16 | −20.05 | 0.01 | 2.00 | 0.15 | 2.33 | 2.85 | 3.32 | 5.94 | −5.77 |
| V | 154I | 0.27 | 1.91 | −1.94 | 0.10 | 1.91 | 0.93 | 1.22 | 1.04 | 1.26 | 2.60 | 1.68 |
| V | 154K | −0.09 | −2.69 | 9.12 | −0.02 | −1.11 | −0.28 | −1.31 | −1.58 | −1.87 | −3.28 | 2.27 |
| V | 154L | 0.03 | 7.02 | 20.22 | 0.01 | 3.43 | 1.04 | 3.85 | 4.56 | 4.85 | 9.72 | −6.82 |
| V | 154N | 0.11 | 4.89 | 6.71 | 0.03 | 1.12 | −0.01 | 1.04 | 1.18 | 1.40 | 3.03 | −2.35 |
| V | 154P | 0.11 | 4.79 | 7.21 | 0.03 | 1.29 | 0.13 | 1.11 | 1.25 | 1.57 | 3.39 | −1.25 |
| V | 154Q | 0.06 | 2.92 | 23.99 | 0.01 | 1.79 | 0.07 | 1.96 | 2.35 | 2.42 | 5.03 | −4.08 |
| V | 154R | 0.03 | 8.79 | −12.66 | 0.01 | 3.54 | 0.87 | 4.13 | 5.08 | 6.01 | 12.55 | −8.23 |
| V | 154S | 0.24 | 1.71 | 7.20 | 0.07 | 1.67 | 0.53 | 1.02 | 0.89 | 1.15 | 2.77 | 1.51 |
| V | 154T | 0.44 | 1.01 | −2.18 | 0.20 | 1.37 | 0.70 | 0.91 | 0.73 | 0.92 | 1.59 | 1.38 |
| V | 154W | −0.02 | −3.72 | 82.69 | 0.00 | −4.66 | −0.57 | −5.34 | −6.56 | −7.90 | −14.32 | 15.20 |
| V | 154Y | 0.15 | 2.42 | −8.25 | 0.04 | 2.82 | 0.49 | 1.54 | 1.18 | 1.65 | 2.86 | −0.37 |
| Q | 155A | 0.40 | 1.15 | 2.30 | 0.23 | 1.55 | 0.97 | 1.13 | 0.67 | 1.16 | 2.01 | 1.59 |
| Q | 155C | 0.38 | 1.11 | 4.61 | 0.19 | 1.43 | 0.87 | 1.09 | 0.92 | 1.12 | 2.09 | 1.48 |
| Q | 155D | −0.18 | −2.84 | −9.57 | −0.04 | −0.90 | −0.09 | −0.76 | −0.88 | −1.05 | −2.17 | −0.77 |
| Q | 155E | 0.50 | 1.08 | 3.25 | 0.24 | 1.16 | 0.72 | 0.85 | 0.93 | 0.95 | 1.43 | 1.08 |
| Q | 155F | 0.16 | 1.96 | 9.92 | 0.06 | 2.79 | 1.24 | 1.85 | 1.89 | 2.05 | 3.95 | 2.75 |
| Q | 155G | 0.08 | 1.51 | 22.16 | 0.02 | 5.04 | 1.91 | 3.33 | 3.19 | 3.58 | 8.07 | 7.32 |
| Q | 155H | 0.22 | 2.18 | 6.93 | 0.09 | 2.71 | 1.53 | 1.96 | 1.59 | 1.90 | 3.41 | 2.91 |
| Q | 155I | 0.49 | 1.41 | 3.69 | 0.31 | 1.65 | 1.32 | 1.38 | 1.03 | 1.28 | 1.66 | 1.61 |
| Q | 155K | −0.01 | −27.72 | −155.83 | 0.00 | −34.45 | −10.37 | −22.44 | −21.51 | −26.69 | −58.72 | −45.56 |
| Q | 155L | 0.24 | 2.18 | 1.51 | 0.11 | 2.63 | 1.48 | 1.85 | 1.08 | 1.81 | 3.48 | 2.79 |
| Q | 155M | 0.57 | 1.23 | 3.22 | 0.46 | 1.33 | 1.07 | 1.12 | 0.73 | 1.09 | 1.54 | 1.33 |
| Q | 155N | 0.02 | 18.30 | 32.39 | 0.00 | 18.63 | 5.46 | 12.99 | 12.31 | 15.26 | 32.07 | 21.95 |
| Q | 155P | −0.18 | 0.21 | −11.62 | −0.04 | −0.57 | −0.06 | −0.63 | −0.76 | −0.95 | −1.67 | −0.53 |
| Q | 155T | 0.28 | 1.71 | 11.12 | 0.11 | 2.15 | 1.26 | 1.50 | 1.20 | 1.52 | 2.79 | 2.18 |
| Q | 155V | 0.42 | 1.52 | 7.70 | 0.24 | 1.85 | 1.33 | 1.46 | 1.15 | 1.39 | 2.09 | 2.02 |
| Q | 155W | 0.17 | 2.61 | 16.14 | 0.07 | 3.47 | 1.91 | 2.47 | 1.73 | 2.38 | 4.34 | 7.27 |
| L | 157A | 0.07 | 5.86 | 35.83 | 0.03 | 5.24 | 1.69 | 2.65 | 1.97 | 3.43 | 6.28 | 5.15 |
| L | 157C | 0.16 | 2.36 | −3.09 | 0.06 | 2.03 | 0.65 | 1.06 | 0.93 | 1.48 | 1.81 | 1.84 |
| L | 157D | −0.09 | −5.40 | −31.77 | −0.02 | −1.23 | −0.12 | −0.81 | −0.80 | −1.71 | −0.20 | −1.27 |
| L | 157E | −0.11 | −2.75 | −37.89 | −0.03 | −2.59 | −0.72 | −1.32 | −1.29 | −2.06 | −3.23 | −2.68 |
| L | 157F | 0.65 | 1.32 | 5.40 | 0.47 | 1.26 | 1.12 | 1.01 | 1.00 | 1.08 | 1.39 | 1.25 |
| L | 157G | −0.04 | −8.73 | −53.43 | −0.01 | −3.27 | −0.53 | −1.86 | −1.82 | −3.58 | −3.12 | −5.57 |
| L | 157H | 0.50 | 1.32 | −0.27 | 0.28 | 1.42 | 1.04 | 0.99 | 0.94 | 1.14 | 1.42 | 1.74 |
| L | 157I | 0.30 | 1.49 | 15.82 | 0.12 | 1.84 | 1.00 | 1.08 | 0.94 | 1.31 | 2.22 | 2.20 |
| L | 157K | 0.04 | 5.99 | 152.15 | 0.01 | 7.37 | 2.21 | 3.54 | 2.85 | 5.32 | 8.39 | 6.46 |
| L | 157L | 0.44 | 1.28 | 1.80 | 0.24 | 1.65 | 1.08 | 1.09 | 0.72 | 1.23 | 1.79 | 1.58 |
| L | 157M | 0.25 | 2.89 | 13.87 | 0.15 | 2.68 | 1.71 | 1.63 | 1.20 | 1.92 | 2.91 | 2.25 |
| L | 157N | −0.07 | −8.62 | −3.77 | −0.02 | −3.29 | −0.35 | −1.74 | −1.59 | −2.90 | −2.32 | −3.26 |
| L | 157P | −0.20 | −1.74 | −1.64 | −0.05 | −0.50 | −0.06 | −0.35 | −0.37 | −0.71 | −0.09 | −0.64 |
| L | 157Q | −0.07 | −5.21 | −29.11 | −0.02 | −3.84 | −1.01 | −2.07 | −2.02 | −3.09 | −4.23 | −2.52 |
| L | 157R | −0.10 | −3.95 | 9.58 | −0.02 | −2.98 | −0.81 | −1.45 | −1.39 | −1.96 | −2.72 | −2.26 |
| L | 157S | −0.08 | −3.68 | −20.11 | −0.02 | −2.96 | −0.55 | −1.51 | −1.50 | −2.47 | −3.25 | −2.40 |
| L | 157T | 0.13 | 2.90 | −4.60 | 0.04 | 3.50 | 1.59 | 1.89 | 1.84 | 2.43 | 4.09 | 3.99 |
| L | 157V | 0.17 | 2.90 | 15.94 | 0.06 | 3.02 | 1.68 | 1.78 | 1.63 | 2.25 | 3.51 | 3.34 |
| L | 157W | 0.03 | 9.22 | 68.50 | 0.01 | 10.79 | 4.50 | 5.64 | 4.28 | 7.56 | 13.55 | 12.21 |
| Y | 158A | 0.67 | 1.31 | −6.49 | 0.67 | 1.37 | 1.11 | 1.15 | 0.84 | 1.25 | 1.34 | 1.06 |
| Y | 158D | −0.18 | −2.33 | −3.67 | −0.04 | −0.77 | −0.08 | −0.51 | −0.52 | −0.94 | −0.30 | −0.62 |
| Y | 158E | −0.02 | −15.31 | 90.10 | −0.01 | −10.95 | −2.80 | −6.52 | −6.24 | −8.92 | −9.04 | −3.06 |
| Y | 158F | 0.24 | 3.07 | −10.60 | 0.11 | 2.46 | 1.20 | 1.68 | 1.45 | 1.48 | 2.79 | 2.21 |
| Y | 158G | 0.02 | 22.25 | 167.13 | 0.00 | 20.74 | 6.43 | 12.35 | 10.70 | 15.43 | 20.43 | 21.85 |
| Y | 158H | 0.26 | 2.28 | 8.54 | 0.13 | 2.39 | 1.34 | 1.82 | 1.73 | 1.70 | 2.74 | 4.78 |
| Y | 158I | 1.03 | 1.12 | −0.01 | 1.14 | 1.05 | 1.08 | 1.22 | 1.02 | 1.09 | 0.95 | 0.99 |
| Y | 158K | −0.10 | −3.43 | 3.85 | −0.02 | −2.67 | −0.28 | −1.39 | −1.17 | −1.99 | −2.21 | −1.52 |
| Y | 158M | 0.83 | 1.34 | −6.14 | 1.14 | 1.28 | 1.09 | 1.20 | 0.68 | 0.91 | 1.15 | 1.14 |
| Y | 158N | −0.09 | −4.38 | 3.40 | −0.03 | −3.20 | −0.55 | −1.74 | −1.31 | −2.33 | −2.61 | −2.32 |
| Y | 158P | −0.16 | −0.77 | −1.64 | −0.03 | −0.62 | −0.05 | −0.45 | −0.47 | −0.95 | 0.10 | −0.75 |
| Y | 158Q | 0.48 | 1.62 | 0.68 | 0.30 | 1.73 | 1.10 | 1.34 | 0.99 | 1.25 | 1.44 | 1.61 |
| Y | 158R | −0.14 | −0.18 | −8.36 | −0.03 | −0.72 | −0.07 | −0.52 | −0.51 | −1.07 | 0.63 | −0.16 |
| Y | 158S | 0.26 | 2.88 | 8.47 | 0.12 | 2.53 | 1.50 | 1.73 | 1.41 | 2.12 | 2.56 | 4.79 |
| Y | 158T | 0.75 | 1.41 | −0.57 | 0.74 | 1.37 | 1.21 | 1.31 | 1.00 | 1.31 | 1.13 | 0.99 |
| Y | 158V | 1.04 | 1.02 | 2.49 | 1.24 | 1.08 | 1.01 | 1.13 | 0.78 | 0.98 | 0.95 | 0.87 |
| Y | 158W | −0.01 | −14.27 | −96.43 | 0.00 | −15.83 | −1.23 | −7.58 | −5.95 | −11.77 | −11.91 | −45.44 |
| Y | 158Y | −0.12 | −1.24 | −26.12 | −0.02 | −1.41 | −0.08 | −0.80 | −0.69 | −1.48 | −0.75 | −0.23 |
| K | 159A | 0.43 | 1.93 | −2.56 | 0.30 | 1.72 | 1.22 | 1.25 | 0.98 | 1.28 | 1.77 | 1.46 |
| K | 159C | 0.37 | 1.62 | 5.48 | 0.22 | 1.76 | 1.16 | 1.34 | 1.29 | 1.33 | 2.03 | 1.83 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| K | 159D | 0.00 | −53.72 | 500.46 | 0.00 | −51.29 | −14.03 | −29.87 | −29.60 | −39.32 | −56.34 | −49.00 |
| K | 159E | 0.19 | 3.09 | 6.04 | 0.09 | 2.87 | 1.54 | 1.92 | 1.87 | 2.07 | 3.37 | 2.51 |
| K | 159F | 0.48 | 1.32 | 2.10 | 0.22 | 1.35 | 0.92 | 1.04 | 1.07 | 1.06 | 1.43 | 1.50 |
| K | 159G | 0.40 | 1.42 | 13.47 | 0.19 | 1.62 | 1.02 | 1.20 | 1.17 | 1.23 | 1.81 | 1.89 |
| K | 159H | 0.51 | 1.66 | 4.95 | 0.31 | 1.53 | 1.21 | 1.27 | 1.23 | 1.27 | 1.85 | 1.60 |
| K | 159I | 0.54 | 1.23 | 3.81 | 0.32 | 1.42 | 1.08 | 1.21 | 1.12 | 1.15 | 1.68 | 1.62 |
| K | 159L | 0.62 | 1.16 | 1.42 | 0.43 | 1.33 | 1.11 | 1.14 | 0.80 | 1.11 | 1.33 | 1.36 |
| K | 159M | 0.57 | 1.52 | −3.97 | 0.48 | 1.47 | 1.18 | 1.18 | 0.90 | 1.15 | 1.32 | 1.54 |
| K | 159N | 0.29 | 1.58 | 2.61 | 0.15 | 1.92 | 1.03 | 1.30 | 1.14 | 1.36 | 1.98 | 1.94 |
| K | 159P | −0.16 | −0.25 | 1.97 | −0.03 | −0.60 | −0.08 | −0.42 | −0.45 | −0.96 | −0.26 | −0.31 |
| K | 159R | 0.79 | 1.09 | 0.08 | 0.57 | 1.10 | 0.98 | 1.05 | 0.96 | 0.96 | 1.04 | 1.14 |
| K | 159S | 0.43 | 1.44 | 14.92 | 0.21 | 1.59 | 1.07 | 1.22 | 1.18 | 1.25 | 1.61 | 1.36 |
| K | 159T | 0.43 | 1.41 | 0.94 | 0.22 | 1.54 | 1.00 | 1.16 | 1.06 | 1.18 | 1.67 | 1.84 |
| K | 159V | 0.44 | 1.56 | 7.97 | 0.23 | 1.60 | 1.12 | 1.29 | 1.07 | 1.22 | 1.83 | 1.65 |
| K | 159W | 0.38 | 1.50 | 12.33 | 0.19 | 1.76 | 1.15 | 1.36 | 1.10 | 1.32 | 1.93 | 1.82 |
| K | 159Y | 0.43 | 1.38 | 8.10 | 0.24 | 1.77 | 1.26 | 1.34 | 0.98 | 1.39 | 1.83 | 1.65 |
| F | 161A | 0.41 | 1.55 | −0.98 | 0.23 | 1.54 | 0.79 | 0.95 | 0.51 | 1.03 | 1.77 | 1.77 |
| F | 161C | 0.20 | 2.50 | −3.01 | 0.08 | 1.88 | 0.54 | 1.05 | 0.72 | 1.19 | 2.36 | 3.16 |
| F | 161D | −0.45 | −0.29 | 4.30 | −0.09 | −0.24 | −0.02 | −0.16 | −0.19 | −0.39 | −0.15 | −0.16 |
| F | 161E | −0.02 | −31.91 | −29.44 | 0.00 | −8.98 | −0.85 | −5.62 | −5.76 | −11.21 | −8.75 | −14.37 |
| F | 161G | 0.27 | 2.30 | −3.36 | 0.11 | 2.00 | 0.91 | 1.20 | 0.83 | 1.38 | 2.75 | 3.16 |
| F | 161H | 0.48 | 1.10 | 3.65 | 0.19 | 1.03 | 0.50 | 0.61 | 0.56 | 0.79 | 1.42 | 1.75 |
| F | 161K | 0.15 | 1.51 | −4.74 | 0.04 | 1.45 | 0.27 | 0.89 | 0.83 | 2.03 | 1.72 | 1.50 |
| F | 161L | 0.16 | 2.07 | 5.24 | 0.05 | 2.85 | 0.87 | 1.43 | 1.27 | 1.90 | 2.68 | 2.18 |
| F | 161M | 0.34 | 1.84 | −3.35 | 0.20 | 1.86 | 1.07 | 1.24 | 0.90 | 1.18 | 1.81 | 1.63 |
| F | 161N | 0.10 | 4.68 | −3.63 | 0.04 | 3.14 | 0.88 | 1.87 | 1.58 | 2.42 | 4.01 | 4.64 |
| F | 161P | −0.14 | −2.15 | 10.65 | −0.04 | −1.12 | −0.08 | −0.57 | −0.67 | −1.31 | −0.68 | −2.24 |
| F | 161Q | −0.07 | −8.03 | −10.59 | −0.02 | −4.50 | −1.08 | −2.53 | −1.98 | −3.52 | −6.42 | −6.46 |
| F | 161R | −0.19 | −2.47 | −7.63 | −0.05 | −0.89 | −0.08 | −0.49 | −0.52 | −0.83 | −1.05 | −1.40 |
| F | 161S | 0.21 | 2.63 | −8.54 | 0.09 | 2.35 | 1.30 | 1.86 | 1.87 | 4.46 | 3.18 | 3.66 |
| F | 161T | −0.01 | −54.49 | −225.25 | 0.00 | −56.18 | −12.17 | −29.31 | −28.00 | −45.81 | −94.71 | −125.02 |
| F | 161Y | 1.05 | 0.63 | 3.17 | 0.99 | 0.94 | 0.85 | 0.79 | 0.63 | 0.81 | 0.79 | 0.69 |
| L | 162A | 0.33 | 1.73 | 33.27 | 0.19 | 1.64 | 0.60 | 1.00 | 0.69 | 0.90 | 1.65 | 0.87 |
| L | 162C | 0.42 | 1.34 | −12.54 | 0.30 | 1.67 | 1.03 | 1.15 | 0.90 | 1.02 | 2.01 | 1.56 |
| L | 162E | 0.08 | 4.61 | 118.03 | 0.03 | 3.54 | 0.71 | 2.12 | 2.04 | 2.10 | 5.57 | 1.22 |
| L | 162F | 0.34 | 1.78 | 104.94 | 0.19 | 1.89 | 0.67 | 1.10 | 0.78 | 0.66 | 1.95 | 1.12 |
| L | 162G | −0.03 | −27.86 | −1378.08 | 0.00 | −8.82 | −1.39 | −6.36 | −7.04 | −7.49 | −14.37 | 1.75 |
| L | 162H | 0.02 | 12.78 | 913.53 | 0.01 | 9.88 | 1.92 | 6.14 | 6.01 | 5.73 | 17.70 | 0.92 |
| L | 162I | 0.54 | 1.31 | 77.34 | 0.40 | 1.45 | 0.98 | 1.08 | 0.87 | 1.06 | 1.65 | 1.58 |
| L | 162K | −0.09 | −0.66 | −172.44 | −0.02 | −1.58 | −1.16 | −2.46 | −2.26 | −12.95 | −3.64 | 1.71 |
| L | 162M | 0.52 | 1.24 | 32.07 | 0.39 | 1.38 | 0.80 | 1.00 | 0.69 | 0.86 | 1.64 | 1.17 |
| L | 162N | −0.04 | −23.66 | −309.24 | −0.01 | −5.91 | −0.37 | −4.52 | −4.88 | −5.35 | −13.53 | 0.99 |
| L | 162P | −0.06 | −9.13 | −572.54 | −0.01 | −3.06 | −0.82 | −2.08 | −2.45 | −2.65 | −6.07 | 4.14 |
| L | 162R | −0.12 | −6.30 | −316.14 | −0.03 | −1.40 | −0.04 | −1.08 | −1.23 | −1.25 | −2.95 | −0.25 |
| L | 162T | −0.04 | −6.81 | 28.66 | −0.02 | −8.64 | −3.30 | −5.38 | −5.55 | −4.99 | −9.68 | −0.69 |
| L | 162V | 0.27 | 1.95 | 62.13 | 0.15 | 2.18 | 1.18 | 1.59 | 1.48 | 1.45 | 2.60 | 1.51 |
| L | 162W | −0.17 | −0.24 | −128.54 | −0.03 | −0.61 | −0.06 | −0.66 | −0.76 | −0.81 | −1.48 | 0.82 |
| L | 162Y | −0.09 | −0.74 | −223.56 | −0.02 | −1.98 | −0.52 | −1.36 | −1.52 | −1.69 | −3.73 | 0.77 |
| R | 164A | 0.82 | 1.14 | −0.32 | 0.78 | 1.12 | 1.02 | 0.98 | 0.66 | 0.96 | 1.08 | 0.90 |
| R | 164F | 0.39 | 1.56 | −10.24 | 0.19 | 1.65 | 1.16 | 1.30 | 1.21 | 1.37 | 1.96 | 2.99 |
| R | 164G | 0.60 | 1.02 | 3.29 | 0.35 | 1.32 | 1.03 | 1.09 | 0.99 | 1.08 | 1.34 | 1.20 |
| R | 164H | 0.76 | 1.00 | −1.17 | 0.55 | 1.10 | 1.01 | 1.04 | 0.90 | 1.03 | 1.15 | 0.93 |
| R | 164I | 0.20 | 0.48 | 16.86 | 0.07 | 2.19 | 1.06 | 1.48 | 1.32 | 1.71 | 2.91 | 2.20 |
| R | 164L | 0.69 | 1.08 | −3.43 | 0.49 | 1.31 | 1.21 | 1.22 | 0.79 | 1.21 | 1.29 | 1.24 |
| R | 164M | 0.95 | 1.07 | 0.35 | 1.00 | 1.02 | 1.03 | 0.96 | 0.50 | 0.92 | 0.99 | 0.82 |
| R | 164N | 0.73 | 1.56 | 3.79 | 0.71 | 1.32 | 1.29 | 1.19 | 0.80 | 1.14 | 1.18 | 1.26 |
| R | 164P | −0.10 | 0.85 | −16.08 | −0.02 | −0.98 | −0.17 | −0.71 | −0.85 | −3.09 | 0.26 | −1.20 |
| R | 164Q | 0.89 | 0.90 | 3.18 | 0.79 | 1.05 | 0.96 | 0.94 | 0.73 | 0.93 | 0.99 | 0.92 |
| R | 164S | 0.79 | 1.07 | −2.88 | 0.57 | 1.19 | 1.04 | 1.05 | 0.77 | 1.01 | 1.09 | 1.12 |
| R | 164T | 0.76 | 1.19 | −7.25 | 0.62 | 1.26 | 1.15 | 1.18 | 0.86 | 1.17 | 1.05 | 1.12 |
| R | 164V | 0.61 | 1.11 | 0.03 | 0.41 | 1.43 | 1.18 | 1.25 | 0.88 | 1.21 | 1.43 | 1.52 |
| R | 164W | 0.51 | 0.98 | −2.45 | 0.28 | 1.48 | 1.08 | 1.12 | 0.77 | 1.18 | 1.50 | 1.26 |
| R | 164Y | 0.53 | 0.85 | −3.23 | 0.30 | 1.47 | 1.04 | 1.09 | 0.71 | 1.11 | 1.46 | 1.44 |
| A | 165C | 0.87 | 1.08 | −30.83 | 0.88 | 1.09 | 1.07 | 1.02 | 0.97 | 1.00 | 1.19 | 1.10 |
| A | 165D | −0.12 | −2.21 | −381.27 | −0.03 | −1.04 | −0.11 | −0.62 | −0.77 | −1.38 | −0.18 | −0.61 |
| A | 165E | −0.11 | 1.59 | 459.98 | −0.03 | −1.07 | −0.15 | −0.65 | −0.80 | −1.43 | −0.38 | −0.76 |
| A | 165F | −0.12 | −1.80 | 321.73 | −0.02 | −1.07 | −0.13 | −0.62 | −0.76 | −1.45 | −0.76 | −1.29 |
| A | 165G | 0.38 | 1.14 | −76.70 | 0.18 | 1.63 | 1.05 | 1.17 | 1.32 | 1.24 | 2.00 | 2.01 |
| A | 165I | 0.57 | 1.24 | −36.69 | 0.43 | 1.56 | 1.46 | 1.33 | 1.31 | 1.42 | 1.70 | 1.55 |
| A | 165K | −0.13 | 5.68 | −376.52 | −0.03 | −0.76 | −0.10 | −0.49 | −0.62 | −1.23 | −0.21 | −0.67 |
| A | 165L | 0.73 | 0.87 | −16.47 | 0.54 | 1.22 | 1.08 | 1.01 | 0.72 | 1.05 | 1.77 | 0.35 |
| A | 165M | 0.67 | 1.14 | −36.47 | 0.62 | 1.31 | 1.18 | 1.07 | 0.69 | 1.04 | 1.29 | 1.46 |
| A | 165N | −1.03 | 0.65 | 86.86 | −0.21 | −0.36 | −2.44 | 0.00 | −0.75 | −0.11 | −0.03 | 0.34 |
| A | 165P | −0.13 | 2.56 | 472.98 | −0.03 | −0.79 | −0.07 | −0.50 | −0.66 | −1.25 | 0.01 | −0.61 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| A | 165Q | 0.08 | −0.54 | −631.49 | 0.03 | 4.42 | 1.72 | 2.56 | 2.65 | 3.00 | 5.35 | 5.87 |
| A | 165R | −0.14 | −0.71 | −301.37 | −0.03 | −0.70 | −0.09 | −0.46 | −0.59 | −1.16 | 0.00 | −1.40 |
| A | 165S | 0.78 | 0.86 | −37.14 | 0.60 | 1.10 | 0.93 | 1.00 | 1.02 | 0.97 | 1.31 | 1.12 |
| A | 165T | 0.74 | 0.89 | 12.12 | 0.56 | 1.17 | 1.08 | 1.08 | 1.13 | 1.10 | 1.36 | 1.17 |
| A | 165V | 0.90 | 0.79 | −18.37 | 0.75 | 1.02 | 1.04 | 0.97 | 0.93 | 1.07 | 1.08 | 1.02 |
| A | 165W | 0.09 | −1.68 | −328.17 | 0.02 | 3.61 | 0.86 | 2.12 | 1.38 | 2.56 | 4.22 | 4.12 |
| A | 165Y | 0.15 | −2.81 | −309.13 | 0.04 | 2.17 | 0.53 | 1.18 | 0.79 | 1.68 | 3.48 | 4.00 |
| N | 167A | 0.88 | 1.25 | 3.88 | 1.04 | 1.18 | 1.19 | 1.12 | 0.86 | 1.12 | 1.09 | 1.00 |
| N | 167C | 0.95 | 0.98 | 3.45 | 0.83 | 0.88 | 0.81 | 0.86 | 0.81 | 0.84 | 0.91 | 0.78 |
| N | 167D | 0.95 | 1.00 | −3.52 | 0.86 | 0.96 | 0.89 | 0.93 | 0.98 | 0.92 | 0.95 | 0.91 |
| N | 167E | 0.83 | 1.22 | −0.59 | 0.80 | 1.08 | 1.06 | 1.07 | 1.11 | 1.10 | 1.10 | 0.93 |
| N | 167F | 0.84 | 1.13 | 0.40 | 0.72 | 1.03 | 0.97 | 1.00 | 1.05 | 0.99 | 1.05 | 1.12 |
| N | 167G | 0.78 | 1.20 | 0.64 | 0.67 | 1.16 | 1.06 | 1.08 | 1.14 | 1.08 | 1.27 | 1.02 |
| N | 167H | 0.97 | 0.87 | 0.25 | 0.93 | 0.98 | 0.94 | 0.95 | 0.93 | 0.91 | 0.96 | 0.89 |
| N | 167I | 0.92 | 0.92 | −2.67 | 0.80 | 0.99 | 0.96 | 0.97 | 0.93 | 1.02 | 0.97 | 0.92 |
| N | 167K | 0.95 | 1.07 | −0.50 | 0.90 | 1.00 | 0.99 | 1.00 | 0.83 | 0.98 | 1.02 | 1.06 |
| N | 167L | 1.05 | 0.74 | −3.73 | 1.02 | 0.96 | 0.94 | 0.93 | 0.57 | 0.96 | 0.89 | 0.89 |
| N | 167M | 0.78 | 1.27 | −1.09 | 0.85 | 1.21 | 1.25 | 1.17 | 0.91 | 1.20 | 1.17 | 1.10 |
| N | 167Q | 0.93 | 1.05 | −1.48 | 0.83 | 1.01 | 0.94 | 0.96 | 1.00 | 0.96 | 0.98 | 1.00 |
| N | 167R | 0.79 | 1.17 | −0.47 | 0.67 | 1.13 | 1.05 | 1.09 | 1.17 | 1.02 | 1.16 | 1.18 |
| N | 167S | 0.94 | 1.00 | −2.95 | 0.79 | 1.00 | 0.94 | 0.96 | 1.02 | 0.97 | 1.03 | 0.94 |
| N | 167T | 0.83 | 1.22 | 2.27 | 0.74 | 1.10 | 1.05 | 1.08 | 1.06 | 1.10 | 1.11 | 1.13 |
| N | 167V | 0.72 | 1.26 | 2.99 | 0.56 | 1.27 | 1.22 | 1.27 | 1.18 | 1.25 | 1.16 | 1.21 |
| N | 167W | 0.84 | 0.88 | −0.91 | 0.64 | 1.02 | 0.93 | 0.98 | 0.85 | 0.98 | 1.03 | 1.02 |
| N | 167Y | 0.90 | 0.84 | −1.26 | 0.84 | 1.07 | 1.04 | 1.03 | 0.67 | 1.01 | 0.92 | 0.95 |
| D | 168C | 0.74 | 1.25 | −18.62 | 0.70 | 1.18 | 1.12 | 1.15 | 1.05 | 1.09 | 1.23 | 1.15 |
| D | 168E | 0.60 | 1.33 | 0.30 | 0.53 | 1.41 | 1.26 | 1.33 | 1.31 | 1.31 | 1.40 | 1.38 |
| D | 168F | 0.75 | 1.17 | 10.18 | 0.62 | 1.16 | 1.08 | 1.14 | 1.12 | 1.07 | 1.24 | 1.09 |
| D | 168G | 0.78 | 1.04 | 2.63 | 0.58 | 1.10 | 1.02 | 1.07 | 1.09 | 1.01 | 1.05 | 1.03 |
| D | 168I | 0.82 | 0.97 | 8.37 | 0.65 | 1.05 | 0.98 | 1.05 | 0.94 | 0.97 | 1.11 | 1.00 |
| D | 168K | 0.75 | 1.08 | −4.92 | 0.57 | 1.16 | 1.05 | 1.11 | 0.97 | 1.07 | 1.28 | 1.09 |
| D | 168L | 0.91 | 0.89 | −26.65 | 0.80 | 1.06 | 1.06 | 1.08 | 0.77 | 1.08 | 1.12 | 0.95 |
| D | 168M | 0.85 | 1.10 | −6.57 | 0.90 | 1.13 | 1.12 | 1.13 | 0.82 | 1.02 | 1.16 | 0.91 |
| D | 168N | 0.71 | 1.25 | −1.91 | 0.62 | 1.20 | 1.06 | 1.10 | 0.97 | 1.07 | 1.14 | 1.09 |
| D | 168P | −0.17 | −1.70 | 7.70 | −0.04 | −0.60 | −0.07 | −0.43 | −0.43 | −0.97 | −0.01 | −0.34 |
| D | 168Q | 0.36 | 0.65 | −4.23 | 0.08 | 0.36 | 0.04 | 0.14 | 0.15 | 0.29 | 0.21 | 0.25 |
| D | 168S | 0.72 | 1.23 | 6.79 | 0.55 | 1.23 | 1.14 | 1.17 | 1.13 | 1.12 | 1.24 | 1.15 |
| D | 168T | 0.57 | 1.38 | −8.57 | 0.38 | 1.43 | 1.23 | 1.36 | 1.22 | 1.31 | 1.47 | 1.48 |
| D | 168V | 0.69 | 1.07 | −9.95 | 0.44 | 1.20 | 1.05 | 1.15 | 0.99 | 1.11 | 1.15 | 1.17 |
| D | 168W | 0.63 | 1.10 | 12.16 | 0.40 | 1.28 | 1.02 | 1.18 | 0.98 | 1.11 | 1.35 | 1.21 |
| D | 168Y | 0.84 | 1.05 | 2.55 | 0.71 | 1.12 | 1.03 | 1.09 | 0.73 | 1.04 | 1.14 | 1.08 |
| G | 169A | −0.11 | −4.91 | −9.42 | −0.03 | −1.26 | −0.06 | −0.85 | −0.90 | −1.64 | −0.53 | −1.08 |
| G | 169C | −0.14 | −2.88 | 19.66 | −0.03 | −0.93 | −0.07 | −0.62 | −0.67 | −1.24 | −0.72 | −2.09 |
| G | 169D | −0.08 | −7.77 | −37.10 | −0.02 | −1.61 | −0.21 | −1.03 | −1.19 | −2.19 | −1.07 | −0.49 |
| G | 169E | −0.44 | −1.50 | 26.99 | −0.11 | −0.31 | −0.10 | −0.29 | −0.36 | −1.29 | −0.20 | −0.39 |
| G | 169F | −0.16 | −0.64 | −7.35 | −0.04 | −0.68 | −0.08 | −0.47 | −0.55 | −0.98 | −0.24 | −0.45 |
| G | 169H | −0.07 | 1.75 | 16.35 | −0.01 | −3.36 | −0.69 | −1.98 | −2.12 | −3.09 | −3.85 | −5.54 |
| G | 169I | −0.22 | 0.41 | 11.04 | −0.04 | −0.42 | −0.03 | −0.31 | −0.36 | −0.69 | −0.34 | −0.66 |
| G | 169K | −0.07 | 0.32 | 61.63 | −0.01 | −2.76 | −0.56 | −1.84 | −1.83 | −2.98 | −2.96 | −3.65 |
| G | 169L | 0.06 | −11.66 | −33.07 | 0.01 | 2.27 | 0.44 | 1.54 | 1.56 | 2.72 | 0.41 | 1.59 |
| G | 169M | −0.11 | −7.46 | −2.76 | −0.03 | −1.37 | −0.12 | −0.93 | −0.94 | −1.66 | −0.57 | −1.18 |
| G | 169N | −0.18 | −0.60 | 8.06 | −0.05 | −1.08 | −0.12 | −0.64 | −0.64 | −1.06 | −1.24 | −0.85 |
| G | 169P | 0.17 | −3.68 | 12.96 | 0.03 | 0.56 | 0.13 | 0.34 | 0.45 | 0.84 | 0.39 | 0.58 |
| G | 169Q | −0.14 | −3.31 | 3.45 | −0.03 | −1.17 | −0.19 | −0.75 | −0.78 | −1.08 | −1.13 | −0.71 |
| G | 169R | −0.15 | −1.74 | −27.57 | −0.03 | −1.00 | −0.15 | −0.64 | −0.71 | −1.12 | −0.52 | −1.39 |
| G | 169S | −0.10 | 1.15 | −43.77 | −0.02 | −1.40 | −0.21 | −0.90 | −1.00 | −1.73 | −1.33 | −0.16 |
| G | 169V | −0.15 | 3.01 | −2.94 | −0.03 | −0.66 | −0.13 | −0.49 | −0.55 | −1.08 | 0.01 | −0.70 |
| G | 169W | −0.18 | 3.14 | 8.77 | −0.04 | −0.57 | −0.09 | −0.42 | −0.49 | −0.90 | −0.54 | −0.91 |
| G | 169Y | −0.09 | 12.08 | 54.82 | −0.02 | −1.45 | −0.21 | −1.09 | −1.13 | −2.13 | 0.06 | −0.53 |
| A | 170C | 0.54 | 1.39 | 0.97 | 0.40 | 1.40 | 1.09 | 1.11 | 1.07 | 1.39 | 1.45 | 1.36 |
| A | 170D | −0.11 | −4.66 | −6.18 | −0.03 | −1.02 | −0.27 | −0.64 | −0.83 | −1.62 | −0.12 | −1.90 |
| A | 170E | −0.05 | −6.93 | −7.56 | −0.01 | −1.97 | −0.49 | −1.42 | −1.91 | −4.11 | −0.18 | −1.15 |
| A | 170G | 0.69 | 1.17 | 1.25 | 0.47 | 1.16 | 0.93 | 0.97 | 0.99 | 1.18 | 1.28 | 1.20 |
| A | 170H | −0.06 | −1.91 | −25.23 | −0.01 | −1.55 | −0.04 | −1.10 | −1.49 | −3.10 | −0.57 | −4.92 |
| A | 170K | −0.13 | −1.48 | −7.00 | −0.03 | −0.74 | 0.00 | −0.51 | −0.68 | −1.37 | 0.13 | −4.70 |
| A | 170L | −0.04 | 3.40 | −11.36 | −0.01 | −2.49 | −0.02 | −1.74 | −2.30 | −4.90 | −0.99 | −5.96 |
| A | 170M | −0.10 | −4.98 | −15.43 | −0.02 | −0.95 | −0.10 | −0.64 | −0.89 | −1.66 | −0.12 | −0.25 |
| A | 170N | 0.00 | 166.24 | 336.35 | 0.00 | 89.98 | 15.71 | 50.01 | 56.21 | 94.37 | 59.02 | 86.61 |
| A | 170P | −0.11 | −2.25 | −12.44 | −0.02 | −0.89 | −0.06 | −0.56 | −0.77 | −1.22 | −0.08 | −1.45 |
| A | 170Q | −0.14 | −1.99 | −5.92 | −0.03 | −0.66 | −0.05 | −0.43 | −0.59 | −1.25 | −0.58 | −0.39 |
| A | 170R | −0.05 | −5.71 | −13.03 | −0.01 | −1.98 | −0.14 | −1.36 | −1.75 | −3.70 | 0.21 | −2.75 |
| A | 170V | 0.29 | 2.14 | 2.82 | 0.14 | 2.26 | 1.55 | 1.72 | 1.54 | 2.09 | 2.38 | 2.25 |
| A | 170W | −0.14 | 0.25 | −5.15 | −0.03 | −0.65 | −0.10 | −0.44 | −0.48 | −1.24 | 0.09 | −0.94 |
| A | 170Y | −0.12 | 0.03 | −7.76 | −0.07 | −0.50 | −0.01 | −0.58 | −0.78 | −1.61 | 0.34 | −0.84 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| D | 171A | 1.07 | 0.79 | 8.66 | 1.10 | 0.88 | 0.82 | 0.86 | 0.60 | 0.85 | 0.96 | 0.92 |
| D | 171C | 0.16 | 3.40 | −12.01 | 0.05 | 2.70 | 1.34 | 1.85 | 1.80 | 2.06 | 2.92 | 1.23 |
| D | 171E | 0.75 | 0.88 | −18.24 | 0.54 | 1.00 | 0.79 | 0.89 | 0.91 | 0.91 | 1.35 | 1.09 |
| D | 171F | 0.34 | 1.92 | −6.12 | 0.14 | 1.72 | 0.94 | 1.30 | 1.33 | 1.31 | 2.19 | 1.85 |
| D | 171G | 0.43 | 1.32 | 2.19 | 0.22 | 1.70 | 1.23 | 1.43 | 1.53 | 1.46 | 2.04 | 1.87 |
| D | 171H | 0.83 | 1.01 | −12.91 | 0.63 | 1.09 | 0.95 | 1.03 | 1.09 | 1.06 | 1.23 | 1.19 |
| D | 171I | 0.58 | 0.82 | −17.75 | 0.32 | 1.25 | 0.92 | 1.06 | 1.03 | 1.04 | 1.58 | 1.41 |
| D | 171L | 0.50 | 1.20 | −13.37 | 0.32 | 1.49 | 1.11 | 1.22 | 1.01 | 1.25 | 1.83 | 1.34 |
| D | 171M | 0.59 | 1.31 | 14.39 | 0.44 | 1.28 | 1.00 | 1.12 | 0.78 | 1.16 | 1.56 | 1.19 |
| D | 171N | 0.75 | 1.20 | −10.80 | 0.74 | 1.13 | 1.11 | 1.17 | 1.01 | 1.16 | 1.35 | 1.33 |
| D | 171P | −0.06 | −2.96 | 21.58 | −0.01 | −1.56 | −0.20 | −1.94 | −2.30 | −2.45 | −5.04 | −1.37 |
| D | 171Q | 0.59 | 1.18 | −10.70 | 0.37 | 1.30 | 1.05 | 1.17 | 1.14 | 1.24 | 1.57 | 1.41 |
| D | 171R | 0.78 | 1.02 | 0.73 | 0.57 | 1.08 | 1.03 | 1.10 | 1.09 | 1.11 | 1.29 | 1.25 |
| D | 171T | −1.27 | 0.13 | −0.21 | −0.23 | −0.30 | −2.04 | −0.47 | −0.11 | −0.19 | −0.28 | −0.07 |
| D | 171V | 0.55 | 1.28 | −12.19 | 0.40 | 1.50 | 1.27 | 1.36 | 1.34 | 1.29 | 1.71 | 1.60 |
| G | 172A | 0.60 | 1.19 | 1.45 | 0.41 | 1.13 | 0.70 | 0.87 | −0.71 | 0.95 | 1.24 | 1.10 |
| G | 172C | 0.12 | 5.95 | 27.31 | 0.03 | 1.38 | 0.02 | 1.32 | 3.21 | 1.80 | 2.99 | 1.20 |
| G | 172D | 0.05 | −1.67 | 20.39 | 0.01 | 2.01 | −0.08 | 2.43 | 2.87 | 3.48 | 5.77 | 0.71 |
| G | 172E | 0.07 | −2.45 | 22.52 | 0.02 | 1.51 | 0.21 | 1.89 | 2.63 | 2.65 | 4.08 | 1.11 |
| G | 172F | 0.07 | −2.58 | 28.58 | 0.02 | 1.57 | 0.11 | 1.83 | 5.59 | 2.68 | 4.44 | 0.92 |
| G | 172H | −0.07 | 0.52 | −1.20 | −0.01 | −1.76 | −0.20 | −2.02 | −3.25 | −2.78 | −5.47 | −1.16 |
| G | 172L | −0.15 | 0.32 | −14.23 | −0.03 | −0.73 | −0.03 | −0.94 | −0.70 | −1.34 | −1.77 | −0.86 |
| G | 172M | 0.00 | −207.59 | −286.40 | 0.00 | −35.47 | −1.35 | −39.27 | −96.95 | −56.16 | −82.36 | −38.51 |
| G | 172P | 0.10 | −0.42 | 13.59 | 0.02 | 1.08 | −0.02 | 1.27 | 3.21 | 1.85 | 2.74 | 0.53 |
| G | 172Q | 0.00 | −148.77 | −1224.90 | 0.00 | −63.73 | −0.80 | −75.14 | −188.29 | −100.84 | −202.44 | −79.41 |
| G | 172R | −0.01 | −13.49 | −79.09 | 0.00 | −7.22 | −0.30 | −8.70 | −10.19 | −11.69 | −16.98 | −8.17 |
| G | 172S | 0.00 | 58.89 | 316.16 | 0.00 | 25.07 | 4.44 | 18.48 | 34.17 | 22.78 | 42.19 | 29.37 |
| G | 172T | −0.05 | 0.41 | −62.74 | −0.01 | −2.69 | −0.41 | −3.00 | −7.79 | −4.19 | −8.85 | −3.05 |
| G | 172V | −0.11 | 2.46 | −11.05 | −0.02 | −1.07 | −0.15 | −1.25 | −3.75 | −1.61 | −2.69 | 0.02 |
| G | 172W | −0.10 | 0.68 | −5.54 | −0.02 | −1.21 | −0.07 | −1.38 | −3.28 | −1.63 | −3.12 | −0.71 |
| G | 172Y | 0.03 | −3.55 | 193.48 | 0.01 | 3.88 | 0.33 | 4.63 | 6.97 | 6.43 | 10.04 | 3.01 |
| F | 173A | 0.00 | −294.71 | −758.76 | 0.00 | −46.94 | −1.61 | −43.52 | −47.69 | −49.03 | −109.89 | 64.48 |
| F | 173C | −0.09 | −7.92 | −29.21 | −0.02 | −1.36 | −0.08 | −1.26 | −1.40 | −1.32 | −3.05 | 2.19 |
| F | 173D | −0.12 | −1.25 | −13.23 | −0.02 | −0.73 | −0.04 | −0.78 | −0.89 | −0.87 | −2.00 | 0.70 |
| F | 173E | −0.17 | −1.41 | −10.36 | −0.03 | −0.54 | −0.07 | −0.57 | −0.66 | −0.65 | −1.65 | 1.34 |
| F | 173G | −0.15 | −1.05 | −4.14 | −0.03 | −0.63 | −0.03 | −0.65 | −0.75 | −0.75 | −2.14 | 0.90 |
| F | 173I | 0.33 | 2.44 | −0.84 | 0.23 | 2.33 | 1.49 | 1.90 | 1.95 | 1.58 | 2.56 | 1.93 |
| F | 173K | −0.15 | 0.17 | 0.64 | −0.03 | −0.60 | −0.06 | −0.67 | −0.75 | −0.76 | −1.80 | 0.86 |
| F | 173M | 0.08 | 5.38 | 8.98 | 0.03 | 4.93 | 1.70 | 3.31 | 2.85 | 3.23 | 7.10 | 3.95 |
| F | 173N | −0.11 | −4.55 | −24.75 | −0.02 | −0.85 | −0.09 | −0.91 | −1.03 | −1.04 | −2.26 | 1.40 |
| F | 173P | −0.14 | −2.77 | −20.20 | −0.03 | −0.67 | −0.05 | −0.71 | −0.82 | −0.81 | −1.63 | 1.16 |
| F | 173Q | −0.15 | −4.01 | −8.57 | −0.03 | −0.61 | −0.02 | −0.62 | −0.73 | −0.71 | −1.54 | 1.21 |
| F | 173R | −0.16 | −0.58 | −8.32 | −0.03 | −0.56 | −0.08 | −0.60 | −0.70 | −0.68 | −1.70 | 1.79 |
| F | 173S | −0.22 | −1.34 | −9.34 | −0.04 | −0.44 | −0.05 | −0.44 | −0.52 | −0.49 | −1.20 | 0.56 |
| F | 173T | −0.26 | −1.84 | −3.19 | −0.05 | −0.49 | −0.04 | −0.41 | −0.46 | −0.43 | −1.19 | 0.51 |
| F | 173V | 0.21 | 2.40 | 4.84 | 0.09 | 2.83 | 1.30 | 2.02 | 2.04 | 1.60 | 3.42 | 2.22 |
| F | 173W | 0.03 | 15.09 | 24.95 | 0.01 | 14.97 | 7.59 | 10.20 | 9.46 | 9.66 | 19.59 | 15.18 |
| F | 173Y | 0.12 | 2.92 | 38.34 | 0.05 | 4.58 | 2.27 | 3.15 | 2.57 | 2.93 | 6.09 | 4.40 |
| R | 174A | 0.86 | 0.62 | −6.59 | 0.17 | 0.11 | 0.01 | 0.15 | 0.17 | 0.20 | 0.37 | 0.76 |
| R | 174C | 0.67 | 0.84 | 0.45 | 0.13 | 0.15 | 0.00 | 0.18 | 0.22 | 0.23 | 0.42 | −0.02 |
| R | 174D | 0.20 | 2.84 | −16.59 | 0.04 | 0.49 | 0.05 | 0.59 | 0.71 | 0.78 | 1.59 | 2.98 |
| R | 174E | 0.10 | 7.45 | −54.45 | 0.02 | 0.96 | −0.01 | 1.19 | 1.44 | 1.54 | 3.17 | 0.83 |
| R | 174G | 0.41 | 0.24 | −21.93 | 0.08 | 0.24 | 0.01 | 0.29 | 0.34 | 0.36 | 0.98 | 0.31 |
| R | 174H | 0.20 | 0.80 | −59.13 | 0.03 | 0.51 | 0.01 | 0.61 | 0.72 | 0.79 | 1.80 | 0.85 |
| R | 174I | −0.01 | −19.93 | −161.83 | 0.00 | −10.21 | −0.58 | −12.56 | −14.86 | −16.35 | −34.99 | −10.63 |
| R | 174K | 0.49 | −0.25 | −4.06 | 0.11 | 0.19 | 0.00 | 0.26 | 0.29 | 0.33 | 0.65 | 0.16 |
| R | 174L | 0.22 | −0.73 | −29.83 | 0.04 | 0.45 | 0.00 | 0.58 | 0.67 | 0.78 | 1.52 | 0.66 |
| R | 174M | 0.50 | 1.16 | −22.51 | 0.09 | 0.19 | 0.00 | 0.25 | 0.30 | 0.34 | 0.83 | 0.20 |
| R | 174P | −0.05 | −11.20 | 101.94 | −0.01 | −2.04 | −0.02 | −2.52 | −2.98 | −3.29 | −5.08 | −2.00 |
| R | 174Q | 0.16 | 1.77 | −31.42 | 0.03 | 0.61 | 0.02 | 0.74 | 0.89 | 1.00 | 2.08 | 0.70 |
| R | 174S | 0.36 | −0.18 | −7.70 | 0.08 | 0.27 | 0.01 | 0.33 | 0.40 | 0.43 | 0.84 | 0.31 |
| R | 174T | −0.08 | −1.83 | 74.04 | −0.02 | −1.27 | −0.21 | −1.56 | −1.85 | −2.05 | −4.10 | −1.24 |
| R | 174V | 0.13 | 0.53 | −61.39 | 0.02 | 0.76 | 0.05 | 0.96 | 1.11 | 1.19 | 2.09 | 0.60 |
| R | 174W | 0.03 | −0.40 | −103.79 | 0.01 | 2.91 | 0.65 | 3.90 | 4.60 | 5.12 | 9.96 | 3.50 |
| R | 174Y | 0.34 | −0.11 | −29.43 | 0.06 | 0.28 | 0.03 | 0.37 | 0.42 | 0.49 | 1.06 | 0.26 |
| F | 175A | 0.04 | 0.12 | 115.46 | 0.01 | 2.80 | 0.09 | 2.75 | 3.31 | 4.12 | 6.28 | 0.67 |
| F | 175C | −0.05 | −3.24 | −87.69 | −0.01 | −2.71 | −0.20 | −2.57 | −3.04 | −3.79 | −5.67 | −13.58 |
| F | 175D | −0.11 | 3.44 | −13.49 | −0.02 | −0.87 | −0.14 | −0.93 | −1.14 | −1.42 | −2.40 | −0.92 |
| F | 175E | −0.08 | 9.57 | −58.74 | −0.02 | −1.31 | −0.40 | −1.36 | −1.69 | −2.13 | −4.14 | −1.52 |
| F | 175G | −0.10 | 4.04 | −27.08 | −0.02 | −1.04 | −0.11 | −1.07 | −1.32 | −1.61 | −3.03 | −1.03 |
| F | 175H | 0.17 | 1.39 | 14.01 | 0.07 | 2.73 | 1.16 | 1.68 | 1.75 | 1.68 | 3.79 | 2.98 |
| F | 175I | −0.09 | 3.15 | −12.41 | −0.02 | −1.88 | −0.30 | −1.53 | −1.64 | −2.17 | −4.13 | −1.22 |
| F | 175K | −0.13 | −0.23 | −13.91 | −0.04 | −1.72 | −0.29 | −1.25 | −1.34 | −1.60 | −3.12 | −1.58 |
| F | 175M | 0.22 | 2.34 | 10.74 | 0.13 | 2.69 | 1.13 | 1.57 | 1.14 | 1.49 | 2.85 | 2.40 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| F | 175N | −0.15 | 1.14 | −9.82 | −0.04 | −0.70 | −0.05 | −0.71 | −0.88 | −1.07 | −1.47 | −0.15 |
| F | 175P | −0.15 | 1.83 | −11.46 | −0.03 | −0.69 | −0.06 | −0.74 | −0.90 | −1.10 | −1.88 | 0.06 |
| F | 175Q | −0.22 | 2.15 | −23.15 | −0.04 | −0.45 | −0.05 | −0.47 | −0.58 | −0.73 | −1.28 | −0.18 |
| F | 175R | −0.11 | 5.45 | −24.55 | −0.03 | −0.87 | 0.00 | −0.95 | −1.15 | −1.51 | −2.05 | −0.65 |
| F | 175T | −0.23 | 1.53 | −6.44 | −0.04 | −0.45 | −0.04 | −0.48 | −0.58 | −0.72 | −1.03 | 0.12 |
| F | 175V | −0.14 | 2.84 | −25.51 | −0.04 | −0.83 | −0.15 | −0.82 | −0.98 | −1.24 | −2.13 | −0.48 |
| F | 175W | 0.11 | 4.90 | 29.96 | 0.06 | 5.74 | 2.71 | 4.00 | 3.15 | 3.34 | 6.38 | 4.88 |
| F | 175Y | 0.87 | 0.93 | 3.68 | 0.77 | 1.07 | 0.99 | 1.00 | 0.83 | 1.00 | 1.12 | 1.16 |
| D | 176A | 0.99 | 0.68 | 45.04 | 0.21 | 0.09 | 0.00 | 0.11 | 0.13 | 0.14 | 0.30 | 0.11 |
| D | 176C | 0.53 | 1.31 | 32.63 | 0.10 | 0.17 | −0.01 | 0.20 | 0.25 | 0.24 | 0.45 | −0.11 |
| D | 176E | 0.21 | 3.39 | 24.93 | 0.04 | 0.43 | 0.03 | 0.51 | 0.61 | 0.64 | 1.24 | 0.57 |
| D | 176F | 0.11 | 2.67 | 452.20 | 0.02 | 0.82 | 0.00 | 0.94 | 1.15 | 1.20 | 2.79 | 1.27 |
| D | 176G | 0.96 | 0.20 | 46.67 | 0.17 | 0.10 | 0.01 | 0.11 | 0.13 | 0.14 | 0.30 | 0.08 |
| D | 176H | 0.47 | 0.38 | 42.84 | 0.09 | 0.19 | 0.03 | 0.23 | 0.27 | 0.29 | 0.66 | 0.24 |
| D | 176I | 0.06 | 3.94 | 50.59 | 0.01 | 1.61 | 0.19 | 1.87 | 2.28 | 2.28 | 4.63 | 1.77 |
| D | 176K | 0.06 | 1.56 | 32.14 | 0.01 | 1.61 | 0.14 | 1.88 | 2.28 | 2.30 | 4.89 | 1.18 |
| D | 176L | 0.21 | −1.24 | 117.82 | 0.04 | 0.42 | 0.05 | 0.53 | 0.64 | 0.71 | 1.26 | 0.52 |
| D | 176M | 0.32 | 2.05 | 156.86 | 0.06 | 0.28 | −0.01 | 0.34 | 0.42 | 0.43 | 0.85 | 0.28 |
| D | 176N | 0.58 | 0.78 | 70.53 | 0.12 | 0.15 | −0.01 | 0.18 | 0.22 | 0.24 | 0.44 | −0.01 |
| D | 176P | −0.11 | −6.97 | −346.67 | −0.02 | −0.85 | 0.06 | −0.95 | −1.21 | −1.17 | −2.48 | −5.36 |
| D | 176Q | 0.45 | 1.09 | 54.04 | 0.08 | 0.20 | 0.01 | 0.23 | 0.28 | 0.29 | 0.48 | 0.32 |
| D | 176R | 0.00 | 209.50 | −588.97 | 0.00 | 30.03 | −0.11 | 33.90 | 41.73 | 42.90 | 103.34 | 27.92 |
| D | 176S | 0.33 | 0.92 | 118.85 | 0.06 | 0.28 | 0.00 | 0.32 | 0.39 | 0.39 | 0.90 | 0.12 |
| D | 176T | 0.38 | 0.49 | 35.80 | 0.07 | 0.23 | 0.04 | 0.27 | 0.33 | 0.32 | 0.66 | 0.05 |
| D | 176V | 0.10 | 0.65 | 61.50 | 0.02 | 0.89 | 0.10 | 1.05 | 1.27 | 1.35 | 2.90 | 0.14 |
| D | 176W | −0.01 | −4.80 | −7665.63 | 0.00 | −15.61 | −3.86 | −18.88 | −23.35 | −24.32 | −50.16 | −16.93 |
| D | 176Y | 0.20 | 0.18 | 175.19 | 0.04 | 0.45 | 0.04 | 0.56 | 0.67 | 0.65 | 1.44 | 0.46 |
| A | 177C | 0.70 | 0.74 | −0.27 | 0.33 | 0.66 | 0.00 | 0.19 | 0.46 | 0.29 | 0.82 | 0.31 |
| A | 177D | 0.83 | 0.28 | 0.90 | 0.18 | 0.13 | 0.01 | 0.15 | 0.41 | 0.22 | 0.35 | 0.06 |
| A | 177E | 0.69 | −0.19 | 3.93 | 0.18 | 0.16 | 0.01 | 0.18 | 0.49 | 0.26 | 0.44 | 0.12 |
| A | 177F | −0.04 | −0.89 | −24.11 | −0.01 | −2.96 | −0.50 | −3.53 | −9.42 | −5.25 | −7.20 | −3.12 |
| A | 177G | 0.65 | 0.54 | 3.32 | 0.14 | 0.22 | 0.00 | 0.21 | 0.16 | 0.29 | 0.86 | 0.92 |
| A | 177H | 0.83 | 0.01 | 1.32 | 0.20 | 0.13 | 0.01 | 0.15 | 0.40 | 0.20 | 0.43 | 0.14 |
| A | 177I | −0.02 | 7.49 | −38.20 | 0.00 | −5.82 | −0.71 | −6.68 | −8.36 | −9.53 | −18.00 | −8.69 |
| A | 177K | 0.84 | 0.09 | 0.12 | 0.20 | 0.12 | 0.02 | 0.15 | 0.38 | 0.22 | 0.39 | 0.10 |
| A | 177L | 0.01 | 3.67 | 65.73 | 0.00 | 9.92 | 1.21 | 12.52 | 28.14 | 17.78 | 24.71 | 8.28 |
| A | 177M | 0.32 | 2.90 | 9.17 | 0.09 | 0.52 | −0.01 | 0.43 | 0.91 | 0.66 | 1.46 | 0.42 |
| A | 177P | −0.64 | −0.73 | −2.00 | −0.15 | −0.17 | 0.00 | −0.07 | −0.20 | −0.27 | −0.47 | −0.08 |
| A | 177Q | 0.32 | −1.36 | 4.79 | 0.07 | 0.33 | 0.02 | 0.40 | 1.02 | 0.62 | 0.84 | 0.17 |
| A | 177R | 0.50 | −0.41 | 2.56 | 0.11 | 0.21 | 0.02 | 0.27 | 0.72 | 0.38 | 0.64 | 0.11 |
| A | 177S | 0.69 | 0.15 | 4.51 | 0.15 | 0.27 | 0.00 | 0.20 | 0.51 | 0.29 | 0.84 | 0.71 |
| A | 177T | −0.17 | −1.91 | −7.29 | −0.05 | −1.43 | 0.03 | −0.69 | −0.68 | −1.02 | −2.59 | −1.11 |
| A | 177V | −0.27 | 0.66 | −2.06 | −0.07 | −0.40 | 0.00 | −0.47 | −0.84 | −0.66 | −1.28 | −0.38 |
| A | 177W | −0.26 | −0.64 | −6.31 | −0.06 | −0.38 | −0.12 | −0.48 | −0.29 | −0.69 | −0.98 | −0.20 |
| A | 177Y | −0.18 | 1.45 | −8.26 | −0.05 | −0.59 | −0.13 | −0.75 | −1.61 | −1.05 | −1.74 | −0.41 |
| A | 178C | 0.32 | 1.28 | 6.95 | 0.21 | 2.18 | 0.64 | 1.23 | 0.96 | 0.57 | 2.08 | 1.23 |
| A | 178D | −0.01 | 19.69 | −77.99 | 0.00 | −9.49 | −0.14 | −10.94 | −13.24 | −12.10 | −25.28 | −10.18 |
| A | 178E | 0.00 | 111.58 | −918.47 | 0.00 | −71.05 | −5.20 | −81.74 | −100.97 | −98.39 | −219.41 | −31.89 |
| A | 178F | −0.04 | 0.88 | −25.09 | −0.01 | −2.32 | −0.71 | −2.67 | −3.18 | −3.05 | −7.15 | −2.74 |
| A | 178G | 0.45 | 1.13 | 2.90 | 0.22 | 1.47 | 0.76 | 0.87 | 0.95 | 0.95 | 1.79 | 1.68 |
| A | 178H | −0.14 | 1.12 | −9.05 | −0.03 | −0.72 | −0.14 | −0.83 | −1.03 | −0.95 | −2.15 | −0.46 |
| A | 178I | −0.04 | −0.03 | −26.48 | −0.01 | −2.64 | −1.15 | −2.97 | −3.61 | −3.54 | −7.27 | −0.76 |
| A | 178K | −0.04 | 2.38 | −57.71 | −0.01 | −2.34 | −0.26 | −2.80 | −3.42 | −3.31 | −7.32 | −2.30 |
| A | 178L | 0.00 | 779.18 | −3252.77 | 0.00 | −289.15 | −7.67 | −258.31 | −300.60 | −245.23 | −693.30 | −166.88 |
| A | 178M | 0.07 | 11.29 | 9.96 | 0.02 | 3.32 | −0.11 | 1.97 | 2.19 | 2.24 | 5.25 | 1.39 |
| A | 178N | −0.02 | −14.38 | −61.01 | 0.00 | −4.80 | 0.41 | −5.52 | −6.83 | −6.66 | −12.72 | −6.01 |
| A | 178P | −0.07 | −2.12 | −10.22 | −0.02 | −1.65 | 0.04 | −1.74 | −2.19 | −2.10 | −5.95 | −0.84 |
| A | 178Q | −0.06 | −11.59 | −2.19 | −0.02 | −2.30 | −0.06 | −1.80 | −2.22 | −2.08 | −4.43 | −0.41 |
| A | 178R | −0.06 | −0.89 | −12.60 | −0.01 | −1.65 | −0.15 | −1.85 | −2.30 | −2.15 | −4.85 | −1.29 |
| A | 178S | 0.30 | 2.09 | 5.57 | 0.19 | 2.71 | 1.21 | 1.60 | 1.48 | 1.27 | 2.44 | 1.69 |
| A | 178T | 0.31 | 1.95 | 2.83 | 0.17 | 2.44 | 0.75 | 1.19 | 1.20 | 1.02 | 2.52 | 1.33 |
| A | 178W | −0.06 | 3.97 | −17.89 | −0.01 | −1.70 | −0.50 | −1.95 | −2.44 | −2.26 | −3.36 | −0.42 |
| A | 178Y | −0.05 | 4.50 | −35.28 | −0.01 | −2.26 | −0.60 | −2.75 | −3.33 | −3.13 | −6.35 | −1.25 |
| D | 179A | 0.89 | 0.85 | 7.62 | 0.58 | 0.66 | 0.20 | 0.23 | 0.15 | 0.24 | 0.97 | 0.41 |
| D | 179C | 0.58 | 0.95 | 0.52 | 0.22 | 0.62 | 0.23 | 0.41 | 0.27 | 0.48 | 1.07 | 0.46 |
| D | 179E | 1.06 | 0.37 | 6.26 | 0.63 | 0.59 | 0.03 | 0.13 | 0.12 | 0.23 | 0.80 | 0.16 |
| D | 179G | 0.73 | 0.90 | 10.80 | 0.35 | 0.76 | 0.11 | 0.24 | 0.18 | 0.26 | 1.21 | 0.20 |
| D | 179H | 0.57 | 1.00 | 14.50 | 0.26 | 0.89 | 0.12 | 0.28 | 0.22 | 0.33 | 1.27 | 0.23 |
| D | 179I | 0.51 | 1.07 | 12.27 | 0.28 | 1.31 | 0.40 | 0.43 | 0.25 | 0.47 | 1.72 | 0.61 |
| D | 179L | 0.32 | 1.65 | 27.76 | 0.17 | 1.76 | 0.60 | 0.91 | 0.41 | 0.79 | 2.34 | 0.98 |
| D | 179M | 0.98 | 0.87 | 9.90 | 0.83 | 0.73 | 0.38 | 0.31 | 0.14 | 0.30 | 0.89 | 0.23 |
| D | 179N | 0.92 | 0.66 | 1.40 | 0.28 | 0.27 | −0.01 | 0.13 | 0.15 | 0.20 | 0.66 | 0.27 |
| D | 179P | 0.09 | 9.96 | 111.90 | 0.02 | 1.41 | −0.08 | 1.24 | 1.47 | 1.99 | 4.21 | 0.47 |
| D | 179Q | 1.09 | 0.32 | 3.63 | 0.48 | 0.40 | 0.00 | 0.11 | 0.12 | 0.16 | 0.72 | 0.07 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| D | 179S | 0.55 | 0.82 | -4.78 | 0.20 | 0.70 | 0.04 | 0.23 | 0.22 | 0.31 | 1.42 | 0.38 |
| D | 179T | 0.46 | 1.31 | 10.06 | 0.21 | 1.12 | 0.11 | 0.31 | 0.28 | 0.40 | 1.77 | 0.31 |
| D | 179V | 0.36 | 2.00 | -3.33 | 0.21 | 1.75 | 0.44 | 0.55 | 0.35 | 0.61 | 2.37 | 0.82 |
| D | 179W | 0.71 | 0.42 | 1.99 | 0.22 | 0.44 | 0.03 | 0.23 | 0.18 | 0.26 | 1.02 | 0.12 |
| D | 179Y | 0.50 | 0.78 | 15.87 | 0.18 | 0.81 | 0.18 | 0.37 | 0.26 | 0.43 | 1.49 | 0.35 |
| H | 180A | 0.10 | 7.37 | -17.51 | 0.03 | 1.06 | 0.02 | 1.29 | 1.50 | 1.76 | 3.65 | 0.95 |
| H | 180C | 0.74 | 0.60 | 1.33 | 0.33 | 0.58 | 0.02 | 0.21 | 0.19 | 0.29 | 0.89 | 0.28 |
| H | 180D | 0.09 | 0.07 | -65.96 | 0.02 | 1.12 | 0.10 | 1.40 | 1.66 | 1.88 | 4.16 | 1.28 |
| H | 180E | 0.02 | 32.23 | -792.59 | 0.00 | 6.16 | 0.66 | 7.51 | 8.93 | 10.05 | 21.32 | 39.47 |
| H | 180F | 0.73 | 0.71 | 0.31 | 0.22 | 0.49 | 0.02 | 0.33 | 0.26 | 0.46 | 0.85 | 0.17 |
| H | 180G | -0.04 | -7.14 | 158.80 | -0.01 | -2.26 | -0.35 | -2.69 | -3.27 | -3.48 | -7.25 | -4.65 |
| H | 180I | -0.02 | 6.63 | 299.93 | 0.00 | -5.02 | 2.26 | -6.14 | -7.31 | -8.06 | -16.16 | -7.41 |
| H | 180K | -0.19 | -0.16 | 13.57 | -0.04 | -0.52 | -0.06 | -0.64 | -0.77 | -0.82 | -1.89 | -0.45 |
| H | 180M | 0.71 | 0.51 | -15.22 | 0.31 | 0.56 | 0.01 | 0.20 | 0.21 | 0.26 | 1.15 | 0.32 |
| H | 180N | 0.54 | 0.73 | -1.34 | 0.17 | 0.52 | 0.00 | 0.24 | 0.26 | 0.31 | 1.35 | 0.25 |
| H | 180P | -0.09 | -5.24 | 105.32 | -0.02 | -1.14 | -0.12 | -1.42 | -1.68 | -1.83 | -3.16 | -2.24 |
| H | 180S | -0.03 | -17.82 | 389.56 | -0.01 | -3.37 | -0.26 | -3.50 | -4.10 | -4.32 | -10.89 | -3.30 |
| H | 180T | -0.22 | 0.87 | 42.92 | -0.04 | -0.44 | -0.04 | -0.55 | -0.66 | -0.72 | -1.27 | -0.39 |
| H | 180V | -0.13 | 1.49 | 59.31 | -0.02 | -0.75 | -0.09 | -0.96 | -1.14 | -1.26 | -2.33 | -0.72 |
| H | 180W | -0.15 | 1.30 | 10.59 | -0.02 | -0.65 | -0.04 | -0.81 | -0.96 | -1.03 | -2.24 | -0.82 |
| H | 180Y | 0.44 | 0.28 | -24.39 | 0.15 | 1.05 | 0.16 | 0.56 | 0.36 | 0.77 | 1.64 | 0.64 |
| I | 181A | 0.15 | 4.92 | 0.34 | 0.05 | 1.75 | 0.17 | 1.11 | 0.98 | 1.28 | 3.09 | 1.20 |
| I | 181C | 0.15 | 4.36 | 11.06 | 0.05 | 1.85 | 0.23 | 1.16 | 1.02 | 1.32 | 2.92 | 1.61 |
| I | 181D | 0.05 | 3.30 | 4.63 | 0.01 | 1.92 | 0.14 | 2.22 | 2.64 | 2.74 | 5.44 | 2.63 |
| I | 181F | -0.06 | -1.00 | -29.13 | -0.01 | -1.75 | -0.05 | -2.03 | -2.44 | -2.45 | -5.67 | -0.60 |
| I | 181G | -0.06 | 1.93 | 13.90 | -0.01 | -1.74 | -0.08 | -1.94 | -2.32 | -2.32 | -5.73 | -1.89 |
| I | 181H | -0.09 | 3.73 | -5.36 | -0.02 | -1.13 | -0.11 | -1.30 | -1.56 | -1.67 | -2.95 | -1.30 |
| I | 181K | -0.09 | 2.74 | -12.45 | -0.02 | -1.15 | -0.14 | -1.34 | -1.57 | -1.69 | -3.03 | -0.87 |
| I | 181L | 0.12 | 1.44 | -8.05 | 0.04 | 2.58 | 0.46 | 1.47 | 1.20 | 1.50 | 4.07 | 1.36 |
| I | 181M | 0.13 | 4.02 | -8.20 | 0.04 | 2.08 | 0.22 | 1.32 | 1.09 | 1.39 | 3.22 | 1.29 |
| I | 181N | 0.04 | 4.33 | -42.26 | 0.01 | 2.58 | 0.39 | 3.03 | 3.62 | 3.88 | 7.51 | 2.93 |
| I | 181R | 0.03 | -7.68 | 6.17 | 0.01 | 3.26 | 0.33 | 3.78 | 4.44 | 3.81 | 9.28 | 0.97 |
| I | 181S | -0.18 | 1.28 | 1.90 | -0.04 | -0.57 | -0.07 | -0.62 | -0.73 | -0.74 | -1.29 | -0.51 |
| I | 181T | 0.00 | 117.01 | 542.82 | 0.00 | 39.59 | 5.11 | 31.07 | 32.77 | 35.81 | 86.63 | 47.86 |
| I | 181V | 0.73 | 1.14 | 1.96 | 0.67 | 1.25 | 1.10 | 1.17 | 1.12 | 1.00 | 1.33 | 1.30 |
| I | 181W | -0.03 | 3.49 | -48.70 | -0.01 | -3.09 | -0.86 | -3.67 | -4.34 | -4.51 | -8.07 | -0.76 |
| I | 181Y | -0.04 | 4.05 | -131.35 | -0.01 | -2.62 | -0.55 | -3.21 | -3.71 | -4.35 | -6.85 | -2.26 |
| E | 182A | 0.13 | 4.19 | 7.06 | 0.03 | 0.76 | 0.15 | 0.84 | 1.11 | 1.40 | 1.42 | -1.47 |
| E | 182C | -0.03 | -19.22 | -30.89 | -0.01 | -3.27 | -0.35 | -3.70 | -4.95 | -5.98 | -8.00 | 5.40 |
| E | 182D | -0.07 | -6.90 | -10.87 | -0.02 | -1.44 | -0.18 | -1.54 | -1.99 | -2.39 | -2.23 | 1.79 |
| E | 182F | -0.02 | -8.81 | -36.38 | -0.01 | -3.90 | -0.35 | -4.07 | -5.49 | -6.34 | -11.32 | 3.87 |
| E | 182G | -0.13 | -0.51 | -11.11 | -0.03 | -0.73 | -0.07 | -0.79 | -1.06 | -1.30 | -2.23 | 1.62 |
| E | 182H | -0.08 | -0.61 | -7.67 | -0.02 | -1.26 | -0.09 | -1.33 | -1.78 | -2.15 | -3.21 | 0.99 |
| E | 182I | -0.13 | -0.47 | -2.47 | -0.03 | -0.74 | -0.03 | -0.79 | -1.03 | -1.26 | -1.63 | 0.95 |
| E | 182K | -0.10 | 0.98 | -10.57 | -0.02 | -0.91 | -0.09 | -0.98 | -1.27 | -1.62 | -2.53 | 0.87 |
| E | 182L | -0.09 | 3.91 | -10.70 | -0.02 | -1.11 | 0.01 | -1.20 | -1.58 | -1.95 | -3.13 | 1.48 |
| E | 182M | -0.02 | -11.95 | -39.65 | 0.00 | -4.22 | -0.45 | -4.68 | -6.07 | -7.69 | -11.31 | 10.77 |
| E | 182N | -0.15 | -1.90 | 0.87 | -0.03 | -0.62 | 0.03 | -0.64 | -0.89 | -1.10 | -1.93 | 1.68 |
| E | 182P | -0.16 | -2.73 | -3.23 | -0.03 | -0.59 | -0.08 | -0.64 | -0.83 | -1.02 | -1.73 | 0.71 |
| E | 182Q | -0.16 | -0.27 | -4.42 | -0.03 | -0.58 | -0.11 | -0.62 | -0.83 | -0.99 | -1.21 | 0.90 |
| E | 182R | -0.15 | -1.63 | -9.36 | -0.03 | -0.74 | -0.83 | -1.68 | -1.56 | 0.00 | -1.78 | 1.15 |
| E | 182S | -0.14 | -1.77 | -2.85 | -0.03 | -0.69 | -0.08 | -0.73 | -0.96 | -1.16 | -1.59 | 1.39 |
| E | 182T | -0.22 | -0.84 | 0.40 | -0.04 | -0.42 | -0.08 | -0.45 | -0.59 | -0.71 | -1.15 | 0.80 |
| E | 182V | -0.17 | -1.45 | -4.19 | -0.03 | -0.55 | -0.11 | -0.61 | -0.80 | -1.04 | -1.35 | 0.64 |
| E | 182W | -0.26 | 0.63 | -3.00 | -0.07 | -0.43 | -0.07 | -0.42 | -0.53 | -0.67 | -0.74 | 0.69 |
| E | 182Y | -0.16 | 0.97 | -5.16 | -0.03 | -0.59 | -0.10 | -0.68 | -0.86 | -1.07 | -1.91 | 1.01 |
| L | 183A | 0.03 | 54.13 | 6.16 | 0.01 | 6.21 | 0.12 | 5.18 | 6.16 | 8.61 | 14.79 | 12.60 |
| L | 183C | 0.04 | 13.45 | 10.65 | 0.01 | 4.36 | 0.41 | 2.72 | 2.60 | 4.01 | 7.06 | 4.22 |
| L | 183D | -0.06 | -7.02 | -17.38 | -0.01 | -1.56 | -0.15 | -1.69 | -2.11 | -2.75 | -2.93 | -2.45 |
| L | 183E | -0.07 | -7.08 | 19.08 | -0.01 | -1.54 | -0.13 | -1.69 | -2.11 | -2.76 | -3.77 | -3.79 |
| L | 183F | -0.06 | -10.42 | -34.93 | -0.02 | -1.90 | -0.25 | -1.82 | -2.25 | -2.75 | -4.25 | -4.70 |
| L | 183G | -0.06 | 6.93 | 4.04 | -0.01 | -1.80 | -0.24 | -1.93 | -2.41 | -3.17 | -5.02 | -3.98 |
| L | 183H | -0.11 | -2.66 | -13.27 | -0.02 | -1.41 | -0.14 | -1.04 | -1.22 | -1.61 | -2.65 | -1.83 |
| L | 183I | -0.08 | -0.89 | 10.99 | -0.02 | -1.72 | -0.30 | -1.52 | -1.77 | -2.29 | -4.69 | -7.84 |
| L | 183K | -0.14 | 4.17 | -19.66 | -0.03 | -0.68 | -0.06 | -0.74 | -0.92 | -1.19 | -1.57 | -1.13 |
| L | 183M | 0.31 | 0.47 | 3.84 | 0.15 | 1.81 | 0.77 | 1.07 | 0.57 | 1.17 | 2.16 | 2.13 |
| L | 183N | -0.15 | -2.89 | -11.11 | -0.03 | -0.65 | -0.06 | -0.67 | -0.88 | -1.17 | -1.06 | -1.05 |
| L | 183P | -0.12 | -2.96 | -23.42 | -0.02 | -0.84 | -0.06 | -0.89 | -1.12 | -1.47 | -2.09 | -3.41 |
| L | 183Q | -0.11 | -7.12 | -30.90 | -0.03 | -1.27 | 0.00 | -1.05 | -1.22 | -1.69 | -3.05 | -0.90 |
| L | 183R | -0.06 | -6.35 | -44.40 | -0.01 | -1.71 | -0.20 | -1.75 | -2.19 | -2.58 | -4.58 | -3.84 |
| L | 183S | -0.11 | 0.11 | -24.12 | -0.02 | -0.90 | -0.07 | -0.96 | -1.19 | -1.49 | -2.15 | 4.24 |
| L | 183T | -0.11 | -2.36 | -26.50 | -0.02 | -1.44 | -0.15 | -1.13 | -1.27 | -1.56 | -2.65 | -0.81 |
| L | 183V | -0.07 | -2.69 | -9.28 | -0.02 | -3.14 | -0.37 | -1.90 | -1.79 | -2.64 | -4.86 | -5.54 |
| L | 183W | -0.13 | 5.38 | -17.31 | -0.02 | -0.76 | -0.13 | -0.83 | -1.04 | -1.34 | -2.21 | -1.18 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| P | 184A | 0.32 | 1.90 | 4.73 | 0.13 | 1.25 | 0.34 | 0.81 | 1.03 | 0.94 | 1.87 | 0.83 |
| P | 184C | 0.27 | 1.70 | 3.56 | 0.10 | 1.04 | 0.17 | 0.75 | 1.42 | 0.90 | 1.77 | 0.86 |
| P | 184D | 0.33 | 1.85 | 2.61 | 0.15 | 1.40 | 0.53 | 0.95 | 1.42 | 1.02 | 1.86 | 1.47 |
| P | 184E | 0.22 | 2.14 | 9.36 | 0.09 | 2.02 | 0.74 | 1.39 | 2.14 | 1.49 | 2.72 | 2.23 |
| P | 184F | 0.10 | 7.29 | 28.62 | 0.03 | 2.15 | 0.25 | 1.69 | 4.04 | 2.07 | 4.31 | 2.32 |
| P | 184G | 0.11 | 5.83 | 22.27 | 0.03 | 2.09 | 0.26 | 1.55 | 3.82 | 2.04 | 4.14 | 1.86 |
| P | 184H | 0.19 | 2.28 | 9.48 | 0.06 | 1.81 | 0.46 | 1.21 | 2.31 | 1.35 | 2.70 | 2.22 |
| P | 184I | 0.14 | 1.80 | 10.71 | 0.04 | 1.98 | 0.38 | 1.36 | 1.83 | 1.68 | 3.24 | 2.07 |
| P | 184K | 0.02 | 7.75 | 59.06 | 0.01 | 8.61 | 1.01 | 6.97 | 17.18 | 9.17 | 17.63 | 12.18 |
| P | 184L | 0.17 | 0.66 | 15.14 | 0.05 | 1.69 | 0.31 | 1.17 | 2.07 | 1.46 | 2.68 | 1.49 |
| P | 184M | 0.12 | 4.04 | 25.31 | 0.05 | 2.50 | 0.51 | 1.70 | 2.66 | 2.14 | 3.65 | 2.45 |
| P | 184N | 0.18 | 2.62 | 7.70 | 0.06 | 1.36 | 0.18 | 1.01 | 2.18 | 1.35 | 2.27 | 1.03 |
| P | 184Q | 0.24 | 2.82 | 11.32 | 0.09 | 1.43 | 0.39 | 0.97 | 1.88 | 1.17 | 2.16 | 1.32 |
| P | 184R | 0.09 | 6.17 | 19.84 | 0.03 | 1.64 | 0.10 | 1.49 | 4.38 | 2.02 | 3.15 | 0.71 |
| P | 184S | 0.02 | 17.23 | 75.11 | 0.01 | 13.29 | 3.36 | 9.01 | 7.66 | 10.26 | 20.40 | 14.71 |
| P | 184T | 0.34 | 1.42 | 6.43 | 0.15 | 1.52 | 0.67 | 1.08 | 0.63 | 1.13 | 2.01 | 1.51 |
| P | 184V | −0.79 | −1.00 | −3.58 | −0.19 | −0.40 | −1.15 | 0.16 | 0.00 | 0.03 | −0.51 | −0.30 |
| P | 184W | 0.10 | 4.53 | 40.70 | 0.03 | 3.30 | 0.78 | 2.34 | 1.76 | 2.63 | 5.43 | 2.68 |
| P | 184Y | 0.00 | 3.17 | 967.83 | 0.00 | 57.89 | 7.85 | 45.43 | 89.40 | 58.16 | 102.88 | 53.91 |
| D | 186A | −0.07 | −3.72 | −41.43 | −0.01 | −1.28 | −0.14 | −1.46 | −1.64 | −1.67 | −3.23 | 2.81 |
| D | 186C | −0.12 | −2.18 | −9.82 | −0.03 | −0.85 | −0.02 | −0.86 | −0.95 | −0.96 | −2.28 | 1.84 |
| D | 186E | 0.82 | 0.88 | 5.10 | 0.53 | 0.86 | 0.64 | 0.76 | 0.64 | 0.66 | 1.08 | 0.84 |
| D | 186F | −0.20 | −2.08 | −10.98 | −0.04 | −0.46 | −0.04 | −0.48 | −0.56 | −0.54 | −1.26 | 1.31 |
| D | 186H | −0.17 | −0.59 | −16.21 | −0.03 | −0.54 | −0.02 | −0.57 | −0.64 | −0.62 | −1.36 | 1.13 |
| D | 186I | −0.16 | −0.87 | −0.67 | −0.03 | −0.56 | −0.03 | −0.59 | −0.67 | −0.65 | −1.48 | 1.07 |
| D | 186K | −0.17 | 0.48 | −4.49 | −0.03 | −0.53 | −0.08 | −0.57 | −0.64 | −0.63 | −1.49 | 1.10 |
| D | 186L | −0.17 | 1.01 | −1.86 | −0.03 | −0.52 | −0.02 | −0.58 | −0.67 | −0.67 | −1.58 | 1.24 |
| D | 186M | −0.07 | −1.46 | −22.57 | −0.01 | −1.29 | −0.10 | −1.44 | −1.66 | −1.76 | −3.57 | 2.70 |
| D | 186N | −0.07 | −3.93 | −22.00 | −0.01 | −1.24 | −0.22 | −1.30 | −1.49 | −1.48 | −3.48 | 2.74 |
| D | 186P | −0.16 | −2.01 | −20.12 | −0.03 | −0.58 | −0.06 | −0.61 | −0.71 | −0.69 | −1.54 | 1.54 |
| D | 186Q | −0.18 | −1.17 | −17.91 | −0.03 | −0.52 | −0.11 | −0.55 | −0.63 | −0.63 | −1.48 | 1.50 |
| D | 186R | −0.17 | −0.45 | −7.98 | −0.03 | −0.57 | −0.17 | −0.58 | −0.68 | −0.66 | −1.58 | 1.04 |
| D | 186S | −0.20 | −0.15 | 3.74 | −0.04 | −0.46 | −0.10 | −0.48 | −0.54 | −0.52 | −1.45 | 1.18 |
| D | 186T | −0.17 | −0.92 | −10.30 | −0.03 | −0.53 | −0.09 | −0.55 | −0.64 | −0.61 | −1.37 | 1.14 |
| D | 186W | −0.30 | 0.31 | −4.86 | −0.06 | −0.31 | −0.03 | −0.33 | −0.37 | −0.37 | −0.74 | 0.71 |
| D | 186Y | −0.17 | 0.39 | −3.61 | −0.03 | −0.58 | −0.03 | −0.61 | −0.70 | −0.69 | −1.88 | 0.98 |
| Y | 189A | 0.00 | 139.43 | 1160.99 | 0.00 | 47.07 | 5.95 | 35.02 | 30.92 | 43.94 | 86.95 | −16.25 |
| Y | 189C | −0.06 | −6.43 | 41.31 | −0.02 | −3.34 | −0.46 | −2.45 | −1.97 | −2.76 | −5.97 | 0.74 |
| Y | 189E | −0.20 | −2.44 | −30.44 | −0.05 | −0.64 | −0.09 | −0.57 | −0.60 | −0.85 | −1.63 | 0.44 |
| Y | 189F | 1.12 | 0.84 | 1.50 | 1.01 | 0.84 | 0.81 | 0.84 | 0.96 | 0.84 | 0.84 | 0.79 |
| Y | 189H | 0.01 | 17.10 | −671.73 | 0.00 | 26.29 | 5.99 | 16.57 | 11.23 | 17.30 | 38.57 | 2.12 |
| Y | 189I | −0.10 | −1.16 | −85.96 | −0.03 | −2.79 | −0.73 | −1.84 | −1.09 | −2.12 | −4.75 | −0.56 |
| Y | 189K | −0.15 | 1.36 | 4.62 | −0.03 | −0.67 | −0.10 | −0.74 | −0.86 | −0.98 | −2.05 | 1.10 |
| Y | 189M | −0.02 | −31.40 | −300.20 | 0.00 | −11.51 | −1.86 | −8.23 | −6.93 | −10.94 | −23.28 | 4.30 |
| Y | 189N | −0.10 | −4.76 | 31.32 | −0.02 | −1.28 | −0.11 | −1.24 | −1.34 | −1.75 | −3.52 | 1.74 |
| Y | 189P | −0.16 | −3.02 | −10.94 | −0.04 | −0.71 | −0.07 | −0.73 | −0.81 | −1.08 | −2.33 | 0.49 |
| Y | 189Q | −0.16 | −3.41 | 30.04 | −0.04 | −0.73 | −0.05 | −0.72 | −0.77 | −0.98 | −1.88 | 1.07 |
| Y | 189R | −0.20 | −0.34 | 16.74 | −0.04 | −0.48 | −0.01 | −0.50 | −0.60 | −0.81 | −1.45 | 0.99 |
| Y | 189S | −0.14 | −3.23 | 57.06 | −0.03 | −1.04 | −0.13 | −0.90 | −0.89 | −1.29 | −1.95 | 0.92 |
| Y | 189T | −0.19 | −2.23 | −25.64 | −0.04 | −0.68 | −0.07 | −0.65 | −0.67 | −0.72 | −1.61 | 0.92 |
| Y | 189V | −0.13 | −0.90 | 13.67 | −0.03 | −1.73 | −0.38 | −1.23 | −0.95 | −1.60 | −3.16 | 0.45 |
| Y | 189W | 0.67 | 1.31 | 1.43 | 0.53 | 1.29 | 1.13 | 1.20 | 0.92 | 1.06 | 1.60 | 1.29 |
| S | 191A | 0.24 | 2.06 | 0.19 | 0.13 | 2.29 | 1.00 | 1.44 | 0.69 | 1.46 | 2.13 | 1.22 |
| S | 191C | 0.00 | 58.24 | 106.09 | 0.00 | 38.37 | 5.72 | 21.17 | 18.89 | 34.09 | 25.65 | 29.58 |
| S | 191D | 0.01 | 36.49 | 17.59 | 0.00 | 40.22 | 7.84 | 20.88 | 16.07 | 29.78 | 41.43 | 35.21 |
| S | 191E | −0.09 | −4.28 | −0.59 | −0.02 | −1.46 | −0.15 | −0.90 | −1.07 | −1.85 | −0.40 | −1.38 |
| S | 191F | −0.11 | −1.26 | 2.39 | −0.02 | −0.90 | −0.12 | −0.65 | −0.82 | −1.34 | 0.24 | −1.57 |
| S | 191I | −0.15 | 0.26 | 3.19 | −0.03 | −0.65 | −0.05 | −0.43 | −0.54 | −0.98 | −0.27 | −1.74 |
| S | 191K | 0.03 | −2.00 | 14.79 | 0.01 | 3.85 | 0.68 | 2.40 | 2.74 | 4.57 | 3.17 | 4.48 |
| S | 191L | 0.07 | −0.86 | −16.67 | 0.01 | 1.36 | 0.18 | 1.01 | 1.29 | 2.23 | 1.34 | 1.89 |
| S | 191M | −0.03 | −13.97 | −0.41 | −0.01 | −4.02 | −0.43 | −2.73 | −3.27 | −5.59 | −1.59 | −6.75 |
| S | 191N | −0.05 | −8.16 | −3.27 | −0.01 | −3.52 | −0.40 | −1.85 | −1.81 | −3.28 | −1.22 | −2.52 |
| S | 191P | −0.05 | −3.29 | 8.44 | −0.01 | −1.80 | −0.27 | −1.31 | −1.80 | −2.72 | 0.06 | −1.73 |
| S | 191Q | −0.07 | −4.36 | −7.41 | −0.02 | −1.74 | −0.20 | −1.04 | −1.28 | −2.16 | −0.10 | −0.38 |
| S | 191R | −0.03 | 3.89 | 14.65 | −0.01 | −4.36 | −0.60 | −2.59 | −2.82 | −4.93 | −1.78 | −3.16 |
| S | 191T | 0.11 | 2.63 | 6.47 | 0.03 | 3.29 | 0.96 | 1.47 | 0.75 | 2.04 | 3.49 | 3.11 |
| S | 191V | −0.10 | 0.52 | 16.06 | −0.02 | −0.96 | −0.12 | −0.70 | −0.92 | −1.45 | −0.31 | −1.49 |
| S | 191W | −0.08 | −2.46 | 8.03 | −0.02 | −1.20 | −0.18 | −0.90 | −1.17 | −1.96 | −0.57 | −1.75 |
| S | 191Y | 0.07 | 0.14 | 25.94 | 0.02 | 1.39 | 0.24 | 1.00 | 1.22 | 2.11 | 0.62 | 1.36 |
| F | 193A | 0.20 | 2.31 | −8.47 | 0.06 | 1.42 | 0.30 | 0.94 | 0.75 | 1.29 | 2.42 | 0.20 |
| F | 193C | −0.05 | −7.46 | −1275.17 | −0.01 | −5.64 | −1.09 | −3.97 | −3.39 | −5.12 | −10.21 | −1.99 |
| F | 193D | −0.11 | −3.30 | −59.00 | −0.02 | −0.87 | −0.10 | −1.00 | −1.17 | −1.57 | −2.49 | 0.77 |
| F | 193E | −0.07 | −1.69 | −110.05 | −0.02 | −1.28 | −0.27 | −1.48 | −1.71 | −2.30 | −2.98 | 3.03 |
| F | 193G | −0.22 | 0.00 | −245.02 | −0.04 | −0.44 | −0.03 | −0.49 | −0.58 | −0.74 | −1.23 | 0.61 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| F | 193H | −0.05 | −3.15 | −243.64 | −0.01 | −3.60 | −0.43 | −2.68 | −2.89 | −3.57 | −6.10 | 1.64 |
| F | 193I | 0.14 | 1.75 | 227.76 | 0.05 | 3.44 | 1.45 | 2.24 | 1.91 | 2.43 | 4.70 | 2.26 |
| F | 193K | −0.18 | 1.38 | −308.67 | −0.04 | −0.52 | −0.06 | −0.60 | −0.72 | −0.92 | −1.28 | 1.02 |
| F | 193L | 0.23 | 2.02 | 139.71 | 0.10 | 2.67 | 1.47 | 1.84 | 1.29 | 1.88 | 3.45 | 1.77 |
| F | 193M | 0.31 | 1.20 | −48.52 | 0.13 | 1.50 | 0.54 | 0.90 | 0.58 | 1.06 | 1.85 | 0.63 |
| F | 193N | −0.07 | −9.50 | −99.31 | −0.02 | −1.65 | −0.13 | −1.64 | −1.94 | −2.62 | −3.95 | 2.97 |
| F | 193P | −0.17 | −0.06 | 38.88 | −0.04 | −0.58 | −0.11 | −0.64 | −0.76 | −1.01 | −1.53 | 1.47 |
| F | 193Q | −0.10 | −3.21 | 3.07 | −0.02 | −0.98 | −0.07 | −1.04 | −1.24 | −1.6$ | −2.18 | 1.43 |
| F | 193R | −0.18 | 0.56 | −234.97 | −0.04 | −0.55 | −0.15 | −0.61 | −0.71 | −1.01 | −1.44 | 0.51 |
| F | 193S | −0.14 | 1.20 | −18.47 | −0.03 | −0.82 | −0.12 | −0.79 | −0.90 | −1.26 | −2.14 | 1.39 |
| F | 193T | −0.16 | −0.61 | 8.85 | −0.03 | −1.19 | −0.17 | −0.88 | −0.89 | −1.27 | −2.46 | 0.72 |
| F | 193V | −0.10 | −3.68 | 283.53 | −0.02 | −3.71 | −1.05 | −2.35 | −2.01 | −2.78 | −5.30 | −1.77 |
| F | 193W | −0.16 | −1.93 | −18.54 | −0.04 | −2.37 | −0.71 | −1.50 | −1.30 | −1.67 | −3.47 | −1.24 |
| F | 193Y | 0.04 | 10.33 | −17.37 | 0.01 | 10.47 | 3.20 | 6.66 | 5.69 | 7.29 | 13.29 | 0.71 |
| W | 194C | −0.12 | −3.66 | 10.24 | −0.02 | −0.84 | −0.08 | −0.95 | −1.11 | −1.43 | −1.73 | 2.63 |
| W | 194F | −0.04 | −10.01 | −48.38 | −0.01 | −7.58 | −1.47 | −4.23 | −3.45 | −4.82 | −10.76 | −2.49 |
| W | 194G | −0.21 | −0.88 | −4.10 | −0.05 | −0.45 | −0.01 | −0.53 | −0.63 | −0.82 | −1.43 | 1.13 |
| W | 194H | −0.12 | 0.53 | −25.04 | −0.03 | −0.91 | −0.09 | −0.96 | −1.15 | −1.40 | −3.06 | 2.99 |
| W | 194I | 0.11 | 2.10 | 17.39 | 0.04 | 3.66 | 1.00 | 1.87 | 1.44 | 1.91 | 5.08 | 2.46 |
| W | 194L | −0.01 | 34.98 | −205.98 | 0.00 | −24.22 | −3.78 | −16.99 | −17.63 | −24.94 | −49.49 | 24.88 |
| W | 194M | −0.07 | −15.47 | −22.38 | −0.02 | −2.40 | −0.08 | −2.03 | −2.16 | −2.86 | −5.92 | 2.99 |
| W | 194N | −0.12 | −4.61 | −9.12 | −0.02 | −0.88 | −0.02 | −1.00 | −1.19 | −1.52 | −2.42 | 1.86 |
| W | 194P | −0.25 | −1.74 | −0.38 | −0.05 | −0.40 | −0.03 | −0.44 | −0.48 | −0.65 | −1.34 | 0.71 |
| W | 194Q | −0.15 | −1.80 | 4.57 | −0.03 | −0.63 | −0.06 | −0.69 | −0.84 | −1.04 | −1.80 | 1.30 |
| W | 194R | −0.12 | −3.21 | −6.62 | −0.03 | −0.83 | −0.05 | −0.91 | −1.06 | −1.42 | −1.92 | 1.42 |
| W | 194S | −0.19 | −1.32 | −4.47 | −0.04 | −0.52 | −0.08 | −0.58 | −0.69 | −0.86 | −1.65 | 1.64 |
| W | 194T | −0.22 | −0.54 | −1.91 | −0.06 | −0.49 | −0.04 | −0.51 | −0.60 | −0.77 | −1.12 | 1.41 |
| W | 194V | −0.09 | −2.10 | −17.28 | −0.02 | −2.37 | −0.30 | −1.54 | −1.55 | −2.00 | −4.17 | 0.93 |
| W | 194Y | −0.06 | −0.13 | −6.13 | −0.02 | −5.38 | −1.14 | −3.40 | −2.68 | −3.52 | −7.45 | 0.34 |
| N | 196A | 0.85 | 1.01 | 0.20 | 0.91 | 1.08 | 0.97 | 0.95 | 0.63 | 0.88 | 1.04 | 1.07 |
| N | 196C | 0.73 | 0.98 | 4.21 | 0.58 | 1.05 | 0.84 | 0.91 | 0.83 | 0.85 | 1.15 | 1.13 |
| N | 196D | 0.39 | 1.52 | 5.41 | 0.25 | 1.73 | 1.23 | 1.44 | 1.44 | 1.52 | 1.98 | 1.89 |
| N | 196E | 0.85 | 1.00 | 1.37 | 0.81 | 1.05 | 0.98 | 1.04 | 1.07 | 1.01 | 1.07 | 1.06 |
| N | 196F | 1.00 | 1.02 | 0.35 | 0.97 | 0.95 | 0.94 | 0.97 | 0.98 | 0.92 | 0.95 | 1.01 |
| N | 196G | 0.38 | 1.25 | 8.32 | 0.19 | 1.73 | 1.09 | 1.29 | 1.24 | 1.32 | 2.15 | 1.54 |
| N | 196H | 0.80 | 0.99 | 2.82 | 0.64 | 1.12 | 1.02 | 1.05 | 1.02 | 1.00 | 1.19 | 1.11 |
| N | 196I | 0.98 | 0.85 | 1.57 | 0.91 | 0.95 | 0.90 | 0.92 | 0.90 | 0.92 | 1.01 | 0.96 |
| N | 196K | 0.84 | 0.89 | 1.60 | 0.65 | 1.05 | 0.95 | 0.98 | 0.83 | 0.95 | 1.16 | 1.10 |
| N | 196L | 0.94 | 0.88 | 1.24 | 0.89 | 1.01 | 0.95 | 0.94 | 0.73 | 0.95 | 1.08 | 0.97 |
| N | 196M | 0.93 | 1.01 | 1.64 | 1.07 | 1.01 | 1.00 | 0.95 | 0.67 | 0.89 | 1.10 | 0.89 |
| N | 196P | −0.15 | −5.00 | 4.00 | −0.04 | −0.83 | −0.03 | −0.80 | −0.89 | −1.19 | −2.00 | 1.30 |
| N | 196Q | 0.77 | 0.98 | 3.67 | 0.69 | 1.08 | 0.99 | 1.02 | 1.01 | 1.00 | 1.16 | 1.11 |
| N | 196R | 0.79 | 1.14 | 2.25 | 0.66 | 1.11 | 1.01 | 1.03 | 1.05 | 0.99 | 1.16 | 1.06 |
| N | 196S | 0.66 | 1.11 | 2.74 | 0.47 | 1.29 | 1.08 | 1.16 | 1.13 | 1.12 | 1.42 | 0.98 |
| N | 196T | 0.78 | 1.26 | 2.49 | 0.77 | 1.25 | 1.25 | 1.27 | 1.23 | 1.25 | 1.33 | 1.22 |
| N | 196V | 0.73 | 1.16 | 1.73 | 0.64 | 1.31 | 1.26 | 1.33 | 1.27 | 1.26 | 1.41 | 1.36 |
| N | 196W | 0.53 | 1.35 | 0.97 | 0.37 | 1.54 | 1.26 | 1.34 | 1.21 | 1.27 | 1.64 | 1.67 |
| N | 196Y | 1.01 | 0.89 | 1.23 | 1.11 | 1.00 | 1.05 | 1.02 | 0.76 | 0.95 | 0.99 | 0.85 |
| I | 197A | 0.44 | 1.26 | 26.37 | 0.26 | 1.37 | 0.91 | 1.04 | 0.73 | 1.14 | 1.68 | 0.88 |
| I | 197C | 0.19 | 2.04 | −107.01 | 0.08 | 2.24 | 0.99 | 1.55 | 1.33 | 1.75 | 2.89 | 1.97 |
| I | 197D | −0.18 | −0.69 | 5.31 | −0.04 | −0.55 | −0.07 | −0.62 | −0.75 | −0.99 | −1.44 | 0.36 |
| I | 197E | −0.07 | −7.99 | −389.34 | −0.02 | −3.30 | −0.62 | −2.38 | −2.56 | −3.12 | −5.59 | 0.97 |
| I | 197F | 0.11 | 3.19 | 16.63 | 0.03 | 4.13 | 1.66 | 2.83 | 2.63 | 2.83 | 5.17 | 2.61 |
| I | 197G | −0.22 | −0.79 | 201.56 | −0.05 | −0.65 | −0.09 | −0.55 | −0.61 | −0.77 | −1.45 | 0.18 |
| I | 197H | −0.31 | 0.71 | 4.96 | −0.06 | −0.42 | −0.07 | −0.37 | −0.44 | −0.55 | −0.95 | 0.59 |
| I | 197K | −0.18 | 0.64 | 288.92 | −0.04 | −0.57 | −0.12 | −0.60 | −0.70 | −0.90 | −1.91 | 1.06 |
| I | 197I | 0.74 | 1.00 | −13.63 | 0.52 | 1.20 | 1.12 | 1.10 | 0.85 | 1.13 | 1.25 | 1.21 |
| I | 197M | 1.16 | 0.76 | −0.96 | 1.40 | 0.89 | 0.93 | 0.80 | 0.53 | 0.85 | 0.89 | 0.77 |
| I | 197N | 0.02 | 19.15 | 232.08 | 0.01 | 8.61 | 1.65 | 6.03 | 5.85 | 8.62 | 15.60 | −7.16 |
| I | 197P | −0.13 | −1.66 | 395.65 | −0.02 | −0.74 | −0.13 | −0.86 | −1.03 | −1.37 | −2.04 | 1.35 |
| I | 197R | −0.08 | 0.33 | −201.57 | −0.02 | −1.07 | −0.23 | −1.24 | −1.45 | −1.85 | −2.93 | 0.38 |
| I | 197S | 0.06 | 4.76 | −380.48 | 0.02 | 6.14 | 1.99 | 3.88 | 3.54 | 4.58 | 8.47 | 2.59 |
| I | 197T | 0.18 | 2.38 | −12.87 | 0.07 | 2.97 | 1.51 | 2.05 | 1.60 | 2.11 | 3.80 | 2.31 |
| I | 197V | 0.85 | 0.79 | −40.75 | 0.63 | 1.09 | 0.93 | 0.93 | 0.65 | 0.93 | 1.09 | 1.08 |
| I | 197W | −0.15 | 0.64 | 222.91 | −0.03 | −0.64 | −0.10 | −0.75 | −0.84 | −1.14 | −1.84 | 1.23 |
| I | 197Y | −0.11 | −0.79 | −95.94 | −0.02 | −2.08 | −0.22 | −1.49 | −1.45 | −1.88 | −3.58 | 0.77 |
| T | 198A | 0.54 | 1.11 | 0.64 | 0.39 | 1.31 | 0.87 | 0.98 | 0.63 | 0.95 | 1.54 | 1.39 |
| T | 198C | 0.75 | 0.83 | 1.72 | 0.56 | 0.99 | 0.79 | 0.83 | 0.78 | 0.83 | 1.11 | 1.27 |
| T | 198D | −0.06 | −7.82 | −9.56 | −0.02 | −2.68 | −0.39 | −2.06 | −2.38 | −2.91 | −6.09 | −0.10 |
| T | 198G | 0.10 | 3.19 | 5.59 | 0.04 | 4.58 | 1.99 | 3.04 | 2.75 | 3.49 | 6.33 | 4.64 |
| T | 198H | 0.07 | 2.48 | 14.43 | 0.02 | 5.20 | 1.68 | 3.36 | 3.08 | 3.84 | 8.95 | 4.08 |
| T | 198I | 0.72 | 0.95 | −0.72 | 0.45 | 1.08 | 0.84 | 0.88 | 0.79 | 0.93 | 1.34 | 1.21 |
| T | 198K | −0.02 | −10.74 | −93.05 | 0.00 | −22.04 | −6.60 | −14.42 | −11.93 | −17.92 | −36.11 | −13.12 |
| T | 198L | 0.90 | 0.59 | 1.63 | 0.66 | 0.91 | 0.72 | 0.73 | 0.36 | 0.82 | 1.06 | 1.17 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| T | 198M | 0.44 | 1.05 | 2.41 | 0.26 | 1.41 | 0.82 | 0.91 | 0.53 | 0.96 | 1.84 | 1.36 |
| T | 198N | 0.09 | 2.75 | 16.92 | 0.03 | 3.82 | 1.21 | 2.50 | 2.17 | 2.90 | 4.74 | 1.39 |
| T | 198P | −0.17 | −3.03 | −5.66 | −0.05 | −0.64 | −0.02 | −0.59 | −0.82 | −1.01 | −1.88 | 0.85 |
| T | 198R | 0.12 | 2.58 | 5.28 | 0.04 | 3.24 | 1.20 | 2.13 | 2.08 | 2.32 | 5.02 | 2.85 |
| T | 198S | 0.48 | 1.04 | 5.40 | 0.26 | 1.38 | 0.97 | 1.18 | 1.10 | 1.62 | 1.68 | 1.61 |
| T | 198V | 0.75 | 0.99 | 0.90 | 0.51 | 1.08 | 0.91 | 0.95 | 0.95 | 0.96 | 1.34 | 1.00 |
| T | 198W | −0.16 | −0.62 | −13.90 | −0.04 | −1.47 | −0.21 | −0.96 | −0.96 | −1.25 | −2.69 | 1.03 |
| T | 198Y | −0.01 | 0.61 | −234.24 | 0.00 | −52.80 | −12.64 | −32.23 | −25.77 | −38.70 | −78.22 | −31.73 |
| F | 204A | 0.19 | 3.71 | −19.30 | 0.06 | 1.51 | 0.29 | 1.02 | 0.95 | 1.42 | 2.22 | 0.92 |
| F | 204C | 0.23 | 1.84 | 35.29 | 0.09 | 1.82 | 0.65 | 1.18 | 1.17 | 1.49 | 2.42 | 2.26 |
| F | 204D | −0.05 | −17.91 | −52.16 | −0.01 | −3.30 | −0.21 | −2.81 | −3.28 | −4.28 | −7.82 | −3.73 |
| F | 204E | 0.16 | 3.90 | 52.66 | 0.04 | 1.44 | 0.23 | 1.04 | 1.15 | 1.48 | 2.71 | 1.65 |
| F | 204G | −0.04 | −5.85 | −202.83 | −0.01 | −2.98 | −0.41 | −2.49 | −2.97 | −3.73 | −5.86 | −3.14 |
| F | 204I | 0.72 | 0.95 | 3.50 | 0.54 | 1.16 | 0.90 | 1.02 | 0.93 | 1.13 | 1.24 | 1.25 |
| F | 204K | 0.03 | 7.48 | −104.55 | 0.01 | 9.21 | 1.72 | 6.40 | 6.18 | 8.74 | 17.22 | 10.24 |
| F | 204L | 0.53 | 1.17 | 4.84 | 0.28 | 1.40 | 0.91 | 1.10 | 0.70 | 1.26 | 1.50 | 1.35 |
| F | 204M | 0.69 | 0.86 | 1.32 | 0.51 | 1.05 | 0.76 | 0.85 | 0.59 | 1.00 | 1.16 | 1.11 |
| F | 204N | 0.02 | 33.32 | −98.45 | 0.01 | 6.65 | 0.79 | 5.26 | 5.82 | 7.86 | 12.46 | 6.28 |
| F | 204P | −1.26 | 0.63 | 6.28 | −0.26 | −0.30 | −2.16 | −0.03 | 0.08 | −0.21 | −0.21 | −0.09 |
| F | 204Q | 0.03 | 12.89 | −41.85 | 0.01 | 7.25 | 1.27 | 4.85 | 5.31 | 6.70 | 12.60 | 7.26 |
| F | 204S | −0.12 | −2.26 | −64.66 | −0.02 | −1.78 | −0.25 | −1.28 | −1.43 | −1.83 | −3.57 | −1.64 |
| F | 204T | 0.07 | 5.89 | −108.94 | 0.02 | 5.62 | 1.66 | 3.66 | 3.77 | 4.71 | 9.17 | 5.78 |
| F | 204V | 0.54 | 1.58 | 11.70 | 0.30 | 1.28 | 0.82 | 1.02 | 0.94 | 1.14 | 1.49 | 1.31 |
| F | 204W | 0.72 | 1.35 | 2.83 | 0.67 | 1.33 | 1.26 | 1.27 | 1.23 | 1.55 | 1.39 | 1.39 |
| F | 204Y | 0.88 | 1.16 | 1.89 | 0.93 | 1.20 | 1.11 | 1.05 | 0.91 | 1.22 | 1.18 | 1.03 |
| Q | 205A | 0.55 | 1.21 | −0.23 | 0.41 | 1.41 | 1.04 | 1.12 | 0.73 | 1.09 | 1.60 | 1.29 |
| Q | 205C | 0.57 | 1.13 | 1.82 | 0.49 | 1.39 | 1.10 | 1.20 | 1.02 | 1.04 | 1.55 | 1.12 |
| Q | 205D | 0.08 | 3.81 | −3.74 | 0.03 | 4.66 | 1.50 | 3.14 | 3.43 | 3.41 | 7.43 | 2.39 |
| Q | 205E | 0.43 | 1.21 | 1.18 | 0.22 | 1.31 | 0.74 | 0.97 | 1.01 | 0.96 | 1.70 | 0.91 |
| Q | 205F | 0.45 | 1.21 | 1.37 | 0.24 | 1.43 | 0.88 | 1.13 | 1.10 | 1.10 | 1.86 | 1.16 |
| Q | 205G | 0.08 | 2.33 | 14.42 | 0.02 | 5.09 | 1.92 | 3.34 | 3.13 | 3.64 | 7.18 | 3.28 |
| Q | 205H | 0.40 | 1.36 | −2.26 | 0.20 | 1.67 | 1.05 | 1.30 | 1.21 | 1.29 | 2.09 | 1.80 |
| Q | 205I | 0.54 | 1.08 | 1.07 | 0.30 | 1.36 | 0.92 | 1.09 | 1.02 | 1.02 | 1.55 | 1.41 |
| Q | 205K | 0.23 | 1.93 | 3.79 | 0.11 | 2.60 | 1.37 | 1.83 | 1.54 | 1.82 | 3.08 | 1.60 |
| Q | 205L | 0.64 | 0.95 | 3.17 | 0.46 | 1.30 | 0.92 | 1.04 | 0.77 | 1.00 | 1.43 | 1.16 |
| Q | 205M | 0.67 | 1.15 | −0.03 | 0.65 | 1.37 | 1.22 | 1.20 | 0.81 | 1.16 | 1.31 | 1.23 |
| Q | 205N | 0.78 | 0.94 | 0.03 | 0.65 | 1.00 | 0.78 | 0.84 | 0.74 | 0.76 | 1.19 | 0.93 |
| Q | 205P | −0.18 | −0.94 | −2.11 | −0.03 | −0.56 | −0.04 | −0.58 | −0.76 | −0.93 | −1.17 | 1.08 |
| Q | 205R | 0.13 | 3.75 | −3.89 | 0.04 | 3.53 | 1.38 | 2.30 | 2.20 | 2.41 | 4.58 | 2.00 |
| Q | 205S | 0.47 | 1.01 | 3.32 | 0.25 | 1.53 | 1.01 | 1.21 | 1.08 | 1.07 | 1.77 | 1.53 |
| Q | 205T | 0.16 | 2.92 | −4.39 | 0.07 | 3.69 | 2.02 | 2.75 | 2.42 | 2.58 | 4.64 | 3.29 |
| Q | 205V | 0.56 | 1.19 | −1.92 | 0.33 | 1.38 | 1.00 | 1.15 | 1.03 | 1.10 | 1.63 | 1.40 |
| Q | 205W | 0.43 | 1.31 | −4.07 | 0.25 | 1.77 | 1.31 | 1.45 | 1.05 | 1.46 | 2.00 | 1.33 |
| Q | 205Y | 0.34 | 1.06 | 0.97 | 0.17 | 2.06 | 1.27 | 1.56 | 0.97 | 1.45 | 2.29 | 1.53 |
| Y | 206A | −0.11 | −5.25 | −55.08 | −0.03 | −0.97 | −0.13 | −1.05 | −1.23 | −1.34 | −2.56 | 2.61 |
| Y | 206C | −0.05 | −16.13 | −423.84 | −0.01 | −3.01 | −0.14 | −2.76 | −3.12 | −3.15 | −9.45 | 0.66 |
| Y | 206D | −0.18 | −1.68 | −31.47 | −0.04 | −0.52 | −0.07 | −0.54 | −0.65 | −0.71 | −1.85 | 0.88 |
| Y | 206E | −0.13 | −0.33 | 8.88 | −0.03 | −0.79 | −0.16 | −0.84 | −1.01 | −1.09 | −1.82 | 1.59 |
| Y | 206F | 0.35 | 1.22 | −13.73 | 0.14 | 1.29 | 0.28 | 0.87 | 0.81 | 0.51 | 1.99 | 1.05 |
| Y | 206G | −0.23 | −0.64 | −34.57 | −0.05 | −0.42 | −0.06 | −0.43 | −0.51 | −0.55 | −1.18 | 0.54 |
| Y | 206H | −0.16 | 0.32 | 63.50 | −0.03 | −0.67 | −0.07 | −0.69 | −0.81 | −0.77 | −2.33 | 1.28 |
| Y | 206K | −0.25 | −0.37 | 86.77 | −0.05 | −0.41 | −0.03 | −0.41 | −0.48 | −0.53 | −1.21 | 0.79 |
| Y | 206M | 0.01 | 119.25 | 923.47 | 0.00 | 42.30 | 1.60 | 29.76 | 29.14 | 30.93 | 92.99 | 22.50 |
| Y | 206N | −0.05 | −7.79 | 2.78 | −0.01 | −2.17 | −0.11 | −2.34 | −2.83 | −2.82 | −6.54 | 4.30 |
| Y | 206P | −0.09 | −1.67 | −33.03 | −0.02 | −1.15 | −0.27 | −1.26 | −1.47 | −1.61 | −3.86 | 2.48 |
| Y | 206Q | −0.06 | 1.86 | −195.05 | −0.01 | −1.65 | −0.19 | −1.76 | −2.07 | −2.27 | −3.13 | 2.28 |
| Y | 206R | −0.13 | −0.91 | 20.60 | −0.03 | −0.76 | −0.19 | −0.82 | −0.98 | −1.06 | −2.23 | 1.73 |
| Y | 206S | −0.14 | −0.35 | −164.69 | −0.02 | −0.75 | −0.04 | −0.78 | −0.91 | −0.93 | −2.03 | 0.64 |
| Y | 206T | −0.16 | −0.13 | 4.24 | −0.03 | −0.64 | −0.08 | −0.67 | −0.78 | −0.83 | −1.93 | 1.17 |
| Y | 206V | −0.05 | −3.17 | 155.71 | −0.01 | −4.27 | −0.15 | −3.20 | −3.18 | −3.12 | −8.30 | −0.69 |
| Y | 206W | 0.00 | 41.02 | 1446.16 | 0.00 | 23.95 | 2.21 | 18.02 | 17.03 | 19.71 | 56.10 | −0.77 |
| G | 207A | 0.86 | 1.54 | 1.71 | 1.63 | 1.52 | 1.00 | 0.96 | 0.67 | 0.51 | 1.08 | 0.81 |
| G | 207C | 0.13 | 4.01 | 23.66 | 0.08 | 5.39 | 0.72 | 1.69 | 1.35 | 1.28 | 4.55 | 2.43 |
| G | 207D | −0.18 | −2.35 | −13.67 | −0.03 | −0.53 | −0.03 | −0.58 | −0.69 | −0.77 | −1.66 | −0.44 |
| G | 207F | −0.06 | −5.13 | −7.02 | −0.02 | −5.38 | −0.23 | −1.98 | −2.23 | −2.05 | −6.26 | −2.04 |
| G | 207H | −0.19 | −1.99 | −5.02 | −0.03 | −0.54 | −0.05 | −0.57 | −0.66 | −0.71 | −1.52 | −0.41 |
| G | 207K | −0.18 | −0.80 | −23.58 | −0.03 | −0.57 | −0.06 | −0.62 | −0.73 | −0.81 | −1.78 | −0.60 |
| G | 207L | −0.16 | −1.91 | 3.30 | −0.04 | −1.61 | −0.06 | −0.85 | −0.88 | −0.96 | −2.64 | −0.97 |
| G | 207M | 0.07 | 5.97 | 11.73 | 0.04 | 8.09 | 1.20 | 3.07 | 2.55 | 2.75 | 8.81 | 3.37 |
| G | 207P | −0.10 | −4.06 | 6.30 | −0.02 | −1.02 | −0.20 | −1.10 | −1.27 | −1.39 | −2.77 | −0.22 |
| G | 207Q | −0.17 | −4.01 | −7.23 | −0.04 | −0.68 | −0.01 | −0.64 | −0.74 | −0.79 | −2.05 | −0.46 |
| G | 207R | −0.25 | −1.55 | −7.79 | −0.04 | −0.39 | −0.09 | −0.43 | −0.51 | −0.54 | −1.33 | −0.32 |
| G | 207S | −0.12 | −4.18 | −31.19 | −0.03 | −4.10 | −0.44 | −1.60 | −1.50 | −1.38 | −4.51 | −1.99 |
| G | 207T | −0.22 | −1.19 | −10.40 | −0.05 | −0.48 | −0.03 | −0.48 | −0.57 | −0.59 | −1.20 | −0.41 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| G | 207V | −0.23 | −0.75 | −5.38 | −0.05 | −0.44 | −0.08 | −0.46 | −0.53 | −0.56 | −1.23 | −0.29 |
| G | 207W | −0.19 | −0.34 | −13.01 | −0.03 | −0.52 | −0.05 | −0.57 | −0.67 | −0.73 | −1.77 | −0.10 |
| G | 207Y | −0.22 | 0.08 | −3.89 | −0.05 | −0.45 | −0.08 | −0.50 | −0.57 | −0.62 | −1.34 | −0.15 |
| E | 208A | 1.34 | 0.11 | 1.86 | 0.28 | 0.08 | −0.01 | 0.09 | 0.11 | 0.12 | 0.23 | 0.05 |
| E | 208C | 0.75 | 0.84 | 1.99 | 0.16 | 0.13 | 0.00 | 0.16 | 0.19 | 0.19 | 0.32 | 0.35 |
| E | 208D | 0.98 | 0.55 | 2.06 | 0.26 | 0.10 | −0.02 | 0.12 | 0.14 | 0.15 | 0.31 | 0.25 |
| E | 208F | 1.02 | −0.04 | 1.87 | 0.20 | 0.10 | 0.00 | 0.11 | 0.14 | 0.14 | 0.27 | 0.10 |
| E | 208G | 0.63 | −0.03 | 2.86 | 0.14 | 0.16 | 0.01 | 0.19 | 0.22 | 0.24 | 0.58 | 0.13 |
| E | 208H | 0.91 | −0.15 | 2.35 | 0.19 | 0.11 | 0.01 | 0.13 | 0.16 | 0.16 | 0.36 | 0.16 |
| E | 208K | 0.29 | −0.91 | 10.04 | 0.06 | 0.34 | 0.03 | 0.41 | 0.50 | 0.50 | 1.02 | 0.34 |
| E | 208L | 0.58 | −0.82 | 4.62 | 0.12 | 0.17 | 0.02 | 0.21 | 0.26 | 0.27 | 0.50 | 0.11 |
| E | 208N | 0.27 | −0.71 | 7.08 | 0.06 | 0.36 | 0.02 | 0.40 | 0.50 | 0.51 | 1.05 | 1.64 |
| E | 208Q | 0.84 | −0.10 | 2.72 | 0.18 | 0.12 | −0.01 | 0.14 | 0.17 | 0.16 | 0.37 | 0.07 |
| E | 208R | 0.08 | −0.23 | 14.52 | 0.02 | 1.35 | 0.19 | 1.45 | 1.83 | 1.72 | 4.03 | 0.95 |
| E | 208S | 0.86 | 0.19 | 1.97 | 0.18 | 0.12 | 0.02 | 0.13 | 0.16 | 0.16 | 0.34 | 0.12 |
| E | 208T | 0.43 | −0.29 | 2.95 | 0.09 | 0.23 | 0.07 | 0.26 | 0.32 | 0.31 | 0.66 | 0.11 |
| E | 208V | 0.78 | −0.29 | 2.28 | 0.17 | 0.13 | 0.03 | 0.15 | 0.18 | 0.18 | 0.38 | 0.07 |
| E | 208Y | 0.98 | −0.09 | 2.81 | 0.20 | 0.10 | 0.02 | 0.12 | 0.15 | 0.15 | 0.27 | 0.04 |
| I | 209A | 0.02 | 42.00 | 69.48 | 0.00 | 7.42 | 0.29 | 6.35 | 6.69 | 8.80 | 15.50 | 10.82 |
| I | 209C | 0.30 | 0.13 | 3.47 | 0.12 | 1.47 | 0.61 | 0.95 | 0.57 | 1.17 | 2.08 | 1.94 |
| I | 209D | −0.09 | −1.87 | −38.23 | −0.02 | −1.19 | −0.23 | −1.22 | −1.52 | −2.01 | −2.87 | −2.64 |
| I | 209E | −0.12 | −4.87 | −17.77 | −0.03 | −0.86 | −0.09 | −0.90 | −1.09 | −1.47 | −2.11 | −1.09 |
| I | 209F | 0.08 | 0.16 | 4.16 | 0.02 | 2.78 | 0.03 | 1.31 | 1.46 | 1.89 | 4.55 | 8.01 |
| I | 209G | −0.07 | −4.30 | 4.60 | −0.01 | −1.46 | −0.38 | −1.50 | −1.84 | −2.38 | −4.02 | −3.50 |
| I | 209H | 0.00 | 173.72 | 176.77 | 0.00 | 685.48 | 48.48 | 387.01 | 382.84 | 468.69 | 1269.52 | 876.99 |
| I | 209K | −0.18 | 0.08 | 3.66 | −0.04 | −1.11 | −0.09 | −0.72 | −0.83 | −1.06 | −2.18 | −0.97 |
| I | 209L | 0.70 | 1.78 | 6.34 | 0.86 | 1.58 | 0.89 | 0.90 | 0.64 | 0.79 | 1.42 | 1.74 |
| I | 209M | 0.32 | 1.03 | 1.25 | 0.18 | 1.97 | 0.24 | 0.64 | 0.42 | 0.60 | 1.81 | 0.98 |
| I | 209N | −0.03 | −1.74 | 32.21 | −0.01 | −9.99 | −1.92 | −7.16 | −6.10 | −8.81 | −17.07 | −14.89 |
| I | 209P | −0.11 | −4.24 | −9.04 | −0.02 | −0.88 | −0.07 | −0.97 | −1.20 | −1.57 | −2.43 | −2.40 |
| I | 209Q | −0.10 | −5.35 | 6.22 | −0.02 | −1.35 | −0.07 | −1.16 | −1.37 | −1.82 | −3.12 | −1.72 |
| I | 209R | −0.14 | −1.05 | −25.29 | −0.02 | −0.71 | −0.09 | −0.75 | −0.94 | −1.27 | −1.67 | −0.75 |
| I | 209S | −0.08 | 1.05 | −27.28 | −0.02 | −3.67 | −0.25 | −1.84 | −1.69 | −2.25 | −6.10 | −4.35 |
| I | 209T | 0.08 | 1.71 | 23.85 | 0.03 | 5.74 | 1.89 | 3.72 | 2.16 | 3.98 | 8.43 | 5.78 |
| I | 209V | 0.70 | 0.68 | 2.42 | 0.36 | 1.03 | 0.91 | 0.80 | 0.71 | 0.99 | 1.22 | 1.27 |
| I | 209W | −0.21 | 2.11 | −22.01 | −0.04 | −0.56 | −0.04 | −0.52 | −0.64 | −0.82 | −1.44 | −0.43 |
| I | 209Y | −0.11 | −0.16 | −6.84 | −0.02 | −1.14 | −0.10 | −1.03 | −1.20 | −1.63 | −2.71 | −1.25 |
| L | 210A | 0.63 | 0.34 | −1.23 | 0.24 | 0.49 | 0.02 | 0.20 | 0.22 | 0.30 | 0.74 | −0.38 |
| L | 210C | 0.73 | 0.32 | −0.24 | 0.20 | 0.29 | 0.03 | 0.25 | 0.24 | 0.27 | 0.72 | 0.17 |
| L | 210D | 0.90 | 0.31 | 0.52 | 0.33 | 0.39 | 0.02 | 0.15 | 0.17 | 0.20 | 0.64 | −0.22 |
| L | 210E | 0.78 | 0.26 | −1.47 | 0.19 | 0.31 | 0.00 | 0.16 | 0.19 | 0.23 | 0.69 | −0.06 |
| L | 210F | 0.45 | 0.61 | 1.11 | 0.11 | 0.54 | 0.04 | 0.30 | 0.32 | 0.38 | 0.98 | −0.22 |
| L | 210G | 0.68 | 0.41 | 0.61 | 0.17 | 0.42 | 0.01 | 0.17 | 0.20 | 0.25 | 0.77 | −0.15 |
| L | 210H | 0.52 | 0.41 | −1.24 | 0.10 | 0.31 | −0.01 | 0.21 | 0.26 | 0.31 | 0.89 | −0.12 |
| L | 210I | 0.92 | 0.80 | 0.20 | 0.59 | 0.80 | 0.69 | 0.61 | 0.64 | 0.67 | 1.03 | 0.74 |
| L | 210K | 0.86 | 0.19 | −1.71 | 0.17 | 0.22 | 0.03 | 0.17 | 0.19 | 0.27 | 0.45 | 0.05 |
| L | 210M | 1.05 | 0.40 | −0.51 | 0.65 | 0.56 | 0.29 | 0.41 | 0.20 | 0.40 | 0.65 | 0.23 |
| L | 210N | 0.76 | 0.28 | −0.43 | 0.24 | 0.37 | 0.03 | 0.15 | 0.19 | 0.24 | 0.65 | −0.21 |
| L | 210Q | 0.81 | 0.30 | −0.51 | 0.33 | 0.53 | 0.05 | 0.18 | 0.19 | 0.26 | 0.66 | −0.15 |
| L | 210R | 0.81 | −0.06 | 0.27 | 0.16 | 0.13 | 0.01 | 0.13 | 0.17 | 0.22 | 0.30 | −0.34 |
| L | 210S | 0.70 | 0.23 | 0.51 | 0.18 | 0.44 | 0.05 | 0.19 | 0.20 | 0.27 | 0.65 | −0.23 |
| L | 210T | 0.76 | 0.56 | 0.01 | 0.26 | 0.65 | 0.33 | 0.23 | 0.21 | 0.26 | 0.88 | −0.24 |
| L | 210V | 0.90 | 0.78 | 0.41 | 0.57 | 0.79 | 0.55 | 0.49 | 0.35 | 0.46 | 0.97 | 0.47 |
| L | 210W | 0.33 | 0.64 | −0.55 | 0.08 | 0.68 | 0.01 | 0.55 | 0.45 | 0.55 | 1.39 | 0.15 |
| Q | 211A | 0.45 | 1.56 | −20.26 | 0.32 | 1.59 | 0.92 | 1.00 | 0.34 | 0.92 | 1.79 | 0.56 |
| Q | 211C | 0.14 | 4.00 | −6.73 | 0.05 | 2.27 | 0.45 | 1.39 | 0.94 | 1.51 | 3.75 | 5.06 |
| Q | 211D | 0.09 | 5.19 | 35.00 | 0.02 | 3.21 | 0.41 | 1.99 | 1.51 | 2.44 | 6.27 | 2.99 |
| Q | 211E | 0.20 | 3.63 | −12.69 | 0.06 | 2.11 | 0.57 | 1.30 | 0.69 | 1.56 | 2.96 | 1.93 |
| Q | 211G | 0.42 | 1.69 | −5.58 | 0.19 | 1.58 | 0.72 | 1.15 | 0.36 | 0.94 | 1.99 | 1.74 |
| Q | 211H | 0.61 | 1.71 | −10.50 | 0.47 | 1.46 | 0.89 | 0.85 | 0.35 | 0.65 | 1.45 | 1.16 |
| Q | 211I | −0.10 | −0.24 | 23.44 | −0.02 | −1.68 | −0.12 | −1.37 | −1.41 | −1.98 | −3.44 | −1.40 |
| Q | 211K | 0.01 | 68.97 | 1947.02 | 0.00 | 55.45 | 7.02 | 32.44 | 24.89 | 36.87 | 94.74 | 41.01 |
| Q | 211L | −0.08 | −0.98 | −27.70 | −0.02 | −1.96 | −0.15 | −1.57 | −1.63 | −2.31 | −4.82 | −1.93 |
| Q | 211M | 0.47 | 0.80 | 1.21 | 0.25 | 1.25 | 0.44 | 0.71 | 0.32 | 0.59 | 1.48 | 0.93 |
| Q | 211N | −1.25 | 0.41 | 5.60 | −0.26 | −0.32 | −2.22 | −0.03 | 0.01 | −0.28 | −0.21 | −0.09 |
| Q | 211P | 0.36 | 1.24 | −12.77 | 0.16 | 1.46 | 0.13 | 0.58 | 0.37 | 0.64 | 1.80 | 1.05 |
| Q | 211S | 0.79 | 1.70 | −10.39 | 1.08 | 1.48 | 1.22 | 1.12 | 0.59 | 0.95 | 1.13 | 1.10 |
| Q | 211T | 1.06 | 1.41 | −3.23 | 1.70 | 1.18 | 0.94 | 0.94 | 0.64 | 0.88 | 0.96 | 0.90 |
| Q | 211V | 0.02 | 19.38 | 109.25 | 0.00 | 15.17 | 0.89 | 9.20 | 8.71 | 12.35 | 22.42 | 12.66 |
| Q | 211W | 0.22 | 2.72 | 41.49 | 0.10 | 2.62 | 1.06 | 1.44 | 0.58 | 1.12 | 2.98 | 2.39 |
| Q | 211Y | 0.45 | 1.70 | 21.69 | 0.28 | 1.75 | 0.93 | 0.97 | 0.32 | 0.71 | 1.76 | 1.62 |
| S | 215A | 0.33 | 1.11 | 5.08 | 0.16 | 1.69 | 0.86 | 1.34 | 0.48 | 1.18 | 2.04 | 2.07 |
| S | 215C | 0.07 | −0.32 | 17.11 | 0.02 | 4.04 | 0.66 | 2.81 | 1.94 | 2.95 | 6.58 | 5.02 |
| S | 215D | 0.01 | 6.07 | 60.33 | 0.00 | 12.44 | 2.45 | 9.49 | 7.08 | 11.89 | 24.08 | 10.33 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| S | 215E | −0.05 | −8.82 | −29.52 | −0.01 | −2.97 | −0.34 | −2.43 | −2.39 | −3.35 | −5.48 | −2.64 |
| S | 215F | −0.08 | −4.76 | −20.86 | −0.02 | −2.06 | −0.17 | −1.60 | −1.60 | −2.13 | −3.53 | −2.08 |
| S | 215G | −0.03 | 8.60 | −62.04 | −0.01 | −9.30 | −1.56 | −6.17 | −3.98 | −6.07 | −13.94 | −10.67 |
| S | 215H | 0.11 | 1.80 | −1.96 | 0.04 | 4.88 | 2.51 | 3.34 | 1.24 | 2.24 | 5.91 | 4.51 |
| S | 215I | −0.15 | −1.13 | 14.81 | −0.03 | −1.01 | −0.09 | −0.73 | −0.88 | −1.15 | −2.01 | −1.53 |
| S | 215K | −0.17 | 0.79 | −13.63 | −0.03 | −0.81 | −0.08 | −0.71 | −0.75 | −1.03 | −1.77 | −0.57 |
| S | 215L | −0.10 | 1.63 | 17.58 | −0.02 | −1.42 | −0.19 | −1.26 | −1.45 | −2.00 | −3.14 | −1.36 |
| S | 215N | −0.03 | −2.49 | −19.34 | −0.01 | −8.63 | −0.64 | −6.41 | −5.11 | −7.40 | −22.10 | −9.70 |
| S | 215P | −0.15 | −2.49 | −5.85 | −0.03 | −0.90 | −0.09 | −0.79 | −0.89 | −1.18 | −2.12 | −1.28 |
| S | 215Q | −0.13 | −2.89 | 4.90 | −0.03 | −1.14 | −0.12 | −0.97 | −1.06 | −1.40 | −2.10 | −0.80 |
| S | 215R | −0.12 | −1.27 | −23.53 | −0.02 | −1.08 | −0.12 | −0.97 | −1.03 | −1.41 | −2.33 | −1.34 |
| S | 21ST | 0.19 | 2.32 | 18.79 | 0.10 | 3.78 | 1.44 | 1.79 | 0.91 | 1.89 | 3.90 | 3.69 |
| S | 215V | −0.08 | 0.36 | −18.33 | −0.02 | −4.04 | −0.63 | −1.99 | −1.61 | −2.32 | −6.15 | −2.03 |
| S | 215W | −0.19 | 0.29 | −12.08 | −0.04 | −0.71 | −0.07 | −0.62 | −0.71 | −0.92 | −1.85 | −0.57 |
| S | 215Y | −0.04 | 4.31 | 10.50 | −0.01 | −6.37 | −0.55 | −4.37 | −4.07 | −5.68 | −10.86 | −6.65 |
| R | 216A | 0.01 | 31.90 | 350.31 | 0.00 | 34.23 | 7.08 | 19.31 | 14.74 | 21.62 | 49.05 | 22.03 |
| R | 216C | 0.09 | 1.43 | 18.11 | 0.03 | 4.18 | 1.18 | 2.59 | 1.75 | 2.41 | 6.29 | 6.21 |
| R | 216D | −0.08 | −6.54 | −15.66 | −0.02 | −2.38 | −0.20 | −1.67 | −1.67 | −2.25 | −4.54 | −1.83 |
| R | 216E | −0.07 | −1.23 | −44.79 | −0.02 | −3.40 | −0.61 | −2.23 | −1.91 | −2.69 | −6.28 | −3.42 |
| R | 216F | −0.09 | −2.21 | −7.37 | −0.02 | −3.03 | −0.51 | −1.93 | −1.59 | −2.07 | −5.29 | −2.89 |
| R | 216G | −0.13 | −1.08 | 0.70 | −0.02 | −1.08 | −0.13 | −0.88 | −1.00 | −1.18 | −2.33 | −2.10 |
| R | 216H | −0.05 | −1.35 | −49.27 | −0.01 | −6.76 | −1.36 | −3.73 | −2.79 | −4.51 | −9.22 | −4.75 |
| R | 216I | −0.02 | 0.24 | −88.86 | −0.01 | −16.20 | −3.46 | −9.37 | −6.49 | −8.41 | −25.52 | −17.38 |
| R | 216K | 0.07 | −1.04 | 76.34 | 0.02 | 6.40 | 2.29 | 4.09 | 2.25 | 3.92 | 8.57 | 9.74 |
| R | 216L | 0.04 | −2.24 | 62.99 | 0.01 | 8.18 | 1.39 | 4.77 | 3.09 | 3.97 | 11.62 | 6.56 |
| R | 216N | 0.04 | 8.88 | 71.37 | 0.01 | 9.95 | 2.29 | 5.44 | 3.59 | 5.67 | 14.28 | 11.41 |
| R | 216P | 0.05 | −0.65 | 60.30 | 0.01 | 7.31 | 2.00 | 4.79 | 2.87 | 5.11 | 10.06 | 7.85 |
| R | 216Q | 0.02 | 10.22 | 57.85 | 0.01 | 17.09 | 3.99 | 10.06 | 6.89 | 10.83 | 24.88 | 17.47 |
| R | 216S | −0.01 | −8.74 | −210.19 | 0.00 | −33.63 | −5.81 | −19.15 | −15.04 | −22.03 | −52.82 | −28.88 |
| R | 216T | −0.09 | 0.87 | −35.23 | −0.02 | −2.71 | −0.27 | −1.68 | −1.51 | −2.07 | −3.80 | −2.25 |
| R | 216V | −0.01 | 5.42 | −778.05 | 0.00 | −91.44 | −12.91 | −54.20 | −38.92 | −51.38 | −136.88 | −89.41 |
| R | 216W | 0.02 | −3.53 | 5.75 | 0.01 | 14.86 | 2.68 | 8.61 | 6.30 | 8.08 | 23.28 | 8.82 |
| R | 216Y | 0.00 | 20.69 | −2188.15 | 0.00 | −207.93 | −30.60 | −124.74 | −94.39 | −131.17 | −328.52 | −230.43 |
| D | 217A | 0.71 | 1.18 | 1.33 | 0.67 | 1.22 | 0.76 | 0.93 | 0.13 | 0.76 | 1.09 | 0.84 |
| D | 217C | 0.51 | 0.95 | 0.99 | 0.27 | 1.10 | 0.65 | 0.73 | 0.33 | 0.70 | 1.14 | 0.87 |
| D | 217E | 1.01 | 0.98 | 0.70 | 1.15 | 0.98 | 1.04 | 0.93 | 0.78 | 1.15 | 0.88 | 0.98 |
| D | 217F | 0.39 | 1.77 | 3.29 | 0.23 | 1.78 | 1.19 | 1.71 | 0.33 | 1.61 | 1.79 | 1.32 |
| D | 217G | 0.29 | 2.18 | 0.63 | 0.14 | 2.15 | 0.92 | 1.34 | 0.34 | 1.53 | 2.08 | 2.07 |
| D | 217I | 0.64 | 1.24 | −0.05 | 0.51 | 1.38 | 1.29 | 1.50 | 0.24 | 1.44 | 1.12 | 0.00 |
| D | 217K | 0.26 | 1.48 | 2.35 | 0.10 | 1.65 | 0.48 | 0.86 | 0.35 | 0.75 | 1.72 | 1.25 |
| D | 217M | 0.87 | 1.34 | 0.81 | 1.24 | 1.26 | 0.96 | 0.92 | 0.17 | 0.89 | 0.92 | 0.80 |
| D | 217N | 0.31 | 1.49 | 0.88 | 0.14 | 1.55 | 0.68 | 1.05 | 0.31 | 1.28 | 1.39 | 1.08 |
| D | 217P | 0.43 | 1.88 | 1.66 | 0.34 | 1.75 | 0.86 | 1.23 | 0.82 | 1.01 | 1.75 | 1.51 |
| D | 217Q | 0.74 | 1.48 | 0.54 | 0.83 | 1.34 | 1.39 | 1.30 | 0.73 | 1.53 | 1.21 | 1.07 |
| D | 217R | 0.16 | 1.71 | 3.06 | 0.05 | 2.06 | 0.50 | 1.02 | 0.74 | 1.65 | 2.06 | 1.03 |
| D | 217S | 0.36 | 1.64 | 1.25 | 0.17 | 1.59 | 1.11 | 1.42 | 0.38 | 1.59 | 1.81 | 1.42 |
| D | 217T | 0.57 | 1.48 | 0.36 | 0.50 | 1.49 | 1.18 | 1.44 | 0.34 | 1.21 | 1.34 | 1.04 |
| D | 217V | 0.41 | 1.49 | 1.87 | 0.23 | 1.60 | 1.11 | 1.59 | 0.52 | 1.16 | 1.56 | 1.03 |
| D | 217W | 0.04 | 10.47 | 22.09 | 0.01 | 9.86 | 2.86 | 6.73 | 2.68 | 6.43 | 8.89 | 9.69 |
| D | 217Y | 0.28 | 2.20 | 2.47 | 0.13 | 1.81 | 0.63 | 1.31 | 0.38 | 1.19 | 1.82 | 1.90 |
| Y | 220A | −0.02 | −7.18 | −3591.31 | 0.00 | −8.28 | −1.11 | −9.01 | −10.44 | −14.18 | −16.00 | 3.11 |
| Y | 220C | −0.14 | −3.07 | −54.41 | −0.03 | −0.78 | −0.11 | −0.84 | −0.97 | −1.32 | −2.03 | 0.99 |
| Y | 220D | −0.05 | 0.43 | 148.30 | −0.01 | −1.79 | −0.22 | −2.00 | −2.39 | −3.17 | −5.05 | 2.52 |
| Y | 220E | −0.08 | −3.36 | −310.90 | −0.02 | −1.11 | −0.25 | −1.23 | −1.46 | −2.02 | −2.89 | 1.57 |
| Y | 220F | 0.12 | 2.61 | −9.31 | 0.04 | 3.21 | 1.06 | 1.91 | 1.11 | 2.25 | 4.64 | 0.88 |
| Y | 220G | −0.08 | −3.54 | −115.46 | −0.02 | −1.18 | 0.08 | −1.30 | −1.55 | −2.09 | −3.84 | 2.87 |
| Y | 220H | −0.16 | 0.58 | −39.96 | −0.04 | −0.71 | −0.12 | −0.70 | −0.80 | −1.06 | −1.68 | 0.97 |
| Y | 220I | −0.12 | 0.34 | −302.96 | −0.03 | −1.11 | −0.08 | −0.94 | −1.05 | −1.39 | −2.70 | 1.34 |
| Y | 220K | −0.12 | 0.81 | −14.88 | −0.02 | −0.77 | −0.03 | −0.88 | −1.04 | −1.34 | −2.26 | 1.09 |
| Y | 220L | −0.11 | 3.64 | −198.61 | −0.02 | −1.11 | −0.17 | −1.07 | −1.18 | −1.59 | −2.65 | 0.17 |
| Y | 220M | 0.01 | 62.90 | 2610.70 | 0.00 | 27.51 | 2.11 | 16.30 | 14.91 | 22.77 | 41.26 | −14.65 |
| Y | 220N | −0.07 | −5.35 | −515.85 | −0.02 | −1.54 | −0.10 | −1.48 | −1.69 | −2.40 | −4.02 | 4.15 |
| Y | 220P | −0.11 | −2.67 | −125.55 | −0.02 | −0.84 | −0.02 | −0.94 | −1.13 | −1.38 | −2.62 | 0.88 |
| Y | 220Q | −0.10 | −5.46 | −647.30 | −0.02 | −1.32 | 0.01 | −1.12 | −1.27 | −1.78 | −3.36 | 2.17 |
| Y | 220R | −0.13 | 0.09 | −87.43 | −0.03 | −0.74 | −0.13 | −0.82 | −0.97 | −1.22 | −2.02 | 1.07 |
| Y | 220T | −0.22 | 1.71 | −175.23 | −0.05 | −0.51 | −0.05 | −0.50 | −0.58 | −0.78 | −1.06 | 0.57 |
| Y | 220V | −0.16 | 1.50 | −162.88 | −0.03 | −0.76 | −0.05 | −0.70 | −0.79 | −1.00 | −1.77 | 0.59 |
| Y | 220W | −0.19 | 0.36 | −79.09 | −0.04 | −0.54 | −0.09 | −0.58 | −0.67 | −0.86 | −1.43 | 0.53 |
| Y | 223A | 0.09 | 6.38 | −23.41 | 0.03 | 3.92 | 0.73 | 2.33 | 1.82 | 2.66 | 6.28 | 3.47 |
| Y | 223C | 0.26 | 1.67 | −4.82 | 0.11 | 1.89 | 0.74 | 1.14 | 0.96 | 1.21 | 2.57 | 1.52 |
| Y | 223D | 0.03 | 31.00 | −27.32 | 0.01 | 6.29 | 0.26 | 4.76 | 4.94 | 5.26 | 13.94 | 4.49 |
| Y | 223E | 0.16 | 2.21 | −21.76 | 0.05 | 2.52 | 0.76 | 1.47 | 1.26 | 1.61 | 3.46 | 2.43 |
| Y | 223F | 1.00 | 0.94 | −2.50 | 1.09 | 1.07 | 1.01 | 0.97 | 0.87 | 0.92 | 1.00 | 1.06 |
| Y | 223G | 0.04 | 7.57 | −10.59 | 0.01 | 8.19 | 1.91 | 4.73 | 4.12 | 5.18 | 13.16 | 7.88 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| Y | 223H | 0.54 | 1.23 | −2.54 | 0.34 | 1.42 | 0.93 | 1.04 | 0.76 | 1.04 | 1.61 | 1.54 |
| Y | 223K | −0.03 | −4.72 | −121.09 | −0.01 | −8.01 | −1.36 | −4.80 | −3.85 | −5.53 | −13.39 | −5.76 |
| Y | 223L | 0.55 | 1.35 | 1.38 | 0.41 | 1.51 | 1.09 | 1.22 | 1.06 | 1.21 | 1.59 | 1.32 |
| Y | 223M | 0.43 | 1.42 | −9.88 | 0.29 | 1.66 | 1.02 | 1.18 | 0.96 | 1.08 | 1.87 | 1.75 |
| Y | 223N | 0.10 | 5.98 | 43.61 | 0.03 | 3.31 | 0.71 | 2.04 | 1.64 | 2.11 | 5.93 | 3.86 |
| Y | 223P | −0.19 | −2.15 | −14.36 | −0.05 | −0.61 | 0.00 | −0.59 | −0.70 | −0.74 | −1.75 | −0.70 |
| Y | 223Q | 0.14 | 3.98 | −17.41 | 0.05 | 2.96 | 0.97 | 1.83 | 1.66 | 2.03 | 3.66 | 3.16 |
| Y | 223R | −0.10 | −5.67 | 29.26 | −0.03 | −2.78 | −0.51 | −1.63 | −1.39 | −1.89 | −4.94 | −2.12 |
| Y | 223S | −0.02 | −18.62 | −14.12 | −0.01 | −12.13 | −2.72 | −7.46 | −7.10 | −8.15 | −19.77 | −10.10 |
| Y | 223T | −0.02 | −27.65 | 15.59 | 0.00 | −20.12 | −5.14 | −12.39 | −11.90 | −13.31 | −31.43 | −16.37 |
| Y | 223V | 0.27 | 2.29 | −8.50 | 0.12 | 2.05 | 1.03 | 1.41 | 1.36 | 1.47 | 2.66 | 2.31 |
| Y | 223W | 0.74 | 1.02 | 0.36 | 0.65 | 1.17 | 1.04 | 1.07 | 0.87 | 1.04 | 1.24 | 1.12 |
| M | 224A | 0.00 | 56.73 | 1455.96 | 0.00 | 15.12 | 0.86 | 13.48 | 10.12 | 12.02 | 28.00 | 0.29 |
| M | 224C | −0.03 | −16.42 | −677.12 | −0.02 | −10.13 | −2.79 | −6.20 | −5.73 | −5.86 | −14.70 | −1.53 |
| M | 224D | −0.09 | −5.52 | −277.12 | −0.02 | −1.19 | −0.10 | −1.28 | −1.54 | −1.61 | −3.82 | 2.27 |
| M | 224E | −0.03 | −3.12 | −239.54 | −0.01 | −3.78 | −0.54 | −3.65 | −4.24 | −4.18 | −9.63 | 4.92 |
| M | 224G | −0.12 | −3.39 | −164.25 | −0.03 | −1.66 | −0.19 | −1.14 | −1.26 | −1.27 | −3.84 | 0.52 |
| M | 224H | −0.17 | −2.68 | −149.95 | −0.04 | −1.01 | −0.12 | −0.73 | −0.82 | −0.78 | −2.25 | 0.78 |
| M | 224I | 0.69 | 1.14 | 28.22 | 0.55 | 1.29 | 0.94 | 1.03 | 0.91 | 0.99 | 1.44 | 1.28 |
| M | 224K | −0.16 | 0.17 | −32.24 | −0.04 | −0.80 | −0.12 | −0.75 | −0.82 | −0.85 | −1.99 | 1.06 |
| M | 224L | 0.39 | 1.54 | 65.45 | 0.22 | 1.82 | 1.18 | 1.36 | 1.06 | 1.37 | 2.14 | 2.10 |
| M | 224N | −0.10 | −7.45 | −151.11 | −0.03 | −1.22 | −0.07 | −1.15 | −1.32 | −1.38 | −3.55 | 2.27 |
| M | 224P | −0.13 | −4.39 | −73.30 | −0.03 | −1.12 | −0.10 | −0.94 | −1.07 | −1.10 | −2.84 | 0.64 |
| M | 224Q | −0.12 | −4.51 | −130.46 | −0.03 | −1.36 | −0.14 | −1.04 | −1.14 | −1.20 | −2.37 | 0.01 |
| M | 224R | −0.20 | −0.41 | 4.45 | −0.05 | −0.45 | −0.10 | −0.48 | −0.56 | −0.59 | −0.62 | 0.72 |
| M | 224S | −0.16 | −2.42 | −72.55 | −0.03 | −1.02 | −0.11 | −0.80 | −0.89 | −0.82 | −2.36 | 1.61 |
| M | 224T | −0.05 | −7.17 | −316.72 | −0.01 | −6.95 | −1.38 | −4.21 | −4.22 | −4.25 | −10.22 | −1.94 |
| M | 224V | 0.35 | 1.96 | −30.68 | 0.19 | 2.12 | 1.34 | 1.60 | 1.53 | 1.37 | 2.29 | 1.62 |
| M | 224Y | 0.09 | 4.47 | 412.15 | 0.04 | 6.18 | 4.35 | 3.84 | 3.45 | 3.64 | 6.80 | 4.37 |
| D | 225A | 0.96 | 0.94 | −42.16 | 0.96 | 0.97 | 0.95 | 0.86 | 0.59 | 0.83 | 0.94 | 0.88 |
| D | 225C | 0.94 | 0.93 | 1.39 | 0.87 | 0.94 | 0.96 | 0.95 | 0.72 | 0.91 | 1.00 | 0.95 |
| D | 225E | 0.70 | 1.16 | −21.25 | 0.47 | 1.12 | 0.91 | 0.92 | 0.84 | 0.92 | 1.21 | 1.40 |
| D | 225F | 0.65 | 1.33 | −50.98 | 0.46 | 1.29 | 1.12 | 1.19 | 1.11 | 1.17 | 1.44 | 1.43 |
| D | 225G | 0.75 | 1.07 | −47.11 | 0.47 | 1.06 | 0.88 | 0.89 | 0.82 | 0.91 | 1.18 | 1.21 |
| D | 225H | 1.17 | 0.81 | −0.52 | 1.07 | 0.85 | 0.86 | 0.86 | 0.82 | 0.88 | 0.94 | 0.92 |
| D | 225I | 0.47 | 1.26 | 16.84 | 0.23 | 1.48 | 0.92 | 1.09 | 0.81 | 1.11 | 1.88 | 1.52 |
| D | 225K | 0.71 | 0.96 | 11.87 | 0.46 | 1.15 | 0.93 | 0.94 | 0.78 | 0.93 | 1.28 | 1.19 |
| D | 225L | 0.61 | 0.98 | −3.12 | 0.34 | 1.25 | 0.88 | 0.96 | 0.73 | 0.97 | 1.29 | 1.28 |
| D | 225M | 0.77 | 1.07 | −1.06 | 0.70 | 1.14 | 1.02 | 0.96 | 0.52 | 0.92 | 1.12 | 1.02 |
| D | 225N | 0.96 | 1.06 | 1.26 | 1.22 | 1.11 | 1.22 | 1.08 | 0.68 | 1.05 | 1.04 | 0.97 |
| D | 225P | 0.55 | 1.42 | 3.03 | 0.43 | 1.61 | 1.05 | 1.11 | 0.93 | 0.87 | 1.40 | 2.40 |
| D | 225Q | 0.70 | 1.35 | 2.08 | 0.56 | 1.28 | 1.10 | 1.13 | 0.82 | 1.04 | 1.24 | 1.23 |
| D | 225S | 1.09 | 0.97 | 2.76 | 1.06 | 0.93 | 0.93 | 0.88 | 0.70 | 0.87 | 0.96 | 0.97 |
| D | 225T | 0.55 | 1.52 | 47.98 | 0.37 | 1.57 | 1.24 | 1.30 | 0.82 | 1.31 | 1.76 | 1.39 |
| D | 225V | 0.66 | 1.17 | 1.42 | 0.41 | 1.24 | 0.91 | 0.98 | 0.61 | 0.98 | 1.29 | 1.26 |
| D | 225W | 0.80 | 1.03 | −5.69 | 0.56 | 1.08 | 0.85 | 0.88 | 0.64 | 0.93 | 1.10 | 1.04 |
| D | 225Y | 0.72 | 1.10 | −9.88 | 0.64 | 1.35 | 1.21 | 1.20 | 0.79 | 1.15 | 1.33 | 1.20 |
| V | 226A | 0.12 | 4.84 | 21.55 | 0.04 | 2.18 | 0.43 | 1.34 | 1.13 | 1.61 | 3.70 | 2.43 |
| V | 226C | 0.36 | 1.51 | 7.33 | 0.15 | 1.49 | 0.93 | 0.98 | 0.92 | 1.09 | 2.08 | 2.29 |
| V | 226D | −0.05 | −7.87 | −10.25 | −0.01 | −1.96 | 0.01 | −2.18 | −2.65 | −2.79 | −6.07 | −0.04 |
| V | 226E | 0.01 | 49.52 | −40.93 | 0.00 | 23.23 | 3.26 | 15.19 | 16.38 | 17.80 | 43.52 | 14.57 |
| V | 226F | 0.14 | 3.43 | −3.28 | 0.04 | 2.96 | 0.99 | 1.87 | 1.76 | 1.75 | 4.41 | 3.69 |
| V | 226G | −1.08 | 0.19 | 3.43 | −0.21 | −0.36 | −2.49 | −0.06 | −0.32 | −0.29 | −0.26 | −0.06 |
| V | 226H | −0.11 | −3.77 | 5.50 | −0.02 | −2.03 | −0.28 | −1.34 | −1.35 | −1.35 | −3.95 | −1.99 |
| V | 226I | 0.86 | 1.39 | −3.85 | 1.06 | 1.31 | 1.15 | 1.22 | 1.21 | 0.96 | 1.16 | 1.09 |
| V | 226K | −0.07 | −1.41 | 29.72 | −0.01 | −1.67 | −0.29 | −1.61 | −1.80 | −1.88 | −4.55 | −1.64 |
| V | 226L | 0.53 | 0.99 | −5.21 | 0.28 | 1.37 | 0.92 | 1.15 | 0.68 | 0.71 | 1.58 | 1.38 |
| V | 226M | 0.33 | 1.67 | −0.44 | 0.15 | 1.51 | 0.78 | 1.05 | 0.65 | 0.87 | 2.15 | 1.50 |
| V | 226P | −0.20 | −1.38 | −24.30 | −0.03 | −0.49 | −0.03 | −0.53 | −0.65 | −0.65 | −1.41 | −0.38 |
| V | 226Q | −0.09 | −4.72 | 5.29 | −0.03 | −3.71 | −0.94 | −2.18 | −1.89 | −2.20 | −5.59 | −4.01 |
| V | 226R | −0.15 | −0.60 | 8.24 | −0.03 | −0.62 | −0.10 | −0.70 | −0.85 | −0.88 | −2.25 | −0.57 |
| V | 226S | −0.10 | −4.08 | 5.01 | −0.02 | −2.18 | −0.47 | −1.62 | −1.47 | −1.52 | −4.24 | −2.23 |
| V | 226T | 0.32 | 1.78 | 0.21 | 0.13 | 1.76 | 1.20 | 1.42 | 1.51 | 1.50 | 2.55 | 2.19 |
| T | 227A | 0.21 | 1.83 | 9.51 | 0.06 | 0.95 | −0.03 | 0.76 | 0.66 | 0.92 | 1.69 | 0.67 |
| T | 227C | 0.39 | 0.54 | 6.35 | 0.16 | 1.02 | 0.33 | 0.74 | 0.38 | 0.86 | 1.65 | 1.10 |
| T | 227D | 0.21 | 1.79 | 11.36 | 0.06 | 0.59 | −0.05 | 0.54 | 0.64 | 0.82 | 1.79 | 0.67 |
| T | 227E | 0.08 | 4.26 | 36.41 | 0.02 | 1.51 | 0.03 | 1.47 | 1.66 | 2.17 | 3.92 | 0.73 |
| T | 227F | −0.01 | −20.16 | −679.33 | 0.00 | −13.89 | −1.02 | −14.16 | −16.65 | −20.96 | −38.02 | −10.29 |
| T | 227G | 0.12 | 0.73 | 14.77 | 0.03 | 1.25 | −0.02 | 0.94 | 1.09 | 1.35 | 3.29 | 0.44 |
| T | 227H | −0.11 | 5.57 | −26.19 | −0.03 | −0.92 | −0.15 | −0.94 | −1.15 | −1.35 | −2.45 | −0.55 |
| T | 227K | −0.09 | 5.07 | 12.61 | −0.02 | −1.18 | −0.08 | −1.26 | −1.54 | −1.92 | −3.00 | −1.19 |
| T | 227L | −0.02 | 33.88 | −92.74 | −0.01 | −7.19 | −1.04 | −6.87 | −7.62 | −10.26 | −17.76 | −9.25 |
| T | 227M | 0.11 | 5.48 | 35.32 | 0.03 | 1.16 | −0.02 | 1.13 | 1.29 | 1.63 | 3.01 | 0.23 |
| T | 227P | 0.04 | 7.54 | 55.07 | 0.01 | 5.88 | 1.37 | 4.29 | 3.46 | 5.87 | 12.02 | 9.95 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| T | 227Q | −0.11 | 2.12 | −6.56 | −0.03 | −0.95 | −0.17 | −0.98 | −1.19 | −1.46 | −2.60 | 0.05 |
| T | 227R | −0.12 | 4.11 | −33.25 | −0.02 | −0.83 | −0.08 | −0.85 | −1.02 | −1.22 | −2.30 | −0.99 |
| T | 227S | 0.39 | 1.22 | 2.87 | 0.23 | 1.62 | 0.58 | 1.26 | 0.69 | 0.97 | 1.95 | 1.44 |
| T | 227V | −0.03 | 5.24 | −74.79 | −0.01 | −6.35 | −1.23 | −5.30 | −4.34 | −7.03 | −15.15 | −3.72 |
| T | 227W | −0.09 | 6.18 | −15.98 | −0.02 | −1.16 | −0.08 | −1.26 | −1.45 | −1.82 | −3.06 | −1.35 |
| T | 227Y | −0.13 | 3.17 | −24.78 | −0.04 | −0.75 | −0.13 | −0.86 | −1.02 | −1.26 | −2.41 | −0.34 |
| A | 228C | 0.43 | 2.22 | −4.15 | 0.33 | 1.72 | 0.70 | 1.18 | 0.73 | 1.15 | 1.72 | 1.36 |
| A | 228D | 0.20 | 2.02 | −9.95 | 0.08 | 1.98 | 0.25 | 1.14 | 0.72 | 1.05 | 2.96 | 1.73 |
| A | 228F | 0.04 | 11.17 | 28.63 | 0.01 | 2.54 | 0.06 | 2.59 | 3.10 | 4.10 | 7.49 | 0.88 |
| A | 228I | 0.02 | 20.11 | 2.70 | 0.00 | 10.97 | 0.53 | 7.38 | 7.16 | 9.53 | 18.03 | 7.04 |
| A | 228L | 0.05 | 2.70 | −75.81 | 0.01 | 4.29 | 0.11 | 3.04 | 2.94 | 4.07 | 8.25 | 3.34 |
| A | 228M | 0.12 | 6.77 | 5.78 | 0.04 | 1.54 | −0.03 | 1.13 | 1.10 | 1.48 | 2.87 | 0.53 |
| A | 228N | 0.23 | 2.81 | −1.47 | 0.09 | 1.55 | 0.34 | 1.13 | 0.78 | 1.17 | 2.29 | 1.77 |
| A | 228P | 0.34 | 1.58 | −9.03 | 0.16 | 1.33 | 0.53 | 1.05 | 0.75 | 1.14 | 1.99 | 1.56 |
| A | 228Q | 0.00 | −297.45 | 825.27 | 0.00 | −55.43 | 0.11 | −45.61 | −50.56 | −55.03 | −130.06 | −64.97 |
| A | 228R | −0.11 | −1.81 | 23.06 | −0.03 | −0.94 | −0.06 | −0.97 | −1.17 | −1.53 | −2.34 | −0.65 |
| A | 228S | 0.38 | 1.66 | −0.69 | 0.23 | 1.89 | 0.93 | 1.47 | 1.05 | 1.27 | 2.13 | 1.61 |
| A | 228T | 0.39 | 1.85 | 0.80 | 0.29 | 1.91 | 0.55 | 1.05 | 0.70 | 0.95 | 1.98 | 1.27 |
| A | 228V | 0.15 | 2.44 | 11.23 | 0.06 | 2.71 | 0.39 | 1.48 | 1.10 | 1.54 | 3.28 | 1.32 |
| A | 228W | 0.00 | −331.96 | −849.05 | 0.00 | 89.83 | 5.85 | 94.03 | 106.64 | 136.93 | 252.50 | 73.41 |
| A | 228Y | −0.03 | 5.03 | 36.88 | −0.01 | −3.07 | −0.25 | −3.65 | −4.30 | −5.60 | −8.32 | −3.82 |
| S | 229C | 0.38 | 0.78 | 2.92 | 0.17 | 1.16 | 0.17 | 0.63 | 0.46 | 0.58 | 1.51 | 0.28 |
| S | 229D | 0.60 | 1.54 | −0.97 | 0.49 | 1.34 | 0.43 | 0.88 | 0.63 | 0.48 | 1.67 | 1.50 |
| S | 229E | 0.65 | 1.12 | 2.83 | 0.44 | 0.97 | 0.07 | 0.25 | 0.25 | 0.29 | 1.50 | 0.45 |
| S | 229F | 0.14 | 1.33 | −3.23 | 0.05 | 2.99 | 0.14 | 1.35 | 1.20 | 1.30 | 4.17 | −1.10 |
| S | 229G | 0.34 | 1.27 | 1.90 | 0.16 | 1.67 | 0.32 | 0.77 | 0.54 | 0.62 | 2.27 | 1.09 |
| S | 229H | 0.51 | 1.05 | 5.23 | 0.28 | 1.25 | 0.32 | 0.61 | 0.46 | 0.35 | 1.48 | 0.50 |
| S | 229K | −0.02 | −2.58 | −62.63 | −0.01 | −17.18 | −0.82 | −6.69 | −6.48 | −8.68 | −22.10 | 1.68 |
| S | 229L | −0.06 | −1.66 | −33.06 | −0.01 | −3.86 | 0.04 | −2.18 | −2.36 | −3.01 | −7.95 | 3.70 |
| S | 229M | 0.25 | 1.99 | 0.07 | 0.16 | 2.43 | 0.22 | 0.84 | 0.58 | 0.82 | 3.33 | 0.79 |
| S | 229N | 0.62 | 1.14 | 1.26 | 0.48 | 1.09 | 0.30 | 0.80 | 0.53 | 0.51 | 1.36 | 1.10 |
| S | 229Q | 0.13 | 1.65 | 2.70 | 0.05 | 3.07 | 0.15 | 1.19 | 0.97 | 1.25 | 4.73 | −0.09 |
| S | 229R | 0.11 | 0.92 | 0.40 | 0.03 | 2.89 | 0.00 | 1.12 | 1.21 | 1.61 | 3.93 | −1.89 |
| S | 229T | 0.73 | 1.39 | 0.45 | 0.66 | 1.31 | 0.67 | 1.15 | 1.01 | 0.92 | 1.19 | 0.71 |
| S | 229V | 0.31 | 2.00 | 3.92 | 0.21 | 2.34 | 0.17 | 0.64 | 0.52 | 0.65 | 2.34 | 0.39 |
| S | 229Y | 0.36 | 0.21 | 5.09 | 0.13 | 1.21 | 0.04 | 0.51 | 0.43 | 0.61 | 1.64 | −0.31 |
| N | 230A | 1.07 | 0.74 | 0.89 | 1.14 | 0.87 | 0.84 | 0.95 | 0.31 | 0.77 | 0.94 | 0.28 |
| N | 230D | 0.82 | 1.01 | 2.56 | 0.68 | 1.09 | 1.05 | 1.04 | 0.75 | 0.86 | 1.20 | 1.12 |
| N | 230E | 0.85 | 1.04 | 1.88 | 0.72 | 0.93 | 1.09 | 1.00 | 0.69 | 0.88 | 1.13 | 1.17 |
| N | 230F | 0.78 | 0.99 | −0.02 | 0.59 | 1.07 | 0.88 | 0.89 | 0.62 | 0.77 | 1.10 | 1.01 |
| N | 230G | 0.50 | 1.13 | 5.05 | 0.31 | 1.50 | 1.04 | 1.47 | 0.69 | 1.15 | 1.67 | 1.62 |
| N | 230H | 0.78 | 1.00 | 2.94 | 0.54 | 1.08 | 0.88 | 1.01 | 0.72 | 0.66 | 1.19 | 1.14 |
| N | 230I | 0.60 | 1.23 | 3.76 | 0.39 | 1.38 | 1.01 | 1.22 | 0.97 | 1.20 | 1.46 | 1.36 |
| N | 230K | 0.75 | 1.16 | −0.30 | 0.59 | 1.22 | 1.07 | 1.16 | 0.71 | 0.79 | 1.33 | 1.24 |
| N | 230M | 0.98 | 0.86 | 0.63 | 1.07 | 1.02 | 0.95 | 0.92 | 0.30 | 0.74 | 0.95 | 0.94 |
| N | 230P | 0.27 | 1.80 | 6.42 | 0.08 | 1.36 | 0.24 | 0.85 | 0.50 | 0.68 | 1.77 | 1.03 |
| N | 230Q | 0.82 | 1.11 | −0.13 | 0.78 | 1.14 | 1.09 | 1.12 | 0.53 | 0.89 | 1.18 | 1.15 |
| N | 230R | 0.92 | 0.99 | 1.71 | 0.83 | 1.03 | 0.86 | 0.97 | 0.47 | 0.71 | 1.04 | 0.85 |
| N | 230S | 0.90 | 0.81 | 1.23 | 0.67 | 0.98 | 0.76 | 0.98 | 0.46 | 0.79 | 0.93 | 0.90 |
| N | 230V | 0.70 | 1.16 | −1.62 | 0.52 | 1.26 | 0.91 | 1.09 | 0.53 | 0.98 | 1.23 | 1.10 |
| N | 230Y | 0.94 | 0.88 | 0.35 | 0.88 | 1.04 | 0.95 | 0.82 | 0.46 | 0.78 | 1.03 | 1.03 |
| Y | 231A | 0.18 | 3.05 | 57.82 | 0.07 | 2.50 | 1.03 | 1.77 | 0.94 | 1.27 | 3.52 | 0.90 |
| Y | 231C | 0.06 | 10.36 | 234.94 | 0.02 | 3.71 | 0.61 | 2.69 | 2.21 | 2.60 | 6.95 | 2.58 |
| Y | 231D | −0.04 | −7.43 | −838.50 | −0.01 | −2.69 | −0.15 | −2.79 | −3.37 | −3.57 | −7.58 | −2.30 |
| Y | 231E | −0.08 | −1.32 | −68.87 | −0.02 | −1.36 | −0.15 | −1.46 | −1.75 | −1.82 | −3.83 | −6.94 |
| Y | 231G | −0.08 | −4.63 | −140.78 | −0.02 | −2.44 | −0.19 | −1.64 | −1.53 | −1.74 | −4.85 | −2.09 |
| Y | 231H | 0.65 | 1.41 | −49.08 | 0.53 | 1.42 | 1.34 | 1.38 | 1.28 | 1.16 | 1.49 | 1.53 |
| Y | 231I | −0.12 | −1.54 | 200.33 | −0.02 | −1.02 | −0.07 | −0.98 | −1.08 | −1.16 | −2.47 | −0.78 |
| Y | 231K | −0.07 | −3.05 | −343.50 | −0.01 | −2.97 | −0.40 | −2.15 | −2.22 | −2.48 | −6.55 | −2.84 |
| Y | 231L | 0.07 | 7.01 | 84.77 | 0.02 | 6.88 | 3.10 | 5.42 | 3.20 | 4.84 | 10.56 | 16.20 |
| Y | 231M | 0.39 | 1.30 | 65.84 | 0.19 | 1.42 | 0.82 | 1.07 | 0.48 | 0.93 | 1.75 | 1.38 |
| Y | 231P | −0.02 | −11.35 | −491.67 | 0.00 | −5.24 | 0.03 | −5.94 | −7.18 | −7.74 | −14.34 | −4.47 |
| Y | 231Q | 0.05 | 10.88 | −45.61 | 0.01 | 5.84 | 1.35 | 3.81 | 2.79 | 3.34 | 9.13 | 4.81 |
| Y | 231R | −0.04 | −2.85 | −504.65 | −0.01 | −2.85 | −0.14 | −3.06 | −3.66 | −4.00 | −7.27 | 0.04 |
| Y | 231S | −0.01 | −76.08 | −2605.66 | 0.00 | −48.32 | −10.82 | −31.74 | −22.75 | −29.06 | −72.95 | −38.43 |
| Y | 231T | −0.10 | −0.19 | 151.12 | −0.02 | −1.41 | −0.13 | −1.24 | −1.31 | −1.42 | −3.51 | −1.06 |
| Y | 231V | −0.01 | −28.39 | −1061.20 | 0.00 | −17.95 | −1.69 | −13.17 | −11.77 | −11.04 | −34.60 | −12.18 |
| Y | 231W | 0.66 | 1.39 | −18.84 | 0.58 | 1.47 | 1.21 | 1.23 | 0.87 | 1.18 | 1.41 | 1.42 |
| G | 232A | 0.30 | 1.34 | 13.18 | 0.13 | 1.58 | 0.30 | 1.08 | 0.71 | 0.68 | 2.29 | 0.84 |
| G | 232C | 0.23 | 2.50 | 5.96 | 0.07 | 1.29 | 0.13 | 0.92 | 0.69 | 0.69 | 2.50 | 1.72 |
| G | 232D | −0.04 | −10.92 | −4.20 | −0.01 | −3.20 | 0.05 | −2.75 | −3.15 | −3.16 | −8.91 | −2.97 |
| G | 232E | −0.03 | −16.19 | −118.71 | −0.01 | −5.08 | 0.08 | −3.88 | −4.33 | −4.45 | −14.53 | −4.07 |
| G | 232F | −0.16 | −2.41 | −18.24 | −0.04 | −0.64 | −0.05 | −0.65 | −0.78 | −0.83 | −1.62 | −0.52 |
| G | 232H | −0.14 | 0.23 | −16.59 | −0.02 | −0.74 | −0.02 | −0.76 | −0.88 | −0.89 | −1.92 | −0.75 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| G | 232I | −0.12 | 0.90 | 26.46 | −0.02 | −0.77 | −0.07 | −0.88 | −1.08 | −1.09 | −2.37 | −0.40 |
| G | 232K | −0.10 | −2.66 | 31.51 | −0.02 | −0.96 | −0.09 | −1.10 | −1.34 | −1.45 | −2.59 | −0.55 |
| G | 232L | −0.19 | −0.59 | −14.02 | −0.04 | −0.47 | −0.05 | −0.57 | −0.67 | −0.72 | −1.68 | −0.48 |
| G | 232M | 0.08 | 10.10 | 27.24 | 0.02 | 1.45 | 0.01 | 1.52 | 1.80 | 1.99 | 3.84 | 0.69 |
| G | 232N | 0.18 | 1.96 | 12.58 | 0.04 | 1.08 | −0.01 | 0.69 | 0.72 | 0.73 | 2.18 | 0.65 |
| G | 232P | −0.01 | −46.31 | −231.84 | 0.00 | −14.55 | −0.85 | −13.82 | −16.37 | −17.58 | −40.26 | −19.24 |
| G | 232Q | 0.05 | 9.15 | 16.08 | 0.01 | 3.58 | 0.02 | 2.46 | 2.59 | 2.87 | 6.74 | 1.16 |
| G | 232R | −0.04 | −0.98 | −44.40 | −0.01 | −2.09 | −0.34 | −2.32 | −2.82 | −3.07 | −6.07 | −0.17 |
| G | 232S | 0.49 | 1.23 | 6.70 | 0.24 | 1.38 | 0.45 | 1.03 | 0.69 | 0.69 | 1.59 | 1.30 |
| G | 232T | 0.04 | 6.89 | −27.62 | 0.01 | 7.45 | 0.48 | 4.20 | 3.26 | 3.49 | 11.10 | 16.64 |
| G | 232W | −0.06 | 0.87 | 20.61 | −0.01 | −1.64 | −0.19 | −1.82 | −2.17 | −2.26 | −4.34 | −0.27 |
| G | 232Y | 0.08 | 2.61 | 26.92 | 0.02 | 2.40 | −0.01 | 1.84 | 1.66 | 1.96 | 5.42 | 2.39 |
| I | 235A | 0.39 | 0.41 | 36.12 | 0.22 | 1.65 | 0.84 | 1.19 | 0.81 | 1.14 | 2.01 | 1.43 |
| I | 235C | 0.48 | 0.97 | 1.19 | 0.26 | 1.25 | 0.69 | 0.91 | 0.71 | 0.79 | 1.56 | 0.94 |
| I | 235D | −0.06 | −6.49 | −96.85 | −0.01 | −1.66 | −0.20 | −1.80 | −2.14 | −2.86 | −5.05 | 4.41 |
| I | 235E | −0.20 | −1.23 | −38.51 | −0.04 | −0.48 | −0.02 | −0.50 | −0.59 | −0.74 | −1.39 | 0.61 |
| I | 235F | 0.09 | 6.55 | −21.05 | 0.03 | 4.58 | 0.64 | 2.58 | 1.96 | 2.54 | 6.49 | 1.87 |
| I | 235G | −0.17 | −1.23 | 29.19 | −0.05 | −0.62 | −0.07 | −0.62 | −0.74 | −0.98 | −1.58 | 1.48 |
| I | 235H | −0.05 | 0.66 | −28.44 | −0.01 | −2.27 | −0.20 | −2.24 | −2.48 | −3.22 | −5.61 | 2.34 |
| I | 235K | −0.09 | 1.55 | −14.72 | −0.02 | −1.07 | −0.05 | −1.18 | −1.34 | −1.83 | −2.64 | 1.87 |
| I | 235L | 1.00 | 1.05 | −1.06 | 1.18 | 1.05 | 1.04 | 1.05 | 0.76 | 0.97 | 1.05 | 1.09 |
| I | 235M | 0.98 | 0.87 | 5.89 | 0.97 | 0.98 | 0.88 | 0.87 | 0.65 | 0.84 | 1.03 | 0.77 |
| I | 235N | −0.07 | −6.88 | −86.52 | −0.02 | −2.62 | −0.18 | −2.19 | −2.30 | −2.12 | −5.11 | 0.83 |
| I | 235P | −0.14 | −0.93 | −37.37 | −0.02 | −0.73 | −0.01 | −0.78 | −0.92 | −1.15 | −2.40 | 1.40 |
| I | 235Q | −0.11 | −1.72 | −45.94 | −0.03 | −2.01 | −0.35 | −1.57 | −1.74 | −1.75 | −2.93 | 0.52 |
| I | 235R | −0.19 | −1.20 | −51.86 | −0.04 | −0.52 | −0.03 | −0.58 | −0.66 | −0.89 | −1.44 | 0.83 |
| I | 235S | −0.16 | −2.90 | 18.99 | −0.04 | −0.99 | −0.13 | −0.84 | −0.94 | −1.14 | −2.28 | 0.64 |
| I | 235T | 0.34 | 1.19 | 0.76 | 0.17 | 1.69 | 0.99 | 1.35 | 1.25 | 1.33 | 2.13 | 1.44 |
| I | 235W | −0.16 | 1.42 | 21.86 | −0.03 | −0.65 | −0.11 | −0.70 | −0.80 | −0.88 | −1.95 | 1.26 |
| I | 235Y | −0.15 | 3.39 | 1.32 | −0.03 | −0.62 | −0.09 | −0.72 | −0.83 | −1.03 | −2.16 | 0.79 |
| R | 236A | 0.69 | 1.42 | −1.95 | 0.56 | 1.17 | 0.83 | 0.94 | 0.59 | 1.03 | 1.17 | 1.49 |
| R | 236C | 0.49 | 1.38 | −0.18 | 0.30 | 1.36 | 0.67 | 0.93 | 0.74 | 1.05 | 1.81 | 1.52 |
| R | 236D | 0.27 | 1.85 | 0.02 | 0.13 | 1.89 | 0.68 | 1.16 | 1.07 | 1.25 | 2.59 | 2.73 |
| R | 236E | 0.31 | 2.09 | −0.74 | 0.16 | 1.90 | 0.94 | 1.21 | 1.11 | 1.42 | 2.30 | 2.53 |
| R | 236F | 0.04 | 10.40 | 17.23 | 0.01 | 5.39 | 0.72 | 3.33 | 3.28 | 3.98 | 8.44 | 0.84 |
| R | 236G | 0.66 | 1.42 | 1.93 | 0.48 | 1.28 | 0.76 | 0.97 | 0.77 | 1.06 | 1.36 | 1.52 |
| R | 236H | 0.30 | 2.60 | −0.70 | 0.14 | 1.86 | 0.83 | 1.34 | 1.00 | 0.73 | 2.44 | 2.20 |
| R | 236I | 0.62 | 1.23 | 3.29 | 0.43 | 1.24 | 0.20 | 0.67 | 0.43 | 0.66 | 1.43 | 1.16 |
| R | 236K | 0.19 | 2.40 | 7.53 | 0.08 | 2.36 | 0.76 | 1.53 | 1.18 | 1.23 | 3.29 | 1.89 |
| R | 236L | 0.78 | 1.08 | 3.09 | 0.68 | 1.10 | 0.69 | 0.94 | 0.53 | 1.01 | 1.21 | 1.37 |
| R | 236M | 0.82 | 1.04 | 1.17 | 0.67 | 0.97 | 0.74 | 0.82 | 0.58 | 0.94 | 1.04 | 1.16 |
| R | 236N | 0.70 | 1.38 | 0.40 | 0.57 | 1.12 | 0.63 | 0.86 | 0.77 | 0.93 | 1.32 | 1.39 |
| R | 236Q | 0.73 | 1.44 | 0.31 | 0.66 | 1.23 | 0.99 | 1.07 | 1.06 | 1.18 | 1.25 | 1.30 |
| R | 236S | 0.43 | 1.47 | 2.21 | 0.24 | 1.49 | 0.89 | 1.16 | 1.10 | 1.21 | 1.84 | 1.90 |
| R | 236T | 0.43 | 1.42 | 2.53 | 0.26 | 1.60 | 0.86 | 1.20 | 1.16 | 1.17 | 1.80 | 1.74 |
| R | 236W | 0.00 | 136.81 | 1196.99 | 0.00 | 98.22 | 18.32 | 63.09 | 53.45 | 68.60 | 158.03 | 40.07 |
| R | 236Y | −0.09 | −0.67 | 21.91 | −0.02 | −2.40 | −0.36 | −1.78 | −1.73 | −2.35 | −5.32 | 0.33 |
| S | 237A | 1.15 | 0.86 | −0.70 | 1.53 | 0.87 | 0.92 | 0.87 | 0.56 | 0.83 | 0.93 | 0.76 |
| S | 237C | 0.90 | 0.87 | 0.61 | 0.84 | 0.94 | 0.97 | 0.90 | 0.70 | 0.87 | 1.01 | 1.00 |
| S | 237D | 0.87 | 1.10 | 0.37 | 0.89 | 1.06 | 1.08 | 1.03 | 0.91 | 1.08 | 1.10 | 1.05 |
| S | 237E | 0.62 | 1.56 | −2.35 | 0.54 | 1.49 | 1.52 | 1.49 | 1.29 | 1.52 | 1.57 | 1.36 |
| S | 237F | 0.91 | 1.00 | −0.89 | 0.74 | 0.98 | 0.91 | 0.96 | 0.86 | 0.94 | 0.98 | 0.91 |
| S | 237G | 0.82 | 1.02 | 1.25 | 0.73 | 1.14 | 1.07 | 1.11 | 1.01 | 1.07 | 1.19 | 0.95 |
| S | 237H | 0.99 | 0.94 | −1.23 | 0.87 | 0.93 | 0.88 | 0.93 | 0.83 | 0.84 | 0.96 | 0.91 |
| S | 237I | 0.78 | 1.03 | 0.56 | 0.61 | 1.20 | 1.12 | 1.17 | 0.96 | 1.10 | 1.18 | 1.19 |
| S | 237K | 0.76 | 0.91 | −0.20 | 0.66 | 1.26 | 1.23 | 1.27 | 1.00 | 1.13 | 1.27 | 1.20 |
| S | 237L | 0.83 | 1.05 | −0.69 | 0.80 | 1.19 | 1.20 | 1.19 | 0.85 | 1.13 | 1.27 | 1.30 |
| S | 237N | 1.18 | 0.83 | −0.18 | 1.47 | 0.90 | 0.91 | 0.88 | 0.54 | 0.81 | 0.84 | 0.80 |
| S | 237P | 0.06 | 2.33 | −0.28 | 0.02 | 6.32 | 1.81 | 3.98 | 2.90 | 3.79 | 7.99 | 1.41 |
| S | 237Q | 0.45 | 1.35 | 4.46 | 0.27 | 1.58 | 1.15 | 1.29 | 0.90 | 1.23 | 1.92 | 1.46 |
| S | 237R | 0.92 | 1.07 | 0.05 | 0.94 | 1.11 | 1.08 | 1.08 | 0.75 | 0.94 | 1.01 | 0.98 |
| S | 237T | 0.98 | 1.05 | −0.71 | 0.92 | 1.05 | 1.02 | 1.03 | 0.73 | 0.95 | 0.97 | 1.04 |
| S | 237V | 1.07 | 0.77 | 0.60 | 0.97 | 0.92 | 0.87 | 0.89 | 0.58 | 0.83 | 0.98 | 0.98 |
| S | 237W | 0.87 | 1.17 | 2.13 | 0.85 | 1.18 | 1.11 | 1.15 | 0.77 | 1.11 | 1.08 | 1.05 |
| S | 237Y | 1.01 | 0.90 | 2.14 | 1.09 | 1.04 | 1.04 | 1.04 | 0.73 | 0.97 | 1.01 | 0.92 |
| A | 238C | 0.71 | 1.15 | 0.10 | 0.62 | 1.27 | 0.99 | 1.03 | 0.81 | 0.95 | 1.39 | 1.13 |
| A | 238D | 0.25 | 2.29 | −0.04 | 0.12 | 2.13 | 0.88 | 1.40 | 1.08 | 1.34 | 2.83 | 2.04 |
| A | 238E | 0.57 | 1.32 | −2.45 | 0.41 | 1.45 | 1.03 | 1.12 | 0.90 | 1.05 | 1.52 | 1.49 |
| A | 238F | 0.36 | 2.02 | −0.95 | 0.21 | 2.10 | 0.96 | 1.27 | 1.05 | 1.15 | 2.18 | 2.10 |
| A | 238G | 0.81 | 1.19 | −2.73 | 0.76 | 1.23 | 1.13 | 1.10 | 0.91 | 1.06 | 1.23 | 1.24 |
| A | 238H | 0.45 | 1.90 | 0.11 | 0.33 | 1.92 | 1.36 | 1.56 | 1.25 | 1.39 | 2.04 | 1.95 |
| A | 238I | 0.49 | 1.26 | −1.88 | 0.28 | 1.48 | 0.86 | 1.08 | 0.91 | 1.03 | 1.72 | 1.40 |
| A | 238L | 0.36 | 1.66 | 3.65 | 0.20 | 2.02 | 1.20 | 1.50 | 1.15 | 1.36 | 2.19 | 2.20 |
| A | 238M | 0.32 | 1.74 | −1.67 | 0.15 | 1.52 | 0.61 | 1.06 | 0.73 | 0.93 | 2.05 | 1.66 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| A | 238N | 0.58 | 1.11 | −2.11 | 0.40 | 1.26 | 0.88 | 1.06 | 0.87 | 0.95 | 1.55 | 1.38 |
| A | 238P | −0.27 | −2.54 | 3.53 | −0.07 | −0.41 | −0.01 | −0.41 | −0.46 | −0.51 | −1.09 | −0.21 |
| A | 238Q | 0.39 | 1.94 | −5.14 | 0.26 | 1.90 | 1.28 | 1.49 | 1.39 | 1.38 | 2.39 | 2.03 |
| A | 238R | 0.32 | 1.66 | −5.75 | 0.14 | 1.89 | 0.98 | 1.41 | 1.27 | 1.23 | 2.38 | 1.97 |
| A | 238S | 0.70 | 1.30 | −1.99 | 0.57 | 1.28 | 1.12 | 1.17 | 1.12 | 1.12 | 1.36 | 1.22 |
| A | 238T | 0.47 | 1.51 | −0.79 | 0.27 | 1.59 | 1.10 | 1.28 | 1.21 | 1.19 | 1.94 | 1.60 |
| A | 238V | 0.46 | 1.56 | −2.17 | 0.26 | 1.54 | 1.10 | 1.25 | 1.12 | 1.21 | 1.89 | 1.65 |
| A | 238W | 0.14 | 3.79 | −5.91 | 0.06 | 3.88 | 1.94 | 2.86 | 2.32 | 2.43 | 5.10 | 4.09 |
| A | 238Y | 0.38 | 1.39 | −1.01 | 0.20 | 1.73 | 0.95 | 1.27 | 0.94 | 1.10 | 2.00 | 1.63 |
| L | 239A | 0.44 | 1.79 | −3.77 | 0.23 | 1.22 | 0.67 | 0.85 | 0.80 | 1.06 | 1.48 | 1.13 |
| L | 239C | −1.18 | 0.34 | 1.86 | −0.24 | −0.32 | −2.21 | −0.19 | 0.30 | −0.18 | −0.23 | −0.07 |
| L | 239D | 0.03 | 4.29 | −11.49 | 0.01 | 3.82 | 0.31 | 4.23 | 5.28 | 7.12 | 11.15 | 3.35 |
| L | 239E | 0.05 | 15.52 | −39.14 | 0.01 | 2.79 | 0.11 | 2.45 | 2.91 | 3.67 | 6.57 | 2.02 |
| L | 239F | 0.26 | 2.45 | −4.13 | 0.06 | 0.62 | 0.09 | 0.50 | 0.61 | 0.70 | 1.37 | 0.70 |
| L | 239I | 0.76 | 0.85 | −0.49 | 0.57 | 1.10 | 0.84 | 0.97 | 0.99 | 1.15 | 1.25 | 1.09 |
| L | 239K | −0.07 | 2.28 | 15.87 | −0.02 | −1.38 | −0.19 | −1.66 | −2.02 | −2.70 | −4.32 | −1.24 |
| L | 239M | 0.83 | 1.01 | −0.86 | 0.79 | 1.02 | 0.94 | 0.91 | 0.74 | 1.10 | 1.09 | 1.05 |
| L | 239N | −0.03 | −28.06 | 76.57 | −0.01 | −5.29 | −0.14 | −4.55 | −5.40 | −6.18 | −13.02 | −6.12 |
| L | 239P | −0.07 | −6.78 | 1.51 | −0.02 | −1.42 | 0.08 | −1.59 | −1.97 | −2.50 | −4.74 | −0.53 |
| L | 239Q | 0.05 | 6.35 | −11.41 | 0.01 | 5.82 | 1.54 | 4.09 | 4.76 | 5.38 | 9.49 | 6.22 |
| L | 239R | −0.06 | 1.81 | −10.23 | −0.01 | −1.55 | −0.11 | −1.73 | −2.20 | −2.80 | −4.90 | −0.29 |
| L | 239S | −0.04 | −12.10 | 83.86 | −0.01 | −5.10 | −0.98 | −3.74 | −4.40 | −5.07 | −10.37 | −6.00 |
| L | 239T | 0.29 | 1.44 | −3.02 | 0.12 | 1.71 | 0.90 | 1.28 | 1.40 | 1.45 | 2.62 | 1.97 |
| L | 239W | −0.11 | 0.73 | 10.67 | −0.02 | −0.90 | −0.08 | −1.05 | −1.30 | −1.63 | −3.02 | −0.92 |
| L | 239Y | −0.05 | 5.40 | 9.11 | −0.01 | −1.93 | −0.27 | −2.26 | −2.74 | −3.56 | −5.37 | −2.21 |
| N | 241A | 1.07 | 1.01 | 1.46 | 1.25 | 0.97 | 0.98 | 0.95 | 0.82 | 0.90 | 0.93 | 0.95 |
| N | 241C | 0.93 | 0.89 | 3.36 | 0.84 | 0.95 | 0.90 | 0.92 | 0.88 | 0.85 | 0.98 | 0.98 |
| N | 241E | 0.97 | 0.92 | 1.57 | 0.88 | 0.96 | 0.96 | 0.96 | 1.02 | 0.87 | 0.99 | 1.07 |
| N | 241F | 0.88 | 1.03 | 5.10 | 0.78 | 1.04 | 0.98 | 1.04 | 1.05 | 0.98 | 1.03 | 1.09 |
| N | 241G | 0.87 | 1.05 | 4.40 | 0.80 | 1.09 | 1.04 | 1.06 | 1.12 | 1.04 | 1.10 | 1.16 |
| N | 241H | 0.85 | 1.09 | 4.43 | 0.85 | 1.10 | 1.07 | 1.15 | 1.16 | 1.00 | 1.16 | 1.18 |
| N | 241K | 0.77 | 1.15 | 6.77 | 0.75 | 1.25 | 1.20 | 1.30 | 1.15 | 1.17 | 1.25 | 1.21 |
| N | 241L | 0.85 | 1.05 | 5.36 | 0.91 | 1.17 | 1.15 | 1.16 | 0.84 | 1.10 | 1.15 | 1.22 |
| N | 241M | 1.04 | 0.91 | 2.50 | 1.16 | 0.97 | 0.98 | 0.92 | 0.82 | 0.87 | 1.00 | 0.80 |
| N | 241P | 0.34 | 1.34 | 8.61 | 0.13 | 1.27 | 0.54 | 0.86 | 0.96 | 0.93 | 1.86 | 1.38 |
| N | 241Q | 0.96 | 0.83 | 4.27 | 0.85 | 0.97 | 0.91 | 0.93 | 0.96 | 0.90 | 0.98 | 0.93 |
| N | 241R | 1.00 | 0.92 | 1.97 | 0.92 | 0.92 | 0.92 | 0.94 | 1.03 | 0.84 | 0.93 | 0.87 |
| N | 241S | 0.57 | 1.77 | 7.08 | 0.54 | 1.65 | 1.58 | 1.66 | 1.74 | 1.61 | 1.70 | 1.71 |
| N | 241T | 0.80 | 1.17 | 5.70 | 0.73 | 1.15 | 1.14 | 1.20 | 1.24 | 1.15 | 1.18 | 1.20 |
| N | 241W | 0.80 | 1.17 | 4.54 | 0.75 | 1.16 | 1.06 | 1.16 | 1.05 | 1.05 | 1.19 | 1.05 |
| N | 241Y | 0.84 | 1.07 | 9.29 | 0.85 | 1.17 | 1.12 | 1.19 | 0.85 | 1.04 | 1.13 | 1.01 |
| R | 242A | 0.84 | 1.15 | −1.13 | 0.86 | 1.12 | 1.11 | 1.01 | 0.75 | 1.01 | 1.08 | 1.00 |
| R | 242C | 0.77 | 1.07 | 0.21 | 0.62 | 1.09 | 1.01 | 0.98 | 0.89 | 0.94 | 1.18 | 1.08 |
| R | 242D | 0.78 | 1.12 | −3.50 | 0.62 | 1.08 | 1.04 | 1.05 | 1.01 | 1.02 | 1.15 | 1.04 |
| R | 242E | 0.87 | 0.91 | −0.17 | 0.72 | 0.98 | 0.92 | 0.89 | 0.88 | 0.89 | 1.02 | 0.93 |
| R | 242F | 0.73 | 1.11 | 0.93 | 0.52 | 1.10 | 1.01 | 1.04 | 1.05 | 1.03 | 1.25 | 1.11 |
| R | 242G | −1.01 | −0.12 | 0.11 | −0.18 | −0.36 | −2.46 | 0.28 | −0.04 | −0.07 | −0.31 | −0.04 |
| R | 242I | 0.65 | 1.20 | 5.07 | 0.45 | 1.28 | 1.02 | 1.15 | 1.11 | 1.14 | 1.42 | 1.23 |
| R | 242K | 0.85 | 1.01 | 5.94 | 0.73 | 1.08 | 1.03 | 1.05 | 0.93 | 1.06 | 1.15 | 1.09 |
| R | 242L | 0.75 | 1.05 | 5.55 | 0.56 | 1.19 | 1.06 | 1.05 | 0.80 | 1.04 | 1.30 | 1.04 |
| R | 242M | 0.86 | 0.98 | 1.99 | 0.81 | 1.05 | 1.01 | 0.91 | 0.67 | 0.91 | 1.04 | 0.96 |
| R | 242Q | 0.85 | 1.49 | 0.51 | 0.74 | 1.03 | 0.99 | 1.00 | 1.01 | 0.99 | 1.08 | 0.98 |
| R | 242S | 0.71 | 1.16 | 3.81 | 0.53 | 1.23 | 1.13 | 1.15 | 1.08 | 1.10 | 1.26 | 1.21 |
| R | 242T | 0.71 | 1.18 | 4.17 | 0.51 | 1.19 | 1.05 | 1.10 | 1.05 | 1.10 | 1.25 | 1.30 |
| R | 242V | 0.68 | 1.20 | 1.29 | 0.48 | 1.24 | 1.07 | 1.12 | 1.07 | 1.15 | 1.45 | 1.17 |
| R | 242W | 0.57 | 1.36 | 5.00 | 0.38 | 1.43 | 1.19 | 1.27 | 1.12 | 1.27 | 1.53 | 1.53 |
| R | 242Y | 0.70 | 1.14 | 4.21 | 0.51 | 1.26 | 1.09 | 1.11 | 0.82 | 1.12 | 1.40 | 1.34 |
| L | 244A | 0.21 | 2.30 | 3.44 | 0.09 | 1.91 | 0.72 | 1.27 | 1.11 | 1.34 | 2.49 | 2.06 |
| L | 244D | −0.08 | 2.02 | −4.21 | −0.01 | −1.15 | −0.09 | −1.19 | −1.47 | −1.93 | −3.71 | −1.84 |
| L | 244E | −0.10 | 0.68 | 0.24 | −0.03 | −1.07 | −0.16 | −1.12 | −1.37 | −1.67 | −2.93 | 0.16 |
| L | 244F | 1.04 | 0.93 | 0.77 | 0.99 | 0.87 | 0.85 | 0.86 | 0.90 | 0.88 | 0.90 | 0.87 |
| L | 244G | −0.03 | 7.30 | 12.00 | −0.01 | −3.73 | −0.51 | −3.43 | −4.22 | −4.56 | −10.01 | −2.78 |
| L | 244H | 0.03 | −4.60 | −19.25 | 0.01 | 5.05 | 0.74 | 3.54 | 4.19 | 4.00 | 9.46 | 6.43 |
| L | 244I | 0.62 | 1.16 | 5.42 | 0.44 | 1.35 | 1.09 | 1.19 | 1.15 | 1.17 | 1.41 | 1.28 |
| L | 244K | −0.06 | 1.76 | 2.79 | −0.01 | −1.60 | −0.21 | −1.69 | −2.03 | −2.43 | −3.97 | −1.46 |
| L | 244M | 0.76 | 1.14 | 0.74 | 0.64 | 1.16 | 1.10 | 1.09 | 0.79 | 1.09 | 1.14 | 1.13 |
| L | 244N | −0.02 | −25.95 | 36.69 | −0.01 | −9.80 | −1.66 | −7.21 | −7.84 | −8.91 | −16.67 | −11.60 |
| L | 244P | −0.03 | −11.80 | −75.30 | −0.01 | −5.44 | −0.56 | −4.52 | −5.29 | −5.91 | −14.10 | −2.97 |
| L | 244Q | 0.00 | −126.94 | 6.65 | 0.00 | −51.49 | −7.05 | −41.32 | −48.13 | −52.63 | −106.65 | −70.29 |
| L | 244R | −0.12 | 3.99 | −39.58 | −0.02 | −0.82 | −0.11 | −0.87 | −1.05 | −1.29 | −1.98 | −0.54 |
| L | 244S | −0.08 | 0.14 | −24.15 | −0.02 | −1.74 | −0.20 | −1.45 | −1.77 | −1.96 | −3.41 | −2.01 |
| L | 244T | 0.14 | 2.66 | 28.58 | 0.04 | 2.82 | 1.05 | 1.81 | 1.97 | 1.99 | 3.91 | 6.33 |
| L | 244V | 0.65 | 1.08 | −2.22 | 0.46 | 1.25 | 1.09 | 1.19 | 1.14 | 1.20 | 1.37 | 1.31 |
| L | 244W | 0.18 | 2.76 | 8.53 | 0.07 | 2.85 | 1.56 | 2.10 | 1.94 | 2.25 | 3.62 | 3.05 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| L | 244Y | 0.43 | 1.09 | 16.45 | 0.25 | 1.63 | 1.16 | 1.30 | 1.08 | 1.30 | 1.97 | 1.69 |
| V | 246A | 1.04 | 0.93 | 1.00 | 1.22 | 0.99 | 0.96 | 0.94 | 0.76 | 0.95 | 0.95 | 0.89 |
| V | 246C | 0.58 | 1.20 | 2.45 | 0.50 | 1.37 | 1.07 | 1.14 | 0.93 | 1.11 | 1.52 | 1.59 |
| V | 246D | 0.57 | 1.20 | -0.93 | 0.42 | 1.31 | 0.93 | 1.02 | 0.84 | 1.01 | 1.52 | 1.38 |
| V | 246E | 0.78 | 1.18 | 0.67 | 0.76 | 1.19 | 1.03 | 1.03 | 0.90 | 1.03 | 1.20 | 1.19 |
| V | 246F | 0.33 | 1.49 | -1.34 | 0.16 | 1.71 | 0.85 | 1.12 | 1.02 | 1.16 | 1.95 | 1.62 |
| V | 246G | 0.58 | 1.30 | 3.91 | 0.45 | 1.46 | 1.15 | 1.16 | 1.01 | 1.15 | 1.59 | 1.57 |
| V | 246H | 0.78 | 1.01 | 3.41 | 0.73 | 1.16 | 0.99 | 1.03 | 0.86 | 0.99 | 1.15 | 1.16 |
| V | 246I | 0.87 | 1.05 | -0.05 | 0.96 | 1.15 | 1.12 | 1.15 | 0.91 | 1.12 | 1.14 | 1.29 |
| V | 246K | 0.90 | 0.92 | 1.26 | 0.91 | 1.05 | 0.93 | 0.96 | 0.74 | 0.92 | 1.07 | 1.01 |
| V | 246L | 0.87 | 0.98 | 0.08 | 0.99 | 1.15 | 1.13 | 1.12 | 0.90 | 1.10 | 1.14 | 1.14 |
| V | 246M | 0.84 | 1.09 | 2.38 | 0.82 | 1.06 | 0.93 | 0.97 | 0.79 | 0.93 | 1.05 | 1.10 |
| V | 246P | 0.38 | 1.57 | 3.53 | 0.22 | 1.58 | 0.91 | 1.18 | 1.12 | 1.15 | 1.89 | 1.71 |
| V | 246Q | 0.60 | 1.35 | -1.61 | 0.49 | 1.36 | 1.14 | 1.18 | 1.15 | 1.19 | 1.50 | 1.38 |
| V | 246R | 0.78 | 1.15 | 2.23 | 0.64 | 1.11 | 0.92 | 0.97 | 0.97 | 0.94 | 1.14 | 1.11 |
| V | 246S | 0.80 | 1.04 | 0.68 | 0.66 | 1.06 | 0.90 | 0.95 | 0.93 | 0.94 | 1.15 | 1.13 |
| V | 246T | 0.80 | 1.06 | 5.21 | 0.71 | 1.08 | 0.97 | 1.06 | 1.05 | 1.06 | 1.13 | 1.18 |
| V | 246W | 0.72 | 0.95 | 0.50 | 0.56 | 1.12 | 0.92 | 1.04 | 0.91 | 1.01 | 1.28 | 1.05 |
| V | 246Y | 0.68 | 0.95 | 1.82 | 0.56 | 1.25 | 1.09 | 1.16 | 0.97 | 1.11 | 1.32 | 1.37 |
| I | 249A | 0.82 | 0.88 | 59.39 | 0.61 | 0.92 | 0.67 | 0.72 | 0.41 | 0.75 | 1.13 | 0.77 |
| I | 249C | 0.81 | 0.75 | 33.13 | 0.64 | 1.03 | 0.83 | 0.88 | 0.53 | 0.89 | 1.14 | 1.08 |
| I | 249D | 0.31 | 0.29 | -14.88 | 0.06 | 0.31 | 0.01 | 0.28 | 0.35 | 0.51 | 0.87 | -0.87 |
| I | 249E | 0.12 | 4.59 | -25.63 | 0.03 | 1.98 | 0.34 | 1.40 | 1.25 | 1.68 | 3.41 | -0.90 |
| I | 249F | 0.53 | 1.08 | 34.70 | 0.30 | 1.32 | 0.87 | 1.09 | 0.77 | 1.03 | 1.41 | 1.38 |
| I | 249H | 0.20 | 2.51 | 146.50 | 0.07 | 2.10 | 0.84 | 1.46 | 1.26 | 1.42 | 2.90 | 1.03 |
| I | 249K | -0.03 | -8.68 | 357.92 | -0.01 | -7.16 | -1.13 | -5.47 | -4.93 | -6.84 | -13.81 | 1.53 |
| I | 249L | 1.02 | 0.92 | 9.62 | 1.35 | 1.05 | 1.12 | 1.03 | 0.63 | 1.06 | 1.00 | 1.06 |
| I | 249M | 0.73 | 0.92 | 34.36 | 0.61 | 1.12 | 0.87 | 0.96 | 0.60 | 0.95 | 1.32 | 0.91 |
| I | 249N | 0.04 | 7.36 | 223.99 | 0.01 | 6.91 | 1.67 | 4.99 | 4.41 | 5.80 | 11.83 | 4.09 |
| I | 249P | 0.22 | 0.62 | 57.79 | 0.06 | 0.46 | 0.03 | 0.35 | 0.45 | 0.71 | 1.29 | -0.71 |
| I | 249Q | -0.05 | -9.07 | -61.81 | -0.02 | -5.50 | -1.48 | -4.02 | -3.65 | -4.55 | -7.75 | -2.84 |
| I | 249R | -0.13 | -4.73 | 22.78 | -0.03 | -1.23 | -0.11 | -1.03 | -1.02 | -1.29 | -2.68 | 0.76 |
| I | 249S | 0.14 | 2.76 | -44.20 | 0.05 | 3.13 | 1.34 | 2.21 | 2.08 | 2.34 | 4.88 | 1.88 |
| I | 249V | 0.86 | 1.04 | 59.23 | 0.75 | 1.05 | 1.00 | 1.04 | 0.98 | 0.98 | 1.05 | 0.96 |
| I | 249W | -0.01 | 24.92 | 750.10 | 0.00 | -6.50 | -0.89 | -6.74 | -7.60 | -10.36 | -16.93 | 9.34 |
| I | 249Y | 0.37 | 0.72 | 72.19 | 0.19 | 1.63 | 1.10 | 1.46 | 0.98 | 1.42 | 2.02 | 1.13 |
| V | 256A | 0.59 | 0.84 | 17.23 | 0.39 | 1.22 | 0.84 | 0.89 | 0.63 | 0.97 | 1.34 | 1.39 |
| V | 256C | 0.59 | 0.86 | 1.85 | 0.37 | 1.14 | 0.82 | 0.94 | 0.75 | 0.91 | 1.35 | 1.11 |
| V | 256D | -0.19 | -2.16 | -11.98 | -0.04 | -0.53 | -0.06 | -0.55 | -0.65 | -0.81 | -1.47 | 0.96 |
| V | 256E | -0.02 | -17.26 | -1.55 | -0.01 | -7.00 | -0.78 | -5.34 | -5.09 | -6.32 | -14.63 | 5.41 |
| V | 256G | -0.12 | -2.27 | -8.00 | -0.02 | -1.62 | -0.23 | -1.23 | -1.20 | -1.74 | -2.98 | 0.57 |
| V | 256H | -0.22 | 0.04 | -7.95 | -0.04 | -0.52 | -0.08 | -0.51 | -0.57 | -0.77 | -1.32 | 1.05 |
| V | 256I | 0.59 | 1.10 | 0.46 | 0.41 | 1.30 | 0.92 | 1.17 | 0.83 | 0.83 | 1.49 | 1.15 |
| V | 256M | 0.26 | 1.69 | 29.81 | 0.12 | 2.19 | 0.91 | 1.47 | 0.71 | 1.25 | 2.69 | 1.71 |
| V | 256N | 0.18 | 1.97 | 20.13 | 0.08 | 2.66 | 1.42 | 1.91 | 1.52 | 1.98 | 3.34 | 1.82 |
| V | 256P | 0.01 | 18.88 | -86.66 | 0.00 | 21.42 | 6.62 | 15.15 | 15.24 | 17.29 | 35.77 | 12.59 |
| V | 256Q | -0.01 | -28.78 | -332.30 | 0.00 | -47.09 | -12.82 | -29.59 | -21.53 | -30.38 | -64.39 | -16.24 |
| V | 256R | -0.15 | -1.31 | -0.25 | -0.03 | -0.86 | -0.11 | -0.81 | -0.87 | -1.15 | -2.07 | 1.29 |
| V | 256T | 0.18 | 1.66 | 1.47 | 0.06 | 2.78 | 1.35 | 1.95 | 1.44 | 1.95 | 3.59 | 2.28 |
| V | 256W | -0.20 | 1.30 | -8.66 | -0.04 | -0.51 | 0.06 | -0.57 | -0.64 | -0.70 | -1.35 | 0.93 |
| V | 256Y | -0.18 | 1.76 | 5.13 | -0.04 | -0.57 | -0.10 | -0.64 | -0.71 | -0.73 | -1.64 | 0.79 |
| A | 258C | 0.74 | 1.02 | 14.40 | 0.56 | 1.09 | 0.96 | 1.01 | 0.82 | 0.91 | 1.08 | 0.90 |
| A | 258D | 0.56 | 0.96 | 13.86 | 0.31 | 1.18 | 0.88 | 1.05 | 0.91 | 0.95 | 1.34 | 1.31 |
| A | 258E | 0.80 | 0.99 | 5.28 | 0.57 | 1.00 | 0.91 | 1.01 | 0.88 | 0.96 | 1.03 | 0.85 |
| A | 258F | 0.15 | 3.04 | 27.98 | 0.05 | 3.94 | 2.38 | 3.02 | 2.72 | 2.66 | 4.93 | 2.96 |
| A | 258G | 0.47 | 1.51 | 5.23 | 0.26 | 1.68 | 1.25 | 1.34 | 1.27 | 1.33 | 1.73 | 1.38 |
| A | 258H | 0.41 | 1.43 | 16.54 | 0.21 | 1.82 | 1.40 | 1.60 | 1.38 | 1.46 | 2.04 | 1.54 |
| A | 258I | 0.22 | 2.05 | -2.35 | 0.09 | 2.71 | 1.72 | 2.22 | 1.87 | 2.24 | 3.41 | 2.76 |
| A | 258K | 0.50 | 1.06 | 5.79 | 0.29 | 1.48 | 1.19 | 1.31 | 0.97 | 1.16 | 1.71 | 1.25 |
| A | 258L | 0.13 | 0.52 | 11.42 | 0.04 | 3.04 | 1.17 | 2.15 | 1.53 | 2.24 | 4.69 | 2.28 |
| A | 258M | 0.43 | 1.41 | 37.98 | 0.24 | 1.58 | 1.06 | 1.19 | 0.69 | 1.14 | 1.62 | 1.52 |
| A | 258N | 0.66 | 1.02 | 6.93 | 0.45 | 1.21 | 0.91 | 0.94 | 0.66 | 0.94 | 1.24 | 0.25 |
| A | 258P | 1.10 | 0.86 | 4.98 | 1.12 | 0.91 | 0.92 | 0.88 | 0.61 | 0.90 | 0.85 | 0.79 |
| A | 258Q | 0.60 | 1.20 | -3.42 | 0.39 | 1.30 | 1.08 | 1.16 | 0.82 | 1.10 | 1.35 | 1.01 |
| A | 258R | 0.57 | 1.28 | 0.16 | 0.34 | 1.37 | 1.06 | 1.12 | 0.78 | 1.00 | 1.47 | 1.12 |
| A | 258S | 0.65 | 1.35 | 2.79 | 0.49 | 1.39 | 1.25 | 1.27 | 0.94 | 1.22 | 1.44 | 1.12 |
| A | 258T | 0.45 | 1.57 | 1.09 | 0.26 | 1.80 | 1.44 | 1.55 | 1.08 | 1.54 | 1.97 | 1.69 |
| A | 258V | 0.60 | 1.26 | -3.40 | 0.37 | 1.47 | 1.23 | 1.29 | 0.87 | 1.24 | 1.56 | 1.26 |
| A | 258W | 0.05 | 4.57 | 48.94 | 0.02 | 10.89 | 5.06 | 7.53 | 5.11 | 7.20 | 13.28 | 9.20 |
| A | 258Y | 0.43 | 1.45 | 4.42 | 0.26 | 1.86 | 1.45 | 1.55 | 0.99 | 1.44 | 1.97 | 1.59 |
| K | 260A | 0.76 | 0.98 | 1.59 | 0.60 | 0.93 | 0.80 | 0.84 | 0.52 | 0.82 | 1.13 | 1.05 |
| K | 260C | 0.61 | 1.03 | 0.10 | 0.45 | 1.25 | 0.96 | 1.02 | 0.78 | 0.95 | 1.42 | 1.50 |
| K | 260D | 0.65 | 0.88 | 3.78 | 0.42 | 1.09 | 0.79 | 0.88 | 0.72 | 0.83 | 1.27 | 1.17 |
| K | 260E | 0.39 | 1.16 | 6.77 | 0.20 | 1.51 | 0.89 | 1.09 | 0.92 | 1.02 | 1.81 | 1.46 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| K | 260F | 0.53 | 1.04 | 0.67 | 0.30 | 1.28 | 0.80 | 0.94 | 0.80 | 0.90 | 1.52 | 1.40 |
| K | 260G | 0.32 | 1.36 | −1.68 | 0.15 | 1.81 | 0.96 | 1.19 | 1.11 | 1.16 | 2.28 | 1.90 |
| K | 260H | 0.87 | 1.03 | −1.02 | 0.81 | 1.15 | 1.06 | 1.04 | 0.85 | 1.00 | 1.10 | 1.16 |
| K | 260I | 0.05 | 6.37 | 0.22 | 0.01 | 6.85 | 1.49 | 4.17 | 3.53 | 3.89 | 11.31 | 4.12 |
| K | 260M | 0.37 | 1.13 | 11.02 | 0.22 | 1.68 | 1.03 | 1.26 | 0.94 | 1.21 | 2.10 | 1.57 |
| K | 260N | 0.70 | 0.97 | −0.13 | 0.48 | 1.00 | 0.75 | 0.91 | 0.78 | 0.86 | 1.09 | 1.10 |
| K | 260P | −0.16 | −4.14 | −10.01 | −0.03 | −0.63 | −0.05 | −0.63 | −0.71 | −0.70 | −1.62 | 1.12 |
| K | 260Q | 0.73 | 1.11 | 1.38 | 0.57 | 1.09 | 1.02 | 1.04 | 1.03 | 1.02 | 1.19 | 1.26 |
| K | 260R | 0.89 | 1.03 | 2.47 | 0.84 | 1.01 | 0.91 | 0.94 | 0.88 | 0.90 | 1.01 | 1.01 |
| K | 260S | 0.61 | 1.10 | 0.36 | 0.43 | 1.29 | 0.98 | 1.06 | 1.06 | 1.05 | 1.45 | 1.37 |
| K | 260T | 0.12 | 3.19 | 8.39 | 0.04 | 3.56 | 1.38 | 2.29 | 2.20 | 2.18 | 4.41 | 3.26 |
| K | 260V | 0.02 | 11.69 | 3.19 | 0.01 | 16.61 | 6.37 | 11.26 | 10.17 | 10.11 | 22.64 | 14.15 |
| K | 260W | 0.14 | 2.03 | 15.67 | 0.05 | 2.92 | 1.12 | 1.92 | 1.82 | 1.84 | 4.14 | 2.69 |
| K | 260Y | 0.52 | 1.10 | 1.08 | 0.31 | 1.40 | 1.01 | 1.12 | 0.93 | 1.07 | 1.65 | 1.51 |
| L | 261A | 0.13 | 3.19 | 23.85 | 0.04 | 2.30 | 0.70 | 1.54 | 1.12 | 1.43 | 4.28 | 0.35 |
| L | 261C | 0.20 | 2.08 | 10.09 | 0.08 | 2.15 | 1.09 | 1.54 | 1.17 | 1.32 | 3.29 | 1.93 |
| L | 261D | −0.17 | −1.09 | 12.93 | −0.03 | −0.55 | −0.04 | −0.55 | −0.63 | −0.63 | −1.44 | 1.49 |
| L | 261E | −0.20 | −1.34 | −5.05 | −0.04 | −0.53 | −0.06 | −0.51 | −0.55 | −0.56 | −1.47 | 0.60 |
| L | 261G | −0.12 | 0.46 | −10.88 | −0.02 | −0.83 | −0.14 | −0.78 | −0.87 | −0.84 | −2.04 | 1.20 |
| L | 261H | 0.00 | −154.07 | 466.59 | 0.00 | −167.37 | −61.19 | −99.64 | −92.92 | −64.64 | −225.98 | −93.98 |
| L | 261I | 0.25 | 2.18 | 1.18 | 0.11 | 2.51 | 1.45 | 1.88 | 1.53 | 1.65 | 2.84 | 2.36 |
| L | 261K | −0.24 | 0.14 | 3.38 | −0.04 | −0.70 | −0.10 | −0.53 | −0.48 | −0.52 | −1.45 | 0.29 |
| L | 261M | 0.59 | 1.08 | 3.15 | 0.42 | 1.21 | 0.95 | 0.98 | 0.43 | 0.96 | 1.42 | 1.52 |
| L | 261N | 0.08 | 5.68 | −5.59 | 0.02 | 4.44 | 1.34 | 2.71 | 2.16 | 2.56 | 7.12 | 3.19 |
| L | 261P | −0.01 | 9.59 | −126.63 | 0.00 | −11.10 | −1.24 | −11.81 | −13.18 | −13.34 | −26.37 | 31.14 |
| L | 261Q | 0.10 | 6.31 | 12.02 | 0.03 | 3.90 | 1.38 | 2.49 | 1.58 | 2.23 | 5.96 | 3.73 |
| L | 261R | −0.17 | −1.39 | −6.73 | −0.03 | −0.65 | −0.09 | −0.63 | −0.66 | −0.73 | −1.57 | 1.57 |
| L | 261S | 0.15 | 2.84 | 13.28 | 0.04 | 2.86 | 0.98 | 1.73 | 1.35 | 1.50 | 4.21 | 2.16 |
| L | 261T | 0.48 | 1.04 | 1.44 | 0.18 | 1.17 | 0.49 | 0.78 | 0.50 | 0.63 | 1.45 | 1.17 |
| L | 261V | 0.27 | 2.27 | −6.43 | 0.09 | 2.09 | 0.94 | 1.34 | 0.87 | 1.15 | 2.32 | 1.70 |
| L | 261W | −0.05 | −4.28 | 15.18 | −0.01 | −4.38 | −0.43 | −2.77 | −2.34 | −2.79 | −8.66 | −0.42 |
| L | 261Y | −0.05 | −5.33 | 14.59 | −0.01 | −5.94 | −0.84 | −3.65 | −2.58 | −3.65 | −10.35 | −2.60 |
| V | 262A | 0.15 | 4.01 | 2.04 | 0.04 | 1.43 | 0.11 | 1.18 | 1.15 | 1.28 | 2.74 | 1.55 |
| V | 262C | 0.13 | 2.39 | −7.54 | 0.05 | 3.27 | 1.16 | 2.55 | 2.38 | 2.24 | 5.19 | 3.23 |
| V | 262D | 0.03 | 10.24 | −60.03 | 0.01 | 3.13 | 0.01 | 3.65 | 4.39 | 4.65 | 9.46 | 18.84 |
| V | 262H | −0.11 | 0.09 | −3.03 | −0.03 | −1.04 | −0.13 | −1.12 | −1.32 | −1.11 | −2.83 | −0.35 |
| V | 262I | 0.77 | 0.92 | −1.91 | 0.55 | 1.11 | 0.97 | 1.03 | 1.03 | 1.01 | 1.21 | 1.05 |
| V | 262K | −0.06 | 8.15 | 33.64 | −0.01 | −2.32 | −0.39 | −2.38 | −2.64 | −2.82 | −5.66 | −3.54 |
| V | 262M | 0.33 | 1.46 | −3.09 | 0.15 | 1.41 | 0.52 | 0.94 | 0.83 | 0.96 | 1.73 | 1.21 |
| V | 262N | −0.05 | −6.09 | −10.55 | −0.01 | −2.24 | 0.05 | −2.47 | −2.84 | −2.97 | −6.52 | −2.13 |
| V | 262P | 0.00 | −56.23 | 212.55 | 0.00 | −53.84 | −6.03 | −61.40 | −74.12 | −74.96 | −173.96 | −49.06 |
| V | 262R | −0.05 | 3.72 | 18.28 | −0.01 | −2.20 | −0.28 | −2.45 | −2.94 | −2.72 | −5.89 | −2.72 |
| V | 262S | −0.11 | 0.07 | −4.95 | −0.03 | −1.00 | −0.14 | −1.03 | −1.24 | −1.18 | −2.27 | −0.81 |
| V | 262T | 0.11 | 2.80 | 17.13 | 0.03 | 3.26 | 1.09 | 2.36 | 2.42 | 2.34 | 5.19 | 3.98 |
| V | 262W | −0.18 | 0.44 | −3.86 | −0.03 | −0.56 | −0.03 | −0.63 | −0.78 | −0.70 | −1.58 | −0.61 |
| V | 262Y | −0.14 | −0.21 | −4.87 | −0.03 | −1.78 | −0.20 | −1.34 | −1.24 | −1.17 | −3.13 | −1.75 |
| T | 263A | 0.45 | 1.46 | 0.75 | 0.33 | 1.66 | 1.25 | 1.37 | 0.84 | 1.31 | 2.02 | 0.76 |
| T | 263C | 0.57 | 1.33 | 0.12 | 0.39 | 1.34 | 0.99 | 1.11 | 0.94 | 1.11 | 1.33 | 1.27 |
| T | 263D | −0.11 | −3.75 | −4.99 | −0.03 | −2.61 | −0.50 | −1.82 | −1.91 | −1.98 | −4.10 | −2.78 |
| T | 263F | −0.02 | −20.88 | 4.43 | −0.01 | −11.50 | −2.50 | −8.63 | −7.81 | −8.54 | −19.66 | −11.99 |
| T | 263G | 0.03 | 10.21 | 17.46 | 0.01 | 12.71 | 4.87 | 9.02 | 8.04 | 8.36 | 16.30 | 12.44 |
| T | 263H | 0.03 | 14.21 | −17.02 | 0.01 | 11.25 | 2.70 | 8.28 | 7.10 | 5.78 | 19.00 | 14.27 |
| T | 263K | −0.09 | 1.22 | −14.50 | −0.02 | −1.84 | −0.27 | −1.71 | −1.83 | −1.75 | −3.43 | −1.21 |
| T | 263L | 0.57 | 1.20 | 1.41 | 0.39 | 1.42 | 1.06 | 1.14 | 0.90 | 1.09 | 1.58 | 1.42 |
| T | 263M | 0.54 | 1.02 | 2.05 | 0.32 | 1.20 | 0.71 | 0.88 | 0.42 | 0.83 | 1.37 | 1.27 |
| T | 263N | 0.15 | 4.40 | 0.55 | 0.05 | 2.41 | 0.61 | 1.58 | 1.26 | 1.53 | 3.57 | 2.15 |
| T | 263P | 0.22 | 2.10 | 3.12 | 0.08 | 2.03 | 0.85 | 1.47 | 1.08 | 1.49 | 2.68 | 1.42 |
| T | 263Q | −0.08 | 1.81 | 4.65 | −0.02 | −1.24 | −0.20 | −1.44 | −1.74 | −1.78 | −3.30 | −0.99 |
| T | 263R | −0.05 | 1.66 | −1.19 | −0.01 | −2.42 | −0.25 | −2.47 | −2.94 | −2.86 | −5.64 | −1.62 |
| T | 263S | 0.66 | 1.28 | −0.30 | 0.52 | 1.43 | 1.36 | 1.36 | 0.93 | 1.34 | 1.50 | 1.41 |
| T | 263V | 0.88 | 1.00 | −0.20 | 0.76 | 1.16 | 1.03 | 1.08 | 0.80 | 1.04 | 1.06 | 1.02 |
| T | 263W | −0.03 | −23.22 | 8.28 | −0.01 | −4.21 | −0.15 | −4.08 | −4.45 | −5.02 | −9.47 | −1.49 |
| T | 263Y | −0.02 | 13.08 | −77.41 | 0.00 | −8.86 | −0.84 | −7.86 | −8.39 | −8.66 | −17.66 | −5.73 |
| W | 264A | 1.18 | 0.50 | 13.89 | 0.66 | 0.42 | 0.02 | 0.16 | 0.13 | 0.15 | 0.57 | 0.26 |
| W | 264C | 0.87 | 0.62 | 26.42 | 0.39 | 0.50 | 0.03 | 0.23 | 0.19 | 0.21 | 0.77 | 0.82 |
| W | 264D | 0.37 | 1.09 | 125.18 | 0.12 | 0.82 | 0.00 | 0.41 | 0.40 | 0.42 | 1.89 | 0.87 |
| W | 264E | 0.47 | 0.76 | 115.55 | 0.16 | 0.74 | −0.01 | 0.29 | 0.30 | 0.30 | 1.27 | 0.32 |
| W | 264F | 1.13 | 0.93 | 43.12 | 1.06 | 0.71 | 0.24 | 0.55 | 0.43 | 0.36 | 0.82 | 0.65 |
| W | 264G | 0.76 | 0.73 | 29.35 | 0.30 | 0.68 | 0.05 | 0.30 | 0.27 | 0.25 | 1.01 | 0.55 |
| W | 264H | 0.67 | 0.83 | 48.90 | 0.26 | 0.70 | 0.04 | 0.28 | 0.25 | 0.22 | 1.15 | 0.48 |
| W | 264I | 0.51 | 1.22 | 31.66 | 0.25 | 1.08 | 0.08 | 0.46 | 0.30 | 0.33 | 1.53 | 0.72 |
| W | 264L | 0.81 | 0.91 | 71.58 | 0.66 | 0.99 | 0.17 | 0.44 | 0.27 | 0.91 | 1.07 | 0.59 |
| W | 264M | 1.01 | 0.94 | 21.44 | 0.93 | 0.72 | 0.12 | 0.36 | 0.20 | 0.28 | 0.80 | 0.54 |
| W | 264N | 0.76 | 0.73 | 30.52 | 0.39 | 0.63 | 0.05 | 0.32 | 0.24 | 0.25 | 1.02 | 0.52 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| W | 264P | −0.07 | −7.75 | −37.01 | −0.01 | −1.49 | 0.10 | −1.46 | −1.80 | −1.74 | −4.10 | −1.41 |
| W | 264Q | 0.81 | 0.46 | 35.81 | 0.26 | 0.41 | 0.00 | 0.16 | 0.18 | 0.18 | 0.80 | 0.27 |
| W | 264R | 0.66 | 0.69 | 40.42 | 0.13 | 0.13 | −0.01 | 0.16 | 0.19 | 0.20 | 0.43 | 0.03 |
| W | 264S | 0.87 | 0.69 | 44.26 | 0.36 | 0.56 | 0.03 | 0.26 | 0.23 | 0.19 | 0.87 | 0.34 |
| W | 264Y | 0.94 | 0.81 | 44.30 | 0.70 | 0.79 | 0.12 | 0.42 | 0.30 | 0.38 | 1.05 | 0.59 |
| V | 265A | 0.36 | 1.38 | 15.59 | 0.20 | 1.74 | 0.98 | 1.35 | 0.88 | 1.27 | 2.08 | 0.86 |
| V | 265C | 0.53 | 1.34 | 2.41 | 0.39 | 1.44 | 1.01 | 1.24 | 0.91 | 1.13 | 1.73 | 1.29 |
| V | 265D | −0.02 | 8.26 | 10.35 | 0.00 | −4.42 | −0.13 | −5.45 | −6.45 | −7.02 | −15.38 | −1.21 |
| V | 265F | 0.21 | 1.83 | −11.20 | 0.07 | 1.94 | 0.13 | 1.14 | 1.01 | 0.84 | 2.98 | 1.89 |
| V | 265G | −0.16 | −4.95 | −52.41 | −0.03 | −0.64 | 0.12 | −0.78 | −0.94 | −1.01 | −2.38 | −0.10 |
| V | 265H | 0.04 | 2.36 | −89.38 | 0.01 | 2.33 | 0.14 | 2.80 | 3.50 | 3.72 | 8.11 | 3.92 |
| V | 265I | −1.31 | −0.13 | 1.57 | −0.25 | −0.30 | −2.02 | −0.48 | −0.32 | −0.19 | −0.23 | −0.04 |
| V | 265K | −1.31 | −0.13 | −0.55 | −0.25 | −0.29 | −2.00 | −0.34 | −0.41 | −0.26 | −0.25 | −0.04 |
| V | 265M | 0.39 | 1.27 | −2.08 | 0.23 | 1.57 | 0.50 | 1.14 | 0.59 | 0.77 | 2.14 | 1.37 |
| V | 265R | −0.02 | 11.98 | 381.83 | 0.00 | −5.69 | −1.12 | −7.24 | −8.43 | −9.54 | −19.23 | −3.06 |
| V | 265S | 0.03 | 10.32 | −277.27 | 0.01 | 10.31 | 2.42 | 6.80 | 6.33 | 6.55 | 16.30 | 9.70 |
| V | 265T | 0.16 | 1.34 | −13.54 | 0.03 | 1.41 | 0.16 | 1.02 | 1.11 | 1.18 | 2.73 | 1.24 |
| V | 265W | −0.07 | −0.28 | −128.70 | −0.02 | −1.44 | −0.03 | −1.80 | −2.09 | −2.26 | −4.96 | −1.52 |
| V | 265Y | 0.24 | 1.39 | −16.30 | 0.08 | 1.98 | 0.26 | 1.36 | 1.02 | 0.83 | 2.73 | 1.42 |
| E | 266A | −0.18 | −1.90 | −0.24 | −0.03 | −0.55 | −0.11 | −0.66 | −0.82 | −3.13 | −1.74 | 0.84 |
| E | 266C | −0.25 | −1.58 | 1.60 | −0.06 | −0.39 | −0.03 | −0.44 | −0.54 | −2.16 | −0.95 | −0.44 |
| E | 266D | −0.12 | −5.30 | −22.13 | −0.03 | −1.85 | −0.03 | −1.45 | −1.50 | −4.56 | −3.55 | −0.96 |
| E | 266F | −0.35 | −0.28 | −3.27 | −0.07 | −0.27 | −0.04 | −0.30 | −0.37 | −1.36 | −0.82 | −0.22 |
| E | 266G | −0.35 | −0.60 | −1.73 | −0.06 | −0.27 | −0.03 | −0.30 | −0.37 | −1.43 | −0.79 | −0.11 |
| E | 266H | −0.28 | −0.86 | 3.29 | −0.05 | −0.36 | −0.03 | −0.40 | −0.50 | −1.68 | −1.11 | −0.39 |
| E | 266I | −0.26 | −0.95 | −7.91 | −0.05 | −0.38 | −0.04 | −0.42 | −0.51 | −1.97 | −1.25 | −0.21 |
| E | 266K | −0.29 | −0.78 | −3.32 | −0.06 | −0.34 | −0.03 | −0.39 | −0.48 | −1.73 | −1.01 | −0.18 |
| E | 266L | −0.33 | −0.06 | −1.77 | −0.06 | −0.30 | −0.02 | −0.35 | −0.42 | −1.54 | −0.92 | −0.15 |
| E | 266M | −0.06 | −2.10 | −2.27 | −0.01 | −1.49 | −0.20 | −1.76 | −2.16 | −8.07 | −4.04 | −1.63 |
| E | 266P | −0.18 | 0.23 | −10.94 | −0.03 | −0.56 | −0.16 | −0.64 | −0.78 | −3.03 | −1.77 | −0.65 |
| E | 266Q | −0.08 | −2.69 | 18.60 | −0.01 | −1.25 | −0.18 | −1.44 | −1.72 | −6.61 | −3.85 | −0.67 |
| E | 266R | −0.14 | −0.32 | −14.25 | −0.03 | −0.71 | −0.19 | −0.78 | −0.95 | −3.81 | −2.10 | −0.88 |
| E | 266S | −0.24 | −0.07 | −6.97 | −0.04 | −0.44 | −0.09 | −0.50 | −0.61 | −2.74 | −1.17 | −0.34 |
| E | 266V | −0.23 | −0.70 | −12.31 | −0.04 | −0.43 | −0.05 | −0.49 | −0.59 | −2.19 | −1.26 | −0.22 |
| E | 266Y | −0.15 | −0.61 | 6.92 | −0.03 | −0.65 | −0.09 | −0.79 | −0.95 | −3.64 | −2.22 | −0.11 |
| S | 267A | 0.69 | 0.76 | 0.40 | 0.40 | 0.86 | 0.10 | 0.50 | 0.33 | 0.86 | 1.05 | 0.30 |
| S | 267C | 0.62 | 1.15 | 2.37 | 0.40 | 1.12 | 0.35 | 0.86 | 0.52 | 1.73 | 1.33 | 0.80 |
| s | 267D | 0.43 | 1.22 | 0.97 | 0.13 | 0.70 | −0.03 | 0.33 | 0.34 | 1.32 | 1.44 | 0.37 |
| S | 267E | −0.05 | −15.64 | −21.22 | −0.01 | −2.64 | 0.16 | −2.79 | −3.46 | −13.06 | −7.56 | −4.06 |
| S | 267F | 0.20 | 3.10 | −12.07 | 0.03 | 0.51 | −0.01 | 0.54 | 0.67 | 2.55 | 1.39 | 0.32 |
| S | 267G | 0.21 | 2.28 | 4.60 | 0.06 | 1.95 | 0.05 | 0.91 | 0.80 | 2.55 | 2.82 | 1.14 |
| S | 267H | 0.10 | 4.36 | −2.97 | 0.02 | 1.75 | −0.05 | 1.25 | 1.46 | 5.60 | 5.23 | 1.54 |
| S | 267I | −0.02 | −18.28 | −81.84 | 0.00 | −11.30 | 0.77 | −9.05 | −10.72 | −39.37 | −32.37 | −8.28 |
| S | 267K | −0.10 | 0.02 | 4.02 | −0.02 | −1.05 | −0.10 | −1.18 | −1.41 | −5.12 | −2.96 | 0.02 |
| S | 267M | 0.36 | 1.78 | 3.92 | 0.08 | 0.40 | −0.07 | 0.34 | 0.39 | 1.44 | 1.24 | 0.04 |
| S | 267N | 0.64 | 0.78 | −0.77 | 0.33 | 0.83 | 0.20 | 0.60 | 0.46 | 1.11 | 1.20 | 1.04 |
| S | 267P | −0.11 | −5.35 | −17.63 | −0.03 | −1.97 | 0.08 | −1.34 | −1.47 | −4.68 | −3.70 | −0.78 |
| S | 267Q | 0.34 | 0.94 | 4.45 | 0.08 | 0.41 | −0.06 | 0.32 | 0.38 | 1.42 | 1.04 | 0.11 |
| S | 267R | −0.20 | −2.88 | −6.64 | −0.05 | −0.51 | 0.01 | −0.50 | −0.61 | −2.42 | −1.59 | −0.59 |
| S | 267T | 0.64 | 1.21 | 6.40 | 0.45 | 1.24 | 0.64 | 1.03 | 1.05 | 0.97 | 1.44 | 1.27 |
| S | 267V | 0.06 | 6.14 | 11.47 | 0.02 | 3.60 | −0.04 | 2.21 | 2.16 | 6.59 | 6.99 | 4.91 |
| S | 267W | −0.05 | −1.27 | −11.88 | −0.01 | −1.80 | −0.25 | −2.05 | −2.44 | −9.24 | −6.84 | −0.59 |
| S | 267Y | 0.39 | −0.34 | 5.56 | 0.08 | 0.27 | 0.00 | 0.30 | 0.35 | 1.35 | 0.79 | 0.00 |
| H | 268A | 0.92 | 0.57 | 0.01 | 0.29 | 0.30 | 0.01 | 0.14 | 0.15 | 0.17 | 0.76 | 0.24 |
| H | 268C | 0.60 | 0.99 | 1.93 | 0.13 | 0.17 | −0.02 | 0.18 | 0.21 | 0.23 | 0.71 | 0.04 |
| H | 268D | 0.50 | 1.11 | −3.34 | 0.10 | 0.21 | −0.02 | 0.21 | 0.26 | 0.25 | 0.58 | 0.13 |
| H | 268E | 0.68 | 0.58 | 0.14 | 0.14 | 0.17 | −0.01 | 0.15 | 0.19 | 0.19 | 0.41 | 0.10 |
| H | 268F | 0.50 | 1.29 | 4.40 | 0.10 | 0.21 | −0.01 | 0.21 | 0.25 | 0.28 | 0.73 | 0.24 |
| H | 268G | 0.63 | 0.65 | 4.61 | 0.15 | 0.36 | −0.01 | 0.17 | 0.21 | 0.21 | 0.85 | 0.16 |
| H | 268K | 0.50 | 0.03 | 2.78 | 0.09 | 0.19 | 0.02 | 0.22 | 0.26 | 0.30 | 0.58 | 0.03 |
| H | 268M | 0.58 | 0.42 | −6.40 | 0.20 | 0.57 | 0.10 | 0.30 | 0.28 | 0.33 | 1.21 | 0.59 |
| H | 268N | 0.59 | 1.03 | −2.49 | 0.13 | 0.17 | −0.02 | 0.18 | 0.21 | 0.22 | 0.65 | 0.15 |
| H | 268P | 0.42 | 1.41 | −1.06 | 0.09 | 0.22 | −0.01 | 0.25 | 0.30 | 0.32 | 0.90 | 0.11 |
| H | 268Q | 0.60 | 0.45 | −4.70 | 0.17 | 0.45 | 0.00 | 0.21 | 0.23 | 0.24 | 1.03 | 0.38 |
| H | 268R | 0.12 | 1.18 | −19.59 | 0.02 | 0.80 | 0.03 | 0.89 | 1.06 | 1.09 | 2.52 | 0.88 |
| H | 268S | 0.88 | 0.20 | −7.07 | 0.24 | 0.29 | 0.00 | 0.13 | 0.15 | 0.16 | 0.71 | 0.15 |
| H | 268T | 0.47 | 0.51 | −12.69 | 0.09 | 0.20 | −0.01 | 0.22 | 0.26 | 0.29 | 0.74 | 0.14 |
| H | 268V | 0.32 | 0.65 | −14.99 | 0.06 | 0.30 | −0.02 | 0.34 | 0.39 | 0.40 | 1.19 | 0.45 |
| H | 268W | −0.14 | 1.21 | 15.18 | −0.03 | −0.66 | −0.06 | −0.75 | −0.91 | −0.86 | −2.29 | −0.78 |
| H | 268Y | 0.38 | −0.55 | −21.47 | 0.07 | 0.25 | 0.07 | 0.39 | 0.42 | 1.60 | 0.63 | 0.07 |
| D | 269A | 1.66 | 0.10 | 0.63 | 0.35 | 0.06 | 0.01 | 0.04 | 0.06 | 0.10 | −0.01 | 0.08 |
| D | 269C | 1.24 | 0.21 | 1.26 | 0.25 | 0.08 | 0.01 | 0.05 | 0.08 | 0.13 | 0.09 | 0.14 |
| D | 269F | 0.99 | 0.19 | −0.38 | 0.20 | 0.09 | 0.01 | 0.06 | 0.09 | 0.15 | 0.02 | 0.21 |
| D | 269H | 0.33 | 2.31 | 0.86 | 0.06 | 0.41 | 0.73 | 0.34 | 0.20 | −0.98 | 0.13 | 0.57 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| D | 269I | 0.95 | −0.33 | 2.50 | 0.18 | 0.10 | 0.01 | 0.06 | 0.10 | 0.16 | 0.03 | −0.34 |
| D | 269K | 1.66 | −0.16 | 2.68 | 0.35 | 0.06 | 0.01 | 0.04 | 0.06 | 0.09 | 0.01 | 0.02 |
| D | 269L | 0.82 | 0.84 | 1.00 | 0.16 | 0.23 | 0.80 | −0.01 | −0.02 | −0.19 | 0.04 | 0.07 |
| D | 269M | 1.58 | 0.15 | 0.60 | 0.33 | 0.06 | 0.01 | 0.04 | 0.06 | 0.10 | −0.01 | 0.80 |
| D | 269N | 1.13 | 0.14 | 1.27 | 0.24 | 0.08 | 0.00 | 0.05 | 0.08 | 0.13 | 0.00 | 0.11 |
| D | 269P | 1.01 | 0.05 | 0.17 | 0.21 | 0.09 | 0.01 | 0.06 | 0.10 | 0.16 | −0.02 | 0.22 |
| D | 269Q | 1.39 | −0.03 | 0.54 | 0.30 | 0.07 | 0.01 | 0.04 | 0.07 | 0.11 | 0.00 | 0.11 |
| D | 269R | 1.60 | −0.14 | 0.57 | 0.35 | 0.06 | 0.00 | 0.04 | 0.06 | 0.09 | 0.01 | 0.03 |
| D | 269S | 1.53 | −0.16 | 0.41 | 0.35 | 0.06 | 0.02 | 0.04 | 0.06 | 0.10 | 0.01 | 0.05 |
| D | 269T | 1.37 | −0.21 | 1.74 | 0.30 | 0.07 | 0.02 | 0.04 | 0.07 | 0.11 | 0.02 | 0.07 |
| D | 269V | 1.02 | −0.23 | 1.71 | 0.21 | 0.09 | 0.01 | 0.06 | 0.09 | 0.15 | 0.00 | 0.10 |
| D | 269W | 0.77 | −0.38 | 3.57 | 0.17 | 0.12 | 0.01 | 0.08 | 0.12 | 0.20 | −0.06 | 0.02 |
| D | 269Y | 0.62 | −0.21 | 0.18 | 0.12 | 0.14 | 0.01 | 0.11 | 0.16 | 0.25 | 0.00 | 0.15 |
| T | 270A | 1.33 | 0.80 | 1.35 | 1.98 | 0.78 | 0.51 | 0.82 | 0.53 | 0.46 | 0.65 | 0.46 |
| T | 270C | 1.30 | 0.69 | 0.91 | 1.32 | 0.68 | 0.34 | 0.45 | 0.46 | 0.37 | 0.74 | 0.55 |
| T | 270D | 1.60 | 0.61 | 0.50 | 1.60 | 0.56 | 0.35 | 0.66 | 0.63 | 0.70 | 0.67 | 0.73 |
| T | 270E | 1.66 | 0.75 | 0.47 | 2.37 | 0.63 | 0.49 | 0.74 | 0.71 | 0.73 | 0.63 | 0.65 |
| T | 270F | 1.61 | 0.89 | 1.21 | 2.69 | 0.76 | 0.80 | 0.75 | 0.89 | 0.66 | 0.65 | 0.63 |
| T | 270G | 0.57 | 1.01 | −1.68 | 0.37 | 1.19 | 0.39 | 1.03 | 0.95 | 0.44 | 1.32 | 0.69 |
| T | 270I | 0.77 | 0.33 | −0.28 | 0.45 | 0.75 | 0.05 | 0.29 | 0.28 | 0.25 | 0.86 | 0.39 |
| T | 270L | 1.02 | 0.81 | −0.37 | 1.27 | 0.95 | 0.39 | 0.79 | 0.62 | 0.48 | 0.87 | 0.57 |
| T | 270M | 0.80 | 0.91 | 0.52 | 0.95 | 1.10 | 0.30 | 0.75 | 0.54 | 0.36 | 0.89 | 0.63 |
| T | 270N | 1.70 | 0.84 | 0.88 | 3.35 | 0.74 | 0.91 | 0.82 | 0.90 | 0.71 | 0.62 | 0.52 |
| T | 270Q | 1.16 | 0.39 | 1.49 | 0.63 | 0.50 | 0.09 | 0.37 | 0.33 | 0.23 | 0.73 | 0.47 |
| T | 270R | 0.12 | 3.37 | −3.61 | 0.03 | 1.25 | −0.02 | 1.10 | 1.27 | 1.31 | 2.92 | 1.20 |
| T | 270S | 1.11 | 0.93 | −1.68 | 1.19 | 0.92 | 0.76 | 1.19 | 1.07 | 0.66 | 0.87 | 0.82 |
| T | 270V | 0.77 | 1.02 | −0.31 | 0.79 | 1.09 | 0.29 | 0.69 | 0.62 | 0.38 | 1.10 | 0.66 |
| T | 270W | −0.13 | 1.90 | 5.02 | −0.03 | −1.29 | 0.00 | −1.06 | −1.19 | −1.12 | −2.53 | −0.57 |
| T | 270Y | 0.16 | 0.57 | 6.98 | 0.04 | 1.62 | 0.00 | 0.94 | 1.00 | 0.95 | 3.01 | 1.36 |
| Y | 271D | −0.15 | −1.89 | 4.87 | −0.04 | −0.62 | −0.06 | −0.71 | −0.88 | −0.99 | −1.76 | −0.53 |
| Y | 271E | −0.12 | −0.91 | 6.61 | −0.03 | −0.84 | −0.21 | −0.96 | −1.21 | −1.52 | −2.71 | −0.59 |
| Y | 271F | 1.36 | 1.04 | −0.07 | 1.99 | 0.84 | 1.06 | 1.04 | 1.05 | 1.32 | 0.81 | 0.82 |
| Y | 271G | −0.07 | 4.45 | 24.61 | −0.02 | −1.39 | −0.28 | −1.57 | −1.97 | −2.15 | −4.57 | −2.79 |
| Y | 271H | −0.20 | 1.67 | 2.33 | −0.04 | −0.51 | −0.05 | −0.57 | −0.69 | −0.86 | −1.47 | −0.27 |
| Y | 271I | −0.30 | 1.25 | 9.89 | −0.06 | −0.32 | −0.02 | −0.37 | −0.46 | −0.56 | −0.95 | −0.24 |
| Y | 271K | −0.27 | 1.32 | −14.45 | −0.06 | −0.35 | 0.07 | −0.42 | −0.51 | −0.66 | −1.16 | −0.29 |
| Y | 271L | −0.23 | 1.71 | 8.53 | −0.05 | −0.45 | −0.08 | −0.52 | −0.62 | −0.65 | −1.56 | −0.09 |
| Y | 271M | −0.14 | −3.90 | 7.76 | −0.04 | −0.85 | 0.00 | −0.87 | −1.03 | −1.27 | −2.19 | −0.28 |
| Y | 271N | −0.07 | −2.58 | 24.58 | −0.01 | −1.37 | −0.11 | −1.55 | −1.93 | −2.43 | −4.05 | −0.71 |
| Y | 271P | −0.17 | 0.87 | −3.01 | −0.04 | −0.59 | −0.06 | −0.65 | −0.83 | −1.04 | −1.66 | −0.09 |
| Y | 271Q | −0.26 | 0.20 | 1.11 | −0.06 | −0.38 | −0.01 | −0.43 | −0.55 | −0.67 | −1.18 | −0.25 |
| Y | 271R | −0.26 | 0.90 | 3.19 | −0.06 | −0.37 | −0.07 | −0.43 | −0.53 | −0.65 | −1.03 | −0.43 |
| Y | 271S | −0.23 | 0.03 | 11.53 | −0.05 | −0.43 | −0.12 | −0.49 | −0.61 | −0.70 | −1.15 | −0.43 |
| Y | 271T | −0.24 | 0.95 | 5.78 | −0.05 | −0.41 | −0.13 | −0.46 | −0.57 | −0.72 | −1.35 | −0.87 |
| Y | 271W | −0.14 | −2.81 | 4.41 | −0.04 | −2.00 | −0.19 | −1.29 | −1.29 | −1.27 | −3.53 | −1.61 |
| A | 272D | 0.02 | 18.05 | −60.18 | 0.01 | 9.26 | 0.18 | 5.60 | 6.20 | 6.90 | 16.92 | −1.62 |
| A | 272G | 1.04 | 1.05 | 1.63 | 1.19 | 1.03 | 1.05 | 1.00 | 1.03 | 1.00 | 1.03 | 1.02 |
| A | 272H | −0.16 | −1.11 | −5.27 | −0.03 | −0.84 | 0.01 | −0.67 | −0.81 | −1.10 | −2.15 | 1.08 |
| A | 272I | 0.49 | 1.95 | 5.25 | 0.38 | 1.47 | 0.29 | 0.75 | 0.59 | 0.38 | 1.67 | 1.08 |
| A | 272K | −0.08 | 3.14 | −55.39 | −0.02 | −1.27 | −0.13 | −1.35 | −1.66 | −2.21 | −3.81 | 3.54 |
| A | 272L | 0.68 | 1.14 | 1.00 | 0.48 | 1.06 | 0.28 | 0.69 | 0.35 | 0.40 | 1.35 | 0.95 |
| A | 272M | 0.32 | 1.53 | −2.19 | 0.17 | 1.59 | 0.27 | 0.92 | 0.68 | 0.62 | 2.15 | 1.45 |
| A | 272N | 0.40 | 1.06 | 2.80 | 0.16 | 1.03 | 0.15 | 0.58 | 0.57 | 0.50 | 1.52 | 0.68 |
| A | 272P | −0.02 | −20.15 | 40.47 | −0.01 | −7.97 | 0.57 | −5.54 | −6.71 | −9.25 | −19.78 | 5.06 |
| A | 272Q | −0.16 | −2.07 | −11.51 | −0.04 | −0.93 | 0.03 | −0.72 | −0.85 | −1.15 | −2.18 | 1.30 |
| A | 272R | −0.23 | −1.51 | −4.59 | −0.05 | −0.42 | −0.02 | −0.45 | −0.56 | −0.77 | −1.18 | 1.04 |
| A | 272S | 0.75 | 1.16 | −1.06 | 0.64 | 1.18 | 1.00 | 1.09 | 1.11 | 0.93 | 1.23 | 1.11 |
| A | 272T | 0.48 | 2.01 | −0.33 | 0.33 | 1.45 | 0.35 | 0.94 | 0.75 | 0.64 | 1.84 | 1.10 |
| A | 272V | 0.57 | 1.90 | 0.60 | 0.50 | 1.33 | 0.31 | 0.82 | 0.64 | 0.39 | 1.66 | 1.06 |
| A | 272W | −0.24 | −0.21 | −7.45 | −0.05 | −0.48 | 0.01 | −0.46 | −0.55 | −0.76 | −1.18 | 0.92 |
| A | 272Y | −0.19 | 1.35 | 5.02 | −0.04 | −0.60 | −0.03 | −0.59 | −0.69 | −1.00 | −1.57 | 0.62 |
| N | 273A | 1.27 | 1.07 | 0.12 | 1.66 | 0.67 | 0.26 | 0.58 | 0.40 | 0.37 | 0.82 | 0.65 |
| N | 273C | 0.89 | 0.32 | 0.62 | 0.31 | 0.38 | 0.03 | 0.20 | 0.22 | 0.23 | 0.68 | −0.03 |
| N | 273D | 1.03 | 0.78 | 0.52 | 0.95 | 0.74 | 0.27 | 0.41 | 0.44 | 0.87 | 0.84 | 0.37 |
| N | 273E | 1.12 | 0.49 | 1.72 | 0.67 | 0.48 | 0.07 | 0.22 | 0.24 | 0.36 | 0.81 | 0.52 |
| N | 273G | 0.93 | 1.00 | 0.70 | 0.79 | 0.85 | 0.47 | 0.77 | 0.75 | 0.71 | 1.09 | 0.81 |
| N | 273H | 1.19 | 0.65 | 2.19 | 1.06 | 0.69 | 0.40 | 0.72 | 0.68 | 0.36 | 0.79 | 0.57 |
| N | 273I | 0.62 | 0.98 | 4.57 | 0.31 | 0.87 | 0.08 | 0.39 | 0.35 | 0.29 | 1.35 | 0.94 |
| N | 273K | 0.88 | 0.46 | 0.97 | 0.38 | 0.57 | 0.10 | 0.44 | 0.44 | 0.31 | 0.98 | 0.45 |
| N | 273L | 0.88 | 0.59 | −1.42 | 0.51 | 0.61 | 0.09 | 0.29 | 0.24 | 0.23 | 1.10 | 0.82 |
| N | 273M | 1.13 | 0.68 | 1.02 | 0.89 | 0.60 | 0.25 | 0.52 | 0.39 | 0.34 | 0.82 | 0.73 |
| N | 273P | 0.42 | 1.69 | 3.61 | 0.16 | 0.92 | 0.05 | 0.55 | 0.48 | 0.47 | 1.98 | 0.87 |
| N | 273Q | 0.91 | 0.75 | 2.86 | 0.55 | 0.69 | 0.12 | 0.31 | 0.31 | 0.39 | 1.04 | 0.79 |
| N | 273R | 0.96 | 0.46 | 2.73 | 0.36 | 0.45 | 0.09 | 0.43 | 0.47 | 0.24 | 0.82 | 0.40 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| N | 273S | 0.95 | 1.21 | 2.77 | 0.86 | 0.84 | 0.30 | 0.65 | 0.60 | 0.53 | 1.04 | 0.66 |
| N | 273T | 0.68 | 1.31 | 5.25 | 0.48 | 0.95 | 0.14 | 0.43 | 0.38 | 0.35 | 1.36 | 0.74 |
| N | 273V | 0.50 | 1.58 | 0.20 | 0.30 | 1.23 | 0.14 | 0.59 | 0.49 | 0.38 | 1.90 | 1.27 |
| N | 273W | 0.50 | 0.35 | 4.96 | 0.10 | 0.39 | 0.00 | 0.26 | 0.27 | 0.37 | 1.17 | 0.30 |
| N | 273Y | 0.79 | 0.91 | 1.66 | 0.46 | 0.77 | 0.13 | 0.37 | 0.27 | 0.24 | 1.24 | 0.89 |
| S | 278A | 0.34 | 1.39 | 6.09 | 0.18 | 1.42 | 0.20 | 0.84 | 0.63 | 0.52 | 1.91 | 0.80 |
| S | 278C | 0.06 | 4.63 | 11.17 | 0.02 | 3.79 | −0.08 | 2.45 | 2.42 | 2.50 | 7.20 | 3.43 |
| S | 278D | 0.03 | 12.87 | 48.91 | 0.01 | 4.70 | −0.45 | 4.04 | 4.88 | 5.49 | 12.51 | 3.94 |
| S | 278E | 0.04 | 8.04 | 38.49 | 0.01 | 3.24 | −0.10 | 2.67 | 3.26 | 3.68 | 6.67 | 2.14 |
| S | 278F | −0.03 | −0.02 | −72.25 | −0.01 | −3.30 | 0.12 | −3.17 | −3.83 | −4.57 | −8.58 | −5.24 |
| S | 278G | −0.03 | −10.21 | −62.06 | −0.01 | −12.18 | −1.04 | −7.54 | −7.77 | −6.31 | −19.50 | −8.67 |
| S | 278H | −0.08 | 0.86 | −44.33 | −0.01 | −1.40 | 0.00 | −1.33 | −1.61 | −1.88 | −3.04 | −1.88 |
| S | 278I | 0.02 | −1.68 | 162.90 | 0.00 | 8.61 | −0.38 | 7.06 | 8.42 | 9.90 | 26.47 | 6.29 |
| S | 278K | −0.04 | −3.61 | −36.31 | −0.01 | −2.36 | −0.08 | −2.39 | −2.89 | −3.43 | −6.35 | −1.86 |
| S | 278M | −0.01 | −44.61 | −95.45 | 0.00 | −12.69 | 0.21 | −11.89 | −13.76 | −15.90 | −32.61 | −6.59 |
| S | 278N | −0.03 | −11.38 | −16.82 | −0.01 | −4.44 | 0.06 | −3.64 | −4.21 | −4.77 | −9.59 | −4.04 |
| S | 278P | −0.07 | −2.95 | −16.94 | −0.01 | −1.82 | 0.15 | −1.68 | −1.95 | −2.15 | −3.62 | −0.63 |
| S | 278Q | −0.04 | −7.57 | −57.26 | −0.01 | −2.86 | −0.05 | −2.68 | −3.23 | −3.53 | −6.83 | −4.31 |
| S | 278R | −0.05 | 3.82 | 31.39 | −0.01 | −2.14 | −0.27 | −2.26 | −2.72 | −4.37 | −4.90 | −2.59 |
| S | 278T | 0.32 | 1.50 | 12.73 | 0.13 | 1.68 | 0.64 | 1.22 | 1.02 | 0.88 | 2.12 | 1.59 |
| S | 278V | 0.04 | 1.73 | 8.80 | 0.01 | 4.65 | −0.01 | 2.86 | 3.28 | 3.80 | 9.81 | 3.54 |
| S | 278W | −0.08 | 1.56 | −35.34 | −0.01 | −1.45 | 0.02 | −1.27 | −1.64 | −1.94 | −3.55 | −0.07 |
| S | 278Y | −0.08 | 1.24 | −26.59 | −0.01 | −1.48 | −0.01 | −1.45 | −1.68 | −2.04 | −3.40 | −1.16 |
| T | 279A | 0.99 | 0.99 | 1.61 | 1.19 | 0.88 | 0.49 | 0.60 | 0.37 | 0.36 | 0.97 | 0.65 |
| T | 279D | 0.41 | 1.65 | 0.08 | 0.23 | 1.55 | 0.73 | 1.19 | 0.93 | 0.70 | 1.89 | 1.33 |
| T | 279E | 0.31 | 2.33 | 9.40 | 0.15 | 1.71 | 0.42 | 1.10 | 0.91 | 0.62 | 2.14 | 1.61 |
| T | 279G | 0.36 | 1.93 | 5.71 | 0.20 | 1.94 | 1.01 | 1.55 | 1.32 | 0.60 | 2.19 | 2.22 |
| T | 279H | 0.55 | 1.51 | 5.17 | 0.34 | 1.24 | 0.37 | 0.74 | 0.62 | 0.29 | 1.58 | 1.37 |
| T | 279I | 0.68 | 1.12 | 2.89 | 0.46 | 1.07 | 0.39 | 0.81 | 0.63 | 0.40 | 1.15 | 0.89 |
| T | 279K | 0.45 | 0.89 | 6.53 | 0.19 | 1.17 | 0.22 | 0.79 | 0.61 | 0.47 | 1.67 | 1.15 |
| T | 279L | 0.66 | 0.99 | 4.01 | 0.43 | 1.11 | 0.43 | 0.86 | 0.58 | 0.54 | 1.37 | 1.13 |
| T | 279M | 0.64 | 0.99 | 1.02 | 0.46 | 1.01 | 0.27 | 0.69 | 0.34 | 0.41 | 1.17 | 0.90 |
| T | 279N | 0.47 | 1.71 | 0.96 | 0.35 | 1.52 | 0.47 | 0.92 | 0.55 | 0.42 | 1.74 | 1.43 |
| T | 279P | 0.42 | 1.26 | 1.72 | 0.23 | 1.61 | 1.01 | 1.26 | 0.85 | 0.57 | 1.72 | 1.77 |
| T | 279Q | 0.49 | 1.28 | 1.42 | 0.25 | 1.10 | 0.29 | 0.73 | 0.50 | 0.44 | 1.73 | 1.30 |
| T | 279R | 0.41 | 1.47 | 4.28 | 0.18 | 1.25 | 0.25 | 0.93 | 0.65 | 0.79 | 1.83 | 1.13 |
| T | 279S | 0.94 | 1.01 | 0.48 | 0.95 | 1.07 | 0.71 | 0.87 | 0.63 | 0.44 | 1.06 | 1.02 |
| T | 279V | 0.96 | 0.97 | 2.80 | 1.06 | 1.07 | 0.90 | 1.09 | 0.74 | 0.58 | 1.02 | 1.10 |
| T | 279W | 0.37 | 1.41 | 6.94 | 0.19 | 1.62 | 0.42 | 1.04 | 0.14 | 0.48 | 2.20 | 1.73 |
| T | 279Y | 0.74 | 0.74 | 1.29 | 0.54 | 1.01 | 0.31 | 0.70 | 0.50 | 0.47 | 1.25 | 1.26 |
| W | 280A | 0.19 | 3.13 | −15.95 | 0.10 | 3.05 | 1.54 | 1.64 | 1.64 | 1.06 | 2.92 | 2.40 |
| W | 280D | 0.34 | 1.92 | −0.46 | 0.17 | 1.72 | 1.12 | 1.13 | 1.25 | 0.64 | 1.97 | 2.05 |
| W | 280E | 0.17 | 2.56 | 5.95 | 0.06 | 2.70 | 1.31 | 1.53 | 1.76 | 0.96 | 3.10 | 3.10 |
| W | 280F | 0.56 | 1.33 | −0.10 | 0.32 | 1.26 | 0.92 | 0.98 | 1.01 | 0.61 | 1.33 | 1.42 |
| W | 280G | 0.32 | 1.89 | 0.59 | 0.14 | 1.97 | 1.19 | 1.36 | 1.39 | 0.74 | 2.00 | 1.81 |
| W | 280H | 0.26 | 2.11 | 3.20 | 0.11 | 2.16 | 1.11 | 1.43 | 1.38 | 0.66 | 2.40 | 2.52 |
| W | 280I | 0.00 | −625.21 | −2871.46 | 0.00 | −685.68 | −227.36 | −374.34 | −329.48 | −265.65 | −753.79 | −695.65 |
| W | 280K | 0.08 | 4.93 | −31.36 | 0.03 | 4.97 | 1.63 | 2.79 | 2.36 | 1.94 | 6.34 | 4.29 |
| W | 280L | 0.09 | 3.44 | 46.91 | 0.03 | 5.36 | 1.87 | 2.84 | 1.96 | 2.00 | 6.75 | 4.84 |
| W | 280M | 0.38 | 1.50 | 0.64 | 0.24 | 1.68 | 0.81 | 0.84 | 0.76 | 0.54 | 1.55 | 1.35 |
| W | 280N | 0.39 | 1.37 | −1.14 | 0.21 | 1.63 | 0.88 | 0.86 | 0.82 | 0.52 | 1.78 | 1.70 |
| W | 280Q | 0.19 | 2.63 | 3.33 | 0.07 | 2.60 | 1.04 | 1.31 | 1.29 | 0.88 | 2.74 | 3.27 |
| W | 280R | 0.10 | 4.16 | 11.42 | 0.03 | 3.86 | 1.01 | 1.79 | 1.90 | 1.53 | 4.24 | 3.28 |
| W | 280S | 0.24 | 2.21 | 2.10 | 0.12 | 2.72 | 1.33 | 1.65 | 1.42 | 0.88 | 2.87 | 2.44 |
| W | 280T | 0.15 | 3.01 | 2.90 | 0.05 | 3.32 | 1.05 | 1.74 | 1.48 | 1.15 | 3.13 | 2.97 |
| W | 280Y | 0.46 | 1.08 | 3.55 | 0.25 | 1.58 | 1.14 | 1.02 | 0.66 | 0.62 | 1.59 | 1.45 |
| M | 281C | 0.58 | 1.07 | 4.60 | 0.44 | 1.27 | 0.99 | 1.11 | 0.99 | 0.83 | 1.43 | 1.33 |
| M | 281D | −0.17 | 2.68 | −0.45 | −0.04 | −0.58 | −0.03 | −0.62 | −0.77 | −0.81 | −1.34 | −0.04 |
| M | 281F | 0.33 | 1.01 | 0.44 | 0.14 | 1.67 | 0.77 | 1.22 | 1.27 | 0.59 | 2.04 | 2.12 |
| M | 281G | −0.06 | −0.68 | −33.04 | −0.01 | −4.15 | −0.48 | −3.01 | −3.42 | −3.24 | −8.64 | −4.09 |
| M | 281H | −0.22 | 1.18 | −19.28 | −0.05 | −0.85 | −0.11 | −0.65 | −0.78 | −0.77 | −1.72 | −0.60 |
| M | 281K | −0.20 | 1.07 | 0.56 | −0.05 | −0.53 | −0.08 | −0.58 | −0.70 | −0.86 | −1.44 | −0.41 |
| M | 281L | 0.73 | 1.29 | 6.71 | 0.68 | 1.37 | 1.39 | 1.43 | 1.10 | 1.23 | 1.44 | 1.52 |
| M | 281N | −0.13 | 1.54 | −14.35 | −0.04 | −0.86 | −0.05 | −0.89 | −1.08 | −1.36 | −2.30 | −0.80 |
| M | 281P | −0.18 | 3.91 | 13.54 | −0.05 | −0.61 | −0.04 | −0.64 | −0.75 | −0.93 | −1.26 | −0.36 |
| M | 281Q | −0.07 | −3.53 | 44.41 | −0.02 | −4.83 | −1.66 | −3.36 | −3.56 | −2.59 | −7.67 | −3.61 |
| M | 281R | −0.15 | 4.43 | −19.27 | −0.04 | −0.68 | −0.10 | −0.72 | −0.88 | −1.09 | −2.72 | −0.65 |
| M | 281T | −0.17 | −1.20 | −4.39 | −0.04 | −1.57 | −0.36 | −1.09 | −1.22 | −1.03 | −2.66 | −2.03 |
| M | 281V | −0.14 | 0.14 | 16.12 | −0.03 | −1.85 | −0.37 | −1.30 | −1.38 | −1.17 | −2.92 | −1.38 |
| M | 281W | −0.20 | 0.45 | −5.37 | −0.04 | −0.54 | −0.08 | −0.60 | −0.72 | −0.89 | −1.31 | −0.19 |
| M | 281Y | −0.02 | −0.04 | −116.45 | 0.00 | −26.36 | −6.41 | −17.65 | −15.68 | −13.88 | −39.62 | −19.65 |
| D | 285A | 0.28 | 1.99 | 8.97 | 0.15 | 2.13 | 0.79 | 1.54 | 1.13 | 1.39 | 2.59 | 1.12 |
| D | 285C | 0.37 | 1.72 | 0.75 | 0.21 | 1.73 | 1.26 | 1.37 | 1.15 | 1.15 | 2.18 | 1.43 |
| D | 285E | 0.65 | 1.34 | 0.82 | 0.50 | 1.29 | 1.19 | 1.16 | 1.06 | 1.16 | 1.42 | 1.27 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| D | 285G | −0.07 | −5.84 | −20.65 | −0.02 | −4.34 | −1.17 | −2.85 | −2.86 | −3.56 | −5.45 | 1.97 |
| D | 285H | 0.45 | 1.66 | 3.67 | 0.24 | 1.60 | 1.22 | 1.36 | 1.15 | 1.29 | 1.87 | 1.71 |
| D | 285I | 0.05 | 6.13 | 14.51 | 0.02 | 8.37 | 3.61 | 5.78 | 5.09 | 5.51 | 11.98 | 5.62 |
| D | 285K | −0.20 | −0.55 | −16.36 | −0.04 | −0.91 | −0.15 | −0.71 | −0.77 | −1.00 | −1.99 | 0.58 |
| D | 285L | 0.24 | 1.86 | 13.00 | 0.12 | 2.71 | 1.78 | 2.00 | 1.47 | 1.73 | 3.30 | 2.25 |
| D | 285M | 0.53 | 1.20 | 3.57 | 0.34 | 1.32 | 0.93 | 0.95 | 0.59 | 0.82 | 1.52 | 1.16 |
| D | 285N | 0.37 | 1.46 | 2.36 | 0.16 | 1.44 | 0.72 | 0.94 | 0.72 | 0.73 | 1.72 | 1.27 |
| D | 285P | −0.05 | −7.28 | −59.89 | −0.01 | −2.33 | −0.18 | −2.29 | −2.83 | −3.81 | −5.62 | 5.39 |
| D | 285Q | 0.50 | 1.38 | 1.61 | 0.28 | 1.43 | 1.00 | 1.08 | 0.82 | 1.00 | 1.65 | 1.28 |
| D | 285R | −0.17 | −0.78 | −13.81 | −0.04 | −0.69 | −0.05 | −0.68 | −0.81 | −1.08 | −1.57 | 1.40 |
| D | 285S | 0.21 | 2.71 | 17.86 | 0.09 | 2.72 | 1.65 | 2.03 | 1.62 | 1.81 | 3.33 | 2.40 |
| D | 285T | 0.28 | 1.65 | 17.25 | 0.12 | 2.29 | 1.29 | 1.65 | 1.21 | 1.53 | 2.85 | 2.32 |
| D | 285V | 0.14 | 3.57 | 12.18 | 0.05 | 3.87 | 1.72 | 2.51 | 1.91 | 2.40 | 5.07 | 2.55 |
| D | 285W | −0.02 | −12.45 | −43.43 | −0.01 | −17.10 | −4.66 | −10.70 | −9.56 | −11.13 | −26.34 | −6.71 |
| D | 285Y | 0.10 | 4.31 | 26.98 | 0.04 | 4.60 | 1.91 | 3.00 | 2.33 | 2.73 | 6.11 | 3.50 |
| I | 286A | 0.34 | 1.28 | 8.59 | 0.17 | 1.50 | 0.61 | 1.02 | 0.80 | 0.93 | 2.13 | 1.14 |
| I | 286C | 0.68 | 1.17 | 1.43 | 0.58 | 1.19 | 0.90 | 0.97 | 0.75 | 0.88 | 1.38 | 1.24 |
| I | 286D | −0.12 | −7.34 | −2.25 | −0.04 | −1.03 | −0.09 | −1.00 | −1.30 | −1.48 | −2.59 | 2.35 |
| I | 286E | −0.07 | −9.83 | −11.38 | −0.02 | −2.81 | −0.43 | −2.12 | −2.49 | −2.55 | −5.30 | −0.65 |
| I | 286F | −0.01 | −194.40 | −115.49 | 0.00 | −27.94 | −3.13 | −24.27 | −29.50 | −30.90 | −54.96 | 46.43 |
| I | 286G | −0.10 | −7.59 | −29.64 | −0.02 | −1.71 | −0.22 | −1.39 | −1.66 | −1.81 | −3.91 | 1.32 |
| I | 286H | −0.14 | −4.45 | −4.52 | −0.03 | −1.26 | −0.19 | −1.02 | −1.19 | −1.21 | −2.55 | −0.55 |
| I | 286L | 1.07 | 1.08 | 0.99 | 1.59 | 1.09 | 1.20 | 1.10 | 0.88 | 1.05 | 1.01 | 1.22 |
| I | 286M | 0.61 | 1.13 | 4.41 | 0.44 | 1.17 | 0.79 | 0.93 | 0.73 | 0.64 | 1.24 | 1.14 |
| I | 286N | 0.09 | 5.27 | 14.64 | 0.03 | 3.23 | 0.79 | 2.27 | 2.50 | 2.33 | 5.26 | 0.81 |
| I | 286P | −0.17 | −3.98 | −12.86 | −0.04 | −0.59 | −0.17 | −0.62 | −0.83 | −0.95 | −1.64 | 2.01 |
| I | 286Q | 0.16 | 3.58 | 1.88 | 0.07 | 2.75 | 1.11 | 1.94 | 2.04 | 1.43 | 3.88 | 2.68 |
| I | 286R | −0.19 | −3.13 | 0.73 | −0.05 | −0.62 | 0.00 | −0.62 | −0.82 | −0.92 | −1.43 | 1.26 |
| I | 286S | −0.16 | −2.77 | 2.10 | −0.05 | −2.10 | −0.60 | −1.41 | −1.59 | −1.44 | −3.24 | −0.80 |
| I | 286T | 0.27 | 1.85 | 1.46 | 0.14 | 2.32 | 1.43 | 1.79 | 1.81 | 1.48 | 2.76 | 2.86 |
| I | 286V | 0.71 | 1.32 | 3.02 | 0.57 | 1.27 | 1.12 | 1.18 | 1.15 | 1.10 | 1.29 | 1.36 |
| I | 286W | −0.28 | 0.09 | 0.84 | −0.07 | −0.49 | −0.04 | −0.46 | −0.58 | −0.59 | −1.05 | 1.05 |
| I | 286Y | −0.17 | 0.00 | 4.68 | −0.04 | −1.31 | −0.14 | −1.01 | −1.09 | −1.08 | −2.08 | 1.04 |
| L | 288A | 0.27 | 2.06 | 24.98 | 0.11 | 1.49 | 0.54 | 0.98 | 0.92 | 1.35 | 2.15 | 1.51 |
| L | 288C | 0.66 | 1.03 | 1.15 | 0.44 | 1.09 | 0.76 | 0.86 | 0.79 | 1.06 | 1.35 | 1.11 |
| L | 288D | −0.01 | 11.87 | −839.85 | 0.00 | −7.23 | −0.03 | −7.87 | −9.64 | −13.10 | −19.28 | −13.43 |
| L | 288E | −0.13 | −4.67 | −69.34 | −0.03 | −0.89 | −0.07 | −0.90 | −1.06 | −1.40 | −2.33 | −1.18 |
| L | 288H | −0.07 | −5.36 | −49.51 | −0.02 | −3.20 | −0.54 | −2.21 | −2.54 | −3.14 | −4.67 | −3.44 |
| L | 288I | 1.10 | 0.93 | −1.11 | 1.15 | 0.93 | 0.95 | 0.94 | 0.88 | 1.20 | 0.94 | 0.92 |
| L | 288K | −0.05 | 6.19 | −14.85 | −0.01 | −2.20 | −0.43 | −2.24 | −2.61 | −3.64 | −5.75 | −1.76 |
| L | 288M | 0.95 | 0.93 | 0.55 | 0.96 | 0.93 | 0.87 | 0.82 | 0.68 | 1.02 | 0.96 | 0.88 |
| L | 288N | 0.01 | 247.17 | 1986.92 | 0.00 | 117.45 | 18.25 | 83.35 | 89.92 | 113.62 | 211.84 | 111.89 |
| L | 288Q | −0.13 | −3.12 | −101.40 | −0.03 | −1.97 | −0.39 | −1.33 | −1.51 | −1.89 | −3.20 | −1.48 |
| L | 288S | −0.17 | −2.94 | −87.28 | −0.03 | −1.19 | −0.22 | −0.88 | −1.02 | −1.29 | −2.50 | −1.08 |
| L | 288T | 0.30 | 1.37 | 26.85 | 0.13 | 1.88 | 1.20 | 1.45 | 1.52 | 1.90 | 2.39 | 1.96 |
| L | 288V | 0.79 | 1.34 | 7.48 | 0.79 | 1.21 | 1.28 | 1.26 | 1.20 | 1.65 | 1.18 | 1.21 |
| L | 288W | −0.29 | 1.57 | −24.25 | −0.06 | −0.48 | −0.05 | −0.44 | −0.51 | −0.68 | −0.96 | −0.24 |
| L | 288Y | −0.09 | 5.15 | −106.25 | −0.02 | −1.37 | −0.23 | −1.46 | −1.64 | −2.34 | −3.63 | −0.64 |
| G | 289A | 0.67 | 1.18 | 1.92 | 0.47 | 1.13 | 0.65 | 0.89 | 0.64 | 0.95 | 1.21 | 1.02 |
| G | 289C | −0.02 | −41.78 | −14.98 | 0.00 | −20.00 | −2.59 | −14.01 | −13.79 | −47.50 | −34.81 | −14.19 |
| G | 289D | −0.14 | −2.73 | −7.33 | −0.02 | −0.71 | −0.06 | −0.76 | −0.93 | −3.80 | −2.24 | −1.40 |
| G | 289E | −0.18 | −4.05 | 15.96 | −0.03 | −0.56 | −0.01 | −0.62 | −0.76 | −3.08 | −1.43 | −0.42 |
| G | 289F | −0.18 | −2.98 | 1.12 | −0.04 | −0.54 | −0.10 | −0.58 | −0.71 | −2.85 | −1.83 | −0.93 |
| G | 289H | −0.22 | −1.01 | −13.10 | −0.04 | −0.45 | −0.05 | −0.48 | −0.60 | −2.31 | −1.38 | −0.47 |
| G | 289I | −0.21 | −0.57 | 11.66 | −0.05 | −0.55 | −0.10 | −0.57 | −0.68 | −2.53 | −1.61 | −0.44 |
| G | 289K | −0.23 | 0.13 | −1.22 | −0.04 | −0.41 | −0.04 | −0.48 | −0.58 | −2.24 | −1.21 | −0.44 |
| G | 289L | −0.14 | −1.79 | 15.65 | −0.03 | −2.03 | −0.25 | −1.28 | −1.23 | −3.61 | −3.47 | −1.63 |
| G | 289M | −0.16 | −5.64 | 3.70 | −0.04 | −0.89 | −0.03 | −0.77 | −0.86 | −3.32 | −2.23 | −0.54 |
| G | 289N | −0.19 | −3.44 | −7.88 | −0.03 | −0.52 | −0.04 | −0.56 | −0.67 | −2.53 | −1.53 | −0.36 |
| G | 289P | −0.27 | −1.91 | 0.47 | −0.05 | −0.36 | −0.08 | −0.40 | −0.49 | −1.85 | −1.12 | −0.26 |
| G | 289Q | −0.22 | −2.94 | −2.16 | −0.04 | −0.49 | −0.07 | −0.52 | −0.63 | −2.31 | −1.42 | 0.13 |
| G | 289R | −0.22 | −3.43 | −0.31 | −0.04 | −0.45 | −0.03 | −0.49 | −0.55 | −2.33 | −1.33 | −0.58 |
| G | 289S | 0.13 | 3.50 | 6.70 | 0.05 | 4.29 | 1.76 | 3.08 | 3.07 | 4.48 | 5.58 | 4.54 |
| G | 289V | −0.27 | −1.43 | 1.48 | −0.06 | −0.42 | −0.05 | −0.43 | −0.52 | −2.00 | −1.05 | −0.09 |
| G | 289W | −0.24 | −0.08 | 0.21 | −0.04 | −0.41 | −0.04 | −0.47 | −0.56 | −2.18 | −1.22 | −0.43 |
| G | 289Y | −0.29 | 0.99 | 6.21 | −0.06 | −0.37 | −0.07 | −0.44 | −0.51 | −1.88 | −1.10 | −0.13 |
| W | 290A | −0.10 | −4.47 | −21.29 | −0.03 | −1.00 | −0.17 | −1.10 | −1.48 | −1.73 | −2.63 | 3.98 |
| W | 290C | −0.15 | −4.29 | −16.91 | −0.04 | −0.72 | −0.09 | −0.79 | −1.06 | −1.22 | −1.84 | 2.33 |
| W | 290D | −0.10 | −0.96 | −19.37 | −0.03 | −1.05 | −0.11 | −1.10 | −1.43 | −1.59 | −3.27 | 2.83 |
| W | 290E | −0.18 | −3.45 | −6.92 | −0.04 | −0.55 | −0.05 | −0.60 | −0.82 | −0.93 | −1.47 | 2.03 |
| W | 290F | 0.45 | 1.17 | 2.83 | 0.25 | 1.39 | 0.93 | 1.15 | 1.18 | 1.24 | 1.76 | 1.52 |
| W | 290G | −0.23 | −1.81 | −4.73 | −0.05 | −0.44 | −0.05 | −0.48 | −0.65 | −0.74 | −1.21 | 0.80 |
| W | 290H | 0.14 | 2.51 | 5.92 | 0.05 | 3.34 | 1.31 | 2.43 | 2.43 | 1.80 | 4.81 | 3.04 |
| W | 290I | −0.17 | 0.22 | 6.01 | −0.04 | −0.69 | −0.13 | −0.67 | −0.89 | −0.98 | −1.64 | 1.68 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| W | 290K | −0.25 | 1.33 | −1.85 | −0.05 | −0.40 | −0.04 | −0.44 | −0.59 | −0.69 | −1.00 | 1.16 |
| W | 290L | −0.27 | 0.62 | −9.08 | −0.07 | −0.42 | −0.08 | −0.45 | −0.58 | −0.67 | −1.08 | 1.04 |
| W | 290M | 0.07 | 6.81 | 34.54 | 0.03 | 5.85 | 2.00 | 3.79 | 3.54 | 4.29 | 8.62 | 1.43 |
| W | 290N | −0.20 | −2.71 | −7.98 | −0.05 | −0.54 | −0.06 | −0.57 | −0.74 | −0.85 | −1.46 | 1.77 |
| W | 290P | −0.29 | −1.43 | −3.58 | −0.07 | −0.33 | −0.01 | −0.37 | −0.49 | −0.58 | −0.87 | 1.23 |
| W | 290Q | −0.24 | −2.07 | −12.17 | −0.06 | −0.59 | −0.05 | −0.55 | −0.70 | −0.75 | −1.14 | 0.57 |
| W | 290R | −0.34 | −0.26 | −2.63 | −0.07 | −0.30 | −0.02 | −0.33 | −0.45 | −0.54 | −0.70 | 0.77 |
| W | 290S | −0.23 | −0.68 | −21.20 | −0.06 | −0.46 | −0.08 | −0.49 | −0.65 | −0.76 | −1.13 | 0.47 |
| W | 290V | −0.28 | 0.32 | −1.65 | −0.07 | −0.40 | −0.04 | −0.44 | −0.58 | −0.73 | −0.91 | 1.00 |
| W | 290Y | 0.67 | 1.04 | 0.06 | 0.58 | 1.36 | 1.17 | 1.23 | 0.90 | 1.15 | 1.40 | 1.19 |
| A | 291C | 0.63 | 1.33 | 33.99 | 0.53 | 1.32 | 1.19 | 1.21 | 1.13 | 1.15 | 1.47 | 1.28 |
| A | 291D | 0.02 | 7.05 | 1115.85 | 0.00 | 4.09 | 0.23 | 4.57 | 5.65 | 5.59 | 13.30 | 0.60 |
| A | 291E | −0.06 | −2.42 | −552.28 | −0.01 | −1.76 | −0.10 | −1.94 | −2.38 | −2.39 | −5.16 | −0.96 |
| A | 291F | 0.05 | 8.27 | −364.91 | 0.02 | 6.08 | 1.90 | 3.93 | 4.46 | 4.36 | 9.83 | 6.01 |
| A | 291G | 0.80 | 0.98 | 29.31 | 0.57 | 1.06 | 0.98 | 1.02 | 1.07 | 0.98 | 1.26 | 1.12 |
| A | 291H | −0.13 | −2.81 | −128.96 | −0.02 | −1.13 | −0.15 | −0.99 | −1.19 | −1.10 | −2.69 | −0.79 |
| A | 291I | 0.09 | 6.00 | −144.51 | 0.03 | 6.71 | 4.91 | 5.05 | 5.20 | 5.02 | 4.56 | 3.05 |
| A | 291K | −0.19 | 0.08 | −80.43 | −0.04 | −0.47 | −0.06 | −0.57 | −0.71 | −0.71 | −1.56 | −0.15 |
| A | 291L | 0.61 | 1.11 | 72.53 | 0.38 | 1.39 | 1.10 | 1.22 | 0.98 | 1.23 | 1.52 | 1.40 |
| A | 291M | 0.20 | 2.79 | 101.25 | 0.09 | 2.69 | 1.48 | 1.88 | 1.57 | 1.96 | 3.67 | 2.43 |
| A | 291N | 0.07 | 5.50 | 180.96 | 0.02 | 4.46 | 1.31 | 2.95 | 3.04 | 3.25 | 7.35 | 4.60 |
| A | 291P | −0.16 | −4.40 | −162.91 | −0.04 | −0.72 | −0.08 | −0.72 | −0.86 | −0.88 | −2.34 | −0.54 |
| A | 291Q | −0.09 | −6.90 | −375.82 | −0.02 | −1.20 | −0.01 | −1.23 | −1.52 | −1.49 | −3.36 | −1.45 |
| A | 291R | −0.11 | 0.55 | −412.57 | −0.02 | −0.85 | −0.04 | −0.94 | −1.18 | −1.20 | −2.91 | −0.95 |
| A | 291S | 0.62 | 1.26 | 16.49 | 0.40 | 1.33 | 1.09 | 1.18 | 1.20 | 1.16 | 1.43 | 1.22 |
| A | 291T | 0.65 | 1.30 | −6.14 | 0.47 | 1.31 | 1.17 | 1.26 | 1.21 | 1.20 | 1.38 | 1.31 |
| A | 291V | 0.30 | 2.12 | 9.82 | 0.14 | 2.45 | 2.21 | 2.10 | 2.06 | 2.13 | 1.62 | 0.93 |
| A | 291W | −0.23 | −0.50 | −94.40 | −0.04 | −0.41 | −0.16 | −0.49 | −0.59 | −0.59 | −1.35 | −0.41 |
| A | 291Y | −0.10 | −2.52 | −477.41 | −0.02 | −2.39 | −0.40 | −1.68 | −1.76 | −1.92 | −4.49 | −2.03 |
| V | 292A | 0.59 | 1.34 | 0.97 | 0.43 | 1.34 | 0.98 | 1.07 | 0.79 | 1.02 | 1.50 | 1.28 |
| V | 292C | 0.75 | 1.01 | 0.01 | 0.57 | 1.04 | 0.83 | 0.91 | 0.82 | 0.88 | 1.12 | 1.04 |
| V | 292D | −0.19 | −2.13 | 5.04 | −0.05 | −0.54 | −0.05 | −0.58 | −0.65 | −0.72 | −1.76 | 0.09 |
| V | 292E | −0.04 | −10.83 | −9.67 | −0.01 | −3.56 | −0.40 | −2.88 | −3.13 | −3.29 | −8.02 | −1.84 |
| V | 292G | −0.13 | −3.21 | −8.42 | −0.03 | −1.79 | −0.30 | −1.26 | −1.40 | −1.40 | −3.36 | −1.94 |
| V | 292H | −0.17 | −2.19 | −8.84 | −0.03 | −1.09 | −0.14 | −0.87 | −0.95 | −0.83 | −2.21 | −1.14 |
| V | 292I | 0.88 | 0.97 | 2.06 | 0.68 | 1.05 | 0.99 | 1.05 | 1.02 | 1.00 | 1.13 | 0.96 |
| V | 292K | −0.18 | 0.00 | 1.56 | −0.04 | −0.63 | −0.07 | −0.66 | −0.75 | −0.79 | −1.75 | −0.70 |
| V | 292L | 0.87 | 0.94 | 3.03 | 0.77 | 1.13 | 1.07 | 1.11 | 0.83 | 1.07 | 1.12 | 1.03 |
| V | 292M | 0.98 | 1.02 | 0.94 | 1.06 | 0.97 | 0.98 | 0.95 | 0.69 | 0.92 | 0.99 | 0.83 |
| V | 292P | −0.50 | −2.17 | 1.67 | −0.13 | −0.22 | −0.04 | −0.30 | −0.30 | −0.95 | −0.57 | −0.17 |
| V | 292Q | −0.07 | −5.29 | −36.46 | −0.02 | −4.30 | −1.49 | −2.92 | −2.99 | −3.06 | −6.66 | −3.85 |
| V | 292R | −0.24 | −0.92 | −8.11 | −0.05 | −0.39 | −0.11 | −0.42 | −0.50 | −0.53 | −1.11 | −0.19 |
| V | 292S | 0.11 | 4.18 | 1.54 | 0.04 | 4.48 | 2.25 | 3.22 | 3.20 | 3.12 | 6.18 | 4.71 |
| V | 292T | 0.52 | 1.51 | 2.53 | 0.29 | 1.43 | 1.05 | 1.22 | 1.18 | 1.16 | 1.69 | 1.50 |
| V | 292W | 0.06 | 8.52 | −22.29 | 0.02 | 7.32 | 3.18 | 5.73 | 5.13 | 5.19 | 10.21 | 6.96 |
| I | 293C | 0.84 | 1.02 | 0.28 | 0.83 | 1.10 | 1.00 | 1.04 | 0.66 | 0.96 | 1.14 | 1.09 |
| I | 293D | 0.11 | 6.59 | 7.25 | 0.03 | 2.48 | 0.46 | 1.61 | 1.58 | 1.65 | 3.72 | 1.72 |
| I | 293E | 0.36 | 1.66 | 4.50 | 0.15 | 1.51 | 0.68 | 0.98 | 0.90 | 0.93 | 2.01 | 1.19 |
| I | 293F | 0.08 | 8.06 | −20.19 | 0.02 | 1.98 | 0.15 | 1.56 | 1.75 | 1.67 | 4.30 | 1.10 |
| I | 293G | 0.12 | 4.50 | −1.61 | 0.03 | 3.05 | 0.86 | 1.86 | 1.80 | 1.93 | 4.41 | 3.02 |
| I | 293H | 0.00 | 128.10 | −47.78 | 0.00 | 46.38 | 5.28 | 31.45 | 33.75 | 27.95 | 85.01 | 31.17 |
| I | 293N | 0.39 | 1.47 | −0.78 | 0.18 | 1.35 | 0.71 | 0.98 | 0.86 | 0.93 | 1.65 | 1.17 |
| I | 293P | −0.02 | −31.48 | −15.34 | 0.00 | −4.80 | −0.27 | −5.23 | −6.46 | −7.01 | −16.23 | −7.35 |
| I | 293Q | 0.13 | 4.02 | 12.11 | 0.03 | 1.82 | 0.30 | 1.24 | 1.35 | 1.20 | 3.49 | 1.78 |
| I | 293R | −0.01 | −33.47 | 6.98 | 0.00 | −6.92 | −0.27 | −7.58 | −9.29 | −9.88 | −19.19 | −2.92 |
| I | 293S | 0.10 | 4.92 | 9.87 | 0.04 | 4.95 | 2.49 | 3.55 | 3.35 | 3.26 | 5.73 | 4.67 |
| I | 293V | 0.86 | 1.17 | 0.86 | 0.86 | 1.13 | 1.13 | 1.17 | 1.07 | 1.11 | 1.11 | 0.96 |
| I | 293W | −0.07 | 2.97 | −30.71 | −0.01 | −1.55 | −0.29 | −1.68 | −2.01 | −2.16 | −4.68 | −1.28 |
| I | 293Y | −0.07 | 1.67 | −42.00 | −0.01 | −1.43 | −0.18 | −1.70 | −1.98 | −2.07 | −4.15 | −1.15 |
| A | 294C | 0.78 | 1.14 | −1.25 | 0.64 | 1.08 | 0.99 | 0.98 | 0.74 | 0.96 | 1.16 | 1.14 |
| A | 294D | −0.14 | −4.87 | −8.02 | −0.03 | −1.26 | −0.01 | −1.02 | −1.10 | −1.25 | −2.85 | −0.89 |
| A | 294E | −0.03 | −15.38 | −49.08 | −0.01 | −10.47 | −3.66 | −7.57 | −6.98 | −8.39 | −16.83 | −11.03 |
| A | 294F | −0.29 | −2.25 | 1.13 | −0.06 | −0.33 | −0.07 | −0.36 | −0.44 | −0.47 | −0.96 | −0.29 |
| A | 294G | 0.65 | 1.40 | −2.11 | 0.51 | 1.47 | 1.35 | 1.33 | 1.18 | 1.34 | 1.50 | 1.46 |
| A | 294H | −0.20 | −0.76 | −8.45 | −0.04 | −0.58 | −0.07 | −0.56 | −0.65 | −0.67 | −1.74 | −0.59 |
| A | 294I | −0.25 | −0.54 | −10.99 | −0.05 | −0.47 | −0.08 | −0.45 | −0.53 | −0.49 | −1.39 | −0.34 |
| A | 294K | −0.18 | −1.05 | −1.61 | −0.03 | −0.53 | −0.06 | −0.60 | −0.71 | −0.81 | −1.75 | −0.44 |
| A | 294L | −0.11 | −0.69 | 5.93 | −0.02 | −1.47 | −0.27 | −1.28 | −1.35 | −1.56 | −3.40 | −0.91 |
| A | 294M | 0.06 | 13.51 | −16.71 | 0.01 | 3.32 | 0.49 | 2.54 | 2.54 | 3.24 | 5.81 | 2.92 |
| A | 294N | 0.10 | 6.44 | −10.55 | 0.03 | 4.88 | 2.06 | 3.26 | 2.37 | 3.48 | 6.09 | 5.15 |
| A | 294P | −0.15 | −2.75 | 8.92 | −0.03 | −0.64 | −0.14 | −0.74 | −0.85 | −0.96 | −2.52 | −0.05 |
| A | 294Q | −0.06 | −8.00 | 16.94 | −0.02 | −3.70 | −0.82 | −2.51 | −2.34 | −2.85 | −6.38 | −2.83 |
| A | 294R | −0.01 | −112.70 | 190.20 | 0.00 | −40.63 | −6.62 | −29.25 | −28.68 | −33.94 | −87.83 | −22.48 |
| A | 294S | 0.61 | 1.37 | 1.57 | 0.45 | 1.50 | 1.24 | 1.26 | 0.96 | 1.22 | 1.56 | 1.57 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| A | 294T | 0.63 | 1.36 | −0.98 | 0.40 | 1.41 | 1.19 | 1.23 | 0.88 | 1.19 | 1.56 | 1.38 |
| A | 294V | 0.39 | 1.65 | 0.09 | 0.18 | 1.67 | 1.15 | 1.29 | 0.94 | 1.29 | 1.96 | 2.08 |
| A | 294W | −0.19 | −0.60 | 9.96 | −0.03 | −0.51 | −0.04 | −0.58 | −0.68 | −0.78 | −1.52 | −0.58 |
| A | 294Y | −0.16 | −1.41 | 4.21 | −0.03 | −0.60 | −0.08 | −0.71 | −0.80 | −0.92 | −1.82 | −0.99 |
| S | 295A | 0.67 | 1.12 | 1.20 | 0.60 | 1.23 | 1.07 | 1.07 | 0.81 | 1.04 | 1.29 | 1.16 |
| S | 295C | 0.54 | 1.14 | 5.59 | 0.38 | 1.31 | 1.01 | 1.13 | 1.09 | 1.14 | 1.60 | 1.42 |
| S | 295D | −0.17 | −4.03 | 1.01 | −0.05 | −0.64 | −0.07 | −0.68 | −0.91 | −1.01 | −1.87 | 1.46 |
| S | 295E | −0.15 | −2.04 | −9.16 | −0.03 | −0.67 | −0.07 | −0.74 | −1.00 | −1.14 | −1.83 | 2.27 |
| S | 295F | −0.25 | −1.03 | −1.32 | −0.05 | −0.41 | −0.04 | −0.45 | −0.60 | −0.69 | −1.09 | 1.05 |
| S | 295G | 0.68 | 1.09 | 3.34 | 0.52 | 1.26 | 1.14 | 1.20 | 1.30 | 1.19 | 1.47 | 1.50 |
| S | 295H | −0.30 | 0.08 | 1.02 | −0.06 | −0.33 | −0.04 | −0.37 | −0.52 | −0.61 | −0.88 | 0.64 |
| S | 295I | −0.24 | −0.28 | −7.28 | −0.06 | −0.45 | −0.08 | −0.48 | −0.63 | −0.75 | −0.91 | 1.20 |
| S | 295M | −0.08 | −9.31 | −1.88 | −0.02 | −1.65 | −0.16 | −1.59 | −2.02 | −2.42 | −4.19 | 2.65 |
| S | 295N | −0.06 | −13.31 | −8.04 | −0.02 | −2.27 | −0.12 | −2.16 | −2.72 | −3.12 | −5.50 | 4.38 |
| S | 295P | 0.02 | 23.57 | −105.33 | 0.01 | 22.12 | 8.35 | 16.94 | 17.42 | 17.91 | 37.68 | 18.78 |
| S | 295Q | −0.24 | −1.35 | −4.32 | −0.05 | −0.41 | −0.10 | −0.45 | −0.62 | −0.68 | −1.05 | 1.19 |
| S | 295R | −0.30 | 0.02 | 0.88 | −0.07 | −0.33 | −0.03 | −0.37 | −0.49 | −0.56 | −1.17 | 0.84 |
| S | 295T | 0.41 | 1.59 | −6.14 | 0.24 | 1.83 | 1.45 | 1.66 | 1.68 | 1.58 | 2.12 | 2.12 |
| S | 295V | −0.21 | −0.90 | 1.62 | −0.05 | −0.95 | −0.17 | −0.76 | −0.90 | −0.94 | −1.71 | 0.94 |
| S | 295W | −0.41 | 0.53 | 6.01 | −0.08 | −0.24 | −0.02 | −0.27 | −0.36 | −0.41 | −0.70 | 0.78 |
| S | 295Y | −0.28 | 0.97 | 0.43 | −0.06 | −0.35 | −0.02 | −0.41 | −0.55 | −0.66 | −0.90 | 0.54 |
| R | 296A | 0.26 | 2.35 | 6.09 | 0.09 | 1.25 | 0.29 | 0.87 | 0.69 | 0.84 | 1.87 | 1.42 |
| R | 296C | 0.05 | 16.09 | 27.30 | 0.02 | 4.45 | 0.71 | 3.41 | 3.13 | 3.17 | 7.88 | 3.58 |
| R | 296D | 0.01 | 139.99 | 158.79 | 0.00 | 23.58 | 1.01 | 21.44 | 24.50 | 22.83 | 55.96 | 21.03 |
| R | 296E | −0.18 | −4.82 | −5.16 | −0.05 | −0.94 | −0.08 | −0.80 | −0.89 | −0.93 | −1.99 | −0.75 |
| R | 296F | 0.20 | 1.85 | 7.90 | 0.06 | 1.48 | 0.27 | 0.99 | 0.96 | 0.93 | 2.39 | 1.26 |
| R | 296G | 0.12 | 3.07 | 18.81 | 0.03 | 2.36 | 0.51 | 1.73 | 1.67 | 1.65 | 4.68 | 1.89 |
| R | 296H | 0.13 | 2.23 | 9.57 | 0.04 | 2.72 | 0.90 | 1.88 | 1.84 | 1.95 | 4.07 | 3.54 |
| R | 296K | 0.24 | 1.24 | 6.85 | 0.09 | 1.93 | 0.95 | 1.55 | 1.36 | 1.42 | 2.66 | 2.16 |
| R | 296M | 0.21 | 1.81 | 7.42 | 0.09 | 2.06 | 0.79 | 1.47 | 1.07 | 1.43 | 2.89 | 2.30 |
| R | 296N | 0.00 | −230.57 | −1337.93 | 0.00 | −185.67 | −47.22 | −146.38 | −140.31 | −146.84 | −299.01 | −211.36 |
| R | 296P | 0.01 | 35.41 | 79.25 | 0.00 | 9.51 | 0.36 | 9.97 | 11.91 | 11.50 | 25.03 | 7.62 |
| R | 296Q | 0.04 | 8.41 | 36.52 | 0.01 | 7.51 | 2.04 | 5.32 | 5.07 | 5.12 | 11.58 | 8.78 |
| R | 296S | 0.03 | 19.25 | 76.36 | 0.01 | 10.36 | 2.77 | 8.23 | 7.64 | 7.42 | 17.46 | 14.50 |
| R | 296T | −0.04 | −5.69 | −38.34 | −0.01 | −6.56 | −1.36 | −4.94 | −4.92 | −4.58 | −10.82 | −5.55 |
| R | 296V | −0.08 | −4.64 | −21.25 | −0.02 | −2.89 | −0.54 | −2.25 | −2.29 | −2.04 | −4.91 | −3.66 |
| R | 296W | −0.12 | −1.38 | −20.81 | −0.03 | −1.15 | −0.14 | −1.17 | −1.25 | −1.23 | −2.76 | −0.85 |
| R | 296Y | −0.01 | −18.67 | −212.79 | 0.00 | −18.04 | −2.43 | −14.29 | −13.97 | −16.61 | −33.21 | −12.23 |
| S | 297A | 0.84 | 0.99 | −2.24 | 0.91 | 1.10 | 1.03 | 1.02 | 0.81 | 1.00 | 1.04 | 0.89 |
| S | 297C | 1.06 | 0.83 | −0.40 | 0.96 | 0.83 | 0.76 | 0.79 | 0.75 | 0.77 | 0.83 | 0.74 |
| S | 297D | 0.83 | 1.11 | 0.37 | 0.73 | 1.07 | 1.05 | 1.09 | 1.11 | 1.10 | 1.15 | 1.20 |
| S | 297E | 0.82 | 1.00 | 7.46 | 0.69 | 1.03 | 0.99 | 1.03 | 1.06 | 0.98 | 1.05 | 0.94 |
| S | 297F | 0.69 | 1.38 | 1.16 | 0.59 | 1.31 | 1.18 | 1.19 | 1.27 | 1.24 | 1.31 | 1.13 |
| S | 297G | 0.75 | 1.12 | −7.75 | 0.55 | 1.13 | 1.01 | 1.02 | 1.05 | 1.08 | 1.35 | 1.14 |
| S | 297H | 0.92 | 0.97 | −6.23 | 0.78 | 1.04 | 1.03 | 1.09 | 1.10 | 1.11 | 1.02 | 1.11 |
| S | 297I | 0.74 | 1.13 | 13.99 | 0.55 | 1.19 | 1.14 | 1.14 | 1.09 | 1.18 | 1.26 | 1.81 |
| S | 297K | 1.22 | 0.79 | −9.35 | 1.32 | 0.89 | 0.97 | 0.99 | 0.89 | 1.07 | 0.91 | 0.81 |
| S | 297L | 0.83 | 0.94 | −15.89 | 0.69 | 1.11 | 1.05 | 1.09 | 0.78 | 1.10 | 1.19 | 1.05 |
| S | 297M | 0.79 | 1.13 | 16.76 | 0.81 | 1.21 | 1.23 | 1.16 | 0.94 | 1.12 | 1.14 | 0.98 |
| S | 297N | 0.85 | 0.97 | −4.60 | 0.86 | 1.04 | 1.04 | 1.06 | 1.03 | 1.04 | 1.03 | 1.77 |
| S | 297P | 0.69 | 1.16 | 0.66 | 0.48 | 1.16 | 1.08 | 1.14 | 1.15 | 1.12 | 1.19 | 1.14 |
| S | 297Q | 0.80 | 1.15 | −7.25 | 0.69 | 1.13 | 1.06 | 1.09 | 1.15 | 1.08 | 1.11 | 1.03 |
| S | 297R | 0.78 | 1.20 | 8.40 | 0.70 | 1.10 | 1.10 | 1.10 | 1.17 | 1.10 | 1.15 | 0.91 |
| S | 297T | 0.77 | 1.26 | −2.30 | 0.63 | 1.17 | 1.10 | 1.13 | 1.13 | 1.12 | 1.05 | 1.16 |
| S | 297V | 0.86 | 1.03 | 2.94 | 0.71 | 1.07 | 1.04 | 1.08 | 1.04 | 1.06 | 1.05 | 0.97 |
| S | 297W | 0.90 | 0.98 | −15.64 | 0.78 | 1.03 | 0.92 | 1.08 | 0.97 | 1.02 | 1.04 | 0.97 |
| S | 297Y | 0.96 | 0.88 | −15.05 | 0.86 | 1.03 | 0.92 | 0.99 | 0.74 | 0.99 | 1.00 | 0.91 |
| G | 298A | 1.19 | 0.85 | 0.99 | 1.45 | 0.84 | 0.95 | 0.88 | 0.58 | 0.83 | 0.86 | 0.60 |
| G | 298C | 0.73 | 1.11 | 2.17 | 0.61 | 1.20 | 1.15 | 1.17 | 0.96 | 1.13 | 1.28 | 1.63 |
| G | 298D | 0.87 | 1.16 | −2.61 | 0.86 | 1.08 | 1.13 | 1.14 | 1.02 | 1.13 | 1.10 | 1.08 |
| G | 298E | 0.89 | 1.12 | 0.23 | 0.82 | 1.08 | 1.12 | 1.15 | 1.04 | 1.11 | 1.10 | 1.18 |
| G | 298F | 0.64 | 1.38 | −3.41 | 0.51 | 1.31 | 1.29 | 1.33 | 1.21 | 1.28 | 1.39 | 1.46 |
| G | 298H | 0.77 | 1.16 | −0.89 | 0.61 | 1.21 | 1.24 | 1.29 | 1.15 | 1.20 | 1.32 | 1.23 |
| G | 298I | 0.63 | 1.25 | 0.80 | 0.42 | 1.35 | 1.26 | 1.30 | 1.03 | 1.21 | 1.33 | 1.54 |
| G | 298K | 0.88 | 0.99 | −1.97 | 0.74 | 1.06 | 1.11 | 1.11 | 0.86 | 1.06 | 1.19 | 1.14 |
| G | 298L | 0.89 | 1.04 | 0.16 | 0.80 | 1.10 | 1.11 | 1.18 | 0.88 | 1.15 | 1.22 | 1.04 |
| G | 298M | 0.91 | 1.03 | 1.60 | 1.20 | 1.18 | 1.31 | 1.17 | 0.61 | 1.12 | 1.14 | 1.15 |
| G | 298N | 0.91 | 0.99 | −0.78 | 0.98 | 1.13 | 1.14 | 1.09 | 0.70 | 1.02 | 1.12 | 1.17 |
| G | 298P | 0.70 | 0.98 | −1.90 | 0.49 | 1.18 | 0.98 | 1.01 | 0.71 | 0.97 | 1.26 | 1.33 |
| G | 298Q | 0.88 | 0.96 | 1.02 | 0.81 | 1.10 | 1.16 | 1.11 | 0.79 | 1.05 | 1.15 | 1.12 |
| G | 298R | 0.83 | 1.07 | 0.80 | 0.82 | 1.22 | 1.27 | 1.21 | 0.85 | 1.10 | 1.24 | 1.16 |
| G | 298S | 0.91 | 0.97 | 2.64 | 0.82 | 1.12 | 1.14 | 1.13 | 0.85 | 1.06 | 1.13 | 1.06 |
| G | 298V | 0.71 | 1.09 | −0.36 | 0.58 | 1.32 | 1.24 | 1.24 | 0.81 | 1.15 | 1.36 | 1.38 |
| G | 298W | 0.90 | 0.97 | −1.71 | 0.80 | 1.09 | 1.07 | 1.12 | 0.77 | 1.10 | 1.13 | 0.65 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| G | 298Y | −0.06 | 4.13 | −48.89 | −0.01 | −1.60 | −0.14 | −1.80 | −2.14 | −2.77 | −4.65 | 0.33 |
| S | 299A | 0.97 | 1.04 | 0.27 | 1.08 | 1.01 | 0.98 | 0.91 | 0.69 | 0.87 | 0.98 | 0.92 |
| S | 299C | 0.72 | 1.10 | 1.33 | 0.59 | 1.14 | 0.95 | 1.00 | 0.93 | 0.93 | 1.37 | 1.12 |
| S | 299D | 0.27 | 1.79 | −0.40 | 0.11 | 1.76 | 0.88 | 1.26 | 1.24 | 1.28 | 2.60 | 1.76 |
| S | 299E | 0.23 | 1.98 | 6.56 | 0.08 | 2.08 | 0.93 | 1.36 | 1.40 | 1.40 | 2.85 | 1.88 |
| S | 299F | 0.12 | 4.29 | 0.40 | 0.04 | 3.24 | 0.99 | 2.10 | 1.96 | 1.93 | 4.71 | 3.85 |
| S | 299G | 0.87 | 1.10 | 0.17 | 0.82 | 1.09 | 1.24 | 1.22 | 1.16 | 1.19 | 1.14 | 1.13 |
| S | 299H | 0.11 | 3.26 | 17.26 | 0.03 | 3.34 | 1.01 | 2.28 | 1.82 | 1.68 | 5.18 | 2.52 |
| S | 299I | 0.57 | 1.46 | 1.66 | 0.36 | 1.33 | 0.92 | 1.16 | 1.12 | 1.07 | 1.44 | 2.38 |
| S | 299K | −0.04 | −9.82 | −19.65 | −0.01 | −5.42 | −0.74 | −3.84 | −4.14 | −4.11 | −10.23 | −4.27 |
| S | 299L | 0.35 | 1.46 | 14.12 | 0.16 | 1.72 | 0.88 | 1.28 | 0.99 | 1.20 | 2.25 | 1.38 |
| S | 299M | 0.43 | 0.99 | 1.16 | 0.21 | 1.26 | 0.63 | 0.86 | 0.61 | 0.75 | 1.67 | 1.23 |
| S | 299N | 0.66 | 1.02 | 1.09 | 0.48 | 1.15 | 0.90 | 0.96 | 0.90 | 0.93 | 1.23 | 1.03 |
| S | 299P | 0.96 | 1.00 | −1.03 | 1.06 | 1.01 | 1.05 | 1.00 | 1.00 | 0.91 | 1.02 | 0.97 |
| S | 299Q | 0.33 | 1.66 | −5.08 | 0.17 | 1.75 | 1.23 | 1.51 | 1.51 | 1.46 | 2.28 | 1.93 |
| S | 299V | 0.73 | 1.16 | 3.85 | 0.60 | 1.20 | 1.00 | 1.10 | 1.07 | 1.06 | 1.25 | 1.15 |
| S | 299W | −0.06 | −6.95 | −37.09 | −0.01 | −5.32 | −1.11 | −3.33 | −3.23 | −3.14 | −8.43 | −3.86 |
| S | 299Y | −0.02 | −7.81 | −265.57 | 0.00 | −12.64 | −1.46 | −9.52 | −9.02 | −9.63 | −27.16 | −10.40 |
| T | 300A | 0.42 | 1.16 | −1.07 | 0.24 | 1.43 | 0.91 | 1.07 | 0.80 | 1.10 | 1.79 | 0.97 |
| T | 300C | 0.49 | 1.39 | −2.68 | 0.35 | 1.48 | 1.18 | 1.26 | 1.07 | 1.24 | 1.66 | 1.52 |
| T | 300E | −0.11 | −3.87 | −4.62 | −0.04 | −3.29 | −1.21 | −2.32 | −2.57 | −2.58 | −4.90 | −1.31 |
| T | 300F | 0.41 | 1.39 | −2.78 | 0.21 | 1.64 | 1.18 | 1.38 | 1.30 | 1.38 | 2.04 | 1.47 |
| T | 300G | −0.22 | −1.09 | 5.88 | −0.05 | −0.90 | −0.16 | −0.71 | −0.86 | −0.92 | −1.73 | 0.70 |
| T | 300H | 0.59 | 1.14 | −5.63 | 0.37 | 1.33 | 1.18 | 1.24 | 1.16 | 1.25 | 1.51 | 1.70 |
| T | 300I | 0.39 | 1.54 | −2.90 | 0.23 | 1.92 | 1.45 | 1.63 | 1.35 | 1.58 | 2.13 | 2.28 |
| T | 300K | 0.56 | 1.07 | −3.95 | 0.41 | 1.51 | 1.28 | 1.36 | 1.21 | 1.42 | 1.57 | 1.77 |
| T | 300L | 0.36 | 1.42 | −6.98 | 0.21 | 2.09 | 1.54 | 1.70 | 1.30 | 1.69 | 2.21 | 2.03 |
| T | 300M | 0.88 | 0.89 | −1.16 | 0.84 | 1.02 | 0.85 | 0.83 | 0.45 | 0.77 | 1.01 | 1.01 |
| T | 300N | 0.41 | 1.37 | −4.01 | 0.24 | 1.62 | 1.05 | 1.16 | 0.82 | 1.22 | 1.97 | 1.51 |
| T | 300P | −0.13 | −1.81 | 2.03 | −0.04 | −2.01 | −0.45 | −1.44 | −1.36 | −1.67 | −3.17 | 0.43 |
| T | 300Q | 0.41 | 1.31 | −1.24 | 0.22 | 1.67 | 1.12 | 1.28 | 1.08 | 1.29 | 2.06 | 1.81 |
| T | 300R | 0.58 | 1.11 | 0.20 | 0.38 | 1.32 | 1.06 | 1.09 | 0.86 | 1.10 | 1.45 | 1.51 |
| T | 300S | 0.41 | 1.63 | −0.69 | 0.25 | 1.95 | 1.46 | 1.57 | 1.31 | 1.57 | 2.18 | 2.04 |
| T | 300V | 0.74 | 0.96 | −2.58 | 0.54 | 1.24 | 1.05 | 1.06 | 0.76 | 1.02 | 1.24 | 1.49 |
| T | 300W | 0.05 | 7.91 | −54.50 | 0.02 | 10.79 | 5.39 | 7.37 | 5.56 | 7.98 | 12.34 | 8.15 |
| T | 300Y | 0.20 | 1.91 | −3.07 | 0.08 | 2.78 | 1.46 | 1.91 | 1.34 | 2.06 | 3.32 | 2.18 |
| P | 301C | 0.61 | 1.28 | −0.52 | 0.49 | 1.25 | 1.01 | 1.05 | 0.93 | 1.04 | 1.25 | 1.19 |
| P | 301D | 0.07 | 5.45 | −12.60 | 0.02 | 4.07 | 1.29 | 2.38 | 2.72 | 3.32 | 4.47 | 11.46 |
| P | 301F | 0.11 | 3.14 | 12.15 | 0.03 | 2.31 | 0.62 | 1.43 | 1.54 | 2.07 | 2.68 | 3.91 |
| P | 301H | 0.23 | 2.53 | 8.26 | 0.09 | 2.15 | 1.21 | 1.67 | 1.28 | 1.82 | 2.54 | 2.28 |
| P | 301I | 0.50 | 1.37 | 2.68 | 0.31 | 1.38 | 1.05 | 1.09 | 0.80 | 1.15 | 1.71 | 1.53 |
| P | 301K | 0.67 | 1.15 | 2.44 | 0.48 | 1.16 | 1.06 | 1.16 | 0.62 | 1.23 | 1.37 | 1.18 |
| P | 301L | 0.46 | 1.11 | −1.56 | 0.29 | 1.53 | 1.20 | 1.19 | 0.63 | 1.29 | 1.69 | 1.48 |
| P | 301M | 0.46 | 1.39 | 4.70 | 0.31 | 1.41 | 1.05 | 1.08 | 0.86 | 1.14 | 1.34 | 1.55 |
| P | 301N | 0.71 | 1.09 | 2.61 | 0.56 | 1.09 | 0.95 | 0.94 | 0.91 | 0.95 | 1.07 | 1.14 |
| P | 301Q | 0.27 | 2.03 | 3.50 | 0.12 | 1.92 | 1.13 | 1.42 | 1.57 | 1.57 | 2.30 | 1.84 |
| P | 301R | 0.06 | 5.14 | 55.79 | 0.02 | 3.71 | 0.96 | 2.28 | 2.63 | 3.69 | 4.13 | 6.12 |
| P | 301T | 0.58 | 1.34 | 2.20 | 0.42 | 1.37 | 1.13 | 1.17 | 1.04 | 1.20 | 1.37 | 1.32 |
| P | 301V | 0.45 | 1.56 | 5.33 | 0.27 | 1.69 | 1.31 | 1.39 | 1.08 | 1.40 | 1.75 | 1.44 |
| P | 301W | −0.14 | −1.91 | −24.68 | −0.03 | −1.26 | −0.16 | −0.71 | −0.89 | −1.35 | −1.85 | −1.97 |
| P | 301Y | −0.08 | −0.72 | −30.43 | −0.02 | −2.16 | −0.37 | −1.41 | −1.43 | −2.39 | −2.09 | −1.45 |
| L | 302A | 0.58 | 0.98 | 1.81 | 0.36 | 1.06 | 0.35 | 0.74 | 0.47 | 0.66 | 1.39 | 1.14 |
| L | 302C | 0.50 | 1.15 | 1.53 | 0.28 | 1.16 | 0.43 | 0.92 | 0.75 | 0.76 | 1.49 | 1.35 |
| L | 302D | −0.13 | −2.82 | −7.77 | −0.03 | −0.93 | −0.07 | −0.57 | −0.72 | −1.39 | −0.74 | −1.03 |
| L | 302E | 0.14 | 1.92 | 5.17 | 0.04 | 1.80 | 0.20 | 1.06 | 1.05 | 1.47 | 2.66 | 2.05 |
| L | 302F | 0.05 | 5.60 | 18.21 | 0.02 | 5.71 | 0.87 | 3.27 | 2.97 | 4.39 | 5.97 | 6.14 |
| L | 302G | 0.13 | 1.30 | 6.35 | 0.03 | 1.85 | 0.12 | 0.79 | 0.76 | 1.44 | 2.05 | 2.05 |
| L | 302H | −0.01 | −18.30 | −49.79 | 0.00 | −17.31 | −3.10 | −9.66 | −9.75 | −12.19 | −17.93 | −28.34 |
| L | 302I | 0.93 | 0.92 | 0.71 | 0.75 | 0.86 | 0.52 | 0.85 | 0.76 | 0.77 | 0.91 | 0.89 |
| L | 302K | 0.11 | −2.26 | 7.62 | 0.02 | 0.86 | 0.09 | 0.61 | 0.80 | 1.76 | 0.09 | 2.33 |
| L | 302M | 0.56 | 1.40 | 2.07 | 0.44 | 1.33 | 0.73 | 1.13 | 0.64 | 0.93 | 1.44 | 1.21 |
| L | 302N | 0.23 | 2.15 | 3.51 | 0.12 | 2.42 | 1.04 | 1.85 | 1.36 | 2.00 | 2.71 | 2.30 |
| L | 302P | −0.13 | −2.73 | −6.84 | −0.03 | −0.73 | −0.12 | −0.47 | −0.64 | −1.31 | 0.22 | −0.82 |
| L | 302Q | 0.00 | −235.94 | −560.99 | 0.00 | −134.28 | −12.60 | −83.33 | −88.38 | −142.42 | −165.92 | −137.23 |
| L | 302R | 0.47 | 0.09 | 2.36 | 0.10 | 0.20 | 0.01 | 0.13 | 0.18 | 0.35 | 0.02 | 0.17 |
| L | 302S | 0.23 | 1.34 | 2.62 | 0.08 | 1.74 | 0.35 | 1.11 | 0.92 | 1.03 | 2.07 | 2.25 |
| L | 302T | 0.53 | 1.08 | 0.69 | 0.25 | 1.08 | 0.41 | 0.89 | 0.77 | 0.75 | 1.28 | 1.48 |
| L | 302V | 0.72 | 0.94 | 0.60 | 0.43 | 0.92 | 0.42 | 0.82 | 0.68 | 0.71 | 1.27 | 1.10 |
| L | 302W | −0.13 | 0.38 | −8.15 | −0.03 | −0.79 | −0.06 | −0.53 | −2.79 | −1.48 | 0.11 | −1.02 |
| L | 302Y | −0.03 | −8.36 | −19.59 | −0.01 | −12.58 | −3.20 | −7.22 | −14.20 | −10.25 | −12.14 | −17.03 |
| F | 303A | −0.12 | −6.55 | −243.62 | −0.04 | −1.05 | −0.02 | −0.98 | −1.11 | −1.23 | −2.44 | 1.75 |
| F | 303C | −0.02 | −43.47 | 443.50 | 0.00 | −8.82 | −0.43 | −8.74 | −10.33 | −10.20 | −22.14 | 6.99 |
| F | 303D | −0.19 | −1.46 | −62.67 | −0.05 | −0.48 | 0.01 | −0.52 | −0.61 | −0.66 | −1.34 | 0.76 |
| F | 303E | −0.14 | −3.47 | −54.76 | −0.03 | −0.69 | −0.07 | −0.73 | −0.86 | −0.93 | −2.03 | 1.25 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| F | 303G | −0.14 | −0.63 | −138.91 | −0.03 | −0.82 | −0.14 | −0.83 | −0.95 | −1.06 | −2.22 | 1.23 |
| F | 303H | −0.11 | −4.63 | −122.18 | −0.02 | −1.48 | −0.17 | −1.19 | −1.36 | −1.35 | −4.01 | 0.36 |
| F | 303I | −0.20 | −0.97 | −137.38 | −0.05 | −0.77 | −0.10 | −0.65 | −0.72 | −0.70 | −1.81 | 0.79 |
| F | 303K | −0.13 | 0.16 | 14.49 | −0.03 | −1.04 | −0.24 | −0.82 | −0.93 | −1.00 | −2.55 | 0.99 |
| F | 303L | 0.27 | 1.58 | 129.56 | 0.14 | 2.20 | 1.08 | 1.60 | 1.22 | 1.31 | 2.62 | 1.85 |
| F | 303M | 0.78 | 1.09 | 20.63 | 0.82 | 1.16 | 0.97 | 0.97 | 0.75 | 0.97 | 1.23 | 1.12 |
| F | 303N | −0.10 | −6.76 | −172.61 | −0.03 | −1.23 | −0.10 | −1.15 | −1.31 | −1.44 | −2.91 | 0.42 |
| F | 303P | −0.10 | −5.57 | −242.66 | −0.02 | −0.98 | −0.06 | −1.03 | −1.20 | −1.32 | −2.88 | 0.36 |
| F | 303Q | −0.12 | −6.39 | −239.77 | −0.03 | −1.15 | −0.03 | −0.98 | −1.14 | −1.18 | −3.19 | 0.25 |
| F | 303R | −0.17 | −0.65 | −116.64 | −0.04 | −0.57 | −0.03 | −0.62 | −0.72 | −0.79 | −1.76 | 1.21 |
| F | 303S | −0.18 | −1.96 | −177.12 | −0.03 | −0.54 | −0.05 | −0.57 | −0.66 | −0.69 | −1.79 | 0.58 |
| F | 303T | −0.25 | 0.06 | −53.58 | −0.05 | −0.40 | −0.05 | −0.43 | −0.49 | −0.52 | −1.17 | 0.87 |
| F | 303V | −0.17 | −1.38 | −41.69 | −0.03 | −0.63 | −0.05 | −0.63 | −0.73 | −0.75 | −1.91 | 1.19 |
| F | 303W | 0.18 | 3.36 | 119.74 | 0.09 | 3.47 | 2.07 | 2.50 | 2.39 | 2.43 | 4.63 | 3.09 |
| F | 303Y | 0.31 | 1.64 | −3.88 | 0.18 | 2.13 | 1.31 | 1.54 | 1.28 | 1.45 | 2.58 | 2.08 |
| F | 304C | 0.12 | 4.60 | 36.82 | 0.03 | 1.98 | 0.21 | 1.38 | 1.63 | 1.43 | 3.86 | 2.01 |
| F | 304D | 0.03 | 3.16 | 59.58 | 0.01 | 3.42 | 0.19 | 4.03 | 5.02 | 5.31 | 11.42 | 1.47 |
| F | 304E | 0.05 | 1.37 | 50.43 | 0.01 | 2.16 | 0.29 | 2.42 | 3.03 | 3.05 | 6.42 | 0.08 |
| F | 304G | 0.06 | 1.30 | 43.27 | 0.01 | 1.48 | 0.22 | 1.57 | 2.01 | 1.98 | 4.28 | 1.64 |
| F | 304H | 0.00 | −108.84 | −1279.53 | 0.00 | −62.39 | −7.62 | −44.87 | −53.77 | −38.91 | −120.87 | −53.92 |
| F | 304I | 0.01 | 27.38 | 345.89 | 0.00 | 11.47 | 0.81 | 9.31 | 11.35 | 9.31 | 24.32 | 10.27 |
| F | 304K | −0.01 | −123.01 | −742.72 | 0.00 | −55.55 | −3.42 | −67.05 | −82.54 | −72.60 | −192.90 | −73.28 |
| F | 304L | 0.81 | 1.03 | 7.50 | 0.66 | 1.11 | 0.90 | 0.96 | 0.78 | 0.21 | 1.19 | 1.14 |
| F | 304M | 0.96 | 1.07 | 0.53 | 0.92 | 0.94 | 0.68 | 0.79 | 0.72 | 0.60 | 0.95 | 0.99 |
| F | 304N | 0.07 | 7.78 | 25.98 | 0.02 | 1.51 | 0.16 | 1.61 | 1.99 | 2.00 | 4.12 | 2.17 |
| F | 304Q | −0.10 | −2.50 | −10.95 | −0.02 | −1.02 | −0.03 | −1.12 | −1.40 | −1.49 | −2.61 | −0.58 |
| F | 304R | −0.04 | 2.52 | −5.80 | −0.01 | −2.85 | −0.36 | −3.28 | −4.12 | −3.19 | −8.60 | −3.81 |
| F | 304V | −0.01 | 197.61 | 1847.33 | 0.00 | 152.57 | 14.59 | 101.49 | 119.54 | 89.55 | 256.45 | 96.38 |
| F | 304W | −0.04 | −9.23 | −18.90 | −0.01 | −4.52 | −0.17 | −3.37 | −3.81 | −3.13 | −9.04 | −2.77 |
| F | 304Y | 0.82 | 1.14 | 5.76 | 0.73 | 1.21 | 1.26 | 1.12 | 0.85 | 1.12 | 1.24 | 1.17 |
| S | 305A | 0.19 | 5.81 | 1.24 | 0.18 | 4.65 | 5.28 | 1.96 | −2.92 | −12.79 | 4.84 | 1.86 |
| S | 305C | 0.01 | 81.31 | −132.57 | 0.00 | 25.52 | 8.78 | 17.57 | 18.15 | 25.30 | 42.12 | 26.82 |
| S | 305E | 0.00 | −918.04 | −1310.77 | 0.00 | −274.44 | −45.92 | −213.05 | −244.37 | −251.45 | −537.75 | −296.85 |
| S | 305F | −0.14 | 3.10 | 11.22 | −0.03 | −0.67 | −0.11 | −0.78 | −0.96 | −1.24 | −2.10 | −0.03 |
| S | 305G | 0.30 | 1.56 | −5.29 | 0.14 | 2.11 | 1.24 | 1.57 | 1.48 | 1.42 | 2.66 | 2.12 |
| S | 305H | −0.09 | 2.43 | −20.18 | −0.02 | −1.37 | −0.15 | −1.31 | −1.59 | −1.72 | −4.01 | −1.93 |
| S | 305I | 0.17 | 3.30 | −8.30 | 0.08 | 3.48 | 1.96 | 2.46 | 2.31 | 1.86 | 4.45 | 4.03 |
| S | 305K | −0.04 | −1.33 | −11.45 | −0.01 | −2.32 | −0.46 | −2.68 | −3.31 | −4.37 | −6.76 | −0.63 |
| S | 305L | −0.10 | 2.43 | −7.11 | −0.02 | −1.58 | −0.16 | −1.44 | −1.62 | −2.07 | −3.64 | −1.17 |
| S | 305M | −1.18 | 0.39 | 0.85 | −0.27 | −0.35 | −2.42 | −0.12 | 0.13 | −0.20 | −0.23 | −0.02 |
| S | 305N | 1.03 | 0.91 | −0.32 | 0.99 | 0.91 | 0.85 | 0.81 | 0.55 | 0.99 | 0.91 | 0.95 |
| S | 305Q | −0.08 | −2.24 | 1.38 | −0.02 | −1.57 | −0.19 | −1.58 | −1.88 | −2.02 | −4.07 | −0.75 |
| S | 305R | −0.10 | 1.52 | −6.08 | −0.02 | −0.97 | −0.19 | −1.12 | −1.40 | −1.81 | −2.93 | −1.11 |
| S | 305T | 0.69 | 1.30 | 0.25 | 0.54 | 1.26 | 1.07 | 1.08 | 0.79 | 1.11 | 1.22 | 1.31 |
| S | 305V | 0.67 | 1.48 | −1.43 | 0.60 | 1.39 | 1.22 | 1.16 | 0.85 | 1.39 | 1.43 | 1.48 |
| S | 305W | −0.18 | 0.05 | 0.71 | −0.04 | −0.54 | −0.18 | −0.66 | −0.79 | −0.93 | −1.67 | −0.51 |
| R | 306A | −0.09 | −7.79 | −10.37 | −0.02 | −1.22 | −0.05 | −1.26 | −1.47 | −5.79 | −3.39 | −0.66 |
| R | 306C | −0.17 | −3.11 | −1.13 | −0.03 | −0.62 | −0.07 | −0.66 | −0.81 | −3.01 | −1.87 | −0.51 |
| R | 306D | −0.27 | −2.43 | −11.57 | −0.06 | −0.34 | 0.01 | −0.38 | −0.46 | −1.72 | −0.91 | 0.03 |
| R | 306E | −0.11 | −3.91 | 12.11 | −0.03 | −0.84 | −0.11 | −0.91 | −1.12 | −4.25 | −2.56 | −0.41 |
| R | 306F | −0.20 | −0.81 | −3.55 | −0.04 | −0.50 | −0.10 | −0.56 | −0.68 | −2.66 | −1.63 | −0.41 |
| R | 306G | −0.26 | −1.79 | 3.50 | −0.05 | −0.38 | −0.07 | −0.42 | −0.51 | −2.17 | −1.32 | −0.32 |
| R | 306H | −0.12 | −3.34 | −23.68 | −0.02 | −2.36 | −0.46 | −1.62 | −1.85 | −4.62 | −4.23 | −2.65 |
| R | 306K | −0.05 | −7.34 | −1.52 | −0.01 | −7.06 | −2.43 | −4.89 | −4.94 | −10.35 | −10.46 | −7.30 |
| R | 306L | −0.29 | 0.42 | −1.97 | −0.05 | −0.35 | −0.02 | −0.40 | −0.49 | −1.82 | −1.01 | −0.07 |
| R | 306M | −0.17 | −0.85 | −3.60 | −0.03 | −0.59 | −0.05 | −0.67 | −0.80 | −3.21 | −1.74 | −0.14 |
| R | 306N | −0.21 | −2.70 | −2.12 | −0.04 | −0.50 | −0.06 | −0.53 | −0.65 | −2.37 | −1.54 | −0.41 |
| R | 306Q | −0.20 | −3.54 | 8.46 | −0.04 | −0.75 | −0.04 | −0.66 | −0.78 | −2.64 | −1.80 | −0.65 |
| R | 306S | −0.25 | −0.50 | −2.00 | −0.05 | −0.43 | −0.02 | −0.45 | −0.54 | −2.06 | −1.44 | −0.28 |
| R | 306V | −0.28 | 0.21 | −1.31 | −0.06 | −0.40 | −0.06 | −0.41 | −0.49 | −1.78 | −1.18 | −0.17 |
| R | 306W | −0.24 | −0.10 | −4.76 | −0.04 | −0.43 | −0.02 | −0.47 | −0.57 | −2.12 | −1.03 | −0.10 |
| R | 306Y | −0.25 | 0.96 | 6.04 | −0.05 | −0.42 | −0.07 | −0.47 | −0.56 | −2.10 | −1.22 | −0.20 |
| P | 307A | 0.26 | 3.29 | 11.14 | 0.12 | 1.86 | 0.67 | 1.17 | 1.05 | 0.78 | 2.47 | 1.75 |
| P | 307C | 0.59 | 1.09 | 1.51 | 0.38 | 1.17 | 0.70 | 0.84 | 0.71 | 0.72 | 1.42 | 1.27 |
| P | 307D | 0.08 | 11.84 | 4.99 | 0.02 | 1.67 | 0.16 | 1.49 | 1.83 | 1.83 | 4.33 | 1.38 |
| P | 307F | −0.37 | −3.04 | −6.48 | −0.07 | −0.40 | −0.71 | −0.44 | −0.29 | 1.26 | −0.86 | −0.22 |
| P | 307H | −0.01 | −8.69 | −409.04 | 0.00 | −8.87 | −0.86 | −10.16 | −12.56 | −13.20 | −29.31 | −10.13 |
| P | 307K | 0.01 | 0.50 | 881.31 | 0.00 | 11.26 | 1.28 | 13.32 | 16.65 | 10.69 | 37.17 | 1.38 |
| P | 307L | 0.03 | −7.82 | 149.99 | 0.01 | 3.17 | 0.51 | 3.52 | 4.17 | 4.83 | 8.75 | 2.49 |
| P | 307M | 0.03 | 28.86 | 115.06 | 0.01 | 4.26 | 0.16 | 4.54 | 5.58 | 6.06 | 11.29 | 2.69 |
| P | 307N | 0.61 | 1.06 | 1.29 | 0.37 | 1.08 | 0.64 | 0.80 | 0.78 | 0.66 | 1.33 | 1.18 |
| P | 307Q | 0.10 | 5.25 | 25.00 | 0.02 | 1.04 | 0.04 | 1.15 | 1.42 | 1.45 | 3.27 | 1.42 |
| P | 307S | 0.05 | 11.95 | 40.42 | 0.01 | 5.05 | 0.91 | 3.55 | 4.16 | 3.06 | 9.00 | 3.35 |
| P | 307T | 0.01 | 78.67 | 381.69 | 0.00 | 46.48 | 8.79 | 30.42 | 35.44 | 21.69 | 79.97 | 42.75 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| P | 307V | 0.20 | 3.35 | 21.37 | 0.08 | 2.36 | 0.96 | 1.62 | 1.66 | 0.88 | 3.16 | 2.33 |
| P | 307W | −0.09 | −3.20 | −30.56 | −0.02 | −1.09 | −0.19 | −1.33 | −1.65 | −1.79 | −3.13 | 0.23 |
| P | 307Y | 0.05 | 3.21 | 151.15 | 0.01 | 1.97 | 0.39 | 2.52 | 3.08 | 3.51 | 5.70 | 1.09 |
| N | 312A | 1.20 | 0.90 | 0.56 | 1.46 | 0.89 | 0.83 | 0.84 | 0.50 | 0.85 | 0.85 | 0.92 |
| N | 312C | 0.98 | 0.91 | 2.00 | 0.97 | 0.95 | 0.81 | 0.82 | 0.64 | 0.80 | 0.86 | 0.77 |
| N | 312D | 0.96 | 1.00 | 1.47 | 0.98 | 1.01 | 0.89 | 0.88 | 0.74 | 0.90 | 0.94 | 0.93 |
| N | 312F | 0.92 | 0.99 | 0.67 | 0.84 | 1.05 | 0.86 | 0.90 | 0.76 | 0.74 | 1.12 | 0.99 |
| N | 312G | 1.00 | 0.98 | 1.02 | 1.01 | 1.05 | 0.98 | 0.95 | 0.87 | 0.94 | 1.03 | 1.01 |
| N | 312H | 0.83 | 1.22 | 1.83 | 0.85 | 1.23 | 1.14 | 1.13 | 1.04 | 1.01 | 1.12 | 1.30 |
| N | 312I | 0.80 | 1.07 | 3.99 | 0.74 | 1.21 | 1.03 | 1.05 | 0.82 | 1.00 | 1.13 | 1.06 |
| N | 312K | 0.95 | 1.01 | 2.09 | 1.13 | 1.13 | 1.09 | 1.08 | 0.70 | 1.01 | 1.04 | 1.06 |
| N | 312L | 0.64 | 1.27 | 0.88 | 0.60 | 1.45 | 1.25 | 1.25 | 1.00 | 1.37 | 1.40 | 1.36 |
| N | 312M | 0.95 | 1.14 | 1.18 | 1.02 | 1.00 | 0.89 | 0.90 | −0.16 | 0.88 | 0.98 | 0.98 |
| N | 312P | 0.80 | 1.06 | 1.61 | 0.70 | 1.05 | 0.62 | 0.84 | 0.84 | 0.65 | 1.14 | 1.10 |
| N | 312Q | 0.80 | 1.20 | 0.08 | 0.81 | 1.16 | 1.09 | 1.13 | 1.06 | 1.12 | 1.10 | 1.13 |
| N | 312R | 0.67 | 1.45 | 2.25 | 0.62 | 1.34 | 1.20 | 1.26 | 1.24 | 1.16 | 1.52 | 1.27 |
| N | 312T | −0.11 | −7.52 | 8.73 | −0.05 | −4.97 | −2.72 | −4.03 | −5.16 | −12.42 | −5.56 | −5.04 |
| N | 312V | 0.80 | 0.97 | 2.28 | 0.71 | 1.10 | 0.97 | 1.03 | 0.98 | 1.00 | 1.09 | 1.12 |
| N | 312W | 0.90 | 1.04 | 0.46 | 0.71 | 0.94 | 0.81 | 0.86 | 0.77 | 0.77 | 0.92 | 0.95 |
| N | 312Y | 0.87 | 0.95 | −1.08 | 0.87 | 1.11 | 1.08 | 1.07 | 0.82 | 0.99 | 1.08 | 1.12 |
| R | 315C | 0.22 | 3.27 | 3.55 | 0.10 | 2.37 | 0.69 | 1.71 | 1.36 | 1.00 | 3.35 | 2.51 |
| R | 315D | 0.34 | 1.58 | 2.71 | 0.15 | 1.45 | 0.33 | 0.96 | 0.83 | 0.61 | 2.04 | 1.14 |
| R | 315E | 0.19 | 2.96 | −7.18 | 0.07 | 2.22 | 0.28 | 1.41 | 1.27 | 1.00 | 3.33 | 1.64 |
| R | 315G | 0.26 | 2.50 | 0.54 | 0.12 | 2.47 | 0.97 | 1.72 | 1.54 | 0.87 | 3.12 | 2.43 |
| R | 315H | 0.15 | 4.28 | 3.24 | 0.05 | 3.50 | 0.78 | 2.15 | 1.97 | 1.12 | 4.68 | 3.06 |
| R | 315I | 0.30 | 2.17 | 7.70 | 0.13 | 1.86 | 0.50 | 1.26 | 1.03 | 0.81 | 2.58 | 1.82 |
| R | 315K | 0.78 | 1.32 | 1.79 | 0.63 | 1.12 | 0.73 | 1.09 | 0.83 | 0.57 | 1.20 | 1.00 |
| R | 315L | 0.21 | 3.03 | 16.83 | 0.08 | 2.76 | 0.88 | 1.98 | 1.35 | 0.99 | 3.75 | 3.01 |
| R | 315M | 0.98 | 1.03 | −1.73 | 1.04 | 0.90 | 0.45 | 0.68 | 0.41 | 0.43 | 1.00 | 0.77 |
| R | 315N | 0.63 | 1.11 | −1.88 | 0.42 | 1.12 | 0.46 | 0.80 | 0.50 | 0.46 | 1.36 | 0.78 |
| R | 315P | 0.88 | 1.07 | −0.77 | 0.82 | 1.05 | 0.66 | 0.92 | 0.59 | 0.71 | 1.15 | 0.91 |
| R | 315Q | 0.96 | 1.14 | −3.22 | 0.97 | 1.06 | 1.03 | 1.05 | 0.75 | 0.95 | 1.00 | 0.88 |
| R | 315T | 0.52 | 1.57 | 1.43 | 0.34 | 1.50 | 0.66 | 1.11 | 0.80 | 0.58 | 1.61 | 1.46 |
| R | 315V | 0.36 | 0.81 | 2.61 | 0.11 | 1.24 | 0.23 | 0.72 | 0.67 | 0.60 | 1.59 | 1.08 |
| R | 315W | −0.27 | −0.81 | −4.23 | −0.05 | −0.64 | −0.03 | −0.55 | −0.57 | −0.56 | −1.27 | −0.41 |
| F | 316A | −0.04 | −9.09 | −116.89 | −0.02 | −6.05 | −0.83 | −3.55 | −2.34 | −3.37 | −10.35 | −7.72 |
| F | 316C | 0.04 | 6.34 | 209.67 | 0.01 | 5.56 | 0.71 | 3.41 | 2.59 | 3.03 | 5.83 | 2.75 |
| F | 316D | 0.08 | 4.84 | 145.91 | 0.03 | 4.82 | 1.31 | 2.75 | 2.30 | 2.06 | 5.14 | 3.75 |
| F | 316G | −0.12 | −1.90 | 69.80 | −0.03 | −2.00 | −0.15 | −1.11 | −0.93 | −1.37 | −1.92 | −1.82 |
| F | 316H | 0.08 | 3.23 | 2.48 | 0.02 | 4.58 | 1.16 | 2.69 | 2.17 | 1.97 | 5.74 | 4.83 |
| F | 316I | 0.13 | 2.22 | −89.48 | 0.04 | 2.73 | 0.55 | 1.55 | 1.18 | 1.26 | 3.02 | 2.72 |
| F | 316K | −0.04 | −6.15 | 260.80 | −0.01 | −4.37 | −0.28 | −2.52 | −2.02 | −3.32 | −3.50 | −1.74 |
| F | 316L | 0.11 | 2.69 | −116.00 | 0.03 | 3.31 | 0.59 | 1.98 | 1.33 | 1.77 | 4.12 | 2.29 |
| F | 316M | 0.10 | 4.48 | −8.69 | 0.04 | 4.58 | 1.31 | 2.90 | 2.10 | 2.16 | 4.40 | 4.12 |
| F | 316P | −0.12 | −3.92 | −35.68 | −0.03 | −1.32 | 0.02 | −0.82 | −0.76 | −1.40 | −1.09 | −0.59 |
| F | 316Q | −0.05 | −5.74 | −19.73 | −0.01 | −4.51 | −0.19 | −2.66 | −2.41 | −3.38 | −3.25 | −2.35 |
| F | 316R | −0.08 | −3.82 | −16.84 | −0.02 | −2.60 | −0.14 | −1.52 | −1.38 | −2.18 | −2.58 | −3.20 |
| F | 316S | −0.10 | −2.51 | 63.82 | −0.02 | −2.55 | −0.31 | −1.43 | −1.32 | −1.48 | −2.98 | −2.26 |
| F | 316T | −0.02 | −17.10 | 313.28 | 0.00 | −12.88 | −1.59 | −7.70 | −6.72 | −7.87 | −11.84 | −14.55 |
| F | 316V | 0.02 | 7.86 | −591.40 | 0.01 | 10.64 | 1.79 | 6.44 | 5.71 | 6.78 | 10.22 | 7.95 |
| F | 316W | 0.82 | 1.00 | −4.10 | 0.68 | 1.04 | 0.80 | 0.99 | 0.79 | 0.79 | 1.13 | 1.03 |
| F | 316Y | 0.68 | 1.17 | −15.62 | 0.51 | 1.29 | 1.07 | 1.20 | 0.82 | 0.78 | 1.40 | 1.28 |
| I | 322A | −0.03 | −27.11 | 9.32 | −0.01 | −5.07 | −0.35 | −4.01 | −4.52 | −4.40 | −10.38 | 5.70 |
| I | 322C | 0.04 | 11.39 | −1.59 | 0.01 | 7.37 | 1.99 | 4.96 | 4.88 | 4.50 | 12.06 | 5.29 |
| I | 322D | −0.13 | −0.76 | −6.87 | −0.02 | −0.72 | −0.04 | −0.82 | −1.02 | −1.09 | −2.53 | −0.16 |
| I | 322E | −0.09 | 0.60 | −7.21 | −0.02 | −0.98 | −0.10 | −1.10 | −1.36 | −1.39 | −3.08 | −0.43 |
| I | 322G | −0.10 | −0.66 | −14.50 | −0.02 | −0.91 | −0.10 | −1.00 | −1.22 | −1.07 | −2.55 | −0.77 |
| I | 322H | −0.09 | 0.70 | −24.71 | −0.02 | −1.14 | −0.14 | −1.22 | −1.49 | −1.55 | −3.25 | −1.41 |
| I | 322K | −0.12 | −1.49 | −30.11 | −0.02 | −0.73 | −0.09 | −0.85 | −1.04 | −1.06 | −2.45 | 0.00 |
| I | 322L | 0.80 | 1.09 | 8.14 | 0.69 | 1.21 | 1.15 | 1.13 | 0.84 | 1.12 | 1.28 | 1.22 |
| I | 322M | 1.05 | 0.97 | −0.17 | 1.41 | 1.03 | 1.12 | 0.96 | 0.53 | 0.97 | 0.92 | 0.86 |
| I | 322N | −0.02 | −34.42 | 22.23 | 0.00 | −5.94 | −0.27 | −6.46 | −7.79 | −8.61 | −22.79 | −4.20 |
| I | 322P | 0.03 | 7.57 | −27.10 | 0.01 | 2.93 | 0.24 | 3.22 | 3.88 | 4.09 | 9.97 | 1.49 |
| I | 322Q | 0.00 | 131.77 | 403.38 | 0.00 | 43.64 | 4.94 | 33.82 | 35.46 | 36.79 | 89.97 | 28.50 |
| I | 322R | −0.04 | −2.67 | 7.32 | −0.01 | −2.17 | −0.47 | −2.56 | −3.03 | −3.16 | −7.70 | −2.30 |
| I | 322S | −0.09 | 0.99 | −21.70 | −0.02 | −1.35 | −0.18 | −1.30 | −1.56 | −1.62 | −3.74 | −1.96 |
| I | 322T | −0.11 | −2.27 | 9.50 | −0.02 | −1.74 | −0.24 | −1.24 | −1.33 | −1.30 | −3.51 | −1.41 |
| I | 322V | 0.69 | 1.14 | 4.04 | 0.42 | 1.20 | 1.00 | 0.99 | 0.72 | 0.92 | 1.43 | 1.30 |
| I | 322W | −0.09 | 0.04 | −21.09 | −0.01 | −1.47 | −0.09 | −1.28 | −1.51 | −1.58 | −4.01 | −0.64 |
| I | 322Y | −0.02 | −21.62 | −68.31 | 0.00 | −5.44 | −0.23 | −5.48 | −6.45 | −6.91 | −14.86 | −1.23 |
| G | 326A | 0.08 | 6.25 | −4.15 | 0.02 | 3.04 | 0.60 | 1.46 | 1.95 | 2.22 | 2.43 | 3.67 |
| G | 326C | −0.17 | −1.91 | −11.24 | −0.04 | −0.56 | −0.05 | −0.37 | −0.58 | −0.90 | 0.12 | −0.43 |
| G | 326D | −0.11 | −3.71 | −9.01 | −0.02 | −0.84 | −0.12 | −0.57 | −0.91 | −1.46 | −0.59 | −5.91 |
| G | 326E | −0.01 | 12.16 | −268.45 | 0.00 | −6.18 | −0.84 | −4.12 | −6.52 | −10.14 | −0.77 | −6.32 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| G | 326F | −0.06 | 2.15 | 2.05 | −0.01 | −1.54 | −0.29 | −1.01 | −1.55 | −2.50 | −0.99 | −7.85 |
| G | 326H | −0.09 | 1.58 | −20.56 | −0.02 | −1.09 | −0.12 | −0.68 | −1.07 | −1.74 | −0.72 | −3.20 |
| G | 326I | −0.17 | 1.35 | −14.69 | −0.03 | −0.53 | −0.04 | −0.36 | −0.57 | −0.92 | 0.00 | −0.77 |
| G | 326K | −0.09 | 3.39 | −12.08 | −0.01 | −1.07 | −0.05 | −0.74 | −1.15 | −1.88 | −0.56 | −1.59 |
| G | 326L | −0.13 | 1.96 | −18.57 | −0.02 | −0.72 | −0.06 | −0.53 | −0.80 | −1.31 | −0.45 | −1.25 |
| G | 326M | −0.07 | −3.31 | 8.63 | −0.02 | −1.39 | −0.07 | −0.92 | −1.49 | −2.24 | −0.53 | −1.26 |
| G | 326N | −0.20 | −1.93 | 0.76 | −0.05 | −0.57 | −0.05 | −0.33 | −0.53 | −0.78 | −0.08 | −0.38 |
| G | 326P | 0.00 | 327.93 | 796.88 | 0.00 | 81.17 | 7.22 | 47.44 | 68.33 | 85.99 | 32.18 | 60.19 |
| G | 326Q | 0.15 | 2.68 | 10.23 | 0.05 | 2.72 | 1.33 | 1.92 | 2.13 | 1.18 | 3.45 | 2.79 |
| G | 326R | −0.17 | −0.22 | −9.53 | −0.03 | −0.55 | −0.18 | −0.36 | −0.56 | −0.87 | −0.07 | −0.88 |
| G | 326S | 0.00 | 370.62 | 2544.53 | 0.00 | 376.81 | 127.65 | 212.68 | 258.62 | 216.53 | 438.00 | 308.62 |
| G | 326T | −0.09 | 2.56 | −9.16 | −0.02 | −1.27 | −0.08 | −0.79 | −1.20 | −1.76 | −0.56 | −2.39 |
| G | 326V | −0.18 | 0.59 | −4.55 | −0.03 | −0.52 | −0.05 | −0.34 | −0.53 | −0.86 | −0.11 | −0.77 |
| G | 326W | −0.15 | 1.06 | −5.06 | −0.03 | −0.62 | −0.07 | −0.42 | −0.68 | −1.03 | −0.53 | −0.71 |
| G | 326Y | −0.12 | 0.61 | 2.45 | −0.02 | −0.79 | −0.06 | −0.59 | −0.89 | −1.40 | −0.75 | −1.60 |
| L | 329A | 0.67 | 1.29 | 0.75 | 0.58 | 1.26 | 0.97 | 0.95 | 0.64 | 1.09 | 1.15 | 0.89 |
| L | 329C | 0.01 | 58.18 | 20.16 | 0.01 | 37.99 | 31.82 | 29.21 | 27.67 | 0.00 | 44.35 | 39.20 |
| L | 329D | 0.17 | 2.61 | 4.76 | 0.07 | 2.66 | 1.20 | 1.64 | 1.44 | 1.99 | 2.67 | 2.91 |
| L | 329E | 0.37 | 1.64 | −0.39 | 0.19 | 1.68 | 1.11 | 1.24 | 1.15 | 1.55 | 1.90 | 1.84 |
| L | 329F | 0.65 | 1.38 | 0.76 | 0.49 | 1.28 | 1.11 | 1.15 | 1.03 | 1.26 | 1.41 | 1.38 |
| L | 329G | 0.15 | 3.94 | 1.35 | 0.06 | 3.81 | 2.03 | 2.50 | 2.27 | 2.94 | 4.24 | 4.11 |
| L | 329H | 0.47 | 1.48 | 1.11 | 0.28 | 1.51 | 1.10 | 1.22 | 1.05 | 1.11 | 1.58 | 1.79 |
| L | 329K | 0.02 | 13.79 | 31.64 | 0.00 | 16.92 | 4.77 | 9.23 | 8.74 | 12.65 | 14.96 | 20.57 |
| L | 329M | 1.01 | 1.01 | 0.73 | 1.26 | 1.00 | 0.99 | 0.86 | 0.44 | 0.94 | 0.95 | 0.77 |
| L | 329N | 0.07 | 11.37 | 9.75 | 0.04 | 8.78 | 6.62 | 7.05 | 6.47 | −1.78 | 9.35 | 7.08 |
| L | 329P | −0.11 | −1.86 | −7.39 | −0.03 | −0.99 | −0.06 | −0.65 | −0.82 | −1.63 | −0.15 | −0.97 |
| L | 329Q | 0.58 | 1.41 | 0.37 | 0.38 | 1.37 | 1.07 | 1.05 | 0.76 | 1.19 | 1.24 | 1.32 |
| L | 329R | 0.07 | 5.01 | 14.70 | 0.02 | 5.23 | 1.69 | 2.79 | 2.31 | 3.50 | 4.57 | 4.44 |
| L | 329S | 0.35 | 2.00 | 1.69 | 0.19 | 2.11 | 1.34 | 1.45 | 1.10 | 1.63 | 2.25 | 1.79 |
| L | 329T | 0.66 | 1.20 | 0.80 | 0.50 | 1.28 | 1.01 | 1.02 | 0.75 | 1.18 | 1.15 | 1.18 |
| F | 330A | 0.06 | 6.57 | 1.42 | 0.02 | 6.48 | 2.73 | 4.29 | 3.32 | 4.74 | 6.72 | 4.27 |
| F | 330C | 0.30 | 1.74 | 34.88 | 0.18 | 2.09 | 1.48 | 1.62 | 1.41 | 1.68 | 2.24 | 1.86 |
| F | 330D | −0.09 | −4.04 | −23.75 | −0.02 | −2.14 | −0.35 | −1.38 | −1.29 | −2.26 | −1.56 | −1.12 |
| F | 330E | −0.09 | −2.99 | −0.75 | −0.02 | −1.24 | −0.18 | −0.89 | −0.86 | −1.87 | −1.55 | −2.34 |
| F | 330G | −0.14 | −1.85 | 22.43 | −0.03 | −1.31 | −0.32 | −0.78 | −0.74 | −1.23 | −1.34 | −0.85 |
| F | 330H | 0.21 | 2.32 | 40.67 | 0.07 | 2.70 | 1.57 | 2.02 | 1.79 | 1.67 | 3.22 | 2.81 |
| F | 330I | −0.09 | −2.88 | 41.87 | −0.02 | −2.40 | −0.40 | −1.43 | −1.34 | −2.08 | −2.30 | −2.40 |
| F | 330K | −0.13 | 1.38 | −59.34 | −0.02 | −0.76 | −0.07 | −0.56 | −0.57 | −1.27 | −0.57 | −1.20 |
| F | 330L | 0.17 | 1.82 | 9.83 | 0.05 | 2.49 | 1.06 | 1.69 | 1.26 | 1.89 | 3.15 | 2.55 |
| F | 330M | 0.31 | 1.85 | −0.25 | 0.19 | 2.16 | 1.45 | 1.55 | 1.09 | 1.56 | 3.47 | 3.24 |
| F | 330N | −0.06 | −6.04 | 33.13 | −0.01 | −4.05 | −0.66 | −2.31 | −2.04 | −3.56 | −4.13 | −4.10 |
| F | 330P | −0.06 | −7.40 | 36.43 | −0.01 | −2.37 | −0.28 | −1.58 | −1.50 | −2.90 | −1.38 | −2.50 |
| F | 330Q | −0.10 | −2.15 | −13.46 | −0.02 | −1.07 | −0.09 | −0.80 | −0.79 | −1.63 | −0.09 | −1.10 |
| F | 330R | −0.18 | 0.22 | 47.28 | −0.04 | −0.55 | −0.06 | −0.41 | −0.39 | −0.86 | 0.10 | −0.14 |
| F | 330S | 0.22 | 2.52 | −24.70 | 0.08 | 2.42 | 1.17 | 1.54 | 1.22 | 1.59 | 2.23 | 2.01 |
| F | 330T | −0.21 | −0.36 | 38.51 | −0.05 | −0.50 | −0.10 | −0.34 | −0.34 | −0.76 | −0.46 | −0.20 |
| F | 330V | −0.03 | −9.54 | −267.58 | −0.01 | −9.46 | −2.02 | −5.55 | −4.58 | −7.14 | −10.78 | −6.61 |
| F | 330W | 0.58 | 1.29 | 2.82 | 0.35 | 1.41 | 1.05 | 1.18 | 0.78 | 1.00 | 1.47 | 1.40 |
| F | 330Y | 0.84 | 1.16 | −18.07 | 0.76 | 1.20 | 1.19 | 1.21 | 0.77 | 1.15 | 1.18 | 1.26 |
| D | 332A | 0.71 | 1.13 | 0.16 | 0.64 | 1.25 | 1.03 | 0.99 | 0.61 | 0.98 | 1.23 | 2.08 |
| D | 332C | 0.80 | 1.05 | −0.97 | 0.81 | 1.21 | 1.11 | 1.04 | 0.81 | 0.97 | 1.15 | 0.96 |
| D | 332E | 0.75 | 1.25 | −1.78 | 0.63 | 1.16 | 0.98 | 0.97 | 0.81 | 0.98 | 1.28 | 1.10 |
| D | 332F | 0.08 | 1.29 | −19.16 | 0.03 | 4.71 | 1.52 | 2.60 | 2.22 | 3.06 | 5.32 | 4.73 |
| D | 332G | 0.58 | 0.80 | 0.38 | 0.37 | 1.23 | 0.93 | 0.98 | 0.74 | 0.94 | 1.44 | 1.33 |
| D | 332H | 0.96 | 0.88 | −0.46 | 0.95 | 0.98 | 0.95 | 0.93 | 0.72 | 0.89 | 1.17 | 0.93 |
| D | 332I | 0.10 | −0.44 | −10.59 | 0.03 | 2.75 | 0.70 | 1.60 | 1.36 | 2.13 | 3.32 | 1.57 |
| D | 332K | 0.32 | 0.52 | 0.91 | 0.15 | 1.47 | 0.83 | 1.07 | 0.81 | 1.13 | 1.87 | 1.96 |
| D | 332L | 0.27 | −0.39 | −15.62 | 0.10 | 1.48 | 0.56 | 0.91 | 0.62 | 1.11 | 1.73 | 1.67 |
| D | 332M | 0.21 | 0.77 | 4.45 | 0.10 | 2.51 | 1.13 | 1.62 | 1.23 | 1.72 | 2.82 | 2.39 |
| D | 332P | −0.14 | −1.53 | −22.63 | −0.03 | −0.69 | −0.03 | −0.49 | −0.58 | −0.94 | −0.88 | −0.09 |
| D | 332Q | 0.56 | 1.11 | −0.72 | 0.43 | 1.41 | 1.12 | 1.20 | 1.18 | 1.18 | 1.60 | 1.35 |
| D | 332R | 0.08 | 1.36 | 9.55 | 0.03 | 4.72 | 1.78 | 2.81 | 2.80 | 2.90 | 6.00 | 4.13 |
| D | 332S | 0.74 | 1.02 | −1.15 | 0.57 | 1.20 | 1.02 | 1.05 | 0.97 | 1.02 | 1.24 | 0.97 |
| D | 332V | 0.14 | −0.97 | −25.23 | 0.05 | 3.32 | 1.65 | 2.23 | 2.01 | 2.40 | 3.63 | 3.16 |
| D | 332W | 0.01 | −51.29 | −127.50 | 0.00 | 31.26 | 7.30 | 19.19 | 16.87 | 26.81 | 31.41 | 24.88 |
| D | 332Y | 0.21 | −0.15 | 0.47 | 0.08 | 2.16 | 0.95 | 1.38 | 1.00 | 1.56 | 2.26 | 2.02 |
| A | 334C | 1.15 | 0.88 | −14.96 | 1.55 | 0.90 | 0.97 | 0.91 | 0.70 | 0.88 | 1.04 | 0.92 |
| A | 334D | 0.70 | 1.02 | 18.44 | 0.67 | 1.32 | 1.13 | 1.06 | 0.91 | 1.08 | 1.40 | 1.21 |
| A | 334F | 0.75 | 0.95 | −65.16 | 0.62 | 1.24 | 1.02 | 0.98 | 0.87 | 1.00 | 1.31 | 1.15 |
| A | 334G | 1.02 | 1.02 | −37.83 | 1.06 | 1.02 | 0.98 | 0.92 | 0.77 | 0.95 | 1.12 | 0.97 |
| A | 334H | 0.64 | 1.10 | −68.47 | 0.56 | 1.46 | 1.17 | 1.10 | 0.96 | 1.12 | 1.61 | 1.39 |
| A | 334I | 0.88 | 1.20 | −32.47 | 0.96 | 1.21 | 1.16 | 1.10 | 0.88 | 1.13 | 1.32 | 1.14 |
| A | 334K | 0.89 | 0.85 | 3.91 | 0.81 | 1.04 | 0.93 | 0.91 | 0.68 | 0.88 | 1.12 | 0.99 |
| A | 334L | 0.91 | 0.88 | 11.20 | 1.03 | 1.15 | 1.11 | 1.03 | 0.82 | 1.06 | 1.17 | 1.13 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| A | 334M | 0.81 | 1.23 | −36.46 | 0.98 | 1.28 | 1.31 | 1.20 | 0.93 | 1.26 | 1.24 | 1.39 |
| A | 334N | 0.81 | 0.89 | 22.78 | 0.83 | 1.17 | 1.07 | 1.04 | 0.96 | 1.07 | 1.16 | 1.22 |
| A | 334Q | 0.84 | 0.97 | −23.95 | 0.80 | 1.09 | 1.03 | 1.01 | 1.04 | 1.03 | 1.21 | 0.93 |
| A | 334R | 0.47 | 1.21 | 157.83 | 0.34 | 1.61 | 1.17 | 1.27 | 1.26 | 1.11 | 1.91 | 1.65 |
| A | 334S | 0.93 | 1.40 | 38.73 | 0.91 | 1.07 | 1.00 | 1.03 | 0.99 | 1.00 | 1.02 | 0.85 |
| A | 334T | 0.74 | 0.97 | 1.39 | 0.66 | 1.28 | 1.19 | 1.19 | 1.16 | 1.17 | 1.36 | 1.21 |
| A | 334V | 1.00 | 0.82 | 22.08 | 1.09 | 1.01 | 0.97 | 0.97 | 0.93 | 0.95 | 1.03 | 0.93 |
| A | 334Y | 0.81 | 0.82 | 9.55 | 0.63 | 1.12 | 0.93 | 0.96 | 0.79 | 1.03 | 1.19 | 1.11 |
| I | 335A | 0.14 | 1.07 | −216.20 | 0.06 | 3.10 | 1.11 | 1.69 | 1.50 | 2.09 | 2.79 | 2.85 |
| I | 335C | −0.98 | 0.72 | 72.13 | −0.20 | −0.37 | −2.44 | −0.70 | −0.67 | −0.19 | −0.02 | −0.13 |
| I | 335D | −0.06 | −1.57 | 34.67 | −0.01 | −1.57 | −0.15 | −1.06 | −1.38 | −2.54 | −0.61 | −2.84 |
| I | 335F | −0.08 | −9.62 | 623.88 | −0.02 | −2.14 | −0.25 | −1.26 | −1.46 | −2.45 | −2.25 | −0.78 |
| I | 335G | −0.06 | −1.12 | 872.30 | −0.01 | −1.85 | −0.28 | −1.16 | −1.40 | −2.40 | −1.05 | −2.03 |
| I | 335H | −0.08 | 2.58 | 380.26 | −0.02 | −1.54 | −0.26 | −0.94 | −1.12 | −1.95 | −1.57 | −2.10 |
| I | 335L | 0.29 | 0.10 | 78.55 | 0.12 | 1.97 | 1.04 | 1.24 | 1.09 | 1.43 | 2.28 | 2.06 |
| I | 335M | 0.45 | 1.27 | −22.00 | 0.37 | 1.85 | 1.50 | 1.49 | 1.19 | 1.55 | 1.96 | 1.93 |
| I | 335N | 0.02 | 17.31 | 121.78 | 0.01 | 25.85 | 12.00 | 16.71 | 16.74 | 20.53 | 31.35 | 22.42 |
| I | 335P | −0.06 | −1.82 | −345.51 | −0.01 | −2.89 | −0.35 | −1.62 | −1.90 | −3.07 | −2.41 | −1.27 |
| I | 335Q | 0.06 | −2.49 | −411.41 | 0.02 | 3.67 | 0.70 | 1.94 | 2.37 | 3.39 | 4.60 | 2.22 |
| I | 335R | −0.13 | 1.91 | 258.65 | −0.03 | −0.72 | −0.08 | −0.50 | −0.63 | −1.28 | −0.28 | −1.44 |
| I | 335S | −0.03 | −3.32 | 3827.95 | −0.01 | −6.44 | −1.25 | −3.72 | −4.39 | −6.12 | −7.62 | −7.27 |
| I | 335T | 0.58 | 0.79 | −11.06 | 0.36 | 1.24 | 0.92 | 1.00 | 1.05 | 1.04 | 1.51 | 1.15 |
| I | 335V | 0.71 | 1.07 | −115.61 | 0.56 | 1.22 | 1.12 | 1.20 | 1.18 | 1.20 | 1.30 | 1.28 |
| I | 335W | −0.15 | 4.45 | −198.80 | −0.03 | −0.78 | −0.06 | −0.48 | −0.59 | −1.06 | −0.35 | −0.48 |
| I | 335Y | −0.08 | 7.48 | 1641.12 | −0.01 | −1.21 | −0.04 | −0.91 | −1.13 | −2.23 | 0.05 | −1.03 |
| T | 336A | 1.05 | 0.98 | 0.23 | 1.30 | 0.99 | 1.05 | 0.95 | 0.59 | 0.94 | 0.88 | 0.79 |
| T | 336C | 0.88 | 1.08 | 0.18 | 0.93 | 1.04 | 1.05 | 1.03 | 0.81 | 1.00 | 1.00 | 1.25 |
| T | 336E | 0.79 | 1.10 | −1.72 | 0.64 | 1.09 | 0.98 | 0.99 | 0.87 | 0.99 | 1.19 | 0.99 |
| T | 336F | 0.65 | 1.30 | 0.09 | 0.42 | 1.22 | 0.96 | 1.00 | 0.89 | 0.99 | 1.27 | 2.28 |
| T | 336G | 0.93 | 1.15 | 2.26 | 0.83 | 1.03 | 0.99 | 0.99 | 0.91 | 1.00 | 0.99 | 0.98 |
| T | 336H | 0.75 | 1.09 | −0.28 | 0.51 | 1.09 | 0.91 | 0.94 | 0.84 | 0.93 | 1.18 | 1.05 |
| T | 336I | 0.90 | 1.21 | 1.21 | 0.82 | 1.06 | 1.06 | 1.06 | 0.92 | 1.08 | 1.07 | 1.16 |
| T | 336K | 0.95 | 1.02 | −0.04 | 0.77 | 0.99 | 0.95 | 0.95 | 0.76 | 0.94 | 1.08 | 1.11 |
| T | 336L | 0.06 | 0.58 | 4.25 | 0.01 | 1.57 | 0.09 | 1.26 | 1.44 | 2.88 | 1.09 | 1.85 |
| T | 336M | 0.98 | 1.10 | 0.62 | 1.17 | 1.04 | 1.06 | 1.00 | 0.47 | 0.97 | 0.95 | 0.53 |
| T | 336N | 0.68 | 1.28 | 0.48 | 0.59 | 1.31 | 1.08 | 1.06 | 0.65 | 1.05 | 1.26 | 1.42 |
| T | 336P | −0.09 | −3.80 | 0.90 | −0.02 | −2.06 | −0.28 | −1.18 | −1.11 | −1.60 | −1.54 | −1.92 |
| T | 336Q | 0.86 | 1.23 | 0.21 | 0.79 | 1.07 | 1.06 | 1.00 | 0.71 | 1.00 | 1.04 | 1.04 |
| T | 336R | 0.94 | 1.11 | −0.05 | 0.92 | 1.06 | 1.05 | 1.00 | 0.72 | 0.94 | 1.02 | 1.03 |
| T | 336S | 1.02 | 1.05 | 0.38 | 0.94 | 1.01 | 0.99 | 0.99 | 0.75 | 0.96 | 0.92 | 1.04 |
| T | 336V | 0.99 | 0.99 | 1.63 | 0.94 | 1.04 | 1.02 | 1.03 | 0.68 | 0.99 | 0.94 | 1.01 |
| T | 336W | 0.64 | 1.06 | 0.08 | 0.43 | 1.28 | 1.05 | 1.03 | 0.67 | 1.03 | 1.46 | 1.48 |
| T | 336Y | 0.83 | 1.07 | 0.17 | 0.67 | 1.12 | 1.00 | 0.98 | 0.64 | 0.95 | 1.17 | 1.08 |
| A | 337D | 0.22 | 2.08 | 3.23 | 0.09 | 2.02 | 0.70 | 1.23 | 1.15 | 1.34 | 2.89 | 1.22 |
| A | 337E | 1.13 | 1.02 | 3.78 | 1.20 | 0.88 | 0.79 | 0.78 | 0.67 | 0.75 | 0.86 | 0.75 |
| A | 337G | 1.08 | 0.94 | 5.15 | 1.09 | 0.94 | 0.89 | 0.85 | 0.72 | 0.83 | 0.92 | 0.82 |
| A | 337H | 0.83 | 1.07 | 6.60 | 0.66 | 1.06 | 0.88 | 0.91 | 0.79 | 0.87 | 1.10 | 1.04 |
| A | 337K | 0.38 | −0.17 | 12.06 | 0.11 | 0.84 | 0.20 | 0.41 | 0.39 | 0.56 | 1.34 | 1.06 |
| A | 337L | 0.48 | 1.08 | 1.15 | 0.27 | 1.42 | 0.89 | 1.05 | 0.85 | 1.03 | 1.80 | 1.18 |
| A | 337N | 0.74 | 1.11 | 2.68 | 0.66 | 1.14 | 0.96 | 1.00 | 0.92 | 0.99 | 1.23 | 1.13 |
| A | 337P | 0.19 | 1.60 | 3.41 | 0.07 | 2.24 | 0.93 | 1.49 | 1.54 | 1.64 | 2.98 | 1.98 |
| A | 337Q | 0.10 | 4.88 | −19.28 | 0.03 | 1.24 | 0.09 | 1.07 | 1.26 | 1.49 | 3.02 | 1.38 |
| A | 337R | 0.31 | 1.00 | 6.47 | 0.14 | 1.92 | 1.16 | 1.37 | 1.39 | 1.39 | 2.62 | 2.37 |
| A | 337S | 0.96 | 0.91 | −3.55 | 0.95 | 1.02 | 0.96 | 0.96 | 0.95 | 0.97 | 0.96 | 0.87 |
| A | 337V | 0.79 | 0.87 | −5.67 | 0.58 | 1.04 | 0.86 | 0.91 | 0.86 | 0.90 | 1.13 | 0.95 |
| A | 337W | 0.78 | 0.89 | 0.05 | 0.54 | 1.04 | 0.88 | 0.95 | 0.82 | 0.93 | 1.08 | 1.26 |
| A | 337Y | 0.60 | 1.02 | −6.95 | 0.37 | 1.26 | 0.96 | 1.05 | 0.81 | 1.04 | 1.47 | 1.10 |
| V | 338C | 1.43 | 0.67 | −3.64 | 1.70 | 0.71 | 0.71 | 0.67 | 0.69 | 0.75 | 0.66 | 0.65 |
| V | 338D | −0.06 | −8.46 | 32.50 | −0.02 | −2.02 | −0.29 | −1.94 | −2.29 | −2.78 | −5.34 | −2.13 |
| V | 338F | 0.46 | 0.63 | 8.23 | 0.13 | 0.74 | 0.20 | 0.36 | 0.39 | 0.50 | 1.18 | 0.89 |
| V | 338G | 0.87 | 0.85 | −5.38 | 0.66 | 1.01 | 0.88 | 0.87 | 0.92 | 0.91 | 1.06 | 0.96 |
| V | 338H | −0.03 | −2.14 | 8.35 | −0.01 | −6.91 | −1.46 | −4.74 | −5.22 | −5.80 | −12.69 | −8.11 |
| V | 338I | 0.97 | 0.91 | −0.42 | 0.95 | 1.00 | 1.00 | 1.03 | 1.01 | 1.00 | 1.03 | 0.92 |
| V | 338K | −0.19 | 1.40 | 31.29 | −0.03 | −0.51 | −0.06 | −0.57 | −0.68 | −0.87 | −1.42 | −0.49 |
| V | 338L | 0.90 | 1.07 | −2.74 | 0.90 | 1.11 | 1.10 | 1.06 | 0.72 | 1.05 | 1.08 | 0.95 |
| V | 338M | 0.95 | 1.18 | −1.48 | 1.17 | 1.08 | 1.13 | 1.03 | 0.80 | 1.00 | 1.02 | 0.95 |
| V | 338N | 0.24 | 2.24 | 27.28 | 0.14 | 2.57 | 1.65 | 1.94 | 1.78 | 1.94 | 2.87 | 2.47 |
| V | 338P | 0.10 | 2.33 | −42.41 | 0.04 | 4.14 | 1.73 | 2.84 | 2.95 | 3.13 | 6.97 | 3.56 |
| V | 338Q | 0.00 | 85.93 | 407.23 | 0.00 | 122.58 | 52.84 | 83.63 | 90.80 | 90.58 | 159.36 | 132.95 |
| V | 338S | 0.83 | 1.05 | 7.09 | 0.68 | 1.14 | 1.11 | 1.06 | 1.09 | 1.10 | 1.21 | 1.03 |
| V | 338T | 0.84 | 1.06 | −4.56 | 0.79 | 1.11 | 1.08 | 1.10 | 1.14 | 1.11 | 1.17 | 1.05 |
| V | 338W | −0.06 | 9.46 | 131.19 | −0.01 | −1.58 | −0.08 | −1.81 | −2.16 | −2.73 | −4.27 | −0.98 |
| V | 338Y | −0.10 | −0.50 | 23.89 | −0.02 | −2.56 | −0.61 | −1.81 | −1.75 | −2.28 | −4.40 | −2.73 |
| N | 339C | 0.53 | 1.24 | 0.25 | 0.37 | 1.46 | 1.11 | 1.20 | 1.00 | 1.21 | 1.40 | 1.46 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| N | 339D | −0.15 | −2.89 | −3.65 | −0.03 | −0.92 | −0.17 | −0.60 | −0.63 | −1.13 | −0.94 | −0.21 |
| N | 339E | −0.12 | 0.65 | 10.81 | −0.02 | −0.78 | −0.12 | −0.58 | −0.66 | −1.36 | −0.02 | −0.33 |
| N | 339F | −0.12 | −2.26 | −6.60 | −0.02 | −0.74 | −0.09 | −0.57 | −0.63 | −1.32 | 0.04 | −0.64 |
| N | 339G | 0.28 | 1.84 | 6.01 | 0.12 | 2.20 | 1.30 | 1.53 | 1.53 | 1.60 | 2.63 | 2.43 |
| N | 339H | −0.11 | 1.99 | 1.15 | −0.02 | −1.03 | −0.18 | −0.65 | −0.74 | −1.39 | −0.68 | −1.38 |
| N | 339I | 0.39 | 1.98 | −10.30 | 0.21 | 1.88 | 1.43 | 1.55 | 1.48 | 1.61 | 2.05 | 1.94 |
| N | 339K | 0.04 | −5.56 | 18.54 | 0.01 | 2.28 | 0.14 | 1.83 | 2.01 | 4.19 | 1.72 | 3.69 |
| N | 339L | −0.01 | −13.19 | 74.01 | 0.00 | −35.30 | −11.49 | −20.37 | −16.40 | −26.59 | −33.11 | −33.18 |
| N | 339M | −0.01 | −30.43 | −80.71 | 0.00 | −16.83 | −1.56 | −9.80 | −8.93 | −15.60 | −10.00 | −14.11 |
| N | 339Q | −0.15 | −1.21 | 3.87 | −0.03 | −0.76 | −0.04 | −0.56 | −0.61 | −0.99 | −0.54 | −0.58 |
| N | 339R | −0.15 | −2.07 | −2.93 | −0.03 | −0.60 | −0.12 | −0.47 | −0.51 | −1.02 | 0.05 | −1.33 |
| N | 339S | 0.42 | 1.50 | −2.18 | 0.25 | 1.70 | 1.20 | 1.35 | 1.27 | 1.37 | 1.94 | 1.56 |
| N | 339T | 0.47 | 1.34 | 3.43 | 0.26 | 1.57 | 1.18 | 1.33 | 1.21 | 1.36 | 1.67 | 1.58 |
| N | 339V | 0.43 | 1.16 | −1.49 | 0.22 | 1.59 | 1.03 | 1.20 | 1.14 | 1.25 | 1.71 | 1.85 |
| N | 339W | −0.09 | 3.87 | 32.52 | −0.02 | −0.99 | −0.18 | −0.78 | −0.88 | −1.63 | −0.78 | −1.11 |
| R | 340D | 0.89 | 1.02 | 0.12 | 0.82 | 1.00 | 0.93 | 0.94 | 0.93 | 0.95 | 1.06 | 0.94 |
| R | 340E | 0.87 | 1.02 | 1.00 | 0.81 | 1.03 | 0.95 | 0.96 | 0.98 | 0.97 | 0.99 | 0.98 |
| R | 340F | 0.76 | 1.27 | 1.18 | 0.66 | 1.23 | 1.17 | 1.19 | 1.20 | 1.18 | 1.20 | 1.24 |
| R | 340G | 0.88 | 0.99 | 2.00 | 0.72 | 1.03 | 0.93 | 0.96 | 0.96 | 0.95 | 0.92 | 0.98 |
| R | 340H | 0.91 | 0.93 | 1.68 | 0.80 | 1.01 | 0.97 | 1.01 | 1.00 | 1.04 | 1.07 | 1.04 |
| R | 340I | 0.94 | 0.95 | 0.83 | 0.82 | 0.96 | 0.94 | 0.95 | 0.93 | 0.98 | 1.00 | 1.03 |
| R | 340K | 0.90 | 1.00 | 0.30 | 0.78 | 0.99 | 0.94 | 0.97 | 0.83 | 0.98 | 1.10 | 1.56 |
| R | 340L | 0.95 | 0.91 | 3.79 | 0.91 | 1.04 | 0.99 | 0.97 | 0.73 | 0.97 | 0.98 | 1.29 |
| R | 340M | 0.87 | 1.07 | 0.51 | 0.95 | 1.13 | 1.10 | 0.99 | 0.80 | 1.03 | 1.00 | 1.05 |
| R | 340N | 0.80 | 1.08 | −1.87 | 0.78 | 1.13 | 1.09 | 1.10 | 1.00 | 1.05 | 1.11 | 1.01 |
| R | 340P | −0.10 | −1.84 | 6.16 | −0.03 | −2.54 | −0.45 | −1.49 | −1.55 | −2.17 | −3.18 | −1.83 |
| R | 340S | 0.71 | 1.22 | −0.68 | 0.56 | 1.22 | 1.11 | 1.16 | 1.23 | 1.16 | 1.29 | 1.26 |
| R | 340T | 0.81 | 1.12 | 0.73 | 0.65 | 1.09 | 0.99 | 1.07 | 1.07 | 1.04 | 1.08 | 1.09 |
| R | 340V | 0.86 | 1.04 | −0.55 | 0.69 | 1.04 | 0.97 | 1.04 | 1.01 | 1.05 | 1.13 | 0.95 |
| R | 340W | 0.75 | 1.07 | 1.09 | 0.59 | 1.21 | 1.15 | 1.20 | 1.04 | 1.21 | 1.21 | 1.27 |
| F | 341A | 0.58 | 1.42 | −4.28 | 0.44 | 1.31 | 1.07 | 1.10 | 0.89 | 1.31 | 1.44 | 1.38 |
| F | 341D | −0.15 | 0.69 | 2.92 | −0.03 | −0.72 | −0.43 | −1.17 | −1.22 | −5.86 | −0.27 | −0.72 |
| F | 341E | −0.13 | 0.38 | −6.70 | −0.04 | −0.87 | −0.19 | −0.60 | −0.70 | −1.23 | −0.35 | −1.15 |
| F | 341H | −0.16 | −2.30 | −0.93 | −0.04 | −1.31 | −0.31 | −0.73 | −0.83 | −1.31 | −0.96 | −1.98 |
| F | 341I | 0.36 | 1.82 | −6.00 | 0.20 | 1.86 | 1.43 | 1.51 | 1.45 | 1.74 | 2.37 | 2.02 |
| F | 341K | −0.14 | −1.24 | 3.07 | −0.02 | −0.74 | −0.04 | −0.51 | −0.65 | −1.25 | −0.20 | −2.70 |
| F | 341L | 0.83 | 0.85 | 1.59 | 0.64 | 1.03 | 0.93 | 0.93 | 0.66 | 0.96 | 1.14 | 1.06 |
| F | 341M | 0.54 | 1.54 | −1.70 | 0.43 | 1.47 | 1.30 | 1.29 | 0.96 | 1.30 | 1.43 | 1.41 |
| F | 341N | −0.22 | −0.60 | −9.85 | −0.06 | −0.53 | −0.03 | −0.36 | −0.43 | −0.77 | −0.10 | −0.06 |
| F | 341Q | −0.14 | −4.41 | 9.16 | −0.03 | −1.50 | −0.27 | −1.02 | −1.15 | −1.73 | −1.60 | −1.89 |
| F | 341R | −0.24 | −0.66 | −37.43 | −0.05 | −0.42 | −0.04 | −0.30 | −0.35 | −0.75 | −0.22 | −0.61 |
| F | 341S | −0.07 | −6.14 | −23.32 | −0.02 | −4.67 | −1.65 | −2.81 | −3.22 | −3.73 | −6.55 | −5.91 |
| F | 341T | −0.15 | −1.90 | −19.24 | −0.03 | −1.71 | −0.40 | −1.05 | −1.17 | −1.71 | −2.13 | −2.76 |
| F | 341V | 0.31 | 2.01 | −0.13 | 0.14 | 2.00 | 1.41 | 1.61 | 1.47 | 1.78 | 2.13 | 2.13 |
| F | 341W | 0.43 | 1.69 | 8.39 | 0.27 | 1.72 | 1.34 | 1.41 | 1.23 | 1.43 | 1.95 | 1.74 |
| F | 341Y | 0.78 | 0.79 | 1.11 | 0.61 | 1.10 | 0.97 | 0.98 | 0.69 | 1.01 | 1.13 | 1.09 |
| H | 342A | 0.61 | 1.36 | 0.61 | 0.45 | 1.22 | 0.98 | 1.03 | 0.79 | 1.05 | 1.35 | 1.08 |
| H | 342D | 0.17 | 4.54 | −11.24 | 0.07 | 2.53 | 1.33 | 1.81 | 1.86 | 2.12 | 2.98 | 3.19 |
| H | 342E | 0.10 | 6.42 | 43.94 | 0.04 | 3.89 | 1.81 | 2.72 | 2.83 | 2.98 | 4.34 | 4.31 |
| H | 342F | 0.37 | 2.07 | −0.18 | 0.20 | 1.78 | 1.31 | 1.55 | 1.60 | 1.55 | 2.11 | 1.73 |
| H | 342G | 0.35 | 2.06 | 8.76 | 0.15 | 1.70 | 1.18 | 1.34 | 1.44 | 1.46 | 1.97 | 2.12 |
| H | 342I | −0.01 | −22.21 | 7.52 | −0.01 | −24.09 | −10.83 | −15.82 | −16.14 | −19.06 | −27.19 | −24.56 |
| H | 342K | 0.95 | 0.71 | −0.53 | 0.73 | 0.93 | 0.94 | 0.95 | 0.85 | 1.04 | 1.04 | 0.94 |
| H | 342L | 0.26 | 1.63 | 4.37 | 0.10 | 2.08 | 1.30 | 1.47 | 1.15 | 1.69 | 2.06 | 2.57 |
| H | 342M | 0.30 | 2.33 | −2.01 | 0.15 | 1.78 | 1.09 | 1.26 | 1.03 | 1.44 | 2.11 | 1.88 |
| H | 342N | 0.64 | 1.53 | −1.54 | 0.47 | 1.25 | 1.08 | 1.16 | 1.06 | 1.14 | 1.38 | 1.31 |
| H | 342P | −0.56 | −0.83 | −1.70 | −0.13 | −0.27 | −0.02 | −0.18 | −0.21 | −0.40 | −0.22 | −0.40 |
| H | 342R | 0.98 | 1.03 | −1.72 | 0.78 | 0.88 | 0.96 | 1.00 | 0.92 | 0.98 | 1.09 | 1.13 |
| H | 342S | 0.44 | 1.70 | 4.31 | 0.22 | 1.62 | 1.30 | 1.43 | 1.49 | 1.46 | 1.71 | 1.76 |
| H | 342V | 0.50 | 1.14 | 0.22 | 0.25 | 1.29 | 0.93 | 1.09 | 1.04 | 1.10 | 1.53 | 1.29 |
| H | 342W | −0.25 | −0.23 | 1.27 | −0.06 | −0.42 | −0.05 | −0.29 | −0.37 | −0.68 | −0.18 | −0.91 |
| H | 342Y | 0.73 | 0.86 | 2.76 | 0.47 | 1.14 | 0.96 | 0.98 | 0.75 | 1.05 | 1.16 | 1.15 |
| N | 343A | 0.76 | 1.12 | 8.42 | 0.79 | 1.25 | 1.19 | 1.12 | 0.73 | 1.10 | 1.56 | 1.06 |
| N | 343C | 0.73 | 0.94 | −22.09 | 0.66 | 1.13 | 1.03 | 0.99 | 0.88 | 0.95 | 1.28 | 1.20 |
| N | 343D | 0.60 | 1.03 | −15.43 | 0.45 | 1.33 | 1.10 | 1.13 | 0.96 | 1.10 | 1.62 | 1.28 |
| N | 343E | 0.50 | 1.38 | 6.65 | 0.36 | 1.64 | 1.42 | 1.42 | 1.28 | 1.49 | 1.65 | 1.59 |
| N | 343F | 0.67 | 1.28 | 95.58 | 0.51 | 1.34 | 1.18 | 1.20 | 1.13 | 1.23 | 1.39 | 1.22 |
| N | 343G | 0.24 | 3.60 | 150.08 | 0.15 | 3.28 | 2.76 | 3.12 | 3.14 | 0.00 | 3.72 | 3.08 |
| N | 343H | 0.67 | 0.96 | 84.51 | 0.51 | 1.25 | 1.11 | 1.13 | 0.99 | 1.15 | 1.49 | 1.33 |
| N | 343I | 0.82 | 1.06 | 64.17 | 0.68 | 1.10 | 1.01 | 1.00 | 0.91 | 1.00 | 1.21 | 1.10 |
| N | 343K | 0.76 | 1.19 | 56.58 | 0.59 | 1.19 | 1.10 | 1.09 | 0.93 | 1.12 | 1.36 | 1.22 |
| N | 343L | 0.94 | 0.75 | 123.96 | 0.89 | 1.09 | 1.04 | 1.03 | 0.74 | 1.05 | 1.19 | 1.05 |
| N | 343M | 1.02 | 0.97 | −45.44 | 1.30 | 1.01 | 1.05 | 0.95 | 0.50 | 0.93 | 0.97 | 0.99 |
| N | 343P | 0.27 | 1.58 | 166.53 | 0.15 | 2.50 | 1.54 | 1.57 | 1.23 | 1.72 | 2.88 | 2.29 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| N | 343Q | 0.70 | 1.34 | 28.98 | 0.61 | 1.36 | 1.24 | 1.17 | 0.84 | 1.21 | 1.38 | 1.23 |
| N | 343R | 0.59 | 0.46 | 68.23 | 0.24 | 0.95 | 0.47 | 0.57 | 0.48 | 0.65 | 1.16 | 0.87 |
| N | 343S | 0.76 | 1.35 | 7.99 | 0.69 | 1.33 | 1.24 | 1.18 | 0.93 | 1.19 | 1.36 | 1.28 |
| N | 343T | 0.97 | 1.12 | 13.31 | 0.93 | 1.04 | 1.05 | 0.99 | 0.74 | 0.99 | 1.12 | 1.09 |
| N | 343V | 0.91 | 0.90 | 62.83 | 0.89 | 1.11 | 1.03 | 0.99 | 0.71 | 0.99 | 1.13 | 0.99 |
| N | 343W | 0.79 | 1.05 | 71.95 | 0.66 | 1.20 | 1.08 | 1.04 | 0.72 | 1.05 | 1.21 | 1.15 |
| N | 343Y | 0.82 | 1.18 | −110.81 | 0.91 | 1.33 | 1.40 | 1.29 | 0.92 | 1.33 | 1.29 | 1.21 |
| V | 344A | 0.24 | 1.73 | 2.34 | 0.11 | 2.03 | 0.86 | 1.18 | 0.82 | 0.82 | 2.16 | 1.96 |
| V | 344C | 1.32 | 0.79 | −0.30 | 1.91 | 0.86 | 0.99 | 0.93 | 0.71 | 0.91 | 0.72 | 0.88 |
| V | 344D | 0.90 | 0.94 | 1.00 | 0.97 | 1.02 | 1.04 | 1.01 | 0.78 | 0.98 | 1.02 | 1.02 |
| V | 344E | 0.96 | 1.03 | 2.72 | 1.01 | 1.05 | 1.01 | 0.96 | 0.77 | 0.92 | 1.00 | 1.02 |
| V | 344F | 1.02 | 1.11 | 0.70 | 1.06 | 0.98 | 1.02 | 1.00 | 0.80 | 0.95 | 1.04 | 1.09 |
| V | 344G | 0.84 | 1.05 | 0.74 | 0.70 | 1.05 | 0.99 | 0.98 | 0.78 | 0.97 | 1.25 | 1.38 |
| V | 344H | 1.08 | 0.92 | 1.12 | 1.07 | 0.95 | 0.93 | 0.89 | 0.69 | 0.85 | 1.00 | 1.00 |
| V | 344I | 0.89 | 1.15 | 0.73 | 0.86 | 1.15 | 1.10 | 1.10 | 0.84 | 1.05 | 1.20 | 1.75 |
| V | 344L | 1.16 | 0.87 | −1.00 | 1.39 | 0.94 | 0.99 | 0.98 | 0.71 | 0.93 | 0.95 | 0.93 |
| V | 344M | 0.83 | 1.23 | 1.48 | 0.93 | 1.25 | 1.22 | 1.20 | 0.85 | 1.16 | 1.20 | 1.19 |
| V | 344N | 0.92 | 1.09 | −0.66 | 0.98 | 1.08 | 1.05 | 1.00 | 0.86 | 0.97 | 1.18 | 1.16 |
| V | 344P | −0.06 | −7.34 | −26.61 | −0.02 | −2.06 | −0.09 | −1.40 | −1.50 | −2.92 | −1.06 | −1.99 |
| V | 344Q | 0.85 | 1.05 | −0.93 | 0.84 | 1.12 | 1.07 | 1.05 | 1.00 | 1.05 | 1.12 | 0.50 |
| V | 344R | 0.95 | 1.09 | 0.55 | 0.94 | 1.02 | 1.03 | 0.99 | 0.96 | 0.96 | 1.16 | 1.23 |
| V | 344S | 0.75 | 1.26 | 0.88 | 0.68 | 1.29 | 1.19 | 1.20 | 1.13 | 1.11 | 1.34 | 1.31 |
| V | 344T | 0.83 | 1.11 | 0.61 | 0.72 | 1.13 | 1.08 | 1.07 | 1.00 | 1.09 | 1.11 | 1.16 |
| V | 344W | 0.90 | 0.90 | 0.42 | 0.75 | 1.00 | 0.96 | 1.00 | 0.80 | 0.94 | 1.10 | 1.07 |
| V | 344Y | 0.53 | 1.70 | 1.38 | 0.36 | 1.63 | 1.28 | 1.31 | 0.96 | 1.50 | 1.66 | 1.53 |
| M | 345A | 0.93 | 0.98 | −1.58 | 0.95 | 0.99 | 0.92 | 0.92 | 0.68 | 0.89 | 1.08 | 1.01 |
| M | 345C | 0.88 | 1.03 | −0.68 | 0.80 | 0.99 | 0.94 | 0.95 | 0.86 | 0.92 | 1.11 | 1.10 |
| M | 345D | 0.08 | 5.78 | −8.27 | 0.03 | 3.91 | 1.23 | 2.72 | 2.83 | 2.91 | 7.30 | 2.31 |
| M | 345E | 0.66 | 1.07 | 0.74 | 0.44 | 1.08 | 0.92 | 0.95 | 0.96 | 0.95 | 1.40 | 1.46 |
| M | 345F | 0.75 | 1.09 | −0.84 | 0.54 | 1.08 | 0.94 | 1.00 | 1.02 | 1.01 | 1.26 | 1.19 |
| M | 345G | 0.50 | 1.29 | 4.22 | 0.24 | 1.35 | 0.99 | 1.12 | 1.18 | 1.11 | 1.75 | 1.66 |
| M | 345H | 0.76 | 1.29 | 2.97 | 0.56 | 1.14 | 1.10 | 1.08 | 1.09 | 1.09 | 1.35 | 1.46 |
| M | 345I | 0.64 | 1.08 | −3.78 | 0.40 | 1.20 | 1.01 | 1.08 | 1.09 | 1.05 | 1.32 | 1.16 |
| M | 345N | 0.64 | 1.29 | 0.27 | 0.50 | 1.29 | 1.13 | 1.13 | 1.03 | 1.12 | 1.66 | 1.26 |
| M | 345Q | 0.65 | 1.22 | −1.85 | 0.43 | 1.21 | 1.07 | 1.10 | 1.11 | 1.10 | 1.38 | 1.52 |
| M | 345R | −0.01 | −56.38 | 146.76 | 0.00 | −45.04 | −19.98 | −30.92 | −32.39 | −33.41 | −70.43 | −53.83 |
| M | 345S | 0.67 | 1.41 | −0.72 | 0.44 | 1.27 | 1.12 | 1.19 | 1.17 | 1.13 | 1.38 | 1.38 |
| M | 345T | 0.69 | 1.37 | 4.44 | 0.51 | 1.25 | 1.13 | 1.19 | 1.19 | 1.14 | 1.49 | 1.14 |
| M | 345V | 0.76 | 1.18 | −2.95 | 0.58 | 1.16 | 1.06 | 1.11 | 1.06 | 1.08 | 1.24 | 1.25 |
| M | 345W | 0.30 | 1.71 | −3.45 | 0.13 | 2.12 | 1.52 | 1.70 | 1.61 | 1.71 | 3.07 | 2.62 |
| M | 345Y | 0.46 | 1.36 | 4.86 | 0.24 | 1.57 | 1.22 | 1.29 | 1.05 | 1.24 | 2.14 | 2.00 |
| Q | 348A | 1.04 | 0.91 | −0.77 | 1.09 | 0.92 | 0.92 | 0.86 | 0.55 | 0.89 | 0.94 | 0.84 |
| Q | 348C | 0.91 | 1.00 | −2.40 | 0.83 | 0.98 | 0.94 | 0.93 | 0.75 | 0.93 | 1.04 | 0.94 |
| Q | 348F | 0.80 | 1.16 | 0.28 | 0.60 | 1.12 | 1.08 | 1.08 | 0.97 | 1.08 | 1.14 | 0.90 |
| Q | 348G | 0.46 | 1.70 | 3.04 | 0.27 | 1.79 | 1.50 | 1.55 | 1.40 | 1.54 | 1.99 | 1.78 |
| Q | 348H | 0.83 | 1.18 | 1.34 | 0.65 | 1.06 | 1.04 | 1.03 | 0.91 | 1.03 | 1.23 | 1.24 |
| Q | 348I | 0.73 | 1.16 | 1.56 | 0.55 | 1.26 | 1.17 | 1.18 | 1.02 | 1.18 | 1.41 | 1.10 |
| Q | 348K | 0.92 | 1.06 | −1.65 | 0.75 | 0.98 | 0.98 | 1.00 | 0.82 | 1.22 | 0.94 | 0.61 |
| Q | 348M | 0.98 | 0.99 | 1.24 | 1.12 | 1.06 | 1.09 | 0.95 | 0.48 | 0.97 | 1.07 | 1.06 |
| Q | 348N | 0.99 | 1.05 | −0.26 | 1.00 | 1.01 | 0.99 | 0.93 | 0.57 | 0.93 | 1.01 | 0.95 |
| Q | 348P | 0.14 | 3.52 | −7.69 | 0.05 | 3.76 | 1.83 | 2.54 | 2.04 | 2.61 | 5.26 | 1.96 |
| Q | 348R | 0.85 | 1.20 | 0.76 | 0.74 | 1.13 | 1.13 | 1.06 | 0.80 | 1.06 | 0.98 | 0.82 |
| Q | 348S | 0.83 | 1.12 | 0.33 | 0.75 | 1.24 | 1.16 | 1.12 | 0.84 | 1.13 | 1.21 | 1.15 |
| Q | 348T | 0.86 | 1.08 | 0.94 | 0.77 | 1.15 | 1.11 | 1.08 | 0.78 | 1.08 | 1.21 | 1.04 |
| Q | 348V | 0.86 | 1.05 | −0.63 | 0.71 | 1.07 | 1.06 | 1.03 | 0.72 | 1.05 | 1.13 | 1.11 |
| Q | 348W | 0.80 | 1.14 | −1.74 | 0.64 | 1.18 | 1.12 | 1.10 | 0.82 | 1.61 | 1.18 | 1.11 |
| Q | 348Y | 0.83 | 1.15 | −2.03 | 0.72 | 1.22 | 1.19 | 1.16 | 0.82 | 1.24 | 1.14 | 0.93 |
| E | 350A | 0.16 | 3.66 | 2089.68 | 0.07 | 2.99 | 1.13 | 1.85 | 1.32 | 2.08 | 4.30 | 2.19 |
| E | 350C | 0.20 | 2.02 | 1581.30 | 0.10 | 2.30 | 1.09 | 1.59 | 1.24 | 1.69 | 3.01 | 2.31 |
| E | 350D | 0.84 | 1.07 | 230.22 | 0.71 | 1.02 | 0.82 | 0.83 | 0.65 | 0.81 | 1.03 | 0.97 |
| E | 350F | −0.01 | 97.77 | 62765.38 | 0.00 | 29.25 | 3.66 | 23.18 | 25.39 | 31.44 | 68.41 | −34.70 |
| E | 350G | 0.00 | −61.02 | −50431.29 | 0.00 | −77.27 | −24.89 | −50.04 | −45.88 | −55.83 | −119.21 | −22.69 |
| E | 350H | −0.07 | −5.26 | −8192.20 | −0.02 | −2.63 | −0.47 | −1.96 | −1.97 | −2.41 | −5.35 | −0.01 |
| E | 350I | −0.08 | −3.86 | −4844.77 | −0.02 | −2.20 | −0.31 | −1.83 | −2.02 | −2.49 | −5.43 | 1.70 |
| E | 350K | −0.22 | 0.17 | −2371.03 | −0.04 | −0.46 | −0.07 | −0.51 | −0.64 | −0.74 | −1.24 | 0.89 |
| E | 350M | −0.03 | −14.49 | 161.98 | −0.01 | −7.08 | −1.43 | −5.01 | −3.93 | −5.97 | −11.96 | −1.41 |
| E | 350N | 0.11 | 2.34 | 561.85 | 0.04 | 2.99 | 1.01 | 2.15 | 1.75 | 2.23 | 4.78 | 2.08 |
| E | 350P | −0.13 | −5.96 | −1302.18 | −0.03 | −1.06 | −0.02 | −0.97 | −1.18 | −1.41 | −2.51 | 1.90 |
| E | 350Q | 0.02 | 14.72 | −3912.03 | 0.01 | 16.71 | 6.86 | 11.97 | 10.58 | 12.44 | 26.59 | 11.10 |
| E | 350R | −0.26 | −2.29 | −1001.06 | −0.04 | −0.42 | −0.06 | −0.44 | −0.56 | −0.65 | −1.22 | 1.19 |
| E | 350S | 0.13 | 1.51 | 2116.94 | 0.05 | 3.49 | 1.68 | 2.43 | 2.31 | 2.47 | 4.45 | 2.20 |
| E | 350T | −0.08 | −0.47 | −2459.36 | −0.02 | −5.27 | −1.76 | −3.78 | −3.56 | −4.07 | −7.68 | −4.14 |
| E | 350V | −0.12 | −1.22 | 141.82 | −0.03 | −2.27 | −0.53 | −1.72 | −1.65 | −2.03 | −4.00 | −0.48 |
| E | 350W | −0.21 | −0.16 | −540.53 | −0.05 | −0.68 | −0.10 | −0.66 | −0.76 | −0.73 | −1.43 | 1.35 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| E | 350Y | -0.17 | -0.64 | 1132.74 | -0.04 | -1.14 | -0.22 | -0.91 | -0.93 | -1.20 | -2.31 | 1.32 |
| E | 351A | 0.97 | 1.02 | -1.25 | 1.07 | 0.89 | 1.00 | 0.94 | 0.70 | 0.89 | 0.98 | 1.48 |
| E | 351C | 1.10 | 0.85 | 5.60 | 1.07 | 0.84 | 0.78 | 0.79 | 0.74 | 0.78 | 0.83 | 0.92 |
| E | 351D | 0.94 | 1.03 | 1.61 | 0.86 | 0.97 | 0.96 | 0.97 | 0.98 | 0.95 | 1.15 | 1.10 |
| E | 351G | 0.99 | 0.90 | 4.88 | 0.76 | 0.92 | 0.87 | 0.88 | 0.92 | 0.88 | 1.00 | 1.02 |
| E | 351H | 0.80 | 1.24 | 11.63 | 0.69 | 1.16 | 1.10 | 1.14 | 1.15 | 1.05 | 1.28 | 1.20 |
| E | 351K | 0.69 | 1.33 | -14.81 | 0.59 | 1.33 | 1.29 | 1.32 | 1.16 | 1.23 | 1.48 | 1.43 |
| E | 351L | 1.00 | 0.90 | -6.20 | 1.00 | 0.99 | 1.12 | 0.99 | 0.72 | 0.85 | 1.04 | 0.96 |
| E | 351M | 0.97 | 0.94 | -4.01 | 0.99 | 0.98 | 0.99 | 0.91 | 0.67 | 0.88 | 0.96 | 0.85 |
| E | 351P | 0.80 | 1.08 | 2.76 | 0.67 | 1.07 | 0.96 | 0.98 | 0.95 | 0.96 | 1.23 | 1.07 |
| E | 351Q | 0.96 | 0.98 | 10.12 | 0.81 | 0.96 | 0.94 | 0.96 | 0.93 | 0.90 | 1.01 | 0.92 |
| E | 351R | 1.03 | 0.93 | -3.04 | 0.84 | 0.90 | 0.88 | 0.88 | 0.89 | 0.81 | 0.98 | 0.94 |
| E | 351S | 0.44 | 2.17 | 46.94 | 0.31 | 1.60 | 0.37 | 0.99 | 0.81 | 0.39 | 2.03 | 1.46 |
| E | 351T | 0.67 | 1.44 | 17.90 | 0.49 | 1.28 | 1.10 | 1.17 | 1.14 | 1.15 | 1.44 | 1.31 |
| E | 351V | 0.80 | 1.15 | -0.36 | 0.63 | 1.15 | 1.04 | 1.08 | 1.02 | 1.05 | 1.22 | 1.19 |
| E | 351W | 0.88 | 1.35 | 12.64 | 0.75 | 1.06 | 0.99 | 1.02 | 0.90 | 1.01 | 1.12 | 1.07 |
| E | 351Y | 0.75 | 1.33 | 17.22 | 0.69 | 1.29 | 1.21 | 1.27 | 0.92 | 1.24 | 1.41 | 1.34 |
| L | 352A | 0.73 | 1.10 | 5.37 | 0.64 | 1.18 | 0.89 | 0.93 | 0.63 | 0.88 | 1.28 | 1.11 |
| L | 352C | 0.89 | 0.90 | 8.03 | 0.84 | 0.99 | 0.81 | 0.83 | 0.63 | 0.80 | 0.98 | 0.86 |
| L | 352D | 0.24 | 2.07 | 23.54 | 0.10 | 1.73 | 0.59 | 1.24 | 1.12 | 2.05 | 2.22 | 1.59 |
| L | 352E | 0.33 | 1.84 | 10.18 | 0.17 | 1.77 | 0.96 | 1.31 | 1.12 | 2.04 | 2.22 | 1.90 |
| L | 352F | 0.93 | 1.00 | 1.73 | 0.90 | 1.04 | 0.95 | 0.90 | 0.75 | 0.92 | 1.05 | 1.01 |
| L | 352G | 0.35 | 1.80 | 12.26 | 0.18 | 1.92 | 1.21 | 1.38 | 1.21 | 1.40 | 2.13 | 1.90 |
| L | 352H | 0.68 | 1.23 | 1.04 | 0.49 | 1.23 | 0.98 | 1.02 | 0.80 | 0.95 | 1.31 | 1.07 |
| L | 352I | 0.92 | 1.03 | 7.73 | 0.91 | 0.98 | 1.03 | 0.97 | 0.79 | 0.98 | 1.03 | 0.98 |
| L | 352K | 0.45 | 1.22 | 10.66 | 0.27 | 1.52 | 0.98 | 1.09 | 0.92 | 1.02 | 1.73 | 1.36 |
| L | 352N | 0.43 | 1.29 | -1.33 | 0.28 | 1.48 | 0.97 | 1.20 | 1.14 | 1.36 | 1.75 | 1.35 |
| L | 352Q | 0.58 | 1.24 | -0.50 | 0.42 | 1.29 | 1.00 | 1.14 | 1.09 | 1.15 | 1.49 | 1.14 |
| L | 352R | 0.32 | 1.43 | -8.34 | 0.16 | 1.81 | 1.02 | 1.30 | 1.24 | 1.31 | 2.14 | 1.62 |
| L | 352T | 0.59 | 1.34 | -4.01 | 0.41 | 1.31 | 1.02 | 1.14 | 1.07 | 1.09 | 1.37 | 1.18 |
| L | 352V | 0.21 | 5.19 | 10.40 | 0.13 | 3.67 | 3.26 | -0.06 | 1.23 | 0.00 | 3.73 | 3.64 |
| L | 352W | 0.30 | 1.90 | 1.79 | 0.14 | 1.86 | 1.15 | 1.44 | 1.29 | 1.46 | 2.12 | 1.55 |
| L | 352Y | 0.51 | 1.02 | -5.63 | 0.35 | 1.46 | 1.12 | 1.18 | 0.88 | 1.12 | 1.58 | 1.41 |
| S | 353A | 1.07 | 0.91 | 14.67 | 1.32 | 0.99 | 0.94 | 0.90 | 0.54 | 0.88 | 0.96 | 0.98 |
| S | 353C | 1.12 | 0.88 | 7.41 | 1.28 | 0.89 | 0.87 | 0.83 | 0.62 | 0.79 | 0.90 | 0.90 |
| S | 353D | 0.99 | 1.00 | 14.61 | 1.02 | 1.00 | 0.90 | 0.86 | 0.69 | 0.85 | 1.04 | 0.98 |
| S | 353E | 0.91 | 1.02 | 23.26 | 0.94 | 1.06 | 0.97 | 0.95 | 0.78 | 0.91 | 1.04 | 1.03 |
| S | 353F | 1.19 | 0.84 | 4.90 | 1.26 | 0.88 | 0.83 | 0.82 | 0.69 | 0.81 | 0.90 | 0.91 |
| S | 353G | 0.89 | 1.17 | -0.03 | 0.91 | 1.13 | 1.05 | 1.05 | 0.90 | 0.99 | 1.10 | 1.12 |
| S | 353I | 0.88 | 1.10 | 14.31 | 0.90 | 1.14 | 1.08 | 1.05 | 0.84 | 0.99 | 1.11 | 1.10 |
| S | 353K | 0.96 | 0.99 | 17.02 | 1.05 | 1.06 | 1.06 | 1.03 | 0.77 | 0.97 | 1.09 | 1.09 |
| S | 353L | 0.92 | 0.97 | 24.76 | 1.05 | 1.12 | 1.12 | 1.08 | 0.75 | 1.07 | 1.15 | 1.04 |
| S | 353M | 0.96 | 0.92 | 13.11 | 1.03 | 1.00 | 0.95 | 0.89 | 0.65 | 0.88 | 1.00 | 1.04 |
| S | 353N | 1.10 | 0.87 | -2.29 | 1.08 | 0.84 | 0.78 | 0.78 | 0.69 | 0.76 | 0.89 | 0.85 |
| S | 353P | -0.07 | -4.78 | -57.60 | -0.02 | -1.39 | -0.11 | -1.48 | -1.78 | -1.80 | -4.28 | -0.75 |
| S | 353Q | 0.84 | 1.11 | 6.15 | 0.81 | 1.10 | 1.01 | 1.02 | 0.99 | 0.98 | 1.14 | 1.02 |
| S | 353R | 1.01 | 0.99 | 11.33 | 1.01 | 0.95 | 0.90 | 0.89 | 0.89 | 0.85 | 0.94 | 0.94 |
| S | 353T | 1.07 | 0.93 | 7.93 | 1.03 | 0.89 | 0.87 | 0.88 | 0.87 | 0.86 | 0.85 | 0.87 |
| S | 353V | 0.94 | 1.04 | 18.99 | 0.82 | 0.98 | 0.91 | 0.93 | 0.87 | 0.84 | 1.08 | 1.02 |
| S | 353W | 0.82 | 1.07 | 13.93 | 0.66 | 1.06 | 0.94 | 1.01 | 0.85 | 0.93 | 1.11 | 1.09 |
| S | 353Y | 1.02 | 0.92 | 18.76 | 1.04 | 0.95 | 1.02 | 0.96 | 0.67 | 0.92 | 1.04 | 1.03 |
| N | 354A | 0.32 | 1.85 | 0.76 | 0.14 | 1.61 | 0.85 | 1.11 | 0.87 | 1.14 | 2.45 | 0.41 |
| N | 354C | 0.39 | 1.64 | 2.76 | 0.21 | 1.50 | 1.04 | 1.20 | 1.04 | 1.14 | 2.21 | 1.99 |
| N | 354D | 0.00 | 248.18 | -521.87 | 0.00 | 202.68 | 73.32 | 136.39 | 138.02 | 149.21 | 316.41 | 200.63 |
| N | 354E | -0.15 | 1.39 | 26.56 | -0.03 | -0.60 | -0.06 | -0.67 | -0.80 | -0.81 | -1.97 | -0.30 |
| N | 354G | -0.13 | -4.95 | 72.01 | -0.03 | -2.12 | -0.55 | -1.42 | -1.50 | -1.59 | -3.86 | -2.12 |
| N | 354H | -0.06 | -6.38 | -29.39 | -0.01 | -4.25 | -1.14 | -2.92 | -3.05 | -3.07 | -7.82 | -4.29 |
| N | 354I | -0.08 | -6.47 | -31.99 | -0.02 | -4.30 | -1.19 | -2.91 | -2.89 | -3.12 | -7.49 | -5.52 |
| N | 354K | -0.24 | -1.26 | 9.65 | -0.04 | -0.97 | -0.18 | -0.70 | -0.73 | -0.85 | -1.75 | -1.21 |
| N | 354L | -0.10 | -1.51 | -35.28 | -0.02 | -1.79 | -0.28 | -1.41 | -1.42 | -1.78 | -3.38 | -2.29 |
| N | 354M | 0.09 | 4.19 | -12.86 | 0.03 | 3.89 | 1.33 | 2.42 | 1.90 | 2.64 | 6.05 | 2.45 |
| N | 354P | 0.09 | 6.09 | 69.83 | 0.03 | 4.55 | 1.77 | 2.98 | 2.52 | 3.16 | 7.07 | 5.75 |
| N | 354Q | 0.27 | 2.37 | -19.73 | 0.11 | 2.18 | 1.22 | 1.48 | 1.24 | 1.56 | 2.68 | 2.41 |
| N | 354R | -0.03 | -16.94 | 166.59 | -0.01 | -7.82 | -1.60 | -5.43 | -5.27 | -6.08 | -13.48 | -3.46 |
| N | 354S | 0.26 | 2.35 | 35.57 | 0.13 | 2.64 | 1.63 | 1.86 | 1.56 | 1.80 | 3.05 | 2.78 |
| N | 354T | 0.43 | 1.54 | 44.09 | 0.20 | 1.71 | 1.07 | 1.23 | 0.99 | 1.19 | 1.83 | 1.95 |
| N | 354W | -0.11 | -1.66 | -20.75 | -0.02 | -1.86 | -0.30 | -1.38 | -1.31 | -1.65 | -3.09 | -2.48 |
| N | 354Y | -0.08 | -3.34 | 3.70 | -0.02 | -1.22 | -0.11 | -1.39 | -1.62 | -1.90 | -3.34 | -1.57 |
| P | 355C | 0.76 | 1.01 | 0.93 | 0.64 | 1.09 | 0.91 | 0.94 | 0.92 | 0.93 | 1.18 | 1.04 |
| P | 355D | 0.24 | 1.68 | 4.18 | 0.10 | 1.82 | 0.81 | 1.27 | 1.43 | 1.41 | 2.44 | 1.57 |
| P | 355E | 0.27 | 1.44 | -4.15 | 0.13 | 2.00 | 1.15 | 1.55 | 1.67 | 1.60 | 2.57 | 1.43 |
| P | 355F | 0.64 | 1.06 | 4.60 | 0.44 | 1.12 | 0.85 | 0.95 | 1.01 | 1.00 | 1.17 | 1.06 |
| P | 355G | 0.42 | 1.43 | 14.54 | 0.22 | 1.56 | 1.03 | 1.19 | 1.31 | 1.23 | 1.81 | 1.46 |
| P | 355H | -0.12 | -2.16 | 14.20 | -0.02 | -0.84 | -0.05 | -0.91 | -1.24 | -1.40 | -2.07 | 1.28 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| P | 355I | 0.76 | 1.07 | −3.80 | 0.59 | 1.14 | 1.01 | 1.06 | 1.03 | 1.07 | 1.25 | 1.14 |
| P | 355K | 0.12 | 3.26 | −28.75 | 0.04 | 3.08 | 1.36 | 2.35 | 2.38 | 2.53 | 4.67 | 2.08 |
| P | 355L | 0.73 | 1.03 | 7.09 | 0.55 | 1.21 | 1.07 | 1.07 | 0.80 | 1.03 | 1.26 | 1.12 |
| P | 355M | 0.53 | 1.33 | 1.80 | 0.45 | 1.51 | 1.29 | 1.34 | 1.10 | 2.47 | 1.42 | 1.31 |
| P | 355N | 0.22 | 1.98 | 16.34 | 0.10 | 2.01 | 0.99 | 1.45 | 1.50 | 1.58 | 2.50 | 1.58 |
| P | 355R | 0.00 | −139.81 | 983.13 | 0.00 | −154.86 | −41.92 | −108.04 | −130.85 | −137.91 | −243.58 | −19.82 |
| P | 355T | 0.44 | 1.70 | −5.62 | 0.25 | 1.75 | 1.38 | 1.51 | 1.63 | 1.52 | 2.07 | 1.91 |
| P | 355V | 0.77 | 1.07 | 6.84 | 0.60 | 1.14 | 1.05 | 1.11 | 1.07 | 1.14 | 1.23 | 1.03 |
| P | 355W | 0.41 | 1.54 | −3.05 | 0.23 | 1.66 | 1.20 | 1.34 | 1.27 | 1.36 | 1.98 | 1.50 |
| P | 355Y | 0.62 | 1.10 | −2.23 | 0.50 | 1.40 | 1.21 | 1.20 | 0.92 | 1.17 | 1.48 | 1.32 |
| N | 356A | 1.43 | 0.76 | 1.78 | 2.09 | 0.80 | 0.94 | 0.88 | 0.69 | 0.92 | 0.69 | 0.72 |
| N | 356C | 0.92 | 0.95 | 1.19 | 0.82 | 0.95 | 0.86 | 0.87 | 0.80 | 0.85 | 0.99 | 0.91 |
| N | 356D | 0.79 | 1.21 | 2.16 | 0.74 | 1.15 | 1.11 | 1.15 | 1.11 | 1.16 | 1.15 | 1.25 |
| N | 356E | 0.96 | 0.90 | −1.38 | 0.86 | 0.91 | 0.89 | 0.93 | 0.93 | 0.92 | 0.90 | 1.03 |
| N | 356F | 0.83 | 1.00 | −2.75 | 0.66 | 1.01 | 0.88 | 0.95 | 0.97 | 0.91 | 1.11 | 0.92 |
| N | 356G | 0.80 | 1.26 | 0.20 | 0.72 | 1.19 | 1.14 | 1.17 | 1.19 | 1.14 | 1.29 | 1.11 |
| N | 356H | 0.94 | 0.91 | 0.72 | 0.84 | 0.98 | 0.94 | 0.97 | 1.00 | 0.90 | 1.06 | 0.90 |
| N | 356I | 0.75 | 1.05 | 1.02 | 0.57 | 1.12 | 0.98 | 1.03 | 1.03 | 1.00 | 1.17 | 1.01 |
| N | 356K | 0.84 | 1.01 | −0.80 | 0.69 | 1.09 | 1.00 | 1.03 | 0.95 | 0.96 | 1.15 | 1.22 |
| N | 356L | 0.87 | 1.02 | −4.80 | 0.78 | 1.08 | 1.00 | 1.01 | 0.80 | 1.03 | 1.10 | 1.18 |
| N | 356M | 0.97 | 1.02 | −0.14 | 1.06 | 1.00 | 1.06 | 0.97 | 0.72 | 0.95 | 0.97 | 0.77 |
| N | 356P | 0.67 | 1.12 | −1.94 | 0.49 | 1.18 | 0.94 | 1.03 | 1.02 | 1.01 | 1.34 | 1.07 |
| N | 356Q | 1.73 | 0.63 | −0.74 | 2.49 | 0.65 | 0.82 | 0.84 | 0.91 | 0.91 | 0.65 | 0.60 |
| N | 356T | 0.73 | 1.19 | −1.93 | 0.63 | 1.20 | 1.10 | 1.15 | 1.20 | 1.12 | 1.26 | 1.05 |
| N | 356W | 0.66 | 1.25 | 6.88 | 0.48 | 1.22 | 1.01 | 1.11 | 1.04 | 0.99 | 1.49 | 1.23 |
| N | 356Y | 0.75 | 1.10 | 1.99 | 0.64 | 1.22 | 1.09 | 1.13 | 0.91 | 1.07 | 1.34 | 1.01 |
| Q | 360A | 1.13 | 0.99 | 0.39 | 1.44 | 0.94 | 0.90 | 0.87 | 0.71 | 0.90 | 0.86 | 0.83 |
| Q | 360C | 0.95 | 1.12 | 0.70 | 1.04 | 1.07 | 1.01 | 0.99 | 0.79 | 1.02 | 1.06 | 1.04 |
| Q | 360D | 0.91 | 1.09 | 1.02 | 0.99 | 1.05 | 0.97 | 0.92 | 0.73 | 0.96 | 1.04 | 0.99 |
| Q | 360E | 1.13 | 0.95 | 0.96 | 1.29 | 0.88 | 0.84 | 0.83 | 0.69 | 0.81 | 0.87 | 0.69 |
| Q | 360F | 0.94 | 1.12 | 0.46 | 1.05 | 1.10 | 1.04 | 1.00 | 0.81 | 0.97 | 1.00 | 2.66 |
| Q | 360H | 0.90 | 1.08 | 0.18 | 0.99 | 1.16 | 1.14 | 1.04 | 0.91 | 0.96 | 1.11 | 1.25 |
| Q | 360I | 0.89 | 0.82 | 0.04 | 0.96 | 1.02 | 0.95 | 0.89 | 0.72 | 0.85 | 0.96 | 0.84 |
| Q | 360L | 0.88 | 0.93 | 0.25 | 1.07 | 1.15 | 1.22 | 1.10 | 0.78 | 1.08 | 1.15 | 0.98 |
| Q | 360M | 0.91 | 1.22 | 0.47 | 0.95 | 1.04 | 0.94 | 1.00 | 0.80 | 0.99 | 1.10 | 1.16 |
| Q | 360N | 0.83 | 1.26 | 1.51 | 0.81 | 1.09 | 1.00 | 1.08 | 0.96 | 1.12 | 1.12 | 1.17 |
| Q | 360P | 0.62 | 1.31 | 1.37 | 0.52 | 1.21 | 0.97 | 1.01 | 0.97 | 1.07 | 1.34 | 1.31 |
| Q | 360R | 0.77 | 1.38 | 0.91 | 0.76 | 1.26 | 1.20 | 1.24 | 1.18 | 1.11 | 1.25 | 1.24 |
| Q | 360T | 0.71 | 1.36 | 1.31 | 0.70 | 1.37 | 1.29 | 1.26 | 1.23 | 1.26 | 1.32 | 1.42 |
| Q | 360W | 0.75 | 1.12 | 0.39 | 0.76 | 1.16 | 1.09 | 1.10 | 0.91 | 1.03 | 1.24 | 1.32 |
| Q | 360Y | 0.83 | 1.05 | 0.46 | 0.87 | 1.17 | 1.13 | 1.06 | 0.74 | 1.05 | 1.17 | 1.10 |
| I | 361A | 0.07 | 4.12 | 12.44 | 0.03 | 4.72 | 1.45 | 3.06 | 2.94 | 3.76 | 6.77 | 0.50 |
| I | 361C | 0.84 | 0.86 | 0.21 | 0.72 | 1.04 | 0.92 | 0.95 | 0.89 | 0.94 | 1.19 | 0.97 |
| I | 361D | 0.00 | 84.20 | 356.36 | 0.00 | 44.16 | 8.31 | 33.08 | 39.57 | 44.37 | 77.76 | −2.88 |
| I | 361G | 0.17 | 1.89 | 9.14 | 0.06 | 3.08 | 1.53 | 2.17 | 2.38 | 2.40 | 4.01 | 2.20 |
| I | 361H | 0.39 | 1.31 | 4.61 | 0.20 | 1.60 | 1.08 | 1.27 | 1.36 | 1.27 | 2.04 | 1.49 |
| I | 361K | −0.13 | −2.27 | −4.43 | −0.03 | −1.77 | −0.34 | −1.30 | −1.51 | −1.68 | −3.25 | 0.25 |
| I | 361L | 0.94 | 0.84 | 1.33 | 0.85 | 1.06 | 1.00 | 0.98 | 0.85 | 0.94 | 1.05 | 1.15 |
| I | 361M | 0.97 | 0.94 | 1.21 | 1.06 | 0.99 | 0.98 | 0.90 | 0.68 | 0.88 | 1.09 | 0.82 |
| I | 361N | 0.57 | 0.95 | 3.24 | 0.39 | 1.22 | 0.94 | 0.99 | 0.94 | 0.97 | 1.40 | 0.93 |
| I | 361Q | 0.56 | 1.09 | 1.78 | 0.35 | 1.28 | 0.98 | 1.13 | 1.17 | 1.12 | 1.49 | 1.29 |
| I | 361R | 0.04 | 9.22 | 14.85 | 0.01 | 9.80 | 3.90 | 6.57 | 7.48 | 7.16 | 13.53 | 1.68 |
| I | 361S | 0.61 | 1.03 | 1.95 | 0.36 | 1.27 | 1.00 | 1.09 | 1.15 | 1.11 | 1.43 | 1.29 |
| I | 361T | 0.84 | 0.99 | 1.35 | 0.71 | 1.06 | 0.97 | 1.02 | 1.05 | 1.00 | 1.13 | 0.95 |
| I | 361V | 0.81 | 0.95 | 0.92 | 0.65 | 1.12 | 1.05 | 1.09 | 1.09 | 1.09 | 1.16 | 0.97 |
| I | 361W | 0.13 | 3.21 | 8.81 | 0.05 | 4.04 | 2.11 | 2.90 | 2.94 | 3.18 | 5.35 | 2.42 |
| I | 361Y | 0.26 | 1.61 | 9.70 | 0.13 | 2.65 | 1.70 | 1.96 | 1.73 | 1.99 | 2.95 | 2.99 |
| F | 362A | 0.68 | 1.05 | −0.15 | 0.55 | 1.19 | 1.02 | 1.04 | 0.77 | 1.03 | 1.22 | 1.11 |
| F | 362C | 0.57 | 1.02 | 2.16 | 0.40 | 1.27 | 1.06 | 1.12 | 1.04 | 1.12 | 1.44 | 1.18 |
| F | 362D | −0.06 | −7.79 | −3.73 | −0.01 | −1.82 | −0.12 | −2.00 | −2.60 | −3.26 | −5.42 | 6.48 |
| F | 362E | 0.06 | 4.83 | 38.88 | 0.02 | 5.31 | 1.73 | 3.85 | 4.40 | 4.59 | 8.45 | 1.17 |
| F | 362G | −0.02 | −9.86 | −104.75 | 0.00 | −21.50 | −8.00 | −15.27 | −17.59 | −17.57 | −33.73 | −12.18 |
| F | 362H | 0.43 | 1.28 | 3.26 | 0.21 | 1.54 | 1.11 | 1.32 | 1.34 | 1.28 | 1.83 | 1.44 |
| F | 362I | 0.68 | 0.96 | 1.07 | 0.44 | 1.17 | 1.00 | 1.08 | 1.08 | 1.07 | 1.33 | 1.13 |
| F | 362K | −0.19 | −0.55 | −10.48 | −0.04 | −0.80 | −0.12 | −0.70 | −0.86 | −0.94 | −1.67 | 1.03 |
| F | 362L | 0.71 | 0.98 | 2.82 | 0.62 | 1.29 | 1.18 | 1.18 | 0.97 | 1.17 | 1.30 | 1.35 |
| F | 362M | 0.45 | 1.25 | −0.15 | 0.30 | 1.52 | 1.09 | 1.17 | 0.85 | 1.16 | 1.59 | 1.23 |
| F | 362N | −0.03 | −9.07 | −15.18 | −0.01 | −9.50 | −3.16 | −6.64 | −6.93 | −7.73 | −15.10 | −0.86 |
| F | 362Q | 0.08 | 2.63 | 12.56 | 0.03 | 5.14 | 2.32 | 3.79 | 4.07 | 4.04 | 8.02 | 3.70 |
| F | 362R | −0.19 | −0.60 | −1.95 | −0.03 | −0.53 | −0.09 | −0.60 | −0.78 | −0.94 | −1.45 | 1.35 |
| F | 362S | 0.24 | 1.69 | 2.76 | 0.10 | 2.51 | 1.51 | 1.89 | 1.98 | 1.99 | 3.10 | 1.99 |
| F | 362T | 0.22 | 2.16 | 5.63 | 0.08 | 2.25 | 1.16 | 1.66 | 1.74 | 1.76 | 3.15 | 2.03 |
| F | 362V | 0.64 | 1.15 | 0.95 | 0.41 | 1.26 | 1.03 | 1.13 | 1.13 | 1.11 | 1.36 | 1.27 |
| F | 362Y | 0.73 | 1.02 | 1.98 | 0.63 | 1.32 | 1.28 | 1.25 | 1.00 | 1.25 | 1.34 | 1.45 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| M | 363A | 0.97 | 1.02 | 0.61 | 1.03 | 0.90 | 0.80 | 0.83 | 0.69 | 0.86 | 0.94 | 0.85 |
| M | 363C | 0.88 | 1.04 | 0.26 | 0.81 | 0.87 | 0.76 | 0.86 | 0.78 | 0.87 | 0.91 | 0.96 |
| M | 363D | 0.61 | 0.66 | 1.80 | 0.25 | 0.44 | 0.14 | 0.25 | 0.27 | 0.34 | 0.74 | 0.48 |
| M | 363E | 0.72 | 1.07 | 1.09 | 0.58 | 0.93 | 0.75 | 0.83 | 0.83 | 0.85 | 1.11 | 0.93 |
| M | 363F | 1.06 | 0.76 | 0.88 | 0.96 | 0.73 | 0.64 | 0.67 | 0.68 | 0.67 | 0.79 | 0.66 |
| M | 363G | 0.77 | 0.70 | -0.31 | 0.53 | 0.78 | 0.55 | 0.57 | 0.58 | 0.58 | 0.90 | 0.87 |
| M | 363H | 0.63 | 0.80 | 1.93 | 0.41 | 0.98 | 0.71 | 0.74 | 0.74 | 0.72 | 1.13 | 1.85 |
| M | 363L | 0.85 | 0.91 | 0.66 | 0.88 | 1.05 | 0.99 | 0.96 | 0.62 | 0.93 | 1.00 | 1.15 |
| M | 363N | 0.23 | 1.42 | 3.86 | 0.12 | 2.00 | 0.98 | 1.36 | 1.33 | 1.50 | 2.69 | 2.28 |
| M | 363P | -0.04 | 1.14 | -46.56 | -0.01 | -5.10 | -0.67 | -2.93 | -3.69 | -6.38 | -12.57 | -6.89 |
| M | 363Q | 0.83 | 1.16 | 1.72 | 0.69 | 1.05 | 0.96 | 0.98 | 1.01 | 1.03 | 1.21 | 1.02 |
| M | 363R | 0.39 | 1.66 | 2.56 | 0.22 | 1.61 | 1.14 | 1.19 | 1.29 | 1.30 | 1.97 | 1.68 |
| M | 363S | 0.58 | 1.46 | -0.26 | 0.44 | 1.40 | 1.22 | 1.22 | 1.28 | 1.26 | 1.51 | 1.45 |
| M | 363V | 0.47 | 1.40 | 1.35 | 0.30 | 1.71 | 1.43 | 1.45 | 1.36 | 1.42 | 1.91 | 1.88 |
| M | 363W | 0.39 | 1.48 | 1.68 | 0.23 | 1.64 | 1.14 | 1.20 | 1.00 | 1.23 | 1.95 | 1.85 |
| M | 363Y | 0.64 | 1.28 | -0.01 | 0.57 | 1.43 | 1.34 | 1.28 | 0.78 | 1.23 | 1.39 | 1.30 |
| N | 364A | 0.75 | 1.19 | 751.03 | 0.76 | 1.36 | 1.24 | 1.24 | 0.91 | 1.02 | 1.16 | 1.09 |
| N | 364C | 0.86 | 1.01 | 341.04 | 0.70 | 1.01 | 0.90 | 0.92 | 0.85 | 0.89 | 1.11 | 1.21 |
| N | 364D | 0.41 | 1.19 | 311.51 | 0.20 | 1.36 | 0.83 | 1.07 | 1.08 | 1.10 | 1.78 | 1.34 |
| N | 364E | 0.14 | 1.54 | 1508.47 | 0.06 | 2.76 | 1.21 | 2.03 | 2.13 | 2.19 | 4.01 | 2.49 |
| N | 364F | -0.23 | -1.89 | -504.60 | -0.04 | -0.40 | -0.08 | -0.42 | -0.54 | -0.66 | -1.11 | 1.20 |
| N | 364G | 0.72 | 0.85 | 102.82 | 0.51 | 1.11 | 0.91 | 0.96 | 1.01 | 0.96 | 1.17 | 1.16 |
| N | 364H | -0.08 | -3.06 | -994.85 | -0.02 | -3.66 | -1.15 | -2.62 | -2.93 | -3.02 | -6.60 | -1.32 |
| N | 364I | 0.65 | 1.17 | 558.66 | 0.51 | 1.39 | 1.21 | 1.30 | 1.26 | 1.24 | 1.40 | 1.61 |
| N | 364K | -0.16 | 3.63 | -1041.61 | -0.04 | -0.72 | -0.06 | -0.74 | -0.93 | -1.08 | -1.65 | 2.13 |
| N | 364L | 0.66 | 1.12 | -485.91 | 0.50 | 1.30 | 1.08 | 1.13 | 0.89 | 1.11 | 1.48 | 1.42 |
| N | 364M | 0.74 | 1.19 | -394.29 | 0.74 | 1.30 | 1.28 | 1.19 | 0.89 | 1.21 | 1.25 | 1.25 |
| N | 364P | -0.20 | -2.36 | -1423.09 | -0.04 | -0.55 | -0.06 | -0.59 | -0.74 | -0.70 | -1.67 | -0.16 |
| N | 364Q | 0.77 | 0.98 | 345.52 | 0.60 | 1.04 | 0.95 | 0.97 | 1.00 | 1.00 | 1.16 | 1.24 |
| N | 364S | 0.64 | 1.28 | 249.89 | 0.47 | 1.33 | 1.13 | 1.20 | 1.24 | 1.20 | 1.36 | 1.52 |
| N | 364T | 0.68 | 0.99 | 401.39 | 0.53 | 1.21 | 1.07 | 1.14 | 1.16 | 1.14 | 1.22 | 1.29 |
| N | 364V | 0.59 | 1.11 | 821.17 | 0.40 | 1.38 | 1.21 | 1.34 | 1.28 | 1.31 | 1.47 | 1.61 |
| N | 364W | -0.31 | 1.00 | -816.80 | -0.05 | -0.32 | -0.02 | -0.37 | -0.48 | -0.56 | -0.90 | 0.73 |
| N | 364Y | -0.29 | 1.01 | -1891.85 | -0.07 | -0.35 | -0.08 | -0.40 | -0.49 | -0.59 | -0.81 | 0.80 |
| Q | 365A | 1.11 | 0.97 | 2.03 | 1.35 | 0.90 | 0.91 | 0.87 | 0.67 | 0.88 | 0.80 | 0.98 |
| Q | 365C | 0.80 | 1.00 | 2.32 | 0.73 | 1.11 | 1.02 | 1.04 | 0.97 | 1.09 | 1.12 | 1.24 |
| Q | 365D | 0.39 | 0.87 | -0.08 | 0.17 | 1.38 | 0.77 | 1.05 | 1.13 | 1.08 | 1.81 | 1.42 |
| Q | 365E | 1.04 | 0.89 | 2.26 | 1.01 | 0.87 | 0.85 | 0.86 | 0.89 | 0.86 | 0.91 | 0.86 |
| Q | 365F | 0.08 | 1.50 | -0.64 | 0.02 | 2.83 | -0.07 | 1.60 | 1.93 | 2.05 | 4.16 | -1.82 |
| Q | 365G | 0.84 | 1.01 | 5.51 | 0.72 | 1.08 | 1.05 | 1.07 | 1.16 | 1.04 | 1.06 | 0.99 |
| Q | 365I | 0.74 | 1.09 | -1.08 | 0.58 | 1.16 | 1.05 | 1.09 | 1.11 | 1.10 | 1.26 | 1.09 |
| Q | 365K | 0.75 | 0.97 | 7.99 | 0.58 | 1.16 | 1.06 | 1.08 | 0.97 | 1.05 | 1.23 | 1.25 |
| Q | 365L | 0.74 | 1.15 | -1.33 | 0.66 | 1.25 | 1.17 | 1.16 | 0.88 | 1.14 | 1.28 | 1.01 |
| Q | 365M | 0.91 | 1.05 | 1.84 | 1.05 | 1.08 | 1.05 | 0.99 | 0.72 | 0.98 | 1.03 | 1.06 |
| Q | 365N | 0.71 | 1.22 | -4.68 | 0.68 | 1.24 | 1.13 | 1.15 | 1.02 | 1.14 | 1.27 | 1.14 |
| Q | 365P | -0.07 | -8.57 | 37.60 | -0.02 | -2.37 | -0.43 | -2.02 | -2.57 | -2.88 | -5.82 | 1.67 |
| Q | 365R | 0.80 | 1.25 | -2.30 | 0.58 | 1.12 | 1.03 | 1.04 | 1.06 | 1.04 | 1.21 | 1.21 |
| Q | 365S | 0.81 | 1.17 | -1.27 | 0.66 | 1.14 | 1.08 | 1.11 | 1.14 | 1.10 | 1.13 | 1.08 |
| Q | 365T | 0.83 | 1.09 | 0.53 | 0.69 | 1.09 | 1.04 | 1.07 | 1.10 | 1.07 | 1.08 | 1.04 |
| Q | 365V | 0.77 | 1.16 | 1.55 | 0.57 | 1.14 | 1.03 | 1.09 | 1.06 | 1.07 | 1.13 | 1.10 |
| Q | 365W | 0.40 | 1.55 | -9.87 | 0.20 | 1.77 | 1.28 | 1.42 | 1.35 | 1.42 | 2.04 | 1.59 |
| Q | 365Y | 0.35 | 1.55 | 19.77 | 0.19 | 2.05 | 1.45 | 1.60 | 1.27 | 1.60 | 2.35 | 1.90 |
| R | 366A | 0.42 | 1.26 | 1.48 | 0.25 | 1.29 | 0.78 | 0.92 | 0.73 | 0.97 | 1.61 | 1.23 |
| R | 366C | 0.25 | 1.77 | 1.32 | 0.12 | 1.65 | 0.85 | 1.14 | 1.05 | 1.30 | 2.39 | 2.74 |
| R | 366D | -0.08 | -2.34 | -12.93 | -0.02 | -1.78 | -0.25 | -1.03 | -1.24 | -2.34 | -3.51 | -1.30 |
| R | 366E | 0.04 | 0.23 | 6.03 | 0.02 | 3.01 | 0.44 | 1.58 | 1.86 | 3.03 | 6.80 | 2.60 |
| R | 366F | 0.11 | 1.83 | 4.70 | 0.05 | 1.63 | 0.42 | 0.82 | 0.97 | 1.33 | 2.80 | 2.01 |
| R | 366G | 0.07 | -0.23 | 5.71 | 0.03 | 3.30 | 1.15 | 1.83 | 1.94 | 2.44 | 5.03 | 4.15 |
| R | 366H | 0.11 | 1.88 | -1.74 | 0.05 | 2.84 | 1.26 | 1.62 | 1.68 | 1.98 | 3.98 | 3.68 |
| R | 366K | 0.43 | 0.80 | 1.22 | 0.25 | 1.22 | 0.84 | 0.86 | 0.74 | 0.93 | 1.52 | 2.12 |
| R | 366L | 0.31 | 1.18 | 0.52 | 0.18 | 1.86 | 1.21 | 1.27 | 0.81 | 1.36 | 2.12 | 2.05 |
| R | 366M | 0.23 | 2.65 | 10.19 | 0.12 | 2.41 | 1.30 | 1.58 | 1.28 | 1.78 | 3.14 | 2.17 |
| R | 366P | -0.02 | -22.55 | -134.79 | 0.00 | -14.12 | -1.91 | -7.31 | -8.43 | -13.11 | -27.83 | -10.47 |
| R | 366S | 0.09 | 4.06 | -5.74 | 0.03 | 5.36 | 2.71 | 3.32 | 3.32 | 3.82 | 7.05 | 5.93 |
| R | 366T | 0.06 | 5.42 | 9.66 | 0.02 | 7.31 | 3.64 | 4.58 | 4.41 | 5.22 | 9.74 | 9.92 |
| R | 366V | 0.21 | 1.61 | 2.80 | 0.09 | 2.46 | 1.46 | 1.77 | 1.58 | 1.82 | 3.04 | 2.63 |
| R | 366W | -0.15 | 1.71 | -3.54 | -0.03 | -1.24 | -0.02 | -0.63 | -0.79 | -1.30 | -2.84 | -1.01 |
| R | 366Y | -0.07 | -3.62 | -9.98 | -0.01 | -5.98 | -1.29 | -3.03 | -2.84 | -4.69 | -10.18 | -9.83 |
| G | 370A | 0.53 | 1.20 | 1.91 | 0.35 | 1.27 | 0.84 | 0.94 | 0.70 | 0.95 | 1.57 | 0.76 |
| G | 370C | -0.07 | -10.21 | -28.74 | -0.02 | -1.91 | -0.18 | -1.67 | -1.97 | -1.98 | -4.29 | -1.15 |
| G | 370D | -0.16 | -1.51 | -6.28 | -0.04 | -0.63 | -0.08 | -0.67 | -0.85 | -0.81 | -1.35 | -0.31 |
| G | 370E | -0.21 | -0.37 | -8.56 | -0.05 | -0.49 | -0.06 | -0.52 | -0.65 | -0.62 | -1.34 | -0.06 |
| G | 370H | -0.22 | -1.30 | -2.24 | -0.04 | -0.72 | -0.10 | -0.59 | -0.70 | -0.68 | -2.09 | -0.67 |
| G | 370I | -0.33 | 0.29 | -4.16 | -0.07 | -0.32 | -0.05 | -0.33 | -0.42 | -0.41 | -0.73 | -0.33 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| G | 370K | −0.34 | −0.25 | −17.82 | −0.06 | −0.30 | −0.04 | −0.33 | −0.42 | −0.41 | −0.97 | −0.33 |
| G | 370L | −0.21 | 0.63 | −58.27 | −0.04 | −0.59 | −0.14 | −0.60 | −0.69 | −0.69 | −1.53 | −0.78 |
| G | 370M | −0.01 | −83.69 | −307.57 | 0.00 | −13.61 | −1.14 | −13.40 | −16.02 | −16.95 | −39.47 | −13.95 |
| G | 370N | −0.12 | −7.80 | −2.31 | −0.03 | −1.12 | −0.10 | −1.02 | −1.21 | −1.24 | −2.53 | −0.88 |
| G | 370P | −0.16 | −1.02 | −2.15 | −0.04 | −0.59 | −0.24 | −0.67 | −0.82 | −0.82 | −1.96 | −0.36 |
| G | 370Q | −0.17 | −0.44 | −6.18 | −0.04 | −0.62 | −0.05 | −0.65 | −0.80 | −0.84 | −1.61 | 1.54 |
| G | 370R | −0.15 | −1.04 | 8.86 | −0.03 | −0.64 | −0.05 | −0.70 | −0.87 | −0.91 | −1.76 | −0.01 |
| G | 370S | −0.10 | −4.71 | −16.80 | −0.03 | −2.75 | −0.63 | −1.85 | −1.92 | −2.10 | −4.32 | −2.56 |
| G | 370T | −0.15 | 0.36 | −15.40 | −0.03 | −0.80 | −0.09 | −0.79 | −0.96 | −0.96 | −2.08 | −0.87 |
| G | 370V | −0.22 | 0.50 | −11.88 | −0.05 | −0.56 | −0.07 | −0.53 | −0.66 | −0.73 | −1.47 | −0.58 |
| G | 370W | −0.21 | −0.71 | −23.69 | −0.05 | −0.53 | −0.08 | −0.56 | −0.67 | −0.69 | −1.42 | −0.17 |
| G | 370Y | −0.17 | −0.99 | −42.70 | −0.04 | −0.68 | −0.14 | −0.71 | −0.86 | −0.94 | −1.68 | −1.50 |
| V | 371A | 0.92 | 0.97 | −0.69 | 1.02 | 1.05 | 1.03 | 0.97 | 0.63 | 0.96 | 1.08 | 1.07 |
| V | 371C | 0.78 | 1.00 | −0.28 | 0.69 | 1.09 | 1.02 | 1.01 | 0.79 | 0.97 | 1.24 | 1.08 |
| V | 371D | −0.10 | −4.03 | −7.88 | −0.02 | −0.99 | −0.17 | −1.07 | −1.44 | −1.68 | −2.21 | 3.13 |
| V | 371E | 0.05 | 7.39 | −8.16 | 0.02 | 8.75 | 4.14 | 6.21 | 6.24 | 6.58 | 14.30 | 8.60 |
| V | 371F | 0.74 | 1.15 | 0.40 | 0.53 | 1.13 | 1.04 | 1.07 | 0.99 | 1.04 | 1.24 | 1.26 |
| V | 371G | 0.39 | 1.62 | 0.91 | 0.22 | 1.92 | 1.40 | 1.55 | 1.48 | 1.57 | 2.19 | 1.92 |
| V | 371H | 0.22 | 1.59 | −1.88 | 0.08 | 2.46 | 1.57 | 1.81 | 1.77 | 1.90 | 2.29 | 0.83 |
| V | 371I | 0.81 | 1.04 | 0.46 | 0.63 | 1.12 | 1.05 | 1.08 | 1.00 | 1.08 | 1.15 | 1.07 |
| V | 371K | 0.04 | 7.47 | 9.26 | 0.01 | 13.63 | 6.83 | 9.65 | 9.60 | 10.19 | 20.80 | 10.97 |
| V | 371L | 0.91 | 0.92 | 0.60 | 0.83 | 1.07 | 1.04 | 1.01 | 0.81 | 0.99 | 1.09 | 1.09 |
| V | 371M | 1.05 | 0.89 | −0.44 | 1.16 | 0.97 | 0.97 | 0.84 | 0.45 | 0.80 | 1.01 | 0.99 |
| V | 371N | 0.74 | 1.09 | −1.01 | 0.66 | 1.22 | 1.08 | 1.03 | 0.67 | 1.01 | 1.21 | 1.14 |
| V | 371P | −0.11 | −4.99 | 0.96 | −0.02 | −0.97 | −0.10 | −1.08 | −1.36 | −1.69 | −2.58 | 2.58 |
| V | 371Q | 0.49 | 1.22 | −0.45 | 0.26 | 1.32 | 0.89 | 0.99 | 0.78 | 1.00 | 1.53 | 1.35 |
| V | 371R | −0.12 | −2.40 | 5.49 | −0.03 | −0.99 | −0.10 | −0.98 | −1.21 | −1.41 | −2.57 | 2.06 |
| V | 371S | 0.82 | 1.11 | 1.17 | 0.65 | 1.20 | 1.00 | 0.99 | 0.77 | 0.99 | 1.12 | 1.19 |
| V | 371T | 0.92 | 1.00 | −0.01 | 0.77 | 1.07 | 0.97 | 0.96 | 0.75 | 0.88 | 1.07 | 1.01 |
| V | 371W | 0.26 | 1.65 | 1.51 | 0.11 | 2.39 | 1.36 | 1.70 | 1.54 | 1.65 | 2.90 | 2.31 |
| V | 371Y | 0.62 | 0.89 | −0.17 | 0.44 | 1.40 | 1.13 | 1.13 | 0.94 | 1.11 | 1.53 | 1.53 |
| V | 372A | 0.88 | 1.19 | 1.11 | 0.96 | 1.14 | 1.06 | 1.02 | 0.62 | 1.00 | 1.16 | 1.21 |
| V | 372C | 0.73 | 1.07 | 0.27 | 0.73 | 1.29 | 1.12 | 1.11 | 0.81 | 1.07 | 1.36 | 1.29 |
| V | 372D | 0.01 | 25.81 | 63.02 | 0.00 | 21.71 | 4.27 | 14.61 | 15.62 | 18.27 | 35.28 | 2.32 |
| V | 372E | 0.00 | −1236.67 | −3997.35 | 0.00 | −1224.43 | −279.58 | −788.60 | −835.90 | −935.63 | −1916.45 | −235.09 |
| V | 372G | 0.37 | 1.57 | 3.50 | 0.18 | 1.76 | 1.07 | 1.27 | 1.14 | 1.34 | 2.16 | 1.58 |
| V | 372H | −0.17 | −3.11 | −6.06 | −0.04 | −0.77 | −0.13 | −0.69 | −0.88 | −1.06 | −1.71 | 0.97 |
| V | 372I | 0.81 | 1.11 | 1.19 | 0.77 | 1.26 | 1.16 | 1.15 | 0.92 | 1.03 | 1.24 | 1.31 |
| V | 372K | −0.15 | −1.68 | −4.97 | −0.04 | −0.84 | −0.14 | −0.79 | −1.00 | −1.27 | −1.93 | 1.58 |
| V | 372L | 0.89 | 1.12 | 2.43 | 1.02 | 1.14 | 1.12 | 1.06 | 0.88 | 0.99 | 1.18 | 1.20 |
| V | 372M | 0.24 | 1.45 | 0.93 | 0.10 | 1.97 | 0.84 | 1.27 | 1.11 | 1.44 | 2.79 | 1.58 |
| V | 372N | 0.65 | 1.12 | 0.44 | 0.50 | 1.20 | 0.94 | 1.02 | 0.90 | 0.99 | 1.44 | 1.10 |
| V | 372Q | 0.28 | 2.13 | 1.78 | 0.14 | 2.17 | 1.25 | 1.58 | 1.67 | 1.59 | 2.76 | 2.30 |
| V | 372R | −0.11 | −4.99 | −12.18 | −0.02 | −0.95 | −0.03 | −1.00 | −1.33 | −1.57 | −2.82 | 2.48 |
| V | 372S | 0.60 | 1.12 | 0.06 | 0.40 | 1.35 | 1.08 | 1.17 | 1.15 | 1.17 | 1.40 | 1.11 |
| V | 372T | 0.80 | 1.01 | 1.47 | 0.67 | 1.11 | 0.97 | 1.02 | 1.00 | 1.01 | 1.11 | 1.01 |
| V | 372W | −0.21 | 1.84 | −4.34 | −0.05 | −0.50 | −0.09 | −0.52 | −0.69 | −0.84 | −1.43 | 1.63 |
| L | 373A | 0.97 | 0.86 | 320.47 | 0.92 | 0.97 | 0.90 | 0.87 | 0.64 | 0.80 | 0.96 | 0.97 |
| L | 373C | 0.74 | 1.19 | 154.16 | 0.60 | 1.18 | 1.09 | 1.11 | 1.01 | 1.08 | 1.30 | 1.09 |
| L | 373E | 0.01 | 43.51 | 40558.81 | 0.00 | 21.06 | 5.84 | 15.76 | 18.29 | 19.62 | 38.40 | 2.46 |
| L | 373F | 0.85 | 1.14 | 108.03 | 0.66 | 1.04 | 0.97 | 1.02 | 1.05 | 1.02 | 1.18 | 1.17 |
| L | 373G | 0.47 | 1.04 | 286.04 | 0.24 | 1.36 | 0.93 | 1.10 | 1.17 | 1.13 | 1.73 | 1.42 |
| L | 373H | −0.16 | −1.33 | 412.71 | −0.04 | −1.59 | −0.35 | −1.14 | −1.34 | −1.45 | −2.74 | 0.07 |
| L | 373I | 0.83 | 1.00 | 488.19 | 0.66 | 1.07 | 1.03 | 1.05 | 1.03 | 1.06 | 1.14 | 1.21 |
| L | 373K | −0.17 | 0.73 | 673.78 | −0.03 | −0.97 | −0.16 | −0.83 | −0.99 | −1.13 | −2.10 | 1.05 |
| L | 373M | 0.89 | 1.07 | 312.46 | 0.95 | 1.12 | 1.12 | 1.05 | 0.77 | 1.03 | 1.11 | 1.03 |
| L | 373N | −0.14 | −2.77 | −1847.98 | −0.04 | −1.35 | −0.20 | −1.04 | −1.19 | −1.34 | −2.67 | 0.67 |
| L | 373P | −0.19 | 0.02 | 514.03 | −0.04 | −0.55 | −0.05 | −0.61 | −0.77 | −0.81 | −1.64 | 1.45 |
| L | 373Q | 0.19 | 1.71 | −1358.09 | 0.08 | 2.39 | 1.26 | 1.79 | 1.84 | 1.87 | 3.17 | 2.02 |
| L | 373R | −0.23 | 0.49 | −209.45 | −0.04 | −0.44 | −0.16 | −0.48 | −0.62 | −0.76 | −1.21 | 0.96 |
| L | 373S | 0.29 | 1.77 | 696.53 | 0.13 | 2.13 | 1.46 | 1.75 | 1.78 | 1.75 | 2.77 | 2.37 |
| L | 373T | 0.57 | 1.27 | 335.37 | 0.34 | 1.34 | 1.06 | 1.17 | 1.16 | 1.19 | 1.24 | 1.27 |
| L | 373V | 0.88 | 0.93 | −27.12 | 0.63 | 1.00 | 0.91 | 0.96 | 0.91 | 0.96 | 1.04 | 1.21 |
| L | 373W | 0.26 | 1.01 | −227.91 | 0.12 | 2.25 | 1.37 | 1.72 | 1.62 | 1.73 | 2.62 | 2.14 |
| L | 373Y | 0.55 | 1.23 | 650.68 | 0.37 | 1.58 | 1.05 | 1.37 | 1.05 | 1.36 | 1.64 | 1.68 |
| A | 374C | 0.88 | 0.97 | −38.32 | 0.81 | 1.01 | 0.93 | 0.93 | 0.75 | 0.84 | 1.02 | 0.97 |
| A | 374E | 0.16 | 2.39 | −3265.10 | 0.07 | 3.23 | 1.83 | 2.45 | 2.35 | 2.52 | 4.20 | 2.86 |
| A | 374F | −0.23 | −2.03 | 1430.54 | −0.05 | −0.52 | −0.06 | −0.50 | −0.63 | −0.73 | −1.32 | 0.79 |
| A | 374G | 0.80 | 1.00 | −200.56 | 0.54 | 1.11 | 0.97 | 1.02 | 0.95 | 1.02 | 1.17 | 1.11 |
| A | 374H | −0.16 | 2.04 | 2461.86 | −0.03 | −0.73 | −0.12 | −0.72 | −0.90 | −1.04 | −1.66 | 1.00 |
| A | 374I | 0.60 | 1.13 | −283.04 | 0.39 | 1.41 | 1.24 | 1.30 | 1.12 | 1.30 | 1.59 | 1.64 |
| A | 374K | −0.26 | 1.00 | 2193.01 | −0.04 | −0.39 | −0.02 | −0.45 | −0.55 | −0.52 | −1.01 | 1.09 |
| A | 374L | 0.43 | 1.50 | −194.61 | 0.25 | 1.81 | 1.47 | 1.56 | 1.21 | 1.54 | 2.02 | 2.07 |
| A | 374M | 0.55 | 1.27 | 501.91 | 0.37 | 1.31 | 0.93 | 0.97 | 0.61 | 0.92 | 1.44 | 1.20 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| A | 374N | 0.42 | 1.31 | -172.32 | 0.22 | 1.54 | 0.96 | 1.11 | 0.82 | 1.10 | 1.69 | 1.63 |
| A | 374P | -0.18 | -1.52 | 156.17 | -0.04 | -0.60 | -0.05 | -0.62 | -0.76 | -0.88 | -1.77 | 0.75 |
| A | 374Q | -0.09 | -5.59 | -6279.45 | -0.02 | -2.66 | -0.44 | -2.02 | -2.19 | -2.63 | -5.52 | 2.43 |
| A | 374S | 0.81 | 1.20 | 464.06 | 0.62 | 1.15 | 1.04 | 1.02 | 0.78 | 0.97 | 1.19 | 1.13 |
| A | 374T | 0.69 | 1.25 | -376.46 | 0.53 | 1.30 | 1.16 | 1.16 | 0.87 | 1.15 | 1.27 | 1.34 |
| A | 374V | 0.79 | 1.27 | -355.62 | 0.68 | 1.27 | 1.22 | 1.18 | 0.85 | 1.12 | 1.19 | 1.39 |
| A | 374W | -0.20 | 0.74 | -647.35 | -0.04 | -0.49 | -0.03 | -0.58 | -0.72 | -0.87 | -1.30 | 1.72 |
| A | 374Y | -0.18 | 1.66 | -645.16 | -0.04 | -0.56 | -0.05 | -0.65 | -0.81 | -1.00 | -1.60 | 1.14 |
| N | 375A | 0.70 | 1.08 | 53.07 | 0.55 | 1.10 | 0.85 | 0.87 | 0.70 | 0.84 | 1.31 | 1.09 |
| N | 375C | 0.94 | 0.78 | 21.41 | 0.78 | 0.89 | 0.78 | 0.79 | 0.76 | 0.76 | 1.03 | 0.85 |
| N | 375D | 0.56 | 1.23 | 32.66 | 0.30 | 1.13 | 0.73 | 0.87 | 0.90 | 0.85 | 1.55 | 1.15 |
| N | 375E | -0.08 | -8.93 | -192.49 | -0.02 | -2.91 | -0.56 | -2.07 | -2.34 | -2.43 | -5.38 | -3.08 |
| N | 375F | 0.77 | 1.09 | 13.15 | 0.57 | 1.11 | 0.94 | 1.00 | 1.02 | 0.92 | 1.23 | 1.10 |
| N | 375G | 0.41 | 1.28 | 7.26 | 0.19 | 1.55 | 0.96 | 1.14 | 1.21 | 1.11 | 1.88 | 1.68 |
| N | 375H | 0.98 | 1.04 | 15.11 | 0.81 | 0.94 | 0.88 | 0.91 | 0.92 | 0.87 | 0.96 | 0.96 |
| N | 375K | -0.02 | -13.29 | -351.51 | 0.00 | -7.22 | -1.02 | -5.58 | -6.14 | -6.29 | -16.26 | -6.73 |
| N | 375L | 0.71 | 0.99 | 17.56 | 0.47 | 1.15 | 0.90 | 0.95 | 0.72 | 0.97 | 1.23 | 1.30 |
| N | 375M | 0.89 | 1.00 | 12.27 | 0.82 | 0.96 | 0.85 | 0.82 | 0.64 | 0.80 | 1.08 | 1.05 |
| N | 375P | -0.14 | -3.96 | -86.81 | -0.03 | -0.71 | -0.07 | -0.74 | -0.89 | -0.99 | -2.11 | -0.53 |
| N | 375Q | 0.70 | 1.06 | 29.86 | 0.51 | 1.13 | 0.93 | 0.98 | 1.03 | 0.95 | 1.32 | 1.19 |
| N | 375S | 0.68 | 1.35 | 16.57 | 0.50 | 1.26 | 1.09 | 1.14 | 1.18 | 1.10 | 1.37 | 1.36 |
| N | 375T | 0.60 | 1.06 | 14.12 | 0.32 | 1.21 | 0.90 | 1.00 | 1.03 | 0.98 | 1.34 | 1.35 |
| N | 375V | 0.49 | 1.28 | 25.38 | 0.24 | 1.40 | 0.99 | 1.13 | 1.12 | 1.12 | 1.75 | 1.69 |
| N | 375W | 0.25 | 2.10 | 81.49 | 0.12 | 2.40 | 1.48 | 1.84 | 1.69 | 1.84 | 3.01 | 3.05 |
| N | 375Y | 0.84 | 0.90 | 25.76 | 0.71 | 1.10 | 0.96 | 1.00 | 0.75 | 0.98 | 1.12 | 1.11 |
| A | 376C | 0.98 | 1.00 | 2.28 | 0.98 | 0.94 | 0.89 | 0.91 | 0.82 | 0.87 | 0.98 | 0.87 |
| A | 376D | 0.07 | 11.04 | -3.97 | 0.04 | 8.70 | 7.46 | 2.62 | 0.00 | 0.00 | 10.15 | 8.16 |
| A | 376E | 0.29 | 1.78 | -8.59 | 0.13 | 1.68 | 0.90 | 1.25 | 1.27 | 1.28 | 2.13 | 2.09 |
| A | 376F | 0.15 | 2.46 | 7.66 | 0.05 | 3.03 | 1.44 | 2.45 | 2.15 | 2.27 | 3.92 | 3.30 |
| A | 376G | 0.92 | 0.84 | -7.83 | 0.69 | 0.94 | 0.88 | 0.92 | 0.96 | 0.93 | 1.00 | 1.47 |
| A | 376H | 0.06 | 2.36 | 14.97 | 0.01 | 6.06 | 1.86 | 4.12 | 4.38 | 3.77 | 9.18 | 5.02 |
| A | 376I | 0.91 | 0.85 | 0.21 | 0.70 | 0.99 | 0.93 | 0.96 | 0.94 | 1.00 | 1.02 | 0.90 |
| A | 376K | -0.10 | 0.53 | 71.71 | -0.02 | -2.05 | -0.37 | -1.62 | -1.75 | -1.90 | -3.65 | -1.72 |
| A | 376L | 0.49 | 1.05 | -7.14 | 0.26 | 1.44 | 1.05 | 1.23 | 0.77 | 1.19 | 1.74 | 1.37 |
| A | 376M | 0.42 | 1.34 | 1.39 | 0.27 | 1.60 | 1.12 | 1.26 | 0.87 | 1.20 | 1.87 | 1.57 |
| A | 376N | 0.51 | 1.09 | -10.32 | 0.31 | 1.32 | 0.93 | 1.08 | 0.93 | 1.05 | 1.54 | 1.31 |
| A | 376P | 0.47 | 1.39 | -10.15 | 0.27 | 1.44 | 1.04 | 1.19 | 1.12 | 1.17 | 1.60 | 1.21 |
| A | 376Q | 0.31 | 0.55 | -11.08 | 0.13 | 1.62 | 0.95 | 1.26 | 1.23 | 1.22 | 1.95 | 1.76 |
| A | 376R | -0.10 | -1.84 | -6.50 | -0.02 | -2.84 | -0.83 | -2.06 | -2.16 | -2.13 | -5.01 | -2.88 |
| A | 376S | 0.77 | 1.07 | -7.65 | 0.61 | 1.20 | 1.09 | 1.12 | 1.11 | 1.09 | 1.23 | 0.32 |
| A | 376T | 0.72 | 1.03 | -5.90 | 0.53 | 1.20 | 1.02 | 1.10 | 1.08 | 1.08 | 1.29 | 1.19 |
| A | 376V | 0.85 | 1.01 | 1.41 | 0.73 | 1.06 | 1.04 | 1.09 | 1.03 | 1.12 | 1.12 | 1.01 |
| A | 376W | -0.12 | 1.92 | 44.60 | -0.02 | -1.22 | -0.16 | -1.03 | -1.15 | -1.36 | -2.55 | -0.91 |
| A | 376Y | 0.00 | 81.01 | -1467.85 | 0.00 | 261.85 | 92.62 | 181.21 | 142.70 | 181.37 | 363.19 | 196.35 |
| G | 377A | 1.20 | 0.89 | 2.44 | 1.41 | 0.86 | 0.81 | 0.73 | 0.44 | 0.78 | 0.79 | 0.93 |
| G | 377C | 0.94 | 1.13 | 0.89 | 1.01 | 1.04 | 0.95 | 0.88 | 0.66 | 0.94 | 1.01 | 0.91 |
| G | 377D | 0.95 | 1.03 | -0.18 | 1.01 | 1.05 | 0.96 | 0.90 | 0.72 | 0.98 | 1.00 | 0.94 |
| G | 377E | 0.90 | 1.16 | 1.76 | 0.89 | 1.04 | 0.91 | 0.88 | 0.75 | 0.90 | 1.00 | 1.03 |
| G | 377F | 0.70 | 1.41 | 4.52 | 0.66 | 1.39 | 1.17 | 1.17 | 0.97 | 1.23 | 1.35 | 1.22 |
| G | 377H | 0.70 | 1.51 | 3.34 | 0.66 | 1.42 | 1.28 | 1.25 | 1.05 | 1.18 | 1.39 | 1.21 |
| G | 377I | 0.44 | 1.83 | 3.84 | 0.32 | 1.84 | 1.52 | 1.53 | 1.32 | 1.74 | 2.86 | 1.86 |
| G | 377K | 0.83 | 1.14 | 2.47 | 0.75 | 1.17 | 1.04 | 1.00 | 0.77 | 1.01 | 1.15 | 1.19 |
| G | 377L | 0.65 | 1.44 | 3.77 | 0.59 | 1.48 | 1.26 | 1.22 | 0.93 | 1.39 | 0.97 | 1.39 |
| G | 377M | 1.04 | 0.85 | 1.78 | 1.14 | 0.92 | 0.83 | 0.80 | 0.59 | 0.84 | 0.90 | 0.91 |
| G | 377N | 0.82 | 0.97 | 0.87 | 0.70 | 1.01 | 0.81 | 0.82 | 0.76 | 0.91 | 1.00 | 0.82 |
| G | 377P | 0.13 | 4.84 | 15.02 | 0.04 | 2.02 | 0.40 | 1.30 | 1.45 | 1.81 | 3.17 | -0.23 |
| G | 377Q | -1.03 | -0.13 | -1.83 | -0.21 | -0.38 | -2.55 | 0.35 | 0.10 | -0.74 | -0.21 | 0.28 |
| G | 377R | 0.92 | 1.06 | 1.06 | 0.77 | 0.98 | 0.84 | 0.87 | 0.83 | 0.83 | 1.05 | 0.87 |
| G | 377T | 0.64 | 1.43 | 3.47 | 0.47 | 1.30 | 1.03 | 1.09 | 1.09 | 1.16 | 1.29 | 1.18 |
| G | 377W | 0.54 | 1.41 | 3.53 | 0.38 | 1.46 | 1.19 | 1.25 | 1.11 | 1.36 | 1.59 | 1.42 |
| G | 377Y | 0.76 | 1.04 | 2.76 | 0.61 | 1.19 | 0.99 | 0.98 | 0.77 | 1.07 | 1.20 | 1.12 |
| S | 379A | 1.25 | 0.86 | -13.85 | 2.11 | 0.98 | 1.13 | 1.00 | 0.61 | 1.02 | 0.85 | 0.96 |
| S | 379C | 1.19 | 0.90 | -0.11 | 1.53 | 0.87 | 0.91 | 0.82 | 0.62 | 0.82 | 0.73 | 0.85 |
| S | 379D | 1.05 | 0.97 | 7.10 | 1.32 | 1.03 | 1.03 | 0.94 | 0.77 | 0.99 | 0.85 | 0.98 |
| S | 379E | 1.12 | 0.97 | 2.29 | 1.43 | 0.95 | 0.98 | 0.92 | 0.81 | 0.90 | 0.78 | 0.86 |
| S | 379F | 1.00 | 1.05 | 0.21 | 1.10 | 1.05 | 1.00 | 0.95 | 0.83 | 0.89 | 1.01 | 0.96 |
| S | 379G | 0.90 | 1.10 | 3.08 | 0.95 | 1.17 | 1.17 | 1.08 | 0.94 | 1.18 | 1.08 | 1.10 |
| S | 379H | 0.87 | 1.15 | 5.41 | 0.92 | 1.18 | 1.18 | 1.15 | 0.93 | 1.14 | 1.10 | 1.32 |
| S | 379I | 0.94 | 1.03 | 5.27 | 0.95 | 1.10 | 1.09 | 1.02 | 0.84 | 1.10 | 1.12 | 1.06 |
| S | 379K | 0.93 | 1.06 | -1.51 | 1.04 | 1.14 | 1.16 | 1.10 | 0.80 | 1.12 | 1.05 | 1.11 |
| S | 379L | 1.10 | 0.93 | -4.99 | 1.40 | 0.99 | 1.09 | 1.01 | 0.70 | 1.08 | 0.98 | 1.00 |
| S | 379N | 1.00 | 0.93 | 3.80 | 1.19 | 0.98 | 0.99 | 0.94 | 0.84 | 0.96 | 0.97 | 0.98 |
| S | 379P | 0.95 | 0.95 | 0.82 | 0.94 | 0.98 | 0.88 | 0.89 | 0.83 | 0.90 | 0.93 | 0.99 |
| S | 379Q | 0.73 | 1.49 | 7.90 | 0.75 | 1.31 | 1.27 | 1.25 | 1.20 | 1.29 | 1.33 | 1.42 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| S | 379R | 0.92 | 1.04 | −4.44 | 0.85 | 1.04 | 0.98 | 0.99 | 0.94 | 0.91 | 1.04 | 1.11 |
| S | 379T | 0.65 | 1.51 | 22.73 | 0.63 | 1.42 | 1.37 | 1.38 | 1.33 | 1.38 | 1.39 | 2.42 |
| S | 379W | 0.76 | 1.19 | 4.91 | 0.70 | 1.17 | 1.09 | 1.11 | 0.96 | 1.01 | 1.24 | 1.22 |
| S | 379Y | 0.81 | 1.13 | 0.61 | 0.77 | 1.18 | 1.12 | 1.11 | 0.84 | 1.14 | 1.20 | 1.20 |
| S | 380A | 1.16 | 0.92 | 0.30 | 1.47 | 0.91 | 0.91 | 0.86 | 0.52 | 0.88 | 0.79 | 0.85 |
| S | 380C | 1.17 | −0.24 | −0.93 | 1.37 | 0.79 | 0.83 | 0.81 | 0.61 | 0.76 | 0.78 | 0.77 |
| S | 380D | 1.22 | 0.93 | 0.14 | 1.42 | 0.85 | 0.82 | 0.79 | 0.63 | 0.81 | 0.83 | 0.80 |
| S | 380E | 0.94 | 1.34 | −0.25 | 1.06 | 1.08 | 1.03 | 1.00 | 0.84 | 1.01 | 0.98 | 1.05 |
| S | 380F | 1.12 | 1.50 | −0.23 | 1.17 | 0.92 | 0.88 | 0.85 | 0.71 | 0.81 | 0.91 | 0.93 |
| S | 380G | 1.01 | 0.95 | 0.82 | 1.17 | 1.02 | 1.03 | 0.98 | 0.84 | 0.96 | 0.99 | 0.94 |
| S | 380H | 1.23 | 0.74 | −0.37 | 1.38 | 0.83 | 0.84 | 0.83 | 0.72 | 0.78 | 0.85 | 0.80 |
| S | 380L | 0.91 | 0.44 | 0.00 | 1.02 | 1.08 | 1.09 | 1.03 | 0.78 | 1.02 | 1.05 | 1.06 |
| S | 380M | 0.12 | 10.93 | −0.31 | 0.12 | 6.72 | 7.53 | −4.29 | −2.62 | −19.42 | 7.09 | 6.68 |
| S | 380N | 0.99 | 0.94 | −0.71 | 1.02 | 0.93 | 0.88 | 0.92 | 0.81 | 0.92 | 1.00 | 0.94 |
| S | 380P | 0.96 | 0.85 | 0.48 | 0.93 | 0.96 | 0.90 | 0.93 | 0.89 | 0.93 | 0.97 | 0.94 |
| S | 380Q | 0.88 | 1.03 | −1.34 | 0.79 | 1.03 | 0.98 | 1.00 | 0.98 | 1.00 | 1.12 | 1.13 |
| S | 380R | 1.02 | 0.96 | −0.94 | 0.96 | 0.94 | 0.86 | 0.90 | 0.88 | 0.84 | 1.01 | 0.89 |
| S | 380T | 0.91 | 1.03 | −0.27 | 0.84 | 0.99 | 0.99 | 1.00 | 0.97 | 0.98 | 1.04 | 1.04 |
| S | 380V | 0.87 | 1.08 | −0.47 | 0.86 | 1.06 | 1.03 | 1.02 | 0.98 | 1.01 | 1.12 | 1.22 |
| S | 380W | 0.88 | 0.95 | −1.18 | 0.82 | 1.01 | 1.00 | 0.99 | 0.88 | 0.95 | 1.03 | 1.08 |
| S | 380Y | 1.06 | 0.87 | −1.59 | 1.15 | 0.95 | 0.98 | 0.92 | 0.71 | 0.89 | 0.94 | 0.89 |
| V | 381A | 1.04 | 1.07 | 1.72 | 1.44 | 1.06 | 1.10 | 0.99 | 0.63 | 0.99 | 0.74 | 0.94 |
| V | 381C | 1.06 | 1.00 | 0.87 | 1.29 | 0.97 | 0.96 | 0.88 | 0.68 | 0.85 | 0.98 | 0.90 |
| V | 381E | 1.05 | 1.00 | 0.64 | 1.21 | 0.97 | 0.94 | 0.89 | 0.78 | 0.86 | 0.84 | 0.87 |
| V | 381F | 1.06 | 0.95 | 3.00 | 1.17 | 0.99 | 0.98 | 0.91 | 0.81 | 0.90 | 0.77 | 0.83 |
| V | 381G | 0.87 | 1.13 | 0.42 | 0.91 | 1.19 | 1.16 | 1.10 | 0.94 | 1.08 | 1.16 | 1.06 |
| V | 381H | −0.96 | 0.24 | 0.19 | −0.21 | −0.38 | −2.43 | −0.20 | −0.50 | −0.57 | −0.32 | −0.15 |
| V | 381I | 0.88 | 0.92 | −0.38 | 0.82 | 1.09 | 0.99 | 0.96 | 0.82 | 0.89 | 1.19 | 1.02 |
| V | 381K | 0.97 | 0.96 | −0.67 | 1.06 | 1.05 | 1.04 | 0.94 | 0.79 | 0.91 | 1.06 | 0.99 |
| V | 381M | 0.98 | 0.98 | 2.00 | 1.13 | 0.98 | 0.95 | 0.88 | 0.67 | 0.85 | 0.90 | 0.86 |
| V | 381N | 1.07 | 0.86 | 0.21 | 1.13 | 0.85 | 0.80 | 0.80 | 0.73 | 0.78 | 0.87 | 0.87 |
| V | 381P | 0.86 | 1.13 | 0.62 | 0.83 | 1.04 | 0.96 | 0.97 | 0.94 | 0.96 | 1.04 | 1.06 |
| V | 381Q | 0.76 | 1.32 | 1.42 | 0.77 | 1.20 | 1.11 | 1.12 | 1.14 | 1.13 | 1.17 | 1.19 |
| V | 381R | 0.94 | 1.03 | 1.62 | 0.88 | 1.03 | 0.97 | 0.97 | 0.97 | 0.88 | 1.11 | 0.87 |
| V | 381S | 0.72 | 1.36 | 1.98 | 0.63 | 1.26 | 1.17 | 1.19 | 1.17 | 1.17 | 1.21 | 1.19 |
| V | 381T | 0.87 | 0.67 | 3.34 | 0.75 | 1.02 | 0.85 | 0.87 | 0.95 | 0.98 | 1.05 | 1.02 |
| V | 381W | 0.76 | 1.23 | 3.67 | 0.70 | 1.15 | 1.09 | 1.10 | 0.97 | 1.07 | 1.27 | 1.02 |
| V | 381Y | 0.87 | 1.01 | 1.05 | 0.90 | 1.15 | 1.14 | 1.09 | 0.91 | 1.04 | 1.08 | 1.03 |
| I | 383A | 0.77 | 1.08 | −0.87 | 0.73 | 1.11 | 0.98 | 0.96 | 0.70 | 0.96 | 1.17 | 0.86 |
| I | 383C | 0.81 | 1.19 | 1.30 | 0.71 | 1.07 | 0.99 | 0.95 | 0.80 | 0.95 | 1.16 | 1.03 |
| I | 383D | −0.05 | −8.46 | 11.75 | −0.01 | −4.63 | −1.02 | −3.39 | −3.92 | −4.29 | −7.75 | −0.69 |
| I | 383E | 0.16 | 3.21 | 5.41 | 0.07 | 3.32 | 1.79 | 2.39 | 2.45 | 2.52 | 4.49 | 3.48 |
| I | 383F | 0.87 | 1.10 | −1.28 | 0.76 | 1.05 | 0.98 | 0.99 | 0.93 | 1.00 | 1.17 | 1.04 |
| I | 383G | 0.21 | 2.21 | 2.47 | 0.09 | 2.74 | 1.61 | 1.98 | 2.03 | 2.07 | 3.49 | 2.63 |
| I | 383H | 0.31 | 1.67 | −1.19 | 0.12 | 1.94 | 1.11 | 1.40 | 1.38 | 1.41 | 2.34 | 1.68 |
| I | 383L | 0.86 | 1.05 | 6.26 | 0.84 | 1.13 | 1.11 | 1.07 | 0.78 | 1.05 | 1.16 | 1.11 |
| I | 383N | 0.30 | 1.63 | −0.08 | 0.14 | 1.76 | 0.81 | 1.12 | 0.94 | 1.20 | 2.57 | 1.10 |
| I | 383P | 0.68 | 1.14 | −2.16 | 0.51 | 1.16 | 0.91 | 0.93 | 0.71 | 0.94 | 1.33 | 0.95 |
| I | 383Q | 0.50 | 1.29 | −1.64 | 0.26 | 1.33 | 0.87 | 0.99 | 0.80 | 1.00 | 1.75 | 1.25 |
| I | 383R | −0.04 | −11.04 | 72.17 | −0.01 | −5.13 | −0.98 | −3.73 | −4.24 | −4.81 | −8.83 | −0.80 |
| I | 383S | 0.44 | 1.60 | −3.75 | 0.24 | 1.69 | 1.10 | 1.23 | 1.04 | 1.21 | 1.85 | 1.53 |
| I | 383T | 0.86 | 1.02 | −4.11 | 0.72 | 1.10 | 0.96 | 0.94 | 0.74 | 0.91 | 1.03 | 0.97 |
| I | 383V | 0.77 | 1.22 | 4.87 | 0.70 | 1.32 | 1.29 | 1.23 | 0.93 | 1.19 | 1.28 | 1.19 |
| I | 383W | 0.39 | 1.56 | 15.92 | 0.20 | 1.81 | 1.15 | 1.30 | 1.06 | 1.28 | 2.14 | 0.90 |
| I | 383Y | 0.40 | 1.54 | 3.55 | 0.23 | 1.87 | 1.30 | 1.40 | 1.09 | 1.37 | 2.13 | 1.83 |
| N | 384A | 0.55 | 1.01 | 3.54 | 0.34 | 1.16 | 0.63 | 0.77 | 0.66 | 0.85 | 1.28 | 0.67 |
| N | 384D | 0.92 | 1.04 | 0.38 | 0.91 | 1.00 | 0.93 | 0.93 | 0.97 | 1.01 | 0.99 | 0.87 |
| N | 384F | 0.98 | 0.99 | 2.04 | 0.82 | 0.92 | 0.82 | 0.84 | 0.88 | 0.89 | 0.90 | 0.87 |
| N | 384G | 0.80 | 1.18 | 1.51 | 0.63 | 1.16 | 1.03 | 1.06 | 1.08 | 1.19 | 1.23 | 1.13 |
| N | 384H | 0.64 | 1.48 | 2.84 | 0.55 | 1.46 | 1.32 | 1.36 | 1.36 | 1.45 | 1.46 | 1.31 |
| N | 384I | 0.72 | 1.32 | 0.39 | 0.58 | 1.26 | 1.12 | 1.16 | 1.14 | 1.25 | 1.30 | 1.49 |
| N | 384K | 0.76 | 1.27 | 3.12 | 0.61 | 1.23 | 1.12 | 1.12 | 1.00 | 1.20 | 1.22 | 1.21 |
| N | 384L | 0.82 | 1.20 | 0.74 | 0.78 | 1.19 | 1.11 | 1.08 | 0.82 | 1.18 | 1.18 | 1.18 |
| N | 384M | 1.03 | 1.01 | 1.85 | 1.20 | 0.97 | 0.96 | 0.85 | 0.68 | 0.92 | 0.90 | 0.84 |
| N | 384P | 0.60 | 1.19 | 2.22 | 0.37 | 1.12 | 0.75 | 0.86 | 0.91 | 0.92 | 1.27 | 0.95 |
| N | 384Q | 0.54 | 1.77 | 5.88 | 0.50 | 1.69 | 1.58 | 1.61 | 1.68 | 1.67 | 1.75 | 1.41 |
| N | 384S | 0.90 | 0.98 | 2.87 | 0.70 | 1.02 | 0.91 | 0.92 | 0.96 | 1.02 | 1.05 | 0.98 |
| N | 384T | 0.82 | 1.16 | 0.84 | 0.68 | 1.13 | 0.99 | 1.04 | 1.03 | 1.17 | 1.09 | 0.94 |
| N | 384V | 0.67 | 1.39 | 4.14 | 0.54 | 1.33 | 1.16 | 1.21 | 1.17 | 1.34 | 1.35 | 1.35 |
| N | 384W | 0.63 | 1.42 | 3.25 | 0.50 | 1.42 | 1.24 | 1.30 | 1.19 | 1.32 | 1.52 | 1.22 |
| T | 387A | 1.06 | 1.00 | 1.58 | 1.33 | 1.03 | 1.04 | 0.98 | 0.56 | 0.97 | 0.92 | 0.95 |
| T | 387C | 1.01 | 0.96 | 1.12 | 1.11 | 0.98 | 0.90 | 0.91 | 0.66 | 0.88 | 0.96 | 1.02 |
| T | 387D | 0.07 | 7.31 | 31.61 | 0.02 | 4.72 | 1.36 | 3.02 | 2.87 | 3.16 | 6.43 | 1.85 |
| T | 387E | 0.10 | 4.29 | 26.66 | 0.03 | 2.99 | 0.78 | 1.91 | 1.94 | 2.01 | 3.96 | 0.82 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| T | 387G | 0.88 | 0.98 | −2.37 | 0.80 | 1.05 | 0.91 | 0.91 | 0.79 | 0.87 | 1.07 | 0.99 |
| T | 387I | 0.89 | 1.03 | 0.87 | 0.89 | 1.11 | 1.07 | 1.06 | 0.91 | 0.93 | 1.06 | 0.99 |
| T | 387L | 0.94 | 0.87 | 1.22 | 0.95 | 1.01 | 0.94 | 0.93 | 0.73 | 0.92 | 1.08 | 0.98 |
| T | 387M | 0.87 | 0.89 | −0.16 | 0.84 | 1.06 | 0.94 | 0.94 | 0.65 | 0.93 | 0.96 | 0.85 |
| T | 387N | 0.83 | 0.93 | 0.04 | 0.70 | 1.01 | 0.85 | 0.89 | 0.77 | 0.90 | 1.07 | 0.78 |
| T | 387P | −0.10 | −3.32 | 12.28 | −0.03 | −3.07 | −0.92 | −2.06 | −2.15 | −2.26 | −4.36 | −1.31 |
| T | 387Q | 0.44 | 1.53 | 1.46 | 0.27 | 1.53 | 1.01 | 1.18 | 1.18 | 1.17 | 1.86 | 1.33 |
| T | 387R | −0.05 | −14.32 | 25.39 | −0.01 | −4.36 | −0.63 | −3.22 | −3.59 | −3.62 | −8.68 | −0.22 |
| T | 387S | 0.94 | 0.96 | 1.84 | 0.87 | 0.99 | 0.93 | 0.96 | 0.94 | 0.92 | 1.02 | 0.82 |
| T | 387W | −0.04 | −10.45 | 57.20 | −0.01 | −7.08 | −1.73 | −4.93 | −5.23 | −5.09 | −13.11 | −4.58 |
| T | 387Y | −0.01 | −19.29 | 188.02 | 0.00 | −26.15 | −8.45 | −16.71 | −16.11 | −17.90 | −41.69 | −11.24 |
| L | 389C | 0.86 | 0.75 | −0.84 | 0.73 | 0.94 | 0.85 | 0.90 | 0.85 | 0.91 | 1.08 | 1.16 |
| L | 389D | −0.02 | −40.79 | 31.83 | −0.01 | −5.27 | −0.23 | −5.12 | −6.13 | −6.59 | −12.46 | 0.61 |
| L | 389E | 0.23 | 2.05 | 2.79 | 0.07 | 1.27 | 0.38 | 0.96 | 1.08 | 1.12 | 2.08 | 1.17 |
| L | 389F | 0.89 | 0.87 | 1.05 | 0.68 | 0.93 | 0.86 | 0.93 | 0.95 | 0.94 | 0.99 | 0.99 |
| L | 389H | 0.12 | −2.31 | −22.76 | 0.04 | 3.51 | 1.47 | 2.51 | 2.88 | 2.65 | 5.12 | 3.73 |
| L | 389I | 1.02 | 0.63 | −0.90 | 0.81 | 0.86 | 0.79 | 0.83 | 0.83 | 0.82 | 0.89 | 0.86 |
| L | 389K | 0.06 | −6.46 | 5.27 | 0.02 | 5.43 | 1.74 | 3.96 | 4.19 | 4.42 | 9.34 | 4.22 |
| L | 389M | 1.14 | 0.94 | −0.47 | 1.18 | 0.80 | 0.79 | 0.79 | 0.58 | 0.80 | 0.85 | 0.77 |
| L | 389N | 0.53 | 0.53 | −1.93 | 0.36 | 1.32 | 0.99 | 1.12 | 1.06 | 1.16 | 1.64 | 1.63 |
| L | 389Q | 0.60 | 0.68 | 1.05 | 0.39 | 1.20 | 0.97 | 1.07 | 1.08 | 1.09 | 1.49 | 1.50 |
| L | 389R | −0.16 | −3.51 | 10.55 | −0.04 | −0.74 | −0.10 | −0.77 | −0.97 | −1.00 | −1.83 | 0.20 |
| L | 389S | 0.48 | 0.62 | 1.30 | 0.25 | 1.45 | 1.02 | 1.18 | 1.22 | 1.19 | 1.76 | 1.49 |
| L | 389T | 0.57 | 0.68 | −3.07 | 0.35 | 1.31 | 1.05 | 1.16 | 1.20 | 1.17 | 1.59 | 1.35 |
| L | 389V | 0.79 | 0.93 | −2.75 | 0.64 | 1.14 | 1.05 | 1.08 | 1.05 | 1.08 | 1.22 | 1.07 |
| L | 389W | 0.37 | 0.75 | −2.44 | 0.25 | 2.02 | 1.66 | 1.77 | 1.65 | 1.80 | 2.39 | 2.07 |
| L | 389Y | 0.20 | −1.38 | 4.43 | 0.08 | 2.53 | 1.28 | 1.77 | 1.57 | 1.91 | 3.25 | 3.04 |
| D | 391A | 0.95 | 1.00 | −0.33 | 1.11 | 1.06 | 1.04 | 0.95 | 0.70 | 1.03 | 1.03 | 0.97 |
| D | 391E | 0.99 | 1.05 | 1.71 | 0.93 | 0.91 | 0.85 | 0.85 | 0.85 | 0.91 | 0.90 | 0.84 |
| D | 391F | 0.74 | 1.27 | 0.53 | 0.62 | 1.21 | 1.07 | 1.09 | 1.12 | 1.14 | 1.23 | 1.27 |
| D | 391G | 0.89 | 0.93 | 2.53 | 0.70 | 1.04 | 0.93 | 0.95 | 0.96 | 1.03 | 1.10 | 1.02 |
| D | 391H | 0.91 | 1.02 | 1.45 | 0.74 | 1.01 | 0.91 | 0.93 | 0.93 | 0.96 | 1.12 | 1.01 |
| D | 391I | 0.85 | 0.98 | 1.18 | 0.68 | 1.04 | 0.92 | 0.94 | 0.93 | 1.03 | 1.11 | 1.13 |
| D | 391K | 0.71 | 1.29 | 0.17 | 0.56 | 1.30 | 1.20 | 1.20 | 1.09 | 1.31 | 1.46 | 1.48 |
| D | 391L | 0.87 | 1.03 | 2.81 | 0.83 | 1.01 | 1.02 | 1.00 | 0.77 | 1.07 | 1.17 | 1.09 |
| D | 391M | 1.12 | 0.82 | −0.63 | 1.27 | 0.88 | 0.87 | 0.78 | 0.56 | 0.83 | 0.87 | 0.90 |
| D | 391N | 0.83 | 1.18 | 1.37 | 0.83 | 1.12 | 1.01 | 1.00 | 0.87 | 1.05 | 1.20 | 1.10 |
| D | 391P | 0.78 | 1.00 | −1.46 | 0.62 | 1.05 | 0.86 | 0.89 | 0.87 | 0.96 | 1.21 | 1.03 |
| D | 391Q | 0.84 | 1.08 | 0.61 | 0.76 | 1.05 | 0.96 | 0.96 | 0.93 | 1.04 | 1.04 | 0.99 |
| D | 391R | 0.76 | 1.34 | −0.50 | 0.63 | 1.20 | 1.06 | 1.07 | 1.06 | 1.10 | 1.34 | 1.36 |
| D | 391S | 0.79 | 1.22 | 0.53 | 0.63 | 1.15 | 1.02 | 1.05 | 1.00 | 1.13 | 1.12 | 1.13 |
| D | 391T | 0.69 | 1.41 | −0.07 | 0.53 | 1.31 | 1.16 | 1.20 | 1.15 | 1.27 | 1.42 | 1.35 |
| D | 391V | 0.81 | 1.06 | 1.53 | 0.57 | 1.09 | 0.95 | 0.99 | 0.92 | 1.06 | 1.18 | 1.20 |
| D | 391W | 0.65 | 1.34 | 1.31 | 0.51 | 1.36 | 1.15 | 1.19 | 1.04 | 1.24 | 1.50 | 1.48 |
| D | 391Y | 0.80 | 1.16 | 1.46 | 0.73 | 1.21 | 1.09 | 1.09 | 0.81 | 1.14 | 1.25 | 1.34 |
| G | 392A | 0.99 | 0.78 | 1.57 | 0.95 | 0.89 | 0.81 | 0.86 | 0.60 | 0.88 | 0.92 | 0.69 |
| G | 392C | 0.92 | 0.75 | −1.14 | 0.81 | 0.92 | 0.84 | 0.86 | 0.71 | 0.87 | 0.93 | 0.92 |
| G | 392D | 0.70 | 0.99 | 0.54 | 0.57 | 1.18 | 1.09 | 1.13 | 1.02 | 1.12 | 1.25 | 1.21 |
| G | 392E | 0.98 | 0.79 | −0.31 | 0.77 | 0.86 | 0.79 | 0.81 | 0.74 | 0.83 | 0.92 | 0.88 |
| G | 392F | 0.67 | 0.89 | −1.60 | 0.46 | 1.16 | 1.02 | 1.07 | 1.02 | 1.06 | 1.27 | 1.31 |
| G | 392H | 0.88 | 0.84 | −0.25 | 0.65 | 0.95 | 0.86 | 0.88 | 0.81 | 0.86 | 1.09 | 0.96 |
| G | 392K | 0.80 | 0.88 | −1.68 | 0.61 | 1.11 | 1.01 | 1.03 | 0.85 | 0.99 | 1.23 | 1.16 |
| G | 392L | 0.87 | 0.64 | −0.79 | 0.69 | 1.05 | 0.94 | 0.95 | 0.71 | 0.93 | 1.10 | 1.00 |
| G | 392M | 1.14 | 0.78 | 0.87 | 1.28 | 0.88 | 0.83 | 0.81 | 0.46 | 0.82 | 0.82 | 0.76 |
| G | 392N | 0.99 | 0.90 | −1.49 | 0.92 | 0.93 | 0.85 | 0.85 | 0.58 | 0.88 | 0.88 | 0.99 |
| G | 392P | −0.01 | 18.66 | 46.58 | 0.00 | −80.56 | −22.02 | −55.63 | −54.14 | −65.17 | −120.59 | −76.34 |
| G | 392Q | 0.98 | 1.00 | 0.14 | 0.85 | 0.94 | 0.88 | 0.89 | 0.66 | 0.89 | 0.92 | 0.93 |
| G | 392R | 0.98 | 1.06 | −0.14 | 0.95 | 1.03 | 1.05 | 0.98 | 0.76 | 0.98 | 0.96 | 1.06 |
| G | 392S | 0.79 | 1.35 | 0.21 | 0.67 | 1.22 | 1.14 | 1.11 | 0.91 | 1.10 | 1.23 | 1.18 |
| G | 392V | 0.83 | 0.29 | −2.69 | 0.41 | 0.79 | 0.49 | 0.59 | 0.48 | 0.52 | 0.91 | 0.95 |
| G | 392Y | 0.86 | 0.91 | 0.04 | 0.78 | 1.14 | 1.06 | 1.01 | 0.66 | 0.99 | 1.10 | 1.03 |
| Y | 394A | 0.86 | 0.90 | 2.60 | 0.80 | 0.99 | 0.78 | 0.77 | 0.64 | 0.81 | 1.08 | 0.95 |
| Y | 394C | 0.91 | 0.86 | 2.26 | 0.90 | 0.98 | 0.86 | 0.83 | 0.68 | 0.84 | 1.08 | 0.98 |
| Y | 394D | 0.05 | 14.47 | 35.55 | 0.02 | 5.08 | 0.54 | 3.26 | 3.62 | 3.54 | 9.06 | 5.07 |
| Y | 394E | 0.43 | 1.43 | 3.06 | 0.24 | 1.43 | 0.77 | 0.95 | 0.87 | 0.94 | 1.56 | 1.60 |
| Y | 394F | 1.04 | 0.91 | 3.28 | 1.12 | 1.02 | 0.95 | 0.92 | 0.80 | 0.95 | 1.01 | 0.95 |
| Y | 394G | 0.05 | 6.48 | 50.76 | 0.01 | 6.12 | 1.16 | 3.74 | 4.13 | 4.25 | 11.36 | 6.04 |
| Y | 394H | 0.94 | 0.95 | 2.08 | 0.91 | 1.05 | 1.01 | 0.97 | 0.83 | 0.96 | 0.98 | 1.08 |
| Y | 394I | 0.88 | 0.82 | 5.14 | 0.83 | 1.10 | 0.95 | 0.95 | 0.80 | 0.96 | 1.15 | 1.03 |
| Y | 394K | 0.65 | 0.96 | 8.28 | 0.48 | 1.27 | 0.95 | 0.97 | 0.86 | 0.87 | 1.49 | 1.41 |
| Y | 394L | 0.99 | 0.89 | 14.19 | 1.17 | 1.06 | 1.09 | 1.03 | 0.82 | 1.02 | 1.05 | 1.02 |
| Y | 394M | 1.11 | 0.77 | −0.98 | 1.20 | 0.86 | 0.80 | 0.77 | 0.64 | 0.77 | 0.89 | 0.95 |
| Y | 394N | 0.23 | 2.42 | −1.38 | 0.12 | 2.21 | 1.07 | 1.53 | 1.49 | 1.47 | 2.94 | 2.17 |
| Y | 394P | 0.32 | 1.30 | 20.75 | 0.17 | 1.75 | 1.00 | 1.25 | 1.27 | 1.29 | 2.37 | 2.46 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| Y | 394Q | 0.70 | 1.20 | 2.16 | 0.54 | 1.14 | 0.90 | 0.96 | 0.97 | 0.95 | 1.26 | 1.21 |
| Y | 394R | 0.40 | 1.42 | 3.18 | 0.19 | 1.54 | 0.88 | 1.09 | 1.14 | 1.10 | 1.94 | 1.96 |
| Y | 394S | 0.34 | 1.52 | 11.37 | 0.18 | 1.82 | 1.11 | 1.33 | 1.38 | 1.33 | 2.24 | 1.88 |
| Y | 394T | 0.52 | 1.37 | −0.14 | 0.32 | 1.36 | 0.96 | 1.08 | 1.06 | 1.07 | 1.73 | 1.38 |
| Y | 394V | 0.89 | 1.06 | 6.65 | 0.83 | 1.03 | 0.97 | 1.00 | 0.93 | 0.98 | 1.11 | 1.07 |
| Y | 394W | 0.93 | 1.00 | 7.17 | 0.86 | 0.98 | 0.98 | 0.98 | 0.89 | 0.96 | 1.02 | 1.01 |
| N | 396A | 0.39 | 1.13 | 10.36 | 0.20 | 1.48 | 0.75 | 1.00 | 0.94 | 1.00 | 1.95 | 1.57 |
| N | 396C | 0.78 | 0.98 | 3.85 | 0.62 | 1.04 | 0.87 | 0.93 | 0.88 | 0.87 | 1.12 | 1.02 |
| N | 396D | 0.80 | 1.06 | 3.99 | 0.72 | 1.07 | 0.98 | 1.01 | 1.05 | 1.01 | 1.20 | 1.15 |
| N | 396E | 0.33 | 1.53 | 5.15 | 0.16 | 1.67 | 1.01 | 1.28 | 1.37 | 1.33 | 2.20 | 1.80 |
| N | 396F | −0.04 | −15.62 | −108.64 | −0.01 | −6.27 | −1.18 | −4.37 | −5.15 | −4.95 | −12.20 | −7.32 |
| N | 396G | 0.15 | 3.25 | 25.05 | 0.05 | 3.20 | 1.46 | 2.17 | 2.41 | 2.20 | 4.05 | 3.40 |
| N | 396H | −0.03 | −8.61 | −170.67 | −0.01 | −8.81 | −2.18 | −5.85 | −6.83 | −6.29 | −15.13 | −10.78 |
| N | 396K | −0.06 | −6.67 | −174.97 | −0.01 | −5.74 | −1.54 | −3.81 | −4.16 | −4.06 | −9.74 | −6.52 |
| N | 396L | 0.02 | 20.77 | 805.63 | 0.01 | 16.71 | 4.33 | 10.88 | 11.47 | 12.31 | 27.14 | 17.98 |
| N | 396M | 0.10 | 5.12 | 39.95 | 0.04 | 3.64 | 1.04 | 2.27 | 2.32 | 2.50 | 5.07 | 3.21 |
| N | 396P | 0.17 | 2.80 | 16.60 | 0.07 | 2.68 | 1.17 | 1.83 | 1.98 | 1.87 | 4.23 | 3.30 |
| N | 396R | −0.17 | −1.87 | −28.16 | −0.04 | −1.69 | −0.43 | −1.12 | −1.32 | −1.21 | −3.03 | −2.46 |
| N | 396S | 0.64 | 1.39 | 6.48 | 0.44 | 1.28 | 1.16 | 1.24 | 1.33 | 1.24 | 1.40 | 1.41 |
| N | 396T | 0.21 | 2.52 | 10.49 | 0.09 | 2.60 | 1.46 | 1.91 | 2.07 | 1.91 | 3.35 | 2.45 |
| N | 396V | −0.21 | −0.55 | −26.69 | −0.04 | −0.44 | −0.08 | −0.50 | −0.62 | −0.57 | −1.41 | −0.51 |
| N | 396W | −0.21 | −1.14 | −42.97 | −0.05 | −0.46 | −0.07 | −0.52 | −0.65 | −0.63 | −1.33 | −0.27 |
| K | 397A | 0.97 | 1.02 | −2.73 | 1.05 | 1.00 | 1.00 | 0.94 | 0.60 | 0.91 | 1.00 | 0.83 |
| K | 397C | 0.84 | 1.13 | −0.79 | 0.81 | 1.06 | 1.00 | 0.97 | 0.76 | 0.96 | 1.06 | 0.97 |
| K | 397D | 0.81 | 1.24 | −1.75 | 0.77 | 1.12 | 1.08 | 1.06 | 0.92 | 1.06 | 1.18 | 1.11 |
| K | 397E | 0.98 | 1.00 | −1.36 | 0.97 | 0.96 | 0.98 | 0.97 | 0.83 | 0.93 | 0.91 | 1.01 |
| K | 397F | 0.92 | 1.14 | −2.34 | 0.76 | 0.98 | 1.00 | 0.98 | 0.88 | 0.95 | 1.10 | 1.04 |
| K | 397G | 0.81 | 0.99 | −2.12 | 0.57 | 1.09 | 0.96 | 1.00 | 0.91 | 0.98 | 1.16 | 1.07 |
| K | 397H | 0.91 | 1.05 | −5.83 | 0.80 | 1.02 | 0.97 | 0.99 | 0.90 | 0.96 | 1.06 | 0.91 |
| K | 397I | 0.79 | 0.96 | −3.95 | 0.62 | 1.13 | 1.04 | 1.07 | 0.93 | 1.06 | 1.21 | 1.08 |
| K | 397L | 0.91 | 1.13 | −7.56 | 0.84 | 1.10 | 1.10 | 1.06 | 0.79 | 1.04 | 1.05 | 0.98 |
| K | 397M | 1.13 | 1.05 | 4.41 | 1.48 | 0.97 | 1.06 | 0.94 | 0.50 | 0.89 | 0.88 | 0.76 |
| K | 397N | 1.12 | 0.92 | −1.20 | 1.32 | 0.91 | 0.93 | 0.88 | 0.54 | 0.84 | 0.83 | 0.75 |
| K | 397P | 0.83 | 1.14 | −1.53 | 0.70 | 1.07 | 0.93 | 0.90 | 0.63 | 0.86 | 1.04 | 1.08 |
| K | 397R | 1.09 | 1.03 | −0.85 | 1.14 | 0.92 | 0.94 | 0.92 | 0.68 | 0.88 | 0.90 | 0.88 |
| K | 397S | 0.88 | 1.17 | −4.06 | 0.76 | 1.14 | 1.06 | 1.05 | 0.79 | 1.00 | 1.09 | 1.00 |
| K | 397T | 0.91 | 0.94 | −6.84 | 0.78 | 1.09 | 1.01 | 0.96 | 0.74 | 0.95 | 1.15 | 1.08 |
| K | 397V | 0.73 | 1.14 | −9.76 | 0.60 | 1.29 | 1.18 | 1.16 | 0.81 | 1.15 | 1.33 | 1.22 |
| K | 397W | 0.93 | 1.06 | −7.70 | 0.88 | 1.07 | 1.09 | 1.04 | 0.69 | 1.02 | 1.06 | 1.08 |
| A | 398C | 0.68 | 1.42 | 1.03 | 0.61 | 1.29 | 1.16 | 1.14 | 0.89 | 1.19 | 1.33 | 1.18 |
| A | 398D | 0.09 | 5.07 | 4.79 | 0.03 | 4.43 | 1.78 | 2.87 | 2.82 | 3.56 | 6.17 | 4.05 |
| A | 398E | 0.21 | 3.05 | 1.03 | 0.08 | 2.34 | 1.16 | 1.56 | 1.50 | 1.82 | 2.89 | 1.28 |
| A | 398F | 0.18 | 2.88 | −3.24 | 0.06 | 2.74 | 1.31 | 1.83 | 1.75 | 2.06 | 3.52 | 2.63 |
| A | 398G | 0.70 | 1.33 | −1.10 | 0.55 | 1.31 | 1.15 | 1.18 | 1.04 | 1.24 | 1.32 | 1.19 |
| A | 398I | 0.29 | 2.22 | 2.43 | 0.15 | 2.38 | 1.50 | 1.71 | 1.55 | 1.87 | 2.62 | 2.16 |
| A | 398K | −0.05 | −3.54 | 6.48 | −0.01 | −6.49 | −1.70 | −4.02 | −3.94 | −5.25 | −10.46 | −4.02 |
| A | 398L | 0.38 | 1.58 | −2.87 | 0.17 | 1.71 | 0.97 | 1.14 | 0.90 | 1.26 | 2.07 | 1.51 |
| A | 398M | 0.41 | 1.32 | 0.87 | 0.22 | 1.51 | 0.81 | 0.93 | 0.62 | 1.06 | 1.79 | 1.21 |
| A | 398N | 0.46 | 1.60 | −0.75 | 0.28 | 1.60 | 1.02 | 1.08 | 0.72 | 1.13 | 1.70 | 1.58 |
| A | 398P | 0.18 | 2.87 | −3.36 | 0.07 | 2.92 | 1.28 | 1.77 | 1.40 | 2.03 | 4.18 | 2.02 |
| A | 398Q | 0.31 | 1.99 | −2.74 | 0.15 | 1.90 | 1.13 | 1.31 | 1.03 | 1.46 | 2.44 | 1.60 |
| A | 398R | 0.15 | 3.54 | 1.44 | 0.04 | 2.78 | 0.98 | 1.65 | 1.46 | 2.00 | 4.26 | 1.91 |
| A | 398S | 0.83 | 1.17 | 1.03 | 0.69 | 1.18 | 1.02 | 0.99 | 0.73 | 1.02 | 1.23 | 1.05 |
| A | 398T | 0.68 | 1.30 | −0.71 | 0.50 | 1.31 | 1.04 | 1.02 | 0.76 | 1.07 | 1.31 | 1.14 |
| A | 398V | 0.60 | 1.40 | 0.36 | 0.42 | 1.35 | 1.12 | 1.13 | 0.81 | 1.24 | 1.49 | 1.34 |
| A | 398W | 0.23 | 2.45 | −2.83 | 0.09 | 2.46 | 1.27 | 1.57 | 1.19 | 1.82 | 3.08 | 2.19 |
| A | 398Y | 0.20 | 2.47 | 4.84 | 0.08 | 2.89 | 1.36 | 1.78 | 1.45 | 2.09 | 3.59 | 2.85 |
| G | 399A | 1.06 | 0.83 | −2.01 | 1.23 | 0.92 | 0.92 | 0.88 | 0.65 | 0.87 | 0.92 | 0.90 |
| G | 399C | 0.89 | 0.99 | 4.11 | 0.83 | 0.99 | 0.92 | 0.95 | 0.90 | 0.92 | 0.99 | 1.00 |
| G | 399D | 1.02 | 0.95 | 0.15 | 0.88 | 0.87 | 0.85 | 0.87 | 0.89 | 0.85 | 0.92 | 0.92 |
| G | 399E | 1.05 | 0.84 | 4.13 | 0.99 | 0.84 | 0.82 | 0.83 | 0.86 | 0.83 | 0.95 | 0.84 |
| G | 399F | 0.83 | 1.05 | 1.42 | 0.64 | 1.08 | 0.97 | 1.02 | 1.04 | 1.00 | 1.14 | 1.01 |
| G | 399H | 0.29 | 2.14 | 5.50 | 0.13 | 2.05 | 0.92 | 1.14 | 1.10 | 0.94 | 2.67 | 2.32 |
| G | 399I | 0.66 | 1.15 | 7.86 | 0.46 | 1.25 | 1.05 | 1.12 | 1.13 | 1.11 | 1.48 | 1.39 |
| G | 399K | 0.92 | 1.00 | 4.57 | 0.73 | 0.98 | 1.01 | 0.94 | 0.86 | 0.91 | 1.03 | 0.98 |
| G | 399L | 0.77 | 1.10 | 16.95 | 0.61 | 1.18 | 1.05 | 1.08 | 0.87 | 1.08 | 1.41 | 1.19 |
| G | 399M | 1.14 | 0.80 | 2.30 | 1.30 | 0.87 | 0.86 | 0.80 | 0.61 | 0.81 | 0.78 | 0.81 |
| G | 399P | 0.47 | 1.28 | −1.41 | 0.29 | 1.43 | 1.00 | 1.13 | 1.16 | 1.12 | 1.55 | 1.57 |
| G | 399Q | −0.01 | −78.49 | −139.12 | 0.00 | −16.84 | −3.56 | −18.05 | −22.61 | −22.68 | −45.78 | −12.76 |
| G | 399R | 0.87 | 1.10 | 1.88 | 0.68 | 1.02 | 0.92 | 0.96 | 0.98 | 0.91 | 1.12 | 1.00 |
| G | 399S | 0.78 | 1.23 | 4.17 | 0.67 | 1.16 | 1.06 | 1.13 | 1.13 | 1.08 | 1.16 | 1.16 |
| G | 399T | 0.79 | 1.23 | −0.03 | 0.61 | 1.12 | 1.02 | 1.08 | 1.06 | 1.06 | 1.23 | 1.24 |
| G | 399V | 0.66 | 1.21 | 6.40 | 0.47 | 1.30 | 1.13 | 1.18 | 1.15 | 1.17 | 1.44 | 1.31 |
| G | 399W | 0.69 | 1.21 | 8.67 | 0.50 | 1.24 | 1.07 | 1.12 | 1.02 | 1.14 | 1.24 | 1.24 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| G | 399Y | 0.84 | 1.03 | 16.72 | 0.72 | 1.14 | 1.11 | 1.05 | 0.83 | 1.07 | 1.29 | 1.10 |
| S | 402A | 1.12 | 0.83 | 2.03 | 1.10 | 0.83 | 0.74 | 0.74 | 0.58 | 0.71 | 0.83 | 0.76 |
| S | 402C | 1.06 | 0.87 | 0.84 | 0.98 | 0.83 | 0.77 | 0.79 | 0.76 | 0.79 | 0.94 | 0.83 |
| S | 402D | 0.83 | 0.86 | −1.83 | 0.76 | 1.04 | 0.99 | 1.04 | 1.05 | 1.04 | 1.06 | 1.07 |
| S | 402E | 0.91 | 0.89 | 0.49 | 0.80 | 0.96 | 0.94 | 0.95 | 0.99 | 0.97 | 1.04 | 0.98 |
| S | 402F | 1.14 | 0.74 | 0.40 | 0.99 | 0.77 | 0.72 | 0.76 | 0.78 | 0.73 | 0.86 | 0.80 |
| S | 402G | 1.04 | 0.87 | −0.69 | 0.96 | 0.90 | 0.85 | 0.86 | 0.92 | 0.84 | 0.93 | 1.01 |
| S | 402H | 0.87 | 0.99 | −1.13 | 0.82 | 1.06 | 1.03 | 1.06 | 1.07 | 0.97 | 1.15 | 1.86 |
| S | 402K | 1.02 | 0.64 | −0.76 | 0.99 | 0.93 | 0.92 | 0.90 | 0.82 | 0.89 | 0.98 | 0.96 |
| S | 402L | 0.90 | 0.87 | −0.35 | 0.98 | 1.11 | 1.12 | 1.08 | 0.84 | 1.06 | 1.13 | 1.10 |
| S | 402M | 0.94 | 0.98 | −1.47 | 1.04 | 1.00 | 1.02 | 0.97 | 0.76 | 0.96 | 1.02 | 0.90 |
| S | 402N | 1.01 | 0.75 | 1.72 | 0.98 | 0.85 | 0.81 | 0.84 | 0.80 | 0.84 | 0.91 | 0.88 |
| S | 402P | 0.91 | 0.84 | −1.00 | 0.81 | 0.94 | 0.90 | 0.93 | 0.97 | 0.93 | 0.99 | 0.92 |
| S | 402Q | 0.96 | 0.88 | −0.68 | 0.79 | 0.93 | 0.90 | 0.94 | 0.97 | 0.97 | 0.98 | 1.09 |
| S | 402R | 0.94 | 0.89 | −0.87 | 0.86 | 0.93 | 0.89 | 0.93 | 1.00 | 0.90 | 1.02 | 0.95 |
| S | 402V | 0.90 | 0.90 | −0.20 | 0.80 | 1.00 | 0.99 | 1.02 | 1.00 | 0.99 | 1.07 | 0.96 |
| S | 402W | −0.05 | 0.31 | 34.34 | −0.01 | −2.65 | −0.16 | −2.47 | −2.96 | −2.93 | −7.07 | −1.02 |
| S | 402Y | 0.88 | 0.76 | −1.64 | 0.79 | 1.13 | 1.16 | 1.08 | 0.86 | 1.05 | 1.07 | 1.06 |
| F | 403A | 0.66 | 1.26 | 1.96 | 0.64 | 1.29 | 1.10 | 1.03 | 0.82 | 1.08 | 1.24 | 1.16 |
| F | 403C | 0.76 | 1.02 | 1.96 | 0.58 | 1.01 | 0.84 | 0.87 | 0.83 | 0.86 | 1.12 | 1.24 |
| F | 403D | −0.12 | −2.88 | −13.05 | −0.03 | −1.11 | −0.10 | −0.65 | −0.78 | −1.20 | −2.82 | −1.24 |
| F | 403E | 0.05 | 7.84 | 14.58 | 0.01 | 3.70 | 0.68 | 2.03 | 2.32 | 3.32 | 6.50 | 3.69 |
| F | 403G | 0.27 | 1.91 | 6.39 | 0.11 | 1.91 | 0.98 | 1.23 | 1.24 | 1.32 | 2.65 | 1.92 |
| F | 403H | 0.62 | 1.20 | 9.02 | 0.39 | 1.18 | 0.87 | 0.95 | 0.96 | 0.97 | 1.36 | 1.40 |
| F | 403I | 0.75 | 1.15 | 3.44 | 0.54 | 1.13 | 0.97 | 0.99 | 0.95 | 0.98 | 1.20 | 1.15 |
| F | 403K | −0.12 | 1.64 | −22.30 | −0.03 | −1.34 | −0.19 | −0.77 | −0.82 | −1.28 | −3.14 | −1.62 |
| F | 403M | 0.85 | 1.21 | 5.69 | 0.96 | 1.11 | 1.13 | 1.03 | 0.80 | 1.07 | 1.01 | 0.87 |
| F | 403N | 0.21 | 1.81 | 10.22 | 0.09 | 1.99 | 0.89 | 1.23 | 1.23 | 1.41 | 2.23 | 1.38 |
| F | 403P | 0.02 | 9.16 | 195.18 | 0.01 | 11.10 | 2.80 | 6.27 | 6.75 | 8.77 | 16.38 | 12.06 |
| F | 403Q | 0.09 | 3.97 | 46.77 | 0.03 | 4.72 | 2.06 | 2.98 | 3.08 | 3.38 | 6.10 | 3.83 |
| F | 403R | −0.19 | 2.32 | −14.56 | −0.04 | −0.52 | −0.05 | −0.33 | −0.41 | −0.78 | −1.42 | −0.14 |
| F | 403S | 0.12 | 5.00 | 33.46 | 0.05 | 4.22 | 2.19 | 2.82 | 2.98 | 3.12 | 5.65 | 4.07 |
| F | 403T | 0.26 | 1.97 | 11.25 | 0.11 | 2.23 | 1.33 | 1.59 | 1.58 | 1.71 | 2.90 | 2.47 |
| F | 403V | 0.67 | 1.13 | 5.46 | 0.48 | 1.22 | 1.04 | 1.08 | 1.03 | 1.10 | 1.23 | 1.31 |
| F | 403W | 0.66 | 1.51 | 4.47 | 0.57 | 1.36 | 1.28 | 1.31 | 1.19 | 1.32 | 1.32 | 1.28 |
| F | 403Y | 0.80 | 1.03 | 3.20 | 0.76 | 1.22 | 1.17 | 1.14 | 0.92 | 1.10 | 1.15 | 1.14 |
| Q | 404A | 1.13 | 0.94 | −4.80 | 1.44 | 0.91 | 0.95 | 0.88 | 0.73 | 0.84 | 0.80 | 0.87 |
| Q | 404D | 0.97 | 0.96 | −1.68 | 0.92 | 0.93 | 0.90 | 0.92 | 0.91 | 0.91 | 0.82 | 1.04 |
| Q | 404E | 0.87 | 1.00 | −19.85 | 0.83 | 1.06 | 1.04 | 1.03 | 1.07 | 1.05 | 1.11 | 1.09 |
| Q | 404F | 0.95 | 0.97 | −9.04 | 0.87 | 0.97 | 0.94 | 0.93 | 1.01 | 0.97 | 0.96 | 0.97 |
| Q | 404G | 0.89 | 1.09 | 14.75 | 0.83 | 1.05 | 0.98 | 1.00 | 1.02 | 0.97 | 1.04 | 1.13 |
| Q | 404H | 0.77 | 1.15 | −10.04 | 0.70 | 1.18 | 1.13 | 1.11 | 1.15 | 1.09 | 1.15 | 1.35 |
| Q | 404I | 0.78 | 1.03 | −1.33 | 0.67 | 1.14 | 1.05 | 1.05 | 1.05 | 1.08 | 1.10 | 1.15 |
| Q | 404K | 0.97 | 0.99 | 0.42 | 0.95 | 0.97 | 0.97 | 0.97 | 0.85 | 0.96 | 0.99 | 0.90 |
| Q | 404L | 0.07 | 3.49 | −217.94 | 0.02 | 4.66 | 1.46 | 2.60 | 2.43 | 3.76 | 4.12 | 4.24 |
| Q | 404M | 1.02 | 1.03 | 0.47 | 1.39 | 1.02 | 1.14 | 1.00 | 0.91 | 1.01 | 0.92 | 1.02 |
| Q | 404N | 0.85 | 1.03 | −19.49 | 0.90 | 1.09 | 1.09 | 1.05 | 1.06 | 1.05 | 1.06 | 1.05 |
| Q | 404P | 0.78 | 1.04 | −4.92 | 0.68 | 1.09 | 0.98 | 1.00 | 1.03 | 1.00 | 1.08 | 1.17 |
| Q | 404R | 0.90 | 1.11 | −9.84 | 0.90 | 1.04 | 1.03 | 1.03 | 1.10 | 0.98 | 1.09 | 1.13 |
| Q | 404T | 0.85 | 1.17 | −2.44 | 0.84 | 1.13 | 1.14 | 1.14 | 1.19 | 1.16 | 1.09 | 1.07 |
| Q | 404V | 0.74 | 1.27 | −2.12 | 0.69 | 1.24 | 1.23 | 1.25 | 1.25 | 1.29 | 1.21 | 1.39 |
| Q | 404W | 0.77 | 1.22 | −6.94 | 0.66 | 1.17 | 1.14 | 1.15 | 1.04 | 1.16 | 1.14 | 1.21 |
| Q | 404Y | 0.89 | 1.09 | −2.27 | 0.97 | 1.14 | 1.18 | 1.12 | 0.86 | 1.09 | 0.97 | 1.11 |
| V | 405A | 1.12 | 0.89 | −1.09 | 1.48 | 0.91 | 0.98 | 0.89 | 0.69 | 0.90 | 0.82 | 0.87 |
| V | 405C | 0.89 | 0.96 | −24.77 | 0.87 | 1.02 | 0.96 | 0.95 | 0.88 | 0.94 | 1.03 | 0.98 |
| V | 405D | −0.04 | −8.93 | −199.23 | −0.01 | −6.01 | −1.33 | −3.52 | −4.02 | −5.28 | −6.32 | −6.27 |
| V | 405E | 0.23 | 1.42 | −29.22 | 0.09 | 1.88 | 0.88 | 1.22 | 1.29 | 1.48 | 2.40 | 2.39 |
| V | 405F | 0.30 | 1.23 | 24.00 | 0.14 | 1.84 | 1.12 | 1.35 | 1.43 | 1.46 | 2.01 | 2.24 |
| V | 405G | 0.57 | 1.22 | −6.10 | 0.37 | 1.36 | 1.09 | 1.13 | 1.21 | 1.19 | 1.45 | 1.54 |
| V | 405H | 0.30 | 1.78 | 2.60 | 0.13 | 1.96 | 1.24 | 1.41 | 1.52 | 1.53 | 2.46 | 2.18 |
| V | 405I | 0.98 | 0.96 | −0.58 | 0.89 | 0.94 | 0.92 | 0.92 | 0.93 | 0.93 | 0.92 | 0.92 |
| V | 405K | 0.21 | 2.26 | 12.71 | 0.09 | 2.83 | 1.74 | 2.05 | 1.95 | 2.22 | 3.45 | 3.31 |
| V | 405M | 0.95 | 0.97 | −14.10 | 1.04 | 0.99 | 0.94 | 0.87 | 0.63 | 0.88 | 0.87 | 0.80 |
| V | 405P | −0.11 | −1.08 | 68.34 | −0.03 | −1.09 | −0.07 | −0.70 | −0.90 | −1.54 | −0.28 | −0.07 |
| V | 405Q | 0.80 | 1.18 | −18.11 | 0.65 | 1.08 | 0.99 | 0.99 | 1.00 | 1.00 | 1.12 | 1.26 |
| V | 405R | −0.11 | −1.95 | −2.38 | −0.03 | −2.86 | −0.92 | −1.68 | −1.78 | −2.24 | −3.00 | −4.60 |
| V | 405S | 0.70 | 1.41 | −17.61 | 0.59 | 1.27 | 1.16 | 1.19 | 1.23 | 1.21 | 1.24 | 1.24 |
| V | 405T | 0.71 | 1.24 | 3.63 | 0.54 | 1.22 | 1.11 | 1.13 | 1.17 | 1.15 | 1.19 | 1.20 |
| V | 405W | −0.08 | −2.64 | 149.58 | −0.02 | −3.69 | −0.98 | −2.11 | −2.28 | −3.08 | −4.02 | −3.34 |
| D | 407A | 0.91 | 1.10 | −0.19 | 1.04 | 1.05 | 1.04 | 0.95 | 0.68 | 0.96 | 1.10 | 1.12 |
| D | 407C | 0.77 | 1.18 | 2.61 | 0.72 | 1.10 | 1.03 | 1.02 | 0.95 | 1.03 | 1.09 | 1.06 |
| D | 407E | 0.43 | 2.64 | 3.16 | 0.29 | 1.78 | 1.69 | 0.68 | 0.63 | −1.31 | 1.81 | 1.62 |
| D | 407F | 0.89 | 1.07 | 0.96 | 0.72 | 0.98 | 0.90 | 0.91 | 0.93 | 0.93 | 1.05 | 1.03 |
| D | 407G | 0.91 | 1.01 | 1.33 | 0.80 | 1.01 | 0.98 | 0.99 | 1.02 | 1.07 | 1.05 | 1.11 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| D | 407H | 0.88 | 1.18 | 5.78 | 0.80 | 1.02 | 0.98 | 0.99 | 0.99 | 1.01 | 1.09 | 1.05 |
| D | 407I | 0.72 | 1.06 | 1.69 | 0.51 | 1.12 | 0.97 | 1.01 | 0.96 | 1.04 | 1.40 | 1.17 |
| D | 407K | 0.72 | 1.23 | 2.18 | 0.62 | 1.25 | 1.20 | 1.16 | 1.05 | 1.20 | 1.40 | 1.19 |
| D | 407M | 0.88 | 1.10 | 1.03 | 0.98 | 1.07 | 1.05 | 0.94 | 0.68 | 0.96 | 1.08 | 1.28 |
| D | 407N | 0.83 | 1.20 | 2.65 | 0.79 | 1.08 | 1.02 | 1.00 | 0.86 | 0.98 | 1.11 | 1.12 |
| D | 407P | 0.14 | 2.92 | −2.68 | 0.05 | 3.22 | 1.50 | 2.10 | 2.03 | 2.35 | 4.84 | 4.01 |
| D | 407Q | 0.74 | 1.29 | 1.42 | 0.61 | 1.16 | 1.11 | 1.12 | 1.07 | 1.12 | 1.31 | 1.15 |
| D | 407R | 0.65 | 1.54 | −0.79 | 0.53 | 1.35 | 1.29 | 1.31 | 1.26 | 1.27 | 1.50 | 1.52 |
| D | 407S | 0.74 | 1.31 | 7.95 | 0.58 | 1.20 | 1.11 | 1.14 | 1.12 | 1.13 | 1.30 | 1.38 |
| D | 407T | 0.74 | 1.26 | 1.56 | 0.59 | 1.18 | 1.07 | 1.10 | 1.04 | 1.15 | 1.25 | 1.43 |
| D | 407V | 0.62 | 1.40 | 0.82 | 0.45 | 1.35 | 1.18 | 1.26 | 1.13 | 1.29 | 1.61 | 1.25 |
| D | 407W | 0.71 | 1.12 | 0.40 | 0.55 | 1.20 | 1.05 | 1.06 | 0.93 | 1.05 | 1.33 | 1.18 |
| D | 407Y | 0.78 | 1.03 | 2.76 | 0.68 | 1.20 | 1.12 | 1.10 | 0.82 | 1.06 | 1.24 | 1.28 |
| G | 408A | 0.84 | 1.11 | 17.50 | 0.86 | 1.13 | 1.07 | 1.01 | 0.80 | 1.01 | 1.24 | 1.00 |
| G | 408C | 0.87 | 1.03 | 15.37 | 0.74 | 0.99 | 0.92 | 0.92 | 0.87 | 0.92 | 1.03 | 0.95 |
| G | 408D | 0.87 | 1.03 | 67.78 | 0.75 | 1.00 | 0.93 | 0.95 | 0.95 | 0.96 | 1.16 | 1.53 |
| G | 408E | 0.71 | 1.20 | −25.45 | 0.62 | 1.23 | 1.16 | 1.19 | 1.24 | 1.19 | 1.22 | 1.13 |
| G | 408F | 0.69 | 1.31 | −25.95 | 0.53 | 1.26 | 1.14 | 1.20 | 1.26 | 1.18 | 1.39 | 1.19 |
| G | 408H | 0.94 | 0.96 | −8.29 | 0.75 | 1.00 | 0.94 | 0.95 | 0.98 | 0.91 | 1.01 | 0.86 |
| G | 408I | 0.24 | 1.50 | −93.17 | 0.10 | 2.33 | 1.33 | 1.66 | 1.63 | 1.71 | 3.06 | 2.09 |
| G | 408K | 0.86 | 0.97 | 46.96 | 0.68 | 1.05 | 1.02 | 1.03 | 0.90 | 0.99 | 1.15 | 1.03 |
| G | 408L | 0.86 | 0.81 | −38.09 | 0.67 | 1.04 | 0.95 | 0.95 | 0.66 | 0.94 | 1.10 | 0.96 |
| G | 408M | 0.87 | 1.03 | −44.70 | 0.86 | 1.09 | 1.00 | 0.94 | 0.70 | 0.95 | 1.14 | 0.94 |
| G | 408N | 0.75 | 1.26 | 32.19 | 0.71 | 1.23 | 1.16 | 1.14 | 1.03 | 1.12 | 1.27 | 1.14 |
| G | 408P | 0.07 | 5.53 | 316.00 | 0.02 | 3.64 | 0.87 | 2.06 | 2.37 | 2.98 | 2.89 | 2.94 |
| G | 408Q | 0.89 | 1.05 | 19.81 | 0.73 | 1.00 | 0.94 | 0.94 | 0.97 | 0.92 | 1.02 | 0.13 |
| G | 408S | 0.87 | 1.01 | −4.19 | 0.68 | 1.03 | 0.97 | 1.00 | 1.03 | 0.97 | 1.08 | 0.95 |
| G | 408T | 0.80 | 1.04 | 1.32 | 0.59 | 1.07 | 0.98 | 1.02 | 1.03 | 1.01 | 1.11 | 1.07 |
| G | 408V | 0.48 | 1.17 | 55.24 | 0.25 | 1.39 | 0.92 | 1.10 | 1.01 | 1.09 | 1.60 | 1.40 |
| G | 408W | 0.73 | 0.95 | 18.71 | 0.50 | 1.13 | 0.97 | 1.04 | 0.91 | 0.97 | 1.22 | 1.08 |
| G | 408Y | 0.77 | 0.97 | −30.88 | 0.60 | 1.03 | 1.01 | 1.02 | 0.74 | 1.02 | 1.06 | 0.83 |
| K | 409A | 0.83 | 1.16 | 10.99 | 0.91 | 1.16 | 1.16 | 1.07 | 0.77 | 1.03 | 1.12 | 0.77 |
| K | 409C | 0.79 | 1.11 | 29.56 | 0.74 | 1.12 | 1.10 | 1.07 | 0.91 | 1.08 | 0.44 | 1.45 |
| K | 409D | 0.81 | 1.15 | 10.32 | 0.70 | 1.10 | 1.05 | 1.08 | 0.94 | 1.04 | 1.13 | 1.01 |
| K | 409E | 0.83 | 1.19 | 37.55 | 0.73 | 1.11 | 1.07 | 1.06 | 0.99 | 1.05 | 1.16 | 0.99 |
| K | 409F | 0.74 | 1.25 | 25.03 | 0.60 | 1.23 | 1.18 | 1.21 | 1.16 | 1.12 | 1.24 | 1.24 |
| K | 409G | 0.84 | 1.08 | 25.75 | 0.64 | 1.07 | 0.99 | 1.01 | 0.95 | 0.94 | 1.14 | 1.08 |
| K | 409H | 0.82 | 1.07 | 43.11 | 0.66 | 1.12 | 1.08 | 1.10 | 1.00 | 1.04 | 1.18 | 1.30 |
| K | 409I | 0.97 | 0.96 | 11.59 | 0.87 | 0.97 | 0.95 | 0.95 | 0.86 | 0.95 | 1.02 | 1.52 |
| K | 409L | 0.85 | 0.98 | 7.20 | 0.78 | 1.16 | 1.16 | 1.13 | 0.82 | 1.12 | 1.19 | 1.05 |
| K | 409M | 0.93 | 1.10 | 16.11 | 1.10 | 1.09 | 1.17 | 1.07 | 0.60 | 1.04 | 1.08 | 0.97 |
| K | 409N | 0.95 | 0.95 | 42.04 | 1.03 | 1.05 | 1.04 | 0.97 | 0.66 | 0.95 | 1.13 | 1.02 |
| K | 409P | −0.02 | −20.07 | −1619.97 | 0.00 | −14.35 | −3.07 | −7.54 | −7.68 | −11.17 | −11.05 | −8.95 |
| K | 409Q | 0.88 | 1.19 | 36.34 | 0.86 | 1.16 | 1.13 | 1.07 | 0.82 | 1.06 | 1.24 | 1.08 |
| K | 409R | 0.81 | 1.26 | 22.30 | 0.77 | 1.12 | 1.24 | 1.19 | 0.94 | 1.12 | 1.19 | 1.25 |
| K | 409S | 0.92 | 1.07 | 50.68 | 0.83 | 1.08 | 1.04 | 1.04 | 0.82 | 0.98 | 1.01 | 0.83 |
| K | 409T | 0.70 | 1.30 | −24.03 | 0.63 | 1.45 | 1.39 | 1.36 | 1.00 | 1.33 | 1.49 | 1.29 |
| K | 409V | 0.83 | 1.11 | 34.88 | 0.78 | 1.20 | 1.19 | 1.16 | 0.84 | 1.16 | 1.21 | 1.05 |
| K | 409W | 0.73 | 1.24 | 16.97 | 0.69 | 1.39 | 1.32 | 1.27 | 1.00 | 1.26 | 1.34 | 1.07 |
| K | 409Y | 0.73 | 1.30 | −52.11 | 0.76 | 1.46 | 1.49 | 1.43 | 0.99 | 1.37 | 1.46 | 1.37 |
| L | 410A | 0.82 | 1.05 | −0.50 | 0.82 | 1.15 | 0.99 | 0.92 | 0.68 | 0.90 | 0.99 | 1.10 |
| L | 410D | −0.09 | −6.16 | 5.35 | −0.02 | −1.03 | 0.07 | −0.72 | −0.96 | −1.60 | −0.09 | −1.96 |
| L | 410E | 0.02 | 27.78 | 23.65 | 0.01 | 4.88 | 0.57 | 3.08 | 3.96 | 5.16 | 3.95 | 8.70 |
| L | 410F | 0.81 | 1.20 | −0.08 | 0.82 | 1.23 | 1.12 | 1.06 | 0.93 | 1.06 | 1.11 | 1.23 |
| L | 410G | 0.16 | 2.13 | 2.33 | 0.05 | 2.41 | 0.81 | 1.28 | 1.25 | 1.60 | 2.48 | 3.04 |
| L | 410H | 0.01 | 24.24 | 76.19 | 0.00 | 12.15 | 1.59 | 7.13 | 8.99 | 13.38 | 5.14 | 9.09 |
| L | 410I | 0.99 | 0.93 | 0.24 | 1.07 | 1.07 | 1.03 | 0.98 | 0.87 | 0.98 | 0.97 | 0.89 |
| L | 410K | 0.14 | 1.25 | 11.49 | 0.04 | 1.67 | 0.28 | 0.88 | 0.98 | 1.45 | 1.44 | 1.49 |
| L | 410N | 0.01 | 43.57 | 30.19 | 0.00 | 21.79 | 2.33 | 11.98 | 13.92 | 18.15 | 13.94 | 20.91 |
| L | 410P | −0.08 | −4.25 | −7.13 | −0.02 | −1.20 | −0.15 | −0.81 | −1.07 | −1.86 | 0.15 | −6.44 |
| L | 410Q | 0.08 | 3.64 | 1.44 | 0.03 | 4.08 | 1.16 | 2.25 | 2.58 | 3.06 | 4.40 | 4.73 |
| L | 410R | −0.07 | −3.95 | −10.73 | −0.01 | −1.39 | −0.12 | −0.96 | −1.28 | −2.12 | −0.68 | −1.58 |
| L | 410S | 0.09 | 3.89 | 14.13 | 0.02 | 2.73 | 0.57 | 1.46 | 1.64 | 2.09 | 2.55 | 2.11 |
| L | 410T | 0.51 | 1.13 | 0.24 | 0.29 | 1.32 | 0.88 | 0.99 | 0.97 | 1.03 | 1.26 | 1.24 |
| L | 410V | 0.81 | 1.03 | 1.40 | 0.73 | 1.13 | 1.05 | 1.07 | 0.99 | 1.08 | 1.11 | 0.91 |
| L | 410W | 0.21 | 1.57 | 8.68 | 0.07 | 1.80 | 0.66 | 1.11 | 1.02 | 1.32 | 1.87 | 1.61 |
| L | 410Y | 0.15 | 1.50 | −4.04 | 0.05 | 2.42 | 0.76 | 1.35 | 1.21 | 1.72 | 1.99 | 2.36 |
| T | 411A | 0.89 | 1.13 | 0.17 | 0.88 | 1.10 | 1.09 | 1.01 | 0.85 | 1.00 | 1.13 | 0.96 |
| T | 411C | 0.98 | 0.91 | 0.52 | 0.92 | 0.90 | 0.85 | 0.85 | 0.80 | 0.84 | 0.84 | 0.81 |
| T | 411D | 0.75 | 1.12 | 1.84 | 0.62 | 1.12 | 1.01 | 1.05 | 1.03 | 1.05 | 1.20 | 1.08 |
| T | 411E | 0.89 | 1.24 | 1.08 | 0.87 | 1.03 | 1.03 | 1.05 | 1.07 | 1.06 | 0.99 | 1.08 |
| T | 411F | 0.82 | 1.04 | 1.66 | 0.77 | 1.11 | 1.05 | 1.10 | 1.13 | 1.08 | 1.15 | 1.04 |
| T | 411G | 0.87 | 1.04 | 2.68 | 0.72 | 1.05 | 0.97 | 0.98 | 0.99 | 0.98 | 1.10 | 1.04 |
| T | 411H | 0.95 | 0.94 | 2.79 | 0.87 | 0.97 | 0.93 | 0.93 | 0.94 | 0.86 | 1.00 | 1.08 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| T | 411I | 0.88 | 0.87 | 0.45 | 0.80 | 1.06 | 1.01 | 1.03 | 0.98 | 1.05 | 1.02 | 1.07 |
| T | 411K | 0.93 | 0.89 | 0.86 | 0.87 | 1.00 | 0.95 | 0.98 | 0.80 | 0.95 | 1.05 | 0.93 |
| T | 411L | 0.98 | 0.85 | 1.44 | 0.99 | 1.02 | 1.00 | 0.97 | 0.67 | 0.96 | 0.95 | 0.94 |
| T | 411M | 0.65 | 1.53 | 0.93 | 0.76 | 1.55 | 1.59 | 1.47 | 1.11 | 1.42 | 1.46 | 1.42 |
| T | 411N | 0.81 | 1.10 | 0.35 | 0.81 | 1.14 | 1.07 | 1.04 | 1.00 | 1.05 | 1.04 | 1.05 |
| T | 411P | −0.06 | −5.74 | −19.23 | −0.02 | −3.32 | −0.58 | −1.90 | −2.19 | −3.01 | −3.23 | −3.63 |
| T | 411Q | 0.79 | 1.33 | 0.44 | 0.74 | 1.14 | 1.11 | 1.12 | 1.15 | 1.13 | 0.46 | 1.15 |
| T | 411R | 0.70 | 1.28 | 0.16 | 0.61 | 1.28 | 1.21 | 1.24 | 1.31 | 1.17 | 1.38 | 1.30 |
| T | 411S | 0.83 | 1.05 | 2.01 | 0.74 | 1.14 | 1.07 | 1.09 | 1.13 | 1.08 | 1.10 | 1.22 |
| T | 411V | 0.82 | 1.02 | −0.24 | 0.66 | 1.12 | 1.02 | 1.05 | 1.03 | 1.07 | 1.18 | 0.90 |
| T | 411W | 0.87 | 0.89 | 1.49 | 0.80 | 1.06 | 1.00 | 1.01 | 0.89 | 0.99 | 1.05 | 1.04 |
| T | 411Y | 0.81 | 0.95 | 2.18 | 0.83 | 1.21 | 1.18 | 1.15 | 0.82 | 1.09 | 1.20 | 15.67 |
| G | 412A | 0.96 | 1.03 | 8.94 | 1.13 | 1.01 | 1.01 | 0.94 | 0.61 | 0.94 | 0.92 | 0.81 |
| G | 412C | 0.81 | 1.05 | 10.89 | 0.66 | 1.01 | 0.87 | 0.87 | 0.72 | 0.89 | 0.91 | 0.99 |
| G | 412D | 0.17 | 2.94 | 66.10 | 0.08 | 3.26 | 1.91 | 2.30 | 2.10 | 2.56 | 3.26 | 4.11 |
| G | 412E | 0.14 | 3.48 | 6.51 | 0.06 | 3.38 | 1.68 | 2.15 | 2.12 | 2.53 | 3.68 | 3.71 |
| G | 412H | 0.07 | 2.94 | 23.72 | 0.03 | 5.58 | 2.43 | 3.52 | 3.46 | 3.81 | 5.81 | 5.65 |
| G | 412I | 0.19 | 2.57 | 48.24 | 0.08 | 3.02 | 1.83 | 2.13 | 2.03 | 2.39 | 3.06 | 3.57 |
| G | 412K | 0.07 | 3.37 | −0.01 | 0.02 | 5.49 | 2.18 | 3.41 | 3.21 | 4.25 | 6.08 | 4.98 |
| G | 412L | 0.29 | 1.77 | −26.69 | 0.14 | 2.11 | 1.35 | 1.51 | 1.26 | 1.67 | 2.29 | 2.43 |
| G | 412M | 0.68 | 1.08 | −7.41 | 0.58 | 1.21 | 0.94 | 0.88 | 0.49 | 0.94 | 1.02 | 1.05 |
| G | 412N | 0.48 | 1.28 | −6.34 | 0.30 | 1.40 | 0.87 | 0.94 | 0.65 | 1.04 | 1.46 | 1.24 |
| G | 412P | −0.01 | −117.76 | 2601.20 | 0.00 | −73.19 | −11.46 | −41.34 | −44.21 | −73.27 | −54.67 | −152.69 |
| G | 412R | 0.08 | 3.70 | 61.23 | 0.02 | 4.67 | 1.56 | 2.55 | 2.39 | 3.23 | 5.12 | 5.62 |
| G | 412S | 0.69 | 1.13 | −6.21 | 0.45 | 1.18 | 0.92 | 0.94 | 0.77 | 0.95 | 1.07 | 1.16 |
| G | 412T | 0.49 | 1.30 | 13.92 | 0.31 | 1.51 | 1.05 | 1.10 | 0.88 | 1.15 | 1.64 | 1.53 |
| G | 412V | 0.32 | 1.52 | −4.43 | 0.16 | 2.04 | 1.24 | 1.36 | 1.09 | 1.49 | 2.21 | 2.04 |
| G | 412W | −0.11 | −1.95 | 83.06 | −0.02 | −1.92 | −0.28 | −1.07 | −1.16 | −1.80 | −1.26 | −1.63 |
| G | 412Y | 0.28 | 1.39 | −48.53 | 0.12 | 2.09 | 1.14 | 1.29 | 1.10 | 1.54 | 2.17 | 2.54 |
| T | 413A | 1.38 | 0.75 | 1.61 | 1.81 | 0.77 | 0.77 | 0.70 | 0.40 | 0.89 | 0.73 | 0.67 |
| T | 413C | 1.11 | 1.01 | 1.92 | 1.26 | 0.88 | 0.82 | 0.77 | 0.59 | 1.01 | 0.84 | 1.37 |
| T | 413D | 1.18 | 0.91 | 1.50 | 1.30 | 0.86 | 0.79 | 0.73 | 0.58 | 0.96 | 0.78 | 0.73 |
| T | 413E | 1.13 | 0.97 | 1.61 | 1.25 | 0.90 | 0.82 | 0.78 | 0.64 | 0.97 | 0.84 | 0.84 |
| T | 413F | 1.21 | 0.97 | 1.12 | 1.27 | 0.86 | 0.78 | 0.73 | 0.62 | 0.93 | 0.82 | 0.91 |
| T | 413G | 1.00 | 0.98 | 0.51 | 0.92 | 0.99 | 0.89 | 0.84 | 0.70 | 1.05 | 1.01 | 0.93 |
| T | 413I | 0.79 | 1.11 | 0.31 | 0.75 | 1.24 | 1.12 | 1.09 | 0.88 | 1.37 | 1.33 | 1.03 |
| T | 413L | 1.04 | 0.92 | 0.43 | 1.24 | 1.01 | 1.02 | 0.96 | 0.79 | 1.20 | 0.91 | 0.98 |
| T | 413M | 1.14 | 0.94 | 1.53 | 1.30 | 0.85 | 0.79 | 0.74 | 0.53 | 0.97 | 0.82 | 0.71 |
| T | 413N | 1.11 | 0.90 | 2.44 | 1.14 | 0.82 | 0.75 | 0.72 | 0.63 | 0.98 | 0.85 | 0.21 |
| T | 413P | 1.02 | 1.03 | 1.75 | 0.99 | 0.91 | 0.79 | 0.79 | 0.75 | 1.02 | 0.95 | 0.87 |
| T | 413R | 1.07 | 1.06 | 1.07 | 0.93 | 0.88 | 0.78 | 0.77 | 0.76 | 0.94 | 0.89 | 0.95 |
| T | 413S | 1.11 | 0.92 | 2.21 | 0.92 | 0.82 | 0.71 | 0.73 | 0.70 | 0.92 | 0.90 | 0.71 |
| T | 413V | 0.87 | 1.23 | 1.13 | 0.78 | 1.03 | 0.93 | 0.95 | 0.90 | 1.21 | 1.10 | 0.98 |
| T | 413W | 0.82 | 1.07 | 0.49 | 0.73 | 1.05 | 0.94 | 0.96 | 0.87 | 1.21 | 1.11 | 1.02 |
| T | 413Y | 1.09 | 0.76 | 0.29 | 1.04 | 0.88 | 0.84 | 0.82 | 0.68 | 1.02 | 0.95 | 0.76 |
| I | 414A | 1.06 | 1.01 | 1.90 | 1.12 | 0.87 | 0.72 | 0.70 | 0.54 | 0.92 | 0.86 | 0.86 |
| I | 414C | 1.03 | 0.89 | 1.42 | 0.93 | 0.83 | 0.71 | 0.72 | 0.67 | 0.93 | 0.85 | 0.81 |
| I | 414D | 0.06 | 11.28 | 27.32 | 0.02 | 4.18 | 0.82 | 2.90 | 3.46 | 5.08 | 7.25 | 3.64 |
| I | 414E | 0.22 | 2.54 | 4.38 | 0.09 | 2.00 | 0.90 | 1.35 | 1.53 | 1.96 | 2.94 | 1.85 |
| I | 414F | 1.11 | 0.94 | −0.22 | 0.92 | 0.79 | 0.69 | 0.70 | 0.74 | 0.94 | 0.82 | 0.74 |
| I | 414G | 0.54 | 1.26 | 0.73 | 0.27 | 1.22 | 0.77 | 0.88 | 0.96 | 1.19 | 1.45 | 1.18 |
| I | 414H | 0.62 | 1.26 | 0.40 | 0.41 | 1.23 | 0.94 | 1.00 | 1.04 | 1.29 | 1.48 | 1.16 |
| I | 414K | 0.03 | 13.33 | −21.26 | 0.01 | 10.67 | 2.62 | 6.87 | 7.62 | 10.55 | 16.89 | 9.54 |
| I | 414L | 0.86 | 1.03 | 1.36 | 0.81 | 1.11 | 1.03 | 1.00 | 0.82 | 1.28 | 1.12 | 0.92 |
| I | 414M | 1.16 | 0.93 | 0.59 | 1.29 | 0.84 | 0.80 | 0.73 | 0.56 | 0.97 | 0.79 | 0.35 |
| I | 414N | 0.76 | 1.00 | 1.60 | 0.56 | 0.98 | 0.73 | 0.77 | 0.74 | 1.04 | 1.19 | 0.91 |
| I | 414P | 0.40 | 1.73 | 3.04 | 0.23 | 1.57 | 0.99 | 1.14 | 1.20 | 1.56 | 1.92 | 1.63 |
| I | 414Q | 0.84 | 1.11 | 1.83 | 0.61 | 0.96 | 0.82 | 0.84 | 0.90 | 1.14 | 1.16 | 1.00 |
| I | 414R | −0.25 | 3.08 | −3.84 | −0.06 | −0.45 | 0.00 | −0.42 | −0.54 | −0.86 | −1.16 | −0.29 |
| I | 414T | 0.84 | 1.25 | 1.25 | 0.64 | 0.99 | 0.86 | 0.89 | 0.90 | 1.16 | 1.03 | 0.87 |
| I | 414V | 0.79 | 1.29 | 0.08 | 0.61 | 1.10 | 0.99 | 1.02 | 1.03 | 1.37 | 1.16 | 1.14 |
| I | 414W | 0.62 | 1.38 | 1.32 | 0.41 | 1.24 | 0.99 | 1.05 | 1.01 | 1.37 | 1.45 | 1.08 |
| N | 415A | 1.03 | 1.02 | 0.83 | 1.12 | 0.91 | 0.93 | 0.95 | 0.71 | 0.93 | 0.97 | 0.77 |
| N | 415D | 0.74 | 1.44 | 0.96 | 0.63 | 1.21 | 1.12 | 1.23 | 1.03 | 1.21 | 1.27 | 1.02 |
| N | 415E | 0.69 | 1.62 | 1.10 | 0.57 | 1.34 | 1.32 | 1.38 | 1.22 | 1.40 | 1.44 | 1.37 |
| N | 415F | 0.75 | 1.32 | 0.16 | 0.63 | 1.19 | 1.14 | 1.16 | 1.03 | 1.11 | 1.22 | 1.26 |
| N | 415G | 0.67 | 1.31 | −0.25 | 0.55 | 1.37 | 1.28 | 1.26 | 1.12 | 1.26 | 1.47 | 1.38 |
| N | 415H | 0.75 | 1.20 | 0.88 | 0.67 | 1.14 | 1.09 | 1.11 | 0.94 | 1.00 | 1.22 | 1.19 |
| N | 415I | 0.70 | 1.15 | 0.17 | 0.56 | 1.27 | 1.17 | 1.15 | 0.89 | 1.13 | 1.33 | 1.36 |
| N | 415K | 0.75 | 1.04 | 0.90 | 0.65 | 1.22 | 1.15 | 1.14 | 0.80 | 1.10 | 1.16 | 1.24 |
| N | 415L | 0.83 | 0.97 | 0.90 | 0.77 | 1.14 | 1.10 | 1.03 | 0.68 | 1.01 | 1.15 | 1.02 |
| N | 415M | 1.26 | 0.87 | 0.46 | 1.48 | 0.87 | 0.91 | 0.95 | 0.67 | 0.95 | 0.89 | 0.78 |
| N | 415P | 0.84 | 1.21 | 1.32 | 0.72 | 1.18 | 1.13 | 1.13 | 0.81 | 1.10 | 1.25 | 1.10 |
| N | 415Q | 0.83 | 1.15 | 0.61 | 0.71 | 1.11 | 1.04 | 1.06 | 0.78 | 1.03 | 1.21 | 0.98 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| N | 415R | 0.81 | 1.22 | 0.98 | 0.75 | 1.21 | 1.17 | 1.09 | 0.82 | 1.02 | 1.32 | 1.12 |
| N | 415V | 0.65 | 1.29 | 1.81 | 0.55 | 1.51 | 1.39 | 1.32 | 0.81 | 1.27 | 1.43 | 1.55 |
| N | 415W | 0.50 | 1.71 | 0.77 | 0.39 | 1.92 | 1.75 | 1.65 | 1.01 | 1.60 | 1.86 | 1.82 |
| A | 416C | 1.19 | 0.87 | 0.64 | 1.57 | 0.84 | 0.94 | 0.83 | 0.64 | 0.83 | 0.81 | 0.76 |
| A | 416D | 1.08 | 0.91 | 1.38 | 1.24 | 0.95 | 0.87 | 0.80 | 0.62 | 0.83 | 0.95 | 0.77 |
| A | 416E | 1.01 | 1.05 | 2.18 | 1.11 | 1.00 | 0.94 | 0.90 | 0.70 | 0.86 | 0.93 | 0.73 |
| A | 416F | 0.99 | 1.04 | 1.72 | 0.98 | 1.02 | 0.92 | 0.86 | 0.71 | 0.87 | 0.95 | 2.13 |
| A | 416H | 0.98 | 0.89 | 2.62 | 0.93 | 1.01 | 0.93 | 0.89 | 0.75 | 0.82 | 0.95 | 0.88 |
| A | 416I | 0.85 | 0.94 | −0.56 | 0.80 | 1.15 | 1.00 | 0.96 | 0.84 | 0.97 | 1.08 | 1.06 |
| A | 416K | 1.05 | 0.81 | 0.75 | 1.21 | 0.98 | 0.97 | 0.88 | 0.75 | 0.85 | 1.04 | 0.98 |
| A | 416L | 1.00 | 0.79 | 3.20 | 1.22 | 1.04 | 1.06 | 0.92 | 0.75 | 0.94 | 1.09 | 1.33 |
| A | 416M | 0.91 | 0.90 | 3.41 | 0.82 | 0.94 | 0.74 | 0.72 | 0.57 | 0.72 | 0.95 | 0.87 |
| A | 416N | 1.13 | 0.86 | 1.13 | 1.19 | 0.84 | 0.78 | 0.78 | 0.69 | 0.79 | 0.86 | 0.79 |
| A | 416P | 0.29 | 1.56 | 1.53 | 0.15 | 2.09 | 1.31 | 1.46 | 1.04 | 1.40 | 0.98 | 0.56 |
| A | 416Q | 0.77 | 1.21 | 1.72 | 0.78 | 1.18 | 1.09 | 1.11 | 1.05 | 1.12 | 1.32 | 0.98 |
| A | 416R | 0.98 | 0.99 | 0.59 | 0.88 | 0.97 | 0.86 | 0.88 | 0.84 | 0.81 | 0.92 | 0.98 |
| A | 416T | 0.97 | 0.92 | 1.85 | 0.87 | 0.92 | 0.86 | 0.85 | 0.84 | 0.87 | 0.91 | 0.88 |
| A | 416V | 0.95 | 0.81 | −0.01 | 0.79 | 0.91 | 0.84 | 0.85 | 0.81 | 0.83 | 0.89 | 0.92 |
| A | 416Y | 0.75 | 0.73 | 2.74 | 0.58 | 1.07 | 0.87 | 0.85 | 0.70 | 0.87 | 1.10 | 1.22 |
| R | 417A | 0.97 | 0.92 | 1.81 | 0.88 | 0.89 | 0.76 | 0.73 | 0.55 | 0.97 | 0.97 | 0.83 |
| R | 417C | 0.68 | 1.10 | 2.43 | 0.53 | 1.14 | 0.96 | 0.97 | 0.90 | 1.27 | 1.36 | 1.09 |
| R | 417D | 0.64 | 1.35 | 1.57 | 0.41 | 1.18 | 0.99 | 1.01 | 1.02 | 1.39 | 1.30 | 1.15 |
| R | 417F | 0.84 | 1.12 | 1.05 | 0.56 | 0.97 | 0.78 | 0.82 | 0.88 | 1.11 | 1.04 | 0.94 |
| R | 417G | 0.83 | 0.96 | −0.72 | 0.55 | 0.99 | 0.88 | 0.89 | 0.96 | 1.19 | 1.04 | 0.97 |
| R | 417H | 0.62 | 1.41 | 1.28 | 0.37 | 1.21 | 0.95 | 1.02 | 1.06 | 1.29 | 1.38 | 1.24 |
| R | 417I | 0.74 | 1.09 | 1.05 | 0.46 | 1.00 | 0.83 | 0.89 | 0.87 | 1.18 | 1.16 | 1.89 |
| R | 417K | 0.82 | 1.07 | −0.59 | 0.53 | 0.97 | 0.83 | 0.86 | 0.79 | 1.11 | 1.05 | 0.85 |
| R | 417M | 0.99 | 0.80 | 2.91 | 0.90 | 0.88 | 0.78 | 0.73 | 0.55 | 0.94 | 0.88 | 0.77 |
| R | 417N | 0.89 | 0.98 | 3.36 | 0.73 | 0.92 | 0.78 | 0.78 | 0.70 | 1.02 | 1.02 | 0.83 |
| R | 417P | 0.23 | 3.01 | 3.16 | 0.10 | 2.22 | 1.17 | 1.55 | 1.58 | 2.10 | 3.17 | 2.21 |
| R | 417Q | 0.71 | 0.81 | 0.69 | 0.37 | 0.93 | 0.68 | 0.74 | 0.79 | 0.97 | 1.16 | 1.01 |
| R | 417S | 0.56 | 1.92 | 3.24 | 0.32 | 1.30 | 1.03 | 1.11 | 1.13 | 1.47 | 1.45 | 1.27 |
| R | 417W | 0.29 | 2.17 | 1.41 | 0.14 | 2.10 | 1.44 | 1.69 | 1.59 | 2.17 | 2.39 | 2.45 |
| R | 417Y | 0.50 | 1.37 | 2.24 | 0.32 | 1.62 | 1.32 | 1.33 | 1.09 | 1.78 | 1.87 | 1.60 |
| S | 418C | 0.83 | 1.12 | 2.07 | 0.74 | 1.06 | 1.00 | 0.97 | 0.76 | 0.95 | 1.13 | 1.20 |
| S | 418D | 0.69 | 1.45 | 1.26 | 0.59 | 1.25 | 1.20 | 1.18 | 1.00 | 1.19 | 1.18 | 1.08 |
| S | 418E | 0.89 | 1.17 | −0.57 | 0.80 | 1.00 | 0.99 | 0.96 | 0.86 | 1.00 | 1.10 | 1.02 |
| S | 418F | 0.69 | 1.38 | 1.05 | 0.51 | 1.18 | 1.08 | 1.09 | 0.96 | 1.10 | 1.24 | 1.38 |
| S | 418H | 0.77 | 1.25 | −0.34 | 0.60 | 1.13 | 1.06 | 1.06 | 0.94 | 1.05 | 1.17 | 1.14 |
| S | 418I | 0.63 | 1.22 | 2.78 | 0.44 | 1.30 | 1.06 | 1.10 | 0.95 | 1.12 | 1.50 | 1.41 |
| S | 418K | 0.77 | 1.22 | 1.31 | 0.60 | 1.13 | 1.03 | 1.04 | 0.82 | 1.06 | 1.22 | 1.28 |
| S | 418M | 0.94 | 1.02 | 1.33 | 1.14 | 1.07 | 1.06 | 0.92 | 0.50 | 0.89 | 0.75 | 0.85 |
| S | 418N | 0.82 | 1.16 | 0.27 | 0.86 | 1.20 | 1.14 | 1.04 | 0.66 | 1.04 | 1.15 | 1.01 |
| S | 418P | 0.00 | −62.14 | 200.16 | 0.00 | 23.12 | 5.06 | 14.67 | 18.70 | 32.07 | 74.24 | 37.22 |
| S | 418Q | 0.80 | 1.17 | −1.03 | 0.72 | 1.10 | 1.06 | 1.01 | 0.74 | 1.02 | 1.07 | 1.12 |
| S | 418R | 0.84 | 1.27 | 1.99 | 0.87 | 1.18 | 1.14 | 1.10 | 0.80 | 1.02 | 1.09 | 1.11 |
| S | 418T | 0.23 | 5.06 | 9.26 | 0.16 | 3.67 | 3.29 | 2.33 | 2.08 | −0.86 | 3.47 | 3.63 |
| S | 418W | 0.69 | 1.24 | 6.49 | 0.54 | 1.33 | 1.16 | 1.08 | 0.75 | 1.18 | 1.45 | 1.23 |
| S | 418Y | 0.70 | 1.11 | 3.72 | 0.69 | 1.41 | 1.36 | 1.27 | 0.87 | 1.28 | 1.38 | 1.22 |
| V | 419A | 0.28 | 0.63 | 14.82 | 0.06 | 0.33 | 0.01 | 0.19 | 0.24 | 0.53 | 0.08 | 0.47 |
| V | 419C | 0.84 | 1.06 | 3.85 | 0.81 | 1.06 | 0.96 | 0.97 | 0.87 | 0.95 | 1.10 | 1.03 |
| V | 419D | 0.37 | 1.40 | 8.04 | 0.16 | 1.37 | 0.73 | 0.94 | 0.93 | 1.06 | 1.53 | 3.17 |
| V | 419E | 0.67 | 1.07 | 3.23 | 0.43 | 1.07 | 0.80 | 0.86 | 0.86 | 0.90 | 1.34 | 1.78 |
| V | 419F | 0.49 | 1.12 | 3.11 | 0.24 | 1.27 | 0.80 | 0.93 | 0.92 | 0.95 | 1.51 | 1.29 |
| V | 419G | 0.64 | 1.10 | −0.56 | 0.36 | 1.09 | 0.77 | 0.84 | 0.86 | 0.88 | 1.15 | 1.11 |
| V | 419H | 0.49 | 1.16 | 6.11 | 0.26 | 1.40 | 0.94 | 1.05 | 1.03 | 1.07 | 1.52 | 1.54 |
| V | 419I | 0.81 | 1.03 | 2.05 | 0.72 | 1.13 | 1.04 | 1.05 | 1.05 | 1.06 | 1.26 | 1.12 |
| V | 419L | 0.77 | 0.93 | 5.26 | 0.71 | 1.22 | 1.12 | 1.05 | 0.85 | 1.06 | 1.18 | 1.10 |
| V | 419M | 0.83 | 0.99 | 2.62 | 0.84 | 1.06 | 0.98 | 0.89 | 0.68 | 0.86 | 1.06 | 1.03 |
| V | 419N | 0.79 | 0.97 | 3.79 | 0.62 | 0.96 | 0.78 | 0.78 | 0.74 | 0.80 | 1.10 | 0.96 |
| V | 419P | 0.73 | 1.20 | 5.78 | 0.59 | 1.14 | 0.97 | 1.03 | 0.94 | 1.02 | 1.22 | 1.13 |
| V | 419Q | 0.80 | 1.03 | 6.06 | 0.59 | 1.00 | 0.85 | 0.89 | 0.91 | 0.91 | 1.04 | 0.35 |
| V | 419R | 0.03 | 9.34 | 12.42 | 0.01 | 7.24 | 1.25 | 4.08 | 4.68 | 6.43 | 6.78 | 8.45 |
| V | 419S | 0.82 | 1.18 | 2.17 | 0.69 | 1.11 | 1.00 | 1.03 | 1.07 | 1.03 | 1.00 | 1.10 |
| V | 419T | 0.84 | 0.99 | −0.79 | 0.69 | 1.08 | 1.01 | 1.03 | 1.05 | 1.02 | 1.04 | 0.08 |
| V | 419W | −0.03 | −4.05 | −30.18 | −0.01 | −10.81 | −2.68 | −6.08 | −6.19 | −8.27 | −12.67 | −11.55 |
| V | 419Y | 0.12 | 3.13 | 26.20 | 0.04 | 3.77 | 1.46 | 2.15 | 1.89 | 2.67 | 3.94 | 3.21 |
| A | 420D | 0.66 | 1.32 | 2.74 | 0.42 | 1.09 | 0.84 | 0.90 | 0.82 | 1.19 | 1.23 | 1.12 |
| A | 420E | 0.75 | 1.34 | 2.63 | 0.46 | 1.01 | 0.78 | 0.83 | 0.78 | 1.10 | 1.15 | 1.18 |
| A | 420F | 0.88 | 1.06 | 0.13 | 0.63 | 0.96 | 0.84 | 0.86 | 0.81 | 1.11 | 1.02 | 0.93 |
| A | 420G | 0.97 | 1.09 | 1.15 | 0.72 | 0.92 | 0.81 | 0.81 | 0.79 | 1.06 | 0.92 | 0.84 |
| A | 420H | 0.91 | 0.96 | 0.30 | 0.62 | 0.92 | 0.77 | 0.80 | 0.75 | 1.02 | 0.99 | 0.91 |
| A | 420I | 0.87 | 1.03 | 1.16 | 0.66 | 1.02 | 0.90 | 0.93 | 0.84 | 1.21 | 1.01 | 1.09 |
| A | 420K | 0.72 | 1.07 | 0.78 | 0.44 | 1.06 | 0.84 | 0.89 | 0.78 | 1.16 | 1.21 | 1.19 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| A | 420L | 0.63 | 1.19 | 1.08 | 0.47 | 1.40 | 1.19 | 1.19 | 0.97 | 1.58 | 1.60 | 1.38 |
| A | 420M | 1.22 | 0.82 | 1.16 | 1.44 | 0.83 | 0.80 | 0.70 | 0.40 | 0.89 | 0.81 | 0.86 |
| A | 420N | 1.14 | 0.86 | 1.17 | 1.10 | 0.82 | 0.74 | 0.70 | 0.47 | 0.88 | 0.87 | 0.71 |
| A | 420P | −0.06 | 4.91 | −20.81 | −0.01 | −2.18 | −0.12 | −1.89 | −2.29 | −3.65 | −5.66 | −2.29 |
| A | 420Q | 0.99 | 0.95 | 0.73 | 0.80 | 0.90 | 0.80 | 0.78 | 0.58 | 1.01 | 0.89 | 0.85 |
| A | 420R | 0.34 | 1.84 | 3.24 | 0.15 | 1.81 | 1.03 | 1.22 | 1.03 | 1.59 | 2.19 | 1.66 |
| A | 420S | 0.87 | 1.01 | 1.46 | 0.75 | 1.07 | 0.95 | 0.94 | 0.74 | 1.21 | 1.05 | 0.88 |
| A | 420T | 0.93 | 1.09 | 0.70 | 0.76 | 1.01 | 0.88 | 0.87 | 0.65 | 1.11 | 0.99 | 0.88 |
| A | 420V | 1.00 | 0.98 | 0.94 | 0.82 | 0.96 | 0.88 | 0.87 | 0.63 | 1.11 | 0.99 | 0.91 |
| A | 420W | 0.74 | 1.05 | 0.26 | 0.57 | 1.22 | 1.02 | 1.01 | 0.73 | 1.34 | 1.29 | 1.03 |
| A | 420Y | 0.92 | 1.00 | 0.73 | 0.86 | 1.07 | 1.01 | 0.94 | 0.72 | 1.21 | 1.08 | 0.89 |
| V | 421A | 0.87 | 1.04 | 2.83 | 0.95 | 1.08 | 1.00 | 0.90 | 0.68 | 0.94 | 1.09 | 1.01 |
| V | 421C | 0.82 | 1.03 | 2.28 | 0.78 | 1.06 | 1.01 | 0.99 | 0.88 | 1.01 | 1.07 | 1.04 |
| V | 421D | −0.04 | −10.39 | −2.27 | −0.01 | −4.02 | −0.48 | −2.36 | −2.79 | −4.37 | −3.03 | −4.83 |
| V | 421E | 0.01 | 49.77 | 400.52 | 0.00 | 18.14 | 2.32 | 10.87 | 12.90 | 21.18 | 7.13 | 3.90 |
| V | 421F | −0.05 | −8.14 | −12.35 | −0.01 | −3.06 | −0.38 | −1.86 | −2.11 | −3.60 | −2.18 | −4.24 |
| V | 421G | 0.05 | 4.87 | 48.06 | 0.01 | 6.94 | 2.43 | 4.13 | 4.52 | 5.29 | 8.05 | 12.32 |
| V | 421H | −0.16 | 0.12 | −50.11 | −0.04 | −0.65 | −0.13 | −0.44 | −0.55 | −0.94 | −0.39 | −1.05 |
| V | 421I | 0.81 | 0.85 | 2.83 | 0.64 | 1.05 | 0.95 | 0.98 | 0.98 | 0.96 | 1.10 | 1.09 |
| V | 421K | −0.16 | 2.44 | −23.53 | −0.03 | −0.58 | −0.05 | −0.42 | −0.52 | −0.98 | 0.05 | −0.80 |
| V | 421L | 0.58 | 0.80 | 5.64 | 0.37 | 1.33 | 1.00 | 1.00 | 0.82 | 1.06 | 1.22 | 1.20 |
| V | 421M | 0.57 | 1.01 | 0.90 | 0.38 | 1.15 | 0.81 | 0.82 | 0.60 | 0.87 | 1.15 | 1.55 |
| V | 421N | 0.02 | 22.56 | 133.99 | 0.01 | 12.28 | 2.25 | 6.88 | 7.62 | 10.40 | 11.30 | 9.18 |
| V | 421Q | −0.04 | −7.45 | −50.85 | −0.01 | −4.05 | −0.53 | −2.54 | −2.91 | −4.33 | −4.00 | −1.86 |
| V | 421R | −0.07 | 0.28 | 22.89 | −0.01 | −1.28 | −0.30 | −0.93 | −1.16 | −2.01 | −0.47 | −1.00 |
| V | 421S | 0.58 | 1.15 | −0.03 | 0.36 | 1.29 | 1.00 | 1.06 | 1.05 | 1.07 | 1.37 | 1.32 |
| V | 421T | 0.71 | 1.15 | −1.12 | 0.52 | 1.19 | 1.03 | 1.09 | 1.04 | 1.07 | 1.30 | 1.02 |
| V | 421W | −0.19 | 1.10 | 8.35 | −0.04 | −0.50 | −0.07 | −0.36 | −0.47 | −0.81 | −0.31 | −1.14 |
| V | 421Y | −0.13 | 1.23 | −28.36 | −0.03 | −0.97 | −0.15 | −0.65 | −0.75 | −1.30 | −0.57 | −0.68 |
| L | 422A | 0.80 | 1.09 | −0.61 | 0.81 | 1.15 | 1.08 | 1.04 | 0.84 | 1.03 | 1.06 | 1.02 |
| L | 422C | 0.85 | 0.97 | 0.65 | 0.77 | 1.04 | 0.95 | 0.95 | 0.88 | 0.96 | 1.00 | 0.84 |
| L | 422D | −0.03 | −12.42 | −27.86 | −0.01 | −3.90 | −0.46 | −2.61 | −3.36 | −5.34 | −0.65 | −7.80 |
| L | 422E | 0.01 | 25.69 | −8.94 | 0.00 | 13.68 | 2.74 | 8.05 | 9.63 | 12.53 | 7.90 | 21.06 |
| L | 422F | 0.78 | 1.13 | 0.70 | 0.65 | 1.18 | 1.11 | 1.14 | 1.17 | 1.15 | 1.10 | 1.12 |
| L | 422G | 0.26 | 1.95 | 6.92 | 0.11 | 2.40 | 1.54 | 1.81 | 1.92 | 1.82 | 2.91 | 2.98 |
| L | 422H | 0.23 | 1.63 | 1.57 | 0.08 | 2.15 | 1.13 | 1.44 | 1.50 | 1.61 | 2.83 | 2.48 |
| L | 422I | 0.70 | 1.02 | 1.12 | 0.53 | 1.25 | 1.17 | 1.21 | 1.16 | 1.20 | 1.22 | 1.21 |
| L | 422K | −0.02 | 10.31 | −26.29 | 0.00 | −5.36 | −1.00 | −3.55 | −4.50 | −7.78 | −2.07 | −10.63 |
| L | 422M | 0.84 | 1.12 | 0.07 | 0.85 | 1.18 | 1.16 | 1.08 | 0.78 | 1.06 | 0.99 | 0.98 |
| L | 422N | 0.14 | 3.01 | −2.22 | 0.08 | 3.05 | 1.81 | 1.86 | 1.78 | 1.90 | 3.22 | 1.99 |
| L | 422P | −0.08 | −2.23 | 22.77 | −0.02 | −1.28 | −0.11 | −0.84 | −1.12 | −1.86 | −0.35 | −1.90 |
| L | 422Q | 0.14 | 1.90 | 5.36 | 0.04 | 2.59 | 0.99 | 1.55 | 1.72 | 1.99 | 3.06 | 2.38 |
| L | 422R | −0.02 | −11.17 | 110.30 | 0.00 | −4.98 | −0.44 | −3.41 | −4.61 | −7.33 | 0.34 | −11.19 |
| L | 422S | 0.54 | 0.93 | 0.34 | 0.28 | 1.28 | 0.92 | 0.99 | 1.00 | 1.04 | 1.32 | 1.36 |
| L | 422T | 0.65 | 1.07 | −0.85 | 0.37 | 1.15 | 0.92 | 1.00 | 0.96 | 1.02 | 1.27 | 1.13 |
| L | 422V | 0.81 | 0.96 | 1.57 | 0.62 | 1.07 | 1.03 | 1.09 | 0.98 | 1.04 | 1.03 | 1.06 |
| L | 422W | 0.59 | 0.95 | −1.07 | 0.34 | 1.25 | 0.98 | 1.04 | 0.88 | 1.06 | 1.44 | 1.56 |
| L | 422Y | 0.63 | 0.98 | −1.15 | 0.43 | 1.32 | 1.11 | 1.12 | 0.78 | 1.09 | 1.38 | 1.15 |
| Y | 423A | 0.91 | 1.03 | −26.57 | 1.01 | 1.14 | 1.09 | 0.99 | 0.57 | 0.96 | 1.08 | 1.03 |
| Y | 423C | 1.00 | 1.02 | 16.40 | 1.08 | 0.99 | 0.97 | 0.89 | 0.66 | 0.93 | 1.13 | 0.98 |
| Y | 423D | 0.69 | 1.22 | 26.61 | 0.59 | 1.25 | 1.05 | 1.01 | 0.80 | 1.04 | 1.53 | 1.48 |
| Y | 423E | 0.82 | 0.99 | −17.32 | 0.75 | 1.09 | 0.99 | 0.95 | 0.77 | 0.95 | 1.16 | 1.06 |
| Y | 423F | 0.94 | 1.01 | −34.24 | 0.96 | 1.07 | 1.02 | 0.98 | 0.82 | 0.93 | 1.14 | 1.06 |
| Y | 423G | 0.89 | 0.95 | −14.72 | 0.83 | 1.10 | 1.03 | 0.99 | 0.79 | 0.96 | 1.32 | 1.26 |
| Y | 423H | 0.89 | 1.04 | 46.64 | 0.83 | 1.08 | 1.02 | 0.98 | 0.79 | 1.01 | 1.06 | 0.34 |
| Y | 423I | 0.84 | 1.08 | −35.58 | 0.83 | 1.18 | 1.12 | 1.07 | 0.82 | 1.08 | 1.29 | 1.14 |
| Y | 423K | 0.77 | 0.93 | −46.27 | 0.58 | 1.09 | 0.95 | 0.91 | 0.70 | 0.88 | 1.28 | 1.27 |
| Y | 423M | 1.03 | 0.99 | 7.67 | 1.16 | 0.95 | 0.95 | 0.89 | 0.62 | 0.90 | 1.04 | 0.95 |
| Y | 423N | 0.87 | 1.00 | 10.19 | 0.79 | 1.02 | 0.93 | 0.93 | 0.80 | 0.95 | 1.17 | 1.14 |
| Y | 423P | 0.07 | 4.14 | 163.26 | 0.02 | 4.82 | 1.61 | 2.82 | 2.85 | 3.52 | 6.61 | 7.27 |
| Y | 423Q | 0.72 | 1.19 | −6.82 | 0.63 | 1.22 | 1.13 | 1.12 | 1.09 | 1.12 | 1.40 | 1.37 |
| Y | 423R | 0.60 | 1.24 | 0.05 | 0.45 | 1.37 | 1.21 | 1.20 | 1.17 | 1.17 | 1.88 | 1.73 |
| Y | 423T | 0.74 | 1.11 | 18.63 | 0.66 | 1.21 | 1.14 | 1.14 | 1.07 | 1.13 | 1.51 | 1.33 |
| Y | 423V | 0.88 | 0.91 | −30.45 | 0.78 | 1.04 | 0.99 | 0.98 | 0.88 | 1.02 | 1.17 | 0.97 |
| Y | 423W | 0.86 | 0.98 | −26.85 | 0.77 | 1.05 | 1.03 | 1.06 | 0.89 | 1.05 | 1.16 | 1.06 |
| P | 424A | 0.95 | 1.07 | −38.12 | 1.03 | 1.03 | 1.00 | 0.94 | 0.72 | 0.96 | 1.15 | 0.97 |
| P | 424C | 0.96 | 0.92 | 55.81 | 0.89 | 0.93 | 0.87 | 0.86 | 0.80 | 0.86 | 1.04 | 0.97 |
| P | 424D | 0.88 | 1.04 | 23.80 | 0.80 | 1.03 | 1.00 | 1.01 | 1.01 | 0.99 | 1.23 | 1.12 |
| P | 424E | 0.85 | 1.04 | −5.37 | 0.75 | 1.08 | 1.03 | 1.02 | 1.05 | 1.03 | 1.17 | 1.17 |
| P | 424G | 0.91 | 0.96 | 16.96 | 0.83 | 1.03 | 1.01 | 1.00 | 1.04 | 1.02 | 1.25 | 1.07 |
| P | 424H | 0.93 | 0.91 | −63.74 | 0.87 | 0.99 | 0.97 | 0.99 | 0.96 | 0.95 | 1.08 | 1.13 |
| P | 424I | 0.93 | 0.88 | 12.19 | 0.84 | 1.02 | 0.98 | 0.98 | 0.92 | 0.99 | 1.15 | 1.07 |
| P | 424K | 0.89 | 0.95 | −10.82 | 0.80 | 1.04 | 1.05 | 1.05 | 0.88 | 1.03 | 1.26 | 1.22 |
| P | 424M | 0.83 | 1.17 | 16.65 | 0.91 | 1.17 | 1.24 | 1.11 | 0.86 | 1.12 | 1.20 | 1.07 |

TABLE 4-continued

Average performance index values for AmyE full length variants

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | Cleaning pH 8 | Cleaning pH 10 |
|---|---|---|---|---|---|---|---|---|---|---|---|---|
| P | 424N | 0.84 | 1.01 | −3.09 | 0.79 | 1.06 | 1.02 | 1.01 | 0.97 | 1.01 | 1.21 | 1.19 |
| P | 424Q | 0.76 | 1.25 | −12.75 | 0.72 | 1.20 | 1.20 | 1.19 | 1.26 | 1.19 | 1.45 | 1.28 |
| P | 424R | 0.81 | 1.15 | 23.39 | 0.75 | 1.11 | 1.10 | 1.08 | 1.20 | 1.07 | 1.28 | 1.34 |
| P | 424S | 0.89 | 1.11 | 12.14 | 0.76 | 0.99 | 1.02 | 1.03 | 1.10 | 1.02 | 1.29 | 1.17 |
| P | 424T | 0.84 | 1.11 | −25.96 | 0.71 | 1.05 | 0.99 | 1.01 | 1.01 | 1.00 | 1.13 | 1.07 |
| P | 424V | 0.70 | 1.12 | −14.41 | 0.56 | 1.26 | 1.23 | 1.23 | 1.18 | 1.25 | 1.40 | 1.34 |
| P | 424W | 0.79 | 0.99 | −36.90 | 0.59 | 1.10 | 1.02 | 1.04 | 0.80 | 1.06 | 1.28 | 1.15 |
| P | 424Y | 0.81 | 1.00 | −51.25 | 0.78 | 1.19 | 1.19 | 1.12 | 0.82 | 1.10 | 1.32 | 1.21 |
| D | 425A | 0.90 | 1.00 | 1.15 | 1.08 | 1.05 | 1.09 | 0.96 | 0.64 | 0.95 | 1.07 | 1.34 |
| D | 425I | 0.74 | 1.01 | 1.28 | 0.60 | 1.19 | 1.10 | 1.08 | 0.94 | 1.07 | 1.36 | 1.44 |
| D | 425K | 0.82 | 1.01 | −0.01 | 0.67 | 1.10 | 1.03 | 1.02 | 0.82 | 1.00 | 1.16 | 1.09 |
| D | 425L | 0.73 | 1.06 | 0.13 | 0.68 | 1.31 | 1.30 | 1.19 | 0.88 | 1.21 | 1.41 | 1.36 |
| D | 425M | 1.21 | 0.79 | −0.20 | 1.80 | 0.88 | 1.04 | 0.86 | 0.46 | 0.87 | 0.83 | 0.75 |
| D | 425N | 1.16 | 0.83 | 0.09 | 1.43 | 0.91 | 0.97 | 0.85 | 0.55 | 0.83 | 0.90 | 0.81 |
| D | 425P | 1.05 | 0.89 | 0.27 | 1.03 | 0.92 | 0.89 | 0.80 | 0.55 | 0.78 | 0.96 | 0.92 |
| D | 425Q | 1.03 | 0.94 | −1.45 | 1.06 | 0.95 | 0.97 | 0.89 | 0.63 | 0.87 | 0.88 | 0.85 |
| D | 425R | 1.08 | 0.89 | −0.57 | 1.10 | 0.93 | 0.95 | 0.88 | 0.65 | 0.79 | 0.99 | 0.92 |
| D | 425S | 0.86 | 1.05 | −0.88 | 0.78 | 1.16 | 1.08 | 1.02 | 0.77 | 0.95 | 1.17 | 1.10 |
| D | 425T | 1.00 | 0.90 | −1.20 | 1.02 | 1.01 | 1.00 | 0.93 | 0.69 | 0.89 | 0.97 | 0.90 |
| D | 425V | 0.86 | 0.99 | −0.78 | 0.80 | 1.13 | 1.08 | 1.03 | 0.69 | 0.99 | 1.20 | 0.99 |
| D | 425W | 1.00 | 0.84 | −0.33 | 1.02 | 1.01 | 0.99 | 0.91 | 0.61 | 0.90 | 0.99 | 0.97 |
| D | 425Y | 0.82 | 0.94 | 4.10 | 0.86 | 1.25 | 1.27 | 1.14 | 0.73 | 1.10 | 1.33 | 1.34 |

TABLE 5

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| L | 001A | 1.333 | 0.786 | 2.032 | 1.989 | 0.855 | 0.987 | 0.930 | 0.652 | 0.877 | 0.94 | 0.83 | 0.71 | 0.97 | 1.05 |
| L | 001C | 0.726 | 0.938 | −6.117 | 0.568 | 1.054 | 0.873 | 0.851 | 0.743 | 0.845 | 0.97 | 0.98 | 0.91 | 0.85 | 0.94 |
| L | 001D | 1.093 | 0.930 | 5.129 | 1.324 | 0.925 | 0.982 | 0.990 | 0.966 | 0.966 | 1.01 | 1.03 | 0.89 | 1.40 | 1.36 |
| L | 001E | 1.276 | 0.768 | 1.739 | 1.471 | 0.835 | 0.903 | 0.992 | 0.948 | 0.925 | 1.02 | 1.06 | 0.96 | 1.04 | 0.76 |
| L | 001F | 1.089 | 0.817 | −1.100 | 1.148 | 0.872 | 0.887 | 0.866 | 0.871 | 0.871 | 1.02 | 1.05 | 1.09 | 0.92 | 1.04 |
| L | 001G | 1.134 | 0.871 | 3.116 | 1.219 | 0.885 | 0.904 | 0.923 | 0.922 | 0.915 | 1.04 | 1.06 | 1.04 | 1.02 | 1.12 |
| L | 001H | 1.262 | 0.802 | 2.643 | 1.595 | 0.849 | 0.943 | 0.992 | 1.008 | 0.942 | 1.09 | 1.12 | 0.72 | 1.09 | 1.00 |
| L | 001K | 1.345 | 0.713 | 3.142 | 1.723 | 0.800 | 0.882 | 0.919 | 0.781 | 0.864 | 1.07 | 0.98 | 0.95 | 1.32 | 0.91 |
| L | 001M | 0.784 | 1.142 | −2.640 | 0.816 | 1.168 | 1.157 | 1.079 | 0.706 | 1.019 | 1.00 | 0.93 | 0.89 | 0.90 | 1.00 |
| L | 001N | 1.121 | 0.865 | −8.483 | 1.405 | 0.904 | 0.980 | 0.943 | 0.868 | 0.875 | 1.03 | 1.02 | 0.78 | 0.92 | 0.89 |
| L | 001Q | 1.305 | 0.807 | 0.987 | 1.691 | 0.806 | 0.895 | 0.922 | 0.944 | 0.869 | 0.99 | 1.07 | 0.82 | 1.13 | 0.85 |
| L | 001R | 0.882 | 1.173 | 0.544 | 0.866 | 1.137 | 1.146 | 1.166 | 1.072 | 1.132 | 1.05 | 1.13 | 1.09 | 1.21 | 1.22 |
| L | 001S | 1.174 | 0.956 | −2.934 | 1.423 | 0.906 | 0.997 | 1.015 | 1.055 | 0.995 | 1.06 | 1.11 | 1.03 | 0.81 | 1.06 |
| L | 001T | 1.242 | 0.855 | 6.591 | 1.385 | 0.822 | 0.892 | 0.934 | 0.933 | 0.913 | 1.05 | 1.05 | 0.91 | 0.94 | 1.04 |
| L | 001V | 0.820 | 1.126 | −4.253 | 0.771 | 1.161 | 1.169 | 1.147 | 1.165 | 1.179 | 1.08 | 1.06 | 1.16 | 0.89 | 1.09 |
| L | 001W | 0.890 | 0.951 | −3.024 | 0.801 | 1.046 | 1.001 | 0.997 | 0.878 | 0.967 | 1.08 | 1.01 | 1.17 | 1.02 | 1.00 |
| L | 001Y | 0.843 | 1.098 | −7.114 | 0.881 | 1.181 | 1.219 | 1.193 | 0.844 | 1.115 | 0.98 | 0.79 | 0.70 | 0.90 | 1.04 |
| T | 002A | 1.288 | 0.924 | 1.536 | 1.910 | 0.849 | 1.020 | 0.954 | 0.536 | 0.927 | 0.93 | 0.74 | 1.02 | 0.60 | 1.12 |
| T | 002C | 0.820 | 0.846 | 1.454 | 0.778 | 1.048 | 0.940 | 0.908 | 0.640 | 0.918 | 0.91 | 0.83 | 0.90 | 0.95 | 0.78 |
| T | 002D | 1.011 | 0.937 | 1.913 | 1.115 | 1.015 | 0.971 | 0.939 | 0.781 | 0.948 | 0.97 | 0.85 | 0.97 | 1.10 | 0.96 |
| T | 002E | 1.200 | 0.973 | 0.873 | 1.526 | 0.901 | 0.946 | 0.911 | 0.789 | 0.901 | 0.93 | 0.84 | 0.85 | 1.23 | 1.05 |
| T | 002F | 0.348 | 0.509 | 2.813 | 0.186 | 1.900 | 1.136 | 1.160 | 1.007 | 1.253 | 0.92 | 0.86 | 0.96 | 0.75 | 1.23 |
| T | 002G | 1.141 | 0.940 | 0.239 | 1.350 | 0.965 | 0.984 | 0.929 | 0.797 | 0.939 | 0.95 | 0.88 | 1.07 | 1.17 | 0.86 |
| T | 002H | 1.197 | 1.071 | 0.267 | 1.429 | 0.920 | 0.978 | 0.920 | 0.791 | 0.921 | 0.90 | 0.83 | 0.98 | 0.88 | 0.79 |
| T | 002I | 0.642 | 0.395 | 1.578 | 0.441 | 1.259 | 0.982 | 0.945 | 0.781 | 0.976 | 0.93 | 0.63 | 1.04 | 0.87 | 0.76 |
| T | 002K | 1.164 | 0.700 | 1.698 | 1.362 | 0.920 | 0.969 | 0.907 | 0.761 | 0.922 | 0.96 | 0.69 | 0.98 | 0.98 | 0.92 |
| T | 002L | 0.837 | 0.601 | 0.890 | 0.765 | 1.103 | 0.982 | 0.907 | 0.745 | 0.949 | 0.91 | 0.45 | 0.92 | 0.87 | 0.84 |
| T | 002M | 0.864 | 0.767 | 0.692 | 0.782 | 0.933 | 0.883 | 0.844 | 0.563 | 0.828 | 0.93 | 0.81 | 0.92 | 0.67 | 0.69 |
| T | 002N | 1.043 | 0.942 | −0.096 | 1.200 | 0.936 | 0.969 | 0.967 | 0.821 | 0.951 | 0.93 | 0.85 | 1.03 | 1.05 | 0.96 |
| T | 002P | 0.859 | 0.550 | 3.083 | 0.681 | 0.910 | 0.743 | 0.770 | 0.746 | 0.808 | 0.88 | 0.86 | 1.17 | 1.11 | 0.69 |
| T | 002Q | 0.985 | 0.981 | 0.799 | 1.142 | 1.034 | 1.050 | 1.058 | 1.034 | 1.020 | 0.96 | 0.95 | 1.16 | 1.16 | 1.02 |
| T | 002R | 0.911 | 1.022 | 0.754 | 0.787 | 0.974 | 0.923 | 0.949 | 0.947 | 0.954 | 0.98 | 0.92 | 1.19 | 1.01 | 1.28 |
| T | 002S | 0.968 | 1.057 | 1.316 | 1.016 | 1.035 | 1.020 | 1.015 | 1.011 | 1.007 | 1.02 | 0.95 | 1.20 | 1.22 | 0.86 |
| T | 002V | 0.925 | 0.691 | −0.140 | 0.857 | 0.996 | 0.950 | 0.955 | 0.905 | 0.976 | 1.02 | 0.95 | 1.03 | 0.90 | 0.88 |
| T | 002W | 0.260 | 0.155 | 1.764 | 0.130 | 2.299 | 1.469 | 1.551 | 1.330 | 1.673 | 0.84 | 0.85 | 1.34 | 0.55 | 0.56 |
| T | 002Y | 0.208 | −1.672 | 8.174 | 0.090 | 2.486 | 1.341 | 1.594 | 1.322 | 1.808 | 0.96 | 0.48 | 1.17 | 1.21 | 0.61 |
| A | 003C | 0.500 | 1.213 | −14.605 | 0.331 | 1.402 | 1.112 | 1.102 | 0.942 | 1.119 | 0.97 | 0.95 | 0.79 | 0.95 | 0.87 |
| A | 003D | 0.847 | 1.162 | −3.162 | 0.834 | 1.081 | 1.094 | 1.064 | 1.052 | 1.062 | 0.97 | 0.99 | 1.07 | 1.14 | 0.72 |
| A | 003E | 0.843 | 1.059 | −0.273 | 0.795 | 1.035 | 1.015 | 1.024 | 1.014 | 1.017 | 1.07 | 1.12 | 1.05 | 1.02 | 0.99 |
| A | 003F | 0.722 | 1.196 | 3.727 | 0.521 | 1.113 | 0.999 | 1.004 | 1.005 | 0.975 | 0.99 | 1.05 | 1.01 | 1.14 | 0.83 |
| A | 003G | 0.918 | 0.998 | −1.722 | 0.780 | 1.022 | 1.003 | 1.001 | 0.997 | 0.997 | 1.01 | 1.01 | 0.89 | 0.66 | 0.78 |
| A | 003H | 0.762 | 1.158 | −4.020 | 0.613 | 1.218 | 1.173 | 1.154 | 1.247 | 1.126 | 1.07 | 1.06 | 1.15 | 1.15 | 1.06 |
| A | 003I | 0.500 | 1.359 | −1.612 | 0.332 | 1.545 | 1.324 | 1.352 | 1.329 | 1.329 | 1.06 | 1.08 | 1.07 | 1.27 | 1.30 |
| A | 003K | 0.787 | 1.003 | −2.962 | 0.649 | 1.145 | 1.089 | 1.094 | 0.915 | 1.060 | 1.03 | 0.97 | 0.67 | 0.90 | 0.99 |
| A | 003L | 0.734 | 1.100 | −4.058 | 0.570 | 1.213 | 1.135 | 1.110 | 0.765 | 1.081 | 1.02 | 0.75 | 0.89 | −0.03 | 1.21 |
| A | 003M | 0.790 | 1.224 | 1.057 | 0.842 | 1.189 | 1.166 | 1.069 | 0.665 | 1.010 | 0.99 | 0.91 | 0.59 | 0.91 | 0.98 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| A | 003N | 0.707 | 1.229 | 1.357 | 0.589 | 1.295 | 1.213 | 1.211 | 1.192 | 1.241 | 1.08 | 1.04 | 0.78 | 1.05 | 1.00 |
| A | 003P | 0.544 | 1.538 | 2.085 | 0.357 | 1.479 | 1.195 | 1.206 | 1.244 | 1.260 | 1.03 | 1.11 | 0.99 | 0.95 | 0.81 |
| A | 003Q | 0.882 | 1.025 | 1.422 | 0.803 | 1.037 | 1.025 | 1.017 | 0.992 | 1.002 | 1.03 | 1.08 | 0.84 | 0.75 | 0.78 |
| A | 003R | 0.520 | 1.173 | 0.930 | 0.294 | 1.419 | 1.126 | 1.122 | 1.030 | 1.143 | 1.01 | 1.06 | 0.95 | 1.28 | 0.82 |
| A | 003S | 0.979 | 0.948 | −5.544 | 0.895 | 1.006 | 0.972 | 0.977 | 0.919 | 0.976 | 0.99 | 1.00 | 0.95 | 0.48 | 0.58 |
| A | 003T | −0.076 | 1.410 | 151.962 | −0.014 | −1.343 | −0.160 | −0.767 | −0.852 | −1.512 | 0.00 | 0.00 | 0.00 | 0.00 | 0.00 |
| A | 003V | 0.693 | 1.139 | 2.513 | 0.499 | 1.228 | 1.099 | 1.129 | 1.015 | 1.086 | 0.90 | 0.90 | 0.82 | 0.81 | 1.14 |
| A | 003W | 0.569 | 1.158 | 4.082 | 0.330 | 1.317 | 1.055 | 1.063 | 0.890 | 1.063 | 1.09 | 1.01 | 0.97 | 0.98 | 0.89 |
| A | 003Y | 0.544 | 1.261 | −9.701 | 0.318 | 1.466 | 1.163 | 1.206 | 0.882 | 1.185 | 0.98 | 0.91 | 1.24 | 0.73 | 1.00 |
| P | 004C | −0.007 | −13.192 | −102.053 | −0.001 | −26.960 | −5.088 | −11.899 | −11.649 | −22.205 | 1.09 | 0.96 | 0.12 | 0.25 | 2.58 |
| P | 004D | 1.097 | 0.922 | −4.274 | 1.450 | 1.006 | 1.014 | 0.948 | 0.772 | 0.967 | 0.89 | 0.80 | 1.18 | 0.86 | 0.93 |
| P | 004E | 0.744 | 1.280 | −0.508 | 0.731 | 1.251 | 1.123 | 1.070 | 0.893 | 1.069 | 1.04 | 0.96 | 0.92 | 0.92 | 1.15 |
| P | 004F | 0.800 | 1.163 | −1.718 | 0.725 | 1.211 | 1.049 | 1.018 | 0.853 | 1.020 | 0.97 | 0.86 | 0.94 | 0.79 | 0.95 |
| P | 004G | 1.182 | 0.967 | −2.334 | 1.493 | 0.965 | 1.014 | 0.979 | 0.822 | 0.992 | 0.99 | 0.88 | 0.99 | 1.17 | 1.17 |
| P | 004H | 0.928 | 1.011 | 1.259 | 1.030 | 1.034 | 1.050 | 0.963 | 0.710 | 0.969 | 0.97 | 0.85 | 0.98 | 0.97 | 0.87 |
| P | 004I | 0.768 | 1.241 | −3.992 | 0.697 | 1.270 | 1.135 | 1.089 | 0.846 | 1.074 | 1.02 | 0.93 | 0.97 | 1.22 | 1.03 |
| P | 004K | 0.955 | 0.963 | 0.696 | 1.117 | 1.091 | 1.151 | 1.128 | 0.845 | 1.141 | 0.97 | 0.84 | 0.96 | 0.91 | 1.14 |
| P | 004L | 0.836 | 0.995 | −9.866 | 0.924 | 1.227 | 1.198 | 1.118 | 0.866 | 1.139 | 0.98 | 0.43 | 1.06 | 0.90 | 0.90 |
| P | 004M | 0.912 | 1.018 | 0.979 | 1.016 | 1.076 | 1.042 | 0.944 | 0.657 | 0.948 | 0.97 | 0.83 | 1.00 | 0.85 | 1.05 |
| P | 004N | 1.055 | 0.906 | 6.267 | 1.243 | 0.939 | 0.946 | 0.928 | 0.790 | 0.922 | 1.03 | 0.93 | 1.07 | 0.88 | 0.98 |
| P | 004Q | 0.938 | 1.082 | −0.268 | 1.052 | 1.052 | 1.051 | 1.026 | 1.015 | 1.054 | 0.99 | 0.93 | 1.20 | 0.82 | 1.22 |
| P | 004R | −0.196 | −2.774 | −7.034 | −0.033 | −0.394 | −0.042 | −0.220 | −0.278 | −0.643 | 0.00 | 0.00 | 0.00 | 0.00 | 0.00 |
| P | 004S | 0.986 | 1.064 | 6.615 | 1.072 | 1.040 | 1.070 | 1.068 | 1.062 | 1.118 | 1.04 | 0.97 | 1.19 | 1.02 | 1.20 |
| P | 004T | 0.858 | 1.157 | 7.648 | 0.885 | 1.184 | 1.221 | 1.212 | 1.157 | 1.209 | 1.09 | 1.00 | 1.48 | 1.08 | 1.04 |
| P | 004V | 0.898 | 1.033 | 3.502 | 0.820 | 1.061 | 1.028 | 1.010 | 0.917 | 1.025 | 1.00 | 0.93 | 1.31 | 0.89 | 0.81 |
| P | 004W | 0.650 | 1.249 | −1.829 | 0.492 | 1.265 | 1.106 | 1.095 | 0.905 | 1.128 | 0.99 | 0.90 | 1.37 | 0.95 | 1.44 |
| P | 004Y | 0.889 | 0.969 | 3.993 | 0.843 | 1.092 | 1.007 | 0.975 | 0.741 | 0.991 | 1.01 | 0.45 | 0.86 | 0.96 | 0.94 |
| S | 005A | 1.239 | 0.957 | 0.286 | 1.753 | 0.952 | 1.052 | 0.977 | 0.642 | 1.012 | 1.01 | 0.93 | 0.77 | 0.87 | 1.18 |
| S | 005C | 0.083 | 3.673 | −0.650 | 0.013 | 0.891 | −0.002 | 0.506 | 0.643 | 1.418 | 0.00 | 0.00 | 0.00 | 0.00 | 0.00 |
| S | 005D | 1.032 | 0.959 | 0.058 | 1.078 | 0.991 | 0.929 | 0.886 | 0.737 | 0.913 | 0.95 | 0.87 | 1.00 | 1.00 | 1.14 |
| S | 005E | 1.204 | 0.932 | −0.020 | 1.447 | 0.909 | 0.955 | 0.894 | 0.808 | 0.934 | 1.11 | 1.03 | 1.15 | 1.10 | 1.48 |
| S | 005F | 1.125 | 0.996 | 0.042 | 1.311 | 0.987 | 1.001 | 0.972 | 0.867 | 0.972 | 0.96 | 0.87 | 1.11 | 0.87 | 1.09 |
| S | 005G | 1.055 | 1.059 | 0.363 | 1.177 | 1.012 | 1.010 | 0.968 | 0.801 | 0.971 | 1.08 | 0.97 | 1.26 | 0.98 | 1.36 |
| S | 005H | 0.378 | −0.094 | 1.032 | 0.056 | 0.188 | 0.007 | 0.061 | 0.055 | 0.274 | −0.07 | −0.14 | −0.65 | 0.01 | −0.13 |
| S | 005I | 0.088 | 4.154 | 7.239 | 0.024 | 4.207 | 1.596 | 2.054 | 1.643 | 2.508 | 1.04 | 0.84 | 0.73 | 1.24 | 0.41 |
| S | 005K | 0.943 | 1.002 | 0.060 | 1.044 | 1.087 | 1.140 | 1.066 | 0.785 | 1.033 | 1.00 | 0.92 | 0.97 | 0.91 | 1.06 |
| S | 005L | 0.536 | 1.073 | 1.433 | 0.307 | 1.280 | 0.820 | 0.785 | 0.597 | 0.843 | 0.96 | 0.93 | 0.84 | 0.70 | 1.08 |
| S | 005N | 0.901 | 1.006 | 0.060 | 0.789 | 0.972 | 0.877 | 0.877 | 0.779 | 0.874 | 0.99 | 0.94 | 0.74 | 0.65 | 1.07 |
| S | 005R | 0.085 | 6.612 | 1.032 | 0.022 | 3.970 | 1.431 | 1.934 | 1.968 | 2.532 | 1.07 | 0.96 | 0.55 | 0.74 | 0.72 |
| S | 005V | 0.762 | 1.348 | −0.368 | 0.693 | 1.235 | 1.180 | 1.163 | 1.095 | 1.156 | 1.02 | 0.92 | 0.67 | 0.58 | 0.93 |
| S | 005W | 1.040 | 0.909 | −0.301 | 1.059 | 0.940 | 0.945 | 0.927 | 0.790 | 0.908 | 0.97 | 0.97 | 0.98 | 0.83 | 1.11 |
| S | 005Y | 0.931 | 1.004 | 0.828 | 0.926 | 1.071 | 1.055 | 0.989 | 0.720 | 0.956 | 0.96 | 0.92 | 0.60 | 0.75 | 0.69 |
| S | 008A | 1.142 | 0.852 | −0.638 | 1.232 | 0.855 | 0.825 | 0.825 | 0.718 | 0.874 | 0.96 | 0.90 | 0.78 | 0.84 | 0.82 |
| S | 008C | 0.395 | 1.607 | −0.123 | 0.216 | 1.570 | 1.060 | 1.084 | 1.005 | 1.080 | 0.94 | 0.92 | 0.57 | 1.27 | 0.83 |
| S | 008E | 0.986 | 1.000 | −3.472 | 0.908 | 0.906 | 0.882 | 0.876 | 0.931 | 0.891 | 1.03 | 1.11 | 0.96 | 1.25 | 1.17 |
| S | 008F | 0.794 | 0.984 | 2.351 | 0.573 | 1.050 | 0.931 | 0.935 | 0.942 | 0.895 | 1.28 | 1.22 | 0.91 | 1.42 | 1.16 |
| S | 008G | 0.750 | 1.106 | 5.465 | 0.545 | 1.196 | 1.117 | 1.101 | 1.056 | 1.091 | 1.13 | 0.99 | 0.78 | 1.37 | 1.06 |
| S | 008H | 0.891 | 1.043 | 8.593 | 0.845 | 1.096 | 1.104 | 1.097 | 1.141 | 1.071 | 1.09 | 1.05 | 0.73 | 0.84 | 0.99 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| S | 008I | 0.797 | 0.983 | 2.888 | 0.622 | 1.126 | 0.983 | 0.987 | 1.027 | 1.033 | 0.94 | 0.96 | 1.28 | 0.94 | 1.15 |
| S | 008K | 1.080 | 0.854 | −4.526 | 1.203 | 0.968 | 1.001 | 1.023 | 0.918 | 0.922 | 1.05 | 0.99 | 0.90 | 1.26 | 0.74 |
| S | 008L | 0.697 | 1.111 | 3.840 | 0.512 | 1.314 | 1.165 | 1.071 | 0.892 | 1.130 | 1.00 | 0.95 | 1.01 | 1.15 | 0.93 |
| S | 008M | 0.941 | 1.070 | −0.785 | 0.969 | 0.979 | 1.009 | 0.912 | 0.707 | 0.947 | 0.95 | 0.90 | 0.84 | 0.92 | 0.73 |
| S | 008N | 0.822 | 1.183 | 2.947 | 0.769 | 1.077 | 1.044 | 0.991 | 0.921 | 0.976 | 0.97 | 0.92 | 0.86 | 1.29 | 0.83 |
| S | 008P | 0.805 | 1.152 | 4.530 | 0.727 | 1.164 | 1.114 | 1.116 | 1.135 | 1.115 | 0.97 | 1.06 | 1.18 | 1.05 | 0.89 |
| S | 008Q | 1.037 | 0.934 | 1.204 | 1.034 | 0.930 | 0.934 | 0.876 | 0.970 | 0.915 | 1.01 | 1.03 | 0.89 | 1.01 | 1.01 |
| S | 008R | 0.907 | 0.978 | 3.556 | 0.772 | 0.967 | 0.895 | 0.922 | 0.962 | 0.880 | 1.02 | 1.03 | 0.70 | 1.10 | 0.94 |
| S | 008T | 0.861 | 1.160 | −7.262 | 0.772 | 1.074 | 1.019 | 1.016 | 1.061 | 0.995 | 1.00 | 1.03 | 0.90 | 1.01 | 0.87 |
| S | 008V | 0.717 | 1.045 | −1.571 | 0.528 | 1.197 | 1.065 | 1.088 | 1.133 | 1.097 | 0.95 | 0.95 | 0.94 | 0.93 | 0.90 |
| S | 008W | 0.309 | 1.955 | −18.190 | 0.146 | 2.192 | 1.493 | 1.524 | 1.419 | 1.495 | 1.06 | 1.01 | 0.58 | 1.13 | 0.57 |
| S | 008Y | 0.702 | 1.022 | 13.190 | 0.554 | 1.264 | 1.142 | 1.111 | 0.881 | 1.021 | 1.12 | 0.92 | 0.86 | 1.07 | 0.72 |
| S | 018A | 0.667 | 0.988 | −1.215 | 0.512 | 1.192 | 0.931 | 0.852 | 0.659 | 0.867 | 0.95 | 0.82 | 0.63 | 0.85 | 0.48 |
| S | 018C | 0.265 | 1.558 | 22.394 | 0.106 | 1.852 | 0.991 | 1.036 | 0.993 | 1.129 | 0.99 | 0.91 | 0.62 | 0.24 | 1.08 |
| S | 018D | 0.582 | 1.395 | 0.316 | 0.365 | 1.229 | 1.056 | 1.026 | 1.043 | 1.063 | 0.98 | 0.95 | 0.70 | 0.83 | 0.56 |
| S | 018E | 0.389 | 1.786 | 7.936 | 0.221 | 1.759 | 1.330 | 1.298 | 1.290 | 1.212 | 1.01 | 1.05 | 1.00 | 0.81 | 1.04 |
| S | 018F | −0.129 | 1.518 | 22.154 | −0.025 | −0.629 | −0.105 | −0.352 | −0.438 | −0.912 | 0.00 | 0.00 | 0.00 | 0.00 | 0.00 |
| S | 018G | 0.817 | 0.988 | 6.398 | 0.661 | 1.189 | 1.064 | 1.080 | 1.103 | 1.025 | 1.04 | 1.06 | 1.24 | 1.08 | 0.65 |
| S | 018H | 0.820 | 1.134 | −0.362 | 0.709 | 1.095 | 1.086 | 1.069 | 1.110 | 0.767 | 1.00 | 1.04 | 0.84 | 0.94 | 1.04 |
| S | 018L | 0.031 | −7.502 | 188.318 | 0.007 | 2.516 | 0.237 | 1.501 | 1.793 | 3.787 | 0.00 | 0.00 | 0.00 | 0.00 | 0.00 |
| S | 018M | 0.024 | 13.373 | −43.062 | 0.008 | 16.008 | 5.778 | 7.335 | 6.115 | 8.760 | 1.18 | 1.01 | 0.68 | 0.43 | 0.21 |
| S | 018N | 1.06 | ND | ND | ND | ND | ND | 0.94 | ND | 0.91 | 0.96 | 0.92 | 0.82 | 0.41 | 1.11 |
| S | 018P | −0.149 | −1.873 | 38.225 | −0.034 | −0.571 | −0.063 | −0.311 | −0.376 | −0.777 | 1.00 | 0.00 | 0.00 | 0.00 | 0.00 |
| S | 018Q | 0.385 | 1.582 | −4.025 | 0.188 | 1.628 | 1.180 | 1.192 | 1.127 | 0.976 | 1.00 | 1.05 | 1.03 | 0.78 | 0.89 |
| S | 018R | 0.509 | 1.554 | −0.506 | 0.323 | 1.583 | 1.267 | 1.200 | 1.202 | 0.651 | 1.09 | 1.13 | 1.16 | 1.55 | 1.25 |
| S | 018T | 0.339 | 1.694 | −11.014 | 0.173 | 1.982 | 1.447 | 1.391 | 1.353 | 1.112 | 0.73 | 0.73 | 0.68 | 0.61 | 0.72 |
| S | 018V | −0.153 | 0.821 | 11.505 | −0.026 | 1.034 | 1.004 | −0.278 | −0.360 | −0.740 | 0.00 | 0.00 | 0.00 | 0.00 | 0.00 |
| S | 018W | −0.301 | −0.414 | −6.300 | −0.055 | −0.523 | −0.054 | −0.161 | −0.209 | −0.391 | 0.00 | 0.00 | 0.00 | 0.00 | 0.00 |
| S | 018Y | −0.129 | −0.492 | −36.066 | −0.024 | −0.257 | −0.142 | −0.496 | −0.537 | −1.015 | 0.00 | 0.00 | 0.00 | 0.00 | 0.00 |
| N | 020A | 1.190 | 0.877 | 2.235 | 1.387 | −1.087 | 0.920 | 0.886 | 0.663 | 0.846 | 0.97 | 0.82 | 0.87 | 1.01 | 0.87 |
| N | 020C | 0.402 | 1.670 | 1.467 | 0.222 | 0.865 | 1.068 | 1.102 | 0.969 | 1.156 | 0.92 | 0.84 | 0.70 | 0.90 | 1.05 |
| N | 020D | 0.911 | 0.908 | 3.420 | 0.862 | 1.524 | 0.925 | 0.861 | 0.599 | 0.837 | 1.04 | 1.02 | 0.82 | 1.15 | 1.01 |
| N | 020F | 0.652 | 1.077 | 5.468 | 0.467 | 0.998 | 1.031 | 1.027 | 1.014 | 1.061 | 1.06 | 1.09 | 1.02 | 1.20 | 1.37 |
| N | 020G | 0.368 | 1.312 | 1.394 | 0.175 | 1.268 | 1.170 | 1.198 | 1.221 | 1.177 | 1.00 | 1.00 | 1.16 | 1.34 | 1.47 |
| N | 020H | 0.881 | 1.709 | −0.784 | 0.744 | 1.812 | 1.271 | 1.267 | 1.337 | 1.358 | 1.00 | 1.00 | 1.20 | 0.99 | 1.16 |
| N | 020I | 1.035 | 1.056 | 11.339 | 0.972 | 1.034 | 1.004 | 1.028 | 1.067 | 0.997 | 1.05 | 1.01 | 0.92 | 1.01 | 1.20 |
| N | 020K | 0.857 | 0.982 | 1.444 | 0.855 | 0.941 | 0.947 | 0.987 | 0.994 | 0.951 | 1.01 | 0.94 | 1.04 | 0.86 | 1.50 |
| N | 020L | 0.924 | 1.012 | −0.330 | 0.948 | 1.133 | 1.189 | 1.204 | 1.079 | 1.159 | 1.01 | 0.93 | 1.11 | 1.06 | 0.80 |
| N | 020M | 1.137 | 0.990 | 1.308 | 1.301 | 1.094 | 1.127 | 1.092 | 0.859 | 1.072 | 0.93 | 0.84 | 0.84 | 0.91 | 0.84 |
| N | 020P | 0.748 | 1.174 | 3.169 | 0.676 | 0.883 | 0.925 | 0.861 | 0.599 | 0.837 | 0.93 | 0.77 | 0.82 | 0.90 | 0.95 |
| N | 020Q | 0.974 | 0.980 | 2.391 | 0.886 | 1.145 | 1.057 | 1.052 | 0.933 | 1.017 | 1.00 | 0.86 | 0.73 | 0.89 | 0.88 |
| N | 020R | 0.973 | 1.029 | 3.409 | 0.921 | 0.931 | 0.949 | 0.932 | 0.908 | 0.951 | 0.97 | 0.98 | 0.87 | 1.11 | 1.39 |
| N | 020S | 0.820 | 1.137 | 1.563 | 0.739 | 0.963 | 0.975 | 0.969 | 0.963 | 0.957 | 1.03 | 0.96 | 0.76 | 1.01 | 0.95 |
| N | 020T | 0.917 | 1.019 | 2.477 | 0.802 | 1.155 | 1.147 | 1.134 | 1.160 | 1.147 | 0.98 | 0.92 | 0.89 | 1.07 | 1.31 |
| N | 020V | 0.880 | 1.058 | 0.510 | 0.814 | 1.013 | 0.983 | 1.019 | 1.015 | 1.015 | 1.01 | 0.96 | 0.95 | 0.92 | 0.95 |
| N | 020W | 0.731 | 1.059 | 1.252 | 0.528 | 1.086 | 1.103 | 1.128 | 1.080 | 1.096 | 1.04 | 0.93 | 0.99 | 0.78 | 1.06 |
| N | 020Y | 0.775 | 1.140 | 1.460 | 0.670 | 1.241 | 1.228 | 1.074 | 0.937 | 1.044 | 0.99 | 0.89 | 0.97 | 0.99 | 1.22 |
| K | 023A | 0.886 | 1.210 | −7.782 | 1.069 | 1.139 | 1.140 | 1.089 | 0.793 | 1.018 | 0.98 | 0.87 | 0.97 | 1.00 | 1.79 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| K | 023C | −0.022 | −19.036 | −92.029 | −0.006 | −17.075 | −7.211 | −9.155 | −8.577 | −11.542 | 0.89 | 0.85 | 0.70 | 1.10 | −1.38 |
| K | 023D | 0.561 | 1.329 | −9.450 | 0.399 | 1.353 | 1.125 | 1.144 | 0.964 | 1.116 | 1.11 | 1.06 | 1.01 | 1.33 | 2.26 |
| K | 023E | 0.819 | 1.059 | −21.748 | 0.665 | 1.111 | 1.042 | 1.049 | 0.940 | 0.992 | 1.11 | 1.11 | 0.99 | 1.25 | 1.61 |
| K | 023F | 0.500 | 1.541 | −2.016 | 0.285 | 1.576 | 1.262 | 1.284 | 1.130 | 1.246 | 0.99 | 0.96 | 1.06 | 0.96 | 1.58 |
| K | 023G | 0.620 | 1.339 | 2.343 | 0.395 | 1.353 | 1.133 | 1.165 | 1.052 | 1.100 | 0.98 | 1.01 | 0.98 | 0.86 | 1.50 |
| K | 023H | 0.718 | 1.156 | −6.848 | 0.538 | 1.178 | 1.147 | 1.157 | 1.030 | 1.185 | 0.95 | 0.92 | 0.94 | 0.93 | 1.65 |
| K | 023I | 0.809 | 1.042 | 3.035 | 0.632 | 1.084 | 1.038 | 1.075 | 0.903 | 1.006 | 1.08 | 1.00 | 0.89 | 0.92 | 1.93 |
| K | 023L | 0.702 | 1.130 | −8.025 | 0.565 | 1.310 | 1.248 | 1.263 | 0.925 | 1.272 | 1.08 | 0.88 | 0.86 | 0.86 | 2.18 |
| K | 023M | 1.086 | 0.944 | −12.754 | 1.319 | 0.933 | 0.957 | 0.892 | 0.578 | 0.814 | 0.93 | 0.76 | 0.72 | 0.91 | 1.54 |
| K | 023N | 0.931 | 1.032 | −9.626 | 1.079 | 1.120 | 1.110 | 1.036 | 0.690 | 0.981 | 0.91 | 0.78 | 0.91 | 0.79 | 1.00 |
| K | 023P | −0.026 | 1.998 | 221.044 | −0.005 | −3.642 | −0.356 | −2.149 | −2.600 | −5.017 | 0.00 | 0.00 | 0.00 | 0.00 | 0.00 |
| K | 023R | 0.977 | 1.113 | −10.655 | 1.046 | 1.099 | 1.129 | 1.117 | 0.846 | 1.011 | 1.02 | 0.99 | 1.12 | 1.40 | 2.08 |
| K | 023S | 0.807 | 1.104 | 0.200 | 0.658 | 1.188 | 1.137 | 1.163 | 1.053 | 1.172 | 1.01 | 0.91 | 1.09 | 1.06 | 1.53 |
| K | 023T | 0.944 | 1.074 | −14.450 | 0.892 | 1.087 | 1.123 | 1.137 | 0.844 | 1.048 | 1.06 | 0.91 | 1.07 | 1.36 | 1.78 |
| K | 023V | 0.748 | 1.050 | −7.307 | 0.551 | 1.187 | 1.123 | 1.120 | 0.792 | 1.046 | 1.07 | 0.90 | 1.02 | 0.83 | 1.87 |
| K | 023W | 0.216 | 1.469 | 4.084 | 0.060 | 2.078 | 1.043 | 1.144 | 1.219 | 1.389 | 0.97 | 0.77 | 0.84 | 1.12 | 1.29 |
| K | 023Y | 0.798 | 1.046 | 1.983 | 0.751 | 1.165 | 1.137 | 1.097 | 0.675 | 1.101 | 1.02 | 0.80 | 0.72 | 0.81 | 2.66 |
| H | 024A | 1.211 | 0.865 | −0.443 | 1.653 | 0.875 | 0.956 | 0.871 | 0.639 | 0.846 | 1.03 | 0.95 | 1.00 | 1.26 | 1.08 |
| H | 024C | 0.214 | 2.540 | −0.661 | 0.103 | 2.678 | 1.720 | 1.789 | 1.463 | 1.933 | 0.99 | 0.90 | 0.53 | 1.25 | 0.67 |
| H | 024D | 1.020 | 0.951 | −1.188 | 1.074 | 0.943 | 0.966 | 0.976 | 0.845 | 0.865 | 1.02 | 0.99 | 0.80 | 0.99 | 0.73 |
| H | 024F | 0.853 | 1.091 | −1.936 | 0.760 | 1.078 | 1.070 | 1.062 | 0.959 | 1.101 | 1.07 | 1.06 | 0.96 | 1.26 | 0.97 |
| H | 024G | 0.947 | 1.149 | −2.206 | 0.861 | 1.017 | 1.007 | 1.035 | 0.948 | 1.033 | 1.13 | 1.10 | 0.88 | 0.99 | 1.13 |
| H | 024H | 0.850 | 1.015 | 2.825 | 0.869 | 1.186 | 1.165 | 1.127 | 0.791 | 1.091 | 1.08 | 1.05 | 0.84 | 1.20 | 1.19 |
| H | 024L | 1.10 | ND | ND | ND | ND | ND | 1.01 | ND | 0.94 | 0.96 | 0.66 | 0.81 | 0.86 | 0.93 |
| H | 024N | 0.924 | 1.085 | 0.812 | 0.828 | 1.042 | 0.997 | 0.999 | 0.933 | 1.031 | 0.96 | 0.89 | 0.72 | 1.05 | 0.79 |
| H | 024P | 0.166 | 2.352 | −6.779 | 0.059 | 2.901 | 1.313 | 1.463 | 1.297 | 1.774 | 0.91 | 0.90 | 0.78 | 0.59 | 0.42 |
| H | 024Q | 1.067 | 0.981 | −1.728 | 1.093 | 0.923 | 1.026 | 0.982 | 0.723 | 0.992 | 1.00 | 0.91 | 0.77 | 0.90 | 0.76 |
| H | 024R | 1.035 | 1.053 | −0.971 | 1.162 | 1.002 | 1.078 | 1.040 | 0.749 | 1.018 | 1.13 | 1.08 | 0.90 | 1.48 | 1.13 |
| H | 024S | 1.061 | 1.043 | −1.325 | 1.102 | 1.011 | 1.005 | 0.998 | 0.755 | 0.980 | 1.07 | 0.98 | 1.03 | 0.91 | 0.94 |
| H | 024T | 1.059 | 1.043 | −0.639 | 1.095 | 0.989 | 0.988 | 0.976 | 0.784 | 0.952 | 1.05 | 0.99 | 0.96 | 1.23 | 1.07 |
| H | 024V | 1.069 | 0.957 | −0.180 | 1.082 | 0.990 | 0.997 | 1.016 | 0.748 | 0.936 | 1.01 | 0.97 | 1.00 | 1.10 | 0.78 |
| H | 024Y | 0.938 | 1.023 | 0.034 | 0.946 | 1.081 | 1.011 | 0.969 | 0.753 | 0.955 | 0.98 | 1.06 | 1.01 | 1.05 | 1.11 |
| N | 025A | 0.847 | 1.079 | 2.666 | 0.875 | 1.080 | 1.085 | 1.053 | 0.783 | 0.988 | 0.99 | 0.88 | 0.81 | 0.77 | 0.65 |
| N | 025C | 0.454 | 0.749 | 4.210 | 0.241 | 1.323 | 1.021 | 1.015 | 0.885 | 1.004 | 0.95 | 0.96 | 0.82 | 0.53 | 0.73 |
| N | 025D | 0.741 | 0.977 | 2.347 | 0.629 | 1.137 | 0.911 | 0.936 | 1.074 | 1.032 | 0.99 | 0.93 | 0.91 | 0.82 | 0.81 |
| N | 025E | 1.306 | 0.856 | 0.874 | 1.684 | 0.807 | 1.028 | 0.990 | 1.009 | 1.038 | 0.94 | 1.06 | 1.01 | 0.92 | 0.90 |
| N | 025F | 0.671 | 1.186 | 2.033 | 0.486 | 1.175 | 0.939 | 0.964 | 1.025 | 0.902 | 1.09 | 1.10 | 0.73 | 1.17 | 1.05 |
| N | 025G | 0.762 | 0.855 | 1.160 | 0.581 | 1.122 | 0.988 | 0.988 | 1.046 | 0.950 | 1.05 | 0.97 | 0.95 | 0.77 | 0.94 |
| N | 025H | 0.906 | 0.868 | 1.285 | 0.787 | 1.021 | 0.995 | 1.016 | 1.036 | 1.003 | 1.01 | 0.99 | 0.76 | 0.82 | 0.95 |
| N | 025I | 0.291 | 0.066 | −0.008 | 0.117 | 1.857 | 1.011 | 0.999 | 1.226 | 0.936 | 1.01 | 0.97 | 1.00 | 1.10 | 0.83 |
| N | 025K | 0.803 | 0.742 | 1.180 | 0.625 | 1.053 | 1.118 | 1.199 | 0.816 | 1.341 | 0.98 | 0.95 | 1.01 | 0.56 | 0.81 |
| N | 025L | 0.665 | 0.855 | 3.961 | 0.538 | 1.287 | 0.963 | 0.940 | 0.781 | 0.696 | 0.95 | 0.83 | 0.82 | 0.89 | 0.71 |
| N | 025R | 0.841 | 0.962 | 2.602 | 0.636 | 0.995 | 1.153 | 1.088 | 1.033 | 1.098 | 0.93 | 0.78 | 0.89 | 0.76 | 1.36 |
| N | 025S | 0.812 | 1.006 | 3.335 | 0.697 | 1.099 | 0.908 | 0.944 | 1.124 | 0.742 | 1.14 | 1.16 | 0.70 | 1.31 | 0.85 |
| N | 025T | 0.771 | 0.978 | 2.398 | 0.662 | 1.135 | 1.023 | 1.062 | 0.746 | 1.053 | 0.97 | 0.96 | 1.11 | 0.73 | 0.78 |
| N | 025V | 0.484 | 1.122 | 2.647 | 0.266 | 1.502 | 1.115 | 1.080 | 1.238 | 1.059 | 1.14 | 1.13 | 0.96 | 0.88 | 1.22 |
| N | 025W | 0.480 | 1.647 | 4.607 | 0.321 | 1.639 | 1.196 | 1.241 | 1.191 | 1.291 | 0.95 | 0.93 | 0.94 | 0.52 | 1.24 |
| N | 025Y | 0.701 | 0.908 | 4.152 | 0.638 | 1.309 | 1.226 | 1.199 | 0.879 | 1.164 | 1.06 | 0.84 | 1.02 | 0.99 | 1.00 |
| | | | | | | | | | | | | | 1.08 | | |
| | | | | | | | | | | | | | 0.93 | | |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 4 | DP3 | DP3 HS | corn flour 30 min | Cleaning pH 8 | Cleaning pH 10 |
|---|---|---|---|---|---|---|---|---|---|---|---|---|---|---|---|
| K | 027A | 1.030 | 0.946 | 0.994 | 1.184 | 0.953 | 0.978 | 0.921 | 0.662 | 0.904 | 1.03 | 0.90 | 0.98 | 1.27 | 0.82 |
| K | 027C | 0.291 | 0.343 | 5.547 | 0.137 | 1.791 | 1.120 | 1.214 | 1.095 | 1.329 | 0.90 | 0.85 | 0.99 | 0.92 | 0.63 |
| K | 027D | 0.859 | 0.898 | 1.600 | 0.826 | 1.005 | 1.057 | 1.058 | 1.025 | 1.079 | 1.02 | 0.98 | 0.93 | 1.08 | 1.02 |
| K | 027E | 0.941 | 0.899 | 1.508 | 0.981 | 1.008 | 1.021 | 1.031 | 1.046 | 1.033 | 1.06 | 1.05 | 1.05 | 1.39 | 1.36 |
| K | 027F | 0.582 | 0.902 | 0.437 | 0.356 | 1.244 | 0.968 | 0.963 | 1.009 | 1.023 | 1.12 | 1.11 | 1.11 | 1.28 | 1.63 |
| K | 027G | 0.912 | 0.837 | 0.471 | 0.817 | 1.033 | 0.994 | 1.001 | 1.031 | 1.012 | 1.03 | 0.99 | 1.06 | 1.37 | 1.36 |
| K | 027H | 0.903 | 0.662 | −0.367 | 0.778 | 1.023 | 0.970 | 0.970 | 0.992 | 0.972 | 1.04 | 0.98 | 1.10 | 1.10 | 0.72 |
| K | 027I | 0.660 | 0.571 | 0.890 | 0.470 | 1.196 | 1.043 | 1.053 | 1.008 | 1.079 | 0.99 | 0.93 | 0.97 | 1.00 | 1.06 |
| K | 027L | 0.729 | 0.662 | 2.395 | 0.586 | 1.212 | 1.038 | 0.969 | 0.808 | 1.024 | 0.99 | 0.68 | 0.84 | 1.21 | 0.70 |
| K | 027M | 0.861 | 0.955 | 1.348 | 0.845 | 1.031 | 0.997 | 0.951 | 0.657 | 0.934 | 1.00 | 0.88 | 1.07 | 1.03 | 0.81 |
| K | 027N | 0.926 | 0.976 | 1.985 | 0.913 | 0.921 | 0.956 | 0.938 | 0.874 | 0.967 | 0.98 | 0.94 | 0.99 | 1.03 | 1.05 |
| K | 027P | 0.906 | 0.953 | 0.243 | 0.879 | 0.968 | 0.999 | 1.014 | 0.994 | 1.015 | 1.02 | 1.01 | 0.94 | 0.65 | 0.82 |
| K | 027R | 0.916 | 0.960 | 0.948 | 0.842 | 1.001 | 1.003 | 1.012 | 1.057 | 1.042 | 1.01 | 1.06 | 0.86 | 1.02 | 1.29 |
| K | 027S | 0.964 | 0.916 | 2.448 | 0.886 | 1.017 | 1.022 | 1.031 | 1.116 | 1.020 | 1.00 | 0.99 | 1.09 | 1.26 | 1.02 |
| K | 027T | 0.730 | 1.108 | 0.239 | 0.540 | 1.163 | 1.043 | 1.046 | 1.061 | 1.070 | 1.01 | 0.95 | 0.91 | 1.25 | 0.73 |
| K | 027V | 0.588 | 0.654 | 1.731 | 0.387 | 1.330 | 1.152 | 1.186 | 1.107 | 1.193 | 1.07 | 1.04 | 1.18 | 1.20 | 1.05 |
| K | 027Y | 0.676 | 0.811 | 3.510 | 0.527 | 1.263 | 1.120 | 1.099 | 0.859 | 1.105 | 1.06 | 0.70 | 1.01 | 1.32 | 0.02 |
| D | 028A | 1.007 | 1.153 | −0.823 | 1.301 | 0.997 | 1.081 | 1.014 | 0.657 | 0.936 | 1.03 | 0.80 | 0.76 | 0.96 | 0.86 |
| D | 028C | 0.354 | 1.704 | 5.680 | 0.191 | 1.838 | 1.271 | 1.316 | 1.002 | 1.307 | 1.10 | 0.94 | 1.13 | 1.39 | 1.11 |
| D | 028F | 0.869 | 1.150 | 1.659 | 0.687 | 1.019 | 0.941 | 0.972 | 0.888 | 0.913 | 0.98 | 1.03 | 1.07 | 1.07 | 0.88 |
| D | 028G | 0.842 | 1.181 | 1.533 | 0.708 | 1.120 | 1.046 | 1.052 | 0.958 | 0.975 | 0.99 | 1.03 | 1.29 | 0.79 | 0.85 |
| D | 028H | 0.853 | 1.285 | −0.961 | 0.768 | 1.125 | 0.999 | 1.121 | 1.045 | 1.022 | 0.98 | 0.99 | 1.11 | 0.96 | 0.88 |
| D | 028I | 0.718 | 1.250 | −2.659 | 0.571 | 1.297 | 1.201 | 1.211 | 1.085 | 1.159 | 1.12 | 1.08 | 1.01 | 1.60 | 1.22 |
| D | 028K | 0.974 | 1.101 | 0.729 | 1.186 | 1.170 | 1.281 | 1.244 | 0.869 | 1.210 | 1.01 | 0.95 | 1.39 | 1.33 | 0.93 |
| D | 028L | 0.934 | 1.018 | −1.756 | 0.915 | 1.108 | 1.101 | 1.077 | 0.816 | 1.006 | 0.98 | 0.68 | 0.90 | 0.97 | 0.75 |
| D | 028M | 1.152 | 0.835 | 0.037 | 1.438 | 0.899 | 0.916 | 0.813 | 0.438 | 0.785 | 0.87 | 0.68 | 0.71 | 1.12 | 0.73 |
| D | 028N | 1.058 | 0.982 | 0.702 | 1.199 | 0.966 | 0.948 | 0.878 | 0.555 | 0.845 | 1.01 | 0.82 | 0.91 | 1.13 | 0.83 |
| D | 028P | 1.097 | 0.980 | 0.985 | 1.260 | 0.951 | 0.954 | 0.976 | 1.040 | 0.985 | 0.97 | 0.86 | 1.05 | 0.96 | 0.70 |
| D | 028Q | 0.923 | 1.334 | 0.935 | 0.978 | 1.140 | 1.164 | 1.131 | 0.806 | 1.046 | 0.99 | 0.90 | 1.06 | 0.49 | 0.92 |
| D | 028R | 1.111 | 1.001 | −1.185 | 1.175 | 0.954 | 0.977 | 0.948 | 0.698 | 0.831 | 1.03 | 0.93 | 0.93 | 1.20 | 0.83 |
| D | 028S | 0.940 | 1.227 | −2.874 | 0.996 | 1.137 | 1.164 | 1.141 | 0.883 | 1.059 | 1.02 | 0.94 | 1.17 | 0.86 | 0.74 |
| D | 028T | 1.029 | 1.075 | −1.330 | 1.029 | 1.023 | 1.012 | 1.018 | 0.746 | 0.939 | 1.04 | 0.87 | 0.73 | 1.00 | 0.86 |
| D | 028V | 0.904 | 1.090 | −1.110 | 0.871 | 1.145 | 1.134 | 1.113 | 0.789 | 1.043 | 1.04 | 0.90 | 1.23 | 0.92 | 0.92 |
| D | 028W | 0.816 | 1.059 | −3.964 | 0.735 | 1.189 | 1.091 | 1.022 | 0.806 | 0.962 | 1.11 | 1.03 | 1.32 | 0.83 | 0.89 |
| D | 028Y | 1.037 | 0.902 | 2.800 | 1.150 | 1.063 | 1.077 | 1.040 | 0.794 | 0.972 | 1.03 | 1.00 | 1.31 | 0.94 | 0.67 |
| H | 030A | 1.239 | 0.830 | 2.436 | 1.648 | 0.876 | 0.916 | 0.881 | 0.530 | 0.853 | 0.88 | 0.75 | 0.80 | 0.73 | 1.34 |
| H | 030C | 0.624 | 0.963 | 0.523 | 0.439 | 1.194 | 0.894 | 0.862 | 0.643 | 0.879 | 0.87 | 0.82 | 0.84 | 0.82 | 1.18 |
| H | 030E | 0.912 | 0.994 | −1.117 | 0.912 | 1.055 | 0.981 | 0.908 | 0.804 | 0.934 | 0.90 | 0.87 | 0.87 | 1.10 | 1.10 |
| H | 030F | 0.782 | 1.059 | 0.068 | 0.729 | 1.205 | 1.048 | 0.971 | 0.849 | 1.026 | 1.00 | 0.97 | 0.97 | 0.70 | 1.22 |
| H | 030G | 1.074 | 0.830 | 0.627 | 1.074 | 0.936 | 0.913 | 0.858 | 0.740 | 0.881 | 0.96 | 0.89 | 1.30 | 0.91 | 1.17 |
| H | 030I | 0.174 | 1.839 | −15.614 | 0.076 | 3.322 | 1.853 | 1.847 | 1.532 | 2.191 | 0.99 | 0.72 | 1.19 | 0.71 | 1.34 |
| H | 030K | 1.148 | 0.766 | −0.354 | 1.220 | 0.888 | 0.909 | 0.868 | 0.688 | 0.873 | 0.94 | 0.52 | 1.06 | 0.81 | 0.93 |
| H | 030L | 0.503 | 1.175 | 4.188 | 0.395 | 1.596 | 1.276 | 1.222 | 0.957 | 1.260 | 0.95 | 0.04 | 1.08 | 0.96 | 1.13 |
| H | 030M | 0.650 | 1.150 | 0.815 | 0.537 | 1.253 | 1.039 | 1.018 | 0.707 | 0.998 | 0.88 | 0.81 | 0.67 | 0.92 | 1.20 |
| H | 030N | 0.852 | 0.980 | −1.486 | 0.786 | 1.051 | 0.940 | 0.963 | 0.849 | 0.934 | 1.04 | 0.96 | 0.85 | 0.94 | 0.99 |
| H | 030P | 0.044 | 6.002 | 17.981 | 0.013 | 7.366 | 2.306 | 3.593 | 3.313 | 4.781 | 1.07 | 1.20 | 0.60 | 1.16 | 3.83 |
| H | 030Q | 0.891 | 0.943 | −1.268 | 0.846 | 1.032 | 0.974 | 0.952 | 0.935 | 0.964 | 0.97 | 1.00 | 1.09 | 0.93 | 1.20 |
| H | 030R | 1.243 | 0.830 | 1.021 | 1.217 | 0.768 | 0.805 | 0.788 | 0.745 | 0.775 | 1.01 | 1.07 | 1.19 | 1.27 | 1.15 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| H | 030S | 0.871 | 0.910 | 0.853 | 0.666 | 0.993 | 0.870 | 0.854 | 0.829 | 0.865 | 0.99 | 0.98 | 1.10 | 0.79 | 1.46 |
| H | 030T | 0.600 | 1.246 | -4.060 | 0.428 | 1.342 | 1.095 | 1.101 | 1.037 | 1.124 | 1.07 | 1.06 | 1.31 | 1.21 | 1.75 |
| H | 030V | 0.708 | 0.935 | -0.172 | 0.480 | 1.113 | 0.924 | 0.910 | 0.853 | 0.952 | 0.98 | 0.86 | 1.36 | 0.77 | 1.05 |
| H | 030W | 0.677 | 1.071 | -5.930 | 0.488 | 1.148 | 0.966 | 0.950 | 0.810 | 0.989 | 0.99 | 0.95 | 1.02 | 0.81 | 1.25 |
| H | 030Y | 0.937 | 0.888 | -6.593 | 0.949 | 1.029 | 1.051 | 1.026 | 0.809 | 1.049 | 1.00 | 0.11 | 1.06 | 1.13 | 1.22 |
| T | 035A | 0.993 | 0.949 | 1.833 | 1.087 | 0.965 | 0.967 | 0.941 | 0.716 | 0.869 | 0.90 | 0.90 | 0.80 | 0.93 | 1.22 |
| T | 035C | 0.349 | 1.532 | 2.281 | 0.177 | 1.725 | 1.103 | 1.176 | 1.069 | 1.210 | 1.08 | 1.08 | 0.84 | 0.77 | 0.84 |
| T | 035F | 0.647 | 1.312 | -0.882 | 0.497 | 1.316 | 1.149 | 1.183 | 1.231 | 1.168 | 0.97 | 1.06 | 0.95 | 1.63 | 1.20 |
| T | 035G | 1.021 | 0.910 | 2.050 | 0.867 | 0.922 | 0.897 | 0.912 | 0.906 | 0.875 | 1.04 | 1.00 | 0.93 | 1.08 | 1.47 |
| T | 035H | 0.893 | 0.897 | -1.027 | 0.752 | 1.006 | 0.939 | 0.961 | 0.919 | 0.902 | 1.00 | 0.99 | 1.00 | 1.06 | 1.52 |
| T | 035I | 0.825 | 1.052 | -0.191 | 0.742 | 1.123 | 1.072 | 1.097 | 1.057 | 1.045 | 0.91 | 0.94 | 0.92 | 0.74 | 0.94 |
| T | 035L | 1.015 | 0.782 | 2.986 | 0.973 | 0.940 | 0.896 | 0.925 | 0.691 | 0.880 | 0.97 | 0.68 | 1.10 | 1.00 | 1.05 |
| T | 035M | 0.647 | 1.291 | 4.895 | 0.581 | 1.332 | 1.226 | 1.192 | 0.866 | 1.108 | 0.88 | 0.83 | 0.74 | 0.78 | 0.69 |
| T | 035N | 0.689 | 1.075 | 6.179 | 0.577 | 1.184 | 1.100 | 1.077 | 0.963 | 1.041 | 0.94 | 0.90 | 0.76 | 0.66 | 1.01 |
| T | 035P | 0.112 | 3.176 | -13.426 | 0.045 | 4.218 | 2.253 | 2.525 | 2.550 | 2.781 | 0.97 | 1.18 | 1.14 | 0.91 | 1.61 |
| T | 035Q | 0.876 | 0.824 | 2.300 | 0.721 | 0.987 | 0.942 | 0.946 | 0.888 | 0.916 | 1.10 | 1.13 | 1.09 | 1.08 | 1.55 |
| T | 035R | 0.962 | 0.911 | 0.998 | 0.837 | 0.921 | 0.918 | 0.926 | 0.948 | 0.860 | 1.03 | 1.06 | 0.82 | 1.26 | 1.27 |
| T | 035S | 1.083 | 0.960 | 2.327 | 1.040 | 0.914 | 0.944 | 0.961 | 1.021 | 0.943 | 1.00 | 1.04 | 0.90 | 0.90 | 1.19 |
| T | 035V | 0.980 | 0.898 | -3.036 | 0.809 | 0.931 | 0.930 | 0.953 | 0.936 | 0.913 | 0.95 | 0.99 | 1.16 | 0.80 | 1.16 |
| T | 035W | 0.831 | 0.920 | -2.876 | 0.744 | 1.108 | 1.061 | 1.057 | 1.015 | 1.130 | 0.90 | 1.02 | 1.20 | 1.07 | 1.25 |
| T | 035Y | 0.406 | 0.999 | -0.773 | 0.193 | 1.528 | 0.950 | 1.036 | 0.803 | 1.065 | 1.05 | 0.59 | 0.84 | 1.09 | 1.43 |
| Q | 044A | 0.769 | 1.093 | 0.883 | 0.702 | 1.209 | 1.197 | 1.222 | 1.183 | 1.218 | 1.04 | 0.83 | 1.12 | 1.03 | 0.91 |
| Q | 044C | 0.328 | 1.331 | -2.405 | 0.157 | 1.671 | 1.007 | 1.053 | 0.997 | 1.137 | 0.94 | 0.79 | 1.08 | 0.69 | 0.68 |
| Q | 044D | 0.884 | 0.857 | 1.990 | 0.740 | 0.933 | 0.837 | 0.792 | 0.790 | 0.832 | 0.94 | 0.77 | 0.74 | 1.04 | 1.20 |
| Q | 044E | 0.959 | 0.967 | 1.168 | 0.883 | 0.987 | 0.978 | 0.981 | 1.011 | 1.001 | 1.13 | 1.07 | 0.91 | 0.68 | 0.95 |
| Q | 044F | 0.537 | 0.924 | 0.569 | 0.279 | 1.288 | 0.916 | 0.950 | 0.998 | 0.961 | 1.06 | 0.99 | 1.35 | 1.24 | 1.00 |
| Q | 044G | 0.898 | 1.000 | 0.848 | 0.758 | 1.031 | 0.857 | 0.866 | 0.761 | 0.820 | 1.04 | 0.62 | 0.54 | 0.90 | 0.73 |
| Q | 044H | 0.889 | 1.055 | 0.220 | 0.768 | 1.088 | 1.020 | 1.082 | 1.147 | 1.034 | 1.03 | 1.01 | 1.10 | 1.04 | 0.82 |
| Q | 044I | 0.270 | 0.948 | 7.514 | 0.109 | 2.193 | 1.401 | 1.440 | 1.428 | 1.536 | 0.96 | 1.07 | 0.98 | 0.68 | 1.16 |
| Q | 044K | 0.886 | 1.027 | -2.105 | 0.819 | 1.087 | 1.056 | 1.071 | 1.003 | 1.056 | 0.99 | 0.95 | 1.22 | 1.24 | 1.09 |
| Q | 044L | 0.390 | 1.341 | -13.716 | 0.251 | 2.062 | 1.642 | 1.553 | 1.205 | 1.587 | 0.87 | 0.63 | 1.02 | 1.62 | 1.04 |
| Q | 044M | 1.035 | 1.026 | 0.290 | 1.163 | 0.930 | 0.954 | 0.903 | 0.714 | 0.873 | 1.00 | 0.82 | 1.06 | 0.74 | 0.76 |
| Q | 044N | 0.998 | 1.082 | 1.864 | 1.097 | 0.947 | 0.974 | 1.003 | 0.911 | 0.934 | 1.04 | 0.93 | 0.93 | 0.79 | 0.94 |
| Q | 044P | 0.671 | 1.147 | 3.803 | 0.430 | 1.129 | 0.803 | 0.832 | 0.749 | 0.854 | 1.00 | 0.76 | 0.54 | 1.37 | 0.83 |
| Q | 044R | 0.906 | 1.197 | 1.231 | 0.841 | 1.052 | 1.060 | 1.000 | 1.142 | 1.002 | 1.09 | 1.28 | 1.55 | 0.59 | 1.32 |
| Q | 044S | 0.811 | 1.193 | 6.684 | 0.697 | 1.155 | 1.077 | 1.087 | 1.153 | 1.052 | 1.02 | 1.05 | 0.86 | 2.22 | 0.85 |
| Q | 044T | 0.737 | 1.008 | 3.758 | 0.549 | 1.182 | 1.081 | 1.082 | 1.105 | 1.043 | 0.98 | 1.04 | 0.90 | 1.36 | 0.83 |
| Q | 044V | 0.246 | 0.671 | 6.132 | 0.085 | 2.114 | 1.191 | 1.300 | 1.349 | 1.426 | 1.05 | 1.19 | 0.91 | 0.93 | 1.16 |
| Q | 044W | 0.347 | 2.002 | 12.602 | 0.213 | 2.212 | 1.677 | 1.787 | 1.571 | 1.914 | 1.00 | 0.77 | 0.73 | 1.32 | 0.85 |
| Q | 044Y | 0.422 | 1.092 | -0.320 | 0.246 | 1.770 | 1.355 | 1.348 | 1.020 | 1.348 | 1.09 | 0.86 | 0.93 | 0.85 | 1.16 |
| V | 045C | 0.296 | 1.601 | -50.663 | 0.156 | 2.117 | 1.165 | 1.150 | 0.951 | 1.275 | 0.86 | 0.68 | 1.20 | 0.97 | 1.23 |
| V | 045D | 0.010 | 48.984 | -928.260 | 0.002 | 12.871 | 1.326 | 5.656 | 6.102 | 12.218 | 0.00 | 0.00 | 0.00 | 1.71 | 0.94 |
| V | 045E | -0.249 | 1.807 | -5.433 | -0.048 | -0.384 | -0.083 | -0.184 | -0.244 | -0.456 | 0.00 | 0.00 | 0.00 | 0.00 | 0.00 |
| V | 045F | 0.610 | 1.167 | -3.418 | 0.496 | 1.464 | 0.892 | 0.902 | 0.608 | 1.027 | 0.79 | 0.43 | 0.70 | 1.28 | 1.32 |
| V | 045G | 0.080 | 3.964 | -49.833 | 0.025 | 5.729 | 1.802 | 2.302 | 1.474 | 2.488 | 0.85 | 0.26 | 0.75 | 1.76 | -0.83 |
| V | 045H | 0.595 | 1.146 | -15.735 | 0.437 | 1.477 | 1.060 | 0.984 | 0.699 | 0.792 | 0.85 | 0.58 | 0.83 | 1.49 | 1.81 |
| V | 045I | 0.717 | 1.080 | -40.090 | 0.594 | 1.305 | 1.060 | 1.073 | 0.735 | 1.028 | 1.01 | 0.72 | 0.85 | 1.52 | 2.61 |
| V | 045K | -0.032 | -9.860 | -13.398 | -0.006 | -4.726 | -0.540 | -5.223 | -4.038 | -8.305 | 0.00 | 0.00 | 0.00 | 0.00 | 0.00 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| V | 045L | 0.261 | 1.508 | −52.841 | 0.130 | 2.404 | 1.147 | 1.247 | 0.672 | 1.030 | 1.13 | 0.04 | 0.61 | 1.22 | 0.57 |
| V | 045M | 0.312 | 1.114 | 4.015 | 0.137 | 1.904 | 0.910 | 1.016 | 0.936 | 1.038 | 1.00 | 0.60 | 0.74 | 1.83 | 0.03 |
| V | 045N | 0.275 | 1.997 | 3.940 | 0.113 | 1.622 | 0.653 | 0.769 | 0.682 | 1.054 | 0.82 | 0.54 | 0.79 | 1.46 | −0.09 |
| V | 045P | 0.092 | 3.293 | −71.512 | 0.033 | 4.446 | 1.458 | 1.996 | 1.879 | 2.706 | 0.78 | 0.66 | 1.21 | 2.67 | −0.47 |
| V | 045Q | 0.058 | 6.643 | −43.972 | 0.017 | 5.539 | 1.573 | 2.412 | 2.201 | 2.910 | 1.10 | 0.80 | 0.90 | 2.52 | −0.91 |
| V | 045R | −0.095 | 1.141 | −137.883 | −0.017 | −0.833 | −0.071 | −0.503 | −0.632 | 1.197 | 0.00 | 0.00 | 0.00 | 0.00 | 0.00 |
| V | 045S | 0.420 | 1.727 | −23.320 | 0.258 | 1.785 | 1.247 | 1.266 | 1.009 | 1.078 | 0.83 | 0.53 | 1.02 | 1.21 | 1.21 |
| V | 045T | 0.499 | 1.350 | 0.344 | 0.334 | 1.656 | 1.236 | 1.122 | 0.939 | −0.463 | 0.99 | 0.70 | 0.83 | 1.17 | 1.82 |
| V | 045W | −0.246 | −0.667 | −5.040 | −0.052 | −0.351 | −0.046 | −0.175 | −0.233 | 4.215 | 0.00 | 0.00 | 0.00 | 0.00 | 0.00 |
| V | 045Y | 0.072 | 4.152 | −43.163 | 0.020 | 5.664 | 1.958 | 3.200 | 2.354 | 0.974 | 0.97 | 0.08 | 0.64 | 1.23 | 0.09 |
| E | 047A | 0.889 | 1.123 | −11.820 | 1.028 | 1.150 | 1.192 | 1.110 | 0.805 | 1.459 | 0.99 | 0.78 | 0.62 | 1.58 | 1.27 |
| E | 047C | 0.212 | −1.135 | 6.856 | 0.093 | 2.295 | 1.230 | 1.245 | 1.163 | 1.272 | 0.94 | 0.80 | 0.82 | 0.78 | 1.18 |
| E | 047D | 0.400 | 1.629 | −10.706 | 0.258 | 1.733 | 1.304 | 1.217 | 1.106 | 0.846 | 0.97 | 0.78 | 0.68 | 1.30 | 1.07 |
| E | 047F | 0.860 | 1.075 | 4.862 | 0.743 | 1.041 | 0.944 | 0.946 | 0.821 | 0.804 | 1.12 | 0.87 | 0.77 | 2.48 | 1.54 |
| E | 047G | 0.751 | 0.367 | 8.421 | 0.506 | 1.106 | 0.905 | 0.865 | 0.746 | 0.667 | 0.89 | 0.58 | 0.62 | 1.97 | 1.35 |
| E | 047H | 0.902 | 0.784 | 0.124 | 0.757 | 0.989 | 0.955 | 0.909 | 0.928 | 0.825 | 0.96 | 0.87 | 1.03 | 1.82 | 1.36 |
| E | 047I | 1.176 | 0.709 | 1.186 | 1.287 | 0.911 | 0.941 | 0.883 | 0.647 | 0.872 | 0.93 | 0.82 | 0.94 | 1.91 | 1.32 |
| E | 047K | 0.512 | 0.181 | −15.249 | 0.312 | 1.472 | 1.126 | 1.004 | 0.822 | 1.556 | 0.86 | 0.59 | 0.63 | 3.25 | 1.79 |
| E | 047L | 0.827 | 0.415 | −12.900 | 0.706 | 1.148 | 1.119 | 0.994 | 0.684 | 0.975 | 0.87 | 0.71 | 0.82 | 1.67 | 1.20 |
| E | 047N | 0.813 | 0.751 | −2.094 | 0.758 | 1.027 | 0.946 | 0.851 | 0.751 | 0.835 | 0.92 | 0.81 | 1.12 | 1.74 | 1.60 |
| E | 047P | 0.672 | 0.631 | −3.322 | 0.560 | 1.242 | 1.126 | 1.236 | 1.089 | 1.315 | 1.00 | 0.79 | 0.88 | 1.98 | 1.21 |
| E | 047R | 0.562 | 0.807 | −4.418 | 0.342 | 1.322 | 1.025 | 0.991 | 0.928 | 0.872 | 0.98 | 0.82 | 0.68 | 3.34 | 3.34 |
| E | 047S | 0.377 | −0.809 | 4.333 | 0.167 | 1.625 | 1.018 | 1.034 | 1.033 | 1.043 | 1.05 | 0.93 | 0.89 | 1.90 | 1.28 |
| E | 047T | 0.91 | ND | ND | ND | ND | ND | 1.09 | ND | 0.96 | 0.95 | 0.86 | 1.09 | 1.86 | 1.56 |
| E | 047V | 0.802 | 0.558 | −11.461 | 0.685 | 1.144 | 1.158 | 1.168 | 1.136 | 1.093 | 0.93 | 0.82 | 0.86 | 1.90 | 1.28 |
| E | 047Y | 0.848 | 0.779 | −4.505 | 0.831 | 1.119 | 1.135 | 1.032 | 0.734 | 0.990 | 0.86 | 0.73 | 0.82 | 1.69 | 1.29 |
| N | 049A | 0.734 | 1.095 | 0.902 | 0.729 | 1.147 | 1.144 | 1.047 | 0.661 | 0.984 | 1.00 | 0.74 | 1.11 | 0.91 | 0.44 |
| N | 049C | 0.215 | 1.035 | 3.313 | 0.084 | 1.990 | 1.198 | 1.315 | 1.144 | 1.515 | 1.05 | 0.96 | 0.83 | 0.62 | 0.40 |
| N | 049D | 0.771 | 0.953 | 0.098 | 0.652 | 1.041 | 1.048 | 1.025 | 0.950 | 1.036 | 0.99 | 0.86 | 0.84 | 0.92 | 0.77 |
| N | 049F | 0.791 | 1.355 | 0.297 | 0.629 | 1.093 | 1.085 | 1.063 | 1.042 | 1.027 | 0.99 | 0.91 | 0.68 | 0.97 | 0.65 |
| N | 049G | 0.725 | 1.105 | 3.201 | 0.496 | 1.155 | 0.951 | 0.919 | 0.894 | 0.804 | 0.84 | 0.67 | 0.79 | 1.02 | 1.08 |
| N | 049H | 0.808 | 0.945 | 1.225 | 0.640 | 1.158 | 1.112 | 1.105 | 1.103 | 0.815 | 0.98 | 0.84 | 0.77 | 1.26 | 1.18 |
| N | 049I | 0.981 | 0.563 | 0.293 | 0.930 | 0.995 | 0.854 | 0.750 | 0.466 | 0.652 | 0.94 | 0.57 | 0.92 | 1.28 | 0.82 |
| N | 049K | 0.614 | 1.155 | −0.055 | 0.437 | 1.306 | 1.242 | 1.206 | 0.988 | 0.900 | 0.98 | 0.76 | 0.70 | 0.96 | 1.09 |
| N | 049L | 0.696 | 0.478 | 0.788 | 0.534 | 1.204 | 1.083 | 1.048 | 0.699 | 0.956 | 1.03 | 0.52 | 0.92 | 1.28 | 0.72 |
| N | 049P | 0.638 | 1.167 | 0.851 | 0.421 | 1.110 | 0.939 | 0.913 | 0.667 | 0.756 | 0.94 | 0.64 | 0.76 | 1.09 | 1.36 |
| N | 049Q | 0.715 | 1.378 | 12.489 | 0.616 | 1.356 | 1.224 | 1.088 | 0.782 | 1.030 | 0.95 | 0.81 | 0.37 | 0.82 | 0.48 |
| N | 049R | 0.743 | 1.188 | 4.767 | 0.545 | 1.109 | 1.059 | 1.025 | 0.913 | 0.810 | 0.79 | 0.67 | 0.69 | 0.97 | 0.70 |
| N | 049S | 0.792 | 0.969 | 1.945 | 0.624 | 1.143 | 1.015 | 1.015 | 0.963 | 0.952 | 1.00 | 0.87 | 0.71 | 1.30 | 0.65 |
| N | 049T | 0.643 | 1.334 | 2.954 | 0.469 | 1.227 | 0.953 | 0.908 | 0.828 | 0.796 | 0.96 | 0.68 | 0.72 | 1.25 | 1.08 |
| N | 049V | 0.586 | 1.043 | 2.832 | 0.368 | 1.288 | 1.058 | 1.080 | 0.868 | 0.943 | 1.03 | 0.67 | 0.57 | 1.23 | 0.93 |
| N | 049W | 0.578 | 0.756 | −0.170 | 0.349 | 1.337 | 0.980 | 0.976 | 0.774 | 0.819 | 0.93 | 0.68 | 0.72 | 1.09 | 0.58 |
| N | 049Y | 0.694 | 0.955 | 3.672 | 0.533 | 1.210 | 1.187 | 1.167 | 0.835 | 1.102 | 0.90 | 0.65 | 0.83 | 1.07 | 1.04 |
| Q | 050A | 1.012 | 1.033 | −0.262 | 1.113 | 1.078 | 1.031 | 0.940 | 0.631 | 0.967 | 1.03 | 0.79 | 1.00 | 1.32 | 0.92 |
| Q | 050C | 0.344 | 2.094 | −5.190 | 0.155 | 1.810 | 1.055 | 1.071 | 0.931 | 1.200 | 0.99 | 0.91 | 0.79 | 0.68 | 0.67 |
| Q | 050E | 0.871 | 1.184 | −0.911 | 0.761 | 1.216 | 1.121 | 1.120 | 1.045 | 1.141 | 1.08 | 1.03 | 1.31 | 0.35 | 0.90 |
| Q | 050F | 0.821 | 1.241 | −2.006 | 0.708 | 1.290 | 1.176 | 1.159 | 1.108 | 1.146 | 1.02 | 0.95 | 0.91 | 0.81 | 0.84 |
| Q | 050G | 0.938 | 1.108 | −0.984 | 0.839 | 1.211 | 1.094 | 1.105 | 1.052 | 1.080 | 1.00 | 0.95 | 1.02 | 1.04 | 0.93 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| Q | 050H | 0.878 | 1.180 | −0.384 | 0.778 | 1.248 | 1.161 | 1.166 | 1.065 | 1.103 | 0.97 | 0.89 | 1.06 | 0.81 | 0.85 |
| Q | 050I | 0.628 | 1.369 | 1.573 | 0.419 | 1.561 | 1.212 | 1.235 | 0.957 | 1.127 | 1.00 | 0.76 | 0.68 | 0.92 | 1.11 |
| Q | 050K | 0.861 | 1.164 | −5.012 | 0.698 | 1.258 | 1.155 | 1.181 | 0.941 | 1.122 | 0.99 | 0.88 | 1.30 | 1.11 | 1.10 |
| Q | 050L | 0.831 | 1.174 | −0.821 | 0.676 | 1.270 | 1.138 | 1.161 | 0.784 | 1.134 | 0.98 | 0.89 | 1.13 | 0.51 | 0.76 |
| Q | 050M | 1.101 | 1.075 | −1.938 | 1.466 | 1.137 | 1.171 | 1.062 | 0.579 | 1.068 | 0.92 | 0.78 | 0.95 | 0.72 | 0.73 |
| Q | 050N | 1.181 | 0.994 | −2.419 | 1.522 | 1.057 | 1.086 | 1.012 | 0.687 | 1.004 | 0.90 | 0.78 | 0.87 | 0.76 | 0.62 |
| Q | 050P | 0.768 | 1.356 | −2.829 | 0.659 | 1.419 | 1.149 | 1.059 | 0.615 | 0.897 | 0.85 | 0.54 | 0.61 | 0.84 | 0.87 |
| Q | 050R | 0.986 | 1.086 | −2.386 | 1.008 | 1.191 | 1.172 | 1.134 | 0.874 | 1.059 | 0.90 | 0.82 | 0.80 | 1.20 | 1.24 |
| Q | 050S | 0.908 | 1.268 | −5.514 | 0.995 | 1.377 | 1.472 | 1.283 | 1.012 | 1.264 | 1.07 | 0.93 | 1.16 | 1.11 | 1.01 |
| Q | 050T | 0.755 | 1.370 | −3.681 | 0.675 | 1.557 | 1.377 | 1.309 | 0.931 | 1.270 | 1.01 | 0.77 | 0.89 | 0.67 | 0.63 |
| Q | 050V | 0.719 | 1.325 | 0.082 | 0.523 | 1.439 | 1.158 | 1.121 | 0.710 | 1.069 | 1.04 | 0.75 | 0.98 | 0.81 | 1.18 |
| Q | 050W | 0.933 | 1.170 | −1.011 | 0.948 | 1.252 | 1.103 | 1.115 | 0.734 | 1.020 | 1.04 | 0.87 | 1.27 | 0.88 | 1.08 |
| Q | 050Y | 1.045 | 1.019 | −5.628 | 1.261 | 1.210 | 1.195 | 1.156 | 0.760 | 1.113 | 0.96 | 0.89 | 1.13 | 0.83 | 0.94 |
| G | 051A | 0.948 | 1.061 | 3.726 | 1.120 | 1.021 | 1.045 | 0.957 | 0.573 | 0.943 | 0.92 | 0.70 | 0.61 | 1.06 | 0.91 |
| G | 051C | 0.266 | 2.833 | 7.792 | 0.105 | 2.106 | 1.212 | 1.272 | 0.903 | 1.322 | 0.93 | 0.63 | 0.49 | 0.98 | 0.79 |
| G | 051D | 0.499 | 1.573 | 3.560 | 0.344 | 1.468 | 1.014 | 0.997 | 0.722 | 1.026 | 0.95 | 0.56 | 0.51 | 0.91 | 0.56 |
| G | 051E | 0.399 | 2.198 | 4.825 | 0.249 | 1.831 | 1.335 | 1.322 | 0.985 | 1.284 | 1.01 | 0.62 | 0.51 | 1.21 | 0.80 |
| G | 051F | 0.505 | 1.608 | 6.538 | 0.324 | 1.507 | 1.259 | 1.217 | 0.950 | 1.058 | 1.10 | 0.79 | 0.77 | 1.22 | 1.51 |
| G | 051H | 0.524 | 1.423 | 4.789 | 0.322 | 1.462 | 1.135 | 1.169 | 0.935 | 1.035 | 0.99 | 0.63 | 0.69 | 1.01 | 0.86 |
| G | 051I | 0.437 | 1.734 | 4.687 | 0.270 | 1.753 | 1.267 | 1.298 | 0.910 | 1.122 | 1.10 | 0.55 | 0.66 | 1.11 | 0.85 |
| G | 051K | 0.583 | 1.243 | 1.294 | 0.372 | 1.369 | 1.062 | 1.072 | 0.761 | 0.853 | 1.09 | 0.69 | 0.75 | 1.30 | 1.32 |
| G | 051L | 0.284 | 1.728 | 1.073 | 0.105 | 1.975 | 1.181 | 1.315 | 1.106 | 1.335 | 0.96 | 0.61 | 0.53 | 1.17 | 1.00 |
| G | 051M | 0.869 | 1.053 | 2.985 | 0.880 | 1.056 | 0.942 | 0.885 | 0.328 | 0.815 | 0.97 | 0.53 | 0.60 | 0.77 | 0.83 |
| G | 051N | 0.778 | 1.048 | 2.736 | 0.670 | 1.128 | 0.928 | 0.859 | 0.438 | 0.789 | 0.92 | 0.53 | 0.57 | 1.00 | 0.81 |
| G | 051P | 0.619 | 1.337 | 4.475 | 0.422 | 1.332 | 0.875 | 0.816 | 0.413 | 0.640 | 0.91 | 0.41 | 0.41 | 1.09 | 0.40 |
| G | 051Q | 0.703 | 1.278 | 2.418 | 0.497 | 1.186 | 1.029 | 1.004 | 0.620 | 0.916 | 1.02 | 0.63 | 0.51 | 1.05 | 1.21 |
| G | 051R | 0.713 | 1.206 | 2.858 | 0.519 | 1.221 | 1.044 | 1.005 | 0.653 | 0.835 | 1.01 | 0.69 | 0.51 | 1.61 | 1.60 |
| G | 051S | 0.827 | 1.060 | 3.995 | 0.706 | 1.165 | 1.036 | 1.021 | 0.723 | 0.987 | 0.99 | 0.71 | 0.78 | 1.19 | 0.97 |
| G | 051T | 0.664 | 1.311 | 1.847 | 0.458 | 1.277 | 1.026 | 1.017 | 0.653 | 0.896 | 1.06 | 0.62 | 0.75 | 1.13 | 1.10 |
| G | 051V | 0.598 | 1.363 | 5.653 | 0.460 | 1.515 | 1.232 | 1.257 | 0.751 | 1.134 | 1.14 | 0.59 | 0.94 | 1.21 | 0.76 |
| G | 051W | 0.595 | 1.325 | 6.424 | 0.427 | 1.388 | 1.045 | 0.978 | 0.659 | 0.791 | 0.99 | 0.63 | 0.62 | 0.84 | 0.60 |
| D | 052A | 1.178 | 0.853 | 0.145 | 1.487 | 0.887 | 0.877 | 0.809 | 0.506 | 0.741 | 0.64 | 0.48 | 0.68 | 0.73 | 0.49 |
| D | 052C | 0.148 | 0.896 | 8.174 | 0.065 | 3.460 | 1.706 | 1.903 | 1.470 | 2.104 | 0.99 | 0.73 | 0.90 | 0.78 | 1.12 |
| D | 052E | 0.907 | 1.096 | −3.505 | 1.080 | 1.170 | 1.162 | 1.108 | 0.998 | 1.097 | 0.95 | 0.73 | 0.95 | 1.30 | 0.78 |
| D | 052F | 0.762 | 0.911 | −1.075 | 0.650 | 1.236 | 1.028 | 0.976 | 0.799 | 0.894 | 0.97 | 0.68 | 0.74 | 1.78 | 0.87 |
| D | 052G | 0.847 | 1.013 | 1.232 | 0.799 | 1.132 | 1.015 | 0.933 | 0.663 | 0.882 | 0.95 | 0.63 | 0.71 | 1.60 | 0.77 |
| D | 052H | 0.885 | 1.048 | −1.404 | 0.931 | 1.242 | 1.184 | 1.153 | 0.943 | 0.912 | 1.01 | 0.77 | 1.00 | 1.67 | 1.14 |
| D | 052I | 0.539 | 1.374 | 1.129 | 0.358 | 1.515 | 1.269 | 1.290 | 1.174 | 1.206 | 1.08 | 0.83 | 1.21 | 1.61 | 1.40 |
| D | 052K | 0.940 | 0.882 | 1.509 | 1.004 | 1.099 | 1.096 | 1.034 | 0.750 | 0.869 | 0.89 | 0.64 | 1.01 | 1.82 | 1.12 |
| D | 052L | 0.905 | 0.861 | −0.895 | 0.992 | 1.141 | 1.117 | 1.088 | 0.813 | 0.961 | 0.90 | 0.38 | 1.05 | 1.22 | 1.13 |
| D | 052M | 0.829 | 1.141 | 3.521 | 0.846 | 1.117 | 1.038 | 0.981 | 0.712 | 0.150 | 0.97 | 0.64 | 1.00 | 0.46 | 0.98 |
| D | 052N | 1.011 | 0.982 | −1.761 | 1.107 | 0.971 | 0.964 | 0.933 | 0.848 | 0.877 | 0.80 | 0.34 | 0.99 | 1.11 | 0.88 |
| D | 052P | 0.097 | 1.835 | −19.190 | 0.040 | 4.672 | 1.585 | 2.018 | 1.585 | 1.443 | 0.92 | 0.84 | 0.54 | 1.16 | 0.79 |
| D | 052Q | 0.724 | 1.330 | −0.010 | 0.699 | 1.310 | 1.215 | 1.199 | 1.165 | 1.104 | 0.99 | 0.79 | 0.94 | 1.15 | 1.08 |
| D | 052R | 0.819 | 1.144 | −3.763 | 0.705 | 1.125 | 1.009 | 0.996 | 1.020 | 0.816 | 0.89 | 0.85 | 1.02 | 2.39 | 1.78 |
| D | 052S | 0.919 | 1.123 | 5.668 | 0.846 | 1.067 | 0.998 | 1.000 | 1.002 | 0.919 | 0.90 | 0.81 | 0.91 | 1.44 | 0.90 |
| D | 052T | 0.650 | 1.053 | −0.315 | 0.506 | 1.406 | 1.189 | 1.183 | 1.149 | 1.067 | 0.95 | 0.81 | 1.03 | 1.52 | 0.99 |
| D | 052V | 0.639 | 1.107 | −1.667 | 0.484 | 1.396 | 1.218 | 1.226 | 1.148 | 1.113 | 1.03 | 0.90 | 1.14 | 1.41 | 1.29 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| D | 052W | 0.411 | 1.301 | −9.652 | 0.263 | 1.853 | 1.359 | 1.399 | 1.048 | 1.131 | 0.96 | 0.64 | 0.85 | 1.42 | 1.19 |
| D | 052Y | 0.597 | 1.108 | 1.089 | 0.466 | 1.437 | 1.232 | 1.212 | 0.861 | 1.066 | 0.92 | 0.42 | 0.72 | 1.32 | 1.20 |
| S | 054A | 1.185 | 0.904 | −6.321 | 1.763 | 0.968 | 1.052 | 0.986 | 0.643 | 0.977 | 0.98 | 0.86 | 0.88 | 0.93 | 0.74 |
| S | 054C | 0.550 | 1.164 | −18.285 | 0.358 | 1.201 | 0.900 | 0.826 | 0.621 | 0.852 | 1.04 | 0.90 | 0.69 | 1.39 | 0.98 |
| S | 054D | 1.079 | 0.964 | 3.427 | 1.465 | 1.047 | 1.103 | 1.016 | 0.871 | 1.083 | 1.06 | 0.98 | 0.63 | 1.03 | 0.65 |
| S | 054F | 0.984 | 1.119 | −3.992 | 1.196 | 1.113 | 1.092 | 0.969 | 0.906 | 0.953 | 0.96 | 0.92 | 1.00 | 1.13 | 1.11 |
| S | 054G | 1.081 | 0.986 | −1.823 | 1.289 | 1.026 | 1.081 | 0.989 | 0.858 | 1.020 | 1.04 | 0.96 | 1.14 | 1.13 | 1.01 |
| S | 054H | 0.783 | 0.963 | −4.630 | 0.626 | 1.167 | 0.946 | 0.868 | 0.753 | 0.827 | 0.99 | 0.96 | 1.14 | 1.27 | 1.13 |
| S | 054I | 1.093 | 0.684 | 3.296 | 1.315 | 1.025 | 1.018 | 0.949 | 0.801 | 0.923 | 0.97 | 0.83 | 0.83 | 1.07 | 0.83 |
| S | 054L | 0.775 | 1.065 | 4.993 | 0.839 | 1.279 | 1.207 | 1.100 | 0.823 | 0.967 | 0.99 | 0.15 | 0.91 | −0.17 | 1.00 |
| S | 054M | 1.014 | 0.957 | −2.703 | 1.001 | 0.939 | 0.835 | 0.792 | 0.566 | 0.763 | 0.94 | 0.80 | 0.70 | 0.85 | 0.73 |
| S | 054N | 1.013 | 0.937 | 0.536 | 1.139 | 0.936 | 0.928 | 0.900 | 0.777 | 0.888 | 1.11 | 1.04 | 0.85 | 1.64 | 1.04 |
| S | 054P | 0.348 | 1.648 | 8.163 | 0.187 | 1.753 | 0.918 | 0.978 | 0.687 | 0.650 | 1.04 | 0.58 | 0.67 | 1.51 | 0.38 |
| S | 054Q | 0.881 | 0.956 | 2.746 | 0.745 | 1.010 | 0.980 | 0.974 | 1.056 | 0.964 | 0.98 | 0.95 | 1.00 | 0.99 | 1.06 |
| S | 054R | 0.983 | 0.981 | 0.991 | 0.912 | 0.990 | 0.922 | 0.882 | 0.871 | 0.796 | 1.05 | 0.99 | 0.94 | 1.18 | 1.25 |
| S | 054T | 0.815 | 1.199 | −1.226 | 0.736 | 1.168 | 1.121 | 1.118 | 1.068 | 1.063 | 1.06 | 1.00 | 0.96 | 0.77 | 1.06 |
| S | 054V | 0.712 | 1.145 | −6.948 | 0.500 | 1.168 | 0.964 | 1.010 | 0.905 | 0.934 | 0.99 | 0.86 | 0.77 | 1.03 | 0.78 |
| S | 054W | 0.537 | 1.459 | −3.288 | 0.397 | 1.526 | 1.231 | 1.185 | 1.011 | 0.955 | 1.00 | 0.92 | 1.28 | 1.06 | 0.87 |
| S | 054Y | 0.738 | 1.030 | −3.933 | 0.633 | 1.219 | 1.114 | 1.031 | 0.805 | 0.931 | 1.00 | 0.71 | 1.09 | 1.36 | 0.82 |
| S | 056A | 1.278 | 0.875 | −1.400 | 1.644 | 0.777 | 0.870 | 0.821 | 0.631 | 0.789 | 0.96 | 0.81 | 0.75 | 0.94 | 0.83 |
| S | 056D | 0.961 | 1.091 | 1.398 | 0.886 | 0.974 | 0.987 | 0.993 | 1.010 | 1.040 | 1.06 | 1.12 | 0.70 | 0.78 | 0.72 |
| S | 056E | 1.143 | 0.986 | 2.499 | 1.128 | 0.834 | 0.729 | 0.860 | 0.885 | 0.877 | 1.10 | 1.22 | 0.84 | 1.27 | 0.91 |
| S | 056F | 0.866 | 1.231 | 0.085 | 0.780 | 1.059 | 0.986 | 1.018 | 1.071 | 0.940 | 1.07 | 1.18 | 1.24 | 0.97 | 0.81 |
| S | 056G | 0.874 | 1.108 | 6.372 | 0.716 | 1.080 | 1.060 | 1.062 | 1.105 | 0.960 | 0.93 | 1.10 | 1.07 | 1.30 | 1.04 |
| S | 056I | 0.818 | 0.972 | 5.130 | 0.619 | 1.093 | 0.991 | 1.034 | 1.023 | 0.995 | 1.12 | 1.13 | 0.74 | 1.14 | 0.80 |
| S | 056K | 0.930 | 0.980 | 0.346 | 0.838 | 1.038 | 1.029 | 1.046 | 0.940 | 0.870 | 0.95 | 0.89 | 0.80 | 1.45 | 0.99 |
| S | 056L | 0.895 | 0.827 | −3.463 | 0.802 | 1.081 | 1.060 | 1.093 | 0.820 | 1.011 | 1.01 | 0.71 | 1.12 | 1.41 | 0.74 |
| S | 056M | 1.163 | 0.968 | −3.114 | 1.495 | 0.887 | 0.947 | 0.849 | 0.624 | 0.812 | 0.99 | 0.81 | 0.75 | 0.85 | 0.98 |
| S | 056N | 0.807 | 1.208 | 1.903 | 0.730 | 1.094 | 1.026 | 0.995 | 0.836 | 0.908 | 0.94 | 0.89 | 0.76 | 0.93 | 0.94 |
| S | 056P | 0.835 | 1.175 | −0.302 | 0.644 | 1.031 | 0.956 | 0.967 | 0.908 | 0.967 | 0.99 | 1.02 | 1.12 | 1.04 | 0.84 |
| S | 056Q | 0.854 | 1.296 | 3.479 | 0.783 | 1.116 | 1.100 | 1.125 | 1.097 | 1.094 | 0.94 | 1.01 | 1.12 | 0.80 | 0.97 |
| S | 056R | 0.882 | 1.218 | 0.491 | 0.739 | 1.066 | 1.037 | 1.058 | 1.051 | 0.824 | 1.02 | 1.10 | 0.93 | 1.27 | 1.12 |
| S | 056T | 0.872 | 1.057 | −0.504 | 0.752 | 1.090 | 1.016 | 1.086 | 1.117 | 1.014 | 1.02 | 1.08 | 1.06 | 1.48 | 0.77 |
| S | 056W | 0.937 | 1.020 | 2.554 | 0.792 | 1.016 | 0.969 | 1.024 | 0.969 | 0.973 | 1.13 | 1.14 | 1.25 | 1.04 | 0.96 |
| S | 056Y | 0.800 | 1.160 | −0.583 | 0.740 | 1.212 | 1.103 | 1.162 | 1.022 | 1.091 | 0.95 | 0.97 | 1.22 | 1.41 | 1.13 |
| Y | 059A | 0.922 | 1.172 | −1.633 | 0.992 | 1.162 | 1.137 | 1.140 | 0.868 | 1.057 | 1.10 | 0.87 | 0.87 | 1.53 | 0.92 |
| Y | 059C | 1.031 | 1.720 | −4.959 | 1.628 | 1.043 | 0.623 | 0.509 | 0.387 | 0.678 | 1.21 | 0.92 | 0.55 | 1.09 | 0.18 |
| Y | 059D | 0.460 | −0.711 | −6.571 | 0.239 | 1.175 | 0.521 | 0.471 | 0.399 | 0.694 | 1.93 | 1.87 | 0.33 | 0.67 | 0.25 |
| Y | 059E | 0.824 | 0.730 | −4.339 | 0.848 | 1.104 | 0.628 | 0.432 | 0.359 | 0.655 | 0.79 | 0.75 | 0.40 | 0.71 | 0.20 |
| Y | 059F | 0.976 | 1.049 | −15.689 | 1.147 | 0.979 | 0.547 | 0.348 | 0.305 | 0.467 | 0.53 | 0.48 | 0.31 | 0.71 | 0.37 |
| Y | 059G | 1.150 | 1.067 | 0.454 | 1.704 | 1.025 | 1.068 | 1.003 | 0.882 | 1.107 | 0.92 | 0.90 | 1.11 | 1.00 | 0.77 |
| Y | 059H | 0.898 | 1.629 | −7.309 | 1.080 | 1.063 | 0.520 | 0.494 | 0.384 | 0.512 | 0.61 | 0.53 | 0.63 | 0.90 | 0.96 |
| Y | 059I | 1.104 | 1.625 | −0.686 | 1.630 | 0.938 | 0.451 | 0.332 | 0.273 | 0.146 | 0.90 | 0.86 | 0.49 | 1.24 | 1.13 |
| Y | 059I | −0.014 | 46.238 | −1155.054 | −0.003 | −12.372 | −0.887 | −4.619 | −4.834 | −9.829 | 0.00 | 0.00 | 0.00 | 0.00 | 0.18 |
| Y | 059K | 1.030 | 0.167 | 3.253 | 1.017 | 0.828 | 0.593 | 0.413 | 0.304 | 0.305 | 0.83 | 0.64 | 0.35 | 0.96 | 0.00 |
| Y | 059L | 0.546 | 1.386 | 0.958 | 0.312 | 1.325 | 0.872 | 0.797 | 0.637 | 0.963 | 0.87 | 0.03 | 0.78 | 0.82 | 0.26 |
| Y | 059N | 0.868 | 1.216 | −11.688 | 0.889 | 0.952 | 0.346 | 0.298 | 0.240 | 0.313 | 1.19 | 1.04 | 0.29 | 0.83 | 0.50 |
| Y | 059P | 0.687 | 1.900 | −4.014 | 0.698 | 1.186 | 0.506 | 0.419 | 0.352 | 0.459 | 1.35 | 1.06 | 0.44 | 0.87 | 0.16 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| Y | 059R | 0.935 | 1.218 | −14.441 | 0.971 | 0.942 | 0.352 | 0.306 | 0.313 | 0.186 | 0.70 | 0.67 | 0.21 | 0.83 | 0.12 |
| Y | 059S | 0.801 | 1.348 | 9.803 | 0.696 | 1.139 | 0.639 | 0.598 | 0.545 | 0.752 | 1.22 | 1.08 | 0.51 | 1.16 | 0.28 |
| Y | 059T | 0.751 | 0.784 | 8.626 | 0.697 | 1.157 | 0.837 | 0.606 | 0.535 | 0.634 | 1.11 | 0.94 | 0.85 | 0.85 | 0.20 |
| Y | 059V | 0.829 | 0.416 | 36.606 | 0.638 | 0.974 | 0.811 | 0.640 | 0.559 | 0.757 | 0.82 | 0.67 | 0.79 | 0.89 | 0.08 |
| Y | 059W | 0.808 | 0.617 | 15.591 | 0.747 | 1.095 | 1.172 | 1.208 | 0.911 | 1.158 | 0.67 | 0.50 | 1.12 | 1.02 | 0.92 |
| Q | 068A | 1.014 | 0.990 | 1.787 | 1.143 | 1.105 | 1.017 | 0.939 | 0.735 | 0.933 | 0.94 | 0.80 | 0.80 | 0.74 | 0.81 |
| Q | 068C | 0.211 | 2.838 | 10.104 | 0.083 | 2.375 | 1.110 | 1.237 | 1.129 | 1.466 | 0.99 | 0.81 | 0.57 | 0.69 | 0.48 |
| Q | 068D | 0.881 | 1.116 | 0.192 | 0.773 | 1.105 | 0.997 | 0.931 | 0.893 | 0.945 | 1.00 | 0.80 | 0.63 | 0.76 | 1.00 |
| Q | 068E | 0.918 | 0.965 | 3.504 | 0.798 | 1.053 | 0.935 | 0.914 | 0.886 | 0.921 | 1.07 | 0.90 | 0.90 | 0.62 | 0.79 |
| Q | 068F | 0.591 | 1.254 | 3.346 | 0.386 | 1.418 | 1.089 | 1.026 | 1.053 | 1.099 | 1.04 | 0.90 | 0.97 | 0.79 | 1.03 |
| Q | 068G | 0.755 | 1.162 | 4.252 | 0.616 | 1.337 | 1.102 | 1.060 | 1.102 | 1.104 | 0.96 | 0.96 | 0.96 | 0.66 | 0.95 |
| Q | 068H | 0.942 | 0.984 | 0.602 | 0.921 | 1.159 | 1.089 | 1.057 | 1.058 | 1.083 | 1.01 | 0.95 | 1.25 | 1.09 | 1.09 |
| Q | 068I | 0.753 | 1.069 | 1.501 | 0.588 | 1.300 | 1.066 | 1.056 | 1.013 | 1.099 | 1.02 | 0.86 | 1.12 | 0.75 | 1.13 |
| Q | 068L | 0.741 | 1.109 | 3.201 | 0.598 | 1.315 | 1.086 | 1.030 | 0.720 | 1.060 | 0.99 | 0.99 | 1.10 | 0.66 | 0.69 |
| Q | 068M | 0.821 | 1.082 | 1.731 | 0.812 | 1.252 | 1.133 | 1.015 | 0.753 | 1.030 | 0.97 | 0.79 | 0.94 | 0.67 | 0.68 |
| Q | 068N | 0.859 | 1.138 | 1.046 | 0.877 | 1.203 | 1.124 | 1.110 | 1.082 | 1.124 | 1.01 | 0.97 | 0.95 | 1.14 | 1.02 |
| Q | 068P | −0.071 | −7.085 | −47.572 | −0.017 | −3.638 | −0.838 | −1.511 | −1.802 | −2.521 | 1.23 | 1.34 | 1.58 | 2.29 | 1.41 |
| Q | 068R | 0.884 | 1.115 | −0.679 | 0.865 | 1.192 | 1.106 | 1.067 | 1.250 | 1.123 | 0.93 | 1.01 | 1.12 | 1.09 | 1.04 |
| Q | 068S | 0.917 | 1.046 | 5.012 | 0.812 | 1.153 | 1.016 | 0.973 | 1.013 | 0.999 | 0.96 | 0.86 | 1.33 | 0.79 | 0.89 |
| Q | 068T | 0.755 | 1.219 | 1.297 | 0.630 | 1.320 | 1.162 | 1.157 | 1.159 | 1.158 | 0.99 | 0.89 | 1.11 | 0.68 | 0.99 |
| Q | 068V | 0.752 | 1.135 | 4.676 | 0.577 | 1.289 | 1.160 | 1.170 | 1.146 | 1.200 | 1.07 | 0.98 | 1.34 | 0.82 | 1.16 |
| Q | 068W | 0.479 | 1.646 | 1.633 | 0.317 | 1.874 | 1.488 | 1.375 | 1.286 | 1.442 | 1.04 | 1.04 | 1.49 | 0.85 | 0.92 |
| Q | 068Y | 0.582 | 1.042 | 8.541 | 0.277 | 0.972 | 0.555 | 0.518 | 0.479 | 0.643 | 1.01 | 0.81 | 1.09 | 0.95 | 1.30 |
| Y | 073A | 0.348 | 2.071 | 2.325 | 0.186 | 1.634 | 0.694 | 0.725 | 0.371 | 0.657 | 0.90 | 0.41 | 0.48 | 0.92 | 1.64 |
| Y | 073C | 0.068 | 9.879 | 17.316 | 0.020 | 3.823 | 0.653 | 1.310 | 1.123 | 1.888 | 1.17 | 0.55 | 0.53 | 1.53 | 0.82 |
| Y | 073D | −0.085 | −6.198 | −10.544 | −0.021 | −1.826 | −0.110 | −0.693 | −0.688 | −1.536 | 0.00 | 0.00 | 0.00 | 0.00 | 0.62 |
| Y | 073E | 0.025 | 21.980 | 17.611 | 0.007 | 10.629 | 2.021 | 3.883 | 3.301 | 5.491 | 0.81 | 0.41 | 0.00 | 0.00 | 2.32 |
| Y | 073F | 0.659 | 1.363 | 1.293 | 0.575 | 1.391 | 0.988 | 0.928 | 0.704 | 0.835 | 1.07 | 0.65 | 0.45 | 1.56 | 1.00 |
| Y | 073G | −0.013 | −41.943 | −22.911 | −0.003 | −19.205 | −3.290 | −6.430 | −5.322 | −9.818 | 0.00 | 0.00 | 0.58 | 1.32 | 0.00 |
| Y | 073H | 0.166 | 3.429 | 1.082 | 0.064 | 3.013 | 1.118 | 1.222 | 0.863 | 0.707 | 1.05 | 0.50 | 0.00 | 0.00 | 0.00 |
| Y | 073I | 0.119 | 3.229 | −3.816 | 0.042 | 3.750 | 1.229 | 1.609 | 1.067 | 1.162 | 1.07 | 0.53 | 0.73 | 1.21 | 0.64 |
| Y | 073K | 0.020 | 15.867 | 23.620 | 0.006 | 18.127 | 5.277 | 6.973 | 5.433 | 7.259 | 0.74 | 0.48 | 0.54 | 1.26 | 1.30 |
| Y | 073L | 0.200 | 2.800 | −4.343 | 0.082 | 2.956 | 1.774 | 1.723 | 1.268 | 1.614 | 0.99 | 0.57 | 0.44 | 1.84 | 1.64 |
| Y | 073M | 0.545 | 1.345 | 1.429 | 0.372 | 1.302 | 0.805 | 0.780 | 0.491 | 0.686 | 1.03 | 0.57 | 0.55 | 1.00 | 0.71 |
| Y | 073P | −0.084 | −5.218 | 5.158 | −0.022 | −2.334 | −0.329 | −0.896 | −0.855 | −1.437 | 0.00 | 0.00 | 0.52 | 1.15 | 0.83 |
| Y | 073R | 0.014 | 28.027 | 5.392 | −0.022 | 16.745 | 2.930 | 6.373 | 5.670 | 8.473 | 0.81 | 0.41 | 0.00 | 0.00 | 0.00 |
| Y | 073S | −0.050 | −8.706 | −1.044 | −0.011 | −2.860 | −0.220 | −1.089 | −1.188 | −2.272 | 0.00 | 0.00 | 0.00 | 0.00 | 1.46 |
| Y | 073T | 0.029 | 15.493 | 10.579 | 0.009 | 11.171 | 2.899 | 4.263 | 3.876 | 5.211 | 1.46 | 0.88 | 0.17 | 0.18 | 0.00 |
| Y | 073V | 0.303 | 0.508 | −1.153 | 0.061 | 0.339 | 0.030 | 0.141 | 0.166 | 0.379 | 0.10 | 0.04 | 1.31 | 1.47 | 1.38 |
| Y | 073W | 0.040 | 7.198 | 5.973 | 0.011 | 8.444 | 2.134 | 3.196 | 2.711 | 2.998 | 0.99 | 0.51 | 0.13 | 0.65 | 0.34 |
| Y | 075A | 0.462 | 1.602 | −0.144 | 0.351 | 1.597 | 0.981 | 0.999 | 0.684 | 0.839 | 1.15 | 0.70 | 0.50 | 1.55 | 1.51 |
| G | 075C | −0.085 | 0.237 | 8.381 | −0.019 | −1.080 | −0.131 | −0.635 | −0.788 | −1.596 | 0.00 | 0.00 | 0.65 | 1.75 | 0.41 |
| G | 075D | −0.126 | 1.536 | −24.150 | −0.019 | −0.675 | −0.028 | −0.404 | −0.497 | −1.037 | 0.00 | 0.00 | 0.00 | 0.00 | 0.00 |
| G | 075E | −0.128 | 0.615 | 9.672 | −0.026 | −0.722 | −0.091 | −0.394 | −0.499 | −0.992 | 0.00 | 0.00 | 0.00 | 0.00 | 0.00 |
| G | 075F | −0.143 | 2.502 | −13.007 | −0.023 | −0.608 | −0.063 | −0.347 | −0.437 | −0.901 | 0.00 | 0.00 | 0.00 | 0.00 | 0.00 |
| G | 075H | −0.147 | 1.777 | −5.953 | −0.024 | −0.579 | −0.083 | −0.328 | −0.420 | −0.875 | 0.00 | 0.00 | 0.00 | 0.00 | 0.00 |
| G | 075I | −0.157 | −0.386 | −23.093 | −0.029 | −0.573 | −0.036 | −0.312 | −0.392 | −0.822 | 0.00 | 0.00 | 0.00 | 0.00 | 0.00 |
| G | 075L | −0.160 | −0.465 | −26.738 | −0.029 | −0.519 | −0.030 | −0.293 | −0.377 | −0.778 | 0.00 | 0.00 | 0.00 | 0.00 | 0.00 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| G | 075K | -0.090 | 0.525 | -43.807 | -0.013 | -0.988 | -0.080 | -0.564 | -0.720 | -1.435 | 0.00 | 0.00 | 0.00 | 0.00 | 0.00 |
| G | 075L | -0.126 | 0.423 | -59.082 | -0.020 | -0.656 | -0.007 | -0.393 | -0.477 | -1.012 | 0.00 | 0.00 | 0.00 | 0.00 | 0.00 |
| G | 075M | -0.058 | 0.356 | 20.505 | -0.012 | -1.677 | -0.212 | -0.995 | -1.160 | -2.448 | 0.00 | 0.00 | 0.00 | 0.00 | 0.00 |
| G | 075N | -0.105 | 3.451 | -2.453 | -0.023 | -0.934 | -0.136 | -0.513 | -0.633 | -1.277 | 0.00 | 0.00 | 0.00 | 0.00 | 0.00 |
| G | 075P | -0.133 | 1.698 | 9.055 | -0.022 | -0.634 | -0.073 | -0.372 | -0.465 | -0.970 | 0.00 | 0.00 | 0.00 | 0.00 | 0.00 |
| G | 075Q | -0.154 | -0.625 | 3.785 | -0.026 | -0.568 | -0.045 | -0.327 | -0.410 | -0.832 | 0.00 | 0.00 | 0.00 | 0.00 | 0.00 |
| G | 075R | -0.154 | 0.717 | 0.606 | -0.023 | -0.577 | -0.052 | -0.324 | -0.403 | -0.817 | 0.00 | 0.00 | 0.00 | 0.00 | 0.00 |
| G | 075S | -0.128 | 2.668 | -30.710 | -0.023 | -0.874 | -0.098 | -0.454 | -0.525 | -1.029 | 0.00 | 0.00 | 0.00 | 0.00 | 0.00 |
| G | 075T | -0.109 | -1.144 | -3.636 | -0.015 | -0.795 | -0.083 | -0.448 | -0.556 | -1.148 | 0.00 | 0.00 | 0.00 | 0.00 | 0.00 |
| G | 075W | -0.157 | -0.959 | -22.827 | -0.024 | -0.533 | -0.048 | -0.316 | -0.381 | -0.799 | 0.00 | 0.00 | 0.00 | 0.00 | 0.00 |
| G | 075Y | -0.173 | -0.951 | -23.493 | -0.027 | -0.492 | -0.022 | -0.312 | -0.342 | -0.760 | 0.00 | 0.00 | 0.00 | 0.00 | 0.00 |
| T | 076A | 0.782 | 1.241 | 8.468 | 0.796 | 1.237 | 1.078 | 0.976 | 0.626 | 0.983 | ND | ND | ND | ND | ND |
| T | 076D | 1.034 | 0.950 | 2.795 | 1.060 | 0.957 | 0.891 | 0.876 | 0.716 | 0.854 | 1.00 | 0.91 | 0.81 | 0.57 | 0.52 |
| T | 076E | 0.673 | 1.200 | 0.106 | 0.585 | 1.244 | 1.121 | 1.017 | 0.685 | 1.058 | 1.00 | 0.91 | 0.95 | 0.83 | 0.79 |
| T | 076F | 0.297 | 2.355 | 21.740 | 0.153 | 2.335 | 1.475 | 1.435 | 1.283 | 1.519 | 1.01 | 0.90 | 1.09 | 0.67 | 0.51 |
| T | 076G | 0.894 | 1.046 | 3.676 | 0.786 | 1.093 | 0.968 | 0.931 | 0.791 | 0.921 | 1.02 | 0.95 | 0.99 | 0.62 | 0.58 |
| T | 076I | 0.390 | 1.601 | -1.151 | 0.194 | 1.389 | 1.073 | 1.048 | 0.906 | 1.133 | 0.99 | 0.95 | 0.94 | 0.67 | 0.17 |
| T | 076L | 0.449 | 1.450 | 3.102 | 0.294 | 1.550 | 1.063 | 0.987 | 0.761 | 1.047 | 0.69 | 0.69 | 0.56 | 0.33 | 0.43 |
| T | 076M | 0.546 | 1.334 | 3.404 | 0.352 | 1.309 | 0.932 | 0.896 | 0.656 | 0.901 | 0.93 | 0.84 | 0.74 | 0.44 | 0.55 |
| T | 076P | 0.579 | 1.503 | -0.235 | 0.352 | 1.264 | 0.948 | 0.937 | 0.912 | 0.952 | 1.06 | 0.97 | 1.16 | 0.62 | 0.62 |
| T | 076Q | 0.648 | 1.393 | 0.711 | 0.475 | 1.245 | 1.039 | 1.034 | 1.007 | 1.038 | 1.04 | 1.01 | 1.04 | 0.63 | 0.63 |
| T | 076R | 0.701 | 1.124 | 2.129 | 0.525 | 1.110 | 0.922 | 0.874 | 0.829 | 0.885 | 0.99 | 0.98 | 1.21 | 1.26 | 0.85 |
| T | 076S | 0.953 | 1.030 | 1.111 | 0.837 | 1.016 | 0.955 | 0.974 | 0.979 | 0.948 | 0.98 | 0.97 | 1.10 | 0.57 | 0.46 |
| T | 076V | 0.416 | 1.260 | 9.415 | 0.219 | 1.479 | 1.059 | 1.063 | 1.008 | 1.113 | 1.01 | 1.00 | 0.93 | 0.88 | 0.38 |
| T | 076Y | 0.579 | 1.221 | -0.705 | 0.389 | 1.389 | 1.040 | 1.016 | 0.811 | 0.972 | 1.07 | 1.09 | 1.06 | 1.09 | 0.89 |
| Q | 078A | 1.182 | 0.874 | 1.006 | 1.491 | 0.857 | 0.866 | 0.825 | 0.660 | 0.848 | 1.02 | 0.93 | 0.89 | 0.90 | 1.09 |
| Q | 078C | 0.095 | 5.201 | 6.157 | 0.021 | 1.345 | 0.116 | 0.593 | 0.674 | 1.358 | 0.74 | 0.67 | 0.69 | 1.50 | 2.91 |
| Q | 078D | 0.852 | 1.181 | 0.098 | 0.728 | 1.093 | 1.071 | 1.070 | 1.086 | 1.084 | 1.09 | 1.09 | 0.93 | 0.91 | 1.43 |
| Q | 078E | 1.093 | 0.871 | 1.028 | 1.187 | 0.871 | 0.907 | 0.927 | 0.961 | 0.917 | 1.00 | 1.02 | 0.80 | 0.86 | 1.10 |
| Q | 078F | 0.918 | 0.766 | 1.016 | 0.731 | 0.901 | 0.733 | 0.718 | 0.853 | 0.784 | 1.02 | 1.01 | 0.74 | 0.94 | 1.08 |
| Q | 078G | 0.974 | 0.949 | 0.235 | 0.926 | 0.982 | 0.928 | 0.923 | 0.953 | 0.932 | 1.02 | 1.05 | 0.85 | 0.99 | 1.18 |
| Q | 078H | 0.681 | 1.215 | 0.971 | 0.534 | 1.250 | 1.097 | 1.068 | 1.050 | 1.034 | 0.94 | 0.95 | 0.84 | 1.00 | 1.03 |
| Q | 078I | 0.915 | 1.042 | 0.993 | 0.872 | 1.020 | 0.965 | 0.999 | 0.928 | 0.997 | 1.03 | 1.03 | 0.99 | 0.94 | 1.21 |
| Q | 078K | 1.055 | 0.859 | 0.936 | 1.076 | 0.932 | 0.904 | 0.938 | 0.826 | 0.926 | 1.05 | 0.99 | 0.97 | 1.35 | 1.17 |
| Q | 078L | 0.973 | 0.880 | 0.630 | 1.055 | 1.024 | 1.006 | 0.999 | 0.745 | 0.989 | 0.99 | 0.97 | 0.77 | 0.91 | 1.14 |
| Q | 078M | 0.865 | 1.107 | -2.119 | 0.802 | 1.110 | 1.122 | 1.058 | 0.781 | 1.035 | 0.00 | 0.00 | 0.00 | 0.00 | 0.00 |
| Q | 078N | 1.020 | 0.917 | 0.609 | 1.091 | 0.918 | 0.923 | 0.901 | 0.854 | 0.915 | 0.97 | 0.99 | 0.79 | 0.63 | 0.97 |
| Q | 078P | 1.018 | 0.857 | 0.210 | 1.000 | 0.910 | 0.828 | 0.839 | 0.906 | 0.885 | 1.09 | 1.14 | 1.11 | 1.13 | 1.43 |
| Q | 078R | 1.031 | 0.886 | 0.478 | 1.010 | 0.898 | 0.903 | 0.902 | 0.980 | 0.877 | 1.03 | 1.08 | 0.79 | 1.39 | 1.43 |
| Q | 078S | 0.85 | ND | ND | ND | ND | ND | 1.22 | ND | 1.17 | 1.16 | 1.28 | 0.99 | 1.04 | 1.36 |
| Q | 078T | 0.824 | 1.070 | 0.590 | 0.685 | 1.097 | 1.011 | 1.020 | 1.017 | 1.018 | 1.13 | 1.13 | 1.04 | 1.16 | 1.07 |
| Q | 078V | 0.961 | 0.850 | 0.942 | 0.837 | 0.955 | 0.905 | 0.939 | 0.848 | 0.940 | 1.02 | 1.01 | 0.83 | 0.89 | 1.07 |
| Q | 078W | 0.737 | 1.120 | 1.189 | 0.590 | 1.234 | 1.141 | 1.144 | 1.004 | 1.100 | 1.02 | 0.98 | 1.08 | 1.05 | 1.30 |
| Q | 078Y | 0.934 | 0.929 | 1.364 | 0.894 | 1.041 | 0.999 | 0.978 | 0.734 | 0.970 | 1.05 | 1.00 | 1.14 | 1.03 | 1.28 |
| A | 085C | -0.162 | -4.349 | -3.778 | -0.049 | -2.063 | -0.742 | -1.015 | -1.033 | -1.449 | 0.00 | 0.00 | 0.00 | 0.00 | 0.00 |
| A | 085D | 1.042 | 0.917 | 0.685 | 1.011 | 0.866 | 0.880 | 0.893 | 0.888 | 0.898 | 1.04 | 1.07 | 0.85 | 0.98 | 1.15 |
| A | 085E | 1.085 | 0.859 | 1.135 | 1.054 | 0.864 | 0.859 | 0.863 | 0.863 | 0.885 | 1.11 | 1.11 | 1.06 | 1.02 | 1.32 |
| A | 085F | 0.879 | 1.090 | 0.715 | 0.708 | 1.010 | 0.967 | 0.973 | 1.051 | 0.988 | 1.03 | 1.14 | 1.13 | 0.94 | 1.28 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| A | 085G | 0.957 | 0.916 | 0.546 | 0.777 | 0.943 | 0.902 | 0.938 | 0.971 | 0.937 | 1.17 | 1.37 | 1.17 | 1.13 | 1.26 |
| A | 085I | 0.959 | 0.990 | 1.103 | 0.826 | 0.961 | 0.936 | 0.951 | 0.912 | 0.938 | 1.08 | 1.16 | 1.15 | 1.03 | 0.89 |
| A | 085K | 0.978 | 0.963 | 0.174 | 0.879 | 1.006 | 0.974 | 0.979 | 0.847 | 0.970 | 1.29 | 1.36 | 1.48 | 1.49 | 1.73 |
| A | 085L | 0.991 | 0.907 | 1.186 | 0.943 | 0.933 | 0.985 | 0.961 | 0.665 | 0.979 | 1.01 | 0.97 | 0.97 | 1.04 | 1.10 |
| A | 085M | 0.915 | 1.098 | 0.411 | 1.029 | 1.057 | 1.076 | 0.995 | 0.734 | 0.972 | 1.04 | 0.91 | 0.80 | 0.86 | 0.85 |
| A | 085N | 1.044 | 0.931 | 1.187 | 1.093 | 0.834 | 0.867 | 0.848 | 0.776 | 0.872 | 1.05 | 1.00 | 0.86 | 0.85 | 0.96 |
| A | 085P | −0.104 | −2.601 | 1.113 | −0.019 | −1.264 | −0.162 | −0.588 | −0.649 | −1.289 | 0.00 | 0.00 | 0.00 | 0.00 | 0.00 |
| A | 085R | 1.009 | 0.938 | 0.535 | 0.874 | 0.893 | 0.869 | 0.880 | 0.882 | 0.871 | 0.97 | 1.10 | 1.13 | 1.04 | 1.01 |
| A | 085S | 0.827 | 1.126 | 1.307 | 0.779 | 1.162 | 1.125 | 1.157 | 1.142 | 1.130 | 1.04 | 1.15 | 1.05 | 1.01 | 1.10 |
| A | 085T | 0.962 | 0.941 | 0.787 | 0.811 | 0.985 | 0.937 | 0.971 | 0.949 | 0.961 | 1.23 | 1.34 | 1.18 | 0.84 | 1.37 |
| A | 085V | 0.914 | 0.920 | 0.823 | 0.821 | 1.046 | 1.006 | 1.019 | 0.959 | 1.008 | 1.37 | 1.56 | 1.21 | 1.23 | 1.34 |
| A | 085W | 0.797 | 1.055 | −0.103 | 0.592 | 1.037 | 0.980 | 1.009 | 0.838 | 0.990 | 1.12 | 1.18 | 1.04 | 1.26 | 1.07 |
| E | 088A | 0.976 | 0.963 | 0.576 | 1.195 | 1.059 | 0.980 | 0.913 | 0.568 | 0.906 | 0.85 | 0.58 | 1.03 | 0.89 | 0.89 |
| E | 088C | 0.093 | 4.647 | 21.612 | 0.037 | 4.602 | 1.950 | 2.285 | 1.887 | 2.813 | 1.04 | 0.92 | 1.80 | 1.04 | 0.11 |
| E | 088D | 1.029 | 0.974 | 3.280 | 1.316 | 1.036 | 1.016 | 0.975 | 0.793 | 0.960 | 0.96 | 0.86 | 1.16 | 1.04 | 0.87 |
| E | 088F | 0.199 | 3.325 | 9.980 | 0.097 | 3.335 | 2.036 | 1.997 | 1.715 | 2.180 | 0.95 | 0.87 | 1.36 | 1.26 | 0.93 |
| E | 088G | 1.046 | 0.940 | 1.226 | 1.051 | 0.986 | 0.931 | 0.892 | 0.772 | 0.895 | 1.03 | 0.92 | 1.43 | 1.14 | 1.05 |
| E | 088H | 0.955 | 1.097 | −2.087 | 0.994 | 1.102 | 1.098 | 1.016 | 0.904 | 1.062 | 1.02 | 0.99 | 1.20 | 1.05 | 0.98 |
| E | 088I | 0.058 | 7.221 | −5.435 | 0.020 | 8.589 | 4.107 | 4.389 | 3.839 | 5.304 | 0.93 | 0.93 | 0.84 | 0.49 | 1.45 |
| E | 088K | 0.863 | 1.105 | 1.167 | 1.060 | 1.199 | 1.296 | 1.224 | 1.055 | 1.221 | 0.94 | 0.82 | 0.99 | 1.16 | 0.78 |
| E | 088L | 0.308 | 1.523 | 6.865 | 0.177 | 2.208 | 1.457 | 1.436 | 1.119 | 1.592 | 0.90 | 0.42 | 0.72 | 0.98 | 1.18 |
| E | 088M | 0.492 | 1.562 | 1.768 | 0.363 | 1.525 | 1.148 | 1.125 | 0.839 | 1.161 | 0.89 | 0.60 | 0.84 | 0.80 | 0.72 |
| E | 088N | 0.855 | 1.058 | −1.946 | 0.975 | 1.116 | 1.089 | 1.093 | 0.980 | 1.077 | 0.99 | 0.93 | 0.80 | 1.04 | 0.84 |
| E | 088Q | 0.916 | 1.100 | −1.181 | 0.964 | 1.024 | 1.004 | 1.024 | 1.032 | 1.001 | 0.99 | 0.99 | 1.35 | 1.35 | 1.00 |
| E | 088R | 0.859 | 1.079 | 2.863 | 0.874 | 1.093 | 1.075 | 1.051 | 1.077 | 1.057 | 1.02 | 1.08 | 1.27 | 1.04 | 0.92 |
| E | 088S | 0.906 | 1.024 | 0.539 | 0.872 | 1.069 | 0.987 | 0.986 | 0.996 | 0.983 | 1.05 | 1.08 | 1.50 | 0.98 | 1.11 |
| E | 088T | 0.591 | 1.403 | −0.470 | 0.429 | 1.471 | 1.191 | 1.195 | 1.186 | 1.216 | 1.05 | 1.01 | 1.35 | 1.07 | 1.13 |
| E | 088V | 0.210 | 2.470 | 11.028 | 0.086 | 2.628 | 1.538 | 1.568 | 1.568 | 1.834 | 1.15 | 1.08 | 0.97 | 0.85 | 1.22 |
| E | 088W | 0.162 | 3.203 | 2.406 | 0.076 | 4.055 | 2.678 | 2.751 | 2.406 | 2.907 | 1.03 | 0.90 | 0.93 | 1.22 | 0.32 |
| E | 088Y | 0.589 | 1.123 | −0.491 | 0.430 | 1.465 | 1.167 | 1.125 | 0.869 | 1.173 | 0.99 | 0.93 | 1.07 | 0.92 | 1.10 |
| E | 089A | 1.049 | 0.969 | 3.732 | 1.357 | 0.995 | 1.026 | 0.904 | 0.695 | 0.914 | 0.90 | 0.81 | 0.68 | 0.91 | 0.95 |
| E | 089C | 0.093 | 4.071 | −0.102 | 0.031 | 3.645 | 1.362 | 1.787 | 1.738 | 2.475 | 1.44 | 1.39 | 0.63 | 2.37 | 1.80 |
| E | 089D | 1.057 | 0.904 | 12.307 | 1.115 | 0.911 | 0.898 | 0.879 | 0.872 | 0.895 | 1.00 | 0.97 | 0.86 | 0.70 | 1.00 |
| E | 089F | 1.466 | 0.793 | 1.295 | 2.080 | 0.828 | 0.898 | 0.865 | 0.804 | 0.901 | 1.03 | 1.02 | 0.91 | 0.85 | 1.05 |
| E | 089G | 0.958 | 1.044 | 3.659 | 0.926 | 1.039 | 1.031 | 1.008 | 1.056 | 1.032 | 1.15 | 1.14 | 1.17 | 1.27 | 1.44 |
| E | 089H | 0.934 | 1.105 | 0.817 | 1.025 | 1.028 | 1.080 | 1.000 | 0.733 | 1.006 | 1.08 | 1.06 | 0.96 | 1.08 | 1.03 |
| E | 089I | 0.943 | 0.869 | 1.707 | 0.833 | 0.984 | 0.953 | 0.988 | 0.927 | 0.970 | 0.90 | 0.87 | 0.95 | 1.05 | 1.10 |
| E | 089K | 1.047 | 1.092 | 0.362 | 1.213 | 1.093 | 1.070 | 0.958 | 0.648 | 0.984 | 1.02 | 0.96 | 0.84 | 0.97 | 1.17 |
| E | 089L | 0.985 | 0.934 | −2.221 | 1.009 | 1.026 | 1.008 | 0.974 | 0.746 | 0.989 | 0.97 | 0.91 | 0.81 | 0.91 | 0.92 |
| E | 089M | 0.918 | 1.064 | −4.017 | 1.061 | 1.065 | 1.063 | 0.946 | 0.732 | 0.951 | 0.98 | 0.87 | 0.89 | 1.12 | 1.01 |
| E | 089N | 0.955 | 0.942 | −5.043 | 1.004 | 0.966 | 0.970 | 0.942 | 0.870 | 0.929 | 1.10 | 1.06 | 1.36 | 1.16 | 1.07 |
| E | 089P | 0.668 | 1.216 | −1.348 | 0.472 | 1.234 | 0.980 | 0.985 | 1.009 | 1.011 | 1.13 | 1.20 | 1.51 | 1.02 | 1.46 |
| E | 089Q | 1.065 | 0.902 | 1.644 | 1.031 | 0.909 | 0.908 | 0.934 | 0.957 | 0.908 | 0.99 | 1.05 | 1.14 | 1.15 | 1.44 |
| E | 089R | 0.955 | 1.044 | 0.294 | 0.904 | 0.993 | 0.994 | 0.971 | 1.075 | 0.977 | 1.01 | 1.06 | 0.87 | 0.89 | 1.54 |
| E | 089S | 1.153 | 0.822 | −4.796 | 1.217 | 0.826 | 0.895 | 0.903 | 0.995 | 0.934 | 1.06 | 1.06 | 1.19 | 1.16 | 1.14 |
| E | 089T | 0.984 | 0.981 | −0.682 | 0.918 | 0.966 | 0.932 | 0.952 | 1.000 | 0.971 | 1.09 | 1.10 | 1.17 | 1.12 | 1.02 |
| E | 089V | 0.886 | 1.103 | 0.727 | 0.811 | 1.017 | 0.945 | 0.921 | 0.823 | 0.939 | 1.10 | 1.10 | 1.22 | 1.04 | 1.10 |
| E | 089W | 0.656 | 1.112 | −6.188 | 0.477 | 1.306 | 1.129 | 1.114 | 1.018 | 1.127 | 1.05 | 0.99 | 1.45 | 1.26 | 1.33 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| E | 089Y | 0.963 | 0.971 | −5.869 | 1.019 | 1.050 | 1.065 | 1.027 | 0.783 | 1.015 | 1.00 | 0.81 | 0.87 | 1.09 | 1.02 |
| Y | 090C | 0.032 | 14.049 | −8.339 | 0.008 | 9.369 | 3.291 | 4.556 | 4.189 | 6.507 | 1.52 | 1.38 | 1.48 | 1.34 | 0.59 |
| Y | 090D | 0.405 | 1.914 | 0.376 | 0.200 | 1.592 | 1.179 | 1.178 | 1.105 | 1.250 | 1.01 | 1.06 | 0.86 | 0.91 | 1.23 |
| Y | 090E | 0.849 | 1.147 | 0.037 | 0.761 | 1.073 | 1.059 | 1.061 | 0.973 | 1.056 | 0.94 | 1.01 | 0.87 | 0.89 | 0.99 |
| Y | 090F | 0.873 | 1.066 | 0.314 | 0.810 | 1.050 | 1.046 | 1.045 | 0.969 | 1.033 | 1.05 | 1.14 | 0.80 | 0.87 | 1.10 |
| Y | 090G | 0.381 | 1.603 | −0.906 | 0.205 | 1.945 | 1.404 | 1.385 | 1.323 | 1.483 | 0.98 | 1.06 | 0.88 | 0.90 | 0.90 |
| Y | 090H | 1.001 | 0.885 | −0.381 | 0.934 | 0.950 | 0.944 | 0.930 | 0.852 | 0.905 | 1.05 | 1.06 | 1.18 | 0.82 | 1.21 |
| Y | 090I | 0.619 | 1.271 | 0.275 | 0.429 | 1.369 | 1.202 | 1.168 | 1.010 | 1.206 | 1.46 | 1.65 | 1.36 | 1.39 | 1.84 |
| Y | 090K | 0.788 | 1.019 | 0.470 | 0.607 | 1.109 | 0.994 | 0.991 | 0.758 | 1.011 | 1.03 | 1.03 | 1.15 | 1.01 | 1.10 |
| Y | 090L | 0.966 | 0.870 | 0.204 | 0.797 | 0.967 | 0.900 | 0.932 | 0.603 | 0.925 | 0.94 | 0.97 | 0.77 | 1.09 | 1.09 |
| Y | 090M | 0.892 | 0.964 | 0.578 | 0.752 | 0.943 | 0.737 | 0.679 | 0.455 | 0.739 | 1.12 | 0.92 | 0.66 | 1.04 | 0.91 |
| Y | 090N | 1.207 | 0.824 | 0.182 | 1.222 | 0.853 | 0.864 | 0.788 | 0.544 | 0.797 | 1.32 | 1.12 | 1.13 | 1.17 | 1.33 |
| Y | 090P | −0.094 | −5.140 | −2.694 | −0.018 | −2.312 | −0.454 | −0.975 | −0.887 | −1.716 | 0.00 | 0.00 | 0.00 | 0.00 | 0.00 |
| Y | 090Q | 0.977 | 1.020 | 0.407 | 0.939 | 1.000 | 1.002 | 0.954 | 0.715 | 0.956 | 1.01 | 0.97 | 0.83 | 0.87 | 0.98 |
| Y | 090R | 0.91 | ND | ND | ND | ND | ND | 1.01 | ND | 1.03 | ND | 1.01 | 1.11 | 0.99 | 1.22 |
| Y | 090S | 0.738 | 1.180 | 0.464 | 0.615 | 1.324 | 1.168 | 1.160 | 0.882 | 1.148 | 0.99 | 0.98 | 1.08 | 0.97 | 1.11 |
| Y | 090T | 0.603 | 1.238 | 1.043 | 0.385 | 1.384 | 1.053 | 0.998 | 0.780 | 1.039 | 1.07 | 1.04 | 1.10 | 0.99 | 1.07 |
| Y | 090V | 0.875 | 1.034 | 0.347 | 0.795 | 1.168 | 1.118 | 1.037 | 0.729 | 1.066 | 1.07 | 1.07 | 0.81 | 1.03 | 1.47 |
| Y | 090W | 0.974 | 0.995 | 0.464 | 1.041 | 1.073 | 1.058 | 1.053 | 0.723 | 1.049 | 1.11 | 1.05 | 1.10 | 1.07 | 1.06 |
| G | 091A | 0.455 | 1.286 | 2.960 | 0.256 | 1.549 | 1.219 | 1.219 | 1.249 | 1.271 | 1.03 | 0.97 | 0.55 | 0.75 | 1.03 |
| G | 091C | 0.127 | 4.442 | −0.381 | 0.031 | 2.254 | 0.608 | 0.968 | 1.035 | 1.454 | 0.98 | 0.93 | −0.25 | 0.46 | 0.28 |
| G | 091D | 1.010 | 0.928 | −0.501 | 0.923 | 0.929 | 0.900 | 0.916 | 0.942 | 0.910 | 1.04 | 1.05 | 1.01 | 0.81 | 1.43 |
| G | 091E | 0.664 | 1.495 | −0.712 | 0.551 | 1.348 | 1.212 | 1.199 | 1.329 | 1.325 | −0.46 | −1.10 | 0.99 | 0.89 | 1.41 |
| G | 091F | 0.204 | 2.476 | 5.068 | 0.054 | 1.706 | 0.630 | 0.796 | 0.919 | 1.053 | 1.08 | 1.09 | −0.11 | 0.41 | 0.59 |
| G | 091H | 0.900 | 0.872 | 0.874 | 0.694 | 0.995 | 0.947 | 0.956 | 0.957 | 0.961 | 1.06 | 1.05 | 0.92 | 0.80 | 1.15 |
| G | 091I | −0.107 | −3.178 | −8.150 | −0.019 | −1.227 | −0.213 | −0.565 | −0.666 | −1.152 | ND | ND | ND | ND | 1.36 |
| G | 091K | 0.993 | 0.881 | 0.586 | 0.914 | 0.943 | 0.947 | 0.944 | 0.834 | 0.929 | 1.08 | 0.97 | 0.94 | 0.81 | −0.32 |
| G | 091L | 0.057 | 7.789 | 26.228 | 0.016 | 6.631 | 2.437 | 2.966 | 2.530 | 3.875 | 1.01 | 0.88 | −0.10 | 1.20 | 1.09 |
| G | 091M | 0.297 | 2.109 | −0.622 | 0.136 | 1.951 | 1.098 | 1.151 | 0.914 | 1.254 | 1.03 | 0.94 | 0.58 | 0.68 | 1.09 |
| G | 091N | 0.954 | 0.985 | 1.056 | 0.855 | 0.947 | 0.917 | 0.892 | 0.862 | 0.899 | 1.14 | 1.12 | 0.98 | 0.78 | 1.05 |
| G | 091P | 0.043 | 11.710 | −8.795 | 0.011 | 7.266 | 2.440 | 3.468 | 3.812 | 4.723 | 1.03 | 1.09 | 0.84 | −0.05 | 2.02 |
| G | 091Q | 0.95 | ND | ND | ND | ND | ND | 0.99 | ND | 1.01 | 0.99 | 1.04 | 0.85 | 0.88 | 1.35 |
| G | 091R | 0.817 | 0.946 | −0.011 | 0.522 | 0.982 | 0.812 | 0.814 | 0.918 | 0.878 | 0.91 | 1.01 | 0.74 | 0.51 | 1.09 |
| G | 091S | 0.718 | 1.223 | 1.109 | 0.451 | 1.151 | 1.024 | 0.996 | 1.101 | 1.040 | 1.13 | 1.18 | 0.72 | 0.98 | 1.04 |
| G | 091T | 0.378 | 1.833 | 2.860 | 0.169 | 1.664 | 1.098 | 1.116 | 1.163 | 1.220 | 1.10 | 1.16 | 0.59 | 0.80 | 1.00 |
| G | 091V | −0.016 | −9.815 | −54.188 | −0.005 | −18.791 | −5.202 | −8.460 | −8.256 | −12.470 | 0.00 | 0.00 | 0.00 | 0.00 | 0.00 |
| G | 091W | −0.057 | −5.907 | −17.862 | −0.012 | −5.049 | −1.546 | −2.347 | −2.257 | −3.228 | 1.60 | 1.52 | 0.05 | 0.99 | 2.26 |
| G | 091Y | 0.315 | 1.846 | 2.404 | 0.131 | 1.832 | 1.066 | 1.052 | 0.811 | 1.169 | 1.10 | 0.97 | 0.71 | 0.72 | 0.47 |
| D | 106A | 0.115 | 3.640 | 4.532 | 0.040 | 3.678 | 1.285 | 1.463 | 0.809 | 1.727 | 1.04 | 0.28 | 0.10 | 1.94 | 0.41 |
| D | 106C | 0.199 | 2.828 | −3.322 | 0.086 | 2.624 | 1.530 | 1.317 | 0.863 | 1.375 | 1.18 | 0.66 | 0.37 | 1.19 | 0.54 |
| D | 106E | 0.549 | 1.486 | 1.936 | 0.339 | 1.418 | 1.169 | 1.052 | 0.889 | 1.042 | 0.94 | 0.71 | 0.86 | 0.87 | 0.87 |
| D | 106F | 0.280 | 1.656 | −0.195 | 0.112 | 2.142 | 1.147 | 0.902 | 0.777 | 0.871 | 1.21 | 0.64 | 0.59 | 1.26 | 1.01 |
| D | 106G | −0.215 | 1.868 | 6.826 | −0.040 | −0.464 | −0.073 | −0.240 | −0.269 | −0.588 | 0.00 | 0.00 | 0.00 | 0.00 | 0.00 |
| D | 106H | 0.263 | 2.362 | 1.152 | 0.111 | 2.353 | 1.492 | 1.452 | 1.096 | 1.107 | 0.95 | 0.56 | 0.66 | 1.71 | 0.67 |
| D | 106I | −0.025 | −18.563 | −35.554 | −0.006 | −15.916 | −4.625 | −5.328 | −4.324 | −7.010 | 1.50 | 0.62 | 0.45 | 1.97 | 1.23 |
| D | 106K | −0.089 | −0.784 | −20.947 | −0.017 | −3.051 | −0.548 | −0.964 | −0.831 | −1.762 | 1.51 | 0.29 | 0.66 | 2.58 | 0.74 |
| D | 106L | −0.102 | −2.118 | 1.213 | −0.021 | −3.004 | −0.609 | −0.930 | −0.748 | −1.614 | 1.13 | 0.32 | 0.51 | 1.52 | 0.52 |
| D | 106M | −0.002 | −303.363 | −1025.447 | 0.000 | −298.463 | −86.670 | −105.331 | −60.532 | −147.260 | 0.99 | 0.23 | 0.03 | 1.64 | 0.21 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| D | 106N | 0.252 | 2.091 | 5.395 | 0.119 | 2.429 | 1.217 | 1.103 | 0.547 | 1.075 | 1.15 | 0.43 | 0.62 | 1.46 | 0.75 |
| D | 106P | -0.189 | 1.198 | 1.869 | -0.038 | -0.421 | -0.029 | -0.293 | -0.316 | -0.701 | 0.00 | 0.00 | 0.00 | 0.00 | 0.00 |
| D | 106Q | 0.166 | 3.707 | 4.430 | 0.060 | 3.260 | 1.477 | 1.416 | 0.810 | 1.490 | 1.05 | 0.36 | 0.55 | 1.51 | 0.70 |
| D | 106R | -0.190 | 1.024 | -5.923 | -0.033 | -0.698 | -0.063 | -0.308 | -0.319 | -0.691 | 1.90 | 0.26 | 0.77 | 2.58 | 1.22 |
| D | 106S | 0.145 | 4.131 | -3.202 | 0.050 | 3.935 | 1.978 | 1.861 | 1.020 | 1.940 | 1.09 | 0.40 | 0.38 | 1.51 | 0.11 |
| D | 106T | 0.069 | 7.413 | -3.553 | 0.024 | 7.407 | 3.311 | 3.223 | 1.839 | 3.230 | 1.07 | 0.38 | 0.50 | 1.21 | 0.40 |
| D | 106V | 0.056 | 6.797 | -0.739 | 0.017 | 8.694 | 2.987 | 2.979 | 1.900 | 3.277 | 1.16 | 0.43 | 0.45 | 1.22 | 0.55 |
| D | 106W | 0.122 | 3.028 | 12.008 | 0.041 | 4.476 | 2.246 | 2.074 | 1.309 | 2.068 | 0.78 | 0.34 | 0.97 | 1.49 | 1.09 |
| D | 106Y | 0.145 | 3.229 | 7.360 | 0.050 | 3.540 | 1.949 | 1.692 | 1.363 | 1.734 | 0.90 | 0.49 | 0.69 | 1.52 | 0.87 |
| Y | 107A | 0.654 | 1.316 | -8.392 | 0.570 | 1.297 | 1.095 | 1.051 | 0.656 | 1.035 | 1.03 | 0.51 | 0.80 | 1.25 | 0.53 |
| Y | 107C | 0.696 | 1.129 | -24.298 | 0.485 | 1.102 | 0.876 | 0.966 | 0.658 | 0.813 | 1.18 | 0.75 | 0.48 | 1.12 | 1.62 |
| Y | 107E | 0.645 | 1.086 | -29.942 | 0.415 | 1.218 | 1.036 | 1.104 | 0.766 | 1.056 | 1.24 | 0.52 | 0.60 | 1.30 | 2.16 |
| Y | 107F | 0.942 | 0.979 | -0.749 | 0.799 | 0.959 | 0.926 | 0.911 | 0.913 | 0.883 | 1.05 | 1.01 | 0.91 | 1.18 | 1.72 |
| Y | 107G | 0.449 | 1.058 | -27.956 | 0.202 | 1.453 | 0.899 | 0.975 | 0.681 | 0.976 | 1.04 | 0.41 | 0.54 | 1.27 | 0.41 |
| Y | 107H | 0.810 | 0.978 | -2.520 | 0.598 | 1.069 | 0.924 | 0.982 | 0.861 | 0.925 | 0.98 | 0.70 | 0.84 | 1.13 | 2.15 |
| Y | 107I | 0.781 | 0.861 | 1.639 | 0.594 | 1.114 | 0.939 | 1.021 | 0.803 | 0.914 | 1.10 | 0.68 | 0.63 | 1.38 | 1.41 |
| Y | 107K | 0.658 | 0.869 | 2.526 | 0.378 | 1.148 | 0.879 | 0.915 | 0.588 | 0.806 | 1.16 | 0.52 | 0.72 | 1.94 | 1.21 |
| Y | 107L | 0.777 | 1.070 | -10.855 | 0.667 | 1.222 | 1.087 | 1.141 | 0.597 | 0.940 | 1.05 | 0.33 | 0.71 | 1.37 | 0.94 |
| Y | 107M | 0.757 | 1.202 | -10.920 | 0.688 | 1.096 | 0.968 | 0.982 | 0.468 | 0.817 | 1.07 | 0.47 | 0.65 | 1.21 | 1.02 |
| Y | 107N | 0.209 | 3.030 | 3.449 | 0.100 | 3.119 | 1.816 | 1.835 | 0.661 | 2.095 | 1.08 | 0.34 | 0.58 | 1.24 | 1.62 |
| Y | 107P | 0.434 | 1.273 | -35.190 | 0.250 | 1.622 | 1.179 | 1.200 | 0.919 | 1.239 | 1.05 | 0.62 | 0.74 | 1.34 | 1.04 |
| Y | 107Q | 0.524 | 1.326 | -66.212 | 0.274 | 1.324 | 0.942 | 1.039 | 0.771 | 1.029 | 1.04 | 0.54 | 0.63 | 1.39 | 1.56 |
| Y | 107R | 0.465 | 1.241 | -80.443 | 0.217 | 1.499 | 0.960 | 1.059 | 0.835 | 0.978 | 1.10 | 0.58 | 0.56 | 1.37 | 2.68 |
| Y | 107S | 0.447 | 1.327 | -7.253 | 0.243 | 1.604 | 1.161 | 1.225 | 0.951 | 1.217 | 1.11 | 0.55 | 0.67 | 1.02 | 0.48 |
| Y | 107T | 0.315 | 1.806 | -28.799 | 0.132 | 1.950 | 1.007 | 1.228 | 0.645 | 1.025 | 1.29 | 0.24 | 0.44 | 0.89 | 1.44 |
| Y | 107W | 0.457 | 1.563 | 0.190 | 0.254 | 1.540 | 1.098 | 1.156 | 0.562 | 1.106 | 1.15 | 0.46 | 0.48 | 1.45 | 1.20 |
| Y | 107V | 0.794 | 1.157 | -0.321 | 0.698 | 1.137 | 1.110 | 1.179 | 0.981 | 1.081 | 1.04 | 0.89 | 0.80 | 0.88 | 2.52 |
| A | 108C | 0.753 | 1.149 | -0.711 | 0.613 | 1.076 | 1.034 | 0.945 | 0.775 | 0.958 | 0.98 | 0.94 | 1.44 | 0.82 | 0.90 |
| A | 108D | 1.100 | 0.903 | -4.165 | 1.178 | 0.875 | 0.964 | 0.917 | 0.838 | 0.947 | 0.97 | 1.01 | 1.44 | 0.63 | 0.74 |
| A | 108E | 0.939 | 1.076 | 1.430 | 0.937 | 1.044 | 1.089 | 1.082 | 1.029 | 1.091 | 1.02 | 1.06 | 1.60 | 0.62 | 0.80 |
| A | 108F | 0.947 | 0.833 | 1.109 | 0.801 | 0.935 | 0.828 | 0.791 | 0.822 | 0.789 | 1.01 | 0.96 | 1.24 | 0.91 | 1.19 |
| A | 108G | 1.006 | 1.015 | 2.464 | 0.982 | 0.995 | 0.989 | 0.993 | 0.953 | 0.992 | 1.00 | 1.00 | 1.47 | 0.97 | 0.86 |
| A | 108H | 0.895 | 1.106 | 0.718 | 0.762 | 1.046 | 1.014 | 1.010 | 0.932 | 0.969 | 0.96 | 0.95 | 1.27 | 0.96 | 0.84 |
| A | 108I | 0.701 | 1.098 | -4.830 | 0.462 | 1.161 | 0.995 | 0.970 | 0.847 | 0.966 | 1.04 | 0.92 | 1.42 | 1.01 | 0.87 |
| A | 108K | 0.851 | 1.044 | 2.289 | 0.683 | 1.097 | 1.077 | 1.062 | 0.819 | 0.973 | 1.04 | 0.91 | 1.24 | 1.32 | 0.99 |
| A | 108L | 0.855 | 1.018 | 4.034 | 0.774 | 1.145 | 1.103 | 1.007 | 0.687 | 1.000 | 1.07 | 1.05 | 1.61 | 1.15 | 1.36 |
| A | 108N | 1.309 | 0.800 | 2.432 | 2.085 | 0.913 | 1.080 | 1.007 | 0.725 | 0.986 | 0.87 | 0.78 | 0.98 | 0.92 | 0.94 |
| A | 108P | 0.684 | 1.191 | 0.887 | 0.565 | 1.333 | 1.082 | 0.913 | 0.562 | 0.820 | 0.96 | 0.72 | 1.13 | 0.99 | 0.52 |
| A | 108Q | 0.019 | 10.530 | -44.707 | 0.004 | 5.428 | 0.621 | 2.742 | 3.003 | 6.436 | 0.00 | 0.00 | 0.00 | 0.00 | 0.00 |
| A | 108R | 0.924 | 1.057 | 5.096 | 0.848 | 1.073 | 1.007 | 0.966 | 0.694 | 0.920 | 0.97 | 0.76 | 1.22 | 1.37 | 1.51 |
| A | 108S | 1.041 | 1.011 | -5.026 | 1.053 | 1.025 | 1.037 | 1.024 | 0.781 | 0.996 | 1.02 | 0.93 | 1.46 | 0.80 | 0.86 |
| A | 108T | 0.858 | 1.119 | 5.825 | 0.794 | 1.144 | 1.118 | 1.057 | 0.765 | 1.060 | 1.01 | 0.85 | 1.60 | 0.98 | 0.78 |
| A | 108V | 0.769 | 1.092 | 3.482 | 0.628 | 1.226 | 1.105 | 1.028 | 0.715 | 1.028 | 0.99 | 0.87 | 1.15 | 0.88 | 0.76 |
| A | 108W | 0.836 | 1.111 | 0.313 | 0.814 | 1.194 | 1.092 | 1.036 | 0.692 | 1.017 | 1.04 | 0.89 | 1.15 | 1.26 | 1.33 |
| A | 108Y | 0.967 | 0.997 | 0.188 | 1.132 | 1.092 | 1.105 | 1.030 | 0.647 | 1.021 | 0.97 | 0.69 | 1.71 | 1.01 | 1.01 |
| A | 109C | 0.685 | 1.130 | -1.715 | 0.496 | 1.124 | 0.970 | 0.918 | 0.844 | 0.953 | 1.03 | 0.95 | 0.74 | 1.06 | 0.51 |
| A | 109D | 0.639 | 1.414 | 4.750 | 0.503 | 1.237 | 0.924 | 0.829 | 0.633 | 0.876 | 1.04 | 0.58 | 0.63 | 1.21 | 0.27 |
| A | 109E | 0.906 | 1.008 | 8.421 | 0.826 | 0.943 | 0.924 | 0.869 | 0.867 | 0.839 | 0.94 | 0.86 | 0.96 | 0.75 | 0.72 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| A | 109F | 0.506 | 1.175 | −2.023 | 0.220 | 1.218 | 0.851 | 0.819 | 0.818 | 0.935 | 0.91 | 0.80 | 0.79 | 0.91 | 0.51 |
| A | 109G | 0.478 | 1.460 | 0.422 | 0.249 | 1.492 | 1.035 | 1.020 | 0.939 | 0.942 | 1.02 | 0.67 | 0.50 | 1.04 | 0.51 |
| A | 109H | 0.676 | 1.237 | 8.871 | 0.420 | 1.206 | 1.006 | 0.953 | 0.903 | 0.786 | 1.05 | 0.87 | 0.79 | 1.21 | 0.79 |
| A | 109I | 0.607 | 1.381 | 7.576 | 0.408 | 1.353 | 1.064 | 1.018 | 0.857 | 0.891 | 1.08 | 0.69 | 0.75 | 0.88 | 0.86 |
| A | 109K | 0.684 | 1.161 | −1.391 | 0.468 | 1.248 | 1.101 | 1.030 | 0.861 | 0.926 | 1.02 | 0.78 | 0.84 | 1.64 | 0.99 |
| A | 109L | 0.941 | 1.106 | −0.122 | 1.108 | 1.080 | 1.086 | 0.900 | 0.329 | 0.801 | 0.98 | 0.63 | 0.61 | 1.25 | 0.56 |
| A | 109M | 0.834 | 1.027 | −4.844 | 0.850 | 1.108 | 1.083 | 0.987 | 0.619 | 0.898 | 0.88 | 0.70 | 0.63 | 0.80 | 0.64 |
| A | 109N | 0.593 | 1.454 | 4.936 | 0.448 | 1.268 | 0.968 | 0.878 | 0.685 | 0.855 | 0.99 | 0.59 | 0.61 | 1.37 | 0.54 |
| A | 109P | 0.124 | 4.573 | −32.459 | 0.036 | 2.689 | 0.974 | 1.228 | 0.907 | 1.680 | 0.97 | 0.37 | 0.52 | 1.55 | −0.35 |
| A | 109R | 0.697 | 0.970 | 2.758 | 0.416 | 1.124 | 0.889 | 0.857 | 0.816 | 0.819 | 1.00 | 0.80 | 0.57 | 1.51 | 1.06 |
| A | 109S | 0.748 | 1.241 | −3.817 | 0.582 | 1.223 | 1.107 | 1.051 | 1.001 | 1.003 | 1.12 | 0.90 | 0.71 | 1.21 | 1.21 |
| A | 109T | 0.452 | 1.520 | 5.556 | 0.215 | 1.524 | 1.008 | 1.024 | 0.964 | 1.050 | 1.04 | 0.79 | 0.84 | 1.04 | 0.83 |
| A | 109V | 0.649 | 1.051 | 12.524 | 0.435 | 1.275 | 1.082 | 1.092 | 0.979 | 1.055 | 0.96 | 0.81 | 0.90 | 0.88 | 0.77 |
| A | 109W | 0.761 | 1.254 | 0.781 | 0.697 | 1.144 | 1.058 | 0.942 | 0.877 | 1.064 | 0.93 | 0.76 | 1.01 | 0.95 | 0.93 |
| A | 109Y | 0.491 | 1.490 | −0.320 | 0.287 | 1.554 | 1.247 | 1.188 | 0.867 | 1.262 | 0.95 | 0.74 | 1.01 | 1.03 | 0.43 |
| N | 112A | 1.263 | 0.866 | 1.635 | 1.807 | 0.890 | 0.989 | 0.905 | 0.529 | 0.966 | 0.91 | 0.75 | 0.97 | 0.78 | 1.00 |
| N | 112C | 0.744 | 1.140 | 4.014 | 0.697 | 1.181 | 1.043 | 0.969 | 0.746 | 1.045 | 0.95 | 0.94 | 0.87 | 0.72 | 0.84 |
| N | 112D | 0.792 | 1.171 | 0.383 | 1.732 | 0.924 | 1.002 | 1.093 | 1.092 | 0.963 | 0.95 | 0.96 | 0.74 | 0.78 | 0.84 |
| N | 112E | 1.209 | 0.915 | 2.195 | 1.225 | 0.991 | 0.994 | 0.953 | 0.775 | 0.877 | 1.01 | 0.86 | 1.01 | 0.95 | 0.87 |
| N | 112F | 1.046 | 0.987 | 2.932 | 1.106 | 1.119 | 1.086 | 0.930 | 0.802 | 0.915 | 0.98 | 0.91 | 0.96 | 1.09 | 0.98 |
| N | 112G | 0.937 | 1.154 | 2.932 | 1.106 | 1.119 | 1.086 | 1.049 | 0.899 | 1.046 | 0.95 | 0.95 | 0.95 | 0.93 | 1.05 |
| N | 112H | 0.470 | 1.624 | 1.783 | 0.319 | 1.674 | 1.204 | 1.153 | 0.921 | 1.211 | 0.97 | 0.82 | 1.15 | 1.19 | 1.13 |
| N | 112I | 0.954 | 0.902 | −6.207 | 0.617 | 1.142 | 1.081 | 1.093 | 1.092 | 1.083 | 0.99 | 0.96 | 1.08 | 1.04 | 0.94 |
| N | 112K | 1.041 | 0.954 | 2.385 | 1.098 | 1.065 | 1.052 | 0.987 | 0.810 | 1.013 | 1.02 | 0.91 | 1.08 | 1.35 | 1.33 |
| N | 112L | 1.093 | 0.922 | −1.429 | 1.342 | 1.040 | 1.146 | 1.067 | 0.883 | 1.082 | 0.95 | 0.65 | 0.97 | 1.12 | 0.93 |
| N | 112M | 1.179 | 0.871 | 2.980 | 1.503 | 1.000 | 1.096 | 1.042 | 0.827 | 1.038 | 0.98 | 0.46 | 0.86 | 0.93 | 0.95 |
| N | 112P | 0.997 | 0.980 | 0.410 | 1.369 | 0.875 | 0.907 | 0.850 | 0.574 | 0.832 | 0.92 | 0.82 | 0.88 | 0.92 | 1.03 |
| N | 112Q | 1.151 | 0.880 | 2.035 | 1.065 | 0.968 | 0.946 | 0.968 | 0.892 | 0.926 | 0.99 | 0.88 | 0.88 | 0.83 | 0.79 |
| N | 112R | 0.868 | 1.129 | 2.653 | 1.378 | 0.860 | 0.875 | 0.892 | 0.849 | 0.880 | 1.02 | 1.01 | 1.03 | 1.69 | 1.57 |
| N | 112S | 0.963 | 1.034 | 0.375 | 0.786 | 1.089 | 1.028 | 1.034 | 1.001 | 1.036 | 1.00 | 0.95 | 1.09 | 0.90 | 1.20 |
| N | 112T | 1.016 | 0.887 | 1.175 | 0.970 | 1.007 | 0.993 | 1.023 | 0.995 | 0.986 | 1.03 | 0.97 | 0.94 | 0.90 | 1.24 |
| N | 112V | 0.819 | 1.006 | 0.344 | 1.038 | 0.933 | 0.925 | 0.933 | 0.930 | 0.938 | 1.02 | 0.98 | 1.09 | 1.08 | 0.90 |
| N | 112W | 0.958 | 1.010 | 1.532 | 0.759 | 1.118 | 1.060 | 1.041 | 0.972 | 1.032 | 1.01 | 0.93 | 0.95 | 1.19 | 1.26 |
| N | 112Y | 1.028 | 0.813 | 1.499 | 1.089 | 0.978 | 1.024 | 1.044 | 0.909 | 0.942 | 1.05 | 1.02 | 1.00 | 1.17 | 1.26 |
| K | 115A | 0.495 | 1.356 | 0.797 | 1.160 | 0.955 | 0.989 | 0.959 | 0.757 | 0.921 | 1.03 | 0.23 | 1.08 | 0.54 | 0.46 |
| K | 115C | 0.673 | 1.033 | 12.967 | 0.525 | 1.192 | 0.902 | 0.858 | 0.460 | 0.962 | 0.91 | 0.60 | 0.61 | 0.60 | 0.55 |
| K | 115D | 0.348 | 1.784 | −18.345 | 0.195 | 1.827 | 1.181 | 1.122 | 0.774 | 1.272 | 0.95 | 0.61 | 0.54 | 0.73 | −0.05 |
| K | 115E | −0.005 | −84.628 | −235.045 | −0.001 | −73.672 | −21.227 | −31.500 | −23.433 | −47.603 | 0.89 | 0.05 | 0.27 | 0.80 | 0.24 |
| K | 115F | 0.022 | 4.300 | 75.307 | 0.005 | 15.407 | 5.901 | 7.140 | 6.263 | 9.879 | 0.97 | 0.28 | 0.47 | 0.66 | 0.61 |
| K | 115G | 0.334 | 1.438 | 5.175 | 0.150 | 1.817 | 1.067 | 1.050 | 0.848 | 1.169 | 0.91 | 0.71 | 0.96 | 0.69 | 0.05 |
| K | 115H | 0.585 | 1.144 | 0.964 | 0.388 | 1.349 | 1.013 | 1.051 | 0.873 | 1.233 | 1.06 | 0.52 | 0.86 | 0.82 | 0.70 |
| K | 115I | 0.655 | 1.119 | −0.127 | 0.492 | 1.349 | 1.198 | 1.134 | 0.731 | 1.037 | 1.07 | 0.78 | 0.90 | 0.65 | 0.80 |
| K | 115L | 1.005 | 0.787 | 4.499 | 1.238 | 1.026 | 1.117 | 1.035 | 0.930 | 1.230 | 0.99 | 0.97 | 1.10 | 0.63 | 0.66 |
| K | 115M | 0.541 | 1.395 | 26.686 | 0.415 | 1.440 | 1.140 | 1.066 | 0.798 | 1.078 | 0.94 | −0.01 | 1.56 | 0.66 | 0.69 |
| K | 115N | 0.279 | 1.947 | −1.599 | 0.154 | 2.130 | 1.350 | 1.384 | 0.669 | 1.122 | 0.89 | 0.64 | 0.66 | 0.63 | 0.53 |
| K | 115P | −0.152 | −3.385 | 26.234 | −0.040 | −0.637 | −0.047 | −0.373 | −0.377 | 1.599 | 0.97 | 0.71 | 0.39 | 0.00 | 0.00 |
| K | 115Q | 0.410 | 1.047 | 1.379 | 0.221 | 1.686 | 1.224 | 1.142 | 1.121 | 1.256 | 0.00 | 0.00 | 0.00 | ND | ND |
| K | 115R | 0.918 | 0.913 | 9.236 | 0.869 | 1.025 | 0.954 | 0.935 | 0.920 | 0.982 | 0.98 | 0.96 | 1.19 | 0.85 | 0.89 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| K | 115S | 0.427 | 1.543 | −5.161 | 0.241 | 1.613 | 1.116 | 1.129 | 1.075 | 1.257 | 1.03 | 0.80 | 0.84 | 0.60 | 0.18 |
| K | 115T | 0.780 | 1.082 | 2.204 | 0.602 | 1.117 | 1.092 | 1.066 | 1.145 | 1.128 | 1.00 | 1.02 | 0.88 | 0.65 | 0.79 |
| K | 115V | 0.561 | 1.194 | 3.626 | 0.397 | 1.403 | 1.197 | 1.167 | 1.114 | 1.261 | 1.04 | 1.06 | 1.11 | 0.50 | 0.77 |
| K | 115W | 0.281 | 1.474 | 7.048 | 0.130 | 2.174 | 1.346 | 1.296 | 1.019 | 1.439 | 1.07 | 0.58 | 0.72 | 0.79 | 0.77 |
| K | 115Y | 0.295 | 1.748 | 10.584 | 0.149 | 2.046 | 1.342 | 1.301 | 0.886 | 1.456 | 1.10 | 0.37 | 0.88 | 0.41 | 0.33 |
| S | 116A | 0.671 | 1.486 | 0.740 | 0.561 | 1.303 | 1.321 | 1.260 | 0.985 | 1.261 | 0.90 | 0.77 | 0.74 | 0.84 | 0.78 |
| S | 116D | 1.049 | 1.032 | 0.465 | 1.196 | 0.996 | 0.961 | 0.926 | 0.771 | 0.885 | 0.99 | 0.89 | 0.85 | 0.74 | 0.72 |
| S | 116E | 1.061 | 1.005 | 2.804 | 1.278 | 1.000 | 0.998 | 0.966 | 0.875 | 0.903 | 0.78 | 0.66 | 0.82 | 0.66 | 0.84 |
| S | 116F | 1.179 | 0.883 | −0.882 | 1.384 | 0.934 | 0.907 | 0.882 | 0.787 | 0.898 | 1.04 | 0.85 | 1.30 | 1.17 | 0.88 |
| S | 116G | 0.892 | 1.132 | 1.584 | 0.870 | 1.067 | 0.980 | 0.937 | 0.774 | 0.942 | 1.07 | 0.96 | 1.14 | 1.11 | 0.92 |
| S | 116H | 0.705 | 1.162 | 1.187 | 0.517 | 1.168 | 1.050 | 1.029 | 1.024 | 1.057 | 1.09 | 0.88 | 1.28 | 1.10 | 0.85 |
| S | 116I | 0.590 | 1.492 | 0.781 | 0.389 | 1.252 | 1.085 | 1.069 | 0.986 | 1.089 | 1.06 | 0.81 | 1.13 | 0.99 | 1.02 |
| S | 116L | 0.543 | 1.802 | 1.436 | 0.379 | 1.499 | 1.348 | 1.335 | 1.279 | 1.340 | 1.03 | 0.57 | 1.41 | 1.04 | 0.86 |
| S | 116N | 1.110 | 0.918 | 1.359 | 1.167 | 0.889 | 0.861 | 0.852 | 0.736 | 0.830 | 1.06 | 0.89 | 0.67 | 1.14 | 1.17 |
| S | 116P | −0.178 | −0.476 | −0.388 | −0.040 | −0.488 | −0.054 | −0.296 | −0.315 | −0.723 | 0.00 | 0.00 | 0.00 | 0.00 | 0.00 |
| S | 116Q | 0.976 | 1.006 | 0.863 | 1.003 | 0.980 | 0.951 | 0.949 | 0.922 | 0.924 | 1.04 | 0.95 | 0.66 | 1.33 | 1.57 |
| S | 116R | 0.986 | 1.043 | 1.226 | 0.933 | 0.964 | 0.942 | 0.935 | 0.910 | 0.894 | 1.08 | 0.97 | 1.06 | 2.35 | 1.63 |
| S | 116T | 0.927 | 1.090 | 1.680 | 0.839 | 1.048 | 0.981 | 0.979 | 0.960 | 0.992 | 1.08 | 0.97 | 0.75 | 1.12 | 0.90 |
| S | 116V | 0.704 | 1.247 | 3.393 | 0.571 | 1.246 | 1.114 | 1.086 | 0.952 | 1.079 | 1.01 | 0.80 | 0.54 | 1.01 | 0.82 |
| S | 116W | −0.178 | −0.476 | 1.291 | 0.694 | 1.108 | 0.960 | 0.962 | 0.825 | 0.948 | 1.11 | 0.90 | 0.73 | 1.09 | 0.93 |
| S | 116Y | 0.787 | 1.151 | 2.050 | 0.468 | 1.371 | 1.079 | 1.032 | 0.809 | 1.044 | 1.17 | 0.62 | 0.69 | 1.47 | 1.01 |
| S | 118A | 0.614 | 1.266 | 0.111 | 0.926 | 1.013 | 0.922 | 0.867 | 0.628 | 0.797 | 1.00 | 0.79 | 0.74 | 0.94 | 0.73 |
| S | 118C | 0.897 | 0.958 | 0.857 | 0.481 | 1.091 | 0.872 | 0.883 | 0.780 | 0.901 | 1.08 | 0.94 | 0.50 | 1.09 | 0.17 |
| P | 118D | 0.673 | 1.012 | 0.559 | 0.889 | 0.884 | 0.835 | 0.858 | 0.801 | 0.827 | 1.06 | 1.00 | 0.49 | 1.41 | 1.32 |
| P | 118E | 0.971 | 0.912 | 0.597 | 0.806 | 1.014 | 1.019 | 0.915 | 0.593 | 0.923 | 1.01 | 0.96 | 0.74 | 1.09 | 0.58 |
| P | 118F | 0.885 | 0.995 | 1.226 | 0.339 | 1.172 | 0.905 | 0.942 | 0.932 | 0.907 | 1.06 | 1.02 | 0.89 | 1.37 | 1.28 |
| P | 118G | 0.586 | 1.298 | 1.226 | 0.396 | 1.445 | 1.184 | 1.137 | 0.799 | 1.151 | 1.06 | 0.63 | 0.72 | 1.12 | 1.07 |
| P | 118H | 0.746 | 1.047 | 2.202 | 0.554 | 1.124 | 0.977 | 1.035 | 1.086 | 1.019 | 1.06 | 1.14 | 0.87 | 1.15 | 0.77 |
| P | 118I | 0.80 | ND | ND | ND | ND | ND | 1.06 | ND | 1.08 | 1.11 | 1.04 | 0.87 | 1.65 | 1.39 |
| P | 118K | 0.705 | 0.799 | 1.825 | 0.439 | 1.085 | 0.860 | 0.893 | 0.797 | 0.918 | 0.95 | 0.81 | 0.85 | 0.77 | 0.58 |
| P | 118L | 0.878 | 1.006 | 1.192 | 0.717 | 1.045 | 0.985 | 0.993 | 0.829 | 0.982 | 1.05 | 0.90 | 0.73 | 1.76 | 1.22 |
| P | 118M | 0.569 | 1.166 | 1.477 | 0.396 | 1.445 | 1.184 | 1.137 | 0.799 | 1.151 | 1.06 | 0.63 | 0.72 | 1.12 | 1.07 |
| P | 118N | 0.738 | 1.188 | −0.320 | 0.635 | 1.112 | 0.945 | 0.876 | 0.593 | 0.900 | 1.03 | 0.78 | 0.76 | 0.96 | 0.85 |
| P | 118Q | 0.936 | 0.908 | 1.715 | 0.843 | 0.915 | 0.837 | 0.828 | 0.751 | 0.855 | 1.11 | 1.00 | 0.57 | 0.87 | 0.99 |
| P | 118R | 0.713 | 0.953 | 2.913 | 0.626 | 1.236 | 1.112 | 1.050 | 1.016 | 1.057 | 1.12 | 1.05 | 1.00 | 1.32 | 1.18 |
| P | 118S | −0.816 | 0.138 | 0.332 | −0.173 | −0.303 | −1.454 | 0.525 | 0.000 | −0.079 | 1.03 | 1.03 | 1.04 | 2.15 | 1.65 |
| P | 118T | 0.834 | 0.955 | 2.766 | 0.628 | 1.037 | 0.916 | 0.933 | 0.967 | 0.984 | 1.09 | 1.04 | 0.75 | 1.21 | 0.76 |
| P | 118V | 0.743 | 1.028 | −0.346 | 0.523 | 1.125 | 0.965 | 0.988 | 0.971 | 1.033 | 1.12 | 1.04 | 0.76 | 1.28 | 1.26 |
| P | 118W | 0.680 | 1.050 | 0.526 | 0.422 | 1.132 | 0.946 | 0.971 | 0.924 | 0.991 | 1.04 | 0.96 | 0.71 | 0.93 | 0.76 |
| P | 118Y | 0.470 | 1.421 | 2.365 | 0.278 | 1.529 | 1.121 | 1.146 | 0.980 | 1.175 | 1.24 | 1.05 | 0.79 | 1.87 | 1.14 |
| P | 119A | 0.462 | 1.581 | 4.345 | 0.330 | 1.715 | 1.419 | 1.374 | 0.973 | 1.373 | 1.08 | 0.81 | 0.86 | 1.40 | 1.12 |
| N | 119C | 0.971 | 1.035 | 2.398 | 1.122 | 1.034 | 0.964 | 0.917 | 0.526 | 0.721 | 1.06 | 0.57 | 0.71 | 0.86 | 0.84 |
| N | 119D | 0.736 | 1.187 | 2.165 | 0.633 | 1.101 | 0.936 | 0.879 | 0.552 | 0.893 | 1.06 | 0.72 | 0.54 | 0.59 | 0.83 |
| N | 119E | 1.075 | 0.969 | 1.428 | 1.290 | 0.982 | 0.949 | 0.926 | 0.721 | 0.968 | 0.99 | 0.88 | 0.57 | 0.84 | 0.79 |
| N | 119F | 1.056 | 0.956 | 2.344 | 1.180 | 0.953 | 0.898 | 0.860 | 0.669 | 0.865 | 1.02 | 0.79 | 0.57 | 1.12 | 0.82 |
| N | 119G | 0.932 | 1.055 | 3.054 | 0.863 | 1.039 | 0.877 | 0.858 | 0.687 | 0.824 | 1.00 | 0.77 | 0.86 | 1.28 | 1.53 |
| N | 119H | 1.095 | 0.902 | 1.592 | 1.150 | 0.952 | 0.908 | 0.876 | 0.591 | 0.870 | 1.01 | 0.55 | 0.81 | 1.02 | 0.98 |
| N | 119H | 0.064 | 3.434 | 16.228 | 0.010 | 1.075 | 0.099 | 0.626 | 0.783 | 1.787 | 0.00 | 0.00 | 0.00 | 0.00 | 0.00 |
| N | 119I | 0.336 | 1.825 | 4.428 | 0.187 | 2.026 | 1.311 | 1.273 | 0.908 | 1.349 | 1.00 | 0.68 | 0.89 | 1.21 | 0.64 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| N | 119K | 0.848 | 1.015 | 1.578 | 0.794 | 1.110 | 0.996 | 0.959 | 0.700 | 0.916 | 0.97 | 0.31 | 0.81 | 1.35 | 1.12 |
| N | 119L | 0.457 | 1.775 | 0.596 | 0.256 | 1.558 | 1.261 | 1.272 | 1.196 | 1.284 | 0.93 | 0.18 | 0.78 | 1.15 | 0.93 |
| N | 119M | 0.802 | 0.911 | 2.506 | 0.624 | 1.029 | 0.921 | 0.880 | 0.824 | 0.866 | 1.08 | 0.78 | 0.60 | 1.08 | 1.00 |
| N | 119P | −0.146 | 0.640 | −5.060 | −0.025 | −0.531 | −0.054 | −0.355 | −0.416 | −0.231 | 0.00 | 0.00 | 0.00 | 0.00 | 0.00 |
| N | 119Q | 0.752 | 0.935 | 0.768 | 0.563 | 1.027 | 0.805 | 0.832 | 0.771 | 0.839 | 0.95 | 0.85 | 0.72 | 1.20 | 0.80 |
| N | 119R | 0.144 | −3.072 | 7.414 | 0.025 | 0.530 | 0.067 | 0.358 | 0.392 | 0.832 | 0.00 | 0.00 | 0.00 | 0.00 | 0.00 |
| N | 119S | 0.638 | 1.393 | 0.075 | 0.494 | 1.370 | 1.180 | 1.189 | 1.108 | 1.209 | 1.04 | 0.89 | 0.86 | 0.91 | 1.09 |
| N | 119T | 0.552 | 1.180 | −0.248 | 0.322 | 1.303 | 0.949 | 0.942 | 0.828 | 1.007 | 1.15 | 0.88 | 0.88 | 1.10 | 0.84 |
| N | 119V | 0.425 | 1.477 | 1.371 | 0.222 | 1.604 | 1.116 | 1.151 | 0.959 | 1.165 | 1.08 | 0.79 | 0.99 | 0.94 | 0.48 |
| N | 119Y | 0.777 | 1.091 | 2.351 | 0.692 | 1.171 | 1.058 | 1.025 | 0.734 | 0.961 | 1.04 | 0.31 | 1.09 | 1.16 | 1.08 |
| G | 123A | −0.071 | −2.942 | −2.720 | −0.018 | −1.187 | −0.131 | −0.829 | −0.891 | −1.625 | 0.00 | 0.00 | 0.00 | 0.00 | 0.00 |
| G | 123C | −0.130 | −3.480 | −15.671 | −0.031 | −0.774 | −0.071 | −0.448 | −0.465 | −0.990 | 0.00 | 0.00 | 0.00 | 0.00 | 0.00 |
| G | 123D | −0.153 | 2.365 | 0.855 | −0.034 | −0.532 | −0.079 | −0.339 | −0.383 | −0.794 | 0.00 | 0.00 | 0.00 | 0.00 | 0.00 |
| G | 123E | 0.154 | 4.727 | 55.397 | 0.108 | 3.782 | 0.113 | 0.727 | 0.906 | 0.261 | 0.00 | 0.00 | 0.00 | 0.00 | 0.00 |
| G | 123F | −0.182 | 2.381 | −3.176 | −0.039 | −0.489 | −0.061 | −0.299 | −0.362 | −0.689 | 0.00 | 0.00 | 0.00 | 0.00 | 0.00 |
| G | 123H | −0.159 | 1.915 | −1.355 | −0.033 | −0.538 | −0.106 | −0.332 | −0.480 | −0.726 | 0.00 | 0.00 | 0.00 | 0.00 | 0.00 |
| G | 123I | −0.185 | 1.203 | −0.357 | −0.030 | −0.408 | −0.006 | −0.273 | −0.320 | −0.649 | 0.00 | 0.00 | 0.00 | 0.00 | 0.00 |
| G | 123K | −0.210 | −0.323 | −8.398 | −0.041 | −0.404 | −0.034 | −0.198 | −0.260 | −0.538 | 0.00 | 0.00 | 0.00 | 0.00 | 0.00 |
| G | 123L | −0.129 | 0.969 | −25.029 | −0.029 | −0.625 | −0.071 | −0.430 | −0.467 | −0.821 | 0.00 | 0.00 | 0.00 | 0.00 | 0.00 |
| G | 123M | −0.053 | −3.017 | 11.724 | −0.014 | −1.541 | −0.073 | −1.041 | −1.212 | −2.342 | 0.00 | 0.00 | 0.00 | 0.00 | 0.00 |
| G | 123N | −0.156 | −0.577 | −7.882 | −0.037 | −0.645 | −0.060 | −0.370 | −0.451 | −0.791 | 0.00 | 0.00 | 0.00 | 0.00 | 0.00 |
| G | 123P | −0.169 | 2.757 | 4.351 | −0.027 | −0.460 | −0.050 | −0.329 | −0.372 | −0.742 | 0.00 | 0.00 | 0.00 | 0.00 | 0.00 |
| G | 123Q | −0.160 | 2.865 | −3.955 | −0.036 | −0.536 | −0.105 | −0.283 | −0.347 | −0.674 | 0.00 | 0.00 | 0.00 | 0.00 | 0.00 |
| G | 123R | −0.172 | 1.960 | −0.230 | −0.024 | −0.551 | −0.051 | −0.373 | −0.445 | −0.785 | 0.00 | 0.00 | 0.00 | 0.00 | 0.00 |
| G | 123S | −0.143 | 1.984 | −3.092 | −0.031 | −0.841 | −0.123 | −0.416 | −0.370 | −0.800 | 0.00 | 0.00 | 0.00 | 0.00 | 0.00 |
| G | 123W | −0.165 | −0.423 | −4.383 | −0.037 | −0.369 | −0.034 | −0.285 | −0.285 | −0.545 | 0.00 | 0.00 | 0.00 | 0.00 | 0.00 |
| G | 123Y | −0.207 | 1.785 | 2.068 | −0.041 | −0.404 | −0.071 | −0.264 | −0.320 | −0.538 | 0.00 | 0.00 | 0.00 | 0.00 | 0.00 |
| G | 123Y | −0.179 | 0.644 | −6.060 | −0.036 | −0.527 | −0.058 | −0.331 | −0.346 | −0.686 | 0.00 | 0.00 | 0.00 | 0.00 | 0.00 |
| G | 123Y | −0.208 | 0.184 | 4.009 | −0.045 | −0.412 | −0.055 | −0.285 | −0.301 | −0.620 | 0.00 | 0.00 | 0.00 | 0.00 | 0.00 |
| N | 124A | 0.481 | 1.674 | 9.655 | 0.310 | 1.571 | 1.021 | 0.958 | 0.164 | 0.911 | 1.00 | 0.02 | 0.00 | 0.62 | 0.48 |
| N | 124C | 0.175 | 2.762 | 3.912 | 0.078 | 2.944 | 1.531 | 1.427 | 0.400 | 1.364 | 1.02 | 0.02 | 0.09 | 0.99 | 0.53 |
| N | 124D | 0.160 | 2.865 | 2.819 | 0.065 | 3.079 | 1.346 | 1.523 | 0.389 | 1.898 | 1.09 | 0.01 | 0.08 | 0.85 | 0.74 |
| N | 124E | 0.053 | 4.161 | 23.912 | 0.014 | 5.452 | 0.811 | 1.623 | 1.026 | 2.766 | 0.00 | 0.00 | 0.00 | 0.00 | 0.00 |
| N | 124F | −0.093 | −2.882 | 42.663 | −0.024 | −2.942 | −0.638 | −1.051 | −0.593 | −1.611 | 1.09 | 0.04 | −0.49 | 1.91 | 1.33 |
| N | 124G | −0.099 | −2.754 | −7.752 | −0.026 | −2.704 | −0.577 | −1.044 | −0.571 | −1.537 | 1.19 | 0.06 | −0.48 | 1.51 | 2.12 |
| N | 124I | 0.010 | 18.750 | 0.450 | 0.004 | 35.763 | 9.981 | 14.153 | 5.479 | 17.285 | 1.66 | 0.01 | −0.16 | 1.45 | 0.48 |
| N | 124K | 0.292 | 2.115 | 5.281 | 0.130 | 1.999 | 0.980 | 1.051 | 0.224 | 0.784 | 1.41 | 0.00 | 0.03 | 1.45 | 0.52 |
| N | 124L | −0.124 | −1.904 | 5.411 | −0.028 | −1.631 | −0.301 | −0.576 | −0.458 | −1.161 | 0.00 | 0.00 | 0.00 | 0.00 | 0.00 |
| N | 124M | −0.060 | −8.372 | −20.182 | −0.018 | −4.528 | −0.921 | −1.676 | −1.031 | −2.630 | 1.03 | 0.04 | −0.36 | 0.36 | 0.74 |
| N | 124Q | 0.042 | 8.604 | 15.161 | 0.015 | 10.002 | 3.586 | 4.787 | 1.522 | 4.878 | 1.28 | 0.02 | −0.01 | 1.37 | 0.83 |
| N | 124R | 0.176 | 3.118 | 4.585 | 0.073 | 2.920 | 1.254 | 1.419 | 0.409 | 1.091 | 1.46 | 0.01 | 0.00 | 1.97 | 0.79 |
| N | 124S | 0.289 | 2.049 | 1.459 | 0.130 | 2.230 | 1.291 | 1.488 | 0.512 | 1.432 | 1.27 | 0.03 | 0.20 | 1.45 | 0.78 |
| N | 124T | 0.269 | 2.417 | −7.472 | 0.131 | 2.182 | 0.948 | 1.205 | 0.362 | 0.923 | 1.73 | 0.01 | −0.02 | 1.53 | 0.50 |
| N | 124V | 0.012 | 26.252 | −81.636 | 0.005 | 26.886 | 7.756 | 10.387 | 3.739 | 12.800 | 1.60 | 0.01 | 0.03 | 1.60 | 0.15 |
| N | 124W | −0.188 | 0.241 | −4.473 | −0.038 | −0.871 | −0.117 | −0.352 | −0.296 | −0.735 | 0.00 | 0.00 | 0.00 | 0.00 | 0.00 |
| N | 124Y | −0.073 | −3.173 | 35.799 | −0.020 | −4.499 | −1.069 | −1.602 | −0.787 | −2.315 | 1.25 | 0.02 | −0.56 | 0.64 | 0.42 |
| T | 125A | 1.203 | 0.872 | −2.389 | 1.652 | 0.930 | 0.929 | 0.632 | 0.274 | 0.621 | 0.87 | 0.26 | 0.38 | 1.18 | 0.82 |
| T | 125D | 1.005 | 0.960 | 2.810 | 1.150 | 0.987 | 0.915 | 0.870 | 0.274 | 0.730 | 1.02 | 0.15 | 0.27 | 0.49 | 0.49 |
| T | 125E | 1.077 | 0.887 | −1.918 | 1.308 | 0.946 | 0.943 | 0.791 | 0.518 | 0.781 | 0.98 | 0.42 | 0.39 | 0.81 | 0.79 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| T | 125F | 1.010 | 0.972 | 6.707 | 0.981 | 0.983 | 0.871 | 0.848 | 0.361 | 0.798 | 1.00 | 0.19 | 0.37 | 1.27 | 0.98 |
| T | 125G | 0.250 | 2.490 | -1.101 | 0.135 | 2.440 | 1.432 | 1.616 | 0.248 | 1.292 | 0.99 | 0.42 | 0.46 | 0.84 | 0.40 |
| T | 125H | 0.967 | 0.919 | 5.270 | 1.035 | 1.040 | 0.948 | 0.899 | 0.408 | 0.753 | 1.02 | 0.24 | 0.54 | 1.07 | 0.61 |
| T | 125I | 0.937 | 1.038 | 3.540 | 0.994 | 1.111 | 1.112 | 1.068 | 0.753 | 1.167 | 0.97 | 0.72 | 0.95 | 1.05 | 0.83 |
| T | 125K | 0.991 | 0.961 | 3.029 | 1.167 | 1.054 | 1.103 | 1.085 | 0.659 | 0.834 | 0.91 | 0.61 | 1.00 | 1.12 | 0.89 |
| T | 125L | 1.059 | 0.716 | -5.481 | 1.237 | 0.991 | 0.998 | 0.921 | 0.360 | 0.861 | 0.94 | 0.12 | 0.46 | 0.89 | 0.93 |
| T | 125M | 1.077 | 0.860 | -2.587 | 1.237 | 1.054 | 0.897 | 0.624 | 0.394 | 0.755 | 0.91 | 0.35 | 0.36 | 1.03 | 0.67 |
| T | 125N | 1.044 | 0.919 | 5.692 | 1.155 | 0.927 | 0.894 | 0.704 | 0.665 | 0.736 | 1.03 | 0.63 | 0.77 | 1.04 | 1.10 |
| T | 125P | 0.215 | 2.239 | 4.485 | 0.088 | 2.343 | 1.106 | 1.141 | 0.991 | 1.311 | 0.00 | 0.00 | 0.00 | 0.00 | 0.00 |
| T | 125Q | 1.037 | 0.907 | 1.635 | 1.039 | 0.894 | 0.893 | 0.877 | 0.901 | 0.791 | 0.99 | 1.00 | 1.21 | 0.89 | 1.07 |
| T | 125R | 0.879 | 1.177 | 1.500 | 0.831 | 1.001 | 0.914 | 0.923 | 0.771 | 0.681 | 0.86 | 0.62 | 1.26 | 1.08 | 0.85 |
| T | 125S | 0.891 | 1.058 | 0.723 | 0.753 | 1.065 | 0.978 | 0.968 | 0.649 | 0.795 | 0.93 | 0.31 | 0.63 | 0.81 | 0.54 |
| T | 125V | 0.975 | 0.929 | 7.829 | 0.960 | 0.992 | 0.959 | 0.933 | 0.812 | 1.012 | 1.02 | 0.72 | 0.87 | 1.22 | 0.85 |
| T | 125W | 0.478 | 1.669 | 2.260 | 0.318 | 1.504 | 0.971 | 1.021 | 0.302 | 0.936 | 0.97 | 0.06 | 0.17 | 0.86 | 0.68 |
| T | 125Y | 0.745 | 1.163 | 8.514 | 0.766 | 1.297 | 1.138 | 1.075 | 0.413 | 1.031 | 0.97 | 0.22 | 0.24 | 0.94 | 0.70 |
| Q | 126A | 0.987 | 1.250 | -11.212 | 1.283 | 1.049 | 0.981 | 0.911 | 0.536 | 0.798 | 1.16 | 0.74 | 0.78 | 1.06 | 0.86 |
| Q | 126C | 0.798 | 0.580 | -12.400 | 0.607 | 0.993 | 0.711 | 0.940 | 0.653 | 0.924 | 1.25 | 0.78 | 0.53 | 0.62 | 0.30 |
| Q | 126D | 0.704 | 2.158 | -1.586 | 0.717 | 1.212 | 0.718 | 0.536 | 0.158 | 0.485 | 1.41 | 0.05 | 0.16 | 1.14 | 0.21 |
| Q | 126F | 0.804 | 1.738 | 3.996 | 0.904 | 1.162 | 0.718 | 1.070 | 0.824 | 1.287 | 1.52 | 0.98 | 0.46 | 1.08 | 0.42 |
| Q | 126G | 0.664 | 1.243 | -0.243 | 0.460 | 1.262 | 0.858 | 0.869 | 0.400 | 0.720 | 1.25 | 0.12 | 0.23 | 0.98 | 0.53 |
| Q | 126H | 0.957 | 1.271 | -3.530 | 0.968 | 1.038 | 0.897 | 0.982 | 1.008 | 0.665 | 1.24 | 0.92 | 0.95 | 1.74 | 1.47 |
| Q | 126K | 0.758 | 0.065 | -13.389 | 0.580 | 1.165 | 0.711 | 1.379 | 1.281 | 0.906 | 0.91 | 1.90 | 1.22 | 1.08 | 1.62 |
| Q | 126L | 0.930 | 0.497 | -1.683 | 0.847 | 1.031 | 1.057 | 1.213 | 1.109 | 1.404 | 0.97 | 1.31 | 1.60 | 1.17 | 1.17 |
| Q | 126N | 0.847 | 1.169 | -1.756 | 0.942 | 1.101 | 0.871 | 0.789 | 0.390 | 0.536 | 1.43 | 0.42 | 0.48 | 1.15 | 0.79 |
| Q | 126P | 1.086 | 1.301 | 7.973 | 1.145 | 0.899 | 0.836 | 0.907 | 1.069 | 1.062 | 1.15 | 1.90 | 2.03 | 0.96 | 0.60 |
| Q | 126R | 1.007 | 0.605 | 4.389 | 0.782 | 0.853 | 0.639 | 1.100 | 1.183 | 0.613 | 0.88 | 1.02 | 1.00 | 0.90 | 0.94 |
| Q | 126S | 0.862 | 1.492 | 2.592 | 0.964 | 1.197 | 1.027 | 0.935 | 0.702 | 0.589 | 1.36 | 0.59 | 0.47 | 1.15 | 0.59 |
| Q | 126T | 0.844 | 1.037 | -4.460 | 0.729 | 1.078 | 0.959 | 0.981 | 0.850 | 0.685 | 1.04 | 0.72 | 0.65 | 1.12 | 0.68 |
| Q | 126V | 0.743 | 0.519 | 1.002 | 0.579 | 1.206 | 1.155 | 1.169 | 1.086 | 1.560 | 0.84 | 0.83 | 1.03 | 0.74 | 0.78 |
| Q | 126W | 0.636 | 1.241 | 25.087 | 0.601 | 1.412 | 0.710 | 1.522 | 1.361 | 0.920 | 1.30 | 1.55 | 0.87 | 0.52 | 0.20 |
| Q | 126Y | 0.745 | 1.607 | -14.753 | 0.788 | 1.307 | 0.866 | 1.169 | 0.469 | 1.286 | 1.21 | 0.51 | 0.31 | 1.22 | 0.42 |
| I | 127A | -0.264 | -2.177 | -0.027 | -0.052 | -0.370 | -0.025 | -0.230 | -0.260 | -0.530 | 0.00 | 0.00 | 0.00 | 0.00 | 0.00 |
| I | 127C | 0.208 | 1.737 | 8.693 | 0.058 | 1.120 | 0.226 | 0.686 | 0.263 | 0.767 | 0.00 | 0.00 | 0.00 | 0.00 | 0.00 |
| I | 127D | -0.078 | 2.009 | -0.463 | -0.013 | -0.990 | -0.091 | -0.740 | -0.758 | -1.726 | 0.00 | 0.00 | 0.00 | 0.00 | 0.00 |
| I | 127E | -0.078 | 0.570 | -7.214 | -0.013 | -1.028 | -0.136 | -0.751 | -0.798 | -1.820 | 0.00 | 0.00 | 0.00 | 0.00 | 0.00 |
| I | 127F | -0.021 | -18.311 | -74.944 | -0.006 | -10.041 | -3.089 | -7.034 | -2.577 | -8.449 | 0.00 | 0.00 | 0.00 | 0.00 | 0.00 |
| I | 127G | -0.179 | -0.515 | 73.784 | -0.028 | -0.437 | -0.037 | -0.269 | -0.307 | -0.662 | 0.00 | 0.00 | 0.00 | 0.00 | 0.00 |
| I | 127H | -0.163 | -0.108 | -4.260 | -0.036 | -0.519 | -0.050 | -0.346 | -0.373 | -0.848 | 0.00 | 0.00 | 0.00 | 0.00 | 0.00 |
| I | 127K | -0.146 | -0.229 | -2.263 | -0.025 | -0.555 | -0.048 | -0.387 | -0.393 | -0.949 | 0.00 | 0.00 | 0.00 | 0.00 | 0.00 |
| I | 127L | 0.131 | 2.440 | -7.378 | 0.039 | 3.013 | 1.302 | 1.391 | 0.447 | 1.640 | 0.64 | 0.04 | 0.23 | 0.73 | -0.03 |
| I | 127M | 0.115 | 5.067 | 14.251 | 0.042 | 3.045 | 1.034 | 1.921 | 0.567 | 1.818 | 1.28 | 0.01 | 0.06 | 0.92 | -0.04 |
| I | 127N | -0.053 | -11.316 | -8.903 | -0.008 | -1.520 | -0.103 | -1.102 | -1.145 | -2.715 | 0.00 | 0.00 | 0.00 | 0.00 | 0.00 |
| I | 127P | -0.128 | -0.115 | -16.822 | -0.022 | -0.615 | -0.061 | -0.467 | -0.455 | -1.064 | 0.00 | 0.00 | 0.00 | 0.00 | 0.00 |
| I | 127Q | -0.127 | -3.708 | -15.719 | -0.027 | -0.762 | -0.048 | -0.482 | -0.458 | -1.074 | 0.00 | 0.00 | 0.00 | 0.00 | 0.00 |
| I | 127R | -0.131 | -4.110 | -4.883 | -0.027 | -0.606 | -0.040 | -0.352 | -0.454 | -0.945 | 0.00 | 0.00 | 0.00 | 0.00 | 0.00 |
| I | 127S | -0.147 | -0.279 | -21.638 | -0.031 | -0.646 | -0.059 | -0.414 | -0.392 | -0.927 | 0.00 | 0.00 | 0.00 | 0.00 | 0.00 |
| I | 127T | -0.007 | -64.799 | 88.876 | -0.001 | -40.083 | -7.287 | -19.167 | -10.107 | -26.506 | 0.00 | 0.00 | 0.07 | 0.69 | 0.28 |
| I | 127V | 0.208 | 1.852 | 0.969 | 0.057 | 1.697 | 0.446 | 0.824 | 0.284 | 0.890 | 1.09 | 0.01 | | | |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| I | 127W | -0.097 | -4.080 | -11.476 | -0.020 | -1.781 | -0.285 | -1.027 | -0.884 | -1.662 | 0.00 | 0.00 | 0.00 | 0.00 | 0.00 |
| I | 127Y | -0.104 | -5.118 | -0.352 | -0.029 | -3.586 | -1.531 | -2.122 | -1.804 | -7.286 | 0.00 | 0.00 | 0.00 | 0.00 | 0.00 |
| S | 131A | 0.928 | 1.033 | 0.293 | 0.894 | 0.992 | 0.979 | 0.925 | 0.732 | 0.935 | 0.87 | 0.86 | 0.94 | 0.88 | 0.84 |
| S | 131C | 1.034 | 0.759 | 3.164 | 0.897 | 0.830 | 0.998 | 0.982 | 0.986 | 0.765 | 0.88 | 0.99 | 0.82 | 0.56 | 0.17 |
| S | 131F | 1.022 | 0.990 | -2.466 | 1.039 | 0.937 | 0.929 | 0.988 | 1.057 | 0.872 | 1.10 | 1.21 | 0.94 | 1.05 | 0.87 |
| S | 131H | 1.101 | 0.682 | 1.923 | 1.049 | 0.866 | 0.785 | 0.777 | 0.626 | 0.803 | 0.92 | 0.62 | 0.56 | 1.21 | 0.84 |
| S | 131I | 0.526 | 1.219 | -1.569 | 0.263 | 1.256 | 0.888 | 1.004 | 0.989 | 0.824 | 1.25 | 1.25 | 0.72 | 0.94 | 1.43 |
| S | 131K | 0.688 | 1.200 | 1.924 | 0.475 | 1.108 | 0.987 | 1.028 | 0.685 | 0.913 | 1.28 | 0.39 | 0.33 | 1.07 | 0.76 |
| S | 131L | 0.836 | 1.025 | -2.908 | 0.729 | 1.132 | 1.165 | 1.227 | 1.020 | 0.929 | 1.04 | 0.91 | 1.00 | 1.01 | 1.26 |
| S | 131M | 0.825 | 1.034 | 2.900 | 0.720 | 1.154 | 1.205 | 1.195 | 1.081 | 1.083 | 1.30 | 1.56 | 1.20 | 0.94 | 0.53 |
| S | 131N | 0.605 | 1.246 | -1.026 | 0.416 | 1.161 | 0.892 | 0.961 | 0.711 | 0.921 | 0.96 | 0.87 | 0.76 | 1.00 | 0.71 |
| S | 131P | 0.859 | 1.155 | -0.443 | 0.941 | 1.148 | 1.186 | 1.173 | 1.093 | 1.125 | 0.89 | 0.96 | 1.00 | 0.92 | 0.72 |
| S | 131Q | -0.038 | -13.244 | 43.421 | -0.009 | -4.216 | -0.641 | -2.253 | -1.562 | -4.098 | 0.00 | 0.00 | 0.00 | 0.00 | 0.00 |
| S | 131R | 0.984 | 1.060 | 0.487 | 0.973 | 0.968 | 1.058 | 1.082 | 1.061 | 1.080 | 1.09 | 1.18 | 0.77 | 0.80 | 0.53 |
| S | 131T | 0.950 | 1.000 | 0.622 | 0.869 | 0.983 | 0.994 | 1.035 | 0.971 | 0.720 | 1.07 | 0.94 | 0.84 | 0.83 | 1.01 |
| S | 131V | 0.908 | 0.921 | 2.171 | 0.903 | 1.111 | 1.086 | 1.092 | 1.011 | 1.013 | 1.10 | 1.07 | 0.96 | 0.98 | 0.93 |
| S | 131W | 0.685 | 1.231 | -0.318 | 0.522 | 1.282 | 1.168 | 1.246 | 0.798 | 1.149 | 1.20 | 0.40 | 0.44 | 0.99 | 0.94 |
| S | 131Y | 0.762 | 1.223 | -6.557 | 0.721 | 1.245 | 1.077 | 1.427 | 1.143 | 1.032 | 1.13 | 0.92 | 1.10 | 1.10 | 1.04 |
| S | 131Y | 0.802 | 1.152 | -0.810 | 0.855 | 1.303 | 1.298 | 1.354 | 0.968 | 1.119 | 1.08 | 0.83 | 0.85 | 0.85 | 0.71 |
| D | 132A | 0.122 | 4.293 | 19.183 | 0.048 | 3.422 | 1.063 | 1.534 | 0.486 | 1.875 | 0.92 | 0.04 | 0.09 | 0.63 | 0.03 |
| D | 132C | 0.836 | 1.112 | 2.817 | 0.882 | 1.131 | 1.071 | 0.973 | 0.703 | 0.950 | 0.94 | 0.67 | 0.74 | 0.63 | 0.61 |
| D | 132E | 0.436 | 1.648 | 4.116 | 0.298 | 1.698 | 1.013 | 1.025 | 0.133 | 1.064 | 0.90 | 0.01 | 0.04 | 1.05 | 0.35 |
| D | 132F | 0.042 | 10.351 | 23.670 | 0.014 | 8.724 | 2.318 | 3.354 | 1.439 | 4.789 | 0.94 | 0.05 | 0.55 | 0.95 | 0.91 |
| D | 132G | -0.105 | -5.411 | -25.490 | -0.022 | -1.479 | -0.191 | -0.685 | -0.569 | -1.399 | 0.00 | 0.00 | 0.00 | 0.00 | 0.00 |
| D | 132H | 0.261 | 2.075 | 9.038 | 0.111 | 2.352 | 1.201 | 1.282 | 0.239 | 1.226 | 0.93 | 0.01 | 0.13 | 1.02 | 0.06 |
| D | 132I | 0.711 | 1.069 | -0.648 | 0.550 | 1.236 | 1.025 | 1.015 | 0.282 | 0.931 | 0.90 | 0.06 | 0.29 | 0.93 | 0.90 |
| D | 132K | 0.009 | 45.047 | 209.722 | 0.002 | 31.693 | 7.831 | 13.524 | 6.929 | 20.493 | 0.51 | 0.05 | -0.28 | -0.11 | -2.57 |
| D | 132L | -0.195 | -1.153 | -7.519 | -0.041 | -1.627 | -0.507 | -0.714 | -0.337 | -1.017 | 1.00 | 0.07 | 0.18 | 1.21 | 0.02 |
| D | 132M | 0.133 | 4.165 | 4.891 | 0.053 | 2.969 | 0.969 | 1.399 | 0.455 | 1.724 | 0.93 | 0.04 | -0.03 | 0.80 | -0.02 |
| D | 132N | 0.911 | 0.996 | 1.059 | 0.940 | 1.006 | 0.926 | 0.906 | 0.189 | 0.850 | 0.89 | 0.04 | 0.22 | 1.18 | 0.64 |
| D | 132P | -0.113 | -4.326 | 5.515 | -0.028 | -0.769 | -0.071 | -0.499 | -0.513 | -1.220 | 0.00 | 0.00 | 0.00 | 0.00 | 0.00 |
| D | 132Q | 0.076 | 5.490 | 12.440 | 0.028 | 5.062 | 1.805 | 2.428 | 0.743 | 3.059 | 0.97 | 0.01 | 0.13 | 1.01 | 0.12 |
| D | 132R | 0.034 | 13.111 | 5.288 | 0.009 | 6.823 | 1.644 | 3.202 | 1.813 | 4.769 | 0.00 | 0.09 | 0.00 | 0.00 | 0.00 |
| D | 132S | 0.907 | 0.939 | 0.054 | 0.785 | 1.029 | 0.981 | 1.004 | 0.378 | 0.931 | 0.97 | 0.00 | 0.23 | 1.22 | 0.92 |
| D | 132T | -0.158 | -2.219 | 12.647 | -0.035 | -1.454 | -0.289 | -0.635 | -0.360 | -1.033 | 0.00 | 0.00 | 0.00 | 0.00 | 0.00 |
| D | 132V | -0.008 | -83.535 | 34.110 | -0.001 | -56.890 | -15.566 | -24.542 | -11.187 | -36.271 | 0.96 | 0.03 | -0.14 | -0.20 | -0.08 |
| D | 132W | 0.311 | 2.042 | -2.297 | 0.155 | 1.988 | 1.164 | 1.268 | 0.205 | 1.288 | 1.03 | 0.03 | 0.11 | 1.22 | 0.45 |
| D | 132Y | 0.042 | 4.934 | -40.968 | 0.011 | 7.050 | 1.857 | 3.097 | 1.365 | 4.428 | 0.87 | 0.08 | -0.04 | 1.32 | -0.19 |
| W | 134C | 0.660 | 0.422 | 6.170 | 0.314 | 0.870 | 0.537 | 0.526 | 0.274 | 0.636 | 0.78 | 0.05 | 0.10 | 0.88 | 0.99 |
| W | 134D | -0.008 | 3.632 | 2.714 | 0.050 | 3.546 | 1.829 | 2.082 | 1.731 | 2.371 | 0.00 | 0.00 | 0.00 | 0.00 | 0.00 |
| W | 134E | 0.131 | 1.073 | 4.797 | 0.479 | 1.199 | 1.082 | 1.066 | 0.511 | 1.141 | 0.88 | 0.06 | 0.25 | 0.58 | 0.99 |
| W | 134F | 0.673 | 1.228 | -0.762 | 0.608 | 1.160 | 1.139 | 1.161 | 0.920 | 1.204 | 0.96 | 0.43 | 0.40 | 0.93 | 0.87 |
| W | 134G | 0.756 | 23.009 | 180.682 | 0.004 | 29.298 | 11.472 | 13.508 | 5.347 | 15.714 | 0.89 | 0.03 | 0.01 | 1.49 | 1.97 |
| W | 134I | 0.015 | -5.651 | -10.425 | -0.013 | -7.511 | -2.731 | -3.667 | -1.910 | -4.420 | 1.82 | 0.04 | -0.06 | 2.63 | 2.71 |
| W | 134K | -0.051 | -5.272 | 8.974 | -0.019 | -1.004 | -0.126 | -0.583 | -0.750 | -1.541 | 0.00 | 0.00 | 0.00 | 0.00 | 0.00 |
| W | 134L | -0.086 | 1.086 | 3.281 | 0.178 | 1.780 | 1.192 | 1.202 | 0.297 | 1.275 | 0.98 | 0.02 | 0.21 | 0.99 | 0.57 |
| W | 134M | 0.379 | 1.145 | -1.133 | 0.572 | 1.161 | 0.988 | 0.941 | 0.159 | 0.950 | 0.90 | 0.02 | 0.21 | 0.87 | 0.89 |
| W | 134N | 0.708 | 1.949 | -1.106 | 0.081 | 2.814 | 1.468 | 1.602 | 0.556 | 1.805 | 0.84 | 0.01 | -0.05 | 0.74 | 0.71 |
| W | 134N | 0.185 | | | | | | | | | | | | | |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| W | 134P | -0.061 | -6.776 | 11.276 | -0.018 | -6.017 | -2.330 | -3.110 | -2.743 | -3.949 | 0.00 | 0.00 | 0.00 | 0.00 | 0.00 |
| W | 134R | 0.839 | 1.050 | -2.247 | 0.651 | 1.073 | 1.029 | 1.016 | 0.464 | 1.075 | 0.88 | 0.07 | 0.18 | 1.10 | 1.01 |
| W | 134S | -0.010 | -28.911 | -217.993 | -0.003 | -44.065 | -17.365 | -20.925 | -7.142 | -23.985 | 1.10 | 0.02 | 0.12 | 1.51 | 1.79 |
| W | 134T | -0.120 | -2.869 | -14.687 | -0.031 | -2.280 | -0.495 | -0.858 | -0.509 | -1.411 | 1.32 | 0.02 | 0.28 | -0.92 | -1.22 |
| W | 134V | -0.131 | -3.091 | -16.937 | -0.030 | -1.688 | -0.411 | -0.725 | -0.472 | -1.207 | 1.50 | 0.25 | 0.43 | 1.44 | 2.75 |
| W | 134Y | 0.914 | 0.938 | -2.096 | 0.756 | 1.054 | 1.042 | 1.055 | 0.582 | 1.112 | 0.96 | 0.40 | 0.46 | 0.87 | 1.24 |
| W | 142A | -0.062 | 0.981 | -26.435 | -0.013 | -2.547 | -0.071 | -0.623 | -1.018 | -2.227 | 0.00 | 0.00 | 0.00 | 0.00 | 0.00 |
| L | 142C | 0.979 | 0.883 | -4.276 | 0.707 | 0.775 | 0.283 | 0.238 | 0.306 | 0.223 | 0.76 | 1.23 | 0.21 | 0.18 | 0.03 |
| L | 142D | 0.932 | 1.771 | -0.774 | 1.552 | 1.221 | 0.816 | 0.439 | 0.382 | 0.606 | 1.79 | 2.23 | 0.08 | 0.13 | 0.12 |
| L | 142F | 1.072 | 1.070 | 1.866 | 1.378 | 0.903 | 0.660 | 0.627 | 0.773 | 0.393 | 1.49 | 2.52 | 1.97 | 1.22 | 0.29 |
| L | 142G | 1.035 | 1.087 | -8.339 | 1.199 | 0.918 | 0.347 | 0.311 | 0.369 | 0.220 | 2.48 | 3.69 | 0.53 | 0.42 | 0.26 |
| L | 142H | 1.094 | 0.697 | -7.539 | 0.761 | 0.615 | 0.211 | 0.165 | 0.206 | 0.189 | 1.57 | 2.43 | 0.74 | 0.80 | 0.63 |
| L | 142I | 0.490 | 2.145 | -13.927 | 0.450 | 1.756 | 0.543 | 0.594 | 0.303 | 0.428 | 1.94 | 0.23 | 0.11 | 1.69 | 0.20 |
| L | 142K | 0.962 | 0.646 | -6.451 | 0.559 | 0.721 | 0.358 | 0.365 | 0.422 | 0.371 | 1.42 | 2.23 | 0.31 | 0.65 | 0.29 |
| L | 142M | 0.837 | 1.138 | -5.440 | 0.919 | 1.157 | 0.451 | 0.307 | 0.370 | 0.497 | 0.60 | 0.82 | 0.58 | 1.26 | -0.21 |
| L | 142P | -0.121 | -2.444 | -30.398 | -0.024 | -0.903 | -0.018 | -0.387 | -0.508 | -1.067 | 0.00 | 0.00 | 0.00 | 0.00 | 0.00 |
| L | 142Q | 0.936 | 1.716 | -0.361 | 1.577 | 1.228 | 0.694 | 0.487 | 0.456 | 0.456 | 2.58 | 3.01 | 0.37 | 0.60 | 0.22 |
| L | 142R | 1.060 | 0.712 | 1.218 | 0.578 | 0.555 | 0.180 | 0.176 | 0.225 | 0.209 | 1.33 | 1.33 | 0.31 | 0.28 | 0.84 |
| L | 142S | 0.879 | 1.646 | -2.529 | 1.258 | 2.177 | 0.508 | 0.373 | 0.340 | 0.269 | 2.04 | 2.23 | 0.46 | 0.40 | 0.29 |
| L | 142T | 0.773 | 1.730 | -5.440 | 1.110 | 1.213 | 0.582 | 0.331 | 0.370 | 0.497 | 1.76 | 0.82 | 0.15 | 0.44 | -0.12 |
| L | 142V | -0.079 | -4.987 | -30.398 | -0.014 | -2.183 | -0.097 | -0.659 | -0.883 | -1.629 | 0.00 | 0.00 | 0.00 | 0.00 | 0.14 |
| L | 142W | 1.040 | 0.464 | 2.870 | 0.569 | 0.615 | 0.346 | 0.313 | 0.367 | 0.526 | 1.16 | 1.87 | 1.74 | 0.74 | 0.04 |
| L | 142Y | 1.014 | 0.826 | -4.143 | 0.992 | 0.918 | 0.796 | 0.473 | 0.517 | 0.640 | 1.01 | 1.74 | 2.21 | 1.16 | 0.25 |
| G | 143A | 0.312 | 1.517 | 4.818 | 0.158 | 1.803 | 0.854 | 0.940 | 0.290 | 0.779 | 1.08 | 0.07 | 0.28 | 0.53 | 0.24 |
| G | 143C | 0.386 | 1.153 | -1.610 | 0.184 | 1.550 | 0.687 | 0.905 | 0.307 | 0.452 | 1.31 | 0.23 | 0.21 | 0.05 | -0.26 |
| G | 143D | 0.279 | 1.917 | 5.487 | 0.158 | 2.177 | 0.445 | 0.668 | 0.250 | 0.243 | 1.63 | 0.08 | 0.11 | -0.06 | -0.14 |
| G | 143F | 0.319 | 0.872 | -1.395 | 0.137 | 2.039 | 0.568 | 1.326 | 0.319 | 0.565 | 1.22 | 0.03 | 0.44 | -0.19 | -0.45 |
| G | 143I | -0.136 | 4.647 | -4.366 | -0.022 | -0.746 | -0.073 | -0.349 | -0.422 | -0.935 | 0.00 | 0.00 | 0.00 | 0.00 | 0.14 |
| G | 143K | 0.226 | 0.253 | 1.309 | 0.072 | 2.277 | 0.930 | 0.994 | 0.438 | 0.638 | 1.12 | 0.13 | 0.43 | 0.15 | 0.24 |
| G | 143L | 0.153 | 0.721 | 1.101 | 0.044 | 2.804 | 0.587 | 0.957 | 0.425 | 0.890 | 1.24 | 0.05 | 0.22 | -0.10 | 0.73 |
| G | 143M | 0.412 | 0.838 | 2.466 | 0.223 | 1.521 | 0.715 | 0.667 | 0.177 | 0.498 | 1.10 | 0.07 | 0.11 | 0.02 | 0.01 |
| G | 143N | 0.417 | 1.562 | 2.360 | 0.253 | 1.677 | 0.570 | 0.672 | 0.173 | 0.441 | 1.17 | 0.07 | 0.27 | 0.31 | -0.04 |
| G | 143P | -0.060 | 0.898 | -17.782 | -0.010 | -1.225 | -0.183 | -0.793 | -0.974 | -2.168 | 0.00 | 0.00 | 0.00 | 0.00 | 0.00 |
| G | 143Q | 0.347 | 1.159 | 3.176 | 0.149 | 1.739 | 0.846 | 0.756 | 0.248 | 0.562 | 1.12 | 0.11 | 0.25 | 0.15 | -0.04 |
| G | 143S | 0.346 | 0.795 | 3.820 | 0.131 | 1.638 | 0.740 | 0.708 | 0.295 | 0.453 | 1.02 | 0.16 | 0.22 | 0.17 | -0.27 |
| G | 143T | 0.503 | 0.920 | 0.060 | 0.248 | 1.393 | 0.758 | 0.924 | 0.322 | 0.703 | 1.19 | 0.10 | 0.36 | 0.34 | -0.08 |
| G | 143V | -0.074 | 1.232 | -0.572 | -0.012 | -2.143 | -0.100 | -0.775 | -0.840 | -1.872 | 0.00 | 0.00 | 0.00 | 0.00 | 0.00 |
| G | 143W | -0.002 | 142.410 | -179.915 | 0.000 | -191.732 | -14.312 | -53.128 | -34.295 | -79.204 | 1.57 | 0.01 | 0.24 | -0.98 | -0.42 |
| T | 152A | 0.969 | 0.930 | -2.837 | 0.072 | 0.951 | 0.990 | 0.960 | 0.561 | 0.911 | 0.87 | 0.79 | 0.71 | 1.00 | 0.93 |
| T | 152C | 0.669 | 1.226 | 2.280 | 0.495 | 1.220 | 1.080 | 1.062 | 0.906 | 1.057 | 0.85 | 1.01 | 0.91 | 0.79 | 0.66 |
| T | 152D | 0.920 | 0.979 | -2.000 | 0.845 | 0.977 | 0.966 | 0.975 | 0.853 | 0.950 | 0.91 | 0.95 | 0.79 | 0.58 | 0.99 |
| T | 152E | 1.002 | 0.834 | 0.905 | 1.072 | 1.021 | 1.012 | 1.015 | 1.091 | 1.041 | 0.98 | 1.03 | 0.83 | 0.66 | 1.26 |
| T | 152F | 0.869 | 1.090 | -4.007 | 0.710 | 1.041 | 0.996 | 0.972 | 0.903 | 0.968 | 0.94 | 0.96 | 0.90 | 1.02 | 1.25 |
| T | 152G | 1.002 | 1.107 | -0.572 | 0.770 | 1.071 | 0.995 | 0.999 | 0.925 | 0.962 | 0.98 | 0.99 | 1.18 | 0.97 | 1.15 |
| T | 152H | 0.877 | 1.041 | -1.890 | 0.696 | 1.106 | 1.081 | 1.108 | 1.010 | 1.057 | 0.88 | 0.90 | 1.18 | 0.70 | 1.16 |
| T | 152I | 0.826 | 0.977 | -2.028 | 0.803 | 1.000 | 1.001 | 1.042 | 0.892 | 0.977 | 0.99 | 0.97 | 1.26 | 0.65 | 1.18 |
| T | 152K | 0.948 | 0.934 | 1.749 | 1.112 | 1.039 | 1.024 | 0.995 | 0.705 | 1.006 | 0.93 | 0.77 | 1.31 | 1.15 | 1.14 |
| T | 152L | 0.975 | 0.907 | -13.631 | 0.928 | 1.033 | 1.063 | 1.033 | 0.749 | 1.006 | 0.88 | 0.66 | 1.01 | 0.93 | 1.00 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| T | 152M | 1.224 | 0.815 | −1.678 | 1.449 | 0.841 | 0.877 | 0.823 | 0.427 | 0.777 | 0.87 | 0.76 | 0.91 | 1.12 | 1.07 |
| T | 152N | 0.923 | 0.980 | −2.038 | 0.845 | 1.031 | 0.983 | 0.952 | 0.599 | 0.927 | 0.87 | 0.79 | 0.74 | 0.76 | 1.23 |
| T | 152P | 1.108 | 0.856 | 0.150 | 1.220 | 0.948 | 0.974 | 0.961 | 0.683 | 0.913 | 0.82 | 0.73 | 0.65 | 0.74 | 0.88 |
| T | 152Q | 1.028 | 0.950 | −0.768 | 0.944 | 0.956 | 0.975 | 0.937 | 0.681 | 0.929 | 0.87 | 0.82 | 0.88 | 0.70 | 1.32 |
| T | 152R | 0.903 | 1.168 | −1.152 | 0.875 | 1.094 | 1.104 | 1.027 | 0.732 | 0.999 | 0.89 | 0.72 | 0.98 | 1.46 | 1.47 |
| T | 152S | 0.872 | 1.212 | −2.014 | 0.929 | 1.198 | 1.112 | 1.083 | 0.827 | 1.072 | 0.99 | 0.89 | 0.96 | 0.69 | 1.09 |
| T | 152V | 0.948 | 1.139 | −2.257 | 1.024 | 1.129 | 1.164 | 1.152 | 1.065 | 1.119 | 0.99 | 0.88 | 1.15 | 0.89 | 1.50 |
| T | 152W | 0.805 | 1.254 | 1.071 | 0.675 | 1.081 | 1.056 | 1.059 | 0.865 | 1.020 | 0.96 | 0.90 | 1.27 | 0.95 | 1.12 |
| T | 152Y | 0.954 | 1.071 | −9.050 | 1.096 | 1.139 | 1.231 | 1.209 | 0.747 | 1.138 | 0.96 | 0.48 | 1.28 | 0.80 | 0.96 |
| Q | 153A | 1.089 | 0.970 | 2.061 | 1.488 | 0.975 | 1.022 | 0.956 | 0.747 | 0.952 | 0.92 | 0.79 | 0.74 | 0.90 | 0.81 |
| Q | 153C | 0.727 | 1.180 | 3.419 | 0.670 | 1.154 | 1.016 | 0.995 | 0.924 | 1.016 | 0.99 | 0.94 | 1.03 | 0.53 | 0.54 |
| Q | 153D | 1.028 | 0.900 | 3.319 | 1.071 | 0.904 | 0.885 | 0.877 | 0.882 | 0.894 | 0.98 | 0.95 | 0.67 | 0.90 | 0.65 |
| Q | 153E | 1.106 | 0.839 | 1.944 | 1.273 | 0.897 | 0.929 | 0.942 | 0.975 | 0.928 | 0.99 | 1.02 | 0.86 | 1.15 | 0.95 |
| Q | 153F | 0.887 | 1.062 | 2.880 | 0.809 | 1.023 | 0.957 | 0.946 | 0.981 | 0.946 | 1.08 | 1.02 | 0.85 | 1.22 | 1.12 |
| Q | 153G | 0.858 | 1.022 | 1.656 | 0.704 | 1.049 | 0.911 | 0.885 | 0.863 | 0.905 | 1.03 | 0.85 | 0.89 | 0.95 | 1.00 |
| Q | 153H | 1.036 | 0.919 | 1.225 | 1.059 | 0.945 | 0.908 | 0.917 | 0.923 | 0.925 | 1.05 | 0.99 | 1.43 | 1.20 | 1.05 |
| Q | 153I | 0.898 | 0.884 | 3.839 | 0.753 | 1.008 | 0.908 | 0.893 | 0.894 | 0.936 | 0.97 | 1.01 | 0.96 | 0.85 | 1.07 |
| Q | 153K | 0.926 | 0.910 | 1.980 | 0.892 | 1.033 | 0.997 | 1.008 | 0.873 | 0.981 | 0.96 | 0.90 | 0.80 | 1.39 | 0.79 |
| Q | 153L | 0.955 | 0.908 | 3.874 | 1.084 | 1.084 | 1.087 | 1.050 | 0.823 | 1.034 | 0.84 | 0.86 | 0.80 | 0.87 | 0.85 |
| Q | 153M | 0.902 | 1.063 | 2.013 | 0.957 | 1.018 | 1.036 | 0.970 | 0.882 | 0.937 | 0.95 | 0.87 | 1.08 | 0.87 | 0.90 |
| Q | 153N | 0.844 | 1.060 | 3.189 | 0.872 | 1.043 | 0.998 | 0.965 | 0.975 | 0.921 | 0.90 | 0.89 | 1.35 | 0.72 | 0.82 |
| Q | 153P | 0.289 | 1.409 | 6.165 | 0.082 | 1.069 | 0.322 | 0.473 | 0.487 | 0.669 | 0.19 | 0.15 | 0.37 | 0.17 | 0.17 |
| Q | 153R | 0.687 | 1.371 | 3.472 | 0.640 | 1.319 | 1.235 | 1.251 | 1.314 | 1.184 | 1.06 | 1.16 | 1.25 | 1.89 | 1.61 |
| Q | 153S | 1.082 | 0.925 | 0.587 | 1.320 | 0.952 | 0.978 | 0.869 | 0.407 | 0.840 | 1.03 | 0.99 | 0.86 | 0.97 | 0.78 |
| Q | 153T | 0.741 | 1.166 | −0.879 | 0.637 | 1.211 | 1.094 | 1.101 | 1.105 | 1.140 | 0.96 | 0.96 | 1.15 | 0.81 | 0.94 |
| Q | 153W | 0.690 | 1.266 | 2.666 | 0.594 | 1.301 | 1.227 | 1.220 | 1.207 | 1.278 | 1.01 | 1.00 | 1.39 | 1.00 | 0.96 |
| Q | 153Y | 0.741 | 1.140 | 1.141 | 0.591 | 1.177 | 1.018 | 1.026 | 0.918 | 1.031 | 0.94 | 0.81 | 1.08 | 1.00 | 0.68 |
| Q | 156A | 0.698 | 1.135 | 0.616 | 0.641 | 1.354 | 1.210 | 1.134 | 0.847 | 1.158 | 0.93 | 0.61 | 1.01 | 0.56 | 0.69 |
| S | 156C | 1.256 | 0.949 | 0.661 | 1.849 | 0.934 | 1.004 | 0.969 | 0.576 | 0.969 | 1.06 | 0.92 | 1.27 | 1.03 | 1.20 |
| S | 156D | 1.031 | 0.981 | 0.674 | 1.126 | 0.943 | 0.885 | 0.810 | 0.619 | 0.843 | 0.96 | 0.86 | 0.95 | 0.80 | 0.96 |
| S | 156E | 1.038 | 1.018 | 0.701 | 1.290 | 1.022 | 1.030 | 0.955 | 0.815 | 0.970 | 0.99 | 0.88 | 0.85 | 0.69 | 0.84 |
| S | 156F | 0.958 | 1.071 | 0.926 | 1.009 | 1.042 | 1.046 | 1.016 | 0.879 | 1.013 | 1.03 | 0.92 | 0.97 | 0.84 | 0.53 |
| S | 156G | 0.849 | 1.226 | 0.786 | 0.801 | 1.201 | 1.110 | 1.011 | 0.846 | 1.037 | 0.95 | 0.81 | 0.98 | 0.85 | 1.27 |
| S | 156I | 1.010 | 0.974 | 0.669 | 0.990 | 1.003 | 0.937 | 0.879 | 0.746 | 0.903 | 1.10 | 0.93 | 1.36 | 0.99 | 1.18 |
| S | 156K | 1.060 | 0.967 | −0.039 | 1.217 | 0.975 | 0.958 | 0.950 | 0.931 | 0.930 | 0.96 | 0.86 | 1.01 | 0.88 | 0.78 |
| S | 156L | 1.048 | 0.984 | 1.375 | 1.049 | 0.921 | 0.917 | 0.911 | 0.908 | 0.943 | 1.02 | 0.79 | 1.08 | 1.19 | 1.61 |
| S | 156N | 1.039 | 0.984 | 1.117 | 1.167 | 1.023 | 1.016 | 0.947 | 0.791 | 0.913 | 0.96 | 0.96 | 0.99 | 0.84 | 0.98 |
| S | 156P | 0.958 | 1.033 | 1.318 | 0.895 | 0.988 | 1.022 | 0.948 | 0.858 | 0.983 | 1.04 | 0.88 | 0.98 | 0.99 | 1.22 |
| S | 156Q | 0.762 | 1.162 | 0.826 | 0.699 | 0.962 | 0.945 | 1.009 | 0.931 | 1.001 | 0.99 | 0.96 | 0.94 | 0.80 | 0.19 |
| S | 156R | 0.853 | 1.054 | 0.557 | 1.496 | 1.094 | 1.114 | 1.071 | 0.788 | 1.040 | 1.06 | 0.90 | 1.05 | 1.09 | 0.93 |
| S | 156T | 1.127 | 0.899 | 0.953 | 1.921 | 1.048 | 1.073 | 0.972 | 0.755 | 0.965 | 1.01 | 0.87 | 0.92 | 1.25 | 1.15 |
| S | 156V | 1.278 | 0.860 | 0.527 | 1.264 | 0.914 | 0.924 | 0.916 | 0.794 | 0.966 | 1.07 | 0.84 | 0.89 | 0.84 | 1.06 |
| S | 156W | 1.085 | 0.965 | 0.376 | 0.000 | 285.848 | 58.948 | 113.783 | 105.651 | 198.778 | 0.91 | 0.41 | 0.66 | 0.78 | −0.97 |
| S | 156Y | 0.000 | 507.540 | 322.712 | 1.118 | 0.923 | 0.911 | 0.913 | 0.885 | 0.909 | 1.01 | 0.95 | 0.90 | 0.98 | 1.21 |
| R | 160A | 1.063 | 0.993 | 0.292 | 1.030 | 0.975 | 0.958 | 0.950 | 0.931 | 0.930 | 0.96 | 0.86 | 1.08 | 1.19 | 1.61 |
| R | 160C | 1.023 | 0.967 | −0.039 | 1.049 | 0.921 | 0.917 | 0.911 | 0.908 | 0.913 | 1.02 | 0.79 | 1.01 | 0.84 | 0.98 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| R | 160D | 1.020 | 0.941 | −1.008 | 0.964 | 0.911 | 0.922 | 0.905 | 0.956 | 0.948 | 0.98 | 1.01 | 1.37 | 0.75 | 0.61 |
| R | 160E | 0.807 | 1.136 | 5.115 | 0.649 | 1.056 | 0.972 | 0.960 | 0.963 | 0.967 | 1.07 | 1.08 | 1.50 | 0.79 | 0.68 |
| R | 160F | 0.669 | 1.134 | −0.561 | 0.426 | 1.156 | 0.948 | 0.976 | 1.014 | 0.999 | 0.98 | 1.05 | 0.78 | 0.81 | 0.73 |
| R | 160G | 0.846 | 1.156 | 0.045 | 0.773 | 1.147 | 1.096 | 1.129 | 1.222 | 1.157 | 1.08 | 1.18 | 1.15 | 0.80 | 0.61 |
| R | 160H | 0.907 | 1.086 | −0.827 | 0.814 | 1.015 | 0.953 | 0.967 | 0.999 | 0.962 | 1.02 | 1.06 | 1.35 | 1.05 | 1.06 |
| R | 160I | 0.523 | 1.307 | −0.107 | 0.337 | 1.511 | 1.223 | 1.202 | 1.173 | 1.246 | 1.07 | 1.02 | 0.99 | 0.72 | 0.94 |
| R | 160K | 0.827 | 0.991 | −0.368 | 0.733 | 1.152 | 1.110 | 1.119 | 0.985 | 1.141 | 1.02 | 0.98 | 1.36 | 1.52 | 1.42 |
| R | 160L | 0.752 | 0.900 | 3.767 | 0.633 | 1.195 | 1.077 | 1.070 | 0.811 | 1.127 | 1.02 | 0.88 | 0.96 | 0.75 | 0.68 |
| R | 160M | 0.835 | 1.162 | 1.106 | 0.940 | 1.170 | 1.126 | 1.040 | 0.769 | 1.050 | 0.93 | 0.80 | 0.94 | 0.69 | 0.72 |
| R | 160N | 1.016 | 0.954 | 0.577 | 1.143 | 0.925 | 0.955 | 0.926 | 0.854 | 0.927 | 0.93 | 0.97 | 0.80 | 0.77 | 1.09 |
| R | 160P | −0.149 | −3.312 | −0.299 | −0.034 | −1.019 | −0.165 | −0.438 | −0.506 | −0.955 | 0.00 | 0.00 | 0.00 | 0.00 | 0.00 |
| R | 160Q | 0.801 | 1.203 | 26.164 | 0.750 | 1.132 | 1.096 | 1.114 | 1.095 | 1.097 | 0.97 | 0.99 | 0.90 | 0.72 | 0.86 |
| R | 160S | 0.890 | 1.118 | 1.123 | 0.821 | 1.071 | 1.045 | 1.085 | 1.077 | 1.087 | 1.16 | 1.24 | 1.30 | 0.86 | 0.75 |
| R | 160T | 0.816 | 1.124 | 2.162 | 0.699 | 1.098 | 1.024 | 1.050 | 1.048 | 1.059 | 1.06 | 1.08 | 1.55 | 0.87 | 0.57 |
| R | 160V | 0.582 | 1.293 | −1.019 | 0.370 | 1.341 | 1.097 | 1.090 | 1.029 | 1.124 | 1.12 | 1.00 | 1.60 | 0.62 | 0.78 |
| R | 160W | 0.483 | 1.453 | 8.920 | 0.292 | 1.610 | 1.195 | 1.209 | 1.089 | 1.292 | 1.05 | 0.94 | 1.04 | 0.79 | 0.63 |
| R | 160Y | 0.770 | 0.845 | 0.229 | 0.574 | 1.006 | 0.868 | 0.816 | 0.772 | 0.855 | 1.05 | 1.01 | 0.88 | 1.06 | 0.81 |
| ED | 163A | 0.969 | 1.087 | 0.327 | 1.166 | 1.048 | 1.095 | 1.048 | 0.737 | 1.069 | 0.89 | 0.84 | 0.67 | 0.97 | 0.74 |
| ED | 163C | 0.857 | 1.088 | 1.555 | 0.842 | 1.101 | 1.085 | 1.017 | 0.871 | 1.020 | 0.99 | 0.95 | 1.01 | 0.96 | 0.75 |
| ED | 163D | 0.751 | 1.016 | −3.616 | 0.616 | 1.150 | 1.051 | 1.009 | 0.893 | 1.026 | 1.00 | 0.92 | 0.91 | 1.31 | 0.86 |
| ED | 163E | 1.069 | 0.927 | −1.247 | 1.082 | 0.906 | 0.979 | 0.944 | 0.892 | 0.936 | 1.01 | 1.07 | 0.77 | 1.14 | 0.86 |
| ED | 163F | 0.922 | 1.075 | −2.228 | 0.588 | 1.053 | 1.094 | 1.050 | 1.001 | 1.001 | 1.06 | 1.05 | 0.80 | 1.31 | 1.18 |
| ED | 163G | 0.841 | 1.108 | 7.070 | 0.885 | 1.168 | 1.109 | 1.058 | 1.048 | 1.038 | 1.01 | 1.06 | 0.99 | 1.56 | 1.18 |
| ED | 163H | 0.924 | 1.092 | −3.974 | 0.735 | 1.120 | 1.176 | 1.192 | 1.012 | 1.090 | 1.02 | 1.00 | 1.05 | 1.32 | 1.06 |
| ED | 163I | 0.927 | 0.995 | 3.370 | 0.920 | 1.070 | 1.116 | 1.112 | 1.103 | 1.072 | 1.00 | 1.04 | 0.85 | 1.09 | 0.96 |
| ED | 163K | 0.804 | 1.093 | −2.281 | 0.912 | 1.205 | 1.154 | 1.145 | 1.038 | 1.081 | 0.96 | 1.02 | 0.95 | 2.02 | 1.19 |
| ED | 163L | 0.990 | 0.853 | −5.220 | 0.658 | 1.054 | 1.187 | 1.056 | 0.968 | 1.023 | 1.05 | 0.98 | 0.97 | 0.89 | 0.96 |
| ED | 163N | 1.073 | 1.025 | 2.390 | 1.003 | 1.046 | 1.075 | 1.063 | 0.884 | 1.029 | 1.07 | 1.02 | 0.96 | 1.27 | 0.82 |
| ED | 163P | −0.044 | −0.645 | 5.023 | 1.475 | 1.060 | 1.180 | 1.059 | 0.744 | 1.047 | 0.90 | 0.86 | 0.63 | 0.00 | 0.00 |
| ED | 163Q | 1.158 | 0.934 | −2.260 | −0.009 | −2.336 | −0.174 | −1.215 | −1.470 | −2.992 | 0.00 | 0.00 | 0.00 | 1.24 | 0.91 |
| ED | 163R | 0.737 | 1.069 | −1.169 | 1.407 | 0.943 | 1.072 | 0.971 | 0.757 | 0.960 | 0.97 | 0.96 | 0.77 | 2.21 | 1.70 |
| ED | 163S | 0.975 | 1.014 | −1.380 | 0.588 | 1.218 | 0.990 | 0.912 | 0.755 | 0.966 | 0.93 | 0.88 | 0.64 | 1.10 | 0.98 |
| ED | 163T | 0.864 | 1.006 | −6.104 | 1.024 | 1.138 | 1.116 | 1.078 | 0.860 | 1.039 | 1.00 | 0.97 | 0.63 | 1.41 | 1.08 |
| ED | 163V | 1.129 | 0.877 | −3.041 | 0.723 | 1.137 | 1.021 | 0.956 | 0.783 | 0.967 | 1.03 | 1.00 | 1.05 | 0.91 | 0.84 |
| ED | 163W | 0.966 | 1.020 | −3.859 | 1.338 | 0.991 | 1.071 | 1.101 | 0.847 | 1.042 | 0.89 | 0.90 | 0.98 | 1.55 | 1.15 |
| ED | 163Y | 1.151 | 0.978 | −6.242 | 1.057 | 1.054 | 1.187 | 1.140 | 0.931 | 1.129 | 1.05 | 1.02 | 1.37 | 1.57 | 1.06 |
| L | 166A | 0.593 | 1.068 | 1.926 | 1.511 | 1.014 | 1.178 | 1.063 | 0.837 | 1.029 | 1.09 | 1.05 | 1.35 | 1.16 | 0.84 |
| L | 166C | 0.575 | 1.089 | 1.286 | 0.406 | 1.170 | 0.750 | 0.730 | 0.454 | 0.840 | 1.07 | 0.74 | 0.83 | 0.96 | 1.49 |
| L | 166D | 0.16 | ND | ND | 0.421 | 1.287 | 0.900 | 0.851 | 0.596 | 0.853 | 1.02 | 0.68 | 0.71 | 0.56 | 1.25 |
| L | 166E | 0.146 | 3.196 | 5.121 | 0.054 | ND | ND | 0.53 | ND | 0.49 | 0.85 | 0.65 | 0.85 | 2.00 | 2.36 |
| L | 166F | 0.267 | 1.704 | 1.648 | 0.113 | 3.297 | 1.333 | 1.571 | 1.327 | 1.562 | 0.98 | 0.77 | 1.08 | 1.14 | 0.48 |
| L | 166G | 0.088 | 4.325 | 12.866 | 0.027 | 2.139 | 0.976 | 1.070 | 1.001 | 1.135 | 1.01 | 0.83 | 1.09 | 1.55 | 1.07 |
| L | 166H | 0.200 | 2.356 | 3.993 | 0.076 | 4.724 | 1.733 | 2.124 | 1.763 | 2.716 | 1.02 | 0.76 | 0.83 | 1.12 | 0.87 |
| L | 166I | 0.831 | 0.982 | 0.306 | 0.809 | 2.685 | 1.225 | 1.349 | 1.109 | 1.367 | 1.02 | 0.81 | 0.91 | 1.55 | 1.18 |
| L | 166K | 0.31 | ND | ND | ND | 1.210 | 1.067 | 1.002 | 0.783 | 0.989 | 0.97 | 0.79 | 0.78 | 1.21 | 0.71 |
| L | 166M | 0.654 | 1.223 | 0.854 | 0.614 | ND | ND | 0.84 | ND | 0.77 | 0.99 | 0.67 | 0.85 | 1.24 | 1.02 |
| L | 166N | 0.129 | 3.011 | −3.768 | 0.045 | 1.272 | 1.093 | 1.040 | 0.718 | 1.004 | 1.03 | 0.74 | 0.82 | 1.16 | 1.16 |
| L | 166P | −0.073 | 0.230 | −9.587 | −0.011 | −1.170 | −0.041 | −0.648 | −0.780 | −1.769 | 0.00 | 0.82 | 0.91 | 0.65 | 1.02 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| L | 166Q | 0.246 | 2.015 | 0.928 | 0.110 | 2.374 | 1.274 | 1.383 | 1.280 | 1.489 | 1.01 | 0.85 | 0.91 | 1.28 | 1.15 |
| L | 166R | 0.202 | 2.017 | 2.160 | 0.075 | 2.568 | 1.148 | 1.308 | 1.216 | 1.496 | 0.96 | 0.77 | 1.24 | 1.14 | 0.86 |
| L | 166S | 0.122 | 3.666 | 1.940 | 0.041 | 4.009 | 1.738 | 2.094 | 1.932 | 2.143 | 1.04 | 0.86 | 1.16 | 1.28 | 1.39 |
| L | 166T | 0.293 | 1.367 | 3.399 | 0.119 | 1.837 | 0.990 | 1.097 | 0.921 | 1.223 | 1.04 | 0.81 | 0.84 | 0.99 | 1.00 |
| L | 166V | 0.65 | ND | ND | ND | ND | ND | 0.92 | ND | 0.89 | 1.04 | 0.80 | 1.07 | 1.14 | 1.07 |
| L | 166W | 0.097 | 2.789 | 4.015 | 0.027 | 3.441 | 1.149 | 1.707 | 1.418 | 1.825 | 1.27 | 1.02 | 1.64 | 0.73 | 1.25 |
| L | 166Y | 0.282 | 1.310 | 4.425 | 0.117 | 1.884 | 0.924 | 1.053 | 0.754 | 1.103 | 1.16 | 0.93 | 0.61 | 1.77 | 1.16 |
| N | 167A | 0.937 | 1.231 | 0.498 | 1.520 | 1.221 | 1.025 | 1.005 | 0.748 | 1.085 | 1.01 | 0.91 | 0.84 | 1.10 | 0.61 |
| N | 167C | 1.031 | 0.869 | −3.155 | 1.029 | 0.904 | 0.885 | 0.677 | 0.830 | 0.881 | 0.97 | 0.98 | 0.71 | 0.61 | 0.89 |
| N | 167E | 1.266 | 0.841 | 0.848 | 1.527 | 0.849 | 0.885 | 0.838 | 0.746 | 0.847 | 0.99 | 0.97 | 0.73 | 0.89 | 0.95 |
| N | 167F | 0.840 | 1.127 | −1.132 | 0.802 | 1.114 | 1.103 | 1.121 | 1.176 | 1.105 | 0.97 | 0.96 | 0.90 | 1.11 | 0.87 |
| N | 167G | 0.942 | 0.949 | −0.620 | 0.862 | 1.007 | 0.967 | 0.925 | 0.996 | 0.948 | 1.15 | 1.09 | 1.22 | 1.17 | 0.87 |
| N | 167H | 1.114 | 0.857 | 1.294 | 1.061 | 0.815 | 0.817 | 0.843 | 0.848 | 0.807 | 0.99 | 0.95 | 0.97 | 0.98 | 0.92 |
| N | 167I | 0.885 | 1.011 | −2.646 | 0.893 | 1.088 | 1.102 | 1.031 | 1.056 | 1.098 | 1.00 | 0.94 | 0.89 | 1.09 | 0.73 |
| N | 167K | 0.968 | 0.886 | −2.115 | 0.992 | 1.000 | 1.027 | 0.963 | 0.868 | 0.988 | 0.96 | 0.89 | 0.86 | 1.05 | 0.90 |
| N | 167L | 1.090 | 0.820 | 1.367 | 1.247 | 0.968 | 1.008 | 0.931 | 0.707 | 0.985 | 1.01 | 0.69 | 1.06 | 0.84 | 0.78 |
| N | 167M | 0.569 | 1.527 | 0.886 | 0.426 | 1.489 | 1.549 | 0.349 | 0.000 | −2.176 | 0.96 | 0.86 | 0.88 | 0.84 | 0.66 |
| N | 167P | −0.197 | −1.709 | 9.217 | −0.042 | −0.421 | −0.053 | −0.242 | −0.326 | −0.663 | 0.00 | 0.00 | 0.00 | 0.00 | 0.00 |
| N | 167Q | 0.931 | 1.103 | −0.905 | 0.894 | 1.037 | 1.056 | 1.052 | 1.124 | 1.010 | 0.96 | 0.86 | 0.95 | 1.00 | 0.98 |
| N | 167R | 1.039 | 0.993 | 1.293 | 1.051 | 0.899 | 0.949 | 0.946 | 1.000 | 0.914 | 1.00 | 1.04 | 0.73 | 1.29 | 0.99 |
| N | 167S | 1.043 | 0.940 | 3.808 | 1.061 | 0.963 | 0.969 | 0.948 | 1.046 | 0.981 | 1.09 | 1.09 | 1.28 | 0.95 | 1.05 |
| N | 167T | 0.965 | 0.961 | 2.578 | 0.949 | 1.004 | 1.002 | 0.975 | 1.041 | 1.015 | 0.99 | 0.98 | 0.84 | 1.06 | 0.84 |
| N | 167V | 0.988 | 0.948 | 1.024 | 0.946 | 0.879 | 0.856 | 0.867 | 0.895 | 0.892 | 1.04 | 1.01 | 0.87 | 1.54 | 1.09 |
| N | 167W | 0.834 | 1.065 | −0.770 | 0.738 | 1.113 | 1.054 | 1.003 | 0.902 | 0.990 | 0.93 | 0.93 | 0.91 | 1.37 | 1.51 |
| N | 167Y | 1.206 | 0.798 | −4.699 | 1.553 | 0.917 | 0.704 | 0.998 | 0.746 | 1.012 | 1.19 | 0.67 | 0.16 | 0.73 | 0.72 |
| P | 184A | 0.177 | 2.955 | 5.317 | 0.062 | 2.151 | 0.704 | 0.964 | 0.389 | 1.166 | 1.19 | 0.08 | 0.16 | 0.84 | 0.60 |
| P | 184C | 0.074 | 6.411 | 7.285 | 0.019 | 3.742 | 0.967 | 1.572 | 0.892 | 2.190 | 0.98 | 0.10 | −0.15 | 0.22 | 0.51 |
| P | 184D | 0.165 | 3.536 | 3.414 | 0.058 | 2.938 | 1.406 | 1.594 | 0.971 | 1.721 | 1.00 | 0.21 | 0.19 | 1.36 | 0.27 |
| P | 184E | 0.173 | 3.157 | 2.464 | 0.056 | 2.500 | 1.102 | 1.361 | 0.920 | 1.448 | 0.97 | 0.27 | 0.39 | 0.69 | 0.84 |
| P | 184F | −0.031 | −15.719 | −20.459 | −0.006 | −6.532 | −1.239 | −2.605 | −1.823 | −4.424 | 1.29 | 0.05 | −0.24 | 1.75 | 0.93 |
| P | 184G | −0.015 | −29.642 | −50.903 | −0.003 | −16.444 | −3.225 | −6.175 | −3.861 | −10.301 | 1.06 | 0.03 | −0.17 | 0.84 | −0.73 |
| P | 184H | 0.052 | 8.434 | 6.161 | 0.013 | 6.135 | 1.750 | 2.577 | 1.655 | 3.312 | 1.03 | 0.13 | 0.00 | 0.22 | −0.17 |
| P | 184I | 0.016 | 19.085 | 19.899 | 0.004 | 15.469 | 3.601 | 6.015 | 3.862 | 9.233 | 1.18 | 0.08 | 0.03 | 1.36 | 0.20 |
| P | 184K | −0.045 | −6.916 | −18.866 | −0.009 | −4.498 | −0.766 | −1.742 | −1.284 | −3.079 | 1.09 | 0.06 | 0.07 | 1.35 | −0.72 |
| P | 184L | 0.036 | 10.360 | 23.863 | 0.009 | 8.745 | 2.395 | 3.509 | 2.218 | 4.938 | 1.10 | 0.06 | 0.26 | 1.58 | −0.73 |
| P | 184M | 0.043 | 11.920 | 16.202 | 0.011 | 4.252 | 0.631 | 1.760 | 1.247 | 2.854 | 1.06 | 0.08 | 0.21 | 1.29 | 0.44 |
| P | 184N | −0.004 | −141.513 | −459.264 | −0.001 | −70.228 | −17.479 | −29.471 | −16.478 | −43.257 | 1.32 | 0.00 | −0.02 | 0.35 | −1.13 |
| P | 184Q | 0.071 | 5.063 | 8.647 | 0.018 | 4.332 | 1.298 | 1.988 | 1.303 | 2.468 | 1.07 | 0.14 | 0.17 | 0.82 | 0.87 |
| P | 184R | −0.075 | −4.243 | −7.897 | −0.014 | −1.703 | −0.163 | −0.716 | −0.644 | −1.563 | 0.00 | 0.00 | 0.00 | 0.75 | 0.00 |
| P | 184S | 0.051 | 7.328 | 25.636 | 0.012 | 6.341 | 1.914 | 2.717 | 1.792 | 3.622 | 1.23 | 0.09 | 0.28 | 1.36 | 0.64 |
| P | 184T | 0.004 | 93.652 | −1640.364 | 0.001 | 90.800 | 35.094 | 43.161 | 18.481 | 51.595 | 1.21 | 0.33 | 0.39 | 1.17 | 0.26 |
| P | 184V | −0.018 | −18.008 | −35.353 | −0.004 | −17.610 | −5.155 | −7.378 | −4.932 | −10.022 | 1.31 | 0.13 | 0.16 | 1.29 | 0.08 |
| P | 184W | 0.025 | 14.748 | 26.626 | 0.007 | 11.072 | 2.870 | 4.469 | 2.883 | 6.368 | 1.47 | 0.10 | 0.08 | 1.42 | 0.38 |
| P | 184Y | 0.030 | 11.013 | 41.147 | 0.007 | 7.812 | 1.413 | 2.936 | 1.704 | 4.756 | 1.43 | 0.01 | 0.86 | 0.75 | −5.28 |
| D | 185A | 0.00 | ND | ND | ND | ND | ND | 0.00 | ND | 0.00 | 0.00 | 0.00 | 0.00 | 0.00 | 0.00 |
| D | 185C | 0.003 | 2634.889 | 4099.857 | 0.000 | 1815.709 | 568.580 | 794.369 | 300.525 | 884.277 | 1.02 | 0.06 | 0.24 | 0.84 | 0.47 |
| D | 185E | 0.284 | 1.997 | 3.863 | 0.119 | 1.828 | 0.890 | 0.975 | 0.191 | 0.841 | 1.09 | 0.04 | 0.30 | 1.73 | 0.28 |
| D | 185F | −0.098 | −3.089 | −13.995 | −0.020 | −1.748 | −0.225 | −0.689 | −0.550 | −1.270 | 0.00 | 0.00 | 0.00 | 0.00 | 0.00 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| D | 185G | −0.067 | −6.616 | −6.252 | −0.014 | −3.579 | −0.619 | −1.293 | −0.822 | −1.921 | 0.00 | 0.00 | 0.00 | 0.00 | 0.00 |
| D | 185H | −0.095 | −3.188 | −12.458 | −0.019 | −2.126 | −0.338 | −0.805 | −0.573 | −1.371 | 0.00 | 0.00 | 0.00 | 0.00 | 0.00 |
| D | 185I | −0.102 | −3.485 | −9.813 | −0.022 | −2.290 | −0.435 | −0.896 | −0.504 | −1.341 | 0.00 | 0.00 | 0.00 | 0.00 | 0.00 |
| D | 185K | −0.125 | −0.858 | −8.833 | −0.025 | −0.809 | −0.122 | −0.391 | −0.413 | −0.976 | 0.00 | 0.00 | 0.00 | 0.00 | 0.00 |
| D | 185L | −0.028 | −8.515 | −29.960 | −0.005 | −7.268 | −0.946 | −2.772 | −2.050 | −4.991 | 0.00 | 0.00 | 0.00 | 0.00 | 0.00 |
| D | 185M | −0.057 | −12.203 | −34.580 | −0.016 | −4.172 | −0.702 | −1.614 | −0.962 | −1.718 | 0.00 | 0.00 | 0.00 | 0.00 | −0.29 |
| D | 185N | 0.139 | 3.610 | 6.359 | 0.043 | 2.746 | 0.947 | 1.226 | 0.374 | 1.475 | 1.25 | 0.04 | 0.37 | 1.00 | 0.00 |
| D | 185P | −0.166 | −0.325 | −2.234 | −0.027 | −0.480 | −0.038 | −0.259 | −0.320 | −0.715 | 0.00 | 0.00 | 0.00 | 0.00 | 0.00 |
| D | 185Q | −0.085 | −3.741 | −4.894 | −0.019 | −2.919 | −0.564 | −1.147 | −0.612 | −1.618 | 0.00 | 0.00 | 0.00 | 0.00 | 0.00 |
| D | 185R | −0.168 | 0.789 | −5.543 | −0.036 | −0.574 | −0.029 | −0.280 | −0.315 | −0.694 | 0.00 | 0.00 | 0.00 | 0.00 | 0.00 |
| D | 185S | 0.153 | 4.005 | 7.821 | 0.055 | 3.370 | 1.541 | 1.715 | 0.345 | 1.816 | 1.18 | 0.01 | 0.64 | 1.32 | 0.89 |
| D | 185T | 0.016 | 20.881 | 44.239 | 0.005 | 23.961 | 8.623 | 10.682 | 3.012 | 12.034 | 1.25 | 0.03 | 0.30 | 2.21 | 0.64 |
| D | 185V | −0.120 | −2.233 | −15.400 | −0.022 | −1.612 | −0.242 | −0.659 | −0.448 | −1.115 | 0.00 | 0.00 | 0.00 | 0.00 | 0.00 |
| D | 185W | −0.111 | −3.002 | −7.536 | −0.021 | −2.162 | −0.348 | −0.875 | −0.515 | −1.091 | 0.00 | 0.00 | 0.00 | 0.00 | 0.00 |
| D | 185Y | −0.110 | −2.927 | −9.640 | −0.021 | −1.502 | −0.179 | −0.611 | −0.489 | −1.167 | 0.00 | 0.00 | 0.00 | 0.00 | 0.00 |
| G | 187A | 1.245 | 0.902 | 1.678 | 1.932 | 0.946 | 1.027 | 0.913 | 0.232 | 0.945 | 0.89 | 0.07 | 0.21 | 0.75 | 0.73 |
| G | 187C | 0.371 | 1.756 | 4.272 | 0.191 | 1.750 | 1.101 | 1.008 | 0.528 | 1.163 | 0.83 | 0.16 | 0.37 | 0.45 | 0.66 |
| G | 187D | 0.716 | 1.135 | 0.554 | 0.157 | 1.341 | 1.144 | 1.024 | 0.445 | 1.078 | 0.92 | 0.25 | 0.35 | 0.72 | 0.79 |
| G | 187E | 0.821 | 1.231 | 2.373 | 0.918 | 1.243 | 1.158 | 1.028 | 0.408 | 1.036 | 0.91 | 0.19 | 0.30 | 1.52 | 1.13 |
| G | 187F | 0.643 | 1.443 | 3.229 | 0.630 | 1.488 | 1.187 | 1.053 | 0.302 | 1.065 | 0.93 | 0.09 | 0.17 | 0.69 | 0.96 |
| G | 187H | 0.715 | 1.079 | 3.030 | 0.614 | 1.264 | 1.010 | 0.884 | 0.222 | 0.888 | 1.01 | 0.11 | 0.32 | 1.32 | 1.18 |
| G | 187I | 0.497 | 1.333 | −1.326 | 0.385 | 1.719 | 1.227 | 1.074 | 0.157 | 1.085 | 0.94 | 0.03 | 0.38 | 1.31 | 1.11 |
| G | 187K | 0.624 | 1.129 | −2.030 | 0.546 | 1.387 | 1.073 | 0.945 | 0.100 | 0.933 | 0.90 | 0.02 | 0.20 | 1.03 | 0.97 |
| G | 187L | 0.391 | 1.687 | 1.477 | 0.255 | 1.891 | 1.318 | 1.137 | 0.261 | 1.252 | 0.92 | 0.04 | 0.23 | 0.82 | 0.85 |
| G | 187M | 0.559 | 1.385 | 0.479 | 0.454 | 1.471 | 1.094 | 0.987 | 0.188 | 1.002 | 0.91 | 0.05 | 0.24 | 1.12 | 0.76 |
| G | 187N | 0.619 | 1.227 | −0.047 | 0.500 | 1.288 | 1.018 | 0.995 | 0.695 | 0.995 | 1.00 | 0.54 | 0.52 | 0.66 | 0.56 |
| G | 187P | 0.757 | 1.276 | 2.852 | 0.746 | 1.232 | 1.065 | 1.004 | 0.309 | 0.961 | 0.88 | 0.08 | 0.17 | 0.84 | 0.73 |
| G | 187Q | 0.559 | 1.297 | 5.029 | 0.404 | 1.322 | 0.917 | 0.896 | 0.286 | 0.916 | 0.96 | 0.08 | 0.12 | 1.14 | 0.63 |
| G | 187R | 0.271 | 2.043 | 4.894 | 0.125 | 2.140 | 1.043 | 1.046 | 0.228 | 1.137 | 1.02 | 0.01 | 0.13 | 0.73 | 0.80 |
| G | 187S | 0.417 | 1.866 | 9.598 | 0.279 | 1.835 | 1.463 | 1.306 | 0.503 | 1.448 | 1.14 | 0.16 | 0.41 | 1.27 | 1.07 |
| G | 187T | 0.247 | 1.591 | −0.791 | 0.104 | 2.115 | 1.074 | 1.107 | 0.238 | 1.191 | 0.95 | 0.01 | 0.49 | 1.01 | 0.44 |
| G | 187V | 0.485 | 1.338 | 3.205 | 0.327 | 1.674 | 1.198 | 1.117 | 0.207 | 1.090 | 0.93 | 0.03 | 0.29 | 1.03 | 0.63 |
| G | 187W | 0.385 | 1.568 | 2.131 | 0.236 | 1.782 | 1.130 | 1.152 | 0.345 | 1.087 | 1.02 | 0.12 | 0.47 | 1.27 | 1.14 |
| G | 187Y | 0.420 | 1.301 | −3.568 | 0.257 | 1.690 | 1.211 | 1.144 | 0.234 | 1.220 | 1.01 | 0.08 | 0.30 | 0.57 | 0.76 |
| S | 188A | 1.034 | 0.900 | 6.542 | 1.157 | 0.946 | 0.984 | 0.706 | 0.492 | 0.926 | 0.95 | 0.60 | 0.43 | 0.96 | 0.64 |
| S | 188C | 0.720 | 1.162 | 0.717 | 0.582 | 1.095 | 1.047 | 0.829 | 0.734 | 0.950 | 0.97 | 0.82 | 1.01 | 0.91 | 0.47 |
| S | 188D | 0.877 | 1.103 | −2.822 | 0.821 | 1.068 | 1.079 | 1.048 | 1.074 | 1.074 | 1.06 | 1.28 | 1.08 | 0.96 | 0.81 |
| S | 188E | 0.967 | 0.976 | 1.851 | 0.894 | 0.953 | 0.964 | 0.952 | 0.786 | 0.916 | 0.92 | 0.80 | 0.49 | 0.78 | 0.89 |
| S | 188F | 0.829 | 1.248 | 12.226 | 0.735 | 1.140 | 1.162 | 1.126 | 1.155 | 1.059 | 1.04 | 1.26 | 1.76 | 0.91 | 1.16 |
| S | 188G | 0.792 | 1.131 | 1.937 | 0.625 | 1.150 | 1.048 | 1.013 | 0.718 | 1.016 | 1.07 | 0.53 | 0.65 | 1.23 | 0.71 |
| S | 188I | 0.893 | 1.017 | −2.242 | 0.801 | 1.067 | 1.059 | 1.030 | 0.560 | 1.033 | 1.01 | 0.34 | 0.37 | 1.29 | 0.95 |
| S | 188K | 0.746 | 1.124 | 8.605 | 0.597 | 1.234 | 1.207 | 1.144 | 1.074 | 1.164 | 0.95 | 0.12 | 0.43 | 1.28 | 1.38 |
| S | 188L | 0.941 | 1.042 | 3.970 | 0.916 | 1.119 | 1.024 | 1.043 | 0.350 | 1.036 | 1.02 | 0.44 | 0.34 | 0.94 | 0.89 |
| S | 188M | 1.067 | 0.910 | 3.568 | 1.355 | 1.089 | 1.162 | 1.043 | 0.435 | 0.867 | 0.90 | 0.20 | 0.60 | 1.08 | 0.65 |
| S | 188N | 0.943 | 0.939 | −3.016 | 0.866 | 0.951 | 0.971 | 0.696 | 0.260 | 0.904 | 0.91 | 0.82 | 1.06 | 0.99 | 0.61 |
| S | 188P | 0.979 | 0.970 | 4.130 | 0.855 | 1.004 | 1.025 | 0.813 | 0.614 | 0.955 | 0.95 | 0.67 | 0.87 | 0.95 | 0.88 |
| S | 188Q | 0.801 | 1.226 | −2.610 | 0.623 | 1.055 | 1.110 | 0.929 | 0.536 | 1.019 | 0.95 | 0.30 | 0.41 | 0.98 | 0.93 |
| S | 188R | 0.739 | 1.134 | 5.083 | 0.568 | 1.264 | 1.145 | 1.059 | 0.244 | 1.015 | 0.98 | 0.09 | 0.27 | 0.86 | 0.84 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| S | 188T | 0.844 | 1.131 | 8.746 | 0.805 | 1.201 | 1.189 | 1.143 | 0.790 | 1.149 | 1.01 | 0.81 | 1.32 | 1.03 | 1.04 |
| S | 188V | 0.896 | 1.063 | 0.521 | 0.869 | 1.202 | 1.199 | 1.165 | 0.484 | 1.121 | 1.04 | 0.43 | 0.44 | 1.13 | 0.73 |
| S | 188W | -0.103 | -3.042 | -13.435 | -0.020 | -2.512 | -0.640 | -1.053 | -1.283 | -1.796 | 0.00 | 0.00 | 0.00 | 0.00 | 0.00 |
| G | 190A | 1.454 | 0.823 | 0.632 | 2.452 | 0.838 | 1.008 | 0.893 | 0.203 | 0.930 | 0.97 | 0.62 | 0.89 | 1.08 | 1.10 |
| G | 190C | 0.719 | 1.003 | 0.741 | 0.611 | 1.206 | 0.951 | 0.822 | 0.110 | 0.884 | 0.97 | 0.26 | 0.46 | 0.98 | 0.81 |
| G | 190D | -0.073 | -8.602 | -3.041 | -0.017 | -2.462 | -0.297 | -0.896 | -0.279 | -1.861 | 0.00 | 0.00 | 0.00 | 0.00 | 0.00 |
| G | 190E | 0.110 | 3.802 | 14.000 | 0.036 | 4.477 | 1.754 | 1.904 | 0.165 | 2.407 | 1.43 | 0.05 | 0.61 | 2.27 | 1.64 |
| G | 190F | 0.280 | 2.157 | 5.406 | 0.127 | 2.317 | 1.251 | 1.209 | 0.103 | 1.387 | 1.01 | 0.06 | 0.65 | 1.04 | 0.51 |
| G | 190H | 0.596 | 0.899 | 1.119 | 0.351 | 1.274 | 0.789 | 0.749 | 0.053 | 0.826 | 1.01 | 0.05 | 0.48 | 1.18 | 0.36 |
| G | 190I | -0.089 | 1.542 | -14.862 | -0.018 | -1.051 | -0.105 | -0.478 | -0.197 | -1.324 | 0.00 | 0.00 | 0.00 | 0.00 | 0.00 |
| G | 190K | 0.581 | 1.066 | 2.894 | 0.417 | 1.411 | 1.107 | 0.978 | 0.045 | 1.057 | 1.02 | 0.05 | 0.41 | 1.09 | 0.24 |
| G | 190L | 0.091 | 2.726 | 26.223 | 0.021 | 2.997 | 0.601 | 0.942 | 0.196 | 1.763 | 0.00 | 0.04 | 0.00 | 0.00 | 0.00 |
| G | 190M | 0.171 | 2.870 | 2.394 | 0.065 | 2.470 | 0.844 | 0.986 | 0.121 | 1.362 | 1.07 | 0.00 | 0.35 | 1.02 | -0.25 |
| G | 190P | -0.026 | -21.330 | -13.738 | -0.005 | -7.119 | -0.790 | -2.721 | -0.797 | -5.332 | 0.00 | 0.00 | 0.00 | 0.00 | 0.00 |
| G | 190Q | -0.731 | 0.289 | -1.055 | -0.127 | -0.334 | -1.472 | -0.170 | 0.000 | -0.014 | 1.07 | 0.07 | 0.32 | 1.38 | 0.90 |
| G | 190R | 0.436 | 1.712 | 13.628 | 0.243 | 1.478 | 1.006 | 0.951 | 0.321 | 1.034 | 0.99 | 0.08 | 0.50 | 1.61 | 0.76 |
| G | 190S | 0.661 | 1.296 | 0.005 | 0.578 | 1.384 | 1.184 | 1.145 | 0.256 | 1.127 | 1.02 | 0.47 | 0.95 | 1.13 | 1.31 |
| G | 190T | -0.069 | -2.206 | -7.087 | -0.012 | -2.037 | -0.215 | -0.789 | -0.262 | -1.751 | 0.00 | 0.00 | 0.00 | 0.00 | 0.00 |
| G | 190V | -0.069 | 0.280 | -15.494 | -0.012 | -1.492 | -0.143 | -0.674 | -0.256 | -1.732 | 0.00 | 0.00 | 0.00 | 0.00 | 0.00 |
| G | 190W | 0.117 | 2.834 | 7.906 | 0.035 | 3.217 | 1.141 | 1.408 | 0.189 | 1.836 | 1.29 | 0.11 | 0.58 | 1.13 | 0.98 |
| G | 190Y | 0.193 | 1.936 | 7.082 | 0.079 | 2.973 | 1.453 | 1.442 | 0.125 | 1.727 | 1.02 | 0.06 | 0.50 | 0.97 | 0.85 |
| Q | 192C | -0.800 | 0.079 | -2.953 | -0.162 | -0.341 | -1.523 | -0.368 | -0.137 | -0.320 | 1.05 | 1.22 | 0.83 | 0.79 | 0.79 |
| Q | 192D | 1.188 | 0.885 | 1.817 | 1.695 | 0.941 | 1.038 | 0.967 | 1.003 | 0.974 | 1.04 | 1.32 | 1.37 | 1.07 | 0.61 |
| Q | 192E | 1.137 | 0.921 | 2.208 | 1.420 | 0.938 | 0.958 | 0.925 | 0.963 | 0.922 | 1.04 | 1.20 | 1.23 | 0.93 | 0.67 |
| Q | 192F | 0.822 | 1.112 | 2.087 | 0.726 | 1.153 | 1.016 | 0.984 | 0.952 | 0.999 | 1.01 | 1.00 | 1.15 | 1.03 | 0.94 |
| Q | 192G | 0.576 | 1.420 | 3.143 | 0.444 | 1.528 | 1.206 | 1.097 | 0.938 | 1.205 | 1.07 | 0.87 | 1.35 | 0.95 | 0.66 |
| Q | 192I | 0.423 | 1.695 | 4.821 | 0.273 | 1.927 | 1.359 | 1.289 | 1.155 | 1.405 | 1.10 | 1.04 | 2.14 | 1.35 | 1.10 |
| Q | 192K | 0.617 | 1.375 | 0.904 | 0.474 | 1.363 | 1.240 | 1.238 | 1.121 | 1.242 | 1.01 | 0.53 | 1.07 | 1.14 | 0.91 |
| Q | 192L | 0.580 | 1.569 | -1.089 | 0.413 | 1.454 | 1.327 | 1.376 | 1.234 | 1.273 | 0.96 | 0.57 | 1.24 | 1.05 | 0.60 |
| Q | 192N | 1.044 | 1.009 | -0.244 | 1.238 | 0.963 | 0.983 | 0.981 | 1.019 | 0.970 | 0.99 | 1.14 | 1.12 | 0.84 | 0.77 |
| Q | 192P | 0.667 | 1.309 | 2.163 | 0.590 | 1.282 | 1.114 | 1.103 | 1.038 | 1.155 | 1.04 | 0.85 | 0.71 | 1.09 | 0.85 |
| Q | 192R | 0.843 | 1.159 | 0.999 | 0.723 | 1.098 | 0.988 | 0.977 | 0.907 | 0.977 | 1.03 | 0.75 | 1.10 | 1.05 | 0.95 |
| Q | 192S | 0.960 | 1.101 | 0.793 | 1.100 | 1.116 | 1.177 | 1.177 | 1.155 | 1.168 | 0.98 | 0.98 | 1.00 | 1.11 | 0.79 |
| Q | 192T | 0.856 | 1.113 | 1.388 | 0.823 | 1.124 | 1.079 | 1.058 | 1.044 | 1.074 | 1.03 | 1.03 | 1.30 | 1.24 | 0.77 |
| Q | 192V | 0.609 | 1.260 | 1.027 | 0.440 | 1.328 | 1.064 | 1.056 | 1.026 | 1.104 | 1.18 | 1.14 | 0.95 | 1.03 | 0.87 |
| Q | 192Y | 0.90 | ND | ND | ND | ND | ND | 0.92 | ND | 0.86 | 0.99 | 0.95 | 1.59 | 1.15 | 0.91 |
| P | 195A | 0.711 | 0.999 | 3.326 | 0.570 | 1.127 | 0.804 | 0.813 | 0.548 | 0.821 | 0.87 | 0.49 | 0.39 | 0.63 | 1.00 |
| P | 195C | 0.429 | 1.517 | 3.366 | 0.254 | 1.536 | 0.976 | 1.001 | 0.700 | 1.031 | 0.87 | 0.42 | 0.54 | 0.92 | 0.50 |
| P | 195D | 0.690 | 1.168 | 2.160 | 0.496 | 1.061 | 0.796 | 0.832 | 0.888 | 0.850 | 0.88 | 0.93 | 1.11 | 0.89 | 1.13 |
| P | 195F | 0.370 | 1.921 | 6.552 | 0.196 | 1.674 | 1.003 | 1.074 | 0.854 | 1.093 | 1.04 | 0.50 | 0.45 | 1.21 | 0.94 |
| P | 195G | 0.501 | 1.076 | 1.740 | 0.280 | 1.436 | 0.963 | 1.013 | 0.947 | 1.011 | 0.93 | 0.72 | 0.53 | 0.87 | 0.91 |
| P | 195H | 0.440 | 1.195 | 3.258 | 0.229 | 1.549 | 0.950 | 0.996 | 0.748 | 1.001 | 0.91 | 0.44 | 0.49 | 0.76 | 1.21 |
| P | 195I | 0.584 | 1.091 | -0.766 | 0.377 | 1.316 | 0.993 | 0.991 | 0.681 | 1.043 | 0.93 | 0.43 | 0.54 | 0.95 | 0.93 |
| P | 195K | 0.502 | 1.111 | 4.313 | 0.314 | 1.487 | 1.004 | 1.055 | 0.480 | 1.040 | 0.88 | 0.23 | 0.42 | 1.02 | 1.00 |
| P | 195L | 0.572 | 1.062 | 3.828 | 0.371 | 1.350 | 0.966 | 0.937 | 0.396 | 0.956 | 0.96 | 0.32 | 0.35 | 0.74 | 0.77 |
| P | 195M | 0.486 | 1.271 | 2.809 | 0.308 | 1.457 | 0.930 | 0.936 | 0.533 | 0.942 | 0.90 | 0.37 | 0.47 | 0.90 | 1.09 |
| P | 195N | 0.433 | 1.295 | 3.138 | 0.246 | 1.409 | 0.859 | 0.900 | 0.653 | 0.946 | 0.88 | 0.40 | 0.51 | 0.86 | 0.99 |
| P | 195Q | 0.556 | 1.230 | 3.636 | 0.364 | 1.291 | 0.916 | 0.950 | 0.783 | 0.963 | 0.93 | 0.56 | 0.50 | 0.89 | 1.02 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 4 | DP3 | DP3 HS | corn flour 30 min | Cleaning pH 8 | Cleaning pH 10 |
|---|---|---|---|---|---|---|---|---|---|---|---|---|---|---|---|
| P | 195R | 0.452 | 1.563 | 4.440 | 0.264 | 1.534 | 0.932 | 0.867 | 0.346 | 0.939 | 1.00 | 0.30 | 0.28 | 1.16 | 1.10 |
| P | 195S | 0.477 | 1.314 | -2.383 | 0.276 | 1.420 | 0.954 | 0.974 | 0.773 | 1.036 | 1.00 | 0.57 | 0.47 | 0.93 | 1.09 |
| P | 195T | 0.420 | 1.502 | 0.679 | 0.227 | 1.649 | 1.148 | 1.144 | 0.873 | 1.221 | 0.96 | 0.45 | 0.59 | 1.07 | 0.86 |
| P | 195V | 0.593 | 1.028 | -0.397 | 0.349 | 1.329 | 1.066 | 1.010 | 0.773 | 1.101 | ND | ND | ND | ND | ND |
| P | 195W | 0.175 | 1.665 | 6.739 | 0.058 | 2.695 | 1.243 | 1.455 | 0.898 | 1.552 | 0.93 | 0.39 | 0.65 | 0.37 | 1.12 |
| P | 195Y | 0.152 | 2.023 | 21.477 | 0.048 | 3.003 | 1.203 | 1.468 | 0.786 | 1.661 | 1.00 | 0.42 | 0.36 | 0.19 | 1.50 |
| N | 199A | 1.053 | 0.882 | 4.986 | 1.212 | 0.962 | 0.967 | 0.904 | 0.673 | 0.877 | 1.01 | 0.92 | 0.73 | 0.57 | 0.66 |
| N | 199C | 0.571 | 1.286 | 5.318 | 0.360 | 1.259 | 0.997 | 0.944 | 0.911 | 0.968 | 0.94 | 0.92 | 0.85 | 0.85 | 1.08 |
| N | 199D | 0.890 | 1.073 | 3.799 | 0.749 | 1.033 | 1.019 | 1.041 | 1.040 | 1.015 | 1.02 | 1.06 | 0.96 | 0.72 | 0.87 |
| N | 199E | 0.730 | 1.162 | 1.046 | 0.501 | 1.111 | 0.995 | 0.970 | 1.007 | 0.993 | 1.01 | 1.01 | 1.15 | 0.58 | 0.61 |
| N | 199F | 0.408 | 1.795 | 5.467 | 0.200 | 1.538 | 1.043 | 1.037 | 1.068 | 1.115 | 1.02 | 0.99 | 0.80 | 1.25 | 0.30 |
| N | 199G | 0.810 | 1.057 | -0.129 | 0.654 | 1.087 | 0.964 | 0.960 | 0.991 | 0.976 | 1.01 | 0.91 | 0.88 | 0.87 | 0.79 |
| N | 199H | 0.780 | 1.160 | -1.206 | 0.625 | 1.116 | 1.035 | 1.026 | 1.043 | 1.027 | 1.04 | 1.01 | 0.79 | 0.99 | 0.79 |
| N | 199I | 0.284 | 1.816 | -6.886 | 0.115 | 1.909 | 1.092 | 1.134 | 1.073 | 1.229 | 1.00 | 0.77 | 0.71 | 0.68 | 0.21 |
| N | 199L | 0.473 | 1.310 | 1.153 | 0.293 | 1.611 | 1.207 | 1.125 | 0.860 | 1.157 | 1.04 | 0.94 | 0.54 | 0.84 | 0.66 |
| N | 199M | 0.714 | 1.158 | 2.841 | 0.572 | 1.168 | 0.982 | 0.878 | 0.703 | 0.904 | 1.00 | 0.87 | 0.61 | 0.43 | 0.43 |
| N | 199P | 0.352 | 1.736 | 5.865 | 0.162 | 1.648 | 1.062 | 1.071 | 1.077 | 1.160 | 1.00 | 0.81 | 0.79 | 0.41 | -0.58 |
| N | 199R | 0.831 | 1.018 | 0.038 | 0.639 | 0.975 | 0.896 | 0.876 | 0.916 | 0.899 | 1.02 | 1.00 | 1.10 | 0.95 | 0.75 |
| N | 199S | 0.778 | 1.144 | 4.172 | 0.593 | 1.176 | 1.071 | 1.061 | 1.159 | 1.077 | 1.17 | 1.20 | 0.90 | 1.12 | 0.88 |
| N | 199T | 0.541 | 0.727 | 3.042 | 0.170 | 0.828 | 0.349 | 0.393 | 0.434 | 0.490 | 0.51 | 0.52 | 0.00 | 0.29 | 0.05 |
| N | 199V | 0.278 | 1.924 | 10.994 | 0.122 | 2.122 | 1.337 | 1.399 | 1.269 | 1.439 | 1.08 | 0.89 | 0.80 | 0.76 | 0.37 |
| N | 199Y | 0.286 | 1.854 | 6.691 | 0.142 | 2.233 | 1.441 | 1.452 | 1.185 | 1.508 | 1.10 | 1.01 | 0.78 | 1.01 | 0.90 |
| N | 200A | 0.190 | 2.757 | 5.129 | 0.077 | 2.603 | 1.228 | 1.417 | 1.031 | 1.587 | 0.85 | 0.56 | 1.01 | 0.79 | 1.04 |
| T | 200C | 0.216 | 1.744 | 6.407 | 0.105 | 2.636 | 1.546 | 1.625 | 1.435 | 1.763 | 0.87 | 0.62 | 0.96 | 1.03 | 0.77 |
| T | 200D | 0.092 | 3.726 | 7.739 | 0.027 | 4.313 | 1.679 | 2.141 | 1.952 | 2.696 | 0.84 | 0.52 | 0.67 | 0.83 | 1.38 |
| T | 200E | 0.075 | 4.552 | 20.334 | 0.020 | 3.770 | 1.060 | 1.622 | 1.561 | 2.368 | 0.83 | 0.47 | 1.09 | 1.25 | 0.81 |
| T | 200F | 0.028 | 11.070 | 35.517 | 0.007 | 12.420 | 4.362 | 5.990 | 5.637 | 7.367 | 0.83 | 0.59 | 0.34 | 1.05 | 0.96 |
| T | 200G | 0.184 | 1.462 | 5.497 | 0.053 | 2.382 | 1.077 | 1.261 | 1.282 | 1.466 | 0.79 | 0.68 | 0.96 | 0.52 | 0.97 |
| T | 200H | 0.221 | 1.780 | -1.754 | 0.078 | 2.539 | 1.412 | 1.528 | 1.486 | 1.511 | 1.01 | 0.88 | 1.20 | 2.18 | 0.91 |
| T | 200I | 0.397 | 1.545 | 1.152 | 0.212 | 1.793 | 1.321 | 1.345 | 1.313 | 1.330 | 0.91 | 0.87 | 1.11 | 1.23 | 0.97 |
| T | 200K | 0.136 | 1.647 | 25.517 | 0.033 | 2.652 | 0.961 | 1.196 | 0.928 | 1.536 | 0.87 | 0.38 | 0.86 | 0.83 | 1.93 |
| T | 200L | 0.138 | 2.272 | 18.509 | 0.039 | 3.219 | 1.374 | 1.620 | 1.161 | 1.858 | 0.86 | 0.73 | 0.89 | 0.55 | 0.37 |
| T | 200M | 0.462 | 1.338 | 0.803 | 0.269 | 1.401 | 0.882 | 0.898 | 0.693 | 0.927 | 0.78 | 0.64 | 0.97 | 0.77 | 0.71 |
| T | 200N | 0.913 | 1.120 | 0.010 | 1.076 | 1.077 | 1.078 | 1.076 | 1.032 | 0.968 | 0.87 | 0.91 | 1.22 | 0.95 | 0.93 |
| T | 200P | 0.101 | 4.259 | 4.348 | 0.030 | 3.388 | 1.175 | 1.614 | 1.303 | 2.049 | 0.79 | 0.34 | 0.64 | 0.92 | 1.10 |
| T | 200Q | 0.028 | -3.286 | 36.641 | 0.005 | 4.663 | 0.674 | 2.246 | 2.447 | 4.575 | 0.30 | 0.23 | -0.22 | 1.66 | 0.48 |
| T | 200R | 0.085 | 5.028 | 5.698 | 0.023 | 4.503 | 1.752 | 2.218 | 1.905 | 2.651 | 0.78 | 0.48 | 0.58 | 0.92 | 0.93 |
| T | 200S | 0.769 | 1.127 | 2.009 | 0.566 | 1.139 | 1.012 | 1.034 | 1.056 | 1.021 | 0.98 | 1.05 | 1.30 | 0.83 | 1.24 |
| T | 200V | 0.341 | 1.561 | 4.818 | 0.152 | 1.986 | 1.289 | 1.218 | 1.084 | 1.214 | 1.00 | 0.83 | 1.37 | 1.21 | 0.94 |
| T | 200W | -0.051 | -10.879 | -3.065 | -0.010 | -4.035 | -0.770 | -1.655 | 1.159 | 1.177 | 0.98 | 0.65 | 3.06 | -0.61 | 3.59 |
| T | 200Y | 0.054 | 5.898 | 0.192 | 0.014 | 6.367 | 2.423 | 3.066 | -1.651 | -2.982 | 1.30 | 0.43 | 0.98 | 0.37 | 0.26 |
| S | 201A | 0.961 | 1.093 | -0.420 | 1.213 | 1.096 | 1.193 | 1.120 | 2.861 | 3.992 | 0.79 | 0.84 | 1.04 | 0.96 | 1.06 |
| S | 201C | 0.874 | 1.040 | -0.017 | 0.815 | 0.974 | 0.932 | 0.922 | 0.860 | 1.105 | 0.99 | 0.80 | 0.88 | 0.86 | 1.12 |
| S | 201D | 0.766 | 1.262 | 0.552 | 0.803 | 1.224 | 1.224 | 1.218 | 0.797 | 0.911 | 0.92 | 0.91 | 1.26 | 0.97 | 1.27 |
| S | 201E | 0.879 | 1.215 | 0.856 | 0.910 | 1.132 | 1.175 | 1.188 | 1.084 | 1.214 | 1.00 | 0.91 | 0.90 | 1.04 | 1.06 |
| S | 201F | 0.424 | 1.798 | -0.714 | 0.234 | 1.760 | 1.352 | 1.325 | 1.159 | 1.177 | 1.02 | 0.92 | 0.98 | 0.60 | 1.30 |
| S | 201G | 0.880 | 1.141 | 0.513 | 0.817 | 1.104 | 1.051 | 1.094 | 1.265 | 1.369 | 0.91 | 0.94 | 1.42 | 0.83 | 1.03 |
| S | 201H | 0.887 | 0.994 | 1.494 | 0.790 | 1.079 | 1.054 | 1.068 | 0.948 | 0.991 | 0.98 | 0.90 | 1.16 | 1.07 | 1.19 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| S | 201I | 0.704 | 1.049 | 0.611 | 0.507 | 1.226 | 1.046 | 1.061 | 0.904 | 1.054 | 0.96 | 0.88 | 1.06 | 0.90 | 1.16 |
| S | 201K | 0.972 | 0.963 | 0.423 | 1.001 | 1.042 | 1.066 | 1.074 | 0.826 | 1.044 | 0.99 | 0.89 | 1.40 | 1.31 | 1.52 |
| S | 201L | 0.622 | 0.995 | -2.102 | 0.414 | 1.391 | 1.173 | 1.184 | 0.772 | 1.148 | 0.97 | 0.86 | 1.12 | 0.92 | 1.00 |
| S | 201M | 1.180 | 0.913 | -1.031 | 1.753 | 0.957 | 1.093 | 1.012 | 0.756 | 1.021 | 0.89 | 0.72 | 0.77 | 0.88 | 0.90 |
| S | 201N | 1.091 | 0.995 | -0.686 | 1.431 | 1.024 | 1.099 | 1.050 | 0.802 | 1.020 | 0.91 | 0.78 | 0.92 | 0.77 | 0.82 |
| S | 201P | 0.814 | 1.217 | -0.047 | 0.787 | 1.204 | 1.135 | 1.112 | 0.836 | 1.065 | 0.86 | 0.76 | 0.80 | 0.84 | 0.77 |
| S | 201Q | 1.000 | 1.129 | 0.674 | 1.115 | 1.043 | 1.076 | 1.032 | 0.801 | 1.017 | 0.95 | 0.84 | 0.78 | 1.08 | 1.11 |
| S | 201R | 1.391 | 0.909 | -0.369 | 2.274 | 0.888 | 1.148 | 1.192 | 1.001 | 1.133 | 0.95 | 0.85 | 0.86 | 1.21 | 1.20 |
| S | 201T | 0.898 | 1.104 | -0.738 | 0.885 | 1.185 | 1.193 | 1.152 | 0.843 | 1.146 | 1.02 | 0.91 | 1.08 | 1.16 | 1.64 |
| S | 201V | 0.814 | 1.031 | 0.034 | 0.728 | 1.208 | 1.113 | 1.101 | 0.756 | 1.060 | 1.00 | 0.85 | 1.02 | 1.05 | 1.19 |
| S | 201W | 0.593 | 1.184 | -1.586 | 0.405 | 1.413 | 1.150 | 1.124 | 0.737 | 1.083 | 1.02 | 0.84 | 1.46 | 1.31 | 1.26 |
| S | 201Y | 0.374 | 1.827 | -0.247 | 0.195 | 1.692 | 1.192 | 1.164 | 1.184 | 1.258 | 0.96 | 0.64 | 0.97 | 0.78 | 1.19 |
| A | 202C | 0.652 | 1.315 | 0.615 | 0.501 | 1.166 | 0.928 | 0.932 | 0.850 | 0.927 | 1.09 | 1.02 | 1.25 | 0.64 | 1.31 |
| A | 202D | -0.072 | -2.117 | -11.615 | -0.016 | -1.978 | -0.326 | -0.933 | -1.053 | -2.034 | 0.00 | 0.00 | 0.00 | 0.00 | 0.00 |
| A | 202E | -0.072 | -7.666 | -4.668 | -0.014 | -2.176 | -0.419 | -1.050 | -1.142 | -2.092 | 0.00 | 0.00 | 0.00 | 0.00 | 0.00 |
| A | 202F | -0.084 | -4.371 | 38.084 | -0.014 | -2.286 | -0.434 | -0.970 | -0.943 | -1.842 | 0.88 | 0.56 | 0.55 | 1.05 | 2.34 |
| A | 202G | 0.262 | 2.074 | 2.793 | 0.080 | 1.801 | 0.859 | 1.004 | 0.991 | 1.155 | 0.93 | 0.78 | 0.87 | 0.32 | 1.29 |
| A | 202H | -0.035 | -8.518 | -27.846 | -0.008 | -7.284 | -1.929 | -3.280 | -3.407 | -5.390 | 0.85 | 0.78 | 0.65 | 0.65 | 0.41 |
| A | 202I | 0.193 | 1.885 | 2.981 | 0.063 | 2.505 | 1.134 | 1.383 | 1.340 | 1.604 | 1.07 | 0.78 | 0.73 | 1.31 | 1.12 |
| A | 202K | -0.015 | -18.957 | -33.788 | -0.003 | -17.128 | -4.377 | -8.245 | -7.803 | -15.428 | 1.46 | 1.13 | 2.39 | 1.91 | 0.42 |
| A | 202L | 0.015 | 27.342 | 18.814 | 0.004 | 23.315 | 7.523 | 10.866 | 9.041 | 14.759 | 1.05 | 0.75 | 1.18 | 0.87 | 1.72 |
| A | 202M | 0.132 | 5.134 | 2.789 | 0.046 | 2.870 | 1.082 | 1.474 | 1.034 | 1.904 | 0.79 | 0.49 | 0.66 | 1.31 | 0.98 |
| A | 202N | 0.143 | -0.261 | 2.315 | 0.026 | 0.534 | 0.029 | 0.344 | 0.416 | 0.942 | 0.00 | 0.00 | 0.00 | 0.00 | 0.00 |
| A | 202P | 0.018 | 26.941 | 28.767 | 0.004 | 13.175 | 3.284 | 5.975 | 6.432 | 9.670 | 0.92 | 0.71 | 0.34 | 0.71 | 1.62 |
| A | 202Q | 0.001 | 118.428 | 344.928 | 0.001 | 111.182 | 33.327 | 55.830 | 56.732 | 79.513 | 1.06 | 0.94 | 0.67 | 0.94 | 1.74 |
| A | 202R | -0.033 | -15.965 | -14.275 | -0.007 | -6.298 | -1.273 | -2.946 | -3.070 | -4.915 | 0.82 | 0.65 | 2.00 | 0.04 | 2.74 |
| A | 202S | 0.378 | 1.684 | 0.774 | 0.183 | 1.790 | 1.232 | 1.311 | 1.289 | 1.377 | 0.99 | 0.92 | 1.03 | 0.77 | 0.95 |
| A | 202T | 0.176 | 2.582 | 1.715 | 0.056 | 2.685 | 1.356 | 1.550 | 1.478 | 1.755 | 1.04 | 0.85 | 0.82 | 1.03 | 1.40 |
| A | 202V | 0.477 | 1.414 | 1.100 | 0.259 | 1.508 | 1.149 | 1.188 | 1.151 | 1.178 | 1.07 | 1.01 | 1.14 | 1.20 | 0.88 |
| A | 202W | -0.087 | -2.695 | -5.936 | -0.016 | -2.283 | -0.418 | -1.074 | -1.041 | -2.066 | 0.00 | 0.00 | 0.00 | 0.00 | 0.00 |
| A | 202Y | -0.094 | -2.578 | -10.062 | -0.019 | -2.514 | -0.545 | -1.124 | -0.997 | -1.895 | 0.89 | 0.52 | 0.54 | 1.16 | 1.96 |
| E | 203A | 0.691 | 1.159 | 0.654 | 0.536 | 1.133 | 0.905 | 0.868 | 0.667 | 0.891 | 0.95 | 0.84 | 1.07 | 1.56 | 1.09 |
| E | 203C | 0.372 | 2.033 | 1.634 | 0.197 | 1.566 | 1.059 | 1.116 | 1.032 | 1.200 | 0.94 | 0.92 | 1.25 | 1.24 | 1.28 |
| E | 203F | 0.311 | 1.999 | 2.148 | 0.136 | 1.901 | 1.187 | 1.282 | 1.308 | 1.375 | 0.87 | 0.85 | 1.53 | 2.68 | 1.50 |
| E | 203G | 0.411 | 1.802 | 0.628 | 0.190 | 1.627 | 1.079 | 1.081 | 1.067 | 1.175 | 0.93 | 0.90 | 1.30 | 0.74 | 0.90 |
| E | 203I | 0.517 | 1.501 | 0.549 | 0.304 | 1.491 | 1.197 | 1.208 | 1.135 | 1.223 | 0.98 | 0.93 | 1.32 | 1.58 | 1.14 |
| E | 203K | 0.575 | 1.282 | 0.801 | 0.364 | 1.369 | 1.136 | 1.115 | 1.038 | 1.173 | 0.99 | 0.93 | 1.54 | 1.58 | 1.75 |
| E | 203L | 0.594 | 1.155 | 1.853 | 0.426 | 1.416 | 1.185 | 1.153 | 0.877 | 1.168 | 1.01 | 0.90 | 1.35 | 1.14 | 1.21 |
| E | 203N | 0.348 | 1.817 | 1.410 | 0.202 | 1.925 | 1.338 | 1.384 | 1.270 | 1.469 | 0.90 | 0.80 | 0.71 | 0.76 | 1.02 |
| E | 203P | 0.021 | 23.813 | 32.728 | 0.006 | 19.723 | 8.595 | 10.717 | 10.142 | 13.151 | 0.87 | 0.73 | 0.56 | 0.90 | 1.62 |
| E | 203Q | 0.717 | 1.226 | 0.526 | 0.509 | 1.153 | 1.045 | 1.048 | 1.053 | 1.065 | 0.99 | 0.97 | 0.99 | 1.12 | 1.26 |
| E | 203R | 0.404 | 1.644 | 0.988 | 0.183 | 1.502 | 0.981 | 1.032 | 1.107 | 1.448 | 0.96 | 0.91 | 0.82 | 1.16 | 1.50 |
| E | 203S | 0.578 | 1.230 | 0.666 | 0.374 | 1.413 | 1.181 | 1.151 | 1.177 | 1.205 | 0.92 | 0.90 | 1.03 | 0.84 | 1.10 |
| E | 203T | 0.675 | 1.166 | -0.438 | 0.482 | 1.225 | 1.021 | 1.038 | 1.043 | 1.072 | 0.98 | 0.87 | 1.10 | 0.73 | 0.98 |
| E | 203V | 0.610 | 1.193 | 1.251 | 0.428 | 1.329 | 1.122 | 1.151 | 1.088 | 1.155 | 0.96 | 0.91 | 1.13 | 1.10 | 1.09 |
| E | 203W | 0.483 | 1.351 | 1.751 | 0.260 | 1.462 | 1.095 | 1.112 | 1.020 | 1.149 | 0.93 | 0.89 | 1.54 | 0.69 | 1.21 |
| E | 203Y | 0.416 | 1.494 | 1.883 | 0.222 | 1.758 | 1.251 | 1.220 | 0.990 | 1.295 | 0.96 | 0.84 | 1.61 | 0.87 | 1.16 |
| D | 212A | 0.222 | 2.273 | 1.781 | 0.092 | 1.997 | 0.858 | 0.973 | 0.305 | 0.901 | 0.63 | 0.01 | -0.03 | 0.75 | 0.14 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| D | 212C | 0.294 | 1.860 | 1.077 | 0.134 | 1.515 | 1.156 | 1.181 | 0.757 | 0.937 | 0.67 | 0.24 | 0.20 | 0.30 | 0.33 |
| D | 212E | 0.124 | 2.742 | -3.751 | 0.034 | 3.146 | 1.381 | 1.751 | 0.476 | 1.309 | 1.00 | 0.01 | 0.06 | 0.38 | 0.15 |
| D | 212F | -0.076 | -4.461 | -4.338 | -0.015 | -2.548 | -0.327 | -1.327 | -0.818 | -1.848 | 0.00 | 0.00 | 0.00 | 0.00 | 0.00 |
| D | 212G | 0.888 | 0.988 | 0.520 | 0.969 | 1.155 | 1.281 | 1.187 | 0.792 | 0.857 | 1.16 | 0.43 | 0.38 | 0.83 | 0.41 |
| D | 212H | -0.011 | -42.037 | 17.885 | -0.002 | -34.088 | -15.377 | -20.448 | -6.928 | -17.006 | 0.63 | 0.02 | 0.01 | 0.09 | 0.52 |
| D | 212I | -0.116 | -1.333 | -1.610 | -0.021 | -1.122 | -0.208 | -0.649 | -0.489 | -1.152 | 0.00 | 0.00 | 0.00 | 0.00 | 0.00 |
| D | 212K | -0.103 | -1.019 | -0.053 | -0.018 | -1.506 | -0.275 | -0.890 | -0.671 | -1.448 | 0.00 | 0.00 | 0.00 | 0.00 | 0.00 |
| D | 212L | -0.115 | -0.472 | -0.581 | -0.020 | -1.264 | -0.169 | -0.750 | -0.534 | -1.243 | 0.00 | 0.00 | 0.00 | 0.00 | 0.00 |
| D | 212N | 0.788 | 0.876 | 0.240 | 0.542 | 1.023 | 1.205 | 1.057 | 0.332 | 0.634 | 0.97 | 0.13 | 0.22 | 0.73 | 0.43 |
| D | 212P | 0.063 | 5.662 | 6.786 | 0.015 | 4.099 | 0.823 | 2.014 | 0.927 | 2.356 | 0.64 | 0.04 | -0.52 | 1.37 | 1.17 |
| D | 212Q | 0.085 | 4.107 | 4.757 | 0.021 | 3.954 | 1.630 | 2.379 | 0.723 | 1.945 | 0.74 | 0.02 | -0.07 | 0.23 | 2.03 |
| D | 212R | -0.030 | -14.546 | -1.570 | -0.005 | -5.383 | -0.775 | -3.332 | -2.031 | -4.860 | 0.00 | 0.00 | 0.00 | 0.00 | 0.00 |
| D | 212S | 0.954 | 0.821 | 0.330 | 0.672 | 0.919 | 0.870 | 0.780 | 0.424 | 0.601 | 0.95 | 0.30 | 0.35 | 0.59 | 0.52 |
| D | 212T | 0.429 | 1.369 | -0.481 | 0.256 | 1.689 | 1.364 | 1.130 | 0.157 | 0.618 | 0.94 | 0.01 | 0.03 | 0.40 | 0.38 |
| D | 212V | -0.057 | -5.249 | 24.183 | -0.010 | -3.383 | -0.489 | -1.706 | -0.999 | -2.274 | 0.00 | 0.00 | 0.00 | 0.00 | 0.00 |
| D | 212W | -0.044 | -5.123 | 3.264 | -0.008 | -3.670 | -0.404 | -2.010 | -1.371 | -3.319 | 0.68 | 0.00 | 0.00 | 0.00 | 0.00 |
| D | 212Y | -0.035 | -4.678 | -6.493 | -0.009 | -7.986 | -1.863 | -3.989 | -1.797 | -4.351 | 0.91 | 0.05 | 0.40 | -1.41 | -0.29 |
| S | 213A | 0.900 | 1.167 | 0.088 | 1.034 | 1.057 | 1.093 | 1.073 | 0.806 | 1.058 | 0.91 | 1.00 | 1.00 | 0.72 | 0.81 |
| S | 213C | 0.921 | 0.935 | 2.916 | 0.801 | 0.897 | 0.969 | 0.975 | 0.757 | 0.829 | 0.96 | 0.95 | 0.56 | 0.47 | 0.39 |
| S | 213D | 1.069 | 0.902 | -1.519 | 1.143 | 0.874 | 0.949 | 0.936 | 0.651 | 0.878 | 0.90 | 0.61 | 0.35 | 0.51 | 0.37 |
| S | 213E | 0.884 | 1.198 | -0.281 | 0.786 | 1.116 | 1.173 | 1.135 | 1.028 | 1.074 | 1.00 | 1.07 | 0.87 | 1.03 | 0.54 |
| S | 213F | 0.801 | 1.278 | -2.142 | 0.684 | 1.158 | 1.160 | 1.181 | 0.880 | 0.933 | 0.92 | 0.62 | 0.63 | 0.77 | 0.65 |
| S | 213G | 0.809 | 1.259 | -2.680 | 0.722 | 1.211 | 1.245 | 1.250 | 0.945 | 1.215 | 0.98 | 0.62 | 0.50 | 0.82 | 0.71 |
| S | 213H | 1.003 | 0.889 | -1.642 | 0.962 | 0.992 | 1.028 | 1.055 | 0.863 | 0.912 | 0.91 | 0.66 | 0.68 | 0.64 | 0.75 |
| S | 213I | 0.732 | 1.188 | 0.903 | 0.617 | 1.267 | 1.256 | 1.227 | 1.055 | 1.109 | 0.98 | 0.85 | 0.82 | 0.43 | 0.83 |
| S | 213K | 0.766 | 1.097 | -5.441 | 0.603 | 1.139 | 1.162 | 1.182 | 0.891 | 1.036 | 0.98 | 0.78 | 1.21 | 0.72 | 1.01 |
| S | 213L | 0.765 | 1.117 | -3.025 | 0.661 | 1.231 | 1.221 | 1.172 | 0.880 | 1.006 | 0.96 | 0.77 | 1.13 | 0.96 | 0.51 |
| S | 213M | 1.039 | 0.967 | -0.728 | 1.343 | 1.018 | 1.055 | 0.924 | 0.589 | 1.283 | 0.84 | 0.81 | 0.73 | 0.91 | 0.85 |
| S | 213P | 0.931 | 0.920 | -0.373 | 0.815 | 0.994 | 1.011 | 1.061 | 0.652 | 1.028 | 0.95 | 0.68 | 0.47 | 0.73 | 0.59 |
| S | 213Q | 1.180 | 0.903 | -1.134 | 1.402 | 0.898 | 0.978 | 0.947 | 0.700 | 0.899 | 0.89 | 0.80 | 0.85 | 0.44 | 0.84 |
| S | 213R | 0.722 | 1.356 | -1.111 | 0.621 | 1.291 | 1.240 | 1.207 | 0.727 | 0.957 | 0.93 | 0.69 | 0.64 | 0.75 | 0.65 |
| S | 213T | 1.197 | 0.889 | -2.588 | 0.832 | 1.206 | 1.244 | 1.183 | 0.770 | 1.026 | 1.03 | 0.77 | 0.78 | 0.90 | 0.71 |
| S | 213V | 0.839 | 1.197 | -1.352 | 0.832 | 1.180 | 1.180 | 1.114 | 0.795 | 1.030 | 0.97 | 0.89 | 0.93 | 1.00 | 0.83 |
| S | 213Y | 0.885 | 0.989 | -3.491 | 0.867 | 1.100 | 1.098 | 1.083 | 0.564 | 0.862 | 0.88 | 0.35 | 0.69 | 0.64 | 0.83 |
| A | 214C | 0.957 | 1.081 | 1.163 | 0.963 | 1.184 | 1.131 | 1.160 | 0.901 | 1.175 | 1.03 | 0.77 | 0.68 | 0.83 | 0.73 |
| A | 214D | 0.752 | 0.953 | 0.854 | 0.633 | 1.579 | 1.138 | 1.395 | 0.162 | 1.187 | 1.25 | 0.00 | 0.01 | 0.86 | 0.93 |
| A | 214F | 0.419 | 1.072 | 2.368 | 0.222 | 1.034 | 0.972 | 1.266 | 1.027 | 1.365 | 1.19 | 0.93 | 0.47 | 1.16 | 0.33 |
| A | 214G | 0.833 | 0.853 | 3.277 | 0.732 | 1.132 | 0.945 | 1.140 | 0.444 | 0.938 | 1.17 | 0.13 | 0.16 | 1.23 | 1.10 |
| A | 214I | 0.761 | 1.021 | 0.430 | 0.558 | 1.041 | 1.224 | 1.246 | 1.676 | 1.223 | 0.98 | 1.79 | 1.98 | 0.96 | 0.47 |
| A | 214K | 0.811 | 1.579 | -1.111 | 0.621 | 1.376 | 1.240 | 1.583 | 0.209 | 1.424 | 1.46 | 0.01 | 0.07 | 0.99 | 1.03 |
| A | 214L | 0.428 | 1.100 | 3.299 | 0.213 | 1.376 | 1.295 | 1.127 | 0.530 | 1.110 | 1.27 | 0.59 | 0.50 | 1.36 | 0.97 |
| A | 214M | 0.828 | 0.963 | 3.152 | 0.839 | 1.621 | 0.893 | 1.132 | 0.513 | 1.066 | 1.22 | 0.47 | 0.31 | 1.08 | 0.92 |
| A | 214N | 0.915 | 1.141 | 1.096 | 0.924 | 1.195 | 0.996 | 1.267 | 0.810 | 1.073 | 1.23 | 0.58 | 0.45 | 0.92 | 0.56 |
| A | 214P | 0.668 | 1.058 | 3.034 | 0.452 | 1.032 | 1.070 | 1.141 | 0.810 | 1.073 | 1.23 | 0.58 | 0.45 | 0.93 | 0.99 |
| A | 214Q | -0.085 | -4.707 | -4.061 | -0.019 | -2.584 | -0.620 | -1.182 | -0.626 | -1.517 | 0.00 | 0.00 | 0.00 | 0.00 | 0.00 |
| A | 214R | 0.950 | 0.996 | 1.880 | 1.250 | 1.139 | 1.183 | 1.183 | 0.407 | 1.168 | 1.02 | 0.45 | 0.42 | 1.05 | 0.88 |
| A | 214S | 0.62 | ND | ND | ND | ND | ND | 1.27 | ND | 0.97 | 1.39 | 0.06 | 0.35 | 1.38 | 0.87 |
| A | 214T | 0.785 | 0.962 | 2.663 | 0.710 | 1.204 | 1.228 | 1.228 | 0.382 | 1.162 | 1.10 | 0.37 | 0.35 | 1.06 | 0.80 |
| A | 214T | 0.960 | 1.142 | 1.574 | 0.980 | 1.045 | 0.948 | 1.075 | 1.160 | 1.114 | 1.08 | 1.12 | 0.83 | 0.80 | 0.81 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| A | 214V | 0.787 | 1.293 | 1.072 | 0.855 | 1.309 | 1.084 | 1.092 | 1.513 | 1.322 | 1.04 | 1.92 | 2.13 | 1.03 | 0.66 |
| A | 214W | 1.022 | 0.799 | 1.481 | 0.909 | 0.826 | 0.736 | 1.012 | 0.971 | 1.168 | 1.27 | 1.53 | 0.92 | 1.03 | 1.06 |
| A | 214Y | 0.694 | 0.881 | 1.990 | 0.539 | 1.248 | 1.084 | 1.356 | 0.871 | 1.479 | 1.14 | 0.93 | 0.54 | 0.95 | 1.12 |
| A | 218C | 0.800 | 1.111 | 1.750 | 0.742 | 1.106 | 1.037 | 1.060 | 1.065 | 1.070 | 0.97 | 1.09 | 1.24 | 0.99 | 0.76 |
| A | 218D | 0.779 | 1.116 | 2.247 | 0.692 | 1.131 | 1.063 | 1.123 | 1.375 | 1.122 | 0.95 | 1.38 | 1.55 | 0.98 | 1.05 |
| A | 218E | 0.895 | 1.071 | 1.752 | 0.852 | 1.024 | 0.995 | 1.017 | 1.184 | 0.999 | 1.10 | 1.43 | 1.55 | 1.20 | 1.14 |
| A | 218F | 0.77 | ND | ND | ND | ND | ND | 1.01 | ND | 0.98 | 1.10 | 0.62 | 0.70 | 1.08 | 1.66 |
| A | 218G | 0.821 | 0.991 | 1.667 | 0.673 | 1.091 | 0.994 | 1.034 | 1.079 | 1.012 | 1.04 | 1.12 | 1.10 | 0.99 | 1.25 |
| A | 218H | 0.798 | 0.940 | 0.197 | 0.622 | 1.101 | 0.905 | 0.915 | 0.894 | 0.970 | 1.03 | 0.84 | 1.13 | 1.31 | 1.02 |
| A | 218I | 0.742 | 1.111 | 1.870 | 0.655 | 1.249 | 1.149 | 1.161 | 1.054 | 1.170 | 1.09 | 0.87 | 1.11 | 1.32 | 1.30 |
| A | 218K | 0.822 | 1.015 | 0.521 | 0.763 | 1.186 | 1.119 | 1.144 | 0.621 | 1.092 | 1.06 | 0.43 | 0.69 | 1.09 | 1.35 |
| A | 218L | 0.815 | 1.132 | 1.486 | 0.841 | 1.228 | 1.238 | 1.218 | 0.759 | 1.199 | 1.10 | 0.80 | 0.78 | 1.21 | 1.12 |
| A | 218M | 1.049 | 0.939 | 1.360 | 1.221 | 0.924 | 0.955 | 0.900 | 0.553 | 0.914 | 1.01 | 0.60 | 0.66 | 0.68 | 1.23 |
| A | 218N | 0.794 | 1.060 | 1.150 | 0.741 | 1.116 | 1.058 | 1.053 | 0.945 | 1.027 | 0.97 | 0.89 | 0.71 | 1.03 | 1.14 |
| A | 218P | 0.606 | 1.298 | 1.167 | 0.419 | 1.283 | 1.076 | 1.068 | 1.108 | 1.121 | 0.96 | 1.03 | 0.99 | 0.96 | 1.07 |
| A | 218Q | 0.820 | 1.162 | 1.106 | 0.724 | 1.104 | 1.064 | 1.107 | 1.013 | 1.051 | 0.98 | 0.86 | 0.66 | 0.98 | 1.12 |
| A | 218R | 0.781 | 1.191 | −0.358 | 0.660 | 1.157 | 1.065 | 1.114 | 0.771 | 1.032 | 1.11 | 0.58 | 0.57 | 1.28 | 1.79 |
| A | 218S | 0.863 | 1.086 | 2.263 | 0.736 | 1.077 | 0.990 | 1.022 | 1.064 | 1.060 | 1.17 | 1.36 | 1.44 | 1.43 | 1.71 |
| A | 218T | 0.990 | 0.944 | 0.838 | 0.944 | 0.960 | 0.922 | 0.962 | 1.016 | 0.941 | 1.03 | 1.31 | 1.60 | 1.14 | 1.16 |
| A | 218V | 0.814 | 0.990 | 0.449 | 0.711 | 1.135 | 1.098 | 1.126 | 0.904 | 1.125 | 1.12 | 0.83 | 0.96 | 1.31 | 1.68 |
| A | 218W | 0.651 | 1.151 | 0.796 | 0.441 | 1.226 | 0.978 | 1.015 | 0.545 | 0.932 | 1.10 | 0.42 | 0.56 | 1.09 | 0.94 |
| A | 218Y | 0.879 | 0.968 | 1.496 | 0.848 | 1.095 | 1.039 | 1.005 | 0.601 | 0.953 | 1.11 | 0.80 | 0.87 | 1.29 | 1.13 |
| A | 219C | 0.392 | 1.669 | 7.034 | 0.210 | 1.707 | 1.192 | 1.247 | 0.710 | 1.071 | 1.06 | 0.36 | 0.29 | 0.63 | 0.42 |
| A | 219D | 0.777 | 1.138 | 1.499 | 0.609 | 1.075 | 1.053 | 1.098 | 0.974 | 1.078 | 1.07 | 0.83 | 0.56 | 0.70 | 0.42 |
| A | 219F | 0.593 | 1.353 | −1.401 | 0.352 | 1.304 | 1.042 | 1.097 | 0.792 | 1.010 | 1.14 | 0.39 | 0.31 | 0.87 | 0.37 |
| A | 219G | 0.950 | 1.049 | 2.893 | 1.004 | 1.110 | 1.074 | 1.012 | 0.883 | 0.942 | 0.93 | 0.55 | 0.63 | 0.99 | 0.60 |
| A | 219H | 0.502 | 1.488 | −2.345 | 0.259 | 1.442 | 1.058 | 1.078 | 0.746 | 0.949 | 1.11 | 0.28 | 0.15 | 0.68 | 0.44 |
| A | 219I | 0.431 | 1.544 | 5.211 | 0.210 | 1.603 | 1.192 | 1.239 | 0.603 | 1.052 | 1.22 | 0.13 | 0.15 | 0.70 | 0.45 |
| A | 219K | 0.290 | 1.820 | −10.654 | 0.116 | 2.119 | 1.248 | 1.333 | 0.183 | 1.113 | 1.27 | 0.00 | −0.12 | 0.87 | 0.63 |
| A | 219L | 0.083 | 5.515 | 32.135 | 0.025 | 5.417 | 2.010 | 2.590 | 0.623 | 2.433 | 1.39 | 0.02 | −0.12 | 0.80 | −0.72 |
| A | 219M | 0.860 | 1.061 | −3.467 | 0.770 | 1.059 | 0.913 | 0.899 | 0.135 | 0.712 | 1.05 | 0.03 | 0.05 | 0.55 | 0.43 |
| A | 219N | 0.378 | 1.814 | 5.062 | 0.223 | 1.866 | 1.320 | 1.347 | 0.535 | 1.282 | 1.14 | 0.16 | 0.31 | 0.59 | 0.42 |
| A | 219P | −0.061 | −6.430 | −3.930 | −0.012 | −4.024 | −1.066 | −1.729 | −0.932 | −2.445 | 0.00 | 0.00 | 0.00 | 0.00 | 0.00 |
| A | 219Q | 0.588 | 1.352 | 3.999 | 0.378 | 1.363 | 1.140 | 1.184 | 0.498 | 1.000 | 1.22 | 0.09 | 0.39 | 0.64 | 0.65 |
| A | 219R | 0.038 | 13.062 | −65.232 | 0.009 | 9.959 | 3.708 | 4.703 | 1.440 | 5.160 | 1.16 | 0.00 | 0.07 | 0.74 | 0.13 |
| A | 219S | 0.709 | 1.310 | −0.468 | 0.521 | 1.277 | 1.162 | 1.195 | 1.055 | 1.123 | 1.11 | 0.84 | 1.22 | 0.72 | 0.79 |
| A | 219T | 0.605 | 1.206 | 0.948 | 0.392 | 1.334 | 1.189 | 1.254 | 1.095 | 1.144 | 1.30 | 0.91 | 1.16 | 0.81 | 0.71 |
| A | 219V | 0.466 | 1.279 | 5.297 | 0.218 | 1.458 | 1.100 | 1.202 | 0.842 | 0.996 | 1.24 | 0.50 | 0.76 | 0.53 | 0.54 |
| A | 219W | 0.166 | 3.660 | −23.875 | 0.064 | 3.547 | 1.926 | 2.126 | 1.011 | 2.104 | 1.22 | 0.21 | 0.24 | 0.49 | 0.46 |
| A | 219Y | 0.467 | 1.349 | 1.042 | 0.276 | 1.737 | 1.281 | 1.321 | 0.581 | 1.154 | 1.19 | 0.32 | 0.23 | 0.81 | 0.28 |
| A | 221C | 0.547 | 1.507 | 1.149 | 0.355 | 1.356 | 0.923 | 0.891 | 0.520 | 0.924 | 1.02 | 0.56 | 0.76 | 0.83 | 0.49 |
| A | 221D | −0.053 | −10.533 | −2.604 | −0.013 | −4.607 | −0.868 | −1.709 | −1.154 | −2.964 | 0.94 | 0.04 | 0.68 | 0.96 | 0.00 |
| A | 221E | 0.217 | 2.590 | 2.840 | 0.091 | 2.492 | 1.258 | 1.232 | 0.875 | 1.480 | 1.02 | 0.39 | 0.83 | 0.75 | 1.17 |
| A | 221F | −0.065 | −11.573 | −18.186 | −0.012 | −1.809 | −0.245 | −0.811 | −0.868 | −1.838 | 0.00 | 0.00 | 0.00 | 0.00 | 0.00 |
| A | 221G | 0.616 | 1.307 | 2.160 | 0.451 | 1.443 | 1.173 | 1.084 | 0.749 | 1.139 | 1.08 | 0.62 | 0.95 | 0.97 | 1.00 |
| A | 221H | −0.137 | −3.814 | −8.643 | −0.025 | −1.122 | −0.152 | −0.448 | −0.411 | −0.946 | 0.00 | 0.00 | 0.00 | 0.00 | 0.00 |
| A | 221I | 0.105 | 5.094 | 10.846 | 0.037 | 5.054 | 2.006 | 2.332 | 1.266 | 2.364 | 1.13 | 0.38 | 0.71 | 0.63 | 0.63 |
| A | 221L | 0.079 | 4.193 | 26.191 | 0.017 | 2.338 | 0.336 | 0.856 | 0.686 | 1.725 | 0.84 | 0.02 | 1.88 | −0.27 | 0.53 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| A | 221M | 0.364 | 2.022 | 2.529 | 0.170 | 1.543 | 0.824 | 0.842 | 0.503 | 0.975 | 1.25 | 0.54 | 0.25 | 0.61 | 0.88 |
| A | 221N | −0.077 | −5.959 | −8.856 | −0.021 | −3.612 | −0.842 | −1.589 | −1.068 | −2.223 | 1.14 | 0.17 | 0.09 | 1.68 | 0.45 |
| A | 221P | −0.082 | −6.095 | −6.192 | −0.017 | −1.948 | −0.176 | −0.749 | −0.697 | −1.608 | 0.00 | 0.00 | 0.00 | 0.00 | 0.00 |
| A | 221Q | 0.290 | 2.433 | 1.476 | 0.119 | 1.924 | 1.125 | 1.144 | 0.986 | 1.314 | 1.17 | 0.67 | 0.54 | 0.81 | 1.30 |
| A | 221R | 0.110 | 5.070 | 5.880 | 0.030 | 3.470 | 1.218 | 1.515 | 1.201 | 2.002 | 1.01 | 0.28 | 0.43 | 0.34 | 0.94 |
| A | 221S | 0.928 | 0.999 | 0.956 | 0.769 | 0.997 | 0.923 | 0.905 | 0.889 | 0.961 | 1.06 | 0.97 | 1.07 | 0.81 | 1.22 |
| A | 221T | 0.355 | 2.200 | 4.048 | 0.212 | 2.070 | 1.375 | 1.396 | 1.069 | 1.256 | 0.99 | 0.59 | 0.76 | 0.82 | 0.90 |
| A | 221V | 0.305 | 1.857 | 6.111 | 0.144 | 1.907 | 0.993 | 1.186 | 0.882 | 1.125 | 1.08 | 0.53 | 0.67 | 1.21 | 0.93 |
| A | 221W | −0.122 | −1.663 | −10.246 | −0.025 | −0.759 | −0.097 | −0.405 | −0.453 | −1.013 | 0.00 | 0.00 | 0.00 | 0.00 | 0.00 |
| A | 221Y | 0.096 | 0.599 | 15.265 | 0.018 | 1.227 | 0.141 | 0.547 | 0.554 | 1.321 | 0.00 | 0.00 | 0.00 | 0.00 | 0.00 |
| N | 222A | 1.047 | 0.987 | 2.196 | 1.116 | 1.002 | 1.042 | 0.965 | 0.879 | 0.984 | 1.02 | 0.93 | 0.60 | 0.91 | 0.96 |
| N | 222C | 0.864 | 1.044 | 1.966 | 0.794 | 1.018 | 0.956 | 0.938 | 0.990 | 0.936 | 0.97 | 1.04 | 0.67 | 0.95 | 0.69 |
| N | 222D | 0.983 | 1.013 | 0.708 | 0.983 | 0.955 | 0.932 | 0.916 | 0.950 | 0.933 | 0.98 | 1.01 | 0.78 | 1.50 | 1.22 |
| N | 222E | 0.97 | ND | ND | ND | ND | ND | 1.16 | ND | 1.03 | 1.03 | 1.29 | 1.02 | 1.31 | 1.16 |
| N | 222F | 0.718 | 1.130 | 2.304 | 0.498 | 1.105 | 0.935 | 0.924 | 1.050 | 0.972 | 1.31 | 1.47 | 1.62 | 1.41 | 1.09 |
| N | 222G | 0.835 | 1.095 | 0.672 | 0.716 | 1.094 | 0.981 | 1.004 | 1.050 | 0.996 | 1.13 | 1.16 | 1.17 | 1.12 | 0.97 |
| N | 222I | 0.782 | 1.082 | 3.262 | 0.639 | 1.138 | 1.057 | 1.060 | 1.077 | 1.086 | 1.08 | 1.13 | 1.32 | 1.06 | 0.95 |
| N | 222K | 1.232 | 0.819 | 1.550 | 1.440 | 0.826 | 0.915 | 0.851 | 0.458 | 0.812 | 1.14 | 0.70 | 0.58 | 1.06 | 1.06 |
| N | 222L | 0.89 | ND | ND | ND | ND | ND | 1.24 | ND | 1.08 | 1.11 | 0.94 | 1.29 | 1.11 | 0.82 |
| N | 222M | 0.941 | 1.039 | −0.074 | 1.074 | 1.024 | 1.045 | 0.992 | 0.908 | 0.963 | 1.09 | 1.07 | 1.02 | 1.03 | 0.91 |
| N | 222P | 0.466 | 1.658 | 5.597 | 0.264 | 1.418 | 1.043 | 0.954 | 0.689 | 1.112 | 0.94 | 0.37 | 0.41 | 0.99 | 0.72 |
| N | 222R | 1.048 | 1.013 | 1.253 | 1.140 | 0.971 | 1.020 | 1.034 | 0.900 | 0.975 | 1.13 | 0.74 | 0.43 | 1.41 | 1.12 |
| N | 222S | 0.927 | 1.004 | 2.164 | 0.788 | 1.027 | 0.941 | 0.960 | 0.999 | 0.931 | 1.10 | 1.09 | 1.06 | 0.89 | 0.79 |
| N | 222T | 0.825 | 1.132 | 1.135 | 0.749 | 1.111 | 1.088 | 1.095 | 1.108 | 1.073 | 1.20 | 1.15 | 1.39 | 1.54 | 0.98 |
| N | 222V | 0.821 | 1.093 | 1.216 | 0.665 | 1.109 | 1.041 | 1.086 | 1.089 | 1.104 | 1.23 | 1.25 | 1.19 | 1.26 | 1.10 |
| N | 222W | 0.56 | ND | ND | ND | ND | ND | 1.06 | ND | 1.04 | 1.16 | 1.08 | 2.03 | 1.56 | 1.37 |
| Y | 223A | 0.028 | 18.361 | 51.507 | 0.008 | 10.573 | 2.617 | 4.007 | 3.048 | 6.440 | 0.96 | 0.29 | 0.27 | 0.88 | 0.79 |
| Y | 223C | 0.106 | 5.230 | 7.751 | 0.034 | 4.023 | 1.785 | 2.054 | 1.858 | 2.531 | 1.03 | 0.75 | 0.61 | 1.28 | 0.34 |
| Y | 223D | −0.078 | −9.265 | −13.473 | −0.014 | −1.761 | −0.228 | −0.796 | −0.771 | −1.713 | 1.07 | 0.12 | 0.49 | 0.96 | 1.15 |
| Y | 223E | 0.011 | 47.451 | 49.182 | 0.003 | 29.577 | 9.770 | 12.794 | 12.115 | 18.838 | 1.06 | 0.62 | 0.36 | 0.63 | 0.53 |
| Y | 223F | 0.928 | 1.037 | 0.556 | 0.856 | 0.998 | 0.978 | 0.961 | 1.089 | 0.963 | 1.02 | 1.13 | 1.24 | 0.92 | 1.13 |
| Y | 223G | −0.351 | −1.893 | −4.691 | −0.060 | −0.334 | −0.045 | −0.153 | −0.165 | −0.340 | 1.05 | 0.11 | 0.72 | −1.88 | 0.22 |
| Y | 223H | 0.390 | 1.728 | 2.427 | 0.187 | 1.643 | 1.099 | 1.102 | 0.912 | 1.185 | 1.14 | 0.69 | 1.03 | 1.03 | 1.23 |
| Y | 223I | 0.060 | 10.400 | 17.528 | 0.023 | 9.097 | 4.979 | 5.352 | 5.090 | 6.039 | 1.02 | 0.96 | 1.40 | 0.92 | 0.76 |
| Y | 223K | −0.091 | −1.736 | −15.525 | −0.019 | −2.801 | −0.566 | −1.026 | −0.643 | −1.729 | 0.95 | 0.06 | 1.14 | 0.63 | −0.02 |
| Y | 223L | 0.575 | 1.300 | 2.611 | 0.362 | 1.401 | 1.043 | 1.013 | 0.783 | 1.049 | 1.11 | 1.02 | 1.12 | 0.74 | 1.08 |
| Y | 223M | 0.540 | 1.334 | 2.324 | 0.311 | 1.234 | 0.728 | 0.747 | 0.645 | 0.770 | 0.97 | 0.83 | 1.06 | 0.80 | 1.02 |
| Y | 223N | −0.029 | −17.148 | −35.914 | −0.007 | −9.487 | −2.325 | −4.113 | −2.921 | −6.041 | 1.18 | 0.30 | 0.31 | 1.31 | 1.19 |
| Y | 223P | −0.190 | −0.505 | −2.861 | −0.030 | −0.382 | −0.031 | −0.220 | −0.295 | −0.624 | 0.00 | 0.00 | 0.00 | 0.00 | 0.00 |
| Y | 223Q | 0.019 | 29.009 | 38.865 | 0.005 | 18.324 | 6.437 | 8.286 | 7.938 | 11.707 | 1.13 | 0.64 | 0.42 | 1.12 | 0.88 |
| Y | 223R | −0.084 | −5.473 | −6.338 | −0.017 | −2.890 | −0.602 | −1.183 | −0.815 | −1.874 | 1.05 | 0.05 | 0.29 | 1.24 | 1.03 |
| Y | 223S | 0.012 | 44.433 | 146.809 | 0.002 | 18.190 | 3.966 | 7.370 | 7.223 | 12.631 | 1.22 | 0.52 | 1.42 | 0.23 | 0.89 |
| Y | 223T | −0.032 | −14.659 | −19.941 | −0.008 | −9.886 | −3.022 | −4.115 | −3.909 | −6.119 | 1.11 | 0.56 | 1.16 | 0.28 | 1.13 |
| Y | 223V | 0.229 | 2.435 | 5.520 | 0.087 | 2.479 | 1.294 | 1.398 | 1.371 | 1.727 | 1.12 | 0.90 | 1.33 | 0.98 | 0.86 |
| Y | 223W | 0.660 | 1.238 | 2.434 | 0.428 | 1.274 | 1.129 | 1.098 | 0.762 | 1.108 | 1.16 | 0.74 | 1.16 | 0.94 | 0.97 |
| H | 233A | 1.048 | 0.958 | 1.007 | 1.245 | 0.974 | 1.080 | 0.996 | 0.242 | 1.166 | 1.09 | 0.82 | 0.76 | 0.95 | 0.58 |
| H | 233C | 0.766 | 1.076 | 1.445 | 0.582 | 1.068 | 1.133 | 1.023 | 0.334 | 1.115 | 0.91 | 0.87 | 0.55 | 0.71 | 0.18 |
| H | 233D | 0.881 | 0.944 | 0.547 | 0.663 | 0.977 | 1.073 | 1.093 | 0.359 | 1.430 | 1.14 | 0.94 | 0.64 | 0.97 | 0.36 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| H | 233E | 0.994 | 0.957 | −0.284 | 0.844 | 0.840 | 1.021 | 0.976 | 0.334 | 1.222 | 1.05 | 0.94 | 0.96 | 0.89 | 0.20 |
| H | 233F | 1.019 | 1.041 | −0.070 | 1.171 | 1.013 | 1.044 | 1.055 | 0.349 | 1.135 | 1.03 | 1.06 | 1.11 | 1.34 | 1.07 |
| H | 233G | 0.841 | 0.907 | 0.958 | 0.638 | 1.058 | 0.958 | 0.928 | 0.318 | 1.223 | 1.05 | 1.00 | 1.15 | 1.23 | 1.38 |
| H | 233I | 0.842 | 0.944 | 0.352 | 0.741 | 1.120 | 1.221 | 1.286 | 0.429 | 1.520 | 1.07 | 1.07 | 1.30 | 1.00 | 0.39 |
| H | 233K | 0.882 | 1.068 | 1.485 | 0.947 | 1.147 | 1.251 | 1.193 | 0.358 | 1.142 | 1.11 | 1.07 | 0.95 | 1.08 | 0.51 |
| H | 233L | 0.417 | 0.853 | 4.249 | 0.178 | 1.424 | 0.903 | 0.906 | 0.237 | 1.106 | 1.14 | 0.94 | 0.70 | 1.03 | 0.45 |
| H | 233M | 0.847 | 1.060 | 1.123 | 0.679 | 1.017 | 1.087 | 0.982 | 0.260 | 1.183 | 1.10 | 0.93 | 0.71 | 0.96 | 0.39 |
| H | 233N | 0.905 | 0.980 | 1.758 | 0.778 | 0.966 | 1.026 | 1.031 | 0.327 | 1.292 | 1.18 | 1.07 | 0.85 | 1.00 | 0.53 |
| H | 233P | −0.047 | −6.186 | −146.160 | −0.012 | −6.258 | −0.723 | −2.368 | −1.400 | −2.864 | 0.79 | 0.07 | 0.04 | 2.24 | −0.13 |
| H | 233Q | 0.891 | 1.086 | 1.081 | 0.739 | 1.025 | 1.083 | 1.066 | 0.371 | 1.285 | 1.07 | 1.02 | 0.99 | 1.08 | 0.46 |
| H | 233R | 0.913 | 1.120 | 1.597 | 0.844 | 1.036 | 1.065 | 1.055 | 0.375 | 0.901 | 0.97 | 0.98 | 0.93 | 0.93 | 0.38 |
| H | 233S | 0.877 | 0.941 | 2.417 | 0.683 | 1.018 | 0.999 | 1.009 | 0.337 | 1.208 | 1.09 | 0.98 | 0.91 | 1.13 | 0.68 |
| H | 233T | 0.831 | 0.985 | 1.091 | 0.669 | 1.095 | 1.153 | 1.192 | 0.386 | 1.416 | 1.07 | 0.91 | 0.85 | 0.87 | 0.47 |
| H | 233V | 1.080 | 0.690 | 0.422 | 0.826 | 0.801 | 0.832 | 0.931 | 1.003 | 1.154 | 1.16 | 0.99 | 1.00 | 1.00 | 0.43 |
| H | 233W | 0.763 | 0.818 | 0.705 | 0.556 | 1.099 | 0.940 | 0.952 | 0.253 | 1.180 | 1.04 | 0.89 | 1.05 | 1.50 | 1.42 |
| H | 233Y | 0.885 | 1.203 | 0.672 | 1.221 | 1.278 | 1.380 | 1.117 | 0.276 | 1.144 | 0.78 | 0.76 | 1.02 | 1.08 | 0.97 |
| S | 234A | 1.135 | 0.901 | −0.302 | 1.290 | 0.914 | 0.947 | 0.953 | 1.003 | 0.992 | 1.00 | 0.85 | 0.87 | 0.83 | 1.10 |
| S | 234C | 0.952 | 0.981 | 0.009 | 0.889 | 0.957 | 0.986 | 0.914 | 0.765 | 0.940 | 0.99 | 0.88 | 0.79 | 0.75 | 0.85 |
| S | 234D | 0.725 | 1.085 | 0.972 | 0.545 | 1.139 | 0.993 | 0.968 | 0.824 | 1.036 | 0.99 | 0.85 | 0.63 | 0.99 | 0.95 |
| S | 234E | 0.808 | 1.158 | −0.512 | 0.694 | 1.118 | 1.102 | 1.047 | 0.967 | 1.132 | 1.04 | 1.05 | 0.72 | 0.90 | 1.04 |
| S | 234F | 0.725 | 1.240 | −0.263 | 0.603 | 1.232 | 1.170 | 1.181 | 1.080 | 1.339 | 0.97 | 0.96 | 1.05 | 1.01 | 1.13 |
| S | 234G | 0.681 | 1.174 | 2.965 | 0.513 | 1.271 | 1.144 | 1.149 | 1.160 | 1.174 | 1.12 | 1.14 | 0.75 | 1.15 | 1.34 |
| S | 234H | 0.881 | 1.070 | 2.288 | 0.798 | 1.053 | 1.032 | 1.041 | 0.925 | 0.931 | 1.03 | 1.16 | 1.24 | 1.13 | 1.24 |
| S | 234I | 0.840 | 1.068 | 0.896 | 0.887 | 1.185 | 1.139 | 1.161 | 1.103 | 1.225 | 1.06 | 1.29 | 1.10 | 1.39 | 1.29 |
| S | 234L | 0.837 | 1.029 | 4.317 | 0.714 | 1.097 | 1.051 | 1.029 | 1.111 | 1.071 | 1.09 | 1.18 | 1.24 | 1.36 | 1.02 |
| S | 234M | 1.411 | 0.879 | 0.448 | 2.533 | 0.841 | 1.109 | 0.942 | 0.619 | 1.123 | 0.93 | 0.76 | 0.70 | 0.64 | 0.97 |
| S | 234N | 1.249 | 0.822 | 0.400 | 1.569 | 0.874 | 0.994 | 0.911 | 0.646 | 0.961 | 1.03 | 0.89 | 0.82 | 0.96 | 1.17 |
| S | 234P | −0.071 | −14.639 | −133.100 | −0.115 | −13.183 | −0.800 | −2.179 | −3.167 | −2.584 | 0.72 | 0.38 | 0.58 | 0.93 | 0.81 |
| S | 234Q | 0.872 | 1.099 | 0.586 | 0.948 | 1.163 | 1.225 | 1.149 | 0.805 | 1.158 | 1.02 | 0.91 | 1.21 | 0.97 | 1.12 |
| S | 234R | 0.948 | 1.046 | 0.015 | 1.116 | 1.073 | 1.108 | 1.047 | 0.691 | 0.918 | 1.06 | 0.82 | 1.12 | 1.20 | 1.40 |
| S | 234T | 0.960 | 1.075 | 0.244 | 1.086 | 1.108 | 1.055 | 1.031 | 0.755 | 1.005 | 1.09 | 1.02 | 1.09 | 0.85 | 1.15 |
| S | 234V | 1.071 | 0.965 | 0.108 | 1.363 | 0.930 | 1.040 | 0.996 | 0.709 | 0.965 | 1.03 | 0.91 | 1.51 | 1.43 | 1.27 |
| S | 234W | 0.818 | 1.023 | 0.533 | 0.816 | 1.042 | 1.078 | 1.101 | 0.721 | 1.236 | 0.96 | 0.91 | 0.81 | 1.26 | 1.44 |
| S | 234Y | 1.000 | 0.831 | 0.748 | 1.023 | 1.210 | 0.947 | 0.902 | 0.563 | 0.985 | 1.01 | 1.05 | 0.95 | 1.24 | 1.02 |
| A | 238C | 0.852 | 0.929 | 13.903 | 0.796 | 1.019 | 0.889 | 0.819 | 0.625 | 0.839 | 1.07 | 0.91 | 1.09 | 0.83 | 1.11 |
| A | 238D | 0.205 | 1.813 | 90.933 | 0.074 | 1.036 | 0.711 | 0.952 | 0.694 | 1.141 | 0.96 | 0.60 | 0.85 | 0.48 | 1.05 |
| A | 238E | 0.945 | 0.822 | 12.833 | 0.976 | 1.996 | 0.998 | 0.930 | 0.802 | 0.940 | 0.99 | 0.73 | 0.66 | 1.03 | 1.18 |
| A | 238F | 0.424 | 1.493 | −6.825 | 0.246 | 1.048 | 0.941 | 0.995 | 0.813 | 0.933 | 0.93 | 0.66 | 0.82 | 0.82 | 0.54 |
| A | 238G | 1.124 | 0.842 | 10.580 | 1.246 | 1.678 | 0.914 | 0.886 | 0.753 | 0.936 | 1.02 | 0.88 | 0.94 | 0.97 | 0.96 |
| A | 238H | 0.852 | 0.918 | 14.267 | 0.756 | 0.930 | 1.040 | 0.996 | 0.661 | 0.863 | 1.01 | 0.80 | 0.69 | 0.81 | 0.77 |
| A | 238I | 0.388 | 1.261 | 21.509 | 0.193 | 1.065 | 0.867 | 0.871 | 0.736 | 1.016 | 0.96 | 0.92 | 0.94 | 1.26 | 1.12 |
| A | 238K | 0.288 | 1.645 | 24.241 | 0.121 | 1.632 | 0.937 | 1.009 | 0.551 | 1.236 | 1.15 | 0.59 | 0.53 | 0.84 | 1.58 |
| A | 238L | 0.283 | 1.724 | 1.797 | 0.096 | 1.836 | 0.947 | 1.095 | 0.731 | 1.020 | 1.01 | 0.72 | 0.66 | 0.71 | 1.14 |
| A | 238M | 0.323 | 1.855 | 27.639 | 0.153 | 1.770 | 0.819 | 0.924 | 0.597 | 1.059 | 1.20 | 0.69 | 0.73 | 0.93 | 1.10 |
| A | 238N | 0.733 | 1.045 | 6.405 | 0.532 | 1.591 | 0.786 | 0.938 | 0.686 | 0.938 | 1.06 | 0.84 | 0.69 | 0.91 | 1.02 |
| A | 238P | −0.133 | −4.691 | 32.932 | −0.031 | 1.041 | 0.804 | 0.839 | −0.462 | 0.794 | 0.00 | 0.00 | 0.00 | 0.00 | 0.00 |
| A | 238Q | 0.512 | 1.315 | 5.199 | 0.346 | 1.427 | 0.999 | −0.356 | 0.982 | −0.881 | 1.06 | 0.88 | 0.86 | 0.66 | 0.89 |
| A | 238R | 0.481 | 0.958 | −16.636 | 0.205 | 1.146 | 0.527 | 0.628 | 0.551 | 1.015 | 1.07 | 0.80 | 0.89 | 0.75 | 1.20 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| A | 238S | 0.832 | 1.030 | 11.005 | 0.727 | 1.057 | 0.956 | 0.967 | 0.962 | 0.965 | 1.03 | 1.01 | 0.90 | 1.10 | 1.00 |
| A | 238T | 0.489 | 1.181 | 12.016 | 0.315 | 1.479 | 1.078 | 1.103 | 1.002 | 1.090 | 1.05 | 0.96 | 0.77 | 0.77 | 0.93 |
| A | 238V | 0.445 | 1.274 | −29.799 | 0.274 | 1.540 | 1.119 | 1.148 | 0.973 | 1.182 | 0.99 | 0.91 | 0.92 | 0.88 | 0.88 |
| A | 238W | 0.163 | 3.534 | 6.752 | 0.058 | 3.252 | 1.662 | 1.905 | 1.741 | 1.781 | 1.05 | 0.76 | 0.62 | 1.06 | 1.15 |
| A | 238Y | 0.327 | 1.418 | 81.655 | 0.179 | 1.913 | 1.137 | 1.251 | 0.762 | 1.130 | 0.99 | 0.73 | 0.67 | 0.96 | 0.92 |
| A | 240A | 1.057 | 0.942 | 16.858 | 1.194 | 0.947 | 0.967 | 0.879 | 0.684 | 0.944 | 1.01 | 0.91 | 1.00 | 1.01 | 0.95 |
| K | 240C | 0.850 | 0.953 | −8.722 | 0.665 | 0.961 | 0.859 | 0.802 | 0.775 | 0.878 | 0.97 | 0.95 | 0.87 | 0.79 | 0.73 |
| K | 240D | 0.787 | 1.107 | 9.761 | 0.598 | 1.040 | 0.969 | 0.901 | 0.961 | 0.956 | 1.01 | 1.01 | 1.02 | 0.77 | 1.03 |
| K | 240E | 0.658 | 1.126 | −2.858 | 0.489 | 1.315 | 1.308 | 1.217 | 1.223 | 1.323 | 0.94 | 1.00 | 0.82 | 0.63 | 0.84 |
| K | 240F | 0.905 | 0.963 | 4.245 | 0.703 | 0.945 | 0.839 | 0.791 | 0.910 | 0.849 | 1.05 | 1.12 | 1.02 | 0.77 | 0.92 |
| K | 240G | 0.641 | 1.268 | 17.558 | 0.397 | 1.261 | 1.068 | 1.046 | 1.026 | 1.107 | 1.06 | 1.06 | 1.02 | 1.20 | 0.95 |
| K | 240H | 1.018 | 0.914 | −3.276 | 0.894 | 0.907 | 0.865 | 0.865 | 0.880 | 0.895 | 1.04 | 1.05 | 0.87 | 0.75 | 0.72 |
| K | 240I | 0.945 | 0.782 | 7.492 | 0.774 | 0.932 | 0.872 | 0.855 | 0.827 | 0.809 | 0.97 | 0.96 | 0.85 | 0.94 | 0.87 |
| K | 240L | 1.003 | 0.728 | 3.482 | 0.925 | 0.972 | 0.957 | 0.878 | 0.672 | 0.932 | 1.09 | 1.01 | 0.80 | 1.06 | 1.02 |
| K | 240M | 0.904 | 0.998 | 1.060 | 0.809 | 0.966 | 0.905 | 0.783 | 0.667 | 0.867 | 1.02 | 0.92 | 0.79 | 1.07 | 0.96 |
| K | 240N | 0.950 | 0.940 | −20.823 | 0.804 | 0.898 | 0.830 | 0.785 | 0.772 | 0.806 | 1.06 | 1.09 | 1.00 | 0.62 | 0.86 |
| K | 240P | −0.169 | −2.263 | 18.319 | −0.025 | −0.892 | −0.131 | −0.380 | −0.402 | −0.833 | 0.00 | 0.00 | 0.00 | 0.00 | 0.00 |
| K | 240Q | 1.008 | 1.057 | 0.532 | 1.054 | 1.044 | 1.067 | 0.976 | 0.802 | 1.151 | 1.02 | 1.08 | 1.16 | 0.70 | 0.96 |
| K | 240R | 1.045 | 0.980 | −10.317 | 0.942 | 0.886 | 0.885 | 0.904 | 0.910 | 0.940 | 1.01 | 1.09 | 1.03 | 0.81 | 1.16 |
| K | 240S | 0.273 | 1.522 | 3.031 | 0.068 | 1.252 | 0.409 | 0.521 | 0.611 | 0.768 | 0.87 | 0.92 | 1.10 | 0.52 | 0.09 |
| K | 240T | 0.660 | 1.132 | −6.973 | 0.426 | 1.207 | 1.006 | 0.958 | 1.061 | 0.988 | 1.06 | 1.07 | 1.12 | 0.85 | 0.93 |
| K | 240W | 0.783 | 1.011 | −5.099 | 0.543 | 1.073 | 0.989 | 0.976 | 0.943 | 0.922 | 1.11 | 1.13 | 1.06 | 0.69 | 0.94 |
| K | 240Y | 0.632 | 0.855 | −6.146 | 0.329 | 1.081 | 0.704 | 0.705 | 0.683 | 0.838 | 1.02 | 0.92 | 0.79 | 0.00 | 0.00 |
| K | 241A | 0.813 | 0.857 | −6.272 | 0.689 | 1.155 | 1.078 | 0.997 | 0.761 | 1.097 | 1.16 | 1.10 | 0.91 | 1.01 | 1.04 |
| K | 241C | 0.962 | 0.932 | −7.342 | 0.968 | 0.983 | 0.962 | 0.908 | 0.708 | 0.908 | 1.01 | 0.89 | 0.82 | 1.06 | 1.00 |
| N | 241D | 0.999 | 0.842 | 8.087 | 0.827 | 0.870 | 0.844 | 0.802 | 0.770 | 0.844 | 1.02 | 0.97 | 0.85 | 0.55 | 0.71 |
| N | 241E | 1.117 | 0.881 | 3.673 | 1.019 | 0.804 | 0.806 | 0.809 | 0.830 | 0.827 | 1.05 | 1.05 | 0.96 | 0.82 | 0.81 |
| N | 241F | 1.138 | 0.807 | 1.509 | 1.067 | 0.813 | 0.818 | 0.819 | 0.867 | 0.830 | 1.02 | 1.08 | 0.84 | 0.80 | 1.00 |
| N | 241G | 1.058 | 0.879 | −1.317 | 0.907 | 0.863 | 0.818 | 0.851 | 0.903 | 0.830 | 0.99 | 1.07 | 0.80 | 0.92 | 1.24 |
| N | 241H | 1.019 | 0.960 | −10.603 | 0.537 | 1.037 | 0.943 | 0.950 | 0.956 | 0.938 | 1.19 | 1.26 | 1.17 | 1.14 | 0.97 |
| N | 241I | 0.790 | 0.936 | −0.820 | 0.897 | 0.910 | 0.894 | 0.922 | 0.953 | 0.893 | 1.07 | 1.08 | 1.00 | 1.08 | 1.03 |
| N | 241L | 0.715 | 1.206 | 20.794 | 0.519 | 1.184 | 1.075 | 1.070 | 1.019 | 1.053 | 1.04 | 1.03 | 0.79 | 0.82 | 0.94 |
| N | 241M | 1.000 | 0.781 | 19.252 | 0.916 | 0.982 | 0.964 | 0.903 | 0.657 | 0.950 | 1.13 | 1.11 | 0.99 | 1.14 | 1.17 |
| N | 241P | 0.738 | 1.140 | −9.005 | 0.581 | 1.115 | 0.929 | 0.879 | 0.638 | 0.860 | 0.97 | 0.85 | 0.89 | 0.95 | 0.80 |
| N | 241R | 0.105 | 5.163 | −9.705 | 0.021 | 2.178 | 0.515 | 0.965 | 1.037 | 1.572 | 0.89 | 0.84 | 0.92 | 0.74 | 0.76 |
| N | 241S | 0.838 | 1.005 | 5.661 | 0.640 | 1.032 | 0.951 | 0.967 | 0.943 | 0.913 | 1.00 | 1.11 | 0.95 | 1.24 | 1.73 |
| N | 241T | 0.944 | 0.987 | −0.372 | 0.788 | 0.997 | 0.947 | 0.967 | 0.974 | 0.969 | 1.15 | 1.23 | 1.30 | 1.21 | 1.12 |
| N | 241V | 1.053 | 0.830 | 1.546 | 0.866 | 0.882 | 0.860 | 0.868 | 0.869 | 0.877 | 1.06 | 1.09 | 1.14 | 0.93 | 0.89 |
| N | 241W | 0.798 | 0.946 | −8.054 | 0.529 | 1.045 | 0.874 | 0.895 | 0.802 | 0.879 | 1.09 | 1.11 | 1.40 | 0.85 | 0.92 |
| N | 241Y | 0.840 | 0.989 | 8.976 | 0.696 | 1.047 | 0.856 | 0.898 | 0.788 | 0.903 | 1.10 | 1.09 | 1.30 | 1.11 | 1.30 |
| N | 243A | 0.645 | 1.191 | 6.495 | 0.510 | 1.392 | 1.207 | 1.172 | 0.842 | 1.162 | 1.08 | 1.08 | 0.96 | 1.03 | 1.14 |
| N | 243C | 0.949 | 0.998 | 0.684 | 0.921 | 1.001 | 0.958 | 0.861 | 0.225 | 0.898 | 1.03 | 0.89 | 0.75 | 0.87 | 0.90 |
| N | 243D | 0.713 | 1.100 | 2.781 | 0.569 | 1.189 | 1.097 | 1.068 | 0.322 | 1.050 | 1.06 | 0.99 | 0.73 | 0.82 | 0.80 |
| N | 243E | 0.838 | 1.094 | 0.452 | 0.747 | 1.106 | 1.149 | 1.142 | 0.389 | 1.146 | 1.03 | 1.03 | 0.85 | 1.02 | 0.81 |
| N | 243F | 0.874 | 1.114 | 0.873 | 0.745 | 1.025 | 1.004 | 0.949 | 0.335 | 0.994 | 1.20 | 1.20 | 1.29 | 1.28 | 1.07 |
| N | 243G | 0.714 | 1.359 | 0.550 | 0.518 | 1.183 | 1.083 | 1.104 | 0.374 | 1.115 | 1.06 | 1.11 | 0.96 | 1.19 | 1.05 |
| N | 243H | 0.602 | 1.201 | 2.312 | 0.390 | 1.316 | 1.120 | 1.082 | 0.382 | 1.147 | 1.20 | 1.26 | 1.21 | 1.77 | 1.39 |
| N | 243I | 0.833 | 1.032 | 1.137 | 0.706 | 1.100 | 1.076 | 1.099 | 0.358 | 1.056 | 1.07 | 1.06 | 1.17 | 1.28 | 1.02 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| N | 243I | 0.796 | 1.190 | 7.029 | 0.659 | 1.159 | 1.024 | 0.942 | 0.813 | 0.981 | 1.12 | 1.02 | 1.42 | 1.02 | 0.93 |
| N | 243K | 0.704 | 1.132 | 0.533 | 0.541 | 1.127 | 1.168 | 1.131 | 0.327 | 1.139 | 1.13 | 1.00 | 1.22 | 1.83 | 1.54 |
| N | 243L | 0.707 | 1.132 | 2.028 | 0.563 | 1.249 | 1.129 | 1.062 | 0.253 | 1.088 | 1.16 | 0.99 | 1.39 | 1.15 | 1.06 |
| N | 243M | 0.754 | 1.224 | 0.451 | 0.706 | 1.262 | 1.216 | 1.107 | 0.254 | 1.110 | 1.04 | 0.89 | 0.79 | 0.95 | 0.92 |
| N | 243P | −0.153 | −1.001 | 2.372 | −0.022 | −0.492 | −0.046 | −0.274 | −0.122 | −0.741 | 0.00 | 0.00 | 0.00 | 0.00 | 0.00 |
| N | 243Q | 0.879 | 1.065 | 0.456 | 0.709 | 0.997 | 0.974 | 0.978 | 0.317 | 0.970 | 1.06 | 1.07 | 1.25 | 1.03 | 0.96 |
| N | 243R | 0.838 | 1.034 | −0.647 | 0.631 | 1.028 | 0.942 | 0.955 | 0.305 | 0.922 | 1.04 | 1.13 | 1.06 | 1.49 | 1.25 |
| N | 243S | 0.899 | 0.840 | 2.029 | 0.773 | 0.980 | 0.956 | 0.971 | 0.999 | 0.951 | 1.12 | 1.09 | 0.96 | 1.39 | 1.29 |
| N | 243T | 0.867 | 0.905 | 0.720 | 0.687 | 1.010 | 0.993 | 1.014 | 0.323 | 0.988 | 1.12 | 1.15 | 1.13 | 1.35 | 0.93 |
| N | 243V | 0.700 | 0.995 | 2.334 | 0.502 | 1.156 | 1.053 | 1.080 | 0.317 | 1.064 | 1.17 | 1.15 | 1.05 | 1.04 | 0.98 |
| N | 243W | 0.706 | 1.001 | −0.395 | 0.525 | 1.212 | 1.020 | 1.026 | 0.294 | 1.059 | 1.11 | 1.07 | 1.29 | 1.33 | 1.30 |
| N | 243Y | 0.730 | 1.099 | 0.729 | 0.651 | 1.310 | 1.198 | 1.192 | 0.285 | 1.158 | 1.11 | 0.99 | 1.18 | 1.15 | 1.00 |
| G | 245A | 0.346 | 2.468 | 2.010 | 0.162 | 1.647 | 1.016 | 1.044 | 0.776 | 1.124 | 0.91 | 0.81 | 1.10 | 0.47 | 0.56 |
| G | 245C | 0.801 | 1.01 | 1.272 | 0.714 | 1.143 | 1.120 | 1.105 | 1.047 | 1.061 | 1.06 | 1.00 | 1.01 | 0.81 | 1.00 |
| G | 245D | 0.840 | 1.119 | 0.393 | 0.688 | 1.041 | 0.990 | 0.951 | 1.059 | 1.017 | 1.02 | 1.05 | 0.82 | 0.60 | 0.93 |
| G | 245F | 0.874 | 1.111 | −0.117 | 0.804 | 1.091 | 1.126 | 1.159 | 1.265 | 1.141 | 1.07 | 1.12 | 0.85 | 1.16 | 1.22 |
| G | 245H | 0.673 | 1.217 | 1.056 | 0.440 | 1.254 | 1.086 | 1.103 | 1.182 | 1.159 | 1.03 | 0.99 | 1.14 | 0.85 | 1.12 |
| G | 245I | 0.904 | 0.999 | 1.121 | 0.833 | 1.061 | 1.085 | 1.124 | 1.067 | 1.092 | 1.08 | 1.05 | 1.04 | 0.86 | 1.21 |
| G | 245L | 0.963 | 0.925 | 1.180 | 0.966 | 1.073 | 1.126 | 1.102 | 0.725 | 1.051 | 1.14 | 0.97 | 1.28 | 0.90 | 0.76 |
| G | 245M | 1.056 | 1.024 | 0.363 | 1.326 | 1.016 | 1.095 | 1.070 | 0.762 | 1.044 | 1.07 | 0.93 | 1.14 | 0.88 | 1.23 |
| G | 245N | 0.977 | 0.952 | 0.595 | 0.915 | 0.977 | 0.992 | 0.938 | 0.884 | 0.980 | 1.15 | 1.10 | 0.96 | 0.57 | 1.72 |
| G | 245P | 0.841 | 1.127 | −0.165 | 0.682 | 1.051 | 0.998 | 1.027 | 0.981 | 1.033 | 1.08 | 0.98 | 1.12 | 0.72 | 1.22 |
| G | 245R | 0.172 | 2.884 | −0.627 | 0.041 | 2.074 | 0.732 | 1.002 | 1.092 | 1.302 | 1.02 | 1.03 | 1.14 | 1.23 | 2.05 |
| G | 245S | 0.010 | −39.624 | 165.529 | 0.003 | 7.146 | 1.819 | 4.086 | 4.777 | 10.095 | 0.00 | 0.00 | 0.00 | 0.00 | 0.00 |
| G | 245T | 0.989 | 0.924 | −0.122 | 0.923 | 0.953 | 1.002 | 1.058 | 0.995 | 1.019 | 1.10 | 1.04 | 1.11 | 0.88 | 1.23 |
| G | 245W | 0.804 | 1.042 | 0.562 | 0.707 | 1.157 | 1.164 | 1.243 | 1.104 | 1.200 | 1.09 | 1.02 | 0.83 | 0.73 | 0.87 |
| G | 245Y | 0.557 | 1.293 | 0.062 | 0.349 | 1.484 | 1.277 | 1.295 | 1.122 | 1.312 | 1.16 | 1.05 | 1.36 | 0.90 | 1.22 |
| S | 247A | 0.834 | 1.015 | 1.097 | 0.725 | 1.213 | 1.139 | 1.141 | 0.795 | 1.144 | 1.14 | 0.97 | 1.18 | 1.04 | 1.11 |
| S | 247C | −0.785 | 0.373 | −0.562 | −0.151 | −0.322 | −1.405 | −0.118 | 0.030 | −0.218 | 0.91 | 0.79 | 0.74 | 0.64 | 0.96 |
| S | 247D | 0.041 | 3.715 | −15.077 | 0.009 | 3.694 | 0.612 | 1.802 | 1.826 | 3.545 | 0.00 | 0.00 | 0.00 | 0.00 | 0.00 |
| S | 247E | 1.143 | 0.842 | 1.302 | 0.912 | 1.133 | 0.943 | 0.923 | 0.873 | 1.079 | 1.00 | 0.95 | 1.16 | 1.22 | 0.85 |
| S | 247F | 0.188 | 0.427 | −0.416 | 1.314 | 0.871 | 1.119 | 1.066 | 0.920 | 0.920 | 0.94 | 0.94 | 0.93 | 0.75 | 0.67 |
| S | 247G | −0.749 | −1.252 | 10.700 | −0.146 | −0.345 | −1.506 | 0.041 | 0.000 | −0.236 | −0.15 | −0.20 | −0.82 | 0.13 | −0.74 |
| S | 247H | 0.807 | 1.233 | −1.109 | 0.034 | 0.354 | 0.050 | 0.161 | 0.190 | 0.614 | 1.06 | 1.05 | 1.24 | 1.31 | 1.09 |
| S | 247I | 0.931 | 1.034 | 2.172 | 0.706 | 1.129 | 1.050 | 1.045 | 1.000 | 1.017 | 1.11 | 1.08 | 1.32 | 0.95 | 0.77 |
| S | 247K | 0.936 | 1.007 | −3.022 | 0.829 | 1.027 | 0.987 | 0.966 | 0.927 | 0.945 | 0.96 | 0.93 | 1.73 | 1.00 | 0.89 |
| S | 247L | 0.763 | 1.214 | 1.751 | 0.854 | 1.012 | 1.000 | 0.982 | 0.920 | 0.962 | 1.02 | 0.96 | 1.40 | 1.14 | 1.01 |
| S | 247M | 0.028 | −0.432 | 115.241 | 0.661 | 1.237 | 1.170 | 1.163 | 1.038 | 1.160 | 0.00 | 0.00 | 0.00 | 0.00 | 0.00 |
| S | 247N | 0.886 | 0.884 | 1.302 | 0.004 | 4.521 | 0.726 | 2.213 | 2.420 | 5.238 | 1.00 | 0.95 | 1.16 | 1.22 | 0.85 |
| S | 247P | 1.186 | 0.427 | −0.583 | 0.912 | 1.133 | 1.119 | 1.066 | 0.771 | 1.079 | 0.90 | 0.75 | 0.65 | 0.82 | 0.59 |
| S | 247Q | 0.421 | 0.896 | 1.011 | −0.146 | 0.896 | 0.956 | 0.892 | 0.599 | 0.867 | 0.94 | 0.79 | 1.21 | 1.06 | 0.82 |
| S | 247R | 0.908 | 0.916 | −2.426 | 1.543 | 0.952 | 0.331 | 0.367 | 0.331 | 0.543 | −0.10 | −0.23 | −0.33 | −0.40 | −0.41 |
| S | 247T | 0.029 | −6.269 | 52.680 | 0.125 | 1.131 | 1.167 | 1.063 | 0.852 | 1.054 | 0.93 | 0.82 | 1.07 | 0.91 | 0.79 |
| S | 247V | 0.859 | 1.143 | 5.739 | 0.005 | 2.394 | 0.425 | 1.528 | 1.836 | 4.167 | 0.00 | 0.00 | 0.00 | 0.00 | 0.00 |
| S | 247Y | 0.852 | 1.137 | 0.470 | 0.931 | 1.229 | 1.242 | 1.202 | 0.916 | 1.172 | 1.01 | 0.92 | 1.15 | 0.82 | 0.83 |
| N | 248A | 1.019 | 1.131 | 2.301 | 0.855 | 1.211 | 1.169 | 1.135 | 0.836 | 1.121 | 1.04 | 1.02 | 1.00 | 1.02 | 0.73 |
| N | 248A | 0.994 | 0.822 | 0.561 | 1.222 | 1.098 | 1.108 | 1.057 | 0.646 | 1.018 | 0.92 | 0.74 | 0.77 | 0.79 | 0.82 |
| N | 248A | 0.994 | 1.032 | 0.561 | 1.166 | 1.021 | 1.091 | 1.029 | 0.849 | 1.006 | 1.01 | 0.87 | 0.66 | 0.94 | 0.75 |
| N | 248C | 0.832 | 1.051 | 1.453 | 0.723 | 1.038 | 0.981 | 0.938 | 0.928 | 0.979 | 1.06 | 1.01 | 0.56 | 0.95 | 0.59 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| N | 248D | −0.801 | −0.178 | −0.617 | −0.148 | −0.314 | −1.417 | −0.388 | 0.097 | −0.404 | 0.00 | 0.00 | 0.00 | 0.00 | 0.00 |
| N | 248E | 0.984 | 1.004 | 2.021 | 0.949 | 0.935 | 0.929 | 0.914 | 0.951 | 0.897 | 1.05 | 1.10 | 1.08 | 1.15 | 0.77 |
| N | 248F | 0.812 | 1.255 | 3.886 | 0.698 | 1.159 | 1.130 | 1.136 | 1.225 | 1.156 | 1.04 | 1.12 | 1.08 | 1.35 | 1.26 |
| N | 248G | 0.867 | 1.136 | 0.065 | 0.763 | 1.097 | 1.061 | 1.102 | 1.175 | 1.121 | 1.10 | 1.21 | 1.00 | 1.09 | 0.90 |
| N | 248H | 0.792 | 0.620 | 0.460 | 0.630 | 1.065 | 0.872 | 0.854 | 0.786 | 0.947 | 1.19 | 1.06 | 0.98 | 1.88 | 1.18 |
| N | 248I | 0.867 | 1.036 | 1.332 | 0.730 | 1.051 | 1.004 | 1.020 | 1.017 | 1.040 | 1.09 | 1.06 | 1.29 | 1.17 | 1.01 |
| N | 248K | 1.048 | 0.835 | 1.711 | 1.238 | 1.034 | 1.019 | 1.088 | 0.878 | 1.056 | 1.08 | 0.97 | 1.22 | 1.38 | 1.38 |
| N | 248L | 0.931 | 1.073 | 2.860 | 0.975 | 1.083 | 1.129 | 0.961 | 0.791 | 1.151 | 1.04 | 0.84 | 0.89 | 0.86 | 0.64 |
| N | 248M | 0.994 | 1.063 | 2.061 | 1.097 | 1.012 | 1.048 | 1.046 | 1.060 | 0.986 | 0.98 | 1.20 | 1.20 | 1.03 | 0.94 |
| N | 248Q | 0.805 | 1.174 | 0.635 | 0.748 | 1.140 | 1.032 | 0.967 | 1.079 | 1.079 | 1.18 | 1.02 | 0.82 | 1.75 | 1.18 |
| N | 248R | 0.867 | 1.203 | −0.432 | 0.786 | 1.106 | 1.076 | 1.129 | 1.113 | 1.118 | 1.01 | 1.08 | 0.99 | 1.45 | 1.51 |
| N | 248S | 0.782 | 1.226 | −0.615 | 0.627 | 1.175 | 1.096 | 1.142 | 1.150 | 1.130 | 1.10 | 1.07 | 0.88 | 0.95 | 0.76 |
| N | 248T | 0.798 | 1.197 | 0.242 | 0.688 | 1.181 | 1.139 | 1.183 | 1.145 | 1.149 | 1.12 | 1.03 | 1.32 | 1.56 | 1.05 |
| N | 248V | 0.874 | 1.113 | 0.980 | 0.799 | 1.076 | 1.074 | 1.095 | 1.052 | 1.080 | 1.06 | 1.03 | 1.05 | 1.22 | 1.15 |
| N | 248W | 0.733 | 1.298 | 0.714 | 0.607 | 1.290 | 1.158 | 1.178 | 1.013 | 1.266 | 1.08 | 1.02 | 0.86 | 1.12 | 0.97 |
| S | 250A | 1.052 | 0.934 | −5.957 | 1.133 | 0.939 | 0.934 | 0.874 | 0.625 | 0.845 | 0.98 | 0.84 | 0.84 | 1.04 | 1.02 |
| S | 250C | 0.693 | 1.316 | 26.560 | 0.496 | 1.194 | 1.081 | 1.036 | 0.798 | 1.002 | 0.98 | 0.91 | 0.84 | 0.42 | 0.89 |
| S | 250E | 1.016 | 0.948 | 5.930 | 0.970 | 0.934 | 0.949 | 0.946 | 0.895 | 0.932 | 1.03 | 1.12 | 1.16 | 0.84 | 0.93 |
| S | 250F | 0.730 | 1.191 | 1.400 | 0.620 | 1.005 | 1.186 | 1.203 | 1.179 | 1.234 | 0.92 | 0.95 | 1.24 | 0.97 | 1.08 |
| S | 250G | 0.846 | 1.013 | −0.205 | 0.585 | 1.027 | 0.853 | 0.859 | 0.792 | 0.860 | 1.08 | 1.02 | 0.98 | 1.10 | 1.10 |
| S | 250H | 0.833 | 1.048 | −2.031 | 0.668 | 1.078 | 0.992 | 1.026 | 0.865 | 0.968 | 1.02 | 1.04 | 1.08 | 1.13 | 1.15 |
| S | 250I | 0.972 | 0.922 | 7.070 | 0.868 | 0.984 | 0.928 | 0.954 | 0.814 | 0.929 | 1.06 | 1.03 | 1.08 | 0.59 | 0.89 |
| S | 250K | 1.013 | 0.889 | −11.458 | 0.946 | 0.947 | 0.937 | 0.957 | 0.695 | 0.922 | 1.11 | 1.00 | 1.22 | 0.98 | 1.30 |
| S | 250L | 0.846 | 1.008 | −0.637 | 0.780 | 1.129 | 1.054 | 1.039 | 0.665 | 1.022 | 1.14 | 1.08 | 1.07 | 1.60 | 1.29 |
| S | 250M | 0.838 | 0.901 | 7.134 | 0.543 | 0.932 | 0.644 | 0.633 | 0.404 | 0.655 | 0.95 | 0.77 | 0.85 | 1.19 | 0.97 |
| S | 250N | 1.138 | 0.849 | 7.740 | 1.141 | 0.899 | 0.899 | 0.824 | 0.538 | 0.827 | 0.98 | 0.83 | 0.70 | 0.67 | 1.03 |
| S | 250P | −0.111 | −4.415 | −31.598 | −0.021 | −1.776 | −0.264 | −0.748 | −0.636 | −1.300 | 0.82 | 0.16 | 0.07 | 0.65 | 0.57 |
| S | 250Q | 0.956 | 0.967 | 18.232 | 0.992 | 1.031 | 0.999 | 0.951 | 0.704 | 0.954 | 0.96 | 0.92 | 0.87 | 0.83 | 0.85 |
| S | 250R | 1.202 | 0.752 | −8.395 | 1.274 | 0.841 | 0.807 | 0.788 | 0.582 | 0.776 | 0.98 | 0.92 | 0.99 | 1.05 | 1.01 |
| S | 250T | 0.928 | 0.968 | −1.193 | 0.889 | 1.107 | 1.039 | 1.007 | 0.766 | 1.071 | 1.07 | 1.02 | 1.45 | 1.23 | 0.97 |
| S | 250V | 1.043 | 0.852 | 2.736 | 1.048 | 1.005 | 0.766 | 0.915 | 0.616 | 0.892 | 1.00 | 0.98 | 0.98 | 0.92 | 0.75 |
| S | 250W | 0.720 | 1.137 | 10.301 | 0.640 | 1.293 | 1.032 | 1.045 | 0.688 | 1.093 | 1.07 | 0.96 | 1.15 | 1.04 | 1.10 |
| S | 250Y | 0.959 | 0.939 | 2.300 | 1.119 | 1.137 | 1.119 | 1.085 | 0.631 | 1.094 | 1.05 | 1.02 | 1.05 | 0.88 | 0.91 |
| H | 251A | 0.991 | 0.980 | 0.273 | 1.093 | 1.023 | 1.081 | 0.993 | 0.728 | 0.955 | 1.04 | 0.97 | 0.79 | 1.10 | 0.92 |
| H | 251C | 0.817 | 0.991 | −0.929 | 0.742 | 1.097 | 1.067 | 1.019 | 0.944 | 1.030 | 1.03 | 1.08 | 0.94 | 0.93 | 0.72 |
| H | 251D | 1.332 | 0.807 | 1.112 | 2.094 | 0.897 | 1.043 | 0.958 | 0.887 | 0.978 | 1.03 | 1.19 | 0.94 | 0.78 | 0.86 |
| H | 251E | 0.937 | 1.004 | −0.315 | 0.870 | 0.985 | 1.014 | 1.001 | 1.067 | 0.989 | 1.08 | 1.22 | 1.02 | 1.31 | 1.27 |
| H | 251G | 0.949 | 0.998 | 0.700 | 0.736 | 1.001 | 1.009 | 1.006 | 1.068 | 0.949 | 1.00 | 1.12 | 0.99 | 1.05 | 0.97 |
| H | 251I | 0.424 | 1.351 | 0.271 | 0.229 | 1.711 | 1.424 | 1.414 | 1.386 | 1.474 | 1.07 | 1.06 | 1.45 | 1.23 | 0.75 |
| H | 251K | 0.752 | 1.053 | 1.496 | 0.558 | 1.186 | 1.122 | 1.101 | 0.967 | 1.093 | 1.05 | 0.80 | 0.98 | 0.92 | 1.10 |
| H | 251L | 0.487 | 1.165 | 1.330 | 0.270 | 1.453 | 1.116 | 1.109 | 1.221 | 1.101 | 1.18 | 1.01 | 1.01 | 0.94 | 0.96 |
| H | 251M | 0.746 | 1.106 | 0.335 | 0.687 | 1.239 | 1.163 | 1.041 | 0.755 | 1.255 | 1.16 | 1.12 | 0.79 | 0.88 | 1.29 |
| H | 251N | 1.066 | 0.916 | 2.214 | 1.135 | 0.944 | 0.980 | 0.957 | 0.860 | 1.047 | 0.93 | 0.84 | 0.82 | 1.10 | 0.84 |
| H | 251P | 0.837 | 0.989 | 1.450 | 0.693 | 1.042 | 0.984 | 0.958 | 0.952 | 0.931 | 1.03 | 1.02 | 1.02 | 1.34 | 0.73 |
| H | 251Q | 0.853 | 1.018 | −7.303 | 0.701 | 1.044 | 1.032 | 1.008 | 1.017 | 0.970 | 1.03 | 1.13 | 0.85 | 1.03 | 0.81 |
| H | 251R | 0.815 | 1.043 | 1.653 | 0.623 | 1.078 | 1.011 | 0.999 | 0.963 | 1.015 | 1.04 | 1.09 | 1.06 | 1.11 | 0.97 |
| H | 251V | 0.672 | 0.981 | −0.381 | 0.443 | 1.183 | 1.054 | 1.073 | 1.026 | 1.000 | 1.09 | 1.03 | 0.82 | 1.18 | 1.11 |
| H | 251Y | 0.832 | 1.241 | 2.912 | 0.800 | 1.230 | 1.210 | 1.167 | 0.931 | 1.083 | 1.08 | 1.08 | 0.99 | 0.86 | 1.02 |
| H | 251Y | | | | | | | | | 1.165 | 1.12 | 1.09 | 0.90 | 1.46 | 1.21 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| Y | 252C | 0.282 | 2.396 | 0.222 | 0.112 | 1.945 | 1.255 | 1.351 | 0.973 | 1.349 | 1.13 | 0.82 | 0.74 | 0.48 | 0.99 |
| Y | 252D | −0.133 | −2.983 | −2.241 | −0.028 | −1.668 | −0.304 | −0.813 | −0.558 | −1.152 | 1.04 | 0.16 | 0.36 | 0.42 | 1.31 |
| Y | 252E | −0.059 | −8.551 | 4.419 | −0.011 | −4.596 | −1.046 | −2.067 | −1.452 | −2.818 | 1.10 | 0.23 | 0.37 | 0.46 | 0.62 |
| Y | 252F | 0.478 | 1.712 | −0.895 | 0.259 | 1.632 | 1.368 | 1.397 | 1.230 | 1.359 | 1.21 | 1.11 | 1.26 | 1.10 | 1.12 |
| Y | 252G | −0.148 | −2.726 | 0.790 | −0.025 | −1.350 | −0.198 | −0.577 | −0.469 | −0.905 | 1.12 | 0.17 | 0.87 | 0.56 | 0.90 |
| Y | 252H | 0.177 | 2.998 | 1.130 | 0.059 | 3.042 | 1.737 | 1.947 | 1.448 | 1.500 | 1.17 | 0.80 | 0.58 | 0.50 | 0.97 |
| Y | 252I | 0.020 | 24.248 | −4.619 | 0.005 | 23.479 | 9.735 | 13.303 | 7.890 | 12.014 | 1.22 | 0.50 | 0.29 | 0.95 | 1.04 |
| Y | 252K | −0.074 | −4.752 | −0.708 | −0.015 | −4.084 | −1.177 | −2.004 | −1.118 | −2.300 | 1.31 | 0.30 | 0.97 | 0.73 | 0.43 |
| Y | 252L | 0.358 | 1.707 | 0.560 | 0.150 | 1.892 | 1.253 | 1.313 | 0.715 | 1.217 | 1.20 | 0.88 | 1.02 | 0.91 | 0.95 |
| Y | 252M | 1.107 | 0.906 | −0.144 | 1.401 | 0.941 | 0.970 | 0.944 | 0.426 | 0.734 | 1.02 | 0.62 | 0.81 | 0.69 | 1.02 |
| Y | 252P | −0.049 | −12.360 | 5.605 | −0.011 | −6.894 | −1.791 | −3.173 | −1.796 | −3.471 | 0.89 | 0.25 | 0.85 | 0.83 | 0.68 |
| Y | 252Q | 0.193 | 3.171 | −1.227 | 0.067 | 2.793 | 1.277 | 1.560 | 0.811 | 1.409 | 1.04 | 0.36 | 0.82 | 0.68 | 0.95 |
| Y | 252R | 0.225 | 2.719 | −0.518 | 0.070 | 2.232 | 1.125 | 1.319 | 0.665 | 1.161 | 1.22 | 0.49 | 0.90 | 0.80 | 1.09 |
| Y | 252S | −0.024 | −16.368 | 5.489 | −0.006 | −14.504 | −3.858 | −6.581 | −3.571 | −7.447 | 1.10 | 0.25 | 0.87 | 0.70 | 0.75 |
| Y | 252T | 0.034 | 15.404 | 6.589 | 0.010 | 13.981 | 6.128 | 7.550 | 3.962 | 7.340 | 1.22 | 0.51 | 0.85 | 0.81 | 1.60 |
| Y | 252V | 0.040 | 11.361 | 0.989 | 0.011 | 11.271 | 4.453 | 5.844 | 2.872 | 5.534 | 1.14 | 0.40 | −0.05 | 0.72 | 0.76 |
| Y | 252W | 0.547 | 1.377 | 0.162 | 0.356 | 1.501 | 1.298 | 1.222 | 0.807 | 1.287 | 1.22 | 1.05 | 1.12 | 0.97 | 1.30 |
| A | 253C | 1.054 | 0.938 | −1.836 | 1.388 | 1.023 | 1.046 | 0.930 | 0.864 | 0.864 | 1.00 | 0.87 | 0.68 | 0.81 | 0.76 |
| A | 253E | 1.202 | 0.948 | −1.427 | 1.615 | 0.934 | 1.016 | 0.973 | 0.706 | 0.991 | 0.99 | 1.01 | 1.01 | 1.05 | 0.76 |
| A | 253F | 0.952 | 0.990 | −2.380 | 1.031 | 1.139 | 1.105 | 1.088 | 0.906 | 1.083 | 1.09 | 0.90 | 0.97 | 0.85 | 1.37 |
| A | 253G | 1.077 | 0.921 | 1.713 | 1.127 | 0.948 | 0.917 | 0.892 | 0.903 | 0.900 | 1.07 | 0.50 | 0.66 | 0.87 | 0.87 |
| A | 253H | 1.231 | 0.845 | −0.079 | 1.558 | 0.918 | 0.962 | 0.942 | 0.549 | 0.926 | 1.05 | 0.97 | 0.91 | 0.93 | 0.93 |
| A | 253I | 0.801 | 1.103 | 5.917 | 0.851 | 1.313 | 1.253 | 1.155 | 0.777 | 1.154 | 1.03 | 1.00 | 0.99 | 1.07 | 1.43 |
| A | 253K | 1.276 | 0.765 | −3.036 | 1.723 | 0.846 | 0.972 | 0.955 | 0.936 | 0.886 | 1.04 | 0.91 | 0.83 | 1.38 | 1.57 |
| A | 253L | 1.161 | 0.848 | 1.667 | 1.778 | 0.985 | 1.105 | 1.009 | 0.640 | 1.053 | 0.98 | 1.00 | 0.74 | 0.88 | 1.01 |
| A | 253M | 1.187 | 0.951 | −1.300 | 1.680 | 0.910 | 0.992 | 0.929 | 0.667 | 0.939 | 1.06 | 0.92 | 1.05 | 1.06 | 1.19 |
| A | 253P | 0.212 | 1.431 | −12.677 | 0.095 | 2.378 | 0.871 | 1.279 | 0.669 | 1.067 | 0.90 | 0.28 | 0.68 | 1.17 | 0.47 |
| A | 253R | 0.713 | 0.969 | 0.646 | 0.501 | 1.212 | 1.074 | 1.090 | 0.793 | 1.035 | 1.04 | 1.02 | 0.91 | 1.22 | 1.33 |
| A | 253S | 0.937 | 0.922 | −2.001 | 0.843 | 0.993 | 0.922 | 0.914 | 1.064 | 0.906 | 1.01 | 0.94 | 0.82 | 0.65 | 0.82 |
| A | 253T | 0.547 | 1.082 | −3.547 | 0.353 | 1.415 | 1.140 | 1.121 | 0.871 | 1.079 | 1.06 | 0.59 | 0.60 | 0.71 | 0.82 |
| A | 253V | 0.882 | 0.917 | 0.768 | 0.809 | 1.054 | 0.965 | 0.957 | 0.804 | 0.906 | 1.00 | 1.00 | 0.80 | 1.00 | 0.88 |
| A | 253W | 0.756 | 1.021 | −0.454 | 0.626 | 1.174 | 1.114 | 1.161 | 0.852 | 0.906 | 0.98 | 0.94 | 0.79 | 1.11 | 1.40 |
| A | 253Y | 1.024 | 0.825 | −1.307 | 1.129 | 0.989 | 1.000 | 0.990 | 0.971 | 1.211 | 1.11 | 1.01 | 0.79 | 1.00 | 1.15 |
| S | 254A | 0.467 | 1.042 | 9.155 | 0.173 | 1.073 | 0.427 | 0.506 | 0.650 | 1.038 | 1.07 | 0.71 | 0.86 | 1.28 | 0.67 |
| S | 254F | 0.531 | 1.984 | −25.022 | 0.544 | 1.933 | 0.972 | 0.779 | 0.591 | 0.630 | 0.71 | 0.02 | 0.43 | 1.31 | 0.26 |
| S | 254G | 0.362 | 1.743 | 0.643 | 0.016 | 1.833 | 1.035 | 1.239 | 0.149 | 0.560 | 0.40 | 0.66 | 1.24 | 1.56 | 1.23 |
| S | 254H | 0.625 | 1.214 | −1.866 | 0.378 | 1.239 | 1.053 | 1.002 | 0.272 | 1.002 | 1.01 | 0.23 | 1.74 | 1.55 | 0.97 |
| S | 254I | 1.042 | 1.394 | 0.171 | 1.720 | 1.244 | 1.084 | 0.945 | 0.328 | 0.830 | 1.07 | 0.84 | 2.15 | 1.46 | 0.87 |
| S | 254K | 0.070 | 5.221 | 16.861 | 0.017 | 5.192 | 1.481 | 2.532 | 1.036 | 0.933 | 0.65 | 0.11 | 0.57 | 1.63 | 1.51 |
| S | 254L | 0.707 | 0.843 | 1.323 | 0.418 | 1.043 | 0.864 | 0.877 | 0.341 | 2.595 | 1.26 | 0.89 | 1.16 | 0.94 | 0.79 |
| S | 254N | 0.477 | 1.859 | −1.108 | 0.298 | 1.582 | 1.175 | 1.169 | 0.171 | 0.846 | 1.22 | 0.85 | 1.17 | 0.81 | 1.11 |
| S | 254P | 0.167 | 2.239 | 10.407 | 0.041 | 2.233 | 0.678 | 1.143 | 1.330 | 1.167 | 0.77 | 0.36 | 0.47 | 1.25 | 1.25 |
| S | 254R | 0.075 | 5.705 | −5.563 | 0.016 | 4.032 | 0.869 | 1.664 | 0.194 | 1.167 | 1.32 | 0.11 | 0.64 | 1.02 | −0.09 |
| S | 254T | 1.251 | 0.855 | −5.120 | 1.555 | 0.927 | 1.023 | 1.047 | 0.274 | 2.067 | 1.13 | 0.55 | 1.07 | 1.30 | 0.81 |
| S | 254V | 1.102 | 0.825 | −1.264 | 1.093 | 0.940 | 0.935 | 1.067 | 0.188 | 0.988 | 1.12 | 1.41 | 1.85 | 2.67 | 0.82 |
| S | 254W | 0.004 | 170.459 | −541.065 | 0.000 | 203.226 | 35.157 | 72.785 | 0.278 | 0.944 | 1.05 | 0.13 | 0.13 | 3.53 | 2.13 |
| S | 254Y | 0.914 | 1.634 | −1.757 | 1.597 | 1.421 | 0.970 | 0.770 | 11.118 | 87.759 | 1.35 | 0.13 | 0.62 | 1.49 | 0.48 |
| D | 255A | 0.879 | 1.175 | −0.615 | 1.076 | 1.131 | 1.157 | 1.067 | 0.347 | 1.070 | 1.09 | 0.23 | 0.20 | 1.12 | 0.77 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| D | 255C | 0.880 | 1.012 | 0.722 | 0.795 | 1.024 | 0.956 | 0.894 | 0.385 | 0.905 | 1.05 | 0.50 | 0.39 | 0.90 | 0.81 |
| D | 255E | 0.831 | 1.293 | 1.008 | 0.778 | 1.115 | 1.103 | 1.113 | 1.045 | 1.145 | 1.03 | 1.07 | 1.24 | 1.30 | 0.73 |
| D | 255F | 0.509 | 1.803 | −0.846 | 0.324 | 1.523 | 1.208 | 1.224 | 0.331 | 1.193 | 1.06 | 0.06 | 0.14 | 1.39 | 1.06 |
| D | 255G | 0.504 | 1.786 | −0.951 | 0.325 | 1.649 | 1.286 | 1.333 | 0.383 | 1.275 | 1.04 | 0.08 | 0.34 | 0.83 | 0.95 |
| D | 255H | −0.848 | −0.257 | 0.741 | −0.151 | −0.302 | −1.355 | −0.605 | −0.026 | −0.341 | 1.07 | 0.13 | 0.37 | 1.11 | 0.67 |
| D | 255I | 0.678 | 1.404 | 2.080 | 0.594 | 1.361 | 1.219 | 1.289 | 0.489 | 1.272 | 1.07 | 0.20 | 0.46 | 1.49 | 0.69 |
| D | 255K | 0.698 | 1.241 | 1.479 | 0.580 | 1.314 | 1.235 | 1.257 | 0.204 | 1.343 | 1.04 | 0.05 | 0.38 | 1.60 | 1.25 |
| D | 255L | 0.826 | 0.951 | −0.418 | 0.638 | 1.083 | 0.918 | 0.972 | 0.548 | 1.020 | 1.02 | 0.05 | 0.36 | 1.32 | 1.06 |
| D | 255N | 0.938 | 1.037 | 0.062 | 0.966 | 1.179 | 0.941 | 0.905 | 0.149 | 0.889 | 1.03 | 0.24 | 0.05 | 1.06 | 0.91 |
| D | 255P | 0.826 | 1.203 | −0.833 | 0.731 | 1.037 | 0.973 | 1.079 | 0.945 | 1.079 | 0.94 | 0.78 | 0.91 | 1.03 | 0.76 |
| D | 255Q | 0.909 | 1.105 | −0.229 | 0.845 | 1.179 | 1.082 | 1.019 | 0.288 | 1.109 | 1.08 | 0.33 | 0.39 | 1.30 | 0.63 |
| D | 255R | 0.569 | 1.494 | 0.908 | 0.384 | 1.446 | 1.185 | 1.162 | 0.159 | 1.207 | 1.02 | 0.02 | 0.26 | 1.55 | 1.27 |
| D | 255S | 0.851 | 1.241 | 0.171 | 0.881 | 1.216 | 1.187 | 1.171 | 0.269 | 1.162 | 1.02 | 0.15 | 0.96 | 0.89 | 0.82 |
| D | 255T | 0.966 | 0.864 | 0.438 | 0.922 | 0.985 | 0.929 | 0.996 | 0.419 | 0.985 | 1.07 | 0.19 | 0.72 | 1.18 | 0.58 |
| D | 255V | 0.895 | 1.179 | −0.636 | 0.989 | 1.210 | 1.192 | 1.192 | 0.426 | 1.221 | 1.00 | 0.34 | 0.81 | 1.43 | 0.75 |
| D | 255W | 0.514 | 1.687 | −0.445 | 0.374 | 1.716 | 1.257 | 1.302 | 0.176 | 1.201 | 1.20 | 0.03 | 0.40 | 1.51 | 0.69 |
| D | 255Y | 1.077 | 0.989 | 0.300 | 1.353 | 1.030 | 1.039 | 1.076 | 0.147 | 1.044 | 1.02 | 0.08 | 0.38 | 1.16 | 0.92 |
| S | 257A | 0.111 | 9.562 | 31.301 | 0.201 | 9.286 | 1.307 | 2.164 | 2.592 | 2.264 | 0.95 | 0.82 | 0.68 | 0.72 | 0.95 |
| S | 257D | 1.097 | 0.888 | 1.664 | 1.246 | 0.959 | 0.962 | 0.910 | 0.778 | 0.920 | 0.96 | 0.94 | 0.79 | 0.56 | 0.94 |
| S | 257E | 0.957 | 1.135 | 1.619 | 1.130 | 1.126 | 1.145 | 1.086 | 1.017 | 1.121 | 0.88 | 1.00 | 1.22 | 0.68 | 0.83 |
| S | 257F | 0.421 | 1.563 | 3.301 | 0.234 | 1.675 | 1.100 | 1.058 | 0.929 | 1.149 | 0.79 | 0.79 | 0.93 | 0.78 | 0.72 |
| S | 257G | 0.187 | 2.508 | −1.605 | 0.076 | 2.954 | 1.727 | 1.851 | 1.937 | 2.024 | 0.95 | 0.75 | 1.94 | 0.04 | 0.88 |
| S | 257H | 1.035 | 0.927 | 0.669 | 0.987 | 1.031 | 0.997 | 0.929 | 0.796 | 0.954 | 0.98 | 0.89 | 1.07 | 0.89 | 1.23 |
| S | 257I | 0.734 | 1.196 | 0.739 | 0.644 | 1.315 | 1.189 | 1.122 | 0.946 | 1.149 | 0.92 | 0.87 | 1.33 | 0.94 | 1.00 |
| S | 257K | 1.110 | 0.797 | 1.061 | 1.393 | 0.976 | 1.029 | 0.960 | 0.742 | 0.963 | 0.93 | 0.59 | 0.99 | 0.68 | 0.79 |
| S | 257L | 0.772 | 0.994 | 3.178 | 0.739 | 1.277 | 1.119 | 1.043 | 0.826 | 1.101 | 0.95 | 0.43 | 1.17 | 0.29 | 0.94 |
| S | 257M | 0.698 | 1.177 | 1.569 | 0.464 | 1.158 | 0.996 | 0.991 | 0.973 | 0.993 | 0.76 | 0.71 | 0.10 | 0.36 | 0.94 |
| S | 257N | 0.904 | 1.018 | 0.552 | 0.910 | 1.032 | 0.979 | 0.964 | 0.860 | 0.985 | 1.03 | 1.01 | 0.66 | 0.61 | 0.80 |
| S | 257P | 1.006 | 0.968 | 1.249 | 1.141 | 1.018 | 1.058 | 1.099 | 1.019 | 1.061 | 0.98 | 0.95 | 1.20 | 0.68 | 0.74 |
| S | 257Q | 1.150 | 0.721 | 1.182 | 1.311 | 0.926 | 0.984 | 0.895 | 0.749 | 0.880 | 0.98 | 0.99 | 1.64 | 0.82 | 1.08 |
| S | 257R | 0.986 | 1.023 | 0.483 | 0.943 | 0.989 | 0.953 | 0.942 | 0.897 | 0.916 | 0.93 | 0.82 | 0.64 | 1.03 | 0.99 |
| S | 257T | 0.955 | 0.996 | −0.271 | 0.892 | 1.010 | 0.978 | 0.970 | 0.931 | 0.970 | 0.99 | 0.97 | 1.44 | 0.67 | 1.22 |
| S | 257V | 0.841 | 0.981 | −0.777 | 0.718 | 1.110 | 1.008 | 0.983 | 0.940 | 1.017 | 0.94 | 0.94 | 0.83 | 0.93 | 1.04 |
| S | 257W | 0.294 | 2.236 | 3.757 | 0.150 | 2.217 | 1.512 | 1.501 | 1.323 | 1.603 | 0.90 | 0.83 | 1.29 | 0.60 | 0.90 |
| S | 259A | 0.746 | 0.936 | 1.268 | 0.656 | 1.247 | 1.021 | 0.962 | 0.789 | 1.082 | 0.88 | 0.72 | 0.64 | 0.90 | 0.84 |
| S | 259E | 0.956 | 1.025 | 0.780 | 0.974 | 1.015 | 1.009 | 1.018 | 1.030 | 1.011 | 0.99 | 1.01 | 1.35 | 0.95 | 0.94 |
| S | 259G | 0.455 | 1.472 | 0.026 | 0.286 | 1.703 | 1.358 | 1.358 | 1.333 | 1.382 | 1.02 | 0.93 | 0.77 | 1.43 | 0.88 |
| S | 259H | 0.783 | 1.052 | −0.427 | 0.654 | 1.176 | 1.069 | 1.081 | 1.071 | 1.074 | 1.07 | 0.96 | 0.66 | 1.15 | 1.06 |
| S | 259I | 0.513 | 1.098 | 2.661 | 0.311 | 1.492 | 1.169 | 1.154 | 1.106 | 1.235 | 0.89 | 0.81 | 0.71 | 0.92 | 0.46 |
| S | 259K | 0.679 | 1.067 | 1.291 | 0.502 | 1.270 | 1.088 | 1.067 | 0.850 | 1.057 | 0.96 | 0.73 | 0.80 | 1.02 | 1.00 |
| D | 259L | 0.512 | 1.231 | 2.070 | 0.323 | 1.582 | 1.196 | 1.116 | 0.819 | 1.187 | 0.94 | 0.57 | 0.74 | 0.94 | 1.07 |
| D | 259M | 0.428 | 1.427 | 0.176 | 0.252 | 1.636 | 1.206 | 1.235 | 1.072 | 1.235 | 0.99 | 0.82 | 0.77 | 0.79 | 1.02 |
| D | 259P | 0.305 | 1.835 | 3.385 | 0.153 | 2.045 | 1.408 | 1.446 | 1.464 | 1.571 | 0.93 | 0.94 | 1.01 | 0.61 | 0.61 |
| D | 259Q | 0.567 | 1.412 | 2.742 | 0.436 | 1.522 | 1.307 | 1.339 | 1.349 | 1.340 | 0.97 | 0.93 | 0.84 | 1.16 | 1.10 |
| D | 259R | 0.480 | 1.503 | 0.349 | 0.307 | 1.588 | 1.297 | 1.318 | 1.307 | 1.318 | 1.04 | 0.89 | 0.74 | 1.50 | 1.34 |
| D | 259S | 0.524 | 1.317 | 2.406 | 0.334 | 1.425 | 1.150 | 1.186 | 1.127 | 1.209 | 1.04 | 0.96 | 0.63 | 1.01 | 0.90 |
| D | 259T | 0.765 | 1.091 | 1.433 | 0.635 | 1.173 | 1.109 | 1.131 | 1.123 | 1.123 | 1.00 | 0.91 | 0.79 | 1.03 | 0.87 |
| D | 259W | 0.563 | 1.421 | 2.982 | 0.373 | 1.460 | 1.192 | 1.236 | 1.016 | 1.223 | 1.10 | 0.95 | 0.83 | 1.55 | 1.31 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| D | 259Y | 0.269 | 1.446 | 1.002 | 0.114 | 2.386 | 1.273 | 1.385 | 1.114 | 1.632 | 0.65 | 0.52 | 0.21 | −4.22 | −2.31 |
| K | 260A | 0.590 | 1.157 | −2.101 | 0.358 | 1.305 | 0.994 | 0.913 | 0.683 | 1.031 | 1.06 | 0.96 | 0.92 | 0.34 | 1.10 |
| K | 260C | 0.329 | 1.122 | −9.899 | 0.149 | 1.734 | 1.010 | 1.009 | 1.008 | 1.152 | 1.01 | 0.98 | 1.07 | 1.22 | 0.13 |
| K | 260D | 0.502 | 1.330 | −2.362 | 0.266 | 1.303 | 1.006 | 0.997 | 1.017 | 1.039 | 1.10 | 1.19 | 1.05 | 1.02 | 1.14 |
| K | 260E | 0.357 | 1.306 | −1.746 | 0.163 | 1.582 | 1.022 | 1.074 | 1.077 | 1.138 | 1.11 | 1.10 | 1.01 | 1.07 | 1.06 |
| K | 260F | 0.388 | 1.381 | −12.368 | 0.185 | 1.559 | 1.022 | 1.030 | 1.106 | 1.157 | 1.20 | 1.26 | 1.23 | 1.51 | 1.41 |
| K | 260G | 0.209 | 1.980 | 0.175 | 0.076 | 2.502 | 1.445 | 1.478 | 1.530 | 1.663 | 1.10 | 1.25 | 1.14 | 1.25 | 1.07 |
| K | 260H | 0.815 | 0.953 | 0.556 | 0.768 | 1.195 | 1.162 | 1.176 | 1.217 | 1.202 | 1.11 | 1.14 | 0.95 | 1.32 | 1.03 |
| K | 260I | −0.088 | −2.723 | −19.594 | −0.018 | −3.294 | −0.894 | −1.391 | −1.173 | −2.055 | 1.23 | 0.68 | 0.73 | 1.67 | 0.78 |
| K | 260L | 0.297 | 1.518 | 9.424 | 0.144 | 2.251 | 1.449 | 1.411 | 0.996 | 1.529 | 1.07 | 0.96 | 0.79 | 0.90 | 0.91 |
| K | 260M | 0.292 | 1.942 | −0.538 | 0.123 | 2.159 | 1.498 | 1.492 | 1.337 | 1.649 | 1.03 | 0.94 | 0.78 | 0.44 | 0.89 |
| K | 260N | 0.697 | 1.199 | −0.761 | 0.561 | 1.203 | 1.071 | 1.024 | 1.008 | 1.103 | 1.24 | 1.28 | 0.95 | 1.29 | 1.16 |
| K | 260P | −0.114 | −5.135 | 33.321 | −0.023 | −1.135 | −0.136 | −0.501 | −0.578 | −1.132 | 0.00 | 0.00 | 0.00 | 0.00 | 0.00 |
| K | 260Q | 0.762 | 1.107 | 1.674 | 0.577 | 1.100 | 1.019 | 1.018 | 1.048 | 1.033 | 1.13 | 1.23 | 0.98 | 1.00 | 1.14 |
| K | 260R | 0.876 | 1.074 | −1.988 | 0.730 | 1.022 | 0.996 | 0.991 | 1.073 | 0.991 | 1.02 | 1.09 | 0.91 | 1.23 | 1.21 |
| K | 260S | 0.493 | 1.268 | 6.420 | 0.269 | 1.430 | 1.105 | 1.135 | 1.173 | 1.188 | 1.12 | 1.22 | 0.91 | 1.14 | 0.93 |
| K | 260T | −0.008 | −42.091 | 72.850 | −0.003 | −44.934 | −19.893 | −23.271 | −21.866 | −28.295 | 1.01 | 0.82 | 0.68 | 0.95 | 0.75 |
| K | 260V | 0.049 | 4.944 | 137.786 | 0.014 | 9.136 | 3.847 | 4.821 | 4.316 | 5.514 | 1.15 | 0.83 | 0.58 | 1.50 | 1.01 |
| K | 260W | −0.005 | −83.886 | −964.374 | −0.001 | −99.706 | −39.366 | −46.775 | −43.041 | −61.265 | 1.19 | 1.08 | 0.89 | 0.43 | 1.99 |
| K | 260Y | 0.403 | 1.395 | −2.148 | 0.195 | 1.713 | 1.252 | 1.233 | 0.999 | 1.321 | 1.15 | 1.06 | 0.77 | 1.08 | 1.20 |
| D | 274A | 0.784 | 1.146 | −3.995 | 0.676 | 1.091 | 0.967 | 1.014 | 0.741 | 0.504 | 0.85 | 0.70 | 0.75 | 0.77 | 0.96 |
| D | 274C | 0.756 | 0.943 | −2.904 | 0.426 | 0.967 | 0.871 | 0.909 | 0.874 | 0.376 | 0.90 | 0.90 | 0.42 | 0.98 | 0.71 |
| D | 274F | 0.910 | 0.909 | 3.548 | 0.920 | 1.084 | 0.998 | 0.995 | 0.629 | 0.239 | 0.83 | 0.82 | 0.78 | 0.93 | 1.40 |
| D | 274G | 0.678 | 1.410 | −0.204 | 0.564 | 1.278 | 1.028 | 1.185 | 1.200 | 0.459 | 0.90 | 0.88 | 0.80 | 1.72 | 0.81 |
| D | 274H | 0.890 | 0.889 | 3.994 | 0.666 | 0.947 | 0.866 | 1.062 | 1.099 | 0.209 | 0.92 | 0.90 | 0.71 | 1.21 | 1.21 |
| D | 274I | 0.780 | 0.861 | 2.669 | 0.542 | 1.072 | 1.001 | 1.088 | 1.035 | 0.328 | 1.18 | 1.15 | 0.86 | 1.44 | 1.02 |
| D | 274K | 0.676 | 0.819 | 2.208 | 0.375 | 1.108 | 0.882 | 1.134 | 1.054 | 0.236 | 1.03 | 1.03 | 0.91 | 1.77 | 1.33 |
| D | 274L | 0.654 | 1.162 | −0.146 | 0.499 | 1.313 | 1.152 | 1.196 | 0.796 | 0.333 | 1.02 | 0.83 | 0.72 | 1.10 | 1.32 |
| D | 274M | 0.830 | 0.992 | −8.237 | 0.823 | 1.080 | 1.002 | 0.972 | 0.755 | 0.383 | 0.93 | 0.77 | 0.76 | 1.07 | 1.25 |
| D | 274N | 0.863 | 1.036 | −1.791 | 0.726 | 1.009 | 0.927 | 0.937 | 0.971 | 0.509 | 1.10 | 1.07 | 0.90 | 1.59 | 1.02 |
| D | 274P | 0.773 | 1.044 | −1.667 | 0.591 | 1.031 | 0.805 | 0.875 | 0.875 | 0.227 | 0.76 | 0.69 | 0.75 | 1.42 | 1.29 |
| D | 274Q | 0.900 | 0.994 | −0.787 | 0.691 | 0.950 | 0.889 | 1.050 | 1.032 | 0.480 | 0.97 | 0.96 | 0.72 | 1.12 | 1.20 |
| D | 274R | 0.804 | 0.942 | 1.502 | 0.702 | 0.883 | 0.779 | 0.883 | 0.689 | 0.168 | 0.87 | 0.98 | 0.80 | 1.10 | 1.67 |
| D | 274S | 0.926 | 0.942 | −0.313 | 0.598 | 0.987 | 0.846 | 0.946 | 0.933 | 0.489 | 0.95 | 0.95 | 0.97 | 1.67 | 1.32 |
| D | 274T | 0.844 | 0.981 | 8.386 | 0.585 | 1.110 | 0.990 | 1.013 | 0.803 | 0.520 | 1.14 | 1.10 | 0.93 | 1.60 | 1.21 |
| D | 274V | 0.793 | 0.850 | 0.378 | 0.589 | 1.044 | 1.006 | 1.115 | 1.060 | 0.360 | 1.13 | 1.18 | 1.06 | 1.05 | 0.99 |
| D | 274W | 0.794 | 0.905 | −5.001 | 0.492 | 1.120 | 0.954 | 0.857 | 0.743 | 0.248 | 0.88 | 0.79 | 1.09 | 1.21 | 1.28 |
| D | 274Y | 0.730 | 1.038 | 3.229 | 0.479 | 1.201 | 0.990 | 1.059 | 0.788 | 0.287 | 0.86 | 0.75 | 0.76 | 0.91 | 1.15 |
| D | 275A | 0.688 | 0.816 | 1.723 | 1.279 | 0.798 | 0.634 | 0.830 | 0.710 | 0.621 | 1.01 | 0.95 | 0.78 | 1.05 | 1.04 |
| D | 275C | 1.160 | 0.665 | 1.253 | 0.751 | 0.694 | 0.594 | 0.781 | 0.779 | 0.413 | 0.78 | 0.82 | 0.48 | 0.52 | 0.32 |
| D | 275E | 1.081 | 0.877 | 1.086 | 1.129 | 0.858 | 0.913 | 0.904 | 0.899 | 0.586 | 1.08 | 1.05 | 0.84 | 1.02 | 0.84 |
| D | 275F | 0.905 | 0.996 | 0.730 | 0.741 | 0.868 | 0.819 | 0.823 | 0.847 | 0.249 | 1.02 | 1.03 | 0.87 | 1.22 | 0.98 |
| D | 275G | 0.863 | 1.048 | −0.154 | 0.793 | 1.043 | 0.990 | 1.063 | 1.093 | 0.613 | 1.03 | 1.06 | 0.96 | 1.24 | 1.28 |
| D | 275H | 0.976 | 0.790 | 1.028 | 0.734 | 0.735 | 0.364 | 0.807 | 0.794 | 0.236 | 1.07 | 1.03 | 0.77 | 1.15 | 1.05 |
| D | 275I | 0.908 | 0.916 | −0.402 | 0.740 | 0.898 | 0.621 | 0.899 | 0.870 | 0.393 | 0.95 | 0.94 | 0.76 | 0.97 | 0.72 |
| D | 275K | 0.859 | 0.864 | 0.106 | 0.683 | 0.878 | 0.435 | 0.943 | 0.912 | 0.393 | 0.80 | 0.88 | 0.60 | 1.19 | 0.48 |
| D | 275L | 0.878 | 0.980 | 2.356 | 0.582 | 0.898 | 0.594 | 0.929 | 0.922 | 0.428 | 0.98 | 0.87 | 0.70 | 1.09 | 0.77 |
| D | 275M | 1.116 | 0.771 | 3.414 | 1.129 | 0.787 | 0.558 | 0.807 | 0.703 | 0.390 | 0.97 | 0.89 | 0.78 | 1.08 | 0.68 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| D | 275N | 0.957 | 0.994 | 3.646 | 0.903 | 0.991 | 0.733 | 0.978 | 0.834 | 0.624 | 1.03 | 1.05 | 0.73 | 1.08 | 1.00 |
| D | 275P | 0.855 | 0.860 | 2.266 | 0.631 | 0.906 | 0.709 | 0.804 | 0.833 | 0.513 | 0.88 | 0.89 | 0.72 | 1.07 | 1.15 |
| D | 275Q | 0.966 | 0.916 | −0.018 | 0.828 | 0.830 | 0.703 | 0.947 | 0.995 | 0.563 | 1.16 | 1.23 | 0.76 | 1.39 | 0.82 |
| D | 275R | 1.105 | 0.711 | 0.358 | 0.659 | 0.584 | 0.225 | 0.771 | 0.817 | 0.255 | 0.93 | 1.16 | 0.76 | 1.34 | 0.59 |
| D | 275S | 0.933 | 0.919 | 2.440 | 0.738 | 0.880 | 0.695 | 0.965 | 0.978 | 0.731 | 1.13 | 1.18 | 0.97 | 1.32 | 1.15 |
| D | 275T | 0.880 | 0.924 | 0.336 | 0.635 | 0.931 | 0.738 | 1.036 | 1.059 | 0.647 | 1.09 | 1.14 | 1.07 | 1.09 | 1.33 |
| D | 275V | 0.782 | 1.001 | −1.433 | 0.541 | 1.008 | 0.688 | 1.053 | 1.015 | 0.520 | 0.97 | 1.07 | 0.85 | 0.85 | 1.12 |
| D | 275W | 0.751 | 1.054 | 0.717 | 0.568 | 1.052 | 0.697 | 1.002 | 0.900 | 0.328 | 1.09 | 0.90 | 0.88 | 0.93 | 1.05 |
| D | 275Y | 0.937 | 0.774 | −0.664 | 0.729 | 0.861 | 0.542 | 0.858 | 0.666 | 0.308 | 0.96 | 0.85 | 0.86 | 1.02 | 0.87 |
| D | 276A | 0.881 | 1.232 | −2.011 | 0.986 | 1.087 | 0.950 | 0.960 | 0.624 | 0.754 | 1.11 | 0.85 | 0.64 | 1.60 | 1.00 |
| D | 276C | 0.805 | 0.881 | −3.254 | 0.621 | 1.001 | 0.835 | 0.874 | 0.688 | 0.710 | 1.09 | 0.95 | 0.81 | 1.31 | 0.83 |
| D | 276D | 0.695 | 1.124 | −1.426 | 0.385 | 0.886 | 0.307 | 0.567 | 0.425 | 0.441 | 0.40 | 0.25 | 0.61 | 2.10 | 0.47 |
| E | 276F | 0.742 | 1.268 | 2.627 | 0.672 | 1.249 | 0.751 | 0.954 | 0.648 | 0.611 | 1.14 | 0.98 | 0.83 | 1.66 | 0.49 |
| E | 276G | 0.800 | 1.389 | −2.738 | 0.741 | 1.118 | 0.767 | 0.927 | 0.817 | 0.564 | 0.96 | 0.87 | 0.75 | 1.86 | 0.95 |
| E | 276H | 0.756 | 1.312 | −2.828 | 0.659 | 1.152 | 0.777 | 1.027 | 0.899 | 0.625 | 1.10 | 1.04 | 0.79 | 2.14 | 0.83 |
| E | 276I | 1.246 | 0.874 | 13.044 | 1.315 | 0.818 | 0.711 | 0.745 | 0.501 | 0.413 | 0.98 | 0.85 | 0.71 | 1.65 | 0.76 |
| E | 276K | 0.746 | 1.258 | −1.831 | 0.658 | 1.201 | 0.931 | 1.108 | 0.856 | 0.983 | 1.12 | 1.02 | 0.92 | 1.85 | 1.37 |
| E | 276L | 0.662 | 1.222 | −8.425 | 0.526 | 1.277 | 0.795 | 0.912 | 0.588 | 0.691 | 1.21 | 1.04 | 0.91 | 1.51 | 1.24 |
| E | 276M | 1.060 | 0.999 | −4.376 | 1.317 | 0.943 | 0.914 | 0.869 | 0.454 | 0.915 | 1.03 | 0.82 | 1.06 | 1.56 | 1.13 |
| E | 276N | 0.828 | 1.359 | −0.311 | 0.882 | 1.114 | 0.723 | 0.860 | 0.504 | 0.367 | 0.89 | 0.62 | 0.91 | 1.56 | 0.75 |
| E | 276P | 0.630 | 1.493 | −5.869 | 0.500 | 1.310 | 0.915 | 0.985 | 0.598 | 0.467 | 0.95 | 0.66 | 0.84 | 1.74 | 0.48 |
| E | 276Q | 0.775 | 1.499 | −5.908 | 0.756 | 1.166 | 0.706 | 0.891 | 0.585 | 0.571 | 1.07 | 0.89 | 0.85 | 1.69 | 0.79 |
| E | 276R | 0.680 | 1.397 | −8.831 | 0.548 | 1.244 | 0.893 | 1.017 | 0.719 | 0.867 | 1.08 | 1.00 | 0.78 | 2.00 | 1.33 |
| E | 276S | 0.847 | 1.319 | −6.099 | 0.904 | 1.196 | 0.943 | 1.062 | 0.757 | 0.615 | 1.04 | 0.94 | 0.80 | 2.09 | 1.20 |
| E | 276T | 0.778 | 1.366 | −3.964 | 0.814 | 1.268 | 1.079 | 1.163 | 0.808 | 0.879 | 1.07 | 0.92 | 0.99 | 2.10 | 1.09 |
| E | 276W | −0.120 | −0.554 | 2.011 | −0.022 | −0.973 | −0.090 | −0.408 | −0.469 | −1.038 | 0.01 | −0.04 | 1.34 | 1.98 | 0.41 |
| E | 276Y | 0.116 | −1.118 | −55.743 | 0.023 | 0.705 | 0.086 | 0.263 | 0.312 | 0.979 | 1.07 | 0.89 | 0.09 | −0.44 | 0.67 |
| E | 277A | 0.828 | 1.168 | −0.584 | 0.996 | 1.207 | 0.728 | 0.897 | 0.523 | 0.534 | 1.04 | 0.85 | 0.73 | 1.57 | 0.89 |
| E | 277C | 0.958 | 1.079 | 0.565 | 1.028 | 0.972 | 0.714 | 0.862 | 0.595 | 0.496 | 0.92 | 0.74 | 0.82 | 1.12 | 0.81 |
| E | 277D | 0.911 | 0.928 | 1.893 | 0.988 | 0.951 | 0.863 | 0.875 | 0.695 | 0.600 | 0.85 | 0.81 | 0.57 | 0.61 | 0.50 |
| E | 277F | 0.824 | 1.156 | 13.245 | 0.761 | 1.046 | 0.929 | 0.981 | 0.706 | 0.570 | 0.87 | 0.76 | 0.98 | 0.99 | 0.75 |
| E | 277M | 0.821 | 1.203 | 0.935 | 0.734 | 1.059 | 0.944 | 0.909 | 0.916 | 0.386 | 0.84 | 0.70 | 0.88 | 1.17 | 0.96 |
| E | 277N | 0.873 | 1.159 | 0.869 | 0.760 | 1.046 | 0.876 | 0.700 | 0.773 | 0.710 | 0.70 | 0.59 | 0.63 | 1.16 | 0.72 |
| E | 277P | 0.775 | 1.164 | 0.579 | 0.733 | 0.959 | 0.718 | 0.983 | 0.594 | 0.366 | 0.54 | 0.40 | 0.42 | 1.62 | 0.57 |
| E | 277F | 0.806 | 0.775 | 0.331 | 0.854 | 1.031 | 0.445 | 0.915 | 1.095 | 0.432 | 0.74 | 0.70 | 0.56 | 1.27 | 0.85 |
| E | 277G | 0.726 | 1.484 | 1.444 | 0.768 | 1.124 | 0.641 | 1.017 | 0.889 | 0.270 | 0.88 | 0.77 | 0.58 | 1.61 | 0.97 |
| E | 277H | 0.797 | 1.291 | 1.255 | 0.604 | 1.200 | 0.639 | 0.926 | 1.178 | 0.362 | 0.94 | 0.79 | 0.95 | 0.92 | 0.70 |
| E | 277I | 0.715 | 1.255 | 0.629 | 0.882 | 1.269 | 0.898 | 1.121 | 1.289 | 0.819 | 0.99 | 0.96 | 1.11 | 1.26 | 0.72 |
| E | 277K | 0.953 | 1.163 | 0.397 | 0.601 | 1.222 | 1.175 | 1.285 | 1.028 | 0.555 | 0.84 | 1.03 | 1.01 | 1.32 | 0.44 |
| E | 277L | 0.786 | 1.042 | 0.429 | 0.988 | 1.044 | 0.663 | 1.047 | 0.973 | 0.657 | 1.02 | 0.85 | 0.95 | 1.12 | 0.75 |
| E | 277Q | 1.056 | 1.409 | 0.651 | 1.141 | 0.886 | 0.834 | 0.983 | 1.062 | 0.874 | 0.86 | 0.87 | 0.83 | 0.62 | 0.91 |
| E | 277R | 0.839 | 0.775 | 0.564 | 0.696 | 0.987 | 0.512 | 0.926 | 0.941 | 0.426 | 0.76 | 0.86 | 0.73 | 1.32 | 0.42 |
| E | 277S | 0.889 | 1.078 | 0.784 | 0.758 | 0.921 | 0.488 | 0.684 | 0.631 | 0.367 | 0.62 | 0.48 | 0.95 | 1.18 | 0.52 |
| E | 277T | 0.759 | 1.300 | 0.840 | 0.683 | 1.176 | 0.863 | 0.998 | 0.973 | 0.495 | 0.81 | 0.75 | 0.85 | 1.25 | 0.67 |
| E | 277V | 0.896 | 1.071 | 0.931 | 0.913 | 1.099 | 0.972 | 1.032 | 1.035 | 0.750 | 0.97 | 1.00 | 1.45 | 1.07 | 0.39 |
| E | 277W | 0.575 | 1.369 | 0.208 | 0.371 | 1.301 | 0.646 | 1.011 | 0.876 | 0.427 | 0.83 | 0.74 | 0.82 | 0.97 | 0.53 |
| E | 277Y | 0.556 | 1.353 | 2.414 | 0.381 | 1.376 | 0.616 | 0.992 | 0.715 | 0.527 | 0.76 | 0.68 | 0.66 | 1.33 | 0.53 |
| S | 282A | 1.283 | 0.848 | 0.334 | 1.947 | 0.894 | 0.985 | 0.886 | 0.613 | 0.919 | 0.99 | 0.83 | 0.61 | 0.88 | 1.21 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| S | 282C | 1.223 | 0.773 | 0.336 | 1.665 | 0.874 | 0.951 | 0.877 | 0.730 | 0.911 | 1.02 | 0.90 | 0.55 | 0.77 | 0.85 |
| S | 282D | 1.171 | 0.834 | 0.748 | 1.501 | 0.887 | 0.914 | 0.872 | 0.740 | 0.863 | 0.95 | 0.84 | 0.77 | 0.73 | 1.15 |
| S | 282E | 1.066 | 0.922 | 17.127 | 1.173 | 0.946 | 0.988 | 0.918 | 0.692 | 0.919 | 1.01 | 0.88 | 0.88 | 0.85 | 1.07 |
| S | 282F | 0.738 | 1.051 | 0.180 | 0.549 | 1.059 | 0.826 | 0.768 | 0.724 | 0.742 | 1.00 | 0.89 | 0.91 | 0.74 | 0.88 |
| S | 282G | 0.309 | 1.681 | 3.584 | 0.138 | 1.862 | 1.031 | 1.015 | 0.889 | 0.875 | 1.02 | 0.89 | 0.80 | 0.80 | 0.90 |
| S | 282H | 1.013 | 1.014 | 0.426 | 1.237 | 1.036 | 1.018 | 0.961 | 0.818 | 0.844 | 1.00 | 0.87 | 0.80 | 0.80 | 1.02 |
| S | 282I | 0.960 | 0.929 | −0.860 | 1.082 | 1.081 | 1.083 | 1.046 | 0.848 | 1.065 | 1.02 | 0.92 | 0.86 | 0.87 | 1.09 |
| S | 282K | 0.957 | 0.880 | 0.080 | 1.167 | 1.058 | 1.123 | 1.048 | 0.778 | 1.040 | 0.97 | 0.86 | 0.93 | 0.66 | 1.22 |
| S | 282L | 0.963 | 0.838 | 0.906 | 1.182 | 1.116 | 1.147 | 1.018 | 0.760 | 1.066 | 0.97 | 0.93 | 0.71 | 0.74 | 1.17 |
| S | 282M | 0.947 | 1.064 | 0.719 | 1.161 | 1.056 | 1.060 | 0.995 | 0.748 | 1.002 | 1.10 | 0.98 | 0.82 | 0.91 | 1.15 |
| S | 282N | 0.273 | 1.099 | −3.760 | 0.104 | 1.405 | 0.607 | 0.693 | 0.671 | 0.864 | 0.91 | 0.83 | 0.66 | 0.81 | 1.18 |
| S | 282P | 0.066 | 5.567 | 3.490 | 0.025 | 6.213 | 2.963 | 3.309 | 3.318 | 2.390 | 1.02 | 0.91 | 0.54 | 0.78 | 2.16 |
| S | 282Q | 0.832 | 1.222 | 2.746 | 0.701 | 1.033 | 1.077 | 1.046 | 1.018 | 1.012 | 1.05 | 1.06 | 0.93 | 0.92 | 1.15 |
| S | 282R | 0.929 | 0.908 | −0.338 | 0.812 | 0.929 | 0.911 | 0.906 | 0.839 | 0.840 | 1.06 | 1.01 | 0.73 | 0.83 | 1.03 |
| S | 282T | 1.314 | 0.817 | 1.822 | 1.512 | 0.763 | 0.865 | 0.843 | 0.682 | 0.815 | 1.12 | 1.08 | 0.96 | 0.85 | 1.04 |
| S | 282V | 0.966 | 0.901 | 0.653 | 1.000 | 0.981 | 0.980 | 0.966 | 0.954 | 0.987 | 1.05 | 0.99 | 0.83 | 0.76 | 1.01 |
| S | 282W | 0.627 | 1.041 | 0.663 | 0.505 | 1.291 | 1.110 | 1.069 | 0.953 | 1.048 | 1.07 | 0.99 | 0.90 | 0.93 | 1.23 |
| S | 282Y | 0.659 | 0.934 | 1.848 | 0.570 | 1.295 | 1.113 | 1.033 | 0.775 | 0.858 | 1.04 | 0.97 | 0.82 | 0.73 | 1.23 |
| D | 283A | 0.093 | 3.176 | 16.660 | 0.023 | 1.698 | 0.228 | 0.724 | 0.751 | 1.485 | 0.26 | 0.17 | −1.42 | −1.43 | −0.55 |
| D | 283C | 0.512 | 1.428 | −11.440 | 0.350 | 1.462 | 1.244 | 1.195 | 0.933 | 0.988 | 0.96 | 0.82 | 0.90 | 0.74 | 1.20 |
| D | 283F | 0.124 | 3.000 | −26.166 | 0.041 | 3.719 | 1.582 | 1.869 | 1.814 | 1.436 | 0.91 | 0.87 | 0.98 | 1.06 | 0.74 |
| D | 283G | 0.592 | 1.294 | 0.003 | 0.394 | 1.468 | 1.103 | 0.906 | 1.012 | 0.938 | 1.05 | 0.97 | 1.71 | 0.91 | 1.06 |
| D | 283H | 0.481 | 1.206 | −15.705 | 0.269 | 1.459 | 1.041 | 1.094 | 0.959 | 0.431 | 1.06 | 1.01 | 1.24 | 0.91 | 1.27 |
| D | 283I | 0.093 | 2.447 | −18.134 | 0.026 | 4.757 | 1.872 | 2.211 | 1.984 | 1.690 | 1.02 | 1.08 | 1.14 | 1.16 | 0.62 |
| D | 283L | 0.101 | 2.177 | 10.931 | 0.028 | 3.851 | 1.491 | 1.824 | 1.424 | 1.516 | 0.99 | 0.91 | 0.54 | 0.37 | 0.59 |
| D | 283M | 0.392 | 0.995 | −0.630 | 0.225 | 1.504 | 0.895 | 0.874 | 0.477 | 0.713 | 0.93 | 0.91 | 0.17 | 0.74 | 0.53 |
| D | 283N | 0.941 | 1.040 | −3.071 | 1.093 | 1.102 | 1.126 | 1.030 | 0.674 | 0.966 | 0.71 | 0.53 | 0.62 | 0.86 | 1.04 |
| D | 283P | 0.566 | 1.021 | −2.866 | 0.380 | 1.577 | 1.072 | 1.036 | 0.703 | 0.665 | 0.96 | 0.82 | 0.61 | 1.28 | 0.74 |
| D | 283R | 0.186 | 2.350 | −18.557 | 0.077 | 3.151 | 1.619 | 1.731 | 1.310 | 0.941 | 0.95 | 0.80 | 0.61 | 1.58 | 1.81 |
| D | 283S | 0.563 | 1.191 | −10.251 | 0.442 | 1.641 | 1.392 | 1.348 | 0.975 | 1.106 | 1.04 | 0.91 | 1.42 | 1.13 | 1.42 |
| D | 283T | 0.461 | 1.385 | −14.813 | 0.290 | 1.794 | 1.300 | 1.275 | 0.905 | 0.904 | 1.05 | 0.88 | 1.44 | 1.33 | 1.04 |
| D | 283V | 0.238 | 1.612 | 1.764 | 0.095 | 2.295 | 1.335 | 1.527 | 1.487 | 1.000 | 0.97 | 0.86 | 0.75 | 1.23 | 0.78 |
| D | 283W | 0.334 | 1.112 | −7.851 | 0.168 | 2.081 | 1.180 | 1.284 | 0.835 | 0.732 | 0.91 | 0.87 | 1.32 | 1.49 | 1.30 |
| D | 283Y | 0.256 | 1.521 | 2.734 | 0.134 | 2.951 | 1.633 | 1.669 | 1.157 | 0.983 | 0.92 | 0.88 | 0.92 | 1.00 | 0.91 |
| D | 284A | 1.049 | 0.906 | −0.612 | 1.148 | 0.907 | 0.907 | 0.810 | 0.642 | 0.869 | 1.11 | 0.97 | 1.07 | 1.02 | 1.34 |
| D | 284C | 0.920 | 0.917 | 0.370 | 0.819 | 0.926 | 0.919 | 0.869 | 0.759 | 0.892 | 1.08 | 1.02 | 1.29 | 0.87 | 0.81 |
| D | 284E | 0.946 | 1.034 | −0.428 | 0.839 | 0.982 | 1.001 | 0.985 | 0.934 | 0.999 | 1.06 | 1.05 | 1.24 | 0.96 | 1.26 |
| D | 284F | 0.679 | 1.010 | −0.962 | 0.414 | 1.152 | 0.963 | 0.969 | 0.906 | 0.966 | 1.13 | 1.13 | 1.91 | 1.02 | 1.37 |
| D | 284G | 0.805 | 1.051 | 0.701 | 0.620 | 1.080 | 1.019 | 1.000 | 0.926 | 0.981 | 1.08 | 1.10 | 1.52 | 0.92 | 1.20 |
| D | 284H | 0.791 | 0.942 | 0.631 | 0.565 | 1.089 | 0.973 | 0.966 | 0.910 | 0.929 | 1.12 | 1.10 | 1.57 | 1.11 | 1.15 |
| D | 284I | 0.769 | 0.818 | −0.605 | 0.610 | 1.165 | 1.080 | 1.062 | 0.944 | 1.057 | 1.09 | 1.05 | 1.32 | 0.92 | 1.35 |
| D | 284K | 0.609 | 0.919 | −1.611 | 0.401 | 1.367 | 1.168 | 1.112 | 0.905 | 1.056 | 1.11 | 1.07 | 1.15 | 1.39 | 1.46 |
| D | 284L | 0.653 | 0.944 | −1.146 | 0.422 | 1.276 | 1.036 | 1.058 | 0.712 | 1.051 | 1.12 | 1.01 | 1.16 | 1.11 | 1.51 |
| D | 284M | 1.049 | 0.845 | −0.392 | 1.148 | 0.973 | 0.969 | 0.864 | 0.546 | 0.876 | 0.98 | 0.82 | 0.90 | 1.08 | 0.93 |
| D | 284N | 1.098 | 0.897 | −0.404 | 1.110 | 0.911 | 0.918 | 0.834 | 0.605 | 0.836 | 0.89 | 0.89 | 1.10 | 0.36 | 1.00 |
| D | 284P | 0.427 | 0.651 | −1.032 | 0.113 | 0.913 | 0.286 | 0.351 | 0.358 | 0.537 | 0.47 | 0.48 | 0.40 | 0.86 | 0.77 |
| D | 284Q | 0.963 | 0.866 | 0.349 | 0.896 | 1.013 | 0.985 | 0.927 | 0.681 | 0.927 | 0.95 | 0.85 | 1.03 | 1.05 | 1.05 |
| D | 284R | 0.673 | 1.124 | −0.487 | 0.479 | 1.265 | 1.071 | 0.997 | 0.764 | 0.937 | 0.99 | 0.92 | 0.79 | 1.79 | 1.61 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| D | 284S | 0.936 | 0.980 | 0.614 | 0.830 | 1.077 | 1.016 | 0.988 | 0.747 | 0.973 | 1.12 | 1.04 | 1.55 | 0.77 | 1.39 |
| D | 284T | 0.863 | 0.951 | −0.924 | 0.776 | 1.171 | 1.115 | 1.059 | 0.818 | 1.076 | 1.14 | 1.06 | 1.39 | 1.38 | 1.51 |
| D | 284V | 0.897 | 0.897 | 0.821 | 0.795 | 1.100 | 1.013 | 0.974 | 0.686 | 0.974 | 1.11 | 0.97 | 1.60 | 1.00 | 1.27 |
| D | 284W | 0.803 | 0.854 | −0.813 | 0.611 | 1.141 | 0.959 | 0.910 | 0.628 | 0.940 | 1.09 | 0.99 | 1.48 | 1.29 | 1.27 |
| D | 284Y | 0.780 | 0.993 | −0.933 | 0.709 | 1.271 | 1.151 | 1.047 | 0.582 | 1.086 | 1.08 | 1.04 | 1.07 | 0.89 | 1.14 |
| R | 287A | 0.623 | 1.199 | −7.413 | 0.368 | 1.297 | 1.096 | 1.044 | 0.736 | 1.048 | 1.07 | 1.00 | 0.98 | 0.87 | 0.85 |
| R | 287C | 0.754 | 1.081 | 2.207 | 0.579 | 1.086 | 0.982 | 0.952 | 0.940 | 0.967 | 1.13 | 1.12 | 1.02 | 1.12 | 1.35 |
| R | 287D | 0.045 | 8.093 | 15.737 | 0.011 | 5.379 | 1.534 | 2.554 | 2.819 | 3.792 | 1.21 | 1.26 | −0.25 | 1.54 | 0.58 |
| R | 287E | 0.645 | 0.932 | 2.607 | 0.349 | 1.065 | 0.824 | 0.803 | 0.866 | 0.851 | 1.11 | 1.15 | 0.97 | 0.83 | 0.94 |
| R | 287F | 0.257 | 1.187 | 5.970 | 0.079 | 1.781 | 0.906 | 1.056 | 1.149 | 1.164 | 1.05 | 1.12 | 1.11 | 1.55 | 0.97 |
| R | 287G | 0.344 | 0.590 | 5.359 | 0.089 | 1.184 | 0.479 | 0.575 | 0.665 | 0.754 | 1.27 | 1.37 | 1.23 | 1.38 | 1.30 |
| R | 287H | 0.52 | ND | ND | ND | ND | ND | 0.98 | ND | 0.90 | 1.06 | 1.13 | 1.28 | 0.99 | 0.82 |
| R | 287I | 0.956 | 0.893 | 2.435 | 0.835 | 0.981 | 0.998 | 0.971 | 0.980 | 0.998 | 1.11 | 1.13 | 0.89 | 0.96 | 0.79 |
| R | 287K | 1.012 | 0.799 | 0.205 | 0.918 | 0.957 | 0.941 | 0.940 | 0.820 | 0.950 | 1.21 | 1.15 | 0.86 | 1.12 | 1.34 |
| R | 287L | 0.703 | 0.889 | 4.956 | 0.521 | 1.291 | 1.166 | 1.103 | 0.783 | 1.124 | 1.30 | 1.17 | 0.94 | 0.64 | 1.44 |
| R | 287M | 0.89 | ND | ND | ND | ND | ND | 1.05 | ND | 1.10 | 1.11 | 0.96 | 0.88 | 0.96 | 0.87 |
| R | 287N | 0.343 | 1.568 | 0.528 | 0.152 | 1.582 | 0.956 | 0.971 | 0.989 | 1.112 | 1.06 | 1.01 | 0.59 | 0.81 | 0.81 |
| R | 287P | −0.041 | −6.529 | 2.237 | −0.009 | −5.784 | −1.603 | −2.705 | −2.894 | −3.977 | 1.43 | 1.42 | −0.30 | −0.06 | 1.42 |
| R | 287Q | 0.687 | 1.191 | 0.050 | 0.510 | 1.227 | 1.119 | 1.140 | 1.153 | 1.136 | 1.13 | 1.13 | 1.02 | 0.72 | 0.80 |
| R | 287S | 0.514 | 1.061 | 0.269 | 0.254 | 1.328 | 0.932 | 0.954 | 1.024 | 1.077 | 1.10 | 1.24 | 1.39 | 0.83 | 1.09 |
| R | 287T | 0.763 | 0.952 | 0.627 | 0.513 | 1.072 | 0.930 | 0.927 | 0.988 | 1.009 | 1.13 | 1.17 | 1.38 | 0.67 | 0.62 |
| R | 287V | 0.822 | 0.879 | 0.860 | 0.630 | 1.072 | 1.022 | 1.018 | 1.015 | 1.054 | 1.18 | 1.13 | 1.28 | 0.69 | 0.99 |
| R | 287W | 0.086 | 2.630 | 1.711 | 0.025 | 5.598 | 2.888 | 3.110 | 2.969 | 3.734 | 1.19 | 1.13 | 1.71 | 0.67 | 0.99 |
| R | 287Y | 0.089 | 3.527 | 1.493 | 0.033 | 5.885 | 3.805 | 3.979 | 3.752 | 4.265 | 1.17 | 1.07 | 0.98 | 0.50 | 1.55 |
| P | 307A | 0.040 | 12.301 | 64.124 | 0.013 | 10.093 | 3.657 | 4.708 | 4.142 | 3.404 | 0.94 | 0.92 | 0.09 | 0.59 | 1.07 |
| P | 307C | 0.328 | 1.749 | −0.443 | 0.147 | 1.625 | 1.003 | 1.017 | 0.860 | 0.916 | 0.87 | 0.83 | 0.57 | 0.82 | 1.02 |
| P | 307D | −0.161 | −3.469 | 8.714 | −0.032 | −0.696 | −0.055 | −0.319 | −0.385 | −0.754 | 0.00 | 0.00 | 0.00 | 0.00 | 0.00 |
| P | 307E | −0.094 | −5.247 | 13.095 | −0.003 | −6.259 | −0.417 | −3.479 | −4.155 | −8.815 | 0.00 | 0.00 | 0.00 | 0.00 | 0.00 |
| P | 307F | −0.177 | −2.799 | 2.458 | −0.018 | −1.721 | −0.213 | −0.706 | −0.790 | −1.227 | 0.00 | 0.00 | 0.00 | 0.00 | 0.00 |
| P | 307G | −0.205 | 0.784 | 9.762 | −0.028 | −0.422 | −0.038 | −0.224 | −0.301 | −0.649 | 0.00 | 0.00 | 0.00 | 0.00 | 0.00 |
| P | 307H | −0.095 | −0.522 | 1.515 | −0.036 | −0.425 | −0.055 | −0.209 | −0.259 | −0.556 | 0.00 | 0.00 | 0.00 | 0.00 | 0.00 |
| P | 307I | −0.141 | −3.834 | 2.308 | −0.034 | −0.336 | −0.056 | −0.176 | −0.230 | −0.496 | 0.00 | 0.00 | 0.00 | 0.00 | 0.00 |
| P | 307K | −0.171 | −1.596 | 5.861 | −0.022 | −0.561 | −0.050 | −0.294 | −0.379 | −0.808 | 0.00 | 0.00 | 0.00 | 0.00 | 0.00 |
| P | 307L | −0.228 | −0.427 | −1.295 | −0.031 | −0.820 | −0.099 | −0.334 | −0.384 | −0.659 | 0.00 | 0.00 | 0.00 | 0.00 | 0.00 |
| P | 307M | −0.121 | 0.421 | −2.384 | −0.035 | −0.331 | −0.017 | −0.170 | −0.233 | −0.512 | 0.00 | 0.00 | 0.00 | 0.00 | 0.00 |
| P | 307N | −0.014 | −1.169 | −5.425 | −0.025 | −0.747 | −0.113 | −0.384 | −0.461 | −1.005 | 0.00 | 0.00 | 0.00 | 0.00 | 0.00 |
| P | 307Q | 0.398 | −1.958 | 13.095 | −0.003 | −6.259 | −0.417 | −3.479 | −4.155 | −8.815 | 0.00 | 0.00 | 0.00 | 0.00 | 0.00 |
| P | 307R | −0.094 | 1.527 | −1.073 | 0.173 | 1.495 | 0.844 | 0.815 | 0.578 | 0.752 | 0.92 | 0.82 | 0.52 | 0.96 | 1.19 |
| P | 307S | −0.113 | −3.834 | −0.828 | −0.023 | −0.722 | −0.035 | −0.376 | −0.474 | −1.039 | 0.00 | 0.00 | 0.00 | 0.00 | 0.00 |
| P | 307T | −0.009 | −37.986 | 37.256 | −0.002 | −30.571 | −6.430 | −11.127 | −10.198 | −13.406 | 1.09 | 0.87 | 0.60 | 0.97 | 2.52 |
| P | 307V | 0.102 | 4.602 | −3.599 | 0.031 | 4.544 | 1.749 | 2.087 | 1.593 | 1.575 | 1.04 | 0.88 | 1.15 | 0.60 | 1.36 |
| P | 307W | −0.064 | −1.150 | −10.478 | −0.011 | −1.197 | −0.069 | −0.647 | −0.817 | −1.905 | 0.00 | 0.00 | 0.00 | 0.00 | 0.00 |
| P | 307Y | −0.121 | 1.467 | −4.917 | −0.019 | −0.638 | −0.069 | −0.370 | −0.439 | −1.028 | 0.00 | 0.00 | 0.00 | 0.00 | 0.00 |
| E | 308A | 1.131 | 0.834 | 1.292 | 1.254 | 0.895 | 0.955 | 0.874 | 0.563 | 0.791 | 1.03 | 0.87 | 0.83 | 0.91 | 0.82 |
| E | 308C | 0.789 | 1.116 | −2.888 | 0.655 | 1.048 | 1.034 | 0.964 | 0.786 | 0.864 | 1.00 | 0.88 | 1.18 | 0.96 | 0.86 |
| E | 308D | 0.849 | 1.027 | 1.765 | 0.761 | 1.022 | 0.966 | 0.944 | 0.834 | 0.904 | 1.07 | 0.98 | 0.77 | 0.83 | 0.78 |
| E | 308F | 0.833 | 1.080 | −2.661 | 0.625 | 1.076 | 1.010 | 0.992 | 0.917 | 0.891 | 1.07 | 1.06 | 1.30 | 1.04 | 0.83 |
| E | 308G | 0.489 | 1.327 | −1.764 | 0.260 | 1.519 | 1.115 | 1.118 | 1.026 | 0.711 | 1.05 | 1.00 | 1.41 | 0.71 | 0.51 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| E | 308H | 0.797 | 1.033 | −0.705 | 0.638 | 1.137 | 1.072 | 1.093 | 1.007 | 0.507 | 1.08 | 1.04 | 1.61 | 0.80 | 0.74 |
| E | 308I | 0.911 | 1.000 | 2.647 | 0.815 | 1.077 | 1.080 | 1.067 | 0.981 | 1.028 | 1.24 | 1.20 | 1.59 | 1.03 | 1.15 |
| E | 308K | 0.868 | 0.954 | −3.528 | 0.782 | 1.119 | 1.125 | 1.150 | 0.948 | 1.019 | 1.06 | 1.00 | 1.20 | 0.99 | 1.03 |
| E | 308L | 0.877 | 0.986 | −2.708 | 0.870 | 1.188 | 1.197 | 1.123 | 0.893 | 1.059 | 1.10 | 1.06 | 1.02 | 1.26 | 0.96 |
| E | 308M | 1.098 | 0.920 | −2.537 | 1.550 | 1.017 | 1.181 | 1.041 | 0.584 | 0.962 | 0.98 | 0.81 | 0.76 | 1.01 | 0.96 |
| E | 308N | 1.030 | 0.913 | −4.071 | 1.005 | 0.989 | 0.982 | 0.906 | 0.599 | 0.797 | 1.01 | 0.83 | 0.93 | 1.21 | 1.02 |
| E | 308P | 0.621 | 1.190 | −1.483 | 0.451 | 1.285 | 0.978 | 0.957 | 0.578 | 0.540 | 1.05 | 0.91 | 1.28 | 0.85 | 0.67 |
| E | 308Q | 1.192 | 0.948 | −3.329 | 1.513 | 0.943 | 1.102 | 1.053 | 0.780 | 0.962 | 1.05 | 0.92 | 1.29 | 0.84 | 0.86 |
| E | 308R | 0.962 | 0.883 | −4.648 | 0.816 | 1.006 | 0.932 | 0.891 | 0.673 | 0.779 | 1.03 | 1.00 | 1.38 | 1.77 | 1.85 |
| E | 308S | 0.762 | 1.163 | −2.482 | 0.653 | 1.319 | 1.239 | 1.161 | 0.888 | 1.073 | 1.12 | 1.05 | 1.34 | 0.86 | 0.91 |
| E | 308T | 1.003 | 0.974 | 2.217 | 0.943 | 0.921 | 0.895 | 0.876 | 0.856 | 0.878 | 1.11 | 1.02 | 1.38 | 0.74 | 0.72 |
| E | 308V | 0.930 | 0.965 | −2.084 | 0.859 | 1.101 | 1.113 | 1.091 | 0.889 | 1.030 | 1.06 | 1.02 | 1.24 | 0.83 | 0.93 |
| E | 308W | 0.835 | 1.037 | −3.256 | 0.685 | 1.154 | 1.055 | 1.026 | 0.810 | 0.812 | 1.05 | 0.99 | 1.21 | 1.02 | 1.14 |
| E | 308Y | 0.909 | 0.962 | −0.843 | 0.944 | 1.176 | 1.180 | 1.115 | 0.826 | 0.938 | 1.02 | 0.97 | 1.13 | 1.04 | 0.85 |
| G | 309A | −0.078 | −1.325 | 5.224 | −0.013 | −2.001 | −0.337 | −0.849 | −0.961 | −1.761 | 0.27 | 0.30 | −0.99 | −1.17 | 0.91 |
| G | 309C | −0.847 | 0.520 | −2.813 | −0.143 | −0.303 | −1.441 | −0.396 | 0.000 | −0.103 | 1.01 | 1.00 | 0.84 | 0.56 | 0.82 |
| G | 309D | 0.741 | 1.195 | 1.451 | 0.598 | 1.188 | 1.145 | 1.171 | 1.173 | 1.121 | 1.02 | 1.05 | 0.91 | 0.45 | 0.60 |
| G | 309E | 0.726 | 1.106 | 2.190 | 0.615 | 1.207 | 1.138 | 1.117 | 1.178 | 0.972 | 0.99 | 1.04 | 0.83 | 0.95 | 1.01 |
| G | 309F | 0.526 | 1.105 | 2.372 | 0.348 | 1.449 | 1.160 | 1.186 | 1.029 | 0.900 | 0.88 | 0.96 | 0.86 | 0.78 | 1.01 |
| G | 309H | 0.674 | 1.359 | 2.707 | 0.477 | 1.303 | 1.170 | 1.204 | 1.203 | 0.735 | 0.99 | 1.00 | 0.96 | 0.96 | 0.92 |
| G | 309I | 0.054 | 4.657 | 53.434 | 0.015 | 8.193 | 4.027 | 4.734 | 4.500 | 3.057 | 1.00 | 0.91 | 0.63 | 0.37 | 0.86 |
| G | 309K | 0.796 | 1.006 | 0.223 | 0.614 | 1.138 | 1.041 | 1.032 | 0.924 | 0.702 | 1.03 | 0.99 | 1.26 | 1.22 | 1.16 |
| G | 309L | −0.116 | 3.196 | −26.535 | −0.024 | −0.690 | −0.062 | −0.482 | −0.588 | −1.262 | 0.00 | 0.00 | 0.00 | 0.00 | 0.00 |
| G | 309M | 0.944 | 0.795 | 1.831 | 0.859 | 1.032 | 0.972 | 0.863 | 0.686 | 0.719 | 0.93 | 0.86 | 0.57 | 0.61 | 0.77 |
| G | 309N | 0.833 | 1.013 | 2.119 | 0.716 | 1.045 | 0.937 | 0.953 | 0.811 | 0.764 | 0.99 | 0.97 | 0.69 | 0.76 | 0.97 |
| G | 309P | −0.172 | −1.935 | 1.931 | −0.039 | −1.380 | −0.291 | −0.701 | −0.671 | −0.810 | 1.08 | 0.89 | −0.11 | −0.08 | 0.62 |
| G | 309R | 0.721 | 1.205 | 0.286 | 0.482 | 1.148 | 1.018 | 1.027 | 1.024 | 0.521 | 0.91 | 0.95 | 0.73 | 0.85 | 0.99 |
| G | 309S | 0.550 | 1.222 | 0.694 | 0.337 | 1.351 | 1.061 | 1.059 | 0.967 | 0.944 | 0.98 | 1.05 | 0.90 | 0.82 | 0.72 |
| G | 309T | 0.372 | 1.385 | 0.721 | 0.175 | 1.759 | 1.229 | 1.309 | 1.289 | 0.692 | 0.92 | 0.89 | 0.69 | 0.48 | 0.81 |
| G | 309V | 0.200 | 1.707 | 0.837 | 0.069 | 2.648 | 1.563 | 1.711 | 1.631 | 0.977 | 1.04 | 0.97 | 0.43 | 0.47 | 0.68 |
| G | 309Y | 0.512 | 1.500 | 1.926 | 0.332 | 1.690 | 1.426 | 1.438 | 1.065 | 1.064 | 1.06 | 0.94 | 0.73 | 0.79 | 1.03 |
| G | 310A | 1.078 | 0.885 | 0.668 | 1.284 | 0.930 | 0.795 | 0.740 | 0.408 | 0.459 | 1.03 | 0.75 | 0.60 | 0.60 | 1.20 |
| G | 310D | 0.130 | 3.009 | −3.300 | 0.041 | 2.789 | 0.881 | 1.283 | 0.981 | 0.959 | 0.95 | 0.65 | 0.49 | 1.46 | 1.49 |
| G | 310E | 0.102 | 3.529 | 17.007 | 0.035 | 3.949 | 1.412 | 1.820 | 1.444 | 1.572 | 0.99 | 0.68 | 0.57 | 1.45 | 1.86 |
| G | 310F | −0.028 | −13.950 | −22.610 | −0.006 | −9.776 | −1.979 | −3.878 | −3.440 | −4.132 | 1.02 | 0.70 | 0.27 | −0.18 | 2.48 |
| G | 310H | 0.179 | 1.951 | −1.434 | 0.057 | 2.452 | 0.830 | 1.059 | 0.929 | 0.626 | 0.96 | 0.68 | 0.87 | 1.15 | 1.27 |
| G | 310I | 0.064 | 4.120 | 14.093 | 0.014 | 3.618 | 0.675 | 1.551 | 1.170 | 1.728 | 0.69 | 0.38 | 0.45 | −0.30 | 0.12 |
| G | 310L | −0.018 | −15.525 | −203.606 | −0.005 | −14.424 | −2.634 | −5.456 | −3.922 | −6.535 | 1.02 | 0.71 | 0.04 | 1.35 | 1.07 |
| G | 310M | 0.068 | 7.657 | 13.212 | 0.019 | 3.968 | 0.745 | 1.707 | 1.265 | 1.734 | 1.21 | 0.72 | −0.06 | 0.90 | 1.27 |
| G | 310N | 0.133 | 3.620 | 3.299 | 0.047 | 2.857 | 1.060 | 1.321 | 1.220 | 1.190 | 1.08 | 0.86 | 0.23 | 1.35 | 1.04 |
| G | 310P | 0.063 | 5.967 | 9.488 | 0.018 | 5.116 | 1.577 | 2.451 | 2.186 | 1.817 | 1.01 | 0.74 | 0.53 | 1.77 | 2.22 |
| G | 310Q | 0.123 | 3.166 | 10.433 | 0.041 | 3.488 | 1.510 | 1.881 | 1.740 | 0.990 | 1.02 | 0.81 | 0.43 | 0.91 | 1.24 |
| G | 310R | −0.011 | −37.076 | −83.078 | −0.002 | −23.540 | −5.366 | −10.362 | −9.813 | −10.300 | 1.09 | 0.80 | −0.10 | 1.12 | 2.94 |
| G | 310S | 0.83 | ND | ND | ND | ND | ND | 0.92 | ND | 0.46 | 0.94 | 0.79 | 0.83 | 0.96 | 1.06 |
| G | 310T | 0.226 | 1.901 | 3.632 | 0.085 | 2.237 | 1.041 | 1.193 | 1.088 | 0.608 | 0.94 | 0.75 | 0.46 | 0.82 | 1.27 |
| G | 310V | 0.24 | ND | ND | ND | ND | ND | 0.74 | ND | 0.04 | 0.97 | 0.60 | −0.04 | 0.82 | 0.23 |
| G | 310W | −0.065 | −3.564 | −16.305 | −0.013 | −3.219 | −0.458 | −1.400 | −1.163 | −1.698 | 0.00 | 0.00 | 0.00 | 0.00 | 0.00 |
| G | 310Y | −0.013 | −22.260 | −63.157 | −0.004 | −18.621 | −4.043 | −7.964 | −5.723 | −7.408 | 1.02 | 0.75 | 0.14 | 1.57 | 0.39 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| G | 311A | 0.914 | 0.772 | 1.406 | 0.825 | 0.960 | 0.664 | 0.654 | 0.491 | 0.312 | 1.02 | 0.78 | 0.76 | 1.41 | 0.91 |
| G | 311C | 0.291 | 2.247 | 5.566 | 0.146 | 2.036 | 1.030 | 1.162 | 0.821 | 0.570 | 1.02 | 0.71 | 0.91 | 0.79 | 0.85 |
| G | 311D | 0.231 | 2.000 | 8.116 | 0.098 | 2.242 | 0.926 | 1.135 | 0.944 | 0.680 | 0.96 | 0.63 | 0.61 | 0.39 | 0.47 |
| G | 311E | 0.490 | 1.338 | 0.679 | 0.274 | 1.425 | 0.868 | 0.902 | 0.772 | 0.435 | 0.96 | 0.69 | 0.66 | 0.89 | 0.97 |
| G | 311F | 0.101 | 2.774 | 8.956 | 0.032 | 4.012 | 1.286 | 1.729 | 1.578 | 1.223 | 0.93 | 0.67 | 0.92 | 1.09 | 1.28 |
| G | 311H | 0.445 | 1.158 | 3.143 | 0.258 | 1.651 | 0.904 | 1.056 | 0.747 | 0.502 | 0.97 | 0.65 | 0.97 | 1.30 | 1.10 |
| G | 311I | 0.009 | 44.933 | −1972.726 | 0.002 | 45.723 | 19.892 | 26.560 | 22.865 | 15.142 | 0.93 | 0.61 | 0.68 | 0.92 | 0.88 |
| G | 311K | 0.463 | 1.082 | 5.915 | 0.312 | 1.577 | 0.992 | 1.064 | 0.659 | 0.400 | 0.95 | 0.64 | 0.73 | 1.30 | 1.09 |
| G | 311L | 0.042 | 4.233 | 44.246 | 0.014 | 9.763 | 3.147 | 4.341 | 3.247 | 3.191 | 1.09 | 0.72 | 0.48 | 1.26 | 1.86 |
| G | 311M | 0.421 | 1.504 | 2.471 | 0.230 | 1.441 | 0.748 | 0.887 | 0.615 | 0.445 | 1.02 | 0.74 | 0.77 | 0.98 | 0.82 |
| G | 311N | 0.49 | ND | ND | ND | ND | ND | 0.92 | ND | 0.20 | 1.01 | 0.80 | 0.66 | 1.29 | 0.82 |
| G | 311P | 0.084 | 1.910 | 10.219 | 0.022 | 3.371 | 0.809 | 1.473 | 1.490 | 1.407 | 0.10 | 0.23 | 0.83 | 0.33 | 1.83 |
| G | 311Q | 0.345 | 1.601 | 1.610 | 0.179 | 1.877 | 1.133 | 1.321 | 1.198 | 0.551 | 1.01 | 0.83 | 0.68 | 0.95 | 0.71 |
| G | 311R | 0.521 | 1.144 | 1.728 | 0.353 | 1.484 | 0.892 | 0.998 | 1.036 | 0.381 | 0.94 | 0.74 | 0.81 | 1.50 | 1.37 |
| G | 311S | 0.437 | 1.268 | 1.548 | 0.240 | 1.549 | 0.952 | 1.008 | 0.929 | 0.487 | 0.96 | 0.80 | 0.72 | 1.00 | 0.86 |
| G | 311T | 0.351 | 1.403 | 7.899 | 0.182 | 1.841 | 1.141 | 1.240 | 1.109 | 0.619 | 0.94 | 0.76 | 0.82 | 0.94 | 0.69 |
| G | 311V | 0.176 | 2.834 | 7.533 | 0.070 | 2.885 | 1.390 | 1.679 | 1.424 | 0.810 | 1.00 | 0.76 | 0.60 | 0.08 | 0.88 |
| G | 311W | −0.017 | −10.958 | −56.572 | −0.004 | −16.932 | −3.862 | −7.338 | −6.384 | −7.438 | 1.42 | 0.89 | 0.91 | 2.48 | 2.64 |
| G | 311Y | 0.244 | 1.352 | 6.070 | 0.099 | 2.178 | 1.023 | 1.200 | 0.816 | 0.589 | 0.99 | 0.76 | 0.55 | 0.81 | 0.78 |
| N | 312A | 1.051 | 0.878 | 0.148 | 1.048 | 0.913 | 0.877 | 0.817 | 0.618 | 0.781 | 1.00 | 0.88 | 0.73 | 0.93 | 0.54 |
| N | 312C | 0.717 | 1.271 | 2.026 | 0.560 | 1.186 | 1.087 | 1.037 | 0.999 | 1.062 | 1.00 | 0.96 | 0.86 | 0.71 | 0.69 |
| N | 312D | 0.693 | 1.431 | 0.244 | 0.555 | 1.234 | 1.117 | 1.081 | 1.089 | 1.100 | 0.94 | 0.95 | 0.87 | 0.81 | 0.37 |
| N | 312E | 0.881 | 1.105 | 0.666 | 0.822 | 1.051 | 1.037 | 1.031 | 1.047 | 1.008 | 1.04 | 1.06 | 0.89 | 0.95 | 0.99 |
| N | 312F | 0.604 | 1.437 | 2.723 | 0.422 | 1.353 | 1.144 | 1.138 | 1.159 | 0.952 | 0.99 | 1.02 | 0.92 | 0.93 | 0.74 |
| N | 312G | 0.845 | 1.234 | 0.568 | 0.682 | 1.109 | 1.020 | 1.039 | 1.052 | 0.978 | 1.06 | 1.10 | 0.85 | 1.15 | 0.72 |
| N | 312H | 0.727 | 1.221 | 2.177 | 0.577 | 1.252 | 1.169 | 1.192 | 1.186 | 1.057 | 1.01 | 1.02 | 0.88 | 1.04 | 0.81 |
| N | 312I | 0.575 | 1.259 | 2.152 | 0.409 | 1.485 | 1.314 | 1.345 | 1.260 | 1.248 | 1.10 | 1.07 | 0.67 | 0.95 | 0.85 |
| N | 312K | 0.875 | 0.949 | −0.316 | 0.786 | 1.113 | 1.043 | 1.076 | 0.911 | 0.986 | 1.01 | 0.98 | 0.70 | 0.88 | 1.18 |
| N | 312L | 0.618 | 0.975 | 1.627 | 0.500 | 1.498 | 1.360 | 1.319 | 0.916 | 1.289 | 1.08 | 0.97 | 0.82 | 0.68 | 0.93 |
| N | 312M | 0.871 | 0.995 | −0.444 | 0.811 | 1.063 | 1.000 | 0.929 | 0.711 | 0.902 | 1.00 | 0.91 | 0.74 | 0.86 | 0.84 |
| N | 312P | 0.260 | 0.212 | −0.480 | 0.064 | 0.292 | 0.020 | 0.148 | 0.167 | 0.431 | 0.51 | 0.53 | 0.36 | 0.57 | −0.10 |
| N | 312Q | 0.909 | 1.019 | −0.495 | 0.749 | 1.010 | 0.955 | 0.954 | 0.946 | 0.934 | 1.01 | 1.02 | 0.74 | 1.26 | 0.83 |
| N | 312R | 0.97 | ND | ND | ND | ND | ND | 1.03 | ND | 0.89 | 0.99 | 1.00 | 0.89 | 1.17 | 0.96 |
| N | 312S | 0.847 | 1.042 | −0.274 | 0.668 | 1.114 | 1.023 | 1.063 | 1.052 | 1.010 | 1.06 | 1.08 | 0.99 | 1.12 | 0.94 |
| N | 312T | 0.746 | 1.022 | −0.698 | 0.545 | 1.184 | 1.066 | 1.101 | 1.066 | 1.029 | 1.11 | 1.12 | 0.93 | 0.92 | 0.64 |
| N | 312V | 0.747 | 0.783 | 0.271 | 0.516 | 1.158 | 1.019 | 1.052 | 1.020 | 0.977 | 1.10 | 1.09 | 1.03 | 0.96 | 0.89 |
| N | 312W | 0.637 | 0.924 | −2.383 | 0.434 | 1.365 | 1.173 | 1.189 | 0.968 | 1.058 | 1.09 | 1.06 | 1.07 | 0.83 | 0.86 |
| N | 312Y | 0.646 | 1.079 | −1.095 | 0.488 | 1.434 | 1.264 | 1.232 | 0.805 | 1.039 | 1.10 | 0.96 | 0.87 | 1.10 | 1.06 |
| G | 313A | 0.637 | 1.237 | 1.909 | 0.505 | 1.222 | 0.885 | 0.889 | 0.676 | 0.735 | 1.11 | 0.95 | 0.79 | 0.80 | 0.99 |
| G | 313C | 0.735 | 1.014 | 1.239 | 0.549 | 1.106 | 0.926 | 0.919 | 0.861 | 0.904 | 0.93 | 0.87 | 0.56 | 0.82 | 0.98 |
| G | 313D | 0.81 | ND | ND | ND | ND | ND | 1.08 | ND | 0.90 | 1.09 | 1.03 | 0.59 | 0.87 | 1.46 |
| G | 313E | 0.703 | 0.981 | 1.967 | 0.473 | 1.065 | 0.854 | 0.882 | 0.844 | 0.725 | 1.16 | 1.05 | 0.69 | 0.99 | 1.21 |
| G | 313F | 0.586 | 1.391 | 1.891 | 0.381 | 1.294 | 1.012 | 1.029 | 1.057 | 0.851 | 1.08 | 1.08 | 0.90 | 0.87 | 1.14 |
| G | 313H | 0.702 | 1.027 | 1.590 | 0.493 | 1.149 | 0.911 | 0.951 | 0.918 | 0.743 | 0.98 | 0.95 | 1.00 | 0.88 | 0.93 |
| G | 313I | 0.201 | 2.049 | 10.489 | 0.068 | 2.312 | 0.966 | 1.198 | 1.098 | 0.803 | 0.99 | 0.77 | 0.37 | 0.97 | 1.04 |
| G | 313K | 0.834 | 0.975 | 2.467 | 0.666 | 1.029 | 0.880 | 0.886 | 0.732 | 0.677 | 1.05 | 0.94 | 1.03 | 1.49 | 1.40 |
| G | 313L | 0.543 | 1.093 | 5.243 | 0.322 | 1.399 | 0.969 | 0.983 | 0.623 | 0.703 | 1.06 | 0.94 | 0.84 | 0.93 | 0.94 |
| G | 313M | 0.772 | 1.040 | 0.220 | 0.683 | 1.066 | 0.877 | 0.854 | 0.604 | 0.725 | 1.06 | 0.90 | 0.96 | 1.03 | 0.98 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| G | 313N | 0.799 | 1.080 | 1.524 | 0.691 | 1.065 | 0.971 | 0.982 | 0.901 | 0.921 | 1.15 | 1.04 | 0.85 | 1.17 | 1.28 |
| G | 313P | 0.257 | 1.905 | 4.159 | 0.092 | 1.855 | 0.836 | 1.078 | 0.957 | 0.578 | 1.03 | 0.81 | 0.62 | 1.31 | 1.56 |
| G | 313Q | 0.705 | 1.139 | 2.445 | 0.467 | 1.080 | 0.891 | 0.915 | 0.936 | 0.727 | 1.17 | 1.13 | 0.97 | 1.03 | 1.06 |
| G | 313R | 0.689 | 1.186 | 0.241 | 0.525 | 1.165 | 0.969 | 0.998 | 1.040 | 0.680 | 1.02 | 1.01 | 0.98 | 1.00 | 1.35 |
| G | 313S | 0.577 | 1.317 | 1.842 | 0.361 | 1.304 | 0.984 | 1.011 | 1.022 | 0.833 | 1.04 | 1.03 | 0.70 | 0.94 | 1.10 |
| G | 313T | 0.101 | 4.434 | 12.075 | 0.025 | 3.337 | 1.104 | 1.497 | 1.501 | 1.721 | 1.45 | 1.39 | 0.14 | 1.00 | 1.41 |
| G | 313V | 0.152 | 3.192 | 7.916 | 0.053 | 3.300 | 1.520 | 1.925 | 1.618 | 1.187 | 1.22 | 0.94 | 0.50 | 1.49 | 1.13 |
| G | 313W | 0.379 | 1.385 | 5.916 | 0.194 | 1.749 | 1.045 | 1.089 | 0.988 | 1.209 | 1.15 | 1.06 | 0.80 | 1.24 | 1.02 |
| G | 313Y | 0.648 | 1.147 | 4.924 | 0.483 | 1.302 | 1.060 | 1.010 | 0.690 | 0.873 | 1.17 | 1.05 | 0.92 | 1.16 | 1.19 |
| V | 314A | 1.207 | 0.791 | -0.130 | 1.029 | 0.774 | 0.701 | 0.782 | 0.584 | 0.614 | 1.04 | 0.84 | 0.69 | 1.10 | 1.02 |
| V | 314C | 0.758 | 1.027 | 0.652 | 0.583 | 1.078 | 0.931 | 0.938 | 0.765 | 0.899 | 1.04 | 0.87 | 0.68 | 0.95 | 1.08 |
| V | 314D | 0.920 | 1.011 | -0.060 | 0.864 | 0.988 | 0.893 | 0.972 | 0.891 | 0.930 | 1.08 | 0.92 | 0.77 | 0.95 | 0.81 |
| V | 314F | 1.058 | 0.846 | 0.882 | 0.865 | 0.860 | 0.844 | 0.795 | 0.742 | 0.681 | 1.02 | 0.95 | 0.99 | 1.16 | 1.50 |
| V | 314G | 0.325 | 1.250 | -0.438 | 0.074 | 0.947 | 0.227 | 0.381 | 0.395 | 0.486 | 0.42 | 0.34 | 0.46 | 0.89 | 0.38 |
| V | 314H | 0.674 | 1.210 | 0.316 | 0.521 | 1.265 | 1.169 | 1.208 | 1.029 | 0.897 | 1.10 | 0.98 | 0.97 | 1.07 | 1.31 |
| V | 314K | 0.836 | 0.951 | 0.482 | 0.759 | 1.134 | 1.090 | 1.099 | 0.821 | 0.875 | 1.09 | 0.99 | 1.09 | 1.41 | 1.35 |
| V | 314L | 0.764 | 1.055 | 0.596 | 0.768 | 1.333 | 1.316 | 1.284 | 0.876 | 1.211 | 1.07 | 0.95 | 1.11 | 0.87 | 1.00 |
| V | 314M | 1.159 | 0.839 | 0.533 | 1.613 | 0.953 | 1.085 | 0.973 | 0.488 | 0.859 | 0.94 | 0.77 | 0.79 | 0.90 | 0.99 |
| V | 314Q | 0.930 | 1.045 | 0.264 | 0.992 | 1.099 | 1.148 | 1.140 | 0.767 | 0.966 | 0.98 | 0.83 | 0.85 | 0.89 | 0.73 |
| V | 314R | 0.779 | 1.221 | 1.697 | 0.618 | 1.078 | 0.950 | 1.080 | 1.093 | 0.820 | 1.04 | 0.87 | 1.05 | 1.36 | 1.14 |
| V | 314S | 0.949 | 0.936 | 0.404 | 0.756 | 0.918 | 0.914 | 0.848 | 0.936 | 0.700 | 1.02 | 0.89 | 1.02 | 1.21 | 0.98 |
| V | 314T | 0.763 | 1.138 | 0.295 | 0.715 | 1.332 | 1.325 | 1.266 | 0.867 | 1.211 | 1.00 | 0.87 | 0.99 | 0.99 | 1.11 |
| V | 314W | 0.527 | 1.348 | 0.619 | 0.370 | 1.582 | 1.274 | 1.225 | 0.751 | 0.994 | 1.05 | 0.89 | 1.37 | 1.40 | 0.91 |
| V | 314Y | 0.683 | 1.168 | 0.008 | 0.661 | 1.497 | 1.412 | 1.336 | 0.638 | 1.106 | 1.02 | 0.90 | 0.97 | 1.06 | 1.06 |
| P | 317A | 1.059 | 0.933 | 0.239 | 1.181 | 0.907 | 0.875 | 0.804 | 0.535 | 0.696 | 1.03 | 0.91 | 0.81 | 0.90 | 1.22 |
| P | 317C | 0.802 | 1.156 | -0.064 | 0.649 | 0.990 | 0.844 | 0.776 | 0.620 | 0.550 | 1.07 | 0.87 | 0.77 | 0.93 | 1.14 |
| P | 317D | 0.703 | 1.242 | 0.210 | 0.569 | 1.191 | 0.973 | 0.970 | 0.799 | 0.733 | 0.98 | 0.84 | 0.83 | 1.01 | 0.50 |
| P | 317E | 0.557 | 1.254 | 0.068 | 0.313 | 1.295 | 0.915 | 0.858 | 0.753 | 0.555 | 0.99 | 0.87 | 1.12 | 0.71 | 0.98 |
| P | 317F | 0.373 | 2.013 | -0.123 | 0.169 | 1.740 | 0.943 | 1.043 | 0.867 | 0.476 | 1.03 | 0.95 | 1.11 | 1.01 | 0.40 |
| P | 317G | 0.674 | 1.218 | 0.778 | 0.445 | 1.201 | 0.946 | 0.942 | 0.869 | 0.611 | 1.10 | 1.01 | 1.05 | 0.80 | 0.95 |
| P | 317H | 0.623 | 1.199 | 0.295 | 0.401 | 1.256 | 0.877 | 0.875 | 0.793 | 0.343 | 1.32 | 1.14 | 1.47 | 1.29 | 1.05 |
| P | 317I | 0.880 | 0.684 | 1.120 | 0.658 | 0.967 | 0.813 | 0.824 | 0.533 | 0.517 | 1.04 | 0.92 | 0.92 | 0.80 | 0.63 |
| P | 317K | 0.709 | 1.059 | 0.928 | 0.522 | 1.209 | 0.962 | 0.895 | 0.741 | 0.483 | 1.10 | 0.99 | 1.19 | 0.83 | 1.15 |
| P | 317L | 0.576 | 1.167 | -0.147 | 0.364 | 1.417 | 0.977 | 0.969 | 0.730 | 0.584 | 1.10 | 1.01 | 1.10 | 1.00 | 0.83 |
| P | 317Q | 0.823 | 1.144 | 0.324 | 0.700 | 1.131 | 0.964 | 0.894 | 0.575 | 0.573 | 0.96 | 0.83 | 0.68 | 1.09 | 0.83 |
| P | 317R | 0.710 | 1.267 | 0.281 | 0.568 | 1.241 | 1.030 | 0.935 | 0.675 | 0.546 | 0.98 | 0.83 | 0.99 | 0.92 | 0.90 |
| P | 317S | 0.604 | 1.384 | 0.833 | 0.448 | 1.373 | 1.116 | 1.020 | 0.683 | 0.559 | 1.01 | 0.93 | 0.83 | 0.78 | 0.88 |
| P | 317T | 0.864 | 1.201 | 0.141 | 0.902 | 1.202 | 1.147 | 1.093 | 0.835 | 0.954 | 1.10 | 0.96 | 1.48 | 0.96 | 0.94 |
| P | 317V | 0.829 | 1.159 | 0.362 | 0.771 | 1.138 | 1.246 | 1.072 | 0.810 | 0.984 | 1.15 | 1.01 | 1.12 | 1.21 | 1.04 |
| P | 317W | 0.664 | 1.454 | 0.377 | 0.527 | 1.419 | 1.074 | 1.130 | 0.832 | 0.970 | 1.14 | 1.01 | 1.02 | 0.79 | 2.30 |
| P | 317Y | 0.633 | 1.102 | 0.865 | 0.467 | 1.421 | 0.997 | 1.009 | 0.684 | 0.625 | 1.10 | 0.95 | 1.38 | 0.87 | 1.17 |
| G | 318A | 0.019 | -7.722 | -0.321 | 0.430 | 1.482 | 0.796 | 0.965 | 0.629 | 0.404 | 1.12 | 1.02 | 0.92 | 0.75 | 0.72 |
| G | 318D | 0.576 | 1.292 | 0.972 | 0.003 | 5.348 | 0.796 | 2.511 | 2.911 | 6.112 | 0.19 | 0.19 | -0.90 | -2.85 | 0.39 |
| G | 318F | 0.808 | 1.072 | -32.126 | 0.766 | 1.146 | 1.091 | 1.136 | 0.947 | 1.048 | 1.00 | 0.94 | 0.80 | 0.48 | 0.63 |
| G | 318H | 0.801 | 1.098 | -0.106 | 0.961 | 1.254 | 1.098 | 1.095 | 0.702 | 0.821 | 0.96 | 0.86 | 1.43 | 0.94 | 0.98 |
| G | 318I | 0.739 | 1.248 | 3.138 | 0.599 | 1.273 | 1.161 | 1.233 | 1.086 | 0.865 | 0.92 | 0.84 | 1.30 | 0.92 | 0.86 |
| G | 318I | 0.683 | 1.263 | 2.516 | 0.487 | 1.291 | 1.022 | 1.150 | 0.941 | 0.834 | 0.99 | 0.82 | 0.70 | 1.12 | 0.83 |
| G | 318K | 0.785 | 1.149 | -0.938 | 0.621 | 1.185 | 1.013 | 1.077 | 0.820 | 0.827 | 0.86 | 0.73 | 1.09 | 1.41 | 1.18 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| G | 318L | 0.741 | 1.268 | 1.390 | 0.644 | 1.306 | 1.107 | 1.175 | 0.789 | 0.971 | 0.93 | 0.78 | 0.82 | 0.92 | 0.74 |
| G | 318M | 0.703 | 1.110 | 0.541 | 0.630 | 1.261 | 1.076 | 1.073 | 0.742 | 0.894 | 0.92 | 0.71 | 0.82 | 0.56 | 0.65 |
| G | 318N | 0.966 | 0.981 | -0.152 | 1.106 | 1.095 | 1.119 | 1.048 | 0.660 | 0.956 | 0.90 | 0.81 | 0.74 | 0.68 | 0.86 |
| G | 318R | 0.671 | 1.342 | 0.155 | 0.565 | 1.456 | 1.281 | 1.323 | 0.939 | 0.922 | 0.95 | 0.82 | 0.72 | 0.91 | 0.93 |
| G | 318S | 0.709 | 1.367 | -0.882 | 0.658 | 1.447 | 1.419 | 1.360 | 0.985 | 1.046 | 0.94 | 0.76 | 1.47 | 1.02 | 0.68 |
| G | 318T | 0.823 | 1.160 | -0.269 | 0.742 | 1.232 | 1.005 | 1.068 | 0.751 | 0.792 | 0.93 | 0.70 | 1.01 | 1.01 | 0.66 |
| G | 318V | 0.728 | 1.288 | -1.480 | 0.625 | 1.413 | 1.154 | 1.230 | 0.842 | 0.936 | 0.90 | 0.68 | 0.72 | 0.82 | 0.71 |
| G | 318W | 0.536 | 1.616 | -2.155 | 0.415 | 1.776 | 1.352 | 1.386 | 0.903 | 0.981 | 0.95 | 0.76 | 1.16 | 1.05 | 1.03 |
| G | 318Y | 0.855 | 1.155 | 0.549 | 0.878 | 1.232 | 1.100 | 1.113 | 0.657 | 0.833 | 0.88 | 0.71 | 0.84 | 0.98 | 0.73 |
| K | 319A | 0.893 | 0.930 | -15.165 | 1.018 | 1.123 | 1.102 | 0.933 | 0.738 | 1.069 | 0.96 | 0.88 | 0.88 | 0.79 | 0.70 |
| K | 319D | 0.881 | 0.944 | -2.103 | 0.841 | 1.052 | 1.000 | 0.990 | 0.863 | 1.068 | 0.95 | 0.90 | 0.90 | 0.84 | 0.71 |
| K | 319F | 0.819 | 0.913 | -7.202 | 0.705 | 1.101 | 1.031 | 0.994 | 0.935 | 1.007 | 1.04 | 1.04 | 0.85 | 1.04 | 0.65 |
| K | 319G | 0.737 | 0.981 | 9.926 | 0.591 | 1.248 | 1.069 | 1.123 | 1.018 | 1.032 | 1.01 | 0.91 | 0.86 | 0.80 | 0.82 |
| K | 319H | 0.849 | 0.714 | 0.449 | 0.721 | 1.088 | 1.036 | 1.071 | 0.959 | 0.979 | 0.96 | 0.91 | 1.04 | 0.84 | 0.60 |
| K | 319L | 0.864 | 0.705 | 1.577 | 0.808 | 1.146 | 1.161 | 1.086 | 0.855 | 1.112 | 1.01 | 0.98 | 1.11 | 0.93 | 0.73 |
| K | 319N | 1.13 | ND | ND | ND | ND | ND | 0.95 | ND | 0.87 | 0.92 | 0.81 | 0.85 | 0.73 | 0.83 |
| K | 319P | 0.784 | 0.864 | 3.381 | 0.676 | 1.151 | 0.962 | 0.868 | 0.627 | 0.886 | 0.94 | 0.82 | 1.06 | 0.91 | 0.72 |
| K | 319Q | 0.909 | 0.985 | 6.316 | 0.914 | 1.088 | 1.053 | 0.986 | 0.749 | 1.023 | 1.03 | 0.95 | 0.84 | 1.18 | 0.85 |
| K | 319S | 0.110 | -13.892 | 143.128 | 0.018 | 0.695 | 0.064 | 0.424 | 0.507 | 1.216 | 0.00 | 0.00 | 0.00 | 0.00 | 0.00 |
| K | 319V | 0.89 | ND | ND | ND | ND | ND | 1.10 | ND | 1.05 | 1.07 | 0.96 | 1.06 | 1.03 | 0.84 |
| K | 319W | 0.864 | 0.880 | 44.704 | 0.839 | 1.159 | 1.115 | 1.047 | 0.786 | 1.032 | 1.04 | 0.91 | 0.94 | 0.95 | 0.72 |
| S | 320A | 0.839 | 1.142 | 1.636 | 0.932 | 1.118 | 0.948 | 0.979 | 0.648 | 0.731 | 0.99 | 0.74 | 0.79 | 0.85 | 0.65 |
| S | 320C | 0.740 | 1.085 | 2.896 | 0.554 | 1.093 | 0.834 | 0.868 | 0.764 | 0.605 | 1.02 | 0.91 | 0.82 | 1.13 | 1.10 |
| S | 320D | 0.334 | 2.144 | 1.335 | 0.154 | 1.841 | 1.112 | 1.235 | 1.163 | 1.117 | 0.95 | 0.89 | 0.76 | 0.82 | 0.70 |
| S | 320F | 0.235 | 2.409 | 3.554 | 0.087 | 2.292 | 1.154 | 1.303 | 1.290 | 0.814 | 0.96 | 0.98 | 0.67 | 1.43 | 0.91 |
| S | 320G | 1.062 | 0.861 | 1.916 | 1.065 | 0.922 | 0.837 | 0.874 | 0.938 | 0.663 | 1.01 | 0.99 | 0.89 | 1.05 | 1.17 |
| S | 320H | 0.456 | 1.487 | 0.946 | 0.270 | 1.649 | 1.101 | 1.072 | 1.078 | 0.620 | 0.96 | 0.90 | 0.65 | 1.01 | 0.99 |
| S | 320I | 0.422 | 1.625 | 2.195 | 0.254 | 1.720 | 1.179 | 1.265 | 1.151 | 0.755 | 0.97 | 0.83 | 0.79 | 1.17 | 0.95 |
| S | 320K | 0.608 | 1.060 | 1.033 | 0.386 | 1.293 | 0.941 | 0.984 | 0.807 | 0.551 | 1.09 | 0.96 | 0.84 | 1.25 | 1.01 |
| S | 320L | 0.374 | 1.447 | 7.375 | 0.184 | 1.801 | 1.056 | 1.031 | 0.730 | 0.684 | 1.02 | 0.85 | 0.80 | 1.16 | 1.02 |
| S | 320M | 0.523 | 1.435 | 3.267 | 0.365 | 1.437 | 0.952 | 0.919 | 0.667 | 0.602 | 0.97 | 0.77 | 0.82 | 0.93 | 1.01 |
| S | 320N | 0.452 | 1.603 | 5.360 | 0.271 | 1.565 | 1.128 | 1.164 | 0.998 | 0.835 | 1.01 | 0.90 | 0.64 | 0.85 | 0.91 |
| S | 320P | 0.563 | 1.430 | -0.968 | 0.368 | 1.336 | 0.972 | 1.014 | 0.900 | 0.566 | 0.90 | 0.82 | 0.67 | 0.94 | 1.15 |
| S | 320Q | 0.525 | 1.428 | 3.146 | 0.339 | 1.459 | 1.056 | 1.064 | 1.021 | 0.716 | 0.94 | 0.90 | 0.81 | 0.98 | 0.60 |
| S | 320R | 0.024 | -4.507 | 32.482 | 0.004 | 3.096 | 0.514 | 1.722 | 2.201 | 4.726 | 0.00 | 0.00 | 0.00 | 0.00 | 0.00 |
| S | 320T | 0.881 | 1.095 | 0.251 | 0.788 | 1.026 | 0.992 | 1.004 | 0.969 | 0.994 | 1.08 | 1.13 | 1.10 | 0.96 | 0.99 |
| S | 320V | 0.333 | 1.470 | 6.003 | 0.111 | 1.496 | 0.638 | 0.749 | 0.731 | 0.721 | 0.00 | 0.95 | 0.79 | 1.09 | 1.31 |
| S | 320W | 0.127 | 4.005 | 69.742 | 0.042 | 3.834 | 1.494 | 1.727 | 1.438 | 1.183 | 0.96 | 0.84 | 1.10 | 0.86 | 0.85 |
| S | 320Y | 0.168 | 2.752 | 11.478 | 0.064 | 3.393 | 1.572 | 1.788 | 1.224 | 0.810 | 0.97 | 0.80 | 1.05 | 1.30 | 1.06 |
| Q | 321A | 1.011 | 1.603 | 5.360 | 1.166 | 0.995 | 1.011 | 0.927 | 0.694 | 0.897 | 0.95 | 0.83 | 0.96 | 1.00 | 1.07 |
| Q | 321C | 0.906 | 0.962 | -4.970 | 0.874 | 1.010 | 0.968 | 0.952 | 0.864 | 0.937 | 0.98 | 0.96 | 1.51 | 0.73 | 0.79 |
| Q | 321D | 0.943 | 0.951 | -4.200 | 0.826 | 0.969 | 0.958 | 0.957 | 0.947 | 0.969 | 1.02 | 1.01 | 1.24 | 0.80 | 1.04 |
| Q | 321E | 1.102 | 0.984 | -0.717 | 1.118 | 0.874 | 0.881 | 0.894 | 0.917 | 0.873 | 1.04 | 1.07 | 1.17 | 0.73 | 1.07 |
| Q | 321F | 0.799 | 0.907 | -5.935 | 0.774 | 1.160 | 1.168 | 1.132 | 1.065 | 1.151 | 1.11 | 1.18 | 1.29 | 0.90 | 1.17 |
| Q | 321G | 0.861 | 1.179 | 0.866 | 0.692 | 1.068 | 0.999 | 1.008 | 1.038 | 0.977 | 1.04 | 1.05 | 1.21 | 1.00 | 1.26 |
| Q | 321H | 0.939 | 1.063 | -5.816 | 0.816 | 1.016 | 1.004 | 1.022 | 1.047 | 0.963 | 1.00 | 1.02 | 0.88 | 0.98 | 0.89 |
| Q | 321I | 0.767 | 1.048 | -4.778 | 0.699 | 1.155 | 1.147 | 1.103 | 1.056 | 1.152 | 0.98 | 0.98 | 0.83 | 0.90 | 0.87 |
| Q | 321K | 0.977 | 0.881 | 3.426 | 0.918 | 1.007 | 1.017 | 1.025 | 0.905 | 0.989 | 1.03 | 0.96 | 0.91 | 1.21 | 1.24 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| Q | 321L | 0.953 | 0.978 | −0.771 | 0.957 | 1.058 | 1.101 | 1.056 | 0.787 | 1.070 | 1.07 | 0.98 | 0.50 | 0.76 | 0.74 |
| Q | 321M | 0.965 | 1.113 | 5.727 | 1.124 | 1.047 | 1.071 | 0.978 | 0.703 | 0.965 | 0.95 | 0.85 | 0.92 | 0.70 | 1.10 |
| Q | 321N | 0.934 | 0.946 | −6.293 | 0.961 | 1.019 | 0.997 | 0.985 | 0.847 | 0.973 | 0.94 | 0.87 | 1.04 | 0.76 | 1.08 |
| Q | 321P | 0.129 | 3.584 | 9.921 | 0.045 | 3.238 | 1.573 | 1.881 | 1.704 | 1.431 | 0.95 | 0.85 | 0.90 | 0.72 | 0.95 |
| Q | 321R | 0.931 | 1.027 | 2.605 | 0.831 | 1.016 | 1.008 | 1.027 | 1.025 | 0.966 | 1.04 | 1.07 | 0.80 | 0.85 | 1.09 |
| Q | 321S | 0.826 | 1.079 | −5.767 | 0.690 | 1.105 | 1.072 | 1.108 | 1.098 | 1.090 | 1.00 | 1.00 | 1.16 | 0.89 | 0.84 |
| Q | 321T | 0.873 | 1.143 | −0.180 | 0.697 | 1.016 | 0.978 | 1.010 | 1.001 | 0.981 | 1.00 | 0.98 | 1.43 | 0.82 | 0.71 |
| Q | 321V | 0.934 | 0.919 | 1.114 | 0.802 | 0.990 | 0.987 | 1.013 | 0.979 | 1.014 | 0.98 | 0.94 | 1.10 | 0.86 | 0.78 |
| Q | 321W | 0.758 | 1.072 | 6.572 | 0.607 | 1.183 | 1.139 | 1.137 | 1.006 | 1.129 | 1.12 | 1.05 | 1.24 | 1.14 | 1.04 |
| G | 323A | 0.263 | 1.933 | 5.968 | 0.115 | 1.893 | 0.817 | 0.937 | 0.713 | 0.683 | 1.10 | 0.66 | 0.99 | 0.41 | 0.82 |
| G | 323C | −0.065 | −10.258 | −26.109 | −0.017 | −2.282 | −0.267 | −0.990 | −1.023 | −1.913 | 0.73 | 0.44 | 2.01 | −2.47 | 1.46 |
| G | 323D | −0.034 | −10.713 | −28.474 | −0.007 | −2.467 | −0.359 | −1.315 | −1.598 | −3.465 | 0.00 | 0.00 | 0.00 | 0.00 | 0.00 |
| G | 323E | −0.015 | −34.909 | −82.854 | −0.003 | −9.483 | −1.294 | −4.157 | −4.398 | −8.114 | 0.00 | 0.00 | 0.00 | 0.00 | 0.00 |
| G | 323F | −0.065 | −6.433 | −27.271 | −0.011 | −1.198 | −0.114 | −0.661 | −0.807 | −1.839 | 0.00 | 0.00 | 0.00 | 0.00 | 0.00 |
| G | 323H | 0.393 | 0.282 | 4.671 | 0.064 | 0.197 | 0.013 | 0.104 | 0.120 | 0.284 | 0.00 | 0.00 | 0.44 | −0.76 | 0.89 |
| G | 323I | −0.073 | 3.444 | −22.859 | −0.013 | −1.069 | −0.098 | −0.591 | −0.708 | −1.597 | 0.00 | 0.00 | 0.00 | 0.00 | 0.00 |
| G | 323K | −0.066 | −3.920 | −10.685 | −0.016 | −2.060 | −0.337 | −0.906 | −0.901 | −1.725 | 0.00 | 0.00 | 0.00 | 0.00 | 0.00 |
| G | 323L | −0.095 | 3.797 | −5.515 | −0.016 | −0.805 | −0.052 | −0.436 | −0.553 | −1.271 | 0.00 | 0.00 | 0.00 | 0.00 | 0.00 |
| G | 323M | −0.023 | −27.422 | −66.618 | −0.006 | −5.117 | −0.612 | −2.482 | −2.616 | −5.126 | 0.00 | 0.00 | 0.00 | 0.00 | 0.00 |
| G | 323N | 0.175 | 2.461 | 4.527 | 0.030 | 0.438 | 0.015 | 0.258 | 0.308 | 0.655 | 0.95 | 0.68 | 0.00 | 0.00 | 0.00 |
| G | 323P | −0.104 | −3.685 | −5.728 | −0.019 | −0.758 | −0.077 | −0.419 | −0.509 | −1.108 | 0.97 | 1.10 | 0.94 | 1.17 | 1.59 |
| G | 323R | 0.102 | 5.236 | 5.056 | 0.050 | 5.481 | 2.818 | 2.977 | 2.511 | 3.073 | 0.98 | 0.58 | 0.90 | 0.79 | 1.01 |
| G | 323S | 0.226 | 2.128 | 4.689 | 0.085 | 2.085 | 1.050 | 1.190 | 1.177 | 0.878 | 0.00 | 0.00 | 0.87 | −0.31 | 1.29 |
| G | 323T | −0.054 | −5.769 | −6.179 | −0.014 | −5.273 | −1.461 | −2.341 | −2.291 | −2.921 | 0.00 | 0.00 | 0.00 | 0.00 | 0.00 |
| G | 323V | −0.142 | 1.043 | −5.405 | −0.025 | −0.517 | −0.051 | −0.303 | −0.348 | −0.786 | 0.00 | 0.00 | 0.00 | 0.00 | 0.00 |
| G | 323W | −0.097 | 0.848 | −11.518 | −0.017 | −0.811 | −0.134 | −0.461 | −0.544 | −1.208 | 0.00 | 0.00 | 0.00 | 0.00 | 0.00 |
| G | 323Y | −0.072 | 4.338 | −7.546 | −0.012 | −1.055 | −0.123 | −0.624 | −0.733 | −1.654 | 0.00 | 0.00 | 0.00 | 0.00 | 0.00 |
| D | 324A | 0.906 | 1.036 | 2.102 | 0.925 | 1.034 | 0.961 | 0.869 | 0.614 | 0.761 | 1.04 | 0.64 | 0.97 | 1.14 | 1.07 |
| D | 324C | 0.747 | 1.036 | 2.513 | 0.601 | 1.061 | 0.879 | 0.865 | 0.777 | 0.739 | 1.00 | 0.68 | 0.97 | 0.78 | 0.69 |
| D | 324E | 1.077 | 0.828 | 1.095 | 1.099 | 0.856 | 0.870 | 0.896 | 0.916 | 0.806 | 1.05 | 0.78 | 0.98 | 0.92 | 0.95 |
| D | 324F | 0.537 | 1.180 | 3.625 | 0.298 | 1.239 | 0.843 | 0.899 | 0.909 | 0.621 | 0.98 | 1.17 | 0.88 | 0.91 | 1.23 |
| D | 324G | 0.696 | 1.047 | 3.613 | 0.444 | 1.180 | 0.925 | 0.936 | 0.933 | 0.776 | 1.00 | 1.00 | 1.12 | 1.12 | 1.08 |
| D | 324H | 0.808 | 1.029 | 2.539 | 0.697 | 1.098 | 0.977 | 0.958 | 0.962 | 0.540 | 0.99 | 1.14 | 1.09 | 0.96 | 1.17 |
| D | 324I | 0.420 | 1.308 | 4.651 | 0.202 | 1.506 | 0.885 | 0.966 | 0.835 | 0.644 | 0.97 | 0.66 | 0.79 | 1.27 | 1.32 |
| D | 324K | 0.699 | 1.040 | 2.552 | 0.541 | 1.167 | 0.903 | 0.924 | 0.665 | 0.553 | 0.96 | 0.62 | 0.66 | 1.04 | 1.15 |
| D | 324L | 0.373 | 1.860 | 7.862 | 0.233 | 1.986 | 1.387 | 1.378 | 0.804 | 0.905 | 0.99 | 0.60 | 0.67 | 1.01 | 1.13 |
| D | 324M | 0.788 | 1.216 | 2.009 | 0.807 | 1.177 | 1.092 | 1.013 | 0.743 | 0.856 | 1.23 | 1.25 | 1.03 | 1.58 | 1.48 |
| D | 324N | 0.866 | 1.144 | 2.730 | 0.803 | 0.996 | 0.903 | 0.903 | 0.809 | 0.745 | 1.08 | 1.21 | 0.95 | 1.11 | 1.05 |
| D | 324P | 0.435 | 1.502 | 3.271 | 0.228 | 1.449 | 0.886 | 0.996 | 0.909 | 0.621 | 1.02 | 1.05 | 0.54 | 0.82 | 0.92 |
| D | 324Q | 1.107 | 0.688 | 0.748 | 1.158 | 0.851 | 0.825 | 0.826 | 0.875 | 0.763 | 1.03 | 1.26 | 0.76 | 0.82 | 1.25 |
| D | 324R | 0.536 | 1.150 | 0.761 | 0.375 | 1.373 | 1.001 | 1.056 | 1.113 | 0.651 | 1.13 | 1.27 | 0.86 | 1.93 | 1.69 |
| D | 324S | 0.787 | 1.022 | 2.866 | 0.575 | 1.097 | 0.953 | 0.971 | 0.995 | 0.846 | 1.15 | 1.34 | 0.95 | 1.12 | 1.15 |
| D | 324T | 0.588 | 1.147 | 2.403 | 0.363 | 1.305 | 0.983 | 1.016 | 1.016 | 0.788 | 1.14 | 1.25 | 1.08 | 1.09 | 1.38 |
| D | 324V | 0.582 | 0.967 | 3.875 | 0.335 | 1.303 | 0.903 | 0.935 | 0.866 | 0.696 | 1.04 | 1.11 | 0.96 | 0.35 | 1.21 |
| D | 324W | 0.630 | 1.065 | 1.905 | 0.456 | 1.327 | 1.062 | 1.091 | 0.912 | 0.903 | 1.06 | 1.16 | 0.86 | 1.08 | 1.07 |
| D | 324Y | 0.434 | 1.554 | 3.008 | 0.273 | 1.781 | 1.325 | 1.302 | 0.831 | 0.937 | 1.06 | 1.05 | 0.88 | 0.97 | 1.14 |
| R | 325A | 1.039 | 0.915 | 1.283 | 1.088 | 0.929 | 0.904 | 0.840 | 0.644 | 0.808 | 1.07 | 0.72 | 1.04 | 0.93 | 0.94 |
| R | 325C | 0.953 | 0.921 | 1.948 | 0.896 | 0.898 | 0.872 | 0.864 | 0.783 | 0.706 | 1.05 | 1.25 | 0.77 | 0.61 | 0.75 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| R | 325D | 0.410 | 1.341 | 3.023 | 0.203 | 1.341 | 0.897 | 0.931 | 0.902 | 0.609 | 1.04 | 1.29 | 0.59 | 0.50 | 1.02 |
| R | 325F | 0.196 | 3.023 | 5.614 | 0.068 | 2.651 | 1.448 | 1.662 | 1.639 | 1.418 | 1.06 | 1.34 | 1.04 | 0.84 | 1.07 |
| R | 325G | 0.532 | 1.178 | 4.040 | 0.262 | 1.289 | 0.929 | 0.945 | 0.981 | 0.792 | 1.05 | 1.41 | 0.93 | 0.69 | 0.87 |
| R | 325H | 0.570 | 1.280 | 2.762 | 0.309 | 1.286 | 1.008 | 0.995 | 1.001 | 0.800 | 1.12 | 1.30 | 1.25 | 0.88 | 1.16 |
| R | 325I | 0.968 | 0.868 | 2.111 | 0.797 | 0.933 | 0.919 | 0.944 | 0.841 | 0.941 | 1.16 | 1.39 | 0.89 | 1.50 | 0.91 |
| R | 325K | 0.987 | 0.958 | 0.873 | 0.938 | 0.977 | 0.987 | 0.998 | 0.796 | 0.960 | 1.10 | 1.23 | 1.07 | 0.80 | 0.98 |
| R | 325L | 0.748 | 1.205 | 3.247 | 0.646 | 1.243 | 1.212 | 1.148 | 0.738 | 1.144 | 1.17 | 1.26 | 1.09 | 1.14 | 0.99 |
| R | 325M | 1.027 | 1.040 | 0.904 | 1.125 | 0.968 | 0.981 | 0.907 | 0.618 | 0.879 | 1.15 | 1.23 | 0.85 | 0.89 | 1.03 |
| R | 325N | 0.412 | 1.546 | 3.720 | 0.199 | 1.452 | 0.945 | 0.974 | 0.826 | 0.707 | 1.01 | 1.16 | 0.43 | 0.45 | 0.71 |
| R | 325P | 0.733 | 1.155 | 0.656 | 0.574 | 1.133 | 1.053 | 1.028 | 0.968 | 1.002 | 1.08 | 1.32 | 0.72 | 0.59 | 0.69 |
| R | 325T | 0.740 | 0.937 | -0.411 | 0.450 | 1.028 | 0.900 | 0.913 | 0.896 | 0.874 | 1.15 | 1.38 | 0.93 | 0.64 | 1.06 |
| R | 325V | 0.833 | 0.999 | 1.506 | 0.685 | 1.055 | 1.026 | 1.052 | 0.961 | 1.027 | 1.36 | 1.54 | 1.25 | 1.05 | 1.20 |
| R | 325W | -0.025 | -5.069 | -39.959 | -0.004 | -9.817 | -2.309 | -4.443 | -4.159 | -6.037 | 1.45 | 1.48 | 1.53 | -0.31 | 2.74 |
| R | 325Y | 0.230 | 2.131 | 4.084 | 0.088 | 2.387 | 1.318 | 1.432 | 0.973 | 1.049 | 1.20 | 1.34 | 0.50 | 0.65 | 1.09 |
| S | 327C | 0.635 | 1.283 | 1.037 | 0.566 | 1.289 | 1.134 | 1.102 | 0.858 | 0.528 | 0.91 | 1.05 | 1.07 | 0.75 | 0.82 |
| S | 327D | 0.966 | 0.754 | 0.652 | 0.846 | 0.872 | 0.844 | 0.836 | 0.909 | 0.847 | 1.02 | 1.18 | 0.99 | 0.64 | 0.62 |
| S | 327F | -0.708 | 0.248 | -0.211 | -0.130 | -0.191 | -0.397 | -0.054 | -0.234 | -0.109 | 1.06 | 1.24 | 1.13 | 0.02 | 1.06 |
| S | 327G | 0.868 | 1.079 | 0.313 | 0.735 | 1.053 | 0.976 | 0.974 | 0.893 | 0.913 | 1.11 | 1.36 | 1.37 | 0.79 | 1.00 |
| S | 327H | 0.546 | 1.200 | 1.075 | -0.007 | 1.323 | 0.979 | 0.996 | 0.895 | 0.269 | 1.06 | 1.20 | 1.32 | 1.00 | 1.37 |
| S | 327I | -0.129 | -1.906 | -7.387 | -0.025 | -1.418 | -0.265 | -0.623 | -0.621 | -0.893 | 0.00 | 0.00 | 0.00 | 0.00 | 0.00 |
| S | 327K | 0.115 | 2.952 | -3.260 | 0.037 | 4.106 | 1.937 | 2.235 | 1.714 | 1.209 | 0.98 | 1.17 | 1.04 | 0.93 | 1.19 |
| S | 327N | 0.611 | 1.121 | 1.110 | 0.352 | 1.197 | 0.788 | 0.763 | 0.545 | 0.624 | 0.92 | 0.99 | 1.22 | 0.88 | 0.93 |
| S | 327P | -0.226 | -1.552 | -4.179 | -0.051 | -0.415 | -0.031 | -0.205 | -0.274 | -0.483 | 0.18 | 0.11 | -1.63 | -1.23 | 1.11 |
| S | 327R | 0.059 | 4.914 | 4.611 | 0.013 | 5.004 | 1.428 | 2.095 | 1.949 | 2.635 | 0.76 | 0.70 | 1.55 | -1.92 | 1.41 |
| S | 327T | 0.593 | 1.248 | -0.131 | 0.330 | 1.226 | 0.935 | 1.090 | 1.066 | 0.796 | 1.07 | 1.12 | 1.09 | 1.13 | 1.37 |
| S | 327V | 0.046 | 4.132 | 9.171 | 0.010 | 6.502 | 1.738 | 2.762 | 2.264 | 2.642 | 0.99 | 0.90 | 0.77 | -0.63 | 1.23 |
| S | 327W | -0.039 | -4.925 | -5.597 | -0.007 | -4.122 | -0.496 | -1.724 | -1.709 | -3.059 | 0.00 | 0.00 | 0.00 | 0.00 | 0.00 |
| S | 327Y | -0.042 | -1.681 | 1.361 | -0.009 | -1.924 | -0.213 | -1.163 | -1.570 | -2.967 | 0.33 | 0.26 | 1.26 | -0.73 | 0.26 |
| A | 328C | 0.906 | 1.072 | 1.639 | 0.872 | 1.025 | 1.001 | 0.953 | 0.916 | 0.968 | 1.03 | 1.02 | 0.77 | 0.74 | 0.87 |
| A | 328D | 0.920 | 1.102 | -0.014 | 0.825 | 0.993 | 1.006 | 1.021 | 0.999 | 0.996 | 1.05 | 1.08 | 0.79 | 0.80 | 0.97 |
| A | 328E | 1.021 | 1.041 | 0.582 | 0.895 | 0.899 | 0.902 | 0.890 | 0.923 | 0.912 | 1.09 | 1.13 | 0.74 | 0.88 | 0.88 |
| A | 328F | 0.737 | 1.374 | 0.814 | 0.509 | 0.934 | 0.904 | 0.905 | 0.881 | 0.866 | 1.13 | 1.18 | 0.85 | 0.71 | 1.10 |
| A | 328G | 0.976 | 1.000 | 1.982 | 0.823 | 1.000 | 0.959 | 0.999 | 1.113 | 0.992 | 1.02 | 1.09 | 0.82 | 1.18 | 0.78 |
| A | 328H | 0.963 | 0.947 | 1.565 | 0.750 | 0.977 | 0.903 | 0.963 | 1.012 | 0.968 | 0.99 | 1.03 | 0.76 | 0.94 | 0.89 |
| A | 328I | 0.828 | 1.040 | 1.490 | 0.635 | 0.951 | 0.990 | 0.911 | 0.914 | 0.885 | 1.04 | 1.05 | 0.77 | 0.94 | 0.87 |
| A | 328K | 0.951 | 0.968 | 0.305 | 0.802 | 1.064 | 0.958 | 0.986 | 0.988 | 0.964 | 1.04 | 1.03 | 0.66 | 1.08 | 0.94 |
| A | 328L | 0.931 | 1.020 | 1.537 | 0.859 | 0.981 | 1.037 | 0.964 | 0.837 | 0.914 | 1.09 | 0.99 | 0.74 | 0.96 | 0.90 |
| A | 328N | 1.008 | 0.976 | 0.537 | 0.982 | 1.045 | 0.922 | 0.985 | 0.727 | 0.913 | 1.10 | 1.06 | 0.74 | 1.14 | 1.06 |
| A | 328P | 0.963 | 0.949 | 0.170 | 0.842 | 0.930 | 0.904 | 0.897 | 0.801 | 0.866 | 1.04 | 1.02 | 0.90 | 0.90 | 0.81 |
| A | 328Q | 0.900 | 1.093 | 1.257 | 0.768 | 0.934 | 0.902 | 0.905 | 0.881 | 0.934 | 1.04 | 1.02 | 0.74 | 0.72 | 0.81 |
| A | 328R | 0.780 | 1.004 | 0.413 | 0.610 | 1.000 | 0.982 | 0.978 | 0.964 | 0.992 | 1.11 | 1.11 | 0.85 | 0.78 | 0.98 |
| A | 328S | 0.990 | 0.975 | 0.511 | 0.839 | 1.142 | 1.072 | 1.087 | 1.035 | 1.028 | 1.01 | 1.06 | 0.81 | 1.04 | 0.98 |
| A | 328T | 0.658 | 0.778 | 0.727 | 0.292 | 0.945 | 0.938 | 0.968 | 0.957 | 0.950 | 1.02 | 1.08 | 0.84 | 0.84 | 1.08 |
| A | 328V | 0.838 | 0.570 | 1.814 | 0.553 | 0.940 | 0.589 | 0.627 | 0.667 | 0.731 | 1.00 | 1.03 | 0.96 | 0.75 | 0.99 |
| A | 328W | 0.774 | 0.954 | 0.456 | 0.513 | 1.005 | 0.833 | 0.878 | 0.818 | 0.913 | 1.04 | 1.02 | 0.97 | 0.94 | 1.06 |
| A | 328Y | 0.785 | 1.034 | 0.800 | 0.664 | 1.088 | 0.901 | 0.904 | 0.832 | 0.833 | 1.06 | 1.01 | 0.81 | 0.71 | 0.85 |
| E | 331C | 1.028 | 0.937 | -0.020 | 1.007 | 0.898 | 0.947 | 0.890 | 0.796 | 0.874 | 1.04 | 0.98 | 0.65 | 0.80 | 0.93 |
| E | 331D | 0.682 | 1.212 | -0.184 | 0.466 | 1.164 | 1.080 | 1.052 | 0.716 | 0.910 | 1.03 | 0.98 | 0.71 | 1.09 | 0.89 |
| E | | | | | | | | | | | 1.08 | 1.03 | 0.84 | 0.80 | 0.82 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| E | 331F | 0.857 | 1.107 | 0.333 | 0.746 | 1.083 | 1.062 | 1.056 | 0.966 | 1.040 | 1.09 | 1.10 | 1.05 | 1.02 | 0.79 |
| E | 331G | 0.867 | 1.035 | 0.540 | 0.710 | 1.051 | 1.003 | 1.013 | 0.926 | 0.970 | 0.91 | 1.00 | 1.13 | 0.78 | 0.56 |
| E | 331I | 0.845 | 0.981 | 0.958 | 0.693 | 1.124 | 1.089 | 1.083 | 0.923 | 1.044 | 1.06 | 1.03 | 0.94 | 1.04 | 1.05 |
| E | 331K | 1.069 | 0.853 | 0.044 | 1.005 | 0.927 | 0.968 | 0.951 | 0.761 | 0.883 | 1.08 | 1.07 | 1.04 | 0.84 | 1.08 |
| E | 331L | 0.829 | 1.054 | 0.667 | 0.710 | 1.133 | 1.101 | 1.110 | 0.973 | 1.079 | 1.04 | 0.99 | 1.13 | 0.94 | 0.79 |
| E | 331M | 1.656 | 0.698 | −0.112 | 2.705 | 0.722 | 0.902 | 0.802 | 0.467 | 0.788 | 0.98 | 0.90 | 0.71 | 0.72 | 0.73 |
| E | 331N | 1.175 | 0.841 | −0.415 | 1.265 | 0.898 | 0.966 | 0.860 | 0.579 | 0.869 | 1.04 | 0.95 | 0.90 | 1.03 | 0.95 |
| E | 331P | −0.202 | −3.331 | −8.754 | −0.052 | −0.642 | −0.097 | −0.318 | −0.390 | −0.615 | 0.00 | 0.00 | 0.00 | 0.00 | 0.00 |
| E | 331Q | 1.111 | 0.924 | 0.222 | 1.185 | 0.953 | 1.063 | 1.012 | 0.749 | 1.021 | 1.09 | 1.04 | 1.14 | 0.84 | 1.24 |
| E | 331R | 1.141 | 0.912 | −0.439 | 1.287 | 0.943 | 1.011 | 0.944 | 0.727 | 0.915 | 0.99 | 0.94 | 0.98 | 0.99 | 1.02 |
| E | 331S | 0.917 | 0.897 | 3.433 | 0.804 | 1.017 | 0.959 | 0.963 | 0.932 | 0.937 | 1.00 | 1.02 | 1.52 | 0.82 | 0.75 |
| E | 331T | 1.086 | 0.900 | 0.845 | 1.141 | 0.973 | 0.995 | 0.973 | 0.728 | 0.943 | 1.04 | 1.01 | 1.29 | 1.15 | 0.85 |
| E | 331V | 0.935 | 0.972 | 0.775 | 0.908 | 1.109 | 1.120 | 1.069 | 0.777 | 1.055 | 0.93 | 0.89 | 1.35 | 0.79 | 0.84 |
| E | 331Y | 1.022 | 0.911 | 0.425 | 1.243 | 1.160 | 1.191 | 1.100 | 0.814 | 1.042 | 0.99 | 0.91 | 1.14 | 0.82 | 0.81 |
| Q | 333C | 0.941 | 1.020 | 0.562 | 1.057 | 1.072 | 1.059 | 0.969 | 0.720 | 1.009 | 0.98 | 0.89 | 0.91 | 0.77 | 0.87 |
| Q | 333D | 0.972 | 1.007 | 0.867 | 0.986 | 1.034 | 1.023 | 0.921 | 0.760 | 0.953 | 1.00 | 0.93 | 1.06 | 0.97 | 0.84 |
| Q | 333F | 1.009 | 0.979 | 1.426 | 0.939 | 0.976 | 0.905 | 0.845 | 0.770 | 0.853 | 0.95 | 0.91 | 1.09 | 1.04 | 0.91 |
| Q | 333G | 0.928 | 1.113 | 1.878 | 0.988 | 1.143 | 1.112 | 1.068 | 0.905 | 1.086 | 1.00 | 0.94 | 1.00 | 0.92 | 0.91 |
| Q | 333H | 1.109 | 0.931 | 0.738 | 1.219 | 0.962 | 0.950 | 0.872 | 0.735 | 0.905 | 0.99 | 0.91 | 1.00 | 0.91 | 1.01 |
| Q | 333I | 1.128 | 0.772 | 0.948 | 1.265 | 0.941 | 0.927 | 0.885 | 0.749 | 0.943 | 1.04 | 0.95 | 1.29 | 1.14 | 0.95 |
| Q | 333K | 1.123 | 0.732 | 1.203 | 1.225 | 0.876 | 0.870 | 0.803 | 0.648 | 0.916 | 0.99 | 0.94 | 0.94 | 1.06 | 0.98 |
| Q | 333L | 0.985 | 0.946 | 0.442 | 1.241 | 1.098 | 1.155 | 1.019 | 0.797 | 0.825 | 0.91 | 1.05 | 0.79 | 0.90 | 1.06 |
| Q | 333M | 1.049 | 1.073 | 0.853 | 1.254 | 0.974 | 0.991 | 0.913 | 0.623 | 1.075 | 0.98 | 0.91 | 0.69 | 0.80 | 0.94 |
| Q | 333N | 1.041 | 1.030 | −0.151 | 1.159 | 0.930 | 0.974 | 0.926 | 0.819 | 0.923 | 0.98 | 0.88 | 0.72 | 0.87 | 1.19 |
| Q | 333P | 1.185 | 0.936 | 0.751 | 1.157 | 0.813 | 0.832 | 0.846 | 0.797 | 0.938 | 0.99 | 0.93 | 0.95 | 1.07 | 0.85 |
| Q | 333R | 0.847 | 0.689 | 0.721 | 0.571 | 0.937 | 0.714 | 0.690 | 0.748 | 0.829 | 0.99 | 0.94 | 0.84 | 0.97 | 1.03 |
| Q | 333S | 0.693 | 0.635 | 1.204 | 0.304 | 0.905 | 0.509 | 0.515 | 0.557 | 0.799 | 0.96 | 0.95 | 0.98 | 1.17 | 1.06 |
| Q | 333T | 0.952 | 1.068 | 1.216 | 0.909 | 1.030 | 0.989 | 1.026 | 0.976 | 0.623 | 0.92 | 0.94 | 0.76 | 0.73 | 1.09 |
| Q | 333V | 1.049 | 0.991 | 1.546 | 1.120 | 0.946 | 0.968 | 0.999 | 0.989 | 0.990 | 1.03 | 1.01 | 0.94 | 1.10 | 1.05 |
| Q | 333W | 0.668 | 1.060 | 1.586 | 0.528 | 1.258 | 1.092 | 1.059 | 1.002 | 1.003 | 1.04 | 0.97 | 0.82 | 1.07 | 0.93 |
| Q | 333Y | 0.913 | 0.967 | 0.235 | 0.992 | 1.115 | 1.092 | 1.038 | 0.806 | 1.087 | 1.01 | 1.00 | 0.75 | 0.99 | 0.99 |
| V | 344A | 1.041 | 0.923 | 1.147 | 1.132 | 0.946 | 0.946 | 0.820 | 0.651 | 0.996 | 0.98 | 1.06 | 0.79 | 1.08 | 1.04 |
| V | 344C | 0.949 | 0.971 | 1.105 | 0.850 | 0.956 | 0.948 | 0.922 | 0.892 | 0.865 | 0.96 | 0.86 | 0.79 | 0.95 | 1.14 |
| V | 344E | 1.042 | 1.011 | 1.117 | 1.008 | 0.902 | 0.913 | 0.933 | 0.957 | 0.897 | 0.99 | 0.90 | 0.98 | 1.05 | 0.82 |
| V | 344F | 0.967 | 1.009 | 1.487 | 0.837 | 0.942 | 0.928 | 0.941 | 0.974 | 0.942 | 1.01 | 1.00 | 0.77 | 1.02 | 1.06 |
| V | 344G | 1.064 | 0.870 | 0.869 | 1.081 | 0.930 | 0.940 | 0.964 | 0.806 | 0.934 | 1.05 | 1.06 | 0.51 | 0.95 | 0.93 |
| V | 344H | 0.983 | 1.129 | 1.423 | 0.857 | 0.996 | 0.935 | 0.965 | 1.023 | 0.976 | 0.90 | 0.91 | 0.60 | 0.71 | 0.86 |
| V | 344I | 0.860 | 0.869 | 1.803 | 0.892 | 1.118 | 1.097 | 1.144 | 1.000 | 0.936 | 1.00 | 1.06 | 0.56 | 1.07 | 1.10 |
| V | 344K | 0.898 | 0.900 | 1.051 | 1.097 | 1.108 | 1.134 | 1.139 | 1.140 | 1.155 | 1.00 | 0.97 | 0.54 | 1.02 | 1.12 |
| V | 344L | 1.045 | 0.864 | 0.726 | 1.311 | 1.003 | 1.010 | 0.986 | 1.034 | 1.125 | 1.09 | 0.94 | 0.57 | 0.73 | 0.77 |
| V | 344M | 1.136 | 0.983 | 0.952 | 1.193 | 0.884 | 0.926 | 0.827 | 0.762 | 0.966 | 1.04 | 0.99 | 0.72 | 0.95 | 1.03 |
| V | 344N | 1.166 | 1.109 | 0.707 | 1.097 | 0.818 | 0.821 | 0.813 | 0.639 | 0.843 | 0.00 | 0.00 | 0.86 | 1.00 | 0.90 |
| V | 344P | −0.123 | −3.046 | −8.140 | −0.022 | −1.323 | −0.232 | −0.616 | −0.660 | −1.144 | 0.00 | 0.00 | 0.00 | 0.00 | 0.00 |
| V | 344Q | 1.085 | 0.899 | 0.696 | 1.108 | 0.895 | 0.924 | 0.942 | 0.981 | 0.934 | 0.98 | 0.98 | 0.74 | 1.10 | 0.88 |
| V | 344R | 1.140 | 0.846 | 0.549 | 1.133 | 0.837 | 0.864 | 0.875 | 0.960 | 0.846 | 1.00 | 1.05 | 0.70 | 0.98 | 1.04 |
| V | 344S | 0.957 | 1.091 | 1.591 | 0.804 | 0.975 | 0.940 | 0.947 | 1.022 | 0.973 | 1.07 | 1.10 | 0.79 | 0.93 | 1.01 |
| V | 344T | 0.911 | 1.052 | 1.521 | 0.756 | 0.997 | 0.953 | 0.976 | 0.986 | 0.983 | 1.05 | 1.03 | 0.81 | 0.99 | 0.98 |
| V | 344W | 0.862 | 0.966 | 1.175 | 0.642 | 1.045 | 0.970 | 0.968 | 0.891 | 0.961 | 1.03 | 0.99 | 0.72 | 1.28 | 0.93 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| V | 344Y | 0.949 | 0.934 | 1.946 | 0.964 | 1.064 | 1.070 | 1.019 | 0.789 | 1.013 | 1.06 | 0.95 | 0.74 | 0.79 | 0.84 |
| A | 346C | 1.237 | 0.912 | 0.823 | 1.583 | 0.896 | 0.943 | 0.902 | 0.715 | 0.914 | 1.03 | 0.97 | 1.12 | 0.84 | 1.03 |
| A | 346D | 1.131 | 0.937 | 0.865 | 1.374 | 1.020 | 0.994 | 0.974 | 0.884 | 0.978 | 0.93 | 0.89 | 1.01 | 0.91 | 0.65 |
| A | 346E | 0.830 | 1.150 | 0.975 | 0.766 | 1.232 | 1.063 | 1.012 | 0.895 | 1.026 | 0.95 | 0.89 | 0.94 | 1.12 | 0.91 |
| A | 346F | 1.182 | 0.948 | 0.817 | 1.442 | 0.954 | 0.993 | 0.975 | 0.875 | 0.927 | 0.97 | 0.91 | 0.91 | 0.98 | 0.94 |
| A | 346H | 1.062 | 0.916 | 1.460 | 1.061 | 0.987 | 0.948 | 0.931 | 0.789 | 0.940 | 0.96 | 0.86 | 1.10 | 0.86 | 0.80 |
| A | 346I | 0.586 | 1.106 | 1.327 | 0.373 | 1.420 | 1.006 | 0.958 | 0.741 | 1.025 | 0.96 | 0.84 | 1.03 | 1.27 | 1.12 |
| A | 346K | 1.015 | 0.857 | 0.733 | 1.073 | 0.991 | 1.012 | 0.959 | 0.591 | 0.992 | 1.02 | 0.86 | 1.00 | 0.96 | 1.26 |
| A | 346L | 0.905 | 1.023 | 1.034 | 1.051 | 1.215 | 1.267 | 1.177 | 0.710 | 1.197 | 1.03 | 1.01 | 0.80 | 1.05 | 1.03 |
| A | 346M | 1.042 | 0.992 | 0.916 | 1.117 | 0.964 | 0.961 | 0.915 | 0.654 | 0.920 | 1.07 | 0.93 | 1.11 | 0.92 | 1.02 |
| A | 346N | 0.938 | 1.067 | 0.734 | 1.009 | 1.116 | 1.041 | 1.040 | 0.938 | 1.042 | 0.96 | 0.92 | 1.01 | 0.96 | 1.00 |
| A | 346P | 0.518 | 1.305 | 2.489 | 0.362 | 1.352 | 1.070 | 0.999 | 0.781 | 1.050 | 0.99 | 0.91 | 0.78 | 1.06 | 0.79 |
| A | 346R | 0.912 | 0.904 | 0.675 | 0.858 | 0.976 | 0.974 | 0.856 | 0.652 | 0.879 | 1.04 | 0.93 | 0.81 | 0.86 | 0.88 |
| A | 346S | 0.928 | 1.003 | 0.264 | 1.012 | 1.033 | 1.074 | 0.954 | 0.692 | 0.970 | 0.90 | 0.87 | 0.99 | 1.13 | 0.95 |
| A | 346T | 0.885 | 1.058 | 1.000 | 0.886 | 1.105 | 1.092 | 1.133 | 1.094 | 1.132 | 0.99 | 0.95 | 0.93 | 0.87 | 0.72 |
| A | 346V | 0.908 | 1.080 | 1.304 | 0.950 | 1.116 | 1.107 | 1.136 | 1.055 | 1.117 | 1.00 | 0.97 | 0.89 | 1.14 | 1.10 |
| A | 346Y | 0.959 | 1.001 | 1.062 | 1.152 | 1.128 | 1.169 | 1.129 | 0.754 | 1.075 | 0.98 | 0.96 | 0.96 | 0.97 | 0.93 |
| G | 347A | 0.928 | 1.108 | -0.141 | 1.072 | 1.044 | 1.023 | 0.939 | 0.636 | 0.957 | 1.02 | 0.89 | 0.97 | 1.05 | 0.95 |
| G | 347C | 0.818 | 1.074 | 0.140 | 0.680 | 1.024 | 0.962 | 0.932 | 0.754 | 0.944 | 0.99 | 0.92 | 0.84 | 0.87 | 0.86 |
| G | 347D | 0.912 | 1.074 | 0.649 | 0.804 | 0.983 | 0.927 | 0.915 | 0.805 | 0.930 | 1.00 | 1.03 | 0.91 | 0.92 | 1.21 |
| G | 347E | 0.800 | 1.023 | -0.232 | 0.584 | 1.049 | 0.923 | 0.889 | 0.860 | 0.922 | 1.00 | 1.02 | 1.04 | 0.93 | 1.07 |
| G | 347F | 0.703 | 1.219 | 0.003 | 0.530 | 1.218 | 1.064 | 1.054 | 0.966 | 1.071 | 1.01 | 1.06 | 0.87 | 1.09 | 1.12 |
| G | 347H | 1.161 | 0.846 | 12.841 | 1.399 | 0.936 | 0.995 | 0.930 | 0.567 | 0.941 | 1.10 | 1.12 | 1.11 | 0.62 | 0.92 |
| G | 347I | 0.544 | 1.466 | -0.403 | 0.413 | 1.512 | 1.318 | 1.305 | 1.137 | 1.326 | 1.04 | 1.08 | 1.09 | 0.86 | 1.09 |
| G | 347K | 0.832 | 0.972 | 0.921 | 0.709 | 1.100 | 1.034 | 1.010 | 0.779 | 1.017 | 1.05 | 0.99 | 0.98 | 0.72 | 1.17 |
| G | 347L | 0.733 | 1.084 | 1.865 | 0.635 | 1.281 | 1.166 | 1.091 | 0.707 | 1.106 | 1.08 | 1.07 | 1.22 | 0.96 | 1.21 |
| G | 347M | 1.166 | 0.829 | -0.094 | 1.470 | 0.880 | 0.884 | 0.782 | 0.421 | 0.801 | 0.99 | 0.84 | 0.98 | 1.18 | 1.50 |
| G | 347N | 1.030 | 0.968 | 0.361 | 1.135 | 0.985 | 1.006 | 0.931 | 0.616 | 0.961 | 0.98 | 0.93 | 0.79 | 0.97 | 0.96 |
| G | 347P | 1.044 | 0.877 | -1.164 | 1.161 | 0.958 | 0.925 | 0.862 | 0.605 | 0.916 | 0.97 | 0.92 | 0.84 | 0.96 | 0.86 |
| G | 347Q | 1.075 | 0.872 | 0.604 | 1.172 | 0.918 | 0.977 | 0.924 | 0.668 | 0.955 | 1.02 | 0.94 | 0.99 | 0.78 | 1.13 |
| G | 347R | 0.855 | 1.164 | 0.200 | 0.844 | 1.167 | 1.176 | 1.103 | 0.792 | 1.083 | 0.97 | 0.92 | 0.98 | 0.94 | 1.04 |
| G | 347S | 0.909 | 1.050 | 0.577 | 0.962 | 1.155 | 1.116 | 1.077 | 0.793 | 1.055 | 1.08 | 1.07 | 1.14 | 0.82 | 0.90 |
| G | 347T | 0.907 | 1.010 | 0.601 | 0.951 | 1.101 | 1.071 | 1.009 | 0.739 | 1.028 | 1.06 | 1.05 | 1.19 | 0.80 | 0.76 |
| G | 347V | 0.829 | 1.009 | 1.087 | 0.739 | 1.152 | 1.057 | 1.007 | 0.703 | 1.034 | 1.01 | 0.99 | 1.19 | 0.92 | 0.88 |
| G | 347W | 0.805 | 1.059 | 0.641 | 0.728 | 1.184 | 1.096 | 1.018 | 0.623 | 1.006 | 1.04 | 0.99 | 1.24 | 0.96 | 1.12 |
| G | 347Y | 1.066 | 0.867 | 2.250 | 1.318 | 1.009 | 0.997 | 0.957 | 0.560 | 0.976 | 1.00 | 1.00 | 1.09 | 0.78 | 1.00 |
| G | 349A | 1.140 | 0.996 | 1.814 | 1.385 | 0.947 | 0.955 | 0.996 | 0.658 | 1.009 | 1.02 | 0.87 | 0.88 | 0.96 | 1.29 |
| HP | 349C | 1.062 | 0.985 | 1.817 | 1.082 | 0.916 | 0.838 | 0.886 | 0.700 | 0.911 | 1.05 | 0.97 | 0.82 | 1.08 | 0.80 |
| HP | 349D | 1.049 | 1.028 | 2.352 | 1.115 | 0.917 | 0.922 | 1.004 | 0.829 | 0.993 | 1.04 | 0.96 | 0.87 | 0.83 | 0.87 |
| HP | 349F | 0.687 | 1.246 | 2.230 | 0.467 | 1.231 | 0.953 | 0.948 | 0.833 | 0.995 | 0.99 | 0.92 | 0.98 | 1.16 | 1.77 |
| HP | 349G | 1.123 | 0.943 | 1.311 | 1.298 | 0.991 | 1.020 | 0.964 | 0.833 | 0.989 | 0.97 | 0.93 | 1.02 | 0.84 | 1.24 |
| HP | 349H | 0.968 | 1.071 | 1.568 | 0.990 | 1.104 | 1.057 | 0.990 | 0.853 | 1.011 | 0.96 | 0.91 | 1.04 | 0.97 | 0.77 |
| HP | 349I | 0.905 | 0.877 | 0.661 | 0.933 | 1.145 | 1.094 | 1.016 | 0.823 | 1.020 | 1.03 | 0.96 | 0.92 | 1.26 | 0.70 |
| HP | 349K | 0.740 | 1.195 | -3.563 | 0.665 | 1.217 | 1.186 | 1.185 | 0.985 | 1.161 | 0.90 | 0.88 | 0.83 | 1.10 | 1.69 |
| HP | 349L | 0.940 | 0.843 | 1.151 | 1.089 | 1.100 | 1.073 | 0.966 | 0.689 | 0.976 | 0.96 | 0.94 | 0.96 | 0.92 | 1.06 |
| HP | 349M | 0.945 | 1.062 | 1.162 | 0.918 | 0.990 | 0.883 | 0.908 | 0.694 | 0.934 | 1.11 | 0.93 | 0.98 | 0.95 | 1.02 |
| HP | 349N | 0.923 | 1.115 | 0.552 | 0.899 | 1.008 | 0.932 | 0.975 | 0.818 | 0.943 | 1.05 | 0.95 | 0.98 | 1.38 | 1.01 |
| HP | 349P | 1.025 | 0.987 | 0.230 | 0.940 | 0.924 | 0.865 | 0.957 | 0.904 | 0.961 | 0.81 | 0.92 | 0.86 | 0.82 | 1.09 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| H | 349Q | 0.879 | 0.987 | 0.254 | 0.756 | 1.037 | 0.933 | 0.975 | 0.991 | 1.006 | 1.03 | 1.02 | 0.84 | 0.77 | 0.99 |
| H | 349R | 0.986 | 0.893 | 0.962 | 0.842 | 0.918 | 0.795 | 0.852 | 0.901 | 0.883 | 1.09 | 1.05 | 0.91 | 1.20 | 1.51 |
| H | 349S | 0.916 | 1.075 | 0.942 | 0.852 | 1.034 | 0.997 | 1.000 | 1.059 | 1.001 | 0.98 | 0.96 | 1.20 | 0.81 | 1.18 |
| H | 349T | 0.923 | 1.306 | 3.055 | 0.982 | 1.110 | 1.069 | 1.056 | 0.875 | 1.030 | 0.99 | 0.99 | 1.04 | 0.90 | 0.73 |
| H | 349V | −0.333 | 1.090 | −1.691 | −0.056 | −0.608 | −2.240 | 1.489 | 0.000 | −0.201 | 0.97 | 1.01 | 1.12 | 0.67 | 0.95 |
| H | 349W | 0.439 | 1.324 | 2.094 | 0.246 | 1.543 | 1.089 | 1.087 | 0.971 | 1.111 | 1.19 | 0.98 | 1.30 | 1.00 | 0.85 |
| H | 349Y | 0.735 | 1.115 | 1.104 | 0.662 | 1.305 | 1.185 | 1.120 | 0.855 | 1.075 | 1.04 | 0.90 | 1.04 | 0.84 | 0.89 |
| G | 357A | 1.029 | 0.898 | 0.802 | 1.157 | 0.957 | 0.968 | 0.902 | 0.719 | 0.902 | 1.03 | 0.91 | 0.66 | 1.13 | 1.22 |
| G | 357C | 0.846 | 0.951 | 0.594 | 0.806 | 1.068 | 1.063 | 1.031 | 1.013 | 1.027 | 0.96 | 1.05 | 0.80 | 0.90 | 0.68 |
| G | 357D | 0.968 | 1.016 | 0.581 | 0.931 | 0.945 | 0.979 | 0.974 | 0.998 | 0.976 | 1.06 | 1.02 | 0.76 | 0.92 | 0.85 |
| G | 357E | 0.976 | 0.835 | 0.454 | 0.903 | 0.963 | 0.982 | 0.985 | 0.998 | 0.981 | 1.01 | 1.02 | 0.79 | 0.91 | 0.71 |
| G | 357F | 0.881 | 1.155 | 1.464 | 0.781 | 1.046 | 0.971 | 0.986 | 1.071 | 1.006 | 1.06 | 1.06 | 0.86 | 0.96 | 1.10 |
| G | 357H | 1.322 | 0.846 | −0.015 | 1.770 | 0.851 | 0.994 | 0.893 | 0.696 | 0.875 | 1.03 | 1.04 | 1.00 | 1.17 | 1.20 |
| G | 357I | 0.553 | 1.127 | 0.934 | 0.349 | 1.322 | 1.072 | 1.082 | 1.024 | 1.105 | 1.03 | 1.03 | 0.90 | 0.90 | 0.92 |
| G | 357K | 0.981 | 1.068 | 0.969 | 0.998 | 0.932 | 0.922 | 0.988 | 0.864 | 0.965 | 1.00 | 0.93 | 0.86 | 1.19 | 1.26 |
| G | 357L | 0.717 | 1.151 | 1.337 | 0.688 | 1.340 | 1.276 | 1.230 | 0.868 | 1.218 | 1.06 | 0.94 | 1.03 | 1.29 | 1.27 |
| G | 357M | 0.876 | 1.020 | 0.846 | 0.925 | 1.094 | 1.095 | 1.011 | 0.837 | 1.051 | 1.03 | 0.89 | 0.68 | 1.01 | 0.97 |
| G | 357N | 0.937 | 0.901 | 0.661 | 0.934 | 0.997 | 1.020 | 1.009 | 0.959 | 1.006 | 1.05 | 0.99 | 0.76 | 1.18 | 1.17 |
| G | 357P | 0.478 | 1.459 | 0.872 | 0.237 | 1.346 | 0.996 | 1.019 | 1.033 | 1.076 | 1.01 | 0.97 | 0.92 | 0.96 | 0.80 |
| G | 357Q | 0.869 | 0.930 | 0.822 | 0.809 | 1.044 | 1.036 | 1.056 | 1.105 | 1.051 | 1.05 | 1.03 | 0.85 | 0.77 | 1.18 |
| G | 357R | 0.711 | 1.157 | 1.102 | 0.576 | 1.178 | 1.105 | 1.131 | 1.211 | 1.118 | 0.98 | 1.00 | 0.76 | 1.69 | 1.84 |
| G | 357S | 0.891 | 0.955 | 0.962 | 0.787 | 1.064 | 1.023 | 1.054 | 1.105 | 1.050 | 1.10 | 1.13 | 0.83 | 1.10 | 0.80 |
| G | 357T | 0.659 | 1.186 | 0.851 | 0.534 | 1.336 | 1.247 | 1.236 | 1.280 | 1.275 | 1.04 | 1.07 | 0.87 | 1.15 | 1.54 |
| G | 357V | 0.536 | 1.173 | 1.427 | 0.361 | 1.449 | 1.237 | 1.252 | 1.224 | 1.295 | 1.06 | 1.06 | 0.85 | 1.06 | 0.89 |
| G | 357W | 0.612 | 1.271 | 0.689 | 0.481 | 1.428 | 1.272 | 1.308 | 1.119 | 1.258 | 1.08 | 1.02 | 1.00 | 1.27 | 1.25 |
| G | 357Y | 0.745 | 1.116 | 1.174 | 0.751 | 1.317 | 1.296 | 1.244 | 0.878 | 1.223 | 1.04 | 0.98 | 0.99 | 1.18 | 0.85 |
| N | 358A | 1.243 | 0.936 | 0.205 | 1.638 | 0.895 | 0.955 | 0.866 | 0.567 | 0.886 | 0.98 | 0.89 | 0.93 | 1.10 | 1.02 |
| N | 358C | 1.001 | 0.983 | 1.833 | 1.130 | 1.015 | 1.020 | 0.944 | 0.734 | 0.929 | 1.01 | 0.93 | 0.75 | 0.65 | 0.50 |
| N | 358D | 1.103 | 0.988 | 2.298 | 1.302 | 0.961 | 0.966 | 0.921 | 0.776 | 0.905 | 1.06 | 0.98 | 1.00 | 0.93 | 1.00 |
| N | 358E | 0.347 | 2.107 | 5.715 | 0.188 | 1.959 | 1.353 | 1.298 | 1.110 | 1.388 | 0.97 | 0.90 | 1.07 | 0.92 | 0.91 |
| N | 358F | 0.896 | 1.178 | 1.775 | 0.983 | 1.180 | 1.175 | 1.085 | 0.972 | 1.089 | 1.00 | 0.99 | 1.15 | 1.18 | 1.07 |
| N | 358G | 0.454 | 1.471 | 9.271 | 0.268 | 1.691 | 1.378 | 1.382 | 1.335 | 1.349 | ND | ND | ND | ND | ND |
| N | 358H | 1.099 | 0.846 | 1.976 | 1.210 | 0.967 | 0.965 | 0.940 | 0.785 | 0.938 | 0.95 | 0.86 | 1.18 | 0.84 | 1.08 |
| N | 358I | 0.698 | 1.110 | −0.289 | 0.506 | 1.257 | 1.119 | 1.094 | 0.978 | 1.077 | 0.96 | 0.88 | 1.10 | 0.87 | 0.66 |
| N | 358K | 0.876 | 1.237 | 4.044 | 0.911 | 1.149 | 1.135 | 1.032 | 0.840 | 1.079 | 0.94 | 0.91 | 1.03 | 0.99 | 1.24 |
| N | 358L | 0.951 | 0.983 | 1.558 | 0.975 | 1.152 | 1.178 | 1.111 | 0.722 | 1.123 | 0.97 | 0.99 | 0.93 | 1.02 | 0.95 |
| N | 358M | 0.888 | 1.217 | 1.580 | 1.001 | 1.146 | 1.127 | 1.042 | 0.805 | 1.063 | 1.05 | 0.93 | 1.05 | 1.06 | 1.15 |
| N | 358P | 0.007 | 268.840 | 400.029 | 0.000 | 190.343 | 60.073 | 83.864 | 90.323 | 117.338 | ND | ND | 0.76 | 1.03 | 1.13 |
| N | 358Q | 0.882 | 1.093 | 0.639 | 0.837 | 1.053 | 1.014 | 1.009 | 0.994 | 1.018 | 1.03 | 1.05 | 0.97 | 1.00 | 0.81 |
| N | 358R | 0.980 | 0.968 | 0.063 | 0.923 | 0.977 | 0.930 | 0.942 | 0.946 | 0.920 | 0.99 | 0.99 | 0.87 | 1.20 | 1.44 |
| N | 358S | 0.909 | 1.130 | 1.057 | 0.852 | 1.060 | 0.969 | 0.984 | 0.970 | 1.000 | 0.98 | 0.98 | 1.14 | 0.96 | 0.85 |
| N | 358T | 0.760 | 1.304 | 0.837 | 0.689 | 1.201 | 1.087 | 1.103 | 1.074 | 1.086 | 0.94 | 0.91 | 0.80 | 0.73 | 0.90 |
| N | 358V | 0.709 | 1.397 | 2.183 | 0.602 | 1.251 | 1.149 | 1.176 | 1.065 | 1.200 | 0.98 | 0.96 | 0.75 | 1.30 | 0.86 |
| N | 358W | 0.713 | 0.988 | 4.710 | 0.556 | 1.218 | 1.058 | 1.041 | 1.041 | 1.007 | 0.99 | 0.97 | 0.63 | 0.92 | 0.99 |
| N | 358Y | 0.690 | 1.210 | −0.102 | 0.564 | 1.291 | 1.135 | 1.073 | 0.711 | 1.043 | 0.99 | 0.91 | 0.76 | 0.95 | 1.02 |
| N | 359A | 1.135 | 0.943 | 1.379 | 1.473 | 0.946 | 1.009 | 0.931 | 0.773 | 0.947 | 1.05 | 0.96 | 0.94 | 0.98 | 0.98 |
| N | 359C | 1.118 | 0.883 | 0.621 | 1.137 | 0.855 | 0.890 | 0.850 | 0.821 | 0.819 | 1.06 | 1.05 | 0.75 | 0.69 | 0.56 |
| N | 359D | 0.949 | 1.059 | 1.114 | 0.923 | 0.984 | 1.012 | 0.991 | 1.010 | 1.006 | 1.09 | 1.12 | 0.87 | 0.99 | 0.80 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 4 | DP3 | DP3 HS | corn flour 30 min | Cleaning pH 8 | Cleaning pH 10 |
|---|---|---|---|---|---|---|---|---|---|---|---|---|---|---|---|
| N | 359E | 0.952 | 1.035 | 0.946 | 0.919 | 0.999 | 1.016 | 0.991 | 1.056 | 1.022 | 1.07 | 1.12 | 0.79 | 0.88 | 0.92 |
| N | 359F | 1.314 | 0.739 | 0.410 | 1.401 | 0.751 | 0.729 | 0.748 | 0.848 | 0.790 | 1.00 | 1.09 | 0.67 | 0.89 | 0.79 |
| N | 359G | 0.716 | 0.975 | 2.049 | 0.419 | 1.054 | 0.820 | 0.807 | 0.893 | 0.847 | 0.98 | 1.02 | 0.87 | 0.97 | 0.82 |
| N | 359H | 0.979 | 0.976 | 1.603 | 0.892 | 0.960 | 0.936 | 0.937 | 1.006 | 0.945 | 0.98 | 1.01 | 0.74 | 0.85 | 1.23 |
| N | 359I | 1.055 | 0.901 | 1.353 | 0.950 | 0.894 | 0.857 | 0.867 | 0.857 | 0.869 | 1.06 | 1.04 | 0.80 | 1.04 | 1.03 |
| N | 359K | 1.063 | 0.898 | 0.567 | 0.947 | 0.884 | 0.851 | 0.854 | 0.741 | 0.852 | 1.00 | 0.95 | 0.59 | 0.97 | 0.87 |
| N | 359L | 0.939 | 0.941 | 1.279 | 0.989 | 1.112 | 1.097 | 1.080 | 0.773 | 1.042 | 1.02 | 0.94 | 0.71 | 0.91 | 1.08 |
| N | 359M | 1.026 | 0.996 | 1.076 | 1.168 | 0.979 | 1.044 | 0.945 | 0.774 | 0.960 | 1.06 | 0.95 | 0.91 | 0.98 | 0.96 |
| N | 359P | 0.870 | 1.069 | 0.755 | 0.841 | 1.069 | 1.060 | 1.057 | 1.049 | 1.069 | 1.07 | 1.06 | 0.85 | 1.05 | 0.96 |
| N | 359Q | 1.043 | 1.019 | 1.189 | 0.980 | 0.900 | 0.894 | 0.900 | 0.914 | 0.895 | 1.05 | 1.07 | 0.85 | 0.85 | 1.19 |
| N | 359R | 1.033 | 0.751 | 0.866 | 0.947 | 0.890 | 0.877 | 0.887 | 0.930 | 0.862 | 1.02 | 1.07 | 0.87 | 1.04 | 1.44 |
| N | 359S | 1.020 | 1.006 | 1.612 | 0.925 | 0.952 | 0.939 | 0.944 | 1.016 | 0.937 | 1.07 | 1.10 | 0.66 | 0.94 | 0.80 |
| N | 359T | 0.478 | 1.769 | 3.402 | 0.349 | 1.778 | 1.271 | 1.236 | 1.118 | 1.622 | 0.74 | 0.53 | 0.62 | 1.30 | 0.69 |
| N | 359V | 0.779 | 1.091 | 2.274 | 0.621 | 1.164 | 1.120 | 1.145 | 1.115 | 1.128 | 1.03 | 1.02 | 0.61 | 0.92 | 0.94 |
| N | 359W | 0.853 | 1.022 | 1.350 | 0.721 | 1.075 | 1.024 | 1.048 | 0.926 | 1.014 | 0.99 | 0.99 | 0.76 | 0.99 | 0.91 |
| N | 359Y | 1.011 | 0.947 | 1.380 | 0.978 | 0.997 | 0.959 | 0.920 | 0.677 | 0.905 | 1.01 | 0.93 | 0.81 | 0.97 | 0.89 |
| G | 367A | 1.082 | 0.925 | 0.950 | 1.177 | 0.972 | 0.907 | 0.821 | 0.638 | 0.844 | 0.94 | 0.87 | 1.01 | 1.02 | 0.93 |
| G | 367C | 0.673 | 1.071 | 1.230 | 0.434 | 1.110 | 0.916 | 0.876 | 0.823 | 0.900 | 0.92 | 0.90 | 0.97 | 0.93 | 0.56 |
| G | 367D | 0.816 | 0.993 | 0.574 | 0.647 | 1.120 | 0.925 | 0.952 | 0.965 | 0.961 | 0.92 | 0.93 | 1.02 | 1.02 | 1.00 |
| G | 367E | 0.955 | 0.807 | 0.694 | 0.721 | 0.954 | 0.778 | 0.758 | 0.832 | 0.818 | 0.95 | 0.96 | 0.81 | 0.94 | 0.89 |
| G | 367F | 0.374 | 1.678 | 1.988 | 0.172 | 1.783 | 1.096 | 1.174 | 1.197 | 1.224 | 0.99 | 0.99 | 0.88 | 1.01 | 0.82 |
| G | 367H | 0.753 | 0.986 | 1.159 | 0.550 | 1.110 | 0.952 | 0.957 | 0.957 | 0.972 | 0.95 | 0.95 | 0.85 | 0.95 | 0.97 |
| G | 367I | 0.099 | 3.440 | 9.300 | 0.033 | 4.506 | 2.206 | 2.580 | 2.399 | 2.877 | 1.04 | 1.01 | 0.76 | 1.55 | 1.67 |
| G | 367K | 0.614 | 0.987 | 1.377 | 0.394 | 1.234 | 1.011 | 1.009 | 0.847 | 1.036 | 0.93 | 0.91 | 0.77 | 1.04 | 0.87 |
| G | 367L | 0.566 | 1.059 | 2.167 | 0.381 | 1.411 | 1.121 | 1.052 | 0.689 | 1.095 | 1.01 | 0.95 | 0.96 | 1.21 | 1.04 |
| G | 367M | 0.604 | 1.451 | 1.457 | 0.427 | 1.298 | 1.076 | 0.983 | 0.767 | 1.023 | 0.99 | 0.91 | 1.06 | 0.98 | 0.93 |
| G | 367N | 0.830 | 0.929 | 1.272 | 0.647 | 1.077 | 0.914 | 0.878 | 0.831 | 0.905 | 0.99 | 0.97 | 1.13 | 1.04 | 0.84 |
| G | 367P | 0.105 | 4.841 | 3.359 | 0.033 | 4.188 | 1.803 | 2.192 | 2.183 | 2.598 | 0.95 | 1.05 | 1.01 | 1.32 | 1.60 |
| G | 367R | 0.693 | 1.065 | 0.492 | 0.513 | 1.057 | 0.887 | 0.867 | 0.782 | 0.871 | 0.95 | 0.98 | 0.83 | 1.23 | 0.97 |
| G | 367S | 0.786 | 1.098 | 1.354 | 0.585 | 1.121 | 1.034 | 1.079 | 1.099 | 1.069 | 1.02 | 1.05 | 1.02 | 1.29 | 0.98 |
| G | 367T | 0.531 | 1.219 | 1.360 | 0.325 | 1.411 | 1.129 | 1.155 | 1.148 | 1.198 | 1.00 | 1.01 | 0.90 | 0.86 | 0.99 |
| G | 367V | 0.234 | 2.053 | 3.618 | 0.095 | 2.459 | 1.556 | 1.640 | 1.529 | 1.779 | 1.07 | 1.08 | 1.28 | 1.48 | 1.36 |
| G | 367W | 0.342 | 1.774 | 2.054 | 0.166 | 2.032 | 1.440 | 1.448 | 1.232 | 1.524 | 1.06 | 1.01 | 0.93 | 1.31 | 0.84 |
| G | 367Y | 0.559 | 1.007 | 3.282 | 0.342 | 1.196 | 0.928 | 0.926 | 0.953 | 0.964 | 1.05 | 0.98 | 0.98 | 1.17 | 1.42 |
| S | 368D | 0.265 | 1.436 | 1.311 | 0.087 | 1.780 | 0.775 | 0.902 | 0.940 | 1.086 | 0.81 | 0.83 | 1.17 | 0.93 | 1.28 |
| S | 368F | 0.820 | 0.900 | 1.384 | 0.719 | 1.034 | 0.988 | 0.962 | 0.954 | 0.943 | 1.00 | 1.05 | 1.13 | 1.04 | 0.84 |
| S | 368G | 0.880 | 1.098 | 1.642 | 0.735 | 1.158 | 1.046 | 1.060 | 1.117 | 1.056 | 0.95 | 0.98 | 1.06 | 1.00 | 0.96 |
| S | 368I | 0.927 | 0.966 | 1.047 | 0.781 | 1.016 | 0.982 | 1.023 | 0.996 | 1.003 | 1.01 | 1.02 | 1.05 | 1.08 | 1.21 |
| S | 368K | 0.942 | 0.923 | 0.329 | 0.802 | 1.047 | 1.006 | 1.036 | 1.148 | 0.993 | 1.03 | 1.05 | 0.88 | 1.27 | 1.06 |
| S | 368L | 0.871 | 0.965 | 1.989 | 0.737 | 1.109 | 1.079 | 1.040 | 0.875 | 1.022 | 1.02 | 1.01 | 1.02 | 1.03 | 1.22 |
| S | 368M | 0.982 | 1.120 | 0.603 | 1.050 | 1.082 | 1.041 | 0.953 | 0.703 | 0.946 | 0.95 | 0.92 | 1.03 | 1.07 | 1.11 |
| S | 368N | 1.012 | 1.018 | 0.451 | 0.989 | 0.996 | 0.931 | 0.901 | 0.691 | 0.916 | 0.96 | 0.89 | 0.97 | 1.07 | 0.96 |
| S | 368P | 0.877 | 1.213 | −0.049 | 0.747 | 1.115 | 1.004 | 1.030 | 0.798 | 1.010 | 0.92 | 0.93 | 0.88 | 1.00 | 0.99 |
| S | 368Q | 0.987 | 0.937 | 0.096 | 0.866 | 1.009 | 0.945 | 0.971 | 0.964 | 0.968 | 1.00 | 0.92 | 0.78 | 0.90 | 1.00 |
| S | 368R | 0.930 | 1.053 | 0.071 | 0.793 | 1.116 | 1.033 | 1.071 | 0.954 | 1.028 | 1.03 | 1.01 | 1.07 | 1.04 | 1.03 |
| S | 368T | 0.890 | 1.060 | 0.008 | 0.743 | 1.058 | 1.064 | 1.111 | 1.062 | 1.098 | 0.98 | 1.02 | 0.92 | 1.18 | 1.00 |
| S | 368V | 0.233 | 2.255 | 1.550 | 0.083 | 2.420 | 1.440 | 1.561 | 1.432 | 1.647 | 1.15 | 1.16 | 0.98 | 1.34 | 1.25 |
| S | 368W | 0.782 | 1.077 | −0.152 | 0.638 | 1.192 | 1.118 | 1.145 | 0.960 | 1.115 | 1.04 | 1.04 | 0.95 | 1.23 | 1.10 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| S | 368Y | 0.927 | 0.960 | 0.997 | 0.847 | 1.048 | 1.063 | 1.028 | 0.692 | 1.016 | 1.03 | 0.95 | 0.83 | 0.97 | 1.10 |
| H | 369A | 1.141 | 0.981 | 0.564 | 1.362 | 0.890 | 0.980 | 0.900 | 0.676 | 0.889 | 0.99 | 0.87 | 0.76 | 0.78 | 0.76 |
| H | 369C | 0.936 | 0.975 | 0.701 | 0.960 | 1.028 | 1.093 | 1.060 | 0.973 | 1.068 | 1.06 | 1.00 | 0.93 | 0.87 | 0.83 |
| H | 369D | 0.706 | 1.085 | 0.111 | 0.570 | 1.298 | 1.216 | 1.225 | 1.172 | 1.248 | 0.98 | 0.97 | 0.74 | 0.86 | 0.80 |
| H | 369E | 0.933 | 1.143 | 1.148 | 0.915 | 1.002 | 1.022 | 1.053 | 1.081 | 1.042 | 1.02 | 1.03 | 0.88 | 0.97 | 0.90 |
| H | 369F | 0.637 | 1.297 | 3.350 | 0.509 | 1.478 | 1.334 | 1.269 | 0.803 | 1.268 | 1.10 | 1.02 | 0.98 | 1.02 | 0.96 |
| HP | 369G | 1.021 | 0.932 | 3.268 | 1.172 | 1.018 | 1.026 | 0.955 | 0.730 | 0.973 | 1.10 | 1.20 | 1.01 | 1.07 | 1.17 |
| H | 369I | 0.871 | 0.992 | 0.827 | 0.776 | 1.076 | 1.072 | 1.107 | 1.084 | 1.103 | 1.09 | 1.10 | 0.91 | 0.94 | 1.03 |
| H | 369K | 0.975 | 0.894 | 0.287 | 0.860 | 0.985 | 0.946 | 0.959 | 0.935 | 0.967 | 1.10 | 1.09 | 0.83 | 1.28 | 1.11 |
| H | 369L | 0.799 | 1.135 | 0.646 | 0.782 | 1.231 | 1.277 | 1.232 | 0.948 | 1.228 | 1.10 | 0.96 | 0.88 | 0.90 | 0.76 |
| H | 369M | 1.172 | 0.886 | 0.799 | 1.308 | 0.858 | 0.903 | 0.851 | 0.578 | 0.813 | 1.04 | 0.89 | 0.75 | 0.84 | 0.76 |
| H | 369N | 1.167 | 0.871 | −0.889 | 1.312 | 0.849 | 0.921 | 0.892 | 0.804 | 0.882 | 1.01 | 0.92 | 0.79 | 0.80 | 1.13 |
| H | 369P | 0.194 | 2.985 | 0.255 | 0.076 | 2.855 | 1.762 | 1.842 | 1.778 | 2.066 | 0.97 | 0.92 | 0.60 | 0.87 | 0.94 |
| H | 369Q | 1.019 | 0.900 | 2.278 | 0.916 | 0.890 | 0.930 | 0.944 | 0.921 | 0.941 | 1.00 | 0.96 | 1.10 | 0.91 | 1.18 |
| H | 369R | 0.882 | 1.085 | 0.835 | 0.718 | 1.041 | 1.020 | 1.026 | 1.005 | 1.009 | 1.00 | 0.91 | 1.06 | 1.07 | 1.02 |
| H | 369S | 0.826 | 1.170 | 0.073 | 0.707 | 1.103 | 1.092 | 1.115 | 1.117 | 1.122 | 1.18 | 1.25 | 1.19 | 1.09 | 1.21 |
| H | 369T | 1.033 | 0.938 | 2.068 | 1.017 | 0.912 | 0.974 | 1.019 | 1.016 | 1.004 | 1.19 | 1.24 | 1.34 | 1.13 | 1.01 |
| H | 369V | 0.951 | 0.890 | 1.523 | 0.793 | 0.953 | 0.957 | 0.989 | 0.964 | 0.998 | 1.09 | 1.09 | 1.22 | 0.75 | 0.84 |
| H | 369W | 0.966 | 0.910 | 0.750 | 1.014 | 1.231 | 1.161 | 1.145 | 1.049 | 1.121 | 1.09 | 1.03 | 1.09 | 1.10 | 1.08 |
| H | 369Y | 0.862 | 0.991 | 0.866 | 0.890 | 0.976 | 0.954 | 0.960 | 0.895 | 0.993 | 1.07 | 1.07 | 1.09 | 1.09 | 1.07 |
| S | 378A | 1.236 | 0.840 | 1.256 | 0.816 | 1.158 | 1.138 | 1.123 | 0.876 | 1.124 | 1.12 | 0.99 | 1.01 | 0.68 | 0.82 |
| S | 378C | 1.028 | 1.002 | 0.514 | 1.780 | 0.895 | 1.019 | 0.942 | 0.748 | 0.962 | 0.92 | 0.80 | 0.72 | 0.97 | 0.93 |
| S | 378D | 1.013 | 1.101 | 0.366 | 1.014 | 0.907 | 1.006 | 0.940 | 0.759 | 0.962 | 1.21 | 1.07 | 1.00 | 0.83 | 0.79 |
| S | 378E | 1.005 | 1.101 | 0.823 | 0.923 | 0.922 | 0.938 | 0.920 | 0.778 | 0.926 | 1.00 | 0.91 | 0.83 | 0.79 | 0.78 |
| S | 378F | 0.603 | 1.421 | 0.566 | 0.383 | 1.279 | 1.154 | 1.108 | 0.936 | 1.094 | 0.98 | 0.86 | 1.06 | 0.70 | 0.85 |
| S | 378G | 0.912 | 1.066 | −0.436 | 0.765 | 1.014 | 1.014 | 1.005 | 0.918 | 0.979 | 0.98 | 0.99 | 1.40 | 1.04 | 1.06 |
| S | 378H | 0.894 | 1.092 | 1.504 | 0.747 | 1.078 | 1.040 | 1.047 | 0.969 | 1.033 | 1.01 | 1.04 | 1.10 | 0.75 | 0.81 |
| S | 378I | 0.703 | 1.134 | 1.566 | 0.504 | 1.252 | 1.161 | 1.145 | 1.049 | 1.121 | 1.03 | 1.03 | 1.36 | 1.10 | 0.74 |
| S | 378K | 0.875 | 1.126 | 0.977 | 0.721 | 1.058 | 1.028 | 1.042 | 0.939 | 1.043 | 1.03 | 1.00 | 1.22 | 0.86 | 1.25 |
| S | 378L | 0.769 | 1.182 | −0.257 | 0.620 | 1.188 | 1.143 | 1.136 | 0.906 | 1.102 | 1.03 | 0.95 | 1.10 | 1.17 | 1.12 |
| S | 378M | 0.631 | 1.116 | 0.148 | 0.453 | 1.444 | 1.258 | 1.157 | 0.872 | 1.156 | 1.17 | 1.09 | 1.04 | 1.05 | 0.76 |
| S | 378N | 1.013 | 1.152 | 0.274 | 1.211 | 1.006 | 1.128 | 0.948 | 0.562 | 0.977 | 0.95 | 0.78 | 0.61 | 0.97 | 1.00 |
| S | 378P | 1.378 | 0.927 | −0.122 | 1.965 | 0.851 | 1.033 | 0.987 | 0.704 | 0.971 | 0.95 | 0.76 | 0.75 | 0.58 | 0.84 |
| S | 378Q | 0.445 | 1.101 | −1.080 | 0.202 | 1.481 | 0.941 | 0.897 | 0.658 | 0.994 | 0.89 | 0.78 | 0.82 | 0.86 | 0.76 |
| S | 378R | −0.764 | −0.008 | 0.144 | −0.137 | −0.325 | −1.454 | −0.203 | 0.029 | 0.008 | 0.95 | 0.81 | 0.79 | 0.75 | 1.06 |
| S | 378T | 0.909 | 1.089 | 0.337 | 0.812 | 1.059 | 1.017 | 0.932 | 0.707 | 0.890 | 0.90 | 0.84 | 0.68 | 0.92 | 1.12 |
| S | 378V | 0.626 | 1.129 | 1.526 | 0.429 | 1.395 | 1.147 | 1.100 | 0.814 | 1.128 | 1.05 | 0.97 | 1.26 | 1.19 | 0.60 |
| S | 378W | 0.890 | 0.928 | 0.544 | 0.873 | 1.164 | 1.159 | 1.112 | 0.830 | 1.112 | 1.03 | 0.96 | 1.15 | 0.87 | 1.08 |
| S | 378Y | 1.005 | 0.928 | 0.371 | 1.018 | 1.027 | 1.014 | 0.975 | 0.721 | 0.951 | 1.07 | 1.02 | 1.20 | 1.05 | 0.99 |
| S | 380A | 0.854 | 0.868 | 4.364 | 0.768 | 1.098 | 1.025 | 1.031 | 0.893 | 0.978 | 1.02 | 0.99 | 0.89 | 1.00 | 0.96 |
| S | 380C | 1.380 | 0.928 | 5.809 | 2.356 | 0.876 | 1.005 | 0.927 | 0.642 | 0.908 | 1.01 | 0.87 | 0.82 | 1.02 | 1.44 |
| S | 380E | 1.183 | 0.902 | 0.904 | 1.494 | 0.950 | 0.986 | 0.905 | 0.754 | 0.660 | 0.96 | 0.92 | 0.63 | 0.73 | 0.96 |
| S | 380F | 1.02 | 0.840 | ND | ND | ND | ND | 0.96 | ND | 1.02 | 1.00 | 0.98 | 1.17 | 1.06 | 0.98 |
| S | 380G | 1.082 | 0.924 | 4.989 | 1.174 | 1.010 | 0.970 | 0.943 | 0.852 | 0.953 | 1.03 | 0.94 | 1.20 | 0.92 | 1.31 |
| S | 380H | 1.092 | 0.967 | −0.310 | 1.321 | 0.989 | 1.070 | 1.027 | 0.932 | 1.047 | 0.99 | 0.92 | 1.11 | 1.08 | 1.03 |
| S | 380I | 1.243 | 0.819 | 0.469 | 1.458 | 0.897 | 0.945 | 0.910 | 0.796 | 0.901 | 0.89 | 0.89 | 0.91 | 0.86 | 1.06 |
| S | 380L | 1.072 | 0.831 | 1.906 | 1.213 | 1.042 | 1.025 | 0.987 | 0.838 | 0.981 | 0.93 | 0.90 | 0.87 | 0.96 | 0.95 |
| S | 380M | 1.170 | 0.906 | 2.322 | 1.592 | 0.975 | 1.063 | 0.979 | 0.731 | 0.957 | 0.95 | 0.93 | 0.83 | 0.83 | 1.21 |
| S | 380M | 1.214 | 0.830 | 1.046 | 1.642 | 0.884 | 0.916 | 0.818 | 0.626 | 0.829 | 1.00 | 0.91 | 0.83 | 0.72 | 1.21 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| S | 380N | 1.00 | ND | ND | ND | ND | ND | 0.99 | ND | 1.02 | 0.99 | 0.95 | 0.81 | 0.73 | 1.05 |
| S | 380P | 0.883 | 1.025 | 2.880 | 0.797 | 1.067 | 1.014 | 0.983 | 1.003 | 1.005 | 1.02 | 0.99 | 0.87 | 1.08 | 0.89 |
| S | 380Q | 1.039 | 0.973 | −1.221 | 1.167 | 0.969 | 0.978 | 0.959 | 0.987 | 0.975 | 1.04 | 1.06 | 0.86 | 1.02 | 1.06 |
| S | 380R | 1.066 | 0.896 | 1.018 | 1.099 | 0.930 | 0.934 | 0.930 | 0.948 | 0.918 | 0.98 | 1.02 | 1.09 | 1.28 | 1.23 |
| S | 380T | 0.93 | ND | ND | ND | ND | ND | 0.99 | ND | 0.99 | 1.01 | 1.00 | 1.00 | 0.77 | 0.78 |
| S | 380V | 0.930 | 1.031 | −4.810 | 0.928 | 1.080 | 1.010 | 1.020 | 0.978 | 1.016 | 1.03 | 0.99 | 0.93 | 0.54 | 0.85 |
| S | 380W | 0.872 | 0.968 | −0.600 | 0.890 | 1.069 | 1.046 | 1.037 | 0.928 | 1.024 | 0.98 | 0.97 | 0.66 | 0.73 | 0.75 |
| S | 380Y | 1.196 | 0.892 | −1.160 | 1.794 | 1.067 | 1.176 | 1.152 | 0.906 | 1.132 | 0.93 | 0.92 | 0.66 | 0.73 | 0.90 |
| S | 382A | 0.96 | ND | ND | ND | ND | ND | 1.06 | ND | 1.12 | 1.09 | 0.98 | 0.72 | 0.67 | 1.28 |
| S | 382C | 1.025 | 0.986 | −0.045 | 1.042 | 0.938 | 0.946 | 0.900 | 0.882 | 0.918 | 0.97 | 0.94 | 0.76 | 0.74 | 2.92 |
| S | 382D | 0.950 | 1.015 | 1.962 | 0.935 | 0.981 | 0.989 | 0.986 | 1.036 | 0.997 | 0.99 | 0.98 | 0.78 | 0.91 | 0.90 |
| S | 382F | 1.133 | 0.875 | 1.656 | 1.318 | 0.901 | 0.969 | 0.998 | 1.054 | 0.988 | 1.06 | 1.10 | 0.90 | 0.99 | 0.95 |
| S | 382G | 0.921 | 1.023 | 7.862 | 0.918 | 1.035 | 1.032 | 1.051 | 1.081 | 1.047 | 1.00 | 1.01 | 0.97 | 0.96 | 0.79 |
| S | 382H | 0.841 | 1.099 | 5.120 | 0.806 | 1.141 | 1.113 | 1.124 | 1.150 | 1.099 | 1.05 | 1.05 | 0.85 | 1.02 | 0.96 |
| S | 382I | 0.831 | 0.979 | −0.605 | 0.724 | 1.157 | 1.123 | 1.030 | 1.035 | 1.018 | 1.04 | 1.03 | 0.60 | 0.65 | 1.15 |
| S | 382K | 0.970 | 0.897 | 2.441 | 0.900 | 0.968 | 0.973 | 1.013 | 0.842 | 0.948 | 1.01 | 1.00 | 0.58 | 1.14 | 1.06 |
| S | 382L | 1.018 | 0.910 | 1.596 | 1.114 | 0.993 | 1.022 | 1.026 | 0.662 | 0.949 | 1.02 | 0.98 | 0.67 | 0.89 | 0.63 |
| S | 382M | 1.046 | 0.977 | 4.004 | 1.384 | 1.020 | 1.070 | 1.119 | 0.769 | 1.000 | 1.00 | 0.90 | 0.73 | 0.86 | 0.90 |
| S | 382N | 0.929 | 0.958 | 4.239 | 0.953 | 1.000 | 1.016 | 0.959 | 0.919 | 0.954 | 1.04 | 0.99 | 0.75 | 0.55 | 1.07 |
| S | 382P | 1.038 | 0.843 | 4.521 | 0.998 | 0.890 | 0.862 | 0.850 | 0.884 | 0.874 | 1.01 | 1.01 | 0.87 | 0.91 | 0.89 |
| S | 382Q | 0.872 | 1.045 | 1.099 | 0.853 | 1.063 | 1.084 | 1.086 | 1.127 | 1.089 | 1.09 | 1.12 | 1.21 | 1.09 | 0.92 |
| S | 382R | 0.855 | 1.099 | 6.041 | 0.831 | 1.111 | 1.113 | 1.110 | 1.184 | 1.102 | 1.04 | 1.15 | 0.90 | 1.43 | 1.37 |
| S | 382T | 0.805 | 1.114 | 1.588 | 0.780 | 1.179 | 1.170 | 1.197 | 1.219 | 1.157 | 1.07 | 1.09 | 1.09 | 1.08 | 1.09 |
| S | 382V | 0.833 | 0.883 | 0.487 | 0.749 | 1.135 | 1.065 | 1.070 | 1.093 | 1.044 | 1.06 | 1.04 | 0.75 | 0.76 | 1.01 |
| S | 382W | 0.729 | 1.241 | −5.865 | 0.702 | 1.279 | 1.297 | 1.331 | 1.167 | 1.266 | 1.07 | 1.05 | 0.70 | 1.29 | 1.05 |
| S | 382Y | 0.782 | 1.027 | 3.156 | 0.775 | 1.326 | 1.250 | 1.195 | 0.816 | 1.143 | 1.07 | 1.02 | 0.77 | 0.95 | 1.12 |
| S | 385A | 1.053 | 0.912 | 0.096 | 1.216 | 1.035 | 1.024 | 0.928 | 0.632 | 0.927 | 0.93 | 0.83 | 1.01 | 1.08 | 0.89 |
| T | 385C | 1.309 | 0.794 | −0.226 | 1.736 | 0.875 | 1.001 | 0.984 | 0.901 | 1.007 | 0.97 | 0.95 | 1.09 | 1.09 | 0.86 |
| T | 385D | 0.973 | 0.984 | −0.070 | 0.830 | 0.994 | 0.924 | 0.919 | 0.814 | 0.919 | 0.93 | 0.89 | 0.97 | 0.90 | 0.89 |
| T | 385E | 0.882 | 0.972 | −0.181 | 0.702 | 1.116 | 1.026 | 1.020 | 0.904 | 1.016 | 0.93 | 0.86 | 1.04 | 0.92 | 0.51 |
| T | 385F | 0.648 | 1.274 | −0.302 | 0.430 | 1.374 | 1.135 | 1.120 | 1.018 | 1.118 | 1.07 | 1.03 | 0.98 | 1.04 | 1.18 |
| T | 385G | 1.082 | 0.722 | 0.119 | 1.027 | 0.945 | 0.911 | 0.842 | 0.670 | 0.853 | 1.00 | 0.97 | 0.94 | 0.66 | 0.91 |
| T | 385H | 0.969 | 0.905 | 0.094 | 0.773 | 0.932 | 0.930 | 0.964 | 0.852 | 0.894 | 0.98 | 0.98 | 1.28 | 1.13 | 0.92 |
| T | 385I | 0.707 | 1.153 | 0.126 | 0.532 | 1.256 | 1.220 | 1.211 | 1.080 | 1.227 | 0.98 | 0.98 | 1.37 | 1.31 | 1.06 |
| T | 385K | 0.865 | 0.817 | 0.055 | 0.673 | 1.046 | 1.005 | 1.003 | 0.792 | 0.973 | 1.04 | 0.93 | 1.17 | 1.31 | 1.17 |
| T | 385L | 0.717 | 1.162 | 0.243 | 0.553 | 1.416 | 1.200 | 1.150 | 0.779 | 1.130 | 1.02 | 0.92 | 0.84 | 1.04 | 1.28 |
| T | 385M | 1.015 | 0.932 | 0.224 | 1.139 | 1.069 | 1.027 | 0.917 | 0.514 | 0.920 | 0.97 | 0.81 | 0.75 | 1.04 | 0.86 |
| T | 385N | 1.309 | 0.780 | 0.113 | 1.420 | 0.882 | 0.884 | 0.818 | 0.561 | 0.812 | 0.96 | 0.80 | 0.92 | 0.96 | 0.91 |
| T | 385P | 0.992 | 0.937 | −0.183 | 0.947 | 1.145 | 1.059 | 1.020 | 0.697 | 0.984 | 0.90 | 0.80 | 1.04 | 0.83 | 0.89 |
| T | 385Q | 1.056 | 0.912 | −0.228 | 1.008 | 1.040 | 0.985 | 0.953 | 0.681 | 0.939 | 1.00 | 0.87 | 1.20 | 1.14 | 0.82 |
| T | 385R | 0.787 | 1.071 | −0.363 | 0.646 | 1.198 | 1.138 | 1.095 | 0.778 | 1.062 | 0.92 | 0.82 | 0.95 | 0.98 | 1.31 |
| T | 385S | 0.972 | 1.024 | −0.047 | 0.911 | 1.184 | 1.076 | 1.061 | 0.764 | 1.021 | 0.95 | 0.89 | 1.24 | 0.77 | 0.88 |
| T | 385V | 1.022 | 0.934 | 0.103 | 0.991 | 1.037 | 1.093 | 1.099 | 0.761 | 1.053 | 1.07 | 0.91 | 1.30 | 1.09 | 0.99 |
| T | 385W | 1.049 | 0.870 | 0.086 | 1.080 | 1.101 | 1.053 | 1.029 | 0.702 | 0.999 | 1.04 | 0.89 | 1.24 | 1.08 | 1.15 |
| T | 385Y | 0.946 | 0.913 | 0.949 | 0.876 | 1.102 | 1.124 | 1.064 | 0.722 | 1.048 | 0.93 | 0.84 | 0.93 | 0.94 | 1.02 |
| A | 386C | 0.885 | 0.956 | 0.680 | 0.803 | 1.005 | 1.006 | 0.987 | 0.943 | 0.950 | 1.05 | 0.96 | 0.72 | 0.92 | 0.23 |
| A | 386D | 0.819 | 1.061 | 0.672 | 0.818 | 1.109 | 1.157 | 1.143 | 1.141 | 1.167 | 1.12 | 1.05 | 0.79 | 1.29 | 0.73 |
| A | 386F | 0.862 | 1.062 | 0.611 | 0.809 | 1.063 | 1.074 | 1.132 | 1.160 | 1.083 | 1.05 | 1.09 | 0.90 | 1.30 | 1.39 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| A | 386G | 0.825 | 1.084 | 0.883 | 0.757 | 1.151 | 1.163 | 1.204 | 1.262 | 1.182 | 1.04 | 1.06 | 0.81 | 1.16 | 1.05 |
| A | 386H | 0.945 | 0.940 | 1.836 | 0.825 | 0.910 | 0.838 | 0.919 | 0.877 | 0.899 | 1.03 | 1.02 | 1.02 | 1.24 | 1.07 |
| A | 386I | 0.844 | 0.962 | 0.919 | 0.760 | 1.126 | 1.109 | 1.143 | 1.084 | 1.105 | 1.06 | 1.03 | 0.91 | 0.91 | 1.09 |
| A | 386L | 0.851 | 0.984 | 1.353 | 0.902 | 1.142 | 1.178 | 1.132 | 0.774 | 1.108 | 1.10 | 1.01 | 1.17 | 1.10 | 0.83 |
| A | 386N | 0.915 | 1.001 | 0.780 | 0.871 | 1.017 | 1.015 | 1.012 | 0.881 | 0.983 | 1.09 | 0.98 | 0.73 | 0.98 | 1.20 |
| A | 386P | 0.843 | 1.047 | 0.779 | 0.808 | 1.093 | 1.125 | 1.135 | 1.086 | 1.128 | 1.03 | 0.95 | 0.87 | 0.99 | 1.05 |
| A | 386R | 0.807 | 1.100 | 0.450 | 0.705 | 1.135 | 1.129 | 1.174 | 1.157 | 1.121 | 1.05 | 1.04 | 0.95 | 1.43 | 2.00 |
| A | 386S | 0.871 | 0.982 | 0.777 | 0.786 | 1.097 | 1.067 | 1.094 | 1.124 | 1.083 | 1.10 | 1.08 | 0.88 | 1.16 | 1.02 |
| A | 386T | 0.767 | 1.078 | 0.529 | 0.672 | 1.233 | 1.238 | 1.274 | 1.241 | 1.236 | 1.07 | 1.06 | 1.05 | 1.15 | 1.23 |
| A | 386V | 0.750 | 1.020 | 0.951 | 0.616 | 1.218 | 1.164 | 1.172 | 1.150 | 1.172 | 1.06 | 1.06 | 0.86 | 1.00 | 1.24 |
| A | 386W | 0.783 | 1.003 | 0.558 | 0.735 | 1.193 | 1.179 | 1.195 | 0.998 | 1.138 | 1.06 | 1.00 | 1.06 | 1.25 | 1.15 |
| A | 386Y | 0.788 | 1.133 | 0.943 | 0.762 | 1.291 | 1.310 | 1.271 | 0.849 | 1.220 | 1.12 | 1.03 | 0.96 | 1.15 | 1.08 |
| K | 388A | 1.198 | 0.880 | 0.637 | 1.577 | 0.913 | 0.930 | 0.858 | 0.601 | 0.836 | 1.01 | 0.93 | 1.04 | 0.96 | 1.01 |
| K | 388C | 0.794 | 0.957 | 1.940 | 0.854 | 1.252 | 1.197 | 1.091 | 0.808 | 1.089 | 0.98 | 0.96 | 0.87 | 0.74 | 0.60 |
| K | 388D | 1.193 | 0.951 | 1.189 | 1.504 | 0.935 | 0.988 | 0.946 | 0.814 | 0.937 | 1.00 | 0.95 | 0.82 | 1.00 | 0.81 |
| K | 388E | 1.025 | 1.110 | 0.987 | 1.247 | 1.060 | 1.112 | 1.073 | 0.951 | 1.054 | 0.99 | 0.90 | 0.92 | 0.96 | 0.78 |
| K | 388F | 1.038 | 0.906 | 1.955 | 1.136 | 1.022 | 1.014 | 0.968 | 0.854 | 0.966 | 0.98 | 0.95 | 0.97 | 0.93 | 0.72 |
| K | 388G | 1.238 | 0.921 | 1.014 | 1.647 | 0.911 | 1.016 | 0.995 | 0.915 | 1.030 | 0.96 | 0.87 | 1.06 | 0.86 | 0.72 |
| K | 388H | 0.931 | 1.031 | 0.103 | 1.049 | 1.133 | 1.144 | 1.073 | 0.895 | 1.078 | 0.99 | 0.89 | 0.93 | 0.79 | 0.79 |
| K | 388I | 0.781 | 0.919 | -0.611 | 0.712 | 1.207 | 1.127 | 1.068 | 0.801 | 1.055 | 0.97 | 0.88 | 1.09 | 0.96 | 0.95 |
| K | 388L | 0.883 | 0.979 | 0.187 | 1.123 | 1.149 | 1.269 | 1.179 | 0.854 | 1.168 | 0.95 | 0.94 | 0.84 | 0.85 | 0.89 |
| K | 388M | 1.048 | 1.013 | 0.071 | 1.177 | 0.977 | 0.944 | 0.887 | 0.708 | 0.905 | 1.05 | 0.97 | 0.77 | 0.98 | 0.78 |
| K | 388N | 0.950 | 1.025 | -0.488 | 0.935 | 0.999 | 0.964 | 0.917 | 0.835 | 0.919 | 0.00 | 0.00 | 0.00 | 0.00 | 0.00 |
| K | 388P | 0.768 | 0.924 | 1.528 | 0.553 | 1.121 | 1.038 | 1.048 | 1.036 | 1.049 | 0.98 | 0.95 | 0.80 | 1.04 | 0.75 |
| K | 388Q | 0.924 | 0.958 | -0.259 | 0.878 | 1.034 | 1.002 | 0.996 | 0.991 | 0.972 | 1.08 | 1.07 | 0.80 | 0.93 | 0.66 |
| K | 388R | 1.007 | 0.983 | 1.372 | 0.993 | 0.974 | 0.957 | 0.936 | 0.931 | 0.928 | 0.97 | 0.97 | 0.91 | 0.97 | 1.00 |
| K | 388S | 0.756 | 1.382 | 0.378 | 0.684 | 1.293 | 1.193 | 1.167 | 1.127 | 1.172 | 1.04 | 1.00 | 0.99 | 0.95 | 0.69 |
| K | 388T | 0.769 | 1.182 | 0.699 | 0.712 | 1.207 | 1.174 | 1.196 | 1.106 | 1.162 | 0.98 | 0.97 | 0.87 | 0.60 | 0.71 |
| K | 388V | 0.814 | 1.171 | 0.621 | 0.725 | 1.143 | 1.058 | 1.050 | 0.948 | 1.043 | 1.00 | 0.95 | 0.76 | 0.78 | 1.07 |
| K | 388W | 0.556 | 1.167 | 0.988 | 0.429 | 1.481 | 1.293 | 1.246 | 1.063 | 1.240 | 1.07 | 0.99 | 0.80 | 0.85 | 0.85 |
| K | 388Y | 0.646 | 1.498 | 2.254 | 0.780 | 1.648 | 1.675 | 1.578 | 1.168 | 1.604 | 0.98 | 0.94 | 0.74 | 0.99 | 0.84 |
| P | 390A | 1.140 | 0.830 | 0.982 | 1.276 | 0.891 | 0.954 | 0.858 | 0.662 | 0.871 | 1.01 | 0.88 | 0.78 | 0.79 | 0.95 |
| P | 390C | 0.868 | 0.969 | 2.507 | 0.632 | 0.951 | 0.850 | 0.900 | 0.791 | 0.923 | 1.00 | 0.91 | 0.75 | 0.94 | 1.05 |
| P | 390D | 1.026 | 0.893 | 0.855 | 0.801 | 0.853 | 0.799 | 0.876 | 0.865 | 0.881 | 0.99 | 0.96 | 0.82 | 0.72 | 1.09 |
| P | 390E | 0.942 | 1.004 | 0.809 | 0.751 | 0.934 | 0.875 | 0.932 | 0.967 | 0.901 | 0.99 | 0.98 | 0.84 | 1.00 | 1.08 |
| P | 390F | 0.904 | 1.019 | 1.150 | 0.756 | 0.983 | 0.917 | 0.963 | 1.016 | 0.963 | 0.98 | 1.05 | 1.07 | 1.16 | 1.14 |
| P | 390G | 0.904 | 0.973 | 1.921 | 0.828 | 1.043 | 1.018 | 1.005 | 1.089 | 1.019 | 0.98 | 0.99 | 0.92 | 0.72 | 0.96 |
| P | 390H | 0.938 | 1.007 | 2.254 | 0.880 | 1.028 | 0.996 | 0.998 | 1.026 | 1.007 | 1.01 | 1.00 | 1.06 | 0.92 | 0.84 |
| P | 390I | 0.935 | 1.030 | -0.222 | 0.862 | 0.967 | 0.950 | 0.956 | 0.972 | 0.927 | 1.00 | 0.96 | 1.15 | 0.88 | 0.83 |
| P | 390K | 0.933 | 0.893 | 0.840 | 0.919 | 1.023 | 1.008 | 1.029 | 0.907 | 0.988 | 0.94 | 0.91 | 0.86 | 1.36 | 1.51 |
| P | 390L | 0.936 | 0.947 | 1.363 | 1.028 | 1.115 | 1.116 | 1.067 | 0.811 | 1.036 | 1.04 | 1.01 | 1.03 | 1.15 | 0.98 |
| P | 390M | 1.082 | 0.908 | 1.356 | 1.078 | 0.879 | 0.854 | 0.870 | 0.674 | 0.872 | 1.09 | 0.93 | 0.84 | 0.97 | 1.05 |
| P | 390N | 0.937 | 1.189 | 1.746 | 0.737 | 0.938 | 0.865 | 0.942 | 0.863 | 0.915 | 1.09 | 1.07 | 1.02 | 1.61 | 1.48 |
| P | 390R | 0.944 | 0.900 | -0.346 | 0.798 | 0.951 | 0.939 | 0.998 | 1.083 | 0.985 | 0.98 | 1.04 | 1.00 | 1.05 | 1.36 |
| P | 390S | 0.960 | 0.958 | 1.164 | 0.853 | 1.008 | 0.956 | 0.980 | 1.068 | 0.986 | 1.04 | 1.09 | 1.10 | 0.88 | 0.91 |
| P | 390T | 0.849 | 1.063 | 1.654 | 0.789 | 1.118 | 1.092 | 1.097 | 1.198 | 1.111 | 0.90 | 0.99 | 1.10 | 0.82 | 0.85 |
| P | 390V | 0.837 | 1.031 | 1.757 | 0.744 | 1.136 | 1.101 | 1.099 | 1.121 | 1.092 | 1.11 | 1.07 | 1.15 | 1.26 | 1.25 |
| P | 390W | 0.732 | 1.059 | 1.829 | 0.606 | 1.259 | 1.176 | 1.165 | 1.065 | 1.124 | 1.04 | 0.98 | 1.22 | 1.32 | 1.36 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| P | 390Y | 0.904 | 0.933 | 1.088 | 0.846 | 1.080 | 1.034 | 0.971 | 0.722 | 0.947 | 1.09 | 0.99 | 1.17 | 0.97 | 0.94 |
| R | 393A | 0.867 | 1.101 | 1.245 | 0.818 | 1.052 | 0.991 | 1.013 | 0.816 | 0.995 | 1.07 | 0.92 | 0.87 | 1.51 | 1.00 |
| R | 393C | 0.888 | 1.025 | 1.919 | 0.673 | 1.001 | 0.912 | 1.008 | 0.895 | 1.000 | 1.20 | 1.15 | 1.19 | 0.86 | 1.04 |
| R | 393D | 0.785 | 1.152 | 0.815 | 0.604 | 1.096 | 1.071 | 1.149 | 1.154 | 1.166 | 1.02 | 1.02 | 1.01 | 0.90 | 0.94 |
| R | 393F | 0.852 | 1.263 | 1.569 | 0.721 | 1.074 | 1.055 | 1.171 | 1.201 | 1.150 | 0.99 | 1.09 | 1.01 | 0.95 | 0.72 |
| R | 393G | 0.989 | 0.892 | 2.222 | 0.975 | 0.924 | 0.913 | 0.886 | 0.972 | 0.911 | 1.19 | 1.21 | 2.51 | 1.10 | 0.87 |
| R | 393H | 0.910 | 0.993 | 0.831 | 0.832 | 1.049 | 1.039 | 1.049 | 1.045 | 1.029 | 1.04 | 1.07 | 1.15 | 0.56 | 0.74 |
| R | 393I | 0.753 | 1.156 | 2.531 | 0.715 | 1.258 | 1.258 | 1.315 | 1.260 | 1.277 | 1.04 | 1.03 | 1.00 | 1.05 | 0.97 |
| R | 393L | 0.830 | 1.083 | 3.053 | 0.848 | 1.208 | 1.279 | 1.226 | 0.915 | 1.205 | 1.12 | 1.04 | 1.23 | 1.54 | 1.29 |
| R | 393M | 0.968 | 0.942 | 0.380 | 0.824 | 0.898 | 0.741 | 0.748 | 0.609 | 0.817 | 0.69 | 0.91 | 0.86 | 0.83 | 0.78 |
| R | 393P | 0.884 | 1.048 | 0.050 | 0.672 | 0.970 | 0.906 | 1.014 | 0.951 | 1.000 | 1.01 | 1.00 | 0.96 | 0.61 | 0.90 |
| R | 393Q | 0.949 | 0.941 | 0.776 | 0.760 | 0.945 | 0.895 | 1.001 | 0.963 | 0.981 | 1.03 | 1.10 | 1.19 | 0.85 | 0.72 |
| R | 393S | 0.836 | 1.080 | 1.070 | 0.728 | 1.118 | 1.080 | 1.102 | 1.126 | 1.084 | 1.04 | 1.05 | 1.14 | 0.73 | 0.83 |
| R | 393T | 0.884 | 0.969 | 0.984 | 0.796 | 1.043 | 1.031 | 1.056 | 1.095 | 1.047 | 1.06 | 1.06 | 1.06 | 0.73 | 2.43 |
| R | 393V | 0.807 | 1.006 | 1.782 | 0.711 | 1.159 | 1.152 | 1.187 | 1.061 | 1.162 | 1.07 | 1.11 | 1.13 | 0.83 | 0.95 |
| R | 393W | 0.644 | 1.230 | 0.697 | 0.484 | 1.351 | 1.261 | 1.231 | 1.127 | 1.265 | 1.08 | 1.08 | 1.34 | 0.91 | 1.25 |
| R | 393Y | 0.766 | 1.107 | 1.620 | 0.770 | 1.329 | 1.359 | 1.273 | 0.897 | 1.235 | 1.12 | 1.05 | 1.04 | 0.88 | 0.96 |
| R | 395A | 1.069 | 0.945 | -0.591 | 1.150 | 0.944 | 0.945 | 0.902 | 0.688 | 0.862 | 1.00 | 0.90 | 0.88 | 0.89 | 0.84 |
| R | 395C | 1.068 | 0.965 | 0.689 | 1.042 | 0.904 | 0.936 | 0.915 | 0.902 | 0.906 | 0.99 | 0.98 | 0.84 | 0.85 | 1.02 |
| D | 395E | 0.20 | ND | ND | ND | ND | ND | 0.84 | ND | 0.38 | 0.29 | 0.28 | 13.30 | 4.28 | 3.23 |
| D | 395F | 0.987 | 1.001 | 0.674 | 0.841 | 0.959 | 0.943 | 0.960 | 1.011 | 0.942 | 0.95 | 1.05 | 1.20 | 0.80 | 1.01 |
| D | 395G | 0.950 | 1.047 | 1.338 | 0.783 | 1.001 | 0.958 | 0.976 | 1.038 | 0.949 | 1.11 | 1.17 | 1.29 | 1.11 | 1.16 |
| D | 395H | 1.037 | 0.951 | -0.121 | 0.851 | 0.917 | 0.902 | 0.920 | 0.924 | 0.854 | 1.08 | 1.10 | 1.13 | 1.00 | 1.24 |
| D | 395I | -0.081 | -10.246 | -7.578 | -0.024 | -6.102 | -3.233 | -3.462 | -3.545 | -4.190 | 1.64 | 2.02 | 0.68 | 2.02 | 2.13 |
| D | 395K | 0.980 | 0.945 | -0.263 | 0.845 | 0.984 | 0.947 | 0.933 | 0.845 | 0.892 | 1.11 | 1.07 | 0.99 | 0.97 | 1.54 |
| D | 395L | 0.962 | 0.965 | 0.737 | 0.979 | 1.079 | 1.040 | 1.063 | 0.789 | 1.025 | 1.11 | 1.00 | 0.80 | 0.84 | 1.00 |
| D | 395M | 0.979 | 1.041 | -0.476 | 1.055 | 1.056 | 1.078 | 0.988 | 0.740 | 0.959 | 0.98 | 0.90 | 0.63 | 0.64 | 0.91 |
| D | 395N | 1.030 | 0.974 | -0.279 | 0.955 | 0.917 | 0.882 | 0.850 | 0.798 | 0.864 | 0.98 | 0.98 | 0.97 | 1.00 | 1.01 |
| D | 395P | 0.97 | ND | ND | ND | ND | ND | 1.06 | ND | 1.07 | 1.03 | 1.03 | 1.03 | 0.89 | 1.10 |
| D | 395Q | 0.947 | 1.008 | -0.849 | 0.812 | 0.992 | 0.973 | 0.978 | 0.927 | 0.968 | 0.99 | 1.04 | 1.09 | 0.89 | 1.36 |
| D | 395R | 0.900 | 1.122 | -0.697 | 0.738 | 1.061 | 1.056 | 1.063 | 1.054 | 0.998 | 1.00 | 1.09 | 0.96 | 1.10 | 1.35 |
| D | 395S | 0.777 | 1.298 | 0.537 | 0.625 | 1.211 | 1.196 | 1.210 | 1.202 | 1.190 | 1.05 | 1.08 | 1.47 | 0.87 | 1.13 |
| D | 395T | 0.865 | 1.130 | 0.454 | 0.737 | 1.081 | 1.091 | 1.103 | 1.085 | 1.098 | 1.09 | 1.12 | 1.08 | 0.82 | 1.10 |
| D | 395V | 0.952 | 0.975 | -0.163 | 0.830 | 0.995 | 0.989 | 0.989 | 0.937 | 0.964 | 1.14 | 1.19 | 1.17 | 1.10 | 1.17 |
| D | 395Y | 0.906 | 1.032 | 0.163 | 0.788 | 1.065 | 1.040 | 1.054 | 0.897 | 0.996 | 1.10 | 1.07 | 1.20 | 0.80 | 1.42 |
| A | 400C | 1.049 | 0.910 | -0.594 | 1.054 | 0.997 | 1.033 | 1.014 | 0.707 | 0.943 | 1.07 | 1.04 | 1.29 | 1.05 | 1.00 |
| A | 400D | 1.009 | 1.058 | -0.964 | 0.924 | 0.873 | 0.912 | 0.866 | 0.704 | 0.848 | 0.98 | 0.92 | 1.22 | 0.70 | 0.94 |
| A | 400E | 0.838 | 1.177 | -1.739 | 0.718 | 1.080 | 1.065 | 0.990 | 0.906 | 1.015 | 0.91 | 0.91 | 1.11 | 0.57 | 0.76 |
| A | 400F | 0.941 | 1.045 | 0.605 | 0.810 | 0.969 | 0.986 | 0.968 | 0.862 | 0.953 | 0.94 | 0.98 | 1.58 | 0.92 | 1.08 |
| A | 400G | 0.949 | 1.041 | -0.996 | 0.770 | 0.977 | 0.948 | 0.933 | 0.863 | 0.914 | 1.01 | 1.06 | 1.32 | 0.75 | 1.03 |
| A | 400H | 0.607 | 1.519 | 3.278 | 0.485 | 1.386 | 1.220 | 1.189 | 1.083 | 1.167 | 1.05 | 1.13 | 1.25 | 0.72 | 0.88 |
| A | 400I | 0.981 | 0.998 | -0.444 | 0.796 | 0.954 | 0.939 | 0.928 | 0.820 | 0.887 | 1.11 | 1.11 | 1.53 | 0.70 | 1.19 |
| A | 400K | 0.839 | 1.179 | -1.133 | 0.707 | 1.122 | 1.103 | 1.047 | 0.949 | 1.062 | 1.10 | 1.02 | 1.44 | 1.07 | 0.96 |
| A | 400L | 0.989 | 0.995 | 0.360 | 0.877 | 0.983 | 0.976 | 0.965 | 0.750 | 0.915 | 1.06 | 1.11 | 1.37 | 0.56 | 1.27 |
| A | 400L | 1.085 | 0.937 | -0.714 | 1.086 | 0.954 | 1.003 | 0.972 | 0.651 | 0.933 | 1.03 | 1.05 | 0.91 | 0.94 | 1.24 |
| A | 400M | 1.344 | 0.851 | -1.222 | 1.948 | 0.850 | 0.998 | 0.884 | 0.570 | 0.882 | 1.00 | 0.84 | 0.69 | 0.65 | 0.71 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| A | 400N | 1.138 | 0.943 | −0.838 | 1.174 | 0.872 | 0.919 | 0.848 | 0.549 | 0.837 | 0.98 | 0.90 | 0.83 | 0.77 | 0.97 |
| A | 400P | 0.988 | 1.072 | −1.450 | 0.938 | 1.029 | 1.027 | 0.945 | 0.656 | 0.956 | 0.96 | 0.88 | 1.02 | 0.68 | 1.06 |
| A | 400Q | 1.098 | 0.913 | −0.813 | 1.092 | 0.945 | 0.974 | 0.921 | 0.651 | 0.909 | 0.96 | 0.89 | 0.87 | 1.02 | 1.15 |
| A | 400R | 1.080 | 1.020 | −1.104 | 1.094 | 0.955 | 0.993 | 0.920 | 0.695 | 0.912 | 1.00 | 0.94 | 1.30 | 1.07 | 1.27 |
| A | 400S | 0.790 | 1.032 | 3.068 | 0.642 | 1.149 | 1.067 | 1.015 | 1.057 | 1.023 | 1.05 | 1.02 | 1.27 | 0.90 | 0.90 |
| A | 400T | 0.874 | 1.068 | −0.218 | 0.799 | 1.062 | 1.057 | 1.021 | 0.727 | 0.983 | 1.11 | 1.05 | 1.45 | 0.87 | 1.32 |
| A | 400V | 1.055 | 0.910 | −0.388 | 1.001 | 0.996 | 0.996 | 0.953 | 0.644 | 0.917 | 1.09 | 1.01 | 1.32 | 1.02 | 0.93 |
| A | 400W | 1.102 | 0.940 | −0.259 | 1.156 | 0.944 | 0.991 | 0.921 | 0.619 | 0.877 | 1.07 | 1.02 | 1.12 | 0.93 | 0.98 |
| A | 400Y | 1.166 | 0.881 | −0.343 | 1.376 | 0.976 | 1.051 | 0.971 | 0.584 | 0.919 | 1.03 | 1.10 | 1.04 | 0.88 | 1.09 |
| G | 401A | 0.838 | 1.097 | 0.216 | 0.863 | 1.127 | 1.098 | 1.096 | 0.674 | 1.074 | 0.74 | 0.91 | 0.79 | 1.69 | 1.65 |
| G | 401C | 0.840 | 1.262 | 1.020 | 0.647 | 0.976 | 0.937 | 0.966 | 0.748 | 0.940 | 1.03 | 0.94 | 0.94 | 1.30 | 0.85 |
| G | 401D | 0.545 | 1.356 | 0.579 | 0.294 | 1.299 | 1.079 | 1.134 | 0.981 | 1.170 | 1.03 | 0.94 | 0.84 | 0.74 | 0.84 |
| G | 401E | 0.830 | 1.082 | −0.148 | 0.632 | 1.074 | 1.006 | 1.106 | 0.929 | 1.088 | 0.99 | 0.99 | 0.85 | 0.63 | 0.96 |
| G | 401F | 0.599 | 1.253 | −0.299 | 0.357 | 1.334 | 1.107 | 1.195 | 1.047 | 1.203 | 1.05 | 1.01 | 1.16 | 0.92 | 1.20 |
| G | 401H | 0.821 | 0.979 | 0.225 | 0.681 | 1.077 | 1.038 | 1.010 | 0.829 | 0.995 | 0.80 | 1.06 | 1.02 | 0.63 | 1.02 |
| G | 401I | 0.344 | 1.535 | −0.584 | 0.179 | 2.065 | 1.573 | 1.545 | 1.237 | 1.569 | 1.13 | 1.02 | 1.18 | 0.82 | 0.86 |
| G | 401K | 0.866 | 0.885 | 0.874 | 0.672 | 1.054 | 0.973 | 0.950 | 0.716 | 0.921 | 1.15 | 1.07 | 1.45 | 1.05 | 1.12 |
| G | 401L | 0.738 | 0.959 | 0.021 | 0.684 | 1.322 | 1.089 | 1.208 | 0.952 | 1.188 | 1.08 | 1.02 | 1.12 | 0.95 | 1.14 |
| G | 401M | 1.014 | 0.871 | 0.031 | 1.040 | 0.902 | 0.924 | 0.934 | 0.791 | 0.892 | 1.08 | 1.02 | 0.82 | 1.33 | 1.59 |
| G | 401N | 0.905 | 1.111 | 0.200 | 1.374 | 1.118 | 1.211 | 1.043 | 0.528 | 1.019 | 0.96 | 0.80 | 0.92 | 0.76 | 1.05 |
| G | 401P | 1.199 | 0.880 | −4.034 | 0.140 | 0.903 | 0.985 | 0.999 | 0.722 | 0.988 | 1.01 | 0.91 | 0.76 | 0.94 | 1.23 |
| G | 401Q | 0.309 | 2.074 | 0.571 | 0.533 | 2.060 | 1.381 | 1.360 | 0.975 | 1.449 | 0.70 | 0.84 | 1.08 | 0.56 | 0.72 |
| G | 401R | 0.721 | 1.169 | −0.352 | 0.672 | 1.219 | 1.089 | 1.080 | 0.952 | 1.109 | 1.06 | 0.98 | 1.08 | 0.85 | 1.02 |
| G | 401S | 0.753 | 1.144 | 0.919 | 0.641 | 1.289 | 1.156 | 1.114 | 0.761 | 1.080 | 1.06 | 1.03 | 0.95 | 1.33 | 1.59 |
| G | 401T | 0.773 | 1.048 | 0.885 | 0.697 | 1.305 | 1.235 | 1.178 | 0.761 | 1.149 | 1.05 | 0.96 | 1.21 | 0.88 | 0.68 |
| G | 401W | 0.560 | 1.272 | 0.943 | 0.379 | 1.560 | 1.316 | 1.221 | 0.804 | 1.274 | 1.07 | 0.97 | 1.08 | 1.06 | 1.02 |
| G | 401Y | 0.694 | 1.146 | 0.792 | 0.499 | 1.218 | 1.057 | 1.037 | 1.013 | 1.039 | 1.12 | 0.93 | 1.16 | 0.94 | 1.13 |
| G | 402A | 0.815 | 1.024 | 1.289 | 0.776 | 1.256 | 1.226 | 1.103 | 0.691 | 1.085 | 0.75 | 0.94 | 1.24 | 0.87 | 1.01 |
| G | 402C | 1.035 | 1.105 | 1.444 | 1.212 | 0.946 | 1.007 | 0.964 | 0.742 | 0.946 | 1.06 | 0.99 | 1.08 | 1.04 | 1.30 |
| G | 402D | 0.902 | 0.962 | 2.689 | 0.868 | 1.013 | 1.010 | 1.016 | 0.951 | 0.928 | 0.89 | 0.79 | 0.72 | 0.80 | 0.73 |
| S | 402E | 0.997 | 0.903 | 0.674 | 0.922 | 0.896 | 0.882 | 0.893 | 0.960 | 0.943 | 0.93 | 0.88 | 0.98 | 0.80 | 0.97 |
| S | 402F | 1.025 | 0.955 | 1.491 | 0.974 | 0.993 | 1.038 | 1.028 | 0.697 | 0.990 | 0.94 | 0.95 | 1.16 | 1.16 | 0.63 |
| S | 402G | 0.844 | 1.237 | 1.236 | 0.785 | 1.117 | 1.133 | 1.172 | 1.247 | 1.171 | 1.02 | 1.02 | 0.94 | 0.78 | 0.89 |
| S | 402I | 0.806 | 1.273 | 0.825 | 0.734 | 1.183 | 1.173 | 1.176 | 1.286 | 1.219 | 1.01 | 1.04 | 0.77 | 1.15 | 1.02 |
| S | 402K | 0.839 | 0.906 | 2.578 | 0.723 | 1.125 | 1.112 | 1.142 | 1.186 | 1.109 | 0.93 | 0.90 | 1.03 | 0.86 | 0.82 |
| S | 402L | 0.802 | 1.070 | 0.082 | 0.709 | 1.196 | 1.211 | 1.210 | 1.113 | 1.203 | 1.00 | 0.92 | 1.10 | 0.60 | 1.14 |
| S | 402M | 0.891 | 1.044 | 1.622 | 0.914 | 1.119 | 1.180 | 1.135 | 0.834 | 1.155 | 0.95 | 0.83 | 0.92 | 0.90 | 1.27 |
| S | 402P | 0.950 | 1.071 | 0.065 | 1.036 | 1.005 | 1.054 | 1.011 | 0.705 | 0.941 | 0.94 | 0.80 | 1.05 | 1.14 | 0.89 |
| S | 402Q | 0.828 | 0.875 | 1.441 | 0.696 | 1.050 | 1.000 | 1.017 | 1.002 | 0.988 | 0.89 | 0.74 | 0.80 | 0.76 | 0.82 |
| S | 402R | 0.957 | 0.954 | 1.481 | 0.896 | 0.979 | 0.994 | 1.008 | 0.994 | 1.004 | 0.91 | 0.87 | 1.05 | 0.63 | 0.56 |
| S | 402T | 0.946 | 0.920 | 1.686 | 0.790 | 0.946 | 0.946 | 0.946 | 0.978 | 0.925 | 0.94 | 0.91 | 0.85 | 0.58 | 0.76 |
| S | 402V | 0.810 | 1.111 | 0.362 | 0.722 | 1.167 | 1.153 | 1.170 | 1.196 | 1.179 | 0.99 | 0.94 | 0.97 | 0.90 | 0.97 |
| S | 402W | 0.783 | 0.965 | −0.495 | 0.658 | 1.184 | 1.167 | 1.201 | 1.166 | 1.160 | 1.06 | 0.96 | 1.03 | 0.57 | 0.62 |
| S | 402Y | 0.759 | 1.109 | −0.949 | 0.624 | 1.210 | 1.195 | 1.206 | 1.075 | 1.177 | 0.90 | 0.78 | 1.04 | 0.77 | 1.03 |
| S | 402Y | 1.115 | 0.875 | 2.060 | 1.286 | 0.948 | 1.038 | 1.044 | 0.791 | 1.002 | 0.87 | 0.72 | 0.97 | 0.62 | 0.73 |
| N | 406D | 1.009 | 1.059 | −1.390 | 1.064 | 0.992 | 1.053 | 1.054 | 0.954 | 1.022 | 0.97 | 0.97 | 0.83 | 0.79 | 0.75 |
| N | | | | | | | | | | | | | | 0.96 | 0.63 |

TABLE 5-continued

Average performance indices of AmyE truncated variants for the properties tested

| Wildtype amino acid | Variant | Expression | Peak Viscosity | Final Viscosity | Iodine | Reducing Ends | Glucose | DP7 pH 5.8 | DP7 pH 5.8 heated | DP7 pH 4 | DP3 | DP3 HS | corn flour 30 min | Cleaning pH 8 | Cleaning pH 10 |
|---|---|---|---|---|---|---|---|---|---|---|---|---|---|---|---|
| N | 406F | 0.801 | 1.075 | -1.444 | 0.662 | 1.149 | 1.103 | 1.103 | 0.990 | 1.075 | 1.02 | 1.05 | 0.89 | 1.02 | 0.76 |
| N | 406L | 0.851 | 0.814 | -2.719 | 0.747 | 1.188 | 1.164 | 1.130 | 0.732 | 1.084 | 1.11 | 1.10 | 1.11 | 1.06 | 1.24 |
| N | 406T | 0.812 | 1.044 | -1.129 | 0.715 | 1.243 | 1.217 | 1.202 | 0.881 | 1.167 | 1.05 | 1.00 | 1.08 | 0.92 | 0.82 |
| N | 406Y | 0.722 | 0.330 | -1.620 | 0.391 | 1.113 | 0.750 | 0.685 | 0.491 | 0.735 | 0.75 | 0.75 | 0.72 | 0.75 | 0.79 |

Based on the relative performance data of AmyE variants for the properties described in Tables 2, 4 and 5, AmyE full-length and truncated positions were classified as follows:

Fully restrictive positions: no neutral mutations for any property tested

Non-fully restrictive positions: at least one neutral mutation for one of the properties tested Non-restrictive positions: ≥20% neutral mutations for at least one property Table 6 shows the non-fully restrictive positions and the identity of the wild-type amino acid residue at each position in the in the truncated AmyE variants, along with the % neutral mutations for each property. All of the positions listed may be mutated to alter performance in the desired manner for any of the properties tested. Table 7 shows the non-fully restrictive positions and the wild-type amino acid residues at each position in the full-length AmyE variants, with the % neutral mutations for each property. Again, all of the positions listed may be mutated to alter performance in the desired manner for any of the properties tested.

TABLE 6

Non-fully restrictive positions in truncated AmyE

| POS | WT AA | cornflour Pi % > 0.5 ss1 | DP3 HS Pi % > 0.5 ss1 | Clean pH 8 Pi % > 0.5 ss1 | Clean pH 10 Pi % > 0.5 ss1 | Bradford PI > 0.5% ss2 TRUNC | Visc Peak PI > 0.5% ss2 TRUNC | PAH BAH PI > 0.5% ss2 TRUNC | Glucose PI > 0.5% ss2 TRUNC | DP7 Unstressed PI > 0.5% ss2 TRUNC | DP7 pH 4 PI > 0.5% ss2 TRUNC | THE R PI > 0.5% ss2 TRUNC |
|---|---|---|---|---|---|---|---|---|---|---|---|---|
| 1 | L | 100% | 100% | 100% | 100% | 100% | 100% | 100% | 100% | 100% | 100% | 100% |
| 2 | T | 100% | 89% | 100% | 100% | 84% | 100% | 100% | 100% | 100% | 100% | 100% |
| 3 | A | 100% | 100% | 89% | 100% | 79% | 95% | 95% | 95% | 95% | 95% | 95% |
| 4 | P | 94% | 88% | 94% | 100% | 89% | 89% | 89% | 89% | 89% | 89% | 89% |
| 5 | S | 93% | 93% | 93% | 86% | 73% | 100% | 87% | 87% | 87% | 87% | 87% |
| 8 | S | 100% | 100% | 100% | 100% | 89% | 100% | 100% | 100% | 100% | 100% | 100% |
| 18 | S | 100% | 100% | 73% | 82% | 31% | 56% | 56% | 56% | 56% | 50% | 56% |
| 20 | N | 100% | 100% | 100% | 100% | 89% | 100% | 100% | 100% | 100% | 100% | 100% |
| 23 | K | 100% | 100% | 100% | 94% | 83% | 89% | 89% | 89% | 89% | 89% | 89% |
| 24 | H | 100% | 100% | 100% | 93% | 85% | 100% | 100% | 100% | 100% | 100% | 100% |
| 25 | N | 100% | 100% | 100% | 100% | 75% | 100% | 100% | 100% | 100% | 100% | 100% |
| 27 | K | 100% | 100% | 100% | 94% | 94% | 100% | 100% | 100% | 100% | 100% | 100% |
| 28 | D | 100% | 100% | 94% | 100% | 94% | 100% | 100% | 100% | 100% | 100% | 100% |
| 30 | H | 100% | 89% | 100% | 100% | 83% | 94% | 94% | 94% | 94% | 94% | 94% |
| 35 | T | 100% | 100% | 100% | 100% | 81% | 100% | 100% | 100% | 100% | 100% | 100% |
| 44 | Q | 100% | 100% | 100% | 100% | 68% | 100% | 100% | 100% | 100% | 100% | 100% |
| 45 | V | 100% | 69% | 100% | 46% | 22% | 72% | 72% | 72% | 72% | 72% | 61% |
| 47 | E | 100% | 100% | 100% | 100% | 73% | 100% | 100% | 100% | 100% | 100% | 100% |
| 49 | N | 94% | 100% | 100% | 82% | 94% | 100% | 100% | 100% | 100% | 100% | 100% |
| 50 | Q | 100% | 100% | 94% | 100% | 94% | 100% | 100% | 100% | 100% | 100% | 100% |
| 51 | G | 89% | 94% | 100% | 94% | 78% | 100% | 100% | 100% | 100% | 94% | 89% |
| 52 | D | 100% | 79% | 95% | 95% | 84% | 100% | 100% | 100% | 100% | 89% | 100% |
| 54 | S | 100% | 94% | 94% | 94% | 88% | 100% | 100% | 100% | 100% | 94% | 100% |
| 56 | S | 100% | 100% | 100% | 100% | 100% | 100% | 100% | 100% | 100% | 100% | 100% |
| 59 | Y | 50% | 81% | 100% | 19% | 82% | 94% | 94% | 65% | 35% | 41% | 94% |
| 68 | Q | 100% | 100% | 100% | 94% | 83% | 94% | 94% | 94% | 89% | 89% | 94% |
| 73 | Y | 57% | 64% | 93% | 86% | 11% | 50% | 44% | 44% | 44% | 22% | 39% |
| 76 | T | 100% | 100% | 86% | 71% | 79% | 100% | 100% | 100% | 100% | 100% | 100% |
| 78 | Q | 100% | 100% | 100% | 100% | 94% | 100% | 100% | 94% | 94% | 94% | 94% |
| 85 | A | 100% | 100% | 100% | 100% | 88% | 88% | 88% | 88% | 88% | 88% | 88% |
| 88 | E | 100% | 94% | 94% | 89% | 61% | 100% | 100% | 100% | 100% | 100% | 100% |
| 89 | E | 100% | 100% | 100% | 100% | 95% | 100% | 100% | 100% | 100% | 100% | 100% |
| 90 | Y | 100% | 100% | 100% | 100% | 76% | 88% | 88% | 88% | 88% | 88% | 88% |
| 91 | G | 76% | 94% | 82% | 82% | 39% | 78% | 78% | 78% | 78% | 67% | 78% |
| 106 | S | 59% | 29% | 100% | 76% | 5% | 63% | 63% | 63% | 63% | 53% | 37% |
| 107 | Y | 83% | 67% | 100% | 89% | 61% | 100% | 100% | 100% | 100% | 100% | 78% |
| 108 | A | 100% | 100% | 100% | 100% | 94% | 94% | 94% | 94% | 94% | 94% | 94% |
| 109 | A | 100% | 94% | 100% | 83% | 83% | 100% | 100% | 100% | 100% | 100% | 94% |
| 112 | N | 100% | 89% | 100% | 100% | 95% | 100% | 100% | 100% | 100% | 100% | 100% |
| 115 | K | 82% | 76% | 88% | 65% | 32% | 84% | 84% | 84% | 84% | 84% | 84% |
| 116 | S | 100% | 100% | 100% | 100% | 94% | 94% | 94% | 94% | 94% | 94% | 94% |
| 118 | P | 89% | 100% | 100% | 95% | 83% | 94% | 94% | 94% | 94% | 94% | 94% |
| 119 | N | 100% | 80% | 100% | 93% | 67% | 94% | 83% | 83% | 83% | 83% | 83% |
| 124 | N | 0% | 0% | 93% | 64% | 6% | 47% | 47% | 47% | 47% | 24% | 0% |
| 125 | T | 47% | 35% | 94% | 88% | 83% | 100% | 100% | 100% | 100% | 100% | 56% |
| 126 | Q | 63% | 81% | 100% | 69% | 100% | 100% | 100% | 100% | 94% | 81% | 75% |
| 127 | I | 0% | 0% | 100% | 0% | 0% | 21% | 21% | 11% | 16% | 0% | 0% |
| 131 | S | 88% | 88% | 100% | 94% | 94% | 88% | 94% | 94% | 94% | 94% | 94% |
| 132 | D | 13% | 7% | 87% | 33% | 21% | 53% | 53% | 53% | 53% | 42% | 5% |
| 134 | W | 0% | 0% | 92% | 92% | 38% | 50% | 56% | 56% | 50% | 50% | 19% |
| 142 | L | 43% | 86% | 57% | 14% | 76% | 82% | 82% | 41% | 12% | 12% | 71% |
| 143 | G | 0% | 0% | 8% | 8% | 7% | 73% | 73% | 67% | 67% | 0% | 0% |
| 152 | T | 100% | 95% | 100% | 100% | 100% | 100% | 100% | 100% | 100% | 100% | 100% |
| 153 | Q | 95% | 95% | 95% | 95% | 95% | 100% | 100% | 95% | 95% | 95% | 95% |
| 156 | S | 100% | 94% | 100% | 89% | 94% | 94% | 94% | 94% | 94% | 94% | 94% |
| 160 | R | 100% | 100% | 94% | 100% | 89% | 95% | 95% | 95% | 95% | 95% | 95% |
| 163 | D | 100% | 100% | 100% | 100% | 94% | 94% | 94% | 94% | 94% | 94% | 94% |

TABLE 6-continued

Non-fully restrictive positions in truncated AmyE

| POS | WT AA | cornflour Pi % > 0.5 ss1 | DP3 HS Pi % > 0.5 ss1 | Clean pH 8 Pi % > 0.5 ss1 | Clean pH 10 Pi % > 0.5 ss1 | Bradford PI > 0.5% ss2 TRUNC | Visc Peak PI > 0.5% ss2 TRUNC | PAH BAH PI > 0.5% ss2 TRUNC | Glucose PI > 0.5% ss2 TRUNC | DP7 Unstressed PI > 0.5% ss2 TRUNC | DP7 pH 4 PI > 0.5% ss2 TRUNC | THE R PI > 0.5% ss2 TRUNC |
|---|---|---|---|---|---|---|---|---|---|---|---|---|
| 166 | L | 100% | 100% | 100% | 94% | 25% | 94% | 94% | 94% | 94% | 88% | 94% |
| 167 | N | 100% | 100% | 100% | 100% | 94% | 94% | 94% | 94% | 89% | 89% | 89% |
| 184 | P | 6% | 0% | 89% | 33% | 0% | 37% | 37% | 37% | 37% | 26% | 11% |
| 185 | D | 20% | 0% | 100% | 40% | 0% | 17% | 17% | 17% | 17% | 6% | 0% |
| 187 | G | 5% | 5% | 95% | 95% | 63% | 100% | 100% | 100% | 100% | 100% | 5% |
| 188 | S | 50% | 56% | 100% | 94% | 94% | 94% | 94% | 94% | 94% | 94% | 53% |
| 190 | G | 58% | 8% | 100% | 75% | 28% | 67% | 67% | 61% | 61% | 61% | 11% |
| 192 | Q | 0% | 0% | 0% | 0% | 86% | 93% | 93% | 93% | 93% | 93% | 93% |
| 195 | P | 47% | 24% | 88% | 94% | 50% | 100% | 100% | 100% | 100% | 100% | 78% |
| 199 | N | 94% | 100% | 81% | 63% | 63% | 100% | 100% | 94% | 94% | 94% | 100% |
| 200 | T | 89% | 68% | 89% | 84% | 16% | 84% | 84% | 84% | 84% | 79% | 84% |
| 201 | S | 100% | 100% | 100% | 100% | 89% | 100% | 100% | 100% | 100% | 100% | 100% |
| 202 | A | 93% | 93% | 87% | 87% | 5% | 42% | 37% | 37% | 37% | 37% | 37% |
| 203 | E | 100% | 100% | 100% | 100% | 44% | 94% | 94% | 94% | 94% | 94% | 94% |
| 212 | D | 0% | 0% | 45% | 36% | 17% | 50% | 50% | 50% | 50% | 6% | 17% |
| 213 | S | 82% | 94% | 82% | 88% | 100% | 100% | 100% | 100% | 100% | 100% | 100% |
| 214 | A | 44% | 56% | 100% | 88% | 81% | 94% | 94% | 94% | 94% | 94% | 50% |
| 218 | A | 100% | 89% | 100% | 100% | 100% | 100% | 100% | 100% | 100% | 100% | 100% |
| 219 | A | 29% | 29% | 94% | 35% | 44% | 89% | 89% | 89% | 89% | 89% | 44% |
| 221 | A | 77% | 54% | 85% | 77% | 17% | 67% | 61% | 56% | 56% | 56% | 39% |
| 222 | N | 0% | 0% | 0% | 0% | 92% | 100% | 100% | 100% | 100% | 100% | 92% |
| 223 | Y | 0% | 0% | 0% | 0% | 21% | 42% | 42% | 42% | 42% | 42% | 42% |
| 233 | H | 95% | 95% | 100% | 42% | 89% | 95% | 95% | 95% | 95% | 95% | 95% |
| 234 | S | 100% | 94% | 100% | 100% | 94% | 94% | 94% | 94% | 94% | 94% | 94% |
| 238 | A | 100% | 100% | 94% | 100% | 32% | 95% | 95% | 95% | 95% | 89% | 89% |
| 240 | K | 100% | 100% | 100% | 94% | 89% | 95% | 95% | 89% | 89% | 89% | 95% |
| 241 | N | 100% | 100% | 100% | 100% | 94% | 100% | 100% | 94% | 94% | 94% | 100% |
| 243 | N | 100% | 100% | 100% | 100% | 95% | 95% | 95% | 95% | 95% | 95% | 95% |
| 245 | G | 100% | 100% | 93% | 100% | 81% | 94% | 94% | 94% | 94% | 94% | 94% |
| 247 | S | 87% | 87% | 87% | 87% | 61% | 72% | 67% | 61% | 61% | 61% | 67% |
| 248 | N | 0% | 0% | 0% | 0% | 94% | 94% | 94% | 94% | 94% | 94% | 94% |
| 250 | S | 94% | 94% | 94% | 100% | 94% | 94% | 94% | 94% | 94% | 94% | 94% |
| 251 | H | 100% | 100% | 100% | 100% | 93% | 100% | 100% | 100% | 100% | 100% | 100% |
| 252 | Y | 76% | 47% | 82% | 94% | 12% | 47% | 47% | 47% | 47% | 47% | 24% |
| 253 | A | 100% | 88% | 100% | 94% | 94% | 100% | 100% | 100% | 100% | 94% | 100% |
| 254 | S | 79% | 57% | 100% | 79% | 50% | 93% | 93% | 86% | 86% | 64% | 50% |
| 255 | D | 0% | 0% | 0% | 0% | 78% | 94% | 94% | 94% | 94% | 94% | 17% |
| 257 | S | 0% | 0% | 0% | 0% | 76% | 100% | 100% | 100% | 100% | 100% | 100% |
| 259 | D | 93% | 100% | 93% | 87% | 53% | 100% | 100% | 100% | 100% | 100% | 100% |
| 260 | K | 100% | 100% | 83% | 94% | 37% | 79% | 79% | 79% | 79% | 79% | 79% |
| 274 | D | 94% | 100% | 100% | 100% | 100% | 100% | 100% | 100% | 100% | 0% | 100% |
| 275 | D | 95% | 100% | 100% | 89% | 100% | 100% | 100% | 74% | 100% | 11% | 100% |
| 276 | E | 95% | 89% | 95% | 79% | 89% | 95% | 89% | 84% | 89% | 37% | 89% |
| 277 | E | 95% | 89% | 100% | 79% | 100% | 100% | 100% | 84% | 100% | 32% | 100% |
| 282 | S | 100% | 100% | 100% | 100% | 84% | 100% | 100% | 100% | 100% | 84% | 100% |
| 283 | D | 88% | 94% | 88% | 94% | 38% | 100% | 100% | 94% | 94% | 38% | 94% |
| 284 | D | 95% | 95% | 95% | 100% | 95% | 100% | 100% | 95% | 95% | 95% | 100% |
| 287 | R | 89% | 100% | 95% | 100% | 59% | 88% | 88% | 82% | 82% | 82% | 88% |
| 307 | P | 80% | 100% | 100% | 100% | 0% | 16% | 16% | 16% | 16% | 5% | 16% |
| 308 | E | 100% | 100% | 100% | 100% | 95% | 100% | 100% | 100% | 100% | 89% | 100% |
| 309 | G | 81% | 94% | 63% | 100% | 53% | 76% | 76% | 76% | 76% | 53% | 76% |
| 310 | G | 31% | 94% | 88% | 81% | 7% | 67% | 67% | 67% | 67% | 0% | 60% |
| 311 | G | 95% | 95% | 84% | 95% | 11% | 83% | 83% | 83% | 83% | 0% | 83% |
| 312 | N | 95% | 100% | 100% | 89% | 94% | 100% | 94% | 94% | 94% | 94% | 94% |
| 313 | G | 84% | 100% | 100% | 100% | 72% | 100% | 100% | 100% | 100% | 83% | 100% |
| 314 | V | 93% | 93% | 100% | 93% | 93% | 100% | 100% | 93% | 93% | 93% | 87% |
| 317 | P | 100% | 100% | 100% | 89% | 94% | 100% | 100% | 100% | 100% | 28% | 100% |
| 318 | G | 93% | 93% | 87% | 93% | 87% | 93% | 93% | 93% | 93% | 93% | 93% |
| 319 | K | 100% | 100% | 100% | 100% | 90% | 100% | 90% | 90% | 90% | 90% | 90% |
| 320 | S | 100% | 100% | 100% | 100% | 44% | 94% | 94% | 94% | 94% | 44% | 94% |
| 321 | Q | 100% | 106% | 106% | 106% | 94% | 100% | 100% | 100% | 100% | 94% | 100% |
| 323 | G | 83% | 67% | 33% | 100% | 0% | 28% | 17% | 17% | 17% | 6% | 17% |
| 324 | D | 100% | 100% | 95% | 100% | 74% | 100% | 100% | 100% | 100% | 68% | 100% |
| 325 | R | 88% | 100% | 88% | 100% | 69% | 94% | 94% | 94% | 94% | 81% | 94% |
| 327 | S | 92% | 83% | 58% | 92% | 43% | 57% | 57% | 57% | 57% | 21% | 57% |
| 328 | A | 100% | 100% | 100% | 100% | 100% | 100% | 100% | 100% | 100% | 100% | 100% |
| 331 | E | 100% | 100% | 100% | 100% | 94% | 94% | 94% | 94% | 94% | 94% | 94% |
| 333 | Q | 100% | 100% | 100% | 100% | 100% | 100% | 100% | 94% | 100% | 100% | 100% |
| 344 | V | 100% | 100% | 100% | 100% | 94% | 94% | 94% | 94% | 94% | 94% | 94% |
| 346 | A | 107% | 107% | 107% | 107% | 94% | 100% | 100% | 100% | 100% | 100% | 100% |
| 347 | G | 100% | 100% | 100% | 100% | 100% | 100% | 100% | 100% | 100% | 100% | 100% |

TABLE 6-continued

Non-fully restrictive positions in truncated AmyE

| POS | WT AA | cornflour Pi % > 0.5 ss1 | DP3 HS Pi % > 0.5 ss1 | Clean pH 8 Pi % > 0.5 ss1 | Clean pH 10 Pi % > 0.5 ss1 | Bradford PI > 0.5% ss2 TRUNC | Visc Peak PI > 0.5% ss2 TRUNC | PAH BAH PI > 0.5% ss2 TRUNC | Glucose PI > 0.5% ss2 TRUNC | DP7 Unstressed PI > 0.5% ss2 TRUNC | DP7 pH 4 PI > 0.5% ss2 TRUNC | THE R PI > 0.5% ss2 TRUNC |
|---|---|---|---|---|---|---|---|---|---|---|---|---|
| 349 | P | 100% | 100% | 100% | 100% | 89% | 94% | 94% | 94% | 94% | 94% | 94% |
| 357 | G | 100% | 100% | 100% | 100% | 95% | 100% | 100% | 100% | 100% | 100% | 100% |
| 358 | N | 100% | 100% | 100% | 100% | 89% | 95% | 95% | 95% | 95% | 95% | 95% |
| 359 | N | 100% | 100% | 100% | 100% | 95% | 100% | 100% | 100% | 100% | 100% | 100% |
| 367 | G | 100% | 100% | 100% | 100% | 72% | 100% | 100% | 100% | 100% | 100% | 100% |
| 368 | S | 100% | 100% | 100% | 100% | 87% | 100% | 100% | 100% | 100% | 100% | 100% |
| 369 | H | 100% | 100% | 100% | 100% | 95% | 100% | 100% | 100% | 100% | 100% | 100% |
| 378 | S | 100% | 100% | 100% | 100% | 89% | 95% | 95% | 95% | 95% | 95% | 95% |
| 380 | S | 100% | 100% | 100% | 100% | 100% | 100% | 100% | 100% | 100% | 100% | 100% |
| 382 | S | 100% | 100% | 100% | 100% | 100% | 100% | 100% | 100% | 100% | 100% | 100% |
| 385 | T | 100% | 100% | 100% | 100% | 100% | 100% | 100% | 100% | 100% | 100% | 95% |
| 386 | A | 100% | 100% | 100% | 93% | 100% | 100% | 100% | 100% | 100% | 100% | 100% |
| 388 | K | 100% | 100% | 100% | 100% | 100% | 100% | 100% | 100% | 100% | 100% | 100% |
| 390 | P | 100% | 100% | 100% | 100% | 100% | 100% | 100% | 100% | 100% | 100% | 100% |
| 393 | R | 100% | 100% | 100% | 100% | 100% | 100% | 100% | 100% | 100% | 100% | 100% |
| 395 | D | 100% | 95% | 100% | 100% | 94% | 94% | 94% | 94% | 94% | 94% | 94% |
| 400 | A | 100% | 100% | 100% | 100% | 100% | 100% | 100% | 100% | 100% | 100% | 100% |
| 401 | G | 100% | 100% | 100% | 100% | 89% | 100% | 100% | 100% | 100% | 100% | 74% |
| 402 | S | 100% | 100% | 100% | 100% | 100% | 100% | 100% | 100% | 100% | 100% | 100% |
| 406 | N | 100% | 100% | 100% | 100% | 100% | 100% | 100% | 100% | 100% | 100% | 100% |

TABLE 7

Non-fully restrictive positions in full-length AmyE

| POS | WT AA | Bradford PI > 0.5% ss2 FULL | Visc Peak PI > 0.5% ss2 FULL | PAH BAH PI > 0.5% ss2 FULL | Glucose PI > 0.5% ss2 FULL | DP7 Unstressed PI > 0.5% ss2 FULL | DP7 pH 4 PI > 0.5% ss2 FULL | Cleaning 8 PI > 0.5% ss2 FULL | Cleaning 10 PI > 0.5% ss2 FULL | THE R PI > 0.5% ss2 FULL |
|---|---|---|---|---|---|---|---|---|---|---|
| 6 | I | 88% | 100% | 100% | 100% | 100% | 100% | 100% | 100% | 100% |
| 7 | K | 44% | 100% | 100% | 100% | 100% | 100% | 100% | 100% | 100% |
| 9 | G | 82% | 100% | 100% | 100% | 100% | 100% | 100% | 100% | 100% |
| 10 | T | 47% | 60% | 60% | 60% | 60% | 60% | 60% | 60% | 60% |
| 11 | I | 25% | 56% | 56% | 50% | 56% | 50% | 56% | 56% | 56% |
| 12 | L | 12% | 18% | 18% | 18% | 18% | 18% | 18% | 18% | 18% |
| 13 | H | 18% | 82% | 47% | 6% | 6% | 6% | 82% | 59% | 76% |
| 14 | A | 22% | 44% | 33% | 28% | 33% | 28% | 44% | 44% | 44% |
| 15 | W | 6% | 13% | 13% | 6% | 6% | 0% | 13% | 13% | 13% |
| 16 | N | 11% | 72% | 72% | 50% | 67% | 0% | 72% | 67% | 72% |
| 17 | W | 0% | 35% | 24% | 6% | 18% | 6% | 35% | 29% | 35% |
| 19 | F | 11% | 50% | 50% | 44% | 50% | 44% | 50% | 50% | 50% |
| 21 | T | 47% | 82% | 82% | 82% | 82% | 76% | 82% | 82% | 76% |
| 22 | L | 25% | 38% | 38% | 38% | 38% | 38% | 38% | 38% | 38% |
| 26 | M | 13% | 31% | 31% | 31% | 31% | 31% | 31% | 31% | 31% |
| 27 | K | 93% | 100% | 100% | 100% | 100% | 100% | 100% | 100% | 100% |
| 29 | I | 19% | 44% | 44% | 38% | 38% | 19% | 44% | 44% | 44% |
| 30 | H | 88% | 100% | 100% | 94% | 100% | 94% | 100% | 100% | 100% |
| 31 | D | 83% | 94% | 94% | 94% | 94% | 94% | 94% | 94% | 94% |
| 32 | A | 12% | 71% | 71% | 53% | 71% | 47% | 71% | 71% | 71% |
| 33 | G | 35% | 94% | 82% | 35% | 65% | 41% | 94% | 88% | 94% |
| 34 | Y | 11% | 26% | 16% | 11% | 16% | 11% | 26% | 21% | 26% |
| 36 | A | 44% | 83% | 83% | 83% | 83% | 83% | 83% | 83% | 83% |
| 37 | I | 13% | 25% | 19% | 19% | 19% | 19% | 25% | 25% | 25% |
| 38 | Q | 0% | 59% | 35% | 0% | 29% | 0% | 59% | 47% | 59% |
| 39 | T | 24% | 53% | 53% | 41% | 47% | 24% | 53% | 47% | 47% |
| 40 | S | 0% | 53% | 47% | 18% | 41% | 6% | 53% | 53% | 41% |
| 41 | P | 0% | 37% | 32% | 0% | 26% | 0% | 37% | 37% | 37% |
| 42 | I | 6% | 28% | 28% | 17% | 28% | 28% | 28% | 28% | 28% |
| 43 | N | 29% | 53% | 53% | 53% | 53% | 53% | 53% | 53% | 53% |
| 45 | V | 0% | 73% | 73% | 67% | 73% | 60% | 73% | 73% | 67% |
| 46 | K | 44% | 94% | 94% | 94% | 94% | 94% | 94% | 94% | 72% |
| 48 | G | 44% | 94% | 94% | 88% | 88% | 0% | 94% | 94% | 56% |
| 52 | D | 89% | 100% | 100% | 94% | 100% | 89% | 100% | 100% | 100% |
| 53 | K | 72% | 94% | 94% | 94% | 94% | 94% | 94% | 94% | 94% |
| 55 | M | 60% | 93% | 93% | 87% | 93% | 47% | 93% | 93% | 93% |

TABLE 7-continued

Non-fully restrictive positions in full-length AmyE

| POS | WT AA | Bradford PI > 0.5% ss2 FULL | Visc Peak PI > 0.5% ss2 FULL | PAH BAH PI > 0.5% ss2 FULL | Glucose PI > 0.5% ss2 FULL | DP7 Unstressed PI > 0.5% ss2 FULL | DP7 pH 4 PI > 0.5% ss2 FULL | Cleaning 8 PI > 0.5% ss2 FULL | Cleaning 10 PI > 0.5% ss2 FULL | THE R PI > 0.5% ss2 FULL |
|---|---|---|---|---|---|---|---|---|---|---|
| 57 | N | 47% | 100% | 100% | 94% | 100% | 41% | 100% | 100% | 94% |
| 58 | W | 6% | 17% | 17% | 0% | 0% | 0% | 17% | 6% | 17% |
| 60 | W | 20% | 93% | 93% | 27% | 7% | 0% | 93% | 87% | 20% |
| 61 | L | 7% | 57% | 50% | 36% | 50% | 21% | 57% | 57% | 57% |
| 62 | Y | 6% | 94% | 6% | 0% | 0% | 0% | 89% | 28% | 78% |
| 63 | Q | 17% | 67% | 50% | 0% | 0% | 0% | 67% | 44% | 56% |
| 64 | P | 11% | 56% | 44% | 0% | 17% | 6% | 56% | 56% | 50% |
| 65 | T | 17% | 61% | 61% | 61% | 61% | 61% | 61% | 61% | 61% |
| 66 | S | 41% | 94% | 94% | 94% | 94% | 94% | 94% | 94% | 94% |
| 67 | Y | 60% | 100% | 100% | 87% | 100% | 80% | 100% | 100% | 87% |
| 69 | I | 12% | 35% | 35% | 24% | 35% | 24% | 35% | 35% | 35% |
| 70 | G | 0% | 31% | 31% | 13% | 31% | 6% | 31% | 31% | 31% |
| 71 | N | 0% | 7% | 7% | 7% | 7% | 7% | 7% | 7% | 7% |
| 72 | R | 89% | 100% | 100% | 100% | 100% | 100% | 100% | 100% | 79% |
| 74 | L | 13% | 44% | 44% | 31% | 44% | 25% | 44% | 44% | 44% |
| 77 | E | 59% | 88% | 88% | 82% | 76% | 82% | 88% | 88% | 59% |
| 79 | E | 33% | 60% | 60% | 60% | 60% | 53% | 60% | 60% | 60% |
| 80 | F | 6% | 28% | 22% | 22% | 22% | 22% | 28% | 28% | 28% |
| 81 | K | 78% | 94% | 94% | 94% | 94% | 89% | 94% | 94% | 94% |
| 82 | E | 81% | 94% | 94% | 94% | 94% | 94% | 94% | 94% | 94% |
| 83 | M | 19% | 38% | 38% | 38% | 38% | 38% | 38% | 38% | 38% |
| 84 | C | 21% | 63% | 63% | 58% | 63% | 53% | 63% | 63% | 63% |
| 86 | A | 88% | 94% | 94% | 88% | 94% | 88% | 94% | 94% | 94% |
| 87 | A | 6% | 24% | 24% | 12% | 12% | 12% | 24% | 24% | 18% |
| 88 | E | 56% | 89% | 89% | 83% | 89% | 83% | 89% | 89% | 89% |
| 89 | E | 94% | 100% | 100% | 100% | 100% | 94% | 100% | 100% | 100% |
| 92 | I | 17% | 28% | 28% | 22% | 28% | 22% | 28% | 28% | 22% |
| 93 | K | 44% | 100% | 100% | 100% | 100% | 100% | 100% | 100% | 100% |
| 94 | V | 6% | 29% | 29% | 24% | 29% | 24% | 29% | 29% | 29% |
| 95 | I | 28% | 33% | 33% | 33% | 33% | 33% | 33% | 33% | 28% |
| 96 | V | 6% | 39% | 39% | 39% | 39% | 39% | 39% | 39% | 33% |
| 98 | A | 6% | 41% | 41% | 41% | 41% | 24% | 41% | 41% | 35% |
| 99 | V | 6% | 71% | 18% | 0% | 6% | 0% | 71% | 29% | 71% |
| 100 | I | 24% | 53% | 53% | 47% | 47% | 41% | 53% | 53% | 53% |
| 103 | T | 24% | 41% | 41% | 41% | 41% | 29% | 41% | 41% | 24% |
| 104 | T | 11% | 16% | 16% | 16% | 16% | 5% | 16% | 16% | 11% |
| 105 | S | 50% | 94% | 94% | 31% | 56% | 13% | 94% | 94% | 94% |
| 110 | I | 6% | 17% | 17% | 11% | 11% | 11% | 17% | 17% | 6% |
| 111 | S | 72% | 100% | 94% | 94% | 94% | 89% | 100% | 94% | 100% |
| 113 | E | 11% | 89% | 89% | 83% | 89% | 72% | 89% | 89% | 89% |
| 114 | V | 13% | 40% | 33% | 33% | 7% | 33% | 33% | 33% | 7% |
| 117 | I | 5% | 42% | 42% | 37% | 42% | 32% | 42% | 42% | 16% |
| 121 | T | 6% | 22% | 22% | 17% | 22% | 11% | 22% | 17% | 6% |
| 122 | H | 0% | 6% | 6% | 6% | 6% | 0% | 6% | 6% | 0% |
| 126 | Q | 100% | 100% | 100% | 100% | 94% | 83% | 100% | 100% | 67% |
| 128 | K | 83% | 94% | 94% | 94% | 94% | 94% | 94% | 94% | 28% |
| 129 | N | 18% | 88% | 88% | 88% | 88% | 88% | 88% | 88% | 6% |
| 130 | W | 31% | 94% | 94% | 94% | 81% | 81% | 94% | 94% | 6% |
| 131 | S | 94% | 94% | 94% | 94% | 94% | 94% | 94% | 94% | 83% |
| 135 | D | 6% | 41% | 41% | 12% | 41% | 6% | 41% | 41% | 18% |
| 136 | V | 6% | 38% | 38% | 19% | 38% | 13% | 38% | 38% | 6% |
| 138 | Q | 0% | 56% | 31% | 6% | 19% | 0% | 56% | 38% | 6% |
| 139 | N | 0% | 41% | 41% | 35% | 41% | 35% | 41% | 41% | 0% |
| 140 | S | 5% | 26% | 16% | 11% | 16% | 5% | 26% | 16% | 5% |
| 141 | L | 58% | 95% | 21% | 0% | 0% | 0% | 79% | 26% | 21% |
| 144 | L | 78% | 89% | 6% | 0% | 0% | 0% | 72% | 22% | 6% |
| 145 | Y | 6% | 6% | 6% | 6% | 6% | 6% | 6% | 6% | 6% |
| 146 | D | 0% | 22% | 6% | 0% | 0% | 0% | 22% | 0% | 17% |
| 147 | W | 13% | 50% | 44% | 31% | 44% | 25% | 50% | 50% | 25% |
| 148 | N | 0% | 50% | 50% | 50% | 50% | 50% | 50% | 50% | 38% |
| 149 | T | 0% | 6% | 6% | 6% | 6% | 6% | 6% | 6% | 0% |
| 150 | Q | 6% | 25% | 25% | 25% | 25% | 25% | 25% | 25% | 0% |
| 151 | N | 63% | 89% | 89% | 89% | 89% | 84% | 89% | 89% | 74% |
| 154 | V | 6% | 53% | 35% | 24% | 35% | 24% | 53% | 29% | 47% |
| 155 | Q | 6% | 75% | 75% | 75% | 75% | 75% | 75% | 75% | 63% |
| 157 | L | 11% | 44% | 44% | 44% | 39% | 44% | 44% | 44% | 39% |
| 158 | Y | 29% | 53% | 53% | 53% | 53% | 53% | 53% | 53% | 53% |
| 159 | K | 28% | 89% | 89% | 89% | 89% | 89% | 89% | 89% | 89% |
| 161 | F | 6% | 63% | 63% | 56% | 44% | 56% | 63% | 63% | 25% |
| 162 | L | 13% | 44% | 44% | 44% | 44% | 25% | 44% | 44% | 44% |
| 164 | R | 80% | 93% | 93% | 93% | 93% | 93% | 93% | 93% | 87% |

TABLE 7-continued

Non-fully restrictive positions in full-length AmyE

| POS | WT AA | Bradford PI > 0.5% ss2 FULL | Visc Peak PI > 0.5% ss2 FULL | PAH BAH PI > 0.5% ss2 FULL | Glucose PI > 0.5% ss2 FULL | DP7 Unstressed PI > 0.5% ss2 FULL | DP7 pH 4 PI > 0.5% ss2 FULL | Cleaning 8 PI > 0.5% ss2 FULL | Cleaning 10 PI > 0.5% ss2 FULL | THE R PI > 0.5% ss2 FULL |
|---|---|---|---|---|---|---|---|---|---|---|
| 165 | A | 39% | 61% | 61% | 56% | 56% | 61% | 61% | 56% | 50% |
| 167 | N | 100% | 100% | 100% | 100% | 100% | 100% | 100% | 100% | 100% |
| 168 | D | 88% | 94% | 88% | 88% | 88% | 88% | 88% | 88% | 88% |
| 169 | G | 0% | 11% | 6% | 0% | 0% | 0% | 0% | 11% | 0% |
| 170 | A | 13% | 20% | 20% | 20% | 20% | 20% | 20% | 20% | 20% |
| 171 | D | 53% | 87% | 87% | 87% | 87% | 87% | 87% | 87% | 87% |
| 172 | G | 6% | 31% | 6% | 6% | 6% | 6% | 31% | 31% | 25% |
| 173 | F | 0% | 24% | 24% | 24% | 24% | 24% | 24% | 24% | 24% |
| 174 | R | 12% | 76% | 0% | 0% | 0% | 0% | 65% | 41% | 41% |
| 175 | F | 6% | 24% | 24% | 24% | 24% | 24% | 24% | 24% | 24% |
| 176 | D | 26% | 84% | 0% | 0% | 0% | 0% | 63% | 21% | 37% |
| 177 | A | 39% | 56% | 6% | 0% | 0% | 0% | 44% | 11% | 11% |
| 178 | A | 0% | 28% | 28% | 22% | 28% | 11% | 28% | 28% | 28% |
| 179 | D | 63% | 100% | 69% | 6% | 6% | 0% | 100% | 31% | 6% |
| 180 | H | 19% | 44% | 6% | 0% | 0% | 0% | 44% | 19% | 13% |
| 181 | I | 6% | 31% | 31% | 6% | 31% | 6% | 31% | 31% | 6% |
| 183 | L | 0% | 11% | 11% | 6% | 11% | 11% | 11% | 11% | 0% |
| 184 | P | 0% | 79% | 79% | 16% | 63% | 5% | 79% | 79% | 68% |
| 186 | D | 6% | 6% | 6% | 6% | 6% | 6% | 6% | 6% | 6% |
| 189 | Y | 13% | 13% | 13% | 13% | 13% | 13% | 13% | 13% | 13% |
| 191 | S | 0% | 24% | 12% | 12% | 6% | 12% | 18% | 24% | 0% |
| 193 | F | 0% | 21% | 21% | 11% | 21% | 16% | 21% | 16% | 11% |
| 194 | W | 0% | 7% | 7% | 7% | 7% | 7% | 7% | 7% | 0% |
| 196 | N | 79% | 95% | 95% | 95% | 95% | 95% | 95% | 95% | 95% |
| 197 | I | 17% | 44% | 44% | 44% | 44% | 44% | 44% | 44% | 44% |
| 198 | T | 31% | 69% | 69% | 69% | 69% | 69% | 69% | 69% | 50% |
| 204 | F | 24% | 59% | 59% | 47% | 59% | 41% | 59% | 59% | 59% |
| 205 | Q | 37% | 95% | 95% | 95% | 95% | 95% | 95% | 95% | 84% |
| 206 | Y | 0% | 6% | 6% | 0% | 6% | 0% | 6% | 6% | 6% |
| 207 | G | 6% | 19% | 19% | 19% | 19% | 0% | 19% | 19% | 19% |
| 208 | E | 73% | 100% | 0% | 0% | 0% | 0% | 40% | 13% | 13% |
| 209 | I | 11% | 32% | 32% | 21% | 21% | 21% | 32% | 32% | 11% |
| 210 | L | 88% | 100% | 18% | 12% | 6% | 6% | 88% | 6% | 35% |
| 211 | Q | 18% | 71% | 71% | 47% | 65% | 12% | 71% | 71% | 6% |
| 215 | S | 0% | 22% | 22% | 17% | 22% | 17% | 22% | 22% | 0% |
| 216 | R | 0% | 11% | 11% | 11% | 11% | 11% | 11% | 11% | 0% |
| 217 | D | 41% | 94% | 94% | 82% | 82% | 82% | 94% | 88% | 12% |
| 220 | Y | 0% | 6% | 6% | 6% | 6% | 6% | 6% | 6% | 0% |
| 223 | Y | 22% | 61% | 61% | 61% | 61% | 44% | 61% | 61% | 50% |
| 224 | M | 6% | 24% | 24% | 24% | 24% | 24% | 24% | 24% | 24% |
| 225 | D | 94% | 100% | 100% | 100% | 100% | 100% | 100% | 100% | 83% |
| 226 | V | 13% | 44% | 44% | 38% | 44% | 19% | 44% | 44% | 25% |
| 227 | T | 0% | 41% | 12% | 6% | 6% | 6% | 41% | 29% | 0% |
| 228 | A | 0% | 53% | 53% | 20% | 47% | 13% | 53% | 53% | 13% |
| 229 | S | 27% | 87% | 87% | 7% | 27% | 7% | 87% | 47% | 33% |
| 230 | N | 87% | 100% | 100% | 93% | 100% | 87% | 100% | 93% | 40% |
| 231 | Y | 12% | 41% | 41% | 35% | 41% | 24% | 41% | 41% | 12% |
| 232 | G | 6% | 39% | 33% | 0% | 28% | 0% | 39% | 39% | 11% |
| 235 | I | 11% | 33% | 33% | 28% | 33% | 22% | 33% | 33% | 28% |
| 236 | R | 41% | 82% | 82% | 76% | 82% | 65% | 82% | 82% | 71% |
| 237 | S | 89% | 100% | 100% | 100% | 100% | 100% | 100% | 100% | 94% |
| 238 | A | 28% | 94% | 94% | 94% | 94% | 89% | 94% | 94% | 94% |
| 239 | L | 13% | 38% | 31% | 25% | 31% | 19% | 38% | 38% | 38% |
| 241 | N | 94% | 100% | 100% | 94% | 100% | 94% | 100% | 100% | 100% |
| 242 | R | 94% | 94% | 94% | 94% | 94% | 94% | 94% | 94% | 94% |
| 244 | L | 22% | 44% | 44% | 44% | 44% | 44% | 44% | 44% | 44% |
| 246 | V | 89% | 100% | 100% | 100% | 100% | 100% | 100% | 100% | 100% |
| 249 | I | 35% | 71% | 59% | 53% | 59% | 53% | 71% | 53% | 47% |
| 256 | V | 20% | 40% | 40% | 40% | 40% | 40% | 40% | 40% | 33% |
| 258 | A | 47% | 95% | 95% | 95% | 95% | 95% | 95% | 89% | 84% |
| 260 | K | 56% | 83% | 83% | 83% | 83% | 83% | 83% | 83% | 83% |
| 261 | L | 6% | 50% | 50% | 44% | 50% | 28% | 50% | 44% | 33% |
| 262 | V | 7% | 36% | 36% | 21% | 36% | 14% | 36% | 36% | 36% |
| 263 | T | 29% | 47% | 47% | 41% | 47% | 41% | 47% | 47% | 29% |
| 264 | W | 88% | 94% | 56% | 0% | 6% | 6% | 88% | 50% | 44% |
| 265 | V | 0% | 43% | 43% | 21% | 36% | 14% | 43% | 43% | 36% |
| 267 | S | 22% | 0% | 44% | 6% | 28% | 0% | 67% | 33% | 39% |
| 268 | H | 65% | 94% | 0% | 0% | 0% | 6% | 88% | 12% | 24% |
| 269 | D | 94% | 47% | 0% | 12% | 0% | 0% | 0% | 12% | 0% |
| 270 | T | 81% | 94% | 81% | 19% | 63% | 31% | 94% | 81% | 94% |
| 271 | Y | 6% | 6% | 6% | 6% | 6% | 6% | 6% | 6% | 6% |

TABLE 7-continued

Non-fully restrictive positions in full-length AmyE

| POS | WT AA | Bradford PI > 0.5% ss2 FULL | Visc Peak PI > 0.5% ss2 FULL | PAH BAH PI > 0.5% ss2 FULL | Glucose PI > 0.5% ss2 FULL | DP7 Unstressed PI > 0.5% ss2 FULL | DP7 pH 4 PI > 0.5% ss2 FULL | Cleaning 8 PI > 0.5% ss2 FULL | Cleaning 10 PI > 0.5% ss2 FULL | THE R PI > 0.5% ss2 FULL |
|---|---|---|---|---|---|---|---|---|---|---|
| 272 | A | 25% | 50% | 50% | 13% | 44% | 13% | 50% | 50% | 38% |
| 273 | N | 83% | 100% | 72% | 0% | 28% | 11% | 100% | 78% | 89% |
| 278 | S | 0% | 17% | 17% | 6% | 17% | 0% | 17% | 17% | 17% |
| 279 | T | 65% | 100% | 100% | 29% | 100% | 12% | 100% | 100% | 76% |
| 280 | W | 13% | 94% | 94% | 94% | 94% | 0% | 94% | 94% | 69% |
| 281 | M | 13% | 20% | 20% | 20% | 20% | 13% | 20% | 20% | 20% |
| 285 | D | 11% | 72% | 72% | 72% | 72% | 67% | 72% | 72% | 67% |
| 286 | I | 22% | 44% | 44% | 44% | 44% | 28% | 44% | 44% | 44% |
| 288 | L | 27% | 40% | 40% | 40% | 40% | 33% | 40% | 40% | 40% |
| 289 | G | 6% | 0% | 11% | 11% | 11% | 0% | 11% | 11% | 11% |
| 290 | W | 6% | 22% | 22% | 22% | 22% | 22% | 22% | 22% | 22% |
| 291 | A | 26% | 53% | 53% | 53% | 53% | 53% | 53% | 53% | 53% |
| 292 | V | 38% | 50% | 50% | 50% | 50% | 50% | 50% | 50% | 50% |
| 293 | I | 14% | 64% | 64% | 43% | 57% | 43% | 64% | 64% | 64% |
| 294 | A | 21% | 37% | 37% | 32% | 37% | 32% | 37% | 37% | 37% |
| 295 | S | 12% | 24% | 24% | 24% | 24% | 24% | 24% | 24% | 24% |
| 296 | R | 0% | 41% | 41% | 18% | 41% | 18% | 41% | 41% | 24% |
| 297 | S | 100% | 100% | 100% | 100% | 100% | 100% | 100% | 100% | 100% |
| 298 | G | 94% | 94% | 94% | 94% | 94% | 94% | 94% | 94% | 89% |
| 299 | S | 41% | 82% | 82% | 82% | 82% | 71% | 82% | 82% | 82% |
| 300 | T | 22% | 78% | 78% | 78% | 78% | 78% | 78% | 78% | 61% |
| 301 | P | 47% | 87% | 87% | 87% | 80% | 87% | 87% | 87% | 67% |
| 302 | L | 37% | 63% | 58% | 21% | 47% | 26% | 58% | 63% | 32% |
| 303 | F | 5% | 21% | 21% | 21% | 21% | 21% | 21% | 21% | 21% |
| 304 | F | 20% | 47% | 27% | 20% | 20% | 7% | 47% | 40% | 47% |
| 305 | S | 19% | 38% | 38% | 38% | 38% | 25% | 38% | 38% | 31% |
| 307 | P | 13% | 47% | 27% | 27% | 27% | 0% | 47% | 47% | 47% |
| 312 | N | 94% | 94% | 94% | 94% | 94% | 88% | 94% | 94% | 88% |
| 315 | R | 40% | 93% | 93% | 53% | 87% | 7% | 93% | 93% | 73% |
| 316 | R | 12% | 41% | 47% | 29% | 47% | 18% | 47% | 47% | 29% |
| 322 | I | 17% | 17% | 17% | 17% | 17% | 17% | 17% | 17% | 11% |
| 326 | G | 0% | 11% | 11% | 5% | 5% | 0% | 11% | 11% | 11% |
| 329 | L | 40% | 80% | 80% | 80% | 80% | 73% | 80% | 80% | 67% |
| 330 | F | 11% | 42% | 42% | 42% | 42% | 42% | 42% | 42% | 42% |
| 332 | D | 41% | 88% | 88% | 88% | 76% | 88% | 88% | 88% | 65% |
| 334 | A | 100% | 100% | 100% | 100% | 100% | 100% | 100% | 100% | 100% |
| 335 | I | 12% | 35% | 35% | 35% | 29% | 35% | 35% | 35% | 35% |
| 336 | T | 89% | 94% | 89% | 89% | 89% | 89% | 94% | 89% | 83% |
| 337 | A | 57% | 100% | 93% | 86% | 86% | 86% | 100% | 100% | 93% |
| 338 | V | 44% | 63% | 63% | 56% | 56% | 56% | 63% | 63% | 63% |
| 339 | N | 6% | 38% | 38% | 38% | 38% | 38% | 38% | 38% | 38% |
| 340 | R | 93% | 93% | 93% | 93% | 93% | 93% | 93% | 93% | 93% |
| 341 | F | 19% | 44% | 44% | 44% | 44% | 44% | 44% | 44% | 44% |
| 342 | H | 31% | 81% | 81% | 81% | 81% | 81% | 81% | 81% | 81% |
| 343 | N | 89% | 100% | 100% | 95% | 95% | 89% | 100% | 100% | 95% |
| 344 | V | 89% | 78% | 94% | 94% | 94% | 89% | 89% | 89% | 89% |
| 345 | M | 75% | 94% | 94% | 94% | 94% | 94% | 94% | 94% | 94% |
| 348 | Q | 88% | 100% | 100% | 100% | 100% | 100% | 100% | 100% | 94% |
| 350 | E | 6% | 28% | 28% | 28% | 28% | 28% | 28% | 28% | 22% |
| 351 | E | 94% | 100% | 100% | 94% | 100% | 94% | 100% | 100% | 100% |
| 352 | L | 50% | 100% | 100% | 94% | 94% | 94% | 100% | 100% | 94% |
| 353 | S | 94% | 94% | 94% | 94% | 94% | 94% | 94% | 94% | 94% |
| 354 | N | 0% | 41% | 41% | 41% | 41% | 41% | 41% | 35% | 41% |
| 355 | P | 44% | 88% | 88% | 88% | 88% | 88% | 88% | 88% | 88% |
| 356 | N | 100% | 100% | 100% | 100% | 100% | 100% | 100% | 100% | 100% |
| 360 | Q | 100% | 100% | 100% | 100% | 100% | 100% | 100% | 100% | 100% |
| 361 | I | 50% | 81% | 81% | 81% | 81% | 81% | 81% | 81% | 81% |
| 362 | F | 35% | 71% | 71% | 71% | 71% | 71% | 71% | 71% | 71% |
| 363 | M | 88% | 94% | 75% | 69% | 69% | 81% | 94% | 88% | 94% |
| 364 | N | 56% | 67% | 67% | 67% | 67% | 67% | 67% | 67% | 67% |
| 365 | Q | 72% | 94% | 94% | 89% | 94% | 89% | 94% | 89% | 94% |
| 366 | R | 13% | 75% | 75% | 63% | 56% | 63% | 75% | 75% | 69% |
| 370 | G | 0% | 6% | 6% | 6% | 6% | 6% | 6% | 6% | 6% |
| 371 | V | 53% | 74% | 74% | 74% | 74% | 74% | 74% | 74% | 68% |
| 372 | V | 44% | 63% | 63% | 63% | 63% | 63% | 63% | 63% | 56% |
| 373 | L | 39% | 67% | 67% | 67% | 67% | 67% | 67% | 67% | 67% |
| 374 | A | 41% | 59% | 59% | 59% | 59% | 59% | 59% | 59% | 53% |
| 375 | N | 65% | 82% | 82% | 82% | 82% | 82% | 82% | 82% | 82% |
| 376 | A | 32% | 79% | 79% | 79% | 79% | 74% | 79% | 74% | 74% |
| 377 | G | 82% | 94% | 94% | 88% | 94% | 88% | 94% | 88% | 94% |
| 379 | S | 100% | 88% | 100% | 100% | 100% | 100% | 100% | 100% | 100% |

TABLE 7-continued

Non-fully restrictive positions in full-length AmyE

| POS | WT AA | Bradford PI > 0.5% ss2 FULL | Visc Peak PI > 0.5% ss2 FULL | PAH BAH PI > 0.5% ss2 FULL | Glucose PI > 0.5% ss2 FULL | DP7 Unstressed PI > 0.5% ss2 FULL | DP7 pH 4 PI > 0.5% ss2 FULL | Cleaning 8 PI > 0.5% ss2 FULL | Cleaning 10 PI > 0.5% ss2 FULL | THE R PI > 0.5% ss2 FULL |
|---|---|---|---|---|---|---|---|---|---|---|
| 380 | S | 94% | 100% | 100% | 100% | 94% | 94% | 100% | 100% | 94% |
| 381 | V | 94% | 94% | 94% | 94% | 94% | 94% | 94% | 94% | 94% |
| 383 | I | 47% | 88% | 88% | 88% | 88% | 88% | 88% | 88% | 88% |
| 384 | N | 100% | 100% | 100% | 100% | 100% | 93% | 100% | 100% | 100% |
| 387 | T | 53% | 73% | 73% | 73% | 73% | 67% | 73% | 73% | 73% |
| 389 | L | 38% | 88% | 88% | 81% | 88% | 81% | 88% | 88% | 88% |
| 391 | D | 100% | 100% | 100% | 100% | 100% | 100% | 100% | 100% | 100% |
| 392 | G | 94% | 94% | 94% | 94% | 94% | 88% | 94% | 94% | 88% |
| 394 | Y | 58% | 89% | 89% | 89% | 89% | 89% | 89% | 89% | 89% |
| 396 | N | 19% | 56% | 56% | 56% | 56% | 56% | 56% | 56% | 56% |
| 397 | K | 100% | 100% | 100% | 100% | 100% | 100% | 100% | 100% | 94% |
| 398 | A | 33% | 94% | 94% | 94% | 94% | 94% | 94% | 94% | 94% |
| 399 | G | 83% | 94% | 94% | 94% | 94% | 89% | 94% | 94% | 94% |
| 402 | S | 94% | 94% | 94% | 94% | 94% | 94% | 94% | 94% | 94% |
| 403 | F | 44% | 78% | 78% | 72% | 72% | 72% | 78% | 78% | 72% |
| 404 | Q | 94% | 100% | 100% | 100% | 100% | 100% | 100% | 100% | 100% |
| 405 | V | 50% | 69% | 75% | 75% | 75% | 75% | 75% | 75% | 75% |
| 407 | D | 89% | 100% | 100% | 100% | 94% | 94% | 100% | 100% | 100% |
| 408 | G | 89% | 94% | 100% | 100% | 94% | 100% | 100% | 94% | 100% |
| 409 | K | 95% | 95% | 95% | 95% | 95% | 95% | 89% | 95% | 89% |
| 410 | L | 29% | 65% | 65% | 53% | 47% | 53% | 65% | 65% | 59% |
| 411 | T | 95% | 95% | 95% | 95% | 95% | 95% | 89% | 95% | 95% |
| 412 | G | 35% | 88% | 88% | 88% | 88% | 88% | 88% | 88% | 82% |
| 413 | T | 100% | 100% | 100% | 100% | 100% | 100% | 100% | 94% | 94% |
| 414 | I | 65% | 82% | 82% | 82% | 82% | 82% | 82% | 76% | 82% |
| 415 | N | 100% | 100% | 100% | 100% | 100% | 100% | 100% | 100% | 100% |
| 416 | A | 94% | 100% | 100% | 100% | 100% | 100% | 100% | 100% | 100% |
| 417 | R | 73% | 100% | 100% | 100% | 100% | 100% | 100% | 100% | 100% |
| 418 | S | 87% | 93% | 93% | 93% | 93% | 87% | 93% | 93% | 93% |
| 419 | V | 72% | 89% | 83% | 83% | 83% | 83% | 83% | 72% | 83% |
| 420 | A | 89% | 94% | 94% | 94% | 94% | 94% | 94% | 94% | 89% |
| 421 | V | 39% | 44% | 44% | 44% | 44% | 44% | 44% | 44% | 44% |
| 422 | L | 53% | 74% | 74% | 74% | 74% | 74% | 74% | 74% | 74% |
| 423 | Y | 94% | 94% | 100% | 100% | 100% | 100% | 100% | 94% | 94% |
| 424 | P | 100% | 94% | 100% | 100% | 100% | 100% | 100% | 100% | 100% |
| 425 | D | 100% | 100% | 100% | 100% | 100% | 100% | 100% | 100% | 100% |

As will be apparent from the foregoing description, certain positions can be mutated in AmyE polypeptides to alter one or more properties without substantially adversely affecting any one property. These mutations are collectively referred to as combinable mutations for surface properties. Such positions are good candidates for making single mutations, and combinations of mutations, since they are generally tolerant to manipulation. On the other hand, mutations at these position impart distinguishable properties on the resulting AmyE variants, indicating that they are important to enzyme structure and/or function. Corresponding positions in other parental amylases, including α-amylase other than AmyE can be similarly mutated. In some cases, where the corresponding position in another parental amylases includes a different amino acid residue, it can be mutated to include an amino acid residue found in a wild-type AmyE polypeptide. The positions are as follows: 052D, 052E, 052I, 052K, 052L, 052N, 052Q, 052R, 052V, 056D, 056E, 056I, 056K, 056L, 056N, 056Q, 056R, 056V, 089D, 089E, 089I, 089K, 089L, 089N, 089Q, 089R, 089V, 152D, 152E, 152I, 152K, 152L, 152N, 152Q, 152R, 152V, 153D, 153E, 153I, 153K, 153L, 153N, 153Q, 153R, 153V, 201D, 201E, 201I, 201K, 201L, 201N, 201Q, 201R, 201V, 251D, 251E, 251I, 251K, 251L, 251N, 251Q, 251R, 251V, 284D, 284E, 284I, 284K, 284L, 284N, 284Q, 284R, 284V, 297D, 297E, 297I, 297K, 297L, 297N, 297Q, 297R, 297V, 308D, 308E, 308I, 308K, 308L, 308N, 308Q, 308R, 308V, 321D, 321E, 321I, 321K, 321L, 321N, 321Q, 321R, 321V, 328D, 328E, 328I, 328K, 328L, 328N, 328Q, 328R, 328V, 347D, 347E, 347I, 347K, 347L, 347N, 347Q, 347R, 347V, 357D, 357E, 357I, 357K, 357L, 357N, 357Q, 357R, 357V, 359D, 359E, 359I, 359K, 359L, 359N, 359Q, 359R, 359V, 369D, 369E, 369I, 369K, 369L, 369N, 369Q, 369R, 369V, 385D, 385E, 385I, 385K, 385L, 385N, 385Q, 385R, 385V, 388D, 388E, 388I, 388K, 388L, 388N, 388Q, 388R, 388V, 391D, 391E, 391I, 391K, 391L, 391N, 391Q, 391R, 391V, 400D, 400E, 400I, 400K, 400L, 400N, 400Q, 400R, 400V, 416D, 416E, 416I, 416K, 416L, 416N, 416Q, 416R, and 416V. Mutations at all these mutations have PI values >0.5 for both protein and activity, demonstrating that the positions can be mutated without destroying protein expression or performance.

Example 17

Liquefaction in the Viscometer

Viscosity reduction of corn flour due to the action of the α-amylase was monitored using a HAAKE Viscotester 550 instrument. The substrate slurry is made up fresh daily in batch mode with 30% corn flour dry solids. The pH was adjusted to 5.8 using sulfuric acid. 50 g of the slurry (15 g dry solids) is weighed out and pre-incubated, with stirring, for 10 minutes to warm up to 70° C. Upon a amylase addition the temperature is immediately ramped up from 70° C. to 85° C. with a rotation speed of 75 rpm. Once the temperature of the slurry and enzyme mixture reaches 85° C., its temperature is held constant and viscosity is monitored for an additional 30 minutes. The viscosity was measured throughout the run and is reported in µNm.

Wild-type AmyE (full-length or truncated) and several variants, thereof, were dosed at from about 0.25 to 1.5 mg/50 g of corn flour slurry and the viscosity recorded.

A typical graph of the viscosity of the slurry over time is shown in FIG. 15, in which the wild-type full-length AmyE, and the AmyE full-length variants I100F and W60M are compared. In other cases, only the peak and final viscosity of the slurry are tabulated. The results for wild-type, full-length AmyE, and the variants L142F, L142G, L142Q, L142S, L142W, L142Y, A214I, A214V, S245Y, Q126F, Q126L, Q126P, Q126V, S131L, and S254I, made in the full-length AmyE background, are shown in Tables 8 and 9. The results for wild-type, truncated AmyE, and the variants W60L, W60M, W60N, I100F, I100M, S105M, S105W, G207A, T270A, T270E, T270L, T270N, T270V, and T279A, made in the truncated AmyE background, are shown in Table 10.

TABLE 8

Peak and final viscosity obtained using truncated wild-type and variant AmyE (corn flour bag F)

| | dose (mg) | peak viscosity | final viscosity |
|---|---|---|---|
| WT | 1.40 | 27300 | 1490 |
| L142F | 0.60 | 26100 | 550 |
| L142G | 0.30 | 29900 | 1925 |
| L142Q | 0.30 | 31400 | 2800 |
| L142S | 0.25 | 30000 | 2495 |
| L142W | 1.40 | 33000 | 570 |
| L142Y | 1.20 | 27800 | 1940 |
| A214I | 1.40 | 24700 | 2330 |
| A214V | 1.40 | 21700 | 560 |
| S245Y | 1.40 | 25800 | 520 |
| Q126F | 0.70 | 32300 | 2540 |
| Q126L | 1.40 | 30900 | 400 |
| Q126P | 1.40 | 25100 | 480 |
| Q126V | 1.40 | 28300 | 520 |
| S131L | 1.40 | 26100 | 450 |

TABLE 9

Peak and final viscosity obtained using truncated wild-type and variant AmyE (corn flour bag G)

| | dose (mg) | peak viscosity | final viscosity |
|---|---|---|---|
| WT | 0.60 | 33600 | 890 |
| L142F | 0.45 | 28000 | 700 |
| L142G | 0.30 | 25300 | 2620 |
| L142Q | 0.30 | 26300 | 4320 |
| L142S | 0.25 | 31200 | 11200 |
| L142Y | 0.60 | 28600 | 570 |
| A214I | 0.60 | 25200 | 780 |
| Q126F | 0.50 | 32400 | 2020 |
| S254I | 0.60 | 32500 | 1320 |

TABLE 10

Peak and final viscosity obtained using truncated wild-type and variant AmyE (corn flour bag H)

| | dose (mg) | peak viscosity | final viscosity |
|---|---|---|---|
| WT | 1.40 | 29800 | 840 |
| W60L | 0.75 | 29200 | 1980 |
| W60M | 1.00 | 29100 | 2220 |
| W60N | 1.00 | 30900 | 4250 |
| I100F | 0.75 | 29600 | 870 |
| I100M | 0.75 | 29200 | 840 |
| S105M | 0.75 | 30300 | 2170 |
| S105W | 0.75 | 30400 | 1960 |
| G207A | 0.75 | 29300 | 1920 |
| T270A | 0.75 | 31100 | 1540 |
| T270E | 1.00 | 33200 | 1300 |
| T270L | 0.85 | 33000 | 1520 |
| T270N | 1.40 | 27700 | 560 |
| T270V | 0.80 | 33900 | 2400 |
| T279A | 0.75 | 29400 | 1280 |

Improved performance in the viscometer assay can be identified using a number of criteria, i.e., decreased peak viscosity, decreased final viscosity, or a decreased enzyme dose required to produce similar peak or final viscosities relative to the dose required for a reference (control) enzyme. The bold highlighted text in Tables 9-10 indicate the criteria in which each variant demonstrates improved performance compared to the respective wild-type control.

Example 18

Thermostability of AmyE Full-length, AmyE-tr and AmyE Variants Using Differential Scanning Calorimetry Excess heat capacity curves were measured using an ultrasensitive scanning high-throughput microcalorimeter, VP-Cap DSC (MicroCal, Inc., Northampton, Mass., USA). The standard procedure for DSC measurements and the theory of the technique is previously published (Freire, E. (1995) Differential Scanning Calorimetry Methods. *Mol. Biol.* 41:191-218). Approximately 500 µL of 0.5 mg/ml of AmyE-tr, or truncated AmyE variants were scanned over 30-120° C. temperature range. The same sample was then re-scanned to check the reversibility of the process. The buffer used was 10 mM sodium acetate, pH 4.0 or pH 5.8. A 200° C./hr scan rate was used to minimize any artifacts that may result from aggregation. The thermal midpoint ($T_m$) of the DSC curves was used as an indicator of the thermal stability. Table 11 shows the $T_m$ values of wildtype truncated AmyE and truncated AmyE variants tested at pH 4.0 and pH 5.8.

TABLE 11

$T_m$ (in ° C.) of wild-type truncated AmyE and truncated AmyE variants

| Variants | $T_m$ at pH 4.0 | $T_m$ at pH 5.8 |
|---|---|---|
| wild type AmyE truncated | 69.9 | 74.9 |
| Q126L | 73 | 78.1 |
| Q126P | 75 | 81 |
| Q126V | 70 | 75.6 |
| L142F | 74.2 | 79.1 |
| L142G | 71 | 77.3 |
| L142Q | 70.1 | 75.7 |
| L142W | 74.1 | 79.6 |

TABLE 11-continued $T_m$ (in ° C.) of wild-type truncated AmyE and truncated AmyE variants

| Variants | $T_m$ at pH 4.0 | $T_m$ at pH 5.8 |
| --- | --- | --- |
| L142Y | 74.3 | 79.5 |
| A214I | 77.4 | 81.6 |
| A214V | 78 | 83 |
| A214W | 71 | 76.3 |

Example 19

Bread Staling

The following example relates to the use of an AmyE polypeptides to reduce bread staling.

A. Recipe for Baking Trials

Baking trials were carried out with a standard white bread sponge and dough recipe for US toast. The sponge dough is prepared from 1400 g of flour "Gold Medal" from General Mills, USA, 800 g of water, 40 g of rape seed oil, 7.5 g GRINDSTED™ SSL P55 Veg, 10 g emulsifier DIMODAN™ PH200 and 60 g of compressed yeast. The sponge is mixed for 1 min. at low speed and subsequently 3 min. at speed 2 on a Hobart spiral mixer. The sponge is subsequently fermented for 3 hours at 25° C., 85% RH.

Thereafter, 600 g of "Gold Medal" flour, 18 g of compressed yeast, 5 g of calcium propionate, 160 g of sucrose, 5 g of calcium propionate, 432 g of water and ascorbic acid (60 ppm final concentration) and ADA (azodicarbonamide; 40 ppm final concentration) are added to the sponge. The resulting dough is mixed for 1 min. at low speed and then 2 min. on high speed on a Diosna mixer. Then 30 g of salt is added to the dough.

The dough is rested for 5 min. at ambient temperature, and then 550 g dough pieces are scaled, moulded on Glimek sheeter with the settings 1:4, 2:4, 3:15, 4:12 and width 8 on both sides and transferred to a baking form. After 65 min. proofing at 43° C. at 95% RH the doughs are baked for 26 min. at 200° C. in an MIWE oven.

B. Protocol for Evaluation of Firmness, Resilience and Cohesiveness

Firmness, resilience and cohesiveness are determined by analysing bread slices by Texture Profile Analysis using a Texture Analyser From Stable Micro Systems, UK. Calculation of firmness and resilience is done according to preset standard supplied by Stable Micro System, UK. The probe used is aluminium 50 mm round.

Bread is sliced with the width of 12.5 mm. The slices are stamped out to a circular piece with a diameter of 45 mm and measured individually.

The following settings are used: Pre Test Speed: 2 mm/s, Test Speed: 2 mm/s, Post Test Speed: 10 mm/s, Rupture Test Distance: 1%, Distance: 40%, Force: 0.098 N, Time: 5.00 sec, Count: 5, Load Cell: 5 kg, Trigger Type: Auto—0.01 N.

The mode of compression is a modification to the one used in Standard method AACC 74-09. The sample is compressed twice in the test.

C Protocol for Evaluation of Firmness

Firmness was determined at 40% compression during the first compression. The figure is the force needed to compress the slice to 40% of the total thickness. The lower the value, the softer the bread. The firmness was expressed as a pressure, for example, in hPa.

D. Improved Handling Properties of Food Products Treated with an AmyE Variant Polypeptides Bread was baked with 0.4 mg/kg of AmyE tr and the firmness of the bread is tested according to the protocol set out above at various times after baking. The firmness of the bread was tested. As a control, firmness of bread baked without any enzyme is also measured.

FIG. 16 shows the results of a baking trial in which firmness of bread treated with AmyE tr was compared to firmness of bread without enzyme. A reduced increase in firmness from day 1 to day 14 in the bread baked with AmyE tr indicated that the enzyme has antistalling effect and can improve the fresh keeping of bread.

What is claimed is:

1. An isolated variant polypeptide having α-amylase activity and at least one altered characteristic that improves enzyme performance, wherein the altered characteristic is selected from the group consisting of increased viscosity reduction, increased amylolytic activity, increased thermostability, increased pH stability and increased stain removal, the isolated variant polypeptide comprising:
   i) a polypeptide having an amino acid sequence at least 90% identical to SEQ ID NO: 1 and a modification at one or more positions selected from the group consisting of 9, 68, 88, 126, 139, 158, 192, 214, and 257 of the amino acid sequence of SEQ ID NO:1; or
   ii) a polypeptide having an amino acid sequence at least 92% identical to SEQ ID NO: 2, and a modification at one or more positions selected from the group consisting of 9, 68, 88, 126, 139, 158, 192, 214, and 257 of the amino acid sequence of SEQ ID NO:2,
   wherein the modification produces a variant polypeptide having a performance index (PI) greater than 1.0 for the at least one altered characteristic that improves enzyme performance.

2. The isolated variant polypeptide of claim 1, wherein the modification is a substitution at one or more positions selected from the group consisting of 9M, 68H, 88K, 126P, 139H, 158I, 192S, 214V, and 257E.

3. The isolated variant polypeptide of claim 2, wherein the variant polypeptide comprises the substitution 9M, and the variant polypeptide exhibits increased ability to convert maltose and maltoheptaose substrates to glucose compared to the parental polypeptide.

4. The isolated variant polypeptide of claim 2, wherein the variant polypeptide comprises the substitution 68H, and the variant polypeptide exhibits increased ability to convert maltose and maltoheptaose substrates to glucose compared to the parental polypeptide.

5. The isolated variant polypeptide of claim 2, wherein the variant polypeptide comprises the substitution 88K, and the variant polypeptide exhibits increased ability to convert maltose and maltoheptaose substrates to glucose compared to the parental polypeptide.

6. The isolated variant polypeptide of claim 2, wherein the variant polypeptide comprises the substitution 126P, and the variant polypeptide exhibits increased ability to convert maltose and maltoheptaose substrates to glucose compared to the parental polypeptide.

7. The isolated variant polypeptide of claim 2, wherein the variant polypeptide comprises the substitution 139H, and the variant polypeptide exhibits increased ability to convert maltose and maltoheptaose substrates to glucose compared to the parental polypeptide.

8. The isolated variant polypeptide of claim 2, wherein the variant polypeptide comprises the substitution 158I, and the variant polypeptide exhibits increased ability to convert maltose and maltoheptaose substrates to glucose compared to the parental polypeptide.

9. The isolated variant polypeptide of claim 2, wherein the variant polypeptide comprises the substitution 192S, and the variant polypeptide exhibits increased ability to convert maltose and maltoheptaose substrates to glucose compared to the parental polypeptide.

10. The isolated variant polypeptide of claim 2, wherein the variant polypeptide comprises the substitution 214V, and the variant polypeptide exhibits increased ability to convert maltose and maltoheptaose substrates to glucose compared to the parental polypeptide.

11. The isolated variant polypeptide of claim 2, wherein the variant polypeptide comprises the substitution 257E , and the variant polypeptide exhibits increased ability to convert maltose and maltoheptaose substrates to glucose compared to the parental polypeptide.

* * * * *

SEQUENCE LISTING

```
<160> NUMBER OF SEQ ID NOS: 17

<210> SEQ ID NO 1
<211> LENGTH: 618
<212> TYPE: PRT
<213> ORGANISM: Bacillus subtilis
<220> FEATURE:
<221> NAME/KEY: misc_feature
<223> OTHER INFORMATION: Full length Bacillus subtilis AmyE amino acid
      sequence. The native signal sequence is not shown.

<400> SEQUENCE: 1

Leu Thr Ala Pro Ser Ile Lys Ser Gly Thr Ile Leu His Ala Trp Asn
1               5                   10                  15

Trp Ser Phe Asn Thr Leu Lys His Asn Met Lys Asp Ile His Asp Ala
            20                  25                  30

Gly Tyr Thr Ala Ile Gln Thr Ser Pro Ile Asn Gln Val Lys Glu Gly
        35                  40                  45

Asn Gln Gly Asp Lys Ser Met Ser Asn Trp Tyr Trp Leu Tyr Gln Pro
    50                  55                  60

Thr Ser Tyr Gln Ile Gly Asn Arg Tyr Leu Gly Thr Glu Gln Glu Phe
65                  70                  75                  80
```

-continued

Lys Glu Met Cys Ala Ala Glu Glu Tyr Gly Ile Lys Val Ile Val
            85                  90                  95
Asp Ala Val Ile Asn His Thr Thr Ser Asp Tyr Ala Ala Ile Ser Asn
        100                 105                 110
Glu Val Lys Ser Ile Pro Asn Trp Thr His Gly Asn Thr Gln Ile Lys
            115                 120                 125
Asn Trp Ser Asp Arg Trp Asp Val Thr Gln Asn Ser Leu Leu Gly Leu
    130                 135                 140
Tyr Asp Trp Asn Thr Gln Asn Thr Gln Val Gln Ser Tyr Leu Lys Arg
145                 150                 155                 160
Phe Leu Asp Arg Ala Leu Asn Asp Gly Ala Asp Gly Phe Arg Phe Asp
                165                 170                 175
Ala Ala Lys His Ile Glu Leu Pro Asp Asp Gly Ser Tyr Gly Ser Gln
            180                 185                 190
Phe Trp Pro Asn Ile Thr Asn Thr Ser Ala Glu Phe Gln Tyr Gly Glu
        195                 200                 205
Ile Leu Gln Asp Ser Ala Ser Arg Asp Ala Ala Tyr Ala Asn Tyr Met
    210                 215                 220
Asp Val Thr Ala Ser Asn Tyr Gly His Ser Ile Arg Ser Ala Leu Lys
225                 230                 235                 240
Asn Arg Asn Leu Gly Val Ser Asn Ile Ser His Tyr Ala Ser Asp Val
                245                 250                 255
Ser Ala Asp Lys Leu Val Thr Trp Val Glu Ser His Asp Thr Tyr Ala
            260                 265                 270
Asn Asp Asp Glu Glu Ser Thr Trp Met Ser Asp Asp Ile Arg Leu
        275                 280                 285
Gly Trp Ala Val Ile Ala Ser Arg Ser Gly Ser Thr Pro Leu Phe Phe
    290                 295                 300
Ser Arg Pro Glu Gly Gly Gly Asn Gly Val Arg Phe Pro Gly Lys Ser
305                 310                 315                 320
Gln Ile Gly Asp Arg Gly Ser Ala Leu Phe Glu Asp Gln Ala Ile Thr
                325                 330                 335
Ala Val Asn Arg Phe His Asn Val Met Ala Gly Gln Pro Glu Glu Leu
            340                 345                 350
Ser Asn Pro Asn Gly Asn Asn Gln Ile Phe Met Asn Gln Arg Gly Ser
        355                 360                 365
His Gly Val Val Leu Ala Asn Ala Gly Ser Ser Ser Val Ser Ile Asn
    370                 375                 380
Thr Ala Thr Lys Leu Pro Asp Gly Arg Tyr Asp Asn Lys Ala Gly Ala
385                 390                 395                 400
Gly Ser Phe Gln Val Asn Asp Gly Lys Leu Thr Gly Thr Ile Asn Ala
                405                 410                 415
Arg Ser Val Ala Val Leu Tyr Pro Asp Asp Ile Ala Lys Ala Pro His
            420                 425                 430
Val Phe Leu Glu Asn Tyr Lys Thr Gly Val Thr His Ser Phe Asn Asp
        435                 440                 445
Gln Leu Thr Ile Thr Leu Arg Ala Asp Ala Asn Thr Thr Lys Ala Val
    450                 455                 460
Tyr Gln Ile Asn Asn Gly Pro Glu Thr Ala Phe Lys Asp Gly Asp Gln
465                 470                 475                 480
Phe Thr Ile Gly Lys Gly Asp Pro Phe Gly Lys Thr Tyr Thr Ile Met
                485                 490                 495
Leu Lys Gly Thr Asn Ser Asp Gly Val Thr Arg Thr Glu Lys Tyr Ser

```
                500                 505                 510
Phe Val Lys Arg Asp Pro Ala Ser Ala Lys Thr Ile Gly Tyr Gln Asn
            515                 520                 525

Pro Asn His Trp Ser Gln Val Asn Ala Tyr Ile Tyr Lys His Asp Gly
        530                 535                 540

Ser Arg Val Ile Glu Leu Thr Gly Ser Trp Pro Gly Lys Pro Met Thr
545                 550                 555                 560

Lys Asn Ala Asp Gly Ile Tyr Thr Leu Thr Leu Pro Ala Asp Thr Asp
                565                 570                 575

Thr Thr Asn Ala Lys Val Ile Phe Asn Asn Gly Ser Ala Gln Val Pro
            580                 585                 590

Gly Gln Asn Gln Pro Gly Phe Asp Tyr Val Leu Asn Gly Leu Tyr Asn
        595                 600                 605

Asp Ser Gly Leu Ser Gly Ser Leu Pro His
                610                 615

<210> SEQ ID NO 2
<211> LENGTH: 425
<212> TYPE: PRT
<213> ORGANISM: Bacillus subtilis
<220> FEATURE:
<221> NAME/KEY: misc_feature
<223> OTHER INFORMATION: Truncated Bacillus subtilis AmyE (AmyE-tr)
      amino acid sequence. The native signal sequence is not shown.

<400> SEQUENCE: 2

Leu Thr Ala Pro Ser Ile Lys Ser Gly Thr Ile Leu His Ala Trp Asn
1               5                   10                  15

Trp Ser Phe Asn Thr Leu Lys His Asn Met Lys Asp Ile His Asp Ala
                20                  25                  30

Gly Tyr Thr Ala Ile Gln Thr Ser Pro Ile Asn Gln Val Lys Glu Gly
            35                  40                  45

Asn Gln Gly Asp Lys Ser Met Ser Asn Trp Tyr Trp Leu Tyr Gln Pro
        50                  55                  60

Thr Ser Tyr Gln Ile Gly Asn Arg Tyr Leu Gly Thr Glu Gln Glu Phe
65                  70                  75                  80

Lys Glu Met Cys Ala Ala Ala Glu Glu Tyr Gly Ile Lys Val Ile Val
                85                  90                  95

Asp Ala Val Ile Asn His Thr Thr Ser Asp Tyr Ala Ala Ile Ser Asn
            100                 105                 110

Glu Val Lys Ser Ile Pro Asn Trp Thr His Gly Asn Thr Gln Ile Lys
        115                 120                 125

Asn Trp Ser Asp Arg Trp Asp Val Thr Gln Asn Ser Leu Leu Gly Leu
    130                 135                 140

Tyr Asp Trp Asn Thr Gln Asn Thr Gln Val Gln Ser Tyr Leu Lys Arg
145                 150                 155                 160

Phe Leu Asp Arg Ala Leu Asn Asp Gly Ala Asp Gly Phe Arg Phe Asp
                165                 170                 175

Ala Ala Lys His Ile Glu Leu Pro Asp Asp Gly Ser Tyr Gly Ser Gln
            180                 185                 190

Phe Trp Pro Asn Ile Thr Asn Thr Ser Ala Glu Phe Gln Tyr Gly Glu
        195                 200                 205

Ile Leu Gln Asp Ser Ala Ser Arg Asp Ala Ala Tyr Ala Asn Tyr Met
    210                 215                 220

Asp Val Thr Ala Ser Asn Tyr Gly His Ser Ile Arg Ser Ala Leu Lys
225                 230                 235                 240
```

```
Asn Arg Asn Leu Gly Val Ser Asn Ile Ser His Tyr Ala Ser Asp Val
            245                 250                 255

Ser Ala Asp Lys Leu Val Thr Trp Val Glu Ser His Asp Thr Tyr Ala
            260                 265                 270

Asn Asp Asp Glu Glu Ser Thr Trp Met Ser Asp Asp Ile Arg Leu
            275                 280                 285

Gly Trp Ala Val Ile Ala Ser Arg Ser Gly Ser Thr Pro Leu Phe Phe
            290                 295                 300

Ser Arg Pro Glu Gly Gly Gly Asn Gly Val Arg Phe Pro Gly Lys Ser
305                 310                 315                 320

Gln Ile Gly Asp Arg Gly Ser Ala Leu Phe Glu Asp Gln Ala Ile Thr
            325                 330                 335

Ala Val Asn Arg Phe His Asn Val Met Ala Gly Gln Pro Glu Glu Leu
            340                 345                 350

Ser Asn Pro Asn Gly Asn Asn Gln Ile Phe Met Asn Gln Arg Gly Ser
            355                 360                 365

His Gly Val Val Leu Ala Asn Ala Gly Ser Ser Ser Val Ser Ile Asn
            370                 375                 380

Thr Ala Thr Lys Leu Pro Asp Gly Arg Tyr Asp Asn Lys Ala Gly Ala
385                 390                 395                 400

Gly Ser Phe Gln Val Asn Asp Gly Lys Leu Thr Gly Thr Ile Asn Ala
            405                 410                 415

Arg Ser Val Ala Val Leu Tyr Pro Asp
            420                 425

<210> SEQ ID NO 3
<211> LENGTH: 659
<212> TYPE: PRT
<213> ORGANISM: Bacillus subtilis
<220> FEATURE:
<221> NAME/KEY: misc_feature
<223> OTHER INFORMATION: Bacillus subtilis alpha-amylase variant Amy31A
      amino acid sequence (UniProtKB/TrEMBL Accession No. O82953).

<400> SEQUENCE: 3

Met Phe Glu Lys Arg Phe Lys Thr Ser Leu Leu Pro Leu Phe Ala Gly
1               5                   10                  15

Phe Leu Leu Leu Phe His Leu Val Leu Ser Gly Pro Ala Ala Ala Asn
            20                  25                  30

Ala Glu Thr Ala Asn Lys Ser Asn Lys Val Thr Ala Ser Ser Val Lys
            35                  40                  45

Asn Gly Thr Ile Leu His Ala Trp Asn Trp Ser Phe Asn Thr Leu Thr
    50                  55                  60

Gln Asn Met Lys Asp Ile Arg Asp Ala Gly Tyr Ala Ala Ile Gln Thr
65                  70                  75                  80

Ser Pro Ile Asn Gln Val Lys Glu Gly Asn Gln Gly Asp Lys Ser Met
            85                  90                  95

Ser Asn Trp Tyr Trp Leu Tyr Gln Pro Thr Ser Tyr Gln Ile Gly Asn
            100                 105                 110

Arg Tyr Leu Gly Thr Glu Gln Glu Phe Lys Asp Met Cys Ala Ala Ala
            115                 120                 125

Glu Lys Tyr Gly Val Lys Val Ile Val Asp Ala Val Ala Asn His Thr
            130                 135                 140

Thr Ser Asp Tyr Gly Ala Ile Ser Asp Glu Ile Lys Arg Ile Pro Asn
145                 150                 155                 160
```

-continued

Trp Thr His Gly Asn Thr Gln Ile Lys Asn Trp Ser Asp Arg Trp Asp
                165                 170                 175

Ile Thr Gln Asn Ala Leu Leu Gly Leu Tyr Asp Trp Asn Thr Gln Asn
            180                 185                 190

Thr Glu Val Gln Ala Tyr Leu Lys Gly Phe Leu Glu Arg Ala Leu Asn
        195                 200                 205

Asp Gly Ala Asp Gly Phe Arg Tyr Asp Ala Ala Lys His Ile Glu Leu
    210                 215                 220

Pro Asp Asp Gly Asn Tyr Gly Ser Gln Phe Trp Pro Asn Ile Thr Asn
225                 230                 235                 240

Thr Ser Ala Glu Phe Gln Tyr Gly Glu Ile Leu Gln Asp Ser Ala Ser
                245                 250                 255

Arg Asp Thr Ala Tyr Ala Asn Tyr Met Asn Val Thr Ala Ser Asn Tyr
            260                 265                 270

Gly His Ser Ile Arg Ser Ala Leu Lys Asn Arg Ile Leu Ser Val Ser
        275                 280                 285

Asn Ile Ser His Tyr Ala Ser Asp Val Ser Ala Asp Lys Leu Val Thr
    290                 295                 300

Trp Val Glu Ser His Asp Thr Tyr Ala Asn Asp Asp Glu Glu Ser Thr
305                 310                 315                 320

Trp Met Ser Asp Asp Asp Ile Arg Leu Gly Trp Ala Val Ile Gly Ser
                325                 330                 335

Arg Ser Gly Ser Thr Pro Leu Phe Phe Ser Arg Pro Glu Gly Gly Gly
            340                 345                 350

Asn Gly Val Arg Phe Pro Gly Lys Ser Gln Ile Gly Asp Arg Gly Ser
        355                 360                 365

Ala Leu Phe Lys Asp Gln Ala Ile Thr Ala Val Asn Gln Phe His Asn
    370                 375                 380

Glu Met Ala Gly Gln Pro Glu Glu Leu Ser Asn Pro Asn Gly Asn Asn
385                 390                 395                 400

Gln Ile Phe Met Asn Gln Arg Gly Ser Lys Gly Val Val Leu Ala Asn
                405                 410                 415

Ala Gly Ser Ser Ser Val Thr Ile Asn Thr Ser Thr Lys Leu Pro Asp
            420                 425                 430

Gly Arg Tyr Asp Asn Arg Ala Gly Ala Gly Ser Phe Gln Val Ala Asn
        435                 440                 445

Gly Lys Leu Thr Gly Thr Ile Asn Ala Arg Ser Ala Ala Val Leu Tyr
    450                 455                 460

Pro Asp Asp Ile Gly Asn Ala Pro His Val Phe Leu Glu Asn Tyr Gln
465                 470                 475                 480

Thr Glu Ala Val His Ser Phe Asn Asp Gln Leu Thr Val Thr Leu Arg
                485                 490                 495

Ala Asn Ala Lys Thr Thr Lys Ala Val Tyr Gln Ile Asn Asn Gly Gln
            500                 505                 510

Glu Thr Ala Phe Lys Asp Gly Asp Arg Leu Thr Ile Gly Lys Glu Asp
        515                 520                 525

Pro Ile Gly Thr Thr Tyr Asn Val Lys Leu Thr Gly Thr Asn Gly Glu
    530                 535                 540

Gly Ala Ser Arg Thr Gln Glu Tyr Thr Phe Val Lys Lys Asp Pro Ser
545                 550                 555                 560

Gln Thr Asn Ile Ile Gly Tyr Gln Asn Pro Asp His Trp Gly Asn Val
                565                 570                 575

Asn Ala Tyr Ile Tyr Lys His Asp Gly Gly Gly Ala Ile Glu Leu Thr

```
                580             585             590
Gly Ser Trp Pro Gly Lys Ala Met Thr Lys Asn Ala Asp Gly Ile Tyr
        595             600             605

Thr Leu Thr Leu Pro Ala Asn Ala Asp Thr Ala Asp Ala Lys Val Ile
        610             615             620

Phe Asn Asn Gly Ser Ala Gln Val Pro Gly Gln Asn His Pro Gly Phe
625             630             635             640

Asp Tyr Val Gln Asn Gly Leu Tyr Asn Asn Ser Gly Leu Asn Gly Tyr
                645             650             655

Leu Pro His

<210> SEQ ID NO 4
<211> LENGTH: 518
<212> TYPE: PRT
<213> ORGANISM: Geobacillus stearothermophilus
<220> FEATURE:
<221> NAME/KEY: misc_feature
<223> OTHER INFORMATION: Truncated Geobacillus stearothermophilus
      alpa-amylase (AmyS) Protein sequence.

<400> SEQUENCE: 4

Met Leu Thr Phe His Arg Ile Ile Arg Lys Gly Trp Met Phe Leu Leu
1               5                   10                  15

Ala Phe Leu Leu Thr Ala Ser Leu Phe Cys Pro Thr Gly Gln His Ala
            20                  25                  30

Lys Ala Ala Ala Pro Phe Asn Gly Thr Met Met Gln Tyr Phe Glu Trp
        35                  40                  45

Tyr Leu Pro Asp Asp Gly Thr Leu Trp Thr Lys Val Ala Asn Glu Ala
    50                  55                  60

Asn Asn Leu Ser Ser Leu Gly Ile Thr Ala Leu Trp Leu Pro Pro Ala
65                  70                  75                  80

Tyr Lys Gly Thr Ser Arg Ser Asp Val Gly Tyr Gly Val Tyr Asp Leu
                85                  90                  95

Tyr Asp Leu Gly Glu Phe Asn Gln Lys Gly Thr Val Arg Thr Lys Tyr
            100                 105                 110

Gly Thr Lys Ala Gln Tyr Leu Gln Ala Ile Gln Ala Ala His Ala Ala
        115                 120                 125

Gly Met Gln Val Tyr Ala Asp Val Val Phe Asp His Lys Gly Gly Ala
    130                 135                 140

Asp Gly Thr Glu Trp Val Asp Ala Val Glu Val Asn Pro Ser Asp Arg
145                 150                 155                 160

Asn Gln Glu Ile Ser Gly Thr Tyr Gln Ile Gln Ala Trp Thr Lys Phe
                165                 170                 175

Asp Phe Pro Gly Arg Gly Asn Thr Tyr Ser Ser Phe Lys Trp Arg Trp
            180                 185                 190

Tyr His Phe Asp Gly Val Asp Trp Asp Glu Ser Arg Lys Leu Ser Arg
        195                 200                 205

Ile Tyr Lys Phe Ile Gly Lys Ala Trp Asp Trp Glu Val Asp Thr Glu
    210                 215                 220

Asn Gly Asn Tyr Asp Tyr Leu Met Tyr Ala Asp Leu Asp Met Asp His
225                 230                 235                 240

Pro Glu Val Val Thr Glu Leu Lys Asn Trp Gly Lys Trp Tyr Val Asn
                245                 250                 255

Thr Thr Asn Ile Asp Gly Phe Arg Leu Asp Ala Val Lys His Ile Lys
            260                 265                 270
```

```
Phe Ser Phe Phe Pro Asp Trp Leu Ser Tyr Val Arg Ser Gln Thr Gly
            275                 280                 285

Lys Pro Leu Phe Thr Val Gly Glu Tyr Trp Ser Tyr Asp Ile Asn Lys
290                 295                 300

Leu His Asn Tyr Ile Thr Lys Thr Asn Gly Thr Met Ser Leu Phe Asp
305                 310                 315                 320

Ala Pro Leu His Asn Lys Phe Tyr Thr Ala Ser Lys Ser Gly Gly Ala
                325                 330                 335

Phe Asp Met Arg Thr Leu Met Thr Asn Thr Leu Met Lys Asp Gln Pro
            340                 345                 350

Thr Leu Ala Val Thr Phe Val Asp Asn His Asp Thr Glu Pro Gly Gln
        355                 360                 365

Ala Leu Gln Ser Trp Val Asp Pro Trp Phe Lys Pro Leu Ala Tyr Ala
370                 375                 380

Phe Ile Leu Thr Arg Gln Glu Gly Tyr Pro Cys Val Phe Tyr Gly Asp
385                 390                 395                 400

Tyr Tyr Gly Ile Pro Gln Tyr Asn Ile Pro Ser Leu Lys Ser Lys Ile
                405                 410                 415

Asp Pro Leu Leu Ile Ala Arg Arg Asp Tyr Ala Tyr Gly Thr Gln His
            420                 425                 430

Asp Tyr Leu Asp His Ser Asp Ile Ile Gly Trp Thr Arg Glu Gly Val
        435                 440                 445

Thr Glu Lys Pro Gly Ser Gly Leu Ala Ala Leu Ile Thr Asp Gly Pro
    450                 455                 460

Gly Gly Ser Lys Trp Met Tyr Val Gly Lys Gln His Ala Gly Lys Val
465                 470                 475                 480

Phe Tyr Asp Leu Thr Gly Asn Arg Ser Asp Thr Val Thr Ile Asn Ser
                485                 490                 495

Asp Gly Trp Gly Glu Phe Lys Val Asn Gly Gly Ser Val Ser Val Trp
            500                 505                 510

Val Pro Arg Lys Thr Thr
        515

<210> SEQ ID NO 5
<211> LENGTH: 1854
<212> TYPE: DNA
<213> ORGANISM: Bacillus subtilis
<220> FEATURE:
<221> NAME/KEY: misc_feature
<223> OTHER INFORMATION: Nucleotide sequence encoding the AmyE of SEQ ID
      NO: 1.

<400> SEQUENCE: 5
cttacagcac cgtcgatcaa aagcggaacc attcttcatg catggaattg gtcgttcaat        60
acgttaaaac acaatatgaa ggatattcat gatgcaggat atacagccat tcagacatct       120
ccgattaacc aagtaaagga agggaatcaa ggagataaaa gcatgtcgaa ctggtactgg       180
ctgtatcagc cgacatcgta tcaaattggc aaccgttact taggtactga acaagaattt       240
aaagaaatgt gtgcagccgc tgaagaatat ggcataaagg tcattgttga cgcggtcatc       300
aatcatacca ccagtgatta tgccgcgatt tccaatgagg ttaagagtat tccaaactgg       360
acacatggaa acacacaaat taaaaactgg tctgatcgat gggatgtcac gcagaattca       420
ttgctcgggc tgtatgactg gaatacacaa atacacaag tacagtccta tctgaaacgg       480
ttcttagaca gggcattgaa tgacgggca gacggttttc gatttgatgc cgccaaacat       540
atagagcttc cagatgatgg cagttacggc agtcaatttt ggccgaatat cacaaataca       600
```

```
tcagcagagt tccaatacgg agaaatcctt caggatagtg cctccagaga tgctgcatat     660
gcgaattata tggatgtgac agcgtctaac tatgggcatt ccataaggtc cgctttaaag     720
aatcgtaatc tgggcgtgtc gaatatctcc cactatgcat ctgatgtgtc tgcggacaag     780
ctagtgacat gggtagagtc gcatgatacg tatgccaatg atgatgaaga gtcgacatgg     840
atgagcgatg atgatatccg tttaggctgg gcggtgatag cttctcgttc aggcagtacg     900
cctcttttct tttccagacc tgagggaggc ggaaatggtg tgaggttccc ggggaaaagc     960
caaataggcg atcgcgggag tgctttattt gaagatcagg ctatcactgc ggtcaataga    1020
tttcacaatg tgatggctgg acagcctgag gaactctcga acccgaatgg aaacaaccag    1080
atatttatga atcagcgcgg ctcacatggc gttgtgctgg caaatgcagg ttcatcctct    1140
gtctctatca atacggcaac aaaattgcct gatggcaggt atgacaataa agctggagcg    1200
ggttcatttc aagtgaacga tggtaaactg acaggcacga tcaatgccag gtctgtagct    1260
gtgctttatc ctgatgatat tgcaaaagcg cctcatgttt tccttgagaa ttacaaaaca    1320
ggtgtaacac attctttcaa tgatcaactg acgattacct gcgtgcaga tgcgaataca    1380 acaaaagccg tttatcaaat caataatgga ccagagacgg cgtttaagga tggagatcaa    1440
ttcacaatcg gaaaaggaga tccatttggc aaaacataca ccatcatgtt aaaaggaacg    1500
aacagtgatg gtgtaacgag gaccgagaaa tacagttttg ttaaaagaga tccagcgtcg    1560
gccaaaacca tcggctatca aaatccgaat cattggagcc aggtaaatgc ttatatctat    1620
aaacatgatg ggagccgagt aattgaattg accggatctt ggcctggaaa accaatgact    1680
aaaaatgcag acggaattta cacgctgacg ctgcctgcgg acacggatac aaccaacgca    1740
aaagtgattt ttaataatgg cagcgcccaa gtgcccggtc agaatcagcc tggctttgat    1800
tacgtgctaa atggtttata taatgactcg ggcttaagcg gttctcttcc ccat          1854

<210> SEQ ID NO 6
<211> LENGTH: 1275
<212> TYPE: DNA
<213> ORGANISM: Bacillus subtilis
<220> FEATURE:
<221> NAME/KEY: misc_feature
<223> OTHER INFORMATION: Nucleotide sequence encoding AmyE-tr (SEQ ID
      NO: 2).

<400> SEQUENCE: 6
cttacagcac cgtcgatcaa aagcggaacc attcttcatg catggaattg gtcgttcaat      60
acgttaaaac acaatatgaa ggatattcat gatgcaggat atacagccat tcagacatct     120
ccgattaacc aagtaaagga agggaatcaa ggagataaaa gcatgtcgaa ctggtactgg     180
ctgtatcagc cgacatcgta tcaaattggc aaccgttact taggtactga acaagaattt     240
aaagaaatgt gtgcagccgc tgaagaatat ggcataaagg tcattgttga cgcggtcatc     300
aatcatacca ccagtgatta tgccgcgatt tccaatgagg ttaagagtat tccaaactgg     360
acacatggaa acacacaaat taaaaactgg tctgatcgat gggatgtcac gcagaattca     420
ttgctcgggc tgtatgactg gaatacacaa aatacacaag tacagtccta tctgaaacgg     480
ttcttagaca gggcattgaa tgacgggca gacggttttc gatttgatgc cgccaaacat     540
atagagcttc cagatgatgg cagttacggc agtcaatttt ggccgaatat cacaaataca     600
tcagcagagt tccaatacgg agaaatcctt caggatagtg cctccagaga tgctgcatat     660
gcgaattata tggatgtgac agcgtctaac tatgggcatt ccataaggtc cgctttaaag     720
```

-continued

```
aatcgtaatc tgggcgtgtc gaatatctcc cactatgcat ctgatgtgtc tgcggacaag    780
ctagtgacat gggtagagtc gcatgatacg tatgccaatg atgatgaaga gtcgacatgg    840
atgagcgatg atgatatccg tttaggctgg gcggtgatag cttctcgttc aggcagtacg    900
cctcttttct tttccagacc tgagggaggc ggaaatggtg tgaggttccc ggggaaaagc    960
caaataggcg atcgcgggag tgctttattt gaagatcagg ctatcactgc ggtcaataga   1020
tttcacaatg tgatggctgg acagcctgag gaactctcga acccgaatgg aaacaaccag   1080
atatttatga atcagcgcgg ctcacatggc gttgtgctgg caaatgcagg ttcatcctct   1140
gtctctatca atacggcaac aaaattgcct gatggcaggt atgacaataa agctggagcg   1200
ggttcatttc aagtgaacga tggtaaactg acaggcacga tcaatgccag gtctgtagct   1260
gtgctttatc ctgat                                                    1275
```

<210> SEQ ID NO 7
<211> LENGTH: 1842
<212> TYPE: DNA
<213> ORGANISM: Bacillus subtilis
<220> FEATURE:
<221> NAME/KEY: misc_feature
<223> OTHER INFORMATION: Nucleotide sequence encoding B. subtilis Amy31A
      (SEQ ID NO: 3).

<400> SEQUENCE: 7

```
tctgttaaaa acggcactat tctgcatgca tggaactgga gctttaacac gctgacccag     60
aacatgaaag atattcgtga cgcgggctat gctgcgatcc aaaccagccc tatcaaccag    120
gtcaaagaag caaccaagg cgacaaatcc atgtccaact ggtactggct gtatcaaccg    180
acgtcctatc agattggcaa ccgttatctg ggcacggagc aagagttcaa agacatgtgt    240
gctgcggctg agaaatatgg tgtgaaagtt atcgtggacg ctgtggtaaa ccacacgacc    300
tctgattatg gtgctattag cgacgagatt aaacgtattc caaattggac ccatggtaat    360
acccagatca aaaattggag cgaccgctgg gacattaccc agaatgcgct gctgggtctg    420
tatgactgga acacgcaaaa caccgaagta caggcatatc tgaagggctt cctggaacgc    480
gctctgaacg atggtgctga tggttttcgc tacgacgccg caaagcatat tgagctgccg    540
gatgacggca actacggttc ccaattctgg ccgaacatca ccaacacctc tgccgaattc    600
cagtacggca gatcctgca agactccgcg agccgtgaca ccgcttatgc caactatatg    660
aacgtaactg cctctaacta tggccattcc attcgttctg cgctgaaaaa tcgtatcctg    720
tccgtgtcca atatctccca ctatgcatcc gacgttttctg ctgacaaact ggtaacttgg    780
gtcgagtctc acgacaccta tgcaaatgat gacgaggaga gcacctggat gagcgatgat    840
gatattcgtc tgggttgggc ggttattggt tctcgctctg gttctactcc gctgttcttt    900
agccgtccgg aaggtggcgg caatggcgtt cgtttcccgg gtaaatctca aattggtgat   960
cgtggctctg cactgtttaa agatcaagct attacggcgg tgaatcagtt ccataatgag   1020
atggcaggtc aacctgaaga actgtccaat ccaaacggta caaccaaat cttcatgaac   1080 cagcgtggca gcaaaggcgt cgtcctggcg aacgccggta gctcttctgt taccatcaac   1140
acgtctacca aactgccaga cggccgctat gataaccgtg cgggtgctgg ttccttcag   1200 gtagccaacg gcaagctgac gggcaccatc aacgctcgtt ctgctgctgt tctgtacccg   1260
gacgacattg caacgctcc gcacgtgttc ctggagaatt accagaccga agcggtacat   1320
agctttaatg accagctgac cgtcactctg cgtgccaacg caaaaaccac gaaagcagtc   1380
tatcagatca ataatggtca agaaactgct ttcaaggatg gcgaccgtct gactattggt   1440
```

```
aaggaggacc cgattggcac cacttataac gttaaactga ctggcaccaa tggcgagggc    1500
gctagccgca ctcaagagta tacgttcgta aagaaagacc cgtctcaaac caacatcatc    1560
ggttaccaga atcctgacca ctggggtaat gtgaacgctt acatctataa acatgatggt    1620
ggcggtgcta tcgaactgac cggctcttgg ccaggtaaag ccatgacgaa aaacgcggat    1680
ggcatctata ccctgaccct gccggccaat gcggataccg cagatgcgaa ggttatcttc    1740
aataacggct ccgcgcaggt tccgggccaa aaccatccgg gctttgacta cgtacaaaat    1800
ggtctgtata caaactctgg cctgaacggt tacctgccgc ac                       1842
```

<210> SEQ ID NO 8
<211> LENGTH: 1452
<212> TYPE: DNA
<213> ORGANISM: Geobacillus stearothermophilus
<220> FEATURE:
<221> NAME/KEY: misc_feature
<223> OTHER INFORMATION: Nucleotide sequence encoding Geobacillus stearothermophilus AmyS (SEQ ID NO: 4).

<400> SEQUENCE: 8

```
gccgcaccgt ttaacggtac catgatgcag tattttgaat ggtacttgcc ggatgatggc      60
acgttatgga ccaaagtggc caatgaagcc aacaacttat ccagccttgg catcaccgct     120
ctttggctgc cgcccgctta caaaggaaca agccgcagcg acgtagggta cggagtatac     180
gacttgtatg acctcggcga attcaatcaa aagggaccg tccgcacaaa atatggaaca      240
aaagctcaat atcttcaagc cattcaagcc gcccacgccg ctggaatgca agtgtacgcc     300
gatgtcgtgt tcgaccataa aggcggcgct gacggcacgg aatgggtgga cgccgtcgaa     360
gtcaatccgt ccgaccgcaa ccaagaaatc tcgggcacct atcaaatcca agcatggacg     420
aaatttgatt ttcccgggcg gggcaacacc tactccagct taagtggcg ctggtaccat      480 tttgacggcg ttgactggga cgaaagccga aaattaagcc gcatttacaa attcatcggc     540
aaagcgtggg attgggaagt agacacagaa aacggaaact atgactactt aatgtatgcc     600
gaccttgata tggatcatcc cgaagtcgtg accgagctga aaaactgggg gaaatggtat     660
gtcaacacaa cgaacattga tgggttccgg cttgatgccg tcaagcatat taagttcagt     720 tttttttcctg attggttgtc gtatgtgcgt tctcagactg gcaagccgct atttaccgtc     780
ggggaatatt ggagctatga catcaacaag ttgcacaatt acattacgaa acaaacgga      840 acgatgtctt tgtttgatgc cccgttacac aacaaatttt ataccgcttc caaatcaggg     900
ggcgcatttg atatgcgcac gttaatgacc aatactctca tgaaagatca accgacattg     960
gccgtcacct tcgttgataa tcatgacacc gaacccggcc aagcgctgca gtcatgggtc    1020
gacccatggt tcaaaccgtt ggcttacgcc tttattctaa ctcggcagga aggatacccg    1080
tgcgtctttt atggtgacta ttatggcatt ccacaatata cattccttc gctgaaaagc     1140 aaaatcgatc cgctcctcat cgcgcgcagg gattatgctt acggaacgca acatgattat    1200
cttgatcact ccgacatcat cgggtggaca agggaagggg tcactgaaaa accaggatcc    1260
gggctggccg cactgatcac cgatgggccg ggaggaagca aatggatgta cgttggcaaa    1320
caacacgctg gaaaagtgtt ctatgacctt accggcaacc ggagtgacac cgtcaccatc    1380
aacagtgatg gatggggggga attcaaagtc aatggcggtt cggtttcggt ttgggttcct    1440
agaaaaacga cc                                                         1452
```

<210> SEQ ID NO 9

```
<211> LENGTH: 41
<212> TYPE: PRT
<213> ORGANISM: Bacillus subtilis
<220> FEATURE:
<221> NAME/KEY: misc_feature
<223> OTHER INFORMATION: Native signal sequence of the AmyE of SEQ ID
      NO: 1.

<400> SEQUENCE: 9

Met Phe Ala Lys Arg Phe Lys Thr Ser Leu Leu Pro Leu Phe Ala Gly
1               5                   10                  15

Phe Leu Leu Leu Phe His Leu Val Leu Ala Gly Pro Ala Ala Ala Ser
            20                  25                  30

Ala Glu Thr Ala Asn Lys Ser Asn Glu
        35                  40

<210> SEQ ID NO 10
<211> LENGTH: 60
<212> TYPE: DNA
<213> ORGANISM: Artificial Sequence
<220> FEATURE:
<223> OTHER INFORMATION: Synthetic primer PSTAMYE-F 5'

<400> SEQUENCE: 10
cttcttgctg cctcattctg cagcttcagc acttacagca ccgtcgatca aaagcggaac      60

<210> SEQ ID NO 11
<211> LENGTH: 57
<212> TYPE: DNA
<213> ORGANISM: Artificial Sequence
<220> FEATURE:
<223> OTHER INFORMATION: Synthetic primer AMYENOPST-R 5'

<400> SEQUENCE: 11
ctggaggcac tatcctgaag gatttctccg tattggaact ctgctgatgt atttgtg        57

<210> SEQ ID NO 12
<211> LENGTH: 57
<212> TYPE: DNA
<213> ORGANISM: Artificial Sequence
<220> FEATURE:
<223> OTHER INFORMATION: Synthetic primer AMYENOPST-F 5'

<400> SEQUENCE: 12
cacaaataca tcagcagagt tccaatacgg agaaatcctt caggatagtg cctccag        57

<210> SEQ ID NO 13
<211> LENGTH: 56
<212> TYPE: DNA
<213> ORGANISM: Artificial Sequence
<220> FEATURE:
<223> OTHER INFORMATION: Synthetic primer HPAIAMYE-R 5'

<400> SEQUENCE: 13
caggaaatcc gtcctctgtt aactcaatgg ggaagagaac cgcttaagcc cgagtc         56

<210> SEQ ID NO 14
<211> LENGTH: 55
<212> TYPE: DNA
<213> ORGANISM: Artificial Sequence
<220> FEATURE:
<223> OTHER INFORMATION: Synthetic primer HPAIAMYE466-R 5'

<400> SEQUENCE: 14
caggaaatcc gtcctctgtt aactcaatca ggataaagca cagctacaga cctgg          55
```

<210> SEQ ID NO 15
<211> LENGTH: 22
<212> TYPE: DNA
<213> ORGANISM: Artificial Sequence
<220> FEATURE:
<223> OTHER INFORMATION: Synthetic primer AMYE SEQ-F1 5'

<400> SEQUENCE: 15
tacacaagta cagtcctatc tg                                              22

<210> SEQ ID NO 16
<211> LENGTH: 22
<212> TYPE: DNA
<213> ORGANISM: Artificial Sequence
<220> FEATURE:
<223> OTHER INFORMATION: Synthetic primer AMYE SEQ-F2 5'

<400> SEQUENCE: 16
catcctctgt ctctatcaat ac                                              22

<210> SEQ ID NO 17
<211> LENGTH: 413
<212> TYPE: PRT
<213> ORGANISM: Artificial Sequence
<220> FEATURE:
<223> OTHER INFORMATION: Synthetic BP-17 variant of Buttiauxiella
      phytase

<400> SEQUENCE: 17

```
Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Gln Lys Phe Gln Gln Gly Ile Leu Ser Gln Gly Ser Cys Pro
65                  70                  75                  80

Thr Pro Asn Ser Ile Tyr Val Trp Ala Asp Val Asp Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Thr Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Phe Leu Ala Leu Met Asn Thr Thr Leu Asn Phe Ser Thr
                165                 170                 175

Ser Ala Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Lys Val
        195                 200                 205

Ala Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240
```

```
His Ser Glu Gln Glu Trp Ala Ser Leu Leu Lys Leu His Asn Val Gln
                245                 250                 255
Phe Asp Leu Met Ala Arg Thr Pro Tyr Ile Ala Arg His Asn Gly Thr
            260                 265                 270
Pro Leu Leu Gln Ala Ile Ser Asn Ala Leu Asn Pro Asn Ala Thr Glu
        275                 280                 285
Ser Lys Leu Pro Asp Ile Ser Pro Asp Asn Lys Ile Leu Phe Ile Ala
    290                 295                 300
Gly His Asp Thr Asn Ile Ala Asn Ile Ala Gly Met Leu Asn Met Arg
305                 310                 315                 320
Trp Thr Leu Pro Gly Gln Pro Asp Asn Thr Pro Pro Gly Gly Ala Leu
                325                 330                 335
Val Phe Glu Arg Leu Ala Asp Lys Ser Gly Lys Gln Tyr Val Ser Val
            340                 345                 350
Ser Met Val Tyr Gln Thr Leu Glu Gln Leu Arg Ser Gln Thr Pro Leu
        355                 360                 365
Ser Leu Asn Gln Pro Ala Gly Ser Val Gln Leu Lys Ile Pro Gly Cys
    370                 375                 380
Asn Asp Gln Thr Ala Glu Gly Tyr Cys Pro Leu Ser Thr Phe Thr Arg
385                 390                 395                 400
Val Val Ser Gln Ser Val Glu Pro Gly Cys Gln Leu Gln
                405                 410
```